United States Patent
Andersen et al.

(12)

(10) Patent No.: US 7,115,624 B1
(45) Date of Patent: Oct. 3, 2006

(54) METHOD OF INHIBITING PROTEIN TYROSINE PHOSPHATASE 1B AND/OR T-CELL PROTEIN TYROSINE PHOSPHATASE 4 AND/OR OTHER PTPASES WITH AN ASP RESIDUE AT POSITION 48

(75) Inventors: Henrik Sune Andersen, Lyngby (DK); Thomas Kruse Hansen, Herlev (DK); Lars Fogh Iversen, Holte (DK); Jesper Lau, Farum (DK); Niels Peter Hundahl Møller, København (DK); Ole Hvilsted Olsen, Brønshøj (DK); Frank Urban Axe, Escondido, CA (US); Yu Ge, San Diego, CA (US); Daniel Dale Holsworth, San Diego, CA (US); Todd Kevin Jones, Solana Beach, CA (US); Luke Milburn Judge, Seattle, WA (US); Wiliam Charles Ripka, San Diego, CA (US); Barry Zvi Shapira, La Jolla, CA (US); Roy Teruyuki Uyeda, San Diego, CA (US)

(73) Assignee: Novo Nordisk A/S, Bagsvaerd (DK)

( * ) Notice: Subject to any disclaimer, the term of this patent is extended or adjusted under 35 U.S.C. 154(b) by 836 days.

(21) Appl. No.: 09/659,622

(22) Filed: Sep. 11, 2000

Related U.S. Application Data

(60) Provisional application No. 60/156,641, filed on Sep. 29, 1999.

(30) Foreign Application Priority Data

Sep. 10, 1999 (DK) ............................... 1999 01279

(51) Int. Cl.
*A01N 43/42* (2006.01)
*A61K 31/44* (2006.01)

(52) U.S. Cl. ............... 514/301; 514/229.8; 514/202; 514/205; 514/208; 514/302; 514/362; 514/363; 514/365; 514/372; 514/374; 514/381; 514/383; 514/364; 514/396; 514/403; 514/414; 514/417; 514/607; 514/621; 514/625; 435/21

(58) Field of Classification Search ................ 514/301, 514/229.8, 202, 205, 208, 302, 362, 363, 514/364, 365, 372, 374, 378, 381, 383, 396, 514/403, 414, 417, 607, 621, 625; 435/21
See application file for complete search history.

(56) References Cited

U.S. PATENT DOCUMENTS

| 3,953,468 | A | 4/1976 | Wechter et al. |
| 6,262,044 | B1 * | 7/2001 | Moller et al. ............... 514/202 |
| 6,410,586 | B1 | 6/2002 | Moller et al. |

FOREIGN PATENT DOCUMENTS

| GB | 1583679 | 1/1981 |
| WO | WO97/40017 | 10/1997 |
| WO | WO99/46236 | 9/1999 |
| WO | WO99/46237 | 9/1999 |
| WO | WO99/46244 | 9/1999 |
| WO | WO99/46267 | 9/1999 |
| WO | WO99/46268 | 9/1999 |

OTHER PUBLICATIONS

Iversen et al., The Journal of Biological Chemistry, 275(14): 10300-10307 (2000).

* cited by examiner

*Primary Examiner*—Fredrick Krass
*Assistant Examiner*—Amy Lewis
(74) *Attorney, Agent, or Firm*—Rosemarie R. Wilk-Orescan; Reza Green; Richard W. Bork

(57) ABSTRACT

The present invention provides a method of inhibiting a member of a family of Protein Tyrosine Phosphatases (PTPases, PTPs) such as PTP1B, TC-PTP, CD45, SHP-1, SHP-2, PTPα, PTPε, PTPμ, PTPδ, PTPσ, PTPζ, PTPβ, PTPD1, PTPD2, PTPH1, PTP-MEG1, PTP-LAR, and HePTP by exposing said Ptpase member by administration to a host or otherwise to at least one compound with certain structural, physical and spatial characteristics that allow for the interaction of said compound with specific residues of the active site of PTP1B and/or TC-PTP. These compounds are indicated in the management or treatment of a broad range of diseases such as autoimmune diseases, acute and chronic inflammation, osteoporosis, various forms of cancer and malignant diseases, and type I diabetes and type II diabetes, as well as in the isolation of PTPases and in elucidation or further elucidation of their biological function.

6 Claims, 4 Drawing Sheets

SEQUENCE LISTING

```
<160> NUMBER OF SEQ ID NOS: 2

<210> SEQ ID NO 1
<211> LENGTH: 7
<212> TYPE: PRT
<213> ORGANISM: Artificial
<220> FEATURE:
<223> OTHER INFORMATION: Synthetic
<220> FEATURE:
<221> NAME/KEY: MISC_FEATURE
<222> LOCATION: (2)..(6)
<223> OTHER INFORMATION: PTP-ase P-Loop

<400> SEQUENCE: 1

Cys Xaa Xaa Xaa Xaa Xaa Arg
1               5

<210> SEQ ID NO 2
<211> LENGTH: 7
<212> TYPE: PRT
<213> ORGANISM: Homo sapiens
<220> FEATURE:
<221> NAME/KEY: MISC_FEATURE
<222> LOCATION: (1)..(7)
<223> OTHER INFORMATION: PTP1B P-Loop

<400> SEQUENCE: 2

Cys Ser Ala Gly Ile Gly Arg
1               5
```

METHOD OF INHIBITING PROTEIN TYROSINE PHOSPHATASE 1B AND/OR T-CELL PROTEIN TYROSINE PHOSPHATASE 4 AND/OR OTHER PTPASES WITH AN ASP RESIDUE AT POSITION 48

This patent application claims the priority of (1) U.S. provisional patent application No. 60/156,641, filed Sep. 29, 1999, (2) Danish Patent Application No. PA 1999 01279, filed Sep. 10, 1999, and (3) U.S. Ser. No. 09/268,490, filed Mar. 11, 1999, now U.S. Pat. No. 6,262,044, which claims the benefit of U.S. Provisional Patent Application Nos. 60/082,915, 60/093,525, and 60/108,747, filed Apr. 24, 1998, Jul. 21, 1998, and Nov. 17, 1998, respectively, and Danish Patent Application Nos. 0344/98, PA 1998 00480, PA 1998 00938, PA 1998 01385, and PA 1998 10612, filed Mar. 12, 1998, Apr. 3, 1998, Jul. 15, 1998, Oct. 28, 1998, and Dec. 7, 1998, respectively, each of which is incorporated herein by reference.

FIELD OF THE INVENTION

This invention relates to a method of inhibiting Protein Tyrosine Phosphatase 1B (PTP1B) and/or T-cell Protein Tyrosine Phosphatase (TC-PTP) and/or Protein Tyrosine Phosphatases (PTPases) having an aspartic acid (Asp) in position 48 (PTP1B numbering, Chernoff et al., *Proc. Natl. Acad. Sci. USA* 87: 2735–2789 (1989)) by exposing such an enzyme to inhibitor compounds, i.e., to compounds possessing certain structural, physico-chemical and spatial characteristics that allow them to interact with specific amino acid residues of the active site (and the vicinity of the active site) of PTP1B and/or TC-PTP and more generally Protein Tyrosine Phosphatases (PTPases) having an aspartic acid (Asp) in position 48. The resulting inhibition of the PTPase enzymatic activity makes these compounds useful for elucidating the function of PTP's e.g., by inhibiting a PTP and observing up- or down-regulation of other proteins. Additionally, such inhibitors serve as early development candidates, development candidates, or prototype drugs for treatment of or paliation of diseases and dysfunctions such as diabetes type I and II and obesity, cancer, immune disorders (including-allergy and abnormal autoimmunity), and conditions involving disturbances in platelet aggregation as well as infectious diseases. This invention also relates to (I) the design and selection of inhibitors which bind to the active site of PTP1B and/or TC-PTP and/or PTPases having an aspartic acid (Asp) in position 48 (II) the synthesis of said inhibitors, methods for their preparation and (III) to compositions comprising the inhibitor compounds.

BACKGROUND OF THE INVENTION

Protein phosphorylation is now well recognized as an important mechanism utilized by cells to transduce and regulate signals during different stages of cellular function (Hunter, *Phil. Trans. R. Soc. Lond. B* 353: 583–605 (1998); Chan et al., *Annu. Rev. Immunol.* 12: 555–592 (1994); Zhang, *Curr. Top. Cell. Reg.* 35: 21–68 (1997); Matozaki and Kasuga, *Cell. Signal.* 8: 113–19 (1996); Fischer et al, *Science* 253:401–6 (1991); Flint et al., *EMBO J.* 12:1937–46 (1993)). The level of tyrosine phosphorylation is balanced by the opposing action of protein tyrosine kinases and protein tyrosine phosphatases. There are at least two major classes of phosphatases: (1) those that dephosphorylate proteins (or peptides) that contain a phosphate group(s) on a serine or threonine moiety (termed Ser/Thr phosphatases) and (2) those that remove a phosphate group(s) from the amino acid tyrosine (termed protein tyrosine phosphatases or PTPases or PTPs).

The PTPases are a family of enzymes that can be classified into two groups: a) intracellular or nontransmembrane PTPases and b) receptor-type or transmembrane PTPases. In addition, dual-specificity phosphatases and low molecular weight phosphatases are able to dephosphorylate phospho tyrosyl proteins. See, e.g., WO 97/39746; WO 97/40017; WO 99/15529; WO 97/08934; WO 98/27065; WO 99/46236; WO 99/46244; WO 99/46267; WO 99/46268 and WO 99/46237.

Intracellular PTPases: Most known intracellular type PTPases contain a single conserved catalytic phosphatase domain consisting of 220–240 amino acid residues. The regions outside the PTPase domains are believed to play important roles in localizing the intracellular PTPases subcellularly (Mauro, L. J. and Dixon, J. E. *TIBS* 19: 151–155 (1994)). The first intracellular PTPase to be purified and characterized was PTP1B, which was isolated from human placenta (Tonks et al., *J. Biol. Chem.* 263: 6722–6730 (1988)). Shortly after, PTP1B was expressed recombinantly (Charbonneau et al., *Proc. Natl. Acad. Sci. USA* 86: 5252–5256 (1989); Chernoff et al., *Proc. Natl. Acad. Sci. USA* 87: 2735–2789 (1989)). Other examples of intracellular PTPases include (1) T-cell PTPase/TC-PTP (Cool et al. *Proc. Natl. Acad. Sci. USA* 86: 5257–5261 (1989)), (2) rat brain PTPase (Guan et al., *Proc. Natl. Acad. Sci. USA* 87:1501–1502 (1990)), (3) neuronal phosphatase STEP (Lombroso et al., *Proc. Natl. Acad. Sci. USA* 88: 7242–7246 (1991)), (4) ezrin-domain containing PTPases: PTPMEG1 (Guet al., *Proc. Natl. Acad. Sci. USA* 88: 5867–57871 (1991)). PTPH1 (Yang and Tonks, *Proc. Natl. Acad. Sci. USA* 88: 5949–5953 (1991)), PTPD1 and PTPD2 (Møller et al., *Proc. Natl. Acad. Sci. USA* 91: 7477–7481 (1994)); FAP-1/BAS (Sato et al., *Science* 268: 411–415 (1995); Banville et al., *J. Biol. Chem.* 269, 22320–22327 (1994); Maekawa et al., *FEBS Letters* 337: 200–206 (1994)), and SH2 domain containing PTPases: PTP1C/SH-PTP1/SHP-1 (Plutzky et al., *Proc. Natl. Acad. Sci. USA* 89: 1123–1127 (1992); Shen et al., *Nature Lond.* 352: 736–739 (1991)) and PTP1D/Syp/SH-PTP2/SHP-2 (Vogel et al., *Science* 259: 1611–1614 (1993); Feng et al., *Science* 259: 1607–1611 (1993); Bastein et al., *Biochem. Biophys. Res. Comm.* 196: 124–133 (1993)).

Receptor-type PTPases consist of a) a putative ligand-binding extracellular domain, b) a transmembrane segment, and c) an intracellular catalytic region. The structures and sizes of the putative ligand-binding extracellular domains of receptor-type PTPases are quite divergent. In contrast, the intracellular catalytic regions of receptor-type PTPases are very homologous to each other and to the intracellular PTPases. Most receptor-type PTPases have two tandemly duplicated catalytic PTPase domains.

The first receptor-type PTPases to be identified were (1) CD45/LCA (Ralph, S. J., *EMBO J.* 6: 1251–1257 (1987)) and (2) LAR (Streuli et al., *J. Exp. Med.* 168: 1523–1530 (1988)) that were recognized to belong to this class of enzymes based on homology to PTP1B (Charbonneau et al., *Proc. Natl. Aced. Sci. USA* 86: 5252–256 (1989)). CD45 is a family of high molecular weight glycoproteins and is one of the most abundant leukocyte cell surface glycoproteins and appears to be exclusively expressed upon cells of the hematopoietic system (Trowbridge and Thomas, *Ann. Rev. Immunol.* 12: 85–116 (1994)).

The identification of CD45 and LAR as members of the PTPase family was quickly followed by identification and cloning of several different members of the receptor-type PTPase group. Thus, 5 different PTPases, (3) PTPα, (4) PTPβ, (5) PTPδ, (6) PTPε, and (7) PTPζ, were identified in one early study (Krueger et al., *EMBO J.* 9: 3241–3252 (1990)). Other examples of receptor-type PTPases include (8) PTPγ(Barnea et al., *Mol. Cell. Biol.* 13: 1497–1506 (1995)) which, like PTPζ (Krueger and Saito, *Proc. Natl. Acad. Sci. USA* 89: 7417–7421 (1992)) contains a carbonic anhydrase-like domain in the extracellular region, (9) PTPμ (Gebbink et al., *FEBS Letters* 290: 123–130 (1991)), (10) PTPκ (Jiang et al., *Mol. Cell. Biol.* 13: 2942–2951 (1993)). Based on structural differences the receptor-type PTPases may be classified into subtypes (Fischer et al., *Science* 253: 401–406 (19991)): (I) CD45; (II) LAR, PTPd, (11) PTPσ; (III) PTPβ, (12) SAP-1 (Matozaki et al., *J. Biol. Chem.* 269: 2075–2081 (1994)), (13) PTP-U2/GLEPP1 (Seimiya et al., *Oncogene* 10: 1731–1738 (1995); Thomas et al., *J. Biol. Chem.* 269: 19953–19962 (1994)), and (14) DEP-1; (IV) PTPα,_PTPε. All receptor-type PTPases except Type III contain two PTPase domains. Novel PTPases are frequently identified, and it is anticipated that between 100 and more than 500 different species will be found in the human genome.

PTPases are the biological counterparts to protein tyrosine kinases (PTKs). Therefore, one important function of PTPases is to control, and especially down-regulate, the activity of PTKs. However, a more complex picture of the function of PTPases has emerged. Thus, several studies indicate that some PTPases act as positive mediators of cellular signaling. As an example, the SH2 domain-containing SHP-2 acts as a positive mediator in insulin-stimulated Ras activation (Noguchi et al., *Mol. Cell. Biol.* 14: 6674–6682 (1994)) and of growth factor-induced mitogenic signal transduction (Xiao et al., *J. Biol. Chem.* 269: 21244–21248 (1994)), whereas the homologous SHP-1 acts as a negative regulator of growth factor-stimulated proliferation (Bignon and Siminovitch, *Clin. Immunol. Immunopathol.* 73: 168–179 (1994)). Another example of PTPases as positive regulators has been provided by studies designed to define the activation of the Src-family of tyrosine kinases. In particular, several lines of evidence indicate that CD45 is positively regulating the activation of hematopoietic cells, and that the mechanism of such positive regulation may involve dephosphorylation of the C-terminal tyrosine of Fyn and Lck (Chan et al., *Annu. Rev. Immunol.* 12: 555–592 (1994)).

The association of many PTPases with cell proliferation, tranformation and differentiation has now been established. PTP1B, a phosphatase whose structure was the first PTPase to be elucidated (Barford et al., *Science* 263:1397–1404 (1994)) has been shown to be involved in insulin-induced oocyte maturation (Flint et al., *The EMBO J.* 12:1937–46 (1993)) and the overexpression of this enzyme has been implicated in $p185^{c-erb\ B2}$-associated breast and ovarian cancers (Weiner, et al., *J. Natl. cancer Inst.* 86:372–8 (1994); Weiner et al., *Am. J. Obstet. Gynecol.* 170:1177–883 (1994)). The association with cancer is on the basis of evidence that overexpression of PTP1B is statistically correlated with increased levels of $p185^{\ c-erb\ B2}$ in ovarian and breast cancer. The role of PTP1B in the etiology and progression of the disease has not yet been elucidated. Inhibitors of PTP1B therefore would help clarify the role of PTP1B in cancer and in some cases provide therapeutic treatment for certain forms of cancer.

PTPases: the Insulin Receptor Signaling Pathway/Diabetes

Insulin is an important regulator of different metabolic processes and plays a key role in the control of blood glucose. Defects related to its synthesis or signaling lead to diabetes mellitus. Binding of insulin to the insulin receptor (IR) causes rapid (auto)phosphorylation of several tyrosine residues in the intracellular part of the β-subunit. Three closely positioned tyrosine residues (the tyrosine-1150 domain) must all be phosphorylated to obtain full activity of the insulin receptor tyrosine kinase (IRTK) which transmits the signal further downstream by tyrosine phosphorylation of other cellular substrates, including insulin receptor substrate-1 (IRS-1) (Wilden et al., *J. Biol. Chem.* 267: 16660–16668 (1992); Myers and White, *Diabetes* 42: 643–650 (1993); Lee and Pilch, *Am. J. Physiol.* 266: C319–C334 (1994); White et al., *J. Biol. Chem.* 263: 2969–2980 (1988)). The structural basis for the function of the tyrosine-triplet has been provided by X-ray crystallographic studies of IRTK that showed the tyrosine-1150 domain to be autoinhibitory in its unphosphorylated state (Hubbard et al, *Nature* 372: 746–754 (1994)) and of the activated IRTK (Hubbard, *EMBO J.* 16: 5572–5581 (1997)).

Several studies clearly indicate that the activity of the auto-phosphorylated IRTK can be reversed by dephosphorylation in vitro (reviewed in Goldstein, *Receptor* 3: 1–15 (1993); Mooney and Anderson, *J. Biol. Chem.* 264: 6850–6857 (1989)), with the tri-phosphorylated tyrosine-1150 domain being the most sensitive target for protein-tyrosine phosphatases (PTPases) as compared to the di- and mono-phosphorylated forms (King et al., *Biochem. J.* 275: 413–418 (1991)). This tyrosine-triplet functions as a control switch of IRTK activity and IRTK appears to be tightly regulated by PTP-mediated dephosphorylation in vivo (Khan et al., *J. Biol. Chem.* 264: 12931–12940 (1989); Faure et al., *J. Biol. Chem.* 267: 11215–11221 (1992); Rothenberg et al., *J. Biol. Chem.* 266: 8302–8311 (1991)). The intimate coupling of PTPases to the insulin signaling pathway is further evidenced by the finding that insulin differentially regulates PTPase activity in rat hepatoma cells (Meyerovitch et al., *Biochemistry* 31: 10338–10344 (1992)) and in livers from alloxan diabetic rats (Boylan et al., *J. Clin. Invest* 90:174–179 (1992)).

Until recently, relatively little was known about the identity of the PTPases involved in IRTK regulation. However, the existence of PTPases with activity towards the insulin receptor can be demonstrated as indicated above. Further, when the strong PTPase-inhibitor pervanadate is added to whole cells an almost full insulin response can be obtained in adipocytes (Fantus et al., *Biochemistry* 28: 8864–8871 (1989); Eriksson et al., *Diabetologia* 39: 235–242 (1995)) and skeletal muscle (Leighton et al., *Biochem: J.* 276: 289–292 (1991)). In addition, other studies show that a new class of peroxovanadium compounds act as potent hypoglycemic compounds in vivo (Posner et al., supra). Two of these compounds were demonstrated to be more potent inhibitors of dephosphorylation of the insulin receptor than of the EGF-receptor, thus indicating that even such relatively unselective inhibitors may show some specificity in regulating different signal transduction pathways.

It was recently found that mice lacking the protein tyrosine phosphatase-1B gene (PTP1B) (Elchebly et al., *Science* 283: 1544–1548 (1999)) yielded healthy mice that showed increased insulin sensitivity and were resistant to diet-induced obesity. These results were confirmed by Kaman at al *Mol. Cell Biol.* 20:5479–5489 (2000). The enhanced insulin sensitivity of the $PTP^{-/-}$ mice was also evident in glucose and insulin tolerance tests.

The PTP-1B knock-out mouse showed many characteristics which would be highly desirable results for an anti-diabetes treatment. Most importantly, the knock-out mice grew normally and were fertile and have exhibited no increased incidence of cancer. Blood glucose and insulin levels were lowered, and insulin sensitivity increased. Moreover, the insulin-stimulated tyrosine phosphorylation levels of IR and IRS-1 were found to be increased/prolonged in muscle and liver—but not in fat tissue. Thus, the main target tissues for this type of approach would appear to be insulin action in liver and muscle.

Several other "diabetic" parameters were also improved, including plasma triglycerides which were decreased in the knock-out mice. The knock-animals also exhibited a resistance to weight gain when placed on a high-fat diet. This is in contrast to the action of the PPARγ agonist class of insulin sensitizers, which rather induce weight gain (Murphy & Nolan, Exp. Opin. Invest. Drugs 9:1347–1361, 2000), and would suggest that inhibition of PTP-1B could be a particularly attractive option for treatment of obese Type II diabetics.

This is also supported by the fact that the heterozygous mice from this study showed many of these desirable features. The reduction in weight gain of the knock-out animals on the high fat diet was found to be due to a decreased fat cell mass, although differences were observed with respect to fat cell number. Leptin levels were also lower in the knock-out mice, presumably as a reflection of the decreased fat mass. Significantly, the Klaman et al group also found that the knock-out animals had an increased energy expenditure of around 20% and an increased respiratory quotient compared to the wild-type; again, heterozygote animals displayed an intermediate level of energy expenditure. Therefore, inhibition of this enzyme may be an effective anti-diabetic and perhaps also anti-obesity therapy.

It should also be rioted that in the PTP-1B knock-out mice the basal tyrosine phosphorylation level of the insulin receptor tyrosine kinase does not appear to be increased, which is in contrast to the situation after insulin treatment where there is an increased or prolonged phosphorylation. This might indicate that other PTPs are controlling the basic phosphorylation state of the insulin receptor in the knock-out mice— and is expected to do so in man.

Also other PTPases have been implicated as regulators of the insulin signaling pathway. Thus, it was found that the ubiquitously expressed SH2 domain containing PTPase, PTP1D/SHP-2 (Vogel et al., 1993, supra), associates with and dephosphorylates IRS-1, but apparently not the IR it self (Kuhné et al., J. Biol. Chem. 268: 11479–11481 (1993); (Kuhné et al., J. Biol. Chem. 269: 15833–15837 (1994)).

Other studies suggest that receptor-type or membrane-associated PTPases are involved in IRTK regulation (Faure et al., J. Biol. Chem. 267: 11215–11221 (1992), (Haring et al., Biochemistry 23: 3298–3306 (1984); Sale, Adv. Prot. Phosphatases 6: 159–186 (1991)).

While previous reports indicate a role of PTPα in signal transduction through src activation (Zheng et al., Nature 359: 336–339 (1992); den Hertog et al., EMBO J. 12: 3789–3798 (1993)) and interaction with GRB-2 (den Hertog et al., EMBO J. 13: 3020–3032 (1994); Su et al., J. Biol. Chem. 269: 18731–18734 (19.94)), Møller, Lammers and coworkers provided results that suggest a function for this phosphatase and its close relative PTPε as negative regulators of the insulin receptor signal (Møller et al., 1995 supra; Lammers, et al., FEBS Lett. 404:37–40 (1997). These studies also indicated that receptor-like PTPases may play a significant role in regulating the IRTK, including through direct influence on the insulin receptor itself.

Other studies have shown that PTP1B and TC-PTP are likely to be involved in the regulation of several other cellular processes in addition to the described regulatory roles in insulin signaling. Therefore, PTP1B and/or TC-PTP as well as other PTPases showing key structural features with PTP1B and TC-PTP are likely to be important therapeutic targets in a variety of human and animal diseases. The compounds of the present invention are useful for modulating or inhibiting PTP1B and/or TC-PTP and/or other PTPases showing key structural features with said PTPases and thus elucidating their function and for treating disease states in which said modulation or inhibition is indicated.

Further, PTPases influence the following hormones or diseases or disease states: somatostatin, the immune system/autoimmunity, cell—cell interactions/cancer, platelet aggregation, osteoporosis, and microorganisms, as disclosed in PCT Publication WO 99/15529.

PTPases: the Immune System/Autoimmunity

Several studies suggest that the receptor-type PTPase CD45 plays a critical role not only for initiation of T cell activation, but also for maintaining the T cell receptor-mediated signaling cascade. These studies are reviewed in: (Weiss A., Ann. Rev. Genet. 25: 487–510 (1991); Chan et al., Annu. Rev. Immunol. 12: 555–592 (1994); Trowbridge and Thomas, Annu. Rev. Immunol. 12: 85–116 (1994)).

CD45 is one of the most abundant of the cell surface glycoproteins and is expressed exclusively on hemopoetic cells. In T cells, it has been shown that CD45 is one of the critical components of the signal transduction machinery of lymphocytes. In particular, there is evidence that CD45 phosphatase plays a pivotal role in antigen-stimulated proliferation of T lymphocytes after an antigen has bound to the T cell receptor (Trowbridge, Ann. Rev. Immunol, 12: 85–116 (1994)). Several studies indicate that the PTPase activity of CD45 plays a role in the activation of Lck, a lymphocyte-specific member of the Src family protein-tyrosine kinase (Mustelin et al., Proc. Natl. Acad. Sci. USA 86: 6302–6306 (1989); Ostergaard et al., Proc. Natl. Acad. Sci. USA 86: 8959–8963 (1989)). Studies using transgenic mice with a mutation for the CD45-exon6 exhibited a lack of mature T cells. These mice did not respond to an antigenic challenge with the typical T cell mediated response (Kishihara et al., Cell 74:143–56 (1993)). Inhibitors of CD45 phosphatase would therefore be very effective therapeutic agents in conditions that are associated with autoimmune diseases, such as rheumatoid arthritis, systemic lupus erythematosus, type I diabetes, and inflammatory bowel disease. Another important function of CD45 phosphatase inhibitors is in effecting immunosuppression, where such a result is indicated, e.g., in transplantation and other conditions in need of immunosuppressive treatment.

CD45 has also been shown to be essential for the antibody mediated degranulation of mast cells (Berger et al., J. Exp. Med. 180:471–6 (1994)). These studies were also done with mice that were CD45-deficient. In this case, an IgE-mediated degranulation was demonstrated in wild type but not CD45-deficient T cells from mice. These data suggest that CD45 inhibitors could also play a role in the symptomatic or therapeutic treatment of allergic disorders, such as asthma, allergic rhinitis, food allergies, eczema, urticaria and anaphylaxis. Another PTPase, an inducible lymphoid-specific protein tyrosine phosphatase (HePTP) has also been implicated in the immune response. This phosphatase is expressed in both resting T and B lymphocytes, but not non-hemopoetic cells. Upon stimulation of these cells, mRNA levels from the HePTP gene increase 10–15 fold (Zanke et al., *Eur. J. Immunol.* 22: 235–239 (1992)).

Likewise, the hematopoietic cell specific SHP-1 acts as a negative regulator and thus appears to play an essential role in immune cell development in accordance with the abovementioned important function of CD45, HePTP and SHP-1, selective PTPase inhibitors are early development candidates or prototype drugs both as immunosuppressors and as immunostimulants. Recent studies illustrate the potential of PTPase inhibitors as immunmodulators by demonstrating the capacity of the vanadium-based relatively nonselective PTPase inhibitor, BMLOV, to induce apparent B cell selective apoptosis compared to T cells (Schieven et al., *J. Biol. Chem.* 270: 20824–20831 (1995)).

PTPases: Cell—Cell Interactions/Cancer

Focal adhesion plaques, an in vitro phenomenon in which specific contact points are formed when fibroblasts grow on appropriate substrates, mimic, in certain respects, cells and their natural surroundings. Several focal adhesion proteins are phosphorylated on tyrosine residues when fibroblasts adhere to and spread on extracellular matrix (Gumbiner, *Neuron* 11: 551–564 (1993)). However, aberrant tyrosine phosphorylation of these proteins can lead to cellular transformation. The intimate association between PTPases and focal adhesions is supported by the finding of several intracellular PTPases with ezrin-like N-terminal domains, e.g. PTPMEG1 (Gu et al., *Proc. Natl. Acad. Sci. USA* 88: 5867–5871 (1991), PTPH1 (Yang and Tonks, *Proc. Natl. Acad. Sci. USA* 88: 5949–5953 (1991)) and PTPD1 (Møller et al., *Proc. Natl. Acad. Sci. USA* 91: 7477–7481 (1994)). The ezrin-like domains show similarity to several proteins that are believed to act as links between the cell membrane and the cytoskeleton. PTPD1 was found to be phosphorylated by and associated with c-src in vitro and is hypothesized to be involved in the regulation of phosphorylation of focal adhesions (Møller et al., supra).

PTPases may oppose the action of tyrosine kinases, including those responsible for phosphorylation of focal adhesion proteins, and may therefore function as natural inhibitors of transformation. TC-PTP, and especially the truncated form of this enzyme (Cool et al., *Proc. Natl. Acad. Sci. USA* 87: 7280–7284 (1990)), can inhibit the transforming activity of v-erb and v-fms (Lammers et al., *J. Biol. Chem.* 268: 22456–22462 (1993), Zander et al., *Oncogene* 8: 1175–1182 (1993)). Moreover, it was found that transformation by the oncogenic form of the HER2/neu gene was suppressed in NIH 3T3 fribroblasts overexpressing PTP1B (Brown-Shimer et al., *Cancer Res.* 52: 478482 (1992)).

The expression level of PTP1B was found to be increased in a mammary cell line transformed with neu (Zhay et al., *Cancer Res.* 53: 2272–2278 (1993)). The intimate relationship between tyrosine kinases and PTPases in the development of cancer is further evidenced by the recent finding that PTPe is highly expressed in murine mammary tumors in transgenic mice over-expressing c-neu and v-Ha-ras, but not c-myc or int-2 (Elson and Leder, *J. Biol. Chem.* 270: 26116–26122 (1995)). Further, the human gene encoding PTPγ was mapped to 3p21, a chromosomal region which is frequently deleted in renal and lung carcinomas (LaForgia et al., *Proc. Natl. Acad. Sci. USA* 88: 5036–5040 (1991)).

PTPases appear to be involved in controlling the growth of fibroblasts. In a recent study it was found that Swiss 3T3 cells harvested at high density contain a membrane-associated PTPase whose activity on an average is 8-fold higher than that of cells harvested at low or medium density (Pallen and Tong, *Proc. Natl. Acad. Sci. USA* 88: 6996–7000 (1991)).

Two closely related receptor-type PTPases, PTPκ and PTPµ, can mediate homophilic cell—cell interaction when expressed in non-adherent insect cells, suggesting that a normal physiological function for these PTPases in cell-to-cell signalling (Gebbink et al., *J. Biol. Chem.* 268: 16101–16104 (1993), Brady-Kalnay et al., *J. Cell Biol.* 122: 961–972 (1993); Sap et al., *Mol. Cell. Biol.* 14: 1–9 (1994)). Interestingly, PTPκ and PTPµ do not bind to each other (PTPκ does self-associate), despite their structural similarity (Zondag et al., *J. Biol. Chem.* 270: 14247–14250 (1995)).

From the studies described above it is apparent that PTPases play an important role in regulating normal cell growth. Additionally, as pointed out above, PTPases may also function as positive mediators of intracellular signaling and thereby induce or enhance mitogenic responses. Increased activity of certain PTPases might therefore result in cellular transformation and tumor formation. See, Zheng, supra; Uchida et al., *J. Biol. Chem.* 269: 12220–12228 (1994 Hunter, *Cell* 80: 225–236 (1995). Inhibitors of specific PTPases are therefore likely to be of significant therapeutic value in the treatment of certain forms of cancer.

PTPases: Platelet Aggregation

PTPases are centrally involved in platelet aggregation. Thus, agonist-induced platelet activation results in calpain-catalyzed cleavage of PTP1B with a concomitant 2-fold stimulation of PTPase activity (Frangioni et al., *EMBO J.* 12: 4843–4856 (1993)). The cleavage of PTP1B leads to subcellular relocation of the enzyme and correlates with the transition from reversible to irreversible platelet aggregation in platelet-rich plasma. In addition, the SH2 domain containing PTPase, SHP-1, was found to translocate to the cytoskeleton in platelets after thrombin stimulation in an aggregation-dependent manner (Li et al., *FEBS Lett.* 343: 89–93 (1994)).

Although some details in the above two studies have been questioned, there is overall agreement that PTP1B and SHP-1 play significant functional roles in platelet aggregation (Ezumi et al., *J. Biol. Chem.* 270: 11927–11934 (1995)). In accordance with these observations, treatment of platelets with the PTPase inhibitor pervanadate leads to significant increase in tyrosine phosphorylation, secretion and aggregation (Pumiglia et al., *Biochem. J.* 286: 441–449 (1992)).

PTPases: Osteoporosis

The rate of bone formation is determined by the number and the activity of osteoblasts. In turn, these are determined by the rate of proliferation and differentiation of osteoblast progenitor cells, respectively. Histomorphometric studies indicate that the osteoblast number is the primary determinant of the rate of bone formation in humans (Gruber et al., *Mineral Electrolyte Metab.* 12: 246–254 (1987), reviewed in Lau et al., *Biochem. J.* 257: 23–36 (1989)). Acid phosphatases/PTPases are implicated in negative regulation of osteoblast proliferation. Thus, fluoride, which has phosphatase inhibitory activity, has been found to increase spinal bone density in osteoporotics by increasing osteoblast proliferation (Lau et al.; supra). Consistent with this observation, an osteoblastic acid phosphatase with PTPase activity was found to be highly sensitive to mitogenic concentrations of fluoride (Lau et al., *J. Biol. Chem.* 260: 4653–4660 (1985), Lau et al., *J. Biol. Chem.* 262: 1389–1397 (1987), Lau et al., *Adv. Protein Phosphatases* 4: 165–198 (1987)). The mitogenic action of fluoride and other phosphatase inhibitors (molybdate and vanadate) may thus be explained by their inhibition of acid phosphatases/PTPases that negatively regulate the cell proliferation of osteoblasts. The complex nature of the involvement of PTPases in bone formation is further suggested by the recent identification of a novel parathyroid regulated, receptor-like PTPase, OST-PTP, expressed in bone and testis (Mauro et al., *J. Biol. Chem.* 269: 30659–30667 (1994)). OST-PTP is up-regulated following differentiation and matrix formation of primary osteoblasts and subsequently down-regulated in the osteoblasts which are actively mineralizing bone in culture. In addition, it was recently observed that vanadate, vanadyl and pervanadate all increased the growth of the osteoblast-like cell line UMR106. Vanadyl and pervanadate were stronger stimulators of cell growth than vanadate. Only vanadate was able to regulate the cell differentiation as measured by cell alkaline phosphatase activity (Cortizo et al., *Mol. Cell. Biochem.* 145: 97–102 (1995)). More important, several studies have shown that biphosphonates, such as alendronate and tiludronate, inhibit PTPase activity in osteoclasts and that the inhibition of PTPase activity correlated with the inhibition of in vitro osteoclast formation and bone resorption. (Scmidt, et al., *Proc. Natl. Acad. Sci. U.S.A.* 93: 3068–3073, 1996; Murakami et al., *Bone* 20:399–404, 1997; Opas et al., *Biochem. Pharmacol.* 54: 721–727, 1997; Skorey et al., *J. Biol. Chem.* 272: 22472–22480, 1997. Thus other PTPase inhibitors are potentially effective in countering osteoclast activity, and thus treating osteoporosis.

PTPases: Microorganisms

Dixon and coworkers have called attention to the fact that PTPases may be a key element in the pathogenic properties of *Yersinia* (reviewed in Clemens et al. *Molecular Microbiology* 5: 2617–2620 (1991)). This finding was rather surprising since tyrosine phosphate is thought to be absent in bacteria. The genus *Yersinia* comprises 3 species: *Y. pestis* (responsible for the bubonic plague), *Y. pseudoturberculosis* and *Y. enterocolitica* (causing enteritis and mesenteric lymphadenitis). A dual-specificity phosphatase, VH1, has been identified in Vaccinia virus (Guan et al., *Nature* 350: 359–263 (1991)). These observations indicate that PTPases may play critical roles in microbial and parasitic infections, and they further point to PTPase inhibitors as a novel, putative treatment principle of infectious diseases. Availibility of PTPase inhibitors would help shed light in all the foregoing speculations about PTPase function because they would enable assaying techniques which would answer some of these questions as will be illustrated below.

SUMMARY OF BACKGROUND

It has been found that PTPases play a major role in the above modulation and regulation of fundamental cellular signaling mechanisms involved in metabolism, growth, proliferation and differentiation (Fisher et al, *Science* 253: 401–6 (1991); Tonks and Neel, *Cell* 87: 365–368 (1966)" Neel and Tonks, *Current Opinion in Cell Biology* 9: 193–204 (1997); Hunter, *Phil. Trans. R. Soc. Lond. B* 353: 583–605 (1998); Hunter, *Cell* 100: 113–120 (2000); Zhang, *Critical Reviews in Biochemistry and Molecular Biology* 33:1–52 (1988)). Reports from many laboratories have shown that PTPases can act both as positive and negative regulators of signal transduction processes. PTPases have been implicated in a variety of human diseases, including diabetes, obesity, autoimmune diseases, acute and chronic inflammation, osteoporosis, proliferative disorders including various forms of cancer, growth disorders, and defective platelet aggregation (WO97/39748, WO97/40017, WO99/1529, WO97/08934, WO98/27065, WO99/46236, WO99/46244, WO99/46267, WO99/46268, WO99/46237). Accordingly there is increasing evidence which suggests that inhibition of these PTPases would help treat or manage these diseases (Hunter, vide supra; Neel and Tonks, vide supra: Frangione et al., *EMBO J.* 12:4843–4856 (1993); Zhang, *Curr. Top. Cell. Reg.* 35, 21–68 (1997): Zhang, vide supra; Evans and Jalian, *Exp. Opinion. Invest Drugs* 8: 139–160 (1999); Burke and Zhang, *Bioploymers (Peptide Science)* 47: 225–241 (1998): Elchebly et al.; *Science* 283: 1544–1548 (1999); Wrobel et al., *J. Med. Chem.* 42: 3199–3202 (1999)). In addition, certain infectious diseases may also be treated or managed by administration PTPase inhibitors (Clemens et al., *Molecular Microbiology* 5: 2617–2620 (1991)).

Both selective PTPase inhibitors and inhibitors that bind to several PTPases (non-selective inhibitors) can be used therapeutically to partially or completely restore PTPase-mediated perturbed signal transduction processes and thus for management, treatment, palliation or prevention of the above diseases.

DESCRIPTION OF THE INVENTION

Figure 1:
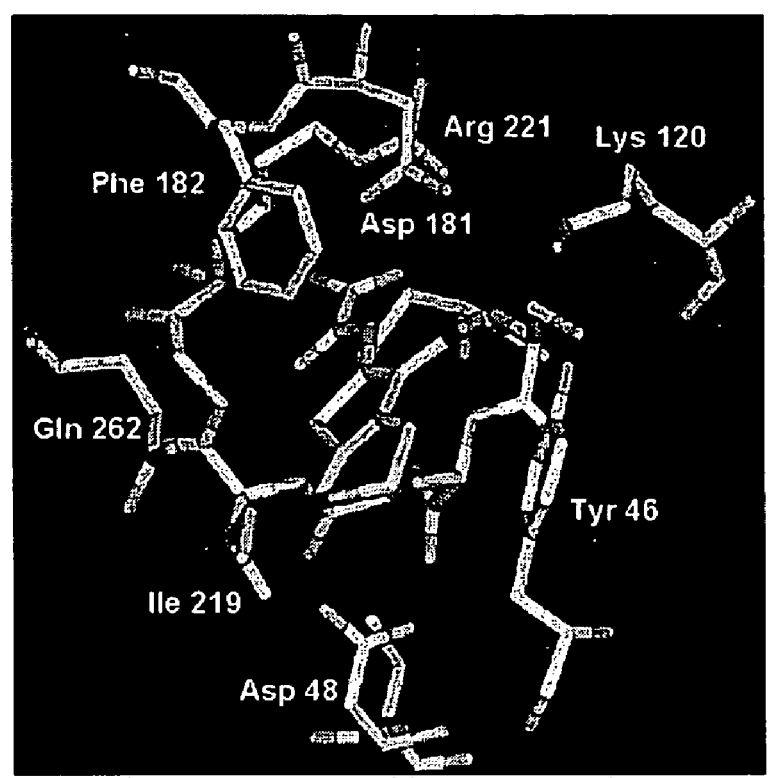
FIG. 1. Active site of Protein Tyrosine Phosphatase 1B complexed with with 2-(oxalyl-amino)-4,5,6,7-tetrahydro-thieno[2,3-c]pyridine-3-carboxylic acid.

The present invention provides a method for inhibiting protein tyrosine phosphatase 1B (PTP1B) and/or T-cell protein tyrosine phosphatase (T-cell PTP/TC-PTP) and/or protein tyrosine phosphatases (PTPases) having an aspartic acid (Asp) in position 48 by exposing said PTPase to a compound having physico-chemical and spatial structural characteristics that interfere with the active site and/or vicinity of the active site of said PTPase thereby inhibiting its enzymatic activity. Specifically, the present inhibitors of PTP1B and/or TC-PTP and/or PTPases having an aspartic acid (Asp) in position 48 interact with two or more residues of the following: arginine 221, glycine 220, lysine 120, tyrosine 46, and phenylalanine/histidine 182 and one or more of the following (residue numbering corresponding to PTP1B will be used through out (Chernoff et al., *Proc. Natl. Acad. Sci. USA* 87: 2735–2789 (1989)):

1. Isoleucine 219 backbone amide nitrogen;
2. Glycine 218 backbone amide nitrogen;
3. Alanine 217 backbone amide nitrogen;
4. Serine 216 backbone amide nitrogen;
5. Cysteine 215 backbone amide nitrogen;
6. The side chain carboxylic acid group of aspartic acid 181;

7. The side chain carboxylic acid group of aspartic acid 48;
8. The side chain guanidinium group of arginine 47;
9. Arginine 47 backbone amide nitrogen;
10. Aspartic acid 48 backbone amide nitrogen;
11. The side chain hydroxy group of tyrosine 46;
12. The side chain amino group of lysine 41;
13. The methylene side chain atoms of lysine 41;
14. The backbone amide carbonyl of asparagine 44;
15. The methylene side chain atoms of arginine 45;
16. The backbone amide carbonyl of arginine 45;
17. The methylene side chain atoms of arginine 47;
18. The methylene side chain atom of aspartic acid 48;
19. The backbone amide carbonyl of aspartic acid 48;
20. The methylene side chain atoms of leucine 88;
21. The side chain hydroxy group of serine 118;
22. The backbone amide carbonyl of leucine 119;
23. The side chain amide nitrogen of glutamine 262;
24. The side chain atoms of methionine 258;
25. The aromatic group of phenylalanine 52;
26. The backbone amide nitrogen of glycine 259;
27. The alpha-methylene atom of glycine 259;
28. The guanidinium group of arginine 254;
29. The methylene side chain atoms of arginine 254;
30. The methylene side chain atoms of arginine 24;
31. The guanidinium group of arginine 24; or
32. Any conserved water molecule in the vicinity of the active site.

Preferably, the present inhibitors of PTP1B and/or TC-PTP and/or PTPases having an aspartic acid (Asp) in position 48 interact with any three or more of the above identified regions of the active site and its vicinity.

In one preference, the inhibitors of PTP1B and/or TC-PTP and/or PTPases having an aspartic acid (Asp) in position 48 interact with arginine 221, glycine 220, lysine 120, tyrosine 46, phenylalanine/histidine 182, aspartic acid 48 and one or more of the following 1. Isoleucine 219 backbone amide nitrogen;
2. Glycine 218 backbone amide nitrogen;
3. Alanine 217 backbone amide nitrogen;
4. Serine 216 backbone amide nitrogen;
5. The side chain carboxylic acid group of aspartic acid 181;
6. The side chain guanidinium group of arginine 47;
7. Arginine 47 backbone amide nitrogen;
8. Aspartic acid 48 backbone amide nitrogen;
9. The side chain hydroxy group of tyrosine 46;
10. The side chain amino group of lysine 41;
11. The methylene side chain atoms of lysine 41;
12. The backbone amide carbonyl of asparagine 44;
13. The methylene side chain atoms of arginine 45;
14. The backbone amide carbonyl of arginine 45;
15. The methylene side chain atoms of arginine 47;
16. The methylene side chain atom of aspartic acid 48;
17. The backbone amide carbonyl of aspartic acid 48;
18. The methylene side chain atoms of leucine 88;
19. The side chain hydroxy group of serine 118;
20. The backbone amide carbonyl of leucine 119;
21. The side chain amide nitrogen of glutamine 262;
22. The side chain atoms of methionine 258;
23. The aromatic group of phenylalanine 52;
24. The backbone amide nitrogen of glycine 259;
25. The alpha-methylene atom of glycine 259;
26. The guanidinium group of arginine 254;
27. The methylene side chain atoms of arginine 254;
28. The methylene side chain atoms of arginine 24;
29. The guanidinium group of arginine 24; or
30. Any conserved water molecule in the vicinity of the active site.

Preferred key structural features of the inhibitors of the present invention include a phosphate isostere (P), a carboxylic acid perferably or a carboxylic acid or ortho-carboxylic acid or o-c acid isostere (B) and a hydrophobic group (A) as shown in Scheme 1.

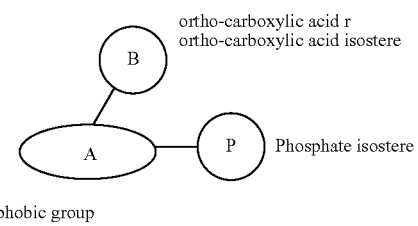

Scheme 1

In a preferred embodiment, the key structural features of the inhibitors of the present invention include a phosphate isostere (P), an ortho-carboxylic acid or an ortho-carboxylic acid isostere (B) and a hydrophobic group (A), preferably a phenyl, naphthyl or thiophenyl as shown in Scheme 1.

In another preferred embodiment the key structural features of the inhibitors of the present invention include an oxalylamide (—NHCOCOOH) (P), an ortho-carboxylic acid or an ortho-carboxylic acid isostere (B) and a hydrophobic group (A).

In another preferred embodiment the key structural features of the inhibitors of the present invention include an oxalylamide (—NHCOCOOH) (P), an ortho-carboxylic acid or an ortho-carboxylic acid isostere (B) and a hydrophobic group (A), preferably a phenyl, naphthyl or thiophenyl as shown in Scheme 1.

In another preferred embodiment the key structural features of the inhibitors of the present invention include a phosphate isostere (P), an ortho-carboxylic acid, or an ortho-carboxylic acid isostere (B), a hydrophobic group (A) and a basic nitrogen (N) as shown in Scheme 2.

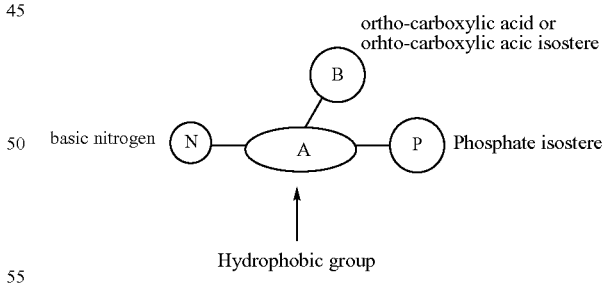

Scheme 2

In another preferred embodiment, the key structural features of the inhibitors of the present invention include an oxalylamide (—NHCOCOOH) (P), an ortho-carboxylic acid or an ortho-carboxylic acid isostere (B), a hydrophobic group (A) and a basic nitrogen (N) as shown in Scheme 2.

In another preferred embodiment the key structural features of the inhibitors of the present invention include an oxalylamide (—NHCOCOOH) (P), an ortho-carboxylic acid or an ortho-carboxylic acid isostere (B), a hydrophobic group (A), preferably a phenyl, naphthyl or thiophenyl and a basic nitrogen (N).

In another preferred embodiment, the key structural features of the inhibitors of the present invention include a basic nitrogen which provides selectivity for PTPases containing an aspartic acid in position 48—via formation of a salt bridge to said aspartic acid 48 and repulsion to PTPases that contain the corresponding asparagine in position 48—a phosphate isostere (P), an ortho-carboxylic acid or an ortho-carboxylic acid isostere (B), a hydrophobic group (A) as shown in Scheme 3.

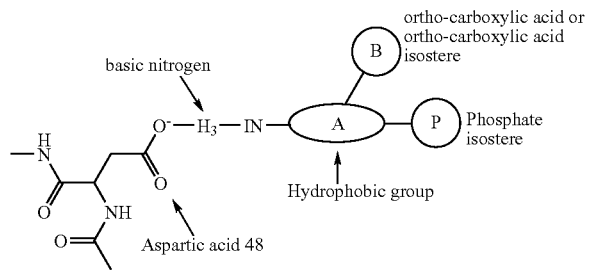

Scheme 3.

In another preferred embodiment, the key structural features of the inhibitors of the present invention include a basic nitrogen which provides selectivity for PTPases containing an aspartic acid in position 48—via formation of a salt bridge to said aspartic acid 48 and repulsion to PTPases that contain the corresponding asparagine in position 48—an oxalylamide (P), an ortho-carboxylic acid or an ortho-carboxylic acid isostere (B), a hydrophobic group (A) as shown in Scheme 3.

In another preferred embodiment, the key structural features of the inhibitors of the present invention include a basic nitrogen which provides selectivity for PTPases containing an aspartic acid in position 48—via formation of a salt bridge to said aspartic acid 48 and repulsion to PTPases that contain the corresponding asparagine in position 48—an oxalylamide (P), an ortho-carboxylic acid or an ortho-carboxylic acid isostere (B), and a hydrophobic group (A), preferably a phenyl, naphthyl or thiophenyl as shown in Scheme 3.

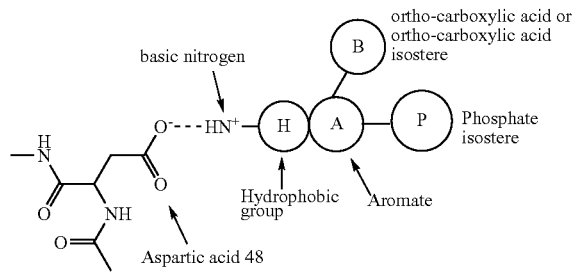

Scheme 4.

In another preferred embodiment, the key structural features of the inhibitors of the present invention include a basic nitrogen which provides selectivity for PTPases containing an aspartic acid in position 48—via formation of a salt bridge to said aspartic acid 48 and repulsion to PTPases that contain the corresponding asparagine in position 48—a phosphate isostere (P), an ortho-carboxylic acid or ortho-carboxylic acid isostere (B), an aromatic group (A), preferably a phenyl or thiophenyl and a hydrophobic group (H) as shown in Scheme 4.

In another preferred embodiment, the key structural features of the inhibitors of the present invention include a basic nitrogen which provides selectivity for PTPases containing an aspartic acid in position 48—via formation of a salt bridge to said aspartic acid 48 and repulsion to PTPases that contain the corresponding asparagine in position 48—an oxalylamide (P), an ortho-carboxylic acid or an ortho-carboxylic acid isostere (B), an aromatic group (A), preferably a phenyl or thiophenyl and a hydrophobic group (H) as shown in Scheme 4.

In another preferred embodiment, the key structural features of the inhibitors of the present invention include a phosphate isostere (P), an ortho-carboxylic acid or an ortho-carboxylic acid isostere (B), an aromatic group (A), preferably a phenyl or thiophenyl and a hydrophobic group (H) which include a basic nitrogen which provides selectivity for PTPases that contain an aspartic acid in position 48—via formation of a salt bridge to said aspartic acid 48 and repulsion to PTPases that contain the corresponding asparagine in position 48—as shown in Scheme 5.

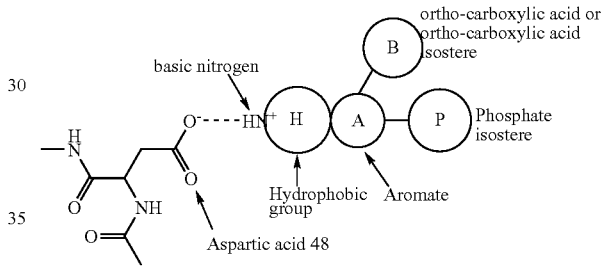

Scheme 5

In another preferred embodiment, the key structural features of the inhibitors of the present invention include an oxalylamide (P), an ortho-carboxylic acid or an ortho-carboxylic acid isostere (B), an aromatic group (A), preferably a phenyl or thiophenyl and a hydrophobic group (H) which include a basic which provides selectivity for PTPases that contain an aspartic acid in position 48—via formation of a salt bridge to said aspartic acid 48 and repulsion to PTPases that contain the corresponding asparagine in position 48—as shown in Scheme 5.

The key structural features of the inhibitors of the present invention described above are linked to each other via covalent bonds.

The compounds of the present invention possess, but are not limited to, a phosphate isostere in which the centroid of the phosphate isostere is 5.0–5.5 Å from the centroid of a carboxylic acid or carboxylic acid isostere, and 4.5–5.1 Å from the centroid of an aromatic group or a hydrophobic group. In a preferred embodiment, the compounds of the present invention possess, but are not limited to, an oxalylamide in which the centroid of the carboxylic acid moiety of said oxalylamide is 5.0–5.5 Å from the centroid of a carboxylic acid or carboxylic acid isostere, and 4.5–5.1 Å from the centroid of an aromatic group or a hydrophobic group.

In an other preferred embodiment the compounds of the present invention possess, but are not limited to, a phosphate isostere in which the centroid of the phosphate isostere is 5.0–5.5 Å from the centroid of a carboxylic acid or carboxylic acid isostere, 4.5–5.1 Å from the centroid of an aromatic group or a hydrophobic group and 8.0–14.0 Å from a basic nitrogen. These features must participate in the appropriate interactions (e.g. hydrogen bonds, salt bridges, hydrophobic interactions, cation-π interactions, or π, π interactions, or aromatic—aromatic interactions) with the PTP1B and/or TC-PTP and/or other PTPases that are structurally similar to PTP1B active site and vicinity e.g. having an aspartic acid (Asp) in position 48. The centroid of the phosphate isostere should be 3.50–4.20 Å from the centroid of the side chain guanidinium group of arginine 221. The centroid of the carboxylic acid or carboxylic acid isostere should be 3.4–4.1 Å from the side chain amino group of lysine 120. The basic nitrogen should be 3.4–4.1 Å from the centroid of aspartic acid 48. The aromatic or, more generally, hydrophobic group should be near the following amino acid side chain atoms with appropriate distance ranges between the centroid of the side chain atoms and the centroid of the aromatic—or hydrophobic group given in parentheses: tyrosine 46 (4.4–5.1 Å) and phenylalanine/histidine 182 (4.4–6.5 Å).

The centroid of the oxalylamide carboxylic acid moiety should be 3.50–4.20 Å from the centroid of the side chain guanidinium group of arginine 221. The centroid of the carboxylic acid or carboxylic acid isostere should be 3.4–4.1 Å from the side chain amino group of lysine 120. The basic nitrogen should be 3.4–4.1 Å from the centroid of aspartic acid 48. The aromatic—or hydrophobic group should be near the following amino acid side chain atoms with appropriate distance ranges between the centroid of the side chain atoms and the centroid of the aromatic—or hydrophobic group given in parentheses: tyrosine 46 (4.4–5.1 Å) and phenylalanine/histidine 182 (4.4–6.5 Å).

In a specific embodiment, the invention is directed to a method of inhibiting at least one intracellular or membrane-associated PTPase that has aspartic acid (Asp) in position 48 using the numbering for PTP1B, the method comprising exposing the PTPase to an inhibitor compound which fits spatially into the active site and the vicinity thereof, said compound comprising the following features and moieties:

I. (a) a phosphate isostere which forms a salt bridge to the guanidinium group of arginine 221 and a hydrogen bond with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.5–4.2 Å, and (III) said glycine 220 backbone amide nitrogen ranges from 2.7–3.5 Å; or (b) an oxalylamide which forms a salt bridge to the guanidinium group of arginine 221 and forms a hydrogen bond with a hydrogen atom donated by the amide nitrogens of arginine 221 and glycine 220 such that the distance between the centroid of the carboxylic acid group of said oxalylamide group and (I) the centroid of said guanidinium group ranges from 3.50–4.20 Å, (II) said arginine 221 amide nitrogen ranges from 3.5–4.2 Å and the distance between the amide carbonyl group of said oxalylamide group and the said glycine 220 amide nitrogen ranges from 2.7–3.5 Å; and II. (a) a carboxylic acid group or (b) a carboxylic acid isostere group selected from the following 5-membered heterocycles wherein said acid or said isostere group forms a salt bridge to the side chain amino group of lysine 120 wherein the distance between the centroid of said carboxylic acid or carboxylic acid isostere and the side chain nitrogen atom of said Lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å;

and at least one of features IV through V:

IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; and V. a hydrophobic group that interacts with the imidazole ring of histidine 182 such that the distance between the centroid of said hydrophobic group and the centroid of the aromatic ring of said histidine 182 ranges from 4.4–6.5 Å; and one or more of the following features VI–XXXVII:

VI. an amino group which forms a salt bridge to the site chain carboxylic acid group of aspartic acid 48 such that the distance between the nitrogen atom of said amino group and the centroid of said site chain carboxylic acid group of aspartic acid 48 ranges from 3.4–4.1 Å; and VII. two oxygen atoms which form hydrogen bonds via a water molecule to the side chain carboxylic acid group of aspartic acid 48 such that the distance between each of the two oxygen atoms and the centroid of said water molecule ranges from 2.5–3.6 Å and that the distance between said water molecule and the centroid of said side chain carboxylic acid group of aspartic acid 48 ranges from 2.5–3.6 Å and that the distance between said two oxygen atoms ranges from 2.5–3.0 Å; and VIII. a hydrophobic group that interacts with the side chain methylene groups of tyrosine 46 such that the distance between the centroid of said hydrophobic group and the centroid of the methylene groups of said tyrosine 46 ranges from 4.4–5.1 Å;

IX. a hydrophilic group that forms a hydrogen bond or forms a salt bridge with aspartic acid 181 such that the distance between the centroid of said hydrophilic group and the centroid of the carboxylic acid of said aspartic acid 181 ranges from 4.4–5.1 Å;

X. a hydrophobic group that interacts with tyrosine 46 and the methylene side chain atoms of arginine 47 such that the distance between the centroid of said hydrophobic group and the centroid of the aromatic ring of said tyrosine 46 is 4.7–5.2 Å and the centroid of the methylene side chain atoms of said arginine 47 ranges from 4.5–5.5 Å;

XI. a hydrophilic group that forms a hydrogen bond with the one or more hydrogen atoms donated by the guanidinium group of arginine 47 such that the distance between the centroid of said hydrophilic group and the guanidinium group of said arginine 47 ranges from 2.7–3.5 Å;

XII. a hydrophilic group that forms a hydrogen bond with the hydrogen atom donated by the backbone amide nitrogen of arginine 47 such that the distance between the centroid of said hydrophilic group and the amide nitrogen group of said arginine 47 is 2 ranges from 7–4.0 Å;

XIII. a hydrophilic group that forms a hydrogen bond with the hydrogen atom donated by the backbone amide nitrogen of aspartic acid 48 such that the distance between the centroid of said hydrophilic group and the amide nitrogen group of said aspartic acid 48 ranges from 2.7–4.0 Å;

XIV. a hydrophilic group that interacts with the backbone amide carbonyl group of asparagine 44 such that the distance between the centroid of said hydrophilic group and the amide carbonyl group of said asparagine 44 ranges from 2.7–4.0 Å;

XV. a hydrophilic group that forms a hydrogen bond with one or more hydrogen atoms donated by the guanidinium group of arginine 45 such that the distance between the centroid of said hydrophilic group and the centroid of the guanidinium group of said arginine 24 ranges from 2.7–4.0 Å;

XVI. a hydrophilic group that forms a salt bridge with the guanidinium group of arginine 45 such that the distance between the centroid of said hydrophilic group and the centroid of the guanidinium group of said arginine 24 ranges from 2.7–4.0 Å;

XVII. a hydrophobic group that reaches a proximity interacts with the side chain methylene groups of arginine 45 such that the distance between the centroid of said hydrophilic group and the centroid of the methylene groups of said arginine 24 ranges from 4.4–5.1 Å;

XVIII. a hydrophilic group that forms a hydrogen bond with the backbone amide carbonyl group of arginine 45 such that the distance between the centroid of said hydrophilic group and the amide carbonyl group of said arginine 45 ranges from 2.7–4.0 Å;

XIX. a hydrophilic group that forms a hydrogen bond with the side chain hydroxy group of tyrosine 46 such that the distance between the centroid of said hydrophilic group and the hydroxy group of said tyrosine 46 ranges from 2.7–4.0 Å;

XX. a hydrophilic group that forms a hydrogen bond with the side chain amino group of lysine 41 such that the distance between the centroid of said hydrophilic group and the amino group of said lysine 41 ranges from 2.7–4.0 Å;

XXI. a hydrophobic group that interacts with the side chain methylene groups of lysine 41 such that the distance between the centroid of said hydrophilic group and the centroid of the methylene groups of said lysine 41 ranges from 4.4–5.1 Å;

XXII. a hydrophobic group that interacts with the side chain methylene groups of leucine 88 such that the distance between the centroid of said hydrophilic group and the centroid of the methylene groups of said leucine 8 ranges from 4.4–5.1 Å;

XXIII. a hydrophilic group that forms a hydrogen bond with the side chain hydroxy group of serine 118 such that the distance between the centroid of said hydrophilic group and the hydroxy group of said serine 118 ranges from 2.7–4.0 Å;

XXIV. a hydrophilic group that forms a hydrogen bond with the backbone amide carbonyl group of leucine 119 such that the distance between the centroid of said hydrophilic group and the amide carbonyl group of said leucine 119 ranges from 2.7–4.0 Å;

XXV. a hydrophilic group that forms a hydrogen bond with the one of the hydrogen atoms donated by the side chain amide nitrogen of glutamine 262 such that the distance between the centroid of said hydrophilic group and the amide nitrogen group of said glutamine 262 ranges from 2.7–4.0 Å;

XXVI. a hydrophilic group that forms a hydrogen bond with the hydrogen atom donated by the backbone amide group nitrogen of glycine 259 such that the distance between the centroid of said hydrophilic group and the amide nitrogen group of said glycine 259 ranges from 2.7–4.0 Å;

XXVII. a hydrophilic group that forms a hydrogen bond with one or more hydrogen atoms donated by the side chain guanidinium group of arginine 254 such that the distance between the centroid of said hydrophilic group and the centroid of the guanidinium group of said arginine 254 ranges from 2.7–4.0 Å;

XXVIII. a hydrophilic group that forms a salt bridge with the guanidinium group of arginine 254 such that the distance between the centroid of said hydrophilic group and the centroid of the guanidinium group of said arginine 254 ranges from 2.7–4.0 Å;

XXIX. a hydrophobic group that interacts with the side chain methylene groups of arginine 254 such that the distance between the centroid of said hydrophilic group and the centroid of the methylene groups of said arginine 254 ranges from 4.4–5.1 Å;

XXX. a hydrophilic group that forms a hydrogen bond with one or more hydrogen atoms donated by the guanidinium group of arginine 24 such that the distance between the centroid of said hydrophilic group and the centroid of the guanidinium group of said arginine 24 ranges from 2.7–4.0 Å;

XXXI. a hydrophilic group that forms a salt bridge with the guanidinium group of arginine 24 such that the distance between the centroid of said hydrophilic group and the centroid of the guanidinium group of said arginine 24 ranges from 2.7–4.0 Å;

XXXII. a hydrophobic group that interacts with the side chain methylene groups of arginine 24 such that the distance between the centroid of said hydrophilic group and the centroid of the methylene groups of said arginine 24 ranges from 4.4–5.1 Å;

XXXIII. a hydrophilic group that forms a hydrogen bond with the backbone amide carbonyl group of aspartic acid 48 such that the distance between the centroid of said hydrophilic group and the backbone amide carbonyl group of said aspartic acid 48 ranges from 2.7–3.5 Å;

XXXIV. a hydrophobic group that interacts with the side chain atoms of methionine 258 such that the distance between the centroid of said hydrophobic group and the centroid of the side chain of said methionine 258 ranges from 4.5–6.2 Å;

XXXV. a hydrophobic group that interacts with glycine 259 such that the distance between the centroid of said hydrophobic group and the centroid of the alpha-carbon atom of said glycine 259 ranges from 4.5–6.2 Å;

XXXVI. a hydrophobic group that interacts with phenylalanine 52 such that the distance between the centroid of said hydrophobic group and the centroid of the aromatic group of said phenylalanine 52 ranges from 4.1–9.1 Å; or XXXVII. a hydrophobic group that interacts with methionine 258, glycine 259 and phenylalanine 52 being part of a hydrophobic pocket such that the distance between the centroid of said hydrophobic group and (i) the centroid of the side chain of said methionine 258 ranges from 4.1–7.2 Å, (ii) the centroid of said glycine 259 ranges from 4.7–7.7 Å, and (iii) the centroid of the side chain of said phenylalanine 52 ranges from 4.1–9.1 Å;

In another embodiment, the invention provides a method of inhibiting at least one PTPase selected from the group consisting of PTP1B, TC-PTP and other PTPase that are structurally similar to PTP1B comprising exposing said PTPase to a compound that fits spatially into the active site of said PTPase and the vicinity therof, said compound comprising the following features and moieties:

I. (a) a phosphate isostere which forms a salt bridge to the guanidinium group of arginine 221 and interacts with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.5–4.2 Å, and (III) said glycine 220 backbone amide nitrogen ranges from 2.7–3.5 Å; or (b) an oxalylamide which forms a salt bridge to the guanidinium group of arginine 221 and forms a hydrogen bond with a hydrogen atom donated by the amide nitrogens of arginine 221 and glycine 220 such that the distance between the centroid of the carboxylic acid group of said oxalylamide group and (I) the centroid of said guanidinium group ranges from 3.50–4.20 Å, (II) said arginine 221 amide nitrogen ranges from 3.5–4.2 Å and the distance between the amide carbonyl group of said oxalylamide group and the said glycine 220 amide nitrogen ranges from 2.7–3.5 Å; and II. (a) a carboxylic acid group or (b) a carboxylic acid isostere group selected from the following 5-membered heterocycles wherein said acid or acid isostere group forms a salt bridge to the side chain amino group of lysine 120 such that the distance between the centroid of said carboxylic acid or carboxylic acid isostere and the side chain nitrogen atom of said lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and one or more of the following features IV and V:

IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; and/or V. a hydrophobic group that interacts with the imidazole ring of histidine 182 such that the distance between the centroid of said hydrophobic group and the centroid of the aromatic ring of said histidine 182 ranges from 4.4–6.5 Å; and one or more of the following features VI through XXX-VII:

VI. an amino group which forms a salt bridge to the side chain carboxylic acid group of aspartic acid 48 such that the distance between the nitrogen atom of said amino group and the centroid of said side chain carboxylic acid group of aspartic acid 48 ranges from 3.4–4.1 Å; and VII. two oxygen atoms which form hydrogen bonds via a water molecule to the side chain carboxylic acid group of aspartic acid 48 such that the distance between each of the two oxygen atoms and the centroid of said water molecule ranges from 2.5–3.6 Å and that the distance between said water molecule and the centroid of said side chain carboxylic acid group of aspartic acid 48 ranges from 2.5–3.6 Å and that the distance between said two oxygen atoms ranges from 2.5–3.0 Å; and VIII. a hydrophobic group that interacts with the side chain methylene groups of tyrosine 46 such that the distance between the centroid of said hydrophobic group and the centroid of the methylene groups of said tyrosine 46 ranges from 4.4–5.1 Å;

IX. a hydrophilic group that forms a salt bridge with aspartic acid 181 such that the distance between the centroid of said hydrophilic group and the centroid of the carboxylic acid of said aspartic acid 181 ranges from 4.4–5.1 Å;

X. a hydrophobic group that interacts with tyrosine 46 and the methylene side chain atoms of arginine 47 such that the distance between the centroid of said hydrophobic group and the centroid of the aromatic ring of said tyrosine 46 ranges from 4.7–5.2 Å and the centroid of the methylene side chain atoms of said arginine 47 ranges from 4.5–5.5 Å;

XI. a hydrophilic group that forms a hydrogen bond with the one or more hydrogen atoms donated by the guanidinium group of arginine 47 such that the distance between the centroid of said hydrophilic group and the guanidinium group of said arginine 47 ranges from 2.7–3.5 Å;

XII. a hydrophilic group that forms a hydrogen bond with the hydrogen atom donated by the backbone amide nitrogen of arginine 47 such that the distance between the centroid of said hydrophilic group and the amide nitrogen group of said arginine 47 ranges from 2.7–4.0 Å;

XIII. a hydrophilic group that forms a hydrogen bond with the hydrogen atom donated by the backbone amide nitrogen of aspartic acid 48 such that the distance between the centroid of said hydrophilic group and the amide nitrogen group of said aspartic acid 48 ranges from 2.7–4.0 Å;

XIV. a hydrophilic group that forms a hydrogen bond with the backbone amide carbonyl group of asparagine 44 such that the distance between the centroid of said hydrophilic group and the amide carbonyl group of said asparagine 44 ranges from 2.7–4.0 Å;

XV. a hydrophilic group that forms a hydrogen bond with one or more hydrogen atoms donated by the guanidinium group of arginine 45 such that the distance between the centroid of said hydrophilic group and the centroid of the guanidinium group of said arginine 24 ranges from 2.7–4.0 Å;

XVI. a hydrophilic group that forms a salt bridge with the guanidinium group of arginine 45 such that the distance between the centroid of said hydrophilic group and the centroid of the guanidinium group of said arginine 24 ranges from 2.7–4.0 Å;

XVII. a hydrophobic group that interacts with the side chain methylene groups of arginine 45 such that the distance between the centroid of said hydrophilic group and the centroid of the methylene groups of said arginine 24 ranges from 4.4–5.1 Å;

XVIII. a hydrophilic group that forms a hydrogen bond with the backbone amide carbonyl group of arginine 45 such that the distance between the centroid of said hydrophilic group and the amide carbonyl group of said arginine 45 ranges from 2.7–4.0 Å;

XIX. a hydrophilic group that forms a hydrogen bond with the side chain hydroxy group of tyrosine 46 such that the distance between the centroid of said hydrophilic group and the hydroxy group of said tyrosine 46 ranges from 2.7–4.0 Å;

XX. a hydrophilic group that forms a hydrogen bond with the side chain amino group of lysine 41 such that the distance between the centroid of said hydrophilic group and the amino group of said lysine 41 ranges from 2.7–4.0 Å;

XXI. a hydrophobic group that interacts with the side chain methylene groups of lysine 41 such that the distance between the centroid of said hydrophilic group and the centroid of the methylene groups of said lysine 41 ranges from 4.4–5.1 Å;

XXII. a hydrophobic group that interacts with the side chain methylene groups of leucine 88 such that the distance between the centroid of said hydrophilic group and the centroid of the methylene groups of said leucine 8 ranges from 4.4–5.1 Å;

XXIII. a hydrophilic group that forms a hydrogen bond with the side chain hydroxy group of serine 118 such that the distance between the centroid of said hydrophilic group and the hydroxy group of said serine 118 ranges from 2.7–4.0 Å;

XXIV. a hydrophilic group that forms a hydrogen bond with the backbone amide carbonyl group of leucine 119 such that the distance between the centroid of said hydrophilic group and the amide carbonyl group of said leucine 119 ranges from 2.7–4.0 Å;

XXV. a hydrophilic group that forms a hydrogen bond with the one of the hydrogen atoms donated by the side chain amide nitrogen of glutamine 262 such that the distance between the centroid of said hydrophilic group and the amide nitrogen group of said glutamine 262 ranges from 2.7–4.0 Å;

XXVI. a hydrophilic group that forms a hydrogen bond with the hydrogen atom donated by the backbone amide group nitrogen of glycine 259 such that the distance between the centroid of said hydrophilic group and the amide nitrogen group of said glycine 259 ranges from 2.7–4.0 Å;

XXVII. a hydrophilic group that forms a hydrogen bond with one or more hydrogen atoms donated by the side chain guanidinium group of arginine 254 such that the distance between the centroid of said hydrophilic group and the centroid of the guanidinium group of said arginine 254 ranges from 2.7–4.0 Å;

XXVIII. a hydrophilic group that forms a salt bridge with the guanidinium group of arginine 254 such that the distance between the centroid of said hydrophilic group and the centroid of the guanidinium group of said arginine 254 ranges from 2.7–4.0 Å;

XXIX. a hydrophobic group that interacts with the side chain methylene groups of arginine 254 such that the distance between the centroid of said hydrophilic group and the centroid of the methylene groups of said arginine 254 ranges from 4.4–5.1 Å;

XXX. a hydrophilic group that forms a hydrogen bond with one or more hydrogen atoms donated by the guanidinium group of arginine 24 such that the distance between the centroid of said hydrophilic group and the centroid of the guanidinium group of said arginine 24 ranges from 2.7–4.0 Å;

XXXI. a hydrophilic group that forms a salt bridge with the guanidinium group of arginine 24 such that the distance between the centroid of said hydrophilic group and the centroid of the guanidinium group of said arginine 24 ranges from 2.7–4.0 Å;

XXXII. a hydrophobic group that interacts with the side chain methylene groups of arginine 24 such that the distance between the centroid of said hydrophilic group and the centroid of the methylene groups of said arginine 24 ranges from 4.4–5.1 Å;

XXXIII. a hydrophilic group that forms a hydrogen bond with the backbone amide carbonyl group of aspartic acid 48 such that the distance between the centroid of said hydrophilic group and the backbone amide carbonyl group of said aspartic acid 48 ranges from 2.7–3.5 Å;

XXXIV. a hydrophobic group that interacts with the side chain atoms of methionine 258 such that the distance between the centroid of said hydrophobic group and the centroid of the side chain of said methionine 258 ranges from 4.5–6.2 Å;

XXXV. a hydrophobic group that interacts with glycine 259 such that the distance between the centroid of said hydrophobic group and the centroid of the alpha-carbon atom of said glycine 259 ranges from 4.5–6.2 Å;

XXXVI. a hydrophobic group that interacts with phenylalanine 52 such that the distance between the centroid of said hydrophobic group and the centroid of the aromatic group of said phenylalanine 52 ranges from 4.1–9.1 Å;

XXXVII. a hydrophobic group that interacts with methionine 258, glycine 259 and phenylalanine 52 being part of a hydrophobic pocket such that the distance between the centroid of said hydrophobic group and the centroid of the side chain of said methionine 258 ranges from 4.1–7.2 Å, the centroid of said glycine 259 ranges from 4.7–7.7 Å, and the centroid of the side chain of said phenylalanine 52 ranges from 4.1–9.1 Å;

In yet another embodiment, the invention provides a method of inhibiting a PTPase selected from the group consisting of PTP1B, TC-PTP and other PTPases that are structurally similar to PTP1B comprising exposing said PTPase to a compound that fits spatially into the active site of said PTPase and the vicinity thereof, said compound comprising the following features and moieties:

I. (a) a phosphate isostere which forms a salt bridge to the guanidinium group of arginine 221 and interacts with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.5–4.2 Å, and (III) said glycine 220 backbone amide nitrogen ranges from 2.7–3.5 Å; or (b) an oxalylamide which forms a salt bridge to the guanidinium group of arginine 221 and forms a hydrogen bond with a hydrogen atom donated by the amide nitrogens of arginine 221 and glycine 220 such that the distance between the centroid of the carboxylic acid group of said oxalylamide group and (I) the centroid of said guanidinium group ranges from 3.50–4.20 Å, (II) said arginine 221 amide nitrogen ranges from 3.5–4.2 Å and the distance between the amide carbonyl group of said oxalylamide group and the said glycine 220 amide nitrogen ranges from 2.7–3.5 Å; and II. (a) a carboxylic acid group or (b) a carboxylic acid isostere group selected from the following 5-membered heterocycles wherein said acid or said isostere group forms a salt bridge to the side chain amino group of lysine 120 such that the distance between the centroid of said carboxylic acid or carboxylic acid isostere and the side chain nitrogen atom of said Lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and at least one of the following features IV and V:

IV. a hydrophobic group that interacts with the aromatic ring of phenylalanine 182 such that the distance between the centroid of said hydrophobic group and the centroid of the aromatic ring of said phenylalanine 182 ranges from 3.55.1 Å; and/or V. a hydrophobic group that interacts with the imidazole ring of histidine 182 such that the distance between the centroid of said hydrophobic group and the centroid of the aromatic ring of said histidine 182 is 4.4–6.5 Å; and one or more of the following features VI–XXXVII VI. two oxygen atoms which form hydrogen bonds via a water molecule to the side chain carboxylic acid group of aspartic acid 48 such that the distance between each of the two oxygen atoms and the centroid of said water molecule ranges from 2.5–3.6 Å and that the distance between said water molecule and the centroid of said side chain carboxylic acid group of aspartic acid 48 ranges from 2.5–3.6 Å and that the distance between said two oxygen atoms ranges from 2.5–3.0 Å;

VII. an amino group which forms a salt bridge to the side chain carboxylic acid group of aspartic acid 48 such that the distance between the nitrogen atom of said amino group and the centroid of said side chain carboxylic acid group of aspartic acid 48 is 3.4–4.1 Å;

VIII. a hydrophobic group that interacts with the side chain methylene groups of tyrosine 46 such that the distance between the centroid of said hydrophobic group and the centroid of the methylene groups of said tyrosine 46 ranges from 4.4–5.1 Å;

IX. a hydrophilic group that forms a hydrogen bond with aspartic acid 181 such that the distance between the centroid of said hydrophilic group and the centroid of the carboxylic acid of said aspartic acid 181 ranges from 4.4–5.1 Å;

X. a hydrophobic group that interacts with tyrosine 46 and the methylene side chain atoms of arginine 47 such that the distance between the centroid of said hydrophobic group and the centroid of the aromatic ring of said tyrosine 46 ranges from 4.7–5.2 Å and the centroid of the methylene side chain atoms of said arginine 47 ranges from 4.5–5.5 Å;

XI. a hydrophilic group that forms a hydrogen bond with the one or more hydrogen atoms donated by the guanidinium group of arginine 47 such that the distance between the centroid of said hydrophilic group and the guanidinium group of said arginine 47 ranges from 2.7–3.5 Å;

XII. a hydrophilic group that forms a hydrogen bond with the hydrogen atom donated by the backbone amide nitrogen of arginine 47 such that the distance between the centroid of said hydrophilic group and the amide nitrogen group of said arginine 47 ranges from 2.7–4.0 Å;

XIII. a hydrophilic group that forms a hydrogen bond with the hydrogen atom donated by the backbone amide nitrogen of aspartic acid 48 such that the distance between the centroid of said hydrophilic group and the amide nitrogen group of said aspartic acid 48 ranges from 2.7–4.0 Å;

XIV. a hydrophilic group that forms a hydrogen bond with the backbone amide carbonyl group of asparagine 44 such that the distance between the centroid of said hydrophilic group and the amide carbonyl group of said asparagine 44 ranges from 2.7–4.0 Å;

XV. a hydrophilic group that forms a hydrogen bond with one or more hydrogen atoms donated by the guanidinium group of arginine 45 such that the distance between the centroid of said hydrophilic group and the centroid of the guanidinium group of said arginine 24 ranges from 2.7–4.0 Å;

XVI. a hydrophilic group that forms a salt bridge with the guanidinium group of arginine 45 such that the distance between the centroid of said hydrophilic group and the centroid of the guanidinium group of said arginine 24 ranges from 2.7–4.0 Å;

XVII. a hydrophobic group that interacts with the side chain methylene groups of arginine 45 such that the distance between the centroid of said hydrophilic group and the centroid of the methylene groups of said arginine 24 ranges from 4.4–5.1 Å;

XVIII. a hydrophilic group that forms a hydrogen bond with the backbone amide carbonyl group of arginine 45 such that the distance between the centroid of said hydrophilic group and the amide carbonyl group of said arginine 45 ranges from 2.7–4.0 Å;

XIX. a hydrophilic group that forms a hydrogen bond with the side chain hydroxy group of tyrosine 46 such that the distance between the centroid of said hydrophilic group and the hydroxy group of said tyrosine 46 ranges from 2.7–4.0 Å;

XX. a hydrophilic group that forms a hydrogen bond with the side chain amino group of lysine 41 such that the distance between the centroid of said hydrophilic group and the amino group of said lysine 41 ranges from 2.7–4.0 Å;

XXI. a hydrophobic group that interacts with the side chain methylene groups of lysine 41 such that the distance between the centroid of said hydrophilic group and the centroid of the methylene groups of said lysine 41 ranges from 4.4–5.1 Å;

XXII. a hydrophobic group that interacts with the side chain methylene groups of leucine 88 such that the distance between the centroid of said hydrophilic group and the centroid of the methylene groups of said leucine 8 ranges from 4.4–5.1 Å;

XXIII. a hydrophilic group that forms a hydrogen bond with the side chain hydroxy group of serine 118 such that the distance between the centroid of said hydrophilic group and the hydroxy group of said serine 118 ranges from 2.7–4.0 Å;

XXIV. a hydrophilic group that forms a hydrogen bond with the backbone amide carbonyl group of leucine 119 such that the distance between the centroid of said hydrophilic group and the amide carbonyl group of said leucine 119 ranges from 2.7–4.0 Å;

XXV. a hydrophilic group that forms a hydrogen bond with the one of the hydrogen atoms donated by the side chain amide nitrogen of glutamine 262 such that the distance between the centroid of said hydrophilic group and the amide nitrogen group of said glutamine 262 ranges from 2.7–4.0 Å;

XXVI. a hydrophilic group that forms a hydrogen bond with the hydrogen atom donated by the backbone amide group nitrogen of glycine 259 such that the distance between the centroid of said hydrophilic group and the amide nitrogen group of said glycine 259 ranges from 2.7–4.0 Å;

XXVII. a hydrophilic group that forms a hydrogen-bond with one or more hydrogen atoms donated by the side chain guanidinium group of arginine 254 such that the distance between the centroid of said hydrophilic group and the centroid of the guanidinium group of said arginine 254 ranges from 2.7–4.0 Å;

XXVIII. a hydrophilic group that forms a salt bridge with the guanidinium group of arginine 254 such that the distance between the centroid of said hydrophilic group and the centroid of the guanidinium group of said arginine 254 ranges from 2.7–4.0 Å;

XXIX. a hydrophobic group that interacts with the side chain methylene groups of arginine 254 such that the distance between the centroid of said hydrophilic group and the centroid of the methylene groups of said arginine 254 ranges from 4.4–5.1 Å;

XXX. a hydrophilic group that forms a hydrogen bond with one or more hydrogen atoms donated by the guanidinium group of arginine 24 such that the distance between the centroid of said hydrophilic group and the centroid of the guanidinium group of said arginine 24 ranges from 2.7–4.0 Å;

XXXI. a hydrophilic group that forms a salt bridge with the guanidinium group of arginine 24 such that the distance between the centroid of said hydrophilic group and the centroid of the guanidinium group of said arginine 24 ranges from 2.7–4.0 Å;

XXXII. a hydrophobic group that interacts with the side chain methylene groups of arginine 24 such that the distance between the centroid of said hydrophilic group and the centroid of the methylene groups of said arginine 24 ranges from 4.4–5.1 Å;

XXXIII. a hydrophilic group that forms a hydrogen bond with the backbone amide carbonyl group of aspartic acid 48 such that the distance between the centroid of said hydrophilic group and the backbone amide carbonyl group of said aspartic acid 48 ranges from 2.7–3.5 Å;

XXXIV. a hydrophobic group that interacts with the side chain atoms of methionine 258 such that the distance between the centroid of said hydrophobic group and the centroid of the side chain of said methionine 258 ranges from 4.5–6.2 Å;

XXXV. a hydrophobic group that interacts with glycine 259 such that the distance between the centroid of said hydrophobic group and the centroid of the alpha-carbon atom of said glycine 259 ranges from 4.5–6.2 Å;

XXXVI. a hydrophobic group that interacts with phenylalanine 52 such that the distance between the centroid of said hydrophobic group and the centroid of the aromatic group of said phenylalanine 52 ranges from 4.1–9.1 Å; or XXXVII. a hydrophobic group that interacts with methionine 258, glycine 259 and phenylalanine 52 being part of a hydrophobic pocket such that the distance between the centroid of said hydrophobic group and the centroid of the side chain of said methionine 258 ranges from 4.1–7.2 Å, the centroid of said glycine 259 is 4.7–7.7 Å, and the centroid of the side chain of said phenylalanine 52 ranges from 4.1–9.1 Å;

Further provided is a method of inhibiting at least one PTPase selected from the group consisting of Protein Tyrosine Phosphatase 1B (PTP1B) and/or T-Cell Protein Tyrosine Phosphatase which (TC-PTP) and/or other PTPases that are structurally similar to PTP1B comprising exposing said PTPase to a compound that fits spatially into the active site of said PTPase and the vicinity thereof, said compound comprising:

I. (a) a phosphate isostere which forms a salt bridge to the guanidinium group of arginine 221 and forms a hydrogen bond with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.54.2 Å, and (III) said glycine 220 backbone amide nitrogen ranges from 2.7–3.5 Å; or (b) an oxalylamide which forms a salt bridge to the guanidinium group of arginine 221 and forms a hydrogen bond with a hydrogen atom donated by the amide nitrogens of arginine 221 and glycine 220 such that the distance between the centroid of the carboxylic acid group of said oxalylamide group and (1) the centroid of said guanidinium group ranges from 3.50–4.20 Å, (II) said arginine 221 amide nitrogen ranges from 3.54.2 Å and the distance between the amide carbonyl group of said oxalylamide group and the said glycine 220 amide nitrogen ranges from 2.7–3.5 Å; and II. (a) a carboxylic acid group or (b) a carboxylic acid isostere group selected from the following 5-membered heterocycles wherein said acid or isostere group forms a salt bridge to the side chain amino group of lysine 120 such that the distance between the centroid of said carboxylic acid or carboxylic acid isostere and the side chain nitrogen atom of said lysine 120 ranges from 3.44.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and at least one of the following features IV and V:

IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; or V. a hydrophobic group that interacts with the imidazole ring of histidine 182 such that the distance between the centroid of said hydrophobic group and the centroid of the aromatic ring of said histidine 182 ranges from 4.4–6.5 Å.

In another specific embodiment, the invention provides a method of inhibiting at least one PTPase selected from the group consisting of Protein Tyrosine Phosphatase 1B (PTP1B), T-Cell Protein Tyrosine Phosphatase (TC-PTP) and other PTPases that are structurally similar to PTP1B which comprises exposing said PTPase to a compound that fits spatially into the active site of said PTPase and the vicinity thereof, said compound comprising:

I. a phosphate isostere which forms a salt bridge to the guanidinium group of arginine 221 and interacts with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.5–4.2 Å, and (III) said glycine 220 backbone amide nitrogen ranges from 2.7–3.5 Å; and II. (a) a carboxylic acid group or (b) a carboxylic acid isostere group selected from the following 5-membered heterocycles wherein said acid or isostere group forms a salt bridge to the side chain amino group of lysine 120 such that the distance between the centroid of said carboxylic acid or carboxylic acid isostere and the side chain nitrogen atom of said lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; or V. a hydrophobic group that interacts with the imidazole ring of histidine 182 such that the distance between the centroid of said hydrophobic group and the centroid of the aromatic ring of said histidine 182 ranges from 4.4–6.5 Å;

wherein the distance between the centroid of the phosphate isostere and the centroid of (I) said carboxylic acid or carboxylic acid isostere ranges from 4.9–5.9 Å, (II) said amino group ranges from 8.0–14.0 Å and between the centroid of said carboxylic acid or carboxylic acid isostere and said amino group ranges from 4.8–5.8 Å or wherein the distance between the centroid of the phosphate isostere and the centroid of (I) said carboxylic acid or carboxylic acid isostere ranges from 4.9–5.9 Å, (II) said oxygen atoms are ranges from 8.0–14.0 Å and between the centroid of said carboxylic acid or carboxylic acid isostere and said oxygen atoms are ranges from 5.0–7.9 Å.

The invention further provides a method of inhibiting at least one PTPase selected from the group consisting of Protein Tyrosine Phosphatase 1B (PTP1B), T-Cell Protein Tyrosine Phosphatase (TC-PTP) and other PTPases that are structurally similar to PTP1B which comprises exposing said PTPase to a compound that fits spatially into the active site of said PTPase and the vicinity thereof, said compound comprising:

I. an oxalylamide which forms a salt bridge to the guanidinium group of arginine 221 and forms a hydrogen bond with a hydrogen atom donated by the amide nitrogens of arginine 221 and glycine 220 such that the distance between the centroid of the carboxylic acid group of said oxalylamide group and (I) the centroid of said guanidinium group ranges from 3.50–4.20 Å, (II) said arginine 221 amide nitrogen ranges from 3.5–4.2 Å and the distance between the amide carbonyl group of said oxalylamide group and the said glycine 220 amide nitrogen ranges from 2.7–3.5 Å; and II. (a) a carboxylic acid group or (b) a carboxylic acid isostere group selected from the following 5-membered heterocycles wherein said acid or isostere group forms a salt bridge to the side chain amino group of lysine 120 such that the distance between the centroid of said carboxylic acid or carboxylic acid isostere and the side chain nitrogen atom of said lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; or V. a hydrophobic group that interacts with the imidazole ring of histidine 182 such that the distance between the centroid of said hydrophobic group and the centroid of the aromatic ring of said histidine 182 ranges from 4.4–6.5 Å; and wherein the distance between the centroid of the carboxylic acid group of said oxalylamide group and the centroid of (I) said carboxylic acid or carboxylic acid isostere ranges from 4.9–5.9 Å, (II) said amino group ranges from 8.0–14.0 Å and between the centroid of said carboxylic acid or carboxylic acid isostere and said amino group ranges from 4.8–5.8 Å or wherein the distance between the centroid of the carboxylic acid group of said oxalylamide group and the centroid of (I) said carboxylic acid or carboxylic acid isostere ranges from 4.9–5.9 Å, (II) said oxygen atoms are ranges from 8.0–14.0 Å and between the centroid of said carboxylic acid or carboxylic acid isostere and said oxygen atoms are ranges from 5.0–7.9 Å.

The hydrophobic groups that interact with tyrosine 46 and phenylalanine/histidine 182 include, but are not limited to, alkyl and aryl groups. These hydrophobic groups include cyclohexyl, phenyl, naphthyl, thiophenyl, pyrrolyl and furanyl. The hydrophobic groups that interact with one or more of the tyrosine 46 and the arginines 24, 45, 47, and 254 include, but are not limited to, alkyl and aryl groups. These hydrophobic groups include cyclohexyl, phenyl, naphthyl, thiophenyl, pyrrolyl and furanyl, optionally substituted The hydrophobic groups that interact with methionine 258, glycine 259 and phenylalanine 52 include, but are not limited to, alkyl and aryl groups groups. These aryl groups include phenyl, thiophenyl, pyrrolyl, furanyl, $C_1$–$C_6$alkyl and aryl$C_1$–$C_6$alkyl which are defined hereinbelow.

The hydrophilic groups that interact with the hydrogen atom donated by the side chain amide nitrogen of arginine 47, aspartic acid 48, leucine 119, glycine 259, lysine 41, lysine 120, the side chain amide hydrogen atom donated by glutamine 262, the hydrogen atoms donated by the guanidinium group of arginine 254, arginine 45 or arginine 24 include, but are not limited to, hydroxy, $C_1$–$C_6$alkyloxy, aminocarbonyl, oxo, SO, $SO_2$, $SONH_2$, $SO_2NH_2$, $SO_2NHCF_3$, COOH or a group selected from the following 5-membered heterocycles

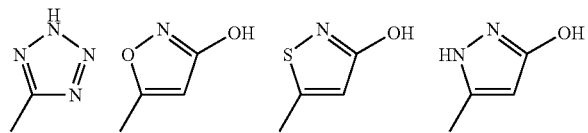

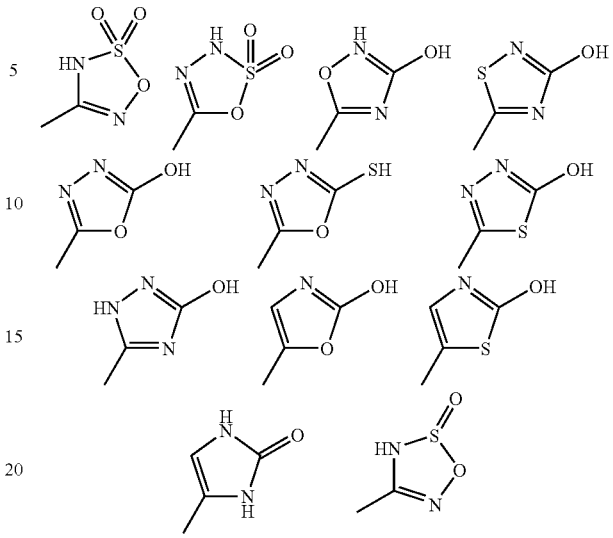

The hydrophilic groups that interact with the side chain amide carbonyl group of asparagine 44, arginine 45 or aspartic acid 48 include, but are not limited to, amino, aminocarbonyl, hydroxy, $SONH_2$, $SO_2NH_2$, or $SO_2NHCF_3$.

The hydrophilic groups that interact with the side chain carboxylic acid group of aspartic acid 181 include, but are not limited to, amino, aminocarbonyl, hydroxy, $C_1$–$C_6$alkyloxy, $SONH_2$, $SO_2NH_2$. The hydrophilic groups that interact with the side chain hydroxy group of serine 118 include, but are not limited to, aminocarbonyl, hydroxy, $C_1$–$C_6$alkyloxy, $SONH_2$, $SO_2NH_2$.

Unique Structural Elements in PTP1B

To identify unique residues or combinations of residues of PTP1B that could be utilised as points of interaction by selective inhibitors, alignment of the primary sequences of the catalytic domains of approximately 105 known vertebrate PTPases (Andersen, J. N. et al., (1999) in preparation) was done (Table 1, below). Using the crystal structure of PTP1B (Andersen, H. S. et al. (1999) J. Biol. Chem. 275:7107–7108 (2000); Barford, D., et al. Science 263: 1397–1404 (1994)), unique combinations of residues in the active site pocket or in its vicinity were identified, i.e. in a distance (3–5.5 Å) that would allow simultaneous binding to the active site and these residues, while still retaining a low molecular weight (for example, below 700 dalton). In particular, the combination of 4 residues seems unique for the PTP1B family: arginine 47, aspartic acid 48, methionine 258, and glycine 259 arginine 47 and aspartic acid 48 contribute significantly to the binding of peptide substrates in PTP1B (Jia, Z. C., et al., Science 268:1754–1758 (1995)). A comparison of these regions in representative members of 14 PTP families, indicates that in particular residue 48 is an attractive binding element for selective PTP1B ligands since this residues is an aspartic acid in PTP1B and an asparagine in many other PTPases. Aspartic acid 48 is well-defined in the published PTP1B structures ((Puius, Y. A. et al. Proc. Natl. Acad. Sci. USA 94:13420–13420 (1997)), (Pannifer, A. D. B., et al., J. Biol. Chem. 273:10454–10462 (1998)) and it is believed to play an important role in positioning substrates correctly relative to the active site (Sarmiento, M., et al., J. Biol. Chem. 273: 26368–26374 (1998)).

TABLE 1

Non-limiting examples of selected amino acid residues at positions in the vicinity of the active site (single letter code - PTP1B numbering)

| Residue | PTP1B | SHP1 | PTP-L1 | PTPD2 | PTPH1 | STEP | IA-2 | PTPβ | PTPα | PTPε | PTP-LAR | PTPμ | CD45 | PTPχ |
|---|---|---|---|---|---|---|---|---|---|---|---|---|---|---|
| 47 | R | K | K | R | K | K | P | N | V | P | A | G | V | I |
| 48 | D | N | N | E | D | T | D | N | N | N | N | N | D | N |
| 258 | M | S | H | M | A | G | P | V | C | P | N | V | C | N |
| 259 | G | G | G | F | M | G | G | H | Q | Q | Y | N | L | Y |

Optimization for Potency

The key structural features of 2-(oxalyl-amino)-benzoic acid (OBA) are the two carboxy groups respectively bound—directly and through a carbonylamino group—to an aromatic ring. Replacement of the phenyl ring in OBA by thiophene, resulted in compounds with little difference in potency between the regioisomer 2-aminothiophene and 3-aminothiophene.

Previous studies have shown that phenyl-based phosphonate inhibitors have little affinity for PTP1B, while addition of a second phenyl ring (e.g. [(1,1-difluoro-1-naphthalenyl)-methyl]phosphonic acid) significantly increased the potency (Burke, T. R. et al., *Biochemistry* 35:15989–15996 (1996)). The enhanced potency of the naphthalene ring system is due to extensive hydrophobic interactions with the side chains of tyrosine 46, valine 49, phenylalanine 182, alanine 217 and isoleucine 219. Similarly, 3-(oxalyl-amino)-naphthalene-2-carboxylic acid interacts with the same residues. It was reasoned that a saturated ring fused to 2-(oxalyl-amino)-thiophene-3-carboxylic acid (2-OTA) and/or 3-(oxalyl-amino)-thiophene-2-carboxylic acid (3-OTA) would serve a similar function and increase the potency. Further, the proposed binding mode of such a compound should bring the saturated ring in close proximity to residues arginine 47 and aspartic acid 48. Introducing a basic nitrogen or polar changes in this saturated ring would allow further interactions with the side chains or backbone amides of arginine 47 and aspartic acid 48. In accordance with the above alignment studies, we anticipated that selectivity for PTP1B and other PTPases with an aspartic acid in position 48 could be obtained by specifically addressing this area of the enzyme.

Consequently, 2-(oxalyl-amino)-4,5,6,7-tetrahydro-benzo[b]thiophene-3-carboxylic acid (2-OBTA) was synthesised and its potency analysed against a set of PTPases. Table II shows that 2-OBTA is about 10-fold more potent against PTP1B than compounds 3-OTA and 2-OTA and 3-fold more potent than OBA when tested at pH 5.5 (the pH optimum for PTP1B using pNPP as substrate). Further, the inhibitory profile against this set of PTPases is almost the same as that of 3-(oxalyl-amino)-naphthalene-2-carboxylic acid. Thus, although 2-OBTA retains the features of a general PTP inhibitor, it already shows some selectivity for PTP1B. These results clearly indicate that 2-OBTA spatially fits in this region of PTP1B. Various substitutions in the saturated ring of 2-OBTA were found to influence the binding affinities for different PTPases (not shown).

TABLE 2

$K_i$ values (μM) - pH 5.5

| | OBA | 3-OTA | 2-OTA | 2-OBTA | 2-OTPyA | 2-OTPA |
|---|---|---|---|---|---|---|
| PTP1B | 20 | 61 | 62 | 5.7 | 0.3 | 15 |
| SHP-1 | 530 | >2000 | 60 | 120 | 900 | 350 |

TABLE 2-continued $K_i$ values (μM) - pH 5.5

| | OBA | 3-OTA | 2-OTA | 2-OBTA | 2-OTPyA | 2-OTPA |
|---|---|---|---|---|---|---|
| PTPα D1 | 700 | 500 | 1700 | 300 | >2000 | 270 |
| PTPε D1 | 125 | 350 | 590 | 45 | 600 | 20 |
| PTPβ | 32 | 160 | 18 | 14 | 150 | 12 |
| CD45 D1D2 | 160 | 250 | 70 | 40 | 110 | 50 |
| LAR D1D2 | >2000 | >2000 | >2000 | 400 | >2000 | 360 |

As indicated above, in comparison with OBA, 2-OBTA showed an approximately 3-fold increase in affinity for most PTPases. It was hypothesised that the saturated ring of 2-OBTA would occupy almost the same position as the distal ring of 3-(oxalyl-amino)-naphthalene-2-carboxylic acid, which was previously shown to bind in the proximity of arginine 47 and aspartic acid 48. Therefore, as expected, there was no apparent change in selectivity in accordance with the notion that the saturated ring makes hydrophobic contact with conserved residues such as tyrosine 46, alanine 217, valine/isoleucine219 and isoleucine/valine 49 (PTP1B numbering).

Optimization for Selectivity

The combination of arginine 47 and aspartic acid 48 offers a rather unique, selective ligand-binding region in PTP1B. The side chains of both residues are charged at neutral pH and are therefore sutiable for salt bridge formation. Introducing a positive charge in 2-OBTA that could form a salt bridge with aspartic acid 48, would not only increase the potency of 20BTA against PTP1B but also—due to repulsive forces between the positive ligand charge and the asparagine side chain found in many other PTPases—decrease the affinity of 20 BTA for these PTPases.

Three side chain rotamer conformations are normally defined for an aspartic acid residue (rota 1: 47.7%, rota 2: 33.6% and rota 3: 15.9%). In the published X-ray structures of PTP1B, two rotamers have been described, rota 1 and 3. The rota 3 conformation is stabilised by an internal hydrogen bond between the side chain and main chain amide with the side chain bending towards the active site pocket. Further, rota 3 seems to be the preferred rotamer for aspartic acid 48. The rota 1 conformation has only been found in four of the eleven published X-ray structures, and in three of these cases the rota 1 position is necessitated due to ligand occupancy. The aspartic acid 48 rota 1 conformation is pointing away from the active site pocket. Thus, rota 3 was found both in the apo-enzyme and in PTP1B complexed with peptide ligands that seem to stabilize this conformation. Further, we have recently co-crystallized PTP1B with OBA and 3 derivatives and found aspartic acid 48 in the rota 3 position in all structures (Andersen, H. S. et al. *J. Biol. Chem.* 275, 7101–7108 (2000)). Based on these observations, it was hypothesized that introduction of a basic nitrogen in the saturated ring in 2-OBTA would be sufficiently close to aspartic acid 48 to allow the formation of a salt bridge. A recent survey of 322 unrelated proteins has shown that aspartic acid and asparagine residues have a strong tendency to form hydrogen bonds with neighboring backbone amides and in both cases with a significant preference for internal hydrogen bonds.

Assuming that asparagine 48 of other PTPases, e.g. PTPα, forms an internal hydrogen bond similar to that observed for aspartic acid 48 in PTP1B, the side chain amide of the asparagine with its positive dipole would be in an unfavourable position to the proposed basic nitrogen and thus cause repulsion.

2-(Oxalyl-amino)-4,5,6,7-tetrahydro-thieno[2,3-c]pyridine-3-carboxylic acid (2-OTPyA)—containing a positively charged tetrahydropyridine ring ($pK_a$>10)—was synthesised in order to test the foregoing hypothesis. In agreement with the predictions, the affinity for PTP1B was increased about 20-fold without any significant increase in molecular weight (Table 2). Further, this compound showed an almost astonishing selectivity for PTP1B versus all other PTPases tested. Again, this is in agreement with the hypothesis that repulsive forces between the basic nitrogen in 2-OTPyA and the positive dipole of the asparagine side chain decrease the potency against other PTPases. CD45, which also contains an aspartic acid in position 48, is a noticeable exception showing only a 2-fold decrease. It is speculated that the preferred rotamer of aspartic acid 48 in CD45 is the rota 1 conformation, which is too far away for salt bridge formation with 2-OTPyA. In addition, CD45 contains a valine in position 47, which may not have the same influence on aspartic acid 48 as an arginine.

2-(Oxalyl-amino)-4,7-dihydro-thieno[2,3-c]pyran-3-carboxylic acid (2-OTPA)—containing a negative dipole in the dihydropyran ring—was synthesised. In agreement with the predictions, the affinity for PTP1B was decreased about 2.5-fold compared to 2-OBTA without any significant increase in molecular weight (Table 2).

Table A (at the end of the specification) discloses the protein coordinates of PTP1B complexed with 2-(oxalyl-amino)-4,5,6,7-tetrahydro-thieno[2,3-c]pyridine-3-carboxylic acid (2-OTPA) and in FIG. 1 is the active site of PTP1B complexed with 2-OTPA shown.

Optimization for Potency Towards Arginine 47 and Aspartic Acid 48

Using further the combination of the 4 unique residues for the PTP1B family: arginine 47, aspartic acid 48, methionine 258, and glycine 259 it was hypothesised that an increase in potency could be obtained by introduction of a hydrogen-bond acceptor side chain that could form one or more hydrogen bonds with the main chain amides of arginine 47 and aspartic acid 48, would increase the potency against PTP1B. 5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid (5-HTPyA) (Example 52)—still containing a positively charged tetrahydropyridine ring and three hydrogen-bond acceptors (oxygen atoms)—was synthesised. In agreement with the predictions, the affinity for PTP1B was increased about 13-fold compared to 2-OTPyA.

Changing the positively charged nitrogen atom with a non charged oxygen atom and still addressing the main chain amides of arginine 47 and aspartic acid 48, it was hypothesised that an increase in general potency could be obtained. Thus, 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (5-HTPA) (Example 4)—containing a non charged dihydropyran ring and three hydrogen-bond acceptor oxygen atoms—was synthesised. In agreement with the predictions, only the general potency was increased compared to 2-OTPyA as shown in Table 3.

Selectivity Via Steric Hindrance

Referring again to the combination of the 4 residues unique for the PTP1B family: arginine 47, aspartic acid 48, methionine 258, and glycine 259, but this time more specifically to the combination of methionine 258 and glycine 259, which form part of a hydrophobic pocket in PTP1B in contrast to most other PTPases where the pocket is filled out: PTPα: cysteine 258-glutamine 259; PTP β: valine 258-histidine 259; PTP-LAR: asparagine 258-tyrosine 259; and CD45: cysteine 258-leucine 259 (PTP1B numbering), it was hypothesised that an increase in potency and selectivity could be obtained by introduction of a hydrophobic side chain that could form hydrophobic interactions to glycine 259 and to the side chain of methionine 258 and at the same time take part in repulsion-/steric hindrance with the same residues in other PTPases. Thus, 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (7-MOTPA) (Example 26)—containing a hydrophobic 1,3-dihydro-isoindol side chain—was synthesised. In agreement with the predictions, both affinity and selectivity for PTP1B was increased as shown in Table 3 compared to 2-OTPA.

TABLE 3

| | $K_i$ values (μM) - pH 7 | | |
|---|---|---|---|
| | 2-OTPA | 7-MOTPA | 5-HTPA |
| PTP1B | 63 | 1.2 | 1.9 |
| PTPα D1 | 1100 | 620 | 93 |
| PTPε D1 | 290 | 330 | 11 |
| PTPβ | 17 | 8.9 | 1.1 |
| CD45 D1D2 | 960 | 380 | 130 |

Figure 2:
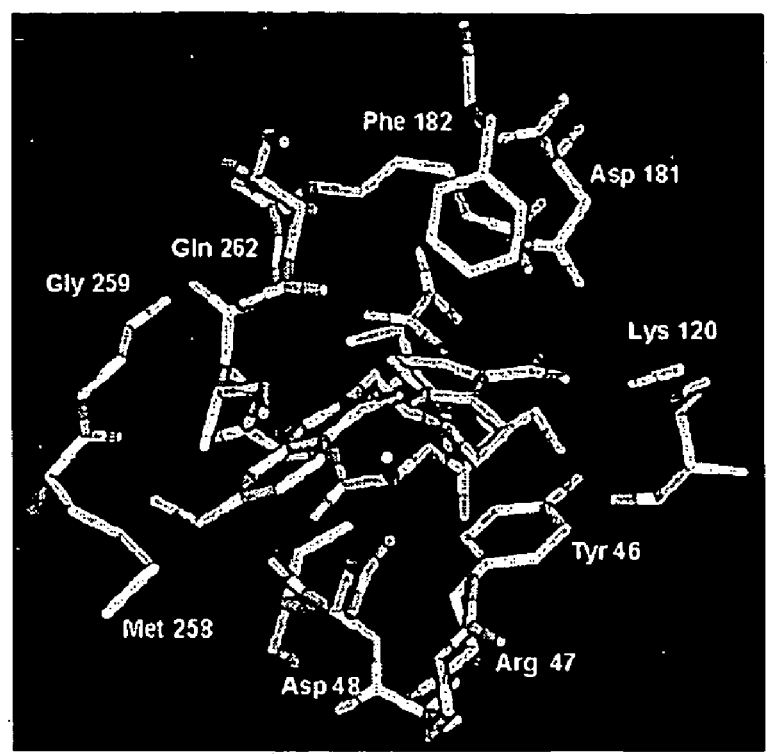
FIG. 2. Active site of Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

Table B (at the end of the specification) discloses the protein coordinates of PTP 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (7-MOTPA) (Example 26), and FIG. 2 shows the crystal structure of the active site of PTP1B complexed with 7-MOTPA.

Figure 3:
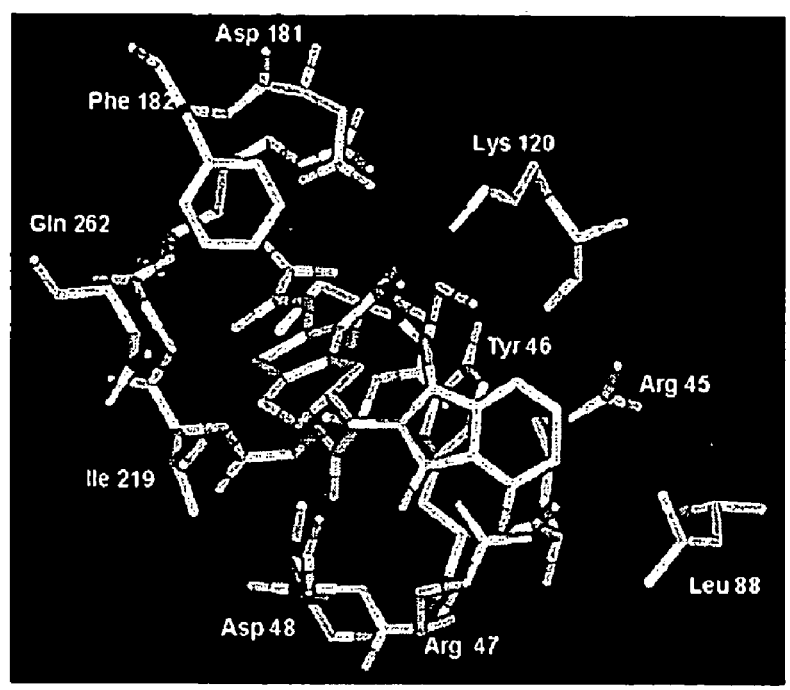
FIG. 3. Active site of Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2, 3-c]pyran-3-carboxylic acid (Example 4).
Figure 4:
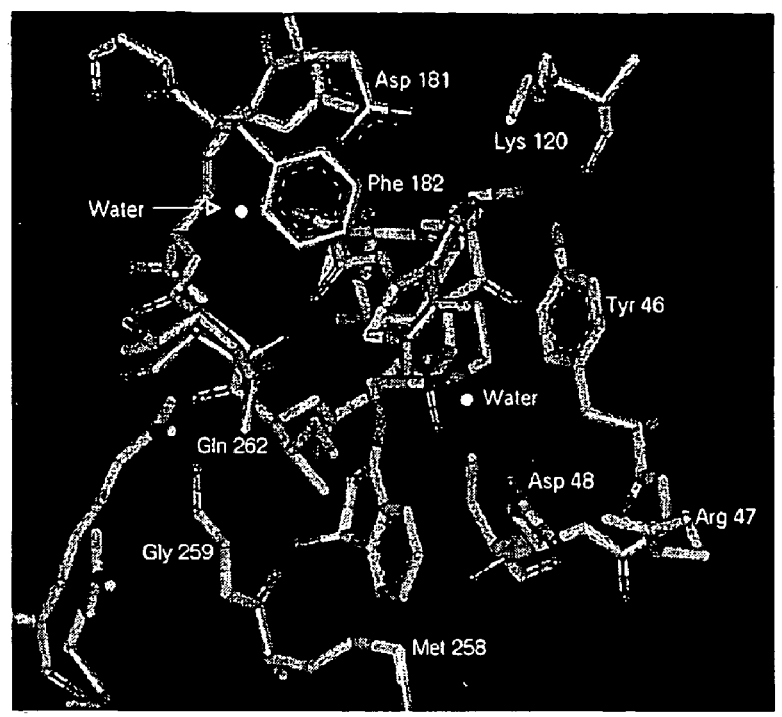
FIG. 4. Active site of Protein Tyrosine Phosphatase 1B complexed with 2-(oxalyl-amino)-7-(1,1,3-trioxo-1H-benzo [d]isothiazol-3-yloxomethyl)-4,7-dihydro-5H-thieno[2,3-c] pyran-3-carboxylic acid (Example 54). Selected water molecules are shown.

Table C (at the end of the specification) discloses the protein coordinates of PTP1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (5-HTPA) (Example 4), and FIG. 3 shows the crystal structure of the active site of PTP1B complexed with 5-HTPA.

Table D (at the end of the specification) discloses the protein coordinates of PTP1B complexed with 2-(oxalyl-amino)-7-(1,1,3-trioxo-1H-benzo [d]isothiazol-3-yloxomethyl)-4,7-dihydro-5H, thieno[2,3-c]pyran-3-carboxylic acid (example 54), including key water molecules. FIG. 2 is the active site with selected water molecules shown.

Specific interactions of certain inhibitors of the present invention at the active site of PTP1B are detailed below.

The carboxy group of the oxamicN acid of 2-(oxalyl-amino)-4,5,6,7-tetrahydro-thieno[2,3-c]pyridine-3-carboxylic acid is positioned 2.9–3.0 Å from the guanidinium group of arginine 221 forming a salt bridge, as well as a hydrogen bond with the main chain amide of arginine 221 and serine 216, and the carbonyl forms a hydrogen bond with the main chain amide of glycine 220. The carboxy group in the 3 position is positioned 2.8 Å from lysine 120 forming a salt bridge. The tetrahydro-thieno[2,3-c]pyridine ring forms hydrophobic interactions with phenylalanine 182, tyrosine 46, valine 49, alanine 217 and isoleucine 219. The basic nitrogen in the tetrahydro-thieno[2,3-c]pyridine ring is positioned 2.8 Å from the carboxy group of aspartic acid 48 forming a salt bridge.

The carboxy group of the oxamic acid of 7-(5-Methoxy-1,3-dioxo-1,3-dihydro-isoindol-2-ylmethyl)-2-(oxalyl-amino)-4,7-dihydro-thieno[2,3-c]pyran-3-carboxylic acid (Example 26) is positioned 2.9–3.0 Å from the guanidinium group of arginine 221 forming a salt bridge, as well as a hydrogen bond with the main chain amide of arginine 221 and serine 216, and the carbonyl forms a hydrogen bond with the main chain amide of glycine 220. The carboxy group in the 3 position is positioned 2.8 Å from lysine 120 forming a salt bridge. The dihydro-thieno[2,3-c]pyran ring forms hydrophobic interactions with phenylalanine 182, tyrosine 46, valine 49, alanine 217 and isoleucine 219. The phenyl ring of the isoindol ring forms a hydrophobic interaction with the side chain methylene atom of aspartic acid 48 and the 5-methoxy substituent forms hydrophobic interactions with the side chain atoms of methionine 258.

The carboxy group of the oxamic acid of 5-(4-hydroxy-1,3-dioxo-1,3-dihydro-isoindol-2-ylmethyl)-2-(oxalyl-amino)-4,7-dihydro-thieno[2,3-c]pyran-3-carboxylic acid (Example 4) is positioned 2.9–3.0 Å from the guanidinium group of arginine 221 forming a salt bridge, as well as a hydrogen bond with the main chain amide of arginine 221 and serine 216, and the carbonyl forms a hydrogen bond with the main chain amide of glycine 220. The the carboxy group in the 3 position is positioned 2.7 Å from lysine 120 forming a salt bridge. The dihydro-thieno[2,3-c]pyran ring forms hydrophobic interactions with phenylalanine 182, tyrosine 46, valine 49, alanine 217 and isoleucine 219. The side chain methylene group at the 5 position of the thieno [2,3-c]pyran forms a hydrophobic interaction the side chain methylene group of aspartic acid 48. The phenyl ring of the isoindol ring forms a hydrophobic interaction with tyrosine 46 and both one of the oxo atoms and the hydroxy group at the isoindole forms hydrogen bonds respectively with the main chain amide of aspartic acid 48 and arginine 47.

To further substantiate the generality in using steric hindrance/steric fit to obtain selectivity for PTP1B, TC-PTP and structurally similar PTPases we also synthesized 7-(1, 1-dioxo-1H-benzo[d]isothiazol-3-yloxymethyl)-2-(oxalyl-amino)-4,7-dihyd ro-5H-thieno[2,3-c]pyran-3-carboxylic acid ("Compound N"). The substitution was introduced in the 7-position to address the region defined by residues 258 and 259. As indicated above, this part of PTP1B forms a hydrophobic pocket with direct access to the active site, whereas the same region is sterically hindered by more bulky side chains, in particular those corresponding to residue 259 in PTP1B. Compound N was synthesized with a substituent in the 7-position of 2-OTPA to sterically fit with this part of PTP1B and TC-PTP, but cause steric hindrance in other PTPs.

To test directly, whether the above compound was addressing the proposed region of PTP1B, Compound N was subjected to detailed enzyme kinetic analyses using a set of wildtype (wt) and mutant PTPs. Two enzymes, PTPα and PTPH1, were chosen as representatives for PTPs with bulky side chains in the 259 position. Using a combination of wt and PTP mutants it has previously been shown that Gln259 in PTPα, in addition to its direct effect, also indirectly influences the binding of inhibitors and substrates, most likely due to a negative influence on the rotational freedom of the side chain of Gln262 (Peters et al., *J. Biol. Chem.* 275: 18201–18209 (2000)). As described above, selectivity can be obtained by introducing a basic nitrogen into 2-(oxalylamino)-4,5,6,7-tetrahydrobenzo[b]thiophene-3-carboxylic acid that causes attraction in PTP1B due to salt bridge formation to Asp48 and repulsion against PTPs with an asparagine in the 48 position, such as PTPα. To analyze if the current approach based on steric hindrance is generally applicable, it was decided to include a PTP with an aspartic acid in position 48. PTPH1, which like PTP1B is an intracellular enzyme with one domain only, was selected for these studies. The results of these studies are shown below (Table 4).

TABLE 4

| Enzyme | Ki values (μM) at pH 7.0 |
| --- | --- |
| PTP1B wt | 0.4 |
| PTP1B G259Q | 65 |
| PTP1B G259M | 55 |
| PTPα wt | >500 |
| PTPα Q259G | 70 |
| PTPH1 wt | 55 |
| PTPH1 M259G | 12 |

It appears that introduction of bulky side chains in the 259 position in PTP1B causes a very significant decrease in affinity for NNC 52–1153. Conversely, replacement of the bulky residues in PTPα and PTPH1 with a glycine increases the affinity. This clearly indicates that NNC 52–1153 addresses the 258–259 region of PTP1B.

Specificity against a broad set of PTPs—It was next analyzed if the side chain of NNC 52–1153 would cause the increased selectivity against other PTPs. NNC 52–1153 was tested against a set of 10 different wt PTP domains (Table 5). It appears from this table that a substantial increase in affinity for PTP1B and TC-PTP has been obtained, while at the same time introducing a very high degree of selectivity against many other PTPs representing a broad spectrum of this class of enzymes (having Asp 48).

TABLE 5

| Enzyme | Ki values (μM) at pH 7.0 |
| --- | --- |
| PTP1B | 0.4 |
| TC-PTP | 0.6 |
| PTPH1 | 55 |
| PTPα | 700 |
| PTPε | 460 |
| CD45 | 500 |
| LAR | 120 |
| GLEPP1 | 150 |
| PTPβ | 15 |

To unequivocally determine the binding mode, x-ray co-crystallization studies of PTP1B and NNC 52–1153 were initiated. A well-suited electron density was identified in the active site pocket. The oxalylamino and o-carboxy groups show the exact same interaction with the PTP signature motif and salt bridge formation to Lys120 as described previously for 2-(oxalylamino)-benzoic acid and the thiophene-based derivatives. Significantly, the side chain of the ligand is positioned in close vicinity to residues 258 and 259. Several interaction points appear to be responsible for the observed significant increase in affinity for PTP1B. Thus, a long hydrogen bond seems to interact with one carbonyl of the ligand side chain. In addition, important van der Waals contacts are made between the aromatic ring of the ligand side chain and the side chain of Met248 and Cβ atom of Asp48.

As described above, we have utilized salt bridge formation to Asp48 to obtain potent and selective PTP1B inhibitors. In these structures, Asp48 was in the so-called rotamer ("rota") 3 position—pointing towards the active site. In contrast, the side chain of Asp48 is pushed away from the active site by the oxygen molecules in NNC 52–1153 (i.e. the rotamer 1 position). This allows a novel water molecule to form a bridge between the two oxygen molecules in the ligand and Asp48. This surprising observation can be used to design additional inhibitors of PTP1B.

The present invention encompasses, but is not limited to, compounds of the Formula 1 wherein n, m, X, Y, $R_1$, $R_2$, $R_3$, $R_4$, $R_5$ and $R_6$ are defined below;

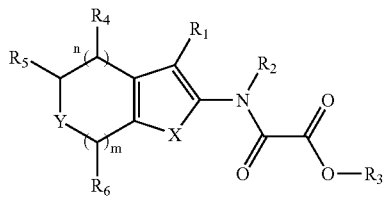

Formula 1

In the above Formula 1 n is 0, 1 or 2 (if m=0 then n is 1 or 2);

m is 0, 1 or 2 (if n=0 then m is 1 or 2);

X is S, O, $NR_8$;

Y is $NR_7$, O, S, SO, $SO_2$;

$R_1$ is hydrogen, $COOR_3$, or selected from the following 5-membered heterocycles:

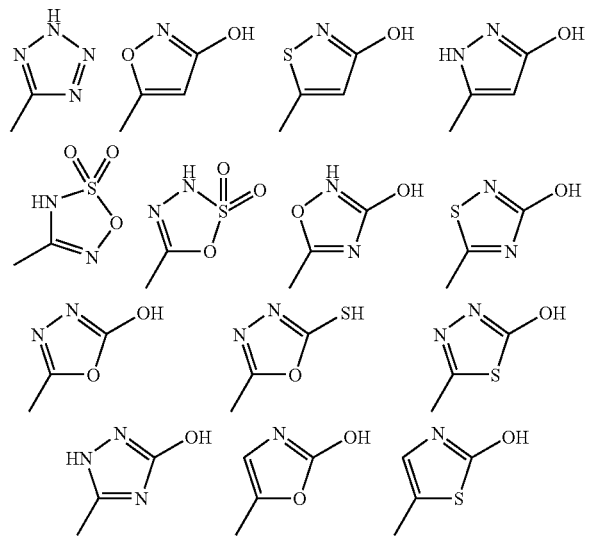

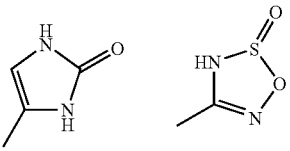

$R_2$ is hydrogen, $C_1$–$C_6$alkyl, hydroxy, $NR_9R_{10}$;

$R_3$ is hydrogen, $C_1$–$C_6$alkyl, aryl$C_1$–$C_6$alkyl, $C_1$–$C_6$alkylcarbonyloxy$C_1$–$C_6$alkyl, $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxy-carbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryloxy $C_1$–$C_6$ alkyl, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_9R_{10}$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy$C_1$–$C_6$-alkyl, arylcarboxy, arylcarboxy$C_1$–$C_6$alkyl, aryl$C_1$–$C_6$alkylcarboxy, aryl$C_1$–$C_6$alkylcarboxy$C_1$–$C_6$alkyl, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{13}$, aryl$C_1$–$C_6$alkylcarbonyl-amino, aryl$C_1$–$C_6$alkylcarbonylamino$C_1$–$C_6$alkyl, arylamino carbonylamino$C_1$–$C_6$ alkyl, arylamino$C_1$–$C_6$ alkyl, arylcarbonylamino $C_1$–$C_6$ alkyl, $CONR_9R_{10}$, $R_8R_9NC_1$–$C_6$ alkyl, or $C_1$–$C_6$alkyl-$CONR_9R_{10}$ wherein the alkyl and aryl groups are optionally substituted and $R_{13}$ is $NR_9R_{10}$, or $C_1$–$C_6$alkyl$NR_9R_{10}$; $R_7$ is hydrogen, $C_1$–$C_6$alkyl, aryl, aryl$C_1$–$C_6$alkyl, $C_1$–$C_6$alkylcarbonyl, $C_1$–$C_6$alkyloxocarbonyl, arylcarbonyl, aryloxocarbonyl, aryl$C_1$–$C_6$alkylcarbonyl, aryl$C_1$–$C_6$alkyloxocarbonyl, $C_1$–$C_6$alkylcarboxy, aryl$C_1$–$C_6$alkylcarboxy, $R_9R_{10}Ncarbonyl C_1$–$C_6$alkyl wherein $R_9$ and $R_0$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy; wherein the alkyl and aryl groups are optionally substituted;

$R_8$ is hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted;

$R_9$ and $R_{10}$ are independently selected from hydrogen, $C_1$–$C_6$alkyl, aryl, aryl$C_1$–$C_6$alkyl, $C_1$–$C_6$alkylcarbonyl, arylcarbonyl, aryl$C_1$–$C_6$alkylcarbonyl, $C_1$–$C_6$alkylcarboxy or aryl$C_1$–$C_6$alkylcarboxy wherein the alkyl and aryl groups are optionally substituted; or $R_9$ and $R_{10}$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one $C_1$–$C_6$alkyl, aryl, aryl$C_1$–$C_6$alkyl, hydroxy, oxo, $C_1$–$C_6$alkyloxy, arylC$_1$–C$_6$alkyloxy, C$_1$–C$_6$alkyloxyC$_1$–C$_6$alkyl, NR$_{11}$R$_{12}$ or C$_1$–C$_6$alkylamino-C$_1$–C$_6$alkyl, wherein R$_{11}$ and R$_{12}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted; or R$_9$ and R$_{10}$ are independently a saturated or partial saturated cyclic 5, 6 or 7 membered amine, imide or lactam or a salt thereof with a pharmaceutically acceptable acid or base, or any optical isomer or mixture of optical isomers, including a racemic mixture, or any tautomeric forms.

The compounds of Formula 1 are oxalylamide compounds having in common key structural features required of non hydrolysable protein tyrosine phosphatase inhibitors, most particularly PTP1B and/or TC-PTP inhibitors. These structural features endow the present compounds with the appropriate molecular shape necessary to fit into the enzymatic active site, to bind to such site in a non covalently way, thereby blocking the site and inhibiting enzymatic biological activity. Referring to Formula 1, such structural features include the oxalylamide and an ortho-carboxylic acid attached to a hydrophobic group, preferably an aryl as defined below The compounds of the invention can be further modified to act as pro-drugs.

It is a well known problem in drug discovery that compounds, such as enzyme inhibitors, may be very potent and selective in biochemical assays, yet be inactive in vivo. This lack of so-called bioavailability may be ascribed to a number of different factors such as lack of or poor absorption in the gut, first pass metabolism in the liver, poor uptake in cells. Although the factors determining bioavailability are not completely understood, there are many examples in the scientific literature—well known to those skilled in the art—of how to modify compounds, which are potent and selective in biochemical assays but show low or no activity in vivo, into drugs that are biologically active. It is within the scope of the invention to modify the compounds of the invention, termed the 'original compound' or "prototype", by attaching chemical groups that will improve the bioavailability of said compounds in such a way that the uptake in cells or mammals is facilitated. Examples of said modifications, which are not intended in any way to limit the scope of the invention, include changing of one or more carboxy groups to esters (for instance methyl esters, ethyl esters, acetoxymethyl esters or other acyloxymethyl esters). Compounds of the invention, original compounds, modified by attaching chemical groups are termed 'modified compounds' Said chemical groups may or may not be apparent in the claims of this invention. Other examples of modified compounds, which are not intended in any way to limit the scope of the invention, are compounds that have been cyclized at specific positions—so called 'cyclic compounds'—which upon uptake in cells or mammals become hydrolyzed at the same specific position(s) in the molecule to yield the compounds of the invention, the original compounds, which are then said to be 'non-cyclic' For the avoidance of doubt, it is understood that the latter original compounds in most cases will contain other cyclic or heterocyclic structures that will not be hydrolyzed after uptake in cells or mammals. Generally, said modified compounds will not show a behavior in biochemical assays similar to that of the original compound, i.e. the corresponding compounds of the invention without the attached chemical groups or said modifications. Said modified compounds may even be inactive in biochemical assays. However, after uptake in cells or mammals these attached chemical groups of the modified compounds may in turn be removed spontaneously or by endogenous enzymes or enzyme systems to yield compounds of the invention, original compounds. 'Uptake' is defined as any process that will lead to a substantial concentration of the compound inside cells or in mammals. After uptake in cells or mammals and after removal of said attached chemical group or hydrolysis of said cyclic compound, the compounds may have the same structure as the original compounds and thereby regain their activity and hence become active in cells and/or in vivo after uptake. A number of procedures, well known to those skilled in the art, may be used to verify that the attached chemical groups have been removed or that the cyclic compound has been hydrolyzed after uptake in cells or mammals. An example, which is not intended in any way to limit the scope of the invention, is given in the following. A mammalian cell line, which can be obtained from the American Tissue Type Collection or other similar governmental or commercial sources, is incubated with said modified compound. After incubation at conditions well known to those skilled in the art, the cells are washed appropriately, lysed and the lysate is isolated. Appropriate controls, well known to those skilled in the art, must be included. A number of different procedures, well known to those skilled in the art, may in turn be used to extract and purify said compound from said lysate. Said compound may or may not retain the attached chemical group or said cyclic compound may or may not have been hydrolyzed. Similarly, a number of different procedures—well known to those skilled in the art—may be used to characterize said purified compound structurally and chemically. Since said purified compound has been isolated from said cell lysate and hence has been taken up by said cell line, a comparison of said structurally and chemically characterized compound with that of the original unmodified compound (i.e. without said attached chemical group or said non-cyclic compound) will immediately provide to those skilled in the art information on whether the attached chemical group as been removed in the cell or whether the cyclic compound has been hydrolyzed. As a further analysis, said purified compound may be subjected to enzyme kinetic analysis as described in detail in the present invention. If the kinetic profile is similar to that of the original compound without said attached chemical group, but different from said modified compound, this confirms that said chemical group has been removed or said cyclic compounds has been hydrolyzed. Similar techniques may be used to analyze compounds of the invention in whole animals and mammals.

Preferred prodrug classes for the present compounds include acyloxymethyl esters or acyloxymethyl carbamates of the compounds of the present invention which may be prepared by the following general, procedure (C. Schultz et al, *J. Biol. Chem.*, 1993, 268, 6316–6322.) and (Alexander, J. et al, *J. Med. Chem.* 1991, 34, 78–81).

A carboxylic acid (1 equivalent) is suspended in dry acetonitrile (2 ml per 0.1 mmol). Diisopropyl amine (3.0 equivalents) is added followed by bromomethyl acetate (1.5 equivalents). The mixture is stirred under nitrogen overnight at room temperature. Acetonitrile is removed under reduced pressure to yield an oil which is diluted in ethyl acetate and washed with water (3×). The organic layer is dried over anhydrous magnesium sulfate. Filtration followed by solvent removal under reduced pressure affords a crude oil. The product is purified by column chromatography on silica gel, using an appropriate solvent system.

Definitions

As used herein, the term "attached" or "—"(e.g. —C(O)—$R_{13}$, which indicates the carbonyl attachment point to the scaffold) signifies a stable covalent bond, certain preferred points of attachment points being apparent to those skilled in the art.

The terms "halogen" or "halo" include fluorine, chlorine, bromine, and iodine.

The term "alkyl" includes $C_1$–$C_6$ straight chain saturated, methylene and $C_2$–$C_6$ unsaturated aliphatic hydrocarbon groups, $C_1$–$C_6$ branched saturated and $C_2$–$C_6$ unsaturated aliphatic hydrocarbon groups, $C_3$–$C_6$ cyclic saturated and $C_5$–$C_6$ unsaturated aliphatic hydrocarbon groups, and $C_1$–$C_6$ straight chain or branched saturated and $C_2$–$C_6$ straight chain or branched unsaturated aliphatic hydrocarbon groups substituted with $C_3$–$C_6$ cyclic saturated and unsaturated aliphatic hydrocarbon groups having the specified number of carbon atoms. For example, this definition shall include but is not limited to methyl (Me), ethyl (Et), propyl (Pr), butyl (Bu), pentyl, hexyl, heptyl, ethenyl, propenyl, butenyl, penentyl, hexenyl, isopropyl (i-Pr), isobutyl (i-Bu), tert-butyl (t-Bu), sec-butyl (s-Bu), isopentyl, neopentyl, cyclopropyl, cyclobutyl, cyclopentyl, cyclohexyl, cyclopentenyl, cyclohexenyl, methylcyclopropyl, ethylcyclohexenyl, butenylcyclopentyl, and the like. The alkyl group as defined above is optionally substituted wherein the substitutents are independently selected from halo, cyano, nitro, trihalomethyl, carbamoyl, hydroxy, oxo, $COOR_3$, $CONR_9R_{10}$, $C_1$–$C_6$alkyl, $C_1$–$C_6$alkyloxy, aryloxy, aryl$C_1$–$C_6$alkyloxy, thio, $C_1$–$C_6$alkylthio, arylthio, aryl$C_1$–$C_6$alkylthio, $NR_9R_{10}$, $C_1$–$C_6$alkylamino, arylamino, aryl$C_1$–$C_6$alkylamino, di(aryl$C_1$–$C_6$alkyl)amino, $C_1$–$C_6$alkylcarbonyl, aryl$C_1$–$C_6$alkylcarbonyl, $C_1$–$C_6$alkylcarboxy, arylcarboxy, aryl$C_1$–$C_6$alkylcarboxy, $C_1$–$C_6$alkylcarbonylamino, —$C_1$–$C_6$alkylamino$COR_{14}$, aryl$C_1$–$C_6$alkylcarbonylamino, tetrahydrofuranyl, morpholinyl, piperazinyl, —$CONR_9R_{10}$, —$C_1$–$C_6$-alkyl$CONR_9R_{10}$, or a saturated or partial saturated cyclic 5, 6 or 7 membered amine, imide or lactam; wherein $R_{14}$ is hydroxy, $C_1$–$C_6$alkyl, aryl, aryl$C_1$–$C_6$alkyl, $C_1$–$C_6$alkyloxy, aryloxy, aryl$C_1$–$C_6$alkyloxy and $R_3$ is defined as above or $NR_9R_{10}$, wherein $R_9$, $R_{10}$ are defined as above.

The term "saturated, partially saturated or aromatic cyclic, bicyclic or tricyclic ring system" represents but are not limit to aziridinyl, pyrrolyl, pyrrolinyl, pyrrolidinyl, imidazolyl, 2-imidazolinyl, imidazolidinyl, pyrazolyl, 2-pyrazolinyl, 1,2,3-triazolyl, 1,2,4-triazolyl, morpholinyl, piperidinyl, thiomorpholinyl, piperazinyl, indolyl, isoindolyl, 1,2,3,4-tetrahydro-quinolinyl, 1,2,3,4-tetrahydro-isoquinolinyl, 1,2,3,4-tetrahydro-quinoxalinyl, indolinyl, indazolyl, benzimidazolyl, benzotriazolyl, purinyl, carbazolyl, acridinyl, phenothiazinyl, phenoxazinyl, iminodibenzyl, iminostilbenyl.

The term "alkyloxy" (e.g. methoxy, ethoxy, propyloxy, allyloxy, cyclohexyloxy) represents an "alkyl" group as defined above having the indicated number of carbon atoms attached through an oxygen bridge. The term "alkyloxyalkyl" represents an "alkyloxy" group attached through an alkyl group as defined above having the indicated number of carbon atoms.

The term "alkyloxyalkyloxy" represents an "alkyloxyalkyl" group attached through an oxygen atom as defined above having the indicated number of carbon atoms.

The term "aryloxy" (e.g. phenoxy, naphthyloxy and the like) represents an aryl group as defined below attached through an oxygen bridge.

The term "arylalkyloxy" (e.g. phenethyloxy, naphthylmethyloxy and the like) represents an "arylalkyl" group as defined below attached through an oxygen bridge.

The term "arylalkyloxyalkyl" represents an "arylalkyloxy" group as defined above attached through an "alkyl" group defined above having the indicated number of carbon atoms.

The term "arylthio" (e.g. phenylthio, naphthylthio and the like) represents an "aryl" group as defined below attached through an sulfur bridge.

The term "alkyloxycarbonyl" (e.g. methylformiat, ethylformiat and the like) represents an "alkyloxy" group as defined above attached through a carbonyl group.

The term "aryloxycarbonyl" (e.g. phenylformiat, 2-thiazolylformiat and the like) represents an "aryloxy" group as defined above attached through a carbonyl group.

The term "arylalkyloxycarbonyl" (e.g. benzylformiat, phenyletylformiat and the like) represents an "arylalkyloxy" group as defined above attached through a carbonyl group.

The term "alkyloxycarbonylalkyl" represents an "alkyloxycarbonyl" group as defined above attached through an "alkyl" group as defined above having the indicated number of carbon atoms.

The term "arylalkyloxycarbonylalkyl" represents an "arylalkyloxycarbonyl" group as defined above attached through an "alkyl" group as defined above having the indicated number of carbon atoms.

The term "alkylthio" (e.g. methylthio, ethylthio, propylthio, cyclohexenylthio and the like) represents an "alkyl" group as defined above having the indicated number of carbon atoms attached through a sulfur bridge. The term "arylalkylthio" (e.g. phenylmethylthio, phenylethylthio, and the like) represents an "arylalkyl" group as defined above having the indicated number of carbon atoms attached through a sulfur bridge.

The term "alkylthioalkyl" represents an "alkylthio" group attached through an alkyl group as defined above having the indicated number of carbon atoms.

The term "arylalkylthioalkyl" represents an "arylalkylthio" group attached through an alkyl group as defined above having the indicated number of carbon atoms.

The term "alkylamino" (e.g. methylamino, diethylamino, butylamino, N-propyl-N-hexylamino, (2-cyclopentyl)propylamino, hexenylamino, pyrrolidinyl, piperidinyl and the like) represents one or two "alkyl" groups as defined above having the indicated number of carbon atoms attached through an amine bridge. The two alkyl groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above. The term "arylalkylamino" (e.g. benzylamino, diphenylethylamino and the like) represents one or two "arylalkyl" groups as defined above having the indicated number of carbon atoms attached through an amine bridge. The two "arylalkyl" groups may be taken together with the nitrogen to which they are attached forming a saturated, partially saturated or aromatic cyclic, bicyclic or tricyclic ring system containing 3 to 14 carbon atoms and 0 to 3 additional heteroatoms selected from nitrogen, oxygen or sulfur, the ring system can optionally be substituted with at least one $C_1$–$C_6$alkyl, aryl, aryl$C_1$–$C_6$alkyl, hydroxy, oxo, $C_1$–$C_6$alkyloxy, $C_1$–$C_6$alkyloxy$C_1$–$C_6$alkyl, $NR_9R_{10}$, $C_1$–$C_6$alkylamino$C_1$–$C_6$alkyl substituent wherein the alkyl and aryl groups are optionally substituted as defined in the definition section and $R_9$ and $R_{10}$ are defined as above.

The term "alkylaminoalkyl" represents an "alkylamino" group attached through an alkyl group as defined above having the indicated number of carbon atoms.

The term "arylalkylaminoalkyl" represents an "arylalkylamino" group attached through an alkyl group as defined above having the indicated number of carbon atoms.

The term "arylalkyl" (e.g. benzyl, phenylethyl) represents an "aryl" group as defined below attached through an alkyl having the indicated number of carbon atoms or substituted alkyl group as defined above.

The term "alkylcarbonyl" (e.g. cyclooctylcarbonyl, pentylcarbonyl, 3-hexenylcarbonyl) represents an "alkyl" group as defined above having the indicated number of carbon atoms attached through a carbonyl group.

The term "arylcarbonyl" (benzoyl) represents an "aryl" group as defined above attached through a carbonyl group.

The term "arylalkylcarbonyl" (e.g. phenylcyclopropylcarbonyl, phenylethylcarbonyl and the like) represents an "arylalkyl" group as defined above having the indicated number of carbon atoms attached through a carbonyl group.

The term "alkylcarbonylalkyl" represents an "alkylcarbonyl" group attached through an "alkyl" group as defined above having the indicated number of carbon atoms.

The term "arylalkylcarbonylalkyl" represents an "arylalkylcarbonyl" group attached through an alkyl group as defined above having the indicated number of carbon atoms.

The term "alkylcarboxy" (e.g. heptylcarboxy, cyclopropylcarboxy, 3-pentenylcarboxy) represents an "alkylcarbonyl" group as defined above wherein the carbonyl is in turn attached through an oxygen bridge.

The term "arylcarboxyalkyl" (e.g. phenylcarboxymethyl) represents an "arylcarbonyl" group defined above wherein the carbonyl is in turn attached through an oxygen bridge to an alkyl chain having the indicated number of carbon atoms.

The term "arylalkylcarboxy" (e.g. benzylcarboxy, phenylcyclopropylcarboxy and the like) represents an "arylalkylcarbonyl" group as defined above wherein the carbonyl is in turn attached through an oxygen bridge.

The term "alkylcarboxyalkyl" represents an "alkylcarboxy" group attached through an "alkyl" group as defined above having the indicated number of carbon atoms.

The term "arylalkylcarboxyalkyl" represents an "arylalkylcarboxy" group attached through an "alkyl" group as defined above having the indicated number of carbon atoms.

The term "alkylcarbonylamino" (e.g. hexylcarbonylamino, cyclopentylcarbonyl-aminomethyl, methylcarbonylaminophenyl) represents an "alkylcarbonyl" group as defined above wherein the carbonyl is in turn attached through the nitrogen atom of an amino group. The nitrogen atom may itself be substituted with an alkyl or aryl group.

The term "arylalkylcarbonylamino" (e.g. benzylcarbonylamino and the like) represents an "arylalkylcarbonyl" group as defined above wherein the carbonyl is in turn attached through the nitrogen atom of an amino group. The nitrogen atom may itself be substituted with an alkyl or aryl group.

The term "alkylcarbonylaminoalkyl" represents an "alkylcarbonylamino" group attached through an "alkyl" group as defined above having the indicated number of carbon atoms. The nitrogen atom may itself be substituted with an alkyl or aryl group.

The term "arylalkylcarbonylaminoalkyl" represents an "arylalkylcarbonylamino" group attached through an "alkyl" group as defined above having the indicated number of carbon atoms. The nitrogen atom may itself be substituted with an alkyl or aryl group.

The term "alkylcarbonylaminoalkylcarbonyl" represents an alkylcarbonylaminoalkyl group attached through a carbonyl group. The nitrogen atom may be further substituted with an "alkyl" or "aryl" group.

The term "aryl" represents a substituted or unsubstituted, mono-, di- or trisubstituted monocyclic, polycyclic, biaryl and heterocyclic aromatic groups covalently attached at any ring position capable of forming a stable covalent bond, certain preferred points of attachment being apparent to those skilled in the art (e.g., 3-indolyl, 4-imidazolyl). The aryl substituents are independently selected from the group consisting of halo, nitro, cyano, trihalo-methyl, $C_1$–$C_6$alkyl, aryl, aryl$C_1$–$C_6$alkyl, hydroxy, $COOR_3$, $CONR_9R_{10}$, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_9R_{10}$, $C_1$–$C_6$-alkylamino, $C_1$–$C_6$alkylamino$C_1$–$C_6$alkyl, arylamino, aryl$C_1$–$C_6$alkylamino, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, aryl$C_1$–$C_6$alkylcarbonyl, aryl$C_1$–$C_6$alkylcarbonyl$C_1$–$C_6$alkyl, $C_1$–$C_6$alkylcarboxy, $C_1$–$C_6$alkylcarboxy-$C_1$–$C_6$alkyl, aryl$C_1$–$C_6$alkylcarboxy, aryl$C_1$–$C_6$alkylcarboxy$C_1$–$C_6$alkyl, carboxy$C_1$–$C_6$alkyloxy, $C_1$–$C_6$alkylcarbonylamino, $C_1$–$C_6$alkylcarbonylamino$C_1$–$C_6$alkyl, -carbonyl$NR_7C_1$–$C_6$alkyl$COR_{14}$, aryl$C_1$–$C_6$alkylcarbonylamino, aryl$C_1$–$C_6$alkylcarbonylamino$C_1$–$C_6$alkyl, —$CONR_9R_{10}$, or —$C_1$–$C_6$alkyl$CONR_9R_{10}$; wherein $R_3$, $R_9$, $R_{10}$, and $R_{14}$ are defined as above and the alkyl and aryl groups contained therein are optionally substituted as defined above. The definition of aryl includes but is not limited to phenyl, biphenyl, indenyl, fluorenyl, naphthyl(1-naphthyl, 2-naphthyl), pyrrolyl(2-pyrrolyl), pyrazolyl(3-pyrazolyl), imidazolyl(1-imidazolyl, 2-imidazolyl, 4-imidazolyl, 5-imidazolyl), triazolyl(1,2,3-triazol-1-yl, 1,2,3-triazol-2-yl, 1,2,3-triazol-4-yl, 1,2,4-triazol-3-yl), oxazolyl(2-oxazolyl, 4-oxazolyl, 5-oxazolyl), isoxazolyl(3-isoxazolyl, 4-isoxazolyl, 5-isoxazolyl), thiazolyl(2-thiazolyl, 4-thiazolyl, 5-thiazolyl), thiophenyl(2-thiophenyl, 3-thiophenyl, 4-thiophenyl, 5-thiophenyl), furanyl(2-furanyl, 3-furanyl, 4-furanyl, 5-furanyl), pyridyl(2-pyridyl, 3-pyridyl, 4-pyridyl, 5-pyridyl), 5-tetrazolyl, pyrimidinyl(2-pyrimidinyl, 4-pyrimidinyl, 5-pyrimidinyl, 6-pyrimidinyl), pyrazinyl, pyridazinyl(3-pyridazinyl, 4-pyridazinyl, 5-pyridazinyl), quinolyl (2-quinolyl, 3-quinolyl, 4-quinolyl, 5-quinolyl, 6-quinolyl, 7-quinolyl, 8-quinolyl), isoquinolyl(1-isoquinolyl, 3-isoquinolyl, 4-isoquinolyl, 5-isoquinolyl, 6-isoquinolyl, 7-isoquinolyl, 8-isoquinolyl), benzo[b]furanyl(2-benzo[b]furanyl, 3-benzo[b]furanyl, 4-benzo[b]furanyl, 5-benzo[b]furanyl, 6-benzo[b]furanyl, 7-benzo[b]furanyl), 2,3-dihydro-benzo[b]furanyl(2-(2,3-dihydro-benzo[b]furanyl), 3-(2,3-dihydro-benzo[b]furanyl), 4-(2,3-dihydro-benzo[b]furanyl), 5-(2,3-dihydro-benzo-[b]furanyl), 6-(2,3-dihydro-benzo-[b]furanyl), 7-(2,3-dihydro-benzo[b]furanyl)), benzo[b]thiophenyl (2-benzo[b]thiophenyl, 3-benzo[b]thiophenyl, 4-benzo[b]thiophenyl, 5-benzo[b]thiophenyl, 6-benzo[b]thiophenyl, 7-benzo[b]thiophenyl), 2,3-dihydro-benzo[b]-thiophenyl(2-(2,3-dihydro-benzo[b]thiophenyl), 3-(2,3-dihydro-benzo[b]-thiophenyl), 4-(2,3-dihydro-benzo[b]thiophenyl), 5-(2,3-dihydro-benzo[b]-thiophenyl), 6-(2,3-dihydro-benzo[b]thiophenyl), 7-(2,3- dihydro-benzo[b]-thiophenyl)), 4,5,6,7-tetrahydro-benzo[b]thiophenyl (2-(4,5,6,7-tetrahydro-benzo-[b]thiophenyl), 3-(4,5,6,7-tetrahydro-benzo-[b]thiophenyl), 4-(4,5,6,7-tetrahydro-benzo[b]thiophenyl), 5-(4,5,6,7-tetrahydro-benzo-[b]thiophenyl), 6-(4,5,6,7-tetrahydro-benzo-[b]thiophenyl), 7-(4,5,6,7-tetrahydro-benzo[b]thiophenyl)), 4,5,6,7-tetrahydro-thieno[2,3-c]pyridyl(4-(4,5,6,7-tetrahydro-thieno[2,3-c pyridyl), 5-4,5,6,7-tetrahydro-thieno[2,3-c]pyridyl), 6-(4,5,6,7-tetrahydro-thieno[2,3-c]pyridyl), 7-(4,5,6,7-tetrahydro-thieno[2,3-c]pyridyl)), indolyl(1-indolyl, 2-indolyl, 3-indolyl, 4-indolyl, 5-indolyl, 6-indolyl, 7-indolyl), isoindolyl (1-isoindolyl, 2-isoindolyl, 3-isoindolyl, 4-isoindolyl, 5-isoindolyl, 6-isoindolyl, 7-isoindolyl), 1,3-dihydro-isoindolyl(1-(1,3-dihydro-isoindolyl), 2-(1,3-dihydro-isoindolyl), 3-(1,3-dihydro-isoindolyl), 4-(1,3-dihydro-isoindolyl), 5-(1,3-dihydro-isoindolyl), 6-(1,3-dihydro-isoindolyl), 7-(1,3-dihydro-isoindolyl)), indazole (1-indazolyl, 3-indazolyl, 4-indazolyl, 5-indazolyl, 6-indazolyl, 7-indazolyl), benzimidazolyl(1-benzimidazolyl, 2-benzimidazolyl, 4-benzimidazolyl, 5-benzimidazolyl, 6-benzimidazolyl, 7-benzimidazolyl, 8-benzimidazolyl), benzoxazolyl(1-benzoxazolyl, 2-benzoxazolyl), benzothiazolyl(1-benzothiazolyl, 2-benzo-thiazolyl, 4-benzothiazolyl, 5-benzothiazolyl, 6-benzothiazolyl, 7-benzothiazolyl), carbazolyl(1-carbazolyl, 2-carbazolyl, 3-carbazolyl, 4-carbazolyl), 5H-dibenz[b,f]azepine (5H-dibenz[b,f]azepin-1-yl, 5H-dibenz-[b,f]azepine-2-yl, 5H-dibenz[b,f]azepine-3-yl, 5H-dibenz-[b,f]azepine-4-yl, 5H-dibenz[b,f]-azepine-5-yl), 10,11-dihydro-5H-dibenz[b,f]azepine (10,11-dihydro-5H-dibenz[b,f]azepine-1-yl, 10,11-dihydro-5H-dibenz[b,f]azepine-2-yl, 10,11-dihydro-5H-dibenz[b,f]azepine-3-yl, 10,11-dihydro-5H-dibenz-[b,f]azepine-4-yl, 10,11-dihydro-5H-dibenz[b,f]azepine-5-yl), piperidinyl(2-piperidinyl, 3-piperidinyl, 4-piperidinyl), pyrrolidinyl(1-pyrrolidinyl, 2-pyrrolidinyl, 3-pyrrolidinyl), phenylpyridyl(2-phenyl-pyridyl, 3-phenyl-pyridyl, 4-phenylpyridyl), phenylpyrimidinyl(2-phenylpyrimidinyl, 4-phenylpyrimidinyl, 5-phenylpyrimidinyl, 6-phenylpyrimidinyl), phenylpyrazinyl, phenylpyridazinyl(3-phenylpyridazinyl, 4-phenylpyridazinyl, 5-phenylpyridazinyl).

The term "arylcarbonyl" (e.g. 2-thiophenylcarbonyl, 3-methoxy-anthrylcarbonyl, oxazolylcarbonyl) represents an "aryl" group as defined above attached through a carbonyl group.

The term "arylalkylcarbonyl" (e.g. (2,3-dimethoxyphenyl)propylcarbonyl, (2-chloronaphthyl)pentenylcarbonyl, imidazolylcyclopentylcarbonyl) represents an "arylalkyl" group as defined above wherein the "alkyl" group is in turn attached through a carbonyl.

The term "aryloxyalkyl" represents an "aryloxy" group as defined above attached through an "alkyl" group defined above having the indicated number of carbon atoms.

The term "arylaminocarbonylaminoalkyl" represents an "arylaminocarbonylamino" group as defined above attached through an "alkyl" group as defined above having the indicated number of carbon atoms.

The term "R8R9Nalkyl" is as defined under "substituted alkyl" or "optionally substituted alkyl".

The term "arylaminoalkyl" represents an "arylamino" group attached through an alkyl group as defined above having the indicated number of carbon atoms.

The term "arylcarbonylaminoalkyl" represents an "arylcarbonylamino" group attached through an alkyl group as defined above having the indicated number of carbon atoms.

As used herein, the term "vicinity" applied with respect to the active site of a PTPase means the space occupied by a half sphere—with its apex pointing towards aspartic acid 48—having its center in the side chain nitrogen atom of the guanidinium group of residue 221 (arginine), which points away from the phosphate binding loop (residue Arg221 to Cys215). The radius of the half sphere is 27 Å.

As used herein, the term "structurally similar" means any PTPase that contains an aspartic acid in residue position 48 (PTP1B numbering—as defined in Chernoff et al, 1989, supra) and is more than 50% identical and preferably more than 65% identical and most preferably more than 80% identical to PTP1B (Chernoff et al., supra) and/or TC-PTP (Cool et al., Proc. Natl. Acad. Sci. U.S.A. 86: 5257–5261 (1989)) at the primary amino acid sequence level in the catalytic domain as defined below. Percent indentity can be determined using standard algorithms e.g. BLAST, BLASTP MEGALIGN, etc using default parameters.

As used herein, the term "catalytic domain" means the primary amino acid sequence of a PTPase that corresponds to the primary amino acid sequence between Asn 40 and Gln 262 (both residues included) in PTP1B (Chernoff et al., supra).

As used herein, the term "centroid" means the position for the stated atoms calculated by averaging the x coordinates of the atoms to obtain the x coordinate of the centroid, averaging the y coordinates of the atoms to obtain the y coordinate of the centroid, and averaging the z coordinates of the atoms to obtain the z coordinate of the centroid.

As used herein, the term "phosphate isostere" means a chemical group, which binds to one or more of the side chains or the main chain of the residues in the so-called P-loop or PTP signature motif of PTPases (i.e. Cys215-Xxx216-Xxx217-Xxx218-Xxx219-Xxx220-Arg221 (SEQ ID NO: 1), where Cys215 and Arg221 are absolutely conserved, whereas Xxx stands for less conserved residues). In PTP1B the P-loop residues are: Cys215-Ser216-Ala217-Gly218-Ile219-Gly220-Arg221 (SEQ ID NO: 2). As a non limiting example the following groups are phosphate isosteres: —CH$_2$PO(OH)$_2$, —CHFPO(OH)$_2$, —CF$_2$PO(OH)$_2$, —NHCOCOOH, —OCH(COOH)$_2$, —OCF(COOH)$_2$, —OCH$_2$COOH, —CONHCH$_2$COOH, —CONHCHFCOOH and —CONHCF$_2$COOH.

As used herein, the term "carboxylic acid isostere" means a compound resembling a carboxy group in its electronic and steric configuration and in its biological action (effecting inhibition of the class of structurally similar PTPases) but having a different chemical structure. As a non limiting example, the following residues and heterocycles are carboxylic acid isosteres: —CONH$_2$, —SONH$_2$, —SO$_2$NH$_2$,

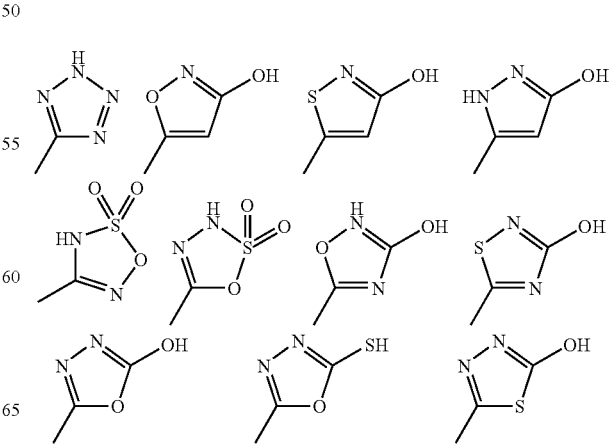

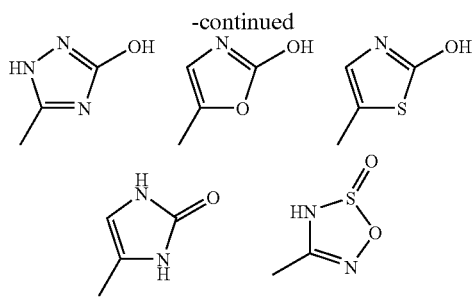

As used herein the term "interact" or "interaction" when used in the context of a moiety or group of an inhibitor interacting with the active site or vicinity thereof of a PTPase, means the formation of noncovalent bonds, such as hydrogen bonds, salt bridges, hydrophobic interactions van der Waals forces, cation π interactions, or π, π interactions, aromatic—aromatic interactions, (Copeland, Enzymes—a practical introduction to structure, mechanism, and data analysis, VCH Publishers, Inc., New York (1996)) or by forming covalent bonds. Preferably, interactions between inhibitors of the invention and PTPs occur through non-covalent bonds.

As used herein, the term "hydrophobic" means a nonpolar chemical group (e.g. phenyl, naphthyl, cyclopropyl, cyclobutyl, cyclohexyl, tert-butyl, isopropyl as nonlimiting examples) when present in the aqueous phase, in the vicinity of an enzyme, its hydrocarbon framework disturbs the degree of randomness of the water molecules, which forces the water molecules to associate by hydrogen bonding to form quasi-crystalline clusters or "ice-bergs". This localized increase in the ordered structure of water will result in a loss of entropy, accompanied by an increase in the free energy of the system. Thus, a driving force operates to reject the hydrocarbon region of the drug/inhibitor from the aqueous phase so that binding to one or more similar hydrocarbon chain(s) within the enzyme molecule is facilitated.

As used herein, the term "hydrogen bond" means an association between an electronegative atom, e.g. fluorine, oxygen, nitrogen, or sulfur, and a hydrogen atom attached to another such electronegative atom.

As used herein, the term "salt bridge" means any electrostatic bond between positively and negatively charged groups.

The compounds of the present invention have asymmetric centers and may occur as racemates, racemic mixtures, and as individual enantiomers or diastereoisomers, with all isomeric forms being included in the present invention as well as mixtures thereof.

Pharmaceutically acceptable salts of the compounds of formula 1, where a basic or acidic group is present in the structure, are also included within the scope of this invention. When an acidic substituent is present, such as —COOH, 5-tetrazolyl or —P(O)(OH)$_2$, there can be formed the ammonium, morpholinium, sodium, potassium, barium, calcium salt, and the like, for use as the dosage form. When a basic group is present, such as amino or a basic heteroaryl radical, such as pyridyl, an acidic salt, such as hydrochloride, hydrobromide, phosphate, sulfate, trifluoroacetate, trichloroacetate, acetate, oxalate, maleate, pyruvate, malonate, succinate, citrate, tartarate, fumarate, mandelate, benzoate, cinnamate, methanesulfonate, ethane sulfonate, picrate and the like, and include acids related to the pharmaceutically acceptable salts listed in Journal of Pharmaceutical Science, 66, 2 (1977) and incorporated herein by reference, can be used as the dosage form.

Also, in the case of the —COOH or —P(O)(OH)$_2$ being present, pharmaceutically acceptable esters can be employed, e.g., methyl, tert-butyl, acetoxymethyl, pivaloyloxymethyl, and the like, and those esters known in the art for modifying solubility or hydrolysis characteristics for use as sustained release or prodrug formulations.

In addition, some of the compounds of the instant invention may form solvates with water or common organic solvents. Such solvates are encompassed within the scope of the invention.

As used herein, "treatment" shall include therapeutic or preventative management, treatment, cure, or palliation of a disease state or a measurable delay in its onset or recurrence or measurable reduction in its severity.

The term "therapeutically effective amount" shall mean that amount of drug or pharmaceutical agent that will elicit the biological or medical response of a tissue, system, animal, or human that is being sought by a researcher, veterinarian, medical doctor or other other biological or clinical investigator. Also included in the present invention is a process for isolation of PTPases via affinity purification procedures based on the use of immobilized compounds of the invention. Isolation can be effected using procedures otherwise well-known to those skilled in the art. Such methods, may be used to identify novel PTPases or other molecules with phosphotyrosine recognition units and to elucidate the function of both novel and previously identified PTPases. As a non-limiting example, compounds of the invention may be immobilized by coupling to a solid-phase support, such as as exemplified in examples 119 and 120. See also Example 121. A tissue sample or a sample from a cell line prepared as a lysate by methods well-known to those skilled in the art may be passed over said solid-phase coupled with a compound of the invention. After appropriate washing procedures designed to remove material that binds nonspecifically to said solid-phase, using standard procedures well known to those skilled in the art, mostly PTPases or other molecules with phosphotyrosine recognition units will be bound to the compounds of the invention coupled to the solid phase. Said PTPases or other molecules with phosphotyrosine recognition units may in turn be released by procedures well-known in the art and further subjected to amino acid sequence analysis according to standard procedures well-known to those skilled in the art. By back-translation of said amino acid sequence into a nucleotide sequence of the corresponding cDNA can be deduced using the appropriate genetic code. Said nucleotide sequence can be used to design and produce an equivalent oligonucleotide, which in turn can be used to identify partial or full-length cDNA clones from appropriate cDNA libraries encoding a protein or glycoprotein corresponding to or similar to the isolated PTPase or molecule with pTyr recognition units. Said oligonucleotide or isolated cDNA clone(s) can similarly be used to isolate genomic clones corresponding to said cDNA clones. Said partial or full-length cDNA can be inserted into appropriate vectors and expressed and purified proteins with procedures well known to those skilled in the art. Said purified proteins, in particular PTPases, may be used to further analyze the inhibitory capacity and selectivity of compounds of the invention as described.

The invention is further directed to compounds of the invention coupled to a suitable solid-phase matrix such as a Wang-resin or a Rink-resin, e.g., for further synthesis, combinational synthesis, or as a support for affinity purification.

The invention is further directed to a method for isolating a protein or a glycoprotein with affinity for a compound according to the invention from a biological sample, comprising:
contacting a compound of the invention immobilized by coupling to a suitable solid-phase matrix with said biological sample in order for said immobilized compound to form a complex by binding said protein or glycoprotein,
removing unbound material from said biological sample and isolating said complex, and
extracting said protein or glycoprotein from said complex.

The invention is further directed to a method for isolating a protein-tyrosine phosphatase with affinity for a compound according to the invention from a biological sample, comprising
contacting a compound of the invention immobilized by coupling to a suitable solid-phase matrix with said biological sample in order for said immobilized compound to form a complex by binding said protein-tyrosine phosphatase
removing unbound material from said biological sample and isolating said complex
extracting said protein-tyrosine phosphatase.

The following compounds are encompassed by the invention:
5-(4-Chloro-1,3-dioxo-1,3-dihydro-isoindol-2-ylmethyl)-2-(oxalylamino)-4,7-dihydro-5H-thieno[2,3-c]pyran-3-carboxylic acid;
7-(2,4-Dioxo-thiazolidin-3-ylmethyl)-2-(oxalyl-amino)-4,7-dihydro-5H-thieno[2,3-c]pyran-3-carboxylic acid;
5-(4,5,6,7-Tetrachloro-1,3-dioxo-1,3-dihydro-isoindol-2-ylmethyl)-2-(oxalyl-amino)-4,7-dihydro-5H-thieno[2,3-c]pyran-3-carboxylic acid;
5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;
5-(1,3-Dioxo-1,3-dihydro-benzo[f]isoindol-2-ylmethyl)-2-(oxalyl-amino)-4,7-dihydro-5H-thieno[2,3-c]pyran-3-carboxylic acid;
Oxalic acid (3-carboxy-2-(oxalyl-amino)-4,7-dihydro-5H-thieno[2,3-c]pyran-5-ylmethyl)ester methyl ester;
Oxalic acid (3-carboxy-2-(oxalyl-amino)-4,7-dihydro-5H-thieno[2,3-c]pyran-5-ylmethyl)ester;
7-Hydroxymethyl-2-(oxalyl-amino)-4,7-dihydro-5H-thieno[2,3-c]pyran-3-carboxylic acid;
7-(((Benzo[1,3]dioxole-5-carbonyl)-amino)-methyl)-2-(oxalyl-amino)-4,7-dihydro-5H-thieno[2,3-c]pyran-3-carboxylic acid;
5-(3-Imidazol-1-yl-2,5-dioxo-pyrrolidin-1-ylmethyl)-2-(oxalyl-amino)-4,7-dihydro-5H-thieno[2,3-c]pyran-3-carboxylic acid;
2-(Oxalyl-amino)-5-phenylcarbamoyl-4,7-dihydro-5H-thieno[2,3-c]pyran-3-carboxylic acid;
2-(Oxalyl-amino)-5-phenylcarbamoyl-4,7-dihydro-5H-thieno[2,3-c]pyran-3-carboxylic acid;
2-(Oxalyl-amino)-4,7-dihydro-5H-thieno[2,3-c]pyran-3,7-dicarboxylic acid 7-ethyl ester;
7-Benzylcarbamoyl-2-(oxalyl-amino)-4,7-dihydro-5H-thieno[2,3-c]pyran-3-carboxylic acid;
5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid;
5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;
7-(1,3-Dioxo-1,3-dihydro-isoindol-2-yloxymethyl)-2-(oxalyl-amino)-4,7-dihydro-5H-thieno[2,3-c]pyran-3-carboxylic acid;
5-(5,7-Dioxo-5,7-dihydro-pyrrolo[3,4-b]pyridin-6-yl methyl)-2-(oxalyl-amino)-4,7-dihydro-5H-thieno[2,3-c]pyran-3-carboxylic acid;
7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;
7-(3-(2,4-Dimethoxy-phenyl)-ureidomethyl)-2-(oxalyl-amino)-4,7-dihydro-5H-thieno[2,3-c]pyran-3-carboxylic acid;
2-((3-Carboxy-2-(oxalyl-amino)-4,7-dihydro-5H-thieno[2,3-c]pyran-5-ylmethyl)-carbamoyl)-nicotinic acid;
5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;
5-(4-Benzyloxy-1,3-dioxo-1,3-dihydro-isoindol-2-ylmethyl)-2-(oxalyl-amino)-4,7-dihydro-5H-thieno[2,3-c]pyran-3-carboxylic acid;
7-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;
7-(5,7-Dioxo-5,7-dihydro-[1,3]dioxolo[4,5-f]isoindol-6-yl methyl2-(oxalyl-amino)-4,7-dihydro-5H-thieno[2,3-c]pyran-3-carboxylic acid;
7-(2,4-Dioxo-5-pyridin-2-ylmethylene-thiazolidin-3-ylmethyl)-2-(oxalyl-amino)-4,7-dihydro-5H-thieno[2,3-c]pyran-3-carboxylic acid;
7-(2,4-Dioxo-5-pyridin-2-ylmethyl-thiazolidin-3-ylmethyl)-2-(oxalyl-amino)-4,7-dihydro-5H-thieno[2,3-c]pyran-3-carboxylic acid;
7-(5-(4-Methoxy-benzylidene)-2,4-dioxo-thiazolidin-3-ylmethyl)-2-(oxalyl-amino)-4,7-dihydro-5H-thieno[2,3-c]pyran-3-carboxylic acid;
7-(5-(4-Acetylamino-benzylidene)-2,4-dioxo-thiazolidin-3-ylmethyl)-2-(oxalyl-amino)-4,7-dihydro-5H-thieno[2,3-c]pyran-3-carboxylic acid;
7-(5-(3,5-Dimethoxy-benzylidene)-2,4-dioxo-thiazolidin-3-ylmethyl)-2-(oxalyl-amino)-4,7-dihydro-5H-thieno[2,3-c]pyran-3-carboxylic acid;
7-(5-(1H-Imidazol-4(5)-ylmethylene)-2,4-dioxo-thiazolidin-3-ylmethyl)-2-(oxalyl-amino)-4,7-dihydro-5H-thieno[2,3-c]pyran-3-carboxylic acid;
7-((2-(4-Methanesulfonyl-phenyl)-acetylamino)-methyl)-2-(oxalyl-amino)-4,7-dihydro-5H-thieno[2,3-c]pyran-3-carboxylic acid;
5-(1,3-Dioxo-4,7-epoxido-1,3,4,5,6,7-hexahydro-isoindol-2-ylmethyl)-2-(oxalyl-amino)-4,7-dihydro-5H-thieno[2,3-c]pyran-3-carboxylic acid;
7-((2-Amino-3-phenyl-propionylamino)methyl)-2-(oxalyl-amino)-4,7-dihydro-5H-thieno[2,3-c]pyran-3-carboxylic acid;
7-(((2R)-2-Amino-3-phenyl-propionylamino)-methyl)-2-(oxalyl-amino)-4,7-dihydro-5H-thieno[2,3-c]pyran-3-carboxylic acid;
7-((2-Acetylamino-3-(4-hydroxy-phenyl)-propionylamino)-methyl)-2-(oxalyl-amino)-4,7-dihydro-5H-thieno[2,3-c]pyran-3-carboxylic acid;

7-((2-Acetylamino-3-methyl-butyrylamino)methyl)-2-(oxalyl-amino)-4,7-dihydro-5H-thieno[2,3-c]pyran-3-carboxylic acid;

5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-c]pyridin-6-ylmethyl)-2-(oxalyl-amino)-4,7-dihydro-5H-thieno[2,3-c]pyran-3-carboxylic acid;

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyran 3-carboxylic acid;

2-(Oxalyl-amino)-7-(3-oxo-3H-benzo[d]isoxazol-2-ylmethyl)-4,7-dihydro-5H-thieno[2,3-c]pyran-3-carboxylic acid;

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

(L)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1-oxo-1,3-dihydro-isoindol-2-ylmethyl)-4,5,6,7-tetrahydro-thieno[2,3-c]pyridine-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

7-(((Benzo[1,3]dioxole-5-carbonyl)amino)methyl)-2-(oxalyl-amino)-4,7-dihydro-5H-thieno[2,3-c]pyran-3-carboxylic acid;

5-(4-(4-Chloro-phenylsulfanyl)-6-methyl-1,3-dioxo-1,3-dihydro-pyrrolo[3,4-c]pyridin-2-yl methyl)-2-(oxalyl-amino)-4,7-dihyro-5H-thieno[2,3-c]pyran-3-carboxylic acid;

7-(3-(2,4-Dimethoxy-phenyl)-ureidomethyl)-2-(oxalyl-amino)-4,7-dihydro-5H-thieno[2,3-c]pyran-3-carboxylic acid;

7-((2-(4-Methanesulfonyl-phenyl)acetylamino)methyl)-2-(oxalyl-amino)-4,7-dihydro-5H-thieno[2,3-c]pyran-3-carboxylic acid;

7-((2-Acetylamino-3-(4-hydroxy-phenyl)propionylamino)methyl)-2-(oxalyl-amino)-4,7-dihydro-5H-thieno[2,3-c]pyran-3-carboxylic acid;

5-(S)-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(S)-(1-oxo-1,3-dihydro-isoindol-2-ylmethyl)-4,5,6,7-tetrahydro-thieno[2,3-c]pyridine-3-carboxylic acid;

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

7-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-5-((2-(5-methoxy-2-methyl-1H-indol-3-yl)-acetylamino)methyl)-2-(oxalyl-amino)-4,5,6,7-tetrahydro-thieno[2,3-c]pyridine-3-carboxylic acid;

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

2-(S)-(Oxalyl-amino)-5-((4-phenoxy-benzylamino)methyl)-4,5,6,7-tetrahydro-thieno[2,3-c]pyridine-3-carboxylic acid;

5-(S)-((4-Acetylamino-benzylamino)methyl)-2-(oxalyl-amino)-4,5,6,7-tetrahydro-thieno[2,3-c]pyridine-3-carboxylic acid;

7-(S)-((Acetyl-(4-phenoxy-benzyl)amino)methyl)-2-(oxalyl-amino)-4,5,6,7-tetrahydro-thieno[2,3-c]pyridine-3-carboxylic acid;

7-(S)-((Acetyl-benzyl-amino)methyl)-2-(oxalyl-amino)-4,5,6,7-tetrahydro-thieno[2,3-c]pyridine-3-carboxylic acid;

5-(S)-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;

7-(R)-Carbamoyl-2-(oxalyl-amino)-4,5,6,7-tetrahydro-thieno[2,3-c]pyridine-3-carboxylic acid;

2-(Oxalyl-amino)-5-(S)-(2-oxo-tetrahydro-thiophen-3-yl-carbamoyl)-4,5,6,7-tetrahydro-thieno[2,3-c]pyridine-3-carboxylic acid;

2-(Oxalyl-amino)-5-(S)-phenylcarbamoyl-4,5,6,7-tetrahydro-thieno[2,3-c]pyridine-3-carboxylic acid;

2-(Oxalyl-amino)-7-(R)-phenylcarbamoyl-4,5,6,7-tetrahydro-thieno[2,3-c]pyridine-3-carboxylic acid;

5-(R),7-(R)-Bis-benzyloxymethyl-2-(oxalyl-amino)-4,5,6,7-tetrahydro-thieno[2,3-c]pyridine-3-carboxylic acid;

6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid; or a pharmaceutically acceptable salt thereof

PHARMACOLOGICAL METHODS

The compounds are evaluated for biological activity with a truncated form of PTP1B (corresponding to the first 321 amino acids), which was expressed in *E. coli* and purified to apparent homogeneity using published procedures well-known to those skilled in the art. The enzyme reactions are carried out using standard conditions essentially as described by Burke et al. (*Biochemistry* 35; 15989–15996 (1996)) incorporated by reference. The assay conditions are as follows. Appropriate concentrations of the compounds of the invention (e.g., 0.1 to 100 μM) are added to the reaction mixtures containing different concentrations of the substrate, p-nitrophenyl phosphate (range: 0.16 to 10 mM—final assay concentration). The buffer used was 50 mM HEPES pH 7.0, 100 mM sodium chloride, 0.1% (w/v) bovine serum albumin, 5 mM glutathione, and 1 mM EDTA. The reaction was started by addition of the enzyme and carried out in microtiter plates at 25° C. for 60 minutes. The reactions are stopped by addition of NaOH. The enzyme activity was determined by measurement of the absorbance at 405 nm with appropriate corrections for absorbance at 405 nm of the compounds and p-nitrophenyl phosphate. The data are analyzed using nonlinear regression fit to classical Michaelis Menten enzyme kinetic models. Inhibition is expressed as $K_i$ values in μM. The results of representative experiments are shown in Table 6.

TABLE 6

Inhibition of classical PTPases by compounds of the invention

| | $K_i$ (μM) at pH 7 | | | | |
|---|---|---|---|---|---|
| Example No. | PTP1B residue 48 Asp | TC-PTP residue 48 Asp | PTP α residue 48 Asn | PTP β residue 48 Asn | PTP ε residue 48 Asn |
| 48 | 0.25 | | 900 | 47 | 380 |
| 49 | 0.085 | | | 8.6 | |
| 50 | 0.07 | | 1000 | 8 | |
| 52 | 1.2 | | >400 | 107 | >500 |

The Synthesis of the Compounds

In accordance with one aspect of the invention, compounds of the invention are prepared as illustrated in the following reaction schemes wherein n, m, X, Y, $R_1$, $R_2$, $R_3$, $R_4$, $R_5$ and $R_6$ are defined as above:

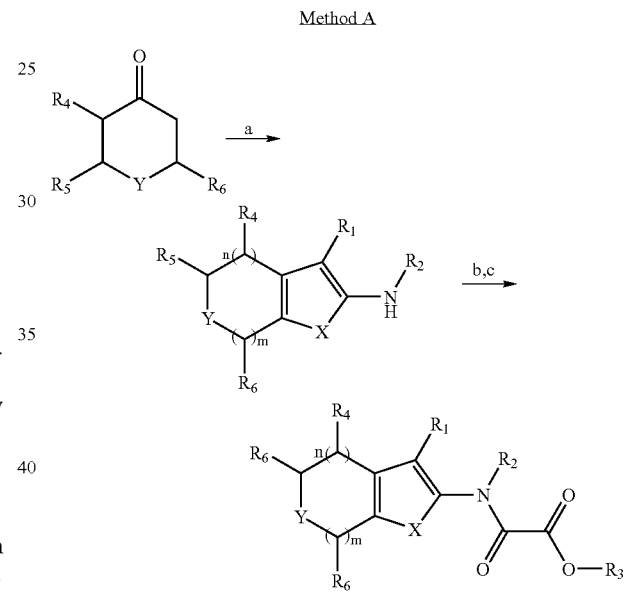

a) NCCH$_2$COOR$_3$, sulphur, morpholine or triethylamine, ethanol; b) R$_3$OCOCOimidazole, tetrahydrofuran; c) 25% trifluoroacetic acid/dichloromethane.

Method B

The pharmaceutical carrier employed may be a conventional solid or liquid carrier. Examples of solid carriers are lactose, terra alba, sucrose, talc, gelatine, agar, pectin, acacia, magnesium stearate and stearic acid. Examples of liquid carriers are syrup, peanut oil, olive oil, water, and physiologic saline.

Similarly, the carrier or diluent may include any material that impacts controlled release of taste-masking properties, known to the art, such as glyceryl monostearate or glyceryl distearate, alone or mixed with a wax.

If a solid carrier for oral administration is used, the preparation can be tabletted, placed in a hard gelatine capsule in powder or pellet form or it can be in the form of a troche or lozenge. The amount of solid carrier will vary widely but will usually be from about 25 mg to about 1 g. If a liquid carrier is used, the preparation may be in the form of a syrup, emulsion, soft gelatin capsule or sterile injectable liquid such as an aqueous or non-aqueous liquid suspension or solution.

Generally, the compounds of this invention are dispensed in unit dosage form comprising 10–200 mg of active ingredient in or together with a pharmaceutically acceptable carrier per unit dosage.

The dosage of the compounds according to this invention is 1–500 mg/day, e.g. about 100 mg per dose, when administered to patients, e.g. humans, as a drug.

A typical tablet that may be prepared by conventional tabletting techniques contains

| Core: | |
|---|---|
| Active compound (as free compound or salt thereof) | 100 mg |
| Colloidal silicon dioxide (Areosil ®) | 1.5 mg |
| Cellulose, microcryst. (Avicel ®) | 70 mg |
| Modified cellulose gum (Ac-Di-Sol ®) | 7.5 mg |
| Magnesium stearate | |

| Coating: | | |
|---|---|---|
| HPMC | approx. | 9 mg |
| *Mywacett ® 9-40 T | approx. | 0.9 mg |

*Acylated monoglyceride used as plasticiser for film coating.

The route of administration may be any route which effectively transports the active compound to the appropriate or desired site of action, such as oral or parenteral e.g. rectal, transdermal, subcutaneous, intranasal, intramuscular, topical, intravenous, intraurethral, ophthalmic solution or an ointment, the oral route being preferred.

EXAMPLES

The process for preparing compounds of Formula 1 and preparations containing them is further illustrated in the following examples, which, however, are not to be construed as limiting.

Hereinafter, TLC is thin layer chromatography, $CDCl_3$ is deuterio chloroform, $CD_3OD$ is tetradeuterio methanol and $DMSO-d_6$ is hexadeuterio dimethylsulfoxide. The structures of the compounds are confirmed by either elemental analysis or NMR, where peaks assigned to characteristic protons in the title compounds are presented where appropriate. $^1$H NMR shifts ($\delta_H$) are given in parts per million (ppm) down field from tetramethylsilane as internal reference standard. M.p.: is melting point and is given in ° C. and is not corrected. Column chromatography was carried out using the technique described by W. C. Still et al., *J. Org. Chem.* 43: 2923 (1978) on Merck silica gel 60 (Art. 9385). HPLC analyses are performed using 5 μm C18 4×250 mm column eluted with various mixtures of water and acetonitrile, flow=1 ml/min, as described in the experimental section.

Wang-resin is polystyrene with a 4-hydroxymethylphenol ether linker. Compounds used as starting material are either known compounds or compounds which can readily be prepared by methods known per se.

Example 1

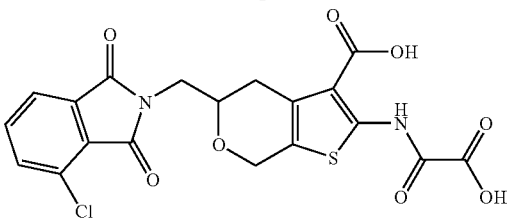

5-(4-Chloro-1,3-dioxo-1,3-dihydro-isoindol-2-ylmethyl)-2-(oxalyl-amino)-4,7-dihydro-5H-thieno[2,3-c]pyran-3-carboxylic acid To a mixture of benzyloxyacetaldehyde (8.3 g, 0.06 mol) in benzene (80 mL) was added 1-methoxy-3-trimethylsilyloxy-1,3-butadiene (10.6 g, 0.06 mol). The reaction mixture was stirred under nitrogen for 15 min., cooled to 0° C. and a solution of 0.5 M zinc chloride (55 ml, 0.03 mol) was added dropwise. The reaction mixture was allowed to warm to room temperature over 16 h and evaporated in vacuo. The resultant oil was diluted with ethyl acetate (100 ml), washed with 1N hydrochloric acid (3×50 ml), saturated sodium bicarbonate (3×50 ml), brine (3×50 ml), dried ($MgSO_4$) and evaporated in vacuo. The resulting oil was subjected to flash chromatography using a mixture of ethyl acetate/hexanes (1:2) as eluant. Pure fractions were collected affording after evaporation in vacuo 7.1 g (60%) of benzyloxy-methyl-2,3-dihydro-pyran-4-one as an oil.

$^1$H NMR (400 MHz, $CDCl_3$) δ 7.39–7.31 (m, 6H), 5.42 (dd, J=6, 1 Hz, <1H), 4.61 (d, J=3 Hz, 1H), 4.57 (m, 1H), 3.70 (m, 2H), 2.74 (dd, J=17 Hz, 14 Hz, 1H), 2.41 (ddd, J=17 Hz, 2 Hz, 1 Hz, 1H).

The above 2,3-dihydro-pyran-4-one (7.1 g, 0.032 mol) and 10% palladium on carbon (0.4 g) in ethyl acetate (50 ml) were placed in a Parr bomb shaker and hydrogenated at 30 psi. The reaction mixture was shaken for 2 h, at which time TLC analysis (methanol/dichloromethane 1:9) indicated the reaction was complete. The reaction mixture was filtered through a pad of Celite and the volatiles evaporated in vacuo. The residue was subjected to flash column chromatography using ethyl acetate as eluant. Pure fractions were collected affording after evaporation in vacuo 3.0 g (75%) of 2-hydroxymethyl-tetrahydro-pyran-4-one as an oil.

$^1$H NMR (400 MHz, $CDCl_3$) δ4.36–4.29 (m, 1H), 3.77–3.66 (m, 3H), 3.61–3.54 (m, 1H), 2.65–2.43 (m, 2H), 2.34–2.27 (m, 2H), 2.04 (bs, 1H, $CH_2OH$).

The above tetrahydro-pyran-4-one (1.90 g, 0.015 mol), tert-butyl cyanoacetate (2.7 g, 0.019 mol), sulfur (0.51 g, 0.016 mol) and morpholine (2.55 ml, 0.03 mol) were dissolved in absolute ethanol (20 ml), and heated to 50° C. for 16 h. The reaction mixture was cooled, filtered and the filtrate evaporated in vacuo. The resultant oil was dissolved in ethyl acetate (50 ml), washed with water (2×50 ml), brine (2×50 m) and dried ($MgSO_4$). The solvent was evaporated in vacuo and the residue was subjected to flash column chromatography using ethyl acetate/hexanes (1:1) as eluant. Pure fractions were collected affording after evaporation in vacuo 3.7 g (90%) of 2-amino-5-hydroxymethyl-4,7-dihydro-5H-thieno[2,3-c]pyran-3-carboxylic acid tert-butyl ester as a solid.

$^1$H NMR (400 MHz, $CDCl_3$) δ 4.64 (s, 2H), 3.80–3.67 (m, 3H), 2.77–2.72 (m, 1H), 2.57–2.53 (m, 1H), 1.54 (s, 9H).

The above carboxylic acid tert-butyl ester (1.0 g, 3.5 mmol), 4-chloro-1,3-dioxo-1,3-dihydro-isoindol (0.67 g, 3.7 mmol) and triphenylphosphine (1.01 g, 3.9 mmol) were dissolved in dry tetrahydrofuran (30 ml) and cooled to 0° C. under a nitrogen atmosphere. Diisopropyl azodicarboxylate (DIAD) (0.62 ml, 3.9 mmol) was added dropwise at 0° C. and the solution allowed to stir overnight, slowly warming to room temperature. The volatiles were evaporated in vacuo and the resultant solid dissolved in ethyl acetate (50 ml). The organic phase was washed with brine (3×50 ml), dried (Na$_2$SO$_4$), filtered and evaporated in vacuo. The residue was subjected to flash column chromatography (300 ml silicagel) using a mixture of ethyl acetate/hexanes (1:3) as eluant. Semi pure fractions were collected affording after evaporation in vacuo 0.7 g which was triturated with diethyl ether. The solid was filtered off and washed with diethyl ether and dried in vacuo affording 0.13 g (27%) of 2-amino-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid. The filtrate was evaporated in vacuo. The residue (0.48 g) was subjected to flash column chromatography (300 ml silicagel) using a mixture of ethyl acetate/hexanes (1:3) as eluant. Pure fractions were collected affording after evaporation in vacuo an additional 0.36 g (23%) of 2-amino-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid.

To the above 4,7-dihydro-5H-thieno[2,3-c]pyran-3-carboxylic acid tert butyl ester (0.36 g, 0.8 mmol) dissolved in tetrahydrofuran (20 ml) was added a mixture of imidazol-1-yl-oxo-acetic acid tert butyl ester (0.31 g, 1.6 mmol) in tetrahydrofuran (3.4 ml) under nitrogen. The reaction mixture was allowed to stir at room temperature for 18 hours. An additional portion of imidazol-1-yl-oxo-acetic acid tert butyl ester (0.3 g, 1.6 mmol) in tetrahydrofuran (2 ml) was added. The reaction mixture was allowed to stir at room temperature for an additional 60 h. The reaction mixture was poured into water (50 ml) and extracted with ethyl acetate (3×50 ml). The combined organic phases were washed with brine (3×50 ml) dried (Na$_2$SO$_4$), filtered and the organic phase evaporated in vacuo. The residue (0.5 g) was purified by column chromatography (300 ml silicagel) using a mixture of ethyl acetate/heptane (1:2) as eluant. Pure fractions were collected and the solvent evaporated in vacuo affording 0.36 g (80%) of 2-(tert-butoxyoxalyl-amino)-5-(4-chloro-1,3-dioxo-1,3-dihydro-isoindol-2-ylmethyl)-4,7-dihydro-5H-thieno[2,3-c]pyran-3-carboxylic acid tert-butyl ester as a solid.

The above di-tert-butyl ester (0.3 g, 0.52 mmol) was dissolved in dichloromethane (1.2 ml) and trifluoroacetic acid (0.5 ml) was added. The reaction was stirred at room temperature for 18 h. The volatiles were evaporated in vacuo and the residue triturated with a mixture of diethyl ether and heptane (1:1) (5 ml). The precipitate was filtered off, washed with heptane and diethyl ether, dried in vacuo at 50° C. for 18 h which afforded 200 mg (69%) of the title compound as a solid.

M.p.: >250° C.

Calculated for C$_{19}$H$_{13}$N$_2$ClO$_8$S; C, 49.09%; H, 2.82%; N, 6.03%. Found: C, 48.79%; H, 2.79%; N, 5.89%.

Example 2

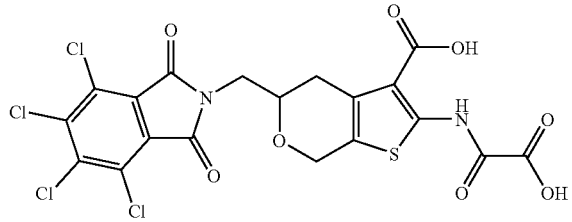

5-(4,5,6,7-Tetrachloro-1,3-dioxo-1,3-dihydro-isoindol-2-ylmethyl)-2-(oxalyl-amino)-4,7-dihydro-5H-thieno[2,3-c]pyran-3-carboxylic acid In a 4 ml scintillating vial, a solution of tetrachloro phthalimide (148 mg, 0.52 mmol) in N,N-dimethylformamide (2.0 ml) was heated to 100° C. for 10 minutes and treated with potassium hydride (55 mg, 0.48 mmol, 35% w/w dispersion in mineral oil). The resulting mixture was stirred until gas generation ended, 2-(tert-butoxyoxalyl-amino)-5-(4-nitro-benzenesulfonyl-oxymethyl)-4,7-dihydro-5H-thieno[2,3-c]pyran-3-carboxylic acid tert-butyl ester (151 mg, 0.25 mmol) and 18-crown-6 ether (31 mg, 0.12 mmol) were added. The solution was flushed with nitrogen gas before being stirred at 80° C. for 25 h. The volatiles were evaporated in vacuo and the residue purified by silica gel chromatography using a mixture of hexanes/ethyl acetate (5:1) as eluant. Pure fractions were collected and the solvent evaporated in vacuo affording 39 mg (23%) of 2-(tert-butoxyoxalyl-amino)-5-(4,5,6,7-tetrachloro-1,3-dioxo-1,3-dihydro-isoindol-2-ylmethyl)-4,7-dihydro-5H-thieno[2,3-c]pyran-3-carboxylic acid tert-butyl ester as a solid.

$^1$H NMR (300 MHz, CDCl$_3$) δ 12.50 (s, 1H), 4.80 (d, J=16, 1H), 4.67 (d, J=14, 1H), 4.14–3.99 (m, 2H), 3.84 (d, J=9, 1H), 2.99 (d, J=17, 1H), 2.70 (dd, J=17, 5, 1H), 1.60 (s, 9H), 1.56 (s, 9H).

HPLC (254.4 nm) R$_t$=5.80 min, 95%.

In a 25 ml round bottom flask, 2-(tert-butoxyoxalyl-amino)-5-(4,5,6,7-tetrachloro-1,3-dioxo-1,3-dihydro-isoindol-2-ylmethyl)-4,7-dihydro-5H-thieno[2,3-c]pyran-3-carboxylic acid tert-butyl ester (39 mg, 0.06 mmol) was dissolved in 20% trifluoroaceetic acid in dichloromethane (4 ml). The solution was left open to the atmosphere without stirring for 24 h. A precipitate was filtered off and washed with diethyl ether, affording after drying 29 mg (90%) of the title compound as a solid.

$^1$H NMR (300 MHz, DMSO-d$_6$) δ 12.32 (s, 1H), 4.76 (d, J=16, 1H), 4.59 (d, J=14, 1H), 4.0–3.6 (m partially obscured by water, 3H), 3.1 (d partially obscured by water, J=17, 1H), 2.61 (dd partially obscured by DMSO, J=20, 11, 1H).

HPLC (254.4 nm) R$_t$=4.15 min, 75%.

Example 3

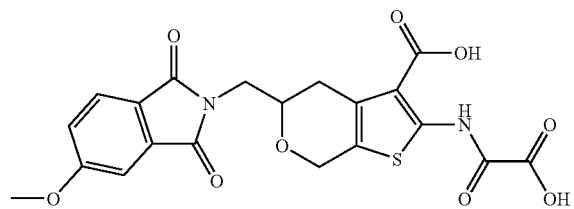

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxyphthalic acid (0.25 g, 1.37 mmol) in anhydrous N,N-dimethylformamide (3 ml) under nitrogen was added sodium hydride (0.22 g, 5.48 mmol). The solution was stirred for 5 minutes and then methyl iodide (0.68 ml) was added and continued stirring for 3 hours. Several drops of water were added to quench the reaction and the mixture was concentrated in vacuo. The crude material was partitioned between ethyl acetate (40 ml) and water (10 ml). The layers were separated and the organic layer washed with brine (2×10 ml), dried (Na$_2$SO$_4$), filtered and the solvent evaporated in vacuo. The resulting oil was dissolved in methanol (8 ml) and 1N sodium hydroxide (4 ml) was added. The reaction was stirred at ambient temperature for 24 h., after which LC-MS indicated only partial hydrolysis. The material was reconstituted in methanol (5 ml) and treated with sodium hydroxide (0.12 g, 3.0 mmol) dissolved in water (1 ml). The reaction mixture was stirred for 48 h., at which time a precipitate had formed. The mixture was acidified with 6N hydrochloric acid until pH=1, causing the solution to become homogeneous. The reaction was concentrated in vacuo and the residue partitioned between ethyl acetate (30 ml) and 0.5N hydrochloric acid (10 ml). The layers were separated and the organic layer concentrated in vacuo to give 100 mg (51%) of 4-methoxy-phthalic acid as a solid.

$^1$H NMR (300 MHz, CD$_3$OD) δ 7.83 (d; J=8, 1H), 7.10–7.06 (m, 2H), 3.87 (s, 3H).

LC-MS: R$_t$=1.45 min, [M+H]$^+$=197.1

A solution of 4-methoxy-phthalic acid (0.10 g, 0.51 mmol), 1-hydroxy-benzotriazole (0.15 g, 1.1 mmol), 1-(3-dimethylaminopropyl)-3-ethyl-carbodiimide hydrochloride (0.22 g, 1.1 mmol), and triethylamine (0.35 ml, 2.5 mmol) was prepared in distilled acetonitrile (4 ml) under nitrogen. 2-Amino-5-aminomethyl-4,7-dihydro-5H-thieno-[2,3-c]pyran-3-carboxylic acid tert-butyl ester (0.11 g, 0.39 mmol) was added in small portions and the reaction was stirred at ambient temperature for 18 h., and then concentrated in vacuo. The crude mixture was diluted in ethyl acetate (30 ml) and washed with 1% hydrochloric acid (5 ml), saturated sodium bicarbonate (5 ml), and brine (5 ml). The organic layer was dried (Na$_2$SO$_4$), filtered, and the solvent evaporated in vacuo. The crude material was purified by silica gel chromatography using a 10% mixture of ethyl acetate/dichloromethane as eluant. Pure fractions were collected and the solvent evaporated in vacuo to give 54 mg (31%) of 2-amino-5-(5-methoxy-1,3-dioxo-1,3-dihydro-isoindol-2-ylmethyl)-4,7-dihydro-5H-thieno-[2,3-c]pyran-3-carboxylic acid tert-butyl ester.

$^1$H NMR (300 MHz, CDCl$_3$) δ 7.76 (d, J=8, 1H), 7.32 (s, 1H), 7.14 (d, J=8, 1H), 4.62–4.48 (m, 2H), 4.00–3.72 (m, 3H), 3.91 (s, 3H), 2.86 (d, J=17, 1H), 2.55 (dd, J=17, 10, 1H), 1.49 (s, 9H).

To a solution of the above 2-amino-5-(5-methoxy-1,3-dioxo-1,3-dihydro-isoindol-2-ylmethyl)-4,7-dihydro-5H-thieno-[2,3-c]pyran-3-carboxylic acid tert-butyl ester (54 mg, 0.12 mmol) in distilled dichloromethane (3 ml) under nitrogen was added midazol-1-yl-oxo-acetic acid tert-butyl ester (0.25 g, 0.36 mmol) and triethylamine (50 μl, 0.36 mmol). The reaction was stirred for 4 h., concentrated in vacuo and the residue reconstituted in ethyl acetate (20 ml). The organic layer was washed with 1% hydrochloric acid (2×5 ml), saturated sodium bicarbonate (5 ml), and brine (5 ml). The organic phase was dried (Na$_2$SO$_4$), filtered, and the solvent evaporated in vacuo. The crude material was purified by silica gel chromatography using a 5% mixture of ethyl acetate/dichloromethane as eluant. Pure fractions were collected and the solvent evaporated in vacuo to give 56 mg (81%) of 2-(tert-butoxyoxalyl-amino)-5-(5-methoxy-1,3-di-oxo-1,3-dihydro-isoindol-2-ylmethyl)-4,7-dihydro-5H-thieno-[2,3-c]pyran-3-carboxylic acid tert-butyl ester.

$^1$H NMR (300 MHz, CDCl$_3$) δ 12.48 (s, 1H), 7.75 (d, J=8, 1H), 7.32 (d, J=2, 1H), 7.15 (dd, J=8, 2, 1H), 4.78 (d, J=15, 1H), 4.65 (d, J=15, 1H), 4.03–3.75 (m, 3H), 3.91 (s, 3H), 2.95 (d, J=17, 1H), 2.66 (dd, J=17, 9, 1H), 1.58 (s, 9H), 1.54 (s, 9H).

APCI-MS: [M+H]$^+$=574

The above 2-(tert-butoxyoxalyl-amino)-5-(5-methoxy-1,3-dioxo-1,3-dihydro-isoindol-2-ylmethyl)-4,7-dihydro-5H-thieno-[2,3-c]pyran-3-carboxylic acid tert-butyl ester (55 mg, 0.096 mmol) was dissolved in a solution of 50% trifluoroacetic acid/dichloromethane (4 ml). The reaction was stirred at ambient temperature for 7 h., concentrated in vacuo and evaporated in vacuo from dichloromethane (3×10 ml). The resulting precipitate was washed with dichloromethane and dried in vacuo to give 17 mg (40%) of the title compound as a solid.

$^1$H NMR (300 MHz, DMSO-d$_6$) δ 12.32 (s, 1H), 7.81 (d, J=8, 1H), 7.40 (d, J=2, 1H), 7.31 (dd, J=8, 2, 1H), 4.75 (d, J=15, 1H), 4.56 (d, J=15, 1H), 3.92 (s, 3H), 3.91–3.69 (m, 3H), 2.98 (d, J=17, 1H), 2.57 (dd, J=17, 9, 1H).

APCI-MS: [M−H]$^−$=459

HPLC (254.4 nm): R$_t$=3.36 min, 98%

Example 4

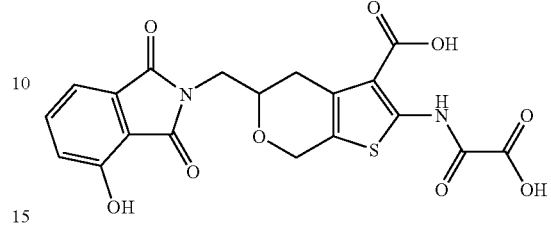

5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid 5-(4-Benzyloxy-1,3-dioxo-1,3-dihydro-isoindol-2-ylmethyl)-2-(tert-butoxyoxalyl-amino)-4,7-dihydro-5H-thieno[2,3-c]pyran-3-carboxylic acid tert-butyl ester was prepared in a similar way as described in Example 1.

To a solution of the above benzylether (0.7 g, 1.08 mmol) in ethyl acetate (50 ml) was added 10% palladium on carbon (0.2 g). The mixture was hydrogenated at 1 atm. for 5 h, filtered and the volatiles evaporated in vacuo. The residue (0.6 g) was purified by column chromatography (500 ml silicagel) using a mixture of ethyl acetate/heptane (1:1) as eluant. Pure fractions were collected and the solvent evaporated in vacuo affording 0.4 g (67%) of 2-(tert-butoxyoxalyl-amino)-5-(4-hydroxy-1,3-dioxo-1,3-dihydro-isoindol-2-yl-methyl)-4,7-dihydro-5H-thieno[2,3-c]pyran-3-carboxylic acid tert-butyl ester as an oil.

TLC: R$_f$=0.2 (ethyl acetate/heptane 1:1)

The above di-tert-butyl ester (0.4 g, 0.72 mmol) was dissolved in 25% trifluoroacetic acid in dichloromethane (25 ml). The reaction was stirred at room temperature for 18 h. The volatiles were evaporated in vacuo and the residue trituated with diethyl ether (5 ml). The precipitate was filtered off, washed with heptane and diethyl ether, dried in vacuo at 50° C. for 18 h which afforded 230 mg (72%) of the title compound as a solid.

M.p.: >250° C.;

Calculated for C$_{19}$H$_{14}$N$_2$O$_9$S, 0.5×H$_2$O; C, 50.11%; H, 3.32%; N, 6.15%. Found: C, 50.06%; H, 3.17%; N, 5.98%.

Example 5

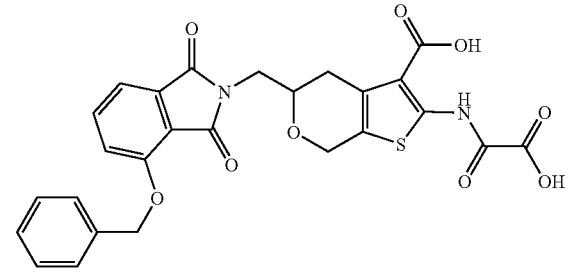

5-(4-Benzyloxy-1,3-dioxo-1,3-dihydro-isoindol-2-ylmethyl)-2-(oxalyl-amino)-4,7-dihydro-5H-thieno[2,3-c]pyran-3-carboxylic acid 5-(4-Benzyloxy-1,3-dioxo-1,3-dihydro-isoindol-2-ylm-ethyl)-2-(tert-butoxyoxalyl-amino)-4,7-dihydro-5H-thieno[2,3-c]pyran-3-carboxylic acid tert-butyl ester (0.7 g, 1.08 mmol) (prepared in a similar way as described in Example 1) was dissolved in 25% trifluoroacetic acid in dichloromethane (25 ml). The reaction was stirred at room temperature for 18 h. The volatiles were evaporated in vacuo and the residue triturated with diethyl ether (25 ml). The precipitate was filtered off, washed with diethyl ether and dried in vacuo at 50° C. for 3 hours which afforded 400 mg (69%) of the title compound as a solid.

M.p.: 194–196° C.;

Calculated for $C_{26}H_{20}N_2O_9S$, $1 \times H_2O$, $0.6 \times CF_3COOH$; C, 52.44%; H, 3.66%; N, 4.50%. Found: C, 52.33%; H, 3.65%; N, 4.62%.

Example 6

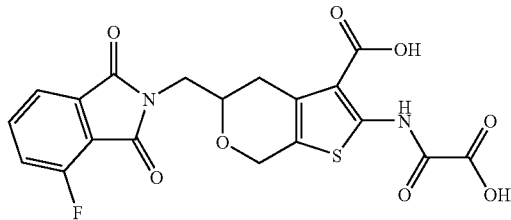

5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid Prepared in a similar way as described in Example 1.
M.p.: >250° C.;
Calculated for $C_{19}H_{13}FN_2O_8S$, $1 \times H_2O$; C, 48.93%; H, 3.24%; N, 6.01%. Found: C, 48.90%; H, 3.15%; N, 5.86%.

Example 7

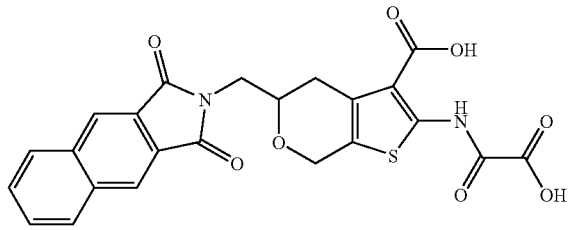

5-(1,3-Dioxo-1,3-dihydro-benzo[f]isoindol-2-ylmethyl)-2-(oxalyl-amino)-4,7-dihydro-5H-thieno[2,3-c]pyran-3-carboxylic acid, In a 4 ml scintillating vial, a solution of benzo[f]isoindole-1,3-dione (145 mg, 0.74 mmol) in N,N-dimethylformamide (2.0 ml) was treated with potassium hydride (55 mg, 0.48 mmol, 35% w/w dispersion in mineral oil). The resulting mixture was stirred until gas generation ended and the resulting precipitate was filtered off and washed with dichloromethane which afforded 121 mg (69%) of benzo[f]isoindole-1,3-dione potassium salt as a solid.

$^1$H NMR (300 MHz, $D_2O$) δ 8.00–7.87 (m, 4H), 7.62 (s, 2H).

In a 4 ml scintillating vial, the above potassium salt (121 mg, 0.5 mmol) in N,N-dimethylformamide (1.5 ml) was treated with 18-crown-6 ether (34 mg, 0.13 mmol) and 2-(tert-butoxyoxalyl-amino)-5-(4-nitro-benzene-sulfonyloxymethyl)-4,7-dihydro-5H-thieno[2,3-c]pyran-3-carboxylic acid tert-butyl ester (148 mg, 0.25 mmol). The solution was flushed with nitrogen gas before being stirred at 80° C. for 7 h. The volatiles were evaporated in vacuo and the residue purified by silica gel chromatography using a mixture of ethyl acetate/dichloromethane (1:49) as eluant. Pure fractions were collected and the solvent evaporated in vacuo affording 85 mg (57%) of 2-(tert-butoxyoxalyl-amino)-5-(1,3-dioxo-1,3-dihydro-benzo[f]isoindole-2-ylmethyl)-4,7-dihydro-5H-thieno[2,3-c]pyran-3-carboxylic acid tert-butyl ester as a solid.

$^1$H NMR (300 MHz, $CDCl_3$) δ 12.52 (s, 1H), 8.37 (s, 2H), 8.08 (m, 2H), 7.72 (m, 2H), 4.84–4.65 (m, 2H), 4.16–3.90 (m, 3H), 3.02 (d, J=17, 1H), 2.73 (dd, J=17, 10, 1H), 1.61 (s, 9H), 1.58 (s, 9H).

In a 25 ml round bottom flask the above 2-(tert-butoxyoxalyl-amino)-5-(1,3-dioxo-1,3-dihydro-benzo[f]isoindole-2-ylmethyl)-4,7-dihydro-5H-thieno[2,3-c]pyran-3-carboxylic acid tert-butyl ester (85 mg, 0.14 mmol) was dissolved in 20% trifluoroacetic acid in dichloromethane (4 ml). The solution was left open to the atmosphere without stirring for 24 h. The precipitate was filtered off and washed with diethyl ether, affording after drying 62 mg (90%) of the title compound as a solid.

$^1$H NMR (300 MHz, DMSO-$d_6$) δ 12.32 (s, 1H), 9.02 (s, 2H) 4.81–4.59 (m, 2H), 3.97–3.81 (m partially obscured by water, 3H), 3.08 (d, J=18, 1H), 2.74–2.53 (m partially obscured by DMSO, 1H).

Example 8

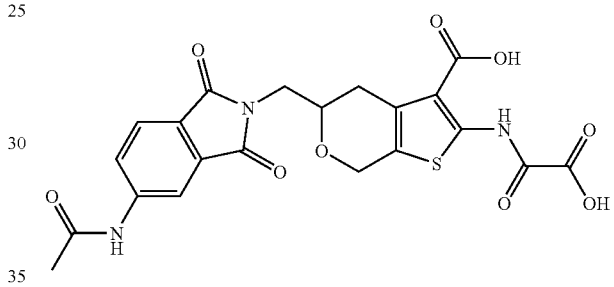

5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid To a solution of N-(1,3-dioxo-2,3-dihydro-1H-isoindol-5-yl)-acetamide (51 mg, 0.25 mmol) in N,N-dimethylformamide (1.5 ml) under nitrogen at room temperature was added potassium hydride (35 wt. % dispersion in mineral oil, 29 mg, 0.25 mmol). The solution was stirred at room temperature for 3 hours. A solid precipitated during this period. 2-(tert-Butoxyoxalyl-amino)-5-(4-nitro-benzene-sulfonyloxymethyl)-4,7-dihydro-5H-thieno[2,3-c]pyran-3-carboxylic acid tert-butyl ester (100 mg, 0.17 mmol) was added to the suspension and the solution was stirred at 80° C. for 12 h. The solvent was evaporated in vacuo, the resulting residue purified by silica gel chromatography using a gradient of ethyl acetate/hexane (10–25%) as eluant. Pure fractions were collected and the solvent evaporated in vacuo affording 50 mg (50%) of 5-(5-acetylamino-1,3-dioxo-1,3-dihydro-isoindol-2-ylmethyl)-2-(tert-butoxyoxalyl-amino)-4,7-dihydro-5H-thieno[2,3-c]pyran-3-carboxylic acid tert-butyl ester as a solid.

$^1$H NMR ($CDCl_3$): δ 12.53 (s, 1H), 8.03 (d, 1H, J=1.5 Hz), 7.91 (dd, 1H, J=7.8, 1.8 Hz) 7.83 (d, 1H, J=8.1 Hz), 7.45 (s, 1H), 4.80 (d, 1H, J=16 Hz), 4.66 (d, 1H, J=16 Hz), 4.03 (m, 2H), 3.83 (q, 1H, J=15 Hz), 2.98 (d, 1H, J=9 Hz), 2.64–2.78 (m, 1H), 2.27 (s, 3H), 1.62 (s, 9H), 1.57 (s, 9H).

To a mixture of trifluoroacetic acid/dichloromethane (2 ml, 1:1) at room temperature was added the above 5-(5-acetylamino-1,3-dioxo-1,3-dihydro-isoindol-2-ylmethyl)-2-(tert-butoxyoxalyl-amino)-4,7-dihydro-5H-thieno[2,3-c]pyran-3-carboxylic acid tert-butyl ester (40 mg, 0.067 mmol).

The solution was stirred for 5 h. at which time the solvent was removed in vacuo. The residue was washed with dichloromethane, filtered off, and dried in vacuo which afforded 23 mg (70%) of the title compound as a solid.

$^1$H NMR (DMSO-d$_6$): δ 12.32 (s, 1H), 10.58 (s, 1H), 8.21 (s, 1H) 7.84 (s, 2H), 4.76 (d, 1H, J=15 Hz), 4.58 (d, 1H, J=15 Hz), 3.80–4.00 (m, 3H), 3.00 (d, 1H, J=17 Hz), 2.58–2.73 (m, 1H), 2.13 (s, 3H).

MS: 488 (M+1).

Example 9

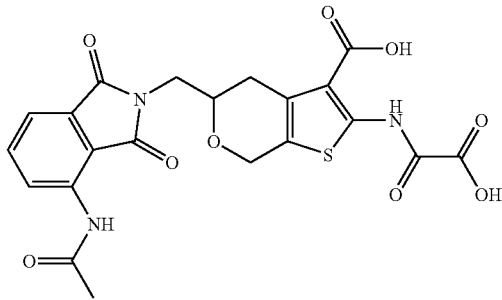

5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid The title compound was prepared in a similar way as described for Example 8.

$^1$H NMR (DMSO-d$_6$): δ 12.32 (s, 1H), 9.76 (s, 1H), 8.45 (d, 1H, J=8.4 Hz) 7.79 (t, 1H, J=8.4 Hz), 7.58 (d, 1H, J=8.4 Hz), 4.77 (d, 1H, J=15 Hz), 4.58 (d, 1H, J=15 Hz), 3.68–3.94 (m, 3H), 3.02 (d, 1H, J=16 Hz), 2.55–2.78 (m, 1H), 2.20 (s, 3H).

MS: 488 (M+1).

Example 10

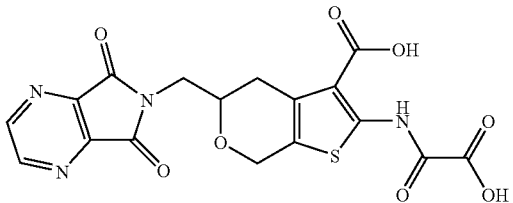

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid In a 4-ml scintillating vial, a solution of 2-amino-5-aminomethyl-4,7-dihydro-5H-thieno[2,3-c]pyran-3-carboxylic acid tert-butyl ester (148 mg, 0.5 mmol) in tetrahydrofuran (1.0 ml) was treated with a solution of pyrazine phthtalic acid anhydride (85 mg, 0.56 mmol) in tetrahydrofuran (1.0 ml) and N,N-dimethylformamide (0.5 ml). The reaction mixture was allowed to stir at room temperature for 1 h. Diisopropylethylamine (220 μl, 0.13 mmol) and 1-(3-dimethylaminopropyl)-3-ethylcarbodiimide hydrochloride (121 mg, 0.6 mmol) were then added. The reaction mixture was shaken vigorously for 10 seconds before being stirred at room temperature for 14 h. The volatiles were evaporated in vacuo and the residue purified by silica gel chromatography using a mixture of dichloromethane/ethyl acetate (3:1) as eluant. Pure fractions were collected and the solvent evaporated in vacuo affording 25 mg (12%) of the 2-amino-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester as a solid.

$^1$H NMR (300 MHz, CDCl$_3$) δ 8.97 (s, 2H), 4.62–4.49 (m, 2H), 4.21–4.04 (m, 2H), 3.94 (dd, J=14, 4, 1H), 2.91 (d, J=17, 1H), 2.63 (dd, J=17, 10, 1H), 1.68 (s, 9H).

In a 4 ml scintillating vial a solution of the above 2-amino-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester (25 mg, 0.06 mmol) in tetrahydrofuran (3 ml) was treated with midazol-1-yl-oxo-acetic acid tert-butyl ester (0.36 mmol). After stirring for 3 hours at room temperature the reaction solution was concentrated to dryness in vacuo. The residue was purified by silica gel chromatography using a mixture of hexanes/ethyl acetate (3:1) as eluant. Pure fractions were collected and the solvent evaporated in vacuo affording 31 mg (95%) of 2-(tert-butoxyoxalyl-amino)-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester as a solid.

$^1$H NMR (300 MHz, CDCl$_3$) δ 12.49 (s, 1H), 8.96 (s, 2H), 4.80–4.61 (m, 2H), 4.21–4.04 (m, 2H), 3.96 (dd, J=14, 4, 1H), 3.03 (d, J=16, 1H), 2.70 (dd, J=17, 10, 1H), 1.60 (s, 9H), 1.59 (s, 9H).

In a 25 ml round bottom flask the above 2-(tert-butoxyoxalyl-amino)-5-(5,7-dioxo-5,7-dihydro-pyrrolo[3,4-b]pyrazin-6-ylmethyl)-4,7-dihydro-5H-thieno[2,3-c]pyran-3-carboxylic acid tert-butyl ester, (31 mg, 0.06 mmol) was dissolved in 20% trifluoroacetic acid in dichloromethane (4 ml). The solution was left open to the atmosphere without stirring for 24 h. A precipitate was filtered off and washed with diethyl ether, affording after drying 22 mg (90%) of the title compound as a solid.

$^1$H NMR (300 MHz, DMSO-d$_6$) δ 12.31 (s, 1H), 9.02 (s, 2), 4.81–4.59 (m, 2H), 3.97–3.81 (m partially obscured by water, 3H), 3.08 (d, J=18, 1H), 2.74–2.53 (m partially obscured by DMSO, 1H).

HPLC (254.4 nm) R$_f$=2.97 min, 89%.

MS (APCI) [M−H] 432.4

Example 11

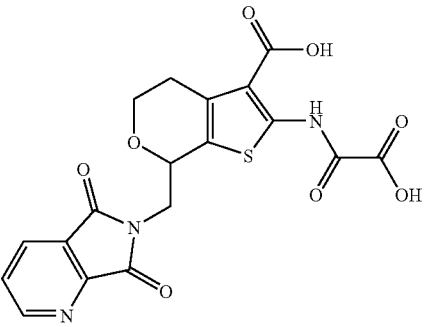

7-(5,7-dihydro-5-pyrrolo[3,4-b]pyridin-6-ylmethyl)-2-(oxalyl-amino)-4,7-dihydro-5H-thieno[2,3-c]pyran-3-carboxylic acid A solution of furo[3,4-b]pyridine-5,7-dione (86.1 mg, 0.58 mmol) and of 2-(tert-butoxyoxalyl-amino)-7-aminomethyl-4,7-dihydro-5H-thieno[2,3-c]pyran-3-carboxylic acid tert-butyl ester (194 mg, 0.47 mmol) in acetonitrile (2.0 ml) was stirred for 10 min. at room temperature. 1-(3-dimethylaminopropyl)-3-ethylcarbodiimide hydrochloride (89.2 mg, 0.564 mmol) and triethylamine (198 μl, 1.41 mmol) were added and the mixture was stirred at room temperature for 20 h. The volatiles were removed in vacuo and the crude product dissolved in dichloromethane (60 ml) and washed with water (3×30 ml). The organic layer was dried (MgSO$_4$), filtered and the solvent removal in vacuo. The residue (338 mg) was purified by column chromatography on silica gel utilizing a mixture of hexane/ethyl acetate (90/10 to 50/50) as gradient which afforded after evaporation of the solvent in vacuo 85 mg (33%) of 2-(tert-butoxyoxalyl-amino)-7-(5, 7-dioxo-5,7-dihydro-pyrrolo[3,4-b]pyridin-6-ylmethyl)-4, 7-dihyd-5H-thieno[2,3-c]pyran-3-carboxylic acid tert-butyl-ester as an oil.

$^1$H NMR (300 MHz, CDCl$_3$), δ 9.00 (d, J=48, 1H), 8.21 (d, J=7.5, 1H), 7.64 (dd, J=4.8, J=6.8, 1H), 5.12 (d, J=7.2, 1H), 4.24–4.1 (m, 2H), 3.97–3.91 (m, 1H), 3.75 (m, 1H), 2.90 (m, 1H), 1.29 (s, 9H), 1.27 (s, 9H).

MS: 544 (M+1).

The above 2-(tert-butoxyoxalyl-amino)-7-(5,7-dioxo-5,7-dihydro-pyrrolo[3,4-b]pyridin-6-ylmethyl)-4,7-dihyd-5H-thieno[2,3-c]pyran-3-carboxylic acid tert-butyl ester (47.4 mg, 0.087 mmol) was stirred in 50% trifluoroacetic acid in dichloromethane (2 ml) at room temperature for 5 h. The solvent was removed in vacuo and the residue was washed with diethyl ether (4×3.0 ml) and dried which afforded 26.5 mg (70%) of the title compound as a solid.

$^1$H NMR (400 MHz, CD$_3$OD): δ 8.96 (d, J=5, 1H), 8.30 (d, J=7.6, 1H), 7.79 (dd, J=5.2, J=5.2, 1H), 5.10 (d, J=6.4, 1H), 4.16 (m, 2H), 3.96 (dd, J=3.2, J=3.6, 1H), 3.78 (m, 1H), 2.95 (m, 2H).

MS: 432 (M+1).

Example 12

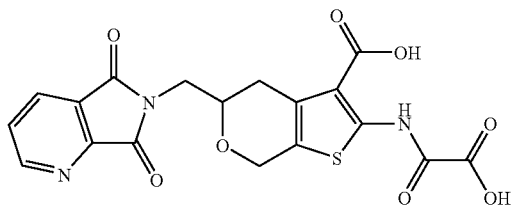

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid Pyrrolo[3,4-b]pyridine-5,7-dione (74.2 mg, 0.5 mmol) was stirred with sodium hydride (60% dispersion in mineral oil, 20.04 mg, 0.5 mmol) in N,N-dimethylformamide (4.0 ml) at room temperature under inert atmosphere. 2-(tert-Butoxyoxalyl-amino)-5-(4-nitro-benzene-sulfonyloxymethyl)-4,7-dihydro-5H-thieno[2,3-c]pyran-3-carboxylic acid tert-butyl ester (198 mg, 0.33 mmol) was added to the sodium salt formed and the reaction was stirred at 80° C. for 20 h. The solvent was removed in vacuo and the crude product was purified by preparative TLC (hexane:ethyl acetate 50:50) which afforded 58 mg (21%) of 2-(tert-butoxyoxalyl-amino)-5-(5,7-dioxo-5,7-dihydro-pyrrolo[3, 4-b]pyridin-6-ylmethyl)-4,7-dihydro-5H-thieno[2,3-c]pyran-3-carboxylic acid tert-butyl ester as a solid.

$^1$H NMR (300 MHz, CDCl$_3$): δ 9.00 (d, J=5, 1H), 8.20 (d, J=7.5, 1H), 7.65 (dd, J=5, J=5, 1H), 4.80 (d, J=14.7, 1H), 4.66 (d, J=14.7, 1H), 4.10 (m, 2H), 3.91 (d, J=13.2, 1H), 3.02 (d, J=16.5, 1H), 2.70 (m, 1H), 1.61 (s, 9H), 1.58 (s, 9H).

MS: 544 (M+1).

The above 2-(tert-butoxyoxalyl-amino)-5-(5,7-dioxo-5,7-dihydro-pyrrolo[3,4-b]pyridin-6-ylmethyl)-4,7-dihydro-5H-thieno[2,3-c]pyran-3-carboxylic acid tert-butyl ester (46.4 mg, 0.09 mmol) was stirred in 20% trifluoroacetic acid in dichloromethane (3.0 ml) at room temperature for 2 h. The volatiles were removed in vacuo and the residue was washed with diethyl ether (5×3 ml) affording 37 mg (99%) of the title compound as a solid.

$^1$H NMR (300 MHz, CDCl$_3$): δ 8.96 (d, J=5.4, 1H), 8.20 (d, J=7.7, 1H), 7.64 (m, 1H), 4.77 (d, J=14.7, 1H), 4.61 (d, J=14.7, 1H), 4.07 (m, 2H), 3.86 (d, J=10.5, 1H), 3.12 (d, J=17.4, 1H), 2.77–2.68 (m, 2H).

MS: 432 (M+1).

Example 13

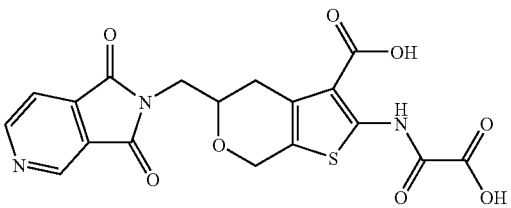

5-(5,7-Dioxo-5,7-dihydro-pyrrolo[3,4-c]pyridin-6-ylmethyl)-2-(oxalyl-amino)-4,7-dihydro-5H-thieno[2,3-c]pyran-3-carboxylic acid To a solution of pyrrolo[3,4-c]pyridine-1,3-dione (74 mg, 0.50 mmol) in N,N-dimethylformamide (1 ml) under nitrogen at room temperature was added potassium hydride (35 wt. % dispersion in mineral oil, 57 mg, 0.50 mmol). The solution was stirred at room temperature for 3 hours. A solid precipitated during this period. 18-Crown-6 (33 mg, 0.13 mmol) and 2-(tert-butoxyoxalyl-amino)-5-(4-nitro-benzene-sulfonyloxymethyl)-4,7-dihydro-5H-thieno[2,3-c]pyran-3-carboxylic acid tert-butyl ester (150 mg, 0.25 mmol) were then added. The solution was stirred at 80° C. for 12 h and the solvent evaporated in vacuo. The residue was purified by silica gel chromatography using a gradient of ethyl acetate/hexane (10–25%) as eluant. Pure fractions were collected and the solvent evaporated in vacuo affording 93 mg (68%) of 2-(tert-butoxyoxalyl-amino)-5-(1,3-dioxo-1,3-dihydro-pyrrolo[3,4-c]pyridin-2-ylmethyl)-4,7-dihydro-5H-thieno[2,3-c]pyran-3-carboxylic acid tert-butyl ester as a solid.

$^1$H NMR (CDCl$_3$): δ 12.49 (s, 1H), 9.20 (s, 1H), 9.11 (d, 2H, J=4.8 Hz) 7.80 (d, 2H, J=4.8 Hz), 4.80 (d, 1H, J=16 Hz), 4.66 (d, 1H, J=16 Hz), 4.00–4.18 (m, 2H), 3.70–3.95 (m, 1H), 3.01 (d, 1H, J=17 Hz), 2.64–2.78 (m, 1H), 1.60 (s, 9H), 1.59 (s, 9H).

To a mixture of trifluoroacetic acid/dichloromethane (1 ml, 1:1) at room temperature was added the above 2-(tert-butoxyoxalyl-amino)-5-(1,3-dioxo-1,3-dihydro-pyrrolo[3, 4-c]pyridin-2-ylmethyl)-4,7-dihydro-5H-thieno[2,3-c]pyran-3-carboxylic acid tert-butyl ester (29 mg, 0.053 mmol). The solution was stirred for 5 h. and the solvent evaporated in vacuo. The residue was washed with dichloromethane afford after drying in vacuo 22 mg (96%) of the title compound as a solid.

$^1$H NMR (DMSO-d$_6$): δ 12.32 (s, 1H), 9.15 (s, 1H), 9.11 (d, 2H, J=4.8 Hz) 7.92 (d, 2H, J=4.8 Hz), 4.76 (d, 1H, J=15 Hz), 4.58 (d, 1H, J=16 Hz), 3.75–4.00 (m, 4H), 3.04 (d, 1H, J=17 Hz).

MS: 432 (M+1).

Example 14

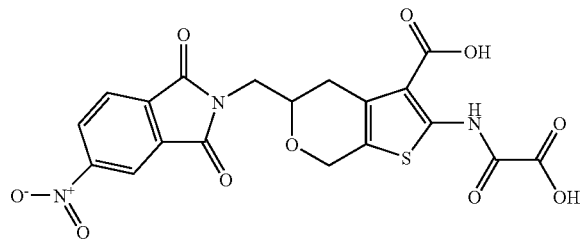

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid In a 4-ml scintillating vial, a solution of 2-amino-5-aminomethyl-4,7-dihydro-5H-thieno[2,3-c]pyran-3-carboxylic acid tert-butyl ester (58 mg, 0.2 mmol) in tetrahydrofuran (2.0 ml) was treated with 4-nitrophthalic acid (63 mg, 0.3 mmol), diisopropylethylamine (190 µl, 1.1 mmol), and 1,3-diisopropylcarbodiimide (120 µl, 0.77 mmol). The reaction mixture was shaken vigorously for 10 seconds before being stirred at 50° C. for 43 hours and at room temperature for 20 h. The solution was diluted with ethyl acetate (25 ml), washed with 0.5N aqueous hydrochloric acid (25 ml), saturated aqueous sodium bicarbonate (25 ml), and brine (25 ml). The organic layer was dried (MgSO$_4$), filtered and the solvent evaporated in vacuo. Crude 2-amino-5-(5-nitro-1,3-dioxo-1,3-dihydro-isoindol-2-ylmethyl)-4,7-dihydro-5H-thieno[2,3-c]pyran-3-carboxylic acid tert-butyl ester was obtained as a solid and used immediately in the next step.

In a 4 ml scintillating vial a solution of the above crude 2-amino-5-(5-nitro-1,3-dioxo-1,3-dihydro-isoindol-2-ylmethyl)-4,7-dihydro-5H-thieno[2,3-c]pyran-3-carboxylic acid tert-butyl ester in dichloromethane (3 ml) was treated with midazol-1-yl-oxo-acetic acid tert-butyl ester (147 mg, 0.75 mmol). After stirring for 2 h. at room temperature the reaction mixture was concentrated to dryness in vacuo. The residue was purified by silica gel chromatography using a mixture of hexanes/ethyl acetate (3:1) as eluant. Pure fractions were collected and the solvent evaporated in vacuo which afforded 30 mg (26%) of 2-(tert-butoxyoxalyl-amino)-5-(5-nitro-1,3-dioxo-1,3-dihydro-isoindol-2-ylmethyl)-4,7-dihydro-5H-thieno[2,3-c]pyran-3-carboxylic acid tert-butyl ester as a solid.

$^1$H NMR (300 MHz, CDCl$_3$) δ 12.47 (s, 1H), 8.71 (s, 1H), 8.64 (d, J=8, 1H), 8.08 (d, J=9, 1H), 4.79 (d, J=14, 1H), 4.65 (d, J=14, 1H), 4.21–3.97 (m, 2H), 3.89 (d, J=12, 1H), 3.01 (d, J=16, 1H), 2.83–2.61 (m, 1H), 1.63 (ds, 18H).

In a 25 ml round bottom flask, the above 2-(tert-butoxyoxalyl-amino)-5-(5-nitro-1,3-dioxo-1,3-dihydro-isoindol-2-ylmethyl)-4,7-dihydro-5H-thieno[2,3-c]pyran-3-carboxylic acid tert-butyl ester (30 mg, 0.05 mmol) was dissolved in a mixture of 20% trifluoroacetic acid in dichloromethane (4 ml). The solution was left open to the atmosphere without stirring of 24 h. A precipitate was filtered off and washed with diethyl ether, affording after drying 22 mg (90%) of the title compound as a solid.

$^1$H NMR (300 MHz, DMSO-d$_6$) δ 12.31 (s, 1H), 8.63 (d, J=8, 1H), 8.15 (d, J=8, 1H), 4.76 (d, J=16, 1H), 4.57 (d, J=16, 1H), 4.42–3.74 (m partially obscured by water, 3H), 3.04 (d partially obscured by water, J=16, 1H), 2.61 (m partially obscured by DMSO, 1H).

HPLC (254.4 nm) R$_f$=3.40 min, 86%.

MS (APCI$^+$) [M+H] 407.6

Example 15

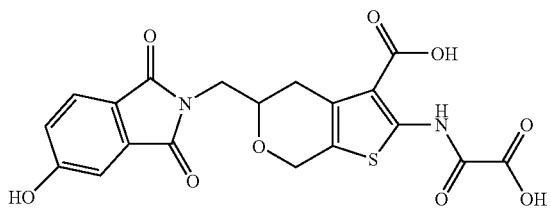

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxyphthalic acid (0.45 g, 2.47 mmol) in anhydrous N,N-dimethylformamide (5 ml) under nitrogen was added chloromethyl methyl ether (1.13 ml, 14.8 mmol) and diisopropylethylamine (2.6 ml, 14.8 mmol). The reaction was stirred at ambient temperature for 18 h. and then concentrated in vacuo. The crude material was partitioned between ethyl acetate (50 ml) and water (15 ml). The layers were separated, the organic layer washed with water (3×10 ml), brine (2×10 ml), dried (Na$_2$SO$_4$), filtered and the solvent evaporated in vacuo. The resulting oil was dissolved in ethanol (5 ml) and sodium hydroxide (0.12 g, 7.4 mmol) dissolved in water (1 ml) was added to the reaction. The solution was stirred at ambient temperature for 48 h. and then concentrated in vacuo affording 4-methoxymethoxy-phthalic acid di-sodium salt which was used without purification.

$^1$H NMR (300 MHz, CD$_3$OD) δ 7.59 (d, J=8, 1H), 7.06 (d, J=3,1H), 6.89 (dd, J=8, 3, 1H), 5.18 (s, 2H), 3.42 (s, 3H).

A solution of 4-methoxymethoxy-phthalic acid di-sodium salt (0.19 g, 0.70 mmol), 1-hydroxybenzotriazole (0.2 g, 3.6 equiv.), 1-(3-dimethylamino-propyl)-3-ethylcarbodiimide hydrochloride (0.28 g, 3.6 equiv.), and triethylamine (0.33 ml, 6 equiv.) was prepared in distilled acetonitrile (5 ml) under nitrogen. The mixture was stirred for 5 minutes before 2-amino-5-aminomethyl-4,7-dihydro-5H-thieno[2,3-c]pyran-3-carboxylic acid tert-butyl ester (115 mg, 0.40 mmol) was added in small portions. The reaction was stirred at ambient temperature for 18 h., then concentrated in vacuo. The crude mixture was diluted with ethyl acetate (30 ml) and washed with 1% hydrochloric acid (5 ml) saturated sodium bicarbonate (5 ml), and brine (5 ml). The organic layer was dried (Na$_2$SO$_4$), filtered, and the solvent evaporated in vacuo. The crude material was purified by silica gel chromatography using a gradient of ethyl acetate/dichloromethane (5 to 10% gradient) as eluant. Pure fractions were collected and the solvent evaporated in vacuo to give 44 mg (23%) of 2-amino-5-(5-methoxy-methoxy-1,3-dioxo-1,3-dihydro-isoindol-2-ylmethyl)-4,7-dihydro-5H-thieno[2,3-c]pyran-3-carboxylic acid tert-butyl ester.

$^1$H NMR (300 MHz, CDCl$_3$) δ 7.75 (d, J=8, 1H), 7.48 (d, J=2, 1H), 7.27 (dd, J=8, 2, 1H), 5.26 (s, 2H), 4.60–4.46 (m, 2H), 3.99–3.71 (m, 3H), 3.47 (s, 3H), 2.85 (d, J=17, 1H), 2.55 (dd, J=17, 9, 1 H), 1.48 (s, 9H).

To a solution of the above 2-amino-5-(5-methoxy-methoxy-1,3-dioxo-1,3-dihydro-isoindol-2-ylmethyl)-4,7-dihydro-5H-thieno[2,3-c]pyran-3-carboxylic acid tert-butyl, ester (44 mg, 0.095 mmol) in distilled dichloromethane (3 ml) under nitrogen was added midazol-1-yl-oxo-acetic acid tert-butyl ester (56 mg, 0.29 mmol) and triethylamine (26 µl, 0.19 mmol). The reaction was stirred for 4 h., concentrated in vacuo and reconstituted in ethyl acetate (20 ml). The organic layer was washed with 1% hydrochloric acid (2×5 ml), saturated sodium bicarbonate (5 ml), and brine (5 ml). The resulting solution was dried (Na$_2$SO$_4$), filtered, and the solvent evaporated in vacuo. The crude material was purified by silica gel chromatography using a 5% mixture of ethyl acetate/dichloromethane as eluant. Pure fractions were collected and the solvent evaporated in vacuo to give 35 mg (63%) of 2-(tert-butoxyoxalyl-amino)-5-(5-methoxymethoxy-1,3-dioxo-1,3-dihydro-isoindol-2-ylmethyl)-4,7-dihydro-5H-thieno[2,3-c]pyran-3-carboxylic acid tert-butyl ester.

$^1$H NMR (300 MHz, CDCl$_3$) δ 12.50 (s, 1H), 7.75 (d, J=8, 1H), 7.49 (d, J=2, 1H), 7.28 (dd, J=8, 2, 1H), 5.26 (s, 2H), 4.77 (d, J=15, 1H), 4.64 (d, J=15, 1H), 4.03–3.74 (m, 3H), 3.47 (s, 3H), 2.95 (d, J=17, 1H), 2.65 (dd, J=17, 9, 1H), 1.58 (s, 9H), 1.54 (s, 9H).

APCI-MS: [M+H]$^+$=603.7

The above 2-(tert-butoxyoxalyl-amino)-5-(5-methoxymethoxy-1,3-dioxo-1,3-dihydro-isoindol-2-ylmethyl)-4,7-dihydro-5H-thieno[2,3-c]pyran-3-carboxylic acid tert-butyl ester (35 mg, 0.058 mmol) was dissolved in a mixture of 50% trifluoroacetic acid/dichloromethane (2.5 ml). The reaction was stirred at ambient temperature for 7 h., concentrated in vacuo and the residue evaporated in vacuo from dichloromethane (3×10 ml). The resulting precipitate was washed with dichloromethane and dried in vacuo to give 20 mg (77%) of the title compound as a solid.

$^1$H NMR (300 MHz, DMSO-d$_6$) δ 12.31 (s, 1H), 10.97 (s, 1H), 7.72 (d, J=8, 1H), 7.18 (s, 1H), 7.10 (d, J=8, 1H), 4.74 (d, J=15, 1H), 4.58 (d, J=15, 1H), 3.96–3.62 (m, 3H), 2.99 (d, J=17, 1H), 2.60–2.50 (m, 1H, partially obscured by DMSO).

APCI-MS: [M–H]$^-$=445.4

HPLC (254.4 nm): R$_t$=2.92 min, 95%

Example 16

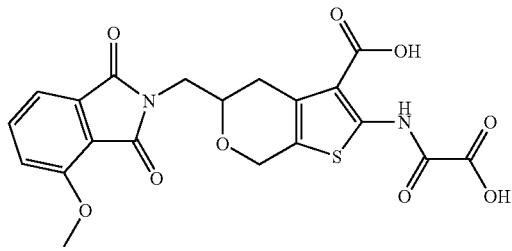

5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxy-isobenzofuran-1,3-dione (195 mg, 1.2 mmol) in anhydrous N,N-dimethylformamide (4 ml) under nitrogen was added minutes and then methyl iodide (0.37 ml, 6.0 mmol) was added. The reaction was stirred for 48 h. and then quenched with saturated ammonium chloride. The mixture was concentrated in vacuo, diluted in ethyl acetate (20 ml) and the organic phase washed with 1N hydrochloric acid (5 ml) and brine (3×5 ml). The organic layer was dried (MgSO$_4$) and concentrated in vacuo. To the crude solid was added methanol causing a precipitate to form. The flask was cooled in an ice bath for 2 h. and the solid filtered off, washed with methanol and dried in vacuo which afforded 0.1 g (47%) of 4-methoxy-isobenzofuran-1,3-dione as a solid.

$^1$H NMR (300 MHz, DMSO-d$_6$) δ 7.95 (t, J=8, 1H), 7.61 (d, J=8, 1H), 7.58 (d, J=8, 1H), 3.99 (s, 3H).

APCI-MS: [M+H]$^+$=179.1

A solution of 2-amino-5-aminomethyl-4,7-dihydro-5H-thieno[2,3-c]pyran-3-carboxylic acid tert-butyl ester (122 mg, 0.43 mmol, prepared as described in Example 17) and 4-methoxy-isobenzofuran-1,3-dione (92 mg, 0.52 mmol) was prepared in distilled tetrahydrofuran (4 ml) under nitrogen. 1-hydroxybenzotriazole (87 mg, 0.65 mmol), 1-(3-dimethyl-aminopropyl)-3-ethylcarbodiimide hydrochloride (123 mg, 0.65 mmol), and triethylamine (0.29 ml, 2.15 mmol) were added. The reaction was stirred at ambient temperature for 18 h., then concentrated in vacuo. The crude mixture was diluted with ethyl acetate (25 ml) and washed with 1N hydrochloric acid (5 ml), saturated sodium bicarbonate (5 ml), and brine (5 ml). The organic layer was dried (Na$_2$SO$_4$), filtered, and the solvent evaporated in vacuo to give 0.18 g (94%) of 2-amino-5-(4-methoxy-1,3-dioxo-1,3-dihydro-isoindol-2-ylmethyl)-4,7-dihydro-5H-thieno[2,3-c]pyran-3-carboxylic acid tert-butyl ester.

$^1$H NMR (300 MHz, CDCl$_3$) δ 7.66 (t, J=7, 1H), 7.43 (d, J=7, 1H), 7.19 (d, J=7, 1H), 4.59–4.46 (m, 2H), 4.06–3.72 (m, 3H), 4.00 (s, 3H), 2.87–2.81 (m, 1H), 2.60–2.51 (m, 1H), 1.48 (s, 9H).

To a solution of the above 2-amino-5-(4-methoxy-1,3-dioxo-1,3-dihydro-isoindol-2-ylmethyl)-4,7-dihydro-5H-thieno[2,3-c]pyran-3-carboxylic acid tert-butyl ester (0.18 g, 0.42 mmol) in distilled dichloromethane (5 ml) under nitrogen was added imidazol-1-yl-oxo-acetic acid tert-butyl ester (0.25 g, 1.26 mmol) and triethylamine (0.23 ml, 1.68 mmol). The reaction was stirred for 12 h., concentrated in vacuo and reconstituted in ethyl acetate (25 ml). The organic layer was washed with 1N hydrochloric acid (2×5 ml), saturated sodium bicarbonate (5 ml), and brine (5 ml). The resulting solution was dried (Na$_2$SO$_4$), filtered, and the solvent evaporated in vacuo. The crude material was purified by silica gel chromatography using a gradient of ethyl acetate/dichloromethane (0 to 10% gradient). Pure fractions were collected and the solvent evaporated in vacuo to give 195 mg (81%) of 2-(tert-butoxyoxalyl-amino)-5-(4-methoxy-1,3-dioxo-1,3-dihydro-isoindol-2-ylmethyl)-4,7-dihydro-5H-thieno[2,3-c]pyran-3-carboxylic acid tert-butyl ester as an oil.

$^1$H NMR (300 MHz, CDCl$_3$) δ 12.48 (s, 1H), 7.65 (t, J=7, 1H), 7.43 (d, J=7, 1H), 7.19 (d, J=7, 1H), 4.77 (d, J=15, 1H), 4.63 (d, J=15, 1H), 4.04–3.75 (m, 3H), 4.00 (s, 3H), 2.94 (d, J=17, 1H), 2.65 (dd, J=17, 10, 1H), 1.58 (s, 9H), 1.53 (s, 9H).

LC-MS: R$_t$=4.17 min, [M+H]$^+$=573.2

The above 2-(tert-butoxyoxalyl-amino)-5-(4-methoxy-1,3-dioxo-1,3-dihydro-isoindol-2-ylmethyl)-4,7-dihydro-5H-thieno[2,3-c]pyran-3-carboxylic acid tert-butyl ester (0.15 g, 0.26 mmol) was dissolved in a mixture of 50% trifluoroacetic acid/dichloromethane (5 ml). The reaction was stirred at ambient temperature for 7 h., concentrated in vacuo and the residue evaporated in vacuo from dichloromethane (3×10 ml). The resulting precipitate was washed with dichloromethane and dried in vacuo to give 100 mg (83%) of the title compound as a solid.

¹H NMR (300 MHz, DMSO-d₆) δ 12.31 (s, 1H), 7.79 (t, J=8, 1H), 7.48 (d, J=8, 1H), 7.42 (d, J=8, 1H), 4.74 (d, J=15, 1H), 4.56 (d, J=15, 1H), 3.95 (s, 3H), 3.91–3.79 (m, 2H), 3.69–3.63 (m, 1H), 2.98 (d, J=17, 1H), 2.57 (dd, J=17, 10, 1H).

LC-MS: $R_t$=1.26 min, [M+H]⁺=461.0

HPLC (254.4 nm): $R_t$=3.10 min, 100%

Example 17

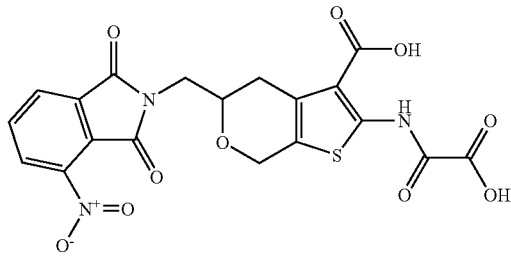

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid In a 50-ml round-bottom flask, a suspension of 2-amino-5-(1,3-dioxo-1,3-dihydro-isoindol-2-ylmethyl)-4,7-dihydro-5H-thieno[2,3-c]pyran-3-carboxylic acid tert-butyl ester (2.00 g, 4.8 mmol) in absolute ethanol (20 ml) was flushed with nitrogen and sealed with a rubber septum. Hydrazine (0.5 ml, 15.9 mmol) was added, followed by an additional portion of absolute ethanol (20 ml) at room temperature. The reaction mixture was heated to 80° C. for 3.5 h., then allowed to stir at room temperature for 14 h. The precipitate was filtered off and washed with absolute ethanol. The filtrate was concentrated in vacuo leaving an oil, which was dissolved in dichloromethane (30 ml) and refiltered. The solvent was evaporated in vacuo affording 1.2 g (86%) of 2-amino-5-aminomethyl-4,7-dihydro-5H-thieno[2,3-c]pyran-3-carboxylic acid tert-butyl ester as a solid.

¹H NMR (300 MHz, CDCl₃) d 5.92 (s, 2H), 4.64 (s, 2H), 3.68–3.60 (m, 1H), 2.98–2.74 (m, 3H), 2.56–2.44 (m, 1H), 1.54 (s, 9H).

MS (APCI⁺) [M+H] 285.3

In a 4-ml scintillating vial, a solution of the above 2-amino-5-aminomethyl-4,7-dihydro-5H-thieno[2,3-c]pyran-3-carboxylic acid tert-butyl ester (63 mg, 0.2 mmol) in tetrahydrofuran (2.0 ml) was treated with 3-nitro-phthalic acid (66 mg, 0.3 mmol), diisopropylethylamine (190 µl, 1.1 mmol), and 1,3-diisopropyl-carbodiimide (120 µl, 0.77 mmol). The reaction mixture was shaken vigorously for 10 seconds before being stirred at 50° C. for 43 hours and at room temperature for 20 h. The reaction mixture was diluted with ethyl acetate (25 ml) and washed with 0.5N aqueous hydrochloric acid (25 ml), saturated sodium bicarbonate (25 ml), and brine (25 ml). The organic layer was dried (MgSO₄), filtered and the solvent evaporated in vacuo affording crude 2-amino-5-(4-nitro-1,3-dioxo-1,3-dihydro-isoindol-2-ylmethyl) 4,7-dihydro-5H-thieno[2,3-c]pyran-3-carboxylic acid tert-butyl ester as a solid.

In a 4 ml scintillating vial a solution of the above crude 2-amino-5 (4-nitro-1,3-dioxo-1,3-dihydro-isoindol-2-ylmethyl)-4,7-dihydro-5H-thieno[2,3-c]pyran-3-carboxylic acid tert-butyl ester in dichloromethane (3 ml) was treated with midazol-1-yl-oxo-acetic acid tert-butyl ester (147 mg, 0.75 mmol). After stirring for 2 h. at room temperature the reaction solution was concentrated to dryness in vacuo. The residue was purified by silica gel chromatography using a mixture of hexanes/ethyl acetate (3:1) as eluant. Pure fractions were collected and the solvent evaporated in vacuo affording 30 mg (26%) of 2-(tert-butoxyoxalyl-amino)-5-(4-nitro-1,3-dioxo-1,3-dihydro-isoindol-2-ylmethyl)-4,7-dihydro-5H-thieno[2,3-c]pyran-3-carboxylic acid tert-butyl ester as a solid.

¹H NMR (300 MHz, CDCl₃) δ 8.17 (d, J=5, 1H), 8.11 (d, J=6, 1H), 7.94 (t, J=8, 1H), 4.80 (d, J=14, 1H), 4.67 (d, J=15, 1H), 4.16–3.97 (m, 3H), 3.88 (d, J=10, 1H), 3.01 (d, J=16, 1H), 2.70 (dd, J=16, 10, 1H), 1.62 (s, 9H), 1.59 (s, 9H).

In a 25 ml round bottom flask, the above 2-(tert-butoxyoxalyl-amino)-5-(4-nitro-1,3-dioxo-1,3-dihydro-isoindol-2-ylmethyl)-4,7-dihydro-5H-thieno[2,3-c]pyran-3-carboxylic acid tert-butyl ester (30 mg, 0.05 mmol) was dissolved in a mixture of 20% trifluoroacetic acid in dichloromethane (4 ml). The solution was left open to the atmosphere without stirring. After standing for 24 h. a precipitate was filtered off and washed with diethyl ether, affording after drying 22 mg (90%) of the title compound as a solid.

¹H NMR (300 MHz, DMSO-d₆) δ 12.33 (s, 1H), 8.32 (d, J=9, 1H), 8.20 (d, J=9, 1H), 8.07 (t, J=9, 1H), 4.77 (d, J=14, 1H), 4.59 (d, J=16, 1H), 4.00–3.65 (m partially obscured by water, 3H), 3.04 (d partially obscured by water, J=16, 1H), 2.63 (dd partially obscured by DMSO, J=17, 13, 1H).

HPLC (254.4 nm) $R_t$=3.33 min, 100%.

MS (APCI⁺) [M+H] 391.6

Example 18

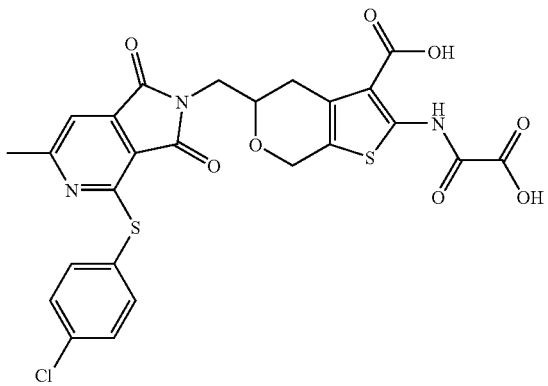

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid Under a nitrogen atmosphere, 4-(4-chloro-phenylsulfanyl)-6-methyl-pyrrolo[3,4-c]-1,3-dione (914 mg, 3.0 mmol), tributylphosphine (1.66 ml, 4.5 mmol) and 2-amino-5-hydroxymethyl-4,7-dihydro-5H-thieno[2,3-c]pyran-3-carboxylic acid tert-butyl ester (855 mg, 3.0 mmol) were successively dissolved in dry benzene (90 ml). Solid azodicarboxylic dipiperidine (1.13 g, 4.5 mmol) was added under stirring at 0° C. to the solution. After stirring for 10 min, the reaction mixture was brought to room temperature and the stirring continued for 4 h. The mixture was cooled on ice, and additional portions of tributylphosphine (1.66 ml, 4.5 mmol) and azodicarboxylic dipiperidine (1.13 g, 4.5 mmol) were added. After stirring for 10 min, the reaction mixture was brought to room temperature and the stirring continued for 18 h. Heptane (30 ml) was added to the reaction and the precipitate filtered off (discard). After evaporation of the solvent the product was purified by flash chromatography to give 1.3 g (76%) of 2-amino-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester as an oil.

Mp: 118–119° C.;

$^1$H NMR (CDCl$_3$) δ 1.55 (s, 9H), 2.50 (s, 3H), 2.50–2.65 (m, 1H), 2.85–2.95 (m, 1H), 3.75–3.85 (m, 1H), 3.95–4.05, (m, 2H), 4.50–4.15 (m, 2H), 5.95 (bs, 2H), 7.30 (s, 1H), 7.40 (d, 2H), 7.55 (d, 2H).

To an ice cooled solution of 2-amino-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester (572 mg, 1 mmol) and dry triethylamine (2 ml) in dry tetrahydrofuran (10 ml) was added imidazol-1-yl-oxo-acetic acid tert-butyl ester (588 mg, 3 mmol). After 10 min, the reaction mixture was brought to room temperature and the stirring continued for 18 h. The mixture was concentrated in vacuo and submitted to flash chromatography using a mixture of toluene/ethyl acetate (30:1) as eluant. Pure fraction were collected and the solvent evaporated in vacuo to give 360 mg (51%) of 2-(tert-butoxyoxalyl-amino)-5-(4-(4-chloro-phenylsulfanyl)-6-methyl-1,3-dioxo-1,3-dihydro-pyrrolo[3,4-c]pyridin-2-yl methyl)-4,7-dihydro-5H-thieno[2,3-c]pyran-3-carboxylic acid tert-butyl ester as a solid.

M.p.: 134–136° C.;

$^1$H NMR (CDCl$_3$) δ 1.60 (s, 9H), 1.63 (s, 9H), 2.50 (s, 3H), 2.65–2.75 (m, 1H), 2.95–3.05 (m, 1H), 3.75–3.90 (m, 1H), 4.00–4.10, (m, 2H), 4.60–4.85 (m, 2H), 7.30 (s, 1H), 7.40 (d, 2H), 7.55 (d, 2H), 12.50 (s, 1H).

To 2-(tert-butoxyoxalyl-amino)-5-(4-(4-chloro-phenylsulfanyl)-6-methyl-1,3-dioxo-1,3-dihydro-pyrrolo[3,4-c]pyridin-2-ylmethyl)-4,7-dihydro-5H-thieno[2,3-c]pyran-3-carboxylic acid tert-butyl ester (324 g, 0.46 mmol) was added a mixture of trifluoroacetic acid (2.5 ml) and dichloromethane (7.5 ml). The mixture was stirred for 5 h, and added petroleum ether/ethyl acetate. The precipitate was isolated off and re-suspended in ethyl acetate. The title compound 136 mg (50%) was isolated by filtration.

Mp: 239–240° C.;

Calculated for $C_{25}H_{18}ClN_3O_8S_2$, 0.75×H$_2$O; C, 49.92%; H, 3.27%; N, 6.99%. Found: C, 49.83%; H, 3.16%; N, 6.85%.

$^1$H NMR (CDCl$_3$) δ 2.48 (s, 3H), 2.65–2.75 (m, 1H), 2.95–3.05 (m, 1H), 3.50–4.00 (m, 3H), 4.50–4.90 (m, 2H), 7.50–7.68 (m, 5H), 12.30 (s, 1H).

Example 19

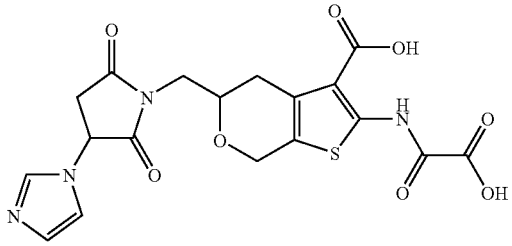

5-(3-Imidazol-1-yl-2,5-dioxo-pyrrolidin-1-ylmethyl)-2-(oxalyl-amino)-4,7-dihydro-5H-thieno[2,3-c]pyran-3-carboxylic acid To a solution of 2-amino-5-aminomethyl-4,7-dihydro-5H-thieno[2,3-c]pyran-3-carboxylic acid tert-butyl ester (0.53 g, 1.86 mmol, prepared as described in Example 17) in tetrahydrofuran (10 ml) was added, maleic acid (0.24 g, 2.05 mmol) and diisopropylcarbodiimide (0.58 ml, 3.72 mmol). The reaction mixture was heated to reflux for 3 hours and then allowed to cool to room temperature over an 18 hour period. The solvent was stripped off in vacuo and the residue diluted into ethyl acetate (50 ml). The organic phase was washed with saturated sodium bicarbonate (2×50 ml), 1% hydrochloric acid (2×20 ml), brine (3×50 ml), dried (MgSO$_4$), filtered, and the solvent evaporated in vacuo affording an oil which was subjected to flash chromatography using a mixture of ethyl acetate/hexanes (6:4) as eluant. Pure fractions (R$_f$=0.25) were collected and the solvent evaporated in vacuo to give 0.60 g (90%) of 2-amino-5-(2,5-dioxo-2,5-dihydro-pyrrol-1-ylmethyl)-4,7-dihydro-5H-thieno[2,3-c]pyran-3-carboxylic acid tert-butyl ester as an oil.

$^1$H NMR (300 MHz, CDCl$_3$) δ 7.31 (d, J=5.7, 1H), 6.63 (d, J=5.4, 1H), 5.94 (bs, 2H), 4.67 (s, 2H), 3.93 (m, 1H), 3.82 (m, 2H), 2.89–2.83 (m, 1H), 2.69–2.60 (m, 1H), 1.54 (s, 9H).

MS: APCI (+): 365.2 (M+H);

To a solution of the above 2-amino-5-(2,5-dioxo-2,5-dihydro-pyrrol-1-ylmethyl)-4,7-dihydro-5H-thieno[2,3-c]pyran-3-carboxylic acid tert-butyl ester (60 mg, 1.64 mmol) in tetrahydrofuran (2 ml) was added midazol-1-yl-oxo-acetic acid tert-butyl ester (50 mg, 2.46 mmol). The solution was stirred at room temperature for 48 h. The solvent was stripped off in vacuo and the resultant oil diluted in ethyl acetate (20 ml), washed with brine (3×25 ml), dried (MgSO$_4$), filtered and the solvent evaporated in vacuo. The residue was subjected preparative thin layer chromatography using a mixture of methanol/dichloromethane (1:9) as eluant which afforded 25 mg (28%) of 2-(tert-butoxyoxalyl-amino)-5-(3-imidazol-1-yl-2,5-dioxo-pyrrolidin-1-ylmethyl)-4,7-dihydro-5H-thieno[2,3-c]pyran-3-carboxylic acid tert-butyl ester as a mixture of diastereoisomers.

$^1$H NMR (300 MHz, CDCl$_3$) δ 7.65 (s, 1H), 6.94 (s, 1H), 5.92 (m, 1H), 5.22 (m, 1H), 4.68–4.53 (m, 2H), 4.00 (m, 3H), 3.71 (m, 1H), 3.47–3.38 (m, 1H), 3.03–2.87 (m, 1H), 2.61 (m, 1H), 1.60 (s, 9H), 1.54 (s, 9H).

MS: APCI (+): 561.2 (M+H).

To the above 2-(tert-butoxyoxalyl-amino)-5-(3-imidazol-1-yl-2,5-dioxo-pyrrolidin-1-ylmethyl)-4,7-dihydro-5H-thieno[2,3-c]pyran-3-carboxylic acid tert-butyl ester (25 mg, 0.05 mmol) was added a mixture of 20% trifluoroacetic acid in dichloromethane (2 ml). The reaction mixture was allowed to stir at room temperature for 2 h., at which time the mixture was concentrated in vacuo. The resultant solid was triturated with diethyl ether (2×) which afforded 13 mg (65%) of the title compound as a solid.

$^1$H NMR (300 MHz, CD$_3$OD) δ9.15 (s, 1H), 7.78 (s, 1H), 7.63 (m, 1H), 5.75 (m, 1H), 4.69 (m, 2H), 4.46 (m, 1H), 3.85 (m, 2H), 3.66 (m, 1H), 3.02 (m, 1H), 2.83 (m, 1H), 2.64 (m, 1H), 2.46 (m, 1H).

MS: ESI (−): 447.4 (M−H).

Example 20

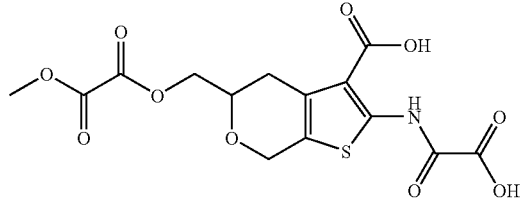

Oxalic acid 3-carboxy-2-(oxalyl-amino)-4,7-dihydro-5H-thieno[2,3-c]pyran-5-ylmethyl ester methyl To a solution of 2-amino-5-hydroxymethyl-4,7-dihydro-5H-thieno[2,3-c]pyran-3-carboxylic acid tert-butyl ester (8.0 g, 28 mmol) in dry tetrahydrofuran (50 ml) was added midazol-1-yl-oxo-acetic acid tert-butyl ester (27.51 g, 0.14 mol) and triethylamine (3.93 ml, 0.14 mol). The reaction mixture was stirred at room temperature for 20 h. The volatiles were removed in vacuo and the crude product was dissolved in ethyl acetate (300 ml) and washed with a saturated solution of sodium bicarbonate (3×100 ml), dilute hydrochloric acid (3×100 ml), water (3×100 ml) and brine (100 ml). The organic layer was dried (MgSO$_4$), filtered and the solvent removed in vacuo affording a foam (16 g) which was purified on column chromatography on silica gel using a gradient of hexane/ethyl acetate (90:10 to 50:50 gradient) as eluant. Pure fractions were collected and the solvent evaporated in vacuo which afforded 11 g (91%) of oxalic acid 2-amino-3-tert-butoxycarbonyl-4,7-dihydro-5H-thieno [2,3-c]pyran-5-ylmethyl ester tert-butyl ester as a solid.

$^1$H NMR (300 MHz, CDCl$_3$): δ 5.94 (s, 2H), 4.86 (d, J=14.7, 1H), 4.77 (d, J=14.4, 1H), 4.64 (m, 1H), 3.82–3.71 (m, 2H), 2.85 (d, J=16.8, 1H), 2.68 (d, J=10.5, 1H), 1.62 (s, 9H), 1.61 (s, 9H).

MS: 414 (M+1).

A solution of the above oxalic acid 2-amino-3-tert-butoxycarbonyl-4,7-dihydro-5H-thieno[2,3-c]pyran-5-ylmethyl ester tert-butyl ester (8.3 g, 20.1 mmol) and potassium carbonate (1.7 g, 12.3 mmol) was stirred in methanol (80 ml) in presence of water (3 ml) at room temperature for 10 min., at which time TLC indicated reaction complete. Methanol was removed in vacuo and the crude product was dissolved in dichloromethane (300 ml) and washed with water (3×150 ml). The organic phase was dried (MgSO$_4$), filtered and the solvent evaporated in vacuo. The residue was purified on flash chromatography on silica gel using a gradient of hexane/ethyl acetate (90:10 to 50:50 gradient) as eluant. Pure fractions were collected and the solvent evaporated in vacuo affording 0.65 g (9%) of oxalic acid 2-amino-3-tert-butoxycarbonyl-4,7-dihydro-5H-thieno[2,3-c]pyran-5-ylmethyl ester methyl ester as a solid.

$^1$H NMR (300 MHz, CDCl$_3$): δ4.86 (d, J=15, 1H), 4.78 (d, J=15, 1H), 4.00 (s, 3H), 3.82–3.70 (m, 3H), 2.86 (d, J=17, 1H), 2.66 (dd, J=10.2, J=10.5, 1H), 1.62 (s, 9H).

MS: 316 (M−55).

To a solution of the above oxalic acid 2-amino-3-tert-butoxycarbonyl-4,7-dihydro-5H-thieno[2,3-c]pyran-5-ylmethyl ester methyl ester (160 mg, 0.43 mmol) in dry tetrahydrofuran (3.0 ml) was added midazol-1-yl-oxo-acetic acid tert-butyl ester (420.4 mg, 2.15 mmol) and triethylamine (120 μl, 0.86 mmol). The resulting mixture was stirred at room temperature for 20 h. The solvent was evaporated in vacuo and the crude product was purified by flash chromatography on silica gel using a gradient of hexane/ethyl acetate (95:5 to 80:20 gradient) as eluant. Pure fractions were collected and the solvent evaporated in vacuo affording 173 mg (81%) of oxalic acid 2-amino-3-tert-butoxycarbonyl-2-(tert-butoxyoxalyl-amino)-4,7-dihydro-5H-thieno[2,3-c]pyran-5-ylmethyl ester methyl ester as a solid.

$^1$H NMR (300 MHz, CDCl$_3$): δ 4.81 (dd, J=14.7, J=14.2, 2H), 4.40 (m, 2H), 4.00 (s, 3H), 2.96 (d, J=15.3, 1H), 2.69 (dd, J=10.8, J=10.8, 1H), 1.61 (s, 9H), 1.57 (s, 9H).

MS: 388.3 (M−11).

The above oxalic acid 2-amino-3-tert-butoxycarbonyl-2-(tert-butoxyoxalyl-amino)-4,7-dihydro-5H-thieno[2,3-c]pyran-5-ylmethyl ester methyl ester (93.8 mg, 0.19 mmol) was stirred in 20% trifluoroacetic acid in dichloromethane (2 ml) for 20 h. at room temperature. The solvent was removal in vacuo which afforded 73 mg (95%) of the title compound as a solid.

$^1$H NMR (300 MHz, CD$_3$OD): δ 4.76 (d, J=5.7, 2H), 4.18 (d, J=4.8, 2H), 3.97 (s, 3H), 2.99 (d, J=16.2, 1H), 2.65 (d, J=10.8, 1H).

MS: 386 (M−1).

Example 21

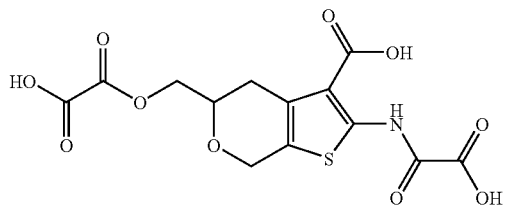

Oxalic acid (3-carboxy-2-(oxalyl-amino)-4,7-dihydro-5H-thieno[2,3-c]pyran-5-ylmethyl)ester To a solution of a mixture of 2-amino-5-hydroxymethyl-4,7-dihydro-5H-thieno[2,3-c]pyran-3-carboxylic acid tert-butyl ester and 2-amino-7-hydroxymethyl-4,7-dihydro-5H-thieno[2,3-c]pyran-3-carboxylic acid tert-butyl ester (1:4 estimated based on $^1$H NMR) (200 mg, 0.70 mmol) and diisopropylethylamine (0.25 ml, 1.4 mmol) in dichloromethane (6.0 ml) cooled to 0° C. under nitrogen was added triethylchlorosilane (0.18 ml, 1.1 mmol). The solution was stirred at 0° C. for 5 min. and then stirred at room temperature for 15 min. The solution was washed with saturated sodium bicarbonate and brine, dried (MgSO$_4$), filtered and the solvent evaporated in vacuo. The residue was purified by silica gel chromatography using a 5% mixture of ethyl acetate/hexane as eluant. Pure fractions were collected and the solvent evaporated in vacuo affording 42 mg (16%) of 2-amino-5-triethylsilanyloxymethy-4,7-dihydro-5H-thieno [2,3-c]pyran-3-carboxylic acid tert-butyl ester (1) and 193 mg (69%) of 2-amino-7-triethylsilanyloxymethy-4,7-dihydro-5H-thieno[2,3-c]pyran-3-carboxylic acid tert-butyl ester (2).

(1) $^1$H NMR (CDCl$_3$): δ 4.58 (m, 1H), 4.18–4.07 (m, 1H), 3.84 (dd, 1H, J=9.6, 6.0 Hz); 3.80–3.70 (m, 1H), 3.60 (dd, 1H, J=9.6, 7.8 Hz), 2.92–2.70 (m, 2H), 1.58 (s, 9H), 0.98 (t, 9H, J=7.8 Hz), 0.64 (q, 6H, J=7.8 Hz);

(2) $^1$H NMR (CDCl$_3$): δ 4.62 (s, 2H), 3.85–3.64 (m, 3H), 2.82 (dm, 1H, J=15 Hz), 2.49 (dd, 1H, J=15, 11 Hz), 1.58 (s, 9H), 0.98 (t, 9H, J=7.8 Hz), 0.64 (q, 6H, J=7.8 Hz).

To a solution of 2-amino-7-triethylsilanyloxymethy-4,7-dihydro-5H-thieno[2,3-c]pyran-3-carboxylic acid tert-butyl ester (6.0 g, 15 mmol) in dichloromethane (10 ml) cooled to 0° C. under the nitrogen was added a solution of imidazol-1-yl-oxo-acetic acid tert-butyl ester (4.5 g, 18 mmol) in dichloromethane. The solution was stirred at 0° C. for 10 min. The reaction was quenched with water (1.0 ml). The solution was washed with brine and dried (MgSO$_4$), filtered and the solvent evaporated in vacuo. The residue was purified by silica gel chromatography using a 10% mixture of ethyl acetate/hexane as eluant. Pure fractions of two compounds were collected and the solvent evaporated in vacuo affording 4.5 g (56%) of 2-(tert-butoxyoxalyl-amino)-7-triethylsilanyloxymethyl-4,7-dihydro-5H-thieno[2,3-c] pyran-3-carboxylic acid tert-butyl ester (A) as a solid and 50 mg of oxalic acid 3-(tert-butoxycarbonyl-2-(tert-butoxyox alyl-amino)-4,7-dihydro-5H-thieno[2,3-c]pyran-3-carboxylic acid tert-butyl ester (B) as a solid.

(A) ¹H NMR (CDCl₃): δ 12.53 (s, 1H), 4.85 (d, 1H, J=12 Hz), 4.65 (d, 1H, J=12 Hz), 3.90–3.60 (m, 3H), 2.94 (d, 1H, J=15 Hz), 2.63 (dd, 1H, J=15, 11 Hz), 1.63 (s, 9H), 1.61 (s, 9H), 0.98 (t, 9H, J=7.8 Hz), 0.64 (q, 6H, J=7.8 Hz).

(B) ¹H NMR (CDCl₃): δ 12.47 (s, 1H), 4.82 (q, 2H, J=14 Hz), 4.43 (m, 2H), 4.01 (m, 1H), 2.97 (d, 1H, J=14 Hz), 2.69 (dd, 1H, J=19, 9 Hz), 1.63 (s, 9H), 1.61 (s, 9H), 1.58 (s, 9H).

To a solution of the above 2-(tert-butoxyoxalyl-amino)-7-triethylsilanyloxymethyl-4,7-dihydro-5H-thieno[2,3-c]pyran-3-carboxylic acid tert-butyl ester (4.5 g, 8.5 mmol) in tetrahydrofuran (10 ml) at room temperature was added 0.5 N hydrochloric acid (2.0 ml). The solution was stirred at room temperature for 0.5 h. Ethyl acetate (100 ml) was added and the resulting solution was washed with saturated sodium bicarbonate, brine, dried (MgSO₄), filtered and the solvent evaporated in vacuo. The residue was purified by silica gel chromatography using a 10% mixture of ethyl acetate/hexane as eluant. Pure fractions were collected and the solvent evaporated in vacuo affording 3.0 g (84%) of 2-(tert-butoxyoxalyl-amino)-7-hydroxymethyl-4,7-dihydro-5H-thieno[2,3-c]pyran-3-carboxylic acid tert-butyl ester as a solid.

¹H NMR (CDCl₃): δ 12.53 (s, 1H), 4.86 (d, 1H, J=12 Hz), 4.60 (d, 1H, J=12 Hz), 3.85–3.65 (m, 3H), 2.85 (d, 1H, J=15 Hz), 2.65 (dd, 1H, J=15, 11 Hz), 1.63 (s, 9H), 1.61 (s, 9H).

To a solution of the above 2-(tert-butoxyoxalyl-amino)-7-hydroxymethyl-4,7-dihydro-5H-thieno[2,3-c]pyran-3-carboxylic acid tert-butyl ester (3.0 g, 7.1 mmol) in dichloromethane (10 ml) at room temperature was added pyridine (2.5 ml, 28.5 mmol) and 4-nitro-benzenesulfonyl chloride (4.7 g, 21.4 mmol). The solution was heated to 50° C. and stirred for 4.5 h. The solution was cooled to room temperature and washed with 0.5 N hydrochloric acid, saturated sodium bicarbonate, brine, dried (MgSO₄), filtered and the solvent evaporated in vacuo. The residue was purified by silica gel chromatography using a gradient of ethyl acetate/hexane (0–100%) as eluant. Pure fractions were collected and the solvent evaporated in vacuo affording 3.6 g (84%) of 2-(tert-butoxyoxalyl-amino)-7-(4-nitro-benzenesulfonyloxymethyl)-4,7-dihydro-5H-thieno[2,3-c]pyran-3-carboxylic acid tert-butyl ester as a solid.

¹H NMR (CDCl₃): δ 12.40 (s, 1H), 8.43 (d, 2H, J=9.0 Hz), 8.17 (d, 2H, J=9.0 Hz), 4.72 (d, 1H, J=14 Hz), 4.64 (d, 1H, J=14 Hz), 4.38–4.24 (m, 2H), 3.98–3.86 (m, 1H), 2.92 (d, 1H, J=17 Hz), 2.65 (dd, 1H, J=17, 12 Hz), 1.63 (s, 9H), 1.61 (s, 9H).

MS: 598 (M−1).

To a solution of 50% trifluoroacetic acid/dichloromethane (1 ml) at room temperature was added oxalic acid 3-(tert-butoxycarbonyl-2-(tert-butoxyoxalyl-amino)-4,7-dihydro-5H-thieno[2,3-c]pyran-3-carboxylic acid tert-butyl ester (50 mg, 0.092 mmol). The solution was stirred for 3 hours. The solvent was removed in vacuo. The residue was washed with dichloromethane affording after filtration 25 mg (73%) of the title compound as a solid.

¹H NMR (DMSO-d₆): δ12.32 (s, 1H), 4.82 (d, 1H, J=15 Hz), 4.68 (d, 1H, J=15 Hz), 4.37 (s, 1H), 3.92 (m, 1H), 2.93 (d, 1H, J=16 Hz), 2.60 (dd, 1H, J=30, 10 Hz).

MS: 372 (M−1).

Example 22

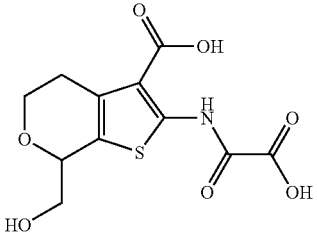

7-Hydroxymethyl-2-(oxalyl-amino)-4,7-dihydro-5H-thieno[2,3-c]pyran-3-carboxylic acid To a mixture of 2-hydroxymethyl-tetrahydro-pyran-4-one (35 g, 0.27 mol), tert-butyl cyanoacetate (58.68 ml g, 0.4 mol), and sulphur (9.47 g, 0.3 mol) in absolute ethanol (400 ml) was added morpholin (47 ml, 0.54 mol), and the resulting mixture was heated to 45° C. for 16 h. The reaction mixture was cooled, filtered and the filtrate evaporated in vacuo. The resultant oil was dissolved in ethyl acetate (600 ml), washed with water (3×200 ml), brine (200 m), dried (Na₂SO₄), filtered and the solvent evaporated in vacuo. The residue was crystallised from diethyl ether (100 ml) followed by addition of a mixture of diethyl ether and heptane (100 ml, 1:1). The precipitate was filtered off, washed with a mixture of diethyl ether and heptane (90 ml, 1:1) and dried in vacuo at 50° C. for 52 h affording 44.51 g of a mixture of 5 and 7 regioisomers according to NMR. The mixture of regioisomers (44.51 g) was suspended in diethyl ether (500 ml) and stirred at room temperature for 96 h. and at reflux temperature for 2 h. After cooling to room temperature the precipitate was filtered off and washed with a mixture of diethyl ether and heptane (100 ml, 1:1) which afforded after drying in vacuo at 50° C., 22.12 g (29%) of 2-amino-5-hydroxymethyl-4,7-dihydro-5H-thieno[2,3-c]pyran-3-carboxylic acid tert-butyl ester as a solid.

All filtrates were pooled and evaporated in vacuo affording 55 g of a mixture of regioisomers. To 40.16 g (0.141 mol) of this regioisomer mixture dissolved in dichloromethane (450 ml) was added diisopropyl-ethylamine (49.5 ml, 0.28 mol) and the mixture was cooled to 0° C. Chlorothiethylsilane (38.2 ml, 0.23 mol) was added dropwise and the mixture was stirred for 10 minutes and for 15 minutes at room temperature. The reaction mixture was washed with saturated aqueous sodium carbonate (3×150 ml), brine (3×150 ml), dried (Na₂SO₄), filtered and the solvent evaporated in vacuo. The residue (70.4 g) was partitioned into two portions which were subjected to flash chromatography (2 l silicagel) using a mixture of ethyl acetate/hexane (1:20) as eluant. Pure fractions of 2-amino-5-triethylsilanyloxymethyl-4,7-dihydro-5H-thieno[2,3-c]pyran-3-carboxylic acid tert-butyl ester and 2-amino-7-triethylsilanylhydroxymethyl-4,7-dihydro-5H-thieno[2,3-c]pyran-3-carboxylic acid tert-butyl ester were collected. A fraction containing both isomers (18.84 g) was re-subjected to flash chromatography (2 l silicagel) using a mixture of ethyl acetate/hexane (1:20) as eluant. A total of 28.1 g (50%) of 2-amino-5-triethylsilanylhydroxymethyl-4,7-dihydro-5H-thieno[2,3-c]pyran-3-carboxylic acid tert-butyl ester was obtained. A total of 18.2 g (32%) of 2-amino-7-triethylsilanylhydroxymethyl-4,7-dihydro-5H-thieno[2,3-c]pyran-3-carboxylic acid tert-butyl ester was obtained.

To the above 2-amino-7-triethylsilanylhydroxymethyl-4,7-dihydro-5H-thieno[2,3-c]pyran-3-carboxylic acid tert-butyl ester (18.2 g, 0.046 mol) dissolved in dichloromethane (200 ml) was added a mixture of imidazol-1-yl-oxo-acetic acid tert butyl ester (17.9 g, 0.091 mol) in dichloromethane (30 ml) under nitrogen. The reaction mixture was allowed to stir at room temperature for 18 h. The reaction mixture was evaporated in vacuo and the residue was dissolved in ethyl acetate (100 ml) and washed with 1 N hydrochloric acid (3×50 ml), brine (3×75 ml), dried (Na$_2$SO$_4$), filtered and the organic phase evaporated in vacuo affording in quantitative yield 2-(tert-butoxyoxalyl-amino)-7-triethylsilanyloxymethyl-4,7-dihydro-5H-thieno[2,3-c]pyran-3-carboxylic acid tert-butyl ester ester as a oil.

To a mixture of the above 7-triethylsilanyl ether (24.0 g, 0.046 mol) in tetrahydrofuran (100 ml) was added 1 N hydrochloric acid (18 ml) and the reaction mixture was stirred at room temperature for 1.5 h. Ethyl acetate (150 ml) was added and the reaction mixture was washed with saturated aqueous sodium carbonate (3×100 ml), brine (3×100 ml), dried (Na$_2$SO$_4$), filtered and the solvent evaporated in vacuo. The residue was tritituated with a mixture of diethyl ether and heptane (1:5) and the precipitate was filtered off, washed with heptane and dried in vacuo at 50.° C. for 16 h affording 13.55 g (57%) of 2-(tert-butoxyoxalyl-amino)-7-hydroxymethyl-4,7-dihydro-5H-thieno[2,3-c]pyran-3-carboxylic acid tert-butyl ester as a solid.

The above 2-(tert-butoxyoxalyl-amino)-7-hydroxymethyl-4,7-dihydro-5H-thieno[2,3-c]pyran-3-carboxylic acid tert-butyl ester (16 mg, 0.033 mmol) was dissolved in 50% trifluoroacetic acid in dichloromethane (1 ml). The reaction was stirred at room temperature for 3 hours. The volatiles were evaporated in vacuo and the residue washed with dichloromethane which afforded 7 mg (73%) of the title compound as a solid.

$^1$H NMR (DMSO-d$_6$): δ 12.32 (s, 1H), 4.62 (s, 1H), 4.12 (m, 1H), 3.62–3.78 (m, 2H), 3.40–3.52 (m, 1H), 2.83 (m, 2H).

MS: 300 (M−1).

Example 23

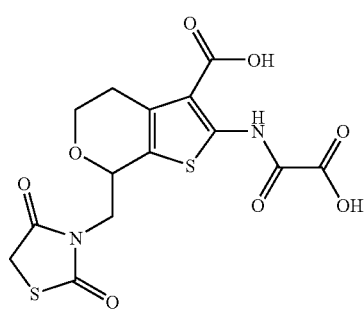

7-(2,4-Dioxo-thiazolidin-3-ylmethyl)-2-(oxalyl-amino)-4,7-dihydro-5H-thieno[2,3-c]pyran-3-carboxylic acid To a solution of 2-amino-7-hydroxymethyl-4,7-dihydro-5H-thieno[2,3-c]pyran-3-carboxylic acid tert-butyl ester (0.13 g, 0.46 mmol) in tetrahydrofuran (3 ml) was added triphenylphosphine (0.13 g, 0.51 mmol), and 2,4-thiazolidinedione (60 mg, 0.51 mmol). The reaction mixture was cooled to 0° C. and diisopropylazodicarboxylate (99 μL, 0.51 mmol) was added via syringe. The resultant mixture was stirred for 18 hours, gradually warming to room temperature. The volatiles were evaporated in vacuo and the resulting oil was diluted in ethyl acetate (50 ml). The organic phase was washed with saturated sodium bicarbonate (3×50 ml), brine (3×50 ml), dried (MgSO$_4$), filtered and the solvent evaporated in vacuo. The residue was subjected to flash chromatography using a mixture of dichloromethane/methanol (9:1) as eluant. Pure fractions were collected (R$_f$=0.70) and the solvent evaporated in vacuo which afforded 89 mg (51%) of 2-amino-7-(2,4-dioxo-thiazolidin-3-ylmethyl)-4,7-dihydro-5H-thieno[2,3-c]pyran-3-carboxylic acid tert-butyl ester as an oil.

$^1$H NMR (300 MHz, CDCl$_3$) δ 6.02 (s, 2H), 4.82 (dm, 1H), 4.13–4.02 (bm, 2H), 3.99 (s, 2H), 3.75–3.67 (m, 1H), 3.60 (dd, 1H, J=14, 3.3,), 2.81–2.74 (m, 2H), 1.54 (s, 9H).

MS: APCI (+): 385.6 (M+H).

To a solution of the above of 2-amino-7-(2,4-dioxo-thiazolidin-3-ylmethyl)-4,7-dihydro-5H-thieno[2,3-c]pyran-3-carboxylic acid tert-butyl ester (89 mg) in tetrahydrofuran (5 ml) was added imidazol-1-yl-oxo-acetic acid tert-butyl ester (79 mg, 0.312 mmol) and the mixture allowed to stir overnight at room temperature. The volatiles were evaporated in vacuo, the residue diluted with ethyl acetate and subjected to preparative chromatography using a mixture of dichloromethane/methanol (9:1) as eluant. Material eluting with R$_f$=0.72 was collected and the solvent evaporated in vacuo affording 40 mg (25%) of 2-(tert-butoxyoxalyl-amino)-7-(2,4-dioxo-thiazolidin-3-ylmethyl)-4,7-dihydro-5H-thieno[2,3-c]pyran-3-carboxylic acid tert-butyl ester as an oil.

$^1$H NMR (300 MHz, CDCl$_3$) δ 12.53 (s, 1H), 5.03 (dm, 1H), 4.12–4.04 (m, 2H), 4.01 (s, 2H), 3.79–3.71 (m, 2H), 2.88 (m, 2H), 1.62 (s, 9H), 1.59 (s, 9H).

MS: APCI (+): 513.3 (M+H).

The above 2-(tert-butoxyoxalyl-amino)-7-(2,4-dioxo-thiazolidin-3-ylmethyl)-4,7-dihydro-5H-thieno[2,3-c]pyran-3-carboxylic acid tert-butyl ester (40 mg) was dissolved in 50% trifluoroacetic acid in dichloromethane (1 ml) and stirred at room temperature for 3 hours. The mixture was concentrated in vacuo, the residue titurated with dichloromethane and methanol which afforded after drying in vacuo 18 mg (87%) of the title compound as a solid.

$^1$H NMR (300 MHz, DMSO-d$_6$+CD$_3$OD) δ 4.98 (dm, 1H), 4.16 (s, 2H), 4.14–4.02 (m, 2H), 3.78–3.72 (m, 2H), 2.91 (m, 2H).

APCI (−): 399 (M−H);
LC-MS: s, 99%.

Example 24

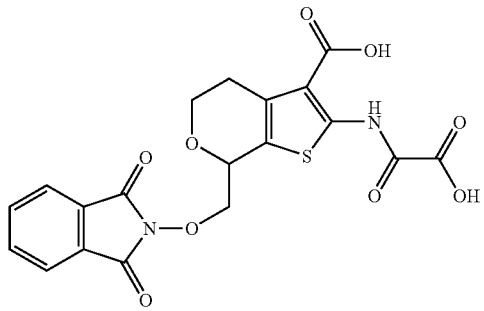

7-(1,3-Dioxo-1,3-dihydro-isoindol-2-yloxymethyl)-2-(oxalyl-amino)-4,7-dihydro-5H-thieno[2,3-c]pyran-3-carboxylic acid To a mixture of 2-(tert-butoxyoxalyl-amino)-7-hydroxymethyl-4,7-dihydro-5H-thieno[2,3-c]pyran-3-carboxylic acid tert-butyl ester (0.5 g, 1.2 mmol), 2-hydroxyisoindole-1,3-dione (0.21 g, 1.3 mmol) and triphenylphosphine (0.35 g, 1.33 mmol) in dry tetrahydrofuran (20 ml) cooled to 0° C. under a nitrogen atmosphere was added diethyl azodicarboxylate (DEAD) (205 μl, 1.33 mmol). The reaction mixture was allowed to stir overnight, slowly warming to room temperature. The volatiles were evaporated in vacuo and the resultant solid dissolved in ethyl acetate (50 ml). The organic phase was washed with saturated aqueous sodium hydrogencarbonate (3×30 ml), water (3×50 ml), dried (Na$_2$SO$_4$), filtered and evaporated in vacuo. The residue (1.02 g) was subjected to flash column chromatography (300 ml silicagel) using a mixture of ethyl acetate/hexane (1:2) as eluant. Pure fractions were collected affording after evaporation in vacuo 0.37 g (54%) of 2-(tert-butoxyoxalyl-amino)-7-(1,3-dioxo-1,3-dihydro-isoindol-2-yloxymethyl)-4,7-dihydro-5H-thieno[2,3-c]pyran-3-carboxylic acid tert-butyl ester as an oil.

The above di-tert-butyl ester (0.33 g, 0.59 mmol) was dissolved in 25% trifluoroacetic acid in dichloromethane (2 ml). The reaction was stirred at room temperature for 6.5 h. The volatiles were evaporated in vacuo and the residue triturated with a mixture of diethyl ether and heptane (5 ml, 1:1). The precipitate was filtered off, washed with heptane and diethyl ether, dried in vacuo at 50° C. for 18 h which afforded 200 mg (77%) of the title compound as a solid.

M.p.: 251.5–254° C.;

Calculated for C$_{19}$H$_{14}$N$_2$O$_9$S; C, 51.12%; H, 3.16%; N, 6.28%. Found: C, 51.46%; H, 3.71%; N, 5.87%.

Example 25

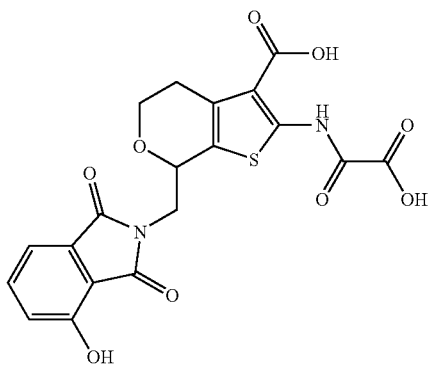

7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid To a solution of 4-hydroxy-isobenzofuran-1,3-dione (0.5 g, 3.03 mmol) in anhydrous N,N-dimethylformamide (6 ml) under nitrogen was added diisopropylethylamine (1.05 ml, 6.06 mmol). The solution was stirred with cooling in an ice bath and chloromethyl methyl ether (0.46 ml, 6.06 mmol) was added. The reaction was allowed to slowly warm to ambient temperature and then stirred for an additional 7 h. The mixture was concentrated in vacuo to a small volume and diluted with ethyl acetate (75 ml). The organic layer was washed with water (2×40 ml), brine (20 ml), dried (Na$_2$SO$_4$), filtered, and the solvent evaporated in vacuo to give 0.6 g (95%) of 4-methoxymethoxy-isobenzofuran-1,3-dione as a solid.

$^1$H NMR (400 MHz, CDCl$_3$) δ 7.81 (t, J=8, 1H), 7.62 (d, J=8, 1H), 7.59 (d, J=8, 1H), 5.43 (s, 2H), 3.55 (s, 3H).

A mixture of 2-amino-7-aminomethyl-4,7-dihydro-5H-thieno[2,3-c]pyran-3-carboxylic acid tert-butyl ester (0.15 g, 0.53 mmol) and 4-methoxymethoxy-isobenzofuran-1,3-dione (135 mg, 0.64 mmol) was dissolved in distilled acetonitrile (7 ml) under nitrogen. The flask was cooled in an ice bath with stirring and 1-(3-dimethylaminopropyl)-3-ethyl-carbodiimide hydrochloride (0.12 g, 0.64 mmol), and triethylamine (0.22 ml, 1.59 mmol) were added. The reaction was warmed to ambient temperature and stirred for 18 h. The solution was concentrated in vacuo and the residue dissolved in ethyl acetate (40 ml). The organic layer was washed with 1% hydrochloric acid (2×10 ml), saturated sodium bicarbonate (10 ml), and brine (10 ml). The resulting solution was dried (Na$_2$SO$_4$), filtered, and the solvent evaporated in vacuo which afforded 0.18 g of a crude 2-amino-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester which was used without further purification.

$^1$H NMR (400 MHz, CDCl$_3$) δ 7.65–7.58 (m, 2H), 7.51 (d, J=8, 1H), 6.00–5.86 (2s, 2H), 5.39 (s, 2H), 4.94–4.89 (m, 1H), 4.18–4.02 (m, 2H), 3.86–3.65 (m, 2H), 3.54 (s, 3H), 2.85–2.73 (m, 2H), 1.55 (s, 9H).

APCI-MS: [M+H]$^+$=475.4

To a solution of crude 2-amino-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester (0.18 g) in distilled dichloromethane (4 ml) under nitrogen was added midazol-1-yl-oxo-acetic acid tert-butyl ester (0.23 g, 1.2 mmol). The reaction was stirred for 3 hours., concentrated in vacuo and reconstituted in ethyl acetate (30 ml). The organic layer was washed with 1% hydrochloric acid (2×5 ml), saturated sodium bicarbonate (5 ml), and brine (5 ml). The resulting solution was dried (Na$_2$SO$_4$), filtered, and the solvent evaporated in vacuo. The crude material was purified by silica gel chromatography using a gradient of ethyl acetate/dichloromethane (0 to 5% gradient) as eluant. Pure fractions were collected and the solvent evaporated in vacuo to give 90 mg (28% in two steps) of 2-(tert-butoxyoxalyl-amino)-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester as an oil.

$^1$H NMR (400 MHz, CDCl$_3$) δ 12.54 (s, 1H), 7.64 (t, J=8, 1H), 7.51 (d, J=8, 1H), 7.46 (d, J=8, 1H), 5.40 (s, 2H), 5.11–5.07 (m, 1H), 4.16–4.08 (m, 2H), 3.84–3.72 (m, 2H), 3.55 (s, 3H), 2.95–2.81 (m, 2H), 1.62 (s, 9H), 1.59 (s, 9H).

APCI-MS: [M+H]$^+$=603.8

The above 2-(tert-butoxyoxalyl-amino)-7-(4-methoxymethoxy-1,3-dioxo-1,3-dihydro-isoindol-2-ylmethyl)-4,7-dihydro-5H-thieno[2,3-c]pyran-3-carboxylic acid tert-butyl ester (86 mg, 0.143 mmol) was dissolved in a solution of 50% trifluoroacetic acid/dichloromethane (4 ml). The reaction was stirred at ambient temperature for 7 h., concentrated in vacuo and evaporated in vacuo from dichloromethane (3×10 ml). The resulting precipitate was washed with dichloromethane and dried in vacuo to give 55 mg (86%) of the title compound as a solid.

$^1$H NMR (400 MHz, d$_6$-DMSO) δ 12.34 (s, 1H), 11.10 (s, 1H), 7.63 (t, J=8, 1H), 7.31 (d, J=8, 1H), 7.22 (d, J=8, 1H), 4.99–4.95 (m, 1H), 4.05–4.00 (m, 1H), 3.91–3.86 (m, 1H), 3.76–3.66 (m, 2H), 2.88–2.80 (m, 2H).

APCI-MS: [M+H]$^+$=447.4

HPLC (254.4 nm): R$_t$=2.921 min, 100%

Example 26

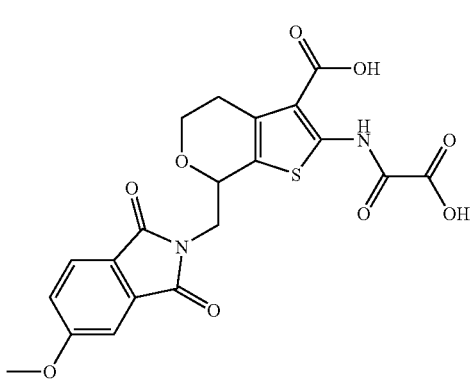

7-(5-Methoxy-1,3-dioxo-1,3-dihydro-isoindol-2-ylmethyl)-2-(oxalyl-amino)-4,7-dihydro-5H-thieno[2,3-c]pyran-3-carboxylic-acid The title compound was prepared in a similar way as described in Example 25.

M.p.: 234–236° C.;

Calculated for $C_{20}H_{16}N_2O_9S$, $0.25 \times H_2O$; C, 51.67%; H, 3.58%; N, 6.03%. Found: C, 51.95%; H, 3.92%; N, 6.06%.

Example 27

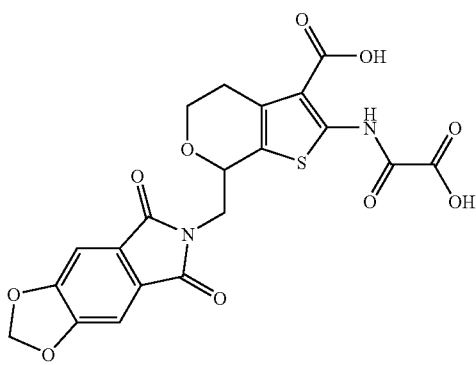

7-(5,7-Dioxo-5,7-dihydro-[1,3]dioxolo[4,5-f]isoindol-6-ylmethyl2-(oxalyl-amino)-4,7-dihydro-5H-thieno[2,3-c]pyran-3-carboxylic acid The title compound was prepared in a similar way as described in Example 25.

M.p.: 239.5–242.5° C.;

Calculated for $C_{20}H_{14}N_2O_{10}S$, $0.1 \times H_2O$; C, 50.45%; H, 3.01%; N, 5.88%. Found: C, 51.06%; H, 3.43%; N, 5.93%.

Example 28

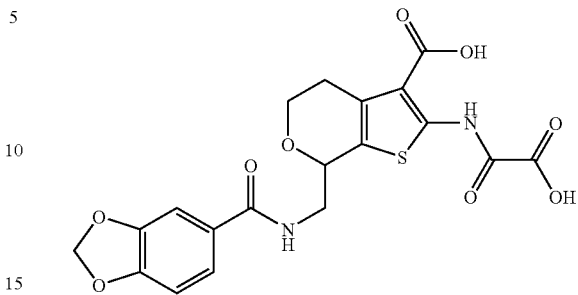

7-(((Benzo[1,3]dioxole-5-carbonyl)-amino)-methyl)-2-(oxalyl-amino)-4,7-dihydro-5H-thieno[2,3-c]pyran-3-carboxylic acid Phthalimidoacetaldehyde diethyl acetal (100 g, 0.38 mol) and 1 N hydrochloric acid (600 ml) was mixture was stirred at reflux temperature for 5 min. or until a homogeneous solution is obtained. The reaction mixture was cooled and the precipitate was filtered off and dried in vacuo at 50° C. for 16 h which afforded 63.3 g (88%) of phthalimidoacetaldehyde as a solid.

$^1$H NMR (300 MHz, CDCl$_3$) δ 4.58 (s, 2H), 7.76–7.78 (m, 2H), 7.90–7.92 (m, 2H), 9.67 (s, 1H).

To a mixture of phthalimidoacetaldehyde (64 g, 0.34 mol) and trans-1-methoxy-3-(trimethylsilyloxy)-1,3-butadiene (81.5 g, 0.38 mol) in benzene (600 ml) stirred for 15 min. under nitrogen was added dropwise a 45% solution of zinc chloride diethyl ether complex in dichloromethane (55.5 ml, 0.17 mol) at 0° C. The reaction was allowed warm up to room temperature overnight. To the reaction mixture was added water (500 ml) and the resulting mixture was extracted with ethyl acetate (200 ml). The organic extract was washed successively with 1.0 N hydrochloric acid (2×200 ml) and brine (200 ml). The organic phase was dried (Na$_2$SO$_4$), filtered and the solvent evaporated in vacuo which afforded a slowly crystallising oil (98 g). To the solid was added a mixture of ethyl acetate and diethyl ether (400 ml, 1:1) and the resulting precipitate was filtered off, washed with a small portion of diethyl ether and dried at 50° C. for 1 h affording 59.8 g (69% of 2-(4-oxo-3,4-dihydro-2H-pyran-2-ylmethyl)-isoindole-1,3-dione as a solid. The filtrate was evaporated in vacuo and the residue purified by column chromatography on silica gel (1 L) using a mixture of ethyl acetate and heptane (1:2) as eluant. Pure fractions were collected and the solvent evaporated in vacuo to almost dryness, the solid was filtered off and dried in vacuo at 50° C. for 16 h affording an additional 15 g (17%) of 2-(4-oxo-3,4-dihydro-2H-pyran-2-ylmethyl)-isoindole-1,3-dione as a solid.

$^1$H NMR (300 MHz, CDCl$_3$) δ 2.61 (d, 2H), 3.85 (dd, 1H), 4.18 (dd, 1H), 4.76 (m, 1H), 5.43 (d, 1H), 7.28 (d, 1H), 7.69–7.77 (m, 2H), 7.84–7.88 (m, 2H).

2-(4-Oxo-3,4-dihydro-2H-pyran-2-ylmethyl)-isoindole-1,3-dione (13 g, 0.051 mol) was dissolved in ethyl acetate (250 ml) and placed in a Parr bottle. 10% Pd/C (1.5 g) was carefully added and the mixture was shaken under a pressure of 30 psi of hydrogen for 6.5 h (Parr apparatus). Filtration followed by evaporation of the ethyl acetate in vacuo afforded a crude 11.5 g of 2-(4-oxo-tetrahydro-pyran-2- ylmethyl)-isoindole-1,3-dione pure enough for the next step. Analytical pure compound could be obtained by purification of a small sample (250 mg) by column chromatography on silica gel, utilising a mixture of hexane/ethyl acetate as a gradient (from 100/0 to 50/50). Pure fractions were collected and the solvent evaporated in vacuo affording 142 mg (55%) of 2-(4-oxo-tetrahydro-pyran-2-ylmethyl)-isoindole-1,3-dione as a solid.

$^1$H NMR (400 MHz, CDCl$_3$) δ 2.30–2.68 (m, 4H), 3.62 (m, 1H), 3.74 (m, 1H), 4.00 (m, 2H), 7.75 (m, 2H), 7.88 (m, 2H).

To a mixture of 2-(4-oxo-tetrahydro-pyran-2-ylmethyl)-isoindole-1,3-dione (11.5 g, 44 mmol), tert-butyl cyanoacetate (6.9 g, 49 mmol) and elemental sulfur (1.6 g, 49 mmol) in ethanol (250 ml) was added morpholin (15 ml) and the resulting mixture was stirred at 50° C. for 16 h. The cooled reaction mixture was filtered and the precipitate filtered off and washed with diethyl ether and dried in vacuo affording 6.5 g (35%) of 2-amino-5-(1,3-dioxo-1,3-dihydro-isoindol-2-ylmethyl)-4,7-dihydro-5H-thieno[2,3-c]pyran-3-carboxylic acid tert-butyl ester as a solid.

The filtrate was evaporated in vacuo and the residue was dissolved in ethyl acetate (200 ml) washed with water (2×100 ml), brine (100 ml), dried (Na$_2$SO$_4$), filtered and the solvent evaporated in vacuo affording 6.0 g (33%) of almost regioisomer pure 2-amino-7-(1,3-dioxo-1,3-dihydro-isoindol-2-ylmethyl)-4,7-dihydro-5H-thieno[2,3-c]pyran-3-carboxylic acid tert-butyl ester as a solid.

2-amino-5-(1,3-dioxo-1,3'-dihydro-isoindol-2-ylmethyl)-4,7-dihydro-5H-thieno[2,3-c]pyran-3-carboxylic acid tert-butyl ester $^1$H NMR (300 MHz, CDCl$_3$) δ1.50 (s, 9H), 2.54–2.63 (m, 1H), 2.84–2.90 (m, 1H), 3.79 (q, 1H), 3.96–4.04 (m, 2H), 4.48–4.62 (m, 2H), 5.91 (bs, 2H, NH$_2$), 7.70 (m, 2H), 7.84 (m, 2H).

2-amino-7-(1,3-dioxo-1,3-dihydro-isoindol-2-ylmethyl)-4,7-dihydro-5H-thieno[2,3-c]pyran-3-carboxylic acid tert-butyl ester $^1$H NMR (300 MHz, CDCl$_3$) δ 1.50 (s, 9H), 2.71–2.90 (m, 2H), 3.67–3.77, (m, 2H), 4.02–4.15 (m, 2H), 4.90 (m, 1H), 6.04 (bs, 2H, NH$_2$), 7.70 (m, 2H), 7.84 (m, 2H).

To a solution of 2-amino-7-(1,3-dioxo-1,3-dihydro-isoindol-2-ylmethyl)-4,7-dihydro-5H-thieno[2,3-c]pyran-3-carboxylic acid tert-butyl ester (6.0 g, 0.014 mol) in ethanol (100 ml) was added hydrazine-hydrate (1.4 ml, 0.029 mol). The mixture was stirred at reflux temperature for 1 h. The cooled reaction mixture was filtered and the solvent evaporated in vacuo. The residue was dissolved in diethyl ether (200 ml) and washed with water (100 ml), brine (100 ml), dried (Na$_2$SO$_4$), filtered and the solvent evaporated in vacuo affording 2.9 g (71%) of 2-amino-7-aminomethyl-4,7-dihydro-5H-thieno[2,3-c]pyran-3-carboxylic acid tert-butyl ester as an oil.

To a ice cooled mixture of 2-amino-7-aminomethyl-4,7-dihydro-5H-thieno[2,3-c]pyran-3-carboxylic acid tert-butyl ester (1.4 g, 4.92 mmol), triethylamine (2 ml) in dichloromethane (100 ml) was added dropwise a solution of benzo[1,3]dioxole-5-carbonyl chloride (1.0 g, 5.41 mmol) in dichloromethane (25 ml) during 1.5 h. The ice cooled reaction mixture was stirred for an additional 0.5 h. The volatiles were evaporated in vacuo and the residue was dissolved in ethyl acetate (200 ml) and washed with water (2×100 ml), brine (100 ml), dried (Na$_2$SO$_4$), filtered and the solvent evaporated in vacuo. The residue (2 g) was subjected to flash column chromatography (1 l silicagel) using a mixture of ethyl acetate/hexane (1:2) as eluant. Pure fractions were collected affording after evaporation in vacuo 0.3 g (14%) of 2-amino-7-(((benzo[1,3]dioxole-5-carbonyl)amino)-methyl)-4,7-dihydro-5H-thieno[2,3-c]pyran-3-carboxylic acid tert-butyl ester as an oil.

TLC: R$_f$=0.44 (ethyl acetate/heptane 1:1)

A mixture of the above 2-amino-7-(((benzo[1,3]dioxole-5-carbonyl)amino)methyl)-4,7-dihydro-5H-thieno[2,3-c]pyran-3-carboxylic acid tert-butyl, ester (0.3 g, 0.69 mmol), imidazol-1-yl-oxo-acetic acid tert-butyl ester (0.16 g, 0.83 mmol) in dry tetrahydrofuran (50 ml) was stirred at room temperature for 16 h. The volatiles were evaporated in vacuo and the residue was dissolved in ethyl acetate (100 ml) and washed with water (2×50 ml), brine (50 ml), dried (Na$_2$SO$_4$), filtered and the solvent evaporated in vacuo. The residue (0.35 g) was subjected to flash column chromatography (500 ml silicagel) using a mixture of ethyl acetate/hexane (1:1) as eluant. Pure fractions were collected and the solvent evaporated in vacuo. The residue was triturated with diethyl ether (5 ml), filtered off and dried in vacuo at 50° C. for 5 h which afforded 0.17 g (44%) of 7-(((benzo[1,3]dioxole-5-carbonyl)amino)methyl)-2-(tert-butoxyoxalyl-amino)-4,7-dihydro-5H-thieno[2,3-c]pyran-3-carboxylic acid tert-butyl ester as a solid.

TLC: R$_f$=0.37 (ethyl acetate/heptane 1.1).

The above di-tert-butyl ester (0.17 g, 0.30 mmol) was dissolved in 25% trifluoroacetic acid in dichloromethane (20 ml). The reaction was stirred at room temperature for 5.5 h. The volatiles were evaporated in vacuo and the residue triturated with diethyl ether (10 ml). The precipitate was filtered off, washed with diethyl ether, dried in vacuo at 50° C. for 72 h which afforded 100 mg (74%) of the title compound as a solid.

M.p.: 277–230° C.

Calculated for $C_{19}H_{16}N_2O_9S$, 0.5×H$_2$O; C, 49.89%; H, 3.75%; N, 6.12%. Found: C, 50.02%; H, 3.68%; N, 5.98%.

Example 29

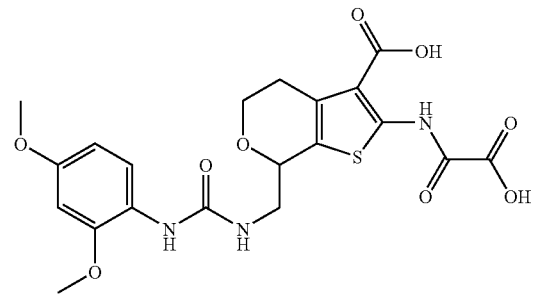

7-[3-(2,4-Dimethoxy-phenyl)-ureidomethyl]-2-(oxalyl-amino)-4,7-dihydro-5H-thieno[2,3-c]pyran-3-carboxylic acid To a solution of 2-amino-7-aminomethyl-4,7-dihydro-5H-thieno[2,3-c]pyran-3-carboxylic acid tert-butyl ester (64 mg, 0.22 mmol) in dichloromethane (1 ml) was added 2,4-dimethoxyphenylisocyanate (40 mg, 0.22 mmol). The reaction mixture was stirred at room temperature for 18 h. The reaction mixture was concentrated in vacuo, diluted with ethyl acetate (30 ml), washed with saturated sodium carbonate (3×25 ml), brine (3×25 ml), dried (MgSO$_4$), filtered and the solvent evaporated in vacuo. The residue was subjected to preparative thin layer chromatography (100% dichloromethane). $R_f$=0.8 was isolated and the solvent evaporated in vacuo which afforded 55 mg (53%) of 2-amino-7-(3-(2,4-dimethoxy-phenyl)ureidomethyl)-4,7-dihydro-5H-thieno[2,3-c]pyran-3-carboxylic acid tert-butyl ester as an oil.

$^1$H NMR (300 MHz, CDCl$_3$) δ 7.75 (d, J=9.6, 1H), 7.62 (d, J=8.1, 1H), 6.45 (m, 3H), 5.00 (bs, 2H), 4.68 (m, 1H), 4.12 (m, 2H), 3.80 (s, 3H), 3.76 (s, 3H), 3.76–3.67 (m, 1H), 3.30 (dd, J=14, 6.9, 1H), 2.76 (m, 2H), 1.55 (s, 9H).

MS: APCI (+): 464.3 (M+H).

To a solution of the above 2-amino-7-(3-(2,4-dimethoxy-phenyl)ureidomethyl)-4,7-dihydro-5H-thieno[2,3-c]pyran-3-carboxylic acid tert-butyl ester (47 mg, 0.11 mmol) in dichloromethane (1 ml) was added triethylamine (28 μl, 0.22 mmol) and midazol-1-yl-oxo-acetic acid tert-butyl ester (40 mg, 0.22 mmol). The mixture allowed to stir at room temperature for 18 h. The volatiles were evaporated in vacuo and the residue diluted with ethyl acetate (35 ml). The organic phase was washed with saturated sodium carbonate (3×25 ml), brine (3×25 ml), dried (MgSO$_4$), filtered, and the solvent evaporated in vacuo. The resultant oil was subjected to preparative thin layer chromatography (60% ethyl acetate/ 40% hexanes). Pure 2-(tert-butoxyoxalyl-amino)-7-(3-(2,4-dimethoxy-phenyl)ureidomethyl)-4,7-dihydro-5H-thieno[2, 3-c]pyran-3-carboxylic acid tert-butyl ester 34 mg (58%) was isolated as an oil.

$^1$H NMR (300 MHz, CDCl$_3$) δ 12.49 (s, 1H), 7.70 (d, J=9.6, 1H), 6.62 (bs, 1H), 6.47 (m, 3H), 5.02 (bs, 1H), 4.84 (m, 1H), 4.19 (dm, 1H), 3.82 (s, 3H), 3.79 (s, 3H), 3.75–3.70 (m, 1H), 3.36 (dd, J=13.5, 7.5, 1H), 2.87 (m, 2H), 1.61 (s, 9H), 1.60 (s, 9H).

MS: APCI (+): 592.4 (M+H).

The above 2-(tert-butoxyoxalyl-amino)-7-(3-(2,4-dimethoxy-phenyl)ureidomethyl)-4,7-dihydro-5H-thieno[2, 3-c]pyran-3-carboxylic acid tert-butyl ester (34 mg) was dissolved in 20% trifluoroacetic acid in dichloromethane (2 ml) and stirred at room temperature for 3 hours. The volatiles were evaporated in vacuo and the residue was titurated with diethyl ether (2×), filtered off and washed with a small amount of dichloromethane which afforded after drying in vacuo 16 mg (89%) of the title compound as a solid.

$^1$H NMR (300 MHz, CD$_3$OD) δ 7.66 (d, J=9, 1H), 6.53 (d, J=2.7, 1H), 6.44 (dd, J=9, 2.7, 2H), 4.82 (m, 1H), 4.2 (m, 2H), 3.82 (s, 3H), 3.76 (s, 3H), 3.67 (dd, J=13, 4.5, 2H), 2.94 (m, 2H).

MS: APCI (+): 480.3 (M+H);

Example 30

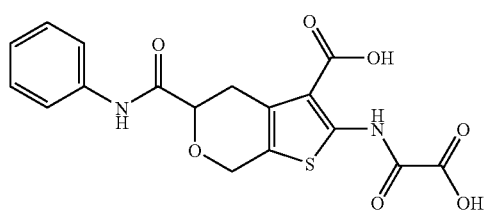

2-(Oxalyl-amino)-5-phenylcarbamoyl-4,7-dihydro-5H-thieno[2,3-c]pyran-3 carboxylic acid A solution of glyoxylic acid ethyl ester, polymer form (2.02 g, 8.9 mmol) and (3-methoxy-1-methylene-allyloxy)- trimethyl-silane (1.9 ml, 8.9 mmol, Danishefsky's diene) in benzene (12 ml) was placed under nitrogen. Zinc chloride (0.5N in tetrahydrofuran, 8.9 ml, 4.45 mmol) was added and the reaction stirred at ambient temperature for 72 h. The mixture was concentrated in vacuo, diluted with ethyl acetate (100 ml) and washed with 1 N hydrochloric acid (20 ml), saturated sodium bicarbonate (20 ml), and brine (20 ml). The organic layer was dried (Na$_2$SO$_4$), filtered, and the solvent evaporated in vacuo. The residue was purified by silica gel chromatography using a mixture of ethyl acetate/ hexane (1:2) as eluant. Pure fractions were collected and the solvent evaporated in vacuo which afforded 1.2 g (75%) of 4-oxo-3,4-dihydro-2H-pyran-2-carboxylic acid ethyl ester as an oil.

$^1$H NMR (400 MHz, CDCl$_3$) δ 7.40 (d, J=6, 1H), 5.48 (d, J=6, 1H), 5.01 (t, J=8, 1H), 4.28 (q, J=7, 2H), 2.85 (d, J=8, 2H), 1.29 (t, J=7, 3H).

To a solution of the above of 4-oxo-3,4-dihydro-2H-pyran-2-carboxylic acid ethyl ester (1.0 g, 5.9 mmol) in ethyl acetate (12 ml) was added 10% palladium on activated carbon (0.15 g). The reaction was shaken on a Parr hydrogenator under a hydrogen atmosphere (30 psi) for 1.5 h. The mixture was filtered through celite and concentrated in vacuo. The residue was purified by silica gel chromatography sing diethyl ether as eluant. Pure fractions were collected and the solvent evaporated in vacuo which affording 0.6 g (60%) of 4-oxo-tetrahydro-2H-pyran-2-carboxylic acid ethyl as an oil.

$^1$H NMR (300 MHz, CDCl$_3$) δ 4.41–4.35 (m, 1H), 4.26 (q, J=7, 2H), 3.81–3.70 (m, 1H), 2.73–2.58 (m, 3H), 2.44–2.36 (m, 1H), 1.29 (t, J=7, 3H).

To a solution of 4-oxo-tetrahydro-2H-pyran-2-carboxylic acid ethyl (0.6 g, 3.5 mmol) in absolute ethanol (6 ml) was added sulfur (0.12 g, 3.85 mmol) and tert-butyl cyanoacetate (0.64 g, 4.55 mmol). The solution was stirred under nitrogen in a 50° C. oil bath and morpholin (0.61 ml, 7.0 mmol) was added. The reaction was stirred for 18 h. and then cooled to ambient temperature and excess sulfur removed by filtration. The filtrate was concentrated in vacuo and reconstituted in ethyl acetate (50 ml). The organic phase was washed with brine (2×10 ml), dried (Na$_2$SO$_4$), filtered, and the solvent evaporated in vacuo. The residue was purified by silica gel chromatography using a gradient of ethyl acetate/hexane (20 to 25% gradient) as eluant. Pure fraction of the two isomers were collected and the solvent evaporated in vacuo which afforded 0.47 g of 2-amino-4,7-dihydro-5H-thieno[2,3-c] pyran-3,5-dicarboxylic acid 3-tert-butyl ester 5-ethyl ester (A) and 0.3 g of 2-amino-4,7-dihydro-5H-thieno[2,3-c]pyran-3,7-dicarboxylic acid 3-tert-butyl ester 7-ethyl ester (B) in 62% combined yield.

(A)
$^1$H NMR (300 MHz, CDCl$_3$) δ 5.96 (bs, 2H), 4.77–4.61 (m, 2H), 4.32–4.18 (m, 3H), 3.19–3.12 (m, 1H), 2.90–2.80 (m, 1H), 1.52 (s, 9H), 1.29 (t, J=7, 3H).

APCI-MS: [M+H]$^+$=272.4 (loss of t-butyl)

(B)
$^1$H NMR (300 MHz, CDCl$_3$) δ5.10 (s, 1H), 4.28–4.13 (m, 3H), 3.98–3.91 (m, 1H), 2.82–2.76 (m, 2H), 1.51 (s, 9H), 1.31 (t, J=7, 3H).

APCI-MS: [M+H]$^+$=272.4 (loss of t-butyl)

The above 2-amino-4,7-dihydro-5H-thieno[2,3-c]pyran-3,5-dicarboxylic acid 3-tert-butyl ester 5-ethyl ester (275 mg, 0.84 mmol) was dissolved in a mixture of ethanol (4 ml) and tetrahydrofuran (1 ml). Sodium hydroxide (1N, 1.6 ml, 1.68 mmol) was added and the reaction stirred at ambient temperature for 5 h. after which TLC analysis indicated that the reaction was complete. The reaction was monitored with a pH meter and neutralized with 1N hydrochloric acid until pH=6.9. The solution was concentrated in vacuo to give 2-amino-4±7-dihydro-5H-thieno[2,3-c]pyran-3,5-dicarboxylic acid 3-tert-butyl ester as a solid. Sodium chloride remained as an impurity.

$^1$H NMR (300 MHz, CD$_3$OD) δ 4.67–4.54 (m, 2H), 4.00–3.95 (m, 1H), 3.20–3.12 (m, 1H), 2.74–2.63 (m, 1H), 1.54 (s, 9H).

APCI-MS: [M+H]$^+$=300.0

To a solution of the above 2-amino-4,7-dihydro-5H-thieno[2,3-c]pyran-3,5-dicarboxylic acid 3-tert-butyl ester (94 mg, 0.31 mmol) and 1-(3-dimethylaminopropyl)-3-ethylcarbodiimide hydrochloride (72 mg, 0.37 mmol) in distilled dichloromethane (4 ml) under nitrogen was added aniline (32 µl, 0.34 mmol) followed by 2,6-lutidine (0.11 ml, 0.93 mmol). The reaction was stirred for 72 h., concentrated in vacuo and reconstituted in ethyl acetate (30 ml). The organic layer was washed with 1% hydrochloric acid (10 ml), saturated sodium bicarbonate (10 ml), brine (10 ml), dried (Na$_2$SO$_4$), filtered, and the solvent evaporated in vacuo to give 51 mg (45%) of 2-amino-5-phenylcarbamoyl-4,7-dihydro-5H-thieno[2,3-c]pyran-3-carboxylic acid tert-butyl ester as a solid.

$^1$H NMR (400 MHz, CDCl$_3$) δ 8.40 (s, 1H), 7.60 (d, 1H, J=7), 7.49 (d, 1H, =8), 7.34 (t, 1H, J=8), 7.32 (t, 1H, J=8), 7.13 (t, 1H, J=7), 6.03 (s, 2H), 4.82–4.73 (m, 2H), 4.25–4.22 (m, 1H), 3.43–3.38 (m, 1H), 2.79–2.72 (m, 1H), 1.54 (s, 9H).

APCI-MS: [M+H]$^+$=375.5

To a solution of the above 2-amino-5-phenylcarbamoyl-4,7-dihydro-5H-thieno[2,3-c]pyran-3-carboxylic acid tert-butyl ester (51 mg, 0.14 mmol) in distilled dichloromethane (3 ml) under nitrogen was added midazol-1-yl-oxo-acetic acid tert-butyl ester (80 mg, 0.42 mmol) and triethylamine (38 µl, 0.28 mmol). The reaction was stirred for 4 h., concentrated in vacuo and reconstituted in ethyl acetate (25 ml). The organic layer was washed with 1% hydrochloric acid (2×5 ml), saturated sodium bicarbonate (5 ml), brine (5 ml), dried (Na$_2$SO$_4$), filtered, and the solvent evaporated in vacuo. The crude material was purified by silica gel chromatography using a 4% mixture of ethyl acetate/dichloromethane as eluant. Pure fractions were collected and the solvent evaporated in vacuo to give 41 mg (26% over two steps) of 2-(tert-butoxyoxalyl-amino)-5-phenylcarbamoyl-4,7-dihydro-5H-thieno[2,3-c]pyran-3-carboxylic acid tert-butyl ester.

$^1$H NMR (300 MHz, CDCl$_3$) δ 12.56 (s, 1H), 8.40 (s, 1H), 7.59 (d, J=8, 2H), 7.33 (t, J=8, 2H), 7.12 (t, J=7, 1H), 5.01–4.85 (m, 2H), 4.27–4.22 (m, 1H), 3.54–3.47 (m, 1H), 3.89–2.79 (m, 1H), 1.60 (s, 9H), 1.58 (s, 9H).

APCI-MS: [M+H]$^+$=503.2

The above 2-(tert-butoxyoxalyl-amino)-5-phenylcarbamoyl-4,7-dihydro-5H-thieno[2,3-c]pyran-3-carboxylic acid tert-butyl ester (37 mg, 0.074 mmol) was dissolved in a solution of 50% trifluoroacetic acid/dichloromethane (3 ml). The reaction was stirred at ambient temperature for 7 h., concentrated in vacuo and evaporated in vacuo from dichloromethane (3×10 ml). The resulting precipitate was washed with ethyl ether and dried in vacuo to give 18 mg (62%) of the title compound.

$^1$H NMR (400 MHz, DMSO-d$_6$) δ 12.32 (s, 1H), 9.85 (s, 1H), 7.69 (d, J=8, 2H), 7.31 (t, J=8, 2H), 7.07 (t, J=7, 1H), 4.98 (d, J=15, 1H), 4.83 (d, J=15, 1H), 4.35–4.31 (m, 1H), 3.23 (t, J=17, 1H), 2.84 (dd, J=17, 10, 1H).

APCI-MS: [M+H]$^+$=391.3

HPLC (254.4 nm): R$_f$=3.22 min, 100%

Example 31

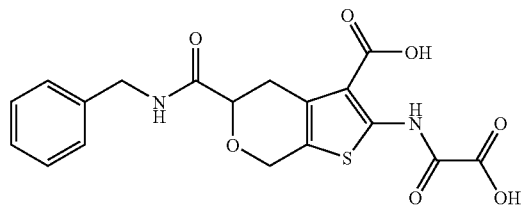

5-Benzylcarbamoyl-2-(oxalyl-amino)-4,7-dihydro-5H-thieno[2,3-c]pyran-3-carboxylic acid To a solution of 2-amino-4,7-dihydro-5H-thieno[2,3-c]pyran-3,5-dicarboxylic acid 3-tert-butyl ester (101 mg, 0.34 mmol, prepared in Example 31) and 1-(3-dimethylaminopropyl)-3-ethylcarbodiimide hydrochloride (78 mg, 0.41 mmol) in distilled dichloromethane (4 ml) under nitrogen was added benzylamine (40 µl, 0.37 mmol) followed by 2,6-lutidine (0.12 ml, 1.02 mmol). The reaction was stirred for 72 h., concentrated in vacuo and reconstituted in ethyl acetate (30 ml). The organic layer was washed with 1% hydrochloric acid (10 ml), saturated sodium bicarbonate (10 ml), brine (10 ml), dried (Na$_2$SO$_4$) over sodium sulfate, filtered, and the solvent evaporated in vacuo to give 72 mg (56%) of 2-amino-5-benzylcarbamoyl-4,7-dihydro-5H-thieno[2,3-c]pyran-3-carboxylic acid tert-butyl ester.

$^1$H NMR (400 MHz, CDCl$_3$) δ 7.36–7.28 (m, 5H), 4.66 (s, 2H), 4.44 (d, J=5, 2H), 4.17–4.13 (m, 1H), 3.40–3.33 (m, 1H), 2.75–2.66 (m, 1H), 1.54 (s, 9H).

APCI-MS: [M+H]$^+$=389.5

To a solution of the above 2-amino-5-benzylcarbamoyl-4,7-dihydro-5H-thieno[2,3-c]pyran-3,carboxylic acid tert-butyl ester (72 mg, 0.19 mmol) in distilled dichloromethane (4 ml) under nitrogen was added midazol-1-yl-oxo-acetic acid tert-butyl ester (0.11 g, 0.57 mmol) and triethylamine (51 µl, 0.38 mmol). The reaction was stirred for 4 h., concentrated in vacuo and reconstituted in ethyl acetate (25 ml). The organic layer was washed with 1% hydrochloric acid (2×5 ml), saturated sodium bicarbonate (5 ml), brine (5 ml), dried (Na$_2$SO$_4$), filtered, and the solvent evaporated in vacuo. The crude material was purified by silica gel chromatography using a gradient of ethyl acetate/dichloromethane (5 to 10% gradient) as eluant. Pure fractions were collected and the solvent evaporated in vacuo to give 42 mg (24% over two steps) of 5-benzylcarbamoyl-2-(tert-butoxyoxalyl-amino)-4,7-dihydro-5H-thieno[2,3-c]pyran-3,carboxylic acid tert-butyl ester as an oil.

$^1$H NMR (400 MHz, CDCl$_3$) δ 12.56 (s, 1H), 7.37–7.29 (m, 5H), 6.97 (t, 1H, J=6), 4.89–4.77 (m, 2H), 4.58–4.46 (m, 2H), 4.20–4.16 (m, 1H), 3.50–3.44 (m, 1H), 2.84–2.76 (m, 1H), 1.61 (s, 9H), 1.60 (s, 9H).

APCI-MS: [M+H]$^+$=517.3

The above 5-benzylcarbamoyl-2-(tert-butoxyoxalyl-amino)-4,7-dihydro-5H-thieno[2,3-c]pyran-3,carboxylic acid tert-butyl ester (36 mg, 0.07 mmol) was dissolved in a solution of 50% trifluoroacetic acid/dichloromethane (3 ml). The reaction was stirred at ambient temperature for 7 h., concentrated in vacuo and evaporated in vacuo from dichloromethane (3×10 ml). The resulting precipitate was washed with dichloromethane and dried in vacuo to give 14 mg (50%) of the title compound as a solid.

$^1$H NMR (400 MHz, DMSO-d$_6$) δ 12.31 (s, 1H), 8.48 (t, J=6, 1H), 7.31–7.20 (m; 5H), 4.91 (d, J=15, 1H), 4.76 (d, J=15, 1H), 4.32–4.29 (m, 2H), 4.20–4.16 (m, 1H); 3.22 (m, 1H, partially obscured by water), 2.70–2.63 (m, 1H).

APCI-MS: [M+H]$^+$=405.2

HPLC (254.4 nm): R$_t$=3.06 min, 100%

Example 32

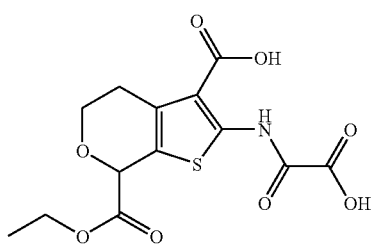

2-(Oxalyl-amino)-4,7-dihydro-5H-thieno[2,3-c]pyran-3,7-dicarboxylic acid 7-ethyl ester To a solution of 2-amino-4,7-dihydro-5H-thieno[2,3-c]pyran-3,7-dicarboxylic acid 3-tert-butyl ester 7-ethyl ester (60 mg, 0.18 mmol) in distilled dichloromethane (3 ml) under nitrogen was added midazol-1-yl-oxo-acetic acid tert-butyl ester (0.11 g, 0.54 mmol) and triethylamine (50 μl, 0.36 mmol). The reaction was stirred for 4 h., concentrated in vacuo and reconstituted in ethyl acetate (20 ml). The organic layer was washed with 1% hydrochloric acid (2×5 ml), saturated sodium bicarbonate (5 ml), brine (5 ml), dried (Na$_2$SO$_4$), filtered, and the solvent evaporated in vacuo. The crude material was purified by silica gel chromatography using a 6% mixture of ethyl acetate/dichloromethane as eluant. Pure fractions were collected and the solvent evaporated in vacuo affording 78 mg (95%) of 2-(tert-butoxyoxalyl-amino)-4,7-dihydro-5H-thieno[2,3-c]pyran-3,7-dicarboxylic acid 3-tert-butyl ester 7-ethyl ester as an oil.

$^1$H NMR (300 MHz, CDCl$_3$) δ 12.54 (s, 1H), 5.28 (s, 1H), 4.27 (q, 2H, J=7), 4.25–4.18 (m, 1H), 4.04–3.96 (m, 1H), 2.96–2.80 (m, 2H), 1.60 (s, 9H), 1.57 (s, 9H).

LC-MS: R$_t$=3.97 min, [M+H]$^+$=456.3

The above 2-(tert-butoxyoxalyl-amino)-4,7-dihydro-5H-thieno[2,3-c]pyran-3,7-dicarboxylic acid 3-tert-butyl ester 7-ethyl ester (72 mg, 0.16 mmol) was dissolved in a solution of 50% trifluoroacetic acid/dichloromethane (4 ml). The reaction was stirred at ambient temperature for 7 h., concentrated in vacuo and the residue evaporated in vacuo from dichloromethane (3×10 ml). The resulting precipitate was washed with dichloromethane and dried in vacuo to give 48 mg (88%) of the title compound as a solid.

$^1$H NMR (400 MHz, DMSO-d$_6$) δ 12.34 (s, 1H), 5.47 (s, 1H), 4.19 (q, J=7, 2H), 3.98–3.94 (m, 2H), 2.90–2.78 (m, 2H), 1.23 (t, J=7, 3H).

APCI-MS: [M+H]$^+$=344.2

HPLC (254.4 nm): R$_t$=2.82 min, 100%

Example 33

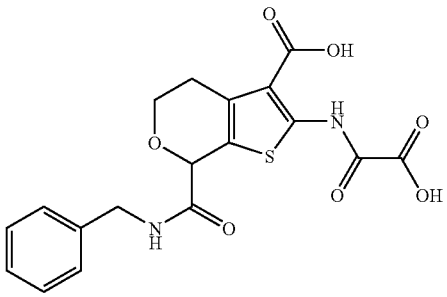

7-Benzylcarbamoyl-2-(oxalyl-amino)-4,7-dihydro-5H-thieno[2,3-c]pyran-3-carboxylic acid To a solution of 2-amino-4,7-dihydro-5H-thieno[2,3-c]pyran-3,7-dicarboxylic acid 3-tert-butyl ester 7-ethyl ester (0.12 g, 0.37 mmol) in ethanol (3 ml) was added potassium hydroxide (56 mg, 1.0 mmol) dissolved in a minimum amount of water. The mixture was stirred for 24 h., then 1N hydrochloric acid was added until pH=7. The solution was concentrated in vacuo and the residue partitioned between ethyl acetate (35 ml) and water (10 ml). The layers were separated and 1% hydrochloric acid (1 ml) was added to the aqueous layer. The aqueous layer was then extracted further with ethyl acetate (3×15 ml) and the combined organic extracts were washed with brine, dried (Na$_2$SO$_4$) and filtered. Triethylamine (3 drops) was added to the solution to stabilize the acid-sensitive compound. The solution was concentrated in vacuo affording 2-amino-4,7-dihydro-5H-thieno[2,3-c]pyran-3,7-dicarboxylic acid 3-tert-butyl ester triethylamine salt (approximately 0.13 g) as a solid.

$^1$H NMR (400 MHz, CDCl$_3$) δ 5.01 (s, 1H), 4.28–4.23 (m, 1H), 3.90–3.85 (m, 1H), 2.88–2.71 (m, 3H), 1.56 (s, 9H).

A solution of the above 2-amino-4,7-dihydro-5H-thieno[2,3-c]pyran-3,7-dicarboxylic acid 3-tert-butyl ester triethylamine salt (0.12 g, 0.30 mmol) and 1-(3-dimethylaminopropyl)-3-ethylcarbodiimide hydrochloride (71 mg, 0.36 mmol) was prepared in distilled acetonitrile under nitrogen. Benzylamine (36 μl, 0.33 mmol) was added followed by 2,6-lutidine (70 μl, 0.60 mmol). The reaction was stirred at ambient temperature for 18 h., then concentrated in vacuo and reconstituted in ethyl acetate (30 ml). The organic layer was washed with 1% hydrochloric acid (2×5 ml), saturated sodium bicarbonate (2×5 ml), and brine (10 ml), dried (Na$_2$SO$_4$), filtered, and the solvent evaporated in vacuo which afforded crude 2-amino-7-benzylcarbamoyl-4,7-dihydro-5H-thieno[2,3-c]pyran-3-carboxylic acid tert-butyl ester which was used without purification.

To a solution of the above crude 2-amino-7-benzylcarbamoyl-4,7-dihydro-5H-thieno[2,3-c]pyran-3-carboxylic acid tert-butyl ester (77 mg, 0.2 mmol) in distilled dichloromethane (3 ml) under nitrogen was added midazol-1-yl-oxo-acetic acid tert-butyl ester (0.11 g, 0.6 mmol) and triethylamine (55 μl, 0.4 mmol). The reaction was stirred for 5 h., concentrated in vacuo and reconstituted in ethyl acetate (20 ml). The organic layer was washed with 1% hydrochloric acid (2×5 ml), saturated sodium bicarbonate (5 ml), brine (5 ml), dried (Na$_2$SO$_4$), filtered, and the solvent evaporated in vacuo. The crude material was purified by silica gel chromatography using a 5% mixture of ethyl acetate/dichloromethane as eluant. Pure fractions were collected and the solvent evaporated in vacuo affording 29 mg (19% over two steps) of 7-benzylcarbamoyl-2-(tert-butoxyoxalyl-amino)-4,7-dihydro-5H-thieno[2,3-c]pyran-3-carboxylic acid tert-butyl ester as an oil.

$^1$H NMR (400 MHz, CDCl$_3$) δ 12.49 (s, 1H), 7.35–7.26 (m, 5H), 6.96 (t, J=6, 1H), 5.20 (s, 1H), 4.55–4.41 (m, 2H), 4.22–4.17 (m, 1H), 3.87–3.81 (m, 1H), 2.97–2.84 (m, 2H), 1.61 (s, 9H), 1.59 (s, 9H).

APCI-MS: [M–H]$^-$=516

The above 7-benzylcarbamoyl-2-(tert-butoxyoxalyl-amino)-4,7-dihydro-5H-thieno[2,3-c]pyran-3-carboxylic acid tert-butyl ester (29 mg, 0.06 mmol) was dissolved in a solution of 50% trifluoroacetic acid/dichloromethane (2 ml). The reaction was stirred at ambient temperature for 7 h., concentrated in vacuo and the residue evaporated in vacuo from dichloromethane (3×10 ml). The resulting precipitate was washed with dichloromethane and dried in vacuo to give 18 mg (80%) of the title compound as an solid.

$^1$H NMR (400 MHz, DMSO-d$_6$) δ 12.33 (s, 1H), 8.67 (t, J=6, 1H), 7.30–7.21 (m, 5H), 5.23 (s, 1H), 4.31–4.28 (m, 2H), 4.13–4.10 (m, 1H), 3.88–3.85 (m, 1H), 2.86 (bs, 2H).

APCI-MS: [M+H]$^+$=405

HPLC (254.4 nm): R$_t$=3.12 min, 94%

Example 34

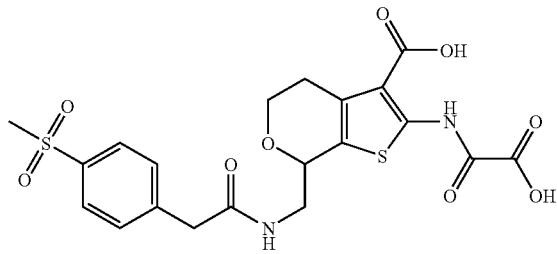

7-((2-(4-Methanesulfonyl-phenyl)-acetylamino)-methyl)-2-(oxalyl-amino)-4,7-dihydro-5H-thieno[2,3-c]pyran-3-carboxylic acid To a solution of (4-methanesulfonyl-phenyl)-acetic acid (90.4 mg, 0.42 mmol) in a mixture of dichloromethane (3 ml) and N,N-dimethylformamide (1 ml) cooled at 0° C. was added diisopropyl-ethylamine (306 µl, 1.76 mmol), diisopropylazodicarboxylate (72 µl, 0.45 mmol) and 1-hydroxybenzotriazole (56.6 mg, 0.42 mmol). After being stirred for 20 minutes, 2-amino-7-aminomethyl-4,7-dihydro-5H-thieno[2,3-c]pyran-3-carboxylic acid tert-butyl ester (100 mg, 0.35 mmol) dissolved in dichloromethane (1 ml) was added via syringe. The reaction mixture was stirred for 18 h. while slowly warming to room temperature. The volatiles were evaporated in vacuo and the residue diluted with ethyl acetate (50 ml). The organic phase was washed with saturated sodium bicarbonate (3×50 ml), 1% hydrochloric acid (3×50 ml), brine (3×50 ml), dried (MgSO$_4$), filtered, and the solvent evaporated in vacuo. The resultant oil was subjected to preparative thin layer chromatography using a mixture of methanol/dichloromethane (1:9) as eluant. Fraction with R$_f$=0.5 was isolated which afforded after evaporating the solvent in vacuo 115 mg (69%) of 2-amino-7-((2-(4-methanesulfonyl-phenyl)acetylamino)-methyl)-4,7-dihydro-5H-thieno[2,3-c]pyran-3-carboxylic acid tert-butyl ester as an oil.

$^1$H NMR (300 MHz, CDCl$_3$) δ 7.87 (d, J=8.7, 2H), 7.39 (d, J=7.5, 2H), 5.91 (bs, 2H), 4.65 (m, 1H), 4.09 (dt, J=7.8, 3.3, 1H), 3.85–3.65 (m, 2H), 3.61 (s, 2H), 3.45–3.38 (m, 2H), 3.05 (s, 3H), 2.75 (m, 2H), 1.56 (s, 9H).

MS: APCI (+): 481 (M+H).

To a solution of the above 2-amino-7-((2-(4-methanesulfonyl-phenyl)acetylamino)-methyl)-4,7-dihydro-5H-thieno[2,3-c]pyran-3-carboxylic acid tert-butyl ester (110 mg, 0.23 mmol) in dichloromethane (3 ml) was added triethylamine (96 µl, 0.69 mmol) and midazol-1-yl-oxoacetic acid tert-butyl ester (134 mg, 0.69 mmol).

The reaction was stirred at room temperature for 18 h. The reaction mixture was concentrated in vacuo, diluted in ethyl acetate (50 ml), washed with saturated sodium carbonate (3×50 ml), brine (3×50 ml), dried (MgSO$_4$), filtered and the solvent evaporated in vacuo. The resultant oil was subjected to preparative thin layer chromatography using a mixture of methanol/dichloromethane (1:9). Fraction with R$_f$=0.5 was collected and the solvent evaporated in vacuo affording 70 mg (50%) of 2-(tert-butoxyoxalyl-amino)-7-((2-(4-methanesulfonyl-phenyl)acetylamino)-methyl)-4,7-dihydro-5H-thieno[2,3-c]pyran-3-carboxylic acid tert-butyl ester as an oil.

$^1$H NMR (300 MHz, CDCl$_3$) δ 12.49 (s, 1H), 7.88 (d, J=8.1, 2H), 7.46 (d, J=8.1, 2H), 5.88 (bs, 1H), 4.78 (m, 1H), 4.15 (dt, J=12, 4, 1H), 3.86–3.71 (m, 2H), 3.64 (s, 2H), 3.42–3.34 (m, 2H), 3.04 (s, 3H), 2.85 (m, 2H), 1.62 (s, 9H), 1.61 (s, 9H).

MS: APCI (+): 609 (M+H)[minor], 497 (–2 tert butyls) [major];

LC-MS: s, 99%

The above 2-(tert-butoxyoxalyl-amino)-7-((2-(4-methanesulfonyl-phenyl)acetylamino)-methyl)-4,7-dihydro-5H-thieno[2,3-c]pyran-3-carboxylic acid tert-butyl ester (60 mg, 0.098 mmol) was dissolved in 50% trifluoroacetic acid in dichloromethane (2 ml) and allowed to stir at room temperature for 3 hours. The reaction mixture was concentrated in vacuo, the residue titurated with diethyl ether (3×), and dried in vacuo which afforded 45 mg (92%) of the title compound as a solid.

$^1$H NMR (300 MHz, DMSO-d$_6$) δ 12.34 (s, 1H), 8.47 (m, 1H), 7.82 (d, J=7.8, 2H), 7.50 (d, J=7.8, 2H), 4.75 (bs, 1H), 4.10 (m, 1H), 3.69 (m, 1H), 3.60 (d, J=3.6, 2H), 3.52 (m, 1H), 3.35 (m, 2H), 3.18 (s, 3H), 2.83 (m, 2H).

MS: APCI (–): 495 (M–H); LC-MS: s, 95%.

Example 35

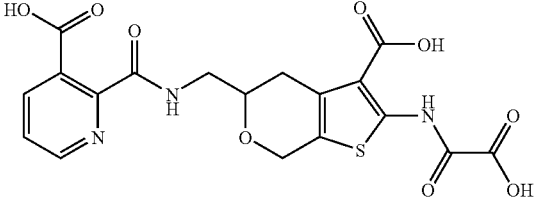

2-((3-Carboxy-2-(oxalyl-amino)-4,7-dihydro-5H-thieno[2,3-c]pyran-5-ylmethyl)carbamoyl)nicotinic acid 2-(tert-Butoxyoxalyl-amino)-5-aminomethyl-4,7-dihydro-5H-thieno[2,3-c]pyran-3-carboxylic acid tert-butyl ester (164 mg, 0.58 mmol) was stirred for 20 h at 80° C. with furo[3,4-b]pyridine-5,7-dione (86.1 mg, 0.58 mmol) in a mixture of tetrahydrofuran (1.0 ml) and N,N-dimethylformamide (0.25 ml). The volatiles were removed in vacuo and the residue was dissolved in ethyl acetate (50 ml) and washed with water (3×30 ml). The organic layer was dried (MgSO$_4$), filtered, and the solvent evaporated in vacuo. The residue (78 mg) was purified by preparative TLC (hexane/ethyl acetate, 50:50) which afforded 2 products: 2-((2-amino-3-tert-butoxycarbonyl-4,7-dihydro-5H-thieno[2,3-c]pyran-5-ylmethyl)carbamoyl)nicotinic acid (A) (27.9 mg, 11%) and 2-amino-5-(5,7-dioxo-5,7-dihydro-pyrrolo[3,4-b]pyridin-6-ylmethyl)-4,7-dihydro-5H-thieno[2,3-c]pyran-3-carboxylic acid tert-butyl ester (B) (21.3 mg, 9%).

(A)

¹H NMR (300 MHz, CDCl₃): δ 9.02 (s, 1H), 8.74 (d, J=3.3, 1H), 8.14 (d, J=7.5, 1H), 7.40 (dd, J=4.8, J=5.1, 1H), 6.71 (m, 1H), 5.98 (s, 2H), 4.63 (s, 2H), 4.00 (m, 1H), 3.42 (m, 1H), 2.90 (dd, J=3.3, J=3.6, 1H), 2.59 (dd, J=11, J=1, 1H), 1.48 (s, 9H).

MS m/z 434 (M+);

(B)

¹H NMR (300 MHz, CDCl₃) δ8.99 (d, J=5.1, 1H), 8.20 (d, J=9, 1H), 7.64 (dd, J=5.7, 4.8, 1H), 5.94 (s, 2H), 4.60 (d, J=14, 1H), 4.51 (d, J=14, 1H), 4.05 (m, 2H), 3.87 (d, J=12.5, H), 2.92 (d, J=17, 1H), 2.61 (m, 1H), 1.53 (s, 9H).

MS: APCI (+): 416 (M+1)[minor], 360 (M-tert-butyl) [major].

To a solution of the above 2-((2-amino-3-tert-butoxycarbonyl-4,7-dihydro-5H-thieno[2,3-c]pyran-5-ylmethyl)carbamoyl)nicotinic acid (27.9 mg, 0.064 mmol) in tetrahydrofuran (2 ml) was added midazol-1-yl-oxo-acetic acid tert-butyl ester (38 mg, 0.193 mmol) and triethylamine (9 µl, 0.064 mmol). The resulting mixture was stirred at room temperature for 20 h. The solvent was removed in vacuo and the residue was dissolved in dichloromethane (20 ml) and washed with water (3×10 ml). The extracts were dried (MgSO₄), filtered and the solvent evaporated in vacuo. The residue was purified by preparative TLC (0.5 mm, hexane/ethyl acetate, 1/1 to 2/3 gradient). After evaporation of the solvent in vacuo 917 mg (46%) of 2-(3-tert-butoxycarbonyl-2-(tert-butoxyoxalyl-amino)-4,7-dihydro-5H-thieno[2,3-c]pyran-5-ylmethyl)carbamoyl)nicotinic acid was isolated as a solid.

¹H NMR (300 MHz, CDCl₃): δ 9.04 (s, 1H), 8.75 (s, 1H), 8.15 (d, J=7.5, 1H), 7.42 (dd, J=6.9, J=5.1, 1H), 6.73 (m, 1H), 4.81 (dd, J=15.3, J=14.4, 2H), 4.03 (m, 1H), 3.83 (m, 1H), 3.47 (m, 1H), 2.99 (d, J=17.1, 1H), 2.59 (dd, J=11.1, J=10.8, 1H), 1.61 (s, 9H), 1.48 (s, 9H).

MS: 506 (M−55).

The above 2-(3-tert-butoxycarbonyl-2-(tert-butoxyoxalyl-amino)-4,7-dihydro-5H-thieno[2,3-c]pyran-5-ylmethyl)carbamoyl)nicotinic acid (13.1 mg, 0.023 mmol) was stirred in 50% trifluoroacetic acid in dichloromethane (2 ml) at room temperature for 7 h. The solvent was evaporated in vacuo which afforded 10 mg (96%) of the title compound as a solid.

¹H NMR (300 MHz, DMSO-d₆): δ 9.04 (s, 1H), 8.77 (d, J=7.7, 1H), 8.16 (d, J=7.5, 1H), 7.60 (d, J=7.8, 1H), 4.88 (d, J=9, 1H), 4.76 (d, J=9, 1H), 3.96 (m, 1H), 3.02 (m, 1H), 2.78 (m, 1H). MS: 481 (M+33).

Example 36

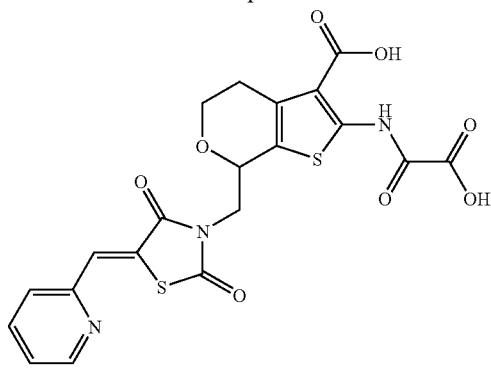

7-(2,4-Dioxo-5-pyridin-2-ylmethylene-thiazolidin-3-ylmethyl)-2-(oxalyl-amino)-4,7-dihydro-5H-thieno[2,3-c]pyran-3-carboxylic acid To a mixture of 2-(tert-butoxyoxalyl-amino)-7-hydroxymethyl-4,7-dihydro-5H-thieno[2,3-c]pyran-3-carboxylic acid tert-butyl ester (1.0 g, 2.42 mmol), 5-pyridin-2-ylmethylene-thiazolidine-2,4-dione (0.55 g, 2.66 mmol, prepared in a similar way as described in J. Med. Chem. 41 (10), 1619–1630 (1998)) and triphenylphosphine (0.7 g, 2.66 mmol) in dry tetrahydrofuran (75 ml) cooled to 0° C. under a nitrogen atmosphere was added diethyl azodicarboxylate (DEAD) (420 µl ml, 2.66 mmol). The reaction mixture was allowed to stir overnight, slowly warming to room temperature. The volatiles were evaporated in vacuo, the resultant solid was washed with diethyl ether, filtered off and dried in vacuo at 50° C. for h affording 1.4 g (96%) of 2-(tert-butoxyoxalyl-amino)-7-(2,4-dioxo-5-pyridin-2-ylmethylene-thiazolidin-3-ylmethyl)-4,7-dihydro-5H-thieno[2,3-c]pyran-3-carboxylic acid tert-butyl ester as a solid.

TLC: R_f 0.46 (ethyl acetate/heptane 1:1).

The above di-tert-butyl ester (1.0 g, 1.66 mmol) was dissolved in 25% trifluoroacetic acid in dichloromethane (30 ml). The reaction was stirred at room temperature for 16 h. The volatiles were evaporated in vacuo and the residue triturated with diethyl ether (50 ml). The precipitate was filtered off, washed with diethyl ether, dried in vacuo at 50° C. for 16 h which afforded 0.8 g of semi pure title compound. The title compound (0.8 g) was suspended in ethylacetate (25 ml) and heated at reflux temperature for 0.5 h. Isopropanol (5 ml) was added and the mixture was cooled to room temperature the precipitate filtered off and dried in vacuo at 50° C. for 16 h which afforded 0.37 g (37%) of the title compound as a solid.

Calculated for C₂₀H₁₅N₃O₈S₂, 0.5×H₂O, 0.75×isopropanol; C, 49.17%; H, 4.08%; N, 7.73%. Found: C, 48.97%; H, 4.03%; N, 7.45%.

Example 37

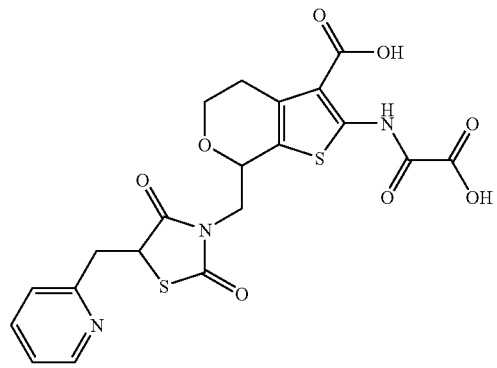

7-(2,4-Dioxo-5-pyridin-2-ylmethyl-thiazolidin-3-ylmethyl)-2-(oxalyl-amino)-4,7-dihydro-5H-thieno[2,3-c]pyran-3-carboxylic acid To a solution of 5-pyridin-2-ylmethylene-thiazolidine-2,4-dione (5.0 g, 0.024 mol, prepared in a similar way as described in J. Med. Chem. 41 (10), 1619–1630 (1998)) in tetrahydrofuran (300 ml) was added 10% palladium on carbon (1 g) and the resulting mixture was hydrogenated. After 50 ml of hydrogen was consumed and additional portion of 10% palladium on carbon (5 g) was added and the hydrogenation was continued at 50 psi for 16 h. The mixture was filtered and the filtrate evaporated in vacuo. The residue was subjected to flash column chromatography (1 l silicagel) using a mixture of ethyl acetate/hexane, (1:1) as eluant. Semi pure fractions were collected and the solvent evaporated in vacuo affording 0.8 g (16,%) of 5-pyridin-2-ylm-ethyl-thiazolidine-2,4-dione as a solid.

To a mixture of 2-(tert-butoxyoxalyl-amino)-7-hydroxymethyl-4,7-dihydro-5H-thieno[2,3-c]pyran-3-carboxylic acid tert-butyl ester (0.7 g, 1.69 mmol), 5-pyridin-2-ylmethyl-thiazolidine-2,4-dione (0.36 g, 1.86 mmol) and triphenylphosphine (0.49 g, 1.86 mmol) in dry tetrahydrofuran (40 ml) cooled to 0° C. under a nitrogen atmosphere was added diethyl was allowed to stir overnight, slowly warming to room temperature. The volatiles were evaporated in vacuo, the resultant residue was subjected to flash column chromatography (0.5 l silica gel) using a mixture of ethyl acetate/hexane (1:2) as eluant. Pure fractions were collected and the solvent evaporated in vacuo affording 0.6 g (59%) of 2-(tert-butoxyoxalyl-amino)-7-(2,4-dioxo-5-pyridin-2-ylmethyl-thiazolidin-3-ylmethyl)-4,7-dihydro-5H-thieno[2,3-c]pyran-3-carboxylic acid tert-butyl ester as a solid.

TLC: $R_f$=0.43 (ethyl acetate/heptane 1:1).

The above di-tert-butyl ester (0.5 g, 0.83 mmol) was dissolved in 25% trifluoroacetic acid in dichloromethane (25 ml). The reaction was stirred at room temperature for 16 h. The volatiles were evaporated in vacuo and the residue trituated with diethyl ether (20 ml). The precipitate was filtered off, washed with diethyl ether, dried in vacuo at 50° C. for 1 h which afforded 0.3 g of semi pure title compound. The title compound (0.3 g) was suspended in isopropanol (15 ml) and heated at reflux temperature for 5 min., cooled to room temperature and the precipitate filtered off and dried in vacuo at 50° C. for 16 h which afforded 0.2 g (49%) of the title compound as a solid.

M.p.: >250° C.;
Calculated for $C_{20}H_{17}N_3O_8S_2$, 0.25×$H_2O$; C, 48.43%; H, 3.56%; N, 8.47% Found: C, 48.41%; H, 3.57%; N, 8.10%

Example 38

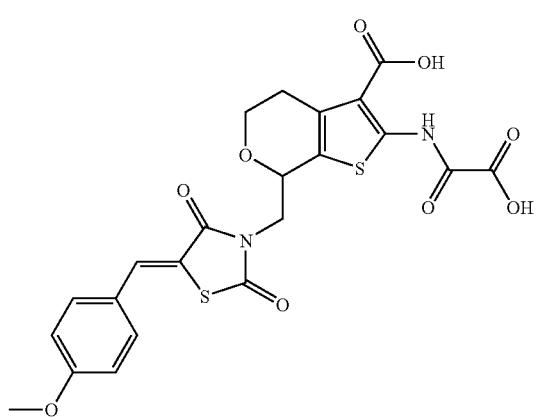

7-(5-(4-Methoxy-benzylidene)-2,4-dioxo-thiazolidin-3-ylmethyl)-2-oxalyl-amino)-4,7-dihydro-5H-thieno[2,3-c]pyran-3-carboxylic acid The title compound was prepared in a similar way as described in Example 37.

M.p.: 236–238° C.;
Calculated for $C_{22}H_{18}N_3O_9S_2$, 0.5×$H_2O$; C, 50.09%; H, 3.63%; N, 5.31%. Found: C, 49.92%; H, 3.59%; N, 5.18%.

Example 39

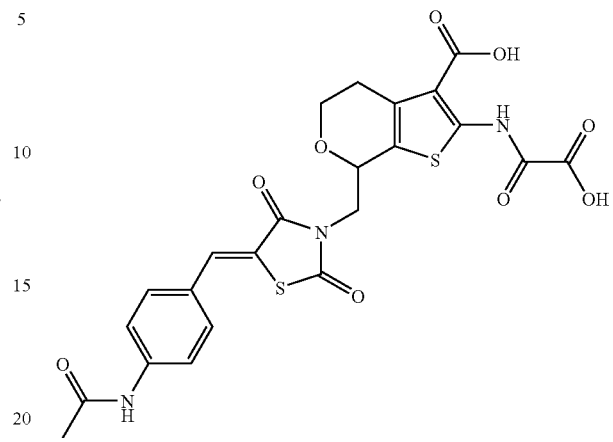

7-[5-(4-Acetylamino-benzylidene)-2,4-dioxo-thiazolidin-3-ylmethyl]-2-(oxalyl-amino)-4,7-dihydro-5H-thieno[2,3-c]pyran-3-carboxylic acid The title compound was prepared in a similar way as described in Example 37.

M.p.: >250° C.;
Calculated for $C_{23}H_{19}N_3O_9S_2$, 2×$H_2O$; C, 47.50%; H, 3.99%; N, 7.23%. Found: C, 47.60%; H, 3.45%; N, 6.80%.

Example 40

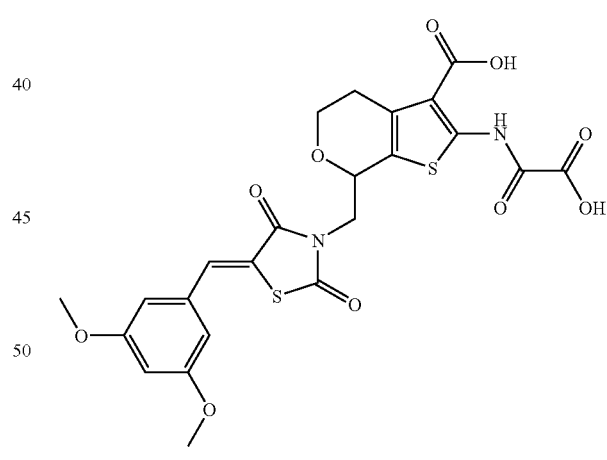

7-[5-(3,5-Dimethoxy-benzylidene)-2,4-dioxo-thiazolidin-3-ylmethyl]-2-(oxalyl-amino)-4,7-dihydro-5H-thieno[2,3-c]pyran-3-carboxylic acid The title compound was prepared in a similar way as described in Example 37.

$^1$H NMR (300 MHz, DMSO-$d_6$) δ 12.37 (s, 1H), 7.92 (s, 1H), 6.80 (d, J=1.8, 2H), 6.66 (t, J=2.1, 1H), 5.00 (m, 1H), 4.06 (bm, 2H), 3.81 (s, 6H), 3.71 (dd, J=6.6, 6, 2H), 2.83 (m, 2H).

MS: APCI (+): 549 (M+H); LC-MS; s, 90%.

Example 41

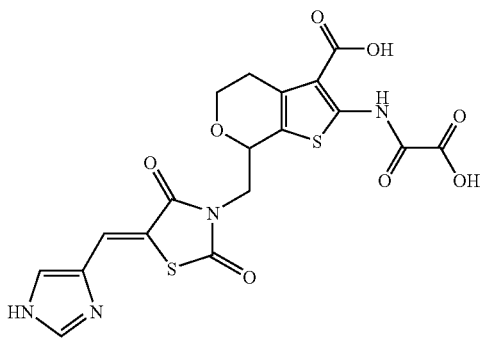

7-[5-(1H-Imidazol-4(5)-ylmethylene)-2,4-dioxo-thiazolidin-3-ylmethyl]-2-(oxalyl-amino)-4,7-dihydro-5H-thieno[2,3-c]pyran-3-carboxylic acid The title compound was prepared in a similar way as described in Example 37.

M.P.: >250° C.;

Calculated for $C_{18}H_{14}N_4O_8S_2$; C, 40.65%; H, 2.56%; N, 9.17%. Found: C, 40.54%; H, 2.55%; N, 9.46%.

Example 42

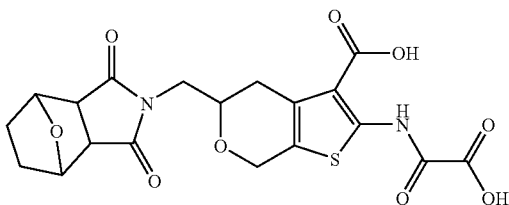

5-(1,3-Dioxo-4,7-epoxido-1,3,4,5,6,7-hexahydro-isoindol-2-ylmethyl)-2-(oxalyl-amino)-4,7-dihydro-5H-thieno[2,3-c]pyran-3-carboxylic acid To a solution of 2-(tert-butoxyoxalyl-amino)-5-hydroxymethyl-4,7-dihydro-5H-thieno[2,3-c]pyran-3-carboxylic acid tert-butyl ester (0.20 g, 0.48 mmol) in tetrahydrofuran (5 ml) was added 10-oxa-4-aza-tricyclo(5,2,1,0,2,6)decane-3,5-dione (81 mg, 0.48 mmol) and triphenylphosphine (126 mg, 0.48 mmol). The mixture was cooled to 0° C. and diisopropylazodicarboxylate (94.5 µl, 0.48 mmol) was added via syringe. The reaction was stirred for 18 h. while slowly warming to room temperature. The volatiles were evaporated in vacuo, and the residue diluted into ethyl acetate (50 ml), washed with saturated sodium bicarbonate (3×50 ml), brine (3×50 ml), dried ($MgSO_4$), filtered and the solvent evaporated in vacuo. The semi-solid residue was subjected to preparative thin layer chromatography using a mixture of ethyl acetate/hexanes (4:1) as eluant. Fraction with $R_f$=0.68 was isolated which afforded 64 mg (24%) of 2-(tert-butoxyoxalyl-amino)-5-(1,3-dioxo-4,7-epoxido-1,3,4,5,6,7-hexahydro-isoindol-2-ylmethyl)-4,7-dihydro-5H-thieno[2,3-c]pyran-3-carboxylic acid tert-butyl ester as a solid.

$^1$H NMR (300 MHz, $CDCl_3$) δ 12.47 (s, 1H), 4.89 (m, 2H), 4.80–4.61 (m, 2H), 3.93–3.86 (m, 1H), 3.83–3.79 (m, 1H), 3.62–3.57 (dd, J=12.6, 3.6, 1H), 2.92 (q, 6.9, 2H), 2.60 (dd, J=17.1, 10.5, 2H), 1.85 (m, 2H), 1.60 (s, 18H).

MS: APCI (−): 561 (M−H).

The above 2-(tert-butoxyoxalyl-amino)-5-(1,3-dioxo-4,7-epoxido-1,3,4,5,6,7-hexahydro-isoindol-2-ylmethyl)-4,7-dihydro-5H-thieno[2,3-c]pyran-3-carboxylic acid tert-butyl ester (51 mg) was dissolved in 50% trifluoroacetic acid in dichloromethane (5 ml) and stirred at room temperature for 2 h. The reaction mixture was evaporated in vacuo and the residue titurated with diethyl ether (3×10 ml). The solid was filtered of and dried affording 30 mg (71%) of the title compound as a solid.

$^1$H NMR (300 MHz, DMSO-$d_6$) δ 12.31 (s, 1H), 7.68 (bs, 1H), 4.69 (s, 2H), 4.67 (d, J=15, 1H), 4.56 (d, J=15, 1H), 3.63 (bm, 1H), 3.50 (d, J=5, 1H), 3.46 (d, J=5, 1H), 3.08 (d, J=15, 2H), 2.94 (d, J=2.4, 1H), 2.89 (m, 1H), 1.64 (s, 4H).

MS: APCI (−): 449 (M−H);

LC-MS: s, 95%

Example 43

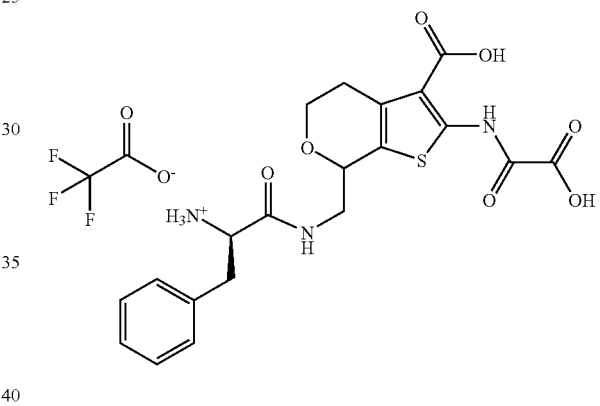

7-(((2R)-2-Amino-3-phenyl-propionylamino)-methyl)-2-(oxalyl-amino)-4,7-dihydro-5H-thieno[2,3-c] pyran-3-carboxylic acid, trifluoroacetic acid salt To a stirred solution of a mixture of 2-amino-7-aminomethyl-4,7-dihydro-5H-thieno[2,3-c]pyran-3-carboxylic acid tert-butyl ester and 2-amino-5-aminomethyl-4,7-dihydro-5H-thieno[2,3-c]pyran-3-carboxylic acid tert-butyl ester (4.7 g, 16 mmol) was added diisopropylethylamine (2.8 ml, 16 mmol) and succinimidyl-2,2,2-trichloroethylcarbonate (4.8 g, 16 mmol) portion wise. The reaction mixture was stirred at room temperature for 18 h, washed with saturated sodium hydrogen carbonate, dried ($MgSO_4$), filtered and the solvent evaporated in vacuo. The residue was chromatographed on silica (90 g) using a mixture of ethyl acetate/heptane (1:1) as eluant. Pure fraction were collected and the solvent evaporated in vacuo affording 6.78 g of crude product which was dissolved in dichloromethane (5 ml) followed by heptane (30 ml) which was added as a top layer. After crystallisation and filtration 5.44 g (74%) of 2-amino-7-((2,2,2-trichloro-ethoxycarbonyl-amino)methyl)-4,7-dihydro-5H-thieno[2,3-c]pyran-3-carboxylic acid tert-butyl ester was obtained as an oil.

$^1$H NMR ($CDCl_3$) δ 1.55 (s, 9H), 2.78 (m, 2H), 3.32 (m, 1H), 3.62 (m, 1H), 3.72 (m, 1H), 4.15 (m, 1H), 4.68 (m, 1H), 4.71 (s, 2H), 6.00 (s, 2H).

The above 2-amino-7-((2,2,2-trichloro-ethoxycarbonylamino)methyl)-4,7-dihydro-5H-thieno[2,3-c]pyran-3-carboxylic acid tert-butyl ester (4.0 g, 8.0 mmol) was dissolved in a mixture of tetrahydrofuran (15 ml) and a aqueous phosphate buffer (pH 3; 5 ml) followed by addition of zinc (16 g, 0.244 mol). The reaction mixture was stirred for 6 h at room temperature at which time the solvent was removed in vacuo. To the residue was added diethyl ether (20 ml) and water (40 ml). Sodium carbonate was added to the aqueous phase until pH=8 and the aqueous phase was extracted with dichloromethane (3×). The combined organic phases were, dried ($MgSO_4$), filtered and the solvent removed in vacuo. The residue was purified by flash chromatography on silica gel (90 g) using a mixture of dichloromethane/ethanol/25% ammonia in water 100:10:0.7 as eluant. Pure fractions were collected and the solvent evaporated in vacuo affording 1.52 g (61%) of 2-amino-7-aminomethyl-4,7-dihydro-5H-thieno[2,3-c]pyran-3-carboxylic acid tert-butyl ester.

$^1$H NMR ($CDCl_3$) δ 1.45 (s, 9H), 2.69 (dt, 2H).

Calculated for $C_{13}H_{20}N_3O_3S$; C, 54.91%; H, 7.09%; N, 9.85%. Found: C, 54.53%; H, 7.19%; N, 9.61%.

LC-MS: Mw=285.2 $R_t$=4.14 min

To a solution of boc-D-phe-OH (0.28 g, 1.05 mmol) in dichloromethane (10 ml) was added 1-hydroxy benzotriazole (0.14 g, 1.05 mmol) and 1-ethyl-3-(3-dimethylaminopropyl) carbodiimide hydrochloride (0.18 g, 1.054-mmol). The reaction mixture was stirred for 15 min at room temperature. 2-Amino-7-aminomethyl-4,7-dihydro-5H-thieno[2,3-c]pyran-3'-carboxylic acid tert-butyl ester (0.30 g, 1.054 mmol) dissolved in dichloromethane (15 ml) was added. Ethyl diisopropylamine (0.18 ml, 1.05 mmol) was added and the reaction mixture was stirred over night at room temperature. The reaction was washed with 10% aqueous citric acid (15 ml), saturated aqueous sodium hydrogencarbonate, dried ($MgSO_4$), filtered and the solvent removed in vacuo affording 594 mg (100%) of 2-amino-7-(((1R)-2-tert-butoxycarbonylamino-3-phenyl-propionylamino)-methyl)-4,7-dihydro-5H-thieno[2,3-c]pyran-3-carboxylic acid tert-butyl ester.

$^1$H NMR($CDCl_3$) δ 1.42 (s, 9H), 1.55 (s, 9H), 2.73 (m, 2H), 3.05 (m, 2H), 3.16 (m, 1H), 4.06 (m, 1H), 4.32 (m, 1H), 5.05 (s, 1H), 6.01 (s, 2H), 6.10 (s, 1H), 7.20 (m, 5H).

LC-MS: Mw=532.2, $R_t$=7.1 1.

2-Amino-7-(((1R)-2-tert-butoxycarbonylamino-3-phenyl-propionylamino)-methyl)-4,7-dihydro-5H-thieno[2,3-c]pyran-3-carboxylic acid tert-butyl ester (0.58 g, 1.09 mmol) was dissolved in dichloromethane (15 ml). Triethylamine (0.3 ml, 2.18 mmol) was added and the reaction mixture was cooled with in a ice bath. Imidazol-1-yl-oxo-acetic acid tert-butyl ester (0.43 g, 2.18 mmol) dissolved in dichloromethane (5 ml) was added to the reaction mixture. The reaction mixture was stirred overnight at room temperature diluted with dichloromethane (20 ml), washed with 1 N hydrochloric acid (15 ml), saturated sodium hydrogencarbonate (15 ml), dried ($MgSO_4$), filtered and the solvent removed in vacuo. The residue was purified by flash chromatography silica gel (40 g) using a mixture of ethyl acetate/heptane 1:1 as eluant. Pure fractions were collected and the solvent evaporated in vacuo affording 512 mg (69%) of 7-((1R)-(2-tert-butoxycarbonylamino-3-phenyl-propionylamino)methyl)-2-(tert-butoxyoxalylamino)-4,7-dihydro-5H-thieno[2,3-c]pyran-3-carboxylic acid tert-butyl ester as an oil.

$^1$H NMR ($CDCl_3$) δ 1.42 (s, 9H), 1.59 (s, 9H), 1.61 (s, 9H), 2.86 (m, 2H), 3.02 (m, 2H), 3.15 (m, 1H), 3.64 (m, 1H), 3.87 (m, 1H), 4.09 (m, 1H), 4.28 (m, 1H), 4.51 (m, 1H), 4.67 (m, 1H), 5.10 (s, 1H), 6.00 (s, 1H), 7.20 (m, 5H), 12.5 (s, 1H).

7-((1R)-(2-tert-Butoxycarbonylamino-3-phenyl-propionylamino)methyl)-2-(tert-butoxyoxalyl-amino)-4,7-dihydro-5H-thieno[2,3-c]pyrran-3-carboxylic acid tert-butyl ester (0.51 g, 0.76 mmol) was dissolved in dichloromethane (5 ml). Trifluoroacetic acid (5 ml) was added and the reaction mixture was stirred for 2 h at room temperature. The solvent was removed in vacuo (stripped 3 times with dichloromethane) which afforded 314 mg (92%) of the title compound.

Calculated for $C_{20}H_{21}N_3O_7S$; 1×$CF_3COOH$, 1×$H_2O$; C, 45.60%; H, 4.17%; N, 7.25%. Found: C, 45.78%; H, 4.20%; N, 7.05%.

LC-MS: RT=3.61/RT=3.77 Mw=448.2

Example 44

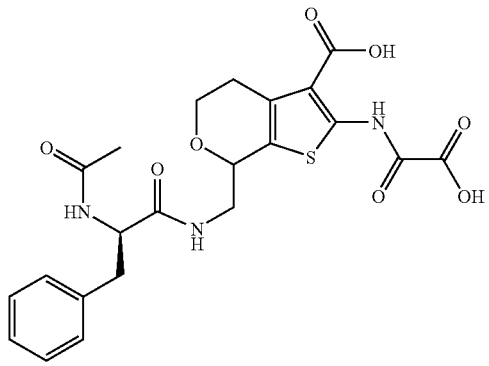

7-((2-Acetylamino-3-(4-hydroxy-phenyl)-propionylamino)-methyl)-2-(oxalyl-amino)-4,7-dihydro-5H-thieno[2,3-c]pyran-3-carboxylic acid To a mixture of Ac-D-Tyr-OH (235 mg, 1.05 mmol) dissolved in dichloromethane (10 ml) was added 1-hydroxybenzotriazole (0.14 g, 1.05 mmol), 1-ethyl-3-(3-dimethylamino propyl)carbodiimide hydrochloride (0.20 g, 1.05 mmol) and the reaction mixture was stirred for 15 min at room temperature. 2-Amino-7-aminomethyl-4,7-dihydro-5H-thieno[2,3-c]pyran-3-carboxylic acid tert-butyl ester (0.3 g, 1.05 mmol) dissolved in dichloromethane (10 ml) was added followed by N,N-diisopropyl-ethylamine (0.18 ml, 1.05 mmol). The resulting reaction mixture was stirred for 18 h at room temperature, diluted with dichloromethane (15 ml) was washed with 10% aqueous citric acid (25 ml), saturated sodium hydrogencarbonate, dried ($MgSO_4$), filtered and the solvent removed in vacuo. The residue was purified by flash chromatography on silica gel (40 g) using ethyl acetate as eluant. Pure fractions were collected and the solvent evaporated in vacuo affording 304 mg (59%) of 7-((2-acetylamino-3-(4-hydroxy-phenyl)propionylamino) methyl)-2-amino-4,7-dihydro-5H-thieno[2,3-c]pyran-3-carboxylic acid tert-butyl ester as an oil.

$^1$H NMR ($CDCl_3$) double set of peaks from diastereomers; selected peaks: δ 1.55 (s, 9H), 1.95 (s, 3H), 2.74 (m, 2H), 2.92 (m, 2H), 3.23 (m, 1H), 3.63 (m, 2H), 6.05 (s, 2H).

LC-MS: $R_t$=5.17, Mw=490.4

7-((2-Acetylamino-3-(4-hydroxy-phenyl)propionylamino)methyl)-2-amino-4,7-dihydro-5H-thieno[2,3-c]pyran-3-carboxylic acid tert-butyl ester (0.3 g, 0.61 mmol) was dissolved in dichloromethane (15 ml). Triethylamine (0.17 ml, 1.22 mmol) was added and the reaction mixture was cooled to 0° C. Imidazol-1-yl-oxo-acetic acid tert-butyl ester (0.24, 1.22 mmol) dissolved in dichloromethane (10 ml) was added dropwise. The resulting reaction mixture was stirred at room temperature for 18 h. Dichloromethane (20 ml) was added and the mixture was washed with 1 N hydrochloric acid (15 ml), saturated sodium hydrogencarbonate (20 ml), dried ($MgSO_4$), filtered and the solvent removed in vacuo. The residue was purified by flash chromatography on silica gel (40 g) using ethyl acetate as eluant. Pure fractions were collected and the solvent evaporated in vacuo affording 208 mg (55%) of 7-((2-acetylamino-3-(4-hydroxy-phenyl)-propionylamino)methyl)-2-(tert-butoxyoxalyl-amino)-4,7-dihydro-5H-thieno[2,3-c]pyran-3-carboxylic acid tert-butyl ester as an oil.

LC-MS: Mw=618.4, $R_t$=6.97

7-((2-Acetylamino-3-(4-hydroxy-phenyl)-propionylamino)methyl)-2-(tert-butoxyoxalyl-amino)-4,7-dihydro-5H-thieno[2,3-c]pyran-3-carboxylic acid tert-butyl ester (0.2 g, 0.32 mmol) was dissolved in dichloromethane (8 ml) and trifluoroacetic acid (4 ml) was added. The reaction mixture was stirred 7 h at room temperature. The solvent was evaporated in vacuo (stripped 3 times with dichloromethane) which afforded 200 mg (100%) of the title compound.

Calculated for $C_{22}H_{23}N_3O_9S$, $3 \times H_2O$; C, 47.22%; H, 5.22%; N, 7.51%. Found: C, 47.05%; H, 4.88%; N, 7.39%.

LC-MS: $R_t$=3.64, Mw=506.4.

Example 45

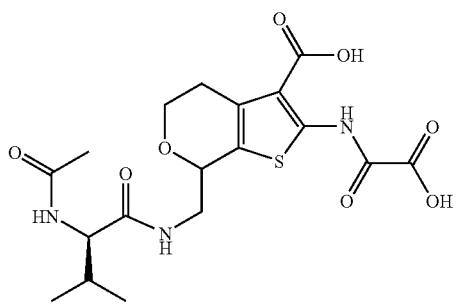

7-((2-Acetylamino-3-methyl-butyrylamino)methyl)-2-(oxalyl-amino)-4,7-dihydro-5H-thieno[2,3-c]pyran-3-carboxylic acid To a solution of Ac-D-Val-OH (0.17 g, 1.09 mmol) dissolved in dichloromethane (15 ml) was added N,N-dimethylformamide (1 Ml), 1-hydroxybenzotriazole (0.15 g, 1.09 mmol) and 1-ethyl-3-(3-dimethylamino-propyl)carbodiimide hydrochloride (0.21 g, 1.09 mmol). The reaction mixture was stirred for 15 min. at room temperature at which time a solution of 2-amino-7-aminomethyl-4,7-dihydro-5H-thieno[2,3-c]pyran-3-carboxylic acid tert-butyl ester (0.31 g, 1.09 mmol) in dichloromethane (10 ml) was added followed by N-N-diisopropylethylamine (0.186 ml, 1.09 mmol). The resulting mixture was stirred over night at room temperature diluted with dichloromethane (10 ml) washed with 10% aqueous citric acid (20 ml), sodium hydrogencarbonate, dried ($MgSO_4$), filtered and the solvent was evaporated in vacuo affording 415 mg (90%) of 7-((2-thieno[2,3-c]pyran-3-carboxylic acid tert-butyl ester as an oil.

$^1$H NMR (CDCl$_3$) δ 0.88 (t, 3H), 0.98 (t, 2H), 1.55 (s, 9) 2.02 (d, 1H), 2.77 m, (2H), 3.40 (m, 1H), 4.14 (m, 1H).

To a mixture of 7-((2-acetylamino-3-methyl-butyrylamino)methyl)-2-amino-4,7-dihydro-5H-thieno[2,3-c]pyran-3-carboxylic acid tert-butyl ester (0.4 g, 0.94 mmol) dissolved in dichloromethane (10 ml) and triethylamine (0.26 g, 1.87 mmol) cooled to 0° C. was added a solution of imidazol-1-yl-oxo-acetic acid tert-butyl ester (0.37 g, 1.87 mmol) in dichloromethane (10 ml). The resulting mixture was stirred for 18 h at room temperature diluted with dichloromethane (20 ml) washed with 1N hydrochloric acid (15 ml), saturated sodium hydrogencarbonate, dried ($MgSO_4$), filtered and the solvent evaporated in vacuo which afforded 515 mg (97%) of 7-((2-acetylamino-3-methyl-butyrylamino)methyl)-2-(tert-butoxyoxalyl-amino)-4,7-dihydro-5H-thieno[2,3-c]pyran-3-carboxylic acid tert-butyl ester as an oil.

LC-MS: $R_t$=7.11, Mw=554.4.

HPLC: $R_t$=34.16, Area (%)=100, %.

To a solution of the above 7-((2-acetylamino-3-methyl-butyrylamino)-methyl)-2-(tert-butoxyoxalyl-amino)-4,7-dihydro-5H-thieno[2,3-c]pyran-3-carboxylic acid tert-butyl ester (0.5 g, 0.90 mmol) dissolved in dichloromethane (3 ml) was added trifluoroacetic acid (1 ml) and the reaction mixture was stirred for 18 h at room temperature. Trifluoroacetic acid (4 ml) was added and the mixture was stirred for an additional 3 hours at room temperature. The volatiles were evaporated in vacuo (and stripped 3 times with dichloromethane) affording 282 mg (71%) of the title compound.

Calculated for $C_{18}H_{23}N_3O_8S$, $2 \times H_2O$; C, 45.28%; H, 5.70%; N, 8.80%. Found: C, 45.20%; H, 5.50%; N, 8.80%.

LC-MS: $R_t$=3.60, Mw=442.2

Example 46

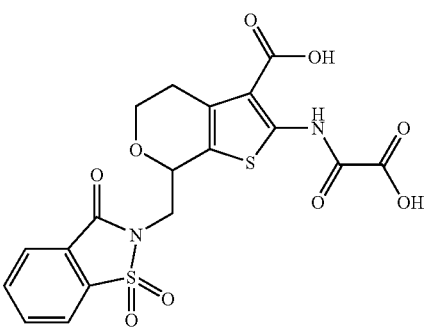

2-(Oxalyl-amino)-7-(1,1,3-trioxo-1,3-dihydro-1H-benzo[d]isothiazol-2-ylmethyl)-4,7-dihydro-5H-thieno[2,3-c]pyran-3-carboxylic acid The title compound was prepared in a similar way as described in Example 25.

M.p.: 210–212° C.;

Calculated for $C_{18}H_{14}N_2O_9S_2$, $0.5 \times H_2O$, $0.75 \times$Ethyl acetate; C, 44.49%; H, 3.83%; N, 5.32%. Found: C, 44.70%; H, 3.61%; N, 4.90%.

Example 47

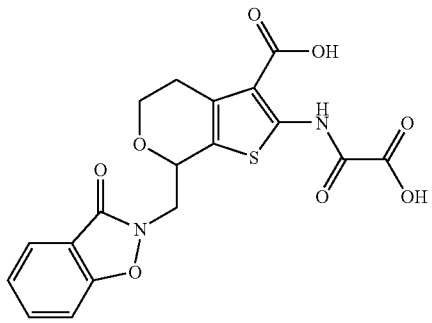

2-(Oxalyl-amino)-7-(3-oxo-3H-benzo[d]isoxazol-2-ylmethyl)-4,7-dihydro-5H-thieno[2,3-c]pyran-3-carboxylic acid The title compound was prepared in a similar way as described in, Example 25.

M.p.: 236–237° C.;

Calculated for $C_{18}H_{14}N_2O_8S$, $0.3 \times H_2O$; C, 51.02%; H, 3.47%; N, 6.61%. Found: C, 51.16%; H, 3.47%; N, 6.31%.

Example 48

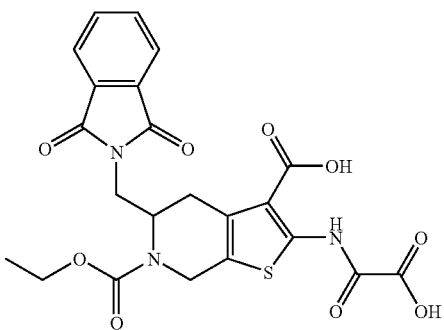

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester To a solution of 1,4-dioxa-8-aza-spiro[4,5]decane (51.5 g, 0.36 moles) in a mixture of dichloromethane (500 ml) and saturated sodium bicarbonate (500 ml) was added di-tert-butyldicarbonate (69.8 g, 0.32 moles) and the reaction was vigorously stirred for 3 hours and the layers separated. The organic layer was washed with 1N hydrochloric acid (2×150 ml), brine (100 ml), dried (MgSO$_4$), filtered and the solvent evaporated in vacuo affording 75.5 g (97%) of 1,4-dioxa-8-aza-spiro[4.5]decane-8-carboxylic acid tert-butyl ester as a crystallizing oil.

$^1$H NMR (400 MHz, CDCl$_3$): δ 3.96 (s, 4H), 3.49 (bm, 4H), 1.65 (bm, 4H), 1.45 (s, 9H).

To the above 1,4-dioxa-8-aza-spiro[4.5]decane-8-carboxylic acid tert-butyl ester (4.0 g, 16.4 mmol) dissolved in dry diethyl ether (32 ml) was added 2,2' bipyridyl (1 mg) and the solution was cooled to −75° C. Tetramethyl-ethylenediamine (3.2 ml, 21.4 mmol) was added followed by dropwise addition of sec-butyl lithium (16.4 ml, 21.4 mmol, 1.3M in cyclohexane). The mixture was stirred at −75° C. for 10 min, then slowly warmed to −20° C. and stirred at that temperature for 0.5 h, then cooled to −30° C. At this temperature, formaldehyde was generated by heating paraformaldehyde at 150° C. and passed through the mixture with dry nitrogen until the color faded to off-white, at which time water (40 ml) was added. The layers were separated, and the aqueous layer was washed diethyl ether (2×50 ml). The combined organic extracts were washed 1N hydrochloric acid (2×75 ml), saturated sodium bicarbonate solution (50 ml), dried (MgSO$_4$), filtered and the solvent evaporated in vacuo. The residue (2.9 g) was purified by silica gel chromatography (hexane/ethyl acetate, 10% ethyl acetate to 30% ethyl acetate, gradient). Pure fractions were collected and the solvent evaporated in vacuo affording 1.3 g (29%) of 7-hydroxy-methyl-1,4-dioxa-8-aza-spiro[4.5]decane-8-carboxylic acid tert-butyl ester as a thick oil.

$^1$H NMR (400 MHz, CDCl$_3$) δ 4.42 (bm, 1H), 4.08–3.96 (m, 5H), 3.96–3.88 (m, 1H), 3.78–3.70 (m, 1H), 3.30–3.16 (bm, 1H), 2.30–1.98 (bs, 1H), 1.96–1.78 (m, 2H), 1.74–1.64 (m, 2H), 1.49 (s, 9H).

To 7-hydroxy-methyl-1,4-dioxa-8-aza-spiro[4.5]decane-8-carboxylic acid tert-butyl ester (0.4 g, 1.5 mmol) dissolved in dry tetrahydrofuran (20 ml) was added phthalimide (0.28 g, 1.9 mmol), triphenylphosphine (0.5 g, 1.9 mmol) and the mixture was cooled to 0° C. in an ice bath.

Diethylazodicarboxylate (0.29 ml, 1.82 mmol) was added dropwise and the mixture was stirred at 0° C. for 0.5 h, then at ambient temperature for 18 h. The solvent was removed in vacuo and the residue was purified by silica gel chromatography (hexane/ethyl acetate, 18% ethyl acetate to 25% ethyl acetate, gradient). Pure fractions were collected and the solvent evaporated in vacuo affording 0.29 g (48%) of 7-(1,3-dioxo-1,3-dihydro-isoindol-2-ylmethyl)-1,4-dioxa-8-aza-spiro[4.5]decane-8-carboxylic acid tert-butyl ester.

$^1$H NMR (400 MHz, CDCl$_3$) δ 7.94–7.80 (bs, 2H), 7.80–7.64 (bd, 2H), 4.96–4.70 (2bs, 1H), 4.66–4.52 (m, 1H), 4.30–4.14 (bm, 1H), 4.12–4.04 (m, 2H), 4.04–3.94 (m, 2H), 3.56–3.32 (m, 2H), 2.04–1.92 (m, 1H), 1.90–1.60 (m, 4H), 1.22–1.0 (2bs, 9H).

MS: (M+1)=403, (M-Boc)=303.

To the above 7-(1,3-dioxo-1,3-dihydro-isoindol-2-ylmethyl)-1,4-dioxa-8-aza-spiro[4.5]decane-8-carboxylic acid tert-butyl ester (1.1 g, 2.7 mmol) dissolved in dichloromethane (6 ml) was added 1.0 N hydrogen chloride in diethyl ether (50 ml) and the solution kept at ambient temperature for 62 h. The precipitate was filtered off and washed with diethyl ether and dried with nitrogen which afforded 0.83 g (90%) of 2-(1,4-dioxa-8-aza-spiro[4.5]dec-7-ylmethyl)-isoindole-1,3-dione hydrochloride as a solid.

$^1$H NMR (400 MHz, DMSO-d$_6$) δ 9.2–8.8 (2bs, 2H), 7.8–8.1 (m, 2H), 4.1–3.6 (m, 5H), 2.9 (bs, 1H), 2.2–1.6 (m, 5H). MS: (M+1)=303.5.

To a suspension of the above 2-(1,4-dioxa-8-aza-spiro[4.5]dec-7-ylmethyl)-isoindole-1,3-dione hydrochloride (0.7 g, 2.1 mmol) and ethyl chloroformate (0.24 ml, 2.5 mmol) in dry tetrahydrofuran (14 ml) cooled in an ice bath under nitrogen was added diisopropylethylamine (0.95 ml, 5.4 mmol) and the reaction mixture was stirred at ambient temperature for 3 hours. The volatiles were removed in vacuo and the residue was partitioned between dichloromethane (25 ml) and 1N hydrochloric acid (25 ml). The layers were separated, and the aqueous layer extracted with dichloromethane (20 ml). The combined organic extracts were washed with a saturated sodium bicarbonate solution (50 ml), dried (MgSO$_4$), filtered and the solvent evaporated in vacuo. The residue was triturated with n-butylchloride, filtered and dried with nitrogen which afforded 0.47 g (61%) of 7-(1,3-dioxo-1,3-dihydro-isoindol-2-ylmethyl)-1,4-dioxa-8-aza-spiro[4.5]decane-8-carboxylic acid ethyl ester.

$^1$H NMR (400 MHz, CDCl$_3$) δ 7.9 (s, 2H), 7.7 (s, 2H), 4.9–4.7 (bs, 1H), 4.7–4.5 (m, 1H) 4.3–3.9 (m, 5H), 3.9–3.6 (bs, 1H), 3.6–3.3 (m, 2H), 2.0–1.9 (m, 1H), 1.9–1.5 (m, 4H), 1.1–0.7 (2bs, 3H). MS: (M−1)=373.

A solution of the above 7-(1,3-dioxo-1,3-dihydro-isoindol-2-ylmethyl)-1,4-dioxa-8-aza-spiro[4.5]decane-8-carboxylic acid ethyl ester (0.44 g, 1.2 mmol) in a mixture of 1N hydrochloric acid (18 ml) and tetrahydrofuran (18 ml) was heated a 75° C. under nitrogen with stirring for 18 h. The tetrahydrofuran was removed in vacuo and the residue was extracted with dichloromethane (2×75 ml). The combined organic extracts were washed with a saturated sodium bicarbonate solution (50 ml), dried (MgSO$_4$), filtered and the solvent removed in vacuo affording 0.42 g (>100%) of 2-(1,3-dioxo-1,3-dihydro-isoindol-2-ylmethyl)-4-oxo-piperidine-1-carboxylic acid ethyl ester as a solid.

$^1$H NMR (400 MHz, CDCl$_3$) δ 7.9 (s, 2H), 7.8 (s, 2H), 5.3–5.0 (bm, 1H), 4.6–4.2 (bm, 1H), 4.0 (m, 2H), 3.8–3.6 (bm, 3H), 2.8 (m, 1H), 2.7–2.4 (bm, 3H), 1.0 (bs, 3H).

MS: (M+1)=330.56.

A mixture of the above 2-(1,3-dioxo-1,3-dihydro-isoindol-2-ylmethyl)-4-oxo-piperidine-1-carboxylic acid ethyl ester (0.39 g, 1.2 mmol), tert-butyl cyanoacetate (0.22 g, 1.55 mmol), sulfur (42 mg, 1.3 mmol) in ethanol (1.5 ml) was degassed. To this mixture, under nitrogen, morpholine (205 µl) was added and the mixture was heated a 50° C. for 13 hours. The solvent was removed in vacuo. The residue (0.74 g) was purified by silica gel chromatography using a mixture of hexane/ethylacetate (7:3) as eluant. Pure fraction were collected and the solvent evaporated in vacuo. The residue (0.29 g) was titurated with acetonitrile, filtered, and dried with nitrogen affording 84 mg (15%) of 2-amino-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester.

$^1$H MNR (400 MHz, CDCl$_3$) δ 7.9–7.7 (2m, 4H), 6.0 (bs, 2H), 5.1–4.8 (bm, 1H), 4.8–4.5 (m, 1H), 4.5–4.2 (m, 1H), 4.1–3.4 (3m, 4H), 3.0 (m, 2H), 1.8–1.4 (m, 10H), 1.1–0.9 (m, 3H).

MS: (M+1)=486.

To the above 2-amino-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester (48 mg, 0.1 mmol) dissolved in dry tetrahydrofuran (1 ml) was added imidazol-1-yl-oxo-acetic acid tert-butyl ester (0.4 ml) and the solution stirred for 18 h. at ambient temperature. The solvent was removed in vacuo and the residue was dissolved in dichloromethane (25 ml) and a saturated sodium bicarbonate solution (25 ml) was added. The layers were separated and the aqueous layer was extracted with dichloromethane (25 ml). The combined organic extracts were dried (Na$_2$SO$_4$), filtered and the solvent evaporated in vacuo. The residue (63 mg) was dissolved in ethyl acetate and passed through 1 g of silica gel and the solvent evaporated in vacuo affording 55 mg (90%) of 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid 3-tert-butyl ester 6-ethyl ester as a solid.

The above 2-(tert-butoxyoxalyl-amino)-5-(1,3-dihydro-isoindol-2-ylmethyl)-4,5,6,7-tetrahydro-thieno[2,3-c]pyridine-3,6-dicarboxylic acid 3-tert-butyl ester 6-ethyl ester (55 mg, 0.09 mmol) was dissolved in 50% trifluoroacetic acid in dichloromethane (2 ml) and stirred at ambient temperature for 18 h. The volatiles were removed in vacuo and the residue was purified by preparative hplc (column: Kromasil C18, 250×4.6 mm, flow: 2 ml/min, gradient: acetonitrile/water, 20% acetonitrile to 60% acetonitrile over 20 min.) affording after evaporation in vacuo 13.8 mg (31%) of the title compound as a solid. (Kromasil™ available from e.g. Richard Scientific Inc, Novato Calif.

$^1$H NMR (400 MHz, DMSO-d$_6$) δ 14–13 (bs, 1H), 12.4 (s, 1H), 7.9 (s, 4H), 4.9 (m, 2H), 4.4 (m, 1H), 4.0–2.8 (m, 13H), 0.8 (m, 3H).

MS: (M+1)=502.

Example 49

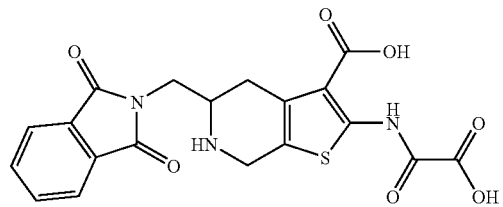

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid 7-(1,3-Dioxo-1,3-dihydro-isoindol-2-ylmethyl)-1,4-dioxa-8-aza-spiro[4.5]decane-8-carboxylic acid tert-butyl ester (353 mg, 0.88 mmol) was cooled in an ice bath and then dissolved in a solution of 20% trifluoroacetic acid/dichloromethane (7 ml). The reaction was stirred for 5 minutes in the ice bath then another 3 hours at ambient temperature, after which it was concentrated in vacuo affording a solid residue. To the solid was added 2N hydrochloric acid (9 ml) and the mixture was heated at 50° C. (oil bath) with stirring for 24 h. The cooled reaction mixture was quenched with saturated sodium bicarbonate solution until the pH was basic. The aqueous layer was extracted with chloroform (3×20 ml) and the combined organic extracts dried (K$_2$CO$_3$), filtered, and the solvent evaporated in vacuo to give 205 mg (91%) of 2-(4-oxo-piperidin-2-ylmethyl)-isoindole-1,3-dione as a solid.

$^1$H NMR (400 MHz, CDCl$_3$) δ 7.90–7.83 (m, 2H), 7.78–7.71 (m, 2H), 3.81–3.73 (m, 2H), 3.43–3.35 (m, 1H), 3.30–3.22 (m, 1H), 2.83 (dt, J=13, 3, 1H), 2.46 (d, J=15, 1H), 2.42–2.32 (m, 2H), 2.21 (dd, J=14, 13, 1H).

APCI-MS: [M+H]$^+$=259

The above 2-(4-oxo-piperidin-2-ylmethyl)-isoindole-1,3-dione (0.20 g, 0.76 mmol) was dissolved in dichloromethane (5 ml). Saturated sodium bicarbonate solution (5 ml) was added followed by di-tert-butyl dicarbonate (0.20 g, 0.91 mmol). The reaction was stirred vigorously for 16 h. after which the organic phase was separated. The aqueous layer was extracted with dichloromethane (2×10 ml) and the combined organic extracts were dried (Na$_2$SO$_4$), filtered, and the solvent evaporated in vacuo. The residue was purified by silica gel chromatography using a gradient of ethyl acetate/dichloromethane (0 to 10% gradient) as eluant. Pure fractions were collected and the solvent evaporated in vacuo affording 0.23 g (85%) of 2-(1,3-dioxo-1,3-dihydro-isoindol-2-ylmethyl)-4-oxo-piperidine-1-carboxylic acid tert-butyl ester.

¹H NMR (400 MHz, CDCl₃) δ 7.86 (bs, 2H), 7.72 (bs, 2H), 5.15–4.98 (m, 1H), 4.23–4.1.4 (m, 1H), 3.90 (t, J=12, 1H), 3.61–3.52 (m, 2H), 2.78–2.70 (m, 1H), 2.57–2.39 (m, 3H), 1.15 (s, 9H)

APCI-MS: [M+H]⁺=359

The above 2-(1,3-dioxo-1,3-dihydro-isoindol-2-ylmethyl)-4-oxo-piperidine-1-carboxylic acid tert-butyl ester (0.43 g, 1.2 mmol) was dissolved in absolute ethanol (9 ml). To the solution was added sulfur (42 mg, 1.32 mmol) and tert-butyl cyanoacetate (0.22 g, 1.56 mmol). The mixture was placed under nitrogen and stirred in a 50° C. oil bath. Morpholine (0.21 ml, 2.4 mmol) was added and the reaction was stirred for 16 h. The precipitate formed was filtered off and washed with acetonitrile (2×3 ml) and dried which afforded 0.18 g of 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (A) (30%). The filtrate was concentrated in vacuo and the residue purified by silica gel chromatography using a gradient of ethyl acetate/hexane (1:4 to 1:3 gradient) as eluant. Pure fractions were collected and the solvent evaporated in vacuo affording 0.3 g of a mixture of 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester. HPLC purification of a small portion of the mixture gave 28 mg of pure 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (B).

(A):
¹H NMR (400 MHz, CDCl₃) δ 7.87–7.82 (m, 2H) 7.73–7.66 (m, 2H), 6.00 (bs, 2H), 5.02–4.87 (m, 1H), 4.72–4.21 (m, 2H), 4.03–3.93 (m, 1H), 3.51 (t, J=14, 1H), 2.97–2.91 (m, 2H), 1.56 (s, 9H), 1.12–1.09 (s, 9H).

LC-MS: R₁=3.96 min, [M+H]⁺=514.4

(B):
¹H NMR (400 MHz, CDCl₃) δ 7.88–7.82 (m, 2H), 7.74–7.66 (m, 2H), 5.39–5.19 (m, 1H), 4.30–4.02 (m, 2H), 3.78–3.70 (m, 1H), 3.33–3.18 (m, 1H), 2.86 (dd, J=18, 4, 1H), 2.75–2.61 (m, 1H), 1.54 (s, 9H), 1.13–1.05 (s, 9H).

LC-MS: R₁=4.01 min, [M+H]⁺=514.4

To a solution of the above 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.097 mmol) in dichloromethane (3 ml) was added midazol-1-yl-oxo-acetic acid tert-butyl ester (60 mg, 0.29 mmol). The reaction was placed under nitrogen and stirred for 3 hours at ambient temperature. The solution was concentrated in vacuo and the residue purified by silica gel chromatography using a 5% mixture of ethyl acetate/dichloromethane as eluant. Pure fractions were collected and the solvent evaporated in vacuo affording 54 mg (87%) of 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester.

¹H NMR (400 MHz, CDCl₃) δ 12.52 (s, 1H), 7.85 (bs, 2H), 7.74–7.67 (m, 2H), 5.08–4.92 (m, 1H), 4.93–4.40 (m, 2H), 3.97–3.87 (m, 1H), 3.53 (t, J=14, 1H), 3.11–2.99 (m, 2H), 1.62 (s, 18H), 1.14–1.12 (2s, 9H).

APCI-MS: [M−H]⁻=641

The above 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (54 mg, 0.084 mmol) was dissolved in a solution of 50% trifluoroacetic acid/dichloromethane (2 ml). The reaction was stirred at ambient temperature for 7 h., concentrated in vacuo and the residue evaporated in vacuo from dichloromethane (3×10 ml). The resulting precipitate was washed with dichloromethane, filtered off and dried in vacuo which afforded 41 mg (90%) of the title compound as a solid.

¹H NMR (400 MHz, DMSO-d₆) δ 12.31 (s, 1H), 9.36 (bs, 2H), 7.93–7.90 (m, 2H), 7.88–7.85 (m, 2H), 4.43 (d, J=16, 1H), 4.26 (d, J=16, 1H), 4.03–3.91 (m, 2H), 3.83–3.76 (m, 1H), 3.31 (dd, J=18, 4, 1H), 2.82 (dd, J=18, 10, 1H).

APCI-MS: [M+H]⁺=430

HPLC (254.4 nm): R₁=6.72 min, 98%

Example 50

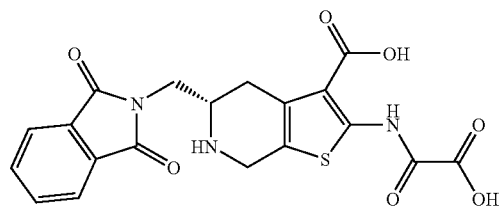

(L)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid To a solution of L-aspartic acid (120 g, 0.90 mol) in methanol (600 ml) cooled to −20° C. was added thionylchoride (93 ml, 1.29 mol) dropwise over 0.5 h. The cooling bath was removed and the mixture was stirred for 1 h, before diethyl ether (1.8 L, containing 50 ml 1 N hydrochloric acid in diethyl ether) was added upon cooling. The resulting precipitate was filtered off and washed with diethyl ether. The product was recrystallized twice:

First recrystallization: The product was dissolved in warm methanol (600 ml) and reprecipitated with 1.8 ml diethyl ether (containing 50 ml 1 N hydrochloric acid in diethyl ether).

Second recrystallization: The product was dissolved in warm methanol (250 ml) and reprecipitated with 1.0 m diethyl ether (containing 50 ml 1 N hydrochloric acid in diethyl ether).

This afforded 75 g (45%) of L-aspartic acid β-methyl ester hydrochloride as a solid.

To a solution of the above β-methyl ester (50 g, 0.27 mol) in water (120 ml) cooled to 0° C. was added triethylamine (95 ml, 0.68 mol) and methyl acrylate (74 ml, 0.82 mol). The reaction mixture was stirred for 3 hours before the cooling bath was removed. After stirring for an additional 1 h the mixture was washed with petrol ether (2×400 ml), before tert-butanol (40 ml) and di-tert-butyl dicarbonate (74 g, 0.34 mol) was added and the reaction mixture was stirred for 16 h. The mixture was washed with petrol ether (2×400 ml), cooled to 0° C. and the pH was adjusted to 3 with concentrated hydrochloric acid. After extraction with ethyl acetate (3×200 ml) the organic phase was washed with brine (200 ml), dried (MgSO₄), filtered and the volatiles evaporated in vacuo. The residue was subjected to column chromatography on silicagel using a mixture of ethyl acetate/hexane/methanol/acetic acid (25:25:2.5:1) as eluant. Pure fractions were collected and the solvent evaporated in vacuo which afforded 60 g (66%) of 2-(tert-butoxycarbonyl-(2-methoxycarbonyl-ethyl)-amino)-succinic acid 4-methyl ester as a solid.

To a solution of the above di-ethyl ester (96.9 g, 0.29 mol) in dry degassed tetrahydrofuran (1.01) was added sodium methoxide (161 ml, 30% solution in methanol) and the reaction mixture was refluxed under nitrogen for 16 h with mechanical stirring. The reaction mixture was cooled to room temperature, the volatiles remove in vacuo until a wet cage was observed. Water (500 ml) was added and the reaction mixture was refluxed for 16 h. The remaining organic solvents were evaporated in vacuo before the pH was adjusted to 2.5 with concentrated hydrochloric acid. The aqueous phase was extracted with ethylacetate (3×3 ml) and the combined organic phases were washed with brine (100 ml), dried (MgSO$_4$) and filtered. tert-Butyl amine (25.36 g, 0.350 mol) was added dropwise under stirring whereupon a off white precipitate was formed. The precipitate was filtered off and washed with ethyl acetate, dried in vacuo affording 74.4 g (81%) of 4-oxo-piperidine-1,2-dicarboxylic acid 1-tert-butyl ester, tert-butyl amine salt as a solid.

Analytically pure compound can be obtained from recrystallisation of the crude product from ethanol-diisopropyl ether by heating the compound in ethanol (ca 100 ml per 10 g compound) and while still hot diisopropyl ether is added (ca 250 ml per 10 g compound). Yield in recrystallisation is approximately 50%.

A solution of the above 4-oxo-piperidine-1,2-dicarboxylic acid 1-tert-butyl ester, tert-butyl amine salt (3.0 g, 9.48 mmol), tert-butyl cyanoacetate (2.01 g, 14.22 mmol), sulfur (0.456 g, 14.22 mmol) and diisopropyl-ethylamine (1.64 ml, 9.48 mmol) was heated to 50° C. under nitrogen for 12 h. The orange-yellow solution was allowed to cool to room temperature before a small precipitate was filtered off. The filtrate was evaporated in vacuo and the residue was divided between ethyl acetate (50 ml) and saturated ammonium chloride (100 ml). The aqueous phase was extracted with ethyl acetate (3×50 m) and the combined organic phases were washed with brine (50 ml), dried (MgSO$_4$), filtered and the solvent evaporated in vacuo. The residue was subjected to column chromatography using a mixture of petrol ether/ethyl acetate/methanol (8:4:1) as eluant. Pure fractions were collected and the solvent evaporated in vacuo affording 2.22 g (58%) of 2-amino-4,5,6,7-tetrahydro-thieno[2,3-c]pyridine-3,5,6-tricarboxylic acid 3,6-di-tert-butyl ester as a solid.

To a solution of the above 3,5,6-tricarboxylic acid 3,6-di-tert-butyl ester (0.63 g, 1.58 mmol) in dimethoxyethane (10 ml) cooled to –20° C. was added N-methylmorpholine (174 ml, 1.58 mmol) followed by isobutylchloroformate (205 ml, 1.58 mmol) and the reaction mixture was stirred for two min. before a precipitate was filtered off. The precipitate was rapidly washed with dimethoxyethane (2×2.5 ml), recooled to –20° C. and a solution of sodium borohydride (90 mg, 2.37 mmol) in water (1 ml) was added in one lot. (Caution—gas evolution).

The reaction mixture was stirred until gas evolution ceases (app. 3 min.) and the mixture was poured into water (25 ml) and extracted with ethyl acetate (10 ml), washed with brine (5 ml), dried (MgSO$_4$), filtered and the solvent evaporated in vacuo affording 0.40 g (66%) of 2-amino-5-hydroxymethyl-4,5,6,7-tetrahydro-thieno[2,3-c]pyridine-3,6-dicarboxylic acid di-tert-butyl ester as a solid.

To a mixture of the above 2-amino-5-hydroxymethyl-4,5,6,7-tetrahydro-thieno[2,3-c]pyridine-3,6-dicarboxylic acid di-tert-butyl ester (2.00 g, 5.20 mmol), phthalimide (0.92 g, 6.24 mmol) and triphenylphosphine (1.64 g, 6.24 mmol) in dry tetrahydrofuran (30 ml) cooled to 0° C. under a nitrogen atmosphere was added diethyl azodicarboxylate (DEAD) (0.98 ml, 6.24 mmol). The reaction mixture was allowed to stir overnight, slowly warming to room temperature. Next day the reaction mixture was again cooled to 0° C. and phthalimide (0.46 g, 3.12 mmol), triphenylphosphine (0.82 g, 3.12 mmol) and diethyl azodicarboxylate (DEAD) (0.49 ml, 3.12 mmol) was added in sequence and the reaction mixture was allowed to stir overnight, slowly warming to room temperature. The volatiles were evaporated in vacuo and the resultant solid dissolved in dichlorormethane (20 ml). The residue was subjected to flash column chromatography using a mixture of ethyl acetate/hexane (1:2) as eluant. Fractions were collected affording after evaporation in vacuo 1.0 g of the desired compound contaminated with phthalimide. Recrystallization from ethanol gave 0.23 g (9%) of pure 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester as a solid.

To the above di-tert-butyl ester (0.20 g, 0.39 mmol) dissolved in dichloromethane (4 ml) was added a mixture of imidazol-1-yl-oxo-acetic acid tert butyl ester (0.23 g, 1.17 mmol) in dichloromethane (1 ml) under nitrogen. The reaction mixture was allowed to stir at room temperature overnight. The reaction mixture was added dichlorormethane (5 ml) and washed with 1% hydrochloric acid (10 ml), dried (Na$_2$SO$_4$), filtered and the organic phase evaporated in vacuo affording 0.25 g (100%) of 2-(tert-butoxyoxalyl-amino)-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester.

The above tri-tert-butyl ester (0.25 g, 0.39 mmol) was dissolved in 20% trifluoroacetic acid in dichloromethane (5 ml). The reaction was stirred at room temperature for 24 h. before diethyl ether (5 ml) was added. The precipitate was filtered off, washed with diethyl ether, dried in vacuo to give 0.150 g of a solid. NMR revealed the presence of a trace amount of material arising from incomplete deprotection. 0.100 g of the crude product was redissolved in 20% trifluoroacetic acid in dichloromethane (5 ml), and stirred at room temperature for 24 h. before diethyl ether (5 ml) was added. The product was filtered off and washed with diethyl ether and dried in vacuo to give 0.05 g (40%) of the title compound as a solid.

M.p.: dec.>240° C.

Calculated for C$_{19}$H$_{15}$N$_3$O$_7$S.⅓.C$_2$HF$_3$O$_2$.½H$_2$O; C, 49.58%; H, 3.46%; N, 8.82%. Found: C, 49.84%; H, 3.83%; N, 8.99%.

Example 51

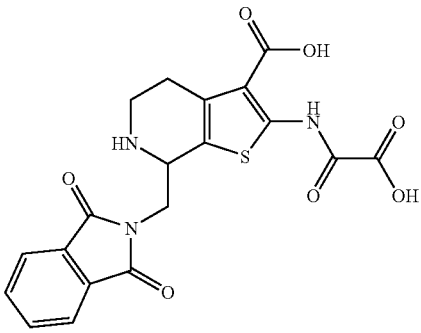

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid To a solution of pure 2-amino-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (28 mg, 0.057 mmol) in dichloromethane (2 ml) was added midazol-1-yl-oxo-acetic acid tert-butyl ester (35 mg, 0.17 mmol). The reaction was placed under nitrogen and stirred for 12 h. at ambient temperature. The volatiles were evaporated in vacuo and the residue was purified by silica gel chromatography using a mixture of ethyl acetate/hexane (1:3) as eluant. Pure fractions were collected and the solvent evaporated in vacuo affording 25 mg (67%) of 2-(tert-butoxyoxalyl-amino)-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester as an oil.

$^1$H NMR (400 MHz, CDCl$_3$) δ 12.59–12.53 (bs, 1H), 7.89–7.84 (m, 2H), 7.75–7.67 (m, 2H), 5.61–5.41 (m, 1H), 4.36–4.15 (m, 1H), 4.12–4.06 (m, 1H), 3.90–3.82 (m, 1H), 3.34–3.21 (m, 1H), 2.99–2.93 (m, 1H), 2.84–2.68 (m, 1H), 1.62–1.59 (s, 18H), 1.12–1.06 (s, 9H).

The above 2-(tert-butoxyoxalyl-amino)-7-(1,3-dioxo-1,3-dihydro-isoindol-2-ylmethyl)-4,5,6,7-tetrahydro-thieno[2,3-c]pyridine-3,6-dicarboxylic acid di-tert-butyl ester (25 mg, 0.039 mmol) was dissolved in a solution of 50% trifluoroacetic acid/dichloromethane (1.5 ml). The reaction was stirred at ambient temperature for 7 h., concentrated in vacuo and the residue evaporated in vacuo from dichloromethane (3×10 ml). The resulting precipitate was washed with dichloromethane, filtered off and dried in vacuo to give 41 mg (85%) of the title compound as a solid.

$^1$H NMR (400 MHz, DMSO-d$_6$) δ 12.32 (s, 1H), 9.48 (bs, 2H), 7.95–7.91 (m, 2H), 7.89–7.84 (m, 2H), 4.89 (s, 1H), 4.15–4.07 (m, 2H), 3.43–3.28 (2m, 2H, partially obscured by water), 3.04 (bs, 2H).

LC-MS: R$_t$=1.51 min, [M−H]$^-$=428.4

Example 52

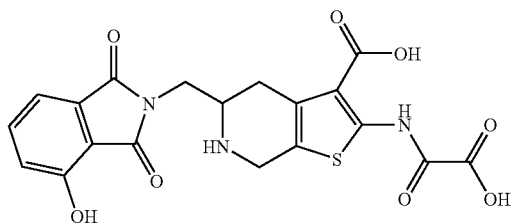

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid 7-(1,3-Dioxo-1,3-dihydro-isoindol-2-ylmethyl)-1,4-dioxa-8-aza-spiro[4.5]decane-8-carboxylic acid tert-butyl ester (1.55 g, 3.85 mmol) was cooled in an ice bath and then dissolved in a solution of 20% trifluoroacetic acid/dichloromethane (15 ml). The reaction was stirred and allowed to slowly warm to ambient temperature during 3 hours. The solution was concentrated in vacuo to give crude 2-(1,4-dioxa-8-aza-spiro[4.5]dec-7-ylmethyl)-isoindole-1,3-dione which was used directly in the following step (assumed 100% yield).

$^1$H NMR (400 MHz, CDCl$_3$) δ 9.26 (bs, 1H), 8.19 (bs, 1H), 7.78–7.75 (m, 2H), 7.74–7.71 (m, 2H), 4.11–3.98 (m, 5H), 3.90–3.79 (m, 3H), 3.26–3.17 (m, 1H), 2.10–2.00 (m, 3H), 1.92–1.88 (m, 1H).

To a suspension of the above 2-(1,4-dioxa-8-aza-spiro[4.5]dec-7-ylmethyl)-isoindole-1,3-dione (3.85 mmol) in absolute ethanol (25 ml) was added hydrazine (0.36 ml, 11.55 mmol). The reaction was stirred at 80° C. (oil bath) for 6 h., then cooled to ambient temperature and stirred for an additional 12 h. The thick precipitate was filtered off and washed with ethanol. The filtrate was concentrated in vacuo and reconstituted in dichloromethane (20 ml), forming a small amount of a second precipitate which was filtered off. The filtrate was evaporated in vacuo and the resulting oil was dissolved in water (10 ml) and basified with 1N sodium hydroxide until pH=10. The aqueous layer was extracted with 20% isopropyl alcohol/chloroform (12×40 ml). The combined organic extracts were dried (K$_2$CO$_3$), filtered and the solvent evaporated in vacuo affording 0.42 g (63%) of (1,4-dioxa-8-aza-spiro[4.5]dec-7-yl)methylamine as an oil.

$^1$H NMR (300 MHz, CDCl$_3$) δ 3.94 (bs, 4H), 3.11–3.05 (m, 1H), 2.81 (dt, J=12, 3, 1H), 2.76–2.65 (m, 2H), 2.58–2.50 (m, 1H), 1.70–1.57 (m, 3H), 1.31 (t, J=12, 1H).

APCI-MS: [M+H]$^+$=173.2

To a solution of 4-hydroxy-isobenzofuran-1,3-dione (0.51 g, 3.09 mmol) in anhydrous N,N-dimethylformamide (7 ml) under nitrogen was added sodium hydride (130 mg, 3.25 mmol). Immediate evolution of gas and bright yellow color was observed. The mixture was stirred for 5 minutes after which benzyl bromide (1.8 ml, 15.45 mmol) was added. The reaction was stirred for 72 h. Saturated sodium bicarbonate (2 ml) was added and the mixture stirred for 2 minutes, diluted in ethyl acetate (35 ml) and washed with saturated sodium bicarbonate (5 ml), 1N hydrochloric acid (5 ml), and brine (2×5 ml). The organic layer was dried (MgSO$_4$), filtered and the solvent evaporated in vacuo. To the crude material was added hexane and the formed precipitate was filtered off, washed further with hexane and dried in vacuo to give 0.54 g (69%) of 4-(benzyloxy)-isobenzofuran-1,3-dione as a solid.

$^1$H NMR (300 MHz, CDCl$_3$) δ 7.74 (t, 1H, J=8 Hz), 7.54 (d, 1H, J=8 Hz), 7.47–7.29 (m, 6H), 5.36 (s, 2H).

A solution of (1,4-dioxa-8-aza-spiro[4.5]dec-7-yl)methylamine (0.19 g, 1.1 mmol) and 4-(benzyloxy)-isobenzofuran-1,3-dione (0.27 g, 1.05 mmol) was prepared in a mixture of distilled dichloromethane (3 ml) and anhydrous N,N-dimethylformamide (2.5 ml) under nitrogen. 1-(3-dimethylaminopropyl)-3-ethylcarbodiimide hydrochloride (0.23 g, 1.21 mmol) was added followed by triethylamine (0.46 ml, 3.3 mmol) and the reaction stirred at ambient temperature for 18 h. The solution was concentrated in vacuo and the residue diluted with ethyl acetate (25 ml) and washed with water (5 ml), saturated sodium bicarbonate (5 ml), and brine (5 ml). The organic layer was evaporated in vacuo and the residue purified by silica gel chromatography using a mixture of 5% methanol/dichloromethane/1% triethylamine as eluant. Pure fractions were collected and the solvent evaporated in vacuo affording 0.22 g (50%) of 4-benzyloxy-2-(1,4-dioxa-8-aza-spiro[4.5]dec-7-ylmethyl)-isoindole-1,3-dione as a semi-solid.

$^1$H NMR (400 MHz, CDCl$_3$) δ7.57 (t, J=8, 1H), 7.48 (d, J=7, 2H), 7.42–7.29 (m, 4H), 7.18 (d, J=8, 1H), 5.31 (s, 2H), 3.94–3.90 (m, 4H), 3.65 (d, J=6, 2H), 3.16–3.09 (m, 1H), 3.07–3.02 (m, 1H), 2.76 (dt, J=13, 3, 1H), 1.78 (d, J=12, 1H), 1.64–1.54 (m, 3H), 1.37 (t, J=12, 1H), 1.08 (t, J=7, 1H).

LC-MS: R$_t$=2.59 min, [M+H]$^+$=409.2

To a solution of the above 4-benzyloxy-2-(1,4-dioxa-8-aza-spiro[4.5]dec-7-ylmethyl)-isoindole-1,3-dione (0.22 g, 0.54 mmol) in 1,4-dioxane (4 ml) was added 4N hydrochloric acid (4 ml) and the reaction stirred in a 65° C. (oil bath) for 6 h. The mixture was basified with saturated sodium bicarbonate until pH=8 and extracted with dichloromethane (3×20 ml). The combined organic extracts were dried (MgSO$_4$), filtered, and the solvent evaporated in vacuo affording crude 4-benzyloxy-2-(4-oxo-piperidin-2-ylmethyl)-isoindole-1,3-dione as an oil. Which was used without further purification or characterization.

The above crude 4-benzyloxy-2-(4-oxo-piperidin-2-ylmethyl)-isoindole-1,3-dione (0.17 g, 0.47 mmol) was dissolved in dichloromethane (4 ml). Saturated sodium bicarbonate (4 ml) was added followed by di-tert-butyl dicarbonate (0.11 g, 0.52 mmol). The reaction was stirred vigorously for 16 h., then the layers were separated. The aqueous layer was extracted with dichloromethane (2×10 ml) and the combined organic phases were dried (MgSO$_4$), filtered and the solvent evaporated in vacuo. The residue was purified by silica gel chromatography using a mixture of ethyl acetate/hexane (1.2) as eluant. Pure fractions were collected and the solvent was evaporated in vacuo affording 0.14 g (64%) of 2-(4-benzyloxy-1,3-dioxo-1,3-dihydro-isoindol-2-ylmethyl)-4-oxo-piperidine-1-carboxylic acid tert-butyl ester.

$^1$H NMR (400 MHz, CDCl$_3$) δ 7.57 (bs, 1H), 7.47–7.31 (m, 6H), 7.18 (bs, 1H), 5.34 (s, 2H), 5.03 (bs, 1H), 4.45–4.14 (m, 1H), 3.89 (t, J=12, 1H), 3.55 (bs, 2H), 2.76–2.71 (m, 1H), 2.57–2.38 (m, 3H), 1.17 (s, 9H).

A solution of 2-(4-benzyloxy-1,3-dioxo-1,3-dihydro-isoindol-2-ylmethyl)-4-oxo-piperidine-1-carboxylic acid tert-butyl ester (0.14 g, 0.30 mmol), sulfur (10.6 mg, 0.33 mmol), and tert-butyl cyanoacetate (55 mg, 0.39 mmol) in absolute ethanol (4 ml) was stirred at 50° C. (oil bath). Morpholine (53 μl, 0.6 mmol) was added and the reaction placed under nitrogen and stirred for 16 h. The solution was cooled to ambient temperature, concentrated in vacuo and the residue purified by silica gel chromatography using a gradient of ethyl acetate/dichloromethane (0 to 5% gradient) as eluant. Pure fractions were collected and the solvent evaporated in vacuo affording a mixture of regioisomers 0.15 g (80%) of 2-amino-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester which were not separable by chromatography.

To a solution of the above mixture of 2-amino-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester and 2-amino-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (0.15 g, 0.24 mmol) in distilled dichloromethane (4 ml) under nitrogen was added imidazol-1-yl-oxo-acetic acid tert-butyl ester (0.14 g, 0.72 mmol) and the reaction mixture was stirred at ambient temperature for 1.5 h. The volatiles were evaporated in vacuo and the crude residue was purified by silica gel chromatography using dichloromethane as eluant. Pure fractions were collected and the solvent evaporated in vacuo affording 50 mg of 2-(tert-butoxyoxalyl-amino)-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (A) and 50 mg of 2-(tert-butoxyoxalyl-amino)-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (B). Another 50 mg remained as a mixture of the two isomers (A) and (B).

(A):

$^1$H NMR (300 μMHz, CDCl$_3$) δ 12.52 (s, 1H), 7.60–7.31 (m, 7H), 7.20–7.10 (m, 1H), 5.33 (s, 2H), 5.05–4.38 (m, 3H), 3.96–3.83 (m, 1H), 3.52–3.41 (m, 1H), 3.01 (bs, 2H), 1.60 (s, 9H), 1.59 (s, 9H), 1.17–1.14 (s, 9H).

LC-MS: R$_t$=4.93 min, [M+H]$^+$=748.1

(B):

$^1$H NMR (300 MHz, CDCl$_3$) δ 12.58–12.52 (s, 1H), 7.60–7.30 (m, 7H), 7.20–7.10 (m, 1H), 5.60–5.39 (m, 1H), 5.34 (s, 2H), 4.36–4.02 (m, 2H), 3.86–3.75 (m, 1H), 3.33–3.18 (m, 1H), 2.97–2.90 (m, 1H), 2.83–2.68 (m, 1H), 1.60 (s, 9H), 1.58–1.57 (s, 9H), 1.15–1.09 (s, 9H)

LC-MS: R$_t$=4.93 min, [M+H]$^+$=748.1

The above 2-(tert-butoxyoxalyl-amino)-5-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.067 mmol) was dissolved in a mixture of ethyl acetate/ethanol (3 ml, 1:1). Palladium on activated carbon (10%, 10 mg) was added and the solution degassed and stirred under hydrogen (1 atm.) for 72 h. TLC analysis indicated that the reaction was incomplete. The mixture was filtered through celite and the filter cake washed with hot ethyl acetate. The filtrate was concentrated in vacuo and purified by silica gel chromatography using a gradient of ethyl acetate/dichloromethane (0 to 5% gradient) as eluant. Pure fractions were collected and the solvent evaporated in vacuo affording 15 mg (30%) of 2-(tert-butoxyoxalyl-amino)-5-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester.

$^1$H NMR (300 MHz, CDCl$_3$) δ 12.50 (s, 1H), 7.61–7.51 (m, 1H), 7.39–7.34 (m, 1H), 7.17–7.09 (m, 1H), 5.04–4.64 (m, 2H), 4.49–4.34 (m, 1H), 3.90–3.78 (m, 1H), 3.51–3.42 (m, 1H), 3.02 (bs, 2H), 1.60 (s, 18H), 1.17–1.14 (2s, 9H).

The above 2-(tert-butoxyoxalyl-amino)-5-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (15 mg, 0.023 mmol) was dissolved in a solution of 50% trifluoroacetic acid/dichloromethane (2 ml). The reaction was stirred at ambient temperature for 12 h., concentrated in vacuo and evaporated in vacuo from dichloromethane (3×10 ml). The resulting precipitate was washed with dichloromethane and dried in vacuo affording 6 mg (47%) of the title compound.

$^1$H NMR (400 MHz, DMSO-d$_6$) δ 12.32 (s, 1H), 11.17 (s, 1H), 9.25 (bs, 2H), 7.64 (t, J=8, 1H), 7.32 (d, J=8, 1H), 7.24 (d, J=8, 1H), 4.41–4.23 (m, 2H), 3.96–3.71 (m, 3H), 3.5–3.2 (obscured by water, 1H), 2.83–2.75 (m, 1H).

LC-MS: R$_t$=1.53 min [M+H]$^+$=446.2

Example 53

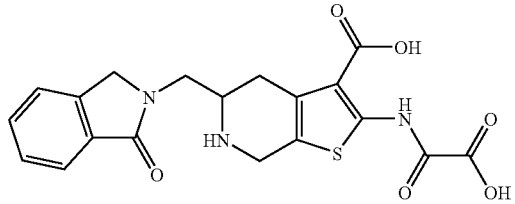

2-(Oxalyl-amino)-5-(1-oxo-1,3-dihydro-isoindol-2-ylmethyl)-4,5,6,7-tetrahydro-thieno[2,3-c]pyridine-3-carboxylic acid 2-Methyl-benzoic acid methyl ester (1.50 g 10 mmol), N-bromosuccinimide (1.96 g, 11 mmol) and 2,2'-azobis(2-methylpropionitrile) (AIBN) (25 mg, 0.15 mmol) were dissolved in chloroform (3 ml). The solution was heated at reflux for 16 h. cooled and the solvent evaporated in vacuo. The residue was purified by silica gel chromatography using a gradient of ethyl acetate/hexane (1–2%) as eluant. Pure fractions were collected and the solvent evaporated in vacuo affording 2.05 g (89%) of 2-bromomethyl-benzoic acid methyl ester as a solid.

¹H NMR (CDCl₃): δ 7.97 (d, 1H, J=7.6 Hz), 7.45–7.52 (m, 2H), 7.38 (dt, 1H, J=1.2, 7.6 Hz), 4.96 (s, 2H), 3.95 (s, 1H).

To a solution of 2-amino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (100 mg, 0.20 mmol) and pyridine (0.18 ml, 2.0 mmol) in acetonitrile (1 ml) at room temperature was added benzyl chloroformate (0.28 ml, 2.0 mmol) in 10 aliquots over 48 h. The solution was then taken into ethyl acetate (30 ml), washed with 0.5 N hydrochloric acid (3×10 ml), saturated sodium bicarbonate (3×10 ml), brine (10 ml), dried (MgSO₄) and filtered. The solvent was evaporated in vacuo. The resulting oil crystallized upon standing for 2 days. The precipitate was filtered off and washed with diethyl ether (3×1 ml) affording after drying in vacuo 59 mg (47,%) of 2-benzyloxy-carbonylamino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester as a solid.

¹H NMR (CDCl₃): δ 10.60 (s, 1H), 7.60–7.92 (m, 4H), 7.38 (m, 5H), 5.26 (s, 2H), 4.30–5.10 (m, 3H), 3.40–4.00 (m, 2H), 1.57 (m, 9H), 1.15 (m, 9H).

To a solution of 1N hydrochloric acid in ethyl acetate (1.0 ml) was added 2-benzyloxy-carbonylamino-5-(1,3-dioxo-1,3-dihydro-isoindol-2-ylmethyl)-4,5,6,7-tetrahydro-thieno[2,3-c]pyridine-3,6-dicarboxylic acid di-tert-butyl ester (52 mg, 0.08 mmol). The solution was stirred at room temperature for 48 h. A precipitate was filtered off which afforded 42 mg (90%) of 2-benzyloxy-carbonylamino-5-(1,3-dioxo-1,3-dihydro-isoindol-2-ylmethyl)-4,5,6,7-tetrahydro-thieno[2,3-c]pyridine-3-carboxylic acid tert-butyl ester hydrochloride as a solid.

¹H NMR (DMSO-d₆): 810.45 (s, 1H), 9.40 (s, 1H), 9.25 (s, 1H), 7.89 (m, 4H), 7.39 (m, 5H), 5.22 (s, 2H), 4.39 (d, 1H, J=15 Hz), 4.28 (m, 1H), 3.95 (m, 2H), 3.79 (m, 1H), 3.20 (m, 1H), 2.70 (m, 1H), 1.48 (s, 9H).

To a solution of the above 2-benzyloxy-carbonylamino-5-(1,3-dioxo-1,3-dihydro-isoindol-2-ylmethyl)-4,5,6,7-tetrahydro-thieno[2,3-c]pyridine-3-carboxylic acid tert-butyl ester hydrochloride (42 mg, 0.072 mmol) in ethanol (0.5 ml) was added hydrazine (68 µl, 0.22 mmol). The solution was stirred at 80° C. for 5 h. and at room temperature for 16 h. The mixture was filtered and the filtrate evaporated in vacuo. The residue was extracted with dichloromethane (5×1 ml). The combined dichloromethane washes were evaporated in vacuo affording 20 mg (67%) of 5-aminomethyl-2-benzyloxy-carbonylamino-4,5,6,7-tetrahydro-thieno[2,3-c]pyridine-3-carboxylic acid tert-butyl ester as an oil.

¹H NMR (CDCl₃): δ 10.55 (bs, 1H), 7.37 (m, 5H), 5.23 (s, 2H), 3.92 (s, 2H), 2.60–3.10 (m, 3H), 1.53 (s, 9H).

To a solution of the above 5-aminomethyl-2-benzyloxy-carbonylamino-4,5,6,7-tetrahydro-thieno[2,3-c]pyridine-3-carboxylic acid tert-butyl ester (20 mg, 0.048 mmol) in acetonitrile (1 ml) at 0° C. was added diisopropylethylamine (18 µl, 0.15 mmol) and 2-bromomethyl-benzoic acid methyl (12 mg, 0.048 mmol). The solution was stirred at 0° C. for 3 hours and at room temperature for 16 h. Di-tert-butyl dicarbonate (21 mg, 0.096 mmol) was then added to the solution. The solution was then stirred at room temperature for 16 h. The solution was taken into ethyl acetate (30 ml), washed with 0.5 N hydrochloric acid (3×10 ml), saturated sodium bicarbonate (3×10 ml) and brine (10 ml), dried (MgSO₄) and filtered. The solvent was evaporated in vacuo. The solid residue was purified by silica gel chromatography using a 5% mixture of ethyl acetate/hexane as eluant. Pure fractions were collected and the solvent evaporated in vacuo affording 10 mg (33%) of 2-benzyloxycarbonylamino-5-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

¹H NMR (CDCl₃): δ 10.59 (s, 1H), 7.81 (m, 1H), 7.52 (m, 1H), 7.39 (m, 7H), 5.25 (s, 1H), 4.22–5.00 (m, 4H), 4.40–4.80 (m, 2H), 2.80–3.10 (m, 2H), 1.55 (s, 9H), 1.25 (s, 9H).

To a solution of the above 2-benzyloxycarbonylamino-5-(1-oxo-1,3-dihydro-isoindol-2-ylmethyl)-4,5,6,7-tetrahydro-thieno[2,3-c]pyridine-3,6-dicarboxylic acid di-tert-butyl ester (9 mg, 0.014 mmol) in methanol (2 ml) was added 10% Pd/C (4 mg). The mixture was stirred under hydrogen (1 atm.) for 3 hours and then filtered. The filtrate was evaporated in vacuo affording 6 mg (93%) of 2-amino-5-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

¹H NMR (CDCl₃): δ 7.80 (m, 1H), 7.50 (m, 1H), 7.44 (m, 2H), 4.22–5.00 (m, 4H), 4.40–4.80 (m, 2H), 2.80–3.10 (m, 2H), 1.63 (s, 9H), 1.25 (s, 9H).

To a solution of the above 2-amino-5-(1-oxo-1,3-dihydro-isoindol-2-ylmethyl)-4,5,6,7-tetrahydro-thieno[2,3-c]pyridine-3,6-dicarboxylic acid di-tert-butyl ester (6 mg, 0.013 mmol) in acetonitrile (0.5 ml) at room temperature was added imidazol-1-yl-oxo-acetic acid tert-butyl ester (27 mg, 0.13 mmol). The solution was stirred for 3 hours at room temperature and then diluted with ethyl acetate (20 ml), washed with 0.5 N hydrochloric acid (2×5 ml), saturated sodium bicarbonate (2×5 ml), brine (5 ml), dried (MgSO₄) and filtered. The solvent was evaporated in vacuo: The residue was purified by silica gel chromatography using a gradient of ethyl acetate/hexane (10–25% gradient) as eluant. Pure fractions were collected and the solvent evaporated in vacuo affording 4 mg (50%) of 2-(tert-butoxyoxalyl-amino-5-(1-oxo-1,3-dihydro-isoindol-2-ylmethyl)-4,5,6,7-tetrahydro-thieno[2,3-c]pyridine-3,6-dicarboxylic acid di-tert-butyl ester as a solid.

¹H NMR (CDCl₃): δ 12.49 (s, 1H), 7.80 (m, 1H), 7.50 (m, 1H), 7.44 (m, 2H), 4.22–5.00 (m, 4H), 4.20–4.90 (m, 2H), 2.90–3.20 (m, 2H), 1.63 (s, 9H), 1.60 (s, 9H), 1.25 (s, 9H).

Example 55

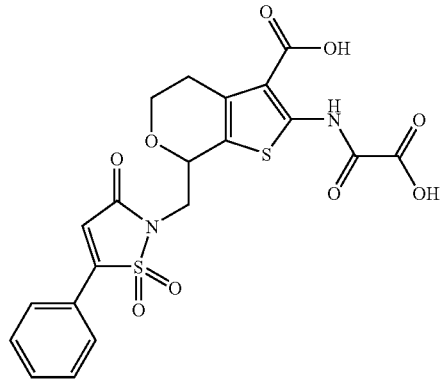

2-(Oxalyl-amino)-7-(1,1,3-trioxo-5-phenyl-1,3-dihydro-isothiazol-2-ylmethyl)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

¹H-NMR (DMSO-d₆) δ 2.85 (bs, 2H), 3.75 (m, 1H), 3.92 (dd, 1H), 4.10 (m, 2H), 5.08 (m, 1H), 7.64 (m, 3H), 7.69 (s, 1H), 7.92 (m, 2H), 12.35 (s, 1H, NHCO).

LC-MS: R$_t$=4.90 min, m/z: 493 [M+H]⁺

Example 56

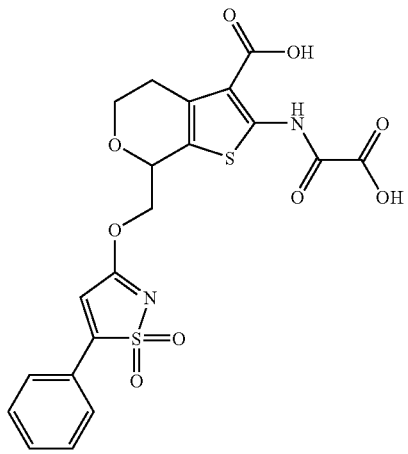

7-(1,1-Dioxo-5-phenyl-1H-isothiazol-3-yloxymethyl)-2-(oxalyl-amino)-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

¹H-NMR (DMSO-d₆) δ 2.86 (bs, 2H), 3.79 (m, 1H), 4.13 (m, 1H), 4.75 (m, 2H), 5.17 (bs, 1H), 7.60 (m, 3H), 7.70 (s, 1H), 7.88 (m, 2H), 12.35 (s, 1H, NHCO).

LC-MS: R$_t$=4.78 min, m/z: 493 [M+H]⁺

Example 57

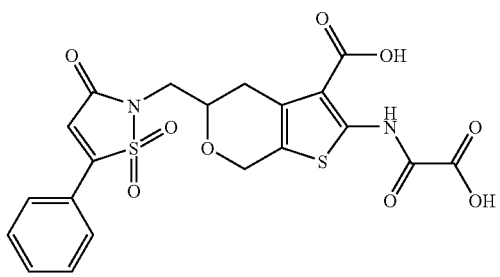

2-(Oxalyl-amino)-5-(1,1,3-trioxo-5-phenyl-1,3-dihydro-isothiazol-2-ylmethyl)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

¹H-NMR (DMSO-d₆) δ 2.62 (dd, 1H), 3.05 (d, 1H), 3.88 (m, 2H), 3.98 (m, 1H), 4.60–4.86 (dd, 2H), 7.6.6 (m, 4H), 7.93 (m, 2H), 12.3 (s, 1H, NHCO).

Example 58

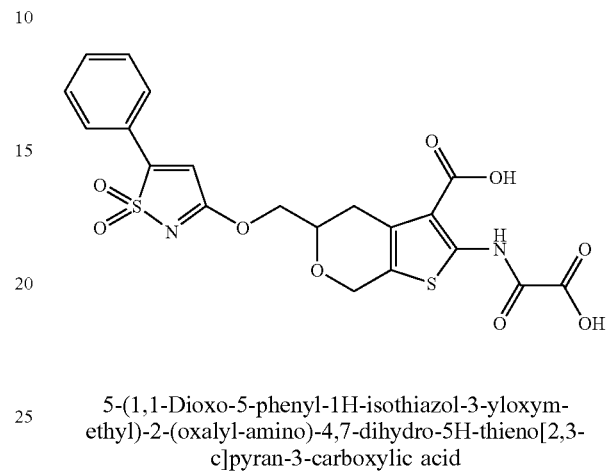

5-(1,1-Dioxo-5-phenyl-1H-isothiazol-3-yloxymethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxo-5-phenyl-1,2-dihydro-1H-isothiazol-3-one as starting material. O- and N-alkylated products were separated by column chromatography.

Mp.: 230–232° C.;

Calculated for C$_{20}$H$_{16}$N$_2$O$_9$S$_2$, 1×H$_2$O; C, 47.06%; H, 3.55%; N, 5.49%. Found: C, 46.88%; H, 3.44%; N, 5.45%.

Example 59

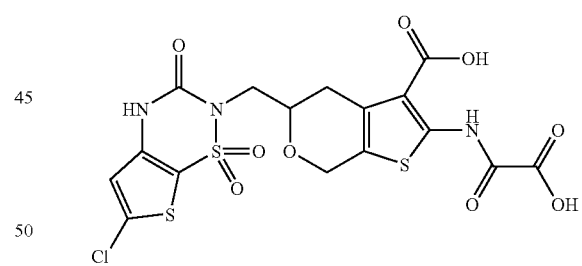

5-(6-Chloro-1,1,3-trioxo-2,3-dihydro-4H-thieno[3,2-e]-1,2,4-thiadiazin-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxide-6-chloro-2,3-dihydro-4H-thieno[3,2-e]-1,2,4-thiadiazine-3-one as starting material. O- and N-alkylated products were separated by column chromatography.

¹H-NMR (DMSO-d₆) δ 2.60 (dd, 1H), 2.98 (d, 1H), 3.87–3.96 (m, 2H), 4.04 (m, 1H), 4.56–4.82 (dd, 2H), 7.0 (s, 1H), 11.95 (s, 1H, NHCO), 12.3 (s, 1H, NHCO).

Example 60

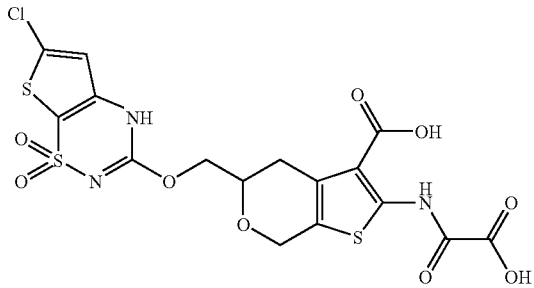

5-(6-Chloro-1,1-dioxo-4H-thieno[3,2-e]-1,2,4-thiadiazine-3-yloxymethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1,1-dioxide-6-chloro-2,3-dihydro-4H-thieno[3,2-e]-1,2,4-thiadiazine-3-one as starting material. O- and N-alkylated products were separated by column chromatography.

Mp.: >250° C.;

Calculated for $C_{16}H_{12}ClN_3O_9S_3$, $0.75 \times H_2O$; C, 35.89%; H, 2.54%; N, 7.85% Found: C, 35.84%; H, 2.36%; N, 7.74%.

Example 61

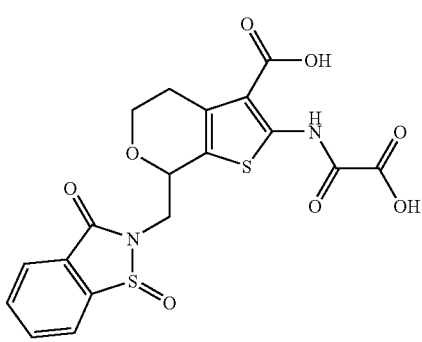

7-(1,3-Dioxo-1,3-dihydro-benzo[d]isothiazol-2-ylmethyl)-2-(oxalyl-amino-4,7-dihydro-5H-thieno[2,3-c]pyran-3-carboxylic acid The title compound was prepared in a similar way as described in Example 23 using 2-amino-7-hydroxymethyl-4,7-dihydro-5H-thieno[2,3-c]pyran-3-carboxylic acid tert-butyl ester and 1-oxo-1,2-dihydro-1H-benzo[d]isothiazol-3-one as starting material. O- and N-alkylated products were separated by column chromatography.

LC-MS: $R_t$=3.82 min, m/z: 451 [M+H]$^+$

Example 62

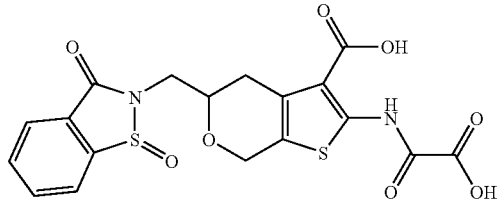

5-(1,3-Dioxo-1,3-dihydro-benzo[d]isothiazol-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 1-oxo-1,2-dihydro-1H-benzo[d]isothiazol-3-one as starting material. O- and N-alkylated products were separated by column chromatography.

Mp.: 230–231° C.;

Calculated for $C_{18}H_{14}N_2O_8S_2$, $0.5 \times H_2O$; C, 47.06%; H, 3.29%; N, 6.10% Found: C, 46.94%; H, 3.42%; N, 6.26%.

Example 63

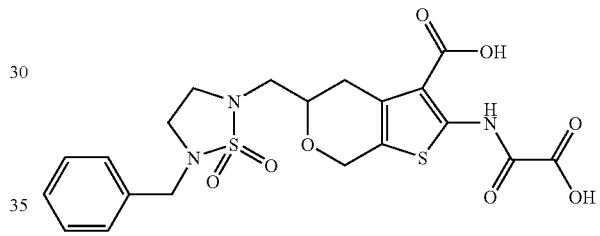

5-(5-Benzyl-1,1-dioxo-[1,2,5]thiadiazolidin-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl-4,7-dihydro-5H-thieno[2,3-c]pyran-3-carboxylic acid tert-butyl ester and 2-benzyl-[1,2,5]thiadiazolidine 1,1-dioxide as starting material.

Mp.: 188–192° C.;

LC-MS: $R_t$=5.00 min, m/z: 496 [M+H]$^+$

Example 64

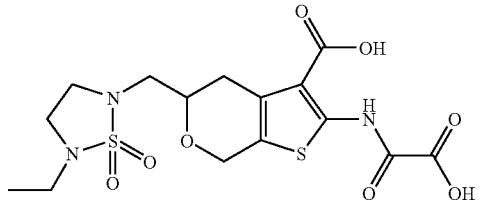

5-(5-Ethyl-1,1-dioxo-[1,2,5]thiadiazolidin-2-ylmethyl)-2-(oxalyl-amino)-4,7-dihydro-5H-thieno[2,3-c]pyran-3-carboxylic acid The title compound was prepared in a similar way as described in Example 23 using 2-amino-5-hydroxymethyl- 4,7-dihydro-5H-thieno[2,3-c]pyran-3-carboxylic acid tert-butyl ester and 2-ethyl-[1,2,5]thiadiazolidine 1,1-dioxide as starting material.

LC-MS: $R_t$=4.18 min, m/z: 434 [M+H]$^+$

Example 65

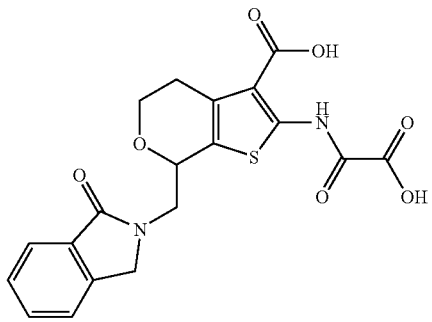

2-(Oxalyl-amino)-7-(1-oxo-1,3-dihydro-isoindol-2-ylmethyl)-4,7-dihydro-5H-thieno[2,3-c]pyran-3-carboxylic acid To a solution of 2-amino-7-aminomethyl-4,7-dihydro-5H-thieno[2,3-c]pyran-3-carboxylic acid tert-butyl ester (100 mg, 0.38 mmol) and N,N-diisopropylethylamine (72 µL, 0.41 mmol) in acetonitrile (6 ml) at 0° C. was added 2-bromomethyl-benzoic acid methyl ester (43 mg, 0.19 mmol). The reaction mixture was stirred for 16 hours and the solvent evaporated in vacuo. The residue was diluted in ethyl acetate (50 ml), washed with 1N hydrochloric acid, saturated sodium bicarbonate, brine, dried (MgSO$_4$), filtered and the solvent evaporated in vacuo, which afforded 50 mg (68%) of 2-amino-7-(1-oxo-1,3-dihydro-isoindol-2-ylmethyl)-4,7-dihydro-5H-thieno[2,3-c]pyran-3-carboxylic acid tert-butyl ester as an oil.

$^1$H-NMR (CDCl$_3$) δ 7.86 (d, 1H, J=8 Hz), 7.55 (t, 1H, J=8 Hz), 7.45 (t, 2H, J=8 Hz), 4.88 (dt, 1H, J=6, 2 Hz), 4.68 (d, 1H, J=17 Hz), 4.48 (d, 1H, J=17 Hz), 4.25–4.10 (m, 1H), 4.03 (dd, 1H, J=17 and J=3 Hz), 3.80–3.75 (m, 2H), 2.92–2.70 (m, 2H), 1.54 (s, 9H).

To a solution of 2-amino-7-(1-oxo-1,3-dihydro-isoindol-2-ylmethyl)-4,7-dihydro-5H-thieno[2,3-c]pyran-3-carboxylic acid tert-butyl ester (50 mg, 0.13 mmol) in tetrahydrofuran (1 ml) was added imidazol-1-yl-oxo-acetic acid tert-butyl ester (100 mg, 0.51 mmol). The mixture was stirred at room temperature for 24 hours. The solvent was removed in vacuo. The residue was taken into ethyl acetate (50 ml), washed with saturated sodium bicarbonate and brine, dried (Na$_2$SO$_4$) and filtered. The solvent was removed in vacuo and the residue was chromatographed using a mixture of 10% ethyl acetate/dichloromethane as eluent, which afforded 55 mg (83%) of 2-(tert-butoxyoxalyl-amino)-7-(1-oxo-1,3-dihydro-isoindol-2-ylmethyl)-4,7-dihydro-5H-thieno[2,3-c]pyran-3-carboxylic acid tert-butyl ester as an oil.

$^1$H-NMR (CDCl$_3$) δ 12.59 (s, 1H), 7.88 (d, 1H, J=7 Hz), 7.54 (t, 1H, J=7 Hz), 7.46 (t, 2H, J=7 Hz), 5.04 (dd, 1H, J=6 Hz and J=2 Hz), 4.69 (d, 1H, J=17 Hz), 4.46 (d, 1H, J=17 Hz), 4.26–4.10 (m, 2H), 3.77 (dd, 1H, J=9 Hz and J=3 Hz), 3.70 (dd, 1H, J=15 Hz and J=9 Hz), 3.02–2.80 (m, 2H), 1.55 (s, 18H).

A solution of 2-(tert-butoxyoxalyl-amino)-7-(1-oxo-1,3-dihydro-isoindol-2-ylmethyl)-4,7-dihydro-5H-thieno[2,3-c]pyran-3-carboxylic acid tert-butyl ester (55 mg, 0.11 mmol) in 50% trifluoroacetic acid/dichloromethane (2 ml) was stirred for 16 hours. The volatiles were removed in vacuo and the residue was washed with dichloromethane and dried, which afforded 29 mg (50%) of the title compound as a solid trifluoroacetate.

$^1$H-NMR (DMSO-d$_6$) δ 12.35 (s, 1H), 7.70 (d, 1H, J=8 Hz), 7.61 (d, 1H, J=3 Hz), 7.52–7.47 (m, 2H), 5.04 (s, 1H), 4.59 (d, 1H, J=18 Hz), 4.58 (d, 1H, J=18 Hz), 4.19–4.08 (m, 1H), 3.88 (d, 1H, J=6 Hz), 3.78–3.66 (m, 1H), 3.38 (q, 1H, J=7 Hz), 2.85 (s, 2H);

LC-MS: $R_t$=2.12 min, m/z: 417 [M+H]$^+$

Example 66

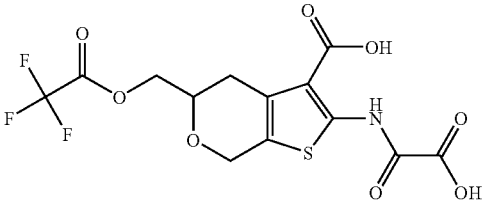

2-(Oxalyl-amino)-5-(2,2,2-trifluoro-acetoxymethyl)-4,7-dihydro-5H-thieno[2,3-c]pyran-3-carboxylic acid 2-(tert-Butoxyoxalyl-amino)-5-hydroxymethyl-4,7-dihydro-5H-thieno[2,3-c]pyran-3-carboxylic acid tert-butyl ester (0.5 g, 1.21 mmol) was dissolved in dichloromethane (9 ml) and trifluoroacetic acid (3 ml) was added. The reaction mixture was stirred 64 hours at room temperature. The precipitate was filtered off and washed with diethyl ether and dried in vacuo at 50° C. for 4 hours, which afforded 180 mg (50%) of the title compound as a solid.

Mp.: 231–233° C.;

Calculated for C$_{13}$H$_{10}$F$_3$NO$_8$S; C, 39.30%; H, 2.56%; N, 3.57%. Found: C, 39.30%; H, 2.54%; N, 3.53%.

Example 67

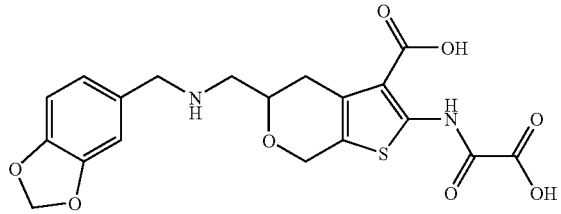

5-(((Benzo[1,3]dioxol-5-ylmethyl)-amino)-methyl)-2-(oxalyl-amino)-4,7-dihydro-5H-thieno[2,3-c]pyran-3-carboxylic acid To a solution of oxalyl chloride (1 ml, 11.13 mmol) in dichloromethane (40 ml) cooled to −78° C. under an atmosphere of nitrogen was added dropwise a solution of dimethylsulfoxide (1.6 ml, 21.78 mmol) in dichloromethane (16 ml) during 5 min. After stirring for 15 min at −78° C. a solution of 2-(tert-butoxyoxalyl-amino)-5-hydroxymethyl-4,7-dihydro-5H-thieno[2,3-c]pyran-3-carboxylic acid tert-butyl ester (2.0 g, 4.84 mmol) in dichloromethane (30 ml) was added dropwise and the resulting mixture was stirred for 0.5 hour at −78° C. N,N-Diisopropylethylamine (4.2 ml, 24.18 mmol) was added and the reaction mixture allowed reaching room temperature at which time heptane (700 ml) was added. The mixture was filtered through anhydrous sodium sulfate and the solvent evaporated in vacuo. The residue (2.71 g) was purified on column chromatography using a mixture of ethyl acetate/heptane (1:4) as eluent which afforded 0.93 g (47%) of 2-(tert-butoxyoxalylamino)-5-formyl-4,7-dihydro-5H-thieno[2,3-c]pyran-3-carboxylic acid tert-butyl ester as an oil.

To a mixture of 2-(tert-butoxyoxalyl-amino)-5-formyl-4,7-dihydro-5H-thieno[2,3-c]pyran-3-carboxylic acid tert-butyl ester (0.46 g, 1.12 mmol) and piperonylamine (145 µl, 1.12 mmol) in 1,2-dichloroethane (25 ml) was added sodium triacetoxyborohydride (0.35 g, 1.57 mmol) and the resulting mixture was stirred at room temperature for 1 hour. The mixture was washed with saturated aqueous sodium hydrogencarbonate (2×30 ml) and dried (Na$_2$SO$_4$), filtered and the solvent evaporated in vacuo. The residue (0.56 g) was purified on column chromatography using a mixture of ethyl acetate/heptane (1:1) as eluent followed by a mixture of 10% triethylamine in ethyl acetate/heptane (1:1) as eluent. Semi pure fractions were collected and the solvent evaporated in vacuo. The residue (180 mg) was subjected to preparative TLC using a mixture of 10% triethylamine in ethyl acetate/ethanol (4:1) as eluent. The desired band was taken off and extracted with methanol (400 ml) for 0.5 hour, filtered and the solvent evaporated in vacuo, which afforded 250 mg (>100%, contains dichloromethane and silicagel) of 5-(((benzo[1,3]dioxol-5-ylmethyl)-amino)methyl)-2-(tert-butoxyoxalyl-amino)-4,7-dihydro-5H-thieno[2,3-c]pyran-3-carboxylic acid tert-butyl ester as an oil.

LC-MS: R$_t$=5.75 min, m/z: 547 [M+H]$^+$.

5-(((Benzo[1,3]dioxol-5-ylmethyl)-amino)methyl)-2-(tert-butoxyoxalyl-amino)-4,7-dihydro-5H-thieno[2,3-c]pyran-3-carboxylic acid tert-butyl ester (250 mg) was dissolved in dichloromethane (9 ml) and trifluoroacetic acid (3 ml) was added. The reaction mixture was stirred 16 hours at room temperature. The volatiles were evaporated in vacuo and the residue triturated with a small portion of diethyl ether. The solid precipitate was filtered off and washed with diethyl ether and dried in vacuo at 50° C. for 16 hours, which afforded 160 mg of the title compound as a solid.

Calculated for C$_{19}$H$_{18}$N$_2$O$_8$S, 2×TFA, 3×H$_2$O; C, 38.56%; H, 3.66%; N, 3.91%. Found: C, 38.61%; H, 3.90%; N, 4.22%.

Example 68

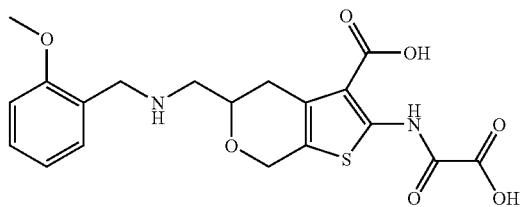

5-((2-Methoxy-benzylamino)methyl)-2-(oxalyl-amino)-4,7-dihydro-5H-thieno[2,3-c]pyran-3-carboxylic acid The title compound was prepared in a similar way as described in Example 66 using 2-(tert-butoxyoxalyl-amino)-5-formyl-4,7-dihydro-5H-thieno[2,3-c]pyran-3-carboxylic acid tert-butyl ester and 2-methoxy-benzylamine as starting material.

Calculated for C$_{19}$H$_{20}$N$_2$O$_7$S, 0.75×TFA; C, 48.67%; H, 4.13%; N, 5.54%. Found: C, 48.61%; H, 4.42%; N, 5.35%.

Example 69

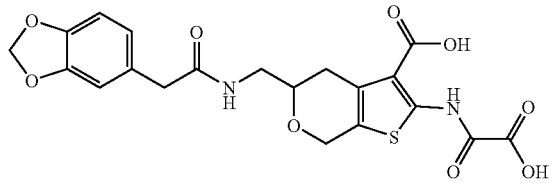

5-((2-Benzo[3,1]dioxol-5-yl-acetylamino)methyl)-2-(oxalyl-amino)-4,7-dihydro-5H-thieno[2,3-c]pyran-3-carboxylic acid To a solution of 3,4-methylenedioxy phenylacetic acid (0.22 g, 1.09 mmol), 1-(3-dimethylaminopropyl)-3-ethylcarbodiimide, hydrochloride (0.27 g, 1.42 mmol) in acetonitrile (6 ml) was added triethylamine (0.46 ml, 3.27 mmol). The resultant mixture was allowed to stir at ambient temperature for 10 min. before 2-amino-5-aminomethyl-4,7-dihydro-5H-thieno-[2,3-c]pyran-3-carboxylic acid tert-butyl ester (0.311 g, 1.09 mmol) was added. The reaction mixture was allowed to stir at ambient temperature for 18 hours and then concentrated in vacuo. To the residue ethyl acetate and water were added and the layers separated. The organic layer was washed with hydrochloric acid (0.5M, (v/v)), saturated sodium bicarbonate (2×25 ml) and brine (2×25 ml). The organic layer was dried (MgSO$_4$), filtered and the solvent evaporated in vacuo. The crude 2-amino-5-((2-benzo[1,3]dioxol-5-yl-acetylamino)-methyl]-4,7-dihydro-5H-thieno[2,3-c]pyran-3-carboxylic acid tert-butyl ester was used immediately in the next step.

$^1$H-NMR (CDCl$_3$) δ 6.78–6.69 (m, 3H), 5.97 (bs, 2H), 5.95 (s, 2H), 4.60–4.58 (m, 1H), 4.53 (s, 2H), 3.73 (ddd, 1H, J=14 Hz, J=7.6 Hz and J=3.2 Hz), 3.65–3.59 (m, 1H), 3.49 (s, 2H), 3.11 (ddd, 1H, J=12.4 Hz, J=4 Hz and J=4.4 Hz), 2.76 (dm, 1H), 2.44 (ddt, 1H, J=19.6 Hz, J=13.2 Hz and J=2.4 Hz), 1.51 (s, 9H).

To a solution of the above crude 2-amino-5-((2-benzo[1,3]dioxol-5-yl-acetylamino)-methyl]-4,7-dihydro-5H-thieno[2,3-c]pyran-3-carboxylic acid tert-butyl ester (0.17 g, 0.38 mmol) in dichloromethane (5 ml) was added imidazol-1-yl-oxo-acetic acid tert-butyl ester (0.22 g, 1.14 mmol). The reaction mixture was stirred at room temperature for 18 hours, the volatiles evaporated in vacuo and the residue diluted with ethyl acetate. The organic layer was washed with hydrochloric acid (1% (v/v), 2×25 ml), saturated sodium bicarbonate (2×25 ml) and brine (2×25 ml). The organic layer was dried (MgSO$_4$), filtered, concentrated in vacuo and the residue subjected to flash chromatography using a mixture of ethyl acetate/hexanes (1:2) as eluent, which afforded 0.12 g (55%) of 2-(tert-butoxyoxalyl-amino)-5-((2-benzo[1,3]dioxol-5-yl-acetylamino)-methyl]-4,7-dihydro-5H-thieno[2,3-c]pyran-3-carboxylic acid tert-butyl ester as an oil.

$^1$H-NMR (CDCl$_3$) δ 12.51 (bs, 1H), 6.78 (d, 1H, J=8 Hz), 6.77 (d, 1H, J=1.6 Hz), 6.71 (dd, 1H, J=8.4 Hz and J=1.6 Hz), 5.96 (s, 2H), 4.70 (m, 2H, J=35 Hz, J=15.2 Hz, J=14.4 Hz and J=2 Hz), 3.77 (ddd, 1H, J=10.8 Hz, J=7.6 Hz and J=3.2 Hz), 3.67–3.62 (m, 1H), 3.50 (s, 2H), 3.15 (ddd, 1H, J=12.8 Hz, J=8.4 Hz and J=4.4 Hz), 2.87 (dt, 1H, J=16 Hz and J=3 Hz), 2.57–2.50 (m, 1H), 1.61 (s, 9H), 1.57 (s, 9H);

LC-MS: m/z: 575.0 [M+H]$^+$ 2-(tert-Butoxyoxalyl-amino)-5-((2-benzo[1,3]dioxol-5-yl-acetylamino)-methyl]-4,7-dihydro-5H-thieno[2,3-c]pyran-3-carboxylic acid tert-butyl ester (0.12 g, 0.20 mmol) was dissolved in a 50% solution of trifluoroacetic acid/dichloromethane (2 ml). The reaction mixture was stirred at ambient temperature for 18 hours, concentrated in vacuo to ⅕ of the volume and the precipitate filtered off and washed with dichloromethane (2×) affording 50 mg (50%) of the title compound as a solid.

¹H-NMR (DMSO-d₆) δ 12.32 (bs, 1H), 8.20 (t, 1H, J=6.8 Hz), 6.81 (m, 2H), 6.70 (m, 1H), 5.95 (s, 2H), 4.80 (d, 1H, J=19.6 Hz), 4.63 (d, 1H, J=20 Hz), 3.65 (m, 1H), 3.34 (s, 2H), 3.30–3.20 (m, 3H), 2.87 (dm, 1H);

LC-MS: m/z: 463.0 [M+H]⁺.

Example 70

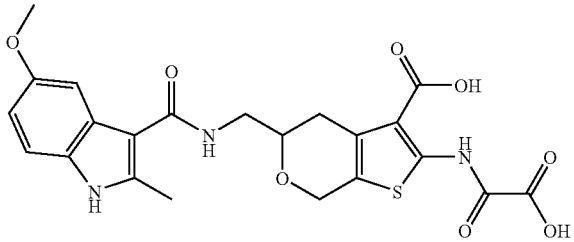

5-(((5-Methoxy-2-methyl-1H-indol-3-carbonyl)amino)methyl)-2-(oxalyl-amino)-4,7-dihydro-5H-thieno[2,3-c]pyran-3-carboxylic acid To a solution of 5-methoxy-2-methyl indole-3-acetic acid (0.26 g, 1.18 mmol), and 1-(3-dimethylaminopropyl)-3-ethylcarbodiimide, hydrochloride (0.27 g, 1.4 mmol) in acetonitrile (10 ml) was added triethylamine (0.46 ml, 3.2 mmol). The reaction mixture was allowed to stir for 10 min at room temperature before compound 2-amino-5-aminomethyl-4,7-dihydro-5H-thieno[2,3-c]pyran-3-carboxylic acid tert-butyl ester (0.307 g, 1.08 mmol) was added. The reaction mixture was allowed to stir for 18 hours and then concentrated in vacuo. Ethyl acetate and water were added and the layers separated. The organic layer was washed with hydrochloric acid (0.5M, (v/v)), saturated sodium bicarbonate (2×25 ml) and brine (2×25 ml). The organic layer was 5-(((5-methoxy-2-methyl-1H-indol-3-carbonyl)amino)-methyl)-4,7-dihydro-5H-thieno[2,3-c]pyran-3-carboxylic acid tert-butyl ester was used immediately in the next step.

¹H-NMR (CDCl₃) δ 7.90 (bs, 1H), 7.19 (d, 1H, J=8.8 Hz), 6.87 (d, 1H, J=2.4 Hz), 6.79 (dd, 1H, J=8.8 Hz and J=2.4 Hz), 6.18 (m, 1H), 5.94 (s, 2H), 4.33 (m, 2H, J=25 Hz, J=14 Hz, J=2.8 Hz and J=1.6 Hz), 3.80 (s, 3H), 3.76 (ddd, 1H, J=14 Hz, J=8 Hz and J=2.8 Hz), 3.65 (s, 3H), 3.53 (m, 1H), 2.99 (ddd, 1H, J=13 Hz, J=5.6 Hz and J=4 Hz), 2.76 (dt, 1H, J=16.8 Hz, J=2.8 Hz), 2.42–2.40 (m, 1H), 2.38 (s, 3H), 1.51 (s, 9H).

To a solution of the crude 2-amino-5-(((5-methoxy-2-methyl-1H-indol-3-carbonyl)amino)methyl)-4,7-dihydro-5H-thieno[2,3-c]pyran-3-carboxylic acid tert-butyl ester (0.35 g, 0.72 mmol) in dichloromethane (5 ml) was added imidazol-1-yl-oxo-acetic acid tert-butyl ester (0.42 g, 2.1 mmol). The reaction mixture was stirred at room temperature for 18 hours. The reaction mixture was concentrated in vacuo and the residue diluted with ethyl acetate. The organic layer was washed with hydrochloric acid (1% (v/v), 2×25 ml), saturated sodium bicarbonate (2×25 ml) and brine (2×25 ml). The organic layer was dried (MgSO₄), filtered, concentrated in vacuo and the residue subjected to flash chromatography using a mixture of ethyl acetate/hexanes (1:1) as eluent, which afforded 0.24 (55%) of 2-(tert-butoxyoxalyl-amino)-5-(((5-methoxy-2-methyl-1H-indol-3-carbonyl)amino)methyl)-4,7-dihydro-5H-thieno[2,3-c]pyran-3-carboxylic acid tert-butyl ester as an oil.

¹H-NMR (CDCl₃) δ 12.50 (bs, 1H), 7.92 (s, 1H), 7.20 (dd, 1H, J=8.4 Hz and J=0.4 Hz), 6.88 (d, 1H, J=2.4 Hz), 6.80 (dd, 1H, J=8.8 Hz and J=2.4 Hz), 6.21 (m, 1H), 4.56 (dd, 1H, J=14.8 Hz and J=2.8 Hz), 4.44 (dt, 1H, J=14.4 Hz and J=2.8 Hz), 4.11 (q, 1H, J=7.2 Hz), 3.81–3.75 (m, 1H), 3.79 (s, 3H), 3.66 (s, 2H), 3.58–3.54 (m, 1H), 3.01 (ddd, 1H, J=14 Hz, J=8.8 Hz and J=4.4 Hz), 2.85 (dt, 1H, J=16.8 Hz and J=6 Hz), 2.52–2.45 (m, 1H), 2.38 (s, 3H), 1.60 (s, 9H), 1.57 (s, 9H);

LC-MS: m/z: 614.1 [M+H]⁺.

2-(tert-Butoxyoxalyl-amino)-5-(((5-methoxy-2-methyl-1H-indol-3-carbonyl)amino)-methyl)-4,7-dihydro-5H-thieno[2,3-c]pyran-3-carboxylic acid tert-butyl ester (0.24 g, 0.39 mmol) was dissolved in a 50% solution of trifluoroacetic acid/dichloromethane (2 ml). The reaction mixture was stirred at ambient temperature for 18 hours, concentrated in vacuo to ⅕ of the volume and the precipitate filtered off. The filtrate was washed with dichloromethane (2×) and dried, which afforded 100 mg (50%) of the title compound as a solid.

¹H-NMR (DMSO-d₆) δ 12.31 (bs, 1H), 10.58 (s, 1H), 7.98 (t, 1H, J=6.8 Hz), 7.08 (d, 1H, J=11.2 Hz), 6.98 (d, 1H, J=2.4 Hz), 6.58 (dd, 1H, J=11.6 Hz and J=2.8 Hz), 5.75 (d, 1H, J=0.8 Hz), 4.77 (d, 1H, J=19.6 Hz), 4.58 (d, 1H, J=20 Hz), 3.69 (s, 3H), 3.64–3.62 (m, 1H), 3.43 (s, 2H), 3.31–3.20 (m, 1H), 2.92–2.84 (m, 1H), 2.52 (m, 1H—partially obscured by DMSO), 2.30 (s, 3H);

LC-MS: m/z: 500.1 [M−H]⁻.

Example 71

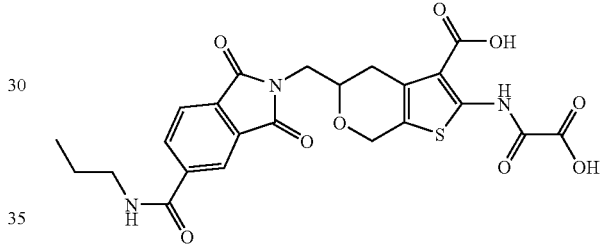

5-(1,3-Dioxo-5-propylcarbamoyl-1,3-dihydro-isoindol-2-ylmethyl)-2-(oxalyl-amino)-4,7-dihydro-5H-thieno[2,3-c]pyran-3-carboxylic acid In a 10-mL scintillating vial, a solution of 2-amino-5-aminomethyl-4,7-dihydro-5H-thieno[2,3-c]pyran-3-carboxylic acid tert-butyl ester (149 mg, 0.5 mmol) in N,N-dimethylformamide (4 mL) was treated with trimellitic anhydride, (120 mg, 0.62 mmol) and stirred at 100° C. for 24 hours. The solution was then diluted with ethyl acetate (25 ml) and washed with 0.5N aqueous hydrogen chloride (25 mL) and brine (25 mL). The organic layer was dried (MgSO₄), filtered, and concentrated in vacuo affording 229 mg (100%) of 2-(2-amino-3-tert-butoxycarbonyl-4,7-dihydro-5H-thieno[2,3-c]pyran-5-ylmethyl)-1,3-dioxo-2,3-dihydro-1H-isoindole-5-carboxylic acid as a solid.

¹H-NMR (300 MHz, CDCl₃) δ 8.58 (s, 1H), 8.49 (d, 1H, J=9 Hz), 8.00 (d, 1H, J=10 Hz), 4.64–4.54 (m, 2H), 4.08–4.02 (m, 2H), 3.88–3.80 (m, 1H), 2.98–2.83 (m, 1H), 2.68–2.54 (m, 1H), 1.57 (s, 9H).

HPLC (254.4 nm) R$_f$=3.98 min.

In a 250 mL round bottom flask, a solution of 2-(2-amino-3-tert-butoxycarbonyl-4,7-dihydro-5H-thieno[2,3-c]pyran-5-ylmethyl)-1,3-dioxo-2,3-dihydro-1H-isoindole-5-carboxylic acid (500 mg, 1.1 mmol) in dichloromethane (7 mL) was treated with a solution of imidazol-1-yl-oxo-acetic acid tert-butyl ester (633 mg, 3.2 mmol) in dichloromethane (1.0 mL). After stirring for 4 hours at room temperature the reaction solution was dissolved in ethyl acetate (100 mL) and washed with distilled water (2×50 mL), 0.5 N aqueous hydrogen chloride (3×50 mL), and brine (50 mL). The organic layer was dried (MgSO$_4$), filtered, and concentrated in vacuo to yield 370 mg (58%) of 2-(2-(tert-butoxyoxalyl-amino)-3-tert-butoxycarbonyl-4,7-dihydro-5H-thieno[2,3-c]pyran-5-ylmethyl)-1,3-dioxo-2,3-dihydro-1H-isoindole-5-carboxylic acid as a solid.

$^1$H-NMR (300 MHz, CDCl$_3$) δ12.49 (s, 1H), 8.58 (s, 1H), 8.50 (d, 1H, J=8 Hz), 8.00 (d, 1H, J=8 Hz), 4.84–4.65 (m, 2H), 4.17–4.00 (m, 2H), 3.92–3.84 (m, 1H), 3.08–2.94 (m, 1H), 2.78–2.64 (m, 1H), 1.61 (s, 9H), 1.57 (s, 9H).

In a 50 mL round bottom flask, a solution of 2-(2-(tert-butoxyoxalyl-amino)-3-tert-butoxycarbonyl-4,7-dihydro-5H-thieno[2,3-c]pyran-5-ylmethyl)-1,3-dioxo-2,3-dihydro-1H-isoindole-5-carboxylic acid (208 mg, 0.36 mmol) in dichloromethane (5.0 mL) was treated with N,N-diisopropyl ethylamine (200 μL, 1.1 mmol) and 1-(3-dimethylamino-propyl)-3-ethylcarbodiimide hydrochloride (84 mg, 0.44 mmol). The solution was allowed to stir for 50 minutes at room temperature before propylamine (30 μL, 0.36 mmol) was added dropwise. The solution was stirred for an additional 18 hours at room temperature. The volatiles were evaporated in vacuo and the residue was purified by silica gel chromatography using a mixture of hexane/ethyl acetate (9:1) as eluent, which afforded 51 mg (23%) of 2-(tert-butoxyoxalyl-amino)-5-(1,3-dioxo-5-propylcarbamoyl-1,3-dihydro-isoindol-2-ylmethyl)-4,7-dihydro-5H-thieno[2,3-c]pyran-3-carboxylic acid tert-butyl ester as a solid.

$^1$H-NMR (300 MHz, CDCl$_3$) δ 12.48 (s, 1H), 8.24–8.16 (m, 2H), 7.93 (d, 1H, J=8 Hz), 6.39 (t, 1H, J=6 Hz), 4.18–4.63 (m, 2H), 4.10–3.96 (m, 2H), 3.92–3.78 (m, 1H), 3.47 (q, 2H, J=7 Hz), 2.99 (d, 1H, J=17), 2.76–2.60 (m, 1H), 1.68 (q, 2H, J=7 Hz), 1.61 (s, 9H), 1.57 (s, 9H), 1.01 (t, 3H, J=7 Hz).

In a 25 mL round bottom flask 2-(tert-butoxyoxalyl-amino)-5-(1,3-dioxo-5-propylcarbamoyl-1,3-dihydro-isoindol-2-ylmethyl)-4,7-dihydro-5H-thieno[2,3-c]pyran-3-carboxylic acid tert-butyl ester (40 mg, 0.07 mmol) was dissolved in 20% trifluoroacetic acid in dichloromethane (4 mL). The solution was left open to the atmosphere without stirring. After 24 hours the precipitate was filtered off and washed with diethyl ether, affording 32 mg (90%) of the title compound as a solid.

$^1$H-NMR (300 MHz, DMSO-d$_6$) δ 12.32 (s, 1H), 8.81 (s, 1H), 8.58 (s, 1H), 8.00 (s, 1H), 4.90–4.48 (m partially obscured by water, 2H), 4.00–3.64 (m partially obscured by water, 3H), 3.36–3.16 (m partially obscured by water, 2H), 3.13–2.90 (d partially obscured by water 1H), 2.69–2.53 (m partially obscured by DMSO, 1H), 1.69–1.38 (m, 2H), 1.00–0.74 (m, 3H).

HPLC (254.4 nm) R$_t$=3.09 min.

MS (APCI$^-$) m/z: 515.4 [M−H]$^-$.

Example 72

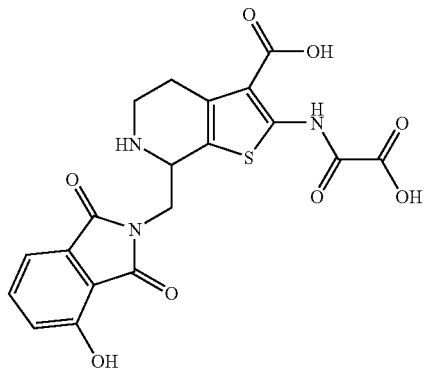

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid 2-(tert-Butoxyoxalyl-amino)-7-(4-benzyloxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (50 mg, 0.067 mmol) was dissolved in a mixture of ethyl acetate/ethanol (3 mL, 1:1). Palladium on activated carbon (10%, 10 mg) was added and the solution degassed and stirred under hydrogen (1 atm) for 72 hours. The mixture was filtered through celite and the filter cake washed with hot ethyl acetate. The filtrate was concentrated in vacuo and the residue purified by silica gel chromatography (10% ethyl acetate/dichloromethane) to obtain 42 mg (95%) of 2-(tert-butoxyoxalyl-amino)-7-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester as an oil.

$^1$H-NMR (400 MHz, CDCl$_3$) δ 12.59–12.53 (2s, 1H), 7.64–7.53 (m, 1H), 7.42–7.36 (m, 1H), 7.19–7.11 (m, 1H), 5.58–5.37 (m, 1H), 4.37–4.00 (m, 2H), 3.86–3.78 (m, 1H), 3.32–3.18 (m, 1H), 2.99–2.94 (m, 1H), 2.84–2.69 (m, 1H), 1.62–1.59 (3s, 18H), 1.17–1.11 (2s, 9H);

LC-MS: R$_t$=4.55 min, m/z: 658 [M+H]$^+$, 2-(tert-Butoxyoxalyl-amino)-7-(4-hydroxy-1,3-dioxo-1,3-dihydro-isoindol-2-ylmethyl)-4,5,6,7-tetrahydro-thieno[2,3-c]pyridine-3,6-dicarboxylic acid di-tert-butyl ester (42 mg, 0.064 mmol) was dissolved in a solution of 50% trifluoroacetic acid/methylene chloride (3 mL). The reaction was stirred at ambient temperature for 7 hours, concentrated in vacuo and evaporated from dichloromethane (10 ml) three times. The resulting precipitate was washed with dichloromethane and dried in vacuo to give 29 mg (81%) of the title compound as a solid trifluoroacetate.

$^1$H-NMR (400 MHz, DMSO-d$_6$) δ 12.32 (bs, 1H), 11.26 (s, 1H), 9.30 (bs, 2H), 7.64 (t, 1H, J=7 Hz), 7.33 (d, 1H, J=7 Hz), 7.25 (d, 1H, J=7 Hz), 4.84 (s, 1H), 4.06–3.96 (m, 2H), 3.56 (m, 2H), 3.05 (bs, 2H),

LC-MS: R$_t$=1.26 min, m/z: [M+H]$^+$,

Example 73

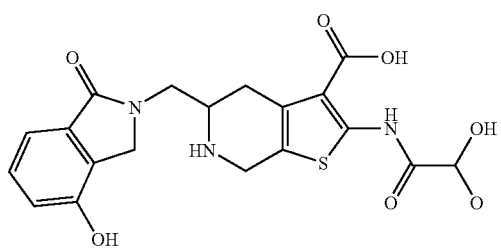

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid Acetyl chloride (5.4 ml, 5.96 g, 76 mmol) was added dropwise to methanol (15 ml) at 0° C. in a sealed 50 ml round-bottom flask. This solution was allowed to warm to room temperature for 1 hour while stirring. To this solution 3-hydroxy-2-methyl-benzoic acid (519 mg, 3.4 mmol) was added and the solution was stirred at room temperature for 42 hours. The reaction was quenched with saturated aqueous sodium bicarbonate and solid sodium bicarbonate. The volatiles were removed in vacuo and the basic aqueous solution was then extracted with dichloromethane (4×40 ml). The combined organic extracts were dried (MgSO$_4$), filtered, and the solvent evaporated in vacuo affording 493 mg (87%) of 3-hydroxy-2-methyl-benzoic acid methyl ester as a solid.

$^1$H-NMR (300 MHz, CDCl$_3$): δ 7.43 (d, 1H, J=9 Hz), 7.12 (t, 1H, J=8 Hz), 6.95 (d, 1H, J=8 Hz), 5.05 (bs, 1H), 3.90 (s, 3H), 2.47 (s, 3H).

To a solution of the above methyl ester (256 mg, 1.54 mmol) and N,N-diisopropylethylamine (530 µl, 3.0 mmol) in dichloromethane (8 ml) at 0° C. methyloxymethyl chloride (175 µl, 2.3 mmol) was added dropwise. The solution was allowed slowly to warm to room temperature and stired for 24 hours. The solution was diluted with dichloromethane (12 ml), washed with water (20 ml), brine (20 ml), dried (MgSO$_4$), filtered, and concentrated in vacuo. The resulting oil was purified by silica gel chromatography using a mixture of hexanes/ethyl acetate (4:1) as eluent, which afforded 269 mg (85%) of 3-methoxymethoxy-2-methyl-benzoic acid methyl ester as an oil.

$^1$H-NMR (300 MHz, CDCl$_3$): δ 7.48 (d, 1H, J=8 Hz), 7.24–7.15 (m, 2H), 5.22 (s, 2H), 3.90 (s, 3H), 3.50 (s, 3H), 2.47 (s, 3H).

In a 25 ml round-bottom flask, N-bromosuccinimide (236 mg, 1.3 mmol) and azobis(cyclohexanecarbonitrile) (33 mg, 0.14 mmol) were added to a solution of 3-methoxymethoxy-2-methyl-benzoic acid methyl ester (265 mg, 1.26 mmol) in carbon tetrachloride (6.5 ml). The reaction was heated to reflux with stirring for 3.5 hours. The volatiles were removed in vacuo and the residue purified by silica gel chromatography using a mixture of hexanes/ethyl acetate (9:1) as eluent, which afforded 364 mg (100%) of 2-bromomethyl-3-methoxymethoxy-benzoic acid methyl ester as a solid.

$^1$H-NMR (300 MHz, CDCl$_3$): δ 7.55 (dd, 1H, J=6, 3 Hz), 7.29 (d, 2H, J=3 Hz), 5.27 (s, 2H), 5.05 (s, 2H), 3.91 (s, 3H), 3.50 (s, 3H).

In a 100 ml round-bottom flask, 2-amino-5-aminomethyl-6-(4-methoxy-benzyl)-4,5,6,7-tetrahydro-thieno[2,3-c]pyridine-3-carboxylic acid tert-butyl ester (298 mg, 0.74 mmol) and N,N-diisopropylethylamine (195 µl, 1.12 mmol) were dissolved in acetonitrile (40 ml). 2-Bromomethyl-3-methoxymethoxy-benzoic acid methyl ester (193 mg, 0.67 mmol) in acetonitrile (5 ml) was slowly added to the amine solution via gastight syringe over 24 hours, followed by stirring at room temperature for an additional 36 hours. The solution was concentrated in vacuo, the residue redissolved in ethyl acetate (25 ml), and washed with saturated aqueous sodium bicarbonate (25 ml) and brine (25 ml). The organic phase was dried (MgSO$_4$), filtered, and the solvent evaporated in vacuo. The residue was purified by silica gel chromatography using a mixture of hexanes/ethyl acetate (1:1) as eluent, which afforded 345 mg (81%) of 2-amino-6-(4-methoxy-benzyl)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR (300 MHz, CDCl$_3$): δ 7.67 (d, 1H, J=8 Hz), 7.57–7.38 (m, 5H), 7.14 (d, 2H, J=8 Hz), 6.96 (m, 2H), 6.77 (d, 2H, J=9 Hz), 6.20 (d, 2H, J=6 Hz), 5.96 (s, 2H), 4.69–2.58 (m, 17H), 1.55 (s, 9H).

In a 50, ml round-bottom flask a solution of 2-amino-6-(4-methoxy-benzyl)-5-(4-methoxymethoxy-1-oxo-1,3-dihydro-isoindol-2-ylmethyl)-4,5,6,7-tetrahydro[2,3-c]pyridine-3-carboxylic acid tert-butyl ester (338 mg, 0.58 mmol) in dichloromethane (20 ml) was treated with imidazol-1-yl-oxo-acetic acid tert-butyl ester (575 mg, 2.9 mmol). After stirring for 18 hours at room temperature, the mixture was concentrated to dryness in vacuo. The residue was purified by silica gel chromatography using a mixture of hexanes/ethyl acetate (1:1) as eluent, which afforded 310 mg (75%) of 2-(tert-Butoxyoxalyl-amino)-6-(4-methoxy-benzyl)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR (300 MHz, CDCl$_3$): δ 12.57 (s, 1H), 7.53 (d, 1H, J=8 Hz), 7.43 (t, 1H, J=8 Hz), 7.26 (d, 1H, J=8 Hz), 7.13 (d, 2H, J=9 Hz), 6.78 (d, 2H, J=9 Hz), 5.28 (s, 2H), 4.47 (q, 2H, J=18 Hz), 4.02–3.44 (m, 11H), 2.97 (dd, 1H, J=18 Hz and J=5 Hz), 2.76 (dd, 1H, J=17 Hz and J=5 Hz), 1.63 (s, 9H), 1.59 (s, 9H).

10% Pd/C (145 mg, 50% by weight) was added to a mixture of 2-(tert-butoxyoxalyl-amino)-6-(4-methoxy-benzyl)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester (283 mg, 0.40 mmol) in 10% formic acid and methanol (10 ml). After stirring at room temperature for 18 hours, more Pd/C (141 mg, 50% by weight) was added to the reaction mixture. After stirring at room temperature for an additional 20 hours, the catalyst was removed via fitration through celite. Fresh Pd/C (255 mg) and ammonium formate (1.0 g) were added to the residue (253 mg, 0.36 mmol) dissolved in 10% formic acid in methanol (10 ml). The solution was heated to 40° C. for 48 hours. Catalyst was removed via filtration through celite and liberal washing with methanol. Purification by chromatotron (ethyl acetate/triethylamine (99:1)) afforded 63 mg (27%) of 2-(tert-butoxyoxalyl-amino)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester A and 46 mg (19%) of 2-(tert-butoxyoxalyl-amino)-5-(4-methoxymethoxy-1-oxo-1,3-dihydro-isoindol-2-ylmethyl)-6-methyl-4,5,6,7-tetrahydro-thieno[2,3-c]pyridine-3-carboxylic acid tert-butyl ester B.

A: $^1$H-NMR (300 MHz, CDCl$_3$): δ 12.54 (s, 1H), 7.50 (d, 1H, J=8 Hz), 7.41 (t, 1H, J=8 Hz), 7.25 (d, 1H, J=8 Hz), 5.27 (s, 2H), 4.52 (dd, 2H, J=30 Hz and J=19 Hz), 4.08–3.90 (m, 2H), 3.86–3.67 (m, 2H), 3.51 (s, 3H), 3.27 (m, 1H), 2.99 (dd, 1H, J=18 Hz and J=4 Hz), 2.53 (dd, 1H, J=18. Hz and J=11 Hz), 1.61 (s, 9H), 1.53 (s, 9H).

LC-MS (APCI$^+$) m/z: 588 [M+H]$^+$; R$_t$=1.32 min.

B: $^1$H-NMR (300 MHz, CDCl$_3$): δ 12.56 (s, 1H), 7.50 (d, 1H, J=7 Hz), 7.41 (t, 1H, J=8 Hz), 7.25 (d, 1H, J=8 Hz), 5.27 (s, 2H), 4.50 (dd, J=28 Hz and J=18 Hz), 3.93–3.68 (m, 4H), 3.51 (s, 1H), 3.51 (s, 3H), 3.31 (m, 1H), 2.88 (dd, 1H, J=18 Hz and J=4 Hz), 2.68 (dd, 1H, J=19 Hz and J=9 Hz), 2.46 (s, 3H), 1.61 (s, 9H), 1.54 (s, 9H).

LC-MS (APCI$^+$) m/z: 602 [M+H]$^+$; R$_t$=1.35 min.

2-(tert-Butoxyoxalyl-amino)-5-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester A (63 mg, 0.11 mmol) was dissolved in 30% trifluoroacetic acid in dichloromethane (4 ml). The solution was left open to the atmosphere without stirring. After 24 hours the precipitate was filtered off and washed with diethyl ether, affording 57 mg (90%) of the title compound as a solid trifluoroacetate.

$^1$H-NMR (300 MHz, DMSO-d$_6$): δ 12.30 (s, 1H), 10.17 (s, 1H), 9.23 (s, 2H, J=5 Hz and J=7 Hz), 7.34 (t, 1H, J=6 Hz), 7.19 (d, 1H, J=5 Hz), 7.03 (d, 1H, J=6 Hz), 5.76 (s, 2H), 4.53 (d, 1H, J=13 Hz), 4.43–4.22 (m, 3H), 4.07 (m, 1H), 3.91 (m, 1H), 3.70 (m, 1H), 3.10 (m, 1H), 2.82 (dd, 1H, J=14 Hz and J=8 Hz).

Example 74

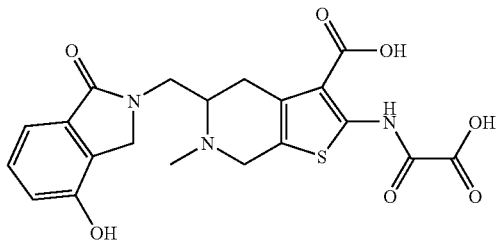

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid The above 2-(tert-butoxyoxalyl-amino)-5-(4-methoxymethoxy-1-oxo-1,3-dihydro-isoindol-2-ylmethyl)-6-methyl-4,5,6,7-tetrahydro-thieno[2,3-c]pyridine-3-carboxylic acid tert-butyl ester B (46 mg; 0.08 mmol) was dissolved in 30% trifluoroacetic acid in dichloromethane (4 ml). The solution was left open to the atmosphere without stirring. After 24 hours the precipitate was filtered off and washed with diethyl ether, affording 41 mg (90%) of the title compound as a solid trifluoroacetate.

$^1$H-NMR (400 MHz, CDCl$_3$): δ 12.39 (s, 1H), 10.19 (s, 1H), 10.10 (s, 1H), 7.32 (t, 1H, J=7.6 Hz), 7.17 (d, 1H, J=7.2 Hz), 7.02 (t, 1H, J=7.2 Hz), 4.55 (d, 2H, J=15 Hz), 4.0–4.5 (m, 4H), 2.95–3.70 (m, 5H), 2.85 (s, 3H).

LC-MS (APCI$^+$) m/z: 446 [M+H]$^+$; R$_t$=1.02 min.

Example 75

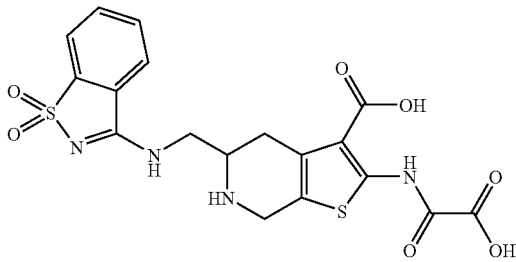

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid Saccharin (8.8 g, 48 mmol) and phosphorous pentachloride (15 g, 72 mmol) were added neat to a round bottom flask equipped with a short path distillation column. The mixture was heated to 175° C. After approximately 0.5 hour, phosphorous oxychloride slowly distilled off. Upon completion of the reaction, the mixture was cooled and the resultant solid recrystallized from benzene affording 3.6 g (37%) of 3-chloro-benzo[d]isothiazole 1,1-dioxide as a solid.

$^1$H-NMR (CDCl$_3$): δ 7.92 (d, 1H, J=6.9 Hz), 7.8 (m, 3H).

To a solution of 2-amino-5-aminomethyl-6-(4-methoxybenzyl)-4,5,6,7-tetrahydro-thieno[2,3-c]pyridine-3-carboxylic acid tert-butyl ester (155 mg, 0.384 mmol) and triethylamine (59 μl, 0.423 mmol) in dichloromethane (2 ml) at 0° C., was added a solution of 3-chloro-benzo[d]isothiazole 1,1-dioxide (85.2 mg, 0.423 mmol) in dichloromethane (2 ml). The reaction mixture was stirred at 0° C. for 1 hour. The reaction was judged complete by tlc (dichloromethane/ethyl acetate (1:1)). The reaction mixture was washed with water (3×20 ml), dried (MgSO$_4$), filtered and the solvent evaporated in vacuo. The crude residue was subjected to flash chromatography using a gradient from 100% dichloromethane to dichloromethane/ethyl acetate (80/20) as eluent, which afforded 200 mg (92%) of 2-amino-5-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as a foam.

$^1$H-NMR (CD$_3$OD): δ 7.99 (m, 1H), 7.87 (m, 1H), 7.79 (m, 2H), 7.19 (d, 2H, J=8.4 Hz), 6.75 (d, 2H, J=8.7 Hz), 3.88–3.79 (m, 2H), 3.75–3.59 (m, 3H), 3.69 (s, 3H), 3.52–3.46 (m, 2H), 2.84 (dd, 1H, J=15.3 Hz and J=5.4 Hz), 2.68 (dd, J=18 Hz and J=4.5 Hz), 1.46 (s, 9H).

LC-MS: R$_t$=2.83, m/z: 569 [M+H]$^+$

To a solution of 2-amino-5-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (129 mg, 0.227 mmol) in tetrahydrofuran (3 ml) was added imidazol-1-yl-oxo-acetic acid tert-butyl ester (1.1 ml, 1.1 mmol, 1 M in tetrahydrofuran). The reaction mixture was stirred at room temperature for 18 hours. The reaction mixture was concentrated in vacuo and the residue subjected to flash chromtography using a mixture of ethyl acetate/dichloromethane (10:90) as eluent, which afforded 142 mg (90%) of 2-(tert-butoxyoxalyl-amino)-5-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as an oil.

$^1$H-NMR (CDCl$_3$): δ 7.92 (d, 1H, J=6.3 Hz), 7.73 (m, 2H), 7.56 (d, 1H, J=5.7 Hz), 7.20 (d, 2H, J=6.3 Hz), 7.05 (bs, 1H), 6.87 (d, 2H, J=6.6 Hz), 3.91 (m, 2H), 3.82–3.72 (m, 2H), 3.79 (s, 3H), 3.61–3.49 (m, 2H), 3.44 (m, 1H), 3.11 (dd, 1H, J=15 Hz and J=3.6 Hz), 2.72 (dd, 1H, J=12 Hz and J=4.2 Hz), 1.63 (s, 18H);

LC-MS: R$_t$=3.48, m/z: 697 [M+H]$^+$ 2-(tert-Butoxyoxalyl-amino)-5-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (120 mg, 0.172 mmol) was dissolved in a mixture of ethanol (4 ml) and formic acid (0.5 ml). 10% Pd—C (20 mg) was added and the reaction mixture stirred at ambient temperature for 4 days (after the second day, 150 mg of additional 10% Pd—C was added). The reaction mixture was filtered through celite and the celite washed with dichloromethane. The organic fractions were combined and concentrated in vacuo. The resultant oil was subjected to preparative thin layer chromatography (dichloromethane/methanol (95:5)), which afforded 17 mg (17%) of 2-(tert-butoxyoxalyl-amino)-5-((1,1-dioxo-1H-benzo[d]isothiazol-3-ylamino)-methyl)-4,5,6,7-tetrahydro-thieno[2,3-c]pyridine-3-carboxylic acid tert-butyl ester as a solid.

$^1$H-NMR (CDCl$_3$): δ 7.91 (m, 1H), 7.72 (m, 3H), 7.34 (bs, 1H), 4.16–4.08 (m, 1H), 4.07 (dd, 2H, J=36.3 Hz and J=8.7 Hz), 3.38–3.30 (m, 1H), 3.22–3.06 (m, 2H), 2.51 (dd, 1H, J=16.8 Hz and J=9.9 Hz), 1.61 (s, 18H).

2-(tert-Butoxyoxalyl-amino)-5-((1,1-dioxo-1H-benzo[d]isothiazol-3-ylamino)-methyl)-4,5,6,7-tetrahydro-thieno[2,3-c]pyridine-3-carboxylic acid tert-butyl ester (15 mg, 0.026 mmol) was dissolved in a solution of 50% trifluoroacetic acid/dichloromethane (3 ml). The reaction mixture was stirred at ambient temperature for 18 hours, concentrated in vacuo and re-evaporated from acetonitrile (2×). The residue was washed with dichloromethane and dried in vacuo to give 16 mg (90%) of the title compound as a solid trifluoroacetate.

$^1$H—NMR (CD$_3$OD): δ 7.98 (d, 1H, 7.2 Hz), 7.92 (d, 1H, J=6.6 Hz), 7.83 (m, 2H), 4.51–4.39 (m, 2H), 4.11–4.08 (m, 1H), 3.97–3.91 (m, 2H), 3.53–3.47 (m, 1H), 3.16–3.10 (m, 1H).

Example 76

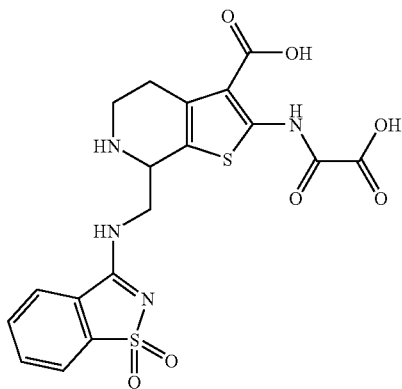

7-((1,1-Dioxo-1H-benzo[d]isothiazol-3-ylamino) methyl)-2-(oxalyl-amino)-4,5,6,7-tetrahydro-thieno [2,3-c]pyridine-3-carboxylic acid 3-Chloro-benzo[d]isothiazole-1,1-dioxide (160 mg, 0.79 mmol) and diisopropylethylamine (1501 µl, 0.86 mmol) were dissolved in dichloromethane (7 ml) at 0° C. 2-Amino-7-aminomethyl-6-(4-methoxy-benzyl)-4,5,6,7-tetrahydro-thieno[2,3-c]pyridine-3-carboxylic acid tert-butyl ester (284 mg, 0.70 mmol) was added and the mixture was stirred for 15 minutes at 0° C., diluted with dichloromethane, (10 ml) and washed with water (20 ml) and brine (20 ml). The organic phase was dried (MgSO$_4$), filtered, and the solvent evaporated in vacuo. The residue was purified by silica gel chromatography using a gradient of hexanes/ethyl acetate (1:1) to pure ethyl acetate as eluent, which afforded 309 mg (77%) of 2-amino-7-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester as an foam.

$^1$H-NMR (300 MHz, CDCl$_3$): δ 7.89 (d, 1H, J=8 Hz), 7.77–7.63 (m, 2H), 7.37 (d, 1H, J=7 Hz), 7.25 (d, 2H, J=10 Hz), 6.82 (d, 2H, J=8 Hz), 6.62 (bs, 1H), 6.08 (s, 2H), 3.91 (m, 1H), 3.71 (s, 3H), 3.49–2.65 (m, 8H), 1.59 (s, 9H).

LC-MS (APCI$^+$) m/z: 569 [M+H]$^+$, [M+Na] 591; R$_t$=2.85 min.

2-Amino-7-((1,1-dioxo-1H-benzo[d]isothiazol-3-ylamino)methyl)-6-(4-methoxy-benzyl)-4,5,6,7-tetrahydro-thieno[2,3-c]pyridine-3-carboxylic acid tert-butyl ester (102 mg, 0.18 mmol) in dichloromethane (10 ml) was treated with imidazol-1-yl-oxo-acetic acid tert-butyl ester (85 mg, 0.43 mmol). After stirring for 18 hours at room temperature, the reaction solution was concentrated to dryness in vacuo. The residue was purified by silica gel chromatography using a gradient of hexanes/ethyl acetate (1:1) to pure ethyl acetate as gradient, which afforded 98 mg (78%) of 2-(tert-butoxy-oxalyl-amino)-7-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester as a solid.

$^1$H-NMR (300 MHz, CDCl$_3$): δ 12.57 (s, 1H), 7.89 (d, 1H, J=8 Hz), 7.77–7.63 (m, 2H), 7.39 (d, 1H, J=7 Hz), 7.25 (d, 2H, J=9 Hz), 6.84 (d, 2H, J=9 Hz), 6.64 (bs, 1H), 3.99–2.76 (m, 12H), 1.64 (s, 9H), 1.63 (s, 9H). 10% Pd/C (100 mg) was added to a mixture of 2-(tert-butoxyoxalyl-amino)-7-((1,1-dioxo-1H-benzo[d]isothiazol-3-ylamino)-methyl)-6-(4-methoxy-benzyl)-4,5,6,7-tetrahydro-thieno[2,3-c]pyridine-3-carboxylic acid tert-butyl ester (98 mg, 0.14 mmol) in 10% formic acid in methanol (10 ml). After stirring at room temperature for 48 hours, the catalyst was removed via filtration through celite and liberal washing with methanol. The volatiles were removed in vacuo and the residue purified by chromatotron (ethyl acetate/triethylamine, 99:1), which afforded 32 mg (40%) of 2-(tert-butoxyoxalyl-amino)-7-((1,1-dioxo-1H-benzo[d]isothiazol-3-ylamino)-methyl)-4,5,6,7-tetrahydro-thieno[2,3-c] pyridine-3-carboxylic acid tert-butyl ester as an oil.

$^1$H-NMR (300 MHz, CDCl$_3$): δ 12.48 (s, 1H), 10.21–9.15 (m, 2H), 8.49–7.42 (m, 3H), 5.62–5.00 (bs, 1H), 4.53–2.87 (m, 8H), 1.61 (s, 18H).

HPLC (254.4 nm) R$_t$=3.67 minutes.

2-(tert-Butoxyoxalyl-amino)-7-((1,1-dioxo-1H-benzo[d] isothiazol-3-ylamino)-methyl)-4,5,6,7-tetrahydro-thieno[2, 3-c]pyridine-3-carboxylic acid tert-butyl ester (32 mg) was dissolved in a mixture of 30% trifluoroacetic acid in dichloromethane (4 ml). The solution was left open to the atmosphere without stirring. After 24 hours the precipitate was filtered off and washed with diethyl ether, affording 29 mg (90%) of the title compound as a solid trifluoroacetate.

$^1$H-NMR (300 MHz, DMSO-d$_6$): δ 12.36 (s, 1H), 9.92 (bs, 1H), 9.73 (bs, 1H), 9.38 (bs, 1H), 8.20 (m, 1H), 8.05 (m, 1H), 7.89 (m, 2H), 4.95 (s, 1H), 4.12–3.00 (m partially obscured by water, 8H).

LC-MS (APCI$^+$) m/z: 466 [M+H]$^+$; R$_t$=0.66 min.

Example 77

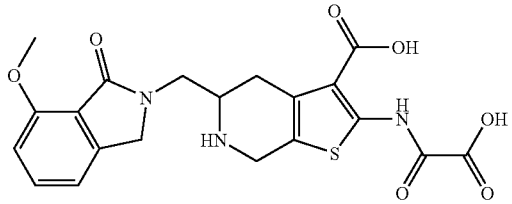

5-(7-Methoxy-1-oxo-1,3-dihydro-isoindol-2-ylm-ethyl)-2-(oxalyl-amino)-4,5,6,7-tetrahydro-thieno[2, 3-c]pyridine-3-carboxylic acid 2-Methoxy-6-methylbenzoic acid ethyl ester (500 mg, 2.67 mmol), N-bromosuccinimide (483.8 mg, 2.72 mmol) and 2,2'-azobis(2-methyl-propionitrile) (30.2 mg, 0.123 mmol) in carbon tetrachloride (10 ml) were heated to reflux. After 18 hours, the reaction mixture was evaporated to dryness in vacuo. The residue was dissolved in dichloromethane (100 ml) and washed with water (2×50 ml). The organic layer was dried (MgSO$_4$), filtered and the solvent evaporated in vacuo. The residue (702 mg) was purified by column chromatography using a mixture of hexanes/dichloromethane (1:1) as eluent, which afforded 573 mg (85%) of 6-bromomethyl-2-methoxy-benzoic acid ethyl ester as an oil.

¹H-NMR (CDCl₃): δ7.37 (t, 1H, J=8.4 Hz), 7.01 (d, 1H, J=8.1 Hz), 6.90 (d, 1H, J=8.4 Hz), 4.54 (s, 2H), 4.45 (q, 2H, J=7.2 Hz), 3.82 (s, 3H), 1.42 (t, 3H, J=9 Hz).

6-Bromomethyl-2-methoxy-benzoic acid ethyl ester (71.1 mg, 0.260 mmol) dissolved in acetonitrile (5 ml) and diisopropylethylamine (453 µl, 2.60 mmol) was stirred at room temperature. To this mixture 2-amino-5-amino-methyl-6-(4-methoxy-benzyl)-4,5,6,7-tetrahydro-thieno[2,3-c]pyridine-3-carboxylic acid tert-butyl ester (200 mg, 0.52 mmol) dissolved in acetonitrile (5 ml) was added syringe pump (0.2 ml/min.). Once addition was complete, the reaction mixture was allowed to stir for 2 hours. The reaction mixture was concentrated in vacuo, and the residue diluted with ethylacetate (50 ml). The organic layer was washed with saturated sodium bicarbonate (2×25 ml) and brine (2×25 ml). The organic layer was dried (MgSO₄), filtered and concentrated in vacuo. The residue (308 mg) was subjected to column chromatography using a gradient of hexane/ethyl acetate (95:5) to (50:50) and then dichloromethane/ethyl acetate (95:5) as eluents, which afforded 106 mg (75%) of 2-amino-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester as an oil.

¹H-NMR (CDCl₃): δ 7.48 (t, 1H, J=7.5 Hz), 7.12 (d, 2H, J=8.4 Hz), 7.01 (d, 1H, J=7.5 Hz), 6.91 (d, 1H, J=8.4 Hz), 6.76 (d, 2H, J=7.8 Hz), 5.95 (bs, 2H), 4.37 (s, 2H), 4.05 (m, 1H), 3.97 (s, 3H), 3.88–3.78 (m, 2H), 3.81 (s, 3H), 3.71–3.39 (m, 4H), 2.90 (dd, 1H, J=18 Hz and J=5.4 Hz), 2.62 (dd, 1H, J=18 Hz and J=5.4 Hz), 1.53 (s, 9H).

To a solution of 2-amino-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester (105 mg, 0.192 mmol) in tetrahydrofuran (3 ml) was added imidazol-1-yl-oxo-acetic acid tert-butyl ester (0.534 ml, 0.534 mmol, 1 M in tetrahydrofuran). The reaction mixture was stirred at room temperature for 18 hours. The reaction mixture concentrated in vacuo and the residue subjected to flash chromtography using a mixture of ethyl acetate/dichloromethane (10:90) as eluent, which afforded 85 mg (66%) of 2-(tert-butoxyoxalyl-amino)-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester.

¹H-NMR (CDCl₃): δ 7.47 (t, 1H, J=5.7 Hz), 7.10 (d, 2H, J=6 Hz), 6.99 (d, 1H, J=5.7 Hz), 6.90 (d, 1H, J=6.3 Hz), 6.76 (d, 2H, J=6.3 Hz), 4.37 (q, 2H, J=11.4 Hz), 3.99–3.92 (m, 1H), 3.97 (s, 3H), 3.79–3.76 (m, 2H), 3.77 (s, 3H), 3.66 (d, 1H, J=12.6 Hz), 3.58–3.50 (m, 3H), 2.95 (dd, 1H, J=13.5 Hz and J=3.6 Hz), 2.70 (dd, 1H, J=13.5 Hz and J=3.6 Hz), 1.61 (d, 9H), 1.57 (s, 9H).

2-(tert-Butoxyoxalyl-amino)-6-(4-methoxy-benzyl)-5-(7-methoxy-1-oxo-1,3-dihydro-isoindol-2-ylmethyl)-4,5,6,7-tetrahydro-thieno[2,3-c]pyridine-3-carboxylic acid tert-butyl ester (66 mg, 0.12 mmol) was dissolved in ethanol (2 ml) and formic acid (0.3 ml). 10% Pd—C (15 mg) was added and the reaction mixture stirred at room temperature for 3 days. TLC (hexane/ethyl acetate (1/1)) indicated reaction complete. The reaction mixture was filtered through celite and the celite washed with dichloromethane. The organic fractions were combined and subjected to preparative thin layer chromatography (hexane/ethyl acetate (1/1) to yield 14.7 mg (22%) of 2-(tert-butoxyoxalyl-amino)-5-(7-methoxy-1-oxo-1,3-dihydro-isoindol-2-ylmethyl)-4,5,6,7-tetrahydro-thieno[2,3-c]pyridine-3-carboxylic acid tert-butyl ester as an oil.

¹H-NMR (CDCl₃): δ 7.48 (t, 1H, J=7.5 Hz), 7.01 (d, 1H, J=7.2 Hz), 6.90 (d, 1H, J=8.4 Hz), 5.50 (d, 2H, J=6.6 Hz), 4.04–3.90 (m, 1H), 3.97 (s, 3H), 3.24 (m, 1H), 3.01–2.95 (m, 1H), 2.57–2.43 (m, 2H), 1.62 (s, 9H), 1.57 (s, 9H).

2-(tert-Butoxyoxalyl-amino)-5-(7-methoxy-1-oxo-1,3-dihydro-isoindol-2-ylmethyl)-4,5,6,7-tetrahydro-thieno[2,3-c] pyridine-3-carboxylic acid tert-butyl ester (14.7 mg, 0.026 mmol) was dissolved in a solution of 50% trifluoroacetic acid/dichloromethane (2 ml). The reaction mixture was stirred at ambient temperature for 18 hours, concentrated in vacuo and re-evaporated from acetonitrile (2×). The resulting precipitate was washed with dichloromethane and dried in vacuo to give 13 mg (89%) of the title compound as a solid trifluoroacetate.

¹H-NMR (CD₃OD): δ 7.56 (t, 1H, J=8.1 Hz), 7.13 (d, 1H, J=7.2 Hz), 7.01 (d, 1H, J=8.1 Hz), 4.87–4.44 (m, 4H), 4.15 (m, 1H), 3.90 (s, 3H), 3.88–3.79 (m, 1H), 3.43 (m, 1H), 2.98 (m, 2H);

LC-MS: R_f=0.71, m/z: 446 [M+H]⁺.

Example 78

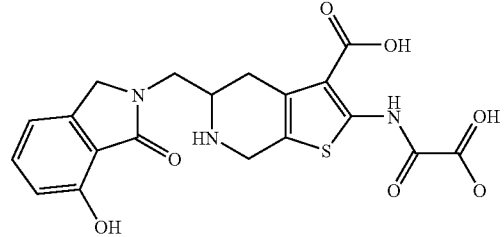

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-hydroxy-6-methyl-benzoic acid ethyl ester (5.00 g, 27.8 mmol) and t-butyl-di-methylsilyl chloride (6.27 g, 41.6 mmol) in dichloromethane (100 ml) was added diisopropyl ethylamine. The solution was stirred at 50° C. for 24 hours, washed with water, brine, dried (MgSO₄), filtered and the solvent evaporated in vacuo, which afforded 7.6 g (93%) of 2-(tert-butyl-dimethyl-silanyloxy)-6-methyl-benzoic acid ethyl ester as an oil.

¹H-NMR (CDCl₃): δ 7.13 (t, 1H, J=7.5 Hz), 6.78 (d, 1H, J=7.5 Hz), 6.67 (d, 1H, J=7.5 Hz), 4.35 (q, 2H, J=7.2 Hz), 2.29 (s, 3H), 1.38 (t, 3H, J=7.2 Hz), 0.97 (s, 9H), 0.23 (s, 6H).

2-(tert-Butyl-dimethyl-silanyloxy)-6-methyl-benzoic acid ethyl ester (7.6 g, 25.8 mmol), N-bromosuccinimide (4.82 g, 27.1 mmol) and azobis(cyclohexanecarbonitrile) (0.32 g, 13 mmol) were dissolved in tetrachlormethane (130 ml). The solution was stirred at room temperature for 60 hours. The solvent was evaporated in vacuo and the residue was chromatographed on silica gel column using a gradient of 1–2% ethyl acetate/hexane as eluent, which afforded 8.0 g (83%) of 6-bromomethyl-2-(tert-butyl-dimethyl-silanyloxy)-benzoic acid ethyl ester as an oil.

¹H-NMR (CDCl₃): δ 7.21 (t, 1H, J=8.4 Hz), 7.00 (d, 1H, J=8.4 Hz), 6.81 (d, 1H, J=8.4 Hz), 4.51 (s, 2H), 4.40 (q, 2H, J=7.2 Hz), 1.42 (t, 3H, J=7.2 Hz), 0.98 (s, 9H), 0.23 (s, 6H).

To a solution of 2-amino-5-aminomethyl-6-(4-methoxy-benzyl)-4,5,6,7-tetrahydro-thieno[2,3-c]pyridine-3-carboxylic acid tert-butyl ester (3.00 g, 7.45 mmol) and diisopropyl ethylamine (1.93 ml, 11.2 mmol) in acetonitrile at room temperature was added a solution of 6-bromomethyl-2-(tert-butyl-dimethyl-silanyloxy)-benzoic acid ethyl ester (2.78 g, 7.45 mmol) in acetonitril over 48 hours. The solution was stirred for 12 hours after the addition was complete. The volatiles were evaporated in vacuo and the residue was taken into ethyl acetate (50 ml) and washed with water, 1 N hydrochloric acid, brine, dried (MgSO$_4$), filtered and the solvent evaporated in vacuo. The residue was chromatographed on silica gel column eluted with a mixture of 20% ethyl acetate/Hexane, which afforded 3.2 g (66. %) of 2-amino-5-(7-(tert-butyl-dimethyl-silanyloxy)-1-oxo-1,3-dihydro-isoindol-2-ylmethyl]-6-(4-methoxy-benzyl)-4,5,6,7-tetrahydro-thieno[2,3-c]pyridine-3-carboxylic acid tert-butyl ester as an oil.

$^1$H-NMR (CDCl$_3$): δ 7.36 (t, 1H, J=8.0 Hz), 7.11 (d, 2H, J=8.8 Hz), 6.99 (d, 1H, J=8.0 Hz), 6.82 (d, 1H, J=8.0 Hz), 6.76 (d, 2H, J=8.8 Hz), 5.94 (s, 2H), 4.48 (d, 1H, J=16.8 Hz), 4.33 (d, 1H, J=16.8 Hz), 3.90–3.45 (m, 7H), 3.78 (s, 3H), 2.95 (dd, 1H, J=17.2 Hz and J=5.2 Hz), 2.72 (dd, 1H, J=17 Hz and J=5.6 Hz), 1.52 (s, 9H), 1.05 (s, 6H).

To a stirred solution of 2-amino-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.37 g, 3.64 mmol) in tetrahydrofuran (50 ml) was added imidazol-1-yl-oxo-acetic acid tert-butyl ester (2.14 mg, 10.9 mmol) in tetrahydrofuran (10 ml). The mixture was stirred at room temperature for 24 hours. The solvent was removed in vacuo. The residue was taken into ethyl acetate (100 ml). The solution was washed with 0.5 N hydrochloric acid solution (2×20 ml), saturated sodium bicarbonate (2×20 ml) and brine (20 ml), dried (MgSO$_4$), filtered and the solvent removed in vacuo. The residue was chromatographed using a gradient of 10–20% ethyl acetate/Hexane as eluent, which afforded 2.40 g (92%) of 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ 12.59 (s, 1H), 7.37 (t, 1H, J=8.0 Hz), 7.10 (d, 2H, J=8.8 Hz), 7.00 (d, 1H, J=8.0 Hz), 6.83 (d, 1H, J=8.0 Hz), 6.77 (d, 2H, J=8.8 Hz), 4.50 (d, 1H, J=16.8 Hz), 4.34 (d, 1H, J=16.8 Hz), 3.90–3.45 (m, 7H), 3.77 (s, 3H), 2.95 (dd, 1H, J=17.2 Hz and J=5.2 Hz), 2.72 (dd, 1H, J=18 and J=5.6 Hz), 1.61 (s, 9H), 1.58 (s, 9H), 1.06 (s, 9H), 0.26 (s, 6H).

To a solution of 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.40 g, 3.34 mmol) in 10% formic acid/methanol (50 ml) at room temperature under nitrogen was added 10% Pd/C (1.2 g). The mixture was stirred for 48 hours. The Pd/C was filtered off and the filtrate was evaporated in vacuo. The residue was dissolved in dichloromethane (10 ml) and the resulting solution was poured into hexane. The precipitate was filtered off and dried in vacuo affording 1.3 g (61%) of 2-(tert-butoxyoxalyl-amino) 5-(7-(tert-butyl-dimethyl-silanyloxy)-1-oxo-1,3-dihydro-isoindol-2-ylmethyl)-4,5,6,7-tetrahydro-thieno[2,3-c]pyridine-3-carboxylic acid tert-butyl ester.

$^1$H-NMR (CDCl$_3$): δ 12.45 (s, 1H), 8.05 (s, 1H), 7.39 (t, 1H, J=8.0 Hz), 7.00 (d, 1H, J=8.0 Hz), 6.83 (d, 1H, J=8.0 Hz), 4.50 (d, 1H, J=16.8 Hz), 4.45 (q, 2H, J=17 Hz), 4.05 (q, 2H, J=17 Hz), 3.82 (dd, 1H, J=17.2 Hz and J=5.2 Hz), 3.72 (dd, 1H, J=17 Hz and J=5.6 Hz), 3.40 (s, 1H), 3.08 (d, 1H, J=17 Hz), 2.61 (dd, 1H, J=18 Hz and J=7.2 Hz), 1.61 (s, 9H), 1.54 (s, 9H), 1.05 (s, 9H), 0.26 (s, 6H).

To a solution of trifluoroacetic acid (33.3 ml) and H$_2$O (2.7 ml) was added 2-(tert-butoxyoxalyl-amino)-5-(7-(tert-butyl-dimethyl-silanyloxy)-1-oxo-1,3-dihydro-isoindol-2-ylmethyl)-4,5,6,7-tetrahydro-thieno[2,3-c]pyridine-3-carboxylic acid tert-butyl ester (0.70 g, 1.04 mmol). The solution was stirred at room temperature for 40 hours. The solvent was poured into ethyl ether (400 ml). The precipitate was filtered off and dried in vacuo which afforded 450 mg (80%) of the title compound as a solid trifluoroacetate.

$^1$H-NMR (DMSO-d$_6$): δ12.30 (s, 1H), 9.71 (s, 1H), 9.20 (s, 2H), 7.39 (t, 1H, J=8.0 Hz), 6.99 (d, 1H, J=8.0 Hz), 6.82 (d, 1H, J=8.0 Hz), 4.52 (d, 1H, J=16.8 Hz), 4.36 (d, 2H, J=17 Hz), 4.22 (d, 2H, J=17 Hz), 4.00 (dd, 1H, J=17.2 Hz and J=5.2 Hz), 3.86 (s, 1H), 3.62 (d, 1H, J=17 Hz), 2.81 (dd, 1H; J=18 Hz and J=7.2 Hz);

LC-MS: R$_t$=1.20 min; m/z=432 [M+H]$^+$

Example 79

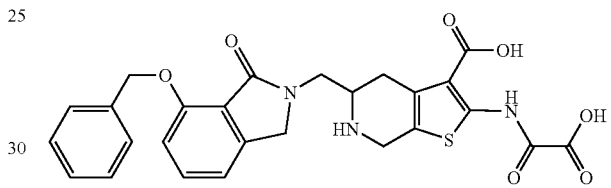

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-tert-butoxyoxalyl-amino)-5-(7-tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (2.40° g, 3.34 mmol) in 10% formic acid/methanol (50 ml) at room temperature under nitrogen was added 10% Pd/C (1.2 g). The mixture was stirred for 48 hours. The Pd/C was filtered off and the filtrate was evaporated in vacuo. The residue was dissolved in dichloromethane (10 ml) and the resulting solution was poured into hexane. The precipitate was filtered off (1.3 g) and the filtrate was evaporated in vacuo. The residual foam (1.1 g) was taken into dichloromethane (50 ml) and treated with di-tert-butyl-dicarbonate (1.1 g, 5.0 mmol) and saturated sodium bicarbonate (20 ml). The mixture was stirred for 2 hours and the organic layer was separated and dried (MgSO$_4$). The solvent was evaporated in vacuo and the residue was chromatographed using a gradient of 10–30% ethyl acetate/Hexane as eluent, which afforded 175 mg of 2-(tert-butoxyoxalyl-amino)-5-(7-hydroxy-1-oxo-1,3-dihydro-isoindol-2-ylmethyl)-4,7-dihydro-5H-thieno[2,3-c]pyridine-3,6-carboxylic acid di-tert-butyl ester.

$^1$H-NMR (CDCl$_3$): δ 12.55 (s, 1H), 8.53 (s, 1H), 7.37 (t, 1H, J=7.6 Hz), 6.92 (d, 1H, J=7.6 Hz), 6.83 (d, 1H, J=7.6 Hz), 4.95 (s, 1H), 4.84 (d, 1H, J=16.4 Hz), 4.72 (d, 1H, J=16.0 Hz), 4.56 (d, 1H, J=16.0 Hz), 4.28 (d, 1H, J=17.6 Hz), 4.13 (m, 1H), 3.68 (s, 0.5H), 3.42 (s, 0.5H), 3.16–2.94 (m, 2H), 1.62 (s, 9H), 1.61 (s, 9H), 1.26 (s, 9H).

To a solution of 2-(tert-butoxyoxalyl-amino)-5-(7-hydroxy-1-oxo-1,3-dihydro-isoindol-2-ylmethyl)-4,7-dihydro- 5H-thieno[2,3-c]pyridine-3,6-carboxylic acid di-tert-butyl ester (16 mg, 0.025 mmol) in N,N-dimethylformamide (0.5 ml) under nitrogen was added sodium hydride (1.0 mg, 0.026 mmol) at room temperature. The solution was stirred for 2 hours and followed by addition of benzyl bromide (5.9 ml, 0.050 mmol). The solution was stirred for 16 hours, diluted with ethyl acetate (20 ml) and washed with 0.5 N hydrochloric acid solution (2×10 ml), saturated sodium bicarbonate (2×10 ml), brine (10 ml), dried (MgSO$_4$), and filtered. The solvent was removed in vacuo. The residue was chromatographed using a gradient of 10–20% ethyl acetate/Hexane as eluent, which afforded 14 mg (76%) of 5-(7-benzyloxy-1-oxo-1,3-dihydro-isoindol-2-ylmethyl)-2-(tert-butoxyoxalyl-amino)-4,7-dihydro-5H-thieno[2,3-c]pyridine-3,6-carboxylic acid di-tert-butyl ester as a solid.

$^1$H-NMR (CDCl$_3$): δ 12.49 (s, 1H), 7.48 (d, 2H, J=7.2 Hz), 7.35 (m, 3H), 7.28 (d; 1H, J=7.2 Hz), 6.97 (d, 1H, J=7.6 Hz), 6.80 (d, 1H, J=7.6 Hz), 5.32 (s, 2H), 4.97 (m, 2H), 4.82–4.62 (m, 2H), 4.45–4.15 (m, 2H), 3.68 (s, 0.5H), 3.48 (s, 0.5H), 3.16–2.94 (m, 2H), 1.62 (s, 9H), 1.60 (s, 9H), 1.26 (s, 9H).

To a solution of trifluoroacetic acid (0.5 ml) and dichloromethane (2.7 ml) was added 5-(7-benzyloxy-1-oxo-1,3-dihydro-isoindol-2-ylmethyl)-2-(tert-butoxyoxalyl-amino)-4,7-dihydro-5H-thieno[2,3-c]pyridine-3,6-carboxylic acid di-tert-butyl ester (14 mg, 0.019 mmol). The solution was stirred at room temperature for 40 hours. The reaction mixture was poured into ethyl ether (20 ml). The precipitate was filtered off and dried in vacuo affording 8.0 mg (68%) of the title compound as a solid trifluoroacetate.

$^1$H-NMR (DMSO-d$_6$): δ 12.25 (s, 1H), 9.28 (s, 1H), 9.02 (s, 1H), 7.53 (m, 3H), 7.39 (t, 2H, J=7.6 Hz), 7.13 (d, 1H, J=7.6 Hz), 7.11 (d, 1H, J=8.4 Hz), 5.27 (m, 2H), 4.54 (d, 1H, J=17.2 Hz), 4.38 (d, 2H, J=17.6 Hz), 4.22 (m, 2H), 4.00 (dd, 1H, J=17.2 Hz and J=5.2 Hz), 3.86 (s, 1H), 3.64 (d, 1H, J=17.2 Hz), 2.81 (dd, 1H, J=18 Hz and J=7.2 Hz);

LC-MS: R$_t$=2.96 min; m/z: 522 [M+H]$^+$

Example 80

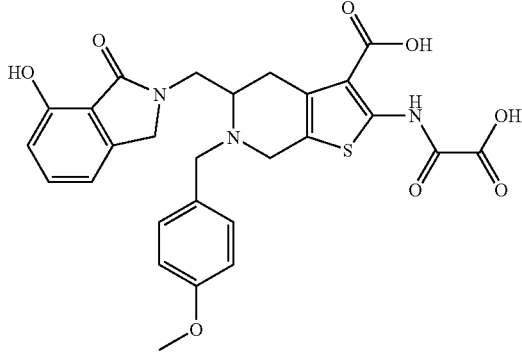

5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a solution of trifluoroacetic acid (0.5 ml) and dichloromethane (0.5 ml) was added 2-(tert-butoxyoxalyl-amino)-5-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (11 mg, 0.014 mmol). The solution was stirred at room temperature for 16 hours. The reaction mixture was poured into ethyl ether (20 ml). The precipitate was filtered off and dried in vacuo, which afforded 7.0 mg (79%) of the title compound as a solid trifluoroacetate.

$^1$H-NMR (DMSO-d$_6$): δ 12.39 (s, 1H), 9.95 (s, 1H), 9.75 (s, 2H), 7.42 (t, 1H, J=8.0 Hz), 7.30 (s, 2H), 7.02 (d, 1H, J=7.2 Hz), 6.96 (s, 2H), 6.85 (d, 1H, J=7.2 Hz), 4.95–3.65 (m, 11H), 3.76 (s, 3H).

LC-MS: R$_t$=1.93 min, m/z: 553 [M+H]$^+$

Example 81

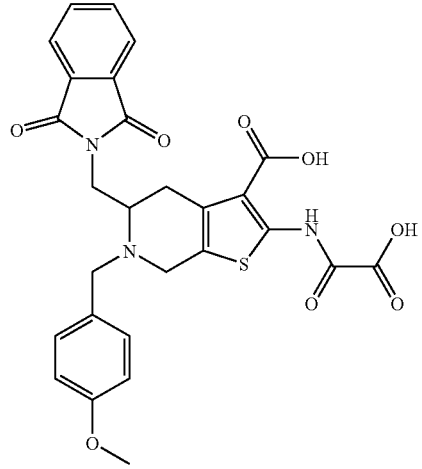

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a stirred solution of 2-amino-5-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (15 mg, 0.028 mmol) in tetrahydrofuran (1.0 ml) was added imidazol-1-yl-oxo-acetic acid tert-butyl ester (27 mg, 0.11 mmol) in tetrahydrofuran (1.0 ml). The mixture was stirred at room temperature for 24 hours. The solvent was removed in vacuo. The residue was taken into ethyl acetate (20 ml). The solution was washed with 0.5 N hydrochloric acid solution (2×10 ml), saturated sodium bicarbonate (2×10 ml) and brine (10 ml), dried (MgSO$_4$) and filtered. The solvent was removed in vacuo. The residue was chromatographed using a gradient of 10–25% ethyl acetate/hexane as eluent, which afforded 17 mg (93%) of 2-(tert-butoxyoxalyl-amino)-5-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ 12.54 (s, 1H), 7.86 (m, 2H), 7.40 (m, 2H), 7.08 (d, 2H J=8.4 Hz), 6.72 (d, 2H, J=8.4 Hz), 4.08 (dd, 1H, J=13.6 Hz and J=8.8 Hz), 3.94 (d, 1H, J=16.8 Hz), 3.82 (d, 1H, J=12.8 Hz), 3.78 (s, 3H), 3.92 (s, 3H), 3.70–3.56 (m, 3H), 3.53 (d, 1H, J=12.8), 2.93 (dd, 1H, J=16.8 Hz and J=4.8 Hz); 2.75 (dd, 1H, J=18.0 Hz and J=5.6 Hz), 1.61 (s, 9H), 1.58 (s, 9H).

To a solution of trifluoroacetic acid (0.5 ml) and dichloromethane (0.5 ml) was added 2-(tert-butoxyoxalyl-amino)-5-(1,3-dioxo-1,3-dihydro-isoindol-2 ylmethyl)-6-(4-methoxy-benzyl)-4,5,6,7-tetrahydro-thieno[2,3-c]pyridine-3-carboxylic acid tert-butyl ester (15 mg, 0.023 mmol). The solution was stirred at room temperature for 40 hours. The reaction mixture was poured into ethyl ether (20 ml). The precipitate was filtered off and dried in vacuo, which afforded 13 mg (87%) of the title compound as a solid trifluoroacetate.

$^1$H-NMR (DMSO-d$_6$): δ 12.38 (s, 1H), 7.89 (d, 4H, J=11.2 Hz), 7.18 (s, 2H), 6.85 (s, 2H), 4.20–3.60 (m, 9H), 3.71 (s, 3H);

LC-MS: R$_t$=2.05 min, m/z: 550 [M+H]$^+$

Example 82

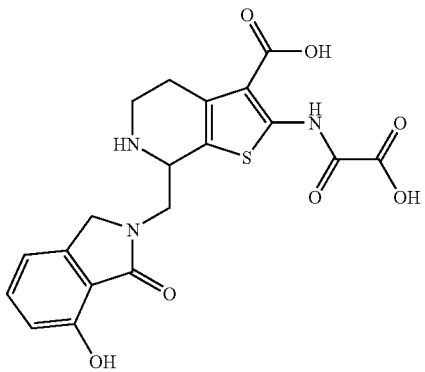

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-amino-7-aminomethyl-6-(4-methoxy-benzyl)-4,5,6,7-tetrahydro-thieno[2,3-c]pyridine-3-carboxylic acid tert-butyl ester (80 mg, 0.20 mmol) and diisopropyl ethylamine (35 μl, 0.40 mmol) in acetonitrile (10 ml) at room temperature as added a solution of 6-bromomethyl-2-(tert-butyl-dimethyl-silanyloxy)-benzoic acid ethyl ester (69 mg, 0.2 mmol). The solution was stirred for 12 hours at room temperature and the solvent was evaporated in vacuo. The residue was dissolved in ethyl acetate (50 ml) and washed with water, 1 N hydrochloric acid, brine, dried (MgSO$_4$), filtered and the solvent evaporated in vacuo. The residue was chromatographed on silica gel column eluted with 20% ethyl acetate/hexane to yield 42 mg (33%) of 2-amino-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as an oil.

$^1$H-NMR (CDCl$_3$): δ 7.64 (d, 1H, J=8.8 Hz), 7.39 (t, 1H, J=8.0 Hz), 7.10–6.80 (m, 5H), 6.09 (s, 2H), 5.04.2 (m, 4H), 3.80 (s, 3H), 3.66–2.92 (m, 3H), 1.55 (s, 9H), 1.04 (s, 9H), 0.22 (s, 6H).

To a stirred solution of 2-amino-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (40 mg, 0.060 mmol) in tetrahydrofuran (1 ml) was added imidazol-1-yl-oxoacetic acid tert-butyl ester (59 mg, 0.30 mmol) in tetrahydrofuran (1 ml). The mixture was stirred at room temperature for 24 hours. The solvent was removed in vacuo. The residue was dissolved in ethyl acetate (20 ml) and the solution was washed with 0.5 N hydrochloric acid (2×20 ml), saturated sodium bicarbonate (2×20 ml), brine (20 ml), dried (MgSO$_4$) and filtered. The solvent was removed in vacuo and the residue was chromatographed using a gradient of 10–20% ethyl acetate/Hexane as eluent, which afforded 40 mg (83%) of 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ 12.52 (s, 1H), 7.37 (t, 1H, J=8.0 Hz), 6.97 (d, 2H, J=8.4 Hz), 6.94 (d, 1H, J=8.0 Hz), 6.83 (d, 1H, J=8.0 Hz), 6.54 (d, 1H, J=8.4 Hz), 4.26 (d, 1H, J=16.8 Hz), 3.93–3.84 (m, 2H), 3.77 (d, 1H, J=16.8 Hz), 3.69 (s, 3H), 3.66–3.48 (m, 3H), 3.42–3.32 (m, 1H), 2.95 (dd, 1H, J=14.4 Hz and J=4.8 Hz), 2.92–2.82 (m, 1H), 2.73 (dd, 1H, J=14.4 Hz and J=4.8 Hz), 1.60 (s, 9H), 1.59 (s, 9H), 1.02 (s, 9H), 0.22 (d, 6H, J=1.6 Hz).

To a solution of 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (4.0 mg, 5.1 μmol) in 10% formic acid/methanol (1 ml) at room temperature under nitrogen was added 10% Pd/C (4 mg). The mixture was stirred for 1 hour. The Pd/C was filtered off and the filtrate was evaporated in vacuo to afford 2.8 mg (82%) of 2-(tert-butoxyoxalyl-amino)-7-(7-(tert-butyl-dimethyl-silanyloxy)-1-oxo-1,3-dihydro-isoindol-2-ylmethyl)-5H-4,5,6,7-tetrahydro-thieno[2,3-c]pyridine-3-carboxylic acid tert-butyl ester as a solid.

$^1$H-NMR (CDCl$_3$): δ 12.45 (s, 1H), 8.05 (s, 1H), 7.39 (t, 1H, J=8.0 Hz), 6.99 (d, 1H, J=8.0 Hz), 6.79 (d, 1H, J=8.0 Hz), 4.50 (d, 1H, J=17.2 Hz), 4.45 (d, 1H, J=17.2 Hz), 4.24 (d, 1H, 8.4 Hz), 4.03 (dd, 1H, J=16.0 Hz and J=7.2 Hz), 3.78–3.68 (m, 2H), 3.38–3.28 (m, 1H), 3.21 (d, 1H, J=18.8 Hz), 3.08–2.98 (m, 1H), 1.57 (s, 9H), 1.56 (s, 9H), 0.98 (s, 9H), 0.15 (d, 6H, J=1 Hz).

To a solution of trifluoroacetic acid (0.5 ml) and dichloromethane (0.5 ml) was added 2-(tert-butoxyoxalyl-amino)-7-(7-(tert-butyl-dimethyl-silanyloxy)-1-oxo-1,3-dihydro-isoindol-2-ylmethyl)-5H-4,5,6,7-tetrahydro-thieno[2,3-c]pyridine-3-carboxylic acid tert-butyl ester (2.8 mg, 0.0042 mmol). The solution was stirred at room temperature for 16 hours. The solvent was removed in vacuo and the residue was washed with dichloromethane affording 1.8 mg (79%) of the title compound as a solid trifluoroacetate.

$^1$H-NMR (DMSO-d$_6$): δ12.30 (s, 1H), 9.76 (s, 1H), 9.40 (s, 1H), 8.95 (s, 1H), 7.40 (t, 1H, J=7.6 Hz), 7.00 (d, 1H, J=7.6 Hz), 6.83 (d, 1H, J=7.6 Hz), 4.92 (s, 1H), 4.54 (d, 1H, J=18.4 Hz), 4.40 (d, 2H, J=18.4 Hz), 4.08–4.00 (m, 1H), 3.91 (d, 1H, J=15.2 Hz), 3.60 (s, 2H), 3.06 (s, 2H);

LC-MS: R$_t$: 1.41 min, m/z: 432 [M+H]$^+$

Example 83

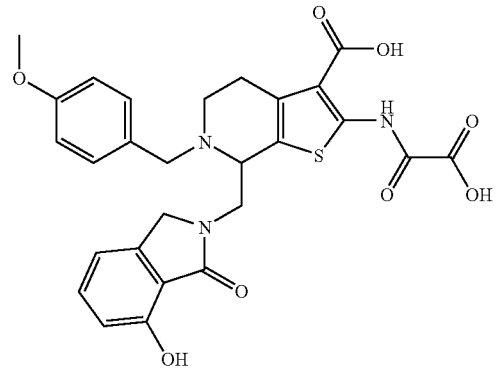

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a solution of trifluoroacetic acid (0.5 ml) and dichloromethane (0.5 ml) was added 2-(tert-butoxyoxalyl-amino)-7-(7-(tert-butyl-dimethyl-silanyloxy)-1-oxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (10 mg, 0.013 mmol). The solution was stirred at room temperature for 16 hours. The solvent was removed in vacuo and the residue was washed with dichloromethane, which afforded 6.8 mg (92%) of the title compound as a solid trifluoroacetate.

$^1$H-NMR (DMSO-d$_6$): δ12.35 (s, 1H), 9.90 (s, 1H), 9.70 (s, 2H), 7.41 (t, 1H, J=8.0 Hz), 7.28 (s, 2H), 7.04 (d, 1H, J=7.2 Hz), 6.92 (s, 2H), 6.83 (d, 1H, J=7.2 Hz), 4.90–3.60 (m, 11H), 3.80 (s, 3H).

LC-MS: R$_t$=1.92 min, m/z: 552 [M+H]$^+$

Example 84

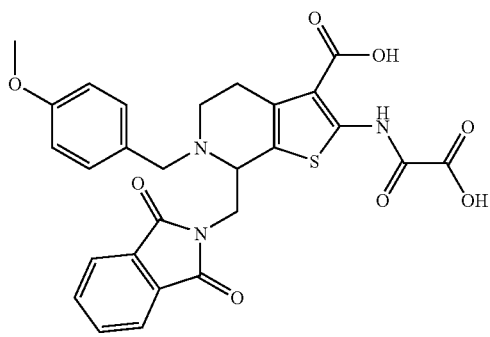

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid To a stirred solution of 2-amino-7-(1,3-dioxo-1,3-dihydro-isoindol-2-ylmethyl-6-(4-methoxy-benzyl)-4,5,6,7-tetrahydro-thieno[2,3-c]pyridine-3-carboxylic acid tert-butyl ester (10 mg, 0.019 mmol) in tetrahydrofuran (1.0 ml) was added imidazol-1-yl-oxo-acetic acid tert-butyl ester (18 mg, 0.092 mmol) in tetrahydrofuran (1.0 ml). The mixture was stirred at room temperature for 24 hours. The solvent was removed in vacuo. The residue was dissolved in ethyl acetate (20 ml) and washed with 0.5 N hydrochloric acid solution (2×10 ml), saturated sodium bicarbonate (2×10 ml), brine (10 ml), dried (MgSO$_4$), and filtered. The solvent was removed in vacuo and the residue was chromatographed using a gradient of 10–25% ethyl acetate/hexane as eluent, which afforded 11 mg (89%) of 2-(tert-butoxyoxalyl-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester as a solid.

$^1$H-NMR (CDCl$_3$): δ 12.54 (s, 1H), 7.76 (m, 4H), 6.82 (d, 2H, J=11.6 Hz), 6.33 (d, 2H, J=11.6 Hz), 4.02 (d, 1H, J=14.4 Hz), 3.98 (d, 1H, J=14.4 Hz), 3.62 (s, 3H), 3.62–3.54 (m, 2H), 3.48–3.34 (m, 2H), 3.02–2.70 (m, 3H), 1.60 (s, 9H), 1.59 (s, 9H).

To a solution of trifluoroacetic acid (0.5 ml) and dichloromethane (0.5 ml) was added 2-(tert-butoxyoxalyl-amino-7-(1,3-dioxo-1,3-dihydro-isoindol-2-ylmethyl)-6-(4-methoxy-benzyl)-4,5,6,7-tetrahydro-thieno[2,3-c]pyridine-3-carboxylic acid tert-butyl ester (10 mg, 0.015 mmol). The solution was stirred at room temperature for 16 hours. The solvent was removed in vacuo and the residue was washed with dichloromethane, which afforded 6.8 mg (80%) of the title compound as a solid trifluoroacetate.

$^1$H-NMR (DMSO-d$_6$): δ 12.38 (s, 1H), 7.86 (m, 4H), 6.82 (s, 2H), 6.30 (s, 2H), 4.00–2.86 (m, 9H), 3.58 (s, 3H);

LC-MS: R$_t$=2.02 min; m/z: 550 [M+H]$^+$

Example 85

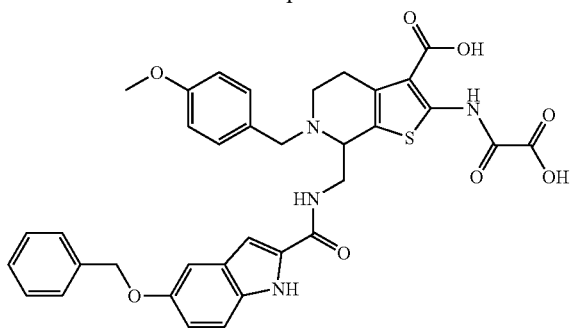

7-(((5-Benzyloxy-1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid 2-Amino-7-aminomethyl-6-(4-methoxy-benzyl)-4,5,6,7-tetrahydro-thieno[2,3-c]pyridine-3-carboxylic acid tert-butyl ester (0.50 g; 1.2 mmol) was dissolved in N,N-dimethylformamide (20 ml). 1-Hydroxy-7-azabenzotriazole (0.19 g; 1.3 mmol) and N-(3-dimethylaminopropyl)-N'-ethylcarbodiimide hydrochloride (0.26 g; 1.3 mmol) and diisopropyl-ethylamine (0.23 ml; 1.3 mmol) were added and the mixture was stirred for 15 min. 5-Benzyloxyindole (0.36 g, 1.3 mmol) was dissolved in N,N-dimethylformamide (20 ml) and added. Diisopropylethylamine (0.23 ml; 1.3 mmol) was added and the mixture was stirred overnight. The solvent was removed in vacuo, the residue dissolved in dichloromethane (30 ml) and the organic phase washed with an aqueous solution of sodium hydrogencarbonate (15 ml). The organic phase was dried (MgSO$_4$), filtered and the solvent removed in vacuo. The residue was chromatographed on silica using ethyl acetate/heptane (1:1) as eluent affording 569 mg of 2-amino-7-(((5-benzyloxy-1H-indole-2-carbonyl)amino)methyl)-6-(4-methoxy-benzyl)-4,5,6,7-tetrahydro-thieno[2,3-c]pyridine-3-carboxylic acid tert-butyl ester as an oil.

The title compound was prepared in a similar way as described in Example 48 using the last two steps.

MS: m/z: 669.4[M+H]$^+$

Calculated for C$_{35}$H$_{32}$N$_4$O$_8$S, ⅔×C$_2$HF$_3$O$_2$, ⅓×H$_2$O; C, 56.77%; H, 4.63%; N, 7.29%. Found: C, 56.43%; H, 4.57%; N, 7.13%.

Example 86

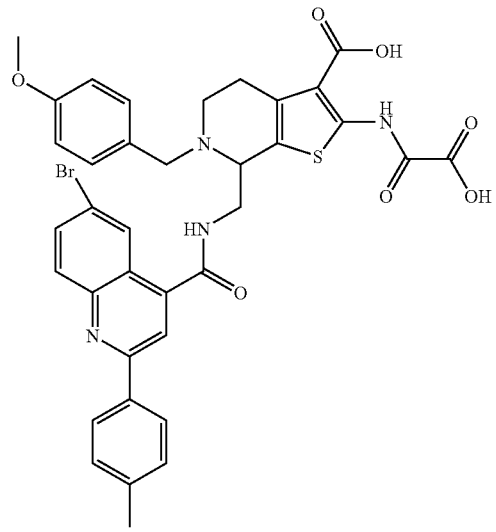

7-(((6-Bromo-2-p-tolyl-quinoline-4-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 6-bromo-2-p-tolyl-quinoline-4-carboxylic acid and 2-amino-7-aminomethyl-6-(4-methoxy-benzyl)-4,5,6,7-tetrahydro-thieno[2,3-c]pyridine-3-carboxylic acid-tert-butyl ester as the starting material.

LC-MS: m/z: 745.2 [M+H]$^+$
Calculated for C$_{36}$H$_{31}$BrN$_4$O$_7$S, 2×C$_2$HF$_3$O$_2$; C, 49.44%; H, 3.42%; N, 5.77%. Found: C, 49.19%; H, 3.59%; N, 6.00%.

Example 87

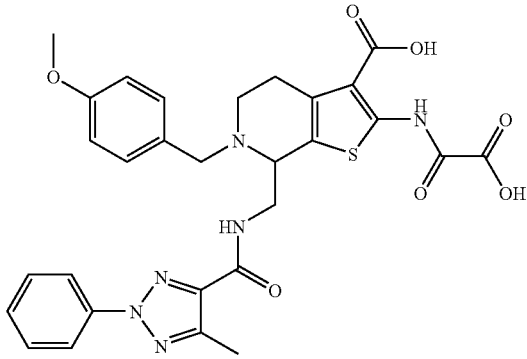

6-(4-Methoxy-benzyl)-7-(((5-methyl-2-phenyl-2H-[1,2,3]triazole-4-carbonyl)amino)-methyl)-2-(oxalyl-amino)-4,5,6,7-tetrahydro-thieno[2,3-c]pyridine-3-carboxylic acid The title compound was prepared in a similar way as in Example 84 using 5-methyl-2-phenyl-2H-[1,2,3]triazole-4-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.
LC-MS: m/z: 605.2 [M+H]$^+$
Calculated for C$_{29}$H$_{28}$N$_6$O$_7$S, 1.3×C$_2$HF$_3$O$_2$, 1.7×H$_2$O; C, 48.14%; H, 3.94%; N, 10.94%. Found: C, 48.35%; H, 4.19%; N, 10.68%.

Example 88

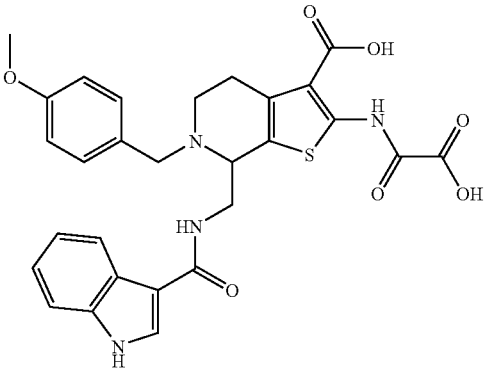

7-(((1H-Indole-3-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 3-indole-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.
LC-MS: m/z: 563.2 [M+H]$^+$
Calculated for C$_{28}$H$_{26}$N$_4$O$_7$S, 5/3×C$_2$HF$_3$O$_2$; C, 49.63%; H, 3.82%; N, 7.35%. Found: C, 50.00%; H, 3.71%; N, 7.44%.

Example 89

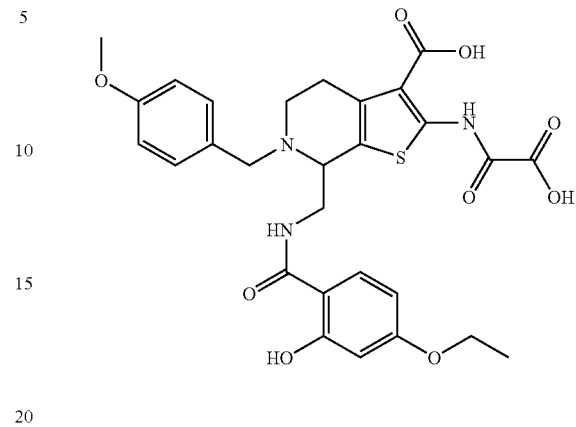

7-((4-Ethoxy-2-hydroxy-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 4-ethoxy-2-hydroxy-benzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.
LC-MS: m/z 584 [M+H]$^+$
HPLC: (B6): 23.8 min.

Example 90

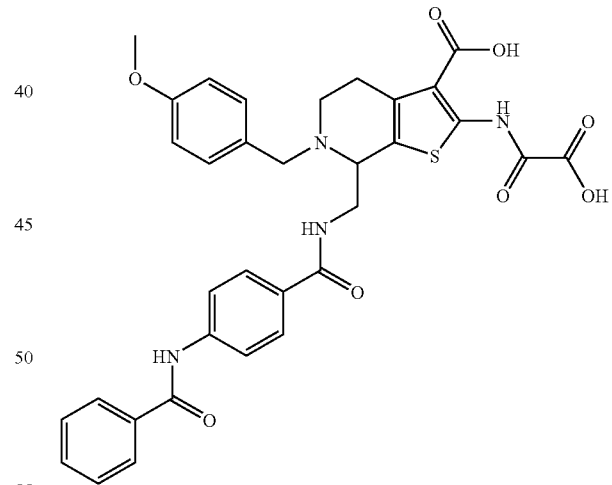

7-((4-Benzoylamino-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 4-benzoylaminobenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.
LC-MS: m/z: 643.1 [M+H]$^+$ Calculated for C$_{33}$H$_{30}$N$_4$O$_8$S, 3×C$_2$HF$_3$O$_2$; C, 47.57%; H, 3.38%; N, 5.69%. Found: C, 47.34%; H, 3.55%; N, 5.62%.

Example 91

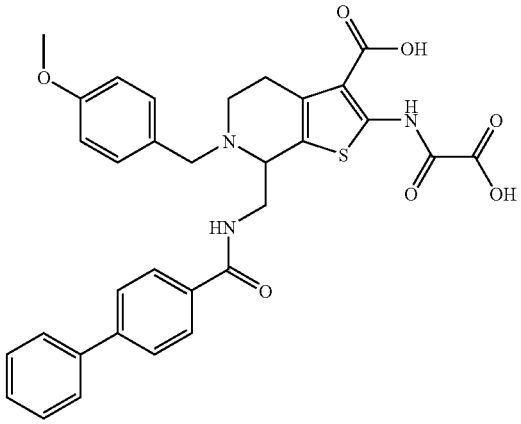

7-(((Biphenyl-4-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 4-phenylbenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 599.0 [M+H]$^+$

Calculated for C$_{32}$H$_{29}$N$_3$O$_7$S, 2×C$_2$HF$_3$O$_2$, 1×H$_2$O; C, 51.13%; H, 3.93%; N, 4.97%. Found: C, 52.02%; H, 4.02%; N, 5.16%.

Example 92

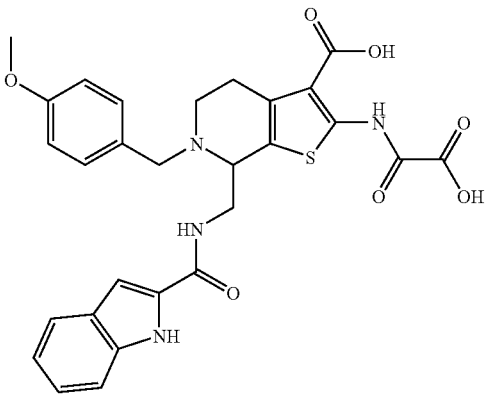

7-(((1H-Indole-2-carbonyl)amino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using indole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 563.2 [M+H]$^+$

HPLC (B6) R$_t$=23.07 min.

Example 93

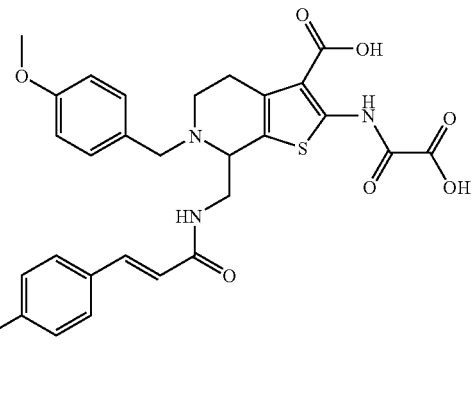

7-((3-Biphenyl-4-yl-acryloylamino)methyl)-6-(4-methoxy-benzyl)-2-(oxalyl-amino)-4,5,6,7-tetrahydro-thieno[2,3-c)pyridine-3-carboxylic acid The title compound was prepared in a similar way as in Example 84 using 3-biphenyl-4-yl-acrylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 626.2 [M+H]$^+$

HPLC (B6) R$_t$=28.74 min.

Calculated for C$_{34}$H$_{31}$N$_3$O$_7$S, 2×C$_2$HF$_3$O$_2$; C, 53.46%; H, 3.90%; N, 4.92%. Found: C, 53.89%; H, 4.23%; N, 5.08%.

Example 94

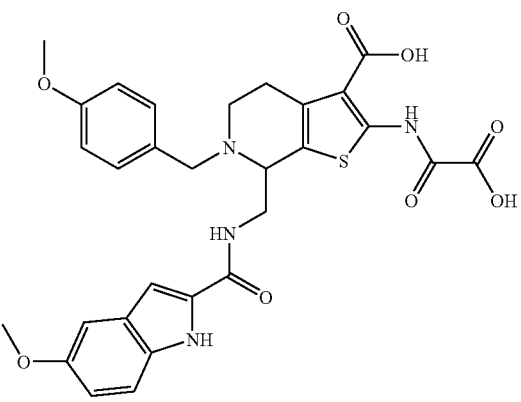

6-(4-Methoxy-benzyl)-7-(((5-methoxy-1H-indole-2-carbonyl)amino)-methyl)-2-(oxalyl-amino)-4,5,6,7-tetrahydro-thieno[2,3-c]pyridine-3-carboxylic acid The title compound was prepared in a similar way as in Example 84 using 5-methoxyindole-2-carboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z: 593.2 [M+H]$^+$

HPLC (B6) R$_t$=21.81 ml.

Example 95

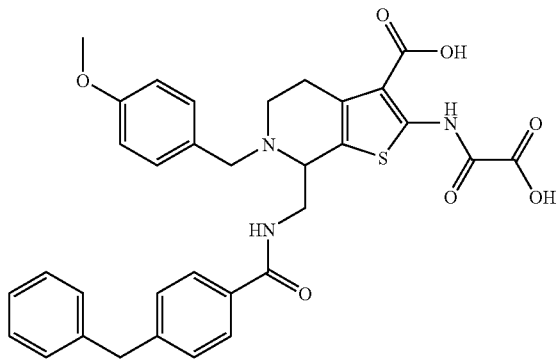

7-((4-Benzyl-benzoylamino)methyl)-6-(4-methoxy-benzyl)-2-(oxalyl-amino)-4,5,6,7-tetrahydro-thieno[2,3-c]pyridine-3-carboxylic acid The title compound was prepared in a similar way as in Example 84 using 4-benzylbenzoic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z 614.2 [M+H]$^+$

HPLC (B6) $R_f$=27.23 min.

Calculated for $C_{33}H_{31}N_3O_7S$, 1.5×$C_2HF_3O_2$; 1×$H_2O$; C, 53.87%; H, 4.33%; N, 5.23%. Found: C, 53.92%; H, 4.24%; N, 5.18%.

Example 95

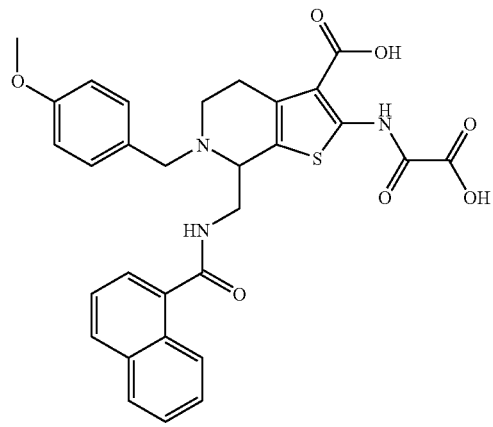

6-(4-Methoxy-benzyl)-7-(((naphthalene-1-carbonyl)amino)methyl)-2-(oxalyl-amino)-4,5,6,7-tetrahydro-thieno[2,3-c]pyridine-3-carboxylic acid The title compound was prepared in a similar way as in Example 84 using 1-napthylcarboxylic acid and 2-amino-7-aminomethyl-6-(4-methoxy-benzyl)-4,5,6,7-tetrahydro-thieno[2,3-c]pyridine-3-carboxylic acid tert-butyl ester as the starting material.

LC-MS: m/z 574.0 [M+H]$^+$

HPLC (B6) $R_f$=22.51 min.

Calculated for $C_{30}H_{27}N_3O_7S$, 2×$C_2HF_3O_2$; C, 50.94%; H, 3.65%; N, 5.24%. Found: C, 51.39%; H, 3.79%; N, 5.16%.

Example 96

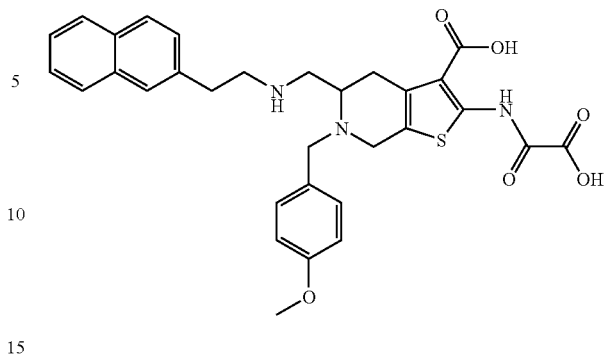

6-(4-Methoxy-benzyl)-5-((2-naphthalen-2-yl-ethylamino)methyl)-2-(oxalyl-amino)-4,5,6,7-tetrahydro-thieno[2,3-c]pyridine-3-carboxylic acid A solution of 2-naphthalen-2-yl-ethanol (1.02 g, 5.8 mmol), 2,2,6,6-tetramethyl-1-piperidinyloxy (TEMPO) (9 mg, 0.058 mmol) and sodium bromide (0.65 g, 6.4 mmol) in a mixture of toluene (18 mL), ethyl acetate (18 mL), and water (3 mL) was cooled to 0° C. and added dropwise over 1 hour a solution containing the following: sodium hypochlorite (17.2 mL, 0.37 M, 6.4 mmol) and sodium hydrogencarbonate (1.46 g, 17.4 mmol). The reaction mixture was stirred at 0° C. for 10 min., and the phases separated. The aqueous layer was extracted with ethyl acetate (150 mL). The combined organic phases were washed with a solution of potassium iodone (0.2 g) in 10,% aqueous potassium hydrogensulfate (150 mL), water (150 mL), brine (150 mL), dried (MgSO$_4$), filtered, and concentrated in vacuo to provide 980 mg of a 3:1 mixture of naphthalen-2-yl-acetaldehyde and 2-naphthalen-2-yl-ethanol.

$^1$H-NMR (CDCl$_3$): δ 9.81 (t, 1H, J=1.5 Hz), 7.92–7.80 (m, 3H), 7.68 (bs, 1H), 7.55–7.42 (m, 3H), 3.87 (d, 2H, J=1.5 Hz).

To a solution of 2-amino-5-aminomethyl-6-(4-methoxy-benzyl)-4,5,6,7-tetrahydro-thieno[2,3-c]pyridine-3-carboxylic acid tert-butyl ester (290 mg, 0.71 mmol) in 1,2-dichloroethane (3 ml) was added the above mixture of 2-naphthyl-acetaldehyde (100 mg, 0.59 mmol), sodium triacetoxyborohydride (190 mg, 0.88 mmol) and the mixture was stirred at room temperature under nitrogen for 2.5 hours. The crude reaction mixture was quenched with saturated sodium bicarbonate (50 ml) and the solution extracted with ethyl acetate (100 ml). The organic phase was dried (MgSO$_4$), filtered, and concentrated in vacuo providing a foam, which was taken directly to the next step. LC-MS showed that 2-amino-6-(4-methoxy-benzyl)-5-((2-naphthalen-2-yl-ethylamino)-methyl)-4,5,6,7-tetrahydro-thieno[2,3-c]pyridine-3-carboxylic acid tert-butyl ester was the major component.

LC-MS: m/z: 558.1 [M+H]$^+$, $R_f$=2.23 min.

To a solution of 2-amino-6-(4-methoxy-benzyl)-5-((2-naphthalen-2-yl-ethylamino)methyl)-4,5,6,7-tetrahydro-thieno[2,3-c]pyridine-3-carboxylic acid tert-butyl-ester in tetrahydrofuran (3 ml) was added di-tert-butyl-dicarbonate (188 mg, 0.85 mmol) and N,N-dimethylformamide (18 mg, 0.14 mmol). The reaction was stirred at room temperature for 7 hours under nitrogen. The crude reaction mixture was diluted with dichloromethane (50 ml) and washed with water (50 ml) and brine-(50 ml). The organic phase was dried (MgSO₄), filtered, and concentrated in vacuo affording a foam, which was used without further purification in the next step.

LC-MS showed that 2-amino-5-((tert-butoxycarbonyl-(2-naphthalen-2-yl-ethyl)-amino)-methyl)-6-(4-methoxy-benzyl)-4,5,6,7-tetrahydro-thieno[2,3-c]pyridine-3-carboxylic acid tert-butyl ester was the major component. $R_f$=2.74, m/z: 658.1 [M+H]⁺, Calculated: 657.4.

To crude 2-amino-5-((tert-butoxycarbonyl-(2-naphthalen-2-yl-ethyl)-amino)-methyl)-6-(4-methoxy-benzyl)-4,5,6,7-tetrahydro-thieno[2,3-c]pyridine-3-carboxylic acid tert-butyl ester was added dichloromethane (5 ml) and imidazol-1-yl-oxo-acetic acid tert-butyl ester (400 mg, 1.78 mmol) and the reaction mixture stirred at room temperature for 12 hours. The crude reaction mixture was added to dichloromethane (50 ml) and washed with water (50 ml) and brine (50 ml). The organic phase was dried (MgSO₄), filtered, and concentrated in vacuo. The residue was purified by flash chromatography using a mixture of dichloromethane/ethyl acetate (10:1) as eluent; which afforded 20.3 mg (39% over tree steps) of 2-(tert-butoxyoxalyl-amino)-5-((tert-butoxycarbonyl-(2-naphthalen-2-yl-ethyl)-amino)methyl)-6-(4-methoxy-benzyl)-4,5,6,7-tetrahydro-thieno[2,3-c]pyridine-3-carboxylic acid tert-butyl ester as a foam.

¹H NMR (CDCl₃) δ 7.99–7.92 (m, 3H), 7.88 (s, 1H), 7.68–7.57 (m, 3H), 7.45 (d, 2H, J=7.8 Hz), 6.99 (d, 2H, J=8.1 Hz), 3.90–3.75 (m, 7H), 3.56–3.42 (m, 5H), 3.19–3.13 (m, 2H), 2.88–2.82 (m, 2H), 1.79 (s, 9H), 1.71 (s, 18H); LC-MS: m/z: 786.2 [M+H]⁺, $R_f$=3.03 min.

To a solution of 2-(tert-butoxyoxalyl-amino)-5-((tert-butoxycarbonyl-(2-naphthalen-2-yl-ethyl)-amino)methyl)-6-(4-methoxy-benzyl)-4,5,6,7-tetrahydro-thieno[2,3-c]pyridine-3-carboxylic acid tert-butyl ester (20 mg, 0.03 mmol) in dry dichloromethane (200 μl) at 0° C. was added 50% trifluoroacetic acid in dichloromethane (2.5 ml). The reaction was stirred for 14 hours at room temperature and then concentrated in vacuo. The resultant solid was re-suspended in dichloromethane, filtered, and dried in vacuo to provide 13 mg (90%) of the title compound as a solid.

¹H NMR-(DMSO-d₆)δ 9.15 (s, 1H), 8.09–8.01 (m, 3H), 7.93 (s, 1H), 7.68–7.57 (m, 3H), 7.45 (d, 2H, J=7.8 Hz), 6.99 (d, 2H, J=8.1 Hz), 4.18–4.12 (m, 2H), 3.90–3.75 (m, 7H), 3.56–3.42 (m, 3H), 3.19–3.13 (m, 2H), 2.88–2.82 (m, 2H); LC-MS: m/z: 574.7 [M+H]⁺, $R_f$=1.36 min.

Example 97

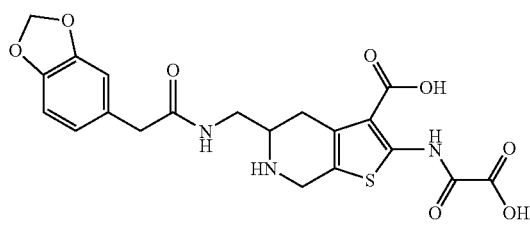

5-((2-Benzo[1,3]dioxol-5-yl-acetylamino)methyl)-2-(oxalyl-amino)-4,5,6,7-tetrahydro-thieno[2,3-c]pyridine-3-carboxylic acid To a mixture of 2-amino-5-aminomethyl-6-(4-methoxy-benzyl)-4,5,6,7-tetrahydro-thieno[2,3-c]pyridine-3-carboxylic acid tert-butyl ester (300 mg, 0.74 mmol), benzo[1,3]dioxol-5-yl-acetic acid (134 mg, 0.74 mmol), 1-hydroxybenzotriazole hydrate (111 mg, 0.82 mmol), and N,N-diisopropyl-ethylamine (258 μL, 1.48 mmol) in acetonitrile (5 ml) at room temperature was added 1-(3-dimethylaminopropyl)-3-ethylcarbodiimide hydrochloride (157 mg, 0.82 mmol). The reaction mixture was stirred for 16 hours and the solvent evaporated in vacuo. The residue was taken into ethylacetate (50 ml), washed with water, 1 N hydrochloric acid, saturated sodium bicarbonate, brine, dried (MgSO₄), filtered and the solvent evaporated in vacuo. The residue was subjected to flash chromatography using a gradient of 10–20% ethylacetate/hexanes as eluent, which afforded 268 mg (64%) of 2-amino-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester as an oil.

¹H-NMR (CDCl₃) δ 6.95 (bs, 2H), 6.75–6.85 (m, 5H), 5.96 (bs, 2H), 5.95 (s, 2H), 3.81 (s, 3H), 3.75–3.30 (m; 5H), 3.53 (s, 2H), 3.18 (bs, 2H), 2.82 (d, 1H, J=17 Hz), 2.52 (d, 1H, J=17 Hz).

To a solution of 2-amino-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester (133 mg, 0.235 mmol) in tetrahydrofuran (1 ml) was added imidazol-1-yl-oxo-acetic acid tert-butyl ester (100 mg, 0.51 mmol). The mixture was stirred at room temperature for 24 hours. The solvent was removed in vacuo. The residue was taken into ethyl acetate (50 ml) washed with saturated sodium bicarbonate, brine, dried (Na₂SO₄) and filtered. The solvent was removed in vacuo and the residue was chromatographed using a gradient of 10–20% ethyl acetate/dichloromethane, which afforded 130 mg (80%) of 2-(tert-butoxyoxalyl-amino)-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester as an oil.

¹H-NMR (CDCl₃) δ 12.50 (s, 1H), 7.95–7.75 (m, 7H), 5.96 (s, 2H), 3.81 (s, 3H), 3.80–3.40 (m, 5H), 3.15 (bs, 2H), 2.90 (d, 1H, J=17 Hz), 2.58 (d, 1H, J=17 Hz), 1.61 (s, 9H), 1.60 (s, 9H).

A solution of 2-(tert-butoxyoxalyl-amino)-5-((2-benzo[1,3]dioxol-5-yl-acetylamino)methyl)-6-(4-methoxy-benzyl)-4,5,6,7-tetrahydro-thieno[2,3-c]pyridine-3-carboxylic acid tert-butyl ester (130 mg, 0.188 mmol) in tetrahydrofuran (2 ml) was passed through a Raney Ni bed (120 mg, 50% Raney Ni-water washed with methanol (6 ml) and tetrahydrofuran (6 ml) and dried before use). The Raney Ni bed was washed with tetrahydrofuran (10 ml). The filtrate and washes were combined and the solvent evaporated in vacuo. The residue was dissolved in 10% formic acid/methanol (6 ml) and stirred with 10% Pd/C (120 mg) for 13 hours. Saturated sodium bicarbonate solution (60 ml) was added to the solution. The mixture was extracted with dichloromethane. The extracts were combined, dried (Na₂SO₄) and filtered. The solvent was removed in vacuo and the residue was washed with 50% hexane/diethyl ether to afford 62 mg (57%) of 2-(tert-butoxyoxalyl-amino)-5-((2-benzo[1,3]dioxol-5-yl-acetylamino)methyl)-4,5,6,7-tetrahydro-thieno[2,3-c]pyridine-3-carboxylic acid tert-butyl ester as an oil.

¹H-NMR (CDCl₃) δ 12.59 (s, 1H), 6.80–6.70 (m, 3H), 5.96 (s, 2H), 4.05 (q, 2H, J=15 Hz), 3.85–3.60 (m, 2H), 3.25–3.00 (m, 4H), 2.58 (m, 1H), 1.61 (s, 9H), 1.59 (s, 9H); LC-MS: R=1.75 min, m/z: 574 [M+H]⁺.

A solution of 2-(tert-butoxyoxalyl-amino)-5-((2-benzo[1,3]dioxol-5-yl-acetylamino)methyl)-4,5,6,7-tetrahydro-thieno[2,3-c]pyridine-3-carboxylic acid tert-butyl ester (62 mg, 0.11 mmol) in 50% trifluoroacetic acid-dichloromethane (2 ml) was left in an open flask over the weekend and then the solvent was removed in vacuo. The residue was washed with dichloromethane and the solid filtered off affording 39 mg (62%) of the title compounds as a solid trifluoroacetate.

$^1$H-NMR (DMSO-d$_6$) δ 12.39 (s, 1H), 9.18 (bs, 1H), 9.10 (bs, 1H), 8.35 (s, 1H), 6.83 (d 1H, J=1.2 Hz), 6.82 (d, 1H, J=8.4 Hz), 6.70 (dd, 1H, J=8.4 Hz and J=1.2 Hz), 5.96 (s, 2H), 4.38 (d, 1H, J=14 Hz), 4.28 (m, 1H), 3.60–3.40 (m, 4H), 3.16 (d, 2H, J=14 Hz), 2.80 (dd, 1H, J=14 Hz and J=11 Hz);

LC-MS: R$_t$=1.11 min, m/z: 462 [M+H]$^+$.

Example 98

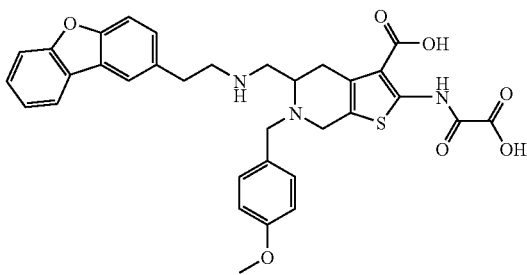

5-((2-Dibenzofuran-2-yl-ethyl)amino)methyl)-6-(4-methoxy-benzyl)-2-(oxalyl-amino)-4,5,6,7-tetrahydro-thieno[2,3-c]pyridine-3-carboxylic acid To a solution of 2-dibenzofuran-2-yl-ethanol (200 mg, 0.94 mmol) and 2,2,6,6-tetramethyl-1-piperidinyloxy (TEMPO) (2 mg, 0.009 mmol) in dichloromethane (2 mL) was added an aqueous solution of sodium bromide (97 mg in 1.3 mL of water for a 0.7M solution, 0.94 mmol) and cooled to 0° C. To this mixture was added dropwise over 30 min., a solution containing the following: sodium hypochlorite (1.4 mL, 0.74 M, 1.03 mmol) and sodium hydrogencarbonate (120 mg, 1.4 mmol) and water (1.4 mL). The reaction mixture was stirred at 0° C. for 0.5 hour and allowed to warm to room temperature. The organic phase and aqueous layer were separated and the aqueous layer extracted with dichloromethane (20 mL). The combined organic phases were washed with a solution of potassium iodone (0.2 g) in 10% aq. Potassium hydrogensulfate (20 mL), water (20 mL), brine (20 mL), dried (MgSO$_4$) filtered, and concentrated in vacuo to provide 198 mg of a 5:1 mixture of dibenzofuran-2-yl-acetaldehyde and 2-dibenzofuran-2-yl-ethanol as an oil.

$^1$H-NMR (CDCl$_3$): δ 9.80 (t, 1H, J=1.5 Hz), 8.02 (d, 2H, J=8.2 Hz), 7.71 (bs, 1H), 7.75–7.42 (m, 4H), 3.82 (d, 2H, J=1.5 Hz).

To a solution of 2-amino-5-aminomethyl-6-(4-methoxy-benzyl)-4,5,6,7-tetrahydro-thieno[2,3-c]pyridine-3-carboxylic acid tert-butyl ester (340 mg, 0.85 mmol) in 1,2-dichloroethane (3 ml) was added the above mixture of dibenzofuran-2-yl-acetaldehyde (150 mg, 0.70 mmol), and sodium triacetoxyborohydride (225 mg, 1.07 mmol) and the mixture was stirred at room temperature under nitrogen for 2.5 hours. The crude reaction mixture was quenched with saturated sodium bicarbonate (50 ml) and the solution extracted with ethylacetate (100 ml). The organic phase was dried (MgSO$_4$), filtered, and the solvent evaporated in vacuo. The crude residue was taken directly to the next step. LC-MS showed that 2-amino-5-((2-dibenzofuran-2-yl-ethylamino)methyl]-6-(4-methoxy-benzyl)-4,5,6,7-tetrahydro-thieno[2,3-c]pyridine-3-carboxylic acid tert-butyl ester was the major component in the crude mixture: m/z: 598.1 [M+H]$^+$, R$_f$=2.40 min).

Crude 2-amino-5-((2-dibenzofuran-2-yl-ethylamino)methyl]-6-(4-methoxy-benzyl)-4,5,6,7-tetrahydro-thieno[2,3-c]pyridine-3-carboxylic acid tert-butyl ester was diluted in tetrahydrofuran (3 ml) and di-tert-butyl dicarbonate (262 mg, 1.20 mmol) and 4-(N,N-dimethylamino)pyridine (25 mg, 0.20 mmol) were added. The reaction was stirred at room temperature for 7 hours under nitrogen. The crude reaction mixture was added to dichloromethane (50 ml) and washed with water (50 ml) and brine (50 ml). The organic phase was dried (MgSO$_4$), filtered, and concentrated in vacuo. The residue was used directly in the next step. LC-MS showed that 2-amino-5-((tert-butoxycarbonyl-(2-dibenzofuran-2-yl-ethyl)amino)-methyl)-6-(4-methoxy-benzyl)-4,5,6,7-tetrahydro-thieno[2,3-c]pyridine-3-carboxylic acid tert-butyl ester was the major component in the crude: R$_f$=2.76, m/z: 698.2 [M+H]$^+$.

To compound 2-amino-5-((tert-butoxycarbonyl-(2-dibenzofuran-2-yl)amino)-methyl)-6-(4'-methoxy-benzyl)-4,5,6,7-tetrahydro-thieno[2,3-c]pyridine-3-carboxylic acid tert-butyl ester was added dichloromethane (5 ml) and imidazol-1-yl-oxo-acetic acid tert-butyl ester (420 mg, 2.12 mmol). The reaction mixture was stirred at room temperature for 12 hours. The crude reaction mixture was added to dichloromethane (50 ml) and washed with water (50 ml) and brine (50 ml). The organic phase was dried (MgSO$_4$), filtered, and concentrated in vacuo. The residue was subjected to flash chromatography using a mixture of dichloromethane/ethyl acetate (10:1) as eluent, which afforded 35.2 mg (51% over 3 steps) of 2-(tert-butoxyoxalyl-amino)-5-((tert-butoxycarbonyl-(2-dibenzofuran-2-yl-ethyl)amino)methyl)-6-(4-methoxy-benzyl)-4,5,6,7-tetrahydro-thieno[2,3-c]pyridine-3-carboxylic acid tert-butyl ester as a foam.

$^1$H-NMR (CDCl$_3$) δ 7.95–7.90 (m, 3H), 7.84 (s, 1H), 7.68–7.57 (m, 3H), 7.45 (d, 2H, J=7.8 Hz), 6.95 (m, 3H), 3.90–3.75 (m, 7H), 3.56–3.42 (m, 5H), 3.19–3.13 (m, 2H), 2.88–2.82 (m, 2H), 1.79 (s, 9H), 1.71 (s, 18H);

LC-MS: R$_f$=3.03 min, m/z: 826.2 [M+H]$^+$.

To a solution of 2-(tert-butoxyoxalyl-amino)-5-((tert-butoxycarbonyl-(2-dibenzofuran-2-yl-ethyl)amino)methyl)-6-(4-methoxy-benzyl)-4,5,6,7-tetrahydro-thieno[2,3-c]pyridine-3-carboxylic acid tert-butyl ester (28 mg, 0.034 mmol) in dry dichloromethane (200 µL) at 0° C. was added 50% trifluoroacetic acid in dichloromethane (2.5 ml). The reaction was stirred for 14 hours at room temperature and then concentrated in vacuo. The resultant solid was re-suspended in dichloromethane, filtered, and dried in vacuo, which afforded 22 mg (90%) of the title compound as a solid trifluoroacetate.

$^1$H-NMR (DMSO-d$_6$), δ9.15 (s, 1H), 8.11–8.21 (m, 3H), 7.93 (s, 1H), 7.68–7.57 (m, 3H), 7.45 (d, 2H, J=7.8 Hz), 6.99 (d, 2H, J=8.1 HZ), 4.18–4.12 (m, 2H), 3.90–3.75 (m, 7H), 3.56–3.42 (m, 3H), 3.19–3.13 (m, 2H), 2.88–2.82 (m, 2H);

LC-MS: R$_f$=3.03, m/z: 614.7 [M+H]$^+$.

Example 99

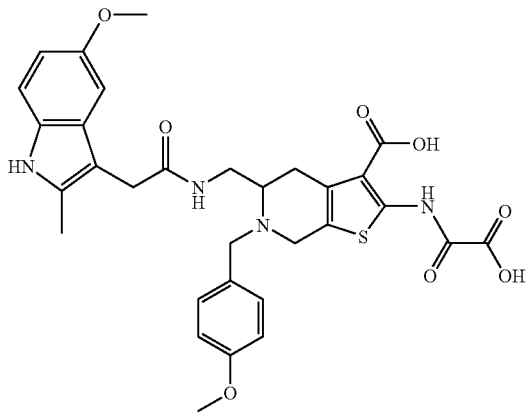

6-(4-Methoxy-benzyl)-5-((2-(5-methoxy-2-methyl-1H-indol-3-yl)-acetylamino)methyl)-2-(oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (202 mg, 0.50 mmol), in N,N-dimethylformamide (4 ml) was added 5-methoxy-2-methyl-3-indole acetic acid (170 mg, 0.74 mmol), 1-(3-dimethylamino-propyl)-3-ethylcarbodiimide, hydrochloride (150 mg, 0.75 mmol), and 1-hydroxybenzotriazole (105 mg, 0.74 mmol). The mixture was stirred at room temperature for 12 hours. The crude reaction mixture was diluted with dichloromethane (100 ml) and washed with water (100 ml), brine (100 ml), dried (MgSO$_4$), filtered, and concentrated in vacuo, which afforded 2-amino-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester as an oil.

$^1$H-NMR (CDCl$_3$) δ 7.16 (d, 2H, J=10.8 Hz), 6.99 (d, 1H, J=2.5 Hz), 6.94 (m, 1H), 6.85 (dd, 1H, J=8.4 Hz and J=1.2 Hz), 6.78 (dd, 1H, J=8.3 Hz and J=1.2 Hz), 6.65 (m, 3H), 6.57 (m, 4H), 3.57 (t, 4H, J=3.0 Hz), 3.53 (m, 6H), 3.59–3.29 (m, 5H), 3.12–2.92 (m, 4H), 2.39 (s, 3H), 1.6 (s, 9H);

LC-MS R$_t$=2.19, m/z: 605 [M+H]$^+$.

To a solution of 2-amino-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester (96 mg, 0.5 mmol) in dichloromethane (5 ml) was added imidazol-1-yl-oxo-acetic acid tert-butyl ester (583 mg, 3.0 mmol) and the reaction stirred at room temperature for 24 hours. The mixture was then concentrated in vacuo. The residue was purified by flash column chromatography (25% ethylacetate/dichloromethane) to give 53 mg (15. %) of 2-(tert-butoxyoxalyl-amino)-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester as an oil.

$^1$H-NMR (CDCl$_3$) δ 7.16 (d, 2H, J=10.8 Hz), 6.99 (d, 1H, J=2.5 Hz), 6.94 (m, 1H), 6.85 (dd, 1H, J=8.4 Hz and J=1.2 Hz), 6.78 (dd, 1H, J=8.3 Hz and J=1.2 Hz), 6.65 (m, 3H), 6.56 (m, 3H), 3.57 (m, 3H), 3.53 (m, 6H), 3.59–3.29 (m, 5H), 3.12–2.92 (m, 4H), 2.39 (s, 3H), 1.6 (s, 18H);

LC-MS R$_t$=2.36 min, m/z: 733 [M+H]$^+$.

2-(tert-Butoxyoxalyl-amino)-6-(4-methoxy-benzyl)-5-((2-(5-methoxy-2-methyl-1H-indol-3-yl)acetylamino)methyl)-4,5,6,7-tetrahydro-thieno[2,3-c]pyridine-3-carboxylic acid tert-butyl ester was dissolved in 50% trifluoroacetic acid/dichloromethane (3 ml) and stirred at room temperature for 48 hours. The solvent was removed in vacuo and the residual trifluoroacetic acid was removed under reduced pressure to give 17 mg (49%) of the title compound as a solid trifluoroacetate.

$^1$H-NMR (DMSO-d$_6$) δ 10.62 (s, 1H), 7.31 (s, 1H), 7.08 (d, 1H, J=10.2 Hz), 6.93 (s, 2H), 6.58 (dd, 1H, J=5.25 Hz and J=2.8 Hz), 3.84–3.44 (m, 19H, partially obscured by solvent), 2.95 (s, 1H), 2.28 (s, 3H), 1.31 (s, 1H), 1.19 (s, 2H);

LC-MS-R$_t$=1.89 min, m/z: 621 [M+H]$^+$.

Example 100

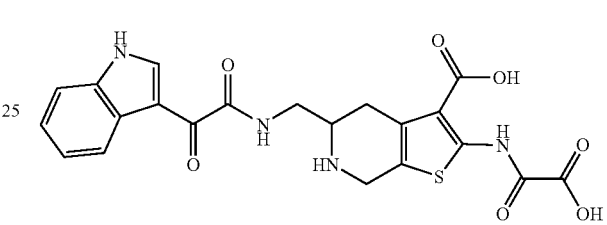

5-((2-(1H-Indol-3-yl)-2-oxo-acetylamino)methyl)-2-(Oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (209 mg, 0.51 mmol) in dry N,N-dimethylformamide (4 ml) was added 3-indole-glyoxylic acid (141 mg, 0.74 mmol), 1-(3-dimethylaminopropyl)-3-ethylcarbodiimide, hydrochloride (152 mg, 0.76 mmol), and 1-hydroxy-benzotriazole (100 mg, 0.74 mmol). The mixture was stirred at room temperature for 16 hours, diluted with dichloromethane (100 ml) and washed with water (100 ml), brine (100 ml), dried (MgSO$_4$), filtered, and concentrated in vacuo. The residue was subjected to flash chromatography using a mixture of ethyl acetate/hexanes (2:5) as eluent, which afforded 143 mg (40. %) of 2-amino-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester as an oil.

LC-MS R$_t$=2.31 min, m/z: 574.9 [M+H]$^+$.

To a solution of 2-amino-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester (143 mg, 0.25 mmol) in dichloromethane (5 ml) was added imidazol-1-yl-oxo-acetic acid tert-butyl ester (144 mg, 0.75 mmol) and the flask was purged with nitrogen. After 24 hours an additional portion of imidazol-1-yl-oxo-acetic acid tert-butyl ester (169 mg, 0.86 mmol) was added and the reaction mixture allowed stirred for an additional 24 hours. The mixture was then concentrated in vacuo. The residue was purified by flash chromatography using a mixture of ethyl acetate/hexanes (2:5) as eluent, which afforded 101 mg (58%) of 2-(tert-butyoxyoxalyl-amino)-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester as a oil.

¹H-NMR (CDCl₃) δ 9.23 (s, 1H); 9.07 (d, 1H, J=3.6 Hz), 8.50 (d, 1H, J=7.6 Hz), 8.15 (d, 1H, J=4.0 Hz), 7.47 (d, 2H, J=7.2 Hz), 7.38–7.27 (m, 6H), 6.89 (d, 2H, J=8.8 Hz), 3.87–3.59 (m, 6H), 3.04 (dd, 2H, J=23.6 Hz), 2.74 (dd, 2H, J=22.4 Hz), 1.62 (s, 18H);

LC-MS R$_t$=2.49 min, m/z: 703 [M+H]⁺.

2-(tert-Butyoxyoxalyl-amino)-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester (101 mg, 0.143 mmol) was dissolved in dry tetrahydrofuran (6 ml) and passed through a pipette, plugged with cotton containing Raney 2800 Nickel (0.38 g). The pipette was flushed with dry tetrahydrofuran (6 ml) and the filtrate was concentrated in vacuo. Pd on carbon (10%, 102 mg, source: Avocado) and formic acid (10% in methanol, 5 ml) were added to the flask containing 2-(tert-Butyoxyoxalyl-amino)-5-((2-(1H-indol-3-yl)-2-oxo-acetylamino)methyl)-6-(4-methoxy-benzyl)-4,5,6,7-tetrahydro-thieno[2,3-c]pyridine-3-carboxylic acid tert-butyl ester. After stirring for 18 hours, the solution was filtered through a pad of celite and concentrated in vacuo. The residue was diluted in ethyl acetate, washed with saturated sodium bicarbonate (2×25 ml), brine (2×25 ml), dried (MgSO₄), filtered and concentrated in vacuo. The residue was subjected to flash chromatography using a mixture of 10% methanol/dichloromethane as eluent, which afforded 2-(tert-butyoxyoxalyl-amino)-5-((2-(1H-indol-3-yl)-2-oxo-acetylamino)methyl)-4,5,6,7-tetrahydro-thieno[2,3-c]pyridine-3-carboxylic acid tert-butyl ester.

¹H-NMR (CDCl₃) δ 9.23 (s, 1H), 9.07 (d, 1H, J=3.6 Hz), 8.50 (d, 1H, J=7.6 Hz), 8.15 (d, 1H, J=4.0 Hz), 7.27 (s, 2H), 7.09 (d, 1H, J=8.8 Hz), 6.81 (d, 1H, J=8.8 Hz), 3.79 (s, 1H), 2.29 (s, 1H), 1.62–1.57 (m, 18H), 0.08 (s, 5H);

LC-MS: R$_t$=2.17 min, m/z: 583 [M+H]⁺.

The above 2-(tert-butyoxyoxalyl-amino)-5-((2-(1H-indol-3-yl)-2-oxo-acetylamino)methyl)-4,5,6,7-tetrahydro-thieno[2,3-c]pyridine-3-carboxylic acid tert-butyl ester was dissolved in 50% trifluoroacetic acid/dichloromethane (3 ml) and stirred at room temperature for 18 hours. The solvent was removed in vacuo and residual trifluoroacetic acid was removed under reduced pressure affording 17.1 mg of the title compound as a solid trifluoroacetate.

¹H-NMR (DMSO-d₆) δ 12.28 (s, 2H), 9.26 (s, 1H), 9.13 (s, 1H), 8.83 (d, 1H, J=2.8 Hz), 8.26 (d, 1H, J=8.8 Hz), 7.55 (d, 0.1H, J=4.8 Hz), 7.27 (d, 2H, J=7.6 Hz), 4.42 (d, 1H, J=15.2 Hz), 4.29 (d, 1H, J=16.4 Hz), 3.76–3.22 (m, 4H, partially obscured by solvent), 2.91–2.834 (m, 1H), 1.23 (s, 1H); LC-MS: R$_t$=0.99 min, m/z 471.4 [M+H]⁺.

General Chiral Synthesis

4-Oxo-1-((S)-1-phenyl-ethyl)-piperidine-(R)-2-carboxylic acid ethyl ester

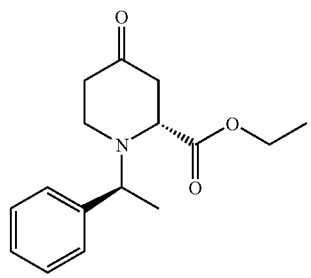

Dichloromethane (1 L) and mol sieves 3 Å (113 g) and amine (S)-(-)-α-methyl-benzylamin (71.7 ml) were mixed in a 2 l three-necked bottle cooled to −5° C. (using a ethanol/water/ice bath). A 50% solution of ethylglyoxylate in toluene (117.6 ml) was added drop wise over 20 min. keeping the temperature between −5° C. and 0° C. The mixture was stirred for 0.5 hour before it was cooled to −30° C. Trifluoroacetic acid (45.2 ml) was added over 3–4 minutes. Boron trifluoride diethyl ether (69.8 ml) was added drop wise over 5 min at −55° C. The ice bath was removed and the mixture was allowed to warm up to −45° C. whereupon 2-trimethylsiloxy)-1,3-butadiene (100 ml) was added drop wise over 10 minutes. During the addition the mixture was cooled and the temperature kept below −20° C. The above additions are all exothermic hence the cooling bath should have sufficient capacity to remove the heat generated during the rapid addition. The reaction mixture was stirred for 2 hours at −15° C. and 1 hour at 0° C. and then poured on ice/water and stirred for 15 minutes. Solid sodium hydrogen carbonate was added until pH 7–8. The mixture was stirred overnight at room temperature. The layers wee separated and the aqueous phase extracted with dichloromethane. The combined organic phases were filtered through a plug of silica eluting with dichloromethane. The relevant fractions were concentrated in vacuo. The residue was dissolved in hot heptane and cooled. This leaves a yellowish gummy material on the side of the flask and crystals starts forming. The heptane solution was heated again to dissolve crystals, leaving the gummy material on the side of the flask and the mixture was filtered hot. The heptane solution was cooled to room temperature and the precipitate was filtered off and dried in vacuo, which afforded 38 g of 4-oxo-1-((S)-1-phenyl-ethyl)-piperidine-(R)-2-carboxylic acid ethyl ester as a solid.

The filtrate was put in a refrigerator and a second crop was formed which was less pure and needed recrystallization from heptane to yield another 7.5 g of 4-oxo-1-((S)-1-phenyl-ethyl)-piperidine-(R)-2-carboxylic acid ethyl ester.

4,4-Diethoxy-1-((S)-1-phenyl-ethyl)-piperidine-(S)-2-carboxylic acid ethyl ester

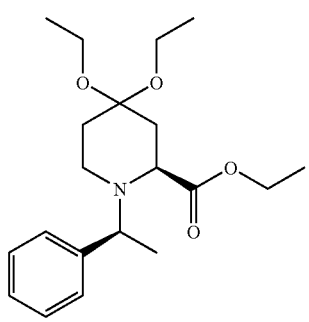

The mother liquor from the above crystallization was concentrated in vacuo. 5.0 g of the resulting material (18.16 mmol) was dissolved in ethanol (100 ml) and triethylorthoformate (26.9 g, 181.6 mmol) and para-toluensulphonic acid (6.9 g, 36.32 mmol) was added. The reaction was stirred at room temperature for 16 hours before the mixture was poured on aqueous sodium hydrogen carbonate (200 ml) and extracted with ethyl acetate (4×75 ml). The combined extracts were concentrated in vacuo and purified by column chromatography (SiO₂, Flash 40, petrol ether-ethyl acetate-10:1). Collection of the first band (R$_f$=0.68) gave 1.14 g (18%) of 4,4-diethoxy-1-((S)-1-phenyl-ethyl)-piperidine-(R)-2-carboxylic acid ethyl ester and collection of the second band (R$_f$=0.4) gave 3.60 g (57%) of the title compound.

4,4-Diethoxy-1-((S)-1-phenyl-ethyl)-piperidine-(R)-2-carboxylic acid ethyl ester

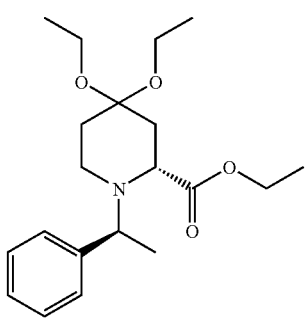

4-Oxo-1-((S)-1-phenyl-ethyl)-piperidine-(R)-2-carboxylic acid ethyl ester (11.0 g, 0.040 mmol) was dissolved in a 1:1 mixture of triethyl orthoformate and ethanol (140 ml) and para-toluene-4-sulphonic acid (15.2 g, 80 mmol) was added and the reaction mixture was stirred for 16 hours. The reaction mixture was neutralized with sodium bicarbonate (to pH 7–8), and extracted with dichloromethane (3×100 ml), dried (MgSO$_4$), filtered and concentrated in vacuo. The residue was purified by column chromatography (SiO$_2$, petrol ether/ethyl acetate 10:1), which afforded 12.0 g (86%) of the title compound as an oil.

4,4-Diethoxy-1-((S)1-phenyl-ethyl)-(R)-2-hydroxymethyl-piperidine

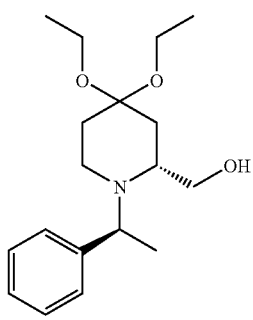

To a solution of 4,4-diethoxy-1-((S)-1-phenyl-ethyl)-piperidine-(R)-2-carboxylic acid ethyl ester (36.0 g, 0.103 mol) in dry diethyl ether (150 ml) was added a suspension of lithium aluminum hydride (5.88 g, 0.155 mol) in dry diethyl ether (300 ml) under an atmosphere of nitrogen at such a rate that the solution gently reflux. The reaction mixture was stirred over night before it was cooled to 0° C. and ethyl acetate (30 ml) was added drop wise to destroy excess lithium aluminum hydride. After stirring for another 0.5 hour, water (12 ml) was added drop wise. After stirring for 10–15 min the precipitate was filtered off through celite and the filter cage was washed with plenty of diethyl ether. The filtrate was washed with brine (100 ml), dried (MgSO$_4$), filtered and the solvent evaporated in vacuo, which afforded 30 g (95%) of the title compound as an oil.

4,4-Diethoxy-1-((S)-1-phenyl-ethyl)-(R)-2-phthalimidomethyl-piperidine

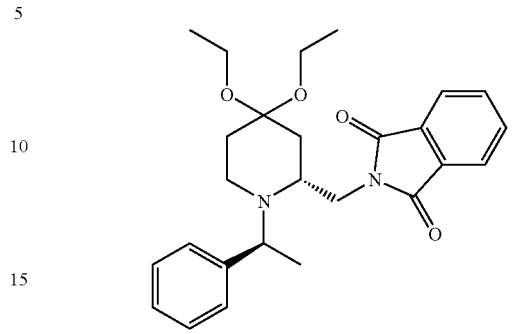

A solution of 4,4-Diethoxy-1-((S)1-phenyl-ethyl)-(R)-2-hydroxymethyl-piperidine (65.35 g, 0.213 mmol), triphenylphosphine (61.3 g, 0.234 mol) and phthalimide (34.4 g, 0.234 mol), in tetrahydrofuran (700 ml) cooled to 0° C. was added diethyl azodicarboxylate over the course of 1.5 hour. The reaction mixture was stirred at 0° C. for another 2 hours before the solvent was removed in vacuo. The residue was dissolved in hot heptane-toluene (3:2) (650 ml) before it was cooled on an ice bath. The precipitate consisting of triphenyl phosphine oxide was filtered off and washed with heptane. The filtrate was concentrated in vacuo and the residue subjected to column chromatography using a mixture of toluene-ethyl acetate-heptane (3:1:3) as eluent. The solvent was evaporated in vacuo whereupon a viscous oil was obtained. Upon addition of light petrol ether the product crystallized to give 67.4 g (73%) of the title compound as a solid.

Example 101

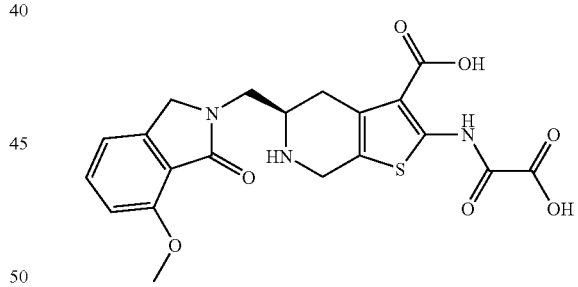

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid A mixture of 4,4-diethoxy-1-((S)-1-phenyl-ethyl)-(R)-2-phthalimidomethyl-piperidine (5.25 g, 12.0 mmol) and hydrazine hydrate (2.92 ml, 60 mmol) was stirred overnight in ethanol (100 ml) at room temperature. The solvent was removed in vacuo and the solid residue was extracted with refluxing diethyl ether. The diethyl ether fractions were combined and evaporated in vacuo, which afforded 3.94 g (94%) of 4,4-diethoxy-1-((S)-1-phenyl-ethyl)-(R)-2-aminomethyl-piperidine as an oil.

4,4-Diethoxy-1-((S)-1-phenyl-ethyl)-(R)-2-aminomethyl-piperidine (2.25 g, 7.37 mmol), and triethyl amine (1.49 g, 14.7 mmol) in acetonitrile (50 ml) was heated to 60° C. before 2-chlormethyl-6-methoxy-benzoic acid methyl ester (1.58 g, 7.37 mmol) in acetonitrile (25 ml) was added over the course of 1.5 hour. After addition the reaction mixture was stirred overnight at 60° C. The solvent was removed in vacuo and the residue was dissolved in dichloromethane (50 ml) and washed with saturated sodium bicarbonate. After drying (MgSO$_4$), filtration and evaporation of the solvent in vacuo the residue was subjected to flash column chromatography (SiO$_2$, ethyl acetate-light petrol ether (1:1)) to give 2.3 g (69%) of 2-(R)-(7-methoxy-2,3-dihydro-isoindol-1-one-2-ylmethyl)-4,4-diethoxy-1-(1-(S)-phenyl-ethyl)-piperidine.

2-(R)-(7-Methoxy-2,3-dihydro-isoindol-1-one-2-ylmethyl)-4,4-diethoxy-1 (1-(S)-phenyl-ethyl)-piperidine (2.0 g, 4.4 mmol) was dissolved in a ice cold mixture of trifluoroacetic acid and water (10 ml, 9:1) and stirred or 0.5 hour on an ice bath. The reaction mixture was poured on aqueous sodium carbonate (100 ml) and extracted with dichloromethane (2×50 ml). The organic phase was dried (MgSO$_4$), filtered and evaporated in vacuo, affording 1.67 g (100%) of 2-(R)-(7-methoxy-2,3-dihydro-isoindol-1-one-2-ylmethyl)-4-oxo-1 (1-(S)-phenyl-ethyl)-piperidine.

2-(R)-(7-Methoxy-2,3-dihydro-isoindol-1-one-2-ylmethyl)-4-oxo-1 (1-(S)-phenyl-ethyl)-piperidine (1.67 g, 4.41 mmol), sulphur (0.155 g, 4.85 mmol), tert-butylcyanoacetate (0.684 g, 4.85 mmol), N-methylmorpholine (0.892 g, 8.82 mmol) and molecular sieves (4 Å, 2 g) was heated to 50° C. in ethanol under an atmosphere of nitrogen for 16 hours. The reaction mixture was filtered through a plug (1 cm) of SiO$_2$, the silica was washed with dichloromethane-ethyl acetate and the solvent was removed in vacuo. The resulting residue was subjected to column chromatography (Flash 40, SiO$_2$, toluene-ethyl acetate (3:1)). Which yielded 1.17 g (50%) of 2-amino-5-(R)-(7-methoxy-1-oxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester and 2-amino-7-(S)-(7-methoxy-1-oxo-1,3-dihydro-isoindol-2-ylmethyl)-6-(1-(S)-phenyl-ethyl)-4,5,6,7-tetrahydrothieno[2,3-c]pyridine-3-carboxylic acid tert-butyl ester as a 3:1 mixture.

The above mixture of 5- and 7-regioisomers (1.17 g, 2.19 mmol) and imidazol-2-yl-oxo-acetic acid tert-butyl ester (1.29 g, 7.57 mmol) and triethylamine (0.66 g, 6.57 mmol) was stirred under an atmosphere of nitrogen in dichloromethane (25 ml) for 16 hours. The solvent was removed in vacuo and the residue was subjected to column chromatography (SiO$_2$, Flash 40, ethyl acetate-petrol ether (1:1)).

Collection of relevant fractions gave 0.61 g (42%) of 2-(tert-butoxyoxalyl-amin)-5-(R)-(7-methoxy-1-oxo-1,3-dihydro-isoindo-2-ylmethyl)-6-(1-(S)-phenyl-ethyl-ethyl)-4,5,6,7-tetrahydro-thieno[2,3-c]pyridine-3-carboxylic acid tert-butyl ester.

2-(tert-Butoxyoxalyl-amin)-5-(R)-(7-methoxy-1-oxo-1,3-dihydro-isoindo-2-ylmethyl)-6-(1-(S)-phenyl-ethyl-ethyl)-4,5,6,7-tetrahydro-thieno[2,3-c]pyridine-3-carboxylic acid tert-butyl ester (0.60 g, 0.91 mmol) was stirred for 16 hours in a mixture of methanol and formic acid (10:1) (20 ml) in the presence of 10% palladium on carbon (50% water). The reaction mixture was filtered through a plug of Celite and washed with methanol. The volatiles were removed in vacuo and the residue was dissolved in dichloromethane (50 ml), washed with semi saturated aqueous sodium carbonate (50 ml), dried (MgSO$_4$), filtered and the solvent evaporated in vacuo. The residue was purified by column chromatography (SiO$_2$, Flash 40, ethyl acetate-methanol (100:15)), which afforded 0.36 g (71%) of 2-(tert-butoxyoxalyl-amin)-5-(R)-(7-methoxy-1-oxo-1,3-dihydro-isoindo-2-ylmethyl)-4,5,6,7-tetrahydro-thieno[2,3-c]pyridine-3-carboxylic acid tert-butyl ester.

2-(tert-Butoxyoxalyl-amin)-5-(R)-(7-methoxy-1-oxo-1,3-dihydro-isoindo-2-ylmethyl)-4,5,6,7-tetrahydro-thieno[2,3-c]pyridine-3-carboxylic acid tert-butyl ester (349 mg, 0.63 mmol) was stirred for 16 hours in a mixture of trifluoroacetic acid and dichloromethane (1:1) (10 ml) whereupon diethyl ether (20 ml) was added. The precipitate was filtered off and washed with diethyl ether, which afforded 215 mg (61%) of the title compound as a solid trifluoroacetate.

LC-MS: R$_f$=1.17 min, m/z: 446 [M+H]$^+$

Calculated for C$_{20}$H$_{19}$N$_3$O$_7$S, C$_2$HF$_3$O$_2$, 0.5×H$_2$O C, 46.48%; H, 3.72%; N, 7.39%; Found: C, 46.45%; H, 3.97%; N, 7.43%;

Example 102

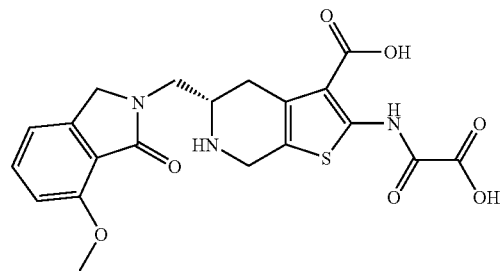

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid A solution of 4,4-diethoxy-1-((S)-1-phenyl-ethyl)-piperidine-(S)-2-carboxylic acid ethyl ester (35.98 g, 0.103 mol) in diethyl ether (150 ml) was added drop wise to a suspension of lithium aluminum hydride (5.88 g, 0.155 mol) in diethyl ether (300 ml) over the course of 1 hour. The reaction mixture was stirred at room temperature overnight before it was cooled on an ice bath and the reaction was quenched by dropwise addition of ethyl acetate (30 ml), followed by drop wise addition of water (12 ml) whereupon a gray precipitate was formed. The mixture was filtered through a plug of Celite and the filter cage was washed with plenty of diethyl ether. The filtrate was dried (MgSO$_4$) before it was filtered and the solvent removed in vacuo, which afforded 24.5 g (79%) of 4,4-diethoxy-1-(1-(S)-phenyl-ethyl)-(S)-2-hydroxymethyl-piperidine as an oil.

A suspension of 4,4-diethoxy-1-(1-(S)-phenyl-ethyl)-(S)-2-hydroxymethyl-piperidine (20 g, 65 mmol), triphenylphosphine (18.76 g, 72 mmol) and phthalimide (10.52 g, 72 mmol) in tetrahydrofurane (200 ml) cooled to 0° C. was added diethyl azodicarboxylate (11.34 ml, 72 mmol) over the course of 1 hour. The reaction mixture was stirred at 0° C. for another 2 hours before the volatiles were removed in vacuo. The residue was dissolve in hot heptane-toluene (3:2) (100 ml) before it was cooled on an ice bath. The precipitate was filtered off and washed with heptane. The filtrate was concentrated in vacuo and the residue subjected to column chromatography using a mixture of toluene/ethyl acetate/heptane (3:1:3) as eluent. The solvent was evaporated in vacuo and the residue was crystallized by addition of light petrol ether (250 ml). The precipitate was filtered off, which afforded 24 g (85%) of 4,4-diethoxy-1-(1-(S)-phenyl-ethyl)-2-(S)-phthalimidomethyl-piperidine as a solid.

4,4-Diethoxy-1-(1-(S)-phenyl-ethyl)-2-(S)-phthalimidomethyl-piperidine (4.0 g, 9.2 mmol) was dissolved in a mixture of trifluoroacetic acid and water (9:1) (100 ml) at 0° C. and stirred for 2 hours at this temperature. The mixture was basified with half saturated aqueous sodium carbonate, extracted with ethyl acetate and dried (MgSO$_4$) for 2 hours. The solvent was removed in vacuo and the residue was dried in a vacuum own at 40° C. for to days. This afforded 3.23 g (98%) of 4-oxo-1-(1-(S)-phenyl-ethyl)-2-(S)-phthalimidomethyl-piperidine pure without further purification (98%). A mixture of 4-oxo-1-(1-(S)-phenyl-ethyl)-2-(S)-phthalimidomethyl-piperidine (17.28 g, 47.73 mmol), tert-butylcyanoacetat (7.41 g, 52.17 mmol), sulphur (1.71 g, 52.17 mmol) and morpholine (8.31 g, 95.46 mmol) in ethanol (150 ml) was heated under an atmosphere of nitrogen at 50° C. The volatiles were removed in vacuo and the residue was subjected to column chromatography on silica gel (heptane-ethyl acetate 5:1). The fractions consisting of a mixture of 5- and 7-isomer were collected and the solvent evaporated in vacuo. The residue was purified on a reverse phase (C$_{18}$) column using a Flash 40 system. The residue was applied in a minimum volume of acetonitrile and eluted with 40% acetonitrile in water containing 0.1% trifluoroacetic acid. When the 5-isomer was collected the eluent was changed to 50% acetonitrile in water with 0.1% trifluoroacetic acid and the 7-isomer was collected. Yield of 2-amino-5-(S)-(1,3-dioxo-1,3-dihydro-isoindol-2-ylmethyl)-6-(1-(S)-phenyl-ethyl)-4, 5, 6, 7-tetrahydro-thieno[2,3-c]pyridine-3-carboxylic acid tert-butyl ester was 7.96 g and yield of 2-amino-7-(R)-(1,3-dioxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester was 3.72 g (47% total).

2-Amino-5-(S)-(1,3-dioxo-1,3-dihydro-isoindol-2-ylmethyl)-6-(1-(S)-phenyl-ethyl)-4,5,6,7-tetrahydro-thieno[2,3-c]pyridine-3-carboxylic-acid tert-butyl ester (7.96 g, 15.4 mmol) and hydrazine hydrate (3.85 g, 77.0 mmol) in ethanol (250 ml) was stirred for 16 hours at room temperature. The solvent was removed in vacuo and the solid residue was extracted with diethyl ether (3×200 ml). The fractions were combined and the solvent removed in vacuo to give 5.9 g (100%) of 2-amino-5-(S)-aminomethyl-6-(1-(S)-phenyl-ethyl)-4,5,6,7-tetrahydrothieno[2,3-c]pyridine-3-carboxylic acid tert-butyl ester.

2-Amino-5-(S)-aminomethyl-6-(1-(S)-phenyl-ethyl)-4,5,6,7-tetrahydro-thieno[2,3-c]pyridine-3-carboxylic acid tert-butyl ester (0.55 g, 1.42 mmol) and triethylamine (396 µl, 2.84 mmol) was heated in acetonitrile (15 ml) under an atmosphere of nitrogen to 60° C. whereupon a solution of 2-chloromethyl-6-methoxy-benzoic acid methyl ester (0.32 g, 1.49 mmol) in acetonitrile (5 ml) was added dropwise over the course of 3 hours, keeping the reaction mixture at 60° C. The reaction was allowed to cool to room temperature and was left for 16 hours before the solvent was evaporated in vacuo. The product was purified by column chromatography (SiO$_2$, Flash 40, ethyl acetate-petrol ether) to give 400 mg (53%) of 2-amino-5-(S)-(7-methoxy-1-oxo-1,3-dihydro-isoindol-2-ylmethyl)-6-((S)-1-phenyl-ethyl)-4,5,6,7-tetrahydro-thieno[2,3-c]pyridine-3-carboxylic acid tert-butyl ester as an oil.

The title compound was obtained as a trifluoroacetate in a similar way as described in example 101 using the last three steps.

Example 103

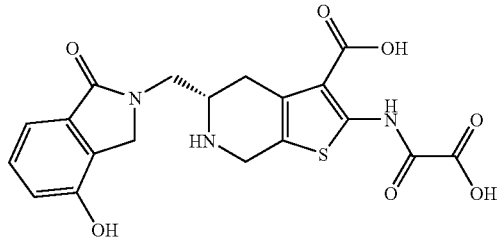

5-(S)-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic-acid 3-Hydroxy-2-methylbenzoic acid (0.5 g, 3.2 mmol) was dissolved in HPLC grade methanol (5 ml) and cooled to 0° C. under nitrogen. Acetyl chloride (5 ml) was added dropwise. Once the addition was complete, the ice bath was removed and the reaction mixture allowed warming to room temperature over a period of 18 hours. The reaction was complete by tlc (R$_f$=0.5, 1:1 ethyl acetate/hexanes) and quenched with saturated sodium bicarbonate. The reaction mixture was concentrated, diluted with dichloromethane and water and the layers separated. The aqueous layer was extracted with dichloromethane (3×). The organic layers were combined, dried (MgSO$_4$), filtered and concentrated in vacuo, which afforded 0.5 g (91%) of 3-hydroxy-2-methylbenzoic acid methyl ester as a solid.

$^1$H-NMR (CDCl$_3$) δ 7.39 (dd, 1H, J=8.1 Hz and J=1.5 Hz), 7.09 (t, 1H, J=8.1 Hz), 6.92 (dd, 1H, J=8.1 Hz and J=1.2 Hz), 5.11 (bs, 1H), 3.87 (s, 3H), 2.43 (s, 3H).

3-Hydroxy-2-methylbenzoic acid methyl ester (0.5 g, 3.01 mmol) in dichloromethane (15 ml) and N,N-diisopropylethylamine (1.57 ml, 9.03 mmol) was cooled to 0° C. under nitrogen. Chloromethyl methyl ether (0.46 ml, 6.02 mmol) was added dropwise and the reaction allowed warming to room temperature over a period of 18 hours. The reaction was judged to be 50% complete by tlc (1:2 ethyl acetate/hexanes, 12) and therefore, N,N-diisopropylethylamine (1.57 ml, 9.03 mmol) was added, the reaction mixture cooled to 0° C. and chloromethyl methyl ether (0.46 ml, 6.02 mmol) added once more. The reaction mixture was warmed to room temperature and stirred for 5 hours. The reaction was quenched with water and the layers separated. The aqueous layer was extracted once with dichloromethane and the organic layers combined, dried (MgSO$_4$), filtered, and concentrated in vacuo. The crude residue was purified by column chromatography (20% ethyl acetate/hexanes) affording 0.44 g (69%) of 3-methoxymethoxy-2-methyl-benzoic acid methyl ester as an oil.

$^1$H-NMR (CDCl$_3$) δ 7.46 (dd, 1H, J=7.6 Hz and J=1.2 Hz), 7.21 (dd, 1H, J=8 Hz and J=1.2 Hz), 7.18 (d, 1H, J=8 Hz), 5.21 (s, 2H), 3.88 (s, 3H), 3.48 (s, 3H), 2.46 (s, 3H).

To a mixture of 3-methoxymethoxy-2-methyl-benzoic acid methyl ester (0.44 g, 2.09 mmol) in carbon tetrachloride (10 ml) was added N-bromosuccinimide (0.39 g, 2.19 mmol) and 1,1'-azo bis(cyclohexane-carbonitrile) (0.051 g, 0.21 mmol). The mixture was heated at reflux for 3 hours, at which time the reaction was judged complete by tlc (1:4 ethyl acetate/hexanes). The reaction mixture was cooled to room temperature and concentrated in vacuo to a solid. The solid was recrystallized from hexane leaving 0.44 g (82%) of 2-bromomethyl-3-methoxymethoxy-benzoic acid methyl ester as a solid.

$^1$H-NMR (CDCl$_3$) δ 7.58 (dd, 1H, J=6.8 Hz and J=2.4 Hz), 7.33–7.29 (m, 2H), 5.30 (s, 2H), 5.07 (s, 2H), 3.94 (s, 3H), 3.52 (s, 3H).

To a stirred mixture of 2-amino-5-(S)-aminomethyl-6-(1-(S)-phenyl-ethyl)-4,5,6,7-tetrahydro-thieno[2,3-c]pyridine-3-carboxylic acid tert-butyl ester (0.24 g, 0.67 mmol) in acetonitrile (30 ml) was added N,N-diisopropylethylamine (0.16 ml, 0.93 mmol) under nitrogen. 2-Bromo-methyl-3-methoxymethoxy-benzoic acid methyl ester (0.16 g, 0.55 mmol) dissolved in acetonitrile, was added via syringe pump at a rate of 0.3 ml/hour. Once the addition was complete, the reaction mixture was stirred at room temperature for 24 hours. Tlc analysis (1:1 ethyl acetate/hexanes) indicated the reaction to be complete. The volatiles were removed in vacuo and the resultant oil dissolved in ethyl acetate/water. The layers were separated and the aqueous layer extracted with ethyl acetate (3×). The organic layers were combined, dried (MgSO$_4$), filtered and the solvebt evaporated in vacuo, which afforded 0.34 g (100%) of 2-amino-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester, which was used without further purification in the next step.

$^1$H-NMR (CDCl$_3$) δ 7.51 (d, 1H, J=6.8 Hz), 7.42 (t, 2H, J=7.6 Hz, 7.23–7.17 (m, 5H), 5.93 (s, 2H), 5.25 (s, 2H), 4.23 (s, 2H), 4.12 (q, 1H, J=7.2 Hz), 3.94 (m, 1H), 3.85 (q, 1H, J=6.4 Hz), 3.66 (d, 1H, J=16.4 Hz), 3.50 (s, 3H), 3.48–3.46 (m, 1H), 3.20 (dd, 1H, J=14 Hz and J=6 Hz), 2.94–2.87 (m, 1H), 2.60 (m, 1H), 1.49 (s, 9H), 1.36 (d, 3H, J=6.4 Hz);

LC-MS: m/z: 564.1 [M+H]$^+$.

To a solution of 2-amino-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester (0.34 g, 0.60 mmol) in dichloromethane (10 ml) was added imidazol-1-yl-oxo-acetic acid tert-butyl ester (0.35 g, 1.8 mmol). The reaction mixture was stirred at room temperature for 18 hours and the solvent concentrated in vacuo. The residue was dissolved in ethyl acetate and washed with water (2×20 ml) and brine (2×25 ml). The organic layer was dried (MgSO$_4$), filtered and the solvent evaporated in vacuo. The residue was subjected to flash chromatography using a mixture of ethyl acetate/hexanes (1:1) as eluent. The obtained residue was then subjected to chromatotron purification (1% methanol/dichloromethane) and later to another flash chromatography (20% ethyl acetate/hexanes to 25% ethyl acetate/hexanes) to obtain 210 mg (50%) of 2-(tert-butoxyoxalyl-amino)-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester as an oil.

$^1$H-NMR (CDCl$_3$) δ 12.50 (s, 1H), 7.51 (dd, 1H, J=6.8 Hz and J=1.2 Hz), 7.42 (t, 2H, J=8 Hz), 7.25–7.17 (m, 5H), 5.23 (s, 2H), 4.24 (q, 2H, J=16.8 Hz), 4.08 (d, 1H, J=16.8 Hz), 4.01 (dd, 1H, J=14 Hz and J=8.8 Hz), 3.89 (d, 1H, J=17.6 Hz), 3.82 (q, 1H, J=6.8 Hz), 3.56 (q, 1H, J=6.4 Hz), 3.51 (s, 3H), 2.28 (dd, 1H, J=14 Hz and J=6.4), 2.98–2.92 (m, 1H), 2.69 (d, 1H, J=17.2), 1.56 (s, 9H), 1.54 (s, 9H), 1.38 (d, 3H, J=6.8 Hz);

LC-MS: m/z: 692.5 [M+H]$^+$.

To a solution of 2-(tert-butoxyoxalyl-amino)-5-(S)-(4-methoxymethoxy-1-oxo-1,3-dihydro-isoindol-2-ylmethyl)-6-(1-(S)-phenyl-ethyl)-4,5,6,7-tetrahydro-thieno[2,3-c]pyridine-3-carboxylic acid tert-butyl ester (0.16 g, 0.23 mmol) in formic acid (10% in methanol, 5 ml total) was added 10% palladium on carbon (85 mg, source: Avacado) and the reaction mixture allowed to stir at room temperature. After 6 hours, tlc (1:1 ethyl acetate/hexanes) analysis indicated reaction complete. The reaction mixture was filtered through a pad of celite and concentrated in vacuo. The crude product was purified via flash chromatography (gradient: 3% isopropyl alcohol/dichloromethane to 5% isopropyl alcohol/dichloromethane (in 1% increments of isopropyl alcohol)) to provide 0.11 g (82%) of 2-(tert-butoxyoxalyl-amino)-5-(S)-(4-methoxymethoxy-1-oxo-1,3-dihydro-isoindol-2-ylm-ethyl)-4,5,6,7-tetrahydro-thieno[2,3-c]pyridine-3-carboxylic acid tert-butyl ester as an oil.

$^1$H-NMR (CDCl$_3$) δ 12.50 (bs, 1H), 7.48 (dd, 1H, J=7.6 Hz and J=0.8 Hz), 7.38 (t, 1H, J=8 Hz), 7.22 (dd, 1H, J=8 Hz and J=0.8 Hz); 5.24 (s, 2H), 4.50 (q, 2H, J=17.3 Hz), 4.02–3.90 (m, 2H), 3.74 (ddd, 2H, J=34 Hz, J=13.6 Hz and J=5.6 Hz), 3.49 (s, 3H), 3.24 (m, 1H), 2.97 (ddd, 1H, J=20 Hz, J=4.4 Hz and J=2.8 Hz), 2.50 (m, 1H), 1.59 (s, 9H), 1.51 (s, 9H);

LC-MS: m/z: 587.8 [M+H]$^+$.

2-(tert-Butoxyoxalyl-amino)-5-(S)-(4-methoxymethoxy-1-oxo-1,3-dihydro-isoindol-2-ylmethyl)-4,5,6,7-tetrahydro-thieno[2,3-c]pyridine-3-carboxylic acid tert-butyl ester (0.11 g, 0.18 mmol) was dissolved in neat trifluoroacetic acid (4 ml) and stirred at room temperature for 48 hours. The reaction mixture was concentrated in vacuo and the resultant solid washed with dichloromethane several times affording 100 mg (83%) of the title compound as a solid trifluoroaceatet.

$^1$H-NMR (DMSO-d$_6$) δ 12.29 (bs, 1H), 10.13 (s, 1H), 9.29 (bs, 1H), 9.10 (bs, 1H), 7.32 (t, 1H, J=7.6 Hz), 7.17 (d, 1H, J=7.2 Hz), 7.01 (d, 1H, J=8 Hz), 4.52 (d, 1H, J=17.2 Hz), 4.40–4.22 (m, 3H), 4.05 (dd, 1H, J=14.4 Hz and J=9.6 Hz), 3.90 (bs, 1H), 3.69 (dm, 1H), 3.22 (dm, 1H), 2.80 (dm, LC-MS: m/z: 432.2 [M+H]$^+$.

Example 104

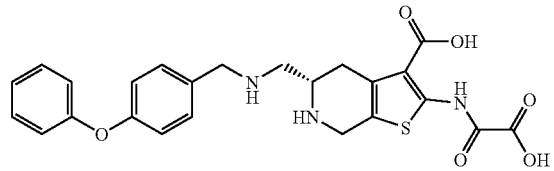

2-(S)-(Oxalyl-amino)-5-((4-phenoxy-benzylamino)methyl)-4,5,6,7-tetrahydro-thieno[2,3-c]pyridine-3-carboxylic acid A solution of 2-amino-5-(S)-aminomethyl-6-(1-(S)-phenyl-ethyl)-4,5,6,7-tetrahydro-thieno[2,3-c]pyridine-3-carboxylic acid tert-butyl ester (500 mg, 1.29 mmol) and 4-phenoxybenzaldehyde (256 mg, 1.29 mmol) was heated to 50° C. in ethanol (50 ml) for 1 hour in the presence of molecular sieves (4 A, 5 ml). The reaction mixture was cooled on an ice bath before sodium borohydride (98 mg, 2.59 mmol) was added in three portions over 45 min. The cooling bath was removed and the reaction mixture was allowed to reach room temperature. The mixture was filtered through a plug of Celite and the filter cage was washed with dichloromethane 3×25 ml). The solvent was removed in vacuo and the residue was redissolved in ethyl acetate (50 ml), washed with sodium bicarbonate (50 ml) and dried (MgSO$_4$). The solvent was removed in vacuo before the residue was redissolved in acetonitrile (20 ml). Triethylamine (130 mg, 1.29 mmol), di-tert-butyl dicarbonate (282 mg, 1.29 mmol) and 4-(N,N-dimethyl-amino)pyridine (5 mg, cat.) was added and the reaction mixture was stirred for 16 hours at room temperature. The volatiles were removed in vacuo and ethyl acetate (50 ml) was added and the solution was washed with saturated sodium bicarbonate (50 ml) and dried (MgSO$_4$). The crude product was purified by column chromatography (SiO$_2$, petroleum ether-ethyl acetate (9:1)) to give 325 mg (38% overall) of 2-amino-5-

(S)-((4-phenoxy-benzylamino)methyl)-6-(1-(S)-phenyl-ethyl)-4,5,6,7-tetrahydro-thieno[2,3-c]pyridine-3-carboxylic acid tert-butyl ester.

The title compound was obtained as a trifluoroacetate in a similar way as described in example 96 using the last three steps.

Oxalation: Standard procedure (16 hours, 82%)
Hydrogenolysis: standard procedure (Pd/C, 10% Pd, methanol-formic acid, 16 hours, ((10:1)) (82% yield)
TFA cleavage: Standard procedure. Yield 150 mg (87%).
LC-MS m/z: 482 [M+H]$^+$, R$_t$=1.87 min
Calculated for C$_{24}$H$_{23}$N$_3$O$_6$S, 2×(C$_2$HF$_3$O$_2$) C, 47.40%; H, 3.55%; N, 5.92%; Found: C, 47.47%; H, 3.87%; N, 5.88%.

Example 105

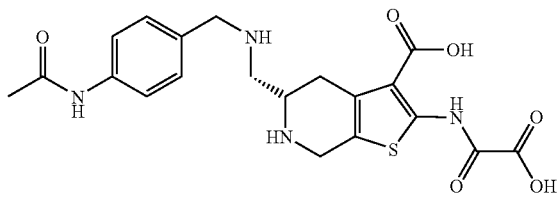

5-(S)-((4-Acetylamino-benzylamino)-methyl)-2-(oxalyl-amino)-4,5,6,7-tetrahydro-thieno[2,3-c]pyridine-3-carboxylic acid The title compound was prepared as a trifluoroacetate in a similar way as described in Example 96 using 2-amino-5-(S)-aminomethyl-6-(1-(S)-phenyl-ethyl)-4,5,6,7-tetrahydro-thieno[2,3-c]pyridine-3-carboxylic acid tert-butyl ester and N-(4-formyl-phenyl)acetamide as the starting material.
Calculated for C$_{20}$H$_{22}$N$_4$O$_6$S, 1.5×C$_2$HF$_3$O$_2$, 1.5×H$_2$O C, 43.78%; H, 3.99%; N, 8.88%; Found: C, 44.20%; H, 4.43%; N, 8.75%.

Example 106

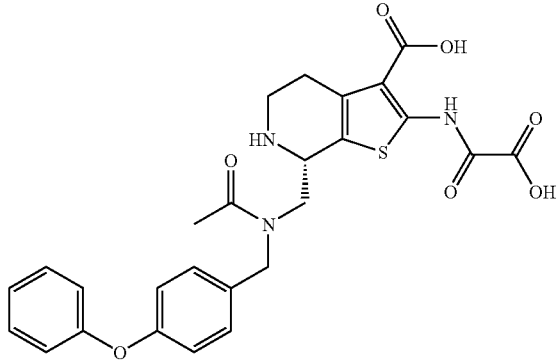

7-(S)-((Acetyl-(4-phenoxy-benzyl)amino)methyl)-2-(oxalyl-amino)-4,5,6,7-tetrahydro-thieno[2,3-c]pyridine-3-carboxylic acid A solution of 2-amino-7-(S)-aminomethyl-6-(1-(S)-phenyl-ethyl)-4,5,6,7-tetrahydro-thieno[2,3-c]pyridine-3-carboxylic aicd tert-butyl ester (500 mg, 1.29 mmol) and 4-phenoxybenzaldehyde (256 mg, 1.29 mmol) was heated to 50° C. in ethanol (50 ml) for 1 hour in the presence of molecular sieves (4 A, 5 ml). The reaction mixture was cooled on an ice bath before sodium borohydride (98 mg, 2.59 mmol) was added in three portions over 45 min. The cooling bath was removed and the reaction mixture was allowed to reach room temperature. The mixture was filtered through a plug of Celite and the filter cage was washed with dichloromethane (3×25 ml). The solvent was removed in vacuo and the residue was redissolved in ethyl acetate (50 ml), washed with sodium bicarbonate (50 ml) and dried (MgSO$_4$). The solvent was removed in vacuo before the product was dissolved in dichloromethane (10 ml). The solution was cooled on an ice bath before di-isopropyl-ethyl amine (101 mg, 1.29 mmol) was added followed by drop wise addition of acetyl chloride (101 mg, 1.29 mmol) in dichloromethane (1 ml). The reaction mixture was stirred 1 hour at 0° C. and the solution was washed with sodium bicarbonate (10 ml) and dried (MgSO$_4$). The crude product was purified by flash column chromatography (SiO$_2$, ethyl acetate-petrol ether 1:3) to give 320 mg (41%) of 7-(S)-((acetyl-(4-phenoxy-benzyl)amino)methyl)-2-amino-6-(1-(S)-phenyl-ethyl)-4,5,6,7-tetrahydro-thieno[2,3-c]pyridine-3-carboxylic acid The title compound was obtained as a trifluoroacetate in a similar way as described in example 96 using the last three steps.

Oxalation: Standard procedure (Yield 69%)
Hydrogenolysis and trifluoroacetic acid cleavage in one step, Standard procedure (Overall yield 6%)
LC-MS m/z=524 [M+H]$^+$, R$_t$=2.58 min
Calculated for C$_{26}$H$_{25}$N$_3$O$_7$S, C$_2$HF$_3$O$_2$, 0.5×H$_2$O C, 52.01%; H, 4.21%; N, 6.50%; Found: C, 51.82%; H, 4.34%; N, 6.36%.

Example 107

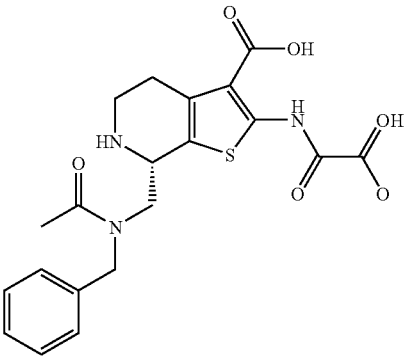

7-(S)-((Acetyl-benzyl-amino)methyl)-2-(oxalyl-amino)-4,5,6,7-tetrahydro-thieno[2,3-c]pyridine-3-carboxylic acid A solution of 2-amino-7-(S)-aminomethyl-6-(1-(S)-phenyl-ethyl)-4,5,6,7-tetrahydro-thieno[2,3-c]pyridine-3-carboxylic aicd tert-butyl ester (400 mg, 1.03 mmol) and benzaldehyde (105 mg, 1.03 mmol) was heated to 50° C. in ethanol (20 ml) for 1 hour in the presence of molecular sieves (4 A, 7 ml). The reaction mixture was cooled on an ice bath before sodium borohydride (78 mg, 2.06 mmol) was added in three portions over 45 min. The cooling bath was removed and the reaction mixture was allowed to reach room temperature. The mixture was filtered through a plug of Celite and the filter cage was washed with dichloromethane (3×25 ml). The solvent was removed in vacuo and the residue was redissolved in ethyl acetate (50 ml), washed with sodium bicarbonate (50 ml) and dried (MgSO$_4$). The solvent was removed in vacuo before the product was dissolved in dichloromethane (20 ml). The solution was cooled on an ice bath before di-isopropyl-ethyl amine (267 mg, 2.06 mmol) was added followed by drop wise addition of acetyl chloride (81 mg, 1.03 mmol) in dichloromethane (1 ml). The reaction mixture was stirred 1 hour at 0° C. before sodium bicarbonate (20 ml) was added. The mixture was extracted with dichloromethane (2×10 ml) and the combined organic fractions were dried (MgSO$_4$). The crude product was purified by flash column chromatography (petrol ether/ethyl acetate (3:1)), which afforded 250 mg (46%) of 7-(S)-((acetyl-benzyl-amino)methyl)-2-amino-6-(1-(S)-phenyl-ethyl)-4,5,6,7-tetrahydro-thieno[2,3-c]pyridine-3-carboxylic acid tert-butyl ester.

The title compound was obtained as a trifluoroacetate in a similar way as described in example 96 using the last three steps.

Oxalation: Standard procedure (54%)
Hydrogenolysis: Standard procedure (methanol-formic acid (10:1)) Yield 38 mg (26%)
Trifluoroacetic acid cleavage: Standard procedure 33 mg (80%)
LC-MS m/z: 432 [M+H]$^+$, R$_f$=1.52 min
Calculated for $C_{20}H_{21}N_3O_6S \times 1.5 \times C_2HF_3O_2$, $2 \times H_2O$ C, 43.26%; H, 4.18%; N, 6.58%; Found: C, 43.19%; H, 3.86%; N, 6.46%.

Example 108

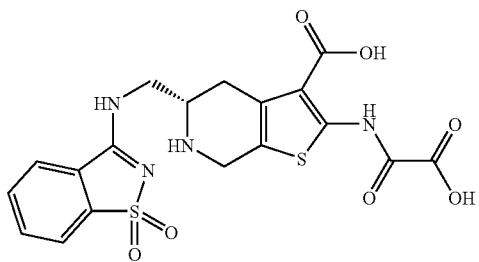

5-(S)-((1-Dioxo-1H-benzo[d]isothiazol-3-ylamino) methyl)-2-(oxalyl-amino)-4,5,6,7-tetrahydro-thieno [2,3-c]pyridine-3-carboxylic acid To a solution of (S)-2-amino-5-aminomethyl-6-(1-(S)-phenyl-ethyl)-4,5,6,7-tetrahydro-thieno[2,3-c]pyridine-3-carboxylic acid tert-butyl ester (1.0 g, 2.58 mmol) in dichloromethane (10 ml) at 0° C. was added N,N-diisopropylethylamine (0.54 ml, 5.16 mmol). A solution of 3-chloro-benzo[d]isothiazole 1,1-dioxide (0.52 g, 2.58 mmol) in dichloromethane (10 ml) was then added dropwise and stirred for 30 min. The solution was warmed to room temperature and washed with water and dried (MgSO$_4$). The solvent was then removed in vacuo. The residue was taken into dichloromethane (15 ml) and imidazol-1-yl-oxo-acetic acid tert-butyl ester (1.0 g, 5.16 mmol) was added. The solution was stirred for 2 hours. The solvent was removed in vacuo. The residue was taken into ethyl acetate (100 ml). The solution was washed with 0.5 N hydrochloric acid solution, saturated sodium bicarbonate and brine, dried (MgSO$_4$) and filtered. The solvent was removed in vacuo. The residue was chromatographed using a mixture of 0–5% ethyl acetate/dichloromethane as eluent, which afforded 0.6 g (34%) of 2-(tert-butoxyoxalyl-amino)-5-(S)-((1,1-dioxo-1H-benzo[d]isothiazol-3-ylamino)methyl)-6-(1-(S)-phenyl-ethyl)-4,5,6,7-tetrahydro-thieno[2,3-c]pyridine-3-carboxylic acid tert-butyl ester as an oil $^1$H-NMR (CDCl$_3$) δ 12.50 (s, 1H), 7.94–7.92 (m, 1H), 7.79–7.71 (m, 2H), 7.59–7.50 (m, 2H), 7.38–7.27 (m, 4H), 6.86 (d, 1H, J=4 Hz), 4.14 (d, 1H, J=12 Hz), 3.95 (d, 1H, J=17 Hz), 3.88 (q, 1H, J=6 Hz), 3.70–3.62 (m, 1H), 3.47 (t, 1H, J=13 Hz), 3.34–3.24 (m, 1H), 3.06 (dd, 1H, J=17, 6 Hz), 2.53 (d, $^1$H, J=17 Hz), 1.62 (s, 9H), 1.61 (s, 9H), 1.44 (d, 3H, J=7 Hz).

A solution of 2-(tert-butoxyoxalyl-amino)-5-(S)-((1,1-dioxo-1H-benzo[d]isothiazol-3-ylamino)methyl)-6-(1-(S)-phenyl-ethyl)-4,5,6,7-tetrahydro-thieno[2,3-c]pyridine-3-carboxylic acid tert-butyl ester (252 mg, 0.37 mmol) in tetrahydrofuran (12 ml) was passed through Raney Ni (0.95 g, 50% Raney Ni-Water washed with methanol (6 ml) and tetrahydrofuran (10 ml) and dried before use). The solvent was removed in vacuo. The residue was dissolved in acetic acid (7 ml) and hydrogenated with 10% Pd/C (250 mg) at 50 psi for 15 hours. The mixture was filtered and the filtrate was added to saturated sodium bicarbonate solution. The solution was then extracted with ethylacetate (3×100 ml). The extracts were combined and dried (MgSO$_4$). The solvent was removed in vacuo. The residue was washed with diethyl ether affording 156 mg (73%) of 2-(tert-butoxyoxalyl-amino)-5-(S)-((1,1-dioxo-1H-benzo[d]isothiazol-3-ylamino)-methyl)-4,5,6,7-tetrahydro-thieno[2,3-c]pyridine-3-carboxylic acid tert-butyl ester as an oil.

$^1$H-NMR (CDCl$_3$) δ 12.59 (s, 1H), 7.94–7.90 (m, 1H), 7.70–7.66 (m, 3H), 7.51 (s, 1H), 4.11 (d, 1H, J=12 Hz), 4.08 (q, 2H, J=17 Hz), 3.40 (dd, 1H, J=12, 6 Hz), 3.26–3.18 (m, 1H), 3.18 (d, 1H, J=17 Hz), 2.55 (dd, 1H, J=12, 6 Hz), 1.62 (s, 18H).

LC-MS: R$_f$=3.58 min, m/z: 577 [M+H]$^+$.

A solution of 2-(tert-butoxyoxalyl-amino)-5-(S)-((1,1-dioxo-1H-benzo[d]isothiazol-3-ylamino)methyl)-4,5,6,7-tetrahydro-thieno[2,3-c]pyridine-3-carboxylic acid tert-butyl ester (149 mg, 0.26 mmol) in 50% trifluoroacetic acid/dichloromethane (1 ml) was left in an open flask for 60 hours. The volatiles were removed in vacuo and the residue was washed with dichloromethane to yield 80 mg (54%) of the title compound as a solid trifluoroacetate.

$^1$H-NMR (DMSO-d$_6$) δ 12.29 (s, 1H), 9.80 (s, 1H), 9.51 (bs, 2H), 8.19 (d, 1H, J=5 Hz), 8.02–8.00 (m, 1H), 7.89–7.84 (m, 2H), 4.46 (d, 1H, J=16 Hz), 4.30 (d, 1H, J=16 Hz), 3.96–3.80 (m, 3H), 3.30 (d, 1H, J=17 Hz), 2.93 (dd, 1H, J=18, 10 Hz);

LC-MS: R$_f$=0.68 min, m/z: 465[M+H]$^+$.

Example 109

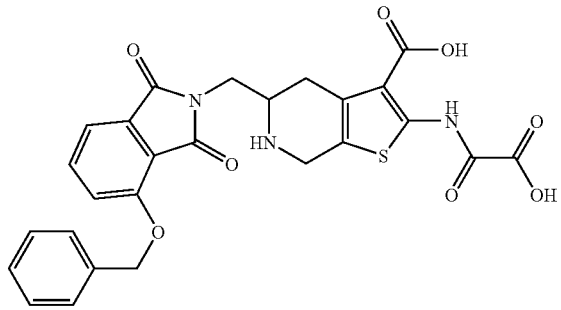

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid The title compound was prepared in a similar way as described in Example 52 as a trifluoroacetate.

$^1$H-NMR (400 MHz, DMSO-d$_6$) δ 12.31 (s, 1H), 9.25 (bs, 2H), 7.80 (t, 1H, J=8 Hz), 7.59–7.32 (m, 7H), 5.37 (s, 2H), 4.42–4.21 (m, 2H), 3.95–3.70 (m, 3H), 3.4–3.2 (obscured by water, 1H), 2.83–2.75 (m, 1H)

LC-MS: R$_f$=2.16 min, m/z: 536.1 [M+H]$^+$

Example 110

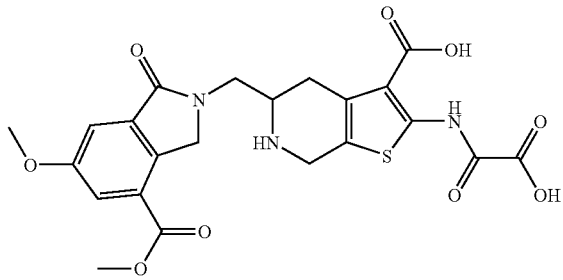

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid To a solution of 2-amino-5-aminomethyl-6-(4-methoxy-benzyl)-4,5,6,7-tetrahydro-thieno[2,3-c]pyridine-3-carboxylic acid tert-butyl ester (57.4 mg, 0.142 mmol) and diisopropyl ethylamine (49 µl, 0.28 mmol) in acetonitrile (20 ml) at room temperature was added 2-bromomethyl-5-methoxy-isophthalic acid dimethyl ester (3.00 g, 7.45 mmol). The solution was stirred for 16 hours and the solvent evaporated in vacuo. The residue was taken into ethyl acetate (50 ml) and washed with water (2×20 ml), 1 N hydrochloric acid (20 ml), brine, dried (MgSO$_4$), filtered and the solvent evaporated in vacuo. The residue was chromatographed on silica gel column using a mixture of ethyl acetate/hexane (1:1) as eluent, which afforded 62 mg (71%) of 2-amino-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR δ (CDCl$_3$): δ 7.75 (d, 1H, J=2.4 Hz), 7.55 (d, 1H, J=2.4 Hz), 7.11 (bs, 2H), 6.74 (d, 2H, J=8.0 Hz), 5.97 (s, 2H), 4.71 (d, 1H, J=18.4 Hz), 4.62 (d, 1H, J=18.4 Hz), 4.09 (m, 1H), 3.93 (s, 3H), 3.92 (s, 3H), 3.80 (m, 1H), 3.76 (s, 3H), 3.66–3.40 (m, 5H), 2.80 (d, 1H, J=17.2 Hz), 2.64 (d, 1H, J=17.2 Hz), 1.52 (s, 9H).

To a stirred solution of 2-amino-6-(4-methoxy-benzyl)-5-(6-methoxy-4-methoxy-carbonyl-1-oxo-1,3-dihydro-isoindol-2-ylmethyl)-4,5,6,7-tetrahydro-thieno[2,3-c]pyridine-3-carboxylic acid tert-butyl ester (60 mg, 0.10 mmol) in tetrahydrofuran (1.0 ml) was added imidazol-1-yl-oxo-acetic acid tert-butyl ester (60 mg, 0.30 mmol) in tetrahydrofuran (1.0 ml). The mixture was stirred at room temperature for 24 hours. The solvent was removed in vacuo. The residue was taken into ethyl acetate (20 ml) and washed with 0.5 N hydrochloric acid (2×10 ml), saturated sodium bicarbonate (2×10 ml) and brine (10 ml), dried (MgSO$_4$) and filtered. The solvent was removed in vacuo and residue was chromatographed using a gradient ethyl acetate/hexane (10–25%) as eluent, which afforded 40 mg (58%) of 2-(tert-butoxyoxalyl-amino)-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR δ (CDCl$_3$): δ 12.54 (s, 1H), 7.75 (d, 1H, J=2.4 Hz), 7.55 (d, 1H, J=2.4 Hz), 7.10 (d, 2H, J=8.0 Hz), 6.74 (d, 2H, J=8.0 Hz), 4.74 (d, 1H, J=18.4 Hz), 4.62 (d, 1H, J=18.4 Hz), 4.05–3.90 (m, 2H), 3.94 (s, 3H), 3.92 (s, 3H), 3.82–3.48 (m, 5H), 3.77 (s, 3H), 2.95 (dd, 1H, J=17.2 Hz and J=5.2 Hz), 2.67 (dd, 1H, J=17.2 Hz and J=5.2 Hz), 1.61 (s, 9H), 1.58 (s, 9H).

To a solution of 2-(tert-butoxyoxalyl-amino)-6-(4-methoxy-benzyl)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester (38 mg, 0.055 mmol) in 10% formic acid/methanol (1.0 ml) at room temperature under nitrogen was added 10% Pd/C (38 mg). The mixture was stirred for 16 hours and the Pd/C was filtered off and the filtrate evaporated in vacuo. The residue was taken into dichloromethane (1.0 ml) poured into hexane. The precipitate was filtered off, affording 28 mg (82%) of 2-(tert-butoxyoxalyl-amino)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester as a solid.

$^1$H-NMR δ (CDCl$_3$): δ 12.45 (s, 1H), 10.90 (s, 1H), 10.69 (s, H), 7.73 (s, 1H), 7.42 (s, 1H), 4.85 (bs, 2H), 4.65 (bs, 1H), 4.42 (bs, 2H), 3.99 (bs, 2H), 3.96 (s, 3H), 3.89 (s, 3H), 3.35 (bs, 1 Hz), 3.21 (bs, 1H), 1.62 (s, 9H), 1.56 (s, 9H).

To a solution of trifluoroacetic acid (0.5 ml) and dichloromethane (0.5 ml) was added 2-(tert-butoxyoxalyl-amino)-5-(6-methoxy-4-methoxycarbonyl-1-oxo-1,3-dihydro-isoindol-2-ylmethyl)-4,5,6,7-tetrahydro-thieno[2,3-c]pyridine-3-carboxylic acid tert-butyl ester (14 mg, 0.023 mmol). The solution was stirred at room temperature for 40 hours. The reaction mixture was poured into diethyl ether (20 ml). The precipitate was filtered off, which afforded 10 mg (75%) of the title compound as a solid trifluoroacetate.

$^1$H-NMR δ (DMSO-d$_6$): δ 12.28 (s, 1H), 9.32 (s, 1H), 9.10 (s, 1H), 7.65 (d, 1H, J=2.4 Hz), 7.50 (d, 1H, J=2.4 Hz), 4.82 (d, 1H, J=17.2 Hz), 4.65 (d, 1H, J=17.6 Hz), 4.40 (d, 1H, J=17.6 Hz), 4.30 (m, 1H), 4.10 (dd, 1H, J=17.2 Hz and J=5.2 Hz), 3.95 (s, 1H), 3.89 (s, 6H), 3.85 (d, 1H, J=17.2 Hz), 2.81 (dd, 1H, J=18 Hz and J=7.2. Hz).

LC-MS: R$_t$=1.30 min; m/z: 504 [M+H]$^+$

Example 111

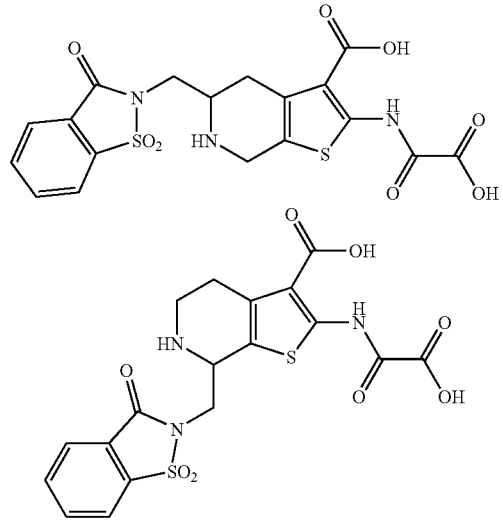

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid and 2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid To a solution of 2-aminomethyl-4-(2-spiro[1,3]dioxolane)-piperidine (193 mg, 1.12 mmol) and diisopropyl ethylamine (0.46 ml, 2.55 mmol) in acetonitrile (10 ml) cooled to 0° C. was added 2-chlorosulfonyl-benzoic acid methyl ester (278 mg. 1.18 mmol). The solution was stirred at 25° C. for 24 hours. Solvent was removed in vacuo and the residue was chromatographed using a mixture of ethyl acetate/hexane (1:3) as eluent, which afforded 199 mg (51%) of 2-(4-(2-spiro[1,3]dioxolane)piperidin-2-ylmethyl)-1,1-dioxo-1,2-dihydro-1H-benzo[d]isothiazol-3-one as a solid.

$^1$H-NMR (CDCl$_3$): δ 7.99–7.96 (m, 1H), 7.66–7.53 (m, 3H), 5.01 (s, 1H), 4.73 (dm, 1H, J=14.4 Hz), 4.06–3.93 (m, 6H), 3.25 (dd, 1H, J=12.6 Hz), 13.06 (td, 1H, J=13.5 Hz and J=3.6 Hz), 1.93 (dd, 1H, J=14.1 Hz and J=5.7 Hz), 1.87 (dd, 1H, J=14.1 Hz and J=3.0 Hz), 1.76 (dd, 1H, J=13.5 Hz and J=5.1 Hz).

LC-MS: R$_t$=1.78; m/z: 339 [M+H]$^+$.

2-(4-(2-Spiro[1,3]dioxolane)piperidin-2-ylmethyl)-1,1-dioxo-1,2-dihydro-1H-benzo[d]isothiazol-3-one (199 mg, 0.588 mmol) was dissolved in 2 M hydrochloric acid (12 ml) and the solution was heated to 50° C. for 24 hours. The volatiles were removed in vacuo and the residue (341 mg) was treated without further purification with saturated sodium carbonate (12 ml), dichloromethane (8 ml) and di-t-butyl-dicarbonate (1.64 g, 7.5 mmol). The mixture was stirred at 35° C. for 3 days and extracted with dichloromethane (30 ml). The organic solution was washed with saturated sodium bicarbonate, brine, dried (MgSO$_4$), filtered and the solvent evaporated in vacuo. The residue was chromatographed on silica gel column using a mixture of ethyl acetate/hexane (1:3) as eluent, which afforded 115 mg (50%) of 4-oxo-2-(1,1,3-trioxo-1,3-dihydro-1H-benzo[d]isothiazol-2-ylmethyl)-piperidine-1-carboxylic acid tert-butyl ester as an oil.

$^1$H-NMR (CDCl$_3$): δ 8.06 (dd, 1H, J=6.0, 1.8 Hz), 7.95–7.80 (m, 3H), 5.02 (bs, 1H), 4.35 (bs, 1H), 3.91 (dd, 1H, J=15.0 Hz and J=8.4 Hz), 3.78 (dd, 1H, J=14.7 Hz and J=5.7 Hz), 3.53 (t, 1H, J=10.8 Hz), 2.74 (dd, 1H, J=15.0 Hz and J=7.5 Hz), 2.60–2.38 (m, 3H), 1.32 (s, 9H).

To a solution of 4-oxo-2-(1,1,3-trioxo-1,3-dihydro-1H-benzo[d]isothiazol-2-ylmethyl)-piperidine-1-carboxylic acid tert-butyl ester (115 mg, 0.292 mmol) in absolute ethanol (5 ml) was added t-butyl cyanoacetate (57 µl, 0.41 mmol), sulfur (13 mg, 0.41 mmol) and morpholine (55 µl, 0.63 mmol). The solution was stirred at 50° C. for 14 hours. The solvent was evaporated in vacuo and the residue was chromatographed on silica gel column using a mixture of ethyl acetate/hexane (1:4) as eluent, which afforded 100 mg (62%) of 2-amino-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-amino-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester as a mixture.

$^1$H-NMR (CDCl$_3$): δ 8.10–8.00 (r, 1H), 7.98–7.77 (m, 2.8H), 7.66–7.58 (m, 0.2H), 6.11 (s, 0.4H), 6.06 (s, 0.6H), 5.59 (m, 0.2H), 5.39 (t, 0.3H, J=5.7 Hz) 5.23 (bs 0.3H), 5.04 (bs, 0.4H), 4.77 (d, 0.4H, J=14.4 Hz), 4.60 (d, 0.4H, J=14.4 Hz), 4.45–4.18 (m, 1H), 4.02–3.82 (m, 1.5H), 3.64 (dd, 0.5H, J=14.7 Hz and J=5.2 Hz), 3.30–2.60 (m, 2H), 1.54 (s, 7H), 1.53 (s, 2H), 1.26 (s, 7H), 1.21 (s, 2H).

To a stirred solution of the above 2-amino-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-amino-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester mixture (100 mg, 0.18 mmol) in acetonitrile (7 ml) was added imidazol-1-yl-oxo-acetic acid tert-butyl ester (290 mg, 1.46 mmol) in acetonitrile (1 ml). The mixture was stirred at room temperature for 16 hours. The solvent was removed in vacuo and the residue was taken into ethyl acetate. The solution was washed with 0.5 N hydrochloric acid solution, saturated sodium bicarbonate, brine, dried MgSO$_4$) and filtered. The solvent was removed in vacuo and the residue was chromatographed on silicagel using a mixture of ethyl acetate/hexane (1:4) as eluent, which provided 98 mg (80%) of a mixture of 2-(tert-butoxyoxalyl-amino)-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-(tert-butoxyoxalyl-amino)-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester as a solid.

$^1$H-NMR (CDCl$_3$): δ 12.60 (s, 0.3H), 12.54 (s, 0.7H), 8.12–8.06 (m, 1H), 7.98–7.80 (m, 2.8H), 7.66–7.58 (m, 0.2H), 5.83 (bs, 0.1H), 5.61 (t, 0.2H), 5.40–4.54 (m, 0.9H), 4.53–4.40 (m, 0.8H), 4.02–3.70 (m, 1.42H), 3.66 (dd, 0.58H, J=14.7 Hz and J=5.2 Hz), 3.30–2.99 (m, 3H), 1.68 (s, 6H), 1.62 (s, 6H), 1.60 (s, 6H), 1.31 (s, 4.5H), 1.25 (s, 4.5H);

LC-MS: R$_t$ 4.45; m/z: 678 [M+H]$^+$.

To a solution of trifluoroacetic acid (4 ml) and dichloromethane (2 ml) was added the mixture of 2-(tert-butoxyoxalyl-amino)-5-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester and 2-(tert-butoxyoxalyl-amino)-7-(1,1,3-trioxo-1,3-dihydro-1H-benzo[d]isothiazol-2-ylmethyl)-4,7-dihydro-5H-thieno[2,3-c]pyridine-3,6-dicarboxylic acid di-tert-butyl ester (78 mg, 0.12 mmol). The solution was stirred at room temperature for 24 hours. The solvent was then evaporated in vacuo, which afforded 50 mg (72%) of the title compounds as a mixture of trifluoroacetates.

$^1$H-NMR (DMSO-d$_6$): δ 12.32 (s, 1H), 9.75–9.20 (m, 2H), 8.40 (t, 1H, J=6.0 Hz), 8.22–8.02 (m, 3H), 5.03 (bs, 0.5H), 4.52 (d, 1H), 4.38–4.10 (m, 2H), 3.88 (bs, 0.5H), 3.70–3.64 (m, 0.5H), 3.44–3.34 (m, 0.5H), 3.20–2.90 (m, 2H).

LC-MS: R$_t$=1.28 min, m/z: 466 [M+H]$^+$

Example 112

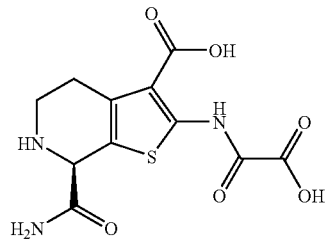

7-(R)-Carbamoyl-2-(oxalyl-amino)-4,5,6,7-tetrahydro-thieno[2,3-c]pyridine-3-carboxylic acid To a solution of 2-(S)-4-oxo-piperidine-1,2-dicarboxylic acid 1-tert butyl ester (18.4 g, 75.6 mmol) and triethylamine (12.65 mL, 90.79 mmol) in tetrahydrofuran (50 mL) cooled to −20° C. was added isobutylchloroformate (11.81 mL, 90.79 mmol) and the mixture was stirred for 10 min at −20° C. before a 25% solution of ammonia in water (100 mL) was added. The temperature was kept at −20° C. for 30 min before the cooling bath was removed and the reaction mixture was allowed to reach room temperature and stirring was continued for another hour. The reaction mixture was extracted with ethyl acetate (6×50 mL) and the combined organic phases were dried (MgSO$_4$). The solvent was removed in vacuo and the residue was purified by column chromatography (SiO$_2$, Flash 40, ethyl acetate) to give 8.51 g (46%) of 2-(S)-carbamoyl-4-oxo-piperidine-1-carboxylic acid 1-tert-butyl ester.

A solution of 2-(S)-carbamoyl-4-oxo-piperidine-1-carboxylic acid 1-tert butyl ester (3.51 g 14.48 mmol), tert-butyl cyanoacetate (2.04 g, 14.48 mmol), sulphur (0.464 g, 14.48 mmol) and diisopropyl ethylamine (2.5 mL, 14.48 mmol) in methanol (20 mL) was heated 16 hours at 40° C. under N$_2$. The volatiles were removed in vacuo and the residue was purified using column chromatography (SiO$_2$, Flash 40, petroleum ether/ethyl acetate 3:1) to give 1.33 g (23%) of a mixture 2-amino-5-(S)-carbamoyl-4,7-dihydro-5H-thieno[2,3-c]pyridine-3,6-di-carboxylic acid di-tert-butyl ester and 2-amino-7-(R)-carbamoyl-4,7-dihydro-5H-thieno[2,3-c]pyridine-3,6-di-carboxylic acid di-tert-butyl ester isomers.

0.5 g (1.25 mmol) of the above mixture was dissolved dichloromethane (10 mL) and imidazole-1-yl-oxo-acetic acid tert-butyl ester (0.74 g, 3.77 mmol) and triethylamine (0.525 mL, 3.77 mmol) was added. The reaction mixture was stirred for 16 hours at room temperature before the volatiles were removed in vacuo. The residue was purified by column chromatography (SiO$_2$, Flash 40, petroleum ether/ethyl acetate (4:1)) too give 75 mg (11%) of 2-(tert-butoxyoxalyl-amino)-7-(R)-carbamoyl-4,7-dithydro-5H-thieno[2,3-c]pyridine-3,6-dicarboxylic acid di-tert-butyl ester. This was dissolved in a mixture of trifluoacetic acid/dichloromethane (1:1) (10 mL) and stirred for 16 hours at room temperature before the solvent was removed in vacuo. The residue was recrystallized from methanol to give 24 mg (39%) of the title compound.

LC-MS; R$_t$=1.56 min, m/z: 314 [M+H]$^+$

Calculated for C$_{11}$H$_{11}$N$_3$O$_6$S, 0.25×C$_2$HF$_3$O$_2$, 0.75×H$_2$O C, 38.88%; H, 3.62%; N, 11.83%; Found: C, 38.92%; H, 3.92%; N, 11.81%.

Example 113

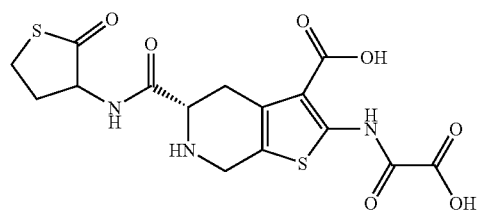

2-(Oxalyl-amino)-5-(S)-(2-oxo-tetrahydro-thiophen-3-ylcarbamoyl)-4,5,6,7-tetrahydro-thieno[2,3-c]pyridine-3-carboxylic acid A solution of 2-amino-4,7-dihydro-5H-thieno[2,3-c]pyridine-3,5-(S),6-tri-carboxylic acid 3,6-di-tert-butyl ester (0.30 g, 0.75 mmol) and triethylamine (0.21 mL, 1.51 mmol) in tetrahydrofuran (10 mL) was cooled to −20° C. before isobutyl chloroformate (0.103 mL, 0.75 mmol) was added. The reaction mixture was stirred 15 min at −20° C. before homocystein hydrochloride (116 mg, 0.75 mmol) was added. The cooling bath was removed and the reaction mixture was left for 16 hours at room temperature. The solvent was removed in vacuo and the residue was subjected to column chromatography (SiO$_2$, Flash 40, heptane/ethyl acetate 2:1) to give 212 mg (56%) of 2-amino-5-(S)-(2-oxo-tetrahydro-thiophen-3-ylcarbamoyl)-4,7-dihydro-5H-thieno[2,3-c]pyridine-3,6-dicarboxylic acid di-tert-butyl ester A solution of 2-amino-5-(S)-(2-oxo-tetrahydro-thiophen-3-ylcarbamoyl)-4,7-dihydro-5H-thieno[2,3-c]pyridine-3,6-dicarboxylic acid di-tert-butyl ester (200 mg, 0.40 mmol), imidazole-1-yl-oxo-acetic acid tert-butyl ester (235 mg, 1.20 mmol) and triethylamine (168 µL, 1.20 mmol) in dichloromethane (10 mL) was stirred for 16 hours at room temperature before the solvent was removed in vacuo. The residue was purified by column chromatography (SiO$_2$, Flash 40, heptane/ethyl acetate 2:1) to give 250 mg (100%) of 2-(tert-butoxyoxalyl-amino)-5-(S)-(2-oxo-tetrahydro-thiophen-3-ylcarbamoyl)-4,7-dihydro-5H-thieno[2,3-c]pyridine-3,6-dicarboxylic acid di-tert-butyl ester.

This was dissolved in a mixture of trifluoroacetic acid/dichloromethane (1:1) (3 mL) and stirred for 16 hours at room temperature before diethyl ether (6 mL) was added. The precipitate was filtered off and washed with diethyl ether to give 172 mg (81%) of the title compound as a solid trifluoroacetate.

LC-MS; R$_t$=0.41 min, m/z: 414 [M+H]$^+$

Calculated for C$_{15}$H$_{15}$N$_3$O$_7$S$_2$, 1.5×C$_2$HF$_3$O$_2$, H$_2$O; C, 35.88%; H, 3.10%; N, 6.97%; Found: C, 35.91%; H, 3.54%; N, 6.97%.

Example 114

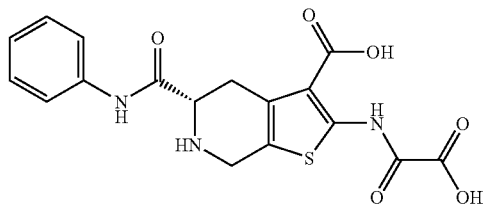

2-(Oxalyl-amino)-5-(S)-phenylcarbamoyl-4,5,6,7-tetrahydro-thieno[2,3-c]pyridine-3-carboxylic acid A solution of 2-amino-4,5,6,7-tetrahydro-thieno[2,3-c]pyridine-3,5-(S),6-tricarboxylic acid 3,5-di-tert-butyl ester (300 mg, 0.75 mmol) and triethylamine (210 µL, 1.51 mmol) in tetrahydrofuran (10 mL) was cooled to −20° C. before isobutylchloroformate (103 mg, 0.75 mmol) was introduced. The reaction mixture was stirred for 20 min before aniline (70 mg, 0.75 mmol) was added. The cooling bath was removed and the reaction was left for 16 hours at room temperature before the solvent was removed in vacuo. The residue was partitioned between ethyl acetate (50 mL) and water (50 mL). The organic phase was dried (MgSO$_4$) and the solvent was removed in vacuo. The residue was dissolved in dichloromethane (10 mL) and imidazole-1-yl-oxoacetic acid tert-butyl ester (443 mg, 2.26 mmol) and triethylamine (315 µL, 2.26 mmol) was added. The reaction mixture was stirred 16 hours at room temperature before the solvent was removed in vacuo. The residue was purified by column chromatography (SiO$_2$, Flash 40, heptane/ethyl acetate (3:1) to give 250 mg 2-(tert-butoxyoxalyl-amino)-

5-(S)-phenylcarbamoyl-4,7-dihydro-5H-thieno[2,3-c]pyridine-3,6-dicarboxylic acid di-tert-butyl ester.

2-(tert-Butoxyoxalyl-amino)-5-(S)-phenylcarbamoyl-4,7-dihydro-5H-thieno[2,3-c]pyridine-3,6-dicarboxylic acid di-tert-butyl ester was dissolved in a mixture of trifluoroacetic acid/dichloromethane (1:1) (3 mL) and stirred for 16 hours at room temperature before diethyl ether (6 mL) was added. The precipitate was filtered off and washed with diethyl ether to give 155 mg (41%) of the title compound as a solid trifluoroacetate.

LC-MS; $R_t$=0.86 min, m/z: 390 [M+H]$^+$

Calculated for $C_{17}H_{15}N_3O_6S$, $1.5 \times C_2HF_3O_2$, $H_2O$; C, 41.53%; H, 3.22%; N, 7.26%; Found: C, 41.77%; H, 3.29%; N, 7.28%.

Example 115

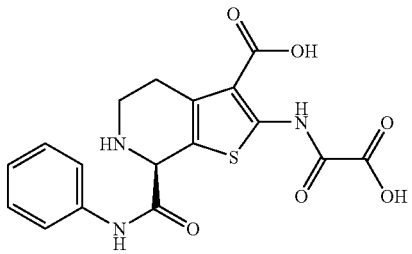

2-(Oxalyl-amino)-7-(R)-phenylcarbamoyl-4,5,6,7-tetrahydro-thieno[2,3-c]pyridine-3-carboxylic acid To a solution of 2-(S)-4-oxo-piperidine-1,2-dicarboxylic acid 1-tert butyl ester (2.06 g, 8.47 mmol) and triethylamine (1.42 mL, 10.16 mmol) in tetrahydrofuran (20 mL) cooled to −20° C. was added isobutylchloroformate (1.39 g, 10.16 mmol) and the mixture was stirred for 10 min at −20° C. before aniline (946 mg, 10.16 mmol) was added. The cooling bath was removed and the reaction mixture was stirred for 16 hours at room temperature before the solvent was removed in vacuo. The residue was divided between water (50 mL) and ethyl acetate (50 mL). The organic phase was washed with saturated sodium chloride (25 mL) and dried (MgSO$_4$). After filtration and concentration in vacuo the residue was purified using column chromatography (SiO$_2$, Flash 40, petroleum ether/ethyl acetate 5:1) to give 1.3 g (48%) of 4-oxo-2-(S)-phenyl-carbamoyl-piperidine-1-carboxylic acid tert-butyl ester.

A solution of 4-oxo-2-(S)-phenylcarbamoyl-piperidine-1-carboxylic acid tert-butyl ester (1.3, 4.08 mmol), tert-butylcyanoacetate (0.58 g, 4.08 mmol), sulphur (0.133 g, 4.08 mmol) and diisopropyl ethylamine (0.7 mL, 4.08 mmol) in methanol (10 mL) was heated under nitrogen to 40° C. for 16 hours before the solvent was removed in vacuo. The residue was subjected to column chromatography (SiO$_2$, Flash 40, petroleum ether/ethyl acetate 6:1) to give 0.70 g (36%) of a mixture of 2-amino-5-(S)-phenylcarbamoyl-4,7-dihydro-5H-thieno[2,3-c]pyridine-3,6-di-carboxylic acid di-tert-butyl ester and 2-amino-7-(R)-phenylcarbamoyl-4,7-dihydro-5H-thieno[2,3-c]pyridine-3,6-di-carboxylic acid di-tert-butyl ester isomers. The above mixture was dissolved in dichloromethane (20 mL) and imidazole-1-yl-oxo-acetic acid tert-butyl ester (872 mg, 4.44 mmol) and triethylamine (618 µL, 4.44 mmol) was added. The reaction mixture was stirred 16 hours before the solvent was removed in vacuo and the residue was subjected to column chromatography (SiO$_2$, Flash 40, petroleum ether/ethyl acetate 5:1) to give 0.50 g (56%) as a mixture of 2-(tert-butoxyoxalyl-amino)-5-(S)-phenylcarbamoyl-4,7-dihydro-5H-thieno[2,3-c]pyridine-3,6-di-carboxylic acid di-tert-butyl ester and 2-(tert-butoxyoxalyl-amino)-7-(R)-phenylcarbamoyl-4,7-dihydro-5H-thieno[2,3-c]pyridine-3,6-di-carboxylic acid di-tert-butyl ester 300 mg of the mixture was dissolved in a mixture of trifluoacetic acid/dichloro-methane (1:1) (6.0 mL) and the solution was stirred for 16 hours at room temperature before the solvent was removed in vacuo. The residue was purified on preparative HPLC to give 70 mg (34%) of the title compound as a solid trifluoroacetate.

LC-MS; $R_t$=0.95 min, m/z: 390 [M+H]$^+$

Calculated for $C_{17}H_{15}N_3O_6S$, $C_2HF_3O_2$, $H_2O$; C, 43.77%; H, 3.48%; N, 8.06%; Found: C, 43.92%; H, 3.44%; N, 7.97%.

Example 116

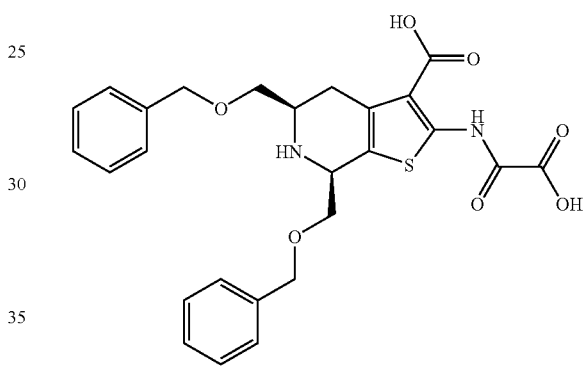

5-(R),7-(R)-Bis-benzyloxymethyl-2-(oxalyl-amino)-4,5,6,7-tetrahydro-thieno[2,3-c]pyridine-3-carboxylic acid Benzyloxyacetaldehyde (0.90 g; 6.0 mmol) and dimethyl (2-oxomethyl)phosphonate (1.0 g; 6.0 mmol) were dissolved in a mixture of tetrahydrofuran (25 ml) and water (20 ml). 1N Aqueous potassium hydroxide (6 ml) was added and the mixture was stirred for 30 min. Dichloromethane (50 ml) was added and the organic phase was separated, dried (MgSO$_4$) and evaporated in vacuo leaving 5-benzyloxypent-3-en-2-one.

$^1$H-NMR: 2.25 (s, 3H); 4.19 (dd, 2H); 4.55 (s, 2H); 6.34 (dt; 1H); 6.70 (dt, 1H); 7.26 (m, 5H).

5-benzyloxypent-3-en-2-one was dissolved in methanol (5 ml) and ammonium acetate (13 mmol, 1.03 g) was mixted together with benzyloxyacetaldehyde (1.8 g; 12 mmol) and acetic acid (0.69 ml) and the mixture was stirred for 2 days. The solvent was removed in vacuo and the residue was chromatographed on silica using gradient elution from 100% dichloromethane to 100% ethyl acetate. A fraction (411 mg) contained (according to LC-MS; m/z 340.4) 2,5-di(benzyloxymethyl)-4-piperidone in an impure state was isolated. The crude mixture was dissolved in ethanol (3 ml) and tert-butylcyanoacetate (400 mg), sulfur (100 mg) and triethylamine was added and the mixture was stirred at room temperature overnight. The mixture was filtered and the solvent removed in vacuo. The residue was chromatographed on silica in a mixture of dichloromethane/(7% of 25% aqueous ammonia in ethanol) (40:1), which afforded 0.14 g of 2-amino-5-(R),7-(R)-bis-benzyloxymethyl-4,5,6,7-tetrahydro-thieno[2,3-c]pyridine-3-carboxylic acid tert-butyl ester as an oil.

LC-MS: $R_t$: 6.03 min; m/z: 495.2 [M+H]$^+$ 2-amino-5-(R),7-(R)-Bis-benzyloxymethyl-4,5,6,7-tetrahydro-thieno[2,3-c]pyridine-3-carboxylic acid tert-butyl ester (0.14 g; 0.28 mmol) was dissolved in dichloromethane (5 ml) and treated with imidazol-1-yl-oxo-acetic acid tert-butyl ester (0.1 g; 0.5 mmol) and triethylamine (70 µl; 0.5 mmol), and stirred overnight, washed with water, dried (MgSO$_4$) and the solvent removed in vacuo. The residue was chromatographed on silica using ethyl acetate/dichloromethane (1:3) as eluent. The residue was treated with trifluoroacetic acid (0.5 ml) in dichloromethane (0.5 ml) and stirred for 4 hours. Evaporation of the solvent in vacuo afforded 37 mg of the title compound.

LC-MS: $R_t$: 4.74 min; m/z: 511.4 [M+H]$^+$.

Example 117

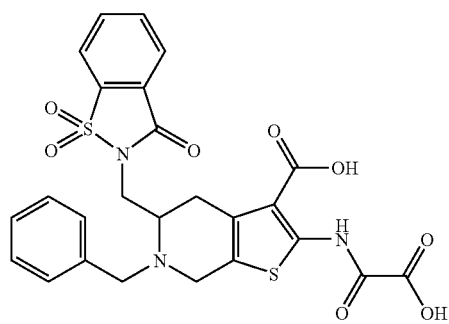

6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid 1-Benzyl-4-oxo-piperidine-2-carboxylic acid ethyl ester (2.9 g; 11.1 mmol) (prepared in a similar way as described in "GENERAL CHIRAL SYNTHESIS" for 4-oxo-1-((S)-1-phenyl-ethyl)-piperidine-(R)-2-carboxylic acid ethyl ester using benzylamine instead of 1-(S)-phenethylamine) was dissolved in abs. ethanol (50 ml) and sulfur (0.35 g, 11.1 mmol), triethylamine (1.6 ml, 11.1 mmol), and tert-butylcyanoacetate (1.7 g, 11.1 mmol) were added and the mixture was stirred 2 days at room temperature. The solvent was removed in vacuo and the residue was chromatographed on silica using a mixture of ethyl actetate/heptane (1:4) as eleuent leaving a mixture (700 mg; 1:1 based on NMR) of 2-amino-6-benzyl-4,5,6,7-tetrahydro-thieno[2,3-c]pyridine-3,7-dicarboxylic acid 3-tert-butyl ester-7-ethyl ester and 2-amino-6-benzyl-4,5,6,7-tetrahydro-thieno[2,3-c]pyridine-3,7-dicarboxylic acid 3-tert-butyl ester 5-ethyl ester which was used in the next step without separation. To this mixture was added tetrahydrofuran (5 ml) and lithium borohydride (1.1 ml of a 2M solution in tetrahydrofuran) and the mixture was stirred 18 hours. More lithium borohydride (5.0 ml of a 2M solution in tetrahydrofuran) was added and the mixture stirred for an additiona 4 days. Ethyl acetate (10 ml) was added dropwise and after 1 hour the mixture was poured onto water (100 ml) and extracted with dichloromethane (2×100 ml) and chromatographed on silica (using ethylacetate/heptane 1:1 as eluent), which afforded a mixture of 2-amino-6-benzyl-7-hydroxymethyl-4,5,6,7-tetrahydro-thieno[2,3-c]pyridine-3-carboxylic acid tert-butyl ester and 2-amino-6-benzyl-5-hydroxymethyl-4,5,6,7-tetrahydro-thieno[2,3-c]pyridine-3-carboxylic acid tert-butyl ester (in total 187 mg). To this mixture was added dry tetrahydrofuran (10 ml), 2,3-dihydro-1,2-benzisothiazol-3-one-1,1-dioxide (100 mg; 0.55 mmol), triphenylphosphine (144 mg 0.55 mmol) and the mixture was cooled with ice. Diethyl azodicarboxylate (86 µl) was added and the mixture was stirred overnight at room temperature. The solvent was evaporated in vacuo and the residue was chromatographed on silica using a mixture of ethyl acetate/heptane (1:1) as eluent leaving 94 mg of 2-amino-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester.

$^1$H-NMR: (CDCl3): 1.52 (s, 9H); 2.75 (dd, 1H); 2.90 (dd, 1H); 3.55 (d, 1H); 3.72 (m, 4H); 3.94 (d, 1H); 4.12 (d, 1H); 5.97 (s, 2H); 7.14–7.37 (m, 5H); 7.80–8.03 (m, 4H).

LC-MS: $R_t$ 5.47 min, m/z: 540.4 [M+H]$^+$

2-Amino-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester (94 mg; 0.17 mmol) was dissolved in dichloromethane (5 ml) and treated with imidazol-1-yl-oxo-acetic acid tert-butyl ester (0.07 g; 0.3 mmol) and triethylamine (49 µl; 0.3 mmol), and stirred overnight, washed with water, 1N aqueous citric acid, dried (MgSO$_4$) and the solvent removed in vacuo leaving 104 mg of 2-(tert-butoxyoxalyl-amino)-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester as an oil.

LC-MS: $R_t$: 5.50 min, m/z: 668.6 [M+H]$^+$ 2-(tert-Butoxyoxalyl-amino)-6-benzyl-5-(1,1,3-trioxo-1,3-dihydro-1,6-benzo[d]isothiazol-2-ylmethyl)-4,5,6,7-tetrahydro-thieno[2,3-c]pyridine-3-carboxylic acid tert-butyl ester (100 mg; 0.15 mmol) was treated with trifluoroacetic acid (1 m) in dichloromethane (4 ml) and stirred for 2 days. Evaporation of the solvent in vacuo afforded 90 mg of the title compound as a solid trifluoroacetate.

Calc. for $C_{25}H_{21}N_3O_8S_2$, $1.5 \times C_2HF_3O_2$, $0.5 \times H_2O$ C, 45.72%; H, 3.22%; N, 5.71%. Found: C, 45.48%; H, 3.46%; N, 5.72%

LC-MS: $R_t$: 4.16 min; m/z: 556.2 [M+H]$^+$

Example 118

Crystallisation of Protein and Protein-Inhibitor Complexes

Co-Crystallization of PTP1B with Inhibitors;

A 6–10 mg/ml preparation of PTP1B in 10 mM Tris pH 7.5, 25 mM NaCl, 0.2 mM EDTA and 3 mM DTT, was used for crystallization. Crystals were grown by the sitting as well as the hanging drop vapor diffusion methods. A 1:10 (PTP1B:inhibitor) molar ratio mixture was prepared at least one hour prior to crystallization. Two µl of PTP1B-inhibitor solution was mixed with 2 µl reservoir solution consisting of: 0.1 M Hepes buffer pH 7.5, 0.3–0.4 M Na-acetate or Mg-acetate, 12–16% Peg 8000 and/or 4% glycerol. The reservoir volume was 1 ml. Crystals grew to the size of 0.3–0.6×0.1–0.3×0.1–0.3 mm over 2–3 days.

Data Collection.

All crystal data collections were performed at 100 K. The following cryo conditions were used: to the hanging or sitting drop 3 µl of 50% glycerol (containing 0.5 mmol inhibitor) were added. The crystal was removed from the drop after 5–30 min. and transferred to 50% glycerol (containing 0.5 mmol inhibitor) and rapidly flash frozen.

Data were collected using a mar345 image plate either at the MAX-lab synchrotron facilities in Lund (Sweden) or in-house equipped with a rotating anode (RU300) and Osmic multilayer mirror system. Typically a 1° oscillation was used for 60 images data sets in the resolution range 2.7–1.8 Å were obtained. The space group was determined to be P3121 for all crystals used.

Refinements.

As P3121 contains a polar axis and, thus, possesses more than one indexing possibility, a molecular replacement solution using Amore [ref] solution was found prior to the refinements. A high resolution PTP1B structure was used as a starting model, with ligand and water molecules omitted from the structure. All refinements were performed with Xplor. v. 3.851 [MSI]. Interchanging cycles of model building using X-build [MSI] and refinement were performed. The 2Fo-Fc maps were inspected by the use of X-ligand [MSI] at a 1.3 sigma level for densities that could correspond to the structures of the inhibitors. In all cases a well-suited inhibitor electron density was identified in the active site pocket, see FIGS. 1–4. No other densities were identified to fit the inhibitors. Water molecules were inserted using the X-solvate program [MSI].

Example 119

Coupling of 2-(oxalyl-amino)-4,5,6,7-tetrahydro-thieno[2,3-c]pyridine-3-carboxylic acid to Epoxy-activated Sepharose 6B This example describes the preparation of an immobilized compound suited for affinity chromatographic purification of PTPases (eg PTP1B or T-cell PTP).

3.5 g Epoxy-activated Sepharose 6B (Pharmacia Biotech) was prepared for coupling according to the manufacturers directions, and divided into 3 portions (3×8 ml gel-suspension, corresponding to 4 ml drained gel each).

8 ml portions of 2-(oxalyl-amino)-4,5,6,7-tetrahydro-thieno[2,3-c]pyridine-3-carboxylic acid dissolved to 10, 1 and 0.1 mM in a 0.2 M sodium carbonate coupling buffer pH 9 were mixed with the gel suspensions and agitated gently overnight at room temperature.

Exces ligand was washed away, the remaining active groups were blocked and the product was washed extensively at alternating pH, all according to the the manufacturers directions.

The products were stored refrigerated in 0.1 M acetate pH 4.0 containing 0.5 M sodium chloride.

Significant inhibition of PTP1B was demonstrated in the 20 μmole ligand/ml gel preparation, when diluted to 1 μl drained gel/ml.

Example 120

Affinity purification of PTP1B using the compound 2-(oxalyl-amino)-4,5,6,7-tetrahydro-thieno[2,3-c] pyridine-3-carboxylic acid coupled to Epoxy-activated Sepharose 6B This example describes the affinity chromatographic purification of a PTPase.

2 ml of the product with 20 μmole ligand/ml described in example 55 was loaded into a 1.6 cm diameter column and equilibrated with a buffer (buffer A) containing
20 mM L-histidine
1 mM EDTA
7 mM Mercaptoethanol
100 mM Sodium chloride and adjusted to pH 6.2 with 1 M HCl.

1.5 mg conventionally purified PTP1B in 5 ml buffer A, was applied to the column at 0.5 ml/min followed by a wash with 10 ml buffer A.

UV absorbing material without PTPase activity, corresponding to approx. 10% of the totally applied material, passed through the column.

The flow direction was reversed, the flow increased to 2 ml/min and linear gradient elution started with a combined salt and pH gradient for 20 minutes using buffer B containing
20 mM L-histidine
1 mM EDTA
7 mM Mercaptoethanol
1 M Sodium chloride and adjusted to pH 9.0 with 1 M NaOH.

Maximum elution took place at approx. 32% buffer B (0.39 M NaCl and pH 6.8) in a broad peak.

The total activity yield in the elution peak was 70%, and the specific activity of the enzyme was improved by a factor 1.4.

Example 121

Use of Compounds of the Invention to Identify Substrates that Are Specifically Dephosphorylated by PTPases that Are Inhibited by the Compounds of the Invention or by Other PTPases The compounds of the invention are unique tools for identification of cellular substrates of the PTPases that are inhibited by the compounds of the invention. Substrates are herein defined as cellular proteins that (i) are phosphorylated on tyrosine residues, (ii) are dephosphorylated by PTPases that are inhibited by compounds of the invention or by other PTPases. If said substrates are dephosphorylated by PTPases that are inhibited by compounds of the invention, administration of the compounds of the invention will result in partial or total prevention of dephosphorylation of said substrates. As a result, a concomitant prolonged or increased activation may be observed of the signal transduction pathway (for definition, vide infra) in which said substrate is involved. Non-limiting examples of substrates are: the insulin receptor β subunit, IRS-1, IRS-2, IRS-3, IRS-4, JAK1, JAK2, shc-2, grb-2 (Hunter, *Cell* 100:113–127 (2000)).

Importantly, the compounds of the invention can also be used to identify novel substrates. When the compounds of the invention have been used to identify the substrates of the PTPases that are inhibited by the compounds of the invention, a person skilled in the arts will be able to use this knowledge to establish animal models that will reflect a human condition or disease in which a compound of the invention will be indicated. Non-limiting example of the usefulness of said compounds of the invention will be in the following disease areas: diabetes, obesity cancer and conditions with unwarranted platelet aggregation.

To identify the substrates of the PTPases that are inhibited by the substrates of the invention the following methods may be employed. Whole animals and/or primary cells and/or cell lines that represent the target organ or tissue may be used for these experiments. Non-limiting examples of animals are: ob/ob mice (worldwide web @ jax.org); db/db mice; Zucker obese rats. Non-limiting examples of target tissues or organs are: skeletal muscle, liver, adipose tissue, pancreas, the spleen, the bone marrow. Non-limiting examples of cell lines are: Chinese hamster ovary (CHO) cells (CHO-K1—American Type Culture Collection (ATCC) Number CCL-61), Baby Hamster Kidney (BHK) cells (ATCC Number CRL-1632), HepG2 cells (ATCC Number HB-8065), C2C12 cells (ATCC Number CRL-1772), L6 cells (ATCC Number CRL-1458), RD cells (ATCC Number CCL-136). Said cells can either be unmanipulated or transfected transiently or permanently with plasmid vectors that encode proteins or substrates. Non-limiting example of a plasmid that allows expression in mammalian cells are: pcDNA1 and pcDNA3 (worldwode web @ invitrogen.com). Non-limiting examples of proteins or substrates that are transfected into said cell lines are: the insulin receptor, the IGF-I receptor, the EGF-R receptor; the PDGF receptor, IRS-1, IRS-2, IRS-3, IRS-4, p56Lck; Jak1, Jak2 (Hunter, supra).

The analysis consists of the following steps:

(A) stimulation of signal transduction pathways with and without the presence of the compounds of the invention. Signal transduction pathways are herein defined as a series of cellular processes that are initiated by a triggering event (such as stimulation of a tissue or cell by a hormone and/or a cytokine and/or cell—cell interaction and/or cell—cell substratum interaction) leading to various cellular effects including metabolic effects, cell differentiation and cell proliferation (Hunter, supra). Non-limiting examples of signal transduction pathways include: the insulin signaling pathway; the leptin signalling pathway; thrombin signalling pathway; the erythropoietin signaling pathway; the epidermal growth factor signaling pathway. Non-limiting examples of the effects of stimulating signal transduction pathways: glucose uptake; glycogen synthesis; cell proliferation; cell differentiation; platelet aggregation.

(B) Analysis and identification of substrates that show increased (or decreased) phosphorylation on tyrosine residues after administration of the compound of the invention in comparison with controls that did not receive the compound.

Step A. Stimulation of Signal Transduction Pathways.

As a non-limiting example, insulin (concentration range: 0.1 to 100 nM, final concentration) is administered to primary hepatocytes in tissue culture plates. The compounds of the invention (concentration range: 10 nM to 100 µM) are administered to half of the plates, with the other plates acting as controls. The plates are incubated at 37° C. for various time periods: Typically for 0, 1, 2, 5, 15, 30 and 60 mins. Following this stimulation, the plates are treated as follows: The medium is rapidly aspirated and the cells washed twice with ice-cold PBS. Two milliliters of ice-cold lysis buffer (see below) is added and the plates are placed on ice for 2 minutes after which the cells are scraped off using a cell scraper ('rubber policeman'). The lysates are placed at 4° C. at a rotary shakerr. Dithiotreitol is added to a final concentration of 10 mM, and the lysates are centrifuged at 20,000 r.p.m. Aliquots of the supernatants, i.e. lysates, are stored at −80° C. until further use.

Lysis buffer—for a total of 20 ml add the following 0.8 ml of 500 mM Tris-Cl, pH 7.4

0.2 ml of 100 mM EDTA 2.0 ml of 1 M NaCl 2.0 ml of 10% (vol/vol) Triton X-100

80 µl of 250 mM PMSF

2 µl of 10 mg/ml aprotinin

20 µl of 1 mg/ml leupeptin 5 mM 100 mM iodoacetate 11.88 ml demineralized water

Step B. Analysis and Identification of Substrates that Show Increased (or Decreased) Phosphorylation on Tyrosine Residues after Administration of the Compound of the Invention in Comparison with Controls that Did not Receive the Compound.

As a non-limiting example, said lysates are subjected to two-dimensional polyacrylamide gel electrophoresis (2-D PAGE) followed by detection of proteins that are phosphorylated on tyrosine residues (pTyr) by western blotting, techniques well-known to those skilled in the art (Marcus et al. *Electrophoresis* 21: 2622–2636 (2000)). Proteins that show increased (or decreased) pTyr are identified by comparing the western blots made from said lysates derived from said hepatocytes treated with both insulin and the compounds of the invention with said control lysates derived from said hepatocytes that were treated with insulin only. Increased pTyr of a protein shows that the said protein is regulated by the PTPase or PTPases that are inhibited by the compounds of the invention. Said protein may either be a direct substrate of the PTPase or PTPases that are inhibited by the compounds of the invention or the substrate of other PTPase(s) which activity is regulated by the PTPase or PTPases that are inhibited by the compounds of the invention. Decreased pTyr of a protein shows that said protein is the substrate of other PTPase(s) that is/are activated, directly or indirectly, by the PTPase or PTPases that are inhibited by the compounds of the invention. Having identified and visualized proteins, i.e. substrates, that show changed pTyr levels, the spots are cut out, digested with trypsin and analyzed by matrix assisted laser desorption/ionization-time of flight-mass spectrometry (MALDI-TOF-MS) (Marcus et al., supra). To identify the nature of said substrate with changed pTyr levels the obtained mass fingerprints are analyzed as described by Marcus et al. (supra) or other methods well-known to those skilled in the art.

Said substrate can either be an already described protein or a novel protein. In both cases, the identification may be followed by cDNA cloning procedures with the aim of obtaining a full-length clone corresponding to said substrate using standard techniques well-known to those skilled in the art (Ausubel, F. M., et al. (ED.). Short Protocols in Molecular Biology, $2^{nd}$ ed, John Wiley and Sons, inc., New York, ISBN0-471-57735-9 (1992)). Said full-length clone may be expressed as recombinant proteins in prokaryotic or eukaryotic expression systems well-known to those skilled in the art (worldwide web @ invitrogen.com; worldwide web @ stratagene.com; worldwide web @ promega.com), and the function of said substrate may in turn be studied both at the biochemical and cellular levels. Further, said recombinant proteins may further be used as an antigen to produce either polyclonal or monoclonal antibodies using techniques well-known to those skilled in the art. As a non-limiting example, with said full-length clone, said antibodies, and the compounds of the invention at hand, those skilled in the art will be able to study the tissue distribution and expression levels of said substrates in normal animals and animal models of diseases, such as diabetes, obesity, cancer and disturbances of platelet aggregation. A person skilled in the art will be able to use this knowledge to establish animal models or use already established animal models that will reflect a human condition or disease in which a compound of the invention will be indicated. Non-limiting example of the usefulness of said compounds of the invention will be in the following disease areas: diabetes, obesity, cancer and conditions with unwarranted platelet aggregation.

Example 122

Identification of Substrates that are Dephosphorylated by PTPases that are Inhibited by the Compounds of the Invention The analysis consists of the following steps: (A) preparation of hyperphosphorylated substrates; (B) identification of said substrates that are dephosphorylated by PTPases that are dephosphorylated by compounds of the invention.

To identify the substrates of the PTPases that are inhibited by the compounds of the invention the following method may be employed. Primary cells and/or cell lines that represent the target organ or tissue may be used for these experiments. Non-limiting examples of target tissues or organs are: skeletal muscle, liver, adipose tissue, pancreas, the spleen, the bone marrow. Non-limiting examples of cell lines are: Chinese hamster ovary (CHO) cells (CHO-K1—American Type Culture Collection (ATCC) Number CCL-61), Baby Hamster Kidney (BHK) cells (ATCC Number CRL-1632), HepG2 cells (ATCC Number HB-8065), C2C12 cells (ATCC Number CRL-1772), L6 cells (ATCC Number CRL-1458), RD cells (ATCC Number CCL-136). Said cells can either be unmanipulated or transfected transiently or permanently with plasmid vectors that encode proteins or substrates. Non-limiting example of a plasmids that allow expression in mammalian cells are: pcDNA1 and pcDNA3 (worldwide web @ invitrogen.com). Non-limiting examples of proteins or substrates that are transfected into said cell lines are: the insulin receptor, the IGF-I receptor, the EGF-R receptor, the PDGF receptor, IRS-1, IRS-2, IRS-3, IRS-4, p56Lck; Jak1, Jak2 (Hunter, supra).

Step A

Said primary cells, tissues or cell lines are exposed to a general inhibitor of PTPases. This treatment results in induction of hyperphosphorylation of a multitude of cellular substrates. A non-limiting example of a general PTPase inhibitor is bisperoxovanadium 1,10 phenanthroline (bpV (phen)) (Posner et al. *J. Biol. Chem.* 269: 4596–4604 (1994)).

A non-limiting example of a hyperphosphorylation protocol: CHO cells that stably overexpress the insulin receptor are grown in 15 cm Petri dishes to 80–90 percent confluence (using F-12 medium with 10 percent fetal calf serum). The culture medium is replaced with medium that does not contain calf serum and are grown for additional 2 hrs at 37° C. The plates are washed twice with phosphate buffered saline (PBS) and incubated for further 2 hours with 100 μM bpV(phen) and 100 nM insulin (Novo Nordisk) (final assay concentrations). Following this stimulation the plates are treated as follows: The medium is rapidly aspirated and the cells washed twice with ice-cold PBS. Two milliliters of ice-cold lysis buffer (see below) is added and the plates are placed on ice for 2 minutes after which the cells are scraped off using a cell scraper ('rubber policeman'). The lysates are placed at 4° C. at a rotary shaker for 1 hour. Dithiotreitol is added to a final concentration of 10 mM, and the lysates are centrifuged for 10 minutes at 20,000 r.p.m. Aliquots of the supernatants, i.e. lysates, are stored at −80° C. until further use.

Lysis buffer—for a total of 20 ml add the following:

0.8 ml of 500 mM Tris-Cl, pH 7.4

0.2 ml of 100 mM EDTA 2.0 ml of 1 M NaCl 2.0 ml of 10% (vol/vol) Triton X-100

80 μl of 250 mM PMSF

2 μl of 10 mg/ml aprotinin

20 μl of 1 mg/ml leupeptin 5 mM 100 mM iodoacetate 11.88 ml demineralized water

Step B

For these studies both novel and known PTPases may be used. The PTPases may be either isolated using the compounds of the invention as described in Example 120 or recombinant proteins. Non-limiting examples of known PTPases that are inhibited by compounds of the invention are PTP1B and TC-PTP. The cDNA for these PTPases are inserted in prokaryotic expression vectors and are expressed in *E. coli*. An overnight culture is diluted 1:25 into a total volume of 2 liters of SOB medium and grown at 37° C. for 3 hours. Isopropyl β-D-thiogalactoside (IPTG) is added to a final concentration of 0.1 mM, and the incubation is continued at room temperature for 3 hrs. The fusion proteins are purified according to the manufacturer's instructions (Amersham Pharmacia Biotech).

Aliquots of said lysates (60 μl) are mixed with said PTPase that is inhibited by said compound of the invention and incubated on ice for 1, 10, and 30 minutes. At each time point, 20 μl aliquots are removed and mixed with SDS loading buffer (20% (v/v) glycerol, 3% (w/v) SDS, 3% (v/v) 2-mercaptoethanol, 10 mM EDTA, 0.05% (w/v) bromophenol blue), heated at 100° C. for 2 minutes and stored at −20° C. until use. Control lysates without addition of PTPase are treated identically.

As a non-limiting example, said lysates are subjected to two-dimensional polyacrylamide gel electrophoresis (2-D PAGE) followed by detection of proteins that are phosphorylated on tyrosine residue (pTyr) by western blotting, techniques well-known to those skilled in the art (Marcus et al. *Electrophoresis* 21: 2622–2636 (2000)). Proteins that show decreased pTyr are identified by comparing the western blots made from said lysates treated with said PTPase with said control lysates. Decreased pTyr of a protein shows that the said protein is a substrate of the PTPase or PTPases that are inhibited by the compounds of the invention. Having identified and visualized proteins, i.e. substrates, that show decreased pTyr levels, the spots are cut out, digested with trypsin and analyzed by matrix assisted laser desorption/ionization-time of flight-mass spectrometry (MALDI-TOF-MS) (Marcus et al., supra). To identify the nature of said substrate with decreased pTyr levels the obtained mass fingerprints are analyzed as described by Marcus et al. (supra) or other methods well-known to those skilled in the art.

Said substrate can either be an already described protein or a novel protein. In both cases, the identification may be followed by cDNA cloning procedures with the aim of obtaining a full-length clone corresponding to said substrate using standard techniques well-know to those skilled in the art (Ausubel, F. M., et al. (ED.). Short protocols in molecular biology, $2^{nd}$ ed, John Wiley and sons, inc., New York, ISBN 0-471-57735-9 (1992)). Further use of the knowledge include analysis in animal models as described in Example 59

Example 123

Analysis for Blood Glucose Lowering Effects

The compounds of the invention are tested for blood glucose lowering effects in diabetic, obese female ob/ob mice. The mice are of similar age and body weights and they are randomized into groups of ten mice. They have free access to food and water during the experiment. The compounds are administered by either by gavage, subcutaneous, intravenous or intraperitoneal injections. The control group receives the same volume of vehicle as the mice that receive the compounds. Non-limiting examples of dose-range: 0.1, 0.3, 1.0, 3.0, 10, 30, 100 mg per kg body weight. The blood glucose levels are measured two times before administration of the compounds of the invention and vehicle (to the control group). After administration of the compound, the blood glucose levels are measured at the following time points: 1, 2, 4, 6, and 8 hours. A positive response is defined either as (i) a more than 25 percent reduction in blood glucose levels in the group receiving the compound of the invention compared to the group receiving the vehicle at any time point or (ii) statistically significant (i.e. $p<0.05$) reduction in the area under the blood glucose curve during the whole period (i.e. 8 hrs) in the group treated with the compounds of the invention compared to the group receiving the vehicle.

All documents cited herein are incorporated by reference in their entirety. In case of conflict in definitions, the present definitions control.

TABLE A

Table of the orthogonal three dimensional coordinates in Ångstroms and B factors ($Å^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1 | GLU | N | 69.819 | 14.736 | 20.949 | 51.88 |
| 2 | GLU | CA | 69.381 | 16.070 | 20.592 | 50.12 |
| 3 | GLU | C | 68.816 | 16.123 | 19.177 | 50.96 |
| 4 | GLU | O | 69.477 | 15.855 | 18.147 | 47.57 |
| 5 | GLU | CB | 70.340 | 17.247 | 20.871 | 48.87 |
| 6 | GLU | CG | 69.694 | 18.607 | 20.512 | 43.78 |
| 7 | GLU | CD | 68.658 | 19.051 | 21.547 | 100.00 |
| 8 | GLU | OE1 | 68.838 | 19.978 | 22.327 | 100.00 |
| 9 | GLU | OE2 | 67.553 | 18.331 | 21.549 | 100.00 |
| 10 | MET | N | 67.550 | 16.476 | 19.190 | 38.96 |
| 11 | MET | CA | 66.810 | 16.619 | 18.000 | 33.41 |
| 12 | MET | C | 67.438 | 17.710 | 17.211 | 32.40 |
| 13 | MET | O | 67.335 | 17.745 | 16.010 | 34.44 |
| 14 | MET | CB | 65.376 | 17.042 | 18.345 | 34.94 |
| 15 | MET | CG | 65.321 | 18.129 | 19.414 | 36.89 |
| 16 | MET | SD | 63.595 | 18.598 | 19.738 | 37.03 |
| 17 | MET | CE | 63.053 | 17.127 | 20.689 | 35.19 |
| 18 | GLU | N | 68.060 | 18.625 | 17.893 | 31.60 |
| 19 | GLU | CA | 68.666 | 19.756 | 17.226 | 34.56 |
| 20 | GLU | C | 69.903 | 19.379 | 16.393 | 37.49 |
| 21 | GLU | O | 70.082 | 19.836 | 15.267 | 37.90 |
| 22 | GLU | CB | 68.955 | 20.859 | 18.236 | 36.57 |
| 23 | GLU | CG | 68.694 | 22.256 | 17.685 | 54.02 |
| 24 | GLU | CD | 68.602 | 23.271 | 18.792 | 84.59 |
| 25 | GLU | OE1 | 68.338 | 22.965 | 19.970 | 60.30 |
| 26 | GLU | OE2 | 68.826 | 24.499 | 18.340 | 56.97 |
| 27 | LYS | N | 70.740 | 18.506 | 16.928 | 34.63 |
| 28 | LYS | CA | 71.925 | 18.073 | 16.173 | 36.36 |
| 29 | LYS | C | 71.504 | 17.225 | 14.995 | 35.30 |
| 30 | LYS | O | 72.071 | 17.271 | 13.926 | 33.46 |
| 31 | LYS | CB | 72.858 | 17.280 | 17.069 | 44.20 |
| 32 | LYS | CG | 73.694 | 18.196 | 17.980 | 95.46 |

TABLE A-continued

Table of the orthogonal three dimensional coordinates in Ångstroms and B factors ($Å^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 33 | LYS | CD | 74.837 | 17.496 | 18.729 | 100.00 |
| 34 | LYS | CE | 74.640 | 17.419 | 20.241 | 98.28 |
| 35 | LYS | NZ | 73.758 | 16.304 | 20.653 | 100.00 |
| 36 | GLU | N | 70.463 | 16.441 | 15.234 | 32.09 |
| 37 | GLU | CA | 69.894 | 15.573 | 14.227 | 31.58 |
| 38 | GLU | C | 69.285 | 16.367 | 13.096 | 33.03 |
| 39 | GLU | O | 69.380 | 16.076 | 11.917 | 33.46 |
| 40 | GLU | CB | 68.841 | 14.653 | 14.863 | 33.60 |
| 41 | GLU | CG | 67.823 | 14.152 | 13.814 | 51.32 |
| 42 | GLU | CD | 66.936 | 13.044 | 14.309 | 61.90 |
| 43 | GLU | OE1 | 66.302 | 13.085 | 15.370 | 49.63 |
| 44 | GLU | OE2 | 66.918 | 12.042 | 13.457 | 46.46 |
| 45 | PHE | N | 68.648 | 17.422 | 13.475 | 31.95 |
| 46 | PHE | CA | 68.008 | 18.269 | 12.488 | 32.19 |
| 47 | PHE | C | 69.072 | 18.712 | 11.539 | 37.60 |
| 48 | PHE | O | 68.928 | 18.630 | 10.309 | 32.52 |
| 49 | PHE | CB | 67.340 | 19.508 | 13.152 | 32.26 |
| 50 | PHE | CG | 66.508 | 20.348 | 12.196 | 30.98 |
| 51 | PHE | CD1 | 65.161 | 20.064 | 11.967 | 29.63 |
| 52 | PHE | CD2 | 67.094 | 21.402 | 11.499 | 29.81 |
| 53 | PHE | CE1 | 64.398 | 20.834 | 11.096 | 31.86 |
| 54 | PHE | CE2 | 66.354 | 22.185 | 10.621 | 32.68 |
| 55 | PHE | CZ | 65.004 | 21.896 | 10.423 | 34.10 |
| 56 | GLU | N | 70.164 | 19.160 | 12.179 | 36.63 |
| 57 | GLU | CA | 71.310 | 19.627 | 11.440 | 36.44 |
| 58 | GLU | C | 71.889 | 18.598 | 10.519 | 37.22 |
| 59 | GLU | O | 72.034 | 18.827 | 9.312 | 41.43 |
| 60 | GLU | CB | 72.309 | 20.346 | 12.308 | 40.39 |
| 61 | GLU | CG | 71.810 | 21.794 | 12.529 | 71.18 |
| 62 | GLU | CD | 71.946 | 22.266 | 13.953 | 100.00 |
| 63 | GLU | OE1 | 72.735 | 21.752 | 14.751 | 100.00 |
| 64 | GLU | OE2 | 71.139 | 23.288 | 14.223 | 100.00 |
| 65 | GLN | N | 72.140 | 17.413 | 11.024 | 31.25 |
| 66 | GLN | CA | 72.622 | 16.443 | 10.091 | 30.97 |
| 67 | GLN | C | 71.717 | 16.227 | 8.911 | 37.58 |
| 68 | GLN | O | 72.187 | 16.205 | 7.798 | 35.23 |
| 69 | GLN | CB | 72.828 | 15.118 | 10.746 | 32.09 |
| 70 | GLN | CG | 73.907 | 15.196 | 11.804 | 59.96 |
| 71 | GLN | CD | 74.286 | 13.786 | 12.123 | 100.00 |
| 72 | GLN | OE1 | 73.653 | 12.854 | 11.579 | 100.00 |
| 73 | GLN | NE2 | 75.309 | 13.631 | 12.975 | 100.00 |
| 74 | ILE | N | 70.403 | 16.026 | 9.164 | 37.32 |
| 75 | ILE | CA | 69.439 | 15.745 | 8.091 | 33.95 |
| 76 | ILE | C | 69.451 | 16.857 | 7.112 | 35.04 |
| 77 | ILE | O | 69.497 | 16.713 | 5.871 | 32.60 |
| 78 | ILE | CB | 68.007 | 15.516 | 8.591 | 33.88 |
| 79 | ILE | CG1 | 67.983 | 14.281 | 9.450 | 33.37 |
| 80 | ILE | CG2 | 67.062 | 15.263 | 7.427 | 27.69 |
| 81 | ILE | CD1 | 66.734 | 14.241 | 10.340 | 41.16 |
| 82 | ASP | N | 69.392 | 17.990 | 7.705 | 31.68 |
| 83 | ASP | CA | 69.374 | 19.138 | 6.893 | 34.74 |
| 84 | ASP | C | 70.643 | 19.193 | 6.028 | 45.86 |
| 85 | ASP | O | 70.614 | 19.383 | 4.778 | 46.01 |
| 86 | ASP | CB | 69.131 | 20.360 | 7.773 | 36.60 |
| 87 | ASP | CG | 67.950 | 21.114 | 7.297 | 41.28 |
| 88 | ASP | OD1 | 67.080 | 20.557 | 6.700 | 43.16 |
| 89 | ASP | OD2 | 67.978 | 22.408 | 7.544 | 44.81 |
| 90 | LYS | N | 71.777 | 19.003 | 6.699 | 41.67 |
| 91 | LYS | CA | 73.008 | 19.033 | 5.954 | 43.82 |
| 92 | LYS | C | 73.035 | 17.928 | 4.864 | 46.27 |
| 93 | LYS | O | 73.357 | 18.177 | 3.709 | 45.13 |
| 94 | LYS | CB | 74.246 | 19.032 | 6.859 | 48.59 |
| 95 | LYS | CG | 74.736 | 17.622 | 7.242 | 93.12 |
| 96 | LYS | CD | 75.455 | 17.518 | 8.604 | 100.00 |
| 97 | LYS | CE | 76.327 | 16.267 | 8.797 | 100.00 |
| 98 | LYS | NZ | 75.740 | 15.262 | 9.683 | 100.00 |
| 99 | SER | N | 72.692 | 16.706 | 5.240 | 40.90 |
| 100 | SER | CA | 72.713 | 15.593 | 4.309 | 41.87 |
| 101 | SER | C | 71.575 | 15.604 | 3.324 | 48.03 |
| 102 | SER | O | 71.464 | 14.678 | 2.502 | 46.24 |
| 103 | SER | CB | 72.726 | 14.225 | 4.998 | 47.13 |
| 104 | SER | OG | 72.148 | 14.254 | 6.292 | 62.32 |
| 105 | GLY | N | 70.729 | 16.629 | 3.441 | 45.84 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 106 | GLY | CA | 69.560 | 16.743 | 2.595 | 46.85 |
| 107 | GLY | C | 68.809 | 15.410 | 2.577 | 51.28 |
| 108 | GLY | O | 68.437 | 14.883 | 1.532 | 56.29 |
| 109 | SER | N | 68.578 | 14.814 | 3.724 | 41.13 |
| 110 | SER | CA | 67.894 | 13.545 | 3.650 | 37.67 |
| 111 | SER | C | 66.529 | 13.420 | 4.344 | 33.83 |
| 112 | SER | O | 66.192 | 12.328 | 4.793 | 32.66 |
| 113 | SER | CB | 68.822 | 12.442 | 4.043 | 39.40 |
| 114 | SER | OG | 69.368 | 12.791 | 5.268 | 49.16 |
| 115 | TRP | N | 65.719 | 14.495 | 4.371 | 28.03 |
| 116 | TRP | CA | 64.390 | 14.413 | 4.947 | 24.69 |
| 117 | TRP | C | 63.521 | 13.375 | 4.242 | 30.79 |
| 118 | TRP | O | 62.773 | 12.639 | 4.915 | 30.44 |
| 119 | TRP | CB | 63.700 | 15.754 | 4.922 | 24.38 |
| 120 | TRP | CG | 64.317 | 16.654 | 5.925 | 24.63 |
| 121 | TRP | CD1 | 65.208 | 17.670 | 5.685 | 27.42 |
| 122 | TRP | CD2 | 64.101 | 16.581 | 7.359 | 22.65 |
| 123 | TRP | NE1 | 65.553 | 18.274 | 6.893 | 27.47 |
| 124 | TRP | CE2 | 64.916 | 17.588 | 7.946 | 28.99 |
| 125 | TRP | CE3 | 63.346 | 15.749 | 8.195 | 21.13 |
| 126 | TRP | CZ2 | 64.926 | 17.778 | 9.345 | 24.85 |
| 127 | TRP | CZ3 | 63.385 | 15.932 | 9.554 | 20.43 |
| 128 | TRP | CH2 | 64.168 | 16.938 | 10.115 | 21.06 |
| 129 | ALA | N | 63.620 | 13.268 | 2.876 | 26.09 |
| 130 | ALA | CA | 62.799 | 12.286 | 2.153 | 24.22 |
| 131 | ALA | C | 63.096 | 10.865 | 2.571 | 28.29 |
| 132 | ALA | O | 62.214 | 10.029 | 2.737 | 27.06 |
| 133 | ALA | CB | 62.920 | 12.477 | 0.652 | 25.69 |
| 134 | ALA | N | 64.363 | 10.580 | 2.794 | 26.20 |
| 135 | ALA | CA | 64.704 | 9.238 | 3.195 | 26.43 |
| 136 | ALA | C | 64.197 | 8.932 | 4.602 | 31.50 |
| 137 | ALA | O | 63.581 | 7.885 | 4.927 | 27.14 |
| 138 | ALA | CB | 66.210 | 9.022 | 3.107 | 26.43 |
| 139 | ILE | N | 64.482 | 9.876 | 5.467 | 28.04 |
| 140 | ILE | CA | 64.042 | 9.728 | 6.826 | 25.50 |
| 141 | ILE | C | 62.562 | 9.449 | 6.863 | 27.81 |
| 142 | ILE | O | 62.053 | 8.525 | 7.520 | 28.96 |
| 143 | ILE | CB | 64.267 | 11.063 | 7.477 | 28.83 |
| 144 | ILE | CG1 | 65.751 | 11.246 | 7.430 | 30.75 |
| 145 | ILE | CG2 | 63.815 | 11.019 | 8.941 | 29.55 |
| 146 | ILE | CD1 | 66.368 | 10.532 | 8.621 | 40.82 |
| 147 | TYR | N | 61.873 | 10.317 | 6.156 | 25.16 |
| 148 | TYR | CA | 60.436 | 10.229 | 6.111 | 24.00 |
| 149 | TYR | C | 59.987 | 8.882 | 5.562 | 28.75 |
| 150 | TYR | O | 59.127 | 8.228 | 6.160 | 24.95 |
| 151 | TYR | CB | 59.814 | 11.445 | 5.419 | 23.47 |
| 152 | TYR | CG | 58.290 | 11.319 | 5.304 | 24.07 |
| 153 | TYR | CD1 | 57.449 | 11.372 | 6.424 | 25.26 |
| 154 | TYR | CD2 | 57.674 | 11.154 | 4.064 | 24.94 |
| 155 | TYR | CE1 | 56.060 | 11.231 | 6.357 | 22.60 |
| 156 | TYR | CE2 | 56.279 | 11.044 | 3.962 | 24.32 |
| 157 | TYR | CZ | 55.470 | 11.103 | 5.101 | 22.19 |
| 158 | TYR | OH | 54.112 | 11.014 | 4.979 | 21.43 |
| 159 | GLN | N | 60.604 | 8.446 | 4.440 | 26.68 |
| 160 | GLN | CA | 60.271 | 7.134 | 3.869 | 25.28 |
| 161 | GLN | C | 60.553 | 6.006 | 4.861 | 26.17 |
| 162 | GLN | O | 59.857 | 4.992 | 4.963 | 26.54 |
| 163 | GLN | CB | 61.021 | 6.871 | 2.543 | 27.78 |
| 164 | GLN | CG | 62.409 | 6.217 | 2.796 | 84.03 |
| 165 | GLN | CD | 63.607 | 6.501 | 1.839 | 100.00 |
| 166 | GLN | OE1 | 64.737 | 6.062 | 2.164 | 98.42 |
| 167 | GLN | NE2 | 63.414 | 7.188 | 0.676 | 76.48 |
| 168 | ASP | N | 61.596 | 6.176 | 5.640 | 24.54 |
| 169 | ASP | CA | 61.862 | 5.128 | 6.590 | 28.47 |
| 170 | ASP | C | 60.721 | 4.997 | 7.550 | 29.84 |
| 171 | ASP | O | 60.290 | 3.884 | 7.886 | 28.51 |
| 172 | ASP | CB | 63.220 | 5.284 | 7.314 | 35.64 |
| 173 | ASP | CG | 64.331 | 5.565 | 6.310 | 80.96 |
| 174 | ASP | OD1 | 64.144 | 5.579 | 5.099 | 89.73 |
| 175 | ASP | OD2 | 65.510 | 5.815 | 6.842 | 91.88 |
| 176 | ILE | N | 60.210 | 6.141 | 7.974 | 24.27 |
| 177 | ILE | CA | 59.060 | 6.052 | 8.889 | 24.52 |
| 178 | ILE | C | 57.903 | 5.367 | 8.255 | 24.70 |
| 179 | ILE | O | 57.252 | 4.522 | 8.841 | 25.35 |
| 180 | ILE | CB | 58.619 | 7.415 | 9.401 | 27.95 |
| 181 | ILE | CG1 | 59.610 | 7.838 | 10.487 | 28.44 |
| 182 | ILE | CG2 | 57.225 | 7.315 | 9.999 | 23.89 |
| 183 | ILE | CD1 | 59.930 | 9.302 | 10.343 | 27.02 |
| 184 | ARG | N | 57.646 | 5.725 | 7.020 | 22.44 |
| 185 | ARG | CA | 56.511 | 5.098 | 6.330 | 22.70 |
| 186 | ARG | C | 56.702 | 3.601 | 6.226 | 26.26 |
| 187 | ARG | O | 55.761 | 2.788 | 6.333 | 23.08 |
| 188 | ARG | CB | 56.366 | 5.662 | 4.905 | 27.59 |
| 189 | ARG | CG | 55.825 | 7.104 | 4.773 | 27.34 |
| 190 | ARG | CD | 55.228 | 7.330 | 3.376 | 30.48 |
| 191 | ARG | NE | 54.182 | 8.369 | 3.362 | 86.57 |
| 192 | ARG | CZ | 53.614 | 8.942 | 2.268 | 100.00 |
| 193 | ARG | NH1 | 53.954 | 8.615 | 1.006 | 100.00 |
| 194 | ARG | NH2 | 52.685 | 9.890 | 2.445 | 33.19 |
| 195 | HIS | N | 57.967 | 3.235 | 5.974 | 26.18 |
| 196 | HIS | CA | 58.297 | 1.840 | 5.840 | 28.26 |
| 197 | HIS | C | 57.980 | 0.991 | 7.099 | 30.43 |
| 198 | HIS | O | 57.474 | −0.179 | 7.075 | 22.68 |
| 199 | HIS | CB | 59.770 | 1.728 | 5.431 | 32.89 |
| 200 | HIS | CG | 60.149 | 0.296 | 5.206 | 42.37 |
| 201 | HIS | ND1 | 60.626 | −0.504 | 6.250 | 47.99 |
| 202 | HIS | CD2 | 60.082 | −0.474 | 4.078 | 47.47 |
| 203 | HIS | CE1 | 60.816 | −1.726 | 5.745 | 48.95 |
| 204 | HIS | NE2 | 60.502 | −1.747 | 4.449 | 48.75 |
| 205 | GLU | N | 58.321 | 1.588 | 8.255 | 30.06 |
| 206 | GLU | CA | 58.143 | 0.866 | 9.524 | 28.09 |
| 207 | GLU | C | 56.806 | 1.041 | 10.196 | 27.30 |
| 208 | GLU | O | 56.503 | 0.399 | 11.193 | 27.94 |
| 209 | GLU | CB | 59.244 | 1.273 | 10.531 | 30.97 |
| 210 | GLU | CG | 60.629 | 1.547 | 9.904 | 54.48 |
| 211 | GLU | CD | 61.444 | 2.586 | 10.685 | 100.00 |
| 212 | GLU | OE1 | 61.742 | 2.444 | 11.872 | 100.00 |
| 213 | GLU | OE2 | 61.812 | 3.644 | 9.973 | 100.00 |
| 214 | ALA | N | 55.999 | 1.936 | 9.673 | 21.78 |
| 215 | ALA | CA | 54.703 | 2.217 | 10.276 | 19.05 |
| 216 | ALA | C | 53.882 | 0.959 | 10.372 | 26.56 |
| 217 | ALA | O | 53.939 | 0.125 | 9.462 | 25.40 |
| 218 | ALA | CB | 53.944 | 3.236 | 9.423 | 20.42 |
| 219 | SER | N | 53.081 | 0.847 | 11.465 | 21.44 |
| 220 | SER | CA | 52.234 | −0.307 | 11.732 | 19.39 |
| 221 | SER | C | 51.225 | −0.517 | 10.663 | 27.89 |
| 222 | SER | O | 50.657 | 0.440 | 10.137 | 25.51 |
| 223 | SER | CB | 51.412 | −0.049 | 12.974 | 21.80 |
| 224 | SER | OG | 52.257 | 0.317 | 14.021 | 26.89 |
| 225 | ASP | N | 50.935 | −1.779 | 10.428 | 27.10 |
| 226 | ASP | CA | 49.936 | −2.129 | 9.448 | 29.07 |
| 227 | ASP | C | 48.895 | −2.997 | 10.125 | 30.02 |
| 228 | ASP | O | 49.166 | −4.133 | 10.484 | 31.00 |
| 229 | ASP | CB | 50.631 | −2.786 | 8.250 | 33.50 |
| 230 | ASP | CG | 49.690 | −3.348 | 7.216 | 50.19 |
| 231 | ASP | OD1 | 48.519 | −3.040 | 7.156 | 46.03 |
| 232 | ASP | OD2 | 50.278 | −4.185 | 6.378 | 67.71 |
| 233 | PHE | N | 47.737 | −2.422 | 10.384 | 20.70 |
| 234 | PHE | CA | 46.675 | −3.127 | 11.085 | 19.53 |
| 235 | PHE | C | 45.446 | −3.117 | 10.216 | 25.93 |
| 236 | PHE | O | 45.307 | −2.281 | 9.357 | 28.17 |
| 237 | PHE | CB | 46.339 | −2.422 | 12.436 | 19.46 |
| 238 | PHE | CG | 47.428 | −2.504 | 13.514 | 18.83 |
| 239 | PHE | CD1 | 47.752 | −3.720 | 14.138 | 19.35 |
| 240 | PHE | CD2 | 48.062 | −1.346 | 13.989 | 17.72 |
| 241 | PHE | CE1 | 48.753 | −3.782 | 15.118 | 19.95 |
| 242 | PHE | CE2 | 49.088 | −1.384 | 14.939 | 21.08 |
| 243 | PHE | CZ | 49.410 | −2.611 | 15.530 | 20.14 |
| 244 | PRO | N | 44.534 | −4.031 | 10.446 | 23.52 |
| 245 | PRO | CA | 43.331 | −4.115 | 9.640 | 21.50 |
| 246 | PRO | C | 42.303 | −3.001 | 9.968 | 23.90 |
| 247 | PRO | O | 42.217 | −2.497 | 11.117 | 22.13 |
| 248 | PRO | CB | 42.675 | −5.448 | 10.030 | 22.86 |
| 249 | PRO | CG | 43.276 | −5.845 | 11.381 | 29.00 |
| 250 | PRO | CD | 44.623 | −5.147 | 11.450 | 24.62 |
| 251 | CYS | N | 41.517 | −2.717 | 8.941 | 19.44 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 252 | CYS | CA | 40.442 | -1.753 | 8.931 | 21.26 |
| 253 | CYS | C | 39.268 | -2.405 | 8.253 | 24.35 |
| 254 | CYS | O | 38.706 | -1.890 | 7.289 | 23.90 |
| 255 | CYS | CB | 40.832 | -0.547 | 8.032 | 24.83 |
| 256 | CYS | SG | 42.442 | 0.202 | 8.391 | 31.37 |
| 257 | ARG | N | 38.910 | -3.578 | 8.709 | 21.13 |
| 258 | ARG | CA | 37.877 | -4.281 | 8.029 | 19.87 |
| 259 | ARC | C | 36.558 | -3.582 | 8.150 | 24.13 |
| 260 | ARG | O | 35.758 | -3.569 | 7.221 | 22.22 |
| 261 | ARG | CB | 37.842 | -5.706 | 8.532 | 29.48 |
| 262 | ARG | CG | 36.735 | -5.804 | 9.576 | 76.36 |
| 263 | ARG | GD | 36.827 | -7.051 | 10.450 | 94.77 |
| 264 | ARG | NE | 36.033 | -6.953 | 11.671 | 78.60 |
| 265 | ARG | CZ | 34.718 | -6.843 | 11.637 | 91.25 |
| 266 | ARG | NH1 | 34.073 | -6.801 | 10.466 | 65.21 |
| 267 | ARG | NH2 | 34.032 | -6.768 | 12.785 | 88.97 |
| 268 | VAL | N | 36.307 | -2.961 | 9.284 | 19.02 |
| 269 | VAL | CA | 35.034 | -2.288 | 9.372 | 17.46 |
| 270 | VAL | C | 34.925 | -1.135 | 8.397 | 21.91 |
| 271 | VAL | O | 33.923 | -0.950 | 7.725 | 25.41 |
| 272 | VAL | CB | 34.726 | -1.775 | 10.740 | 17.65 |
| 273 | VAL | CG1 | 33.338 | -1.205 | 10.712 | 17.50 |
| 274 | VAL | CG2 | 34.778 | -2.908 | 11.719 | 19.97 |
| 275 | ALA | N | 35.964 | -0.367 | 8.277 | 17.06 |
| 276 | ALA | CA | 35.933 | 0.744 | 7.364 | 17.17 |
| 277 | ALA | C | 35.664 | 0.295 | 5.949 | 26.79 |
| 278 | ALA | O | 35.129 | 1.038 | 5.135 | 23.44 |
| 279 | ALA | CB | 37.320 | 1.378 | 7.356 | 16.97 |
| 280 | LYS | N | 36.118 | -0.899 | 5.645 | 21.85 |
| 281 | LYS | CA | 35.993 | -1.403 | 4.299 | 23.03 |
| 282 | LYS | C | 34.718 | -2.121 | 4.012 | 26.65 |
| 283 | LYS | O | 34.497 | -2.565 | 2.898 | 29.21 |
| 284 | LYS | CB | 37.201 | -2.228 | 3.868 | 28.38 |
| 285 | LYS | CG | 38.442 | -1.359 | 3.651 | 30.93 |
| 286 | LYS | CD | 38.066 | -0.075 | 2.926 | 50.71 |
| 287 | LYS | CE | 39.121 | 0.512 | 1.999 | 52.15 |
| 288 | LYS | NZ | 38.518 | 1.459 | 1.033 | 53.44 |
| 289 | LEU | N | 33.855 | -2.250 | 4.983 | 26.04 |
| 290 | LEU | CA | 32.594 | -2.885 | 4.664 | 24.42 |
| 291 | LEU | C | 31.830 | -2.075 | 3.603 | 30.28 |
| 292 | LEU | O | 31.830 | -0.856 | 3.588 | 26.94 |
| 293 | LEU | CB | 31.754 | -2.820 | 5.907 | 25.29 |
| 294 | LEU | CG | 31.721 | -4.091 | 6.733 | 31.05 |
| 295 | LEU | CD1 | 32.743 | -5.118 | 6.282 | 30.64 |
| 296 | LEU | CD2 | 31.726 | -3.789 | 8.213 | 25.61 |
| 297 | PRO | N | 31.131 | -2.743 | 2.705 | 33.21 |
| 298 | PRO | CA | 30.345 | -2.081 | 1.660 | 32.26 |
| 299 | PRO | C | 29.470 | -0.982 | 2.155 | 29.80 |
| 300 | PRO | O | 29.435 | 0.086 | 1.598 | 28.50 |
| 301 | PRO | CB | 29.358 | -3.139 | 1.155 | 35.94 |
| 302 | PRO | CG | 29.790 | -4.443 | 1.815 | 42.24 |
| 303 | PRO | CD | 31.159 | -4.194 | 2.448 | 36.58 |
| 304 | LYS | N | 28.732 | -1.278 | 3.191 | 29.93 |
| 305 | LYS | CA | 27.805 | -0.291 | 3.727 | 29.87 |
| 306 | LYS | C | 28.449 | 1.003 | 4.192 | 32.15 |
| 307 | LYS | O | 27.751 | 2.019 | 4.352 | 29.62 |
| 308 | LYS | CB | 26.915 | -0.840 | 4.835 | 28.99 |
| 309 | LYS | CG | 27.683 | -1.496 | 5.963 | 32.04 |
| 310 | LYS | CD | 26.911 | -1.359 | 7.260 | 40.42 |
| 311 | LYS | CE | 27.142 | -2.452 | 8.303 | 54.33 |
| 312 | LYS | NZ | 26.267 | -2.273 | 9.466 | 72.90 |
| 313 | ASN | N | 29.760 | 0.960 | 4.440 | 25.44 |
| 314 | ASN | CA | 30.439 | 2.153 | 4.930 | 24.36 |
| 315 | ASN | C | 31.136 | 2.942 | 3.817 | 25.64 |
| 316 | ASN | O | 31.853 | 3.900 | 4.038 | 22.73 |
| 317 | ASN | CB | 31.454 | 1.740 | 6.025 | 21.85 |
| 318 | ASN | CG | 30.756 | 1.221 | 7.234 | 27.10 |
| 319 | ASN | OD1 | 29.741 | 1.774 | 7.597 | 21.43 |
| 320 | ASN | ND2 | 31.308 | 0.206 | 7.912 | 22.00 |
| 321 | LYS | N | 30.958 | 2.531 | 2.601 | 23.30 |
| 322 | LYS | CA | 31.685 | 3.175 | 1.546 | 23.68 |
| 323 | LYS | C | 31.498 | 4.684 | 1.542 | 26.11 |
| 324 | LYS | O | 32.434 | 5.476 | 1.385 | 22.38 |
| 325 | LYS | CB | 31.187 | 2.608 | 0.225 | 26.88 |
| 326 | LYS | CG | 32.036 | 2.987 | -0.968 | 54.66 |
| 327 | LYS | CD | 32.007 | 1.947 | -2.079 | 92.45 |
| 328 | LYS | CE | 31.689 | 2.503 | -3.474 | 100.00 |
| 329 | LYS | NZ | 31.185 | 1.538 | -4.438 | 100.00 |
| 330 | ASN | N | 30.233 | 5.068 | 1.662 | 22.80 |
| 331 | ASN | CA | 29.878 | 6.469 | 1.650 | 21.26 |
| 332 | ASN | C | 30.177 | 7.203 | 2.973 | 24.59 |
| 333 | ASN | O | 29.802 | 8.367 | 3.135 | 21.48 |
| 334 | ASN | CB | 28.430 | 6.739 | 1.159 | 19.81 |
| 335 | ASN | CG | 27.389 | 6.329 | 2.191 | 32.17 |
| 336 | ASN | OD1 | 27.700 | 5.966 | 3.344 | 25.99 |
| 337 | ASN | ND2 | 26.147 | 6.335 | 1.765 | 32.33 |
| 338 | ARG | N | 30.877 | 6.548 | 3.904 | 20.39 |
| 339 | ARG | CA | 31.241 | 7.201 | 5.150 | 18.64 |
| 340 | ARG | C | 32.702 | 7.535 | 5.136 | 20.09 |
| 341 | ARG | O | 33.225 | 8.042 | 6.113 | 20.82 |
| 342 | ARG | CB | 30.866 | 6.366 | 6.369 | 15.80 |
| 343 | ARG | CG | 29.337 | 6.275 | 6.511 | 24.13 |
| 344 | ARG | CD | 28.894 | 5.471 | 7.752 | 21.03 |
| 345 | ARG | NE | 27.448 | 5.428 | 7.873 | 21.48 |
| 346 | ARG | CZ | 26.841 | 5.336 | 9.030 | 28.21 |
| 347 | ARG | NH1 | 27.509 | 5.294 | 10.182 | 18.63 |
| 348 | ARG | NH2 | 25.519 | 5.288 | 9.033 | 23.12 |
| 349 | ASN | N | 33.389 | 7.218 | 4.039 | 18.29 |
| 350 | ASN | CA | 34.816 | 7.469 | 3.950 | 17.44 |
| 351 | ASN | C | 35.125 | 8.452 | 2.881 | 20.28 |
| 352 | ASN | O | 34.710 | 8.264 | 1.761 | 19.07 |
| 353 | ASN | CB | 35.593 | 6.181 | 3.663 | 15.55 |
| 354 | ASN | CG | 35.466 | 5.220 | 4.807 | 17.95 |
| 355 | ASN | OD1 | 35.682 | 5.568 | 5.952 | 17.27 |
| 356 | ASN | ND2 | 35.117 | 3.964 | 4.489 | 18.68 |
| 357 | ARG | N | 35.848 | 9.504 | 3.241 | 17.03 |
| 358 | ARG | CA | 36.149 | 10.550 | 2.276 | 16.04 |
| 359 | ARG | C | 37.140 | 10.084 | 1.227 | 21.28 |
| 360 | ARG | O | 37.000 | 10.388 | 0.049 | 17.65 |
| 361 | ARG | CB | 36.633 | 11.840 | 2.983 | 13.55 |
| 362 | ARG | CG | 37.024 | 12.938 | 2.016 | 13.76 |
| 363 | ARG | CD | 37.420 | 14.200 | 2.774 | 16.51 |
| 364 | ARG | NE | 36.224 | 14.791 | 3.392 | 18.16 |
| 365 | ARG | CZ | 35.306 | 15.542 | 2.703 | 26.85 |
| 366 | ARG | NH1 | 35.365 | 15.811 | 1.381 | 20.84 |
| 367 | ARG | NH2 | 34.234 | 16.012 | 3.341 | 16.64 |
| 368 | TYR | N | 38.164 | 9.354 | 1.679 | 17.86 |
| 369 | TYR | CA | 39.233 | 8.872 | 0.832 | 15.41 |
| 370 | TYR | C | 39.411 | 7.359 | 0.980 | 22.83 |
| 371 | TYR | O | 39.443 | 6.781 | 2.075 | 16.42 |
| 372 | TYR | CB | 40.562 | 9.498 | 1.157 | 14.29 |
| 373 | TYR | CG | 40.539 | 11.006 | 1.106 | 18.83 |
| 374 | TYR | CD1 | 40.543 | 11.605 | -0.152 | 18.23 |
| 375 | TYR | CD2 | 40.543 | 11.799 | 2.270 | 17.14 |
| 376 | TYR | CE1 | 40.467 | 12.989 | -0.282 | 17.99 |
| 377 | TYR | CE2 | 40.519 | 13.195 | 2.150 | 16.12 |
| 378 | TYR | CZ | 40.508 | 13.767 | 0.872 | 18.16 |
| 379 | TYR | OH | 40.491 | 15.147 | 0.711 | 18.89 |
| 380 | ARG | N | 39.483 | 6.735 | -0.189 | 21.95 |
| 381 | ARG | CA | 39.577 | 5.315 | -0.261 | 21.42 |
| 382 | ARG | C | 40.844 | 4.775 | 0.390 | 18.55 |
| 383 | ARG | O | 40.869 | 3.647 | 0.838 | 20.34 |
| 384 | ARG | CB | 39.306 | 4.858 | -1.720 | 21.50 |
| 385 | ARG | CG | 40.427 | 4.051 | -2.346 | 62.10 |
| 386 | ARG | CD | 41.233 | 4.684 | -3.494 | 83.64 |
| 387 | ARG | NE | 42.611 | 4.161 | -3.438 | 100.00 |
| 388 | ARG | CZ | 43.771 | 4.841 | -3.523 | 100.00 |
| 389 | ARG | NH1 | 43.842 | 6.149 | -3.796 | 52.01 |
| 390 | ARG | NH2 | 44.910 | 4.155 | -3.451 | 95.71 |
| 391 | ASP | N | 41.862 | 5.576 | 0.492 | 14.95 |
| 392 | ASP | CA | 43.082 | 5.093 | 1.065 | 15.39 |
| 393 | ASP | C | 43.336 | 5.554 | 2.490 | 20.93 |
| 394 | ASP | O | 44.434 | 5.386 | 3.007 | 20.89 |
| 395 | ASP | CB | 44.260 | 5.583 | 0.229 | 16.63 |
| 396 | ASP | CG | 44.232 | 7.082 | 0.082 | 22.24 |
| 397 | ASP | OD1 | 43.217 | 7.738 | 0.070 | 21.30 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 398 | ASP | OD2 | 45.394 | 7.561 | −0.238 | 19.13 |
| 399 | VAL | N | 42.347 | 6.156 | 3.118 | 16.50 |
| 400 | VAL | CA | 42.521 | 6.606 | 4.512 | 15.25 |
| 401 | VAL | C | 41.410 | 6.066 | 5.346 | 14.75 |
| 402 | VAL | O | 40.238 | 6.504 | 5.271 | 14.44 |
| 403 | VAL | CB | 42.451 | 8.123 | 4.686 | 17.27 |
| 404 | VAL | CG1 | 42.721 | 8.517 | 6.182 | 13.83 |
| 405 | VAL | CG2 | 43.493 | 8.755 | 3.753 | 16.91 |
| 406 | SER | N | 41.767 | 5.113 | 6.158 | 15.99 |
| 407 | SER | CA | 40.760 | 4.485 | 6.993 | 17.42 |
| 408 | SER | C | 41.244 | 4.320 | 8.405 | 19.32 |
| 409 | SER | O | 42.424 | 4.173 | 8.656 | 18.77 |
| 410 | SER | CB | 40.514 | 3.028 | 6.484 | 22.19 |
| 411 | SER | OG | 40.054 | 3.029 | 5.131 | 21.85 |
| 412 | PRO | N | 40.292 | 4.229 | 9.316 | 17.04 |
| 413 | PRO | CA | 40.684 | 3.951 | 10.686 | 14.95 |
| 414 | PRO | C | 40.991 | 2.428 | 10.873 | 21.72 |
| 415 | PRO | O | 40.275 | 1.571 | 10.353 | 21.93 |
| 416 | PRO | CB | 39.423 | 4.252 | 11.548 | 14.87 |
| 417 | PRO | CG | 38.238 | 4.153 | 10.604 | 18.96 |
| 418 | PRO | CD | 38.800 | 4.338 | 9.177 | 15.06 |
| 419 | PHE | N | 42.019 | 2.096 | 11.691 | 19.00 |
| 420 | PHE | CA | 42.266 | 0.711 | 12.046 | 16.26 |
| 421 | PHE | C | 41.099 | 0.239 | 12.907 | 20.51 |
| 422 | PHE | O | 40.517 | 0.996 | 13.712 | 18.21 |
| 423 | PHE | CB | 43.484 | 0.629 | 12.972 | 16.62 |
| 424 | PHE | CG | 44.768 | 0.998 | 12.290 | 16.69 |
| 425 | PHE | CD1 | 45.003 | 0.566 | 10.991 | 17.42 |
| 426 | PHE | CD2 | 45.748 | 1.751 | 12.951 | 16.19 |
| 427 | PHE | CE1 | 46.217 | 0.883 | 10.383 | 17.05 |
| 428 | PHE | CE2 | 46.957 | 2.090 | 12.351 | 17.24 |
| 429 | PHE | CZ | 47.157 | 1.686 | 11.030 | 15.76 |
| 430 | ASP | N | 40.774 | −1.056 | 12.819 | 19.69 |
| 431 | ASP | CA | 39.725 | −1.541 | 13.645 | 19.38 |
| 432 | ASP | C | 40.050 | −1.394 | 15.135 | 22.03 |
| 433 | ASP | O | 39.169 | −1.155 | 15.966 | 20.90 |
| 434 | ASP | CB | 39.442 | −3.033 | 13.331 | 21.07 |
| 435 | ASP | CG | 38.887 | −3.204 | 11.964 | 26.66 |
| 436 | ASP | OD1 | 38.132 | −2.404 | 11.443 | 25.86 |
| 437 | ASP | OD2 | 39.391 | −4.217 | 11.336 | 29.95 |
| 438 | HIS | N | 41.288 | −1.623 | 15.513 | 16.04 |
| 439 | HIS | CA | 41.509 | −1.608 | 16.924 | 16.58 |
| 440 | HIS | C | 41.355 | −0.281 | 17.634 | 25.32 |
| 441 | HIS | O | 41.100 | −0.239 | 18.870 | 24.53 |
| 442 | HIS | CB | 42.856 | −2.240 | 17.272 | 15.76 |
| 443 | HIS | CG | 44.037 | −1.338 | 17.088 | 17.63 |
| 444 | HIS | ND1 | 44.449 | −0.441 | 18.079 | 19.17 |
| 445 | HIS | CD2 | 44.890 | −1.230 | 16.041 | 16.56 |
| 446 | HIS | CE1 | 45.560 | 0.159 | 17.644 | 17.00 |
| 447 | HIS | NE2 | 45.831 | −0.298 | 16.427 | 17.69 |
| 448 | SER | N | 41.535 | 0.808 | 16.896 | 18.44 |
| 449 | SER | CA | 41.467 | 2.102 | 17.571 | 17.07 |
| 450 | SER | C | 40.307 | 2.966 | 17.101 | 24.02 |
| 451 | SER | O | 40.171 | 4.125 | 17.523 | 19.51 |
| 452 | SER | CB | 42.776 | 2.867 | 17.350 | 17.91 |
| 453 | SER | OG | 43.130 | 2.848 | 15.967 | 18.63 |
| 454 | ARG | N | 39.469 | 2.429 | 16.223 | 18.61 |
| 455 | ARG | CA | 38.403 | 3.278 | 15.711 | 17.44 |
| 456 | ARG | C | 37.438 | 3.714 | 16.763 | 21.37 |
| 457 | ARG | O | 37.179 | 2.969 | 17.729 | 21.12 |
| 458 | ARG | CB | 37.602 | 2.640 | 14.577 | 20.23 |
| 459 | ARG | CG | 36.621 | 1.515 | 15.009 | 21.54 |
| 460 | ARG | CD | 35.968 | 0.725 | 13.835 | 24.77 |
| 461 | ARG | NE | 34.948 | −0.234 | 14.300 | 23.61 |
| 462 | ARG | CZ | 33.667 | 0.024 | 14.419 | 28.43 |
| 463 | ARG | NH1 | 33.166 | 1.215 | 14.106 | 17.26 |
| 464 | ARG | NH2 | 32.865 | −0.945 | 14.886 | 22.24 |
| 465 | ILE | N | 36.814 | 4.891 | 16.529 | 20.42 |
| 466 | ILE | CA | 35.777 | 5.390 | 17.455 | 17.73 |
| 467 | ILE | C | 34.431 | 4.780 | 17.042 | 23.53 |
| 468 | ILE | O | 34.021 | 4.855 | 15.864 | 19.57 |
| 469 | ILE | CB | 35.640 | 6.925 | 17.449 | 18.61 |
| 470 | ILE | CG1 | 36.949 | 7.648 | 17.816 | 16.90 |
| 471 | ILE | CG2 | 34.493 | 7.340 | 18.369 | 19.54 |
| 472 | ILE | CD1 | 37.390 | 7.446 | 19.280 | 23.50 |
| 473 | LYS | N | 33.724 | 4.181 | 18.014 | 17.77 |
| 474 | LYS | CA | 32.479 | 3.661 | 17.638 | 19.44 |
| 475 | LYS | C | 31.329 | 4.585 | 18.080 | 23.14 |
| 476 | LYS | O | 31.307 | 5.073 | 19.222 | 23.03 |
| 477 | LYS | CB | 32.343 | 2.312 | 18.288 | 25.11 |
| 478 | LYS | CG | 33.271 | 1.269 | 17.706 | 28.50 |
| 479 | LYS | CD | 32.904 | −0.078 | 18.301 | 42.01 |
| 480 | LYS | CE | 34.060 | −1.057 | 18.404 | 50.09 |
| 481 | LYS | NZ | 33.628 | −2.377 | 18.900 | 65.13 |
| 482 | LEU | N | 30.358 | 4.822 | 17.187 | 19.37 |
| 483 | LEU | CA | 29.173 | 5.650 | 17.536 | 19.21 |
| 484 | LEU | C | 28.311 | 4.790 | 18.451 | 30.47 |
| 485 | LEU | O | 28.311 | 3.555 | 18.264 | 27.66 |
| 486 | LEU | CB | 28.346 | 5.917 | 16.283 | 18.17 |
| 487 | LEU | CG | 29.225 | 6.632 | 15.268 | 20.04 |
| 488 | LEU | CD1 | 28.533 | 6.828 | 13.952 | 17.50 |
| 489 | LEU | CD2 | 29.630 | 7.998 | 15.864 | 17.41 |
| 490 | HIS | N | 27.616 | 5.406 | 19.435 | 24.92 |
| 491 | HIS | CA | 26.790 | 4.616 | 20.333 | 23.96 |
| 492 | HIS | C | 25.439 | 4.506 | 19.717 | 34.63 |
| 493 | HIS | O | 24.491 | 5.195 | 20.064 | 38.67 |
| 494 | HIS | CB | 26.695 | 5.217 | 21.719 | 24.41 |
| 495 | HIS | CG | 28.030 | 5.381 | 22.372 | 29.98 |
| 496 | HIS | ND1 | 28.197 | 6.121 | 23.570 | 33.91 |
| 497 | HIS | CD2 | 29.258 | 4.908 | 21.994 | 31.10 |
| 498 | HIS | CE1 | 29.504 | 6.052 | 23.881 | 33.12 |
| 499 | HIS | NE2 | 30.159 | 5.332 | 22.951 | 32.31 |
| 500 | GLN | N | 25.367 | 3.685 | 18.712 | 38.08 |
| 501 | GLN | CA | 24.103 | 3.522 | 18.003 | 41.99 |
| 502 | GLN | C | 24.077 | 2.125 | 17.437 | 46.43 |
| 503 | GLN | O | 25.111 | 1.523 | 17.202 | 42.03 |
| 504 | GLN | CB | 23.751 | 4.631 | 16.958 | 43.94 |
| 505 | GLN | CG | 24.597 | 4.425 | 15.691 | 50.12 |
| 506 | GLN | CD | 24.204 | 5.284 | 14.508 | 78.89 |
| 507 | GLN | OE1 | 24.235 | 6.526 | 14.622 | 72.88 |
| 508 | GLN | NE2 | 23.934 | 4.636 | 13.354 | 62.05 |
| 509 | GLU | N | 22.876 | 1.603 | 17.293 | 50.52 |
| 510 | GLU | CA | 22.676 | 0.234 | 16.832 | 53.51 |
| 511 | GLU | C | 22.637 | 0.058 | 15.328 | 53.08 |
| 512 | GLU | O | 23.006 | −0.999 | 14.825 | 48.73 |
| 513 | GLU | CB | 21.441 | −0.418 | 17.510 | 56.24 |
| 514 | GLU | CG | 21.550 | −0.429 | 19.051 | 74.99 |
| 515 | GLU | CD | 20.383 | −1.136 | 19.705 | 100.00 |
| 516 | GLU | OE1 | 19.203 | −0.939 | 19.368 | 100.00 |
| 517 | GLU | OE2 | 20.768 | −2.009 | 20.636 | 100.00 |
| 518 | ASP | N | 22.170 | 1.083 | 14.619 | 50.94 |
| 519 | ASP | CA | 22.101 | 0.990 | 13.183 | 52.56 |
| 520 | ASP | C | 23.492 | 0.706 | 12.532 | 50.81 |
| 521 | ASP | O | 23.723 | −0.285 | 11.795 | 54.32 |
| 522 | ASP | CB | 21.388 | 2.250 | 12.634 | 57.77 |
| 523 | ASP | CG | 21.808 | 2.668 | 11.243 | 94.02 |
| 524 | ASP | OD1 | 21.577 | 1.977 | 10.250 | 99.87 |
| 525 | ASP | OD2 | 22.439 | 3.847 | 11.214 | 100.00 |
| 526 | ASN | N | 24.444 | 1.597 | 12.808 | 34.60 |
| 527 | ASN | CA | 25.773 | 1.475 | 12.236 | 28.07 |
| 528 | ASN | C | 26.669 | 2.345 | 13.088 | 29.15 |
| 529 | ASN | O | 26.536 | 3.556 | 13.101 | 30.48 |
| 530 | ASN | CB | 25.734 | 2.022 | 10.803 | 19.62 |
| 531 | ASN | CG | 27.024 | 1.823 | 10.062 | 27.76 |
| 532 | ASN | OD1 | 28.067 | 1.547 | 10.679 | 22.79 |
| 533 | ASN | ND2 | 26.967 | 1.995 | 8.729 | 21.65 |
| 534 | ASP | N | 27.600 | 1.752 | 13.806 | 22.25 |
| 535 | ASP | CA | 28.430 | 2.534 | 14.667 | 20.02 |
| 536 | ASP | C | 29.676 | 3.124 | 14.011 | 22.15 |
| 537 | ASP | O | 30.575 | 3.603 | 14.710 | 22.95 |
| 538 | ASP | CB | 28.858 | 1.548 | 15.757 | 21.84 |
| 539 | ASP | CG | 29.803 | 0.461 | 15.282 | 26.22 |
| 540 | ASP | OD1 | 30.328 | 0.421 | 14.195 | 26.63 |
| 541 | ASP | OD2 | 30.146 | −0.355 | 16.235 | 35.64 |
| 542 | TYR | N | 29.794 | 3.001 | 12.697 | 19.04 |
| 543 | TYR | CA | 31.033 | 3.440 | 12.034 | 16.92 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 544 | TYR | C | 31.184 | 4.931 | 11.701 | 22.03 |
| 545 | TYR | O | 30.325 | 5.601 | 11.107 | 22.84 |
| 546 | TYR | CB | 31.149 | 2.733 | 10.691 | 16.06 |
| 547 | TYR | CG | 32.412 | 3.169 | 9.987 | 17.61 |
| 548 | TYR | CD1 | 33.645 | 2.670 | 10.425 | 20.91 |
| 549 | TYR | CD2 | 32.403 | 4.043 | 8.886 | 16.20 |
| 550 | TYR | CE1 | 34.857 | 3.065 | 9.828 | 19.50 |
| 551 | TYR | CE2 | 33.596 | 4.460 | 8.282 | 13.17 |
| 552 | TYR | CZ | 34.818 | 3.973 | 8.769 | 14.97 |
| 553 | TYR | OH | 36.004 | 4.360 | 8.214 | 18.92 |
| 554 | ILE | N | 32.319 | 5.440 | 12.061 | 19.32 |
| 555 | ILE | CA | 32.752 | 6.780 | 11.682 | 17.75 |
| 556 | ILE | C | 34.257 | 6.676 | 11.366 | 16.65 |
| 557 | ILE | O | 35.022 | 5.912 | 11.984 | 14.78 |
| 558 | ILE | CB | 32.460 | 7.883 | 12.709 | 18.72 |
| 559 | ILE | CG1 | 32.923 | 9.269 | 12.196 | 17.13 |
| 560 | ILE | CG2 | 33.132 | 7.524 | 14.066 | 19.79 |
| 561 | ILE | CD1 | 32.357 | 10.364 | 13.106 | 16.24 |
| 562 | ASN | N | 34.721 | 7.445 | 10.394 | 14.05 |
| 563 | ASN | CA | 36.134 | 7.408 | 10.072 | 12.04 |
| 564 | ASN | C | 36.861 | 8.263 | 11.062 | 18.49 |
| 565 | ASN | O | 37.028 | 9.462 | 10.808 | 16.53 |
| 566 | ASN | CB | 36.392 | 7.908 | 8.637 | 10.31 |
| 567 | ASN | CG | 37.806 | 7.615 | 8.161 | 18.51 |
| 568 | ASN | OD1 | 38.803 | 7.928 | 8.840 | 17.25 |
| 569 | ASN | ND2 | 37.914 | 7.096 | 6.948 | 13.86 |
| 570 | ALA | N | 37.206 | 7.670 | 12.215 | 15.81 |
| 571 | ALA | CA | 37.822 | 8.363 | 13.318 | 15.05 |
| 572 | ALA | C | 38.551 | 7.400 | 14.203 | 17.50 |
| 573 | ALA | O | 38.093 | 6.297 | 14.414 | 15.99 |
| 574 | ALA | CB | 36.768 | 9.111 | 14.121 | 15.21 |
| 575 | SER | N | 39.670 | 7.856 | 14.752 | 13.78 |
| 576 | SER | CA | 40.518 | 7.002 | 15.565 | 14.32 |
| 577 | SER | C | 40.915 | 7.650 | 16.857 | 16.94 |
| 578 | SER | O | 41.210 | 8.834 | 16.908 | 18.12 |
| 579 | SER | CB | 41.859 | 6.766 | 14.820 | 15.23 |
| 580 | SER | OG | 41.642 | 6.232 | 13.488 | 17.37 |
| 581 | LEU | N | 41.046 | 6.853 | 17.898 | 15.51 |
| 582 | LEU | CA | 41.503 | 7.396 | 19.161 | 15.13 |
| 583 | LEU | C | 43.015 | 7.175 | 19.229 | 22.22 |
| 584 | LEU | O | 43.454 | 6.029 | 19.128 | 21.68 |
| 585 | LEU | CB | 40.801 | 6.641 | 20.374 | 16.59 |
| 586 | LEU | CG | 41.333 | 6.988 | 21.784 | 19.94 |
| 587 | LEU | CD1 | 41.053 | 8.438 | 22.118 | 20.86 |
| 588 | LEU | CD2 | 40.611 | 6.204 | 22.847 | 21.37 |
| 589 | ILE | N | 43.797 | 8.247 | 19.421 | 17.07 |
| 590 | ILE | CA | 45.219 | 8.168 | 19.506 | 16.19 |
| 591 | ILE | C | 45.524 | 8.335 | 20.995 | 24.53 |
| 592 | ILE | O | 45.338 | 9.380 | 21.568 | 22.94 |
| 593 | ILE | CB | 45.845 | 9.330 | 18.796 | 18.65 |
| 594 | ILE | CG1 | 45.927 | 9.229 | 17.286 | 18.37 |
| 595 | ILE | CG2 | 47.265 | 9.378 | 19.290 | 21.51 |
| 596 | ILE | CD1 | 44.791 | 8.564 | 16.611 | 25.42 |
| 597 | LYS | N | 45.955 | 7.285 | 21.664 | 20.46 |
| 598 | LYS | CA | 46.162 | 7.350 | 23.092 | 20.79 |
| 599 | LYS | C | 47.630 | 7.299 | 23.390 | 24.25 |
| 600 | LYS | O | 48.236 | 6.260 | 23.159 | 24.06 |
| 601 | LYS | CB | 45.396 | 6.160 | 23.699 | 24.07 |
| 602 | LYS | CG | 44.960 | 6.286 | 25.154 | 48.81 |
| 603 | LYS | CD | 44.128 | 5.081 | 25.617 | 70.96 |
| 604 | LYS | CE | 44.276 | 4.756 | 27.109 | 99.34 |
| 605 | LYS | NZ | 44.076 | 3.328 | 27.445 | 100.00 |
| 606 | MET | N | 48.201 | 8.455 | 23.822 | 22.51 |
| 607 | MET | CA | 49.625 | 8.581 | 24.124 | 20.07 |
| 608 | MET | C | 49.859 | 8.290 | 25.599 | 27.14 |
| 609 | MET | O | 49.758 | 9.141 | 26.462 | 24.51 |
| 610 | MET | CB | 50.266 | 9.882 | 23.647 | 19.62 |
| 611 | MET | CG | 50.032 | 10.097 | 22.162 | 21.13 |
| 612 | MET | SD | 50.570 | 8.761 | 21.081 | 23.27 |
| 613 | MET | CE | 52.316 | 9.093 | 21.055 | 18.81 |
| 614 | GLU | N | 50.136 | 7.023 | 25.830 | 28.15 |
| 615 | GLU | CA | 50.280 | 6.525 | 27.160 | 29.78 |
| 616 | GLU | C | 51.248 | 7.321 | 28.030 | 34.27 |
| 617 | GLU | O | 50.881 | 7.991 | 29.015 | 33.62 |
| 618 | GLU | CB | 50.621 | 5.054 | 27.058 | 30.77 |
| 619 | GLU | CG | 50.491 | 4.307 | 28.379 | 42.42 |
| 620 | GLU | CD | 50.541 | 2.833 | 28.160 | 86.17 |
| 621 | GLU | OE1 | 51.464 | 2.282 | 27.586 | 100.00 |
| 622 | GLU | OE2 | 49.454 | 2.226 | 28.584 | 100.00 |
| 623 | GLU | N | 52.506 | 7.246 | 27.649 | 30.68 |
| 624 | GLU | CA | 53.546 | 7.943 | 28.396 | 31.16 |
| 625 | GLU | C | 53.243 | 9.397 | 28.518 | 35.90 |
| 626 | GLU | O | 53.388 | 9.913 | 29.567 | 36.43 |
| 627 | GLU | CB | 54.865 | 7.737 | 27.681 | 33.02 |
| 628 | GLU | CG | 56.142 | 8.220 | 28.385 | 46.68 |
| 629 | GLU | CD | 57.242 | 8.086 | 27.353 | 78.67 |
| 630 | GLU | OE1 | 57.023 | 7.823 | 26.163 | 59.52 |
| 631 | GLU | OE2 | 58.437 | 8.258 | 27.835 | 84.75 |
| 632 | ALA | N | 52.800 | 10.068 | 27.441 | 34.48 |
| 633 | ALA | CA | 52.488 | 11.493 | 27.524 | 31.47 |
| 634 | ALA | C | 51.242 | 11.736 | 28.308 | 33.12 |
| 635 | ALA | O | 51.028 | 12.820 | 28.781 | 31.13 |
| 636 | ALA | CB | 52.294 | 12.082 | 26.132 | 31.22 |
| 637 | GLN | N | 50.354 | 10.764 | 28.383 | 32.47 |
| 638 | GLN | CA | 49.116 | 11.014 | 29.114 | 35.37 |
| 639 | GLN | C | 48.196 | 12.076 | 28.454 | 39.78 |
| 640 | GLN | O | 47.700 | 13.026 | 29.072 | 40.91 |
| 641 | GLN | CB | 49.434 | 11.386 | 30.560 | 39.09 |
| 642 | GLN | CG | 50.174 | 10.260 | 31.290 | 72.08 |
| 643 | GLN | CD | 49.157 | 9.374 | 31.957 | 100.00 |
| 644 | GLN | OE1 | 48.700 | 9.687 | 33.092 | 100.00 |
| 645 | GLN | NE2 | 48.738 | 8.341 | 31.206 | 99.83 |
| 646 | ARG | N | 47.979 | 11.913 | 27.140 | 28.50 |
| 647 | ARG | CA | 47.086 | 12.751 | 26.374 | 23.58 |
| 648 | ARG | C | 46.524 | 11.885 | 25.282 | 24.24 |
| 649 | ARG | O | 47.232 | 11.052 | 24.744 | 26.56 |
| 650 | ARG | CB | 47.779 | 13.904 | 25.722 | 23.27 |
| 651 | ARG | CG | 46.780 | 14.899 | 25.126 | 26.99 |
| 652 | ARG | CD | 47.361 | 16.299 | 24.960 | 26.70 |
| 653 | ARG | NE | 47.293 | 17.043 | 26.199 | 23.46 |
| 654 | ARG | CZ | 47.954 | 18.135 | 26.422 | 24.69 |
| 655 | ARG | NH1 | 48.785 | 18.663 | 25.532 | 22.83 |
| 656 | ARG | NH2 | 47.826 | 18.721 | 27.596 | 23.63 |
| 657 | SER | N | 45.249 | 12.005 | 25.019 | 19.60 |
| 658 | SER | CA | 44.632 | 11.302 | 23.912 | 18.87 |
| 659 | SER | C | 44.089 | 12.361 | 22.960 | 23.27 |
| 660 | SER | O | 43.869 | 13.515 | 23.332 | 20.11 |
| 661 | SER | CB | 43.455 | 10.478 | 24.343 | 21.80 |
| 662 | SER | OG | 43.930 | 9.552 | 25.250 | 30.13 |
| 663 | TYR | N | 43.820 | 11.959 | 21.724 | 21.22 |
| 664 | TYR | CA | 43.211 | 12.812 | 20.702 | 17.17 |
| 665 | TYR | C | 42.381 | 11.892 | 19.853 | 21.01 |
| 666 | TYR | O | 42.734 | 10.702 | 19.695 | 20.98 |
| 667 | TYR | CB | 44.261 | 13.337 | 19.707 | 18.74 |
| 668 | TYR | CG | 45.522 | 13.929 | 20.298 | 16.73 |
| 669 | TYR | CD1 | 46.618 | 13.125 | 20.576 | 17.39 |
| 670 | TYR | CD2 | 45.619 | 15.309 | 20.511 | 16.87 |
| 671 | TYR | CE1 | 47.790 | 13.694 | 21.079 | 18.92 |
| 672 | TYR | CE2 | 46.773 | 15.899 | 21.033 | 17.15 |
| 673 | TYR | CZ | 47.854 | 15.067 | 21.332 | 23.78 |
| 674 | TYR | OH | 49.001 | 15.602 | 21.876 | 23.03 |
| 675 | ILE | N | 41.328 | 12.435 | 19.274 | 17.07 |
| 676 | ILE | CA | 40.554 | 11.723 | 18.279 | 16.38 |
| 677 | ILE | C | 40.866 | 12.407 | 16.961 | 19.66 |
| 678 | ILE | O | 40.778 | 13.628 | 16.850 | 19.42 |
| 679 | ILE | CB | 39.027 | 11.735 | 18.509 | 21.59 |
| 680 | ILE | CG1 | 38.653 | 10.894 | 19.775 | 21.73 |
| 681 | ILE | CG2 | 38.255 | 11.292 | 17.209 | 19.23 |
| 682 | ILE | CD1 | 37.204 | 11.104 | 20.239 | 19.35 |
| 683 | LEU | N | 41.336 | 11.645 | 16.006 | 15.32 |
| 684 | LEU | CA | 41.675 | 12.234 | 14.715 | 14.26 |
| 685 | LEU | C | 40.656 | 11.756 | 13.748 | 18.37 |
| 686 | LEU | O | 40.389 | 10.571 | 13.738 | 16.49 |
| 687 | LEU | CB | 43.066 | 11.848 | 14.198 | 13.33 |
| 688 | LEU | CG | 44.175 | 12.803 | 14.642 | 17.41 |
| 689 | LEU | CD1 | 45.534 | 12.403 | 13.995 | 16.26 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 690 | LEU | CD2 | 44.281 | 12.897 | 16.182 | 15.86 |
| 691 | THR | N | 40.050 | 12.645 | 12.963 | 14.18 |
| 692 | THR | CA | 39.024 | 12.145 | 12.076 | 13.33 |
| 693 | THR | C | 39.116 | 12.910 | 10.755 | 16.62 |
| 694 | THR | O | 39.788 | 13.946 | 10.696 | 15.02 |
| 695 | THR | CB | 37.644 | 12.338 | 12.815 | 15.01 |
| 696 | THR | OG1 | 36.550 | 11.816 | 12.090 | 15.33 |
| 697 | THR | CG2 | 37.396 | 13.829 | 13.035 | 11.94 |
| 698 | GLN | N | 38.432 | 12.417 | 9.692 | 15.62 |
| 699 | GLN | CA | 38.460 | 13.162 | 8.437 | 14.08 |
| 700 | GLN | C | 37.474 | 14.358 | 8.490 | 16.44 |
| 701 | GLN | O | 36.541 | 14.444 | 9.358 | 16.22 |
| 702 | GLN | CB | 38.017 | 12.224 | 7.323 | 13.86 |
| 703 | GLN | CG | 36.562 | 11.804 | 7.547 | 18.12 |
| 704 | GLN | CD | 35.915 | 10.847 | 6.544 | 19.07 |
| 705 | GLN | OE1 | 34.655 | 10.690 | 6.513 | 19.98 |
| 706 | GLN | NE2 | 36.756 | 10.142 | 5.818 | 11.61 |
| 707 | GLY | N | 37.556 | 15.222 | 7.487 | 15.42 |
| 708 | GLY | CA | 36.598 | 16.340 | 7.384 | 12.58 |
| 709 | GLY | C | 35.252 | 15.724 | 7.143 | 16.22 |
| 710 | GLY | O | 35.067 | 14.965 | 6.204 | 14.03 |
| 711 | PRO | N | 34.274 | 16.005 | 7.986 | 16.60 |
| 712 | PRO | CA | 32.950 | 15.389 | 7.745 | 15.78 |
| 713 | PRO | C | 32.405 | 15.529 | 6.317 | 20.52 |
| 714 | PRO | O | 32.677 | 16.525 | 5.642 | 19.37 |
| 715 | PRO | CB | 32.010 | 16.071 | 8.734 | 15.66 |
| 716 | PRO | CG | 32.902 | 16.749 | 9.800 | 17.67 |
| 717 | PRO | CD | 34.316 | 16.772 | 9.281 | 14.44 |
| 718 | LEU | N | 31.620 | 14.505 | 5.898 | 16.55 |
| 719 | LEU | CA | 30.962 | 14.416 | 4.631 | 14.43 |
| 720 | LEU | C | 29.522 | 14.909 | 4.834 | 22.58 |
| 721 | LEU | O | 29.029 | 14.985 | 5.933 | 20.15 |
| 722 | LEU | CB | 30.952 | 12.997 | 4.038 | 14.77 |
| 723 | LEU | CG | 32.352 | 12.481 | 3.728 | 18.92 |
| 724 | LEU | CD1 | 32.333 | 10.957 | 3.798 | 20.45 |
| 725 | LEU | CD2 | 32.799 | 12.968 | 2.329 | 19.10 |
| 726 | PRO | N | 28.852 | 15.291 | 3.742 | 23.61 |
| 727 | PRO | CA | 27.526 | 15.812 | 3.867 | 23.49 |
| 728 | PRO | C | 26.616 | 14.852 | 4.520 | 26.41 |
| 729 | PRO | O | 25.574 | 15.258 | 4.934 | 30.17 |
| 730 | PRO | CB | 27.017 | 16.030 | 2.454 | 25.04 |
| 731 | PRO | CG | 28.057 | 15.523 | 1.480 | 29.04 |
| 732 | PRO | CD | 29.290 | 15.276 | 2.312 | 23.33 |
| 733 | ASN | N | 26.973 | 13.586 | 4.607 | 21.62 |
| 734 | ASN | CA | 26.068 | 12.632 | 5.237 | 17.84 |
| 735 | ASN | C | 26.608 | 12.193 | 6.557 | 22.95 |
| 736 | ASN | O | 25.978 | 11.361 | 7.233 | 23.70 |
| 737 | ASN | CB | 25.861 | 11.386 | 4.362 | 18.60 |
| 738 | ASN | CG | 27.174 | 10.691 | 3.998 | 24.49 |
| 739 | ASN | OD1 | 28.160 | 11.365 | 3.684 | 24.35 |
| 740 | ASN | ND2 | 27.214 | 9.338 | 4.017 | 24.03 |
| 741 | THR | N | 27.791 | 12.714 | 6.939 | 16.40 |
| 742 | THR | CA | 28.325 | 12.237 | 8.220 | 15.19 |
| 743 | THR | C | 28.433 | 13.364 | 9.223 | 21.17 |
| 744 | THR | O | 29.095 | 13.234 | 10.219 | 19.70 |
| 745 | THR | CB | 29.694 | 11.529 | 8.112 | 18.74 |
| 746 | THR | OG1 | 30.690 | 12.447 | 7.709 | 19.88 |
| 747 | THR | CG2 | 29.683 | 10.379 | 7.103 | 16.93 |
| 748 | CYS | N | 27.783 | 14.491 | 8.970 | 16.82 |
| 749 | CYS | CA | 27.883 | 15.573 | 9.943 | 18.20 |
| 750 | CYS | C | 27.174 | 15.247 | 11.228 | 19.02 |
| 751 | CYS | O | 27.613 | 15.697 | 12.308 | 20.16 |
| 752 | CYS | CB | 27.325 | 16.925 | 9.410 | 19.21 |
| 753 | CYS | SG | 28.252 | 17.458 | 7.951 | 23.17 |
| 754 | GLY | N | 26.054 | 14.501 | 11.125 | 17.59 |
| 755 | GLY | CA | 25.352 | 14.185 | 12.370 | 16.40 |
| 756 | GLY | C | 26.210 | 13.222 | 13.189 | 18.70 |
| 757 | GLY | O | 26.279 | 13.293 | 14.394 | 18.52 |
| 758 | HIS | N | 26.865 | 12.306 | 12.499 | 17.15 |
| 759 | HIS | CA | 27.754 | 11.319 | 13.158 | 17.16 |
| 760 | HIS | C | 28.925 | 12.017 | 13.833 | 20.07 |
| 761 | HIS | O | 29.404 | 11.647 | 14.889 | 20.41 |
| 762 | HIS | CB | 28.393 | 10.342 | 12.120 | 18.16 |
| 763 | HIS | CG | 27.384 | 9.635 | 11.299 | 19.12 |
| 764 | HIS | ND1 | 27.704 | 9.228 | 9.989 | 22.15 |
| 765 | HIS | CD2 | 26.096 | 9.300 | 11.596 | 17.48 |
| 766 | HIS | CE1 | 26.596 | 8.639 | 9.509 | 20.83 |
| 767 | HIS | NE2 | 25.620 | 8.661 | 10.438 | 20.03 |
| 768 | PHE | N | 29.491 | 13.003 | 13.166 | 17.15 |
| 769 | PHE | CA | 30.592 | 13.729 | 13.736 | 15.25 |
| 770 | PHE | C | 30.214 | 14.331 | 15.139 | 22.13 |
| 771 | PHE | O | 30.894 | 14.098 | 16.171 | 21.51 |
| 772 | PHE | CB | 31.025 | 14.822 | 12.736 | 15.12 |
| 773 | PHE | CG | 32.096 | 15.740 | 13.307 | 14.74 |
| 774 | PHE | CD1 | 31.746 | 16.887 | 14.020 | 15.97 |
| 775 | PHE | CD2 | 33.466 | 15.466 | 13.140 | 15.95 |
| 776 | PHE | CE1 | 32.734 | 17.739 | 14.539 | 16.67 |
| 777 | PHE | CE2 | 34.475 | 16.298 | 13.663 | 17.69 |
| 778 | PHE | CZ | 34.095 | 17.428 | 14.398 | 14.91 |
| 779 | TRP | N | 29.096 | 15.088 | 15.168 | 19.55 |
| 780 | TRP | CA | 28.632 | 15.704 | 16.421 | 18.79 |
| 781 | TRP | C | 28.147 | 14.656 | 17.418 | 21.85 |
| 782 | TRP | O | 28.289 | 14.839 | 18.633 | 21.13 |
| 783 | TRP | CB | 27.576 | 16.758 | 16.169 | 16.67 |
| 784 | TRP | CG | 28.210 | 17.904 | 15.491 | 16.11 |
| 785 | TRP | CD1 | 27.962 | 18.318 | 14.214 | 18.99 |
| 786 | TRP | CD2 | 29.206 | 18.776 | 16.023 | 14.97 |
| 787 | TRP | NE1 | 28.768 | 19.412 | 13.916 | 18.96 |
| 788 | TRP | CE2 | 29.547 | 19.692 | 15.015 | 18.62 |
| 789 | TRP | CE3 | 29.867 | 18.880 | 17.250 | 16.41 |
| 790 | TRP | CZ2 | 30.506 | 20.686 | 15.213 | 17.94 |
| 791 | TRP | CZ3 | 30.823 | 19.869 | 17.428 | 16.16 |
| 792 | TRP | CH2 | 31.165 | 20.737 | 16.412 | 16.86 |
| 793 | GLU | N | 27.626 | 13.536 | 16.911 | 17.79 |
| 794 | GLU | CA | 27.268 | 12.489 | 17.811 | 16.48 |
| 795 | GLU | C | 28.499 | 12.004 | 18.561 | 20.28 |
| 796 | GLU | O | 28.480 | 11.817 | 19.780 | 18.97 |
| 797 | GLU | CB | 26.530 | 11.293 | 17.103 | 17.70 |
| 798 | GLU | CG | 26.576 | 10.108 | 18.107 | 18.51 |
| 799 | GLU | CD | 25.985 | 8.904 | 17.457 | 36.95 |
| 800 | GLU | OE1 | 25.635 | 8.939 | 16.304 | 24.52 |
| 801 | GLU | OE2 | 25.828 | 7.845 | 18.231 | 22.85 |
| 802 | MET | N | 29.622 | 11.855 | 17.813 | 16.81 |
| 803 | MET | CA | 30.873 | 11.423 | 18.408 | 15.42 |
| 804 | MET | C | 31.414 | 12.466 | 19.451 | 21.03 |
| 805 | MET | O | 31.916 | 12.180 | 20.552 | 17.41 |
| 806 | MET | CB | 31.905 | 11.171 | 17.275 | 15.36 |
| 807 | MET | CG | 33.296 | 10.921 | 17.815 | 15.60 |
| 808 | MET | SD | 34.527 | 10.644 | 16.486 | 19.45 |
| 809 | MET | CE | 34.636 | 12.330 | 15.779 | 16.29 |
| 810 | VAL | N | 31.345 | 13.741 | 19.059 | 17.81 |
| 811 | VAL | CA | 31.809 | 14.761 | 19.961 | 15.34 |
| 812 | VAL | C | 31.027 | 14.648 | 21.239 | 20.80 |
| 813 | VAL | O | 31.512 | 14.740 | 22.361 | 21.08 |
| 814 | VAL | CB | 31.555 | 16.117 | 19.308 | 18.34 |
| 815 | VAL | CG1 | 31.720 | 17.289 | 20.311 | 17.11 |
| 816 | VAL | CG2 | 32.560 | 16.297 | 18.112 | 16.59 |
| 817 | TRP | N | 29.760 | 14.465 | 21.061 | 23.24 |
| 818 | TRP | CA | 28.891 | 14.345 | 22.223 | 25.45 |
| 819 | TRP | C | 29.223 | 13.143 | 23.061 | 25.99 |
| 820 | TRP | O | 29.403 | 13.249 | 24.269 | 25.20 |
| 821 | TRP | CB | 27.412 | 14.241 | 21.777 | 27.30 |
| 822 | TRP | CG | 26.523 | 14.219 | 22.984 | 30.45 |
| 823 | TRP | CD1 | 26.111 | 13.118 | 23.651 | 33.52 |
| 824 | TRP | CD2 | 25.979 | 15.340 | 23.673 | 31.02 |
| 825 | TRP | NE1 | 25.370 | 13.477 | 24.740 | 33.46 |
| 826 | TRP | CE2 | 25.283 | 14.838 | 24.787 | 36.13 |
| 827 | TRP | CE3 | 26.031 | 16.723 | 23.459 | 35.07 |
| 828 | TRP | CZ2 | 24.642 | 15.693 | 25.691 | 36.39 |
| 829 | TRP | CZ3 | 25.390 | 17.583 | 24.335 | 37.49 |
| 830 | TRP | CH2 | 24.716 | 17.061 | 25.452 | 38.40 |
| 831 | GLU | N | 29.254 | 11.979 | 22.430 | 20.77 |
| 832 | GLU | CA | 29.484 | 10.733 | 23.165 | 19.32 |
| 833 | GLU | C | 30.849 | 10.628 | 23.808 | 24.59 |
| 834 | GLU | O | 30.997 | 10.008 | 24.836 | 22.28 |
| 835 | GLU | CB | 29.255 | 9.492 | 22.281 | 20.24 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 836 | GLU | CG | 27.769 | 9.267 | 21.915 | 22.70 |
| 837 | GLU | CD | 27.538 | 8.382 | 20.721 | 31.58 |
| 838 | GLU | OE1 | 28.422 | 7.828 | 20.071 | 28.77 |
| 839 | GLU | OE2 | 26.263 | 8.280 | 20.456 | 22.97 |
| 840 | GLN | N | 31.853 | 11.228 | 23.201 | 19.41 |
| 841 | GLN | CA | 33.216 | 11.131 | 23.689 | 18.18 |
| 842 | GLN | C | 33.531 | 12.204 | 24.662 | 20.10 |
| 843 | GLN | O | 34.595 | 12.205 | 25.267 | 21.48 |
| 844 | GLN | CB | 34.246 | 11.110 | 22.532 | 18.95 |
| 845 | GLN | CG | 33.923 | 9.996 | 21.532 | 19.84 |
| 846 | GLN | CD | 33.991 | 8.651 | 22.246 | 39.40 |
| 847 | GLN | CE1 | 34.851 | 8.438 | 23.105 | 28.56 |
| 848 | GLN | NE2 | 33.079 | 7.739 | 21.948 | 26.05 |
| 849 | LYS | N | 32.598 | 13.105 | 24.794 | 19.33 |
| 850 | LYS | CA | 32.677 | 14.184 | 25.768 | 18.87 |
| 851 | LYS | C | 33.789 | 15.161 | 25.514 | 22.27 |
| 852 | LYS | O | 34.337 | 15.793 | 26.422 | 19.41 |
| 853 | LYS | CB | 32.735 | 13.639 | 27.188 | 21.88 |
| 854 | LYS | CG | 31.398 | 13.126 | 27.651 | 19.83 |
| 855 | LYS | CD | 31.426 | 12.036 | 28.700 | 45.14 |
| 856 | LYS | CE | 30.008 | 11.554 | 29.070 | 76.91 |
| 857 | LYS | NZ | 29.545 | 10.345 | 28.337 | 96.48 |
| 858 | SER | N | 34.066 | 15.353 | 24.244 | 20.79 |
| 859 | SER | CA | 35.092 | 16.316 | 23.892 | 17.81 |
| 860 | SER | C | 34.624 | 17.729 | 24.205 | 21.92 |
| 861 | SER | O | 33.428 | 18.054 | 24.168 | 21.51 |
| 862 | SER | CB | 35.467 | 16.186 | 22.410 | 19.18 |
| 863 | SER | OG | 35.724 | 14.822 | 22.082 | 17.75 |
| 864 | ARG | N | 35.604 | 18.554 | 24.504 | 17.92 |
| 865 | ARG | CA | 35.383 | 19.949 | 24.807 | 16.44 |
| 866 | ARG | C | 35.798 | 20.801 | 23.627 | 19.96 |
| 867 | ARG | O | 35.360 | 21.920 | 23.437 | 19.40 |
| 868 | ARG | CB | 36.288 | 20.356 | 25.943 | 18.45 |
| 869 | ARG | CG | 35.931 | 21.718 | 26.512 | 32.13 |
| 870 | ARG | CD | 36.767 | 22.844 | 26.008 | 47.45 |
| 871 | ARG | NE | 36.397 | 24.110 | 26.645 | 78.03 |
| 872 | ARG | CZ | 35.147 | 24.537 | 26.840 | 72.70 |
| 873 | ARG | NH1 | 34.080 | 23.841 | 26.491 | 57.33 |
| 874 | ARG | NH2 | 34.975 | 25.713 | 27.412 | 58.72 |
| 875 | GLY | N | 36.733 | 20.313 | 22.843 | 18.99 |
| 876 | GLY | CA | 37.197 | 21.150 | 21.735 | 17.48 |
| 877 | GLY | C | 37.354 | 20.376 | 20.447 | 20.79 |
| 878 | GLY | O | 37.564 | 19.146 | 20.464 | 17.85 |
| 879 | VAL | N | 37.263 | 21.126 | 19.331 | 16.59 |
| 880 | VAL | CA | 37.432 | 20.590 | 17.992 | 13.96 |
| 881 | VAL | C | 38.479 | 21.445 | 17.339 | 19.19 |
| 882 | VAL | O | 38.287 | 22.668 | 17.275 | 20.97 |
| 883 | VAL | CB | 36.129 | 20.735 | 17.192 | 15.20 |
| 884 | VAL | CG1 | 36.421 | 20.354 | 15.742 | 14.08 |
| 885 | VAL | CG2 | 35.021 | 19.821 | 17.752 | 15.12 |
| 886 | VAL | N | 39.576 | 20.856 | 16.870 | 13.97 |
| 887 | VAL | CA | 40.603 | 21.610 | 16.157 | 11.79 |
| 888 | VAL | C | 40.457 | 21.284 | 14.648 | 18.77 |
| 889 | VAL | O | 40.570 | 20.121 | 14.232 | 18.28 |
| 890 | VAL | CB | 41.958 | 21.180 | 16.675 | 12.96 |
| 891 | VAL | CG1 | 43.076 | 21.854 | 15.888 | 14.53 |
| 892 | VAL | CG2 | 42.053 | 21.591 | 18.138 | 13.41 |
| 893 | MET | N | 40.169 | 22.317 | 13.833 | 17.03 |
| 894 | MET | CA | 40.019 | 22.225 | 12.360 | 15.40 |
| 895 | MET | C | 41.205 | 22.846 | 11.677 | 18.09 |
| 896 | MET | O | 41.430 | 24.034 | 11.821 | 19.11 |
| 897 | MET | CB | 38.727 | 22.916 | 11.923 | 14.55 |
| 898 | MET | CG | 38.502 | 22.833 | 10.454 | 15.42 |
| 899 | MET | SD | 36.823 | 23.344 | 10.018 | 19.36 |
| 900 | MET | CE | 36.836 | 23.095 | 8.223 | 17.20 |
| 901 | LEU | N | 41.979 | 22.048 | 10.954 | 10.88 |
| 902 | LEU | CA | 43.193 | 22.584 | 10.379 | 10.33 |
| 903 | LEU | C | 43.143 | 22.854 | 8.877 | 13.92 |
| 904 | LEU | O | 44.145 | 23.245 | 8.271 | 14.65 |
| 905 | LEU | CB | 44.326 | 21.595 | 10.679 | 13.36 |
| 906 | LEU | CG | 44.519 | 21.273 | 12.178 | 16.29 |
| 907 | LEU | CD1 | 45.594 | 20.155 | 12.274 | 14.38 |
| 908 | LEU | CD2 | 45.006 | 22.542 | 12.913 | 13.63 |
| 909 | ASN | N | 41.968 | 22.712 | 8.311 | 13.55 |
| 910 | ASN | CA | 41.826 | 22.925 | 6.905 | 17.04 |
| 911 | ASN | C | 40.701 | 23.897 | 6.601 | 18.91 |
| 912 | ASN | O | 39.965 | 24.258 | 7.509 | 17.09 |
| 913 | ASN | CB | 41.343 | 21.584 | 6.310 | 18.53 |
| 914 | ASN | CG | 39.949 | 21.183 | 6.753 | 18.64 |
| 915 | ASN | OD1 | 38.953 | 21.213 | 5.995 | 19.54 |
| 916 | ASN | ND2 | 39.867 | 20.701 | 7.964 | 12.69 |
| 917 | ARG | N | 40.583 | 24.340 | 5.325 | 16.20 |
| 918 | ARG | CA | 39.429 | 25.199 | 4.934 | 18.31 |
| 919 | ARG | C | 38.419 | 24.316 | 4.226 | 23.61 |
| 920 | ARG | O | 38.770 | 23.219 | 3.769 | 20.22 |
| 921 | ARG | CB | 39.765 | 26.336 | 3.973 | 19.06 |
| 922 | ARG | CG | 40.782 | 27.259 | 4.610 | 27.14 |
| 923 | ARG | CD | 40.998 | 28.568 | 3.854 | 35.02 |
| 924 | ARG | NE | 41.400 | 28.489 | 2.457 | 76.50 |
| 925 | ARG | CZ | 42.181 | 27.557 | 1.889 | 100.00 |
| 926 | ARG | NH1 | 42.629 | 26.485 | 2.605 | 100.00 |
| 927 | ARG | NH2 | 42.425 | 27.679 | 0.574 | 74.39 |
| 928 | VAL | N | 37.162 | 24.772 | 4.126 | 17.39 |
| 929 | VAL | CA | 36.162 | 23.961 | 3.451 | 18.47 |
| 930 | VAL | C | 36.529 | 23.752 | 1.972 | 24.72 |
| 931 | VAL | O | 36.433 | 22.657 | 1.424 | 20.57 |
| 932 | VAL | CB | 34.781 | 24.569 | 3.651 | 20.83 |
| 933 | VAL | CG1 | 33.815 | 24.070 | 2.560 | 18.89 |
| 934 | VAL | CG2 | 34.319 | 24.222 | 5.084 | 18.54 |
| 935 | MET | N | 37.039 | 24.816 | 1.331 | 21.78 |
| 936 | MET | CA | 37.494 | 24.680 | -0.054 | 22.02 |
| 937 | MET | C | 39.008 | 24.831 | -0.154 | 23.31 |
| 938 | MET | O | 39.563 | 25.775 | 0.348 | 21.11 |
| 939 | MET | CB | 36.915 | 25.735 | -0.970 | 24.02 |
| 940 | MET | CG | 37.613 | 25.464 | -2.292 | 33.60 |
| 941 | MET | SD | 36.695 | 26.151 | -3.672 | 42.56 |
| 942 | MET | CE | 35.122 | 25.238 | -3.576 | 37.18 |
| 943 | GLU | N | 39.697 | 23.938 | -0.824 | 18.74 |
| 944 | GLU | CA | 41.128 | 24.062 | -0.945 | 18.84 |
| 945 | GLU | C | 41.474 | 23.440 | -2.263 | 26.07 |
| 946 | GLU | O | 40.841 | 22.451 | -2.688 | 29.43 |
| 947 | GLU | CB | 41.877 | 23.271 | 0.166 | 21.64 |
| 948 | GLU | CG | 41.562 | 23.754 | 1.595 | 24.84 |
| 949 | GLU | CD | 42.242 | 22.902 | 2.628 | 27.45 |
| 950 | GLU | OE1 | 42.453 | 21.723 | 2.501 | 25.26 |
| 951 | GLU | OE2 | 42.525 | 23.545 | 3.714 | 24.68 |
| 952 | LYS | N | 42.458 | 24.000 | -2.901 | 22.86 |
| 953 | LYS | CA | 42.899 | 23.487 | -4.187 | 23.50 |
| 954 | LYS | C | 41.742 | 23.348 | -5.204 | 29.15 |
| 955 | LYS | O | 41.767 | 22.481 | -6.061 | 30.13 |
| 956 | LYS | CB | 43.790 | 22.226 | -4.009 | 26.67 |
| 957 | LYS | CG | 45.143 | 22.628 | -3.333 | 33.73 |
| 958 | LYS | CD | 46.022 | 21.518 | -2.773 | 52.09 |
| 959 | LYS | CE | 47.424 | 22.009 | -2.422 | 39.14 |
| 960 | LYS | NZ | 48.324 | 22.031 | -3.581 | 76.66 |
| 961 | GLY | N | 40.695 | 24.167 | -5.076 | 23.79 |
| 962 | GLY | CA | 39.609 | 24.073 | -6.010 | 21.74 |
| 963 | GLY | C | 38.631 | 23.039 | -5.693 | 24.19 |
| 964 | GLY | O | 37.690 | 22.826 | -6.457 | 29.23 |
| 965 | SER | N | 38.860 | 22.368 | -4.620 | 16.90 |
| 966 | SER | CA | 37.939 | 21.336 | -4.250 | 19.52 |
| 967 | SER | C | 37.336 | 21.506 | -2.901 | 22.34 |
| 968 | SER | O | 37.870 | 22.237 | -2.070 | 20.15 |
| 969 | SER | CB | 38.620 | 20.006 | -4.177 | 25.21 |
| 970 | SER | OG | 38.845 | 19.720 | -5.538 | 47.69 |
| 971 | LEU | N | 36.239 | 20.761 | -2.693 | 15.65 |
| 972 | LEU | CA | 35.596 | 20.819 | -1.374 | 14.31 |
| 973 | LEU | C | 36.183 | 19.731 | -0.502 | 21.78 |
| 974 | LEU | O | 35.871 | 18.558 | -0.677 | 26.91 |
| 975 | LEU | CB | 34.104 | 20.610 | -1.481 | 15.29 |
| 976 | LEU | CG | 33.470 | 21.756 | -2.283 | 21.97 |
| 977 | LEU | CD1 | 31.980 | 21.527 | -2.467 | 21.98 |
| 978 | LEU | CD2 | 33.677 | 23.043 | -1.468 | 26.21 |
| 979 | LYS | N | 37.037 | 20.122 | 0.436 | 17.45 |
| 980 | LYS | CA | 37.741 | 19.191 | 1.299 | 14.44 |
| 981 | LYS | C | 37.009 | 18.778 | 2.566 | 17.63 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 982 | LYS | O | 37.488 | 17.920 | 3.313 | 16.36 |
| 983 | LYS | CB | 39.043 | 19.830 | 1.755 | 14.89 |
| 984 | LYS | CG | 39.990 | 20.179 | 0.609 | 20.49 |
| 985 | LYS | CD | 40.109 | 19.031 | −0.365 | 21.67 |
| 986 | LYS | CE | 41.374 | 18.235 | −0.210 | 30.52 |
| 987 | LYS | NZ | 41.699 | 17.355 | −1.379 | 24.68 |
| 988 | CYS | N | 35.889 | 19.384 | 2.848 | 16.47 |
| 989 | CYS | CA | 35.155 | 19.078 | 4.070 | 16.96 |
| 990 | CYS | C | 33.741 | 19.677 | 3.961 | 19.21 |
| 991 | CYS | O | 33.563 | 20.642 | 3.244 | 18.82 |
| 992 | CYS | CB | 35.948 | 19.897 | 5.159 | 16.39 |
| 993 | CYS | SG | 35.331 | 19.703 | 6.887 | 18.71 |
| 994 | ALA | N | 32.760 | 19.154 | 4.700 | 16.15 |
| 995 | ALA | CA | 31.415 | 19.714 | 4.739 | 14.64 |
| 996 | ALA | C | 31.396 | 20.957 | 5.690 | 19.23 |
| 997 | ALA | O | 32.233 | 21.145 | 6.585 | 17.35 |
| 998 | ALA | CB | 30.467 | 18.651 | 5.231 | 13.19 |
| 999 | GLN | N | 30.461 | 21.869 | 5.475 | 21.44 |
| 1000 | GLN | CA | 30.365 | 23.045 | 6.336 | 24.00 |
| 1001 | GLN | C | 29.591 | 22.536 | 7.463 | 24.84 |
| 1002 | GLN | O | 28.375 | 22.686 | 7.394 | 24.39 |
| 1003 | GLN | CB | 29.530 | 24.166 | 5.663 | 26.72 |
| 1004 | GLN | CG | 29.391 | 25.440 | 6.544 | 22.81 |
| 1005 | GLN | CD | 30.676 | 25.983 | 7.104 | 25.37 |
| 1006 | GLN | OE1 | 30.793 | 26.198 | 8.315 | 30.89 |
| 1007 | GLN | NE2 | 31.616 | 26.296 | 6.240 | 21.26 |
| 1008 | TYR | N | 30.266 | 21.838 | 8.409 | 17.99 |
| 1009 | TYR | CA | 29.535 | 21.156 | 9.487 | 15.44 |
| 1010 | TYR | C | 29.151 | 21.957 | 10.748 | 22.11 |
| 1011 | TYR | O | 28.643 | 21.358 | 11.740 | 18.91 |
| 1012 | TYR | CB | 30.286 | 19.866 | 9.883 | 16.63 |
| 1013 | TYR | CG | 31.599 | 20.198 | 10.522 | 17.61 |
| 1014 | TYR | CD1 | 32.752 | 20.328 | 9.749 | 16.52 |
| 1015 | TYR | CD2 | 31.683 | 20.328 | 11.910 | 15.79 |
| 1016 | TYR | CE1 | 33.967 | 20.657 | 10.340 | 15.78 |
| 1017 | TYR | CE2 | 32.904 | 20.620 | 12.511 | 12.70 |
| 1018 | TYR | CZ | 34.026 | 20.821 | 11.722 | 18.43 |
| 1019 | TYR | OH | 35.226 | 21.088 | 12.310 | 18.28 |
| 1020 | TRP | N | 29.389 | 23.282 | 10.79 | 19.64 |
| 1021 | TRP | CA | 29.017 | 24.082 | 11.885 | 20.07 |
| 1022 | TRP | C | 28.335 | 25.344 | 11.398 | 20.86 |
| 1023 | TRP | O | 28.609 | 25.785 | 10.296 | 18.14 |
| 1024 | TRP | CB | 30.274 | 24.405 | 12.737 | 19.79 |
| 1025 | TRP | CG | 31.146 | 25.427 | 12.111 | 20.56 |
| 1026 | TRP | CD1 | 31.114 | 26.769 | 12.391 | 23.88 |
| 1027 | TRP | CD2 | 32.177 | 25.255 | 11.089 | 19.89 |
| 1028 | TRP | NE1 | 32.061 | 27.448 | 11.631 | 23.47 |
| 1029 | TRP | CE2 | 32.720 | 26.554 | 10.813 | 23.19 |
| 1030 | TRP | CE3 | 32.680 | 24.162 | 10.363 | 21.33 |
| 1031 | TRP | CZ2 | 33.724 | 26.765 | 9.888 | 21.55 |
| 1032 | TRP | CZ3 | 33.681 | 24.396 | 9.418 | 21.71 |
| 1033 | TRP | CH2 | 34.190 | 25.681 | 9.187 | 22.67 |
| 1034 | PRO | N | 27.472 | 25.933 | 12.244 | 19.83 |
| 1035 | PRO | CA | 26.755 | 27.155 | 11.892 | 19.59 |
| 1036 | PRO | C | 27.657 | 28.375 | 11.800 | 23.09 |
| 1037 | PRO | O | 28.534 | 28.630 | 12.627 | 24.72 |
| 1038 | PRO | CB | 25.736 | 27.390 | 13.013 | 20.41 |
| 1039 | PRO | CG | 26.142 | 26.514 | 14.203 | 24.23 |
| 1040 | PRO | CD | 27.223 | 25.561 | 13.671 | 19.47 |
| 1041 | GLN | N | 27.361 | 29.188 | 10.787 | 20.72 |
| 1042 | GLN | CA | 28.094 | 30.394 | 10.583 | 24.35 |
| 1043 | GLN | C | 27.360 | 31.604 | 11.131 | 30.18 |
| 1044 | GLN | O | 27.958 | 32.680 | 11.285 | 28.65 |
| 1045 | GLN | CB | 28.440 | 30.572 | 9.138 | 25.68 |
| 1046 | GLN | CG | 29.324 | 29.390 | 8.712 | 36.40 |
| 1047 | GLN | CD | 29.769 | 29.566 | 7.304 | 56.84 |
| 1048 | GLN | OE1 | 28.981 | 29.299 | 6.359 | 45.16 |
| 1049 | GLN | NE2 | 30.999 | 30.080 | 7.175 | 51.88 |
| 1050 | LYS | N | 26.094 | 31.422 | 11.446 | 24.00 |
| 1051 | LYS | CA | 25.374 | 32.529 | 12.050 | 23.16 |
| 1052 | LYS | C | 24.547 | 32.118 | 13.199 | 19.74 |
| 1053 | LYS | O | 23.907 | 31.078 | 13.158 | 22.04 |
| 1054 | LYS | CB | 24.653 | 33.411 | 11.123 | 28.65 |
| 1055 | LYS | CG | 23.416 | 32.791 | 10.569 | 74.23 |
| 1056 | LYS | CD | 23.256 | 33.389 | 9.195 | 100.00 |
| 1057 | LYS | CE | 24.577 | 33.985 | 8.716 | 100.00 |
| 1058 | LYS | NZ | 25.063 | 33.363 | 7.463 | 100.00 |
| 1059 | GLU | N | 24.612 | 32.988 | 14.210 | 19.68 |
| 1060 | GLU | CA | 23.924 | 32.760 | 15.437 | 18.75 |
| 1061 | GLU | C | 22.542 | 32.373 | 15.160 | 22.72 |
| 1062 | GLU | O | 22.083 | 31.334 | 15.615 | 21.78 |
| 1063 | GLU | CB | 23.897 | 34.027 | 16.333 | 20.49 |
| 1064 | GLU | CG | 25.250 | 34.370 | 17.051 | 17.63 |
| 1065 | GLU | CD | 26.224 | 35.178 | 16.201 | 22.34 |
| 1066 | GLU | OE1 | 26.156 | 35.277 | 14.996 | 23.40 |
| 1067 | GLU | OE2 | 27.088 | 35.835 | 16.877 | 20.11 |
| 1068 | GLU | N | 21.820 | 33.237 | 14.433 | 18.53 |
| 1069 | GLU | CA | 20.418 | 32.935 | 14.214 | 19.99 |
| 1070 | GLU | C | 20.107 | 31.763 | 13.281 | 27.09 |
| 1071 | GLU | O | 18.937 | 31.405 | 13.088 | 23.53 |
| 1072 | GLU | CB | 19.614 | 34.172 | 13.817 | 20.56 |
| 1073 | GLU | CG | 20.050 | 34.671 | 12.449 | 21.72 |
| 1074 | GLU | CD | 21.264 | 35.493 | 12.560 | 32.26 |
| 1075 | GLU | OE1 | 22.170 | 35.239 | 13.292 | 30.85 |
| 1076 | GLU | OE2 | 21.209 | 36.560 | 11.870 | 46.23 |
| 1077 | LYS | N | 21.136 | 31.153 | 12.687 | 24.09 |
| 1078 | LYS | CA | 20.821 | 30.032 | 11.815 | 25.40 |
| 1079 | LYS | C | 21.462 | 28.780 | 12.346 | 32.06 |
| 1080 | LYS | O | 22.539 | 28.413 | 11.875 | 34.08 |
| 1081 | LYS | CB | 21.378 | 30.287 | 10.448 | 25.92 |
| 1082 | LYS | CG | 20.579 | 31.355 | 9.738 | 53.04 |
| 1083 | LYS | CD | 20.028 | 30.875 | 8.415 | 61.11 |
| 1084 | LYS | CE | 18.577 | 30.432 | 8.487 | 81.13 |
| 1085 | LYS | NZ | 18.161 | 29.607 | 7.339 | 100.00 |
| 1086 | GLU | N | 20.846 | 28.148 | 13.337 | 24.74 |
| 1087 | GLU | CA | 21.437 | 26.950 | 13.921 | 24.02 |
| 1088 | GLU | C | 21.324 | 25.780 | 12.983 | 28.33 |
| 1089 | GLU | O | 20.606 | 25.824 | 12.017 | 25.06 |
| 1090 | GLU | CB | 20.762 | 26.410 | 15.183 | 25.15 |
| 1091 | GLU | CG | 19.726 | 27.239 | 15.866 | 51.90 |
| 1092 | GLU | CD | 18.497 | 27.376 | 15.063 | 40.35 |
| 1093 | GLU | OE1 | 17.593 | 26.572 | 15.036 | 36.72 |
| 1094 | GLU | OE2 | 18.492 | 28.538 | 14.496 | 33.99 |
| 1095 | MET | N | 21.986 | 24.679 | 13.350 | 24.61 |
| 1096 | MET | CA | 21.950 | 23.455 | 12.553 | 21.48 |
| 1097 | MET | C | 21.326 | 22.368 | 13.373 | 27.14 |
| 1098 | MET | O | 21.641 | 22.217 | 14.572 | 26.22 |
| 1099 | MET | CB | 23.369 | 22.980 | 12.072 | 21.43 |
| 1100 | MET | CG | 23.958 | 23.895 | 11.019 | 22.29 |
| 1101 | MET | SD | 25.666 | 23.460 | 10.592 | 26.20 |
| 1102 | MET | CE | 25.256 | 22.169 | 9.435 | 23.94 |
| 1103 | ILE | N | 20.444 | 21.594 | 12.707 | 27.52 |
| 1104 | ILE | CA | 19.811 | 20.472 | 13.387 | 28.07 |
| 1105 | ILE | C | 20.179 | 19.186 | 12.668 | 32.13 |
| 1106 | ILE | O | 20.079 | 19.113 | 11.435 | 30.18 |
| 1107 | ILE | CB | 18.293 | 20.602 | 13.485 | 32.74 |
| 1108 | ILE | CG1 | 17.977 | 21.495 | 14.686 | 32.67 |
| 1109 | ILE | CG2 | 17.799 | 19.197 | 13.784 | 32.86 |
| 1110 | ILE | CD1 | 16.777 | 22.374 | 14.453 | 40.14 |
| 1111 | PHE | N | 20.657 | 18.208 | 13.416 | 23.83 |
| 1112 | PHE | CA | 21.041 | 16.959 | 12.785 | 23.10 |
| 1113 | PHE | C | 19.998 | 15.956 | 13.154 | 25.20 |
| 1114 | PHE | O | 20.027 | 15.383 | 14.223 | 23.48 |
| 1115 | PHE | CB | 22.477 | 16.491 | 13.147 | 22.44 |
| 1116 | PHE | CG | 23.457 | 17.603 | 12.869 | 21.09 |
| 1117 | PHE | CD1 | 23.901 | 17.863 | 11.574 | 21.96 |
| 1118 | PHE | CD2 | 23.914 | 18.415 | 13.901 | 20.96 |
| 1119 | PHE | CE1 | 24.802 | 18.889 | 11.307 | 19.88 |
| 1120 | PHE | CE2 | 24.819 | 19.449 | 13.666 | 21.74 |
| 1121 | PHE | CZ | 25.240 | 19.692 | 12.360 | 18.52 |
| 1122 | GLU | N | 19.041 | 15.794 | 12.276 | 26.50 |
| 1123 | GLU | CA | 17.949 | 14.903 | 12.589 | 27.86 |
| 1124 | GLU | C | 18.330 | 13.470 | 12.781 | 32.08 |
| 1125 | GLU | O | 17.727 | 12.809 | 13.608 | 35.43 |
| 1126 | GLU | CB | 16.877 | 14.981 | 11.517 | 30.62 |
| 1127 | GLU | CG | 16.580 | 16.453 | 11.155 | 62.94 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1128 | GLU | CD | 15.389 | 16.595 | 10.252 | 100.00 |
| 1129 | GLU | OE1 | 15.483 | 16.977 | 9.084 | 100.00 |
| 1130 | GLU | OE2 | 14.265 | 16.211 | 10.846 | 100.00 |
| 1131 | ASP | N | 19.299 | 12.959 | 12.012 | 25.73 |
| 1132 | ASP | CA | 19.656 | 11.567 | 12.181 | 23.02 |
| 1133 | ASP | C | 20.185 | 11.281 | 13.545 | 28.07 |
| 1134 | ASP | O | 19.956 | 10.200 | 14.084 | 29.11 |
| 1135 | ASP | CB | 20.632 | 11.086 | 11.107 | 25.54 |
| 1136 | ASP | CG | 21.905 | 11.885 | 11.021 | 37.00 |
| 1137 | ASP | OD1 | 22.084 | 12.993 | 11.515 | 30.66 |
| 1138 | ASP | OD2 | 22.789 | 11.248 | 10.330 | 34.51 |
| 1139 | THR | N | 20.935 | 12.242 | 14.102 | 22.93 |
| 1140 | THR | CA | 21.496 | 12.004 | 15.402 | 20.67 |
| 1141 | THR | C | 20.850 | 12.755 | 16.525 | 23.97 |
| 1142 | THR | O | 21.319 | 12.650 | 17.645 | 24.14 |
| 1143 | THR | CB | 23.011 | 12.160 | 15.438 | 24.59 |
| 1144 | THR | OG1 | 23.323 | 13.466 | 15.015 | 22.89 |
| 1145 | THR | CG2 | 23.629 | 11.120 | 14.521 | 20.72 |
| 1146 | ASN | N | 19.789 | 13.480 | 16.239 | 25.41 |
| 1147 | ASN | CA | 19.071 | 14.191 | 17.312 | 27.59 |
| 1148 | ASN | C | 19.850 | 15.245 | 18.085 | 29.45 |
| 1149 | ASN | O | 19.714 | 15.298 | 19.304 | 27.48 |
| 1150 | ASN | CB | 18.408 | 13.208 | 18.326 | 36.52 |
| 1151 | ASN | CG | 17.000 | 13.621 | 18.723 | 67.20 |
| 1152 | ASN | OD1 | 16.346 | 14.422 | 18.030 | 53.22 |
| 1153 | ASN | ND2 | 16.539 | 13.115 | 19.867 | 60.40 |
| 1154 | LEU | N | 20.633 | 16.084 | 17.377 | 24.61 |
| 1155 | LEU | CA | 21.440 | 17.164 | 17.988 | 23.07 |
| 1156 | LEU | C | 21.206 | 18.521 | 17.335 | 26.63 |
| 1157 | LEU | O | 21.001 | 18.634 | 16.126 | 23.32 |
| 1158 | LEU | CB | 22.937 | 16.857 | 17.853 | 21.58 |
| 1159 | LEU | CG | 23.337 | 15.645 | 18.637 | 25.34 |
| 1160 | LEU | CD1 | 24.640 | 15.072 | 18.051 | 25.68 |
| 1161 | LEU | CD2 | 23.514 | 16.058 | 20.088 | 25.96 |
| 1162 | LYS | N | 21.305 | 19.557 | 18.160 | 23.08 |
| 1163 | LYS | CA | 21.182 | 20.874 | 17.655 | 21.49 |
| 1164 | LYS | C | 22.505 | 21.524 | 17.940 | 22.10 |
| 1165 | LYS | O | 23.066 | 21.305 | 18.982 | 23.53 |
| 1166 | LYS | CB | 20.067 | 21.662 | 18.336 | 21.09 |
| 1167 | LYS | CG | 19.870 | 23.030 | 17.657 | 21.83 |
| 1168 | LYS | CD | 18.540 | 23.701 | 18.050 | 20.42 |
| 1169 | LYS | CE | 18.579 | 24.236 | 19.482 | 27.34 |
| 1170 | LYS | NZ | 17.233 | 24.626 | 19.969 | 28.39 |
| 1171 | LEU | N | 22.992 | 22.343 | 17.032 | 21.33 |
| 1172 | LEU | CA | 24.283 | 22.965 | 17.219 | 21.43 |
| 1173 | LEU | C | 24.163 | 24.452 | 16.940 | 23.20 |
| 1174 | LEU | O | 23.767 | 24.857 | 15.847 | 23.59 |
| 1175 | LEU | CB | 25.209 | 22.322 | 16.142 | 22.80 |
| 1176 | LEU | CG | 26.646 | 22.855 | 16.136 | 23.00 |
| 1177 | LEU | CD1 | 27.324 | 22.527 | 17.442 | 20.39 |
| 1178 | LEU | CD2 | 27.437 | 22.271 | 14.965 | 24.15 |
| 1179 | THR | N | 24.498 | 25.276 | 17.874 | 20.33 |
| 1180 | THR | CA | 24.330 | 26.697 | 17.621 | 20.96 |
| 1181 | THR | C | 25.596 | 27.533 | 17.770 | 20.29 |
| 1182 | THR | O | 26.356 | 27.291 | 18.686 | 22.10 |
| 1183 | THR | CB | 23.364 | 27.260 | 18.679 | 21.96 |
| 1184 | THR | OG1 | 22.155 | 26.543 | 18.666 | 22.75 |
| 1185 | THR | CG2 | 23.137 | 28.739 | 18.365 | 21.55 |
| 1186 | LEU | N | 25.777 | 28.540 | 16.915 | 16.73 |
| 1187 | LEU | CA | 26.914 | 29.399 | 17.000 | 17.12 |
| 1188 | LEU | C | 26.594 | 30.412 | 18.199 | 25.18 |
| 1189 | LEU | O | 25.599 | 31.140 | 18.144 | 21.33 |
| 1190 | LEU | CB | 27.158 | 30.194 | 15.745 | 18.33 |
| 1191 | LEU | CG | 28.269 | 31.272 | 15.781 | 22.75 |
| 1192 | LEU | CD1 | 29.625 | 30.638 | 16.105 | 25.53 |
| 1193 | LEU | CD2 | 28.418 | 31.874 | 14.386 | 20.81 |
| 1194 | ILE | N | 27.430 | 30.433 | 19.251 | 22.62 |
| 1195 | ILE | CA | 27.231 | 31.325 | 20.365 | 18.73 |
| 1196 | ILE | C | 28.105 | 32.558 | 20.189 | 25.51 |
| 1197 | ILE | O | 27.689 | 33.684 | 20.405 | 24.71 |
| 1198 | ILE | CB | 27.524 | 30.585 | 21.640 | 17.81 |
| 1199 | ILE | CG1 | 26.543 | 29.420 | 21.797 | 17.68 |
| 1200 | ILE | CG2 | 27.447 | 31.544 | 22.811 | 19.05 |
| 1201 | ILE | CD1 | 25.088 | 29.851 | 21.734 | 20.62 |
| 1202 | SER | N | 29.319 | 32.399 | 19.729 | 20.59 |
| 1203 | SER | CA | 30.136 | 33.576 | 19.528 | 22.30 |
| 1204 | SER | C | 31.333 | 33.201 | 18.738 | 28.89 |
| 1205 | SER | O | 31.682 | 32.043 | 18.682 | 27.38 |
| 1206 | SER | CB | 30.663 | 34.191 | 20.812 | 28.97 |
| 1207 | SER | OG | 31.304 | 33.178 | 21.542 | 43.41 |
| 1208 | GLU | N | 31.978 | 34.183 | 18.172 | 28.09 |
| 1209 | GLU | CA | 33.164 | 33.904 | 17.391 | 31.06 |
| 1210 | GLU | C | 34.245 | 34.958 | 17.494 | 36.63 |
| 1211 | GLU | O | 33.982 | 36.166 | 17.532 | 39.50 |
| 1212 | GLU | CB | 32.762 | 33.570 | 15.962 | 33.57 |
| 1213 | GLU | CG | 33.016 | 34.695 | 14.975 | 57.41 |
| 1214 | GLU | CD | 32.296 | 34.494 | 13.672 | 87.92 |
| 1215 | GLU | OE1 | 32.149 | 33.405 | 13.128 | 58.92 |
| 1216 | GLU | OE2 | 31.820 | 35.627 | 13.204 | 100.00 |
| 1217 | ASP | N | 35.473 | 34.500 | 17.545 | 25.81 |
| 1218 | ASP | CA | 36.614 | 35.390 | 17.665 | 25.56 |
| 1219 | ASP | C | 37.560 | 35.177 | 16.468 | 33.25 |
| 1220 | ASP | O | 38.298 | 34.191 | 16.394 | 31.20 |
| 1221 | ASP | CB | 37.249 | 35.034 | 19.028 | 29.04 |
| 1222 | ASP | CG | 38.528 | 35.708 | 19.390 | 43.28 |
| 1223 | ASP | OD1 | 38.845 | 36.806 | 18.949 | 44.46 |
| 1224 | ASP | OD2 | 39.272 | 34.945 | 20.175 | 48.31 |
| 1225 | ILE | N | 37.495 | 36.089 | 15.490 | 30.26 |
| 1226 | ILE | CA | 38.260 | 36.014 | 14.247 | 30.37 |
| 1227 | ILE | C | 39.612 | 36.677 | 14.347 | 31.11 |
| 1228 | ILE | O | 39.742 | 37.831 | 14.692 | 31.83 |
| 1229 | ILE | CB | 37.472 | 36.612 | 13.070 | 34.71 |
| 1230 | ILE | CG1 | 36.091 | 35.991 | 12.955 | 36.33 |
| 1231 | ILE | CG2 | 38.216 | 36.607 | 11.722 | 35.66 |
| 1232 | ILE | CD1 | 34.977 | 36.984 | 13.317 | 65.27 |
| 1233 | LYS | N | 40.627 | 35.937 | 14.049 | 22.86 |
| 1234 | LYS | CA | 41.961 | 36.472 | 14.069 | 23.68 |
| 1235 | LYS | C | 42.448 | 36.470 | 12.610 | 25.39 |
| 1236 | LYS | O | 41.705 | 36.091 | 11.707 | 25.60 |
| 1237 | LYS | CB | 42.921 | 35.769 | 15.050 | 24.58 |
| 1238 | LYS | CG | 42.498 | 35.848 | 16.530 | 30.43 |
| 1239 | LYS | CD | 42.894 | 37.206 | 17.140 | 56.04 |
| 1240 | LYS | CE | 42.275 | 37.473 | 18.509 | 77.38 |
| 1241 | LYS | NZ | 43.040 | 38.439 | 19.321 | 100.00 |
| 1242 | THR | N | 43.669 | 36.907 | 12.395 | 22.88 |
| 1243 | THR | CA | 44.215 | 36.986 | 11.049 | 23.70 |
| 1244 | THR | C | 44.240 | 35.654 | 10.392 | 30.85 |
| 1245 | THR | O | 43.898 | 35.565 | 9.210 | 34.77 |
| 1246 | THR | CB | 45.696 | 37.481 | 10.942 | 30.00 |
| 1247 | THR | OG1 | 46.602 | 36.842 | 11.798 | 35.80 |
| 1248 | THR | CG2 | 45.878 | 38.999 | 10.992 | 61.05 |
| 1249 | TYR | N | 44.743 | 34.649 | 11.108 | 21.60 |
| 1250 | TYR | CA | 44.882 | 33.376 | 10.456 | 18.56 |
| 1251 | TYR | C | 44.143 | 32.244 | 11.082 | 25.54 |
| 1252 | TYR | O | 44.324 | 31.078 | 10.663 | 28.06 |
| 1253 | TYR | CB | 46.334 | 33.048 | 10.304 | 18.65 |
| 1254 | TYR | CG | 46.986 | 32.802 | 11.597 | 20.73 |
| 1255 | TYR | CD1 | 47.329 | 33.853 | 12.463 | 21.11 |
| 1256 | TYR | CD2 | 47.327 | 31.498 | 11.937 | 20.37 |
| 1257 | TYR | CE1 | 48.003 | 33.584 | 13.661 | 20.41 |
| 1258 | TYR | CE2 | 47.992 | 31.216 | 13.130 | 21.74 |
| 1259 | TYR | CZ | 48.327 | 32.257 | 13.994 | 29.63 |
| 1260 | TYR | OH | 49.006 | 31.917 | 15.159 | 23.15 |
| 1261 | TYR | N | 43.337 | 32.562 | 12.101 | 21.11 |
| 1262 | TYR | CA | 42.551 | 31.528 | 12.759 | 22.22 |
| 1263 | TYR | C | 41.350 | 32.139 | 13.375 | 24.48 |
| 1264 | TYR | O | 41.326 | 33.342 | 13.534 | 23.41 |
| 1265 | TYR | CB | 43.342 | 30.705 | 13.792 | 23.10 |
| 1266 | TYR | CG | 43.742 | 31.476 | 15.028 | 22.92 |
| 1267 | TYR | CD1 | 44.930 | 32.194 | 15.073 | 20.83 |
| 1268 | TYR | CD2 | 42.959 | 31.415 | 16.177 | 24.45 |
| 1269 | TYR | CE1 | 45.287 | 32.851 | 16.247 | 21.19 |
| 1270 | TYR | CE2 | 43.297 | 32.082 | 17.354 | 21.53 |
| 1271 | TYR | CZ | 44.483 | 32.785 | 17.378 | 21.56 |
| 1272 | TYR | OH | 44.815 | 33.471 | 18.512 | 22.47 |
| 1273 | THR | N | 40.369 | 31.311 | 13.688 | 20.51 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1274 | THR | CA | 39.136 | 31.768 | 14.317 | 20.65 |
| 1275 | THR | C | 38.791 | 30.762 | 15.378 | 25.40 |
| 1276 | THR | O | 38.905 | 29.535 | 15.158 | 21.46 |
| 1277 | THR | CB | 37.933 | 31.848 | 13.303 | 25.48 |
| 1278 | THR | OG1 | 38.230 | 32.801 | 12.320 | 23.97 |
| 1279 | THR | CG2 | 36.650 | 32.293 | 13.969 | 17.96 |
| 1280 | VAL | N | 38.318 | 31.309 | 16.488 | 19.73 |
| 1281 | VAL | CA | 37.851 | 30.530 | 17.623 | 17.86 |
| 1282 | VAL | C | 36.371 | 30.790 | 17.799 | 23.43 |
| 1283 | VAL | O | 35.931 | 31.937 | 17.908 | 23.75 |
| 1284 | VAL | CB | 38.557 | 30.926 | 18.924 | 22.90 |
| 1285 | VAL | CG1 | 38.176 | 29.946 | 20.012 | 23.85 |
| 1286 | VAL | CG2 | 40.057 | 30.808 | 18.737 | 23.85 |
| 1287 | ARG | N | 35.609 | 29.713 | 17.805 | 20.09 |
| 1288 | ARG | CA | 34.172 | 29.781 | 17.953 | 19.44 |
| 1289 | ARG | C | 33.699 | 29.002 | 19.174 | 23.12 |
| 1290 | ARG | O | 34.205 | 27.901 | 19.557 | 20.13 |
| 1291 | ARG | CB | 33.431 | 29.182 | 16.745 | 16.93 |
| 1292 | ARG | CG | 33.792 | 29.938 | 15.473 | 24.10 |
| 1293 | ARG | CD | 33.027 | 29.483 | 14.215 | 26.79 |
| 1294 | ARG | NE | 33.620 | 30.035 | 12.964 | 35.76 |
| 1295 | ARG | CZ | 34.769 | 29.584 | 12.421 | 51.01 |
| 1296 | ARG | NH1 | 35.509 | 28.558 | 12.930 | 52.65 |
| 1297 | ARG | NH2 | 35.199 | 30.195 | 11.337 | 44.38 |
| 1298 | GLN | N | 32.711 | 29.625 | 19.799 | 16.92 |
| 1299 | GLN | CA | 32.040 | 28.948 | 20.858 | 20.12 |
| 1300 | GLN | C | 30.679 | 28.456 | 20.290 | 23.98 |
| 1301 | GLN | O | 29.851 | 29.207 | 19.711 | 23.75 |
| 1302 | GLN | CB | 31.889 | 29.796 | 22.106 | 23.97 |
| 1303 | GLN | CG | 31.076 | 29.015 | 23.134 | 41.20 |
| 1304 | GLN | CD | 30.559 | 29.958 | 24.176 | 67.03 |
| 1305 | GLN | OE1 | 31.089 | 31.100 | 24.332 | 52.88 |
| 1306 | GLN | NE2 | 29.502 | 29.485 | 24.841 | 56.56 |
| 1307 | LEU | N | 30.494 | 27.148 | 20.356 | 17.61 |
| 1308 | LEU | CA | 29.310 | 26.552 | 19.806 | 18.88 |
| 1309 | LEU | C | 28.563 | 25.874 | 20.920 | 26.36 |
| 1310 | LEU | O | 29.175 | 25.420 | 21.914 | 29.37 |
| 1311 | LEU | CB | 29.714 | 25.412 | 18.853 | 19.47 |
| 1312 | LEU | CG | 30.632 | 25.859 | 17.719 | 24.78 |
| 1313 | LEU | CD1 | 31.236 | 24.593 | 17.132 | 23.14 |
| 1314 | LEU | CD2 | 29.825 | 26.634 | 16.632 | 19.35 |
| 1315 | GLU | N | 27.268 | 25.770 | 20.753 | 20.30 |
| 1316 | GLU | CA | 26.490 | 25.073 | 21.753 | 19.19 |
| 1317 | GLU | C | 25.861 | 23.866 | 21.128 | 23.29 |
| 1318 | GLU | O | 25.154 | 23.934 | 20.078 | 25.61 |
| 1319 | GLU | CB | 25.419 | 25.931 | 22.471 | 22.13 |
| 1320 | GLU | CG | 24.553 | 25.130 | 23.502 | 24.76 |
| 1321 | GLU | CD | 23.408 | 26.017 | 23.909 | 45.63 |
| 1322 | GLU | OE1 | 23.525 | 26.834 | 24.760 | 51.61 |
| 1323 | GLU | OE2 | 22.343 | 25.925 | 23.137 | 62.26 |
| 1324 | LEU | N | 26.125 | 22.751 | 21.814 | 21.06 |
| 1325 | LEU | CA | 25.635 | 21.497 | 21.378 | 22.31 |
| 1326 | LEU | C | 24.546 | 21.016 | 22.327 | 27.67 |
| 1327 | LEU | O | 24.761 | 20.942 | 23.522 | 26.01 |
| 1328 | LEU | CB | 26.852 | 20.528 | 21.268 | 24.03 |
| 1329 | LEU | CG | 26.539 | 19.163 | 20.645 | 23.92 |
| 1330 | LEU | CD1 | 26.152 | 19.220 | 19.149 | 20.97 |
| 1331 | LEU | CD2 | 27.784 | 18.312 | 20.815 | 23.65 |
| 1332 | GLU | N | 23.403 | 20.711 | 21.735 | 25.02 |
| 1333 | GLU | CA | 22.302 | 20.214 | 22.466 | 26.18 |
| 1334 | GLU | C | 21.791 | 18.886 | 21.998 | 33.77 |
| 1335 | GLU | O | 21.443 | 18.671 | 20.844 | 34.24 |
| 1336 | GLU | CB | 21.070 | 21.145 | 22.382 | 28.09 |
| 1337 | GLU | CG | 19.918 | 20.621 | 23.287 | 31.05 |
| 1338 | GLU | CD | 18.778 | 21.580 | 23.311 | 37.23 |
| 1339 | GLU | OE1 | 18.856 | 22.616 | 22.768 | 35.92 |
| 1340 | GLU | OE2 | 17.717 | 21.235 | 23.997 | 32.19 |
| 1341 | ASN | N | 21.623 | 18.021 | 22.954 | 34.04 |
| 1342 | ASN | CA | 21.013 | 16.727 | 22.728 | 35.49 |
| 1343 | ASN | C | 19.536 | 17.002 | 22.721 | 35.58 |
| 1344 | ASN | O | 18.959 | 17.366 | 23.723 | 36.35 |
| 1345 | ASN | CB | 21.368 | 15.757 | 23.883 | 44.05 |
| 1346 | ASN | CG | 20.671 | 14.415 | 23.812 | 52.92 |
| 1347 | ASN | OD1 | 19.515 | 14.311 | 23.355 | 44.48 |
| 1348 | ASN | ND2 | 21.363 | 13.396 | 24.335 | 42.29 |
| 1349 | LEU | N | 18.930 | 16.882 | 21.595 | 29.96 |
| 1350 | LEU | CA | 17.542 | 17.220 | 21.535 | 30.39 |
| 1351 | LEU | C | 16.669 | 16.255 | 22.278 | 44.87 |
| 1352 | LEU | O | 15.455 | 16.484 | 22.392 | 46.33 |
| 1353 | LEU | CB | 17.041 | 17.273 | 20.108 | 28.60 |
| 1354 | LEU | CG | 17.610 | 18.466 | 19.424 | 34.04 |
| 1355 | LEU | CD1 | 17.221 | 18.478 | 17.959 | 34.74 |
| 1356 | LEU | CD2 | 17.091 | 19.717 | 20.120 | 39.55 |
| 1357 | THR | N | 17.269 | 15.169 | 22.738 | 43.23 |
| 1358 | THR | CA | 16.475 | 14.185 | 23.405 | 45.55 |
| 1359 | THR | C | 16.335 | 14.567 | 24.850 | 50.45 |
| 1360 | THR | O | 15.215 | 14.792 | 25.347 | 50.59 |
| 1361 | THR | CB | 17.157 | 12.816 | 23.285 | 71.99 |
| 1362 | THR | OG1 | 17.334 | 12.446 | 21.931 | 84.31 |
| 1363 | THR | CG2 | 16.334 | 11.768 | 24.000 | 76.78 |
| 1364 | THR | N | 17.522 | 14.663 | 25.474 | 44.41 |
| 1365 | THR | CA | 17.631 | 14.986 | 26.856 | 42.87 |
| 1366 | THR | C | 17.421 | 16.444 | 27.075 | 48.48 |
| 1367 | THR | O | 16.952 | 16.882 | 28.107 | 52.02 |
| 1368 | THR | CB | 18.984 | 14.575 | 27.417 | 55.05 |
| 1369 | THR | OG1 | 20.046 | 15.266 | 26.798 | 63.24 |
| 1370 | THR | CG2 | 19.150 | 13.086 | 27.255 | 59.51 |
| 1371 | GLN | N | 17.784 | 17.191 | 26.081 | 41.45 |
| 1372 | GLN | CA | 17.729 | 18.616 | 26.132 | 38.83 |
| 1373 | GLN | C | 18.894 | 19.129 | 26.948 | 39.20 |
| 1374 | GLN | O | 18.978 | 20.280 | 27.345 | 40.16 |
| 1375 | GLN | CB | 16.416 | 19.191 | 26.628 | 41.08 |
| 1376 | GLN | CG | 15.319 | 19.228 | 25.576 | 61.17 |
| 1377 | GLN | CD | 14.099 | 19.968 | 26.091 | 89.86 |
| 1378 | GLN | OE1 | 13.915 | 20.136 | 27.317 | 69.61 |
| 1379 | GLN | NE2 | 13.273 | 20.437 | 25.155 | 100.00 |
| 1380 | GLU | N | 19.813 | 18.252 | 27.212 | 35.40 |
| 1381 | GLU | CA | 21.012 | 18.645 | 27.881 | 35.65 |
| 1382 | GLU | C | 21.902 | 19.442 | 26.872 | 35.40 |
| 1383 | GLU | O | 21.846 | 19.311 | 25.623 | 30.83 |
| 1384 | GLU | CB | 21.695 | 17.380 | 28.399 | 38.29 |
| 1385 | GLU | CG | 23.069 | 17.598 | 29.043 | 53.86 |
| 1386 | GLU | CD | 23.653 | 16.237 | 29.306 | 86.06 |
| 1387 | GLU | OE1 | 22.927 | 15.190 | 29.234 | 47.15 |
| 1388 | GLU | OE2 | 24.973 | 16.313 | 29.499 | 61.60 |
| 1389 | THR | N | 22.711 | 20.331 | 27.382 | 30.84 |
| 1390 | THR | CA | 23.466 | 21.110 | 26.458 | 30.66 |
| 1391 | THR | C | 24.932 | 21.176 | 26.816 | 36.12 |
| 1392 | THR | O | 25.281 | 21.143 | 28.021 | 33.20 |
| 1393 | THR | CB | 22.790 | 22.467 | 26.411 | 39.57 |
| 1394 | THR | OG1 | 22.486 | 22.795 | 25.083 | 53.77 |
| 1395 | THR | CG2 | 23.565 | 23.531 | 27.180 | 23.13 |
| 1396 | ARG | N | 25.775 | 21.267 | 25.751 | 30.39 |
| 1397 | ARG | CA | 27.226 | 21.319 | 25.923 | 29.24 |
| 1398 | ARG | C | 27.878 | 22.407 | 25.096 | 25.15 |
| 1399 | ARG | O | 27.469 | 22.689 | 23.981 | 24.36 |
| 1400 | ARG | CB | 27.876 | 19.985 | 25.554 | 35.10 |
| 1401 | ARG | CG | 27.814 | 18.914 | 26.635 | 47.54 |
| 1402 | ARG | CD | 28.971 | 17.902 | 26.645 | 35.93 |
| 1403 | ARG | NE | 28.439 | 16.717 | 27.258 | 45.02 |
| 1404 | ARG | CZ | 28.503 | 15.548 | 26.702 | 70.35 |
| 1405 | ARG | NH1 | 29.148 | 15.393 | 25.541 | 42.87 |
| 1406 | ARG | NH2 | 27.922 | 14.522 | 27.339 | 59.02 |
| 1407 | GLU | N | 28.876 | 23.022 | 25.717 | 22.49 |
| 1408 | GLU | CA | 29.661 | 24.057 | 25.109 | 21.66 |
| 1409 | GLU | C | 30.904 | 23.440 | 24.481 | 24.49 |
| 1410 | GLU | O | 31.646 | 22.763 | 25.168 | 21.92 |
| 1411 | GLU | CB | 30.223 | 25.020 | 26.131 | 23.64 |
| 1412 | GLU | CG | 31.072 | 26.050 | 25.395 | 37.97 |
| 1413 | GLU | CD | 31.821 | 26.929 | 26.332 | 70.67 |
| 1414 | GLU | OE1 | 31.279 | 27.585 | 27.207 | 100.00 |
| 1415 | GLU | OE2 | 33.108 | 26.854 | 26.147 | 87.35 |
| 1416 | ILE | N | 31.145 | 23.707 | 23.201 | 20.06 |
| 1417 | ILE | CA | 32.319 | 23.179 | 22.541 | 19.28 |
| 1418 | ILE | C | 33.071 | 24.345 | 21.942 | 22.12 |
| 1419 | ILE | O | 32.454 | 25.302 | 21.437 | 21.81 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1420 | ILE | CB | 31.898 | 22.286 | 21.385 | 22.39 |
| 1421 | ILE | CG1 | 30.838 | 21.236 | 21.764 | 21.96 |
| 1422 | ILE | CG2 | 33.122 | 21.719 | 20.656 | 20.30 |
| 1423 | ILE | CD1 | 31.341 | 20.178 | 22.720 | 24.63 |
| 1424 | LEU | N | 34.376 | 24.265 | 21.944 | 16.47 |
| 1425 | LEU | CA | 35.137 | 25.326 | 21.321 | 16.94 |
| 1426 | LEU | C | 35.661 | 24.796 | 20.041 | 21.55 |
| 1427 | LEU | O | 36.126 | 23.648 | 19.980 | 20.21 |
| 1428 | LEU | CB | 36.341 | 25.704 | 22.198 | 18.75 |
| 1429 | LEU | CG | 35.902 | 26.118 | 23.634 | 26.04 |
| 1430 | LEU | CD1 | 37.112 | 26.450 | 24.540 | 27.16 |
| 1431 | LEU | CD2 | 35.041 | 27.336 | 23.494 | 24.28 |
| 1432 | HIS | N | 35.635 | 25.621 | 19.021 | 16.36 |
| 1433 | HIS | CA | 36.118 | 25.183 | 17.703 | 14.50 |
| 1434 | HIS | C | 37.275 | 26.073 | 17.333 | 20.44 |
| 1435 | HIS | O | 37.118 | 27.293 | 17.360 | 20.81 |
| 1436 | HIS | CB | 34.956 | 25.388 | 16.717 | 15.22 |
| 1437 | HIS | CG | 35.150 | 24.834 | 15.350 | 17.70 |
| 1438 | HIS | ND1 | 35.394 | 25.650 | 14.280 | 18.12 |
| 1439 | HIS | CD2 | 35.045 | 23.553 | 14.893 | 18.74 |
| 1440 | HIS | CE1 | 35.513 | 24.853 | 13.225 | 17.96 |
| 1441 | HIS | NE2 | 35.316 | 23.575 | 13.552 | 17.01 |
| 1442 | PHE | N | 38.456 | 25.476 | 17.039 | 14.68 |
| 1443 | PHE | CA | 39.642 | 26.223 | 16.705 | 14.36 |
| 1444 | PHE | C | 39.905 | 25.964 | 15.252 | 18.76 |
| 1445 | PHE | O | 40.224 | 24.844 | 14.924 | 19.29 |
| 1446 | PHE | CB | 40.854 | 25.765 | 17.540 | 14.14 |
| 1447 | PHE | CG | 40.543 | 25.886 | 19.001 | 15.56 |
| 1448 | PHE | CD1 | 40.812 | 27.078 | 19.679 | 19.52 |
| 1449 | PHE | CD2 | 39.966 | 24.812 | 19.687 | 19.04 |
| 1450 | PHE | CE1 | 40.493 | 27.165 | 21.038 | 21.39 |
| 1451 | PHE | CE2 | 39.691 | 24.853 | 21.057 | 21.60 |
| 1452 | PHE | CZ | 39.956 | 26.053 | 21.711 | 19.12 |
| 1453 | HIS | N | 39.729 | 26.988 | 14.398 | 16.34 |
| 1454 | HIS | CA | 39.850 | 26.842 | 12.954 | 16.68 |
| 1455 | HIS | C | 41.036 | 27.540 | 12.393 | 22.59 |
| 1456 | HIS | O | 41.056 | 28.776 | 12.342 | 20.03 |
| 1457 | HIS | CB | 38.597 | 27.462 | 12.336 | 18.43 |
| 1458 | HIS | CG | 38.504 | 27.092 | 10.899 | 22.05 |
| 1459 | HIS | ND1 | 37.487 | 27.555 | 10.113 | 21.32 |
| 1460 | HIS | CD2 | 39.322 | 26.311 | 10.139 | 23.08 |
| 1461 | HIS | CE1 | 37.665 | 27.073 | 8.892 | 20.85 |
| 1462 | HIS | NE2 | 38.738 | 26.297 | 8.857 | 22.16 |
| 1463 | TYR | N | 42.029 | 26.753 | 11.977 | 17.95 |
| 1464 | TYR | CA | 43.277 | 27.301 | 11.440 | 17.43 |
| 1465 | TYR | C | 43.022 | 27.495 | 9.978 | 23.32 |
| 1466 | TYR | O | 42.787 | 26.542 | 9.283 | 19.33 |
| 1467 | TYR | CB | 44.414 | 26.250 | 11.602 | 16.22 |
| 1468 | TYR | CG | 45.848 | 26.801 | 11.601 | 19.15 |
| 1469 | TYR | CD1 | 46.322 | 27.564 | 10.527 | 21.35 |
| 1470 | TYR | CD2 | 46.732 | 26.525 | 12.639 | 19.74 |
| 1471 | TYR | CE1 | 47.633 | 28.058 | 10.473 | 20.97 |
| 1472 | TYR | CE2 | 48.053 | 26.987 | 12.600 | 20.96 |
| 1473 | TYR | CZ | 48.500 | 27.758 | 11.521 | 24.03 |
| 1474 | TYR | OH | 49.771 | 28.237 | 11.483 | 27.87 |
| 1475 | THR | N | 43.075 | 28.699 | 9.495 | 19.92 |
| 1476 | THR | CA | 42.722 | 28.877 | 8.099 | 22.16 |
| 1477 | THR | C | 43.882 | 29.154 | 7.134 | 28.45 |
| 1478 | THR | O | 43.647 | 29.392 | 5.946 | 29.06 |
| 1479 | THR | CB | 41.656 | 30.007 | 8.008 | 25.85 |
| 1480 | THR | OG1 | 42.260 | 31.210 | 8.473 | 23.68 |
| 1481 | THR | CG2 | 40.470 | 29.686 | 8.925 | 20.99 |
| 1482 | THR | N | 45.126 | 29.138 | 7.580 | 21.17 |
| 1483 | THR | CA | 46.174 | 29.416 | 6.619 | 20.89 |
| 1484 | THR | C | 47.190 | 28.284 | 6.556 | 28.24 |
| 1485 | THR | O | 48.385 | 28.506 | 6.365 | 28.74 |
| 1486 | THR | CB | 46.906 | 30.686 | 7.023 | 27.18 |
| 1487 | THR | OG1 | 47.257 | 30.490 | 8.372 | 25.28 |
| 1488 | THR | CG2 | 46.033 | 31.944 | 6.834 | 22.60 |
| 1489 | TRP | N | 46.743 | 27.029 | 6.778 | 21.40 |
| 1490 | TRP | CA | 47.670 | 25.898 | 6.710 | 18.45 |
| 1491 | TRP | C | 47.214 | 25.059 | 5.472 | 23.97 |
| 1492 | TRP | O | 46.155 | 24.444 | 5.460 | 19.44 |
| 1493 | TRP | CB | 47.520 | 25.065 | 7.977 | 15.94 |
| 1494 | TRP | CG | 48.522 | 23.957 | 8.065 | 15.20 |
| 1495 | TRP | CD1 | 49.281 | 23.420 | 7.059 | 17.12 |
| 1496 | TRP | CD2 | 48.839 | 23.238 | 9.266 | 15.16 |
| 1497 | TRP | NE1 | 50.080 | 22.423 | 7.592 | 16.60 |
| 1498 | TRP | CE2 | 49.810 | 22.295 | 8.937 | 19.35 |
| 1499 | TRP | CE3 | 48.376 | 23.353 | 10.604 | 16.48 |
| 1500 | TRP | CZ2 | 50.290 | 21.421 | 9.907 | 20.83 |
| 1501 | TRP | CZ3 | 48.843 | 22.520 | 11.569 | 17.13 |
| 1502 | TRP | CH2 | 49.763 | 21.536 | 11.205 | 19.65 |
| 1503 | PRO | N | 47.948 | 25.153 | 4.377 | 20.91 |
| 1504 | PRO | CA | 47.535 | 24.503 | 3.150 | 19.93 |
| 1505 | PRO | C | 47.609 | 22.996 | 3.191 | 21.72 |
| 1506 | PRO | O | 48.534 | 22.409 | 3.802 | 19.55 |
| 1507 | PRO | CB | 48.501 | 24.984 | 2.021 | 23.28 |
| 1508 | PRO | CG | 49.570 | 25.796 | 2.717 | 28.22 |
| 1509 | PRO | CD | 49.234 | 25.901 | 4.224 | 21.68 |
| 1510 | ASP | N | 46.667 | 22.415 | 2.435 | 20.26 |
| 1511 | ASP | CA | 46.638 | 20.993 | 2.325 | 17.54 |
| 1512 | ASP | C | 48.007 | 20.561 | 1.755 | 23.68 |
| 1513 | ASP | O | 48.601 | 21.308 | 0.939 | 21.00 |
| 1514 | ASP | CB | 45.449 | 20.625 | 1.461 | 15.69 |
| 1515 | ASP | CG | 45.196 | 19.140 | 1.667 | 19.13 |
| 1516 | ASP | OD1 | 45.886 | 18.423 | 2.440 | 20.93 |
| 1517 | ASP | OD2 | 44.249 | 18.644 | 0.903 | 18.68 |
| 1518 | PHE | N | 48.544 | 19.411 | 2.224 | 16.97 |
| 1519 | PHE | CA | 49.870 | 18.965 | 1.826 | 20.13 |
| 1520 | PHE | C | 50.957 | 19.945 | 2.133 | 25.12 |
| 1521 | PHE | O | 52.103 | 19.742 | 1.643 | 22.55 |
| 1522 | PHE | CB | 49.924 | 18.631 | 0.326 | 26.08 |
| 1523 | PHE | CG | 49.104 | 17.401 | 0.246 | 35.80 |
| 1524 | PHE | CD1 | 49.297 | 16.474 | 1.282 | 48.33 |
| 1525 | PHE | CD2 | 48.084 | 17.211 | −0.681 | 40.42 |
| 1526 | PHE | CE1 | 48.566 | 15.292 | 1.405 | 48.19 |
| 1527 | PHE | CE2 | 47.393 | 15.996 | −0.632 | 45.67 |
| 1528 | PHE | CZ | 47.618 | 15.075 | 0.407 | 46.93 |
| 1529 | GLY | N | 50.632 | 21.004 | 2.915 | 20.53 |
| 1530 | GLY | CA | 51.683 | 21.971 | 3.227 | 19.53 |
| 1531 | GLY | C | 52.004 | 22.104 | 4.708 | 21.83 |
| 1532 | GLY | O | 51.696 | 21.221 | 5.531 | 18.25 |
| 1533 | VAL | N | 52.661 | 23.217 | 5.033 | 18.02 |
| 1534 | VAL | CA | 53.016 | 23.487 | 6.390 | 16.83 |
| 1535 | VAL | C | 52.534 | 24.857 | 6.791 | 24.11 |
| 1536 | VAL | O | 52.177 | 25.662 | 5.955 | 24.27 |
| 1537 | VAL | CB | 54.512 | 23.437 | 6.545 | 20.78 |
| 1538 | VAL | CG1 | 54.973 | 22.026 | 6.244 | 19.08 |
| 1539 | VAL | CG2 | 55.079 | 24.462 | 5.559 | 22.82 |
| 1540 | PRO | N | 52.473 | 25.117 | 8.096 | 21.39 |
| 1541 | PRO | CA | 52.081 | 26.441 | 8.616 | 20.99 |
| 1542 | PRO | C | 53.080 | 27.518 | 8.157 | 26.47 |
| 1543 | PRO | O | 54.203 | 27.218 | 7.754 | 25.08 |
| 1544 | PRO | CB | 52.116 | 26.310 | 10.170 | 21.11 |
| 1545 | PRO | CG | 52.245 | 24.819 | 10.510 | 21.50 |
| 1546 | PRO | CD | 52.674 | 24.115 | 9.211 | 19.66 |
| 1547 | GLU | N | 52.696 | 28.777 | 8.213 | 24.24 |
| 1548 | GLU | CA | 53.593 | 29.831 | 7.749 | 23.61 |
| 1549 | GLU | C | 54.886 | 29.923 | 8.532 | 28.04 |
| 1550 | GLU | O | 55.907 | 30.309 | 7.997 | 26.16 |
| 1551 | GLU | CB | 52.881 | 31.191 | 7.690 | 25.09 |
| 1552 | GLU | CG | 51.548 | 31.090 | 6.895 | 64.56 |
| 1553 | GLU | CD | 50.479 | 32.181 | 7.111 | 100.00 |
| 1554 | GLU | OE1 | 49.716 | 32.227 | 8.113 | 79.43 |
| 1555 | GLU | OE2 | 50.381 | 33.007 | 6.070 | 91.77 |
| 1556 | SER | N | 54.859 | 29.633 | 9.821 | 22.79 |
| 1557 | SER | CA | 56.080 | 29.729 | 10.605 | 20.38 |
| 1558 | SER | C | 55.893 | 28.889 | 11.822 | 23.57 |
| 1559 | SER | O | 54.788 | 28.588 | 12.204 | 24.21 |
| 1560 | SER | CB | 56.352 | 31.159 | 11.079 | 23.98 |
| 1561 | SER | OG | 55.221 | 31.636 | 11.819 | 21.35 |
| 1562 | PRO | N | 56.970 | 28.495 | 12.436 | 22.91 |
| 1563 | PRO | CA | 56.805 | 27.775 | 13.649 | 23.08 |
| 1564 | PRO | C | 56.050 | 28.657 | 14.655 | 26.93 |
| 1565 | PRO | O | 55.238 | 28.194 | 15.396 | 25.45 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1566 | PRO | CB | 58.230 | 27.505 | 14.170 | 24.65 |
| 1567 | PRO | CG | 59.143 | 27.550 | 12.965 | 28.02 |
| 1568 | PRO | CD | 58.397 | 28.442 | 11.979 | 23.89 |
| 1569 | ALA | N | 56.300 | 29.973 | 14.661 | 23.54 |
| 1570 | ALA | CA | 55.629 | 30.881 | 15.613 | 21.90 |
| 1571 | ALA | C | 54.118 | 30.891 | 15.479 | 20.92 |
| 1572 | ALA | O | 53.348 | 30.851 | 16.457 | 19.69 |
| 1573 | ALA | CB | 56.248 | 32.309 | 15.569 | 21.00 |
| 1574 | SER | N | 53.675 | 30.917 | 14.234 | 20.18 |
| 1575 | SER | CA | 52.201 | 30.957 | 14.031 | 21.57 |
| 1576 | SER | C | 51.539 | 29.677 | 14.476 | 24.10 |
| 1577 | SER | O | 50.457 | 29.670 | 15.047 | 23.15 |
| 1578 | SER | CB | 51.769 | 31.348 | 12.606 | 25.87 |
| 1579 | SER | OG | 52.780 | 31.001 | 11.688 | 40.00 |
| 1580 | PHE | N | 52.229 | 28.573 | 14.201 | 19.09 |
| 1581 | PHE | CA | 51.685 | 27.283 | 14.553 | 15.85 |
| 1582 | PHE | C | 51.650 | 27.200 | 16.075 | 21.97 |
| 1583 | PHE | O | 50.659 | 26.814 | 16.684 | 20.90 |
| 1584 | PHE | CB | 52.611 | 26.166 | 13.984 | 18.25 |
| 1585 | PHE | CG | 52.293 | 24.814 | 14.607 | 18.09 |
| 1586 | PHE | CD1 | 51.234 | 24.063 | 14.104 | 16.30 |
| 1587 | PHE | CD2 | 53.032 | 24.327 | 15.687 | 19.26 |
| 1588 | PHE | CE1 | 50.907 | 22.860 | 14.722 | 18.09 |
| 1589 | PHE | CE2 | 52.685 | 23.149 | 16.344 | 23.27 |
| 1590 | PHE | CZ | 51.600 | 22.423 | 15.850 | 21.69 |
| 1591 | LEU | N | 52.774 | 27.544 | 16.720 | 20.33 |
| 1592 | LEU | CA | 52.866 | 27.418 | 18.177 | 19.90 |
| 1593 | LEU | C | 51.888 | 28.318 | 18.868 | 23.96 |
| 1594 | LEU | O | 51.233 | 27.949 | 19.866 | 23.17 |
| 1595 | LEU | CB | 54.290 | 27.689 | 18.661 | 20.12 |
| 1596 | LEU | CG | 55.212 | 26.537 | 18.324 | 22.21 |
| 1597 | LEU | CD1 | 56.679 | 26.965 | 18.499 | 22.08 |
| 1598 | LEU | CD2 | 54.843 | 25.331 | 19.215 | 23.19 |
| 1599 | ASN | N | 51.778 | 29.520 | 18.303 | 22.18 |
| 1600 | ASN | CA | 50.801 | 30.490 | 18.835 | 21.35 |
| 1601 | ASN | C | 49.403 | 29.847 | 18.865 | 21.98 |
| 1602 | ASN | O | 48.693 | 29.928 | 19.870 | 21.88 |
| 1603 | ASN | CB | 50.785 | 31.816 | 18.027 | 20.82 |
| 1604 | ASN | CG | 49.807 | 32.839 | 18.619 | 24.28 |
| 1605 | ASN | OD1 | 49.974 | 33.256 | 19.783 | 21.90 |
| 1606 | ASN | ND2 | 48.763 | 33.220 | 17.844 | 19.52 |
| 1607 | PHE | N | 49.044 | 29.156 | 17.743 | 18.21 |
| 1608 | PHE | CA | 47.745 | 28.501 | 17.628 | 14.93 |
| 1609 | PHE | C | 47.666 | 27.300 | 18.571 | 19.31 |
| 1610 | PHE | O | 46.638 | 27.092 | 19.233 | 19.07 |
| 1611 | PHE | CB | 47.530 | 28.099 | 16.167 | 15.26 |
| 1612 | PHE | CG | 46.276 | 27.312 | 15.946 | 19.10 |
| 1613 | PHE | CD1 | 45.072 | 27.942 | 15.602 | 22.25 |
| 1614 | PHE | CD2 | 46.280 | 25.910 | 16.038 | 14.28 |
| 1615 | PHE | CE1 | 43.887 | 27.210 | 15.433 | 20.75 |
| 1616 | PHE | CE2 | 45.122 | 25.167 | 15.823 | 12.24 |
| 1617 | PHE | CZ | 43.919 | 25.815 | 15.533 | 13.08 |
| 1618 | LEU | N | 48.750 | 26.511 | 18.662 | 18.17 |
| 1619 | LEU | CA | 48.729 | 25.368 | 19.546 | 17.98 |
| 1620 | LEU | C | 48.499 | 25.780 | 21.000 | 21.46 |
| 1621 | LEU | O | 47.707 | 25.217 | 21.756 | 18.26 |
| 1622 | LEU | CB | 50.052 | 24.635 | 19.403 | 18.33 |
| 1623 | LEU | CG | 50.151 | 23.515 | 20.450 | 21.15 |
| 1624 | LEU | CD1 | 51.503 | 22.791 | 20.311 | 23.59 |
| 1625 | LEU | CD2 | 48.978 | 22.520 | 20.359 | 15.46 |
| 1626 | PHE | N | 49.225 | 26.808 | 21.416 | 20.08 |
| 1627 | PHE | CA | 49.049 | 27.353 | 22.789 | 21.32 |
| 1628 | PHE | C | 47.628 | 27.968 | 23.006 | 24.42 |
| 1629 | PHE | O | 47.052 | 27.870 | 24.091 | 24.60 |
| 1630 | PHE | CB | 50.175 | 28.286 | 23.244 | 20.93 |
| 1631 | PHE | CG | 51.389 | 27.451 | 23.568 | 25.75 |
| 1632 | PHE | CD1 | 51.876 | 26.502 | 22.666 | 24.29 |
| 1633 | PHE | CD2 | 52.059 | 27.590 | 24.788 | 33.03 |
| 1634 | PHE | CE1 | 52.958 | 25.669 | 22.967 | 25.19 |
| 1635 | PHE | CE2 | 53.152 | 26.773 | 25.100 | 36.27 |
| 1636 | PHE | CZ | 53.595 | 25.799 | 24.198 | 30.54 |
| 1637 | LYS | N | 47.012 | 28.564 | 21.981 | 19.37 |
| 1638 | LYS | CA | 45.650 | 29.029 | 22.169 | 19.01 |
| 1639 | LYS | C | 44.755 | 27.830 | 22.565 | 23.16 |
| 1640 | LYS | O | 43.965 | 27.875 | 23.510 | 20.57 |
| 1641 | LYS | CB | 45.064 | 29.654 | 20.900 | 20.68 |
| 1642 | LYS | CG | 44.966 | 31.167 | 21.019 | 54.23 |
| 1643 | LYS | CD | 43.679 | 31.660 | 21.671 | 58.81 |
| 1644 | LYS | CE | 43.329 | 33.110 | 21.340 | 79.60 |
| 1645 | LYS | NZ | 42.204 | 33.258 | 20.403 | 90.92 |
| 1646 | VAL | N | 44.903 | 26.725 | 21.833 | 18.90 |
| 1647 | VAL | CA | 44.143 | 25.527 | 22.117 | 17.53 |
| 1648 | VAL | C | 44.447 | 25.027 | 23.508 | 21.15 |
| 1649 | VAL | O | 43.558 | 24.712 | 24.284 | 19.52 |
| 1650 | VAL | CB | 44.432 | 24.450 | 21.047 | 17.34 |
| 1651 | VAL | CG1 | 43.692 | 23.154 | 21.348 | 16.63 |
| 1652 | VAL | CG2 | 44.052 | 24.997 | 19.628 | 15.16 |
| 1653 | ARG | N | 45.712 | 24.939 | 23.832 | 20.55 |
| 1654 | ARG | CA | 46.047 | 24.444 | 25.161 | 19.47 |
| 1655 | ARG | C | 45.455 | 25.327 | 26.259 | 21.39 |
| 1656 | ARG | O | 44.954 | 24.911 | 27.288 | 21.16 |
| 1657 | ARG | CB | 47.560 | 24.512 | 25.353 | 17.77 |
| 1658 | ARG | CG | 48.312 | 23.372 | 24.672 | 24.26 |
| 1659 | ARG | CD | 49.824 | 23.590 | 24.620 | 22.42 |
| 1660 | ARG | NE | 50.439 | 22.292 | 24.419 | 26.10 |
| 1661 | ARG | CZ | 51.464 | 21.787 | 25.113 | 40.08 |
| 1662 | ARG | NH1 | 52.063 | 22.472 | 26.095 | 23.77 |
| 1663 | ARG | NH2 | 51.909 | 20.558 | 24.796 | 21.91 |
| 1664 | GLU | N | 45.604 | 26.581 | 26.047 | 20.31 |
| 1665 | GLU | CA | 45.141 | 27.497 | 27.028 | 21.25 |
| 1666 | GLU | C | 43.668 | 27.493 | 27.214 | 26.86 |
| 1667 | GLU | O | 43.228 | 27.801 | 28.314 | 30.19 |
| 1668 | GLU | CB | 45.646 | 28.874 | 26.753 | 23.38 |
| 1669 | GLU | CG | 47.087 | 28.893 | 27.173 | 37.92 |
| 1670 | GLU | CD | 47.736 | 30.184 | 26.883 | 65.18 |
| 1671 | GLU | OE1 | 47.282 | 30.979 | 26.063 | 63.04 |
| 1672 | GLU | OE2 | 48.853 | 30.321 | 27.578 | 59.99 |
| 1673 | SER | N | 42.897 | 27.123 | 26.213 | 20.78 |
| 1674 | SER | CA | 41.438 | 27.087 | 26.408 | 20.46 |
| 1675 | SER | C | 41.009 | 26.041 | 27.387 | 30.52 |
| 1676 | SER | O | 39.864 | 25.951 | 27.744 | 37.57 |
| 1677 | SER | CB | 40.714 | 26.707 | 25.130 | 17.75 |
| 1678 | SER | OG | 40.998 | 25.358 | 24.799 | 21.13 |
| 1679 | GLY | N | 41.850 | 25.128 | 27.755 | 27.53 |
| 1680 | GLY | CA | 41.324 | 24.128 | 28.636 | 24.97 |
| 1681 | GLY | C | 40.817 | 22.896 | 27.894 | 35.66 |
| 1682 | GLY | O | 40.571 | 21.813 | 28.504 | 38.98 |
| 1683 | SER | N | 40.733 | 23.002 | 26.556 | 26.31 |
| 1684 | SER | CA | 40.241 | 21.873 | 25.787 | 23.11 |
| 1685 | SER | C | 41.002 | 20.591 | 25.925 | 33.29 |
| 1686 | SER | O | 40.402 | 19.563 | 25.614 | 33.64 |
| 1687 | SER | CB | 40.151 | 22.177 | 24.303 | 24.92 |
| 1688 | SER | OG | 39.263 | 23.274 | 24.065 | 24.93 |
| 1689 | LEU | N | 42.318 | 20.630 | 26.294 | 30.38 |
| 1690 | LEU | CA | 43.103 | 19.378 | 26.359 | 30.40 |
| 1691 | LEU | C | 43.108 | 18.701 | 27.742 | 38.35 |
| 1692 | LEU | O | 43.678 | 17.631 | 27.992 | 38.03 |
| 1693 | LEU | CB | 44.513 | 19.515 | 25.757 | 29.26 |
| 1694 | LEU | CG | 44.530 | 20.316 | 24.461 | 31.07 |
| 1695 | LEU | CD1 | 45.948 | 20.591 | 24.014 | 27.31 |
| 1696 | LEU | CD2 | 43.820 | 19.572 | 23.354 | 34.10 |
| 1697 | SER | N | 42.463 | 19.367 | 28.644 | 34.73 |
| 1698 | SER | CA | 42.363 | 18.870 | 29.968 | 34.22 |
| 1699 | SER | C | 41.847 | 17.426 | 30.022 | 36.01 |
| 1700 | SER | O | 40.925 | 17.051 | 29.369 | 31.19 |
| 1701 | SER | CB | 41.501 | 19.801 | 30.780 | 39.43 |
| 1702 | SER | OG | 41.658 | 19.437 | 32.131 | 55.74 |
| 1703 | PRO | N | 42.456 | 16.621 | 30.848 | 39.48 |
| 1704 | PRO | CA | 42.093 | 15.228 | 31.048 | 39.86 |
| 1705 | PRO | C | 40.730 | 15.105 | 31.735 | 38.86 |
| 1706 | PRO | O | 40.123 | 14.050 | 31.847 | 37.15 |
| 1707 | PRO | CB | 43.162 | 14.696 | 31.998 | 42.88 |
| 1708 | PRO | CG | 43.756 | 15.909 | 32.728 | 48.04 |
| 1709 | PRO | CD | 43.253 | 17.145 | 31.996 | 43.33 |
| 1710 | GLU | N | 40.212 | 16.194 | 32.214 | 32.75 |
| 1711 | GLU | CA | 38.901 | 16.068 | 32.791 | 33.48 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1712 | GLU | C | 37.828 | 16.086 | 31.693 | 31.63 |
| 1713 | GLU | O | 36.656 | 16.014 | 31.931 | 31.89 |
| 1714 | GLU | CB | 38.647 | 17.159 | 33.840 | 37.32 |
| 1715 | GLU | CG | 38.309 | 18.559 | 33.240 | 65.45 |
| 1716 | GLU | CD | 39.318 | 19.626 | 33.589 | 92.79 |
| 1717 | GLU | OE1 | 40.366 | 19.358 | 34.151 | 100.00 |
| 1718 | GLU | OE2 | 39.027 | 20.832 | 33.145 | 79.45 |
| 1719 | HIS | N | 38.217 | 16.238 | 30.459 | 23.47 |
| 1720 | HIS | CA | 37.246 | 16.264 | 29.407 | 21.41 |
| 1721 | HIS | C | 37.579 | 15.102 | 28.544 | 24.76 |
| 1722 | HIS | O | 38.664 | 14.584 | 28.727 | 24.90 |
| 1723 | HIS | CB | 37.581 | 17.439 | 28.476 | 23.84 |
| 1724 | HIS | CG | 37.356 | 18.755 | 29.102 | 29.53 |
| 1725 | HIS | ND1 | 36.121 | 19.085 | 29.633 | 32.52 |
| 1726 | HIS | CD2 | 38.191 | 19.824 | 29.252 | 34.49 |
| 1727 | HIS | CE1 | 36.203 | 20.348 | 30.081 | 33.65 |
| 1728 | HIS | NE2 | 37.441 | 20.813 | 29.875 | 35.22 |
| 1729 | GLY | N | 36.738 | 14.774 | 27.539 | 20.61 |
| 1730 | GLY | CA | 37.086 | 13.704 | 26.621 | 18.66 |
| 1731 | GLY | C | 38.225 | 14.238 | 25.771 | 24.63 |
| 1732 | GLY | O | 38.659 | 15.427 | 25.902 | 26.39 |
| 1733 | PRO | N | 38.720 | 13.391 | 24.886 | 20.23 |
| 1734 | PRO | CA | 39.824 | 13.749 | 23.973 | 16.08 |
| 1735 | PRO | C | 39.406 | 14.853 | 23.015 | 16.63 |
| 1736 | PRO | O | 38.315 | 14.885 | 22.519 | 21.70 |
| 1737 | PRO | CB | 40.065 | 12.516 | 23.099 | 18.85 |
| 1738 | PRO | CG | 39.214 | 11.419 | 23.667 | 23.51 |
| 1739 | PRO | CD | 38.245 | 12.018 | 24.690 | 21.40 |
| 1740 | VAL | N | 40.277 | 15.758 | 22.729 | 17.27 |
| 1741 | VAL | CA | 39.952 | 16.799 | 21.788 | 16.61 |
| 1742 | VAL | C | 39.821 | 16.100 | 20.459 | 20.32 |
| 1743 | VAL | O | 40.473 | 15.057 | 20.168 | 20.45 |
| 1744 | VAL | CB | 41.125 | 17.820 | 21.737 | 20.35 |
| 1745 | VAL | CG1 | 42.315 | 17.135 | 21.117 | 22.42 |
| 1746 | VAL | CG2 | 40.889 | 19.002 | 20.793 | 20.42 |
| 1747 | VAL | N | 38.972 | 16.637 | 19.619 | 16.18 |
| 1748 | VAL | CA | 38.847 | 16.060 | 18.263 | 13.46 |
| 1749 | VAL | C | 39.700 | 16.901 | 17.328 | 20.85 |
| 1750 | VAL | O | 39.635 | 18.187 | 17.316 | 22.85 |
| 1751 | VAL | CB | 37.396 | 16.152 | 17.783 | 16.77 |
| 1752 | VAL | CG1 | 37.337 | 15.760 | 16.317 | 16.82 |
| 1753 | VAL | CG2 | 36.566 | 15.164 | 18.549 | 16.12 |
| 1754 | VAL | N | 40.549 | 16.250 | 16.565 | 16.13 |
| 1755 | VAL | CA | 41.389 | 17.029 | 15.642 | 14.73 |
| 1756 | VAL | C | 41.154 | 16.603 | 14.236 | 19.68 |
| 1757 | VAL | O | 41.111 | 15.408 | 13.968 | 18.53 |
| 1758 | VAL | CB | 42.844 | 16.737 | 15.897 | 16.28 |
| 1759 | VAL | CG1 | 43.703 | 17.511 | 14.901 | 17.56 |
| 1760 | VAL | CG2 | 43.184 | 17.097 | 17.349 | 17.81 |
| 1761 | HIS | N | 40.996 | 17.532 | 13.289 | 15.11 |
| 1762 | HIS | CA | 40.798 | 17.040 | 11.911 | 12.07 |
| 1763 | HIS | C | 41.283 | 18.025 | 10.893 | 18.30 |
| 1764 | HIS | O | 41.478 | 19.204 | 11.185 | 18.91 |
| 1765 | HIS | CB | 39.337 | 16.682 | 11.545 | 13.93 |
| 1766 | HIS | CG | 38.478 | 17.919 | 11.267 | 15.77 |
| 1767 | HIS | ND1 | 38.367 | 18.469 | 9.979 | 15.86 |
| 1768 | HIS | CD2 | 37.681 | 18.652 | 12.088 | 16.69 |
| 1769 | HIS | CE1 | 37.560 | 19.518 | 10.045 | 16.85 |
| 1770 | HIS | NE2 | 37.137 | 19.670 | 11.291 | 18.34 |
| 1771 | CYS | N | 41.470 | 17.478 | 9.681 | 16.12 |
| 1772 | CYS | CA | 41.899 | 18.201 | 8.547 | 13.36 |
| 1773 | CYS | C | 40.993 | 17.660 | 7.461 | 17.96 |
| 1774 | CYS | O | 39.874 | 17.322 | 7.714 | 14.94 |
| 1775 | CYS | CB | 43.356 | 18.020 | 8.128 | 12.46 |
| 1776 | CYS | SG | 44.095 | 16.346 | 8.360 | 18.95 |
| 1777 | SER | N | 41.479 | 17.548 | 6.218 | 15.33 |
| 1778 | SER | CA | 40.606 | 16.949 | 5.208 | 15.04 |
| 1779 | SER | C | 40.523 | 15.407 | 5.439 | 18.57 |
| 1780 | SER | O | 39.439 | 14.799 | 5.469 | 17.07 |
| 1781 | SER | CB | 41.042 | 17.237 | 3.766 | 14.15 |
| 1782 | SER | OG | 40.022 | 16.672 | 2.921 | 17.05 |
| 1783 | ALA | N | 41.695 | 14.781 | 5.624 | 14.98 |
| 1784 | ALA | CA | 41.676 | 13.317 | 5.798 | 13.26 |
| 1785 | ALA | C | 41.900 | 12.903 | 7.242 | 18.49 |
| 1786 | ALA | O | 41.702 | 11.727 | 7.613 | 17.47 |
| 1787 | ALA | CB | 42.793 | 12.703 | 4.988 | 14.41 |
| 1788 | GLY | N | 42.343 | 13.867 | 8.075 | 16.70 |
| 1789 | GLY | CA | 42.600 | 13.538 | 9.471 | 15.45 |
| 1790 | GLY | C | 43.930 | 12.809 | 9.660 | 18.39 |
| 1791 | GLY | O | 44.071 | 11.993 | 10.600 | 16.53 |
| 1792 | ILE | N | 44.929 | 13.082 | 8.789 | 13.74 |
| 1793 | ILE | CA | 46.226 | 12.446 | 8.919 | 11.49 |
| 1794 | ILE | C | 47.402 | 13.347 | 8.720 | 18.18 |
| 1795 | ILE | O | 48.386 | 13.343 | 9.475 | 19.37 |
| 1796 | ILE | CB | 46.405 | 11.141 | 8.141 | 16.27 |
| 1797 | ILE | CG1 | 46.367 | 11.366 | 6.605 | 17.55 |
| 1798 | ILE | CG2 | 45.308 | 10.153 | 8.566 | 15.49 |
| 1799 | ILE | CD1 | 46.493 | 10.057 | 5.781 | 14.58 |
| 1800 | GLY | N | 47.379 | 14.148 | 7.683 | 16.11 |
| 1801 | GLY | CA | 48.606 | 14.939 | 7.449 | 16.70 |
| 1802 | GLY | C | 48.766 | 16.139 | 8.371 | 19.48 |
| 1803 | GLY | O | 49.669 | 16.167 | 9.200 | 20.37 |
| 1804 | ARG | N | 47.898 | 17.159 | 8.203 | 14.27 |
| 1805 | ARG | CA | 47.981 | 18.302 | 9.086 | 14.68 |
| 1806 | ARG | C | 47.634 | 17.835 | 10.502 | 17.73 |
| 1807 | ARG | O | 48.295 | 18.218 | 11.470 | 19.43 |
| 1808 | ARG | CB | 47.114 | 19.444 | 8.599 | 12.68 |
| 1809 | ARG | CG | 47.672 | 20.033 | 7.287 | 13.57 |
| 1810 | ARG | CD | 46.645 | 20.986 | 6.671 | 11.34 |
| 1811 | ARG | NE | 45.594 | 20.244 | 5.930 | 16.97 |
| 1812 | ARG | CZ | 44.676 | 20.854 | 5.129 | 31.69 |
| 1813 | ARG | NH1 | 44.618 | 22.185 | 4.971 | 16.84 |
| 1814 | ARG | NH2 | 43.766 | 20.109 | 4.490 | 15.94 |
| 1815 | SER | N | 46.626 | 16.986 | 10.647 | 15.68 |
| 1816 | SER | CA | 46.298 | 16.517 | 12.015 | 14.86 |
| 1817 | SER | C | 47.460 | 15.831 | 12.671 | 17.12 |
| 1818 | SER | O | 47.726 | 16.037 | 13.863 | 16.53 |
| 1819 | SER | CB | 45.169 | 15.510 | 11.989 | 17.35 |
| 1820 | SER | OG | 44.028 | 16.136 | 11.424 | 17.53 |
| 1821 | GLY | N | 48.157 | 14.979 | 11.913 | 15.45 |
| 1822 | GLY | CA | 49.301 | 14.268 | 12.486 | 11.73 |
| 1823 | GLY | C | 50.394 | 15.213 | 12.935 | 17.63 |
| 1824 | GLY | O | 51.056 | 15.041 | 13.964 | 17.72 |
| 1825 | THR | N | 50.627 | 16.231 | 12.100 | 16.30 |
| 1826 | THR | CA | 51.651 | 17.225 | 12.377 | 15.64 |
| 1827 | THR | C | 51.360 | 17.997 | 13.664 | 19.70 |
| 1828 | THR | O | 52.171 | 18.184 | 14.543 | 17.95 |
| 1829 | THR | CB | 51.794 | 18.168 | 11.171 | 23.66 |
| 1830 | THR | OG1 | 52.110 | 17.428 | 9.987 | 19.58 |
| 1831 | THR | CG2 | 52.870 | 19.217 | 11.433 | 19.33 |
| 1832 | PHE | N | 50.158 | 18.420 | 13.807 | 15.63 |
| 1833 | PHE | CA | 49.780 | 19.140 | 14.983 | 15.63 |
| 1834 | PHE | C | 49.909 | 18.259 | 16.248 | 20.88 |
| 1835 | PHE | O | 50.425 | 18.670 | 17.305 | 20.45 |
| 1836 | PHE | CB | 48.260 | 19.563 | 14.772 | 17.22 |
| 1837 | PHE | CG | 47.593 | 20.201 | 15.997 | 17.55 |
| 1838 | PHE | CD1 | 47.575 | 21.585 | 16.155 | 17.33 |
| 1839 | PHE | CD2 | 46.967 | 19.435 | 16.983 | 17.40 |
| 1840 | PHE | CE1 | 46.983 | 22.172 | 17.278 | 17.10 |
| 1841 | PHE | CE2 | 46.361 | 20.001 | 18.114 | 18.42 |
| 1842 | PHE | CZ | 46.365 | 21.392 | 18.257 | 14.40 |
| 1843 | CYS | N | 49.390 | 17.033 | 16.193 | 17.18 |
| 1844 | CYS | CA | 49.432 | 16.201 | 17.366 | 14.77 |
| 1845 | CYS | C | 50.843 | 15.806 | 17.694 | 21.33 |
| 1846 | CYS | O | 51.225 | 15.694 | 18.842 | 20.61 |
| 1847 | CYS | CB | 48.573 | 14.933 | 17.191 | 18.22 |
| 1848 | CYS | SG | 46.804 | 15.307 | 17.081 | 23.37 |
| 1849 | LEU | N | 51.643 | 15.520 | 16.693 | 19.44 |
| 1850 | LEU | CA | 52.998 | 15.101 | 17.015 | 18.15 |
| 1851 | LEU | C | 53.714 | 16.200 | 17.797 | 19.49 |
| 1852 | LEU | O | 54.425 | 15.954 | 18.786 | 19.58 |
| 1853 | LEU | CB | 53.792 | 14.823 | 15.705 | 16.40 |
| 1854 | LEU | CG | 55.288 | 14.537 | 15.965 | 18.63 |
| 1855 | LEU | CD1 | 55.482 | 13.249 | 16.751 | 16.35 |
| 1856 | LEU | CD2 | 55.942 | 14.240 | 14.617 | 19.47 |
| 1857 | ALA | N | 53.571 | 17.449 | 17.313 | 16.69 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 1858 | ALA | CA | 54.249 | 18.534 | 18.012 | 15.40 |
| 1859 | ALA | C | 53.697 | 18.630 | 19.431 | 19.18 |
| 1860 | ALA | O | 54.419 | 18.775 | 20.406 | 16.89 |
| 1861 | ALA | CB | 54.115 | 19.859 | 17.273 | 14.90 |
| 1862 | ASP | N | 52.390 | 18.527 | 19.557 | 19.72 |
| 1863 | ASP | CA | 51.781 | 18.658 | 20.893 | 17.54 |
| 1864 | ASP | C | 52.338 | 17.650 | 21.887 | 20.70 |
| 1865 | ASP | O | 52.697 | 17.949 | 23.038 | 19.79 |
| 1866 | ASP | CB | 50.237 | 18.552 | 20.829 | 15.42 |
| 1867 | ASP | CG | 49.674 | 18.953 | 22.159 | 24.54 |
| 1868 | ASP | OD1 | 50.072 | 19.914 | 22.820 | 19.87 |
| 1869 | ASP | OD2 | 48.833 | 18.076 | 22.624 | 22.29 |
| 1870 | THR | N | 52.385 | 16.427 | 21.396 | 16.78 |
| 1871 | THR | CA | 52.782 | 15.309 | 22.210 | 14.97 |
| 1872 | THR | C | 54.217 | 15.416 | 22.614 | 18.91 |
| 1873 | THR | O | 54.563 | 15.159 | 23.809 | 16.57 |
| 1874 | THR | CB | 52.438 | 13.929 | 21.591 | 19.52 |
| 1875 | THR | OG1 | 51.035 | 13.752 | 21.566 | 22.01 |
| 1876 | THR | CG2 | 53.027 | 12.780 | 22.446 | 15.17 |
| 1877 | CYS | N | 55.074 | 15.710 | 21.605 | 16.93 |
| 1878 | CYS | CA | 56.498 | 15.818 | 21.947 | 16.87 |
| 1879 | CYS | C | 56.751 | 16.927 | 22.968 | 20.74 |
| 1880 | CYS | O | 57.647 | 16.825 | 23.812 | 19.23 |
| 1881 | CYS | CB | 57.335 | 16.123 | 20.706 | 18.21 |
| 1882 | CYS | SG | 57.376 | 14.721 | 19.578 | 21.43 |
| 1883 | LEU | N | 55.983 | 17.999 | 22.886 | 17.24 |
| 1884 | LEU | CA | 56.208 | 19.110 | 23.805 | 16.36 |
| 1885 | LEU | C | 55.758 | 18.707 | 25.185 | 22.13 |
| 1886 | LEU | O | 56.343 | 19.082 | 26.201 | 21.35 |
| 1887 | LEU | CB | 55.501 | 20.411 | 23.335 | 15.49 |
| 1888 | LEU | CG | 56.258 | 21.020 | 22.155 | 16.90 |
| 1889 | LEU | CD1 | 55.474 | 22.152 | 21.560 | 18.67 |
| 1890 | LEU | CD2 | 57.642 | 21.489 | 22.581 | 19.42 |
| 1891 | LEU | N | 54.709 | 17.914 | 25.244 | 18.58 |
| 1892 | LEU | CA | 54.187 | 17.454 | 26.563 | 19.33 |
| 1893 | LEU | C | 55.127 | 16.424 | 27.211 | 20.57 |
| 1894 | LEU | O | 55.403 | 16.398 | 28.406 | 17.16 |
| 1895 | LEU | CB | 52.758 | 16.888 | 26.411 | 20.29 |
| 1896 | LEU | CG | 52.083 | 16.494 | 27.720 | 23.78 |
| 1897 | LEU | CD1 | 51.799 | 17.757 | 28.557 | 22.08 |
| 1898 | LEU | CD2 | 50.756 | 15.824 | 27.386 | 26.13 |
| 1899 | LEU | N | 55.661 | 15.528 | 26.417 | 20.05 |
| 1900 | LEU | CA | 56.607 | 14.567 | 27.014 | 22.38 |
| 1901 | LEU | C | 57.798 | 15.295 | 27.539 | 21.44 |
| 1902 | LEU | O | 58.333 | 14.922 | 28.548 | 18.07 |
| 1903 | LEU | CB | 57.204 | 13.588 | 25.971 | 23.67 |
| 1904 | LEU | CG | 56.223 | 12.489 | 25.668 | 30.34 |
| 1905 | LEU | CD1 | 56.535 | 11.952 | 24.272 | 35.67 |
| 1906 | LEU | CD2 | 56.358 | 11.418 | 26.732 | 23.09 |
| 1907 | MET | N | 58.247 | 16.315 | 26.802 | 17.46 |
| 1908 | MET | CA | 59.411 | 17.026 | 27.246 | 21.88 |
| 1909 | MET | C | 59.093 | 17.791 | 28.540 | 23.63 |
| 1910 | MET | O | 59.925 | 17.939 | 29.443 | 21.17 |
| 1911 | MET | CB | 60.016 | 17.837 | 26.046 | 26.35 |
| 1912 | MET | CG | 60.123 | 19.321 | 26.201 | 31.09 |
| 1913 | MET | SD | 61.319 | 20.100 | 25.086 | 31.12 |
| 1914 | MET | CE | 61.218 | 18.941 | 23.667 | 24.10 |
| 1915 | ASP | N | 57.837 | 18.250 | 28.614 | 21.37 |
| 1916 | ASP | CA | 57.357 | 18.992 | 29.777 | 19.58 |
| 1917 | ASP | C | 57.355 | 18.111 | 31.012 | 26.30 |
| 1918 | ASP | O | 57.669 | 18.490 | 32.147 | 25.46 |
| 1919 | ASP | CB | 55.936 | 19.493 | 29.486 | 18.02 |
| 1920 | ASP | CG | 55.662 | 20.778 | 30.190 | 23.00 |
| 1921 | ASP | OD1 | 56.518 | 21.337 | 30.864 | 26.14 |
| 1922 | ASP | OD2 | 54.428 | 21.203 | 30.067 | 21.46 |
| 1923 | LYS | N | 56.941 | 16.910 | 30.809 | 26.75 |
| 1924 | LYS | CA | 56.835 | 15.971 | 31.911 | 27.98 |
| 1925 | LYS | C | 58.142 | 15.701 | 32.588 | 30.57 |
| 1926 | LYS | O | 58.233 | 15.653 | 33.824 | 29.41 |
| 1927 | LYS | CB | 56.113 | 14.673 | 31.511 | 31.11 |
| 1928 | LYS | CG | 56.050 | 13.703 | 32.679 | 62.81 |
| 1929 | LYS | CD | 54.796 | 12.831 | 32.771 | 87.49 |
| 1930 | LYS | CE | 54.830 | 11.905 | 34.006 | 100.00 |
| 1931 | LYS | NZ | 54.107 | 10.613 | 33.862 | 100.00 |
| 1932 | ARG | N | 59.175 | 15.573 | 31.790 | 29.07 |
| 1933 | ARG | CA | 60.454 | 15.266 | 32.352 | 31.74 |
| 1934 | ARG | C | 61.458 | 16.356 | 32.286 | 38.39 |
| 1935 | ARG | O | 62.576 | 16.155 | 32.699 | 42.73 |
| 1936 | ARG | CB | 61.007 | 14.104 | 31.574 | 42.79 |
| 1937 | ARG | CG | 60.626 | 14.244 | 30.128 | 44.98 |
| 1938 | ARG | CD | 61.065 | 13.064 | 29.267 | 65.93 |
| 1939 | ARG | NE | 60.195 | 11.933 | 29.445 | 74.57 |
| 1940 | ARG | CZ | 59.885 | 10.983 | 28.560 | 88.88 |
| 1941 | ARG | NH1 | 60.356 | 10.889 | 27.280 | 42.03 |
| 1942 | ARG | NH2 | 59.037 | 10.075 | 29.022 | 91.14 |
| 1943 | LYS | N | 61.090 | 17.490 | 31.753 | 28.22 |
| 1944 | LYS | CA | 62.065 | 18.538 | 31.662 | 25.40 |
| 1945 | LYS | C | 63.354 | 18.059 | 31.041 | 28.13 |
| 1946 | LYS | O | 64.435 | 18.477 | 31.438 | 25.94 |
| 1947 | LYS | CB | 62.253 | 19.262 | 32.958 | 26.58 |
| 1948 | LYS | CG | 60.936 | 19.905 | 33.457 | 27.81 |
| 1949 | LYS | CD | 60.409 | 21.051 | 32.575 | 14.64 |
| 1950 | LYS | CE | 59.256 | 21.768 | 33.219 | 19.71 |
| 1951 | LYS | NZ | 58.583 | 22.690 | 32.312 | 24.14 |
| 1952 | ASP | N | 63.240 | 17.207 | 30.024 | 22.76 |
| 1953 | ASP | CA | 64.428 | 16.721 | 29.406 | 22.09 |
| 1954 | ASP | C | 64.228 | 16.564 | 27.898 | 30.50 |
| 1955 | ASP | O | 63.820 | 15.533 | 27.405 | 33.52 |
| 1956 | ASP | CB | 64.769 | 15.377 | 30.068 | 24.25 |
| 1957 | ASP | CG | 65.984 | 14.741 | 29.416 | 34.47 |
| 1958 | ASP | OD1 | 66.675 | 15.328 | 28.608 | 33.87 |
| 1959 | ASP | OD2 | 66.182 | 13.489 | 29.778 | 42.04 |
| 1960 | PRO | N | 64.523 | 17.584 | 27.151 | 24.81 |
| 1961 | PRO | CA | 64.355 | 17.595 | 25.725 | 25.70 |
| 1962 | PRO | C | 65.131 | 16.551 | 24.997 | 31.12 |
| 1963 | PRO | O | 64.707 | 16.018 | 23.971 | 31.92 |
| 1964 | PRO | CB | 64.832 | 18.944 | 25.251 | 29.74 |
| 1965 | PRO | CG | 64.947 | 19.803 | 26.511 | 32.73 |
| 1966 | PRO | CD | 65.066 | 18.845 | 27.678 | 26.52 |
| 1967 | SER | N | 66.264 | 16.244 | 25.538 | 29.07 |
| 1968 | SER | CA | 67.077 | 15.273 | 24.890 | 31.78 |
| 1969 | SER | C | 66.479 | 13.911 | 24.933 | 37.92 |
| 1970 | SER | O | 66.793 | 13.023 | 24.150 | 45.55 |
| 1971 | SER | CB | 68.530 | 15.309 | 25.381 | 42.27 |
| 1972 | SER | OG | 69.183 | 16.449 | 24.808 | 59.55 |
| 1973 | SER | N | 65.580 | 13.735 | 25.830 | 28.18 |
| 1974 | SER | CA | 64.970 | 12.446 | 25.947 | 28.28 |
| 1975 | SER | C | 63.888 | 12.202 | 24.886 | 32.74 |
| 1976 | SER | O | 63.293 | 11.107 | 24.796 | 34.35 |
| 1977 | SER | CB | 64.304 | 12.317 | 27.328 | 30.87 |
| 1978 | SER | OG | 63.068 | 13.050 | 27.357 | 38.21 |
| 1979 | VAL | N | 63.544 | 13.269 | 24.191 | 26.20 |
| 1980 | VAL | CA | 62.453 | 13.223 | 23.204 | 23.76 |
| 1981 | VAL | C | 62.902 | 12.743 | 21.809 | 26.52 |
| 1982 | VAL | O | 63.645 | 13.435 | 21.074 | 28.45 |
| 1983 | VAL | CB | 61.667 | 14.568 | 23.186 | 25.58 |
| 1984 | VAL | CG1 | 60.555 | 14.594 | 22.126 | 25.16 |
| 1985 | VAL | CG2 | 61.053 | 14.793 | 24.553 | 24.66 |
| 1986 | ASP | N | 62.404 | 11.567 | 21.409 | 21.57 |
| 1987 | ASP | CA | 62.732 | 11.009 | 20.111 | 19.61 |
| 1988 | ASP | C | 61.521 | 11.154 | 19.182 | 26.16 |
| 1989 | ASP | O | 60.569 | 10.318 | 19.178 | 26.94 |
| 1990 | ASP | CB | 63.073 | 9.533 | 20.320 | 22.22 |
| 1991 | ASP | CG | 63.559 | 8.879 | 19.072 | 34.42 |
| 1992 | ASP | OD1 | 63.392 | 9.325 | 17.935 | 28.99 |
| 1993 | ASP | OD2 | 64.139 | 7.760 | 19.353 | 40.03 |
| 1994 | ILE | N | 61.550 | 12.245 | 18.381 | 23.48 |
| 1995 | ILE | CA | 60.414 | 12.608 | 17.503 | 19.92 |
| 1996 | ILE | C | 59.899 | 11.503 | 16.616 | 24.71 |
| 1997 | ILE | O | 58.701 | 11.191 | 16.558 | 22.68 |
| 1998 | ILE | CB | 60.775 | 13.880 | 16.762 | 20.09 |
| 1999 | ILE | CG1 | 60.992 | 14.906 | 17.875 | 22.40 |
| 2000 | ILE | CG2 | 59.660 | 14.316 | 15.820 | 17.07 |
| 2001 | ILE | CD1 | 61.365 | 16.303 | 17.382 | 33.15 |
| 2002 | LYS | N | 60.844 | 10.882 | 15.909 | 20.78 |
| 2003 | LYS | CA | 60.402 | 9.864 | 14.960 | 21.92 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 2004 | LYS | C | 59.744 | 8.711 | 15.639 | 21.66 |
| 2005 | LYS | O | 58.801 | 8.086 | 15.176 | 24.06 |
| 2006 | LYS | CB | 61.517 | 9.349 | 14.047 | 22.87 |
| 2007 | LYS | CG | 62.275 | 10.451 | 13.370 | 20.42 |
| 2008 | LYS | CD | 63.483 | 9.834 | 12.671 | 33.57 |
| 2009 | LYS | CE | 64.772 | 10.122 | 13.443 | 43.45 |
| 2010 | LYS | NZ | 65.169 | 9.089 | 14.399 | 74.10 |
| 2011 | LYS | N | 60.328 | 8.382 | 16.736 | 19.22 |
| 2012 | LYS | CA | 59.802 | 7.275 | 17.481 | 21.33 |
| 2013 | LYS | C | 58.418 | 7.643 | 18.006 | 22.92 |
| 2014 | LYS | O | 57.563 | 6.767 | 18.082 | 18.47 |
| 2015 | LYS | CB | 60.804 | 6.907 | 18.595 | 26.85 |
| 2016 | LYS | CG | 60.510 | 5.641 | 19.360 | 57.18 |
| 2017 | LYS | CD | 61.693 | 5.220 | 20.236 | 74.44 |
| 2018 | LYS | CE | 61.283 | 4.289 | 21.393 | 100.00 |
| 2019 | LYS | NZ | 61.528 | 4.824 | 22.754 | 100.00 |
| 2020 | VAL | N | 58.209 | 8.943 | 18.386 | 20.32 |
| 2021 | VAL | CA | 56.880 | 9.344 | 18.869 | 19.06 |
| 2022 | VAL | C | 55.878 | 9.249 | 17.713 | 19.98 |
| 2023 | VAL | O | 54.733 | 8.767 | 17.821 | 19.01 |
| 2024 | VAL | CB | 56.868 | 10.755 | 19.474 | 21.25 |
| 2025 | VAL | CG1 | 55.427 | 11.187 | 19.850 | 18.14 |
| 2026 | VAL | CG2 | 57.734 | 10.742 | 20.750 | 21.39 |
| 2027 | LEU | N | 56.348 | 9.643 | 16.566 | 15.76 |
| 2028 | LEU | CA | 55.460 | 9.554 | 15.431 | 15.06 |
| 2029 | LEU | C | 55.086 | 8.101 | 15.149 | 21.46 |
| 2030 | LEU | O | 53.940 | 7.742 | 14.839 | 18.74 |
| 2031 | LEU | CB | 56.111 | 10.260 | 14.217 | 14.15 |
| 2032 | LEU | CG | 55.289 | 10.130 | 12.916 | 18.24 |
| 2033 | LEU | CD1 | 53.915 | 10.764 | 13.092 | 16.76 |
| 2034 | LEU | CD2 | 56.004 | 10.808 | 11.711 | 17.04 |
| 2035 | LEU | N | 56.064 | 7.209 | 15.275 | 20.58 |
| 2036 | LEU | CA | 55.762 | 5.798 | 15.021 | 18.54 |
| 2037 | LEU | C | 54.783 | 5.290 | 16.042 | 21.57 |
| 2038 | LEU | O | 53.935 | 4.472 | 15.713 | 22.28 |
| 2039 | LEU | CB | 57.015 | 4.889 | 14.955 | 19.53 |
| 2040 | LEU | CG | 57.819 | 5.029 | 13.630 | 24.40 |
| 2041 | LEU | CD1 | 59.230 | 4.498 | 13.813 | 22.15 |
| 2042 | LEU | CD2 | 57.127 | 4.319 | 12.437 | 21.17 |
| 2043 | ASP | N | 54.883 | 5.775 | 17.297 | 17.91 |
| 2044 | ASP | CA | 53.905 | 5.330 | 18.301 | 16.81 |
| 2045 | ASP | C | 52.538 | 5.845 | 17.897 | 19.40 |
| 2046 | ASP | O | 51.528 | 5.181 | 17.996 | 21.08 |
| 2047 | ASP | CB | 54.203 | 5.840 | 19.767 | 19.29 |
| 2048 | ASP | CG | 53.470 | 5.056 | 20.894 | 46.92 |
| 2049 | ASP | OD1 | 53.626 | 3.832 | 21.196 | 39.76 |
| 2050 | ASP | OD2 | 52.681 | 5.849 | 21.576 | 67.80 |
| 2051 | MET | N | 52.465 | 7.082 | 17.466 | 17.80 |
| 2052 | MET | CA | 51.146 | 7.550 | 17.093 | 18.08 |
| 2053 | MET | C | 50.586 | 6.785 | 15.902 | 19.16 |
| 2054 | MET | O | 49.360 | 6.544 | 15.802 | 19.67 |
| 2055 | MET | CB | 51.294 | 9.000 | 16.640 | 23.05 |
| 2056 | MET | CG | 51.750 | 9.946 | 17.756 | 33.10 |
| 2057 | MET | SD | 51.452 | 11.712 | 17.338 | 37.23 |
| 2058 | MET | CE | 50.717 | 12.236 | 18.903 | 32.15 |
| 2059 | ARG | N | 51.471 | 6.425 | 14.953 | 16.98 |
| 2060 | ARG | CA | 50.996 | 5.690 | 13.759 | 18.78 |
| 2061 | ARG | C | 50.448 | 4.309 | 14.082 | 20.60 |
| 2062 | ARG | O | 49.921 | 3.625 | 13.227 | 18.40 |
| 2063 | ARG | CB | 51.817 | 5.867 | 12.441 | 25.17 |
| 2064 | ARG | CG | 52.747 | 7.091 | 12.429 | 48.25 |
| 2065 | ARG | CD | 52.842 | 8.056 | 11.215 | 60.15 |
| 2066 | ARG | NE | 52.920 | 7.361 | 9.965 | 30.10 |
| 2067 | ARG | CZ | 53.076 | 7.701 | 8.652 | 25.89 |
| 2068 | ARG | NH1 | 53.321 | 8.890 | 8.086 | 27.29 |
| 2069 | ARG | NH2 | 53.031 | 6.649 | 7.819 | 19.72 |
| 2070 | LYS | N | 50.600 | 3.877 | 15.366 | 17.55 |
| 2071 | LYS | CA | 50.018 | 2.617 | 15.750 | 16.12 |
| 2072 | LYS | C | 48.516 | 2.808 | 15.804 | 23.50 |
| 2073 | LYS | O | 47.753 | 1.864 | 15.744 | 21.94 |
| 2074 | LYS | CB | 50.439 | 2.157 | 17.165 | 14.21 |
| 2075 | LYS | CG | 51.927 | 1.901 | 17.250 | 18.36 |
| 2076 | LYS | CD | 52.363 | 1.502 | 18.666 | 21.09 |
| 2077 | LYS | CE | 53.863 | 1.184 | 18.762 | 28.07 |
| 2078 | LYS | NZ | 54.278 | 1.049 | 20.179 | 30.77 |
| 2079 | PHE | N | 48.066 | 4.046 | 15.996 | 17.28 |
| 2080 | PHE | CA | 46.649 | 4.276 | 16.181 | 17.04 |
| 2081 | PHE | C | 45.896 | 4.765 | 14.955 | 19.33 |
| 2082 | PHE | O | 44.665 | 4.622 | 14.894 | 17.66 |
| 2083 | PHE | CB | 46.469 | 5.282 | 17.315 | 17.60 |
| 2084 | PHE | CG | 47.096 | 4.756 | 18.576 | 17.54 |
| 2085 | PHE | CD1 | 46.372 | 3.897 | 19.407 | 19.62 |
| 2086 | PHE | CD2 | 48.368 | 5.176 | 18.950 | 18.66 |
| 2087 | PHE | CE1 | 46.943 | 3.369 | 20.570 | 21.35 |
| 2088 | PHE | CE2 | 48.910 | 4.698 | 20.145 | 22.41 |
| 2089 | PHE | CZ | 48.214 | 3.787 | 20.946 | 19.04 |
| 2090 | ARG | N | 46.598 | 5.382 | 14.053 | 13.88 |
| 2091 | ARG | CA | 45.967 | 5.775 | 12.828 | 13.48 |
| 2092 | ARG | C | 47.051 | 5.809 | 11.774 | 16.22 |
| 2093 | ARG | O | 48.163 | 6.250 | 11.973 | 15.25 |
| 2094 | ARG | CB | 45.321 | 7.172 | 12.939 | 16.93 |
| 2095 | ARG | CG | 44.544 | 7.632 | 11.689 | 16.86 |
| 2096 | ARG | CD | 43.697 | 8.897 | 12.048 | 18.74 |
| 2097 | ARG | NE | 42.861 | 9.407 | 10.923 | 16.22 |
| 2098 | ARG | CZ | 41.658 | 8.932 | 10.504 | 27.02 |
| 2099 | ARG | NH1 | 41.047 | 7.860 | 11.071 | 15.47 |
| 2100 | ARG | NH2 | 41.056 | 9.547 | 9.443 | 17.92 |
| 2101 | MET | N | 46.715 | 5.395 | 10.564 | 18.09 |
| 2102 | MET | CA | 47.684 | 5.410 | 9.516 | 18.05 |
| 2103 | MET | C | 47.968 | 6.814 | 8.978 | 20.84 |
| 2104 | MET | O | 47.145 | 7.697 | 9.055 | 18.35 |
| 2105 | MET | CB | 47.079 | 4.556 | 8.343 | 19.02 |
| 2106 | MET | CG | 45.812 | 5.199 | 7.720 | 21.47 |
| 2107 | MET | SD | 45.180 | 4.334 | 6.222 | 26.31 |
| 2108 | MET | CE | 44.495 | 2.762 | 6.841 | 24.21 |
| 2109 | GLY | N | 49.125 | 6.961 | 8.363 | 15.59 |
| 2110 | GLY | CA | 49.540 | 8.083 | 7.529 | 18.21 |
| 2111 | GLY | C | 49.743 | 9.433 | 8.135 | 21.75 |
| 2112 | GLY | O | 49.791 | 10.451 | 7.402 | 18.48 |
| 2113 | LEU | N | 49.925 | 9.400 | 9.463 | 18.42 |
| 2114 | LEU | CA | 50.072 | 10.648 | 10.204 | 14.70 |
| 2115 | LEU | C | 51.314 | 11.339 | 9.720 | 18.00 |
| 2116 | LEU | O | 52.374 | 10.727 | 9.794 | 19.18 |
| 2117 | LEU | CB | 50.061 | 10.371 | 11.712 | 14.05 |
| 2118 | LEU | CG | 48.786 | 9.649 | 12.191 | 17.72 |
| 2119 | LEU | CD1 | 48.869 | 9.460 | 13.706 | 17.55 |
| 2120 | LEU | CD2 | 47.507 | 10.393 | 11.817 | 15.18 |
| 2121 | ILE | N | 51.159 | 12.596 | 9.295 | 15.02 |
| 2122 | ILE | CA | 52.219 | 13.420 | 8.703 | 15.09 |
| 2123 | ILE | C | 52.350 | 12.891 | 7.295 | 20.09 |
| 2124 | ILE | O | 52.785 | 11.728 | 7.088 | 16.03 |
| 2125 | ILE | CB | 53.538 | 13.451 | 9.423 | 17.27 |
| 2126 | ILE | CG1 | 53.244 | 14.065 | 10.772 | 16.88 |
| 2127 | ILE | CG2 | 54.476 | 14.391 | 8.650 | 17.72 |
| 2128 | ILE | CD1 | 54.453 | 14.681 | 11.446 | 18.43 |
| 2129 | GLN | N | 51.917 | 13.710 | 6.331 | 18.36 |
| 2130 | GLN | CA | 51.887 | 13.223 | 4.941 | 19.19 |
| 2131 | GLN | C | 53.025 | 13.540 | 3.983 | 22.72 |
| 2132 | GLN | O | 53.040 | 13.026 | 2.871 | 20.09 |
| 2133 | GLN | CB | 50.522 | 13.582 | 4.326 | 19.65 |
| 2134 | GLN | CG | 49.371 | 12.674 | 4.858 | 22.65 |
| 2135 | GLN | CD | 49.367 | 11.349 | 4.113 | 26.84 |
| 2136 | GLN | OE1 | 49.184 | 11.364 | 2.900 | 17.52 |
| 2137 | GLN | NE2 | 49.600 | 10.236 | 4.801 | 19.94 |
| 2138 | THR | N | 53.911 | 14.414 | 4.397 | 21.73 |
| 2139 | THR | CA | 55.045 | 14.841 | 3.612 | 20.72 |
| 2140 | THR | C | 56.262 | 15.010 | 4.495 | 23.82 |
| 2141 | THR | O | 56.210 | 15.236 | 5.721 | 21.43 |
| 2142 | THR | CB | 54.876 | 16.140 | 2.852 | 21.33 |
| 2143 | THR | CG1 | 55.050 | 17.211 | 3.777 | 23.48 |
| 2144 | THR | CG2 | 53.520 | 16.222 | 2.174 | 16.62 |
| 2145 | ALA | N | 57.378 | 14.910 | 3.844 | 22.77 |
| 2146 | ALA | CA | 58.601 | 15.018 | 4.587 | 23.01 |
| 2147 | ALA | C | 58.801 | 16.403 | 5.105 | 22.21 |
| 2148 | ALA | O | 59.447 | 16.639 | 6.154 | 24.06 |
| 2149 | ALA | CB | 59.776 | 14.531 | 3.763 | 24.53 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 2150 | ASP | N | 58.259 | 17.354 | 4.370 | 20.66 |
| 2151 | ASP | CA | 58.422 | 18.724 | 4.858 | 20.24 |
| 2152 | ASP | C | 57.595 | 18.934 | 6.129 | 23.29 |
| 2153 | ASP | O | 57.899 | 19.740 | 7.024 | 23.21 |
| 2154 | ASP | CB | 58.049 | 19.778 | 3.806 | 23.48 |
| 2155 | ASP | CG | 58.591 | 21.167 | 4.207 | 30.38 |
| 2156 | ASP | OD1 | 59.693 | 21.282 | 4.763 | 31.02 |
| 2157 | ASP | OD2 | 57.785 | 22.190 | 3.885 | 34.64 |
| 2158 | GLN | N | 56.525 | 18.194 | 6.208 | 18.19 |
| 2159 | GLN | CA | 55.712 | 18.298 | 7.413 | 17.86 |
| 2160 | GLN | C | 56.513 | 17.759 | 8.615 | 23.26 |
| 2161 | GLN | O | 56.369 | 18.212 | 9.768 | 21.57 |
| 2162 | GLN | CB | 54.325 | 17.569 | 7.239 | 17.92 |
| 2163 | GLN | CG | 53.295 | 18.409 | 6.448 | 18.27 |
| 2164 | GLN | CD | 52.071 | 17.609 | 6.116 | 19.07 |
| 2165 | GLN | OE1 | 52.036 | 16.389 | 6.390 | 18.84 |
| 2166 | GLN | NE2 | 51.071 | 18.282 | 5.541 | 16.62 |
| 2167 | LEU | N | 57.349 | 16.727 | 8.369 | 20.85 |
| 2168 | LEU | CA | 58.148 | 16.126 | 9.423 | 17.29 |
| 2169 | LEU | C | 59.161 | 17.115 | 9.838 | 21.68 |
| 2170 | LEU | O | 59.368 | 17.386 | 11.015 | 21.08 |
| 2171 | LEU | CB | 58.770 | 14.818 | 8.982 | 16.92 |
| 2172 | LEU | CG | 59.679 | 14.141 | 10.018 | 18.94 |
| 2173 | LEU | CD1 | 58.866 | 13.624 | 11.231 | 17.31 |
| 2174 | LEU | CD2 | 60.409 | 12.959 | 9.351 | 15.70 |
| 2175 | ARG | N | 59.781 | 17.705 | 8.820 | 20.27 |
| 2176 | ARG | CA | 60.792 | 18.727 | 9.101 | 19.02 |
| 2177 | ARG | C | 60.181 | 19.859 | 9.932 | 22.20 |
| 2178 | ARG | O | 60.689 | 20.361 | 10.947 | 21.23 |
| 2179 | ARG | CB | 61.327 | 19.293 | 7.792 | 15.51 |
| 2180 | ARG | CG | 62.568 | 20.163 | 8.046 | 21.78 |
| 2181 | ARG | CD | 63.127 | 20.785 | 6.770 | 27.88 |
| 2182 | ARG | NE | 64.351 | 21.523 | 7.038 | 33.02 |
| 2183 | ARG | CZ | 64.355 | 22.814 | 7.227 | 31.22 |
| 2184 | ARG | NH1 | 63.242 | 23.517 | 7.186 | 23.06 |
| 2185 | ARG | NH2 | 65.508 | 23.412 | 7.478 | 31.35 |
| 2186 | PHE | N | 59.007 | 20.291 | 9.471 | 20.79 |
| 2187 | PHE | CA | 58.378 | 21.345 | 10.214 | 18.33 |
| 2188 | PHE | C | 58.180 | 20.945 | 11.680 | 23.47 |
| 2189 | PHE | O | 58.375 | 21.746 | 12.588 | 22.26 |
| 2190 | PHE | CB | 57.065 | 21.789 | 9.582 | 16.79 |
| 2191 | PHE | CG | 56.399 | 22.920 | 10.381 | 21.31 |
| 2192 | PHE | CD1 | 56.681 | 24.267 | 10.126 | 21.18 |
| 2193 | PHE | CD2 | 55.431 | 22.654 | 11.355 | 21.09 |
| 2194 | PHE | CE1 | 56.063 | 25.309 | 10.814 | 22.40 |
| 2195 | PHE | CE2 | 54.836 | 23.698 | 12.074 | 22.51 |
| 2196 | PHE | CZ | 55.164 | 25.025 | 11.833 | 19.57 |
| 2197 | SER | N | 57.752 | 19.714 | 11.884 | 20.57 |
| 2198 | SER | CA | 57.496 | 19.183 | 13.233 | 19.79 |
| 2199 | SER | C | 58.704 | 19.438 | 14.082 | 22.01 |
| 2200 | SER | O | 58.617 | 19.894 | 15.216 | 21.53 |
| 2201 | SER | CB | 57.252 | 17.666 | 13.321 | 16.35 |
| 2202 | SER | OG | 55.984 | 17.531 | 12.733 | 31.09 |
| 2203 | TYR | N | 59.841 | 19.086 | 13.544 | 20.69 |
| 2204 | TYR | CA | 61.030 | 19.291 | 14.365 | 19.51 |
| 2205 | TYR | C | 61.207 | 20.766 | 14.689 | 21.92 |
| 2206 | TYR | O | 61.557 | 21.130 | 15.818 | 20.31 |
| 2207 | TYR | CB | 62.273 | 18.913 | 13.583 | 19.52 |
| 2208 | TYR | CG | 62.654 | 17.464 | 13.682 | 24.16 |
| 2209 | TYR | CD1 | 61.877 | 16.472 | 13.074 | 24.17 |
| 2210 | TYR | CD2 | 63.872 | 17.095 | 14.281 | 26.60 |
| 2211 | TYR | CE1 | 62.245 | 15.126 | 13.119 | 24.68 |
| 2212 | TYR | CE2 | 64.261 | 15.750 | 14.311 | 25.92 |
| 2213 | TYR | CZ | 63.440 | 14.771 | 13.749 | 24.97 |
| 2214 | TYR | OH | 63.827 | 13.469 | 13.819 | 32.37 |
| 2215 | LEU | N | 60.985 | 21.623 | 13.670 | 19.51 |
| 2216 | LEU | CA | 61.150 | 23.020 | 13.916 | 17.52 |
| 2217 | LEU | C | 60.225 | 23.486 | 15.031 | 26.06 |
| 2218 | LEU | O | 60.606 | 24.304 | 15.892 | 25.65 |
| 2219 | LEU | CB | 60.860 | 23.865 | 12.721 | 16.93 |
| 2220 | LEU | CG | 61.898 | 23.718 | 11.592 | 26.47 |
| 2221 | LEU | CD1 | 61.535 | 24.606 | 10.412 | 24.45 |
| 2222 | LEU | CD2 | 63.302 | 24.080 | 12.029 | 28.00 |
| 2223 | ALA | N | 58.990 | 23.004 | 15.018 | 19.08 |
| 2224 | ALA | CA | 58.051 | 23.437 | 16.041 | 16.99 |
| 2225 | ALA | C | 58.424 | 22.901 | 17.408 | 20.57 |
| 2226 | ALA | O | 58.287 | 23.551 | 18.424 | 19.60 |
| 2227 | ALA | CB | 56.587 | 23.121 | 15.708 | 16.41 |
| 2228 | VAL | N | 58.905 | 21.698 | 17.488 | 17.68 |
| 2229 | VAL | CA | 59.206 | 21.230 | 18.835 | 17.05 |
| 2230 | VAL | C | 60.448 | 21.893 | 19.395 | 23.15 |
| 2231 | VAL | O | 60.592 | 22.155 | 20.616 | 21.24 |
| 2232 | VAL | CB | 59.378 | 19.694 | 18.826 | 20.45 |
| 2233 | VAL | CG1 | 59.865 | 19.096 | 20.165 | 18.27 |
| 2234 | VAL | CG2 | 58.084 | 19.006 | 18.357 | 19.14 |
| 2235 | ILE | N | 61.405 | 22.100 | 18.504 | 21.22 |
| 2236 | ILE | CA | 62.661 | 22.702 | 18.937 | 20.04 |
| 2237 | ILE | C | 62.420 | 24.090 | 19.475 | 25.88 |
| 2238 | ILE | O | 62.999 | 24.462 | 20.493 | 25.47 |
| 2239 | ILE | CB | 63.639 | 22.794 | 17.766 | 24.05 |
| 2240 | ILE | CG1 | 64.232 | 21.403 | 17.511 | 25.87 |
| 2241 | ILE | CG2 | 64.736 | 23.758 | 18.113 | 22.69 |
| 2242 | ILE | CD1 | 64.839 | 21.250 | 16.118 | 27.49 |
| 2243 | GLU | N | 61.577 | 24.877 | 18.781 | 19.27 |
| 2244 | GLU | CA | 61.260 | 26.237 | 19.213 | 17.92 |
| 2245 | GLU | C | 60.385 | 26.224 | 20.480 | 22.75 |
| 2246 | GLU | O | 60.556 | 27.020 | 21.388 | 20.84 |
| 2247 | GLU | CB | 60.510 | 26.936 | 18.054 | 19.09 |
| 2248 | GLU | CG | 59.998 | 28.359 | 18.389 | 20.36 |
| 2249 | GLU | CD | 61.125 | 29.327 | 18.744 | 29.49 |
| 2250 | GLU | OE1 | 62.316 | 29.183 | 18.463 | 23.96 |
| 2251 | GLU | OE2 | 60.693 | 30.344 | 19.428 | 26.29 |
| 2252 | GLY | N | 59.423 | 25.296 | 20.515 | 20.31 |
| 2253 | GLY | CA | 58.498 | 25.189 | 21.643 | 18.63 |
| 2254 | GLY | C | 59.259 | 24.833 | 22.907 | 23.95 |
| 2255 | GLY | O | 58.870 | 25.127 | 24.072 | 18.97 |
| 2256 | ALA | N | 60.356 | 24.110 | 22.677 | 23.58 |
| 2257 | ALA | CA | 61.188 | 23.677 | 23.804 | 23.19 |
| 2258 | ALA | C | 61.565 | 24.862 | 24.682 | 23.67 |
| 2259 | ALA | O | 61.732 | 24.708 | 25.900 | 25.14 |
| 2260 | ALA | CB | 62.471 | 22.961 | 23.330 | 23.30 |
| 2261 | LYS | N | 61.747 | 26.038 | 24.042 | 19.35 |
| 2262 | LYS | CA | 62.155 | 27.232 | 24.809 | 19.49 |
| 2263 | LYS | C | 61.196 | 27.564 | 25.955 | 25.32 |
| 2264 | LYS | O | 61.575 | 27.937 | 27.090 | 22.02 |
| 2265 | LYS | CB | 62.225 | 28.423 | 23.883 | 21.56 |
| 2266 | LYS | CG | 63.349 | 28.249 | 22.857 | 24.29 |
| 2267 | LYS | CD | 63.327 | 29.437 | 21.907 | 28.63 |
| 2268 | LYS | CE | 64.359 | 29.447 | 20.820 | 33.79 |
| 2269 | LYS | NZ | 63.978 | 30.470 | 19.839 | 63.50 |
| 2270 | PHE | N | 59.922 | 27.482 | 25.608 | 20.00 |
| 2271 | PHE | CA | 58.858 | 27.740 | 26.571 | 17.26 |
| 2272 | PHE | C | 58.834 | 26.622 | 27.598 | 23.66 |
| 2273 | PHE | O | 58.789 | 26.847 | 28.791 | 23.24 |
| 2274 | PHE | CB | 57.543 | 27.740 | 25.772 | 19.05 |
| 2275 | PHE | CG | 56.407 | 27.958 | 26.718 | 23.90 |
| 2276 | PHE | CD1 | 55.800 | 26.859 | 27.315 | 30.06 |
| 2277 | PHE | CD2 | 56.014 | 29.242 | 27.087 | 25.49 |
| 2278 | PHE | CE1 | 54.788 | 27.010 | 28.262 | 31.06 |
| 2279 | PHE | CE2 | 54.982 | 29.400 | 28.015 | 30.43 |
| 2280 | PHE | CZ | 54.380 | 28.294 | 28.612 | 28.57 |
| 2281 | ILE | N | 58.841 | 25.369 | 27.139 | 21.16 |
| 2282 | ILE | CA | 58.815 | 24.235 | 28.070 | 21.71 |
| 2283 | ILE | C | 60.001 | 24.330 | 29.014 | 26.83 |
| 2284 | ILE | O | 59.949 | 23.959 | 30.185 | 28.05 |
| 2285 | ILE | CB | 59.014 | 22.890 | 27.335 | 24.04 |
| 2286 | ILE | CG1 | 57.843 | 22.495 | 26.446 | 24.85 |
| 2287 | ILE | CG2 | 59.269 | 21.758 | 28.309 | 26.71 |
| 2288 | ILE | CD1 | 56.488 | 23.121 | 26.760 | 22.80 |
| 2289 | MET | N | 61.117 | 24.785 | 28.524 | 21.30 |
| 2290 | MET | CA | 62.205 | 24.825 | 29.440 | 23.12 |
| 2291 | MET | C | 62.325 | 26.098 | 30.299 | 28.91 |
| 2292 | MET | O | 63.398 | 26.410 | 30.748 | 31.20 |
| 2293 | MET | CB | 63.520 | 24.378 | 28.836 | 25.89 |
| 2294 | MET | CG | 63.303 | 23.037 | 28.171 | 29.97 |
| 2295 | MET | SD | 63.168 | 21.686 | 29.352 | 29.79 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 2296 | MET | CE | 64.744 | 21.950 | 30.149 | 26.41 |
| 2297 | GLY | N | 61.278 | 26.868 | 30.528 | 24.26 |
| 2298 | GLY | CA | 61.489 | 27.964 | 31.450 | 24.71 |
| 2299 | GLY | C | 61.414 | 29.354 | 30.933 | 25.55 |
| 2300 | GLY | O | 61.441 | 30.290 | 31.708 | 24.08 |
| 2301 | ASP | N | 61.338 | 29.535 | 29.658 | 21.90 |
| 2302 | ASP | CA | 61.207 | 30.919 | 29.246 | 22.03 |
| 2303 | ASP | C | 59.786 | 31.173 | 28.742 | 27.04 |
| 2304 | ASP | O | 59.433 | 31.017 | 27.567 | 29.25 |
| 2305 | ASP | CB | 62.264 | 31.272 | 28.189 | 25.34 |
| 2306 | ASP | CG | 62.034 | 32.645 | 27.603 | 36.54 |
| 2307 | ASP | OD1 | 61.228 | 33.466 | 28.063 | 40.88 |
| 2308 | ASP | OD2 | 62.728 | 32.823 | 26.512 | 33.74 |
| 2309 | SER | N | 58.906 | 31.542 | 29.605 | 24.08 |
| 2310 | SER | CA | 57.570 | 31.757 | 29.101 | 26.04 |
| 2311 | SER | C | 57.474 | 32.994 | 28.153 | 33.52 |
| 2312 | SER | O | 56.550 | 33.100 | 27.360 | 33.01 |
| 2313 | SER | CB | 56.523 | 31.840 | 30.246 | 28.08 |
| 2314 | SER | OG | 56.595 | 30.689 | 31.114 | 27.62 |
| 2315 | SER | N | 58.412 | 33.948 | 28.264 | 28.61 |
| 2316 | SER | CA | 58.379 | 35.156 | 27.472 | 26.34 |
| 2317 | SER | C | 58.298 | 34.830 | 25.956 | 32.58 |
| 2318 | SER | O | 57.816 | 35.629 | 25.094 | 30.04 |
| 2319 | SER | CB | 59.651 | 35.942 | 27.768 | 22.72 |
| 2320 | SER | OG | 60.712 | 35.599 | 26.864 | 34.10 |
| 2321 | VAL | N | 58.812 | 33.647 | 25.599 | 28.26 |
| 2322 | VAL | CA | 58.797 | 33.246 | 24.170 | 28.99 |
| 2323 | VAL | C | 57.356 | 33.239 | 23.563 | 32.46 |
| 2324 | VAL | O | 57.093 | 33.549 | 22.403 | 28.95 |
| 2325 | VAL | CB | 59.628 | 31.965 | 23.969 | 29.56 |
| 2326 | VAL | CG1 | 58.841 | 30.740 | 24.349 | 27.83 |
| 2327 | VAL | CG2 | 60.017 | 31.836 | 22.548 | 31.39 |
| 2328 | GLN | N | 56.370 | 32.942 | 24.425 | 30.24 |
| 2329 | GLN | CA | 54.974 | 32.874 | 24.017 | 29.27 |
| 2330 | GLN | C | 54.503 | 34.187 | 23.477 | 30.84 |
| 2331 | GLN | O | 53.777 | 34.236 | 22.506 | 27.71 |
| 2332 | GLN | CB | 54.073 | 32.406 | 25.207 | 32.06 |
| 2333 | GLN | CG | 52.561 | 32.481 | 24.958 | 56.39 |
| 2334 | GLN | CD | 51.805 | 31.561 | 25.885 | 51.02 |
| 2335 | GLN | OE1 | 52.229 | 31.337 | 27.004 | 34.74 |
| 2336 | GLN | NE2 | 50.703 | 31.010 | 25.403 | 62.41 |
| 2337 | ASP | N | 54.895 | 35.262 | 24.140 | 29.32 |
| 2338 | ASP | CA | 54.505 | 36.602 | 23.691 | 30.87 |
| 2339 | ASP | C | 55.136 | 36.911 | 22.333 | 30.01 |
| 2340 | ASP | O | 54.530 | 37.499 | 21.433 | 31.24 |
| 2341 | ASP | CB | 54.906 | 37.629 | 24.756 | 35.79 |
| 2342 | ASP | CG | 54.358 | 37.219 | 26.082 | 65.63 |
| 2343 | ASP | OD1 | 53.170 | 36.998 | 26.227 | 71.17 |
| 2344 | ASP | OD2 | 55.278 | 37.034 | 27.014 | 80.27 |
| 2345 | GLN | N | 56.374 | 36.460 | 22.194 | 25.78 |
| 2346 | GLN | CA | 57.108 | 36.574 | 20.948 | 26.06 |
| 2347 | GLN | C | 56.384 | 35.851 | 19.806 | 30.03 |
| 2348 | GLN | O | 56.246 | 36.357 | 18.715 | 26.89 |
| 2349 | GLN | CB | 58.455 | 35.924 | 21.120 | 27.67 |
| 2350 | GLN | CG | 59.317 | 36.611 | 22.198 | 44.36 |
| 2351 | GLN | CD | 60.751 | 36.116 | 22.147 | 77.73 |
| 2352 | GLN | OE1 | 61.283 | 35.846 | 21.053 | 88.38 |
| 2353 | GLN | NE2 | 61.357 | 35.952 | 23.326 | 61.19 |
| 2354 | TRP | N | 55.906 | 34.644 | 20.070 | 26.22 |
| 2355 | TRP | CA | 55.195 | 33.953 | 19.048 | 23.95 |
| 2356 | TRP | C | 53.959 | 34.709 | 18.716 | 27.74 |
| 2357 | TRP | O | 53.590 | 34.825 | 17.557 | 29.34 |
| 2358 | TRP | CB | 54.752 | 32.529 | 19.487 | 22.50 |
| 2359 | TRP | CG | 55.887 | 31.639 | 19.847 | 21.30 |
| 2360 | TRP | CD1 | 57.167 | 31.756 | 19.417 | 23.75 |
| 2361 | TRP | CD2 | 55.842 | 30.526 | 20.763 | 19.48 |
| 2362 | TRP | NE1 | 57.927 | 30.767 | 19.994 | 23.42 |
| 2363 | TRP | CE2 | 57.143 | 30.005 | 20.849 | 22.89 |
| 2364 | TRP | CE3 | 54.820 | 29.939 | 21.517 | 20.00 |
| 2365 | TRP | CZ2 | 57.464 | 28.895 | 21.668 | 20.62 |
| 2366 | TRP | CZ3 | 55.119 | 28.829 | 22.299 | 20.58 |
| 2367 | TRP | CH2 | 56.418 | 28.303 | 22.365 | 20.81 |
| 2368 | LYS | N | 53.273 | 35.191 | 19.732 | 25.02 |
| 2369 | LYS | CA | 52.051 | 35.913 | 19.449 | 23.72 |
| 2370 | LYS | C | 52.279 | 37.141 | 18.512 | 32.33 |
| 2371 | LYS | O | 51.536 | 37.430 | 17.531 | 28.38 |
| 2372 | LYS | CB | 51.390 | 36.292 | 20.731 | 24.86 |
| 2373 | LYS | CG | 50.049 | 36.954 | 20.489 | 36.15 |
| 2374 | LYS | CD | 49.612 | 37.791 | 21.672 | 56.07 |
| 2375 | LYS | CE | 48.105 | 37.986 | 21.748 | 94.91 |
| 2376 | LYS | NZ | 47.664 | 38.697 | 22.968 | 100.00 |
| 2377 | GLU | N | 53.319 | 37.895 | 18.808 | 32.11 |
| 2378 | GLU | CA | 53.630 | 39.036 | 17.969 | 35.38 |
| 2379 | GLU | C | 54.028 | 38.602 | 16.559 | 36.31 |
| 2380 | GLU | O | 53.557 | 39.097 | 15.540 | 38.26 |
| 2381 | GLU | CB | 54.813 | 39.855 | 18.548 | 39.32 |
| 2382 | GLU | CG | 54.559 | 40.416 | 19.974 | 69.72 |
| 2383 | GLU | CD | 53.542 | 41.540 | 19.993 | 100.00 |
| 2384 | GLU | OE1 | 53.826 | 42.742 | 19.907 | 100.00 |
| 2385 | GLU | OE2 | 52.311 | 41.071 | 20.086 | 100.00 |
| 2386 | LEU | N | 54.930 | 37.668 | 16.477 | 29.59 |
| 2387 | LEU | CA | 55.371 | 37.218 | 15.175 | 29.45 |
| 2388 | LEU | C | 54.297 | 36.602 | 14.316 | 34.02 |
| 2389 | LEU | O | 54.438 | 36.402 | 13.095 | 34.53 |
| 2390 | LEU | CB | 56.402 | 36.124 | 15.389 | 30.02 |
| 2391 | LEU | CG | 57.673 | 36.730 | 15.958 | 37.18 |
| 2392 | LEU | CD1 | 58.611 | 35.621 | 16.448 | 36.22 |
| 2393 | LEU | CD2 | 58.332 | 37.541 | 14.834 | 39.33 |
| 2394 | SER | N | 53.238 | 36.196 | 14.951 | 26.99 |
| 2395 | SER | CA | 52.226 | 35.561 | 14.179 | 27.01 |
| 2396 | SER | C | 51.217 | 36.583 | 13.608 | 33.85 |
| 2397 | SER | O | 50.359 | 36.208 | 12.843 | 33.74 |
| 2398 | SER | CB | 51.521 | 34.632 | 15.134 | 28.99 |
| 2399 | SER | OG | 50.444 | 35.407 | 15.648 | 44.35 |
| 2400 | HIS | N | 51.275 | 37.855 | 14.034 | 33.50 |
| 2401 | HIS | CA | 50.355 | 38.935 | 13.604 | 36.33 |
| 2402 | HIS | C | 48.945 | 38.510 | 13.663 | 34.53 |
| 2403 | HIS | O | 48.221 | 38.641 | 12.668 | 29.05 |
| 2404 | HIS | CB | 50.574 | 39.458 | 12.177 | 41.53 |
| 2405 | HIS | CG | 52.003 | 39.597 | 11.966 | 50.56 |
| 2406 | HIS | ND1 | 52.683 | 38.801 | 11.043 | 55.72 |
| 2407 | HIS | CD2 | 52.889 | 40.377 | 12.656 | 55.69 |
| 2408 | HIS | CE1 | 53.978 | 39.152 | 11.158 | 56.62 |
| 2409 | HIS | NE2 | 54.131 | 40.085 | 12.120 | 56.78 |
| 2410 | GLU | N | 48.528 | 38.023 | 14.795 | 31.47 |
| 2411 | GLU | CA | 47.172 | 37.560 | 14.773 | 32.57 |
| 2412 | GLU | C | 46.110 | 38.585 | 14.659 | 35.60 |
| 2413 | GLU | O | 44.984 | 38.253 | 14.397 | 35.07 |
| 2414 | GLU | CB | 46.886 | 36.568 | 15.881 | 34.05 |
| 2415 | GLU | CG | 47.343 | 37.124 | 17.210 | 29.10 |
| 2416 | GLU | CD | 46.766 | 36.272 | 18.291 | 44.34 |
| 2417 | GLU | OE1 | 46.803 | 35.044 | 18.311 | 28.10 |
| 2418 | GLU | OE2 | 46.156 | 36.987 | 19.183 | 42.70 |
| 2419 | ASP | N | 46.433 | 39.851 | 14.841 | 38.45 |
| 2420 | ASP | CA | 45.375 | 40.870 | 14.777 | 78.44 |
| 2421 | ASP | C | 45.114 | 41.525 | 13.428 | 73.26 |
| 2422 | ASP | O | 46.027 | 41.652 | 12.620 | 57.37 |
| 2423 | ASP | CB | 45.440 | 41.851 | 15.949 | 80.14 |
| 2424 | ASP | CG | 45.045 | 41.139 | 17.215 | 99.39 |
| 2425 | ASP | OD1 | 43.981 | 40.514 | 17.333 | 100.00 |
| 2426 | ASP | OD2 | 45.979 | 41.210 | 18.148 | 100.00 |
| 2427 | HOH | O | 38.401 | 17.896 | 24.639 | 19.06 |
| 2428 | HOH | O | 42.880 | −2.994 | 13.734 | 22.22 |
| 2429 | HOH | O | 37.909 | 0.024 | 10.420 | 18.06 |
| 2430 | HOH | O | 34.283 | 3.652 | 13.551 | 16.99 |
| 2431 | HOH | O | 31.031 | 7.792 | 20.003 | 21.22 |
| 2432 | HOH | O | 56.762 | 16.414 | 35.819 | 23.22 |
| 2433 | HOH | O | 38.520 | 4.591 | 3.340 | 17.34 |
| 2434 | HOH | O | 38.706 | 8.875 | 4.448 | 19.05 |
| 2435 | HOH | O | 48.541 | 17.369 | 4.500 | 18.16 |
| 2436 | HOH | O | 22.375 | 24.091 | 20.022 | 27.04 |
| 2437 | HOH | O | 50.383 | 3.090 | 10.757 | 19.44 |
| 2438 | HOH | O | 56.581 | 20.545 | 34.028 | 23.47 |
| 2439 | HOH | O | 44.023 | 22.433 | 27.502 | 26.90 |
| 2440 | HOH | O | 23.678 | 29.248 | 15.041 | 26.35 |
| 2441 | HOH | O | 30.955 | 16.693 | 24.220 | 25.48 |

TABLE A-continued

Table of the orthogonal three dimensional coordinates in Ångstroms and B factors (Å²) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 2442 | HOH | O | 36.539 | −2.273 | 15.479 | 27.62 |
| 2443 | HOH | O | 60.199 | 22.714 | 6.928 | 25.25 |
| 2444 | HOH | O | 42.799 | 15.905 | 24.284 | 24.08 |
| 2445 | HOH | O | 58.854 | 31.126 | 13.755 | 28.34 |
| 2446 | HOH | O | 25.489 | 12.276 | 9.898 | 29.35 |
| 2447 | HOH | O | 44.868 | 21.909 | 30.537 | 27.95 |
| 2448 | HOH | O | 19.794 | 30.078 | 16.536 | 27.05 |
| 2449 | HOH | O | 41.421 | 3.661 | 14.164 | 17.35 |
| 2450 | HOH | O | 41.884 | 2.616 | 3.383 | 21.00 |
| 2451 | HOH | O | 34.858 | 3.969 | 20.688 | 28.33 |
| 2452 | HOH | O | 53.734 | 2.425 | 13.962 | 22.10 |
| 2453 | HOH | O | 60.930 | 9.816 | 23.103 | 29.63 |
| 2454 | HOH | O | 42.886 | 3.496 | 20.674 | 24.24 |
| 2455 | HOH | O | 30.810 | 36.766 | 18.288 | 26.91 |
| 2456 | HOH | O | 59.810 | 32.233 | 32.172 | 26.16 |
| 2457 | HOH | O | 57.738 | 17.405 | 1.262 | 32.83 |
| 2458 | HOH | O | 36.660 | 27.108 | 5.425 | 23.54 |
| 2459 | HOH | O | 32.265 | 17.633 | 1.767 | 24.56 |
| 2460 | HOH | O | 66.198 | 17.107 | 2.407 | 38.58 |
| 2461 | HOH | O | 57.752 | 28.197 | 31.074 | 29.94 |
| 2462 | HOH | O | 41.286 | 15.987 | 26.904 | 32.37 |
| 2463 | HOH | O | 36.669 | 27.749 | 2.270 | 31.44 |
| 2464 | HOH | O | 39.624 | −4.625 | 16.505 | 28.88 |
| 2465 | HOH | O | 45.398 | 24.023 | 0.668 | 27.71 |
| 2466 | HOH | O | 51.673 | 32.445 | 21.771 | 23.43 |
| 2467 | HOH | O | 53.099 | 24.833 | 2.471 | 29.74 |
| 2468 | HOH | O | 54.526 | 19.450 | 2.810 | 28.76 |
| 2469 | HOH | O | 27.105 | 36.172 | 19.570 | 24.82 |
| 2470 | HOH | O | 36.334 | 30.259 | 9.265 | 30.82 |
| 2471 | HOH | O | 56.626 | 24.387 | 33.815 | 30.17 |
| 2472 | HOH | O | 42.738 | 29.954 | 24.494 | 35.73 |
| 2473 | HOH | O | 57.220 | 13.971 | 0.977 | 32.27 |
| 2474 | HOH | O | 65.256 | 29.469 | 30.089 | 39.20 |
| 2475 | HOH | O | 49.786 | 39.709 | 16.909 | 43.80 |
| 2476 | HOH | O | 52.863 | 6.253 | 24.788 | 35.18 |
| 2477 | HOH | O | 35.798 | −5.535 | 5.469 | 31.13 |
| 2478 | HOH | O | 50.331 | 22.923 | −0.657 | 36.76 |
| 2479 | HOH | O | 36.765 | 3.406 | 1.739 | 42.22 |
| 2480 | HOH | O | 26.434 | 4.890 | 5.483 | 35.83 |
| 2481 | HOH | O | 34.613 | 32.955 | 20.594 | 43.11 |
| 2482 | HOH | O | 27.837 | 3.167 | 1.403 | 42.94 |
| 2483 | HOH | O | 32.582 | 9.372 | −0.315 | 36.58 |
| 2484 | HOH | O | 45.800 | 3.147 | 2.702 | 31.42 |
| 2485 | HOH | O | 33.763 | 0.985 | 2.765 | 30.40 |
| 2486 | HOH | O | 29.040 | 1.300 | 20.110 | 50.77 |
| 2487 | HOH | O | 42.199 | −4.222 | 6.234 | 38.97 |
| 2488 | HOH | O | 21.619 | 20.058 | 9.321 | 40.28 |
| 2489 | HOH | O | 53.500 | 20.656 | 27.642 | 27.42 |
| 2490 | HOH | O | 16.860 | 27.164 | 18.394 | 26.90 |
| 2491 | HOH | O | 43.874 | 0.861 | 20.343 | 25.50 |
| 2492 | HOH | O | 29.683 | −0.569 | 10.390 | 26.21 |
| 2493 | HOH | O | 28.054 | 11.908 | 26.787 | 41.40 |
| 2494 | HOH | O | 50.466 | 28.546 | 28.067 | 42.56 |
| 2495 | HOH | O | 28.502 | 21.053 | 3.156 | 30.33 |
| 2496 | HOH | O | 63.942 | 27.419 | 17.604 | 28.20 |
| 2497 | HOH | O | 22.109 | 21.232 | 30.110 | 48.48 |
| 2498 | HOH | O | 49.254 | 32.003 | 23.342 | 40.08 |
| 2499 | HOH | O | 24.641 | 7.692 | 4.830 | 53.24 |
| 2500 | HOH | O | 63.797 | 11.089 | 16.405 | 27.62 |
| 2501 | HOH | O | 53.333 | 9.033 | 24.881 | 28.87 |
| 2502 | HOH | O | 37.700 | 0.242 | 19.127 | 49.32 |
| 2503 | HOH | O | 24.665 | 29.142 | 9.720 | 48.36 |
| 2504 | HOH | O | 54.352 | −3.114 | 9.194 | 44.58 |
| 2505 | HOH | O | 62.613 | 5.916 | 11.920 | 39.76 |
| 2506 | HOH | O | 63.952 | 28.080 | 27.641 | 38.19 |
| 2507 | HOH | O | 65.802 | 19.783 | 33.411 | 38.59 |
| 2508 | HOH | O | 57.255 | 27.489 | 7.852 | 41.05 |
| 2509 | HOH | O | 19.030 | 25.560 | 24.767 | 57.85 |
| 2510 | HOH | O | 64.201 | 13.583 | 18.348 | 29.38 |
| 2511 | HOH | O | 55.852 | −0.427 | 22.999 | 50.13 |
| 2512 | HOH | O | 36.898 | −5.489 | 16.055 | 67.33 |
| 2513 | HOH | O | 33.905 | 27.753 | 6.095 | 27.01 |
| 2514 | HOH | O | 27.382 | −1.372 | 13.747 | 35.80 |
| 2515 | HOH | O | 33.489 | −3.895 | 15.708 | 41.00 |
| 2516 | HOH | O | 24.559 | 2.258 | 7.150 | 41.23 |
| 2517 | HOH | O | 65.779 | 15.180 | 21.392 | 35.84 |
| 2518 | HOH | O | 65.553 | 25.125 | 21.639 | 47.37 |
| 2519 | HOH | O | 32.513 | 19.611 | 26.519 | 62.17 |
| 2520 | HOH | O | 33.651 | 17.294 | 28.933 | 55.49 |
| 2521 | HOH | O | 41.137 | 19.611 | −7.004 | 52.94 |
| 2522 | HOH | O | 66.395 | 21.128 | 4.224 | 47.91 |
| 2523 | HOH | O | 23.251 | 11.180 | 19.061 | 48.42 |
| 2524 | HOH | O | 39.259 | 33.229 | 22.025 | 51.45 |
| 2525 | HOH | O | 36.119 | 32.908 | 9.928 | 44.34 |
| 2526 | HOH | O | 53.725 | 36.111 | 5.937 | 100.00 |
| 2527 | HOH | O | 63.179 | 35.153 | 24.999 | 55.42 |
| 2528 | HOH | O | 35.968 | 6.586 | −0.582 | 43.18 |
| 2529 | HOH | O | 21.346 | 7.913 | 13.010 | 56.07 |
| 2530 | HOH | O | 19.175 | 28.875 | 19.382 | 53.38 |
| 2531 | HOH | O | 22.715 | 7.898 | 10.565 | 50.52 |
| 2532 | HOH | O | 47.395 | 34.116 | 21.423 | 47.24 |
| 2533 | HOH | O | 32.765 | 7.633 | 26.983 | 64.04 |
| 2534 | HOH | O | 54.471 | 34.005 | 11.028 | 47.55 |
| 2535 | HOH | O | 72.465 | 12.809 | 15.523 | 46.13 |
| 2536 | HOH | O | 47.441 | 6.136 | −1.870 | 46.53 |
| 2537 | HOH | O | 43.416 | 18.301 | −3.456 | 49.44 |
| 2538 | HOH | O | 65.579 | 21.420 | 21.981 | 50.95 |
| 2539 | HOH | O | 47.751 | 7.411 | 2.407 | 40.84 |
| 2540 | HOH | O | 32.644 | 8.712 | 8.756 | 15.74 |
| 2541 | HOH | O | 33.023 | 11.570 | 8.792 | 15.03 |
| 2542 | HOH | O | 44.089 | 25.927 | 7.019 | 19.82 |
| 2543 | HOH | O | 58.775 | 26.249 | 32.830 | 26.89 |
| 2544 | HOH | O | 51.112 | 4.543 | 8.642 | 20.55 |
| 2545 | HOH | O | 62.946 | 25.839 | 15.605 | 26.99 |
| 2546 | HOH | O | 40.881 | −6.288 | 14.710 | 22.12 |
| 2547 | HOH | O | 52.351 | 8.308 | 5.018 | 25.66 |
| 2548 | HOH | O | 61.224 | 24.419 | 33.190 | 30.44 |
| 2549 | HOH | O | 28.243 | −3.909 | 4.213 | 32.48 |
| 2550 | HOH | O | 62.221 | 27.938 | 13.810 | 30.53 |
| 2551 | HOH | O | 39.610 | −6.610 | 12.431 | 30.17 |
| 2552 | HOH | O | 54.043 | 16.770 | 35.701 | 34.80 |
| 2553 | HOH | O | 15.219 | 28.439 | 20.359 | 31.31 |
| 2554 | HOH | O | 64.424 | 20.767 | 35.354 | 32.43 |
| 2555 | HOH | O | 14.987 | 23.468 | 24.936 | 33.81 |
| 2556 | HOH | O | 21.319 | 29.054 | 23.219 | 34.70 |
| 2557 | HOH | O | 30.027 | −1.696 | 12.465 | 39.40 |
| 2558 | HOH | O | 25.366 | 15.033 | 7.774 | 33.88 |
| 2559 | HOH | O | 66.346 | 11.979 | 1.208 | 42.20 |
| 2560 | HOH | O | 17.665 | 23.698 | 26.769 | 54.87 |
| 2561 | HOH | O | 51.859 | 5.861 | 4.981 | 38.52 |
| 2562 | HOH | O | 24.749 | 29.791 | 25.560 | 42.21 |
| 2563 | HOH | O | 57.813 | 3.867 | 18.815 | 41.01 |
| 2564 | HOH | O | 63.315 | 26.715 | 7.503 | 46.17 |
| 2565 | HOH | O | 53.229 | 27.524 | 4.226 | 50.52 |
| 2566 | HOH | O | 63.148 | 7.825 | 9.883 | 44.30 |
| 2567 | HOH | O | 26.879 | 19.362 | 7.236 | 22.65 |
| 2568 | HOH | O | 67.878 | 17.615 | 34.499 | 44.34 |
| 2569 | HOH | O | 54.054 | 30.226 | 31.561 | 25.96 |
| 2570 | HOH | O | 54.931 | 12.873 | 0.470 | 42.81 |
| 2571 | HOH | O | 44.558 | 8.294 | −3.296 | 70.17 |
| 2572 | HOH | O | 26.495 | 26.387 | 25.981 | 49.19 |
| 2573 | HOH | O | 45.561 | 9.651 | 27.926 | 47.40 |
| 2574 | HOH | O | 33.903 | −6.440 | 2.953 | 64.63 |
| 2575 | HOH | O | 64.772 | 6.818 | 21.874 | 47.22 |
| 2576 | HOH | O | 38.599 | 3.739 | 20.598 | 47.72 |
| 2577 | HOH | O | 40.578 | 33.268 | 10.218 | 43.71 |
| 2578 | HOH | O | 23.004 | 14.669 | 9.548 | 41.06 |
| 2579 | HOH | O | 18.520 | 21.210 | 10.100 | 82.04 |
| 2580 | HOH | O | 54.443 | 0.368 | 6.856 | 46.46 |
| 2581 | HOH | O | 53.301 | 3.094 | 5.341 | 55.82 |
| 2582 | HOH | O | 62.577 | 30.234 | 15.315 | 50.03 |
| 2583 | HOH | O | 58.940 | 24.723 | 5.711 | 51.05 |
| 2584 | HOH | O | 20.726 | 3.366 | 15.601 | 78.38 |
| 2585 | HOH | O | 43.027 | 13.430 | 27.118 | 54.39 |
| 2586 | HOH | O | 62.195 | 28.464 | 10.795 | 46.23 |
| 2587 | HOH | O | 50.510 | 34.226 | 10.824 | 39.07 |

TABLE A-continued

Table of the orthogonal three dimensional coordinates in Ångstroms and B factors (Å$^2$) for Protein Tyrosine Phosphatase 1B complexed with 2-(oxalyl-amino)-4,5,6,7-tetrahydro-thieno[2,3-c]pyridine-3-carboxylic acid.

| No | Amino acid | | X | Y | Z | B |
|---|---|---|---|---|---|---|
| 2588 | HOH | O | 40.918 | −2.815 | 21.009 | 65.28 |
| 2589 | HOH | O | 43.587 | 26.925 | −2.428 | 47.56 |
| 2590 | HOH | O | 13.754 | 15.204 | 18.843 | 53.86 |
| 2591 | HOH | O | 31.164 | 30.490 | 3.629 | 56.80 |
| 2592 | HOH | O | 64.794 | 14.809 | 1.227 | 46.20 |
| 2593 | HOH | O | 65.739 | 6.902 | 9.576 | 42.14 |
| 2594 | HOH | O | 22.779 | 9.377 | 7.806 | 74.52 |
| 2595 | HOH | O | 35.536 | 1.247 | 20.572 | 58.11 |
| 2596 | HOH | O | 48.720 | 41.298 | 14.904 | 65.02 |
| 2597 | HOH | O | 41.886 | 8.125 | 26.131 | 43.72 |
| 2598 | HOH | O | 21.553 | 25.706 | 8.779 | 67.26 |
| 2599 | HOH | O | 47.438 | 24.713 | −1.762 | 68.04 |
| 2600 | HOH | O | 59.462 | 2.577 | 16.912 | 44.01 |
| 2601 | HOH | O | 34.650 | 13.050 | 10.584 | 15.74 |
| 2602 | HOH | O | 44.151 | 3.876 | 10.554 | 20.85 |
| 2603 | HOH | O | 30.226 | 8.145 | 9.680 | 20.38 |
| 2604 | HOH | O | 50.795 | 5.197 | 23.429 | 23.53 |
| 2605 | HOH | O | 55.241 | 24.256 | 1.478 | 43.03 |
| 2606 | HOH | O | 13.876 | 26.053 | 19.951 | 39.87 |
| 2607 | HOH | O | 37.440 | 7.794 | 22.997 | 34.34 |
| 2608 | HOH | O | 36.776 | 4.942 | 22.481 | 44.54 |
| 2609 | HOH | O | 49.204 | 6.833 | 4.042 | 59.47 |
| 2610 | HOH | O | 46.016 | 15.869 | 28.666 | 53.22 |
| 2611 | HOH | O | 52.597 | 14.225 | 35.410 | 44.55 |
| 2612 | HOH | O | 55.717 | 8.332 | 23.770 | 40.53 |
| 2613 | HOH | O | 35.617 | 38.541 | 15.729 | 45.63 |
| 2614 | HOH | O | 24.347 | 36.908 | 13.597 | 48.19 |
| 2615 | HOH | O | 37.734 | 23.590 | 30.260 | 62.04 |
| 2616 | HOH | O | 59.359 | 7.814 | 23.351 | 51.17 |
| 2617 | HOH | O | 40.870 | −8.615 | 10.301 | 39.22 |
| 2618 | HOH | O | 55.653 | −1.953 | 5.995 | 52.57 |
| 2619 | HOH | O | 51.582 | 1.831 | 22.838 | 43.21 |
| 2620 | HOH | O | 23.536 | 16.687 | 3.287 | 66.26 |
| 2621 | HOH | O | 27.390 | 9.583 | 26.222 | 66.80 |
| 2622 | HOH | O | 26.006 | 26.772 | 7.979 | 55.20 |
| 2623 | HOH | O | 48.629 | 36.281 | 9.258 | 53.85 |
| 2624 | HOH | O | 54.312 | 1.731 | 24.312 | 49.12 |
| 2625 | HOH | O | 64.534 | 7.113 | 16.407 | 42.12 |
| 2626 | HOH | O | 43.617 | 30.982 | 3.143 | 48.34 |
| 2627 | HOH | O | 22.572 | 13.132 | 27.363 | 70.18 |
| 2628 | HOH | O | 70.408 | 21.965 | 2.674 | 89.51 |
| 2629 | HOH | O | 63.931 | 33.405 | 22.517 | 55.19 |
| 2630 | HOH | O | 48.600 | 32.735 | 29.774 | 71.55 |
| 2631 | HOH | O | 34.250 | 14.917 | 30.699 | 46.61 |
| 2632 | HOH | O | 43.731 | 33.337 | 6.158 | 93.58 |
| 2633 | HOH | O | 60.489 | 31.207 | 10.548 | 55.19 |
| 2634 | HOH | O | 50.155 | 2.150 | 6.615 | 54.57 |
| 2635 | HOH | O | 25.514 | 6.559 | 24.332 | 75.79 |
| 2636 | HOH | O | 31.745 | 30.209 | 9.802 | 50.27 |
| 2637 | HOH | O | 35.679 | 10.169 | 26.838 | 65.87 |
| 2638 | HOH | O | 13.764 | 16.372 | 28.336 | 78.20 |
| 2639 | HOH | O | 17.554 | 19.418 | 30.248 | 64.92 |
| 2640 | HOH | O | 65.875 | 16.089 | 34.874 | 64.83 |
| 2641 | HOH | O | 68.340 | 17.620 | 27.806 | 60.04 |
| 2642 | HOH | O | 36.275 | 32.819 | 22.710 | 48.84 |
| 2643 | HOH | O | 63.468 | 8.121 | 24.078 | 51.50 |
| 2644 | HOH | O | 39.850 | 34.128 | 24.551 | 67.42 |
| 2645 | HOH | O | 22.019 | 12.665 | 7.060 | 70.82 |
| 2646 | HOH | O | 30.890 | −4.164 | 13.154 | 65.28 |
| 2647 | HOH | O | 23.362 | 5.115 | 3.428 | 51.03 |
| 2648 | HOH | O | 41.079 | 12.774 | 28.276 | 77.64 |
| 2649 | HOH | O | 32.157 | 37.768 | 15.682 | 60.54 |
| 2650 | HOH | O | 37.346 | 12.911 | 33.109 | 69.06 |
| 2651 | HOH | O | 60.400 | −0.560 | 17.559 | 60.23 |
| 1 | 95 | C1 | 45.324 | 12.023 | 1.856 | 20.00 |
| 2 | 95 | S2 | 45.841 | 12.927 | 3.269 | 20.00 |
| 3 | 95 | C3 | 44.986 | 14.367 | 2.692 | 20.00 |
| 4 | 95 | C4 | 44.391 | 14.159 | 1.498 | 20.00 |
| 5 | 95 | C5 | 44.709 | 12.824 | 0.981 | 20.00 |
| 6 | 95 | N6 | 44.964 | 15.620 | 3.482 | 20.00 |
| 7 | 95 | C7 | 45.489 | 15.733 | 4.720 | 20.00 |
| 8 | 95 | C8 | 45.238 | 16.996 | 5.547 | 20.00 |
| 9 | 95 | O9 | 44.228 | 17.659 | 5.375 | 20.00 |
| 10 | 95 | O10 | 45.978 | 17.336 | 6.420 | 20.00 |
| 11 | 95 | O11 | 46.159 | 14.860 | 5.251 | 20.00 |
| 12 | 95 | C12 | 43.503 | 15.119 | 0.776 | 20.00 |
| 13 | 95 | O13 | 43.428 | 15.102 | −0.452 | 20.00 |
| 14 | 95 | O14 | 42.803 | 15.898 | 1.358 | 20.00 |
| 15 | 95 | C18 | 44.232 | 12.358 | −0.368 | 20.00 |
| 16 | 95 | C19 | 44.430 | 10.836 | −0.521 | 20.00 |
| 17 | 95 | N20 | 45.675 | 10.345 | 0.087 | 20.00 |
| 18 | 95 | C21 | 45.756 | 10.616 | 1.531 | 20.00 |

TABLE B

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1 | GLU | N | 39.465 | 52.977 | 54.384 | 50.84 |
| 2 | GLU | CA | 38.798 | 51.719 | 54.051 | 51.38 |
| 3 | GLU | C | 39.109 | 51.267 | 52.590 | 49.72 |
| 4 | GLU | O | 38.944 | 52.002 | 51.620 | 49.04 |
| 5 | GLU | GB | 37.270 | 51.855 | 54.252 | 53.79 |
| 6 | GLU | CG | 36.557 | 50.495 | 54.416 | 57.54 |
| 7 | GLU | CD | 36.972 | 49.698 | 55.707 | 62.60 |
| 8 | GLU | OE1 | 36.770 | 50.216 | 56.799 | 64.63 |
| 9 | GLU | OE2 | 37.518 | 48.585 | 55.616 | 64.40 |
| 10 | MET | N | 39.495 | 49.971 | 52.496 | 46.10 |
| 11 | MET | CA | 39.753 | 49.178 | 51.264 | 42.61 |
| 12 | MET | C | 38.547 | 49.091 | 50.363 | 40.49 |
| 13 | MET | O | 38.640 | 48.979 | 49.159 | 38.08 |
| 14 | MET | CB | 40.128 | 47.730 | 51.640 | 41.62 |
| 15 | MET | CG | 39.190 | 47.107 | 52.716 | 40.45 |
| 16 | MET | SD | 39.645 | 45.471 | 53.299 | 35.84 |
| 17 | MET | CE | 41.295 | 45.867 | 53.958 | 39.51 |
| 18 | GLU | N | 37.419 | 49.189 | 51.051 | 40.04 |
| 19 | GLU | CA | 36.086 | 49.198 | 50.457 | 41.99 |
| 20 | GLU | C | 35.767 | 50.510 | 49.639 | 41.64 |
| 21 | GLU | O | 35.409 | 50.486 | 48.472 | 42.33 |
| 22 | GLU | CB | 35.156 | 48.876 | 51.627 | 43.82 |
| 23 | GLU | CG | 33.862 | 48.113 | 51.292 | 47.17 |
| 24 | GLU | CD | 33.244 | 47.563 | 52.607 | 49.31 |
| 25 | GLU | OE1 | 33.732 | 47.923 | 53.672 | 48.56 |
| 26 | GLU | OE2 | 32.301 | 46.761 | 52.564 | 51.19 |
| 27 | LYS | N | 36.000 | 51.696 | 50.213 | 40.99 |
| 28 | LYS | CA | 35.753 | 52.839 | 49.308 | 41.50 |
| 29 | LYS | C | 36.854 | 52.957 | 48.192 | 39.57 |
| 30 | LYS | O | 36.534 | 53.231 | 47.054 | 39.12 |
| 31 | LYS | GB | 35.643 | 54.142 | 50.104 | 45.89 |
| 32 | LYS | CG | 34.578 | 54.185 | 51.248 | 51.71 |
| 33 | LYS | CD | 35.008 | 55.173 | 52.386 | 56.13 |
| 34 | LYS | CE | 34.450 | 54.867 | 53.793 | 59.81 |
| 35 | LYS | NZ | 35.323 | 55.409 | 54.876 | 62.35 |
| 36 | GLU | N | 38.147 | 52.704 | 48.526 | 38.42 |
| 37 | GLU | CA | 39.236 | 52.572 | 47.517 | 37.30 |
| 38 | GLU | C | 38.888 | 51.620 | 46.385 | 34.58 |
| 39 | GLU | O | 39.054 | 51.964 | 45.238 | 33.74 |
| 40 | GLU | CB | 40.601 | 52.140 | 48.101 | 40.63 |
| 41 | GLU | CG | 41.526 | 51.508 | 47.019 | 46.16 |
| 42 | GLU | CD | 43.077 | 51.484 | 47.114 | 49.22 |
| 43 | GLU | OE1 | 43.672 | 50.792 | 47.941 | 50.86 |
| 44 | GLU | OE2 | 43.723 | 52.146 | 46.288 | 51.79 |
| 45 | PHE | N | 38.395 | 50.433 | 46.755 | 31.46 |
| 46 | PHE | CA | 37.835 | 49.488 | 45.799 | 30.49 |
| 47 | PHE | C | 36.777 | 50.107 | 44.857 | 33.05 |
| 48 | PHE | O | 36.828 | 49.954 | 43.648 | 31.17 |
| 49 | PHE | CB | 37.148 | 48.330 | 46.531 | 26.00 |
| 50 | PHE | CG | 36.682 | 47.268 | 45.560 | 23.39 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 51 | PHE | CD1 | 37.608 | 46.321 | 45.069 | 24.75 |
| 52 | PHE | CD2 | 35.388 | 47.202 | 45.084 | 23.83 |
| 53 | PHE | CE1 | 37.277 | 45.364 | 44.109 | 21.69 |
| 54 | PHE | CE2 | 35.064 | 46.263 | 44.099 | 23.15 |
| 55 | PHE | CZ | 35.985 | 45.348 | 43.603 | 22.50 |
| 56 | GLU | N | 35.818 | 50.823 | 45.452 | 34.78 |
| 57 | GLU | CA | 34.725 | 51.349 | 44.619 | 36.92 |
| 58 | GLU | C | 35.092 | 52.587 | 43.702 | 34.88 |
| 59 | GLU | O | 34.771 | 52.673 | 42.529 | 34.89 |
| 60 | GLU | CB | 33.592 | 51.542 | 45.609 | 42.69 |
| 61 | GLU | CG | 33.191 | 50.163 | 46.129 | 51.81 |
| 62 | GLU | CD | 32.044 | 50.199 | 47.121 | 58.22 |
| 63 | GLU | OE1 | 31.735 | 51.274 | 47.661 | 60.76 |
| 64 | GLU | OE2 | 31.467 | 49.123 | 47.337 | 60.88 |
| 65 | GLN | N | 35.875 | 53.523 | 44.252 | 32.17 |
| 66 | GLN | CA | 36.614 | 54.515 | 43.493 | 32.79 |
| 67 | GLN | C | 37.270 | 53.878 | 42.281 | 32.59 |
| 68 | GLN | O | 37.068 | 54.411 | 41.198 | 33.38 |
| 69 | GLN | CB | 37.684 | 55.103 | 44.398 | 38.01 |
| 70 | GLN | CG | 38.460 | 56.386 | 44.041 | 46.72 |
| 71 | GLN | CD | 39.538 | 56.621 | 45.198 | 54.60 |
| 72 | GLN | CE1 | 40.705 | 56.281 | 45.103 | 58.48 |
| 73 | GLN | NE2 | 39.104 | 57.129 | 46.335 | 57.65 |
| 74 | ILE | N | 37.995 | 52.752 | 42.495 | 30.75 |
| 75 | ILE | CA | 38.784 | 52.110 | 41.427 | 29.79 |
| 76 | ILE | C | 37.944 | 51.513 | 40.345 | 29.61 |
| 77 | ILE | O | 38.222 | 51.644 | 39.164 | 28.92 |
| 78 | ILE | CB | 39.820 | 51.020 | 41.780 | 28.01 |
| 79 | ILE | CG1 | 40.944 | 51.578 | 42.625 | 26.65 |
| 80 | ILE | CG2 | 40.547 | 50.559 | 40.485 | 24.67 |
| 81 | ILE | CD1 | 41.717 | 50.482 | 43.321 | 30.61 |
| 82 | ASP | N | 36.941 | 50.841 | 40.826 | 30.56 |
| 83 | ASP | CA | 36.056 | 50.131 | 39.941 | 34.30 |
| 84 | ASP | C | 35.275 | 51.174 | 39.066 | 36.61 |
| 85 | ASP | O | 35.220 | 51.032 | 37.847 | 37.72 |
| 86 | ASP | CB | 35.183 | 49.189 | 40.820 | 34.23 |
| 87 | ASP | CG | 35.372 | 47.692 | 40.610 | 34.09 |
| 88 | ASP | OD1 | 36.406 | 47.266 | 40.156 | 34.45 |
| 89 | ASP | OD2 | 34.468 | 46.917 | 40.892 | 35.24 |
| 90 | LYS | N | 34.750 | 52.271 | 39.708 | 38.57 |
| 91 | LYS | CA | 34.018 | 53.296 | 38.901 | 40.78 |
| 92 | LYS | C | 34.892 | 53.932 | 37.806 | 40.89 |
| 93 | LYS | O | 34.499 | 54.071 | 36.665 | 41.19 |
| 94 | LYS | CB | 33.321 | 54.430 | 39.687 | 44.73 |
| 95 | LYS | CG | 34.160 | 55.716 | 39.765 | 49.46 |
| 96 | LYS | CD | 33.790 | 56.625 | 40.936 | 52.61 |
| 97 | LYS | CE | 34.890 | 57.651 | 41.277 | 51.86 |
| 98 | LYS | NZ | 36.251 | 57.064 | 41.269 | 49.92 |
| 99 | SER | N | 36.087 | 54.345 | 38.162 | 39.93 |
| 100 | SER | CA | 36.820 | 54.789 | 37.003 | 41.11 |
| 101 | SER | C | 37.425 | 53.593 | 36.217 | 41.60 |
| 102 | SER | O | 37.968 | 53.748 | 35.149 | 44.13 |
| 103 | SER | CB | 37.986 | 55.539 | 37.561 | 41.13 |
| 104 | SER | OG | 38.877 | 54.652 | 38.356 | 43.06 |
| 105 | GLY | N | 37.399 | 52.386 | 36.767 | 39.95 |
| 106 | GLY | CA | 38.129 | 51.274 | 36.127 | 36.83 |
| 107 | GLY | C | 39.671 | 51.290 | 36.223 | 35.39 |
| 108 | GLY | O | 40.316 | 50.783 | 35.320 | 37.15 |
| 109 | SER | N | 40.279 | 51.841 | 37.301 | 32.66 |
| 110 | SER | CA | 41.780 | 51.938 | 37.308 | 31.67 |
| 111 | SER | C | 42.598 | 50.665 | 37.811 | 29.26 |
| 112 | SER | O | 43.741 | 50.778 | 38.218 | 28.04 |
| 113 | SER | CB | 42.337 | 53.166 | 38.097 | 32.05 |
| 114 | SER | OG | 41.454 | 54.345 | 38.032 | 36.33 |
| 115 | TRP | N | 42.019 | 49.485 | 37.773 | 26.65 |
| 116 | TRP | CA | 42.787 | 48.357 | 38.207 | 21.95 |
| 117 | TRP | C | 44.128 | 48.196 | 37.429 | 21.43 |
| 118 | TRP | O | 45.199 | 48.050 | 38.019 | 21.86 |
| 119 | TRP | CB | 41.882 | 47.101 | 38.149 | 22.70 |
| 120 | TRP | CG | 40.932 | 47.148 | 39.318 | 20.91 |
| 121 | TRP | CD1 | 39.592 | 47.426 | 39.181 | 21.20 |
| 122 | TRP | CD2 | 41.184 | 47.089 | 40.757 | 21.02 |
| 123 | TRP | NE1 | 39.031 | 47.559 | 40.408 | 21.97 |
| 124 | TRP | CE2 | 39.970 | 47.310 | 41.388 | 20.57 |
| 125 | TRP | CE3 | 42.283 | 46.789 | 41.551 | 18.68 |
| 126 | TRP | CZ2 | 39.847 | 47.294 | 42.770 | 20.86 |
| 127 | TRP | CZ3 | 42.185 | 46.754 | 42.958 | 16.67 |
| 128 | TRP | CH2 | 40.956 | 46.981 | 43.559 | 19.85 |
| 129 | ALA | N | 44.103 | 48.273 | 36.096 | 21.75 |
| 130 | ALA | CA | 45.413 | 48.072 | 35.405 | 21.29 |
| 131 | ALA | C | 46.515 | 49.117 | 35.696 | 19.48 |
| 132 | ALA | O | 47.664 | 48.776 | 35.736 | 17.73 |
| 133 | ALA | CB | 45.192 | 47.958 | 33.915 | 21.57 |
| 134 | ALA | N | 46.103 | 50.326 | 35.925 | 21.34 |
| 135 | ALA | CA | 46.952 | 51.428 | 36.319 | 20.36 |
| 136 | ALA | C | 47.471 | 51.300 | 37.816 | 20.18 |
| 137 | ALA | O | 48.633 | 51.406 | 38.160 | 23.47 |
| 138 | ALA | CB | 45.932 | 52.549 | 36.136 | 21.69 |
| 139 | ILE | N | 46.537 | 50.973 | 38.753 | 20.36 |
| 140 | ILE | CA | 47.001 | 50.649 | 40.115 | 20.21 |
| 141 | ILE | C | 48.074 | 49.511 | 40.105 | 19.21 |
| 142 | ILE | O | 49.155 | 49.583 | 40.676 | 20.20 |
| 143 | ILE | CB | 45.776 | 50.220 | 40.970 | 21.58 |
| 144 | ILE | CG1 | 44.697 | 51.339 | 41.220 | 25.33 |
| 145 | ILE | CG2 | 46.173 | 49.573 | 42.320 | 23.50 |
| 146 | ILE | CD1 | 45.051 | 52.343 | 42.267 | 26.28 |
| 147 | TYR | N | 47.688 | 48.424 | 39.421 | 18.90 |
| 148 | TYR | CA | 48.574 | 47.264 | 39.255 | 16.59 |
| 149 | TYR | C | 49.878 | 47.625 | 38.498 | 19.69 |
| 150 | TYR | O | 50.967 | 47.421 | 38.997 | 21.05 |
| 151 | TYR | CB | 47.748 | 46.176 | 38.592 | 15.48 |
| 152 | TYR | CG | 48.537 | 44.932 | 38.537 | 15.58 |
| 153 | TYR | CD1 | 48.907 | 44.209 | 39.665 | 15.71 |
| 154 | TYR | CD2 | 48.960 | 44.470 | 37.316 | 17.07 |
| 155 | TYR | CE1 | 49.695 | 43.057 | 39.598 | 15.33 |
| 156 | TYR | CE2 | 49.775 | 43.341 | 37.218 | 18.24 |
| 157 | TYR | CZ | 50.173 | 42.628 | 38.344 | 17.83 |
| 158 | TYR | OH | 50.982 | 41.544 | 38.105 | 16.43 |
| 159 | GLN | N | 49.759 | 48.251 | 37.330 | 20.71 |
| 160 | GLN | CA | 50.882 | 48.930 | 36.627 | 23.54 |
| 161 | GLN | C | 51.839 | 49.705 | 37.616 | 21.33 |
| 162 | GLN | O | 53.047 | 49.495 | 37.568 | 22.52 |
| 163 | GLN | CB | 50.268 | 49.816 | 35.499 | 29.74 |
| 164 | GLN | CG | 49.671 | 49.057 | 34.238 | 43.77 |
| 165 | GLN | CD | 48.539 | 49.650 | 33.267 | 50.76 |
| 166 | GLN | OE1 | 47.671 | 50.472 | 33.495 | 53.37 |
| 167 | GLN | NE2 | 48.508 | 49.076 | 32.066 | 51.41 |
| 168 | ASP | N | 51.244 | 50.451 | 38.587 | 22.69 |
| 169 | ASP | CA | 51.903 | 51.194 | 39.649 | 23.75 |
| 170 | ASP | C | 52.715 | 50.305 | 40.609 | 21.78 |
| 171 | ASP | O | 53.932 | 50.387 | 40.718 | 21.26 |
| 172 | ASP | CB | 50.890 | 52.087 | 40.353 | 26.73 |
| 173 | ASP | CG | 50.646 | 53.429 | 39.655 | 31.02 |
| 174 | ASP | OD1 | 51.574 | 53.975 | 39.025 | 31.00 |
| 175 | ASP | OD2 | 49.544 | 53.975 | 39.841 | 32.48 |
| 176 | ILE | N | 52.020 | 49.333 | 41.202 | 20.63 |
| 177 | ILE | CA | 52.741 | 48.290 | 41.962 | 19.38 |
| 178 | ILE | C | 53.874 | 47.578 | 41.116 | 19.66 |
| 179 | ILE | O | 54.989 | 47.370 | 41.576 | 18.07 |
| 180 | ILE | CB | 51.688 | 47.279 | 42.579 | 19.75 |
| 181 | ILE | CG1 | 50.762 | 48.016 | 43.509 | 19.61 |
| 182 | ILE | CG2 | 52.236 | 46.021 | 43.304 | 16.65 |
| 183 | ILE | CD1 | 49.363 | 47.437 | 43.437 | 21.44 |
| 184 | ARG | N | 53.565 | 47.169 | 39.884 | 19.64 |
| 185 | ARG | CA | 54.567 | 46.484 | 39.085 | 22.20 |
| 186 | ARG | C | 55.816 | 47.437 | 39.067 | 22.74 |
| 187 | ARG | O | 56.932 | 46.979 | 39.099 | 20.20 |
| 188 | ARG | CB | 54.023 | 46.237 | 37.637 | 23.80 |
| 189 | ARG | CG | 53.320 | 44.918 | 37.290 | 29.28 |
| 190 | ARG | CD | 53.204 | 44.519 | 35.775 | 38.17 |
| 191 | ARG | NE | 52.689 | 43.130 | 35.686 | 47.71 |
| 192 | ARG | CZ | 53.098 | 42.163 | 34.783 | 46.22 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 193 | ARG | NH1 | 53.704 | 42.464 | 33.629 | 51.10 |
| 194 | ARG | NH2 | 52.965 | 40.881 | 35.132 | 39.82 |
| 195 | HIS | N | 55.615 | 48.784 | 39.064 | 24.89 |
| 196 | HIS | CA | 56.730 | 49.740 | 38.862 | 28.65 |
| 197 | HIS | C | 57.493 | 50.276 | 40.108 | 27.86 |
| 198 | HIS | O | 58.673 | 50.654 | 40.038 | 29.52 |
| 199 | HIS | CB | 56.179 | 50.983 | 38.193 | 36.09 |
| 200 | HIS | CG | 56.811 | 51.114 | 36.834 | 47.89 |
| 201 | HIS | ND1 | 58.149 | 50.961 | 36.592 | 52.16 |
| 202 | HIS | CD2 | 56.145 | 51.425 | 35.625 | 50.80 |
| 203 | HIS | CE1 | 58.303 | 51.179 | 35.262 | 54.85 |
| 204 | HIS | NE2 | 57.113 | 51.465 | 34.656 | 55.16 |
| 205 | GLU | N | 56.716 | 50.341 | 41.204 | 24.60 |
| 206 | GLU | CA | 57.222 | 50.671 | 42.538 | 23.35 |
| 207 | GLU | C | 57.907 | 49.520 | 43.236 | 20.84 |
| 208 | GLU | O | 58.770 | 49.755 | 44.059 | 20.77 |
| 209 | GLU | CB | 56.078 | 51.097 | 43.441 | 25.78 |
| 210 | GLU | CG | 55.482 | 52.418 | 43.015 | 34.71 |
| 211 | GLU | CD | 54.294 | 52.679 | 43.916 | 41.97 |
| 212 | GLU | OE1 | 54.457 | 52.660 | 45.153 | 47.08 |
| 213 | GLU | OE2 | 53.218 | 52.905 | 43.375 | 42.03 |
| 214 | ALA | N | 57.458 | 48.299 | 42.919 | 20.22 |
| 215 | ALA | CA | 58.071 | 47.145 | 43.572 | 18.85 |
| 216 | ALA | C | 59.618 | 47.108 | 43.413 | 19.60 |
| 217 | ALA | O | 60.137 | 47.773 | 42.539 | 21.31 |
| 218 | ALA | CB | 57.514 | 45.879 | 42.928 | 17.65 |
| 219 | SER | N | 60.263 | 46.351 | 44.323 | 17.44 |
| 220 | SER | CA | 61.700 | 46.463 | 44.627 | 17.65 |
| 221 | SER | C | 62.475 | 45.590 | 43.693 | 20.44 |
| 222 | SER | O | 61.875 | 44.737 | 43.028 | 20.82 |
| 223 | SER | CB | 61.987 | 45.892 | 46.086 | 16.87 |
| 224 | SER | OG | 60.908 | 46.087 | 47.088 | 17.03 |
| 225 | ASP | N | 63.806 | 45.769 | 43.757 | 23.65 |
| 226 | ASP | CA | 64.608 | 44.993 | 42.881 | 25.32 |
| 227 | ASP | C | 65.953 | 44.653 | 43.545 | 24.00 |
| 228 | ASP | O | 66.834 | 45.495 | 43.638 | 25.47 |
| 229 | ASP | CB | 64.577 | 45.897 | 41.647 | 30.03 |
| 230 | ASP | CG | 65.409 | 45.356 | 40.505 | 35.94 |
| 231 | ASP | OD1 | 65.782 | 44.168 | 40.576 | 37.82 |
| 232 | ASP | OD2 | 65.652 | 46.122 | 39.542 | 40.50 |
| 233 | PHE | N | 66.128 | 43.392 | 44.016 | 20.26 |
| 234 | PHE | CA | 67.429 | 43.035 | 44.653 | 17.74 |
| 235 | PHE | C | 68.199 | 42.026 | 43.725 | 19.63 |
| 236 | PHE | O | 67.571 | 41.347 | 42.920 | 18.88 |
| 237 | PHE | CB | 67.148 | 42.482 | 46.088 | 15.74 |
| 238 | PHE | CG | 66.400 | 43.443 | 47.024 | 14.99 |
| 239 | PHE | CD1 | 67.009 | 44.602 | 47.475 | 14.29 |
| 240 | PHE | CD2 | 65.081 | 43.181 | 47.458 | 11.07 |
| 241 | PHE | CE1 | 66.294 | 45.491 | 48.252 | 13.28 |
| 242 | PHE | CE2 | 64.379 | 44.048 | 48.267 | 12.04 |
| 243 | PHE | CZ | 64.998 | 45.216 | 48.653 | 14.86 |
| 244 | PRO | N | 69.545 | 41.908 | 43.722 | 19.03 |
| 245 | PRO | CA | 70.154 | 40.759 | 43.057 | 17.74 |
| 246 | PRO | C | 69.576 | 39.346 | 43.319 | 17.59 |
| 247 | PRO | O | 69.475 | 38.926 | 44.441 | 18.11 |
| 248 | PRO | CB | 71.601 | 40.765 | 43.541 | 17.29 |
| 249 | PRO | CG | 71.547 | 41.671 | 44.730 | 17.67 |
| 250 | PRO | CD | 70.462 | 42.691 | 44.470 | 17.97 |
| 251 | CYS | N | 69.285 | 38.589 | 42.224 | 16.91 |
| 252 | CYS | CA | 69.204 | 37.088 | 42.281 | 16.83 |
| 253 | CYS | C | 70.495 | 36.319 | 41.751 | 17.10 |
| 254 | CYS | O | 70.471 | 35.519 | 40.790 | 15.98 |
| 255 | CYS | CB | 68.007 | 36.580 | 41.502 | 17.42 |
| 256 | CYS | SG | 66.580 | 37.626 | 41.691 | 21.76 |
| 257 | ARG | N | 71.667 | 36.666 | 42.348 | 17.15 |
| 258 | ARG | CA | 72.970 | 36.242 | 41.791 | 19.32 |
| 259 | ARG | C | 73.119 | 34.699 | 41.788 | 19.49 |
| 260 | ARG | O | 73.496 | 34.047 | 40.814 | 19.32 |
| 261 | ARG | CB | 74.079 | 36.850 | 42.622 | 24.18 |
| 262 | ARG | CG | 74.980 | 37.833 | 41.912 | 34.75 |
| 263 | ARG | CD | 75.311 | 39.152 | 42.663 | 42.80 |
| 264 | ARG | NE | 75.471 | 39.097 | 44.113 | 51.13 |
| 265 | ARG | CZ | 74.828 | 39.887 | 45.009 | 51.47 |
| 266 | ARG | NH1 | 74.701 | 41.151 | 44.646 | 48.86 |
| 267 | ARG | NH2 | 74.350 | 39.441 | 46.136 | 48.27 |
| 268 | VAL | N | 72.830 | 34.041 | 42.924 | 17.97 |
| 269 | VAL | CA | 72.998 | 32.576 | 42.948 | 16.80 |
| 270 | VAL | C | 71.992 | 31.806 | 41.998 | 15.05 |
| 271 | VAL | O | 72.306 | 30.779 | 41.377 | 15.45 |
| 272 | VAL | CB | 73.273 | 32.034 | 44.312 | 18.01 |
| 273 | VAL | CG1 | 72.573 | 30.756 | 44.520 | 15.99 |
| 274 | VAL | CG2 | 72.876 | 32.942 | 45.388 | 17.07 |
| 275 | ALA | N | 70.819 | 32.430 | 41.831 | 14.53 |
| 276 | ALA | CA | 69.795 | 31.819 | 41.038 | 14.43 |
| 277 | ALA | C | 70.213 | 31.697 | 39.659 | 15.46 |
| 278 | ALA | O | 69.747 | 30.800 | 38.995 | 16.10 |
| 279 | ALA | CB | 68.535 | 32.680 | 41.126 | 12.61 |
| 280 | LYS | N | 71.076 | 32.655 | 39.323 | 17.52 |
| 281 | LYS | CA | 71.665 | 32.762 | 37.982 | 17.70 |
| 282 | LYS | C | 72.998 | 32.019 | 37.847 | 19.60 |
| 283 | LYS | O | 73.580 | 32.004 | 36.776 | 22.60 |
| 284 | LYS | CB | 71.858 | 34.261 | 37.582 | 19.24 |
| 285 | LYS | CG | 70.573 | 35.200 | 37.622 | 19.97 |
| 286 | LYS | CD | 69.498 | 34.765 | 36.639 | 21.69 |
| 287 | LYS | CE | 68.278 | 35.680 | 36.497 | 24.74 |
| 288 | LYS | NZ | 67.268 | 34.860 | 35.757 | 26.46 |
| 289 | LEU | N | 73.581 | 31.431 | 38.936 | 20.39 |
| 290 | LEU | CA | 74.928 | 30.843 | 38.665 | 19.13 |
| 291 | LEU | C | 74.792 | 29.677 | 37.700 | 21.96 |
| 292 | LEU | O | 73.908 | 28.875 | 37.880 | 20.82 |
| 293 | LEU | CB | 75.585 | 30.242 | 39.923 | 18.89 |
| 294 | LEU | CG | 75.924 | 31.268 | 40.972 | 17.87 |
| 295 | LEU | CD1 | 76.848 | 32.313 | 40.400 | 19.14 |
| 296 | LEU | CD2 | 76.506 | 30.672 | 42.266 | 17.39 |
| 297 | PRO | N | 75.721 | 29.419 | 36.742 | 23.61 |
| 298 | PRO | CA | 75.299 | 28.411 | 35.767 | 24.44 |
| 299 | PRO | C | 75.014 | 27.017 | 36.391 | 22.23 |
| 300 | PRO | O | 74.374 | 26.171 | 35.790 | 23.82 |
| 301 | PRO | CB | 76.375 | 28.491 | 34.687 | 26.16 |
| 302 | PRO | CG | 76.896 | 29.926 | 34.822 | 27.75 |
| 303 | PRO | CD | 76.869 | 30.196 | 36.324 | 26.72 |
| 304 | LYS | N | 75.512 | 26.800 | 37.638 | 22.30 |
| 305 | LYS | CA | 75.166 | 25.529 | 38.233 | 22.26 |
| 306 | LYS | C | 73.654 | 25.317 | 38.489 | 22.91 |
| 307 | LYS | O | 73.187 | 24.168 | 38.569 | 25.95 |
| 308 | LYS | CB | 76.067 | 25.121 | 39.358 | 23.13 |
| 309 | LYS | CG | 75.991 | 25.832 | 40.660 | 24.19 |
| 310 | LYS | CD | 76.895 | 25.038 | 41.664 | 27.45 |
| 311 | LYS | CE | 77.506 | 25.823 | 42.852 | 31.65 |
| 312 | LYS | NZ | 77.983 | 24.871 | 43.905 | 37.10 |
| 313 | ASN | N | 72.908 | 26.422 | 38.604 | 20.49 |
| 314 | ASN | CA | 71.547 | 26.288 | 39.034 | 18.95 |
| 315 | ASN | C | 70.578 | 26.384 | 37.886 | 19.83 |
| 316 | ASN | O | 69.364 | 26.402 | 38.110 | 16.61 |
| 317 | ASN | CB | 71.326 | 27.301 | 40.083 | 15.32 |
| 318 | ASN | CG | 72.319 | 27.082 | 41.210 | 18.08 |
| 319 | ASN | OD1 | 72.774 | 25.998 | 41.593 | 16.89 |
| 320 | ASN | ND2 | 72.630 | 28.223 | 41.762 | 17.04 |
| 321 | LYS | N | 71.115 | 26.261 | 36.653 | 19.50 |
| 322 | LYS | CA | 70.198 | 26.533 | 35.517 | 20.65 |
| 323 | LYS | C | 68.970 | 25.582 | 35.499 | 17.99 |
| 324 | LYS | O | 67.827 | 25.897 | 35.252 | 17.79 |
| 325 | LYS | CB | 71.102 | 26.415 | 34.280 | 24.77 |
| 326 | LYS | CG | 70.705 | 27.324 | 33.113 | 35.23 |
| 327 | LYS | CD | 71.780 | 27.296 | 31.993 | 43.17 |
| 328 | LYS | CE | 71.506 | 28.319 | 30.877 | 48.79 |
| 329 | LYS | NZ | 72.095 | 27.908 | 29.585 | 51.89 |
| 330 | ASN | N | 69.249 | 24.336 | 35.828 | 16.87 |
| 331 | ASN | CA | 68.139 | 23.356 | 35.844 | 17.37 |
| 332 | ASN | C | 67.428 | 23.162 | 37.209 | 14.52 |
| 333 | ASN | O | 67.042 | 22.047 | 37.553 | 14.87 |
| 334 | ASN | CB | 68.758 | 22.008 | 35.522 | 17.56 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 335 | ASN | CG | 69.723 | 21.326 | 36.476 | 21.16 |
| 336 | ASN | OD1 | 70.099 | 21.716 | 37.568 | 23.28 |
| 337 | ASN | ND2 | 70.132 | 20.210 | 35.940 | 22.37 |
| 338 | ARG | N | 67.435 | 24.272 | 37.960 | 13.45 |
| 339 | ARG | CA | 66.851 | 24.363 | 39.265 | 14.08 |
| 340 | ARG | C | 65.834 | 25.455 | 39.226 | 11.72 |
| 341 | ARG | O | 64.908 | 25.455 | 39.985 | 11.90 |
| 342 | ARG | CB | 67.927 | 24.635 | 40.349 | 14.72 |
| 343 | ARG | CG | 68.808 | 23.399 | 40.637 | 15.03 |
| 344 | ARG | CD | 69.531 | 23.566 | 41.958 | 13.22 |
| 345 | ARG | NE | 70.329 | 22.382 | 42.127 | 14.96 |
| 346 | ARG | CZ | 70.786 | 22.027 | 43.336 | 15.87 |
| 347 | ARG | NH1 | 70.387 | 22.635 | 44.429 | 14.76 |
| 348 | ARG | NH2 | 71.629 | 21.021 | 43.409 | 16.81 |
| 349 | ASN | N | 65.990 | 26.376 | 38.305 | 12.70 |
| 350 | ASN | CA | 64.823 | 27.286 | 38.125 | 12.44 |
| 351 | ASN | C | 63.866 | 26.703 | 37.067 | 12.58 |
| 352 | ASN | O | 64.316 | 26.017 | 36.196 | 11.79 |
| 353 | ASN | CB | 65.333 | 28.584 | 37.553 | 15.34 |
| 354 | ASN | CG | 66.254 | 29.036 | 38.579 | 15.14 |
| 355 | ASN | OD1 | 65.853 | 29.008 | 39.721 | 13.40 |
| 356 | ASN | ND2 | 67.478 | 29.375 | 38.192 | 15.01 |
| 357 | ARG | N | 62.602 | 26.959 | 37.101 | 11.31 |
| 358 | ARG | CA | 61.750 | 26.422 | 36.097 | 10.21 |
| 359 | ARG | C | 61.344 | 27.550 | 35.032 | 11.77 |
| 360 | ARG | O | 60.942 | 27.244 | 33.909 | 10.43 |
| 361 | ARG | CB | 60.569 | 25.882 | 36.926 | 10.53 |
| 362 | ARG | CG | 59.435 | 25.507 | 35.982 | 9.14 |
| 363 | ARG | CD | 58.083 | 25.567 | 36.545 | 10.01 |
| 364 | ARG | NE | 57.805 | 24.437 | 37.372 | 10.47 |
| 365 | ARG | CZ | 57.604 | 23.255 | 36.784 | 10.78 |
| 366 | ARG | NH1 | 57.345 | 22.981 | 35.539 | 11.53 |
| 367 | ARG | NH2 | 57.847 | 22.305 | 37.582 | 10.00 |
| 368 | TYR | N | 61.531 | 28.839 | 35.419 | 12.06 |
| 369 | TYR | CA | 61.406 | 29.958 | 34.471 | 10.98 |
| 370 | TYR | C | 62.644 | 30.880 | 34.512 | 13.59 |
| 371 | TYR | O | 63.313 | 31.085 | 35.519 | 15.53 |
| 372 | TYR | CB | 60.188 | 30.734 | 34.879 | 9.94 |
| 373 | TYR | CG | 58.902 | 29.947 | 34.781 | 11.54 |
| 374 | TYR | CD1 | 58.528 | 29.222 | 33.627 | 11.75 |
| 375 | TYR | CD2 | 58.104 | 29.917 | 35.903 | 10.70 |
| 376 | TYR | CE1 | 57.373 | 28.429 | 33.600 | 12.58 |
| 377 | TYR | CE2 | 56.968 | 29.113 | 35.885 | 11.42 |
| 378 | TYR | CZ | 56.577 | 28.348 | 34.738 | 12.61 |
| 379 | TYR | OH | 55.482 | 27.467 | 34.686 | 13.20 |
| 380 | ARG | N | 63.021 | 31.360 | 33.315 | 13.40 |
| 381 | ARG | CA | 64.268 | 32.148 | 33.315 | 16.28 |
| 382 | ARG | C | 63.947 | 33.436 | 34.160 | 14.00 |
| 383 | ARG | O | 64.804 | 34.093 | 34.720 | 16.44 |
| 384 | ARG | CB | 64.600 | 32.319 | 31.810 | 17.48 |
| 385 | ARG | CG | 65.513 | 33.475 | 31.434 | 23.38 |
| 386 | ARG | CD | 65.168 | 34.185 | 30.101 | 28.56 |
| 387 | ARG | NE | 63.860 | 34.904 | 30.168 | 32.94 |
| 388 | ARG | CZ | 63.004 | 34.975 | 29.117 | 34.20 |
| 389 | ARG | NH1 | 63.482 | 34.836 | 27.908 | 33.58 |
| 390 | ARG | NH2 | 61.715 | 35.089 | 29.282 | 33.15 |
| 391 | ASP | N | 62.671 | 33.824 | 34.184 | 12.94 |
| 392 | ASP | CA | 62.305 | 35.149 | 34.663 | 12.52 |
| 393 | ASP | C | 61.714 | 35.183 | 36.027 | 12.63 |
| 394 | ASP | O | 61.194 | 36.232 | 36.433 | 11.75 |
| 395 | ASP | CB | 61.233 | 35.719 | 33.744 | 13.44 |
| 396 | ASP | CG | 61.768 | 36.276 | 32.470 | 15.48 |
| 397 | ASP | OD1 | 62.985 | 36.503 | 32.404 | 14.91 |
| 398 | ASP | OD2 | 60.953 | 36.507 | 31.556 | 17.68 |
| 399 | VAL | N | 61.838 | 34.020 | 36.724 | 12.12 |
| 400 | VAL | CA | 61.386 | 33.871 | 38.121 | 11.29 |
| 401 | VAL | C | 62.363 | 33.150 | 39.073 | 9.78 |
| 402 | VAL | O | 62.300 | 31.998 | 39.482 | 11.48 |
| 403 | VAL | CB | 59.862 | 33.736 | 38.326 | 16.11 |
| 404 | VAL | CG1 | 59.564 | 33.071 | 39.708 | 15.44 |
| 405 | VAL | CG2 | 59.003 | 33.367 | 37.026 | 14.33 |
| 406 | SER | N | 63.292 | 34.043 | 39.508 | 10.16 |
| 407 | SER | CA | 64.351 | 33.658 | 40.430 | 11.16 |
| 408 | SER | C | 64.044 | 34.235 | 41.838 | 9.64 |
| 409 | SER | O | 63.282 | 35.201 | 41.980 | 11.51 |
| 410 | SER | CB | 65.674 | 34.207 | 39.868 | 10.81 |
| 411 | SER | OG | 65.795 | 34.206 | 38.393 | 12.18 |
| 412 | PRO | N | 64.652 | 33.603 | 42.890 | 8.67 |
| 413 | PRO | CA | 64.679 | 34.069 | 44.300 | 10.79 |
| 414 | PRO | C | 65.739 | 35.174 | 44.607 | 13.35 |
| 415 | PRO | O | 66.863 | 35.054 | 44.167 | 14.81 |
| 416 | PRO | CB | 65.070 | 32.742 | 45.027 | 10.00 |
| 417 | PRO | CG | 65.954 | 31.994 | 44.070 | 10.77 |
| 418 | PRO | CD | 65.350 | 32.343 | 42.713 | 9.16 |
| 419 | PHE | N | 65.333 | 36.312 | 45.288 | 13.59 |
| 420 | PHE | CA | 66.396 | 37.309 | 45.592 | 12.71 |
| 421 | PHE | C | 67.463 | 36.637 | 46.469 | 12.31 |
| 422 | PHE | O | 67.099 | 35.793 | 47.313 | 12.68 |
| 423 | PHE | CB | 65.827 | 38.538 | 46.324 | 9.81 |
| 424 | PHE | CG | 64.721 | 39.284 | 45.705 | 10.06 |
| 425 | PHE | CD1 | 64.796 | 39.648 | 44.360 | 9.58 |
| 426 | PHE | CD2 | 63.667 | 39.689 | 46.481 | 9.41 |
| 427 | PHE | CE1 | 63.839 | 40.478 | 43.828 | 10.26 |
| 428 | PHE | CE2 | 62.712 | 40.531 | 45.935 | 10.02 |
| 429 | PHE | CZ | 62.810 | 40.954 | 44.617 | 8.64 |
| 430 | ASP | N | 68.731 | 37.039 | 46.301 | 11.62 |
| 431 | ASP | CA | 69.699 | 36.442 | 47.229 | 12.07 |
| 432 | ASP | C | 69.336 | 36.779 | 48.740 | 12.27 |
| 433 | ASP | O | 69.471 | 35.939 | 49.614 | 15.21 |
| 434 | ASP | CB | 71.090 | 36.960 | 46.918 | 13.40 |
| 435 | ASP | CG | 71.585 | 36.819 | 45.512 | 14.25 |
| 436 | ASP | OD1 | 71.510 | 35.755 | 45.001 | 15.72 |
| 437 | ASP | OD2 | 72.114 | 37.776 | 44.954 | 12.79 |
| 438 | HIS | N | 68.891 | 37.987 | 49.110 | 12.16 |
| 439 | HIS | CA | 68.936 | 38.332 | 50.537 | 12.71 |
| 440 | HIS | C | 68.037 | 37.415 | 51.373 | 13.92 |
| 441 | HIS | O | 68.357 | 37.023 | 52.468 | 15.61 |
| 442 | HIS | CB | 68.619 | 39.807 | 50.639 | 12.05 |
| 443 | HIS | CG | 67.189 | 40.229 | 50.532 | 10.80 |
| 444 | HIS | ND1 | 66.218 | 40.158 | 51.532 | 11.89 |
| 445 | HIS | CD2 | 66.595 | 40.810 | 49.442 | 10.89 |
| 446 | HIS | CE1 | 65.078 | 40.670 | 51.055 | 9.38 |
| 447 | HIS | NE2 | 65.292 | 41.065 | 49.801 | 11.30 |
| 448 | SER | N | 66.911 | 37.032 | 50.727 | 13.43 |
| 449 | SER | CA | 65.732 | 36.268 | 51.219 | 12.13 |
| 450 | SER | C | 65.616 | 34.786 | 50.742 | 12.76 |
| 451 | SER | O | 64.852 | 33.988 | 51.280 | 13.37 |
| 452 | SER | CB | 64.459 | 36.969 | 50.655 | 10.16 |
| 453 | SER | CG | 64.073 | 36.712 | 49.237 | 10.34 |
| 454 | ARG | N | 66.289 | 34.396 | 49.662 | 11.78 |
| 455 | ARG | CA | 66.110 | 33.011 | 49.184 | 13.97 |
| 456 | ARG | C | 66.308 | 32.030 | 50.330 | 13.85 |
| 457 | ARG | O | 67.052 | 32.388 | 51.228 | 11.86 |
| 458 | ARG | CB | 67.182 | 32.758 | 48.072 | 12.96 |
| 459 | ARG | CG | 68.663 | 32.686 | 48.534 | 13.81 |
| 460 | ARG | CD | 69.587 | 31.920 | 47.602 | 13.20 |
| 461 | ARG | NE | 70.951 | 31.816 | 48.184 | 14.78 |
| 462 | ARG | CZ | 71.552 | 30.688 | 48.524 | 15.00 |
| 463 | ARG | NH1 | 70.936 | 29.557 | 48.478 | 11.82 |
| 464 | ARG | NH2 | 72.784 | 30.639 | 48.884 | 17.64 |
| 465 | ILE | N | 65.654 | 30.828 | 50.300 | 14.21 |
| 466 | ILE | CA | 65.948 | 29.645 | 51.217 | 12.58 |
| 467 | ILE | C | 67.155 | 28.748 | 50.720 | 14.61 |
| 468 | ILE | O | 67.216 | 28.241 | 49.587 | 15.26 |
| 469 | ILE | CB | 64.722 | 28.774 | 51.313 | 13.58 |
| 470 | ILE | CG1 | 63.510 | 29.500 | 51.879 | 13.29 |
| 471 | ILE | CG2 | 64.977 | 27.447 | 52.006 | 13.64 |
| 472 | ILE | OD1 | 63.571 | 29.924 | 53.338 | 13.30 |
| 473 | LYS | N | 68.150 | 28.621 | 51.612 | 15.82 |
| 474 | LYS | CA | 69.276 | 27.764 | 51.318 | 15.98 |
| 475 | LYS | C | 69.096 | 26.360 | 51.954 | 17.60 |
| 476 | LYS | O | 68.984 | 26.265 | 53.135 | 19.95 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 477 | LYS | CB | 70.448 | 28.373 | 52.073 | 17.28 |
| 478 | LYS | CG | 70.639 | 29.851 | 51.912 | 17.24 |
| 479 | LYS | CD | 72.028 | 30.137 | 52.423 | 22.81 |
| 480 | LYS | CE | 72.374 | 31.627 | 52.475 | 26.05 |
| 481 | LYS | NZ | 73.787 | 31.719 | 52.904 | 31.86 |
| 482 | LEU | N | 69.186 | 25.284 | 51.179 | 17.25 |
| 483 | LEU | CA | 69.191 | 23.986 | 51.803 | 18.29 |
| 484 | LEU | C | 70.420 | 23.813 | 52.707 | 20.34 |
| 485 | LEU | O | 71.463 | 24.451 | 52.542 | 19.70 |
| 486 | LEU | CB | 69.326 | 23.009 | 50.654 | 18.28 |
| 487 | LEU | CG | 68.077 | 22.606 | 49.875 | 18.66 |
| 488 | LEU | CD1 | 68.503 | 22.354 | 48.425 | 17.13 |
| 489 | LEU | CD2 | 66.905 | 23.584 | 50.003 | 14.98 |
| 490 | HIS | N | 70.327 | 22.853 | 53.607 | 22.86 |
| 491 | HIS | CA | 71.473 | 22.568 | 54.469 | 25.86 |
| 492 | HIS | C | 72.376 | 21.544 | 53.818 | 30.06 |
| 493 | HIS | O | 72.823 | 20.636 | 54.478 | 31.82 |
| 494 | HIS | CB | 71.011 | 22.101 | 55.889 | 26.12 |
| 495 | HIS | CG | 70.169 | 23.121 | 56.652 | 25.12 |
| 496 | HIS | ND1 | 69.669 | 22.796 | 57.857 | 25.76 |
| 497 | HIS | CD2 | 69.771 | 24.443 | 56.370 | 24.91 |
| 498 | HIS | CE1 | 68.999 | 23.876 | 58.293 | 25.52 |
| 499 | HIS | NE2 | 69.054 | 24.883 | 57.439 | 26.33 |
| 500 | GLN | N | 72.654 | 21.694 | 52.528 | 32.94 |
| 501 | GLN | CA | 73.476 | 20.669 | 51.845 | 36.50 |
| 502 | GLN | C | 74.845 | 21.250 | 51.490 | 37.97 |
| 503 | GLN | O | 74.997 | 22.462 | 51.350 | 37.18 |
| 504 | GLN | CB | 72.785 | 19.969 | 50.653 | 37.95 |
| 505 | GLN | CG | 72.220 | 20.893 | 49.533 | 40.06 |
| 506 | GLN | CD | 71.786 | 20.148 | 48.187 | 44.06 |
| 507 | GLN | OE1 | 72.396 | 20.225 | 47.103 | 46.49 |
| 508 | GLN | NE2 | 70.689 | 19.404 | 48.371 | 41.49 |
| 509 | GLU | N | 75.833 | 20.321 | 51.371 | 41.15 |
| 510 | GLU | CA | 77.175 | 20.785 | 50.982 | 41.70 |
| 511 | GLU | C | 77.356 | 20.946 | 49.420 | 39.31 |
| 512 | GLU | O | 78.061 | 21.828 | 48.944 | 38.68 |
| 513 | GLU | CB | 78.182 | 19.780 | 51.511 | 45.57 |
| 514 | GLU | CG | 78.185 | 19.584 | 53.033 | 54.22 |
| 515 | GLU | CD | 78.719 | 18.188 | 53.518 | 60.23 |
| 516 | GLU | OE1 | 79.014 | 17.293 | 52.706 | 63.36 |
| 517 | GLU | OE2 | 78.813 | 18.019 | 54.741 | 62.48 |
| 518 | ASP | N | 76.708 | 20.105 | 48.601 | 38.53 |
| 519 | ASP | CA | 77.055 | 20.312 | 47.192 | 37.73 |
| 520 | ASP | C | 76.579 | 21.706 | 46.692 | 33.50 |
| 521 | ASP | O | 77.309 | 22.594 | 46.250 | 35.46 |
| 522 | ASP | CB | 76.361 | 19.144 | 46.491 | 43.21 |
| 523 | ASP | CG | 76.711 | 19.135 | 45.008 | 49.96 |
| 524 | ASP | OD1 | 77.838 | 19.533 | 44.702 | 53.55 |
| 525 | ASP | OD2 | 75.843 | 18.784 | 44.184 | 52.89 |
| 526 | ASN | N | 75.262 | 21.863 | 46.853 | 28.37 |
| 527 | ASN | CA | 74.553 | 23.027 | 46.358 | 21.99 |
| 528 | ASN | C | 73.354 | 23.441 | 47.299 | 20.24 |
| 529 | ASN | O | 72.312 | 22.805 | 47.353 | 21.87 |
| 530 | ASN | CB | 74.099 | 22.536 | 44.960 | 19.04 |
| 531 | ASN | CG | 73.717 | 23.704 | 44.039 | 18.04 |
| 532 | ASN | OD1 | 73.456 | 24.765 | 44.530 | 19.25 |
| 533 | ASN | ND2 | 73.728 | 23.588 | 42.734 | 15.06 |
| 534 | ASP | N | 73.466 | 24.546 | 48.022 | 18.00 |
| 535 | ASP | CA | 72.332 | 25.033 | 48.836 | 18.78 |
| 536 | ASP | C | 71.151 | 25.681 | 48.030 | 17.35 |
| 537 | ASP | O | 70.225 | 26.206 | 48.623 | 18.81 |
| 538 | ASP | CB | 72.886 | 26.053 | 49.861 | 19.48 |
| 539 | ASP | CG | 73.288 | 27.453 | 49.333 | 23.10 |
| 540 | ASP | OD1 | 72.887 | 27.851 | 48.256 | 24.35 |
| 541 | ASP | OD2 | 73.983 | 28.207 | 50.021 | 29.58 |
| 542 | TYR | N | 71.212 | 25.740 | 46.675 | 16.55 |
| 543 | TYR | CA | 70.199 | 26.452 | 45.895 | 12.98 |
| 544 | TYR | C | 68.875 | 25.687 | 45.783 | 12.27 |
| 545 | TYR | O | 68.835 | 24.576 | 45.292 | 12.81 |
| 546 | TYR | CB | 70.772 | 26.662 | 44.525 | 10.36 |
| 547 | TYR | CG | 69.834 | 27.547 | 43.751 | 12.42 |
| 548 | TYR | CD1 | 69.670 | 28.900 | 44.065 | 10.55 |
| 549 | TYR | CD2 | 69.026 | 27.003 | 42.736 | 11.80 |
| 550 | TYR | CE1 | 68.666 | 29.636 | 43.411 | 11.79 |
| 551 | TYR | CE2 | 68.002 | 27.711 | 42.094 | 10.71 |
| 552 | TYR | CZ | 67.821 | 29.072 | 42.453 | 9.67 |
| 553 | TYR | OH | 66.838 | 29.931 | 41.987 | 10.99 |
| 554 | ILE | N | 67.843 | 26.362 | 46.233 | 13.06 |
| 555 | ILE | CA | 66.470 | 26.037 | 45.852 | 12.41 |
| 556 | ILE | C | 65.728 | 27.348 | 45.344 | 11.32 |
| 557 | ILE | O | 66.023 | 28.445 | 45.836 | 12.19 |
| 558 | ILE | CB | 65.643 | 25.321 | 46.943 | 12.98 |
| 559 | ILE | CG1 | 64.216 | 25.028 | 46.401 | 8.76 |
| 560 | ILE | CG2 | 65.631 | 26.109 | 48.238 | 10.91 |
| 561 | ILE | CD1 | 63.534 | 23.768 | 46.941 | 9.88 |
| 562 | ASN | N | 64.802 | 27.274 | 44.373 | 9.16 |
| 563 | ASN | CA | 63.961 | 28.432 | 44.113 | 9.65 |
| 564 | ASN | C | 62.777 | 28.477 | 45.134 | 10.37 |
| 565 | ASN | O | 61.669 | 28.001 | 44.902 | 10.07 |
| 566 | ASN | CB | 63.409 | 28.368 | 42.689 | 9.08 |
| 567 | ASN | CG | 62.854 | 29.669 | 42.094 | 9.54 |
| 568 | ASN | OD1 | 62.064 | 30.411 | 42.717 | 10.96 |
| 569 | ASN | ND2 | 63.215 | 29.836 | 40.823 | 9.06 |
| 570 | ALA | N | 63.053 | 29.245 | 46.232 | 9.41 |
| 571 | ALA | CA | 62.074 | 29.518 | 47.285 | 10.05 |
| 572 | ALA | C | 62.490 | 30.729 | 48.081 | 11.58 |
| 573 | ALA | O | 63.684 | 31.012 | 48.161 | 12.92 |
| 574 | ALA | CB | 62.248 | 28.369 | 48.268 | 7.50 |
| 575 | SER | N | 61.501 | 31.398 | 48.688 | 10.51 |
| 576 | SER | CA | 61.767 | 32.622 | 49.448 | 11.23 |
| 577 | SER | C | 60.986 | 32.733 | 50.725 | 10.85 |
| 578 | SER | O | 59.810 | 32.408 | 50.715 | 12.48 |
| 579 | SER | CB | 61.240 | 33.808 | 48.570 | 7.55 |
| 580 | SER | OG | 61.832 | 33.943 | 47.206 | 10.45 |
| 581 | LEU | N | 61.665 | 33.227 | 51.759 | 11.48 |
| 582 | LEU | CA | 61.028 | 33.484 | 53.026 | 12.53 |
| 583 | LEU | C | 60.459 | 34.863 | 52.839 | 13.15 |
| 584 | LEU | O | 61.162 | 35.801 | 52.745 | 13.65 |
| 585 | LEU | CB | 62.100 | 33.317 | 54.125 | 13.18 |
| 586 | LEU | CG | 61.714 | 33.026 | 55.617 | 15.58 |
| 587 | LEU | CD1 | 60.346 | 32.465 | 56.032 | 15.45 |
| 588 | LEU | CD2 | 61.990 | 34.242 | 56.446 | 15.90 |
| 589 | ILE | N | 59.142 | 34.963 | 52.710 | 12.91 |
| 590 | ILE | CA | 58.433 | 36.244 | 52.854 | 13.87 |
| 591 | ILE | C | 58.199 | 36.410 | 54.383 | 16.47 |
| 592 | ILE | O | 57.520 | 35.626 | 55.029 | 16.73 |
| 593 | ILE | CB | 57.078 | 36.103 | 52.126 | 13.55 |
| 594 | ILE | CG1 | 57.058 | 36.090 | 50.580 | 12.82 |
| 595 | ILE | CG2 | 56.084 | 37.173 | 52.640 | 16.67 |
| 596 | ILE | CD1 | 58.184 | 35.285 | 49.937 | 12.75 |
| 597 | LYS | N | 58.754 | 37.425 | 54.954 | 16.38 |
| 598 | LYS | CA | 58.733 | 37.584 | 56.393 | 19.03 |
| 599 | LYS | C | 57.916 | 38.848 | 56.792 | 18.79 |
| 600 | LYS | O | 58.361 | 39.997 | 56.871 | 18.39 |
| 601 | LYS | CB | 60.193 | 37.663 | 56.758 | 24.89 |
| 602 | LYS | CG | 60.382 | 37.380 | 58.215 | 36.70 |
| 603 | LYS | CD | 61.837 | 37.012 | 58.412 | 45.35 |
| 604 | LYS | CE | 62.107 | 36.507 | 59.815 | 49.89 |
| 605 | LYS | NZ | 63.542 | 36.156 | 59.861 | 53.29 |
| 606 | MET | N | 56.632 | 38.598 | 57.069 | 17.44 |
| 607 | MET | CA | 55.789 | 39.713 | 57.508 | 17.07 |
| 608 | MET | C | 56.013 | 39.963 | 59.034 | 17.04 |
| 609 | MET | O | 55.491 | 39.236 | 59.879 | 16.87 |
| 610 | MET | CB | 54.344 | 39.363 | 57.116 | 15.46 |
| 611 | MET | CG | 54.239 | 38.984 | 55.611 | 15.47 |
| 612 | MET | SD | 55.075 | 40.191 | 54.531 | 16.71 |
| 613 | MET | CE | 53.670 | 41.304 | 54.490 | 12.89 |
| 614 | GLU | N | 56.792 | 41.029 | 59.352 | 20.27 |
| 615 | GLU | CA | 57.059 | 41.404 | 60.754 | 22.54 |
| 616 | GLU | C | 55.827 | 42.015 | 61.552 | 22.33 |
| 617 | GLU | O | 55.304 | 41.421 | 62.490 | 24.08 |
| 618 | GLU | CB | 58.262 | 42.322 | 60.762 | 26.36 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 619 | GLU | CG | 58.891 | 42.457 | 62.173 | 35.25 |
| 620 | GLU | CD | 59.916 | 43.590 | 62.166 | 40.00 |
| 621 | GLU | OE1 | 59.477 | 44.700 | 61.830 | 43.15 |
| 622 | GLU | OE2 | 61.096 | 43.345 | 62.480 | 43.54 |
| 623 | GLU | N | 55.283 | 43.165 | 61.103 | 23.41 |
| 624 | GLU | CA | 54.028 | 43.623 | 61.715 | 24.81 |
| 625 | GLU | C | 52.959 | 42.499 | 61.936 | 24.74 |
| 626 | GLU | O | 52.437 | 42.295 | 63.015 | 24.77 |
| 627 | GLU | CB | 53.482 | 44.704 | 60.837 | 26.99 |
| 628 | GLU | CG | 52.576 | 45.679 | 61.608 | 35.79 |
| 629 | GLU | CD | 51.974 | 46.718 | 60.634 | 45.06 |
| 630 | GLU | OE1 | 52.430 | 46.765 | 59.511 | 48.32 |
| 631 | GLU | OE2 | 51.091 | 47.475 | 61.022 | 49.68 |
| 632 | ALA | N | 52.665 | 41.750 | 60.868 | 22.17 |
| 633 | ALA | CA | 51.673 | 40.706 | 60.947 | 21.64 |
| 634 | ALA | C | 52.213 | 39.523 | 61.660 | 22.46 |
| 635 | ALA | O | 51.470 | 38.690 | 62.105 | 24.05 |
| 636 | ALA | CB | 51.310 | 40.191 | 59.565 | 20.53 |
| 637 | GLN | N | 53.508 | 39.446 | 61.797 | 23.74 |
| 638 | GLN | CA | 53.951 | 38.375 | 62.649 | 27.80 |
| 639 | GLN | C | 53.494 | 36.942 | 62.164 | 26.92 |
| 640 | GLN | O | 53.212 | 36.073 | 62.988 | 27.71 |
| 641 | GLN | CB | 53.604 | 38.695 | 64.142 | 32.88 |
| 642 | GLN | CG | 54.557 | 39.626 | 64.990 | 40.36 |
| 643 | GLN | CD | 55.637 | 38.789 | 65.755 | 47.19 |
| 644 | GLN | OE1 | 55.413 | 38.194 | 66.807 | 52.84 |
| 645 | GLN | NE2 | 56.809 | 38.690 | 65.144 | 46.59 |
| 646 | ARG | N | 53.576 | 36.814 | 60.781 | 23.43 |
| 647 | ARG | CA | 53.512 | 35.548 | 59.983 | 18.91 |
| 648 | ARG | C | 54.532 | 35.508 | 58.799 | 16.84 |
| 649 | ARG | O | 54.660 | 36.485 | 58.081 | 17.96 |
| 650 | ARG | CB | 52.108 | 35.410 | 59.417 | 18.58 |
| 651 | ARG | CG | 51.983 | 33.974 | 58.874 | 16.36 |
| 652 | ARG | CD | 50.561 | 33.599 | 58.555 | 17.70 |
| 653 | ARG | NE | 49.917 | 33.327 | 59.836 | 17.29 |
| 654 | ARG | CZ | 48.629 | 33.215 | 59.998 | 15.94 |
| 655 | ARG | NH1 | 47.869 | 33.433 | 58.973 | 13.68 |
| 656 | ARG | NH2 | 48.184 | 32.917 | 61.156 | 18.40 |
| 657 | SER | N | 55.331 | 34.440 | 58.582 | 13.82 |
| 658 | SER | CA | 56.164 | 34.277 | 57.366 | 12.48 |
| 659 | SER | C | 55.588 | 33.151 | 56.471 | 11.37 |
| 660 | SER | O | 54.899 | 32.287 | 56.921 | 13.16 |
| 661 | SER | CB | 57.601 | 33.787 | 57.603 | 12.86 |
| 662 | SER | OG | 58.317 | 33.977 | 58.878 | 19.01 |
| 663 | TYR | N | 56.004 | 33.108 | 55.215 | 11.99 |
| 664 | TYR | CA | 55.704 | 31.895 | 54.458 | 10.12 |
| 665 | TYR | C | 56.953 | 31.593 | 53.701 | 10.62 |
| 666 | TYR | O | 57.730 | 32.497 | 53.459 | 11.32 |
| 667 | TYR | CB | 54.616 | 32.184 | 53.384 | 10.39 |
| 668 | TYR | CG | 53.469 | 33.063 | 53.849 | 10.08 |
| 669 | TYR | CD1 | 53.696 | 34.400 | 54.011 | 10.55 |
| 670 | TYR | CD2 | 52.208 | 32.580 | 54.154 | 10.53 |
| 671 | TYR | CE1 | 52.769 | 35.233 | 54.522 | 12.90 |
| 672 | TYR | CE2 | 51.239 | 33.420 | 54.642 | 12.10 |
| 673 | TYR | CZ | 51.530 | 34.723 | 54.834 | 13.13 |
| 674 | TYR | OH | 50.524 | 35.465 | 55.346 | 13.22 |
| 675 | ILE | N | 57.104 | 30.369 | 53.235 | 10.35 |
| 676 | ILE | CA | 58.077 | 30.153 | 52.147 | 7.97 |
| 677 | ILE | C | 57.178 | 30.151 | 50.851 | 9.78 |
| 678 | ILE | O | 56.263 | 29.348 | 50.833 | 10.25 |
| 679 | ILE | CB | 58.953 | 28.883 | 52.458 | 9.05 |
| 680 | ILE | CG1 | 59.740 | 29.088 | 53.740 | 10.20 |
| 681 | ILE | CG2 | 59.957 | 28.496 | 51.397 | 8.37 |
| 682 | ILE | CD1 | 60.474 | 27.819 | 54.246 | 8.33 |
| 683 | LEU | N | 57.403 | 31.084 | 49.833 | 8.73 |
| 684 | LEU | CA | 56.855 | 30.922 | 48.465 | 8.66 |
| 685 | LEU | C | 57.905 | 30.236 | 47.526 | 11.10 |
| 686 | LEU | O | 59.110 | 30.576 | 47.552 | 12.49 |
| 687 | LEU | CB | 56.561 | 32.244 | 47.860 | 9.65 |
| 688 | LEU | CG | 55.257 | 32.826 | 48.326 | 10.58 |
| 689 | LEU | CD1 | 54.913 | 34.147 | 47.565 | 11.19 |
| 690 | LEU | CD2 | 55.270 | 32.940 | 49.838 | 12.47 |
| 691 | THR | N | 57.402 | 29.203 | 46.761 | 10.83 |
| 692 | THR | CA | 58.299 | 28.363 | 45.895 | 8.06 |
| 693 | THR | C | 57.668 | 28.097 | 44.482 | 9.10 |
| 694 | THR | O | 56.489 | 28.380 | 44.264 | 8.53 |
| 695 | THR | CB | 58.859 | 27.100 | 46.647 | 8.87 |
| 696 | THR | OG1 | 59.976 | 26.366 | 45.972 | 11.27 |
| 697 | THR | CG2 | 57.803 | 26.211 | 47.344 | 8.63 |
| 698 | GLN | N | 58.506 | 27.610 | 43.519 | 7.55 |
| 699 | GLN | CA | 57.990 | 27.172 | 42.176 | 7.51 |
| 700 | GLN | C | 57.437 | 25.750 | 42.219 | 8.15 |
| 701 | GLN | O | 57.723 | 24.997 | 43.143 | 9.26 |
| 702 | GLN | CB | 59.060 | 27.244 | 41.087 | 7.72 |
| 703 | GLN | CG | 60.130 | 26.188 | 41.317 | 7.48 |
| 704 | GLN | CD | 61.257 | 26.336 | 40.384 | 7.54 |
| 705 | GLN | OE1 | 61.977 | 25.398 | 40.166 | 13.65 |
| 706 | GLN | NE2 | 61.511 | 27.505 | 39.888 | 6.16 |
| 707 | GLY | N | 56.603 | 25.377 | 41.221 | 8.70 |
| 708 | GLY | CA | 56.238 | 23.982 | 41.272 | 8.95 |
| 709 | GLY | C | 57.520 | 23.130 | 41.108 | 10.89 |
| 710 | GLY | O | 58.254 | 23.333 | 40.156 | 12.56 |
| 711 | PRO | N | 57.762 | 22.179 | 42.005 | 11.90 |
| 712 | PRO | CA | 58.999 | 21.445 | 41.898 | 10.45 |
| 713 | PRO | C | 59.179 | 20.901 | 40.444 | 12.59 |
| 714 | PRO | O | 58.192 | 20.527 | 39.776 | 12.30 |
| 715 | PRO | CB | 58.889 | 20.400 | 42.984 | 10.51 |
| 716 | PRO | CG | 57.757 | 20.889 | 43.873 | 11.89 |
| 717 | PRO | CD | 56.917 | 21.895 | 43.147 | 9.07 |
| 718 | LEU | N | 60.423 | 20.963 | 39.954 | 13.19 |
| 719 | LEU | CA | 60.928 | 20.422 | 38.711 | 14.02 |
| 720 | LEU | C | 61.288 | 18.972 | 38.994 | 13.93 |
| 721 | LEU | O | 61.401 | 18.617 | 40.157 | 12.95 |
| 722 | LEU | CB | 62.178 | 21.303 | 38.472 | 13.39 |
| 723 | LEU | CG | 62.181 | 22.123 | 37.185 | 14.69 |
| 724 | LEU | CD1 | 62.862 | 23.432 | 37.390 | 13.28 |
| 725 | LEU | CD2 | 60.808 | 22.403 | 36.589 | 12.21 |
| 726 | PRO | N | 61.492 | 18.060 | 38.006 | 16.81 |
| 727 | PRO | CA | 61.666 | 16.641 | 38.394 | 17.34 |
| 728 | PRO | C | 62.962 | 16.281 | 39.104 | 16.85 |
| 729 | PRO | O | 63.122 | 15.247 | 39.688 | 18.24 |
| 730 | PRO | CB | 61.517 | 15.864 | 37.116 | 17.12 |
| 731 | PRO | CG | 60.922 | 16.848 | 36.100 | 19.47 |
| 732 | PRO | CD | 61.300 | 18.261 | 36.556 | 16.45 |
| 733 | ASN | N | 63.900 | 17.198 | 39.011 | 15.30 |
| 734 | ASN | CA | 65.204 | 16.949 | 39.638 | 14.86 |
| 735 | ASN | C | 65.487 | 17.673 | 40.952 | 15.36 |
| 736 | ASN | O | 66.603 | 17.703 | 41.410 | 15.84 |
| 737 | ASN | CB | 66.197 | 17.452 | 38.620 | 14.48 |
| 738 | ASN | CG | 65.975 | 18.909 | 38.203 | 16.03 |
| 739 | ASN | OD1 | 65.058 | 19.216 | 37.443 | 19.68 |
| 740 | ASN | ND2 | 66.878 | 19.774 | 38.721 | 15.67 |
| 741 | THR | N | 64.484 | 18.374 | 41.425 | 15.02 |
| 742 | THR | CA | 64.442 | 19.135 | 42.712 | 12.29 |
| 743 | THR | C | 63.211 | 18.662 | 43.532 | 11.96 |
| 744 | THR | O | 62.712 | 19.350 | 44.385 | 11.69 |
| 745 | THR | CB | 64.049 | 20.608 | 42.328 | 10.87 |
| 746 | THR | OG1 | 62.724 | 20.721 | 41.769 | 10.92 |
| 747 | THR | CG2 | 64.891 | 21.218 | 41.196 | 10.49 |
| 748 | CYS | N | 62.634 | 17.505 | 43.321 | 14.04 |
| 749 | CYS | CA | 61.483 | 17.193 | 44.179 | 14.17 |
| 750 | CYS | C | 62.088 | 16.768 | 45.539 | 12.97 |
| 751 | CYS | O | 61.464 | 16.855 | 46.615 | 13.90 |
| 752 | CYS | CB | 60.644 | 16.031 | 43.646 | 13.16 |
| 753 | CYS | SG | 59.565 | 16.488 | 42.264 | 15.24 |
| 754 | GLY | N | 63.405 | 16.394 | 45.404 | 13.25 |
| 755 | GLY | CA | 64.191 | 15.974 | 46.563 | 14.11 |
| 756 | GLY | C | 64.788 | 17.158 | 47.402 | 14.77 |
| 757 | GLY | O | 64.846 | 17.059 | 48.598 | 15.71 |
| 758 | HIS | N | 65.185 | 18.303 | 46.789 | 15.04 |
| 759 | HIS | CA | 65.415 | 19.657 | 47.379 | 13.49 |
| 760 | HIS | C | 64.101 | 20.265 | 47.972 | 14.38 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 761 | HIS | O | 64.083 | 20.721 | 49.105 | 15.19 |
| 762 | HIS | CB | 65.898 | 20.682 | 46.344 | 12.89 |
| 763 | HIS | CG | 67.036 | 20.181 | 45.457 | 14.63 |
| 764 | HIS | ND1 | 67.075 | 20.421 | 44.117 | 13.48 |
| 765 | HIS | CD2 | 68.117 | 19.333 | 45.753 | 16.55 |
| 766 | HIS | CE1 | 68.090 | 19.729 | 43.613 | 14.33 |
| 767 | HIS | NE2 | 68.744 | 19.084 | 44.580 | 15.87 |
| 768 | PHE | N | 62.967 | 20.201 | 47.261 | 12.72 |
| 769 | PHE | CA | 61.732 | 20.613 | 47.958 | 12.68 |
| 770 | PHE | C | 61.548 | 19.898 | 49.353 | 13.22 |
| 771 | PHE | O | 61.483 | 20.497 | 50.423 | 12.12 |
| 772 | PHE | CB | 60.586 | 20.347 | 46.968 | 12.82 |
| 773 | PHE | CG | 59.235 | 20.806 | 47.480 | 9.60 |
| 774 | PHE | CD1 | 58.367 | 19.945 | 48.151 | 8.18 |
| 775 | PHE | CD2 | 58.819 | 22.104 | 47.261 | 8.54 |
| 776 | PHE | CE1 | 57.135 | 20.383 | 48.629 | 11.79 |
| 777 | PHE | CE2 | 57.551 | 22.497 | 47.662 | 11.03 |
| 778 | PHE | CZ | 56.712 | 21.647 | 48.354 | 10.70 |
| 779 | TRP | N | 61.531 | 18.566 | 49.377 | 12.17 |
| 780 | TRP | CA | 61.277 | 17.960 | 50.667 | 12.15 |
| 781 | TRP | C | 62.426 | 18.110 | 51.675 | 12.77 |
| 782 | TRP | O | 62.267 | 17.797 | 52.824 | 12.89 |
| 783 | TRP | CB | 60.914 | 16.499 | 50.457 | 13.28 |
| 784 | TRP | CG | 59.487 | 16.421 | 49.968 | 13.46 |
| 785 | TRP | CD1 | 59.176 | 16.003 | 48.715 | 13.99 |
| 786 | TRP | CD2 | 58.238 | 16.857 | 50.571 | 12.69 |
| 787 | TRP | NE1 | 57.858 | 16.174 | 48.514 | 13.76 |
| 788 | TRP | CE2 | 57.224 | 16.674 | 49.611 | 12.21 |
| 789 | TRP | CE3 | 57.892 | 17.354 | 51.835 | 11.54 |
| 790 | TRP | CZ2 | 55.928 | 17.024 | 49.845 | 11.49 |
| 791 | TRP | CZ3 | 56.569 | 17.707 | 52.119 | 12.46 |
| 792 | TRP | CH2 | 55.598 | 17.545 | 51.099 | 11.61 |
| 793 | GLU | N | 63.588 | 18.588 | 51.263 | 13.48 |
| 794 | GLU | CA | 64.731 | 18.763 | 52.162 | 12.78 |
| 795 | GLU | C | 64.458 | 20.064 | 52.881 | 13.54 |
| 796 | GLU | O | 64.488 | 20.065 | 54.123 | 13.56 |
| 797 | GLU | CB | 66.084 | 18.779 | 51.401 | 11.88 |
| 798 | GLU | CG | 67.269 | 19.356 | 52.235 | 15.11 |
| 799 | GLU | CD | 68.554 | 19.518 | 51.499 | 17.43 |
| 800 | GLU | OE1 | 68.577 | 19.290 | 50.284 | 19.12 |
| 801 | GLU | OE2 | 69.547 | 19.872 | 52.101 | 19.81 |
| 802 | MET | N | 63.973 | 21.049 | 51.994 | 11.71 |
| 803 | MET | CA | 63.546 | 22.379 | 52.486 | 12.23 |
| 804 | MET | C | 62.389 | 22.312 | 53.511 | 11.68 |
| 805 | MET | O | 62.291 | 22.943 | 54.555 | 11.24 |
| 806 | MET | CB | 63.108 | 23.239 | 51.328 | 9.82 |
| 807 | MET | CG | 62.214 | 24.420 | 51.724 | 11.63 |
| 808 | MET | SD | 61.999 | 25.602 | 50.392 | 15.04 |
| 809 | MET | CE | 60.555 | 24.934 | 49.564 | 11.38 |
| 810 | VAL | N | 61.422 | 21.461 | 53.168 | 12.17 |
| 811 | VAL | CA | 60.354 | 21.227 | 54.164 | 10.63 |
| 812 | VAL | C | 60.941 | 20.624 | 55.438 | 13.77 |
| 813 | VAL | O | 60.589 | 21.011 | 56.523 | 14.26 |
| 814 | VAL | CB | 59.220 | 20.388 | 53.522 | 10.58 |
| 815 | VAL | CG1 | 58.576 | 21.226 | 52.398 | 8.22 |
| 816 | VAL | CG2 | 58.132 | 19.960 | 54.487 | 10.48 |
| 817 | TRP | N | 61.857 | 19.696 | 55.332 | 13.52 |
| 818 | TRP | CA | 62.368 | 19.071 | 56.546 | 14.59 |
| 819 | TRP | C | 63.063 | 20.108 | 57.515 | 15.04 |
| 820 | TRP | O | 62.665 | 20.298 | 58.672 | 16.22 |
| 821 | TRP | CB | 63.263 | 17.908 | 56.111 | 12.97 |
| 822 | TRP | CG | 63.663 | 17.210 | 57.352 | 17.46 |
| 823 | TRP | CD1 | 64.811 | 17.506 | 58.070 | 21.61 |
| 824 | TRP | CD2 | 62.942 | 16.235 | 58.122 | 19.79 |
| 825 | TRP | NE1 | 64.831 | 16.777 | 59.222 | 23.85 |
| 826 | TRP | CE2 | 63.721 | 15.974 | 59.290 | 22.70 |
| 827 | TRP | CE3 | 61.749 | 15.593 | 57.954 | 21.09 |
| 828 | TRP | CZ2 | 63.300 | 15.074 | 60.220 | 21.76 |
| 829 | TRP | CZ3 | 61.323 | 14.679 | 58.916 | 21.15 |
| 830 | TRP | CH2 | 62.094 | 14.409 | 60.031 | 21.23 |
| 831 | GLU | N | 64.079 | 20.742 | 56.935 | 16.06 |
| 832 | GLU | CA | 65.024 | 21.609 | 57.615 | 15.05 |
| 833 | GLU | C | 64.396 | 22.880 | 58.008 | 16.50 |
| 834 | GLU | O | 64.758 | 23.461 | 59.019 | 18.37 |
| 835 | GLU | CB | 66.099 | 21.948 | 56.599 | 13.43 |
| 836 | GLU | CG | 66.738 | 20.660 | 56.125 | 13.77 |
| 837 | GLU | CD | 67.820 | 20.935 | 55.146 | 14.43 |
| 838 | GLU | OE1 | 67.899 | 22.007 | 54.586 | 15.87 |
| 839 | GLU | OE2 | 68.632 | 20.038 | 54.975 | 15.61 |
| 840 | GLN | N | 63.390 | 23.283 | 57.230 | 14.99 |
| 841 | GLN | CA | 62.612 | 24.477 | 57.635 | 14.10 |
| 842 | GLN | C | 61.510 | 24.226 | 58.676 | 14.79 |
| 843 | GLN | O | 60.879 | 25.146 | 59.160 | 14.03 |
| 844 | GLN | CB | 62.048 | 25.170 | 56.347 | 13.84 |
| 845 | GLN | CG | 63.212 | 25.595 | 55.375 | 14.77 |
| 846 | GLN | CD | 64.194 | 26.544 | 56.098 | 20.12 |
| 847 | GLN | OE1 | 63.694 | 27.506 | 56.665 | 21.85 |
| 848 | GLN | NE2 | 65.471 | 26.331 | 56.071 | 18.11 |
| 849 | LYS | N | 61.251 | 22.954 | 59.012 | 14.24 |
| 850 | LYS | CA | 60.227 | 22.483 | 59.980 | 15.01 |
| 851 | LYS | C | 58.797 | 22.890 | 59.696 | 12.96 |
| 852 | LYS | O | 57.994 | 22.992 | 60.604 | 13.31 |
| 853 | LYS | CB | 60.584 | 22.912 | 61.402 | 19.21 |
| 854 | LYS | CG | 62.055 | 22.609 | 61.711 | 21.85 |
| 855 | LYS | CD | 62.235 | 22.379 | 63.198 | 29.47 |
| 856 | LYS | CE | 63.661 | 22.216 | 63.640 | 31.82 |
| 857 | LYS | NZ | 64.341 | 23.105 | 62.727 | 37.86 |
| 858 | SER | N | 58.495 | 23.079 | 58.406 | 14.72 |
| 859 | SER | CA | 57.092 | 23.282 | 58.019 | 14.22 |
| 860 | SER | C | 56.246 | 22.042 | 58.300 | 15.12 |
| 861 | SER | O | 56.655 | 20.897 | 58.189 | 14.48 |
| 862 | SER | CB | 57.124 | 23.649 | 56.489 | 12.78 |
| 863 | SER | OG | 58.109 | 24.701 | 56.039 | 13.54 |
| 864 | ARG | N | 55.046 | 22.316 | 58.638 | 13.87 |
| 865 | ARG | CA | 53.889 | 21.469 | 58.787 | 14.62 |
| 866 | ARG | C | 52.900 | 21.380 | 57.558 | 14.77 |
| 867 | ARG | O | 52.279 | 20.349 | 57.295 | 13.72 |
| 868 | ARG | CB | 53.162 | 22.084 | 59.989 | 14.39 |
| 869 | ARG | CG | 52.448 | 21.021 | 60.790 | 23.02 |
| 870 | ARG | CD | 51.000 | 20.993 | 60.443 | 27.49 |
| 871 | ARG | NE | 50.286 | 20.242 | 61.462 | 30.20 |
| 872 | ARG | CZ | 50.380 | 18.916 | 61.652 | 29.90 |
| 873 | ARG | NH1 | 51.307 | 18.211 | 60.950 | 31.36 |
| 874 | ARG | NH2 | 49.427 | 18.304 | 62.133 | 30.49 |
| 875 | GLY | N | 52.739 | 22.450 | 56.827 | 15.17 |
| 876 | GLY | CA | 51.776 | 22.626 | 55.799 | 13.10 |
| 877 | GLY | C | 52.462 | 22.850 | 54.485 | 12.93 |
| 878 | GLY | O | 53.449 | 23.538 | 54.399 | 12.18 |
| 879 | VAL | N | 51.894 | 22.272 | 53.426 | 13.38 |
| 880 | VAL | CA | 52.274 | 22.713 | 52.082 | 10.87 |
| 881 | VAL | C | 50.983 | 23.124 | 51.461 | 9.66 |
| 882 | VAL | O | 50.002 | 22.387 | 51.541 | 10.04 |
| 883 | VAL | CB | 52.870 | 21.528 | 51.228 | 10.73 |
| 884 | VAL | CG1 | 54.155 | 20.840 | 51.773 | 11.72 |
| 885 | VAL | CG2 | 53.136 | 21.897 | 49.737 | 10.72 |
| 886 | VAL | N | 51.007 | 24.297 | 50.825 | 8.51 |
| 887 | VAL | CA | 49.805 | 24.732 | 50.087 | 7.91 |
| 888 | VAL | C | 50.113 | 24.799 | 48.608 | 8.39 |
| 889 | VAL | O | 50.967 | 25.546 | 48.186 | 9.71 |
| 890 | VAL | CB | 49.346 | 26.112 | 50.615 | 6.14 |
| 891 | VAL | CG1 | 48.848 | 26.046 | 52.098 | 7.70 |
| 892 | VAL | CG2 | 48.214 | 26.748 | 49.800 | 6.32 |
| 893 | MET | N | 49.389 | 24.005 | 47.841 | 8.82 |
| 894 | MET | CA | 49.534 | 23.899 | 46.386 | 8.53 |
| 895 | MET | C | 48.365 | 24.505 | 45.638 | 9.29 |
| 896 | MET | O | 47.289 | 23.983 | 45.711 | 9.66 |
| 897 | MET | CB | 49.534 | 22.412 | 46.115 | 8.63 |
| 898 | MET | CG | 49.584 | 22.144 | 44.622 | 9.02 |
| 899 | MET | SD | 50.458 | 20.629 | 44.313 | 13.59 |
| 900 | MET | CE | 50.211 | 20.435 | 42.521 | 7.30 |
| 901 | LEU | N | 48.591 | 25.598 | 44.954 | 8.05 |
| 902 | LEU | CA | 47.428 | 26.275 | 44.340 | 6.79 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 903 | LEU | C | 47.172 | 26.020 | 42.785 | 8.29 |
| 904 | LEU | O | 46.566 | 26.877 | 42.182 | 8.17 |
| 905 | LEU | CB | 47.688 | 27.800 | 44.449 | 8.82 |
| 906 | LEU | CG | 47.991 | 28.331 | 45.842 | 9.33 |
| 907 | LEU | CD1 | 46.842 | 28.070 | 46.813 | 6.68 |
| 908 | LEU | CD2 | 48.214 | 29.832 | 45.771 | 8.69 |
| 909 | ASN | N | 47.920 | 25.017 | 42.200 | 8.85 |
| 910 | ASN | CA | 48.020 | 24.702 | 40.735 | 10.85 |
| 911 | ASN | C | 47.769 | 23.175 | 40.514 | 10.96 |
| 912 | ASN | O | 48.012 | 22.421 | 41.451 | 11.52 |
| 913 | ASN | CB | 49.393 | 25.060 | 40.117 | 10.56 |
| 914 | ASN | CG | 50.568 | 24.084 | 40.487 | 10.18 |
| 915 | ASN | OD1 | 51.127 | 23.276 | 39.749 | 13.30 |
| 916 | ASN | ND2 | 51.129 | 24.353 | 41.654 | 6.84 |
| 917 | ARG | N | 47.424 | 22.750 | 39.274 | 12.81 |
| 918 | ARG | CA | 47.423 | 21.308 | 38.970 | 12.84 |
| 919 | ARG | C | 48.776 | 20.954 | 38.393 | 13.06 |
| 920 | ARG | O | 49.452 | 21.835 | 37.869 | 13.72 |
| 921 | ARG | CB | 46.231 | 20.948 | 38.085 | 15.06 |
| 922 | ARG | CG | 44.960 | 21.740 | 38.453 | 23.73 |
| 923 | ARG | CD | 43.614 | 21.096 | 38.015 | 34.40 |
| 924 | ARG | NE | 43.483 | 20.691 | 36.595 | 44.56 |
| 925 | ARG | CZ | 43.334 | 21.619 | 35.619 | 51.42 |
| 926 | ARG | NH1 | 43.467 | 22.892 | 35.787 | 54.99 |
| 927 | ARG | NH2 | 42.994 | 21.256 | 34.403 | 53.99 |
| 928 | VAL | N | 49.195 | 19.695 | 38.452 | 13.43 |
| 929 | VAL | CA | 50.346 | 19.256 | 37.704 | 16.12 |
| 930 | VAL | C | 50.278 | 19.565 | 36.147 | 16.48 |
| 931 | VAL | O | 51.114 | 20.226 | 35.584 | 14.56 |
| 932 | VAL | CB | 50.559 | 17.783 | 38.070 | 14.79 |
| 933 | VAL | CG1 | 50.930 | 17.661 | 39.553 | 14.80 |
| 934 | VAL | CG2 | 51.639 | 17.182 | 37.160 | 16.58 |
| 935 | MET | N | 49.229 | 19.073 | 35.453 | 17.62 |
| 936 | MET | CA | 48.799 | 19.616 | 34.173 | 19.41 |
| 937 | MET | C | 47.577 | 20.606 | 34.287 | 17.22 |
| 938 | MET | O | 46.471 | 20.315 | 34.733 | 16.41 |
| 939 | MET | CB | 48.548 | 18.474 | 33.180 | 22.53 |
| 940 | MET | CG | 48.920 | 18.893 | 31.711 | 30.44 |
| 941 | MET | SD | 48.488 | 17.626 | 30.498 | 36.43 |
| 942 | MET | CE | 46.891 | 18.345 | 30.183 | 32.23 |
| 943 | GLU | N | 47.925 | 21.768 | 33.762 | 17.49 |
| 944 | GLU | CA | 47.082 | 22.928 | 33.568 | 18.64 |
| 945 | GLU | C | 47.552 | 23.550 | 32.237 | 17.88 |
| 946 | GLU | O | 48.753 | 23.611 | 31.959 | 18.32 |
| 947 | GLU | CB | 47.409 | 24.092 | 34.512 | 16.54 |
| 948 | GLU | CG | 47.652 | 23.731 | 35.929 | 16.82 |
| 949 | GLU | CD | 47.619 | 24.979 | 36.772 | 15.94 |
| 950 | GLU | OE1 | 48.517 | 25.821 | 36.630 | 15.52 |
| 951 | GLU | OE2 | 46.727 | 25.093 | 37.611 | 15.98 |
| 952 | LYS | N | 46.605 | 23.992 | 31.444 | 19.17 |
| 953 | LYS | CA | 46.693 | 24.610 | 30.148 | 20.14 |
| 954 | LYS | C | 47.513 | 23.739 | 29.202 | 18.74 |
| 955 | LYS | O | 48.351 | 24.244 | 28.449 | 18.86 |
| 956 | LYS | CB | 47.304 | 25.984 | 30.368 | 21.50 |
| 957 | LYS | CG | 46.267 | 26.889 | 31.035 | 24.11 |
| 958 | LYS | CD | 46.770 | 28.322 | 31.089 | 28.82 |
| 959 | LYS | CE | 45.657 | 29.354 | 31.107 | 30.30 |
| 960 | LYS | NZ | 44.532 | 28.741 | 31.820 | 32.58 |
| 961 | GLY | N | 47.273 | 22.392 | 29.319 | 18.79 |
| 962 | GLY | CA | 47.911 | 21.493 | 28.344 | 17.83 |
| 963 | GLY | C | 49.363 | 21.124 | 28.602 | 19.02 |
| 964 | GLY | O | 49.889 | 20.163 | 28.022 | 18.80 |
| 965 | SER | N | 49.994 | 21.951 | 29.434 | 16.08 |
| 966 | SER | CA | 51.417 | 21.727 | 29.690 | 17.76 |
| 967 | SER | C | 51.563 | 21.319 | 31.153 | 16.07 |
| 968 | SER | O | 50.624 | 21.508 | 31.921 | 15.80 |
| 969 | SER | CB | 52.195 | 22.984 | 29.281 | 21.32 |
| 970 | SER | OG | 51.454 | 23.745 | 28.215 | 29.95 |
| 971 | LEU | N | 52.706 | 20.665 | 31.433 | 16.19 |
| 972 | LEU | CA | 53.044 | 20.095 | 32.721 | 14.22 |
| 973 | LEU | C | 53.814 | 21.162 | 33.523 | 14.90 |
| 974 | LEU | O | 54.937 | 21.513 | 33.212 | 16.30 |
| 975 | LEU | CB | 53.928 | 18.847 | 32.505 | 13.16 |
| 976 | LEU | CG | 53.098 | 17.636 | 32.063 | 12.66 |
| 977 | LEU | CD1 | 52.255 | 17.105 | 33.249 | 15.43 |
| 978 | LEU | CD2 | 53.993 | 16.510 | 31.569 | 13.88 |
| 979 | LYS | N | 53.070 | 21.738 | 34.484 | 14.30 |
| 980 | LYS | CA | 53.355 | 22.962 | 35.234 | 11.19 |
| 981 | LYS | C | 54.103 | 22.727 | 36.555 | 10.51 |
| 982 | LYS | O | 54.480 | 23.691 | 37.202 | 11.24 |
| 983 | LYS | CB | 51.969 | 23.563 | 35.492 | 11.90 |
| 984 | LYS | CG | 51.377 | 24.141 | 34.173 | 15.22 |
| 985 | LYS | CD | 52.251 | 25.323 | 33.894 | 16.86 |
| 986 | LYS | CE | 51.945 | 26.341 | 32.815 | 20.26 |
| 987 | LYS | NZ | 52.785 | 27.477 | 33.270 | 18.45 |
| 988 | CYS | N | 54.265 | 21.458 | 36.919 | 10.35 |
| 989 | CYS | CA | 54.800 | 21.085 | 38.199 | 10.12 |
| 990 | CYS | C | 55.093 | 19.570 | 38.124 | 13.34 |
| 991 | CYS | O | 54.346 | 18.872 | 37.449 | 13.61 |
| 992 | CYS | CB | 53.752 | 21.438 | 39.298 | 13.04 |
| 993 | CYS | SG | 54.171 | 21.096 | 41.056 | 11.06 |
| 994 | ALA | N | 56.092 | 19.102 | 38.912 | 11.84 |
| 995 | ALA | CA | 56.384 | 17.664 | 39.115 | 11.47 |
| 996 | ALA | C | 55.350 | 16.986 | 39.954 | 13.20 |
| 997 | ALA | O | 54.725 | 17.565 | 40.853 | 10.87 |
| 998 | ALA | CB | 57.698 | 17.551 | 39.874 | 9.90 |
| 999 | GLN | N | 55.227 | 15.685 | 39.755 | 12.25 |
| 1000 | GLN | CA | 54.380 | 14.965 | 40.731 | 13.18 |
| 1001 | GLN | C | 55.285 | 14.601 | 41.907 | 13.71 |
| 1002 | GLN | O | 55.974 | 13.592 | 41.922 | 14.92 |
| 1003 | GLN | CB | 53.719 | 13.735 | 40.112 | 13.64 |
| 1004 | GLN | CG | 52.758 | 12.973 | 41.060 | 14.19 |
| 1005 | GLN | CD | 51.427 | 13.725 | 41.216 | 14.78 |
| 1006 | GLN | OE1 | 50.905 | 13.910 | 42.309 | 20.52 |
| 1007 | GLN | NE2 | 50.901 | 14.217 | 40.086 | 13.59 |
| 1008 | TYR | N | 55.306 | 15.502 | 42.891 | 12.19 |
| 1009 | TYR | CA | 56.373 | 15.447 | 43.967 | 11.14 |
| 1010 | TYR | C | 55.940 | 14.903 | 45.328 | 10.72 |
| 1011 | TYR | O | 56.779 | 14.953 | 46.207 | 12.61 |
| 1012 | TYR | CB | 56.928 | 16.825 | 44.297 | 10.70 |
| 1013 | TYR | CG | 55.892 | 17.745 | 44.873 | 12.19 |
| 1014 | TYR | CD1 | 55.710 | 17.845 | 46.233 | 10.21 |
| 1015 | TYR | CD2 | 55.141 | 18.558 | 44.050 | 11.16 |
| 1016 | TYR | CE1 | 54.801 | 18.729 | 46.793 | 12.37 |
| 1017 | TYR | CE2 | 54.213 | 19.435 | 44.555 | 10.83 |
| 1018 | TYR | CZ | 54.033 | 19.497 | 45.943 | 11.09 |
| 1019 | TYR | OH | 53.050 | 20.302 | 46.488 | 11.70 |
| 1020 | TRP | N | 54.662 | 14.460 | 45.484 | 11.94 |
| 1021 | TRP | CA | 54.108 | 13.696 | 46.608 | 12.84 |
| 1022 | TRP | C | 53.453 | 12.393 | 46.058 | 14.59 |
| 1023 | TRP | O | 53.073 | 12.404 | 44.901 | 14.57 |
| 1024 | TRP | CB | 53.090 | 14.582 | 47.358 | 12.85 |
| 1025 | TRP | CG | 51.796 | 14.668 | 46.559 | 13.65 |
| 1026 | TRP | CD1 | 50.660 | 13.882 | 46.775 | 14.58 |
| 1027 | TRP | CD2 | 51.462 | 15.520 | 45.460 | 12.43 |
| 1028 | TRP | NE1 | 49.663 | 14.196 | 45.908 | 14.02 |
| 1029 | TRP | CE2 | 50.123 | 15.214 | 45.098 | 12.63 |
| 1030 | TRP | CE3 | 52.186 | 16.429 | 44.734 | 13.32 |
| 1031 | TRP | CZ2 | 49.544 | 15.874 | 44.043 | 12.31 |
| 1032 | TRP | CZ3 | 51.623 | 17.068 | 43.649 | 11.49 |
| 1033 | TRP | CH2 | 50.298 | 16.797 | 43.312 | 14.96 |
| 1034 | PRO | N | 53.291 | 11.284 | 46.898 | 16.00 |
| 1035 | PRO | CA | 52.633 | 10.039 | 46.450 | 15.76 |
| 1036 | PRO | C | 51.096 | 10.056 | 46.250 | 16.40 |
| 1037 | PRO | O | 50.249 | 10.513 | 47.021 | 18.51 |
| 1038 | PRO | CB | 53.112 | 8.965 | 47.400 | 12.06 |
| 1039 | PRO | CG | 53.352 | 9.784 | 48.636 | 15.79 |
| 1040 | PRO | CD | 53.814 | 11.162 | 48.256 | 15.75 |
| 1041 | GLN | N | 50.762 | 9.495 | 45.124 | 18.99 |
| 1042 | GLN | CA | 49.356 | 9.444 | 44.808 | 21.65 |
| 1043 | GLN | C | 48.588 | 8.192 | 45.388 | 22.14 |
| 1044 | GLN | O | 47.377 | 8.070 | 45.250 | 20.49 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1045 | GLN | CB | 49.477 | 9.419 | 43.309 | 26.00 |
| 1046 | GLN | CG | 49.582 | 10.837 | 42.765 | 32.71 |
| 1047 | GLN | CD | 49.147 | 10.778 | 41.328 | 36.57 |
| 1048 | GLN | OE1 | 49.811 | 10.217 | 40.486 | 35.28 |
| 1049 | GLN | NE2 | 47.927 | 11.228 | 41.111 | 40.87 |
| 1050 | LYS | N | 49.312 | 7.229 | 46.019 | 20.39 |
| 1051 | LYS | CA | 48.578 | 6.239 | 46.799 | 19.10 |
| 1052 | LYS | C | 49.447 | 5.480 | 47.773 | 16.46 |
| 1053 | LYS | O | 50.649 | 5.374 | 47.569 | 16.58 |
| 1054 | LYS | CB | 48.004 | 5.271 | 45.819 | 22.59 |
| 1055 | LYS | CG | 49.022 | 4.477 | 44.999 | 24.94 |
| 1056 | LYS | CD | 48.247 | 3.613 | 44.031 | 30.53 |
| 1057 | LYS | CE | 46.873 | 4.187 | 43.585 | 32.07 |
| 1058 | LYS | NZ | 46.151 | 3.195 | 42.750 | 40.14 |
| 1059 | GLU | N | 48.770 | 4.939 | 48.805 | 15.88 |
| 1060 | GLU | CA | 49.282 | 4.619 | 50.076 | 15.37 |
| 1061 | GLU | C | 50.274 | 3.498 | 49.993 | 15.69 |
| 1062 | GLU | O | 51.310 | 3.575 | 50.666 | 13.68 |
| 1063 | GLU | CB | 48.129 | 4.329 | 50.969 | 16.72 |
| 1064 | GLU | CG | 47.224 | 5.504 | 51.264 | 14.29 |
| 1065 | GLU | CD | 46.086 | 5.726 | 50.288 | 18.80 |
| 1066 | GLU | OE1 | 46.254 | 5.591 | 49.071 | 21.62 |
| 1067 | GLU | OE2 | 44.996 | 6.034 | 50.720 | 21.27 |
| 1068 | GLU | N | 50.001 | 2.488 | 49.145 | 18.42 |
| 1069 | GLU | CA | 50.982 | 1.369 | 48.868 | 20.95 |
| 1070 | GLU | C | 52.285 | 1.728 | 48.121 | 20.76 |
| 1071 | GLU | O | 53.234 | 0.936 | 48.094 | 20.49 |
| 1072 | GLU | CB | 50.407 | 0.309 | 47.934 | 20.78 |
| 1073 | GLU | CG | 48.890 | 0.282 | 47.935 | 25.93 |
| 1074 | GLU | CD | 48.253 | 1.097 | 46.847 | 25.99 |
| 1075 | GLU | OE1 | 48.672 | 0.948 | 45.699 | 28.63 |
| 1076 | GLU | OE2 | 47.378 | 1.916 | 47.165 | 25.53 |
| 1077 | LYS | N | 52.277 | 2.922 | 47.470 | 21.38 |
| 1078 | LYS | CA | 53.466 | 3.451 | 46.700 | 21.50 |
| 1079 | LYS | C | 54.120 | 4.756 | 47.250 | 21.97 |
| 1080 | LYS | O | 53.847 | 5.847 | 46.775 | 22.57 |
| 1081 | LYS | CB | 53.121 | 3.583 | 45.211 | 22.92 |
| 1082 | LYS | CG | 53.120 | 2.175 | 44.507 | 27.23 |
| 1083 | LYS | CD | 53.566 | 1.981 | 43.052 | 35.59 |
| 1084 | LYS | CE | 54.901 | 2.700 | 42.698 | 43.39 |
| 1085 | LYS | NZ | 56.064 | 2.530 | 43.615 | 46.48 |
| 1086 | GLU | N | 54.995 | 4.585 | 48.246 | 21.26 |
| 1087 | GLU | CA | 55.858 | 5.703 | 48.687 | 22.94 |
| 1088 | GLU | C | 56.922 | 6.019 | 47.618 | 21.77 |
| 1089 | GLU | O | 57.224 | 5.216 | 46.703 | 23.33 |
| 1090 | GLU | CB | 56.631 | 5.472 | 50.033 | 22.83 |
| 1091 | GLU | CG | 56.303 | 4.151 | 50.740 | 28.82 |
| 1092 | GLU | CD | 56.755 | 2.950 | 49.946 | 29.12 |
| 1093 | GLU | OE1 | 57.947 | 2.882 | 49.726 | 33.37 |
| 1094 | GLU | OE2 | 55.910 | 2.091 | 49.582 | 28.44 |
| 1095 | MET | N | 57.395 | 7.255 | 47.918 | 18.83 |
| 1096 | MET | CA | 58.502 | 7.859 | 47.186 | 17.54 |
| 1097 | MET | C | 59.720 | 7.939 | 48.072 | 19.07 |
| 1098 | MET | O | 59.583 | 8.268 | 49.240 | 20.58 |
| 1099 | MET | CB | 58.083 | 9.281 | 46.771 | 16.27 |
| 1100 | MET | CG | 57.088 | 9.220 | 45.629 | 16.56 |
| 1101 | MET | SD | 56.497 | 10.824 | 45.225 | 19.88 |
| 1102 | MET | CE | 57.882 | 11.386 | 44.232 | 18.70 |
| 1103 | ILE | N | 60.896 | 7.720 | 47.557 | 18.63 |
| 1104 | ILE | CA | 62.108 | 7.877 | 48.322 | 20.60 |
| 1105 | ILE | C | 63.025 | 8.809 | 47.514 | 20.37 |
| 1106 | ILE | O | 63.395 | 8.568 | 46.393 | 23.05 |
| 1107 | ILE | CB | 62.691 | 6.493 | 48.661 | 24.01 |
| 1108 | ILE | CG1 | 61.881 | 5.871 | 49.811 | 25.81 |
| 1109 | ILE | CG2 | 64.181 | 6.578 | 49.065 | 24.90 |
| 1110 | ILE | CD1 | 61.992 | 4.357 | 49.909 | 27.88 |
| 1111 | PHE | N | 63.380 | 9.944 | 48.145 | 19.97 |
| 1112 | PHE | CA | 64.224 | 10.949 | 47.503 | 18.46 |
| 1113 | PHE | C | 65.685 | 10.633 | 47.905 | 19.73 |
| 1114 | PHE | O | 66.114 | 10.938 | 49.001 | 18.94 |
| 1115 | PHE | CB | 63.753 | 12.370 | 47.917 | 16.35 |
| 1116 | PHE | CG | 62.290 | 12.582 | 47.628 | 14.87 |
| 1117 | PHE | CD1 | 61.851 | 12.931 | 46.357 | 13.55 |
| 1118 | PHE | CD2 | 61.348 | 12.399 | 48.607 | 16.14 |
| 1119 | PHE | CE1 | 60.511 | 13.044 | 46.035 | 14.72 |
| 1120 | PHE | CE2 | 60.000 | 12.519 | 48.297 | 14.63 |
| 1121 | PHE | CZ | 59.565 | 12.811 | 47.004 | 14.92 |
| 1122 | GLU | N | 66.423 | 9.955 | 47.009 | 23.42 |
| 1123 | GLU | CA | 67.730 | 9.355 | 47.371 | 27.04 |
| 1124 | GLU | C | 68.809 | 10.381 | 47.518 | 26.67 |
| 1125 | GLU | O | 69.611 | 10.299 | 48.440 | 27.77 |
| 1126 | GLU | CB | 68.229 | 8.253 | 46.431 | 32.84 |
| 1127 | GLU | CG | 67.362 | 6.947 | 46.395 | 43.59 |
| 1128 | GLU | CD | 68.029 | 5.711 | 45.646 | 52.36 |
| 1129 | GLU | OE1 | 68.362 | 5.845 | 44.439 | 54.69 |
| 1130 | GLU | OE2 | 68.199 | 4.647 | 46.298 | 55.07 |
| 1131 | ASP | N | 68.765 | 11.386 | 46.636 | 25.27 |
| 1132 | ASP | CA | 69.664 | 12.544 | 46.813 | 24.77 |
| 1133 | ASP | C | 69.573 | 13.322 | 48.180 | 24.82 |
| 1134 | ASP | O | 70.550 | 13.880 | 48.657 | 26.69 |
| 1135 | ASP | CB | 69.487 | 13.507 | 45.649 | 25.87 |
| 1136 | ASP | CG | 68.195 | 14.296 | 45.612 | 28.11 |
| 1137 | ASP | OD1 | 67.142 | 13.727 | 45.835 | 27.95 |
| 1138 | ASP | OD2 | 68.296 | 15.481 | 45.365 | 30.09 |
| 1139 | THR | N | 68.365 | 13.360 | 48.766 | 22.69 |
| 1140 | THR | CA | 68.270 | 13.979 | 50.054 | 20.10 |
| 1141 | THR | C | 67.933 | 13.020 | 51.178 | 20.10 |
| 1142 | THR | O | 67.943 | 13.373 | 52.347 | 20.15 |
| 1143 | THR | CB | 67.476 | 15.268 | 50.010 | 18.17 |
| 1144 | THR | OG1 | 66.041 | 14.985 | 49.980 | 15.16 |
| 1145 | THR | CG2 | 68.214 | 16.309 | 49.052 | 16.50 |
| 1146 | ASN | N | 67.735 | 11.756 | 50.863 | 21.38 |
| 1147 | ASN | CA | 67.628 | 10.783 | 51.969 | 23.28 |
| 1148 | ASN | C | 66.346 | 10.889 | 52.861 | 23.35 |
| 1149 | ASN | O | 66.353 | 10.887 | 54.078 | 24.28 |
| 1150 | ASN | CB | 68.918 | 10.815 | 52.831 | 27.97 |
| 1151 | ASN | CG | 69.285 | 9.445 | 53.414 | 32.19 |
| 1152 | ASN | OD1 | 68.963 | 8.394 | 52.899 | 34.42 |
| 1153 | ASN | ND2 | 70.048 | 9.471 | 54.465 | 31.14 |
| 1154 | LEU | N | 65.246 | 10.944 | 52.152 | 22.74 |
| 1155 | LEU | CA | 63.923 | 11.233 | 52.687 | 21.67 |
| 1156 | LEU | C | 62.917 | 10.253 | 52.009 | 20.94 |
| 1157 | LEU | O | 62.978 | 9.941 | 50.835 | 21.39 |
| 1158 | LEU | CB | 63.586 | 12.665 | 52.212 | 21.84 |
| 1159 | LEU | CG | 63.600 | 13.787 | 53.240 | 23.27 |
| 1160 | LEU | CD1 | 64.055 | 15.113 | 52.656 | 17.13 |
| 1161 | LEU | CD2 | 64.224 | 13.472 | 54.596 | 21.62 |
| 1162 | LYS | N | 61.974 | 9.802 | 52.783 | 21.10 |
| 1163 | LYS | CA | 60.920 | 8.934 | 52.328 | 19.53 |
| 1164 | LYS | C | 59.609 | 9.681 | 52.550 | 18.34 |
| 1165 | LYS | O | 59.486 | 10.402 | 53.520 | 20.22 |
| 1166 | LYS | CB | 61.135 | 7.645 | 53.185 | 20.94 |
| 1167 | LYS | CG | 59.973 | 6.657 | 53.250 | 22.87 |
| 1168 | LYS | CD | 60.414 | 5.282 | 53.669 | 29.27 |
| 1169 | LYS | CE | 59.161 | 4.429 | 53.683 | 32.16 |
| 1170 | LYS | NZ | 59.380 | 3.130 | 54.360 | 36.84 |
| 1171 | LEU | N | 58.659 | 9.543 | 51.618 | 16.41 |
| 1172 | LEU | CA | 57.406 | 10.345 | 51.727 | 16.41 |
| 1173 | LEU | C | 56.161 | 9.462 | 51.429 | 16.89 |
| 1174 | LEU | O | 56.112 | 8.863 | 50.367 | 16.71 |
| 1175 | LEU | CB | 57.542 | 11.526 | 50.777 | 15.09 |
| 1176 | LEU | CG | 56.271 | 12.369 | 50.729 | 13.98 |
| 1177 | LEU | CD1 | 56.382 | 13.211 | 49.453 | 15.42 |
| 1178 | LEU | CD2 | 56.090 | 13.271 | 51.990 | 16.75 |
| 1179 | THR | N | 55.183 | 9.368 | 52.377 | 17.65 |
| 1180 | THR | CA | 54.124 | 8.352 | 52.362 | 17.51 |
| 1181 | THR | C | 52.766 | 9.036 | 52.409 | 16.95 |
| 1182 | THR | O | 52.566 | 9.943 | 53.206 | 16.10 |
| 1183 | THR | CB | 54.424 | 7.325 | 53.497 | 15.94 |
| 1184 | THR | OG1 | 55.871 | 7.204 | 53.749 | 15.73 |
| 1185 | THR | CG2 | 54.295 | 5.897 | 53.009 | 17.67 |
| 1186 | LEU | N | 51.815 | 8.672 | 51.504 | 15.85 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1187 | LEU | CA | 50.464 | 9.240 | 51.601 | 16.51 |
| 1188 | LEU | C | 49.849 | 8.492 | 52.784 | 19.83 |
| 1189 | LEU | O | 49.757 | 7.284 | 52.720 | 20.59 |
| 1190 | LEU | CB | 49.614 | 9.054 | 50.317 | 15.58 |
| 1191 | LEU | CG | 48.211 | 9.745 | 50.328 | 15.08 |
| 1192 | LEU | CD1 | 47.345 | 9.428 | 49.092 | 13.12 |
| 1193 | LEU | CD2 | 48.368 | 11.251 | 50.477 | 15.75 |
| 1194 | ILE | N | 49.561 | 9.233 | 53.881 | 18.46 |
| 1195 | ILE | CA | 48.795 | 8.626 | 54.964 | 18.30 |
| 1196 | ILE | C | 47.299 | 8.487 | 54.699 | 18.81 |
| 1197 | ILE | O | 46.786 | 7.492 | 55.168 | 19.41 |
| 1198 | ILE | CB | 49.008 | 9.309 | 56.286 | 17.44 |
| 1199 | ILE | CG1 | 50.497 | 9.177 | 56.670 | 16.16 |
| 1200 | ILE | CG2 | 48.030 | 8.763 | 57.336 | 17.37 |
| 1201 | ILE | OD1 | 51.109 | 7.804 | 56.438 | 15.26 |
| 1202 | SER | N | 46.772 | 9.561 | 54.052 | 18.02 |
| 1203 | SER | CA | 45.404 | 9.579 | 53.498 | 19.40 |
| 1204 | SER | C | 45.002 | 10.838 | 52.741 | 21.38 |
| 1205 | SER | O | 45.731 | 11.814 | 52.767 | 22.64 |
| 1206 | SER | CB | 44.410 | 9.580 | 54.635 | 21.28 |
| 1207 | SER | OG | 44.258 | 10.789 | 55.488 | 24.51 |
| 1208 | GLU | N | 43.804 | 10.869 | 52.157 | 22.91 |
| 1209 | GLU | CA | 43.247 | 12.165 | 51.666 | 25.57 |
| 1210 | GLU | C | 41.728 | 12.456 | 51.777 | 25.11 |
| 1211 | GLU | O | 40.921 | 11.581 | 51.933 | 28.12 |
| 1212 | GLU | CB | 43.646 | 12.377 | 50.247 | 27.94 |
| 1213 | GLU | CG | 43.357 | 11.238 | 49.297 | 32.29 |
| 1214 | GLU | CD | 44.066 | 11.603 | 47.994 | 38.30 |
| 1215 | GLU | OE1 | 44.307 | 12.793 | 47.744 | 43.02 |
| 1216 | GLU | OE2 | 44.430 | 10.703 | 47.259 | 41.87 |
| 1217 | ASP | N | 41.337 | 13.722 | 51.692 | 20.31 |
| 1218 | ASP | CA | 39.977 | 14.185 | 51.811 | 18.75 |
| 1219 | ASP | C | 39.742 | 15.051 | 50.582 | 19.30 |
| 1220 | ASP | O | 40.185 | 16.193 | 50.485 | 17.85 |
| 1221 | ASP | CB | 40.000 | 14.960 | 53.115 | 21.92 |
| 1222 | ASP | CG | 38.796 | 15.833 | 53.455 | 28.13 |
| 1223 | ASP | OD1 | 37.691 | 15.542 | 52.994 | 28.01 |
| 1224 | ASP | OD2 | 38.979 | 16.828 | 54.204 | 33.77 |
| 1225 | ILE | N | 39.104 | 14.403 | 49.603 | 19.47 |
| 1226 | ILE | CA | 38.862 | 15.024 | 48.297 | 20.98 |
| 1227 | ILE | C | 37.511 | 15.728 | 48.182 | 22.51 |
| 1228 | ILE | O | 36.486 | 15.086 | 48.315 | 25.15 |
| 1229 | ILE | CB | 38.844 | 13.927 | 47.248 | 22.51 |
| 1230 | ILE | CG1 | 40.112 | 13.113 | 47.366 | 22.32 |
| 1231 | ILE | CG2 | 38.613 | 14.468 | 45.803 | 23.73 |
| 1232 | ILE | CD1 | 40.193 | 12.123 | 46.229 | 22.61 |
| 1233 | LYS | N | 37.553 | 17.021 | 47.906 | 21.11 |
| 1234 | LYS | CA | 36.359 | 17.863 | 47.866 | 20.45 |
| 1235 | LYS | C | 36.188 | 18.316 | 46.391 | 20.80 |
| 1236 | LYS | O | 37.064 | 18.038 | 45.587 | 22.26 |
| 1237 | LYS | CB | 36.663 | 18.921 | 48.924 | 22.37 |
| 1238 | LYS | CG | 36.755 | 18.276 | 50.320 | 25.62 |
| 1239 | LYS | CD | 35.354 | 18.201 | 50.911 | 29.83 |
| 1240 | LYS | CE | 35.212 | 17.510 | 52.277 | 33.05 |
| 1241 | LYS | NZ | 33.797 | 17.735 | 52.656 | 35.32 |
| 1242 | THR | N | 35.094 | 18.956 | 45.972 | 19.82 |
| 1243 | THR | CA | 34.963 | 19.315 | 44.853 | 21.59 |
| 1244 | THR | C | 35.971 | 20.151 | 44.101 | 20.83 |
| 1245 | THR | O | 36.245 | 19.955 | 42.922 | 22.59 |
| 1246 | THR | CB | 33.646 | 20.055 | 44.669 | 24.13 |
| 1247 | THR | OG1 | 33.609 | 21.266 | 45.395 | 24.73 |
| 1248 | THR | CG2 | 32.537 | 19.144 | 45.139 | 30.44 |
| 1249 | TYR | N | 36.550 | 21.088 | 44.859 | 17.73 |
| 1250 | TYR | CA | 37.522 | 21.987 | 44.234 | 15.97 |
| 1251 | TYR | C | 38.926 | 22.037 | 44.888 | 15.46 |
| 1252 | TYR | O | 39.790 | 22.830 | 44.552 | 15.86 |
| 1253 | TYR | CB | 36.862 | 23.362 | 44.168 | 12.55 |
| 1254 | TYR | CG | 36.787 | 24.053 | 45.510 | 12.56 |
| 1255 | TYR | CD1 | 35.748 | 23.758 | 46.416 | 14.70 |
| 1256 | TYR | CD2 | 37.745 | 25.026 | 45.793 | 14.86 |
| 1257 | TYR | CE1 | 35.638 | 24.506 | 47.593 | 15.48 |
| 1258 | TYR | CE2 | 37.676 | 25.747 | 47.000 | 16.69 |
| 1259 | TYR | CZ | 36.598 | 25.497 | 47.858 | 16.96 |
| 1260 | TYR | OH | 36.474 | 26.267 | 48.979 | 15.71 |
| 1261 | TYR | N | 39.089 | 21.152 | 45.889 | 14.74 |
| 1262 | TYR | CA | 40.333 | 21.010 | 46.643 | 14.03 |
| 1263 | TYR | C | 40.453 | 19.639 | 47.315 | 16.12 |
| 1264 | TYR | O | 39.469 | 18.949 | 47.536 | 17.82 |
| 1265 | TYR | CB | 40.575 | 22.195 | 47.613 | 12.74 |
| 1266 | TYR | CG | 39.769 | 22.161 | 48.905 | 15.40 |
| 1267 | TYR | CD1 | 40.334 | 21.536 | 50.033 | 13.77 |
| 1268 | TYR | CD2 | 38.479 | 22.734 | 48.947 | 18.58 |
| 1269 | TYR | CE1 | 39.560 | 21.424 | 51.207 | 15.81 |
| 1270 | TYR | CE2 | 37.715 | 22.646 | 50.134 | 17.84 |
| 1271 | TYR | CZ | 38.266 | 21.965 | 51.235 | 16.69 |
| 1272 | TYR | OH | 37.544 | 21.811 | 52.389 | 18.92 |
| 1273 | THR | N | 41.697 | 19.226 | 47.627 | 14.21 |
| 1274 | THR | CA | 41.956 | 17.974 | 48.377 | 15.42 |
| 1275 | THR | C | 42.951 | 18.234 | 49.465 | 15.44 |
| 1276 | THR | O | 43.955 | 18.887 | 49.248 | 15.14 |
| 1277 | THR | CB | 42.630 | 16.919 | 47.491 | 16.15 |
| 1278 | THR | OG1 | 41.761 | 16.554 | 46.440 | 16.75 |
| 1279 | THR | CG2 | 43.128 | 15.643 | 48.159 | 15.21 |
| 1280 | VAL | N | 42.638 | 17.716 | 50.607 | 14.25 |
| 1281 | VAL | CA | 43.604 | 17.716 | 51.687 | 15.61 |
| 1282 | VAL | C | 44.212 | 16.325 | 51.849 | 15.76 |
| 1283 | VAL | O | 43.534 | 15.320 | 51.815 | 16.87 |
| 1284 | VAL | CB | 42.971 | 18.215 | 53.028 | 15.56 |
| 1285 | VAL | CG1 | 42.210 | 19.534 | 52.861 | 17.93 |
| 1286 | VAL | CG2 | 44.018 | 18.329 | 54.147 | 15.84 |
| 1287 | ARG | N | 45.545 | 16.296 | 51.981 | 15.23 |
| 1288 | ARG | CA | 46.259 | 15.034 | 52.198 | 12.90 |
| 1289 | ARG | C | 47.094 | 15.095 | 53.452 | 14.57 |
| 1290 | ARG | O | 47.669 | 16.099 | 53.852 | 14.51 |
| 1291 | ARG | CB | 47.213 | 14.689 | 51.060 | 12.22 |
| 1292 | ARG | CG | 46.431 | 14.664 | 49.771 | 14.22 |
| 1293 | ARG | CD | 47.328 | 14.307 | 48.603 | 17.43 |
| 1294 | ARG | NE | 46.522 | 14.288 | 47.372 | 19.70 |
| 1295 | ARG | CZ | 46.343 | 15.286 | 46.563 | 18.02 |
| 1296 | ARG | NH1 | 46.936 | 16.433 | 46.719 | 20.75 |
| 1297 | ARG | NH2 | 45.562 | 15.101 | 45.583 | 22.30 |
| 1298 | GLN | N | 47.167 | 13.949 | 54.075 | 15.95 |
| 1299 | GLN | CA | 48.177 | 13.855 | 55.083 | 15.20 |
| 1300 | GLN | C | 49.286 | 12.980 | 54.578 | 14.98 |
| 1301 | GLN | O | 49.094 | 11.915 | 54.000 | 15.16 |
| 1302 | GLN | CB | 47.425 | 13.295 | 56.248 | 19.99 |
| 1303 | GLN | CG | 48.352 | 12.986 | 57.366 | 24.39 |
| 1304 | GLN | CD | 47.446 | 12.294 | 58.357 | 33.29 |
| 1305 | GLN | OE1 | 46.290 | 11.917 | 58.100 | 36.18 |
| 1306 | GLN | NE2 | 48.061 | 12.057 | 59.508 | 32.20 |
| 1307 | LEU | N | 50.472 | 13.510 | 54.813 | 14.40 |
| 1308 | LEU | CA | 51.690 | 12.890 | 54.351 | 16.50 |
| 1309 | LEU | C | 52.629 | 12.588 | 55.537 | 17.55 |
| 1310 | LEU | O | 52.702 | 13.268 | 56.555 | 18.19 |
| 1311 | LEU | CB | 52.425 | 13.840 | 53.397 | 16.87 |
| 1312 | LEU | CG | 52.057 | 14.029 | 51.920 | 19.16 |
| 1313 | LEU | CD1 | 52.220 | 15.473 | 51.494 | 18.62 |
| 1314 | LEU | CD2 | 50.780 | 13.408 | 51.439 | 19.45 |
| 1315 | GLU | N | 53.373 | 11.519 | 55.358 | 16.26 |
| 1316 | GLU | CA | 54.428 | 11.311 | 56.300 | 16.63 |
| 1317 | GLU | C | 55.754 | 11.455 | 55.632 | 15.84 |
| 1318 | GLU | O | 56.066 | 10.787 | 54.676 | 17.35 |
| 1319 | GLU | CB | 54.304 | 9.947 | 56.958 | 17.38 |
| 1320 | GLU | CG | 55.477 | 9.848 | 57.928 | 23.65 |
| 1321 | GLU | CD | 55.430 | 8.583 | 58.764 | 30.56 |
| 1322 | GLU | OE1 | 54.547 | 8.475 | 59.626 | 31.25 |
| 1323 | GLU | OE2 | 56.295 | 7.734 | 58.553 | 32.96 |
| 1324 | LEU | N | 56.529 | 12.352 | 56.152 | 17.81 |
| 1325 | LEU | CA | 57.907 | 12.582 | 55.715 | 19.00 |
| 1326 | LEU | C | 58.902 | 11.990 | 56.739 | 21.54 |
| 1327 | LEU | O | 59.000 | 12.436 | 57.883 | 19.81 |
| 1328 | LEU | CB | 58.084 | 14.121 | 55.646 | 17.55 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1329 | LEU | CG | 59.011 | 14.839 | 54.653 | 19.65 |
| 1330 | LEU | CD1 | 59.999 | 13.982 | 53.910 | 20.83 |
| 1331 | LEU | CD2 | 59.611 | 16.118 | 55.230 | 17.35 |
| 1332 | GLU | N | 59.677 | 11.018 | 56.242 | 24.40 |
| 1333 | GLU | CA | 60.757 | 10.444 | 57.062 | 24.80 |
| 1334 | GLU | C | 62.183 | 10.790 | 56.622 | 25.64 |
| 1335 | GLU | O | 62.666 | 10.593 | 55.508 | 24.49 |
| 1336 | GLU | CB | 60.566 | 8.923 | 57.182 | 24.55 |
| 1337 | GLU | CG | 61.533 | 8.201 | 58.134 | 26.49 |
| 1338 | GLU | CD | 61.368 | 6.701 | 58.012 | 28.97 |
| 1339 | GLU | OE1 | 60.447 | 6.223 | 57.350 | 33.55 |
| 1340 | GLU | OE2 | 62.199 | 5.969 | 58.536 | 32.02 |
| 1341 | ASN | N | 62.873 | 11.339 | 57.617 | 26.33 |
| 1342 | ASN | CA | 64.303 | 11.526 | 57.452 | 28.36 |
| 1343 | ASN | C | 65.008 | 10.195 | 57.582 | 29.60 |
| 1344 | ASN | O | 65.247 | 9.741 | 58.682 | 31.34 |
| 1345 | ASN | CB | 64.793 | 12.543 | 58.488 | 27.93 |
| 1346 | ASN | CG | 66.295 | 12.759 | 58.412 | 30.21 |
| 1347 | ASN | OD1 | 67.105 | 11.921 | 58.046 | 28.62 |
| 1348 | ASN | ND2 | 66.668 | 13.937 | 58.851 | 31.76 |
| 1349 | LEU | N | 65.339 | 9.597 | 56.434 | 30.56 |
| 1350 | LEU | CA | 65.970 | 8.276 | 56.397 | 31.30 |
| 1351 | LEU | C | 67.360 | 8.191 | 57.066 | 35.28 |
| 1352 | LEU | O | 67.827 | 7.146 | 57.488 | 35.62 |
| 1353 | LEU | CB | 66.080 | 7.880 | 54.942 | 28.95 |
| 1354 | LEU | CG | 65.153 | 6.811 | 54.458 | 29.38 |
| 1355 | LEU | CD1 | 65.096 | 6.740 | 52.927 | 27.85 |
| 1356 | LEU | CD2 | 63.794 | 6.896 | 55.086 | 30.00 |
| 1357 | THR | N | 68.009 | 9.367 | 57.192 | 37.71 |
| 1358 | THR | CA | 69.278 | 9.474 | 57.935 | 41.16 |
| 1359 | THR | C | 69.130 | 9.189 | 59.443 | 43.17 |
| 1360 | THR | O | 70.010 | 8.733 | 60.157 | 45.18 |
| 1361 | THR | CB | 69.921 | 10.888 | 57.739 | 44.16 |
| 1362 | THR | OG1 | 70.079 | 11.267 | 56.353 | 45.45 |
| 1363 | THR | CG2 | 71.278 | 11.033 | 58.430 | 44.74 |
| 1364 | THR | N | 67.912 | 9.502 | 59.928 | 43.51 |
| 1365 | THR | CA | 67.627 | 9.396 | 61.373 | 40.76 |
| 1366 | THR | C | 66.443 | 8.517 | 61.738 | 41.34 |
| 1367 | THR | O | 66.193 | 8.141 | 62.866 | 43.02 |
| 1368 | THR | CB | 67.386 | 10.777 | 62.009 | 39.25 |
| 1369 | THR | OG1 | 66.206 | 11.364 | 61.461 | 42.09 |
| 1370 | THR | CG2 | 68.536 | 11.758 | 61.802 | 37.92 |
| 1371 | GLN | N | 65.653 | 8.252 | 60.722 | 40.94 |
| 1372 | GLN | CA | 64.289 | 7.831 | 61.000 | 41.20 |
| 1373 | GLN | C | 63.388 | 8.708 | 61.881 | 38.70 |
| 1374 | GLN | O | 62.322 | 8.304 | 62.315 | 38.13 |
| 1375 | GLN | CB | 64.284 | 6.380 | 61.408 | 45.37 |
| 1376 | GLN | CG | 64.898 | 5.645 | 60.250 | 51.51 |
| 1377 | GLN | CD | 64.977 | 4.182 | 60.571 | 56.44 |
| 1378 | GLN | CE1 | 65.018 | 3.741 | 61.710 | 58.04 |
| 1379 | GLN | NE2 | 65.051 | 3.403 | 59.497 | 61.09 |
| 1380 | GLU | N | 63.785 | 9.974 | 62.092 | 37.29 |
| 1381 | GLU | CA | 62.727 | 10.920 | 62.488 | 37.74 |
| 1382 | GLU | C | 61.627 | 11.026 | 61.422 | 35.73 |
| 1383 | GLU | O | 61.806 | 10.869 | 60.217 | 34.94 |
| 1384 | GLU | CB | 63.277 | 12.311 | 62.903 | 43.18 |
| 1385 | GLU | CG | 62.269 | 13.276 | 63.617 | 51.01 |
| 1386 | GLU | CD | 62.855 | 14.683 | 63.932 | 57.11 |
| 1387 | GLU | OE1 | 64.057 | 14.771 | 64.282 | 59.70 |
| 1388 | GLU | OE2 | 62.106 | 15.688 | 63.812 | 59.23 |
| 1389 | THR | N | 60.452 | 11.227 | 61.976 | 33.44 |
| 1390 | THR | CA | 59.253 | 11.210 | 61.132 | 31.67 |
| 1391 | THR | C | 58.364 | 12.397 | 61.416 | 30.34 |
| 1392 | THR | O | 58.213 | 12.814 | 62.569 | 31.62 |
| 1393 | THR | CB | 58.498 | 9.890 | 61.287 | 29.52 |
| 1394 | THR | OG1 | 58.650 | 9.203 | 60.065 | 31.41 |
| 1395 | THR | CG2 | 57.054 | 9.944 | 61.745 | 27.83 |
| 1396 | ARG | N | 57.809 | 12.940 | 60.314 | 27.40 |
| 1397 | ARG | CA | 56.900 | 14.072 | 60.476 | 22.96 |
| 1398 | ARG | C | 55.656 | 14.011 | 59.676 | 19.60 |
| 1399 | ARG | O | 55.670 | 13.570 | 58.544 | 18.08 |
| 1400 | ARG | CB | 57.517 | 15.400 | 60.125 | 24.02 |
| 1401 | ARG | CG | 58.772 | 15.656 | 60.892 | 27.06 |
| 1402 | ARG | CD | 59.108 | 17.126 | 60.821 | 30.34 |
| 1403 | ARG | NE | 60.299 | 17.280 | 61.631 | 31.08 |
| 1404 | ARG | CZ | 61.259 | 18.051 | 61.210 | 33.27 |
| 1405 | ARG | NH1 | 61.083 | 18.824 | 60.138 | 28.01 |
| 1406 | ARG | NH2 | 62.397 | 17.980 | 61.904 | 34.77 |
| 1407 | GLU | N | 54.607 | 14.560 | 60.263 | 19.61 |
| 1408 | GLU | CA | 53.391 | 14.722 | 59.470 | 20.49 |
| 1409 | GLU | C | 53.307 | 16.068 | 58.787 | 18.35 |
| 1410 | GLU | O | 53.451 | 17.113 | 59.403 | 19.50 |
| 1411 | GLU | CB | 52.147 | 14.576 | 60.334 | 23.73 |
| 1412 | GLU | CG | 50.804 | 14.805 | 59.633 | 30.58 |
| 1413 | GLU | CD | 49.709 | 15.110 | 60.669 | 37.37 |
| 1414 | GLU | OE1 | 49.895 | 15.928 | 61.586 | 42.91 |
| 1415 | GLU | OE2 | 48.642 | 14.550 | 60.567 | 39.95 |
| 1416 | ILE | N | 53.037 | 15.988 | 57.502 | 17.31 |
| 1417 | ILE | CA | 52.824 | 17.183 | 56.671 | 15.44 |
| 1418 | ILE | C | 51.428 | 17.188 | 56.122 | 13.03 |
| 1419 | ILE | O | 50.984 | 16.205 | 55.574 | 13.73 |
| 1420 | ILE | CB | 53.864 | 17.224 | 55.509 | 14.77 |
| 1421 | ILE | CG1 | 55.351 | 17.051 | 55.964 | 13.99 |
| 1422 | ILE | CG2 | 53.605 | 18.469 | 54.616 | 13.81 |
| 1423 | ILE | CD1 | 56.011 | 18.081 | 56.937 | 13.39 |
| 1424 | LEU | N | 50.739 | 18.290 | 56.267 | 9.92 |
| 1425 | LEU | CA | 49.468 | 18.427 | 55.596 | 10.85 |
| 1426 | LEU | C | 49.617 | 19.120 | 54.238 | 12.45 |
| 1427 | LEU | O | 50.280 | 20.137 | 54.100 | 13.72 |
| 1428 | LEU | CB | 48.604 | 19.334 | 56.441 | 11.52 |
| 1429 | LEU | CG | 47.671 | 18.670 | 57.476 | 17.76 |
| 1430 | LEU | CD1 | 47.397 | 19.618 | 58.652 | 14.86 |
| 1431 | LEU | CD2 | 48.036 | 17.234 | 57.826 | 15.60 |
| 1432 | HIS | N | 48.967 | 18.556 | 53.225 | 10.68 |
| 1433 | HIS | CA | 49.032 | 19.147 | 51.860 | 11.55 |
| 1434 | HIS | C | 47.653 | 19.632 | 51.485 | 12.79 |
| 1435 | HIS | O | 46.691 | 18.863 | 51.473 | 14.70 |
| 1436 | HIS | CB | 49.509 | 18.015 | 50.971 | 11.04 |
| 1437 | HIS | CG | 49.846 | 18.414 | 49.500 | 9.68 |
| 1438 | HIS | ND1 | 49.049 | 18.115 | 48.481 | 10.25 |
| 1439 | HIS | CD2 | 50.975 | 19.042 | 49.048 | 10.64 |
| 1440 | HIS | CE1 | 49.666 | 18.552 | 47.378 | 12.62 |
| 1441 | HIS | NE2 | 50.846 | 19.126 | 47.727 | 11.21 |
| 1442 | PHE | N | 47.569 | 20.948 | 51.199 | 12.23 |
| 1443 | PHE | CA | 46.274 | 21.521 | 50.815 | 10.89 |
| 1444 | PHE | C | 46.347 | 21.882 | 49.348 | 13.34 |
| 1445 | PHE | O | 47.133 | 22.727 | 48.947 | 13.55 |
| 1446 | PHE | CB | 45.985 | 22.804 | 51.608 | 10.80 |
| 1447 | PHE | CG | 46.010 | 22.514 | 53.082 | 11.64 |
| 1448 | PHE | CD1 | 47.239 | 22.635 | 53.771 | 11.60 |
| 1449 | PHE | CD2 | 44.825 | 22.131 | 53.751 | 14.48 |
| 1450 | PHE | CE1 | 47.320 | 22.342 | 55.132 | 12.91 |
| 1451 | PHE | CE2 | 44.901 | 21.852 | 55.142 | 15.96 |
| 1452 | PHE | CZ | 46.143 | 21.936 | 55.791 | 13.40 |
| 1453 | HIS | N | 45.551 | 21.162 | 48.554 | 11.63 |
| 1454 | HIS | CA | 45.637 | 21.261 | 47.102 | 10.69 |
| 1455 | HIS | C | 44.419 | 21.873 | 46.463 | 11.28 |
| 1456 | HIS | O | 43.339 | 21.303 | 46.375 | 10.79 |
| 1457 | HIS | CB | 45.985 | 19.871 | 46.547 | 11.78 |
| 1458 | HIS | CG | 46.316 | 19.861 | 45.068 | 10.24 |
| 1459 | HIS | ND1 | 46.407 | 20.911 | 44.219 | 13.45 |
| 1460 | HIS | CD2 | 46.596 | 18.751 | 44.321 | 9.09 |
| 1461 | HIS | CE1 | 46.724 | 20.470 | 42.970 | 8.49 |
| 1462 | HIS | NE2 | 46.847 | 19.132 | 43.028 | 12.97 |
| 1463 | TYR | N | 44.598 | 23.139 | 46.037 | 10.13 |
| 1464 | TYR | CA | 43.496 | 23.797 | 45.360 | 11.53 |
| 1465 | TYR | C | 43.543 | 23.415 | 43.888 | 12.75 |
| 1466 | TYR | O | 44.543 | 23.620 | 43.217 | 11.94 |
| 1467 | TYR | CB | 43.699 | 25.310 | 45.529 | 12.91 |
| 1468 | TYR | CG | 42.453 | 26.186 | 45.414 | 14.41 |
| 1469 | TYR | CD1 | 41.617 | 26.161 | 44.267 | 12.62 |
| 1470 | TYR | CD2 | 42.190 | 27.059 | 46.496 | 14.67 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1471 | TYR | CE1 | 40.497 | 27.009 | 44.203 | 14.22 |
| 1472 | TYR | CE2 | 41.062 | 27.896 | 46.437 | 15.77 |
| 1473 | TYR | CZ | 40.224 | 27.857 | 45.292 | 16.57 |
| 1474 | TYR | OH | 39.121 | 28.676 | 45.247 | 18.08 |
| 1475 | THR | N | 42.470 | 22.797 | 43.411 | 13.66 |
| 1476 | THR | CA | 42.557 | 22.223 | 42.056 | 14.87 |
| 1477 | THR | C | 41.794 | 22.989 | 40.931 | 16.37 |
| 1478 | THR | O | 41.788 | 22.650 | 39.752 | 19.74 |
| 1479 | THR | CB | 42.122 | 20.752 | 42.107 | 13.92 |
| 1480 | THR | OG1 | 40.780 | 20.610 | 42.619 | 14.21 |
| 1481 | THR | CG2 | 43.091 | 19.964 | 42.981 | 14.13 |
| 1482 | THR | N | 41.108 | 24.086 | 41.337 | 17.79 |
| 1483 | THR | CA | 40.223 | 24.849 | 40.406 | 17.71 |
| 1484 | THR | C | 40.545 | 26.343 | 40.315 | 17.22 |
| 1485 | THR | O | 39.717 | 27.169 | 39.955 | 19.49 |
| 1486 | THR | CB | 38.737 | 24.756 | 40.818 | 20.00 |
| 1487 | THR | OG1 | 38.645 | 25.274 | 42.134 | 22.57 |
| 1488 | THR | CG2 | 38.165 | 23.331 | 40.809 | 17.86 |
| 1489 | TRP | N | 41.824 | 26.648 | 40.637 | 13.24 |
| 1490 | TRP | CA | 42.325 | 28.014 | 40.474 | 11.42 |
| 1491 | TRP | C | 43.192 | 28.106 | 39.219 | 11.23 |
| 1492 | TRP | O | 44.305 | 27.599 | 39.146 | 13.88 |
| 1493 | TRP | CB | 43.175 | 28.346 | 41.714 | 10.59 |
| 1494 | TRP | CG | 43.522 | 29.827 | 41.830 | 10.86 |
| 1495 | TRP | CD1 | 43.572 | 30.834 | 40.839 | 10.44 |
| 1496 | TRP | CD2 | 43.944 | 30.486 | 43.029 | 11.23 |
| 1497 | TRP | NE1 | 43.985 | 32.030 | 41.334 | 11.38 |
| 1498 | TRP | CE2 | 44.223 | 31.860 | 42.696 | 11.59 |
| 1499 | TRP | CE3 | 44.121 | 30.010 | 44.341 | 12.73 |
| 1500 | TRP | CZ2 | 44.674 | 32.751 | 43.694 | 9.06 |
| 1501 | TRP | CZ3 | 44.569 | 30.912 | 45.324 | 11.86 |
| 1502 | TRP | CH2 | 44.846 | 32.248 | 45.002 | 9.08 |
| 1503 | PRO | N | 42.673 | 28.737 | 38.174 | 11.63 |
| 1504 | PRO | CA | 43.454 | 28.717 | 36.926 | 12.03 |
| 1505 | PRO | C | 44.752 | 29.544 | 36.926 | 10.91 |
| 1506 | PRO | O | 44.841 | 30.605 | 37.525 | 11.74 |
| 1507 | PRO | CB | 42.440 | 29.259 | 35.916 | 15.45 |
| 1508 | PRO | CG | 41.096 | 29.392 | 36.622 | 16.92 |
| 1509 | PRO | CD | 41.398 | 29.448 | 38.084 | 12.40 |
| 1510 | ASP | N | 45.746 | 29.023 | 36.201 | 9.83 |
| 1511 | ASP | CA | 46.936 | 29.819 | 36.018 | 13.50 |
| 1512 | ASP | C | 46.686 | 31.178 | 35.371 | 15.42 |
| 1513 | ASP | O | 45.875 | 31.324 | 34.474 | 16.15 |
| 1514 | ASP | CB | 47.954 | 29.031 | 35.195 | 14.19 |
| 1515 | ASP | CG | 49.381 | 29.475 | 35.461 | 17.10 |
| 1516 | ASP | OD1 | 49.628 | 30.416 | 36.256 | 16.38 |
| 1517 | ASP | OD2 | 50.271 | 28.847 | 34.883 | 16.84 |
| 1518 | PHE | N | 47.308 | 32.203 | 35.958 | 15.66 |
| 1519 | PHE | CA | 46.951 | 33.601 | 35.630 | 13.22 |
| 1520 | PHE | C | 45.496 | 34.007 | 35.774 | 13.65 |
| 1521 | PHE | O | 45.036 | 34.974 | 35.189 | 14.13 |
| 1522 | PHE | CB | 47.522 | 33.989 | 34.243 | 15.03 |
| 1523 | PHE | CG | 49.046 | 33.819 | 34.221 | 16.37 |
| 1524 | PHE | CD1 | 49.875 | 34.865 | 34.737 | 12.85 |
| 1525 | PHE | CD2 | 49.590 | 32.627 | 33.669 | 15.04 |
| 1526 | PHE | CE1 | 51.275 | 34.714 | 34.723 | 10.54 |
| 1527 | PHE | CE2 | 50.986 | 32.515 | 33.639 | 12.82 |
| 1528 | PHE | CZ | 51.798 | 33.547 | 34.161 | 12.68 |
| 1529 | GLY | N | 44.790 | 33.186 | 36.600 | 12.17 |
| 1530 | GLY | CA | 43.402 | 33.477 | 36.870 | 12.74 |
| 1531 | GLY | C | 43.130 | 33.699 | 38.349 | 13.53 |
| 1532 | GLY | O | 44.023 | 33.939 | 39.149 | 12.80 |
| 1533 | VAL | N | 41.854 | 33.622 | 38.691 | 14.29 |
| 1534 | VAL | CA | 41.352 | 33.878 | 40.056 | 13.36 |
| 1535 | VAL | C | 40.477 | 32.685 | 40.533 | 15.85 |
| 1536 | VAL | O | 39.970 | 31.920 | 39.707 | 16.84 |
| 1537 | VAL | CB | 40.533 | 35.165 | 40.144 | 12.64 |
| 1538 | VAL | CG1 | 39.246 | 35.111 | 39.297 | 13.96 |
| 1539 | VAL | CG2 | 41.357 | 36.379 | 39.842 | 12.56 |
| 1540 | PRO | N | 40.310 | 32.541 | 41.888 | 16.09 |
| 1541 | PRO | CA | 39.326 | 31.553 | 42.374 | 14.29 |
| 1542 | PRO | C | 37.904 | 31.850 | 41.841 | 16.70 |
| 1543 | PRO | O | 37.538 | 32.942 | 41.394 | 15.47 |
| 1544 | PRO | CB | 39.425 | 31.709 | 43.893 | 12.24 |
| 1545 | PRO | CG | 40.797 | 32.289 | 44.158 | 11.83 |
| 1546 | PRO | CD | 41.011 | 33.237 | 42.981 | 14.99 |
| 1547 | GLU | N | 37.091 | 30.811 | 41.895 | 18.37 |
| 1548 | GLU | CA | 35.721 | 30.970 | 41.414 | 20.99 |
| 1549 | GLU | C | 34.895 | 32.053 | 42.123 | 22.01 |
| 1550 | GLU | O | 34.014 | 32.699 | 41.571 | 24.26 |
| 1551 | GLU | CB | 34.978 | 29.614 | 41.414 | 22.54 |
| 1552 | GLU | CG | 35.941 | 28.443 | 41.162 | 31.50 |
| 1553 | GLU | CD | 36.522 | 27.764 | 42.465 | 36.66 |
| 1554 | GLU | OE1 | 37.244 | 28.386 | 43.315 | 31.28 |
| 1555 | GLU | OE2 | 36.201 | 26.562 | 42.601 | 36.17 |
| 1556 | SER | N | 35.218 | 32.225 | 43.432 | 20.38 |
| 1557 | SER | CA | 34.520 | 33.218 | 44.274 | 17.88 |
| 1558 | SER | C | 35.369 | 33.535 | 45.449 | 15.08 |
| 1559 | SER | O | 36.146 | 32.701 | 45.885 | 14.67 |
| 1560 | SER | CB | 33.107 | 32.739 | 44.793 | 16.14 |
| 1561 | SER | OG | 33.172 | 31.454 | 45.419 | 13.25 |
| 1562 | PRO | N | 35.198 | 34.731 | 46.003 | 17.02 |
| 1563 | PRO | CA | 35.695 | 34.996 | 47.370 | 16.44 |
| 1564 | PRO | C | 35.343 | 33.936 | 48.410 | 16.53 |
| 1565 | PRO | O | 36.174 | 33.495 | 49.169 | 15.74 |
| 1566 | PRO | CB | 35.085 | 36.348 | 47.744 | 16.53 |
| 1567 | PRO | CG | 34.912 | 37.008 | 46.367 | 18.72 |
| 1568 | PRO | CD | 34.518 | 35.878 | 45.431 | 16.72 |
| 1569 | ALA | N | 34.112 | 33.456 | 48.396 | 16.66 |
| 1570 | ALA | CA | 33.729 | 32.357 | 49.341 | 16.12 |
| 1571 | ALA | C | 34.496 | 31.057 | 49.241 | 15.23 |
| 1572 | ALA | O | 34.901 | 30.462 | 50.211 | 15.53 |
| 1573 | ALA | CB | 32.226 | 31.970 | 49.232 | 15.29 |
| 1574 | SER | N | 34.701 | 30.625 | 48.006 | 15.32 |
| 1575 | SER | CA | 35.478 | 29.414 | 47.823 | 15.79 |
| 1576 | SER | C | 36.944 | 29.511 | 48.170 | 13.45 |
| 1577 | SER | O | 37.543 | 28.637 | 48.804 | 13.08 |
| 1578 | SER | CB | 35.222 | 28.779 | 46.447 | 17.95 |
| 1579 | SER | OG | 35.486 | 29.689 | 45.407 | 26.88 |
| 1580 | PHE | N | 37.464 | 30.720 | 47.831 | 13.85 |
| 1581 | PHE | CA | 38.864 | 31.032 | 48.219 | 12.76 |
| 1582 | PHE | C | 39.021 | 31.081 | 49.708 | 12.10 |
| 1583 | PHE | O | 39.917 | 30.465 | 50.247 | 14.79 |
| 1584 | PHE | CB | 39.297 | 32.409 | 47.672 | 14.01 |
| 1585 | PHE | CG | 40.660 | 32.843 | 48.229 | 12.89 |
| 1586 | PHE | CD1 | 41.853 | 32.277 | 47.736 | 10.70 |
| 1587 | PHE | CD2 | 40.701 | 33.811 | 49.277 | 15.33 |
| 1588 | PHE | CE1 | 43.092 | 32.636 | 48.324 | 13.65 |
| 1589 | PHE | CE2 | 41.935 | 34.193 | 49.864 | 13.88 |
| 1590 | PHE | CZ | 43.111 | 33.585 | 49.388 | 14.38 |
| 1591 | LEU | N | 38.112 | 31.849 | 50.367 | 13.17 |
| 1592 | LEU | CA | 38.075 | 32.020 | 51.857 | 11.98 |
| 1593 | LEU | C | 37.823 | 30.760 | 52.651 | 11.69 |
| 1594 | LEU | O | 38.520 | 30.483 | 53.608 | 10.86 |
| 1595 | LEU | CB | 37.066 | 33.104 | 52.284 | 11.49 |
| 1596 | LEU | CG | 37.504 | 34.528 | 51.922 | 9.71 |
| 1597 | LEU | CD1 | 38.642 | 35.024 | 52.815 | 12.65 |
| 1598 | LEU | CD2 | 36.326 | 35.472 | 51.928 | 12.34 |
| 1599 | ASN | N | 36.872 | 29.960 | 52.146 | 13.52 |
| 1600 | ASN | CA | 36.726 | 28.586 | 52.660 | 14.70 |
| 1601 | ASN | C | 38.019 | 27.745 | 52.629 | 13.68 |
| 1602 | ASN | O | 38.453 | 27.118 | 53.596 | 13.48 |
| 1603 | ASN | CB | 35.555 | 27.891 | 51.921 | 15.31 |
| 1604 | ASN | CG | 35.254 | 26.492 | 52.493 | 16.04 |
| 1605 | ASN | OD1 | 34.760 | 26.270 | 53.576 | 17.67 |
| 1606 | ASN | ND2 | 35.582 | 25.465 | 51.694 | 15.77 |
| 1607 | PHE | N | 38.701 | 27.785 | 51.452 | 12.27 |
| 1608 | PHE | CA | 39.997 | 27.082 | 51.440 | 11.60 |
| 1609 | PHE | C | 41.052 | 27.661 | 52.365 | 11.61 |
| 1610 | PHE | O | 41.697 | 26.908 | 53.084 | 13.15 |
| 1611 | PHE | CB | 40.490 | 27.042 | 49.979 | 11.94 |
| 1612 | PHE | CG | 41.868 | 26.456 | 49.776 | 11.78 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1613 | PHE | CD1 | 43.009 | 27.294 | 49.766 | 14.00 |
| 1614 | PHE | CD2 | 42.033 | 25.070 | 49.586 | 11.64 |
| 1615 | PHE | CE1 | 44.296 | 26.727 | 49.592 | 10.61 |
| 1616 | PHE | CE2 | 43.329 | 24.515 | 49.407 | 12.07 |
| 1617 | PHE | CZ | 44.460 | 25.345 | 49.407 | 10.24 |
| 1618 | LEU | N | 41.208 | 29.021 | 52.358 | 10.72 |
| 1619 | LEU | CA | 42.131 | 29.689 | 53.281 | 10.36 |
| 1620 | LEU | C | 41.892 | 29.328 | 54.775 | 11.41 |
| 1621 | LEU | O | 42.776 | 29.036 | 55.575 | 8.72 |
| 1622 | LEU | CB | 42.039 | 31.214 | 53.107 | 9.30 |
| 1623 | LEU | CG | 42.908 | 32.004 | 54.144 | 11.24 |
| 1624 | LEU | CD1 | 42.781 | 33.509 | 53.999 | 9.97 |
| 1625 | LEU | CD2 | 44.376 | 31.595 | 54.123 | 8.08 |
| 1626 | PHE | N | 40.589 | 29.343 | 55.118 | 13.37 |
| 1627 | PHE | CA | 40.178 | 28.962 | 56.483 | 14.13 |
| 1628 | PHE | C | 40.391 | 27.509 | 56.789 | 14.10 |
| 1629 | PHE | O | 40.855 | 27.222 | 57.866 | 16.46 |
| 1630 | PHE | CB | 38.766 | 29.443 | 56.760 | 14.59 |
| 1631 | PHE | CG | 38.772 | 30.884 | 57.201 | 17.38 |
| 1632 | PHE | CD1 | 39.357 | 31.890 | 56.414 | 17.66 |
| 1633 | PHE | CD2 | 38.132 | 31.220 | 58.421 | 20.46 |
| 1634 | PHE | CE1 | 39.363 | 33.222 | 56.859 | 17.85 |
| 1635 | PHE | CE2 | 38.121 | 32.566 | 58.855 | 21.97 |
| 1636 | PHE | CZ | 38.761 | 33.551 | 58.091 | 19.00 |
| 1637 | LYS | N | 40.227 | 26.595 | 55.788 | 14.03 |
| 1638 | LYS | CA | 40.694 | 25.200 | 56.007 | 13.68 |
| 1639 | LYS | C | 42.139 | 25.064 | 56.362 | 13.76 |
| 1640 | LYS | O | 42.514 | 24.340 | 57.275 | 13.17 |
| 1641 | LYS | CB | 40.525 | 24.284 | 54.793 | 17.74 |
| 1642 | LYS | CG | 39.416 | 23.233 | 54.857 | 26.69 |
| 1643 | LYS | CD | 39.759 | 21.835 | 55.418 | 32.82 |
| 1644 | LYS | CE | 38.482 | 20.926 | 55.564 | 34.45 |
| 1645 | LYS | NZ | 38.794 | 19.520 | 55.920 | 39.18 |
| 1646 | VAL | N | 43.001 | 25.790 | 55.589 | 13.89 |
| 1647 | VAL | CA | 44.422 | 25.885 | 55.972 | 11.86 |
| 1648 | VAL | C | 44.678 | 26.442 | 57.355 | 11.86 |
| 1649 | VAL | O | 45.304 | 25.794 | 58.182 | 11.98 |
| 1650 | VAL | CB | 45.238 | 26.728 | 54.971 | 12.00 |
| 1651 | VAL | CG1 | 44.967 | 26.260 | 53.509 | 11.88 |
| 1652 | VAL | CG2 | 46.748 | 26.651 | 55.285 | 12.37 |
| 1653 | ARG | N | 44.126 | 27.628 | 57.609 | 12.93 |
| 1654 | ARG | CA | 44.218 | 28.196 | 58.973 | 14.48 |
| 1655 | ARG | C | 43.774 | 27.269 | 60.139 | 16.45 |
| 1656 | ARG | O | 44.486 | 27.063 | 61.113 | 17.22 |
| 1657 | ARG | CB | 43.366 | 29.447 | 59.011 | 13.76 |
| 1658 | ARG | CG | 44.037 | 30.657 | 58.430 | 12.22 |
| 1659 | ARG | CD | 43.028 | 31.823 | 58.494 | 13.67 |
| 1660 | ARG | NE | 43.712 | 33.077 | 58.134 | 15.68 |
| 1661 | ARG | CZ | 43.554 | 34.198 | 58.799 | 14.21 |
| 1662 | ARG | NH1 | 42.626 | 34.342 | 59.706 | 12.91 |
| 1663 | ARG | NH2 | 44.379 | 35.143 | 58.580 | 12.03 |
| 1664 | GLU | N | 42.622 | 26.635 | 59.960 | 16.23 |
| 1665 | GLU | CA | 42.097 | 25.723 | 60.976 | 16.92 |
| 1666 | GLU | C | 42.975 | 24.566 | 61.298 | 16.63 |
| 1667 | GLU | O | 43.037 | 24.051 | 62.388 | 17.05 |
| 1668 | GLU | CB | 40.849 | 25.081 | 60.476 | 21.77 |
| 1669 | GLU | CG | 39.696 | 26.051 | 60.316 | 30.11 |
| 1670 | GLU | CD | 38.885 | 26.144 | 61.587 | 37.62 |
| 1671 | GLU | OE1 | 38.166 | 27.160 | 61.732 | 42.75 |
| 1672 | GLU | OE2 | 38.978 | 25.220 | 62.436 | 39.25 |
| 1673 | SER | N | 43.731 | 24.148 | 60.295 | 16.50 |
| 1674 | SER | CA | 44.592 | 22.981 | 60.481 | 17.63 |
| 1675 | SER | C | 45.788 | 23.113 | 61.450 | 20.41 |
| 1676 | SER | O | 46.550 | 22.181 | 61.695 | 21.90 |
| 1677 | SER | CB | 45.172 | 22.503 | 59.108 | 14.84 |
| 1678 | SER | OG | 46.254 | 23.396 | 58.735 | 13.92 |
| 1679 | GLY | N | 46.011 | 24.359 | 61.919 | 20.72 |
| 1680 | GLY | CA | 47.237 | 24.604 | 62.671 | 20.75 |
| 1681 | GLY | C | 48.494 | 24.856 | 61.883 | 22.62 |
| 1682 | GLY | O | 49.516 | 25.236 | 62.431 | 25.75 |
| 1683 | SER | N | 48.416 | 24.672 | 60.541 | 20.77 |
| 1684 | SER | CA | 49.659 | 24.779 | 59.772 | 20.37 |
| 1685 | SER | C | 50.360 | 26.137 | 59.773 | 22.30 |
| 1686 | SER | O | 51.559 | 26.233 | 59.585 | 22.94 |
| 1687 | SER | CB | 49.485 | 24.400 | 58.287 | 17.21 |
| 1688 | SER | OG | 49.026 | 23.044 | 58.151 | 16.17 |
| 1689 | LEU | N | 49.548 | 27.204 | 59.963 | 22.44 |
| 1690 | LEU | CA | 50.024 | 28.615 | 59.942 | 25.58 |
| 1691 | LEU | C | 50.572 | 29.143 | 64.293 | 29.18 |
| 1692 | LEU | O | 50.849 | 30.302 | 61.553 | 34.54 |
| 1693 | LEU | CB | 48.951 | 29.616 | 59.439 | 23.62 |
| 1694 | LEU | CG | 48.548 | 29.235 | 58.027 | 22.66 |
| 1695 | LEU | CD1 | 49.689 | 29.422 | 57.098 | 23.63 |
| 1696 | LEU | CD2 | 47.444 | 30.047 | 57.437 | 25.59 |
| 1697 | SER | N | 50.649 | 28.205 | 62.203 | 27.88 |
| 1698 | SER | CA | 50.934 | 28.588 | 63.544 | 28.98 |
| 1699 | SER | C | 52.365 | 28.767 | 63.829 | 29.17 |
| 1700 | SER | O | 53.212 | 28.114 | 63.230 | 29.28 |
| 1701 | SER | CB | 50.428 | 27.503 | 64.367 | 29.56 |
| 1702 | SER | OG | 49.070 | 27.851 | 64.442 | 38.82 |
| 1703 | PRO | N | 52.649 | 29.669 | 64.766 | 28.99 |
| 1704 | PRO | CA | 54.068 | 29.983 | 64.955 | 28.15 |
| 1705 | PRO | C | 54.893 | 28.912 | 65.712 | 27.34 |
| 1706 | PRO | O | 56.103 | 28.986 | 65.759 | 28.43 |
| 1707 | PRO | CB | 53.940 | 31.338 | 65.624 | 29.14 |
| 1708 | PRO | CG | 52.734 | 31.150 | 66.539 | 28.91 |
| 1709 | PRO | CD | 51.769 | 30.350 | 65.692 | 28.77 |
| 1710 | GLU | N | 54.222 | 27.885 | 66.248 | 25.89 |
| 1711 | GLU | CA | 54.930 | 26.738 | 66.757 | 27.19 |
| 1712 | GLU | C | 55.561 | 25.818 | 65.688 | 26.00 |
| 1713 | GLU | O | 56.405 | 24.951 | 65.946 | 25.89 |
| 1714 | GLU | CB | 54.031 | 26.017 | 67.792 | 33.55 |
| 1715 | GLU | CG | 52.691 | 25.276 | 67.504 | 41.02 |
| 1716 | GLU | CD | 51.512 | 26.145 | 67.001 | 47.74 |
| 1717 | GLU | OE1 | 51.521 | 27.382 | 67.117 | 49.25 |
| 1718 | GLU | OE2 | 50.550 | 25.570 | 66.459 | 51.04 |
| 1719 | HIS | N | 55.110 | 26.077 | 64.437 | 21.92 |
| 1720 | HIS | CA | 55.663 | 25.415 | 63.239 | 18.96 |
| 1721 | HIS | C | 56.588 | 26.312 | 62.464 | 17.83 |
| 1722 | HIS | O | 56.466 | 27.528 | 62.564 | 17.07 |
| 1723 | HIS | CB | 54.545 | 25.023 | 62.270 | 20.94 |
| 1724 | HIS | CG | 53.668 | 24.065 | 63.047 | 20.70 |
| 1725 | HIS | ND1 | 52.366 | 24.242 | 63.288 | 22.42 |
| 1726 | HIS | CD2 | 54.077 | 22.872 | 63.652 | 19.89 |
| 1727 | HIS | CE1 | 51.937 | 23.170 | 64.033 | 18.97 |
| 1728 | HIS | NE2 | 52.998 | 22.336 | 64.244 | 19.93 |
| 1729 | GLY | N | 57.430 | 25.669 | 61.628 | 16.31 |
| 1730 | GLY | CA | 58.102 | 26.449 | 60.582 | 14.07 |
| 1731 | GLY | C | 57.110 | 27.069 | 59.607 | 12.35 |
| 1732 | GLY | O | 55.911 | 26.804 | 59.695 | 13.46 |
| 1733 | PRO | N | 57.602 | 27.933 | 58.693 | 11.56 |
| 1734 | PRO | CA | 56.641 | 28.612 | 57.833 | 13.06 |
| 1735 | PRO | C | 55.989 | 27.621 | 56.834 | 12.70 |
| 1736 | PRO | O | 56.633 | 26.687 | 56.321 | 13.68 |
| 1737 | PRO | CB | 57.455 | 29.724 | 57.210 | 11.82 |
| 1738 | PRO | CG | 58.892 | 29.277 | 57.324 | 12.42 |
| 1739 | PRO | CD | 58.963 | 28.340 | 58.496 | 11.92 |
| 1740 | VAL | N | 54.674 | 27.911 | 56.610 | 12.70 |
| 1741 | VAL | CA | 53.984 | 27.163 | 55.557 | 12.91 |
| 1742 | VAL | C | 54.744 | 27.391 | 54.248 | 13.19 |
| 1743 | VAL | O | 55.220 | 28.484 | 53.926 | 11.64 |
| 1744 | VAL | CB | 52.499 | 27.578 | 55.507 | 13.06 |
| 1745 | VAL | CG1 | 51.592 | 26.621 | 54.745 | 14.25 |
| 1746 | VAL | CG2 | 52.321 | 28.992 | 54.937 | 13.39 |
| 1747 | VAL | N | 54.874 | 26.281 | 53.520 | 12.59 |
| 1748 | VAL | CA | 55.295 | 26.380 | 52.106 | 11.98 |
| 1749 | VAL | C | 54.101 | 26.584 | 51.151 | 12.38 |
| 1750 | VAL | O | 53.183 | 25.771 | 51.097 | 15.24 |
| 1751 | VAL | CB | 56.061 | 25.107 | 51.706 | 9.51 |
| 1752 | VAL | CG1 | 57.319 | 24.946 | 52.599 | 9.49 |
| 1753 | VAL | CG2 | 56.454 | 25.144 | 50.213 | 10.06 |
| 1754 | VAL | N | 54.126 | 27.689 | 50.434 | 10.51 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1755 | VAL | CA | 53.077 | 27.963 | 49.445 | 10.15 |
| 1756 | VAL | C | 53.712 | 27.938 | 48.046 | 11.07 |
| 1757 | VAL | O | 54.761 | 28.530 | 47.785 | 11.12 |
| 1758 | VAL | CB | 52.435 | 29.351 | 49.698 | 9.24 |
| 1759 | VAL | CG1 | 51.958 | 29.592 | 51.143 | 8.57 |
| 1760 | VAL | CG2 | 51.325 | 29.657 | 48.689 | 9.28 |
| 1761 | HIS | N | 53.032 | 27.235 | 47.133 | 10.38 |
| 1762 | HIS | CA | 53.504 | 27.236 | 45.747 | 8.48 |
| 1763 | HIS | C | 52.373 | 27.222 | 44.762 | 10.06 |
| 1764 | HIS | O | 51.254 | 26.782 | 45.047 | 9.96 |
| 1765 | HIS | CB | 54.558 | 26.153 | 45.458 | 8.91 |
| 1766 | HIS | CG | 53.991 | 24.769 | 45.162 | 8.64 |
| 1767 | HIS | ND1 | 53.572 | 24.395 | 43.919 | 7.44 |
| 1768 | HIS | CD2 | 53.803 | 23.723 | 46.048 | 8.51 |
| 1769 | HIS | CE1 | 53.098 | 23.130 | 43.981 | 9.19 |
| 1770 | HIS | NE2 | 53.243 | 22.739 | 45.290 | 11.46 |
| 1771 | CYS | N | 52.695 | 27.766 | 43.579 | 10.31 |
| 1772 | CYS | CA | 51.889 | 27.543 | 42.384 | 8.62 |
| 1773 | CYS | C | 52.821 | 26.996 | 41.318 | 9.41 |
| 1774 | CYS | O | 53.697 | 26.240 | 41.661 | 9.11 |
| 1775 | CYS | CB | 51.158 | 28.783 | 41.966 | 9.94 |
| 1776 | CYS | SG | 52.104 | 30.295 | 42.054 | 10.94 |
| 1777 | SER | N | 52.652 | 27.373 | 40.056 | 9.15 |
| 1778 | SER | CA | 53.690 | 26.848 | 39.157 | 8.78 |
| 1779 | SER | C | 55.026 | 27.639 | 39.274 | 8.55 |
| 1780 | SER | O | 56.127 | 27.100 | 39.390 | 8.15 |
| 1781 | SER | CB | 53.108 | 26.847 | 37.734 | 7.93 |
| 1782 | SER | OG | 54.103 | 26.437 | 36.830 | 8.26 |
| 1783 | ALA | N | 54.879 | 28.997 | 39.335 | 8.61 |
| 1784 | ALA | CA | 56.088 | 29.824 | 39.571 | 7.66 |
| 1785 | ALA | C | 56.362 | 30.302 | 41.022 | 8.82 |
| 1786 | ALA | O | 57.443 | 30.767 | 41.388 | 11.75 |
| 1787 | ALA | CB | 55.994 | 31.024 | 38.665 | 7.00 |
| 1788 | GLY | N | 55.332 | 30.135 | 41.872 | 8.66 |
| 1789 | GLY | CA | 55.504 | 30.616 | 43.255 | 8.32 |
| 1790 | GLY | C | 55.306 | 32.127 | 43.454 | 9.76 |
| 1791 | GLY | O | 55.810 | 32.695 | 44.413 | 10.12 |
| 1792 | ILE | N | 54.593 | 32.756 | 42.493 | 11.14 |
| 1793 | ILE | CA | 54.394 | 34.217 | 42.519 | 12.07 |
| 1794 | ILE | C | 52.948 | 34.722 | 42.312 | 10.76 |
| 1795 | ILE | O | 52.428 | 35.499 | 43.094 | 12.85 |
| 1796 | ILE | CB | 55.434 | 34.998 | 41.644 | 8.68 |
| 1797 | ILE | CG1 | 55.274 | 34.717 | 40.134 | 9.17 |
| 1798 | ILE | CG2 | 56.862 | 34.670 | 42.093 | 8.98 |
| 1799 | ILE | CD1 | 56.328 | 35.365 | 39.216 | 7.46 |
| 1800 | GLY | N | 52.269 | 34.172 | 41.269 | 10.38 |
| 1801 | GLY | CA | 50.932 | 34.709 | 40.970 | 9.10 |
| 1802 | GLY | C | 49.783 | 34.383 | 41.944 | 10.90 |
| 1803 | GLY | O | 49.349 | 35.185 | 42.763 | 10.20 |
| 1804 | ARG | N | 49.366 | 33.089 | 41.810 | 11.01 |
| 1805 | ARG | CA | 48.418 | 32.462 | 42.759 | 10.63 |
| 1806 | ARG | C | 48.954 | 32.468 | 44.215 | 10.18 |
| 1807 | ARG | O | 48.254 | 32.844 | 45.134 | 10.97 |
| 1808 | ARG | CB | 48.025 | 31.034 | 42.275 | 9.12 |
| 1809 | ARG | CG | 47.247 | 31.120 | 40.967 | 9.78 |
| 1810 | ARG | CD | 47.007 | 29.785 | 40.293 | 7.58 |
| 1811 | ARG | NE | 48.188 | 29.323 | 39.636 | 8.89 |
| 1812 | ARG | CZ | 48.221 | 28.218 | 38.919 | 9.55 |
| 1813 | ARG | NH1 | 47.173 | 27.474 | 38.805 | 10.16 |
| 1814 | ARG | NH2 | 49.286 | 27.911 | 38.225 | 9.68 |
| 1815 | SER | N | 50.258 | 32.092 | 44.358 | 10.07 |
| 1816 | SER | CA | 50.854 | 32.120 | 45.724 | 8.26 |
| 1817 | SER | C | 50.864 | 33.513 | 46.362 | 10.19 |
| 1818 | SER | O | 50.529 | 33.638 | 47.522 | 10.34 |
| 1819 | SER | CB | 52.294 | 31.691 | 45.717 | 8.89 |
| 1820 | SER | OG | 52.445 | 30.356 | 45.240 | 11.05 |
| 1821 | GLY | N | 51.192 | 34.586 | 45.584 | 10.44 |
| 1822 | GLY | CA | 51.137 | 35.968 | 46.103 | 8.60 |
| 1823 | GLY | C | 49.743 | 36.409 | 46.483 | 9.62 |
| 1824 | GLY | O | 49.523 | 37.100 | 47.455 | 11.83 |
| 1825 | THR | N | 48.755 | 35.971 | 45.676 | 11.37 |
| 1826 | THR | CA | 47.324 | 36.271 | 45.940 | 10.02 |
| 1827 | THR | C | 46.841 | 35.647 | 47.237 | 11.10 |
| 1828 | THR | O | 46.328 | 36.337 | 48.121 | 9.82 |
| 1829 | THR | CB | 46.392 | 35.796 | 44.796 | 9.53 |
| 1830 | THR | OG1 | 46.832 | 36.337 | 43.530 | 10.14 |
| 1831 | THR | CG2 | 44.927 | 36.128 | 45.095 | 8.73 |
| 1832 | PHE | N | 47.096 | 34.326 | 47.377 | 9.10 |
| 1833 | PHE | CA | 46.838 | 33.635 | 48.636 | 10.60 |
| 1834 | PHE | C | 47.384 | 34.332 | 49.931 | 10.58 |
| 1835 | PHE | O | 46.702 | 34.625 | 50.911 | 11.24 |
| 1836 | PHE | CB | 47.311 | 32.168 | 48.478 | 8.88 |
| 1837 | PHE | CG | 47.118 | 31.324 | 49.741 | 9.58 |
| 1838 | PHE | CD1 | 45.907 | 30.608 | 49.935 | 11.54 |
| 1839 | PHE | CD2 | 48.151 | 31.261 | 50.713 | 11.23 |
| 1840 | PHE | CE1 | 45.741 | 29.809 | 51.090 | 6.44 |
| 1841 | PHE | CE2 | 47.985 | 30.464 | 51.879 | 9.94 |
| 1842 | PHE | CZ | 46.787 | 29.741 | 52.023 | 6.47 |
| 1843 | CYS | N | 48.703 | 34.583 | 49.832 | 10.70 |
| 1844 | CYS | CA | 49.413 | 35.190 | 50.962 | 10.02 |
| 1845 | CYS | C | 49.027 | 36.625 | 51.272 | 10.89 |
| 1846 | CYS | O | 48.945 | 37.006 | 52.423 | 12.32 |
| 1847 | CYS | CB | 50.929 | 35.091 | 50.816 | 12.17 |
| 1848 | CYS | SG | 51.574 | 33.397 | 50.718 | 15.41 |
| 1849 | LEU | N | 48.766 | 37.424 | 50.215 | 10.01 |
| 1850 | LEU | CA | 48.287 | 38.785 | 50.451 | 10.37 |
| 1851 | LEU | C | 46.994 | 38.815 | 51.257 | 10.12 |
| 1852 | LEU | O | 46.890 | 39.510 | 52.246 | 9.30 |
| 1853 | LEU | CB | 48.149 | 39.524 | 49.125 | 9.12 |
| 1854 | LEU | CG | 47.758 | 40.996 | 49.225 | 11.23 |
| 1855 | LEU | OD1 | 47.427 | 41.612 | 47.834 | 11.32 |
| 1856 | LEU | CD2 | 48.778 | 41.823 | 50.020 | 11.96 |
| 1857 | ALA | N | 46.015 | 37.982 | 50.789 | 10.91 |
| 1858 | ALA | CA | 44.724 | 37.906 | 51.492 | 10.80 |
| 1859 | ALA | C | 44.906 | 37.426 | 52.955 | 11.33 |
| 1860 | ALA | O | 44.454 | 38.026 | 53.923 | 10.76 |
| 1861 | ALA | CB | 43.764 | 36.998 | 50.732 | 7.83 |
| 1862 | ASP | N | 45.678 | 36.373 | 53.117 | 11.75 |
| 1863 | ASP | CA | 45.996 | 35.908 | 54.497 | 11.91 |
| 1864 | ASP | C | 46.600 | 36.952 | 55.469 | 11.55 |
| 1865 | ASP | O | 46.156 | 37.208 | 56.590 | 11.95 |
| 1866 | ASP | CB | 46.840 | 34.628 | 54.482 | 10.16 |
| 1867 | ASP | CG | 46.956 | 34.094 | 55.912 | 13.48 |
| 1868 | ASP | OD1 | 45.954 | 33.856 | 56.609 | 12.31 |
| 1869 | ASP | OD2 | 48.073 | 33.934 | 56.360 | 12.63 |
| 1870 | THR | N | 47.625 | 37.598 | 54.924 | 10.97 |
| 1871 | THR | CA | 48.347 | 38.815 | 55.751 | 11.02 |
| 1872 | THR | C | 47.504 | 39.800 | 55.982 | 11.79 |
| 1873 | THR | O | 47.502 | 40.323 | 57.088 | 11.99 |
| 1874 | THR | CB | 49.692 | 39.040 | 55.137 | 11.07 |
| 1875 | THR | OG1 | 50.625 | 37.985 | 55.158 | 11.80 |
| 1876 | THR | CG2 | 50.336 | 40.218 | 55.881 | 10.36 |
| 1877 | CYS | N | 46.764 | 40.247 | 54.943 | 10.65 |
| 1878 | CYS | CA | 45.827 | 41.365 | 55.230 | 10.63 |
| 1879 | CYS | C | 44.740 | 41.106 | 56.320 | 12.96 |
| 1880 | CYS | O | 44.486 | 41.919 | 57.205 | 13.56 |
| 1881 | CYS | CB | 45.123 | 41.924 | 53.999 | 10.48 |
| 1882 | CYS | SG | 46.329 | 42.755 | 52.937 | 13.42 |
| 1883 | LEU | N | 44.189 | 39.876 | 56.268 | 10.64 |
| 1884 | LEU | CA | 43.255 | 39.449 | 57.316 | 11.23 |
| 1885 | LEU | C | 43.865 | 39.322 | 58.731 | 12.65 |
| 1886 | LEU | O | 43.280 | 39.757 | 59.707 | 14.44 |
| 1887 | LEU | CB | 42.560 | 38.133 | 56.873 | 9.49 |
| 1888 | LEU | CG | 41.665 | 38.328 | 55.653 | 8.57 |
| 1889 | LEU | CD1 | 40.477 | 39.186 | 55.978 | 10.68 |
| 1890 | LEU | CD2 | 41.173 | 37.002 | 55.114 | 11.48 |
| 1891 | LEU | N | 45.089 | 38.753 | 58.780 | 13.24 |
| 1892 | LEU | CA | 45.873 | 38.751 | 60.039 | 12.90 |
| 1893 | LEU | C | 46.154 | 40.116 | 60.664 | 13.36 |
| 1894 | LEU | O | 45.961 | 40.401 | 61.827 | 15.00 |
| 1895 | LEU | CB | 47.209 | 38.118 | 59.142 | 12.90 |
| 1896 | LEU | CG | 47.717 | 37.083 | 60.724 | 17.31 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 1897 | LEU | CD1 | 47.104 | 37.072 | 62.115 | 17.90 |
| 1898 | LEU | CD2 | 49.240 | 37.021 | 60.648 | 17.91 |
| 1899 | LEU | N | 46.613 | 41.024 | 59.811 | 14.06 |
| 1900 | LEU | CA | 46.725 | 42.436 | 60.177 | 15.83 |
| 1901 | LEU | C | 45.461 | 43.107 | 60.760 | 15.86 |
| 1902 | LEU | O | 45.460 | 43.682 | 61.849 | 15.48 |
| 1903 | LEU | CB | 47.201 | 43.234 | 58.964 | 15.91 |
| 1904 | LEU | CG | 48.624 | 43.774 | 58.904 | 18.29 |
| 1905 | LEU | CD1 | 49.052 | 43.573 | 57.469 | 20.36 |
| 1906 | LEU | CD2 | 49.641 | 43.305 | 59.923 | 16.23 |
| 1907 | MET | N | 44.375 | 42.978 | 59.989 | 14.06 |
| 1908 | MET | CA | 43.106 | 43.427 | 60.510 | 16.10 |
| 1909 | MET | C | 42.674 | 42.850 | 61.894 | 18.37 |
| 1910 | MET | O | 42.126 | 43.531 | 62.759 | 17.82 |
| 1911 | MET | CB | 42.118 | 43.137 | 59.401 | 17.90 |
| 1912 | MET | CG | 40.713 | 43.550 | 59.741 | 22.88 |
| 1913 | MET | SD | 39.601 | 43.214 | 58.369 | 27.93 |
| 1914 | MET | CE | 40.671 | 43.783 | 57.014 | 21.01 |
| 1915 | ASP | N | 42.996 | 41.548 | 62.049 | 17.66 |
| 1916 | ASP | CA | 42.752 | 40.766 | 63.290 | 18.72 |
| 1917 | ASP | C | 43.468 | 41.301 | 64.551 | 20.72 |
| 1918 | ASP | O | 42.988 | 41.449 | 65.670 | 18.46 |
| 1919 | ASP | CB | 43.151 | 39.310 | 62.959 | 15.77 |
| 1920 | ASP | CG | 42.280 | 38.294 | 63.654 | 15.78 |
| 1921 | ASP | OD1 | 41.335 | 38.723 | 64.270 | 15.30 |
| 1922 | ASP | OD2 | 42.563 | 37.090 | 63.595 | 12.03 |
| 1923 | LYS | N | 44.725 | 41.679 | 64.309 | 22.67 |
| 1924 | LYS | CA | 45.442 | 42.083 | 65.515 | 26.79 |
| 1925 | LYS | C | 45.030 | 43.365 | 66.118 | 27.91 |
| 1926 | LYS | O | 45.173 | 43.640 | 67.292 | 27.25 |
| 1927 | LYS | CB | 46.939 | 42.117 | 65.368 | 31.63 |
| 1928 | LYS | CG | 47.623 | 43.011 | 64.367 | 36.21 |
| 1929 | LYS | CD | 49.088 | 42.561 | 64.344 | 41.15 |
| 1930 | LYS | CE | 49.122 | 41.080 | 63.907 | 45.83 |
| 1931 | LYS | NZ | 49.950 | 40.195 | 64.789 | 48.52 |
| 1932 | ARG | N | 44.496 | 44.183 | 65.244 | 29.18 |
| 1933 | ARG | CA | 44.107 | 45.458 | 65.814 | 30.25 |
| 1934 | ARG | C | 42.610 | 45.701 | 65.816 | 28.51 |
| 1935 | ARG | O | 42.101 | 46.694 | 66.298 | 29.83 |
| 1936 | ARG | CB | 44.909 | 46.490 | 65.022 | 35.96 |
| 1937 | ARG | CG | 44.730 | 46.304 | 63.509 | 35.60 |
| 1938 | ARG | CD | 45.670 | 47.261 | 62.794 | 39.72 |
| 1939 | ARG | NE | 47.048 | 46.827 | 62.880 | 44.72 |
| 1940 | ARG | CZ | 47.922 | 47.107 | 61.918 | 49.49 |
| 1941 | ARG | NH1 | 47.618 | 47.655 | 60.744 | 46.55 |
| 1942 | ARG | NH2 | 49.174 | 46.847 | 62.219 | 54.27 |
| 1943 | LYS | N | 41.920 | 44.731 | 65.188 | 24.03 |
| 1944 | LYS | CA | 40.522 | 44.893 | 64.863 | 22.66 |
| 1945 | LYS | C | 40.206 | 46.220 | 64.139 | 22.19 |
| 1946 | LYS | O | 39.223 | 46.916 | 64.337 | 22.54 |
| 1947 | LYS | CB | 39.649 | 44.455 | 66.104 | 23.45 |
| 1948 | LYS | CG | 39.743 | 42.957 | 66.570 | 20.10 |
| 1949 | LYS | CD | 39.208 | 41.813 | 65.634 | 20.71 |
| 1950 | LYS | CE | 39.159 | 40.316 | 66.166 | 17.94 |
| 1951 | LYS | NZ | 38.787 | 39.163 | 65.278 | 27.72 |
| 1952 | ASP | N | 41.140 | 46.551 | 63.222 | 21.48 |
| 1953 | ASP | CA | 41.082 | 47.870 | 62.548 | 22.85 |
| 1954 | ASP | C | 41.316 | 47.877 | 61.015 | 21.41 |
| 1955 | ASP | O | 42.375 | 48.119 | 60.444 | 21.48 |
| 1956 | ASP | CB | 41.986 | 48.893 | 63.285 | 25.58 |
| 1957 | ASP | CG | 41.991 | 50.280 | 62.654 | 29.64 |
| 1958 | ASP | OD1 | 41.113 | 50.584 | 61.818 | 31.77 |
| 1959 | ASP | OD2 | 42.919 | 51.024 | 62.980 | 30.41 |
| 1960 | PRO | N | 40.247 | 47.578 | 60.311 | 20.58 |
| 1961 | PRO | CA | 40.371 | 47.322 | 58.886 | 22.04 |
| 1962 | PRO | C | 40.829 | 48.515 | 58.129 | 24.22 |
| 1963 | PRO | O | 41.512 | 48.463 | 57.118 | 22.77 |
| 1964 | PRO | CB | 38.944 | 47.032 | 58.454 | 23.82 |
| 1965 | PRO | CG | 38.145 | 46.699 | 59.709 | 22.76 |
| 1966 | PRO | CD | 38.893 | 47.416 | 60.819 | 22.17 |
| 1967 | SER | N | 40.411 | 49.657 | 58.676 | 26.49 |
| 1968 | SER | CA | 40.771 | 50.891 | 57.983 | 29.21 |
| 1969 | SER | C | 42.244 | 51.221 | 58.015 | 28.16 |
| 1970 | SER | O | 42.769 | 51.948 | 57.184 | 30.98 |
| 1971 | SER | CB | 39.918 | 52.100 | 58.446 | 32.36 |
| 1972 | SER | OG | 38.686 | 52.172 | 57.658 | 37.57 |
| 1973 | SER | N | 42.922 | 50.561 | 58.956 | 25.94 |
| 1974 | SER | CA | 44.384 | 50.605 | 58.947 | 23.97 |
| 1975 | SER | C | 45.142 | 49.677 | 58.018 | 23.07 |
| 1976 | SER | O | 46.361 | 49.640 | 58.035 | 23.41 |
| 1977 | SER | CB | 44.987 | 50.283 | 60.317 | 24.53 |
| 1978 | SER | OG | 44.902 | 48.866 | 60.519 | 26.18 |
| 1979 | VAL | N | 44.421 | 48.864 | 57.246 | 22.45 |
| 1980 | VAL | CA | 45.137 | 48.031 | 56.270 | 21.20 |
| 1981 | VAL | C | 45.123 | 48.557 | 54.850 | 21.26 |
| 1982 | VAL | O | 44.092 | 48.802 | 54.231 | 22.49 |
| 1983 | VAL | CB | 45.002 | 46.493 | 56.466 | 22.58 |
| 1984 | VAL | CG1 | 44.884 | 45.658 | 55.190 | 20.76 |
| 1985 | VAL | CG2 | 44.174 | 46.080 | 57.682 | 17.17 |
| 1986 | ASP | N | 46.355 | 48.833 | 54.405 | 19.92 |
| 1987 | ASP | CA | 46.605 | 49.285 | 53.043 | 19.98 |
| 1988 | ASP | C | 47.081 | 48.123 | 52.164 | 17.61 |
| 1989 | ASP | O | 48.232 | 47.702 | 52.203 | 18.51 |
| 1990 | ASP | CB | 47.639 | 50.404 | 53.178 | 21.39 |
| 1991 | ASP | CG | 47.956 | 51.130 | 51.885 | 25.31 |
| 1992 | ASP | OD1 | 47.820 | 50.542 | 50.821 | 23.58 |
| 1993 | ASP | OD2 | 48.409 | 52.287 | 51.944 | 32.08 |
| 1994 | ILE | N | 46.134 | 47.556 | 51.413 | 18.00 |
| 1995 | ILE | CA | 46.483 | 46.335 | 50.680 | 16.17 |
| 1996 | ILE | C | 47.626 | 46.519 | 49.725 | 16.20 |
| 1997 | ILE | O | 48.485 | 45.657 | 49.701 | 16.71 |
| 1998 | ILE | CB | 45.244 | 45.758 | 49.959 | 18.69 |
| 1999 | ILE | CG1 | 44.185 | 45.428 | 51.013 | 20.07 |
| 2000 | ILE | CG2 | 45.559 | 44.493 | 49.131 | 16.13 |
| 2001 | ILE | CD1 | 42.889 | 44.877 | 50.407 | 22.35 |
| 2002 | LYS | N | 47.646 | 47.644 | 48.951 | 15.61 |
| 2003 | LYS | CA | 48.796 | 47.807 | 48.039 | 16.12 |
| 2004 | LYS | C | 50.135 | 47.931 | 48.716 | 15.62 |
| 2005 | LYS | O | 51.153 | 47.394 | 48.321 | 15.12 |
| 2006 | LYS | CB | 48.689 | 49.055 | 47.235 | 18.84 |
| 2007 | LYS | CG | 47.447 | 49.010 | 46.334 | 31.31 |
| 2008 | LYS | CD | 47.091 | 50.385 | 45.684 | 37.73 |
| 2009 | LYS | CE | 47.284 | 51.463 | 46.766 | 43.40 |
| 2010 | LYS | NZ | 46.243 | 52.480 | 46.893 | 47.06 |
| 2011 | LYS | N | 50.099 | 48.648 | 49.820 | 16.19 |
| 2012 | LYS | CA | 51.282 | 48.662 | 50.657 | 17.17 |
| 2013 | LYS | C | 51.745 | 47.323 | 51.261 | 15.81 |
| 2014 | LYS | O | 52.929 | 47.020 | 51.262 | 13.38 |
| 2015 | LYS | CB | 51.004 | 49.698 | 51.724 | 21.47 |
| 2016 | LYS | CG | 52.262 | 50.268 | 52.260 | 26.41 |
| 2017 | LYS | CD | 52.080 | 51.628 | 52.944 | 32.75 |
| 2018 | LYS | CE | 51.717 | 52.861 | 52.072 | 37.01 |
| 2019 | LYS | NZ | 52.068 | 54.091 | 52.860 | 41.44 |
| 2020 | VAL | N | 50.779 | 46.493 | 51.746 | 15.38 |
| 2021 | VAL | CA | 51.243 | 45.153 | 52.147 | 13.40 |
| 2022 | VAL | C | 51.721 | 44.256 | 51.029 | 12.42 |
| 2023 | VAL | O | 52.682 | 43.538 | 51.174 | 12.19 |
| 2024 | VAL | CB | 50.424 | 44.394 | 53.259 | 17.62 |
| 2025 | VAL | CG1 | 50.125 | 42.920 | 53.057 | 13.70 |
| 2026 | VAL | CG2 | 49.369 | 45.253 | 53.949 | 14.26 |
| 2027 | LEU | N | 51.133 | 44.416 | 49.870 | 11.53 |
| 2028 | LEU | CA | 51.731 | 43.742 | 48.691 | 12.42 |
| 2029 | LEU | C | 53.154 | 44.176 | 48.316 | 11.91 |
| 2030 | LEU | O | 54.046 | 43.392 | 48.055 | 10.65 |
| 2031 | LEU | CB | 50.805 | 4a.927 | 47.497 | 12.94 |
| 2032 | LEU | CG | 51.267 | 43.151 | 46.270 | 14.51 |
| 2033 | LEU | CD1 | 50.310 | 43.372 | 45.083 | 14.86 |
| 2034 | LEU | CD2 | 51.468 | 41.649 | 46.603 | 12.64 |
| 2035 | LEU | N | 53.356 | 45.507 | 48.366 | 14.10 |
| 2036 | LEU | CA | 54.728 | 46.026 | 48.214 | 13.57 |
| 2037 | LEU | C | 55.705 | 45.555 | 49.289 | 11.98 |
| 2038 | LEU | O | 56.801 | 45.159 | 48.950 | 10.15 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 2039 | LEU | CB | 54.659 | 47.567 | 48.096 | 15.92 |
| 2040 | LEU | CG | 54.751 | 48.229 | 46.702 | 18.96 |
| 2041 | LEU | CD1 | 53.794 | 49.403 | 46.600 | 18.76 |
| 2042 | LEU | CD2 | 54.861 | 47.323 | 45.482 | 20.15 |
| 2043 | ASP | N | 55.280 | 45.511 | 50.587 | 13.06 |
| 2044 | ASP | CA | 56.110 | 44.828 | 51.584 | 12.70 |
| 2045 | ASP | C | 56.460 | 43.385 | 51.230 | 11.44 |
| 2046 | ASP | O | 57.602 | 42.960 | 51.239 | 11.16 |
| 2047 | ASP | CB | 55.726 | 44.946 | 53.135 | 15.05 |
| 2048 | ASP | CG | 57.045 | 45.344 | 53.997 | 23.08 |
| 2049 | ASP | OD1 | 57.469 | 46.507 | 54.030 | 22.88 |
| 2050 | ASP | OD2 | 57.754 | 44.542 | 54.624 | 24.92 |
| 2051 | MET | N | 55.430 | 42.623 | 50.818 | 13.08 |
| 2052 | MET | CA | 55.755 | 41.284 | 50.344 | 12.59 |
| 2053 | MET | C | 56.726 | 41.161 | 49.161 | 10.76 |
| 2054 | MET | O | 57.544 | 40.258 | 49.155 | 9.86 |
| 2055 | MET | CB | 54.494 | 40.507 | 49.955 | 14.18 |
| 2056 | MET | CG | 53.772 | 39.803 | 51.043 | 20.95 |
| 2057 | MET | SD | 52.297 | 39.007 | 50.399 | 25.25 |
| 2058 | MET | CE | 51.819 | 38.502 | 52.033 | 24.15 |
| 2059 | ARG | N | 56.616 | 42.061 | 48.195 | 11.81 |
| 2060 | ARG | CA | 57.544 | 42.017 | 47.025 | 14.09 |
| 2061 | ARG | C | 59.018 | 42.435 | 47.298 | 14.19 |
| 2062 | ARG | O | 59.958 | 42.214 | 46.558 | 15.37 |
| 2063 | ARG | CB | 57.006 | 42.765 | 45.786 | 15.27 |
| 2064 | ARG | CG | 55.506 | 42.740 | 45.458 | 20.41 |
| 2065 | ARG | CD | 54.800 | 42.082 | 44.276 | 22.57 |
| 2066 | ARG | NE | 55.067 | 42.731 | 43.066 | 21.00 |
| 2067 | ARG | CZ | 54.603 | 42.591 | 41.803 | 19.36 |
| 2068 | ARG | NH1 | 53.481 | 42.040 | 41.379 | 17.30 |
| 2069 | ARG | NH2 | 55.419 | 43.076 | 40.926 | 15.47 |
| 2070 | LYS | N | 59.216 | 42.912 | 48.567 | 12.82 |
| 2071 | LYS | CA | 60.619 | 42.962 | 49.027 | 11.88 |
| 2072 | LYS | C | 61.320 | 41.630 | 49.166 | 11.52 |
| 2073 | LYS | O | 62.519 | 41.494 | 49.116 | 12.87 |
| 2074 | LYS | CB | 60.733 | 43.761 | 50.344 | 10.90 |
| 2075 | LYS | CG | 60.143 | 45.169 | 50.220 | 10.61 |
| 2076 | LYS | CD | 60.078 | 45.786 | 51.630 | 16.89 |
| 2077 | LYS | CE | 59.704 | 47.286 | 51.748 | 18.25 |
| 2078 | LYS | NZ | 59.840 | 47.665 | 53.175 | 18.64 |
| 2079 | PHE | N | 60.530 | 40.573 | 49.403 | 11.46 |
| 2080 | PHE | CA | 61.062 | 39.240 | 49.651 | 10.66 |
| 2081 | PHE | C | 60.961 | 38.264 | 48.481 | 10.63 |
| 2082 | PHE | O | 61.718 | 37.304 | 48.372 | 11.08 |
| 2083 | PHE | CB | 60.312 | 38.582 | 50.824 | 10.87 |
| 2084 | PHE | CG | 60.347 | 39.458 | 52.036 | 10.74 |
| 2085 | PHE | CD1 | 61.470 | 39.374 | 52.899 | 14.67 |
| 2086 | PHE | CD2 | 59.277 | 40.336 | 52.321 | 13.16 |
| 2087 | PHE | CE1 | 61.505 | 40.174 | 54.080 | 14.61 |
| 2088 | PHE | CE2 | 59.312 | 41.139 | 53.481 | 11.84 |
| 2089 | PHE | CZ | 60.439 | 41.068 | 54.334 | 12.78 |
| 2090 | ARG | N | 59.991 | 38.503 | 47.589 | 11.78 |
| 2091 | ARG | CA | 60.048 | 37.752 | 46.323 | 11.12 |
| 2092 | ARG | C | 59.438 | 38.615 | 45.199 | 10.70 |
| 2093 | ARG | O | 58.427 | 39.277 | 45.416 | 11.00 |
| 2094 | ARG | CB | 59.361 | 36.360 | 46.491 | 9.05 |
| 2095 | ARG | CG | 59.547 | 35.389 | 45.310 | 8.54 |
| 2096 | ARG | CD | 58.829 | 34.077 | 45.618 | 8.35 |
| 2097 | ARG | NE | 58.807 | 33.096 | 44.485 | 8.45 |
| 2098 | ARG | CZ | 59.812 | 32.305 | 44.135 | 8.44 |
| 2099 | ARG | NH1 | 60.967 | 32.419 | 44.711 | 8.74 |
| 2100 | ARG | NH2 | 59.670 | 31.395 | 43.187 | 9.54 |
| 2101 | MET | N | 60.064 | 38.542 | 43.986 | 11.10 |
| 2102 | MET | CA | 59.514 | 39.256 | 42.833 | 10.52 |
| 2103 | MET | C | 58.123 | 38.755 | 42.342 | 12.21 |
| 2104 | MET | O | 57.716 | 37.596 | 42.401 | 11.69 |
| 2105 | MET | CB | 60.515 | 39.57 | 41.664 | 12.40 |
| 2106 | MET | CG | 60.688 | 37.693 | 41.161 | 13.12 |
| 2107 | MET | SD | 61.708 | 37.587 | 39.673 | 12.49 |
| 2108 | MET | CE | 63.258 | 38.266 | 40.330 | 14.52 |
| 2109 | GLY | N | 57.384 | 39.697 | 41.822 | 11.82 |
| 2110 | GLY | CA | 56.244 | 39.387 | 40.947 | 10.69 |
| 2111 | GLY | C | 55.014 | 38.778 | 41.578 | 11.80 |
| 2112 | GLY | O | 54.118 | 38.340 | 40.868 | 11.81 |
| 2113 | LEU | N | 54.995 | 38.855 | 42.924 | 11.43 |
| 2114 | LEU | CA | 53.802 | 38.497 | 43.681 | 11.39 |
| 2115 | LEU | C | 52.518 | 39.174 | 43.279 | 12.20 |
| 2116 | LEU | O | 52.384 | 40.390 | 43.261 | 12.24 |
| 2117 | LEU | CB | 54.050 | 38.674 | 45.197 | 10.83 |
| 2118 | LEU | CG | 55.281 | 37.955 | 45.738 | 9.47 |
| 2119 | LEU | CD1 | 55.323 | 36.465 | 45.320 | 9.16 |
| 2120 | LEU | CD2 | 55.336 | 38.148 | 47.254 | 10.38 |
| 2121 | ILE | N | 51.588 | 38.296 | 42.897 | 10.54 |
| 2122 | ILE | CA | 50.396 | 38.717 | 42.153 | 11.17 |
| 2123 | ILE | C | 50.699 | 39.082 | 40.678 | 13.75 |
| 2124 | ILE | O | 51.436 | 40.016 | 40.396 | 13.91 |
| 2125 | ILE | CB | 49.557 | 39.790 | 42.868 | 11.11 |
| 2126 | ILE | CG1 | 49.177 | 39.212 | 44.233 | 9.13 |
| 2127 | ILE | CG2 | 48.312 | 40.138 | 42.008 | 14.38 |
| 2128 | ILE | CD1 | 48.073 | 39.967 | 44.918 | 8.65 |
| 2129 | GLN | N | 50.157 | 38.291 | 39.721 | 13.18 |
| 2130 | GLN | CA | 50.662 | 38.385 | 38.342 | 12.31 |
| 2131 | GLN | C | 49.766 | 39.112 | 37.360 | 14.51 |
| 2132 | GLN | O | 50.188 | 39.490 | 36.276 | 14.93 |
| 2133 | GLN | CB | 51.037 | 36.985 | 37.828 | 12.10 |
| 2134 | GLN | CG | 52.401 | 36.558 | 38.336 | 13.08 |
| 2135 | GLN | CD | 53.427 | 37.182 | 37.460 | 14.33 |
| 2136 | GLN | OE1 | 53.477 | 36.854 | 36.292 | 16.45 |
| 2137 | GLN | NE2 | 54.248 | 38.058 | 38.029 | 11.97 |
| 2138 | THR | N | 48.519 | 39.356 | 37.823 | 14.47 |
| 2139 | THR | CA | 47.567 | 40.130 | 37.057 | 13.82 |
| 2140 | THR | C | 46.787 | 41.158 | 37.866 | 15.31 |
| 2141 | THR | O | 46.656 | 41.081 | 39.092 | 15.21 |
| 2142 | THR | CB | 46.554 | 39.229 | 36.350 | 12.44 |
| 2143 | THR | OG1 | 45.588 | 38.765 | 37.287 | 13.84 |
| 2144 | THR | CG2 | 47.152 | 38.042 | 35.581 | 12.80 |
| 2145 | ALA | N | 46.231 | 42.152 | 37.125 | 16.12 |
| 2146 | ALA | CA | 45.346 | 43.159 | 37.762 | 17.15 |
| 2147 | ALA | C | 44.035 | 42.573 | 38.343 | 17.06 |
| 2148 | ALA | O | 43.495 | 43.018 | 39.351 | 16.84 |
| 2149 | ALA | CB | 44.987 | 44.299 | 36.780 | 15.40 |
| 2150 | ASP | N | 43.567 | 41.485 | 37.685 | 16.67 |
| 2151 | ASP | CA | 42.388 | 40.777 | 38.209 | 16.05 |
| 2152 | ASP | C | 42.651 | 39.978 | 39.460 | 14.16 |
| 2153 | ASP | O | 41.818 | 39.960 | 40.360 | 13.25 |
| 2154 | ASP | CB | 41.797 | 39.833 | 37.180 | 16.36 |
| 2155 | ASP | CG | 40.336 | 39.658 | 37.485 | 18.91 |
| 2156 | ASP | OD1 | 39.640 | 40.638 | 37.769 | 19.27 |
| 2157 | ASP | OD2 | 39.876 | 38.522 | 37.453 | 19.47 |
| 2158 | GLN | N | 43.857 | 39.397 | 39.542 | 12.74 |
| 2159 | GLN | CA | 44.257 | 38.815 | 40.853 | 12.47 |
| 2160 | GLN | C | 44.351 | 39.857 | 41.984 | 13.42 |
| 2161 | GLN | O | 43.906 | 39.646 | 43.101 | 13.68 |
| 2162 | GLN | CB | 45.579 | 38.040 | 40.754 | 10.94 |
| 2163 | GLN | CG | 45.467 | 36.777 | 39.876 | 10.93 |
| 2164 | GLN | CD | 46.795 | 36.101 | 39.634 | 11.89 |
| 2165 | GLN | OE1 | 47.863 | 36.660 | 39.815 | 13.27 |
| 2166 | GLN | NE2 | 46.739 | 34.859 | 39.129 | 10.17 |
| 2167 | LEU | N | 44.892 | 41.066 | 41.654 | 15.21 |
| 2168 | LEU | CA | 44.818 | 42.209 | 42.611 | 13.64 |
| 2169 | LEU | C | 43.408 | 42.567 | 43.025 | 14.41 |
| 2170 | LEU | O | 43.078 | 42.676 | 44.201 | 15.65 |
| 2171 | LEU | CB | 45.560 | 43.441 | 42.074 | 12.86 |
| 2172 | LEU | CG | 45.681 | 44.598 | 43.045 | 13.02 |
| 2173 | LEU | CD1 | 46.174 | 45.889 | 42.389 | 12.87 |
| 2174 | LEU | CD2 | 46.540 | 44.205 | 44.235 | 12.32 |
| 2175 | ARG | N | 42.543 | 42.691 | 41.995 | 13.43 |
| 2176 | ARG | CA | 41.161 | 42.989 | 42.303 | 13.38 |
| 2177 | ARG | C | 40.433 | 41.964 | 43.135 | 14.16 |
| 2178 | ARG | O | 39.716 | 42.292 | 44.066 | 14.64 |
| 2179 | ARG | CB | 40.407 | 43.216 | 41.022 | 13.46 |
| 2180 | ARG | CG | 38.925 | 43.525 | 41.286 | 13.29 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 2181 | ARG | CD | 38.171 | 43.714 | 39.976 | 16.52 |
| 2182 | ARG | NE | 36.823 | 44.228 | 40.247 | 20.17 |
| 2183 | ARG | CZ | 35.772 | 43.485 | 40.354 | 19.49 |
| 2184 | ARG | NH1 | 35.807 | 42.186 | 40.332 | 20.88 |
| 2185 | ARG | NH2 | 34.650 | 44.103 | 40.484 | 21.32 |
| 2186 | PHE | N | 40.683 | 40.692 | 42.778 | 13.41 |
| 2187 | PHE | CA | 40.279 | 39.551 | 43.612 | 13.00 |
| 2188 | PHE | C | 40.781 | 39.564 | 45.054 | 12.42 |
| 2189 | PHE | O | 40.006 | 39.259 | 45.937 | 14.84 |
| 2190 | PHE | CB | 40.652 | 38.200 | 42.969 | 12.87 |
| 2191 | PHE | CG | 40.024 | 37.029 | 43.724 | 13.08 |
| 2192 | PHE | CD1 | 38.719 | 36.588 | 43.410 | 15.82 |
| 2193 | PHE | CD2 | 40.732 | 36.435 | 44.792 | 13.48 |
| 2194 | PHE | CE1 | 38.069 | 35.621 | 44.224 | 14.88 |
| 2195 | PHE | CE2 | 40.074 | 35.497 | 45.610 | 14.71 |
| 2196 | PHE | CZ | 38.737 | 35.123 | 45.347 | 13.48 |
| 2197 | SER | N | 42.069 | 39.939 | 45.279 | 12.86 |
| 2198 | SER | CA | 42.661 | 40.146 | 46.627 | 13.82 |
| 2199 | SER | C | 41.892 | 41.095 | 47.511 | 15.06 |
| 2200 | SER | O | 41.566 | 40.755 | 48.633 | 15.36 |
| 2201 | SER | CB | 44.037 | 40.790 | 46.596 | 11.50 |
| 2202 | SER | OG | 44.867 | 39.808 | 46.005 | 19.07 |
| 2203 | TYR | N | 41.541 | 42.275 | 46.959 | 14.37 |
| 2204 | TYR | CA | 40.568 | 43.166 | 47.642 | 13.98 |
| 2205 | TYR | C | 39.191 | 42.565 | 47.958 | 14.72 |
| 2206 | TYR | O | 38.720 | 42.678 | 49.061 | 16.92 |
| 2207 | TYR | CB | 40.237 | 44.390 | 46.809 | 15.56 |
| 2208 | TYR | CG | 41.257 | 45.499 | 46.833 | 15.10 |
| 2209 | TYR | CD1 | 42.504 | 45.344 | 46.171 | 15.01 |
| 2210 | TYR | CD2 | 40.898 | 46.710 | 47.477 | 16.69 |
| 2211 | TYR | CE1 | 43.433 | 46.405 | 46.232 | 17.26 |
| 2212 | TYR | CE2 | 41.786 | 47.793 | 47.473 | 17.79 |
| 2213 | TYR | CZ | 43.052 | 47.618 | 46.872 | 18.91 |
| 2214 | TYR | OH | 43.970 | 48.651 | 46.941 | 22.03 |
| 2215 | LEU | N | 38.561 | 41.892 | 46.996 | 14.60 |
| 2216 | LEU | CA | 37.297 | 41.190 | 47.263 | 13.80 |
| 2217 | LEU | C | 37.350 | 40.153 | 48.419 | 13.84 |
| 2218 | LEU | O | 36.585 | 40.029 | 49.351 | 15.22 |
| 2219 | LEU | CB | 36.998 | 40.456 | 45.966 | 15.22 |
| 2220 | LEU | CG | 35.889 | 40.943 | 45.032 | 17.91 |
| 2221 | LEU | CD1 | 36.181 | 40.536 | 43.608 | 17.36 |
| 2222 | LEU | CD2 | 35.469 | 42.386 | 45.200 | 17.38 |
| 2223 | ALA | N | 38.419 | 39.344 | 48.343 | 13.18 |
| 2224 | ALA | CA | 38.629 | 38.360 | 49.433 | 12.65 |
| 2225 | ALA | C | 38.897 | 38.956 | 50.826 | 14.16 |
| 2226 | ALA | O | 38.371 | 38.463 | 51.807 | 14.00 |
| 2227 | ALA | CB | 39.768 | 37.370 | 49.099 | 13.02 |
| 2228 | VAL | N | 39.721 | 40.035 | 50.884 | 11.78 |
| 2229 | VAL | CA | 39.918 | 40.769 | 52.138 | 12.53 |
| 2230 | VAL | C | 38.651 | 41.510 | 52.651 | 13.82 |
| 2231 | VAL | O | 38.291 | 41.427 | 53.828 | 12.86 |
| 2232 | VAL | CB | 41.111 | 41.728 | 52.070 | 11.66 |
| 2233 | VAL | CG1 | 42.380 | 40.915 | 51.747 | 13.24 |
| 2234 | VAL | CG2 | 41.316 | 42.491 | 53.376 | 9.92 |
| 2235 | ILE | N | 37.962 | 42.204 | 51.727 | 12.29 |
| 2236 | ILE | CA | 36.692 | 42.836 | 52.151 | 13.94 |
| 2237 | ILE | C | 35.643 | 41.821 | 52.683 | 14.15 |
| 2238 | ILE | O | 35.051 | 42.017 | 53.733 | 14.06 |
| 2239 | ILE | CB | 36.150 | 43.725 | 50.998 | 13.50 |
| 2240 | ILE | CG1 | 37.132 | 44.878 | 50.705 | 14.91 |
| 2241 | ILE | CG2 | 34.736 | 44.246 | 51.344 | 12.74 |
| 2242 | ILE | CD1 | 36.837 | 45.561 | 49.370 | 13.99 |
| 2243 | GLU | N | 35.524 | 40.682 | 51.982 | 13.27 |
| 2244 | GLU | CA | 34.623 | 39.640 | 52.511 | 12.79 |
| 2245 | GLU | C | 35.054 | 38.960 | 53.810 | 14.22 |
| 2246 | GLU | O | 34.348 | 38.838 | 54.812 | 14.98 |
| 2247 | GLU | CB | 34.469 | 38.619 | 51.428 | 11.88 |
| 2248 | GLU | CG | 33.577 | 37.436 | 51.758 | 12.69 |
| 2249 | GLU | CD | 32.144 | 37.802 | 52.097 | 18.61 |
| 2250 | GLU | OE1 | 31.662 | 38.871 | 51.750 | 19.68 |
| 2251 | GLU | OE2 | 31.437 | 37.016 | 52.719 | 20.07 |
| 2252 | GLY | N | 36.351 | 38.579 | 53.807 | 14.10 |
| 2253 | GLY | CA | 36.996 | 38.012 | 55.024 | 11.35 |
| 2254 | GLY | C | 36.903 | 38.905 | 56.279 | 12.42 |
| 2255 | GLY | O | 36.792 | 38.436 | 57.408 | 14.09 |
| 2256 | ALA | N | 36.936 | 40.244 | 56.035 | 12.11 |
| 2257 | ALA | CA | 36.786 | 41.194 | 57.129 | 13.24 |
| 2258 | ALA | C | 35.555 | 40.936 | 57.966 | 14.50 |
| 2259 | ALA | O | 35.567 | 41.104 | 59.163 | 15.74 |
| 2260 | ALA | CB | 36.717 | 42.628 | 56.649 | 12.85 |
| 2261 | LYS | N | 34.522 | 40.415 | 57.318 | 15.43 |
| 2262 | LYS | CA | 33.316 | 40.077 | 58.087 | 17.97 |
| 2263 | LYS | C | 33.511 | 39.126 | 59.305 | 18.17 |
| 2264 | LYS | O | 33.007 | 39.309 | 60.412 | 16.72 |
| 2265 | LYS | CB | 32.232 | 39.479 | 57.184 | 17.36 |
| 2266 | LYS | CG | 31.843 | 40.457 | 56.080 | 20.89 |
| 2267 | LYS | CD | 30.798 | 39.777 | 55.206 | 19.35 |
| 2268 | LYS | CE | 30.249 | 40.618 | 54.078 | 21.45 |
| 2269 | LYS | NZ | 29.750 | 39.613 | 53.147 | 28.58 |
| 2270 | PHE | N | 34.298 | 38.096 | 58.987 | 17.06 |
| 2271 | PHE | CA | 34.710 | 37.136 | 60.018 | 17.26 |
| 2272 | PHE | C | 35.681 | 37.783 | 61.042 | 17.65 |
| 2273 | PHE | O | 35.418 | 37.750 | 62.227 | 17.35 |
| 2274 | PHE | CB | 35.243 | 35.871 | 59.313 | 16.04 |
| 2275 | PHE | CG | 35.710 | 34.853 | 60.327 | 18.17 |
| 2276 | PHE | CD1 | 36.999 | 34.982 | 60.906 | 18.77 |
| 2277 | PHE | CD2 | 34.842 | 33.806 | 60.681 | 17.46 |
| 2278 | PHE | CE1 | 37.423 | 34.059 | 61.897 | 18.56 |
| 2279 | PHE | CE2 | 35.280 | 32.867 | 61.642 | 17.26 |
| 2280 | PHE | CZ | 36.551 | 33.006 | 62.234 | 16.76 |
| 2281 | ILE | N | 36.741 | 38.443 | 60.524 | 17.16 |
| 2282 | ILE | CA | 37.667 | 39.052 | 61.474 | 16.95 |
| 2283 | ILE | C | 36.960 | 40.030 | 62.419 | 18.22 |
| 2284 | ILE | O | 37.307 | 40.294 | 63.547 | 19.58 |
| 2285 | ILE | CB | 38.752 | 39.831 | 60.687 | 16.65 |
| 2286 | ILE | CG1 | 39.499 | 39.025 | 59.668 | 15.20 |
| 2287 | ILE | CG2 | 39.745 | 40.510 | 61.608 | 17.33 |
| 2288 | ILE | CD1 | 40.138 | 37.768 | 60.180 | 16.00 |
| 2289 | MET | N | 35.924 | 40.676 | 61.869 | 17.76 |
| 2290 | MET | CA | 35.293 | 41.696 | 62.708 | 17.15 |
| 2291 | MET | C | 34.125 | 41.213 | 63.554 | 18.59 |
| 2292 | MET | O | 33.271 | 42.006 | 63.936 | 18.92 |
| 2293 | MET | CB | 34.850 | 42.902 | 61.856 | 18.33 |
| 2294 | MET | CG | 36.096 | 43.579 | 61.237 | 18.10 |
| 2295 | MET | SD | 37.293 | 44.167 | 62.479 | 22.98 |
| 2296 | MET | CE | 36.332 | 45.615 | 62.928 | 22.14 |
| 2297 | GLY | N | 34.007 | 39.878 | 63.787 | 17.81 |
| 2298 | GLY | CA | 33.117 | 39.341 | 64.764 | 19.24 |
| 2299 | GLY | C | 31.932 | 38.467 | 64.303 | 18.12 |
| 2300 | GLY | O | 31.162 | 37.852 | 65.052 | 18.31 |
| 2301 | ASP | N | 31.751 | 38.493 | 62.977 | 16.53 |
| 2302 | ASP | CA | 30.662 | 37.671 | 62.462 | 17.00 |
| 2303 | ASP | C | 31.116 | 36.272 | 62.108 | 18.13 |
| 2304 | ASP | O | 31.346 | 35.891 | 60.957 | 19.06 |
| 2305 | ASP | CB | 29.981 | 38.377 | 61.275 | 18.82 |
| 2306 | ASP | CG | 28.755 | 37.606 | 60.749 | 20.22 |
| 2307 | ASP | OD1 | 28.315 | 36.651 | 61.382 | 19.51 |
| 2308 | ASP | OD2 | 28.234 | 37.955 | 59.688 | 23.56 |
| 2309 | SER | N | 31.276 | 35.460 | 63.182 | 18.73 |
| 2310 | SER | CA | 31.804 | 34.126 | 62.883 | 16.96 |
| 2311 | SER | C | 30.962 | 33.233 | 61.948 | 18.39 |
| 2312 | SER | O | 31.432 | 32.300 | 61.284 | 18.33 |
| 2313 | SER | CB | 32.076 | 33.353 | 64.164 | 17.13 |
| 2314 | SER | OG | 33.211 | 33.889 | 64.866 | 14.25 |
| 2315 | SER | N | 29.647 | 33.584 | 61.904 | 17.50 |
| 2316 | SER | CA | 28.726 | 32.804 | 61.055 | 18.74 |
| 2317 | SER | C | 28.994 | 32.849 | 59.528 | 17.75 |
| 2318 | SER | O | 28.665 | 31.927 | 58.776 | 16.68 |
| 2319 | SER | CB | 27.259 | 33.169 | 61.335 | 19.67 |
| 2320 | SER | OG | 26.885 | 34.432 | 60.758 | 21.88 |
| 2321 | VAL | N | 29.690 | 33.918 | 59.107 | 17.27 |
| 2322 | VAL | CA | 30.098 | 33.858 | 57.707 | 18.22 |

TABLE B-continued

Table of the orthogonal three dimensional coordinates in Ångstroms and B factors (Å²) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid |  | X | Y | Z | B |
|---|---|---|---|---|---|---|
| 2323 | VAL | C | 30.893 | 32.658 | 57.299 | 18.73 |
| 2324 | VAL | O | 30.749 | 32.254 | 56.163 | 19.63 |
| 2325 | VAL | CB | 30.851 | 35.081 | 57.155 | 20.69 |
| 2326 | VAL | CG1 | 32.145 | 35.419 | 57.906 | 17.79 |
| 2327 | VAL | CG2 | 29.886 | 36.225 | 56.907 | 23.70 |
| 2328 | GLN | N | 31.676 | 32.100 | 58.244 | 18.28 |
| 2329 | GLN | CA | 32.498 | 30.973 | 57.851 | 19.78 |
| 2330 | GLN | C | 31.709 | 29.809 | 57.296 | 23.25 |
| 2331 | GLN | O | 31.866 | 29.325 | 56.194 | 25.12 |
| 2332 | GLN | CB | 33.350 | 30.549 | 59.027 | 20.56 |
| 2333 | GLN | CG | 34.279 | 29.396 | 58.650 | 24.84 |
| 2334 | GLN | CD | 35.223 | 29.031 | 59.768 | 27.26 |
| 2335 | GLN | OE1 | 35.456 | 29.725 | 60.745 | 31.04 |
| 2336 | GLN | NE2 | 35.798 | 27.883 | 59.602 | 29.42 |
| 2337 | ASP | N | 30.649 | 29.485 | 58.075 | 25.31 |
| 2338 | ASP | CA | 29.810 | 28.447 | 57.454 | 27.02 |
| 2339 | ASP | C | 28.987 | 28.769 | 56.202 | 25.79 |
| 2340 | ASP | O | 28.680 | 27.943 | 55.345 | 25.32 |
| 2341 | ASP | CB | 29.058 | 27.677 | 58.540 | 35.78 |
| 2342 | ASP | CG | 30.060 | 26.695 | 59.218 | 44.92 |
| 2343 | ASP | OD1 | 30.644 | 25.807 | 58.529 | 50.04 |
| 2344 | ASP | OD2 | 30.268 | 26.816 | 60.445 | 50.59 |
| 2345 | GLN | N | 28.684 | 30.074 | 56.081 | 23.38 |
| 2346 | GLN | CA | 28.196 | 30.539 | 54.780 | 24.32 |
| 2347 | GLN | C | 29.105 | 30.389 | 53.573 | 23.16 |
| 2348 | GLN | O | 28.683 | 29.998 | 52.488 | 21.27 |
| 2349 | GLN | CB | 27.869 | 31.970 | 54.845 | 28.00 |
| 2350 | GLN | CG | 26.784 | 32.237 | 55.878 | 35.72 |
| 2351 | GLN | CD | 26.555 | 33.724 | 55.747 | 43.13 |
| 2352 | GLN | OE1 | 26.549 | 34.281 | 54.641 | 48.57 |
| 2353 | GLN | NE2 | 26.403 | 34.395 | 56.909 | 43.82 |
| 2354 | TRP | N | 30.382 | 30.678 | 53.819 | 20.29 |
| 2355 | TRP | CA | 31.346 | 30.362 | 52.750 | 19.31 |
| 2356 | TRP | C | 31.466 | 28.909 | 52.431 | 19.07 |
| 2357 | TRP | O | 31.450 | 28.527 | 51.271 | 19.20 |
| 2358 | TRP | CB | 32.784 | 30.779 | 53.114 | 19.26 |
| 2359 | TRP | CG | 32.909 | 32.243 | 53.480 | 15.65 |
| 2360 | TRP | CD1 | 32.161 | 33.289 | 52.953 | 14.94 |
| 2361 | TRP | CD2 | 33.865 | 32.827 | 54.394 | 15.85 |
| 2362 | TRP | NE1 | 32.572 | 34.480 | 53.472 | 15.54 |
| 2363 | TRP | CE2 | 33.623 | 34.245 | 54.377 | 15.86 |
| 2364 | TRP | CE3 | 34.912 | 32.297 | 55.183 | 14.86 |
| 2365 | TRP | CZ2 | 34.420 | 35.102 | 55.179 | 16.78 |
| 2366 | TRP | CZ3 | 35.699 | 33.183 | 55.951 | 14.37 |
| 2367 | TRP | CH2 | 35.460 | 34.572 | 55.969 | 15.56 |
| 2368 | LYS | N | 31.535 | 28.079 | 53.466 | 21.19 |
| 2369 | LYS | CA | 31.490 | 26.660 | 53.154 | 24.17 |
| 2370 | LYS | C | 30.299 | 26.154 | 52.302 | 25.28 |
| 2371 | LYS | O | 30.419 | 25.380 | 51.350 | 26.15 |
| 2372 | LYS | CB | 31.535 | 25.905 | 54.461 | 26.43 |
| 2373 | LYS | CG | 31.670 | 24.409 | 54.259 | 32.00 |
| 2374 | LYS | CD | 31.629 | 23.919 | 55.676 | 38.87 |
| 2375 | LYS | CE | 31.917 | 22.442 | 55.805 | 45.47 |
| 2376 | LYS | NZ | 31.660 | 22.084 | 57.228 | 51.74 |
| 2377 | GLU | N | 29.117 | 26.663 | 52.680 | 26.22 |
| 2378 | GLU | CA | 27.928 | 26.358 | 51.891 | 27.87 |
| 2379 | GLU | C | 27.975 | 26.877 | 50.455 | 26.53 |
| 2380 | GLU | O | 27.835 | 26.148 | 49.496 | 30.42 |
| 2381 | GLU | CB | 26.659 | 26.888 | 52.548 | 34.80 |
| 2382 | GLU | CG | 26.313 | 26.343 | 53.949 | 47.61 |
| 2383 | GLU | CD | 25.599 | 24.966 | 53.934 | 55.88 |
| 2384 | GLU | OE1 | 24.348 | 24.925 | 53.838 | 59.76 |
| 2385 | GLU | OE2 | 26.294 | 23.937 | 54.064 | 61.03 |
| 2386 | LEU | N | 28.258 | 28.163 | 50.302 | 24.19 |
| 2387 | LEU | CA | 28.499 | 28.736 | 48.972 | 23.43 |
| 2388 | LEU | C | 29.566 | 28.108 | 48.071 | 24.08 |
| 2389 | LEU | O | 29.553 | 28.130 | 46.848 | 22.85 |
| 2390 | LEU | CB | 29.014 | 30.112 | 49.163 | 25.02 |
| 2391 | LEU | CG | 27.980 | 31.163 | 49.085 | 25.39 |
| 2392 | LEU | CD1 | 28.441 | 32.350 | 49.899 | 27.03 |
| 2393 | LEU | CD2 | 26.614 | 30.675 | 49.478 | 28.40 |
| 2394 | SER | N | 30.563 | 27.564 | 48.762 | 23.22 |
| 2395 | SER | CA | 31.652 | 26.937 | 48.040 | 24.53 |
| 2396 | SER | C | 31.401 | 25.574 | 47.438 | 26.87 |
| 2397 | SER | O | 32.174 | 25.053 | 46.642 | 26.47 |
| 2398 | SER | CB | 32.858 | 26.864 | 48.941 | 23.92 |
| 2399 | SER | OG | 32.879 | 25.591 | 49.577 | 27.33 |
| 2400 | HIS | N | 30.272 | 24.958 | 47.865 | 29.80 |
| 2401 | HIS | CA | 29.907 | 23.613 | 47.358 | 33.13 |
| 2402 | HIS | C | 30.966 | 22.498 | 47.442 | 33.64 |
| 2403 | HIS | O | 31.210 | 21.764 | 46.489 | 31.30 |
| 2404 | HIS | CB | 29.302 | 23.669 | 45.909 | 36.51 |
| 2405 | HIS | CG | 28.204 | 24.708 | 45.783 | 40.71 |
| 2406 | HIS | ND1 | 28.213 | 25.693 | 44.854 | 43.97 |
| 2407 | HIS | CD2 | 27.063 | 24.893 | 46.600 | 42.68 |
| 2408 | HIS | CE1 | 27.113 | 26.502 | 45.078 | 43.60 |
| 2409 | HIS | NE2 | 26.408 | 26.006 | 46.157 | 42.67 |
| 2410 | GLU | N | 31.619 | 22.430 | 48.620 | 35.19 |
| 2411 | GLU | CA | 32.799 | 21.567 | 48.661 | 36.70 |
| 2412 | GLU | C | 32.611 | 20.063 | 48.720 | 38.60 |
| 2413 | GLU | O | 33.525 | 19.304 | 48.448 | 37.53 |
| 2414 | GLU | CB | 33.697 | 21.992 | 49.795 | 35.82 |
| 2415 | GLU | CG | 32.956 | 21.874 | 51.117 | 36.20 |
| 2416 | GLU | CD | 33.983 | 21.924 | 52.224 | 38.96 |
| 2417 | GLU | OE1 | 34.913 | 22.725 | 52.123 | 36.60 |
| 2418 | GLU | OE2 | 33.890 | 21.139 | 53.176 | 41.14 |
| 2419 | ASP | N | 31.402 | 19.658 | 49.089 | 42.63 |
| 2420 | ASP | CA | 31.156 | 18.226 | 49.154 | 46.40 |
| 2421 | ASP | C | 30.772 | 17.554 | 47.818 | 47.19 |
| 2422 | ASP | O | 30.066 | 18.144 | 46.977 | 46.38 |
| 2423 | ASP | CB | 30.260 | 17.938 | 50.394 | 50.98 |
| 2424 | ASP | CG | 31.161 | 17.875 | 51.659 | 57.85 |
| 2425 | ASP | OD1 | 32.063 | 17.001 | 51.717 | 60.50 |
| 2426 | ASP | OD2 | 30.999 | 18.696 | 52.591 | 61.02 |
| 2427 | ASP | OXT | 31.255 | 16.438 | 47.575 | 48.57 |
| 1 | TIP3 | OH2 | 60.719 | 23.664 | 43.966 | 20.00 |
| 2 | TIP3 | 1H | 60.985 | 23.573 | 44.873 | 20.00 |
| 3 | TIP3 | 2H | 60.658 | 24.587 | 43.766 | 20.00 |
| 4 | TIP3 | OH2 | 40.411 | 32.301 | 35.797 | 20.00 |
| 5 | TIP3 | 1H | 40.442 | 31.973 | 36.704 | 20.00 |
| 6 | TIP3 | 2H | 39.543 | 32.682 | 35.681 | 20.00 |
| 7 | TIP3 | OH2 | 45.842 | 40.160 | 69.804 | 20.00 |
| 8 | TIP3 | 1H | 46.390 | 40.196 | 70.592 | 20.00 |
| 9 | TIP3 | 2H | 46.479 | 40.472 | 69.181 | 20.00 |
| 10 | TIP3 | OH2 | 53.379 | 29.910 | 58.076 | 20.00 |
| 11 | TIP3 | 1H | 54.092 | 29.933 | 58.712 | 20.00 |
| 12 | TIP3 | 2H | 53.330 | 30.805 | 57.725 | 20.00 |
| 13 | TIP3 | OH2 | 65.665 | 24.233 | 43.388 | 20.00 |
| 14 | TIP3 | 1H | 66.318 | 23.787 | 43.947 | 20.00 |
| 15 | TIP3 | 2H | 66.089 | 25.124 | 43.306 | 20.00 |
| 16 | TIP3 | OH2 | 53.559 | 24.650 | 58.363 | 20.00 |
| 17 | TIP3 | 1H | 54.093 | 24.160 | 58.947 | 20.00 |
| 18 | TIP3 | 2H | 53.867 | 25.523 | 58.315 | 20.00 |
| 19 | TIP3 | OH2 | 64.454 | 48.312 | 45.244 | 20.00 |
| 20 | TIP3 | 1H | 64.267 | 48.158 | 46.175 | 20.00 |
| 21 | TIP3 | 2H | 63.857 | 49.038 | 45.064 | 20.00 |
| 22 | TIP3 | OH2 | 65.964 | 24.398 | 54.095 | 20.00 |
| 23 | TIP3 | 1H | 65.412 | 24.176 | 54.850 | 20.00 |
| 24 | TIP3 | 2H | 65.297 | 24.761 | 53.591 | 20.00 |
| 25 | TIP3 | OH2 | 45.682 | 25.930 | 65.899 | 20.00 |
| 26 | TIP3 | 1H | 46.136 | 26.039 | 66.729 | 20.00 |
| 27 | TIP3 | 2H | 45.378 | 26.840 | 65.851 | 20.00 |
| 28 | TIP3 | OH2 | 41.439 | 40.049 | 69.937 | 20.00 |
| 29 | TIP3 | 1H | 41.192 | 39.958 | 70.811 | 20.00 |
| 30 | TIP3 | 2H | 40.941 | 40.831 | 69.745 | 20.00 |
| 31 | TIP3 | OH2 | 44.346 | 6.948 | 53.731 | 20.00 |
| 32 | TIP3 | 1H | 44.331 | 7.414 | 54.574 | 20.00 |
| 33 | TIP3 | 2H | 43.897 | 7.661 | 53.211 | 20.00 |
| 34 | TIP3 | OH2 | 69.712 | 33.601 | 44.219 | 20.00 |
| 35 | TIP3 | 1H | 69.242 | 33.254 | 44.983 | 20.00 |
| 36 | TIP3 | 2H | 69.119 | 34.180 | 43.748 | 20.00 |
| 37 | TIP3 | OH2 | 58.068 | 40.012 | 37.522 | 20.00 |

TABLE B-continued

Table of the orthogonal three dimensional coordinates in Ångstroms and B factors (Å$^2$) for Protein Tyrosine Phosphatase 1B complexed with 7-(5-methoxy-1,3-dioxo-1,3-dihydro-isoindol-2-ylmethyl)-2-(oxalyl-amino)-4,7-dihydro-5H-thieno[2,3-c]pyran-3-carboxylic acid (Example 26).

| No | Amino acid | | X | Y | Z | B |
|---|---|---|---|---|---|---|
| 38 | TIP3 | 1H | 57.605 | 39.244 | 37.688 | 20.00 |
| 39 | TIP3 | 2H | 57.929 | 40.200 | 36.598 | 20.00 |
| 40 | TIP3 | OH2 | 38.179 | 37.107 | 67.391 | 20.00 |
| 41 | TIP3 | 1H | 38.128 | 37.041 | 68.351 | 20.00 |
| 42 | TIP3 | 2H | 38.342 | 38.026 | 67.301 | 20.00 |
| 43 | TIP3 | OH2 | 53.580 | 42.001 | 38.764 | 20.00 |
| 44 | TIP3 | 1H | 53.963 | 41.667 | 39.579 | 20.00 |
| 45 | TIP3 | 2H | 53.329 | 42.839 | 39.103 | 20.00 |
| 46 | TIP3 | OH2 | 41.144 | 36.980 | 35.497 | 20.00 |
| 47 | TIP3 | 1H | 41.796 | 37.172 | 36.184 | 20.00 |
| 48 | TIP3 | 2H | 41.093 | 37.769 | 34.947 | 20.00 |
| 49 | TIP3 | OH2 | 63.542 | 14.613 | 42.941 | 20.00 |
| 50 | TIP3 | 1H | 63.904 | 14.292 | 43.762 | 20.00 |
| 51 | TIP3 | 2H | 63.730 | 15.559 | 42.948 | 20.00 |
| 52 | TIP3 | OH2 | 64.565 | 20.375 | 61.477 | 20.00 |
| 53 | TIP3 | 1H | 64.349 | 19.937 | 62.304 | 20.00 |
| 54 | TIP3 | 2H | 64.342 | 21.308 | 61.630 | 20.00 |
| 55 | TIP3 | OH2 | 73.801 | 37.858 | 38.356 | 20.00 |
| 56 | TIP3 | 1H | 73.658 | 37.517 | 39.241 | 20.00 |
| 57 | TIP3 | 2H | 73.755 | 38.813 | 38.502 | 20.00 |
| 58 | TIP3 | OH2 | 68.073 | 28.759 | 56.071 | 20.00 |
| 59 | TIP3 | 1H | 68.526 | 28.682 | 56.924 | 20.00 |
| 60 | TIP3 | 2H | 68.460 | 29.576 | 55.744 | 20.00 |
| 61 | TIP3 | OH2 | 66.813 | 32.500 | 36.292 | 20.00 |
| 62 | TIP3 | 1H | 66.619 | 33.294 | 36.779 | 20.00 |
| 63 | TIP3 | 2H | 67.059 | 32.915 | 35.452 | 20.00 |
| 64 | TIP3 | OH2 | 63.409 | 36.906 | 54.912 | 20.00 |
| 65 | TIP3 | 1H | 63.720 | 36.671 | 55.795 | 20.00 |
| 66 | TIP3 | 2H | 63.757 | 37.774 | 54.745 | 20.00 |
| 67 | TIP3 | OH2 | 75.979 | 37.116 | 45.918 | 20.00 |
| 68 | TIP3 | 1H | 75.933 | 36.923 | 46.791 | 20.00 |
| 69 | TIP3 | 2H | 75.587 | 37.969 | 45.865 | 20.00 |
| 70 | TIP3 | OH2 | 44.663 | 41.751 | 34.799 | 20.00 |
| 71 | TIP3 | 1H | 45.028 | 41.787 | 35.676 | 20.00 |
| 72 | TIP3 | 2H | 44.876 | 42.631 | 34.493 | 20.00 |
| 73 | TIP3 | OH2 | 26.251 | 25.219 | 59.180 | 20.00 |
| 74 | TIP3 | 1H | 26.739 | 25.004 | 59.969 | 20.00 |
| 75 | TIP3 | 2H | 26.454 | 26.133 | 58.987 | 20.00 |
| 76 | TIP3 | OH2 | 43.204 | 25.421 | 36.259 | 20.00 |
| 77 | TIP3 | 1H | 42.767 | 24.692 | 36.714 | 20.00 |
| 78 | TIP3 | 2H | 42.761 | 26.233 | 36.519 | 20.00 |
| 79 | TIP3 | OH2 | 48.443 | 47.491 | 57.210 | 20.00 |
| 80 | TIP3 | 1H | 48.360 | 47.421 | 58.167 | 20.00 |
| 81 | TIP3 | 2H | 48.503 | 48.418 | 56.985 | 20.00 |
| 82 | TIP3 | OH2 | 61.254 | 29.798 | 38.553 | 20.00 |
| 83 | TIP3 | 1H | 61.103 | 29.506 | 39.441 | 20.00 |
| 84 | TIP3 | 2H | 60.395 | 30.126 | 38.301 | 20.00 |
| 85 | TIP3 | OH2 | 76.145 | 33.804 | 35.273 | 20.00 |
| 86 | TIP3 | 1H | 76.871 | 33.620 | 35.878 | 20.00 |
| 87 | TIP3 | 2H | 76.462 | 34.565 | 34.787 | 20.00 |
| 88 | TIP3 | OH2 | 55.588 | 41.658 | 31.859 | 20.00 |
| 89 | TIP3 | 1H | 55.460 | 41.366 | 32.756 | 20.00 |
| 90 | TIP3 | 2H | 55.098 | 42.494 | 31.943 | 20.00 |
| 91 | TIP3 | OH2 | 44.487 | 25.053 | 41.030 | 20.00 |
| 92 | TIP3 | 1H | 44.965 | 24.874 | 41.840 | 20.00 |
| 93 | TIP3 | 2H | 43.913 | 25.788 | 41.262 | 20.00 |
| 94 | TIP3 | OH2 | 50.573 | 33.176 | 62.732 | 20.00 |
| 95 | TIP3 | 1H | 51.351 | 32.774 | 63.106 | 20.00 |
| 96 | TIP3 | 2H | 50.818 | 33.516 | 61.865 | 20.00 |
| 97 | TIP3 | OH2 | 49.953 | 52.982 | 34.749 | 20.00 |
| 98 | TIP3 | 1H | 49.992 | 52.859 | 35.691 | 20.00 |
| 99 | TIP3 | 2H | 49.758 | 53.917 | 34.634 | 20.00 |
| 100 | TIP3 | OH2 | 47.275 | 17.995 | 39.661 | 20.00 |
| 101 | TIP3 | 1H | 48.071 | 17.850 | 40.167 | 20.00 |
| 102 | TIP3 | 2H | 47.429 | 18.857 | 39.243 | 20.00 |
| 103 | TIP3 | OH2 | 71.352 | 29.089 | 36.878 | 20.00 |
| 104 | TIP3 | 1H | 71.322 | 29.074 | 37.839 | 20.00 |
| 105 | TIP3 | 2H | 71.180 | 29.979 | 36.603 | 20.00 |
| 106 | TIP3 | OH2 | 29.430 | 35.859 | 66.439 | 20.00 |
| 107 | TIP3 | 1H | 29.726 | 35.302 | 67.151 | 20.00 |
| 108 | TIP3 | 2H | 29.413 | 36.763 | 66.780 | 20.00 |
| 109 | TIP3 | OH2 | 60.271 | 6.760 | 44.654 | 20.00 |
| 110 | TIP3 | 1H | 60.468 | 6.649 | 45.591 | 20.00 |
| 111 | TIP3 | 2H | 60.190 | 7.711 | 44.594 | 20.00 |
| 112 | TIP3 | OH2 | 37.294 | 40.087 | 40.715 | 20.00 |
| 113 | TIP3 | 1H | 36.898 | 40.267 | 41.578 | 20.00 |
| 114 | TIP3 | 2H | 37.588 | 40.958 | 40.472 | 20.00 |
| 115 | TIP3 | OH2 | 43.748 | 16.614 | 44.085 | 20.00 |
| 116 | TIP3 | 1H | 44.120 | 16.513 | 44.960 | 20.00 |
| 117 | TIP3 | O2H | 43.925 | 17.542 | 44.004 | 20.00 |
| 118 | TIP3 | OH2 | 68.520 | 39.888 | 46.997 | 20.00 |
| 119 | TIP3 | 1H | 67.991 | 39.691 | 47.769 | 20.00 |
| 120 | TIP3 | 2H | 67.978 | 40.491 | 46.494 | 20.00 |
| 121 | TIP3 | OH2 | 58.983 | 37.779 | 38.817 | 20.00 |
| 122 | TIP3 | 1H | 59.166 | 37.703 | 39.753 | 20.00 |
| 123 | TIP3 | 2H | 58.959 | 38.722 | 38.652 | 20.00 |
| 1 | NO_H | O1 | 56.508 | 33.999 | 33.158 | 0.00 |
| 2 | NO_H | C2 | 56.195 | 34.428 | 34.475 | 0.00 |
| 3 | NO_H | C3 | 55.272 | 33.387 | 34.975 | 0.00 |
| 4 | NO_H | C4 | 55.005 | 32.237 | 34.328 | 0.00 |
| 5 | NO_H | C5 | 55.802 | 31.748 | 33.139 | 0.00 |
| 6 | NO_H | C6 | 57.040 | 32.661 | 33.064 | 0.00 |
| 7 | NO_H | S11 | 54.303 | 33.664 | 36.352 | 0.00 |
| 8 | NO_H | C12 | 53.738 | 31.989 | 36.222 | 0.00 |
| 9 | NO_H | C13 | 54.015 | 31.430 | 35.040 | 0.00 |
| 10 | NO_H | C14 | 53.373 | 30.194 | 34.527 | 0.00 |
| 11 | NO_H | O15 | 53.544 | 29.898 | 33.386 | 0.00 |
| 12 | NO_H | O16 | 52.655 | 29.368 | 35.270 | 0.00 |
| 13 | NO_H | N17 | 52.959 | 31.222 | 37.208 | 0.00 |
| 14 | NO_H | C18 | 52.258 | 31.692 | 38.256 | 0.00 |
| 15 | NO_H | O19 | 52.471 | 32.753 | 38.871 | 0.00 |
| 16 | NO_H | C20 | 51.099 | 30.781 | 38.736 | 0.00 |
| 17 | NO_H | O21 | 50.031 | 31.233 | 39.053 | 0.00 |
| 18 | NO_H | O22 | 51.286 | 29.429 | 38.924 | 0.00 |
| 19 | NO_H | C23 | 55.687 | 35.865 | 34.517 | 0.00 |
| 20 | NO_H | N25 | 56.853 | 36.772 | 34.366 | 0.00 |
| 21 | NO_H | C31 | 57.312 | 37.239 | 33.194 | 0.00 |
| 22 | NO_H | C32 | 58.507 | 38.073 | 33.403 | 0.00 |
| 23 | NO_H | C33 | 58.662 | 38.076 | 34.763 | 0.00 |
| 24 | NO_H | C34 | 57.674 | 37.221 | 35.392 | 0.00 |
| 25 | NO_H | O35 | 57.690 | 36.879 | 36.554 | 0.00 |
| 26 | NO_H | O36 | 56.825 | 36.836 | 32.137 | 0.00 |
| 27 | NO_H | C37 | 59.400 | 38.796 | 32.575 | 0.00 |
| 28 | NO_H | C38 | 60.492 | 39.457 | 33.192 | 0.00 |
| 29 | NO_H | C39 | 60.621 | 39.444 | 34.609 | 0.00 |
| 30 | NO_H | C40 | 59.698 | 38.714 | 35.403 | 0.00 |
| 31 | NO_H | O44 | 61.631 | 40.169 | 35.326 | 0.00 |
| 32 | NO_H | C45 | 61.145 | 40.731 | 36.599 | 0.00 |

TABLE C

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1 | GLU | N | 59.958 | 70.181 | 38.145 | 50.84 |
| 2 | GLU | CA | 58.803 | 69.268 | 38.132 | 51.38 |
| 3 | GLU | C | 58.809 | 68.319 | 36.855 | 49.72 |
| 4 | GLU | O | 59.460 | 68.640 | 35.857 | 49.04 |
| 5 | GLU | CB | 57.591 | 70.243 | 38.223 | 53.79 |
| 6 | GLU | CG | 56.243 | 69.633 | 38.610 | 57.54 |
| 7 | GLU | CD | 56.368 | 68.679 | 39.828 | 62.60 |
| 8 | GLU | OE1 | 56.347 | 69.190 | 40.946 | 64.63 |
| 9 | GLU | OE2 | 56.479 | 67.454 | 39.647 | 64.40 |
| 10 | GLU | HA | 58.898 | 68.637 | 39.019 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 11 | GLU | 1HB | 57.526 | 70.850 | 37.323 | 20.00 |
| 12 | GLU | 2HB | 57.818 | 70.928 | 39.043 | 20.00 |
| 13 | GLU | 1HG | 55.736 | 69.097 | 37.823 | 20.00 |
| 14 | GLU | 2HG | 55.552 | 70.439 | 38.879 | 20.00 |
| 15 | MET | N | 57.987 | 67.209 | 36.871 | 46.10 |
| 16 | MET | CA | 57.535 | 66.645 | 35.550 | 42.61 |
| 17 | MET | C | 56.699 | 67.639 | 34.673 | 40.49 |
| 18 | MET | O | 56.698 | 67.589 | 33.457 | 38.08 |
| 19 | MET | CB | 56.671 | 65.360 | 35.644 | 41.62 |
| 20 | MET | CG | 55.206 | 65.625 | 36.082 | 40.45 |
| 21 | MET | SD | 54.276 | 64.127 | 36.149 | 35.84 |
| 22 | MET | CE | 55.232 | 63.264 | 37.441 | 39.51 |
| 23 | MET | H | 57.559 | 66.997 | 37.759 | 20.00 |
| 24 | MET | HA | 58.440 | 66.400 | 35.000 | 20.00 |
| 25 | MET | 1HB | 57.157 | 64.654 | 36.311 | 20.00 |
| 26 | MET | 2HB | 56.626 | 64.870 | 34.671 | 20.00 |
| 27 | MET | 1HG | 54.645 | 66.290 | 35.422 | 20.00 |
| 28 | MET | 2HG | 55.188 | 66.074 | 37.082 | 20.00 |
| 29 | MET | 1HE | 55.510 | 63.974 | 38.230 | 20.00 |
| 30 | MET | 2HE | 56.154 | 62.833 | 37.052 | 20.00 |
| 31 | MET | 3HE | 54.636 | 62.486 | 37.923 | 20.00 |
| 32 | GLU | N | 55.933 | 68.506 | 35.346 | 40.04 |
| 33 | GLU | CA | 55.048 | 69.427 | 34.645 | 41.99 |
| 34 | GLU | C | 55.841 | 70.396 | 33.686 | 41.64 |
| 35 | GLU | O | 55.416 | 70.753 | 32.599 | 42.33 |
| 36 | GLU | CB | 54.205 | 70.086 | 35.723 | 43.82 |
| 37 | GLU | CG | 52.967 | 70.759 | 35.105 | 47.17 |
| 38 | GLU | CD | 51.943 | 71.122 | 36.194 | 49.31 |
| 39 | GLU | OE1 | 52.375 | 71.686 | 37.179 | 48.56 |
| 40 | GLU | OE2 | 50.736 | 70.869 | 36.056 | 51.19 |
| 41 | GLU | H | 55.891 | 68.348 | 36.331 | 20.00 |
| 42 | GLU | HA | 54.387 | 68.813 | 34.030 | 20.00 |
| 43 | GLU | 1HB | 54.780 | 70.799 | 36.314 | 20.00 |
| 44 | GLU | 2HB | 53.860 | 69.333 | 36.440 | 20.00 |
| 45 | GLU | 1HG | 52.473 | 70.118 | 34.379 | 20.00 |
| 46 | GLU | 2HG | 53.234 | 71.688 | 34.607 | 20.00 |
| 47 | LYS | N | 57.077 | 70.711 | 34.138 | 40.99 |
| 48 | LYS | CA | 58.115 | 71.521 | 33.434 | 41.50 |
| 49 | LYS | C | 58.730 | 70.802 | 32.190 | 39.57 |
| 50 | LYS | O | 58.673 | 71.310 | 31.076 | 39.12 |
| 51 | LYS | CB | 59.261 | 71.933 | 34.428 | 45.89 |
| 52 | LYS | CG | 58.918 | 73.024 | 35.497 | 51.71 |
| 53 | LYS | CD | 59.986 | 73.136 | 36.630 | 56.13 |
| 54 | LYS | CE | 59.423 | 73.478 | 38.036 | 59.81 |
| 55 | LYS | NZ | 60.210 | 72.951 | 39.186 | 62.35 |
| 56 | LYS | H | 57.200 | 70.440 | 35.092 | 20.00 |
| 57 | LYS | HA | 57.601 | 72.409 | 33.064 | 20.00 |
| 58 | LYS | 1HB | 60.122 | 72.290 | 33.861 | 20.00 |
| 59 | LYS | 2HB | 59.590 | 71.028 | 34.944 | 20.00 |
| 60 | LYS | 1HG | 57.935 | 72.822 | 35.923 | 20.00 |
| 61 | LYS | 2HG | 58.812 | 73.990 | 35.000 | 20.00 |
| 62 | LYS | 1HD | 60.756 | 73.854 | 36.348 | 20.00 |
| 63 | LYS | 2HD | 60.497 | 72.177 | 36.711 | 20.00 |
| 64 | LYS | 1HE | 58.404 | 73.085 | 38.137 | 20.00 |
| 65 | LYS | 2HE | 59.313 | 74.564 | 38.135 | 20.00 |
| 66 | LYS | 1HZ | 61.199 | 73.268 | 39.140 | 20.00 |
| 67 | LYS | 2HZ | 60.194 | 71.902 | 39.141 | 20.00 |
| 68 | LYS | 3HZ | 59.783 | 73.242 | 40.090 | 20.00 |
| 69 | GLU | N | 59.247 | 69.571 | 32.450 | 38.42 |
| 70 | GLU | CA | 59.583 | 68.656 | 31.386 | 37.30 |
| 71 | GLU | C | 58.523 | 68.608 | 30.274 | 34.58 |
| 72 | GLU | O | 58.814 | 68.798 | 29.094 | 33.74 |
| 73 | GLU | CB | 59.912 | 67.281 | 31.966 | 40.63 |
| 74 | GLU | CG | 60.000 | 66.235 | 30.835 | 46.16 |
| 75 | GLU | CD | 60.673 | 64.854 | 31.065 | 49.22 |
| 76 | GLU | OE1 | 60.508 | 64.271 | 32.105 | 50.86 |
| 77 | GLU | OE2 | 61.374 | 64.376 | 30.167 | 51.79 |
| 78 | GLU | H | 59.306 | 69.279 | 33.408 | 20.00 |
| 79 | GLU | HA | 60.487 | 69.052 | 30.916 | 20.00 |
| 80 | GLU | 1HB | 59.208 | 66.970 | 32.737 | 20.00 |
| 81 | GLU | 2HB | 60.879 | 67.339 | 32.462 | 20.00 |
| 82 | GLU | 1HG | 60.482 | 66.668 | 29.959 | 20.00 |
| 83 | GLU | 2HG | 58.967 | 66.050 | 30.534 | 20.00 |
| 84 | PHE | N | 57.266 | 68.373 | 30.681 | 31.46 |
| 85 | PHE | CA | 56.238 | 68.253 | 29.653 | 30.49 |
| 86 | PHE | C | 56.102 | 69.457 | 28.733 | 33.05 |
| 87 | PHE | O | 56.072 | 69.315 | 27.517 | 31.17 |
| 88 | PHE | CB | 54.928 | 67.999 | 30.280 | 26.00 |
| 89 | PHE | CG | 53.774 | 67.886 | 29.306 | 23.39 |
| 90 | PHE | CD1 | 53.283 | 66.628 | 28.992 | 24.75 |
| 91 | PHE | CD2 | 53.136 | 69.002 | 28.777 | 23.83 |
| 92 | PHE | CE1 | 52.145 | 66.498 | 28.272 | 21.69 |
| 93 | PHE | CE2 | 52.023 | 68.860 | 27.977 | 23.15 |
| 94 | PHE | CZ | 51.514 | 67.599 | 27.755 | 22.50 |
| 95 | PHE | H | 57.145 | 68.129 | 31.644 | 20.00 |
| 96 | PHE | HA | 56.531 | 67.409 | 29.021 | 20.00 |
| 97 | PHE | 1HB | 54.687 | 68.795 | 30.988 | 20.00 |
| 98 | PHE | 2HB | 54.998 | 67.080 | 30.860 | 20.00 |
| 99 | PHE | HD1 | 53.805 | 65.747 | 29.338 | 20.00 |
| 100 | PHE | HD2 | 53.488 | 70.001 | 29.012 | 20.00 |
| 101 | PHE | HE1 | 51.759 | 65.506 | 28.091 | 20.00 |
| 102 | PHE | HE2 | 51.544 | 69.725 | 27.536 | 20.00 |
| 103 | PHE | HZ | 50.632 | 67.461 | 27.165 | 20.00 |
| 104 | GLU | N | 56.018 | 70.665 | 29.336 | 34.78 |
| 105 | GLU | CA | 55.897 | 71.897 | 28.527 | 36.92 |
| 106 | GLU | C | 57.122 | 72.019 | 27.553 | 34.88 |
| 107 | GLU | O | 57.053 | 72.444 | 26.408 | 34.89 |
| 108 | GLU | CB | 55.852 | 73.091 | 29.484 | 42.69 |
| 109 | GLU | CG | 54.488 | 73.612 | 30.017 | 51.81 |
| 110 | GLU | CD | 54.564 | 75.215 | 30.166 | 58.22 |
| 111 | GLU | OE1 | 55.679 | 75.818 | 30.045 | 60.76 |
| 112 | GLU | OE2 | 53.497 | 75.845 | 30.355 | 60.88 |
| 113 | GLU | H | 55.958 | 70.729 | 30.335 | 20.00 |
| 114 | GLU | HA | 54.994 | 71.824 | 27.915 | 20.00 |
| 115 | GLU | 1HB | 56.246 | 73.911 | 28.885 | 20.00 |
| 116 | GLU | 2HB | 56.555 | 72.973 | 30.310 | 20.00 |
| 117 | GLU | 1HG | 54.203 | 73.129 | 30.954 | 20.00 |
| 118 | GLU | 2HG | 53.684 | 73.380 | 29.316 | 20.00 |
| 119 | GLN | N | 58.282 | 71.586 | 28.060 | 32.17 |
| 120 | GLN | CA | 59.556 | 71.631 | 27.323 | 32.79 |
| 121 | GLN | C | 59.615 | 70.636 | 26.126 | 32.59 |
| 122 | GLN | O | 60.173 | 71.008 | 25.095 | 33.38 |
| 123 | GLN | CB | 60.597 | 71.291 | 28.375 | 38.01 |
| 124 | GLN | CG | 62.059 | 71.020 | 27.998 | 46.72 |
| 125 | GLN | CD | 62.634 | 70.285 | 29.249 | 54.60 |
| 126 | GLN | OE1 | 62.587 | 69.070 | 29.367 | 58.48 |
| 127 | GLN | NE2 | 63.129 | 71.080 | 30.204 | 57.65 |
| 128 | GLN | H | 58.242 | 71.334 | 29.034 | 20.00 |
| 129 | GLN | HA | 59.693 | 72.651 | 26.984 | 20.00 |
| 130 | GLN | 1HB | 60.256 | 70.391 | 28.865 | 20.00 |
| 131 | GLN | 2HB | 60.549 | 72.041 | 29.167 | 20.00 |
| 132 | GLN | 1HG | 62.601 | 71.953 | 27.837 | 20.00 |
| 133 | GLN | 2HG | 62.187 | 70.379 | 27.126 | 20.00 |
| 134 | GLN | 1HE2 | 63.670 | 70.582 | 30.873 | 20.00 |
| 135 | GLN | 2HE2 | 62.955 | 72.054 | 30.303 | 20.00 |
| 136 | ILE | N | 59.048 | 69.416 | 26.317 | 30.75 |
| 137 | ILE | CA | 58.941 | 68.342 | 25.297 | 29.79 |
| 138 | ILE | C | 57.992 | 68.730 | 24.090 | 29.61 |
| 139 | ILE | O | 58.254 | 68.655 | 22.886 | 28.92 |
| 140 | ILE | CB | 58.520 | 66.966 | 25.824 | 28.01 |
| 141 | ILE | CG1 | 59.648 | 66.484 | 26.709 | 26.65 |
| 142 | ILE | CG2 | 58.389 | 65.988 | 24.623 | 24.67 |
| 143 | ILE | CD1 | 59.272 | 65.414 | 27.633 | 30.61 |
| 144 | ILE | H | 58.661 | 69.264 | 27.231 | 20.00 |
| 145 | ILE | HA | 59.984 | 68.125 | 25.132 | 20.00 |
| 146 | ILE | HB | 57.585 | 67.027 | 26.380 | 20.00 |
| 147 | ILE | 1HG1 | 60.041 | 67.301 | 27.314 | 20.00 |
| 148 | ILE | 2HG1 | 60.483 | 66.163 | 26.083 | 20.00 |
| 149 | ILE | 1HG2 | 59.307 | 65.970 | 24.039 | 20.00 |
| 150 | ILE | 2HG2 | 57.582 | 66.246 | 23.946 | 20.00 |
| 151 | ILE | 3HG2 | 58.243 | 64.972 | 24.970 | 20.00 |
| 152 | ILE | 1HD1 | 58.868 | 64.551 | 27.108 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 153 | ILE | 2HD1 | 58.551 | 65.761 | 28.375 | 20.00 |
| 154 | ILE | 3HD1 | 60.223 | 65.162 | 28.094 | 20.00 |
| 155 | ASP | N | 56.856 | 69.222 | 24.608 | 30.56 |
| 156 | ASP | CA | 55.774 | 69.774 | 23.845 | 34.30 |
| 157 | ASP | C | 56.317 | 70.948 | 23.013 | 36.61 |
| 158 | ASP | O | 56.305 | 70.858 | 21.794 | 37.72 |
| 159 | ASP | CB | 54.623 | 70.039 | 24.829 | 34.23 |
| 160 | ASP | CG | 53.266 | 69.515 | 24.380 | 34.09 |
| 161 | ASP | OD1 | 53.161 | 68.398 | 23.871 | 34.45 |
| 162 | ASP | OD2 | 52.282 | 70.192 | 24.584 | 35.24 |
| 163 | ASP | H | 56.711 | 69.214 | 25.597 | 20.00 |
| 164 | ASP | HA | 55.509 | 68.998 | 23.135 | 20.00 |
| 165 | ASP | 1HB | 54.530 | 71.096 | 25.058 | 20.00 |
| 166 | ASP | 2HB | 54.782 | 69.545 | 25.769 | 20.00 |
| 167 | LYS | N | 56.891 | 71.996 | 23.669 | 38.57 |
| 168 | LYS | CA | 57.394 | 73.143 | 22.870 | 40.78 |
| 169 | LYS | C | 58.187 | 72.746 | 21.598 | 40.89 |
| 170 | LYS | O | 57.821 | 73.058 | 20.475 | 41.19 |
| 171 | LYS | CB | 58.195 | 74.152 | 23.704 | 44.73 |
| 172 | LYS | CG | 59.737 | 74.010 | 23.716 | 49.46 |
| 173 | LYS | CD | 60.389 | 74.662 | 24.948 | 52.61 |
| 174 | LYS | CE | 61.863 | 74.244 | 25.156 | 51.86 |
| 175 | LYS | NZ | 62.098 | 72.811 | 24.890 | 49.92 |
| 176 | LYS | H | 56.748 | 71.985 | 24.653 | 20.00 |
| 177 | LYS | HA | 56.492 | 73.642 | 22.511 | 20.00 |
| 178 | LYS | 1HB | 57.810 | 74.129 | 24.724 | 20.00 |
| 179 | LYS | 2HB | 57.962 | 75.153 | 23.339 | 20.00 |
| 180 | LYS | 1HG | 60.175 | 74.398 | 22.793 | 20.00 |
| 181 | LYS | 2HG | 59.978 | 72.965 | 23.809 | 20.00 |
| 182 | LYS | 1HD | 59.811 | 74.375 | 25.827 | 20.00 |
| 183 | LYS | 2HD | 60.301 | 75.749 | 24.895 | 20.00 |
| 184 | LYS | 1HE | 62.176 | 74.480 | 26.182 | 20.00 |
| 185 | LYS | 2HE | 62.505 | 74.843 | 24.502 | 20.00 |
| 186 | LYS | 1HZ | 61.912 | 72.594 | 23.887 | 20.00 |
| 187 | LYS | 2HZ | 61.421 | 72.194 | 25.397 | 20.00 |
| 188 | LYS | 3HZ | 63.067 | 72.497 | 25.108 | 20.00 |
| 189 | SER | N | 59.282 | 72.003 | 21.844 | 39.93 |
| 190 | SER | CA | 60.160 | 71.674 | 20.742 | 41.11 |
| 191 | SER | C | 59.713 | 70.466 | 19.823 | 41.60 |
| 192 | SER | O | 60.502 | 69.985 | 19.006 | 44.13 |
| 193 | SER | CB | 61.342 | 71.196 | 21.527 | 41.13 |
| 194 | SER | OG | 60.972 | 70.326 | 22.646 | 43.06 |
| 195 | SER | H | 59.394 | 71.615 | 22.757 | 20.00 |
| 196 | SER | HA | 60.414 | 72.549 | 20.149 | 20.00 |
| 197 | SER | 1HB | 61.840 | 72.111 | 21.923 | 20.00 |
| 198 | SER | 2HB | 62.201 | 70.871 | 20.872 | 20.00 |
| 199 | SER | HG | 60.144 | 69.739 | 22.668 | 20.00 |
| 200 | GLY | N | 58.471 | 69.970 | 20.020 | 39.95 |
| 201 | GLY | CA | 58.004 | 68.791 | 19.312 | 36.83 |
| 202 | GLY | C | 58.868 | 67.488 | 19.463 | 35.39 |
| 203 | GLY | O | 59.151 | 66.807 | 18.529 | 37.15 |
| 204 | GLY | H | 57.818 | 70.556 | 20.489 | 20.00 |
| 205 | GLY | 1HA | 57.969 | 69.018 | 18.241 | 20.00 |
| 206 | GLY | 2HA | 57.004 | 68.542 | 19.656 | 20.00 |
| 207 | SER | N | 59.300 | 67.067 | 20.659 | 32.66 |
| 208 | SER | CA | 60.096 | 65.891 | 20.842 | 31.67 |
| 209 | SER | C | 59.562 | 64.556 | 21.564 | 29.26 |
| 210 | SER | O | 60.362 | 63.696 | 21.864 | 28.04 |
| 211 | SER | CB | 61.523 | 66.205 | 21.262 | 32.05 |
| 212 | SER | OG | 61.785 | 67.365 | 22.072 | 36.33 |
| 213 | SER | H | 58.976 | 67.617 | 21.428 | 20.00 |
| 214 | SER | HA | 60.276 | 65.532 | 19.858 | 20.00 |
| 215 | SER | 1HB | 62.162 | 66.169 | 20.334 | 20.00 |
| 216 | SER | 2HB | 61.990 | 65.313 | 21.767 | 20.00 |
| 217 | SER | HG | 61.143 | 68.124 | 22.244 | 20.00 |
| 218 | TRP | N | 58.263 | 64.341 | 21.705 | 26.65 |
| 219 | TRP | CA | 57.678 | 63.094 | 22.236 | 21.95 |
| 220 | TRP | C | 58.092 | 61.836 | 21.456 | 21.43 |
| 221 | TRP | O | 58.398 | 60.796 | 21.999 | 21.86 |
| 222 | TRP | CB | 56.162 | 63.309 | 22.226 | 22.70 |
| 223 | TRP | CG | 55.712 | 64.329 | 23.250 | 20.91 |
| 224 | TRP | CD1 | 55.145 | 65.601 | 23.071 | 21.20 |
| 225 | TRP | CD2 | 55.791 | 64.152 | 24.658 | 21.02 |
| 226 | TRP | NE1 | 54.895 | 66.197 | 24.287 | 21.97 |
| 227 | TRP | CE2 | 55.270 | 65.323 | 25.295 | 20.57 |
| 228 | TRP | CE3 | 56.277 | 63.109 | 25.402 | 18.68 |
| 229 | TRP | CZ2 | 55.184 | 65.387 | 26.676 | 20.86 |
| 230 | TRP | CZ3 | 56.215 | 63.188 | 26.788 | 16.67 |
| 231 | TRP | CH2 | 55.658 | 64.311 | 27.429 | 19.85 |
| 232 | TRP | H | 57.686 | 65.143 | 21.597 | 20.00 |
| 233 | TRP | HA | 58.058 | 62.950 | 23.247 | 20.00 |
| 234 | TRP | 1HB | 55.644 | 62.373 | 22.446 | 20.00 |
| 235 | TRP | 2HB | 55.835 | 63.613 | 21.232 | 20.00 |
| 236 | TRP | HD1 | 54.914 | 66.062 | 22.121 | 20.00 |
| 237 | TRP | HE1 | 54.495 | 67.092 | 24.417 | 20.00 |
| 238 | TRP | HE3 | 56.679 | 62.229 | 24.906 | 20.00 |
| 239 | TRP | HZ2 | 54.819 | 66.296 | 27.119 | 20.00 |
| 240 | TRP | HZ3 | 56.622 | 62.372 | 27.369 | 20.00 |
| 241 | TRP | HH2 | 55.652 | 64.334 | 28.506 | 20.00 |
| 242 | ALA | N | 58.142 | 61.898 | 20.137 | 21.75 |
| 243 | ALA | CA | 58.747 | 60.754 | 19.397 | 21.29 |
| 244 | ALA | C | 60.219 | 60.530 | 19.762 | 19.48 |
| 245 | ALA | O | 60.614 | 59.444 | 20.080 | 17.73 |
| 246 | ALA | CB | 58.536 | 60.943 | 17.876 | 21.57 |
| 247 | ALA | H | 57.792 | 62.693 | 19.657 | 20.00 |
| 248 | ALA | HA | 58.226 | 59.852 | 19.697 | 20.00 |
| 249 | ALA | 1HB | 59.132 | 61.760 | 17.471 | 20.00 |
| 250 | ALA | 2HB | 57.493 | 61.183 | 17.683 | 20.00 |
| 251 | ALA | 3HB | 58.789 | 60.035 | 17.340 | 20.00 |
| 252 | ALA | N | 61.000 | 61.573 | 19.777 | 21.34 |
| 253 | ALA | CA | 62.397 | 61.371 | 20.129 | 20.36 |
| 254 | ALA | C | 62.640 | 60.772 | 21.579 | 20.18 |
| 255 | ALA | O | 63.307 | 59.773 | 21.765 | 23.47 |
| 256 | ALA | CB | 62.920 | 62.788 | 20.000 | 21.69 |
| 257 | ALA | H | 60.646 | 62.340 | 19.255 | 20.00 |
| 258 | ALA | HA | 62.858 | 60.692 | 19.413 | 20.00 |
| 259 | ALA | 1HB | 62.433 | 63.449 | 20.701 | 20.00 |
| 260 | ALA | 2HB | 62.763 | 63.151 | 18.988 | 20.00 |
| 261 | ALA | 3HB | 63.990 | 62.798 | 20.177 | 20.00 |
| 262 | ILE | N | 61.932 | 61.425 | 22.576 | 20.36 |
| 263 | ILE | CA | 61.790 | 60.947 | 23.989 | 20.21 |
| 264 | ILE | C | 61.398 | 59.404 | 24.061 | 19.21 |
| 265 | ILE | O | 62.077 | 58.599 | 24.654 | 20.20 |
| 266 | ILE | CB | 60.737 | 61.851 | 24.792 | 21.58 |
| 267 | ILE | CG1 | 60.968 | 63.384 | 24.927 | 25.33 |
| 268 | ILE | CG2 | 60.518 | 61.317 | 26.196 | 23.50 |
| 269 | ILE | CD1 | 62.410 | 63.607 | 25.264 | 26.28 |
| 270 | ILE | H | 61.488 | 62.254 | 22.255 | 20.00 |
| 271 | ILE | HA | 62.789 | 61.058 | 24.405 | 20.00 |
| 272 | ILE | HB | 59.791 | 61.736 | 24.267 | 20.00 |
| 273 | ILE | 1HG1 | 60.325 | 63.814 | 25.692 | 20.00 |
| 274 | ILE | 2HG1 | 60.743 | 63.949 | 24.032 | 20.00 |
| 275 | ILE | 1HG2 | 61.434 | 61.342 | 26.788 | 20.00 |
| 276 | ILE | 2HG2 | 60.157 | 60.290 | 26.217 | 20.00 |
| 277 | ILE | 3HG2 | 59.791 | 61.912 | 26.743 | 20.00 |
| 278 | ILE | 1HD1 | 63.073 | 63.217 | 24.492 | 20.00 |
| 279 | ILE | 2HD1 | 62.691 | 63.122 | 26.198 | 20.00 |
| 280 | ILE | 3HD1 | 62.627 | 64.673 | 25.357 | 20.00 |
| 281 | TYR | N | 60.231 | 59.064 | 23.403 | 18.90 |
| 282 | TYR | CA | 59.663 | 57.728 | 23.212 | 16.59 |
| 283 | TYR | C | 60.620 | 56.761 | 22.628 | 19.69 |
| 284 | TYR | O | 60.722 | 55.641 | 23.044 | 21.05 |
| 285 | TYR | CB | 58.346 | 57.810 | 22.413 | 15.48 |
| 286 | TYR | CG | 57.722 | 56.420 | 22.275 | 15.58 |
| 287 | TYR | CD1 | 57.298 | 55.713 | 23.438 | 15.71 |
| 288 | TYR | CD2 | 57.586 | 55.775 | 21.044 | 17.07 |
| 289 | TYR | CE1 | 56.771 | 54.396 | 23.415 | 15.33 |
| 290 | TYR | CE2 | 57.097 | 54.458 | 20.983 | 18.24 |
| 291 | TYR | CZ | 56.694 | 53.755 | 22.144 | 17.83 |
| 292 | TYR | OH | 56.243 | 52.455 | 21.973 | 16.43 |
| 293 | TYR | H | 59.824 | 59.847 | 22.928 | 20.00 |
| 294 | TYR | HA | 59.466 | 57.370 | 24.214 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 295 | TYR | 1HB | 58.526 | 58.248 | 21.425 | 20.00 |
| 296 | TYR | 2HB | 57.651 | 58.450 | 22.951 | 20.00 |
| 297 | TYR | HD1 | 57.367 | 56.218 | 24.392 | 20.00 |
| 298 | TYR | HD2 | 57.892 | 56.285 | 20.136 | 20.00 |
| 299 | TYR | HE1 | 56.386 | 54.090 | 24.384 | 20.00 |
| 300 | TYR | HE2 | 56.999 | 53.996 | 20.016 | 20.00 |
| 301 | TYR | HH | 56.824 | 51.863 | 22.447 | 20.00 |
| 302 | GLN | N | 61.366 | 57.183 | 21.632 | 20.71 |
| 303 | GLN | CA | 62.379 | 56.353 | 21.092 | 23.54 |
| 304 | GLN | C | 63.491 | 56.092 | 22.091 | 21.33 |
| 305 | GLN | O | 63.866 | 54.931 | 22.226 | 22.52 |
| 306 | GLN | CB | 62.737 | 56.837 | 19.717 | 29.74 |
| 307 | GLN | CG | 61.480 | 56.551 | 18.818 | 43.77 |
| 308 | GLN | CD | 61.124 | 57.664 | 17.789 | 50.76 |
| 309 | GLN | OE1 | 61.317 | 58.863 | 17.906 | 53.37 |
| 310 | GLN | NE2 | 60.647 | 57.254 | 16.639 | 51.41 |
| 311 | GLN | H | 61.282 | 58.134 | 21.330 | 20.00 |
| 312 | GLN | HA | 61.918 | 55.375 | 20.947 | 20.00 |
| 313 | GLN | 1HB | 63.576 | 56.262 | 19.335 | 20.00 |
| 314 | GLN | 2HB | 63.034 | 57.885 | 19.731 | 20.00 |
| 315 | GLN | 1HG | 60.567 | 56.384 | 19.385 | 20.00 |
| 316 | GLN | 2HG | 61.648 | 55.643 | 18.247 | 20.00 |
| 317 | GLN | 1HE2 | 60.739 | 58.175 | 16.252 | 20.00 |
| 318 | GLN | 2HE2 | 60.319 | 56.444 | 16.170 | 20.00 |
| 319 | ASP | N | 63.890 | 57.146 | 22.820 | 22.69 |
| 320 | ASP | CA | 64.915 | 56.979 | 23.869 | 23.75 |
| 321 | ASP | C | 64.453 | 55.995 | 24.956 | 21.78 |
| 322 | ASP | O | 65.227 | 55.192 | 25.428 | 21.26 |
| 323 | ASP | CB | 65.301 | 58.315 | 24.526 | 26.73 |
| 324 | ASP | CG | 65.718 | 59.428 | 23.564 | 31.02 |
| 325 | ASP | OD1 | 66.369 | 59.105 | 22.550 | 31.00 |
| 326 | ASP | OD2 | 65.408 | 60.604 | 23.837 | 32.48 |
| 327 | ASP | H | 63.674 | 58.089 | 22.539 | 20.00 |
| 328 | ASP | HA | 65.794 | 56.545 | 23.392 | 20.00 |
| 329 | ASP | 1HB | 66.116 | 58.169 | 25.233 | 20.00 |
| 330 | ASP | 2HB | 64.466 | 58.694 | 25.112 | 20.00 |
| 331 | ILE | N | 63.136 | 56.005 | 25.269 | 20.63 |
| 332 | ILE | CA | 62.626 | 54.892 | 26.106 | 19.38 |
| 333 | ILE | C | 62.664 | 53.512 | 25.346 | 19.66 |
| 334 | ILE | O | 63.081 | 52.492 | 25.913 | 18.07 |
| 335 | ILE | CB | 61.192 | 55.230 | 26.711 | 19.75 |
| 336 | ILE | CG1 | 61.197 | 56.210 | 27.894 | 19.61 |
| 337 | ILE | CG2 | 60.570 | 54.008 | 27.384 | 16.65 |
| 338 | ILE | CD1 | 59.917 | 57.001 | 28.052 | 21.44 |
| 339 | ILE | H | 62.684 | 56.835 | 24.927 | 20.00 |
| 340 | ILE | HA | 63.327 | 54.768 | 26.932 | 20.00 |
| 341 | ILE | HB | 60.568 | 55.595 | 25.907 | 20.00 |
| 342 | ILE | 1HG1 | 61.987 | 56.937 | 27.696 | 20.00 |
| 343 | ILE | 2HG1 | 61.490 | 55.748 | 28.838 | 20.00 |
| 344 | ILE | 1HG2 | 61.179 | 53.628 | 28.194 | 20.00 |
| 345 | ILE | 2HG2 | 60.422 | 53.213 | 26.655 | 20.00 |
| 346 | ILE | 3HG2 | 59.582 | 54.249 | 27.768 | 20.00 |
| 347 | ILE | 1HD1 | 59.114 | 56.434 | 28.480 | 20.00 |
| 348 | ILE | 2HD1 | 59.594 | 57.364 | 27.080 | 20.00 |
| 349 | ILE | 3HD1 | 60.051 | 57.880 | 28.668 | 20.00 |
| 350 | ARG | N | 62.162 | 53.475 | 24.066 | 19.64 |
| 351 | ARG | CA | 62.288 | 52.251 | 23.267 | 22.20 |
| 352 | ARG | C | 63.742 | 51.742 | 23.370 | 22.74 |
| 353 | ARG | O | 63.964 | 50.589 | 23.705 | 20.20 |
| 354 | ARG | CB | 61.788 | 52.370 | 21.795 | 23.80 |
| 355 | ARG | CG | 60.263 | 52.326 | 21.416 | 29.28 |
| 356 | ARG | CD | 59.846 | 51.771 | 19.966 | 38.17 |
| 357 | ARG | NE | 58.356 | 51.345 | 19.989 | 47.71 |
| 358 | ARG | CZ | 57.194 | 51.166 | 19.228 | 46.22 |
| 359 | ARG | NH1 | 57.118 | 51.134 | 17.914 | 51.10 |
| 360 | ARG | NH2 | 56.016 | 50.979 | 19.791 | 39.82 |
| 361 | ARG | H | 61.917 | 54.354 | 23.659 | 20.00 |
| 362 | ARG | HA | 61.656 | 51.528 | 23.768 | 20.00 |
| 363 | ARG | 1HB | 62.257 | 51.547 | 21.248 | 20.00 |
| 364 | ARG | 2HB | 62.258 | 53.237 | 21.335 | 20.00 |
| 365 | ARG | 1HG | 59.801 | 53.297 | 21.613 | 20.00 |
| 366 | ARG | 2HG | 59.896 | 51.626 | 22.154 | 20.00 |
| 367 | ARG | 1HD | 60.387 | 50.786 | 19.796 | 20.00 |
| 368 | ARG | 2HD | 60.080 | 52.412 | 19.161 | 20.00 |
| 369 | ARG | HE | 58.008 | 51.167 | 20.902 | 20.00 |
| 370 | ARG | 1HH1 | 56.227 | 51.223 | 17.478 | 20.00 |
| 371 | ARG | 2HH1 | 57.905 | 50.928 | 17.355 | 20.00 |
| 372 | ARG | 1HH2 | 55.262 | 50.537 | 19.303 | 20.00 |
| 373 | ARG | 2HH2 | 55.845 | 51.282 | 20.734 | 20.00 |
| 374 | HIS | N | 64.746 | 52.610 | 23.202 | 20.00 |
| 375 | HIS | CA | 66.074 | 51.898 | 23.241 | 20.00 |
| 376 | HIS | C | 66.658 | 51.767 | 24.678 | 20.00 |
| 377 | HIS | O | 67.428 | 50.861 | 24.973 | 20.00 |
| 378 | HIS | CB | 67.188 | 52.616 | 22.410 | 20.00 |
| 379 | HIS | CG | 66.701 | 53.751 | 21.532 | 20.00 |
| 380 | HIS | ND1 | 66.063 | 53.572 | 20.339 | 20.00 |
| 381 | HIS | CD2 | 66.954 | 55.115 | 21.693 | 20.00 |
| 382 | HIS | CE1 | 65.963 | 54.797 | 19.797 | 20.00 |
| 383 | HIS | NE2 | 66.488 | 55.736 | 20.591 | 20.00 |
| 384 | HIS | H | 64.728 | 53.577 | 22.922 | 20.00 |
| 385 | HIS | HA | 65.925 | 50.904 | 22.851 | 20.00 |
| 386 | HIS | 1HB | 67.950 | 53.016 | 23.105 | 20.00 |
| 387 | HIS | 2HB | 67.710 | 51.887 | 21.787 | 20.00 |
| 388 | HIS | HD1 | 65.792 | 52.727 | 19.934 | 20.00 |
| 389 | HIS | HD2 | 67.557 | 55.565 | 22.468 | 20.00 |
| 390 | HIS | HE1 | 65.731 | 54.961 | 18.764 | 20.00 |
| 391 | GLU | N | 66.332 | 52.581 | 25.699 | 24.60 |
| 392 | GLU | CA | 66.817 | 52.241 | 27.039 | 23.35 |
| 393 | GLU | C | 66.236 | 50.854 | 27.523 | 20.84 |
| 394 | GLU | O | 66.743 | 50.234 | 28.462 | 20.77 |
| 395 | GLU | CB | 66.563 | 53.445 | 27.980 | 25.78 |
| 396 | GLU | CG | 67.579 | 54.531 | 27.671 | 34.71 |
| 397 | GLU | CD | 67.550 | 55.857 | 28.464 | 41.97 |
| 398 | GLU | OE1 | 67.473 | 55.873 | 29.688 | 47.08 |
| 399 | GLU | OE2 | 67.723 | 56.887 | 27.831 | 42.03 |
| 400 | GLU | H | 65.826 | 53.435 | 25.569 | 20.00 |
| 401 | GLU | HA | 67.896 | 52.124 | 26.937 | 20.00 |
| 402 | GLU | 1HB | 66.656 | 53.140 | 29.019 | 20.00 |
| 403 | GLU | 2HB | 65.552 | 53.848 | 27.866 | 20.00 |
| 404 | GLU | 1HG | 67.556 | 54.790 | 26.615 | 20.00 |
| 405 | GLU | 2HG | 68.561 | 54.116 | 27.863 | 20.00 |
| 406 | ALA | N | 65.138 | 50.381 | 26.878 | 20.22 |
| 407 | ALA | CA | 64.425 | 49.305 | 27.596 | 18.85 |
| 408 | ALA | C | 65.171 | 47.952 | 27.675 | 19.60 |
| 409 | ALA | O | 66.080 | 47.612 | 26.913 | 21.31 |
| 410 | ALA | CB | 62.979 | 49.307 | 27.198 | 17.65 |
| 411 | ALA | H | 64.736 | 50.905 | 26.129 | 20.00 |
| 412 | ALA | HA | 64.411 | 49.635 | 28.630 | 20.00 |
| 413 | ALA | 1HB | 62.886 | 49.086 | 26.128 | 20.00 |
| 414 | ALA | 2HB | 62.566 | 50.300 | 27.380 | 20.00 |
| 415 | ALA | 3HB | 62.406 | 48.566 | 27.755 | 20.00 |
| 416 | SER | N | 64.735 | 47.217 | 28.738 | 17.44 |
| 417 | SER | CA | 65.303 | 45.958 | 29.138 | 17.65 |
| 418 | SER | C | 65.080 | 44.926 | 28.069 | 20.44 |
| 419 | SER | O | 64.118 | 44.975 | 27.295 | 20.82 |
| 420 | SER | CB | 64.662 | 45.552 | 30.486 | 16.87 |
| 421 | SER | OG | 64.525 | 46.634 | 31.510 | 17.03 |
| 422 | SER | H | 63.945 | 47.581 | 29.221 | 20.00 |
| 423 | SER | HA | 66.386 | 46.074 | 29.221 | 20.00 |
| 424 | SER | 1HB | 65.308 | 44.740 | 30.885 | 20.00 |
| 425 | SER | 2HB | 63.712 | 44.975 | 30.299 | 20.00 |
| 426 | SER | HG | 64.529 | 47.621 | 31.322 | 20.00 |
| 427 | ASP | N | 65.958 | 43.934 | 28.082 | 23.65 |
| 428 | ASP | CA | 65.585 | 42.963 | 27.136 | 25.32 |
| 429 | ASP | C | 66.051 | 41.684 | 27.689 | 24.00 |
| 430 | ASP | O | 67.238 | 41.557 | 27.964 | 25.47 |
| 431 | ASP | CB | 66.321 | 43.342 | 25.827 | 30.03 |
| 432 | ASP | CG | 66.013 | 42.208 | 24.837 | 35.94 |
| 433 | ASP | OD1 | 64.835 | 41.789 | 24.742 | 37.82 |
| 434 | ASP | OD2 | 66.971 | 41.731 | 24.221 | 40.50 |
| 435 | ASP | H | 66.864 | 43.946 | 28.494 | 20.00 |
| 436 | ASP | HA | 64.508 | 42.853 | 26.973 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 437 | ASP | 1HB | 67.406 | 43.380 | 25.994 | 20.00 |
| 438 | ASP | 2HB | 66.013 | 44.285 | 25.384 | 20.00 |
| 439 | PHE | N | 65.113 | 40.763 | 27.872 | 20.26 |
| 440 | PHE | CA | 65.402 | 39.506 | 28.474 | 17.74 |
| 441 | PHE | C | 64.786 | 38.500 | 27.583 | 19.63 |
| 442 | PHE | O | 63.886 | 38.850 | 26.811 | 18.88 |
| 443 | PHE | CB | 64.780 | 39.359 | 29.899 | 15.74 |
| 444 | PHE | CG | 65.255 | 40.400 | 30.868 | 14.99 |
| 445 | PHE | CD1 | 66.433 | 40.210 | 31.547 | 14.29 |
| 446 | PHE | CD2 | 64.503 | 41.531 | 31.095 | 11.07 |
| 447 | PHE | CE1 | 66.871 | 41.163 | 32.441 | 13.28 |
| 448 | PHE | CE2 | 64.910 | 42.478 | 32.012 | 12.04 |
| 449 | PHE | CZ | 66.114 | 42.290 | 32.698 | 14.86 |
| 450 | PHE | H | 64.258 | 40.990 | 27.405 | 20.00 |
| 451 | PHE | HA | 66.483 | 39.375 | 28.481 | 20.00 |
| 452 | PHE | 1HB | 64.945 | 38.372 | 30.333 | 20.00 |
| 453 | PHE | 2HB | 63.697 | 39.445 | 29.816 | 20.00 |
| 454 | PHE | HD1 | 67.024 | 39.314 | 31.395 | 20.00 |
| 455 | PHE | HD2 | 63.562 | 41.653 | 30.585 | 20.00 |
| 456 | PHE | HE1 | 67.800 | 41.004 | 32.982 | 20.00 |
| 457 | PHE | HE2 | 64.290 | 43.328 | 32.250 | 20.00 |
| 458 | PHE | HZ | 66.455 | 43.015 | 33.431 | 20.00 |
| 459 | PRO | N | 65.253 | 37.196 | 27.759 | 19.03 |
| 460 | PRO | CA | 64.636 | 36.040 | 27.082 | 17.74 |
| 461 | PRO | C | 63.151 | 35.749 | 27.411 | 17.59 |
| 462 | PRO | O | 62.694 | 35.796 | 28.535 | 18.11 |
| 463 | PRO | CB | 65.582 | 34.833 | 27.412 | 17.29 |
| 464 | PRO | CG | 66.564 | 35.298 | 28.571 | 17.67 |
| 465 | PRO | CD | 66.467 | 36.813 | 28.562 | 17.97 |
| 466 | PRO | HA | 64.674 | 36.227 | 26.012 | 20.00 |
| 467 | PRO | 1HB | 66.190 | 34.622 | 26.529 | 20.00 |
| 468 | PRO | 2HB | 65.034 | 33.928 | 27.683 | 20.00 |
| 469 | PRO | 1HG | 66.200 | 34.943 | 29.539 | 20.00 |
| 470 | PRO | 2HG | 67.592 | 34.936 | 28.459 | 20.00 |
| 471 | PRO | 1HD | 67.323 | 37.192 | 28.014 | 20.00 |
| 472 | PRO | 2HD | 66.501 | 37.258 | 29.556 | 20.00 |
| 473 | CYS | N | 62.429 | 35.432 | 26.359 | 16.91 |
| 474 | CYS | CA | 61.116 | 34.821 | 26.476 | 16.83 |
| 475 | CYS | C | 61.155 | 33.441 | 25.799 | 17.10 |
| 476 | CYS | O | 60.446 | 33.139 | 24.838 | 15.98 |
| 477 | CYS | CB | 60.141 | 35.734 | 25.788 | 17.42 |
| 478 | CYS | SG | 60.311 | 37.521 | 26.025 | 21.76 |
| 479 | CYS | H | 62.845 | 35.661 | 25.483 | 20.00 |
| 480 | CYS | HA | 60.833 | 34.706 | 27.525 | 20.00 |
| 481 | CYS | 1HB | 59.112 | 35.435 | 26.009 | 20.00 |
| 482 | CYS | 2HB | 60.247 | 35.600 | 24.709 | 20.00 |
| 483 | CYS | HG | 61.234 | 38.020 | 25.205 | 20.00 |
| 484 | ARG | N | 62.055 | 32.618 | 26.311 | 17.15 |
| 485 | ARG | CA | 62.240 | 31.246 | 25.729 | 19.32 |
| 486 | ARG | C | 61.030 | 30.297 | 25.783 | 19.49 |
| 487 | ARG | O | 60.747 | 29.643 | 24.808 | 19.32 |
| 488 | ARG | CB | 63.463 | 30.474 | 26.274 | 24.18 |
| 489 | ARG | CG | 64.803 | 30.648 | 25.474 | 34.75 |
| 490 | ARG | CD | 66.027 | 31.366 | 26.099 | 42.80 |
| 491 | ARG | NE | 65.822 | 31.308 | 27.538 | 51.13 |
| 492 | ARG | CZ | 66.692 | 31.456 | 28.527 | 51.47 |
| 493 | ARG | NH1 | 67.986 | 31.573 | 28.252 | 48.86 |
| 494 | ARG | NH2 | 66.143 | 31.494 | 29.730 | 48.27 |
| 495 | ARG | H | 62.418 | 32.881 | 27.211 | 20.00 |
| 496 | ARG | HA | 62.407 | 31.422 | 24.671 | 20.00 |
| 497 | ARG | 1HB | 63.253 | 29.408 | 26.156 | 20.00 |
| 498 | ARG | 2HB | 63.505 | 30.537 | 27.360 | 20.00 |
| 499 | ARG | 1HG | 64.620 | 31.011 | 24.461 | 20.00 |
| 500 | ARG | 2HG | 65.175 | 29.633 | 25.308 | 20.00 |
| 501 | ARG | 1HD | 66.058 | 32.421 | 25.820 | 20.00 |
| 502 | ARG | 2HD | 66.979 | 30.904 | 25.819 | 20.00 |
| 503 | ARG | HE | 64.881 | 31.300 | 27.880 | 20.00 |
| 504 | ARG | 1HH1 | 68.672 | 31.709 | 28.970 | 20.00 |
| 505 | ARG | 2HH1 | 68.274 | 31.511 | 27.301 | 20.00 |
| 506 | ARG | 1HH2 | 66.703 | 31.481 | 30.549 | 20.00 |
| 507 | ARG | 2HH2 | 65.138 | 31.551 | 29.794 | 20.00 |
| 508 | VAL | N | 60.319 | 30.155 | 26.945 | 17.97 |
| 509 | VAL | CA | 59.174 | 29.238 | 26.975 | 16.80 |
| 510 | VAL | C | 58.113 | 29.793 | 26.009 | 15.05 |
| 511 | VAL | O | 57.497 | 29.009 | 25.329 | 15.45 |
| 512 | VAL | CB | 58.828 | 28.750 | 28.462 | 18.01 |
| 513 | VAL | CG1 | 57.372 | 28.681 | 28.911 | 15.99 |
| 514 | VAL | CG2 | 59.711 | 29.222 | 29.601 | 17.07 |
| 515 | VAL | H | 60.614 | 30.724 | 27.716 | 20.00 |
| 516 | VAL | HA | 59.553 | 28.350 | 26.498 | 20.00 |
| 517 | VAL | HB | 59.085 | 27.690 | 28.412 | 20.00 |
| 518 | VAL | 1HG1 | 56.744 | 28.248 | 28.134 | 20.00 |
| 519 | VAL | 2HG1 | 56.988 | 29.671 | 29.154 | 20.00 |
| 520 | VAL | 3HG1 | 57.249 | 28.037 | 29.790 | 20.00 |
| 521 | VAL | 1HG2 | 59.485 | 30.243 | 29.907 | 20.00 |
| 522 | VAL | 2HG2 | 60.768 | 29.174 | 29.338 | 20.00 |
| 523 | VAL | 3HG2 | 59.588 | 28.576 | 30.471 | 20.00 |
| 524 | ALA | N | 57.929 | 31.159 | 25.879 | 14.53 |
| 525 | ALA | CA | 56.893 | 31.736 | 24.965 | 14.43 |
| 526 | ALA | C | 57.034 | 31.215 | 23.579 | 15.46 |
| 527 | ALA | O | 56.026 | 30.897 | 22.995 | 16.10 |
| 528 | ALA | CB | 56.950 | 33.283 | 24.793 | 12.61 |
| 529 | ALA | H | 58.489 | 31.728 | 26.477 | 20.00 |
| 530 | ALA | HA | 55.936 | 31.377 | 25.317 | 20.00 |
| 531 | ALA | 1HB | 57.978 | 33.586 | 24.605 | 20.00 |
| 532 | ALA | 2HB | 56.694 | 33.786 | 25.717 | 20.00 |
| 533 | ALA | 3HB | 56.439 | 33.685 | 23.923 | 20.00 |
| 534 | LYS | N | 58.297 | 31.191 | 23.122 | 17.52 |
| 535 | LYS | CA | 58.835 | 30.716 | 21.906 | 17.70 |
| 536 | LYS | C | 58.993 | 29.228 | 21.723 | 19.60 |
| 537 | LYS | O | 59.486 | 28.823 | 20.702 | 22.60 |
| 538 | LYS | CB | 60.168 | 31.413 | 21.780 | 19.24 |
| 539 | LYS | CG | 60.083 | 32.927 | 21.737 | 19.97 |
| 540 | LYS | CD | 59.064 | 33.361 | 20.674 | 21.69 |
| 541 | LYS | CE | 59.193 | 34.787 | 20.078 | 24.74 |
| 542 | LYS | NZ | 58.108 | 35.143 | 19.082 | 26.46 |
| 543 | LYS | H | 58.962 | 31.547 | 23.782 | 20.00 |
| 544 | LYS | HA | 58.145 | 31.021 | 21.117 | 20.00 |
| 545 | LYS | 1HB | 60.687 | 31.055 | 20.890 | 20.00 |
| 546 | LYS | 2HB | 60.838 | 31.130 | 22.595 | 20.00 |
| 547 | LYS | 1HG | 61.064 | 33.367 | 21.526 | 20.00 |
| 548 | LYS | 2HG | 59.740 | 33.340 | 22.686 | 20.00 |
| 549 | LYS | 1HD | 58.049 | 33.228 | 21.050 | 20.00 |
| 550 | LYS | 2HD | 59.142 | 32.677 | 19.824 | 20.00 |
| 551 | LYS | 1HE | 60.168 | 34.871 | 19.582 | 20.00 |
| 552 | LYS | 2HE | 59.209 | 35.527 | 20.883 | 20.00 |
| 553 | LYS | 1HZ | 57.167 | 35.181 | 19.539 | 20.00 |
| 554 | LYS | 2HZ | 58.096 | 34.490 | 18.275 | 20.00 |
| 555 | LYS | 3HZ | 58.222 | 36.119 | 18.723 | 20.00 |
| 556 | LEU | N | 58.600 | 28.321 | 22.639 | 20.39 |
| 557 | LEU | CA | 58.649 | 26.874 | 22.415 | 19.13 |
| 558 | LEU | C | 57.499 | 26.495 | 21.561 | 21.96 |
| 559 | LEU | O | 56.401 | 27.065 | 21.641 | 20.82 |
| 560 | LEU | CB | 58.382 | 26.108 | 23.763 | 18.89 |
| 561 | LEU | CG | 59.526 | 26.182 | 24.733 | 17.87 |
| 562 | LEU | CD1 | 60.698 | 25.466 | 24.168 | 19.14 |
| 563 | LEU | CD2 | 59.172 | 25.541 | 26.090 | 17.39 |
| 564 | LEU | H | 58.246 | 28.683 | 23.495 | 20.00 |
| 565 | LEU | HA | 59.615 | 26.655 | 21.958 | 20.00 |
| 566 | LEU | 1HB | 58.175 | 25.056 | 23.593 | 20.00 |
| 567 | LEU | 2HB | 57.485 | 26.522 | 24.240 | 20.00 |
| 568 | LEU | HG | 59.806 | 27.235 | 24.855 | 20.00 |
| 569 | LEU | 1HD1 | 61.105 | 25.936 | 23.272 | 20.00 |
| 570 | LEU | 2HD1 | 60.454 | 24.433 | 23.933 | 20.00 |
| 571 | LEU | 3HD1 | 61.510 | 25.440 | 24.897 | 20.00 |
| 572 | LEU | 1HD2 | 58.924 | 24.482 | 25.978 | 20.00 |
| 573 | LEU | 2HD2 | 58.292 | 26.034 | 26.506 | 20.00 |
| 574 | LEU | 3HD2 | 59.988 | 25.638 | 26.811 | 20.00 |
| 575 | PRO | N | 57.678 | 25.487 | 20.700 | 23.61 |
| 576 | PRO | CA | 56.624 | 25.246 | 19.703 | 24.44 |
| 577 | PRO | C | 55.294 | 24.893 | 20.278 | 22.23 |
| 578 | PRO | O | 54.301 | 25.224 | 19.668 | 23.82 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 579 | PRO | CB | 57.127 | 24.113 | 18.808 | 26.16 |
| 580 | PRO | CG | 58.632 | 24.213 | 19.010 | 27.75 |
| 581 | PRO | CD | 58.950 | 24.825 | 20.348 | 26.72 |
| 582 | PRO | HA | 56.514 | 26.154 | 19.103 | 20.00 |
| 583 | PRO | 1HB | 56.822 | 24.188 | 17.756 | 20.00 |
| 584 | PRO | 2HB | 56.800 | 23.128 | 19.167 | 20.00 |
| 585 | PRO | 1HG | 59.145 | 23.261 | 18.859 | 20.00 |
| 586 | PRO | 2HG | 59.017 | 24.887 | 18.240 | 20.00 |
| 587 | PRO | 1HD | 59.763 | 25.549 | 20.239 | 20.00 |
| 588 | PRO | 2HD | 59.256 | 24.094 | 21.089 | 20.00 |
| 589 | LYS | N | 55.275 | 24.280 | 21.486 | 22.30 |
| 590 | LYS | CA | 53.990 | 23.915 | 22.172 | 22.26 |
| 591 | LYS | C | 53.174 | 25.094 | 22.666 | 22.91 |
| 592 | LYS | O | 51.958 | 24.974 | 22.806 | 25.95 |
| 593 | LYS | CB | 54.084 | 22.876 | 23.305 | 23.13 |
| 594 | LYS | CG | 54.925 | 23.304 | 24.549 | 24.19 |
| 595 | LYS | CD | 54.938 | 22.261 | 25.694 | 27.45 |
| 596 | LYS | CE | 55.785 | 22.825 | 26.873 | 31.65 |
| 597 | LYS | NZ | 55.815 | 22.067 | 28.141 | 37.10 |
| 598 | LYS | H | 56.127 | 23.877 | 21.799 | 20.00 |
| 599 | LYS | HA | 53.394 | 23.472 | 21.378 | 20.00 |
| 600 | LYS | 1HB | 54.522 | 21.963 | 22.895 | 20.00 |
| 601 | LYS | 2HB | 53.080 | 22.604 | 23.629 | 20.00 |
| 602 | LYS | 1HG | 54.556 | 24.257 | 24.934 | 20.00 |
| 603 | LYS | 2HG | 55.948 | 23.498 | 24.234 | 20.00 |
| 604 | LYS | 1HD | 55.299 | 21.288 | 25.356 | 20.00 |
| 605 | LYS | 2HD | 53.903 | 22.109 | 26.017 | 20.00 |
| 606 | LYS | 1HE | 55.373 | 23.814 | 27.106 | 20.00 |
| 607 | LYS | 2HE | 56.810 | 23.019 | 26.530 | 20.00 |
| 608 | LYS | 1HZ | 56.128 | 21.082 | 28.050 | 20.00 |
| 609 | LYS | 2HZ | 54.827 | 22.030 | 28.497 | 20.00 |
| 610 | LYS | 3HZ | 56.381 | 22.529 | 28.880 | 20.00 |
| 611 | ASN | N | 53.890 | 26.227 | 22.879 | 20.49 |
| 612 | ASN | CA | 53.214 | 27.434 | 23.253 | 18.95 |
| 613 | ASN | C | 52.746 | 28.350 | 22.087 | 19.83 |
| 614 | ASN | O | 52.113 | 29.392 | 22.300 | 16.61 |
| 615 | ASN | CB | 54.191 | 28.118 | 24.160 | 15.32 |
| 616 | ASN | CG | 54.146 | 27.319 | 25.455 | 18.08 |
| 617 | ASN | OD1 | 53.155 | 26.658 | 25.743 | 16.89 |
| 618 | ASN | ND2 | 55.231 | 27.426 | 26.237 | 17.04 |
| 619 | ASN | H | 54.866 | 26.232 | 22.663 | 20.00 |
| 620 | ASN | HA | 52.284 | 27.169 | 23.748 | 20.00 |
| 621 | ASN | 1HB | 53.876 | 29.132 | 24.406 | 20.00 |
| 622 | ASN | 2HB | 55.207 | 28.155 | 23.763 | 20.00 |
| 623 | ASN | 1HD2 | 55.118 | 26.972 | 27.105 | 20.00 |
| 624 | ASN | 2HD2 | 56.036 | 27.928 | 25.914 | 20.00 |
| 625 | LYS | N | 53.052 | 27.988 | 20.818 | 19.50 |
| 626 | LYS | CA | 52.880 | 28.993 | 19.736 | 20.65 |
| 627 | LYS | C | 51.462 | 29.515 | 19.709 | 17.99 |
| 628 | LYS | O | 51.176 | 30.690 | 19.685 | 17.79 |
| 629 | LYS | CB | 53.224 | 28.321 | 18.344 | 24.77 |
| 630 | LYS | CG | 53.732 | 29.255 | 17.235 | 35.23 |
| 631 | LYS | CD | 54.019 | 28.612 | 15.850 | 43.17 |
| 632 | LYS | CE | 54.433 | 29.565 | 14.731 | 48.79 |
| 633 | LYS | NZ | 54.133 | 29.061 | 13.411 | 51.89 |
| 634 | LYS | H | 53.580 | 27.148 | 20.703 | 20.00 |
| 635 | LYS | HA | 53.557 | 29.817 | 19.962 | 20.00 |
| 636 | LYS | 1HB | 52.351 | 27.791 | 17.957 | 20.00 |
| 637 | LYS | 2HB | 53.960 | 27.534 | 18.498 | 20.00 |
| 638 | LYS | 1HG | 54.655 | 29.727 | 17.587 | 20.00 |
| 639 | LYS | 2HG | 53.003 | 30.061 | 17.104 | 20.00 |
| 640 | LYS | 1HD | 53.098 | 28.115 | 15.541 | 20.00 |
| 641 | LYS | 2HD | 54.759 | 27.817 | 15.949 | 20.00 |
| 642 | LYS | 1HE | 55.496 | 29.890 | 14.790 | 20.00 |
| 643 | LYS | 2HE | 53.870 | 30.569 | 14.815 | 20.00 |
| 644 | LYS | 1HZ | 53.097 | 29.011 | 13.287 | 20.00 |
| 645 | LYS | 2HZ | 54.453 | 28.080 | 13.339 | 20.00 |
| 646 | LYS | 3HZ | 54.503 | 29.603 | 12.605 | 20.00 |
| 647 | ASN | N | 50.566 | 28.527 | 19.762 | 16.87 |
| 648 | ASN | CA | 49.107 | 28.843 | 19.726 | 17.37 |
| 649 | ASN | C | 48.464 | 29.507 | 21.029 | 14.52 |
| 650 | ASN | O | 47.248 | 29.727 | 21.164 | 14.87 |
| 651 | ASN | CB | 48.373 | 27.533 | 19.306 | 17.56 |
| 652 | ASN | CG | 48.272 | 26.488 | 20.402 | 21.16 |
| 653 | ASN | OD1 | 48.877 | 26.514 | 21.451 | 23.28 |
| 654 | ASN | ND2 | 47.525 | 25.472 | 20.024 | 22.37 |
| 655 | ASN | H | 50.925 | 27.620 | 19.959 | 20.00 |
| 656 | ASN | HA | 48.961 | 29.568 | 18.921 | 20.00 |
| 657 | ASN | 1HB | 48.842 | 27.093 | 18.437 | 20.00 |
| 658 | ASN | 2HB | 47.350 | 27.783 | 19.013 | 20.00 |
| 659 | ASN | 1HD2 | 47.520 | 24.710 | 20.667 | 20.00 |
| 660 | ASN | 2HD2 | 47.013 | 25.510 | 19.175 | 20.00 |
| 661 | ARG | N | 49.398 | 29.743 | 21.971 | 13.45 |
| 662 | ARG | CA | 49.080 | 30.421 | 23.219 | 14.08 |
| 663 | ARG | C | 49.442 | 31.897 | 23.164 | 11.72 |
| 664 | ARG | O | 49.239 | 32.606 | 24.120 | 11.90 |
| 665 | ARG | CB | 49.812 | 29.746 | 24.405 | 14.72 |
| 666 | ARG | CG | 49.139 | 28.440 | 24.752 | 15.03 |
| 667 | ARG | CD | 49.763 | 27.746 | 25.988 | 13.22 |
| 668 | ARG | NE | 48.959 | 26.521 | 26.267 | 14.96 |
| 669 | ARG | CZ | 48.858 | 25.909 | 27.402 | 15.87 |
| 670 | ARG | NH1 | 49.281 | 26.474 | 28.507 | 14.76 |
| 671 | ARG | NH2 | 48.299 | 24.741 | 27.436 | 16.81 |
| 672 | ARG | H | 50.337 | 29.472 | 21.776 | 20.00 |
| 673 | ARG | HA | 48.004 | 30.372 | 23.369 | 20.00 |
| 674 | ARG | 1HB | 49.727 | 30.401 | 25.279 | 20.00 |
| 675 | ARG | 2HB | 50.877 | 29.631 | 24.213 | 20.00 |
| 676 | ARG | 1HG | 49.197 | 27.772 | 23.893 | 20.00 |
| 677 | ARG | 2HG | 48.078 | 28.628 | 24.920 | 20.00 |
| 678 | ARG | 1HD | 49.685 | 28.396 | 26.850 | 20.00 |
| 679 | ARG | 2HD | 50.798 | 27.458 | 25.812 | 20.00 |
| 680 | ARG | HE | 48.517 | 26.130 | 25.480 | 20.00 |
| 681 | ARG | 1HH1 | 49.168 | 26.032 | 29.395 | 20.00 |
| 682 | ARG | 2HH1 | 49.705 | 27.377 | 28.439 | 20.00 |
| 683 | ARG | 1HH2 | 48.173 | 24.251 | 28.303 | 20.00 |
| 684 | ARG | 2HH2 | 47.960 | 24.316 | 26.599 | 20.00 |
| 685 | ASN | N | 49.996 | 32.318 | 22.035 | 12.70 |
| 686 | ASN | CA | 50.406 | 33.706 | 21.870 | 12.44 |
| 687 | ASN | C | 49.508 | 34.267 | 20.783 | 12.58 |
| 688 | ASN | O | 49.360 | 33.682 | 19.731 | 11.79 |
| 689 | ASN | CB | 51.893 | 33.770 | 21.499 | 15.34 |
| 690 | ASN | CG | 52.706 | 33.250 | 22.622 | 15.14 |
| 691 | ASN | OD1 | 52.540 | 33.681 | 23.718 | 13.40 |
| 692 | ASN | ND2 | 53.664 | 32.406 | 22.420 | 15.01 |
| 693 | ASN | H | 50.101 | 31.681 | 21.265 | 20.00 |
| 694 | ASN | HA | 50.227 | 34.257 | 22.794 | 20.00 |
| 695 | ASN | 1HB | 52.211 | 34.789 | 21.274 | 20.00 |
| 696 | ASN | 2HB | 52.099 | 33.162 | 20.620 | 20.00 |
| 697 | ASN | 1HD2 | 54.227 | 32.167 | 23.194 | 20.00 |
| 698 | ASN | 2HD2 | 53.844 | 32.004 | 21.533 | 20.00 |
| 699 | ARG | N | 48.922 | 35.407 | 21.070 | 11.31 |
| 700 | ARG | CA | 48.157 | 36.050 | 20.031 | 10.21 |
| 701 | ARG | C | 49.030 | 36.735 | 18.938 | 11.77 |
| 702 | ARG | O | 48.660 | 36.681 | 17.785 | 10.43 |
| 703 | ARG | CB | 47.337 | 37.044 | 20.779 | 10.53 |
| 704 | ARG | CG | 46.560 | 37.866 | 19.869 | 9.14 |
| 705 | ARG | CD | 45.810 | 38.876 | 20.590 | 10.01 |
| 706 | ARG | NE | 44.644 | 38.387 | 21.426 | 10.47 |
| 707 | ARG | CZ | 43.536 | 38.042 | 20.725 | 10.78 |
| 708 | ARG | NH1 | 43.385 | 38.316 | 19.382 | 11.53 |
| 709 | ARG | NH2 | 42.642 | 37.281 | 21.300 | 10.00 |
| 710 | ARG | H | 48.857 | 35.623 | 22.040 | 20.00 |
| 711 | ARG | HA | 47.516 | 35.294 | 19.567 | 20.00 |
| 712 | ARG | 1HB | 47.990 | 37.689 | 21.376 | 20.00 |
| 713 | ARG | 2HB | 46.686 | 36.526 | 21.493 | 20.00 |
| 714 | ARG | 1HG | 45.916 | 37.234 | 19.260 | 20.00 |
| 715 | ARG | 2HG | 47.204 | 38.380 | 19.156 | 20.00 |
| 716 | ARG | 1HD | 45.508 | 39.367 | 19.671 | 20.00 |
| 717 | ARG | 2HD | 46.466 | 39.497 | 21.205 | 20.00 |
| 718 | ARG | HE | 44.748 | 38.186 | 22.399 | 20.00 |
| 719 | ARG | 1HH1 | 42.596 | 37.960 | 18.878 | 20.00 |
| 720 | ARG | 2HH1 | 44.085 | 38.855 | 18.925 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 721 | ARG | 1HH2 | 41.874 | 36.942 | 20.748 | 20.00 |
| 722 | ARG | 2HH2 | 42.724 | 37.024 | 22.270 | 20.00 |
| 723 | TYR | N | 50.170 | 37.367 | 19.339 | 12.06 |
| 724 | TYR | CA | 51.144 | 38.065 | 18.550 | 10.98 |
| 725 | TYR | C | 52.522 | 37.481 | 18.816 | 13.59 |
| 726 | TYR | O | 52.966 | 37.428 | 19.960 | 15.53 |
| 727 | TYR | CB | 51.220 | 39.576 | 18.875 | 9.94 |
| 728 | TYR | CG | 49.859 | 40.250 | 18.678 | 11.54 |
| 729 | TYR | CD1 | 49.044 | 40.145 | 17.523 | 11.75 |
| 730 | TYR | CD2 | 49.380 | 40.989 | 19.752 | 10.70 |
| 731 | TYR | CE1 | 47.808 | 40.784 | 17.473 | 12.58 |
| 732 | TYR | CE2 | 48.142 | 41.590 | 19.752 | 11.42 |
| 733 | TYR | CZ | 47.339 | 41.494 | 18.578 | 12.61 |
| 734 | TYR | OH | 46.051 | 41.986 | 18.423 | 13.20 |
| 735 | TYR | H | 50.266 | 37.312 | 20.329 | 20.00 |
| 736 | TYR | HA | 50.862 | 37.907 | 17.513 | 20.00 |
| 737 | TYR | 1HB | 51.984 | 40.094 | 18.317 | 20.00 |
| 738 | TYR | 2HB | 51.550 | 39.711 | 19.903 | 20.00 |
| 739 | TYR | HD1 | 49.336 | 39.506 | 16.724 | 20.00 |
| 740 | TYR | HD2 | 49.993 | 41.106 | 20.635 | 20.00 |
| 741 | TYR | HE1 | 47.172 | 40.704 | 16.611 | 20.00 |
| 742 | TYR | HE2 | 48.011 | 42.008 | 20.763 | 20.00 |
| 743 | TYR | HH | 45.857 | 42.735 | 18.985 | 20.00 |
| 744 | ARG | N | 53.153 | 37.103 | 17.699 | 13.40 |
| 745 | ARG | CA | 54.543 | 36.623 | 17.580 | 16.28 |
| 746 | ARG | C | 55.474 | 37.666 | 18.247 | 14.00 |
| 747 | ARG | O | 56.454 | 37.285 | 18.895 | 16.44 |
| 748 | ARG | CB | 54.915 | 36.428 | 16.068 | 17.48 |
| 749 | ARG | CG | 56.305 | 36.675 | 15.419 | 23.38 |
| 750 | ARG | CD | 56.316 | 37.199 | 13.926 | 28.56 |
| 751 | ARG | NE | 55.326 | 36.527 | 13.052 | 32.94 |
| 752 | ARG | CZ | 54.135 | 36.980 | 12.495 | 34.20 |
| 753 | ARG | NH1 | 53.971 | 38.258 | 12.223 | 33.15 |
| 754 | ARG | NH2 | 53.182 | 36.079 | 12.237 | 33.58 |
| 755 | ARG | H | 52.559 | 37.155 | 16.908 | 20.00 |
| 756 | ARG | HA | 54.579 | 35.718 | 18.147 | 20.00 |
| 757 | ARG | 1HB | 54.506 | 35.533 | 15.621 | 20.00 |
| 758 | ARG | 2HB | 54.611 | 37.441 | 15.734 | 20.00 |
| 759 | ARG | 1HG | 56.835 | 37.432 | 16.015 | 20.00 |
| 760 | ARG | 2HG | 56.937 | 35.799 | 15.540 | 20.00 |
| 761 | ARG | 1HD | 56.210 | 38.289 | 13.888 | 20.00 |
| 762 | ARG | 2HD | 57.315 | 36.970 | 13.512 | 20.00 |
| 763 | ARG | HE | 55.560 | 35.563 | 12.998 | 20.00 |
| 764 | ARG | 1HH2 | 52.331 | 36.288 | 11.752 | 20.00 |
| 765 | ARG | 2HH2 | 53.301 | 35.150 | 12.559 | 20.00 |
| 766 | ARG | 1HH1 | 53.238 | 38.710 | 11.709 | 20.00 |
| 767 | ARG | 2HH1 | 54.784 | 38.793 | 12.502 | 20.00 |
| 768 | ASP | N | 55.116 | 38.934 | 18.094 | 12.94 |
| 769 | ASP | CA | 55.973 | 40.036 | 18.616 | 12.52 |
| 770 | ASP | C | 55.797 | 40.445 | 20.096 | 12.63 |
| 771 | ASP | O | 56.452 | 41.331 | 20.648 | 11.75 |
| 772 | ASP | CB | 55.837 | 41.278 | 17.706 | 13.44 |
| 773 | ASP | CG | 56.220 | 41.009 | 16.226 | 15.48 |
| 774 | ASP | OD1 | 57.040 | 40.145 | 15.911 | 14.91 |
| 775 | ASP | OD2 | 55.608 | 41.579 | 15.347 | 17.68 |
| 776 | ASP | H | 54.485 | 39.225 | 17.376 | 20.00 |
| 777 | ASP | HA | 56.988 | 39.663 | 18.528 | 20.00 |
| 778 | ASP | 1HB | 56.501 | 42.075 | 18.023 | 20.00 |
| 779 | ASP | 2HB | 54.831 | 41.662 | 17.752 | 20.00 |
| 780 | VAL | N | 54.876 | 39.733 | 20.803 | 12.12 |
| 781 | VAL | CA | 54.573 | 40.057 | 22.191 | 11.29 |
| 782 | VAL | C | 54.455 | 38.762 | 22.960 | 9.78 |
| 783 | VAL | O | 53.550 | 37.945 | 22.857 | 11.48 |
| 784 | VAL | CB | 53.595 | 41.270 | 22.522 | 16.11 |
| 785 | VAL | CG1 | 52.686 | 41.008 | 23.691 | 15.44 |
| 786 | VAL | CG2 | 53.024 | 42.155 | 21.436 | 14.33 |
| 787 | VAL | H | 54.326 | 39.100 | 20.257 | 20.00 |
| 788 | VAL | HA | 55.521 | 40.473 | 22.533 | 20.00 |
| 789 | VAL | HB | 54.260 | 42.006 | 22.986 | 20.00 |
| 790 | VAL | 1HG1 | 53.241 | 40.703 | 24.580 | 20.00 |
| 791 | VAL | 2HG1 | 51.975 | 40.213 | 23.479 | 20.00 |
| 792 | VAL | 3HG1 | 52.106 | 41.885 | 23.978 | 20.00 |
| 793 | VAL | 1HG2 | 52.256 | 41.649 | 20.862 | 20.00 |
| 794 | VAL | 2HG2 | 53.807 | 42.481 | 20.755 | 20.00 |
| 795 | VAL | 3HG2 | 52.569 | 43.058 | 21.839 | 20.00 |
| 796 | SER | N | 55.506 | 38.663 | 23.758 | 10.16 |
| 797 | SER | CA | 55.834 | 37.561 | 24.654 | 11.16 |
| 798 | SER | C | 56.196 | 38.081 | 26.070 | 9.64 |
| 799 | SER | O | 56.758 | 39.170 | 26.254 | 11.51 |
| 800 | SER | CB | 57.105 | 36.786 | 24.050 | 10.81 |
| 801 | SER | OG | 56.905 | 36.279 | 22.695 | 12.18 |
| 802 | SER | H | 56.131 | 39.440 | 23.769 | 20.00 |
| 803 | SER | HA | 54.941 | 36.921 | 24.712 | 20.00 |
| 804 | SER | 1HB | 57.272 | 35.928 | 24.740 | 20.00 |
| 805 | SER | 2HB | 58.081 | 37.304 | 24.285 | 20.00 |
| 806 | SER | HG | 56.412 | 36.740 | 21.950 | 20.00 |
| 807 | PRO | N | 55.880 | 37.202 | 27.077 | 8.67 |
| 808 | PRO | CA | 56.329 | 37.300 | 28.414 | 10.79 |
| 809 | PRO | C | 57.824 | 36.995 | 28.517 | 13.35 |
| 810 | PRO | O | 58.237 | 35.943 | 28.085 | 14.81 |
| 811 | PRO | CB | 55.432 | 36.259 | 29.103 | 10.00 |
| 812 | PRO | CG | 55.263 | 35.208 | 28.112 | 10.77 |
| 813 | PRO | CD | 55.042 | 36.035 | 26.923 | 9.16 |
| 814 | PRO | HA | 56.203 | 38.308 | 28.764 | 20.00 |
| 815 | PRO | 1HB | 54.379 | 36.441 | 29.197 | 20.00 |
| 816 | PRO | 2HB | 55.825 | 35.933 | 30.055 | 20.00 |
| 817 | PRO | 1HG | 56.174 | 34.610 | 28.028 | 20.00 |
| 818 | PRO | 2HG | 54.446 | 34.516 | 28.338 | 20.00 |
| 819 | PRO | 1HD | 54.004 | 36.311 | 26.766 | 20.00 |
| 820 | PRO | 2HD | 55.499 | 35.527 | 26.092 | 20.00 |
| 821 | PHE | N | 58.603 | 37.926 | 29.144 | 13.59 |
| 822 | PHE | CA | 59.917 | 37.512 | 29.662 | 12.71 |
| 823 | PHE | C | 59.764 | 36.228 | 30.513 | 12.31 |
| 824 | PHE | O | 58.819 | 36.148 | 31.282 | 12.68 |
| 825 | PHE | CB | 60.730 | 38.634 | 30.385 | 9.81 |
| 826 | PHE | CG | 60.773 | 39.907 | 29.668 | 10.06 |
| 827 | PHE | CD1 | 61.171 | 39.952 | 28.332 | 9.58 |
| 828 | PHE | CD2 | 60.557 | 41.099 | 30.342 | 9.41 |
| 829 | PHE | CE1 | 61.489 | 41.196 | 27.800 | 10.26 |
| 830 | PHE | CE2 | 60.848 | 42.337 | 29.786 | 10.02 |
| 831 | PHE | CZ | 61.354 | 42.399 | 28.543 | 8.64 |
| 832 | PHE | H | 58.157 | 38.782 | 29.377 | 20.00 |
| 833 | PHE | HA | 60.489 | 37.218 | 28.782 | 20.00 |
| 834 | PHE | 1HB | 61.767 | 38.289 | 30.303 | 20.00 |
| 835 | PHE | 2HB | 60.716 | 38.738 | 31.460 | 20.00 |
| 836 | PHE | HD1 | 61.347 | 39.055 | 27.761 | 20.00 |
| 837 | PHE | HD2 | 60.194 | 41.061 | 31.361 | 20.00 |
| 838 | PHE | HE1 | 61.915 | 41.252 | 26.806 | 20.00 |
| 839 | PHE | HE2 | 60.710 | 43.231 | 30.370 | 20.00 |
| 840 | PHE | HZ | 61.689 | 43.349 | 28.141 | 20.00 |
| 841 | ASP | N | 60.707 | 35.281 | 30.364 | 11.62 |
| 842 | ASP | CA | 60.799 | 34.068 | 31.244 | 12.07 |
| 843 | ASP | C | 60.796 | 34.428 | 32.811 | 12.27 |
| 844 | ASP | O | 60.121 | 33.789 | 33.631 | 15.21 |
| 845 | ASP | CB | 62.118 | 33.232 | 30.924 | 13.40 |
| 846 | ASP | CG | 62.097 | 32.558 | 29.567 | 14.25 |
| 847 | ASP | OD1 | 60.970 | 32.119 | 29.186 | 15.72 |
| 848 | ASP | OD2 | 63.206 | 32.476 | 28.952 | 12.79 |
| 849 | ASP | H | 61.362 | 35.357 | 29.624 | 20.00 |
| 850 | ASP | HA | 59.915 | 33.471 | 31.028 | 20.00 |
| 851 | ASP | 1HB | 62.233 | 32.436 | 31.648 | 20.00 |
| 852 | ASP | 2HB | 63.005 | 33.861 | 31.009 | 20.00 |
| 853 | HIS | N | 61.645 | 35.431 | 33.141 | 12.16 |
| 854 | HIS | CA | 61.906 | 35.743 | 34.515 | 12.71 |
| 855 | HIS | C | 60.622 | 36.197 | 35.245 | 13.92 |
| 856 | HIS | O | 60.428 | 35.970 | 36.418 | 15.61 |
| 857 | HIS | CB | 63.111 | 36.710 | 34.678 | 12.05 |
| 858 | HIS | CG | 62.763 | 38.170 | 34.481 | 10.80 |
| 859 | HIS | ND1 | 62.180 | 38.950 | 35.412 | 11.89 |
| 860 | HIS | CD2 | 63.026 | 38.996 | 33.393 | 10.89 |
| 861 | HIS | CE1 | 62.091 | 40.203 | 34.920 | 9.38 |
| 862 | HIS | NE2 | 62.587 | 40.256 | 33.707 | 11.30 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 863 | HIS | H | 62.189 | 35.808 | 32.392 | 20.00 |
| 864 | HIS | HA | 62.205 | 34.800 | 34.956 | 20.00 |
| 865 | HIS | 1HB | 63.930 | 36.436 | 34.003 | 20.00 |
| 866 | HIS | 2HB | 63.521 | 36.613 | 35.682 | 20.00 |
| 867 | HIS | HD1 | 61.951 | 38.686 | 36.324 | 20.00 |
| 868 | HIS | HD2 | 63.513 | 38.693 | 32.486 | 20.00 |
| 869 | HIS | HE1 | 61.660 | 41.067 | 35.402 | 20.00 |
| 870 | SER | N | 59.723 | 36.834 | 34.519 | 13.43 |
| 871 | SER | CA | 58.552 | 37.448 | 35.230 | 12.13 |
| 872 | SER | C | 57.176 | 36.863 | 34.862 | 12.76 |
| 873 | SER | O | 56.104 | 37.349 | 35.336 | 13.37 |
| 874 | SER | CB | 58.525 | 38.196 | 34.846 | 10.16 |
| 875 | SER | OG | 58.653 | 39.016 | 33.381 | 10.34 |
| 876 | SER | H | 59.957 | 37.166 | 33.600 | 20.00 |
| 877 | SER | HA | 58.674 | 37.373 | 36.302 | 20.00 |
| 878 | SER | 1HB | 59.441 | 39.363 | 35.292 | 20.00 |
| 879 | SER | 2HB | 57.743 | 39.503 | 35.420 | 20.00 |
| 880 | SER | HG | 57.994 | 38.636 | 32.702 | 20.00 |
| 881 | ARG | N | 57.244 | 35.805 | 34.022 | 11.78 |
| 882 | ARG | CA | 55.939 | 35.373 | 33.508 | 13.97 |
| 883 | ARG | C | 55.153 | 34.605 | 34.601 | 13.85 |
| 884 | ARG | O | 55.744 | 33.997 | 35.513 | 11.86 |
| 885 | ARG | CB | 56.173 | 34.471 | 32.280 | 12.96 |
| 886 | ARG | CG | 56.702 | 33.069 | 32.654 | 13.81 |
| 887 | ARG | CD | 57.016 | 32.181 | 31.428 | 13.20 |
| 888 | ARG | NE | 57.632 | 30.888 | 31.874 | 14.78 |
| 889 | ARG | CZ | 57.094 | 29.687 | 32.079 | 15.00 |
| 890 | ARG | NH1 | 55.822 | 29.488 | 31.874 | 11.82 |
| 891 | ARG | NH2 | 57.838 | 28.727 | 32.565 | 17.64 |
| 892 | ARG | H | 58.122 | 35.460 | 33.703 | 20.00 |
| 893 | ARG | HA | 55.398 | 36.266 | 33.193 | 20.00 |
| 894 | ARG | 1HB | 56.888 | 34.953 | 31.615 | 20.00 |
| 895 | ARG | 2HB | 55.248 | 34.372 | 31.713 | 20.00 |
| 896 | ARG | 1HG | 55.959 | 32.540 | 33.249 | 20.00 |
| 897 | ARG | 2HG | 57.586 | 33.156 | 33.285 | 20.00 |
| 898 | ARG | 1HD | 57.745 | 32.661 | 30.777 | 20.00 |
| 899 | ARG | 2HD | 56.126 | 31.982 | 30.828 | 20.00 |
| 900 | ARG | HE | 58.614 | 30.885 | 32.076 | 20.00 |
| 901 | ARG | 1HH1 | 55.444 | 28.561 | 32.028 | 20.00 |
| 902 | ARG | 2HH1 | 55.229 | 30.225 | 31.600 | 20.00 |
| 903 | ARG | 1HH2 | 57.363 | 27.856 | 32.770 | 20.00 |
| 904 | ARG | 2HH2 | 58.819 | 28.824 | 32.735 | 20.00 |
| 905 | ILE | N | 53.823 | 34.541 | 34.371 | 14.21 |
| 906 | ILE | CA | 53.015 | 33.695 | 35.241 | 12.58 |
| 907 | ILE | C | 52.784 | 32.276 | 34.706 | 14.61 |
| 908 | ILE | O | 52.311 | 31.983 | 33.572 | 15.26 |
| 909 | ILE | CB | 51.692 | 34.404 | 35.385 | 13.58 |
| 910 | ILE | CG1 | 51.914 | 35.909 | 35.670 | 13.29 |
| 911 | ILE | CG2 | 50.687 | 33.768 | 36.382 | 13.64 |
| 912 | ILE | CD1 | 51.819 | 36.312 | 37.125 | 13.30 |
| 913 | ILE | H | 53.450 | 35.070 | 33.611 | 20.00 |
| 914 | ILE | HA | 53.491 | 33.658 | 36.221 | 20.00 |
| 915 | ILE | HB | 51.217 | 34.358 | 34.405 | 20.00 |
| 916 | ILE | 1HG1 | 51.085 | 36.426 | 35.186 | 20.00 |
| 917 | ILE | 2HG1 | 52.780 | 36.386 | 35.222 | 20.00 |
| 918 | ILE | 1HG2 | 51.116 | 33.664 | 37.379 | 20.00 |
| 919 | ILE | 2HG2 | 50.394 | 32.762 | 36.074 | 20.00 |
| 920 | ILE | 3HG2 | 49.777 | 34.367 | 36.452 | 20.00 |
| 921 | ILE | 1HD1 | 52.673 | 35.943 | 37.695 | 20.00 |
| 922 | ILE | 2HD1 | 50.909 | 35.966 | 37.616 | 20.00 |
| 923 | ILE | 3HD1 | 51.834 | 37.400 | 37.195 | 20.00 |
| 924 | LYS | N | 53.090 | 31.420 | 35.677 | 15.82 |
| 925 | LYS | CA | 52.968 | 29.984 | 35.485 | 15.98 |
| 926 | LYS | C | 51.581 | 29.539 | 35.986 | 17.60 |
| 927 | LYS | O | 51.237 | 29.849 | 37.111 | 19.95 |
| 928 | LYS | CB | 54.154 | 29.264 | 36.206 | 17.28 |
| 929 | LYS | CG | 55.459 | 30.029 | 36.021 | 17.24 |
| 930 | LYS | CD | 56.580 | 29.154 | 36.468 | 22.81 |
| 931 | LYS | CE | 57.923 | 29.820 | 36.118 | 26.05 |
| 932 | LYS | NZ | 59.002 | 28.881 | 36.461 | 31.86 |
| 933 | LYS | H | 53.331 | 31.776 | 36.578 | 20.00 |
| 934 | LYS | HA | 53.041 | 29.782 | 34.419 | 20.00 |
| 935 | LYS | 1HB | 54.240 | 28.241 | 35.827 | 20.00 |
| 936 | LYS | 2HB | 53.945 | 29.180 | 37.272 | 20.00 |
| 937 | LYS | 1HG | 55.449 | 30.949 | 36.604 | 20.00 |
| 938 | LYS | 2HG | 55.572 | 30.305 | 34.972 | 20.00 |
| 939 | LYS | 1HD | 56.527 | 28.185 | 35.965 | 20.00 |
| 940 | LYS | 2HD | 56.506 | 28.962 | 37.538 | 20.00 |
| 941 | LYS | 1HE | 58.051 | 30.780 | 36.631 | 20.00 |
| 942 | LYS | 2HE | 57.975 | 30.045 | 35.049 | 20.00 |
| 943 | LYS | 1HZ | 58.861 | 27.982 | 35.937 | 20.00 |
| 944 | LYS | 2HZ | 58.998 | 28.698 | 37.481 | 20.00 |
| 945 | LYS | 3HZ | 59.917 | 29.296 | 36.191 | 20.00 |
| 946 | LEU | N | 50.885 | 28.827 | 35.063 | 17.25 |
| 947 | LEU | CA | 49.701 | 28.023 | 35.305 | 18.29 |
| 948 | LEU | C | 50.164 | 26.889 | 36.218 | 20.34 |
| 949 | LEU | O | 51.156 | 26.241 | 35.911 | 19.70 |
| 950 | LEU | CB | 49.199 | 27.455 | 33.986 | 18.28 |
| 951 | LEU | CG | 48.053 | 28.245 | 33.290 | 18.66 |
| 952 | LEU | CD1 | 47.989 | 27.995 | 31.755 | 17.13 |
| 953 | LEU | CD2 | 47.828 | 29.708 | 33.707 | 14.98 |
| 954 | LEU | H | 51.364 | 28.759 | 34.195 | 20.00 |
| 955 | LEU | HA | 48.963 | 28.629 | 35.838 | 20.00 |
| 956 | LEU | 1HB | 48.868 | 26.443 | 34.106 | 20.00 |
| 957 | LEU | 2HB | 50.029 | 27.419 | 33.293 | 20.00 |
| 958 | LEU | HG | 47.157 | 27.754 | 33.671 | 20.00 |
| 959 | LEU | 1HD1 | 48.064 | 26.933 | 31.522 | 20.00 |
| 960 | LEU | 2HD1 | 48.811 | 28.517 | 31.259 | 20.00 |
| 961 | LEU | 3HD1 | 47.039 | 28.334 | 31.374 | 20.00 |
| 962 | LEU | 1HD2 | 48.762 | 30.260 | 33.691 | 20.00 |
| 963 | LEU | 2HD2 | 47.441 | 29.754 | 34.725 | 20.00 |
| 964 | LEU | 3HD2 | 47.112 | 30.213 | 33.062 | 20.00 |
| 965 | HIS | N | 49.467 | 26.676 | 37.346 | 22.86 |
| 966 | HIS | CA | 49.798 | 25.580 | 38.220 | 25.86 |
| 967 | HIS | C | 49.188 | 24.299 | 37.604 | 30.06 |
| 968 | HIS | O | 48.407 | 23.576 | 38.179 | 31.82 |
| 969 | HIS | CB | 49.207 | 25.838 | 39.607 | 26.12 |
| 970 | HIS | CG | 49.625 | 27.147 | 40.252 | 25.12 |
| 971 | HIS | ND1 | 48.983 | 27.623 | 41.360 | 25.76 |
| 972 | HIS | CD2 | 50.620 | 28.085 | 39.869 | 24.91 |
| 973 | HIS | CE1 | 49.574 | 28.827 | 41.642 | 25.52 |
| 974 | HIS | NE2 | 50.566 | 29.138 | 40.757 | 26.33 |
| 975 | HIS | H | 48.586 | 27.148 | 37.402 | 20.00 |
| 976 | HIS | HA | 50.880 | 25.472 | 38.282 | 20.00 |
| 977 | HIS | 1HB | 49.461 | 25.018 | 40.278 | 20.00 |
| 978 | HIS | 2HB | 48.122 | 25.837 | 39.553 | 20.00 |
| 979 | HIS | HD1 | 48.204 | 27.201 | 41.765 | 20.00 |
| 980 | HIS | HD2 | 51.269 | 27.996 | 39.010 | 20.00 |
| 981 | HIS | HE1 | 49.292 | 29.465 | 42.470 | 20.00 |
| 982 | GLN | N | 49.608 | 23.987 | 36.392 | 32.94 |
| 983 | GLN | CA | 49.271 | 22.663 | 35.842 | 36.50 |
| 984 | GLN | C | 50.532 | 21.955 | 35.351 | 37.97 |
| 985 | GLN | O | 51.618 | 22.541 | 35.302 | 37.18 |
| 986 | GLN | CB | 48.147 | 22.806 | 34.854 | 37.95 |
| 987 | GLN | CG | 48.266 | 24.086 | 34.021 | 40.06 |
| 988 | GLN | CD | 47.360 | 23.885 | 32.822 | 44.06 |
| 989 | GLN | OE1 | 47.592 | 22.903 | 32.119 | 46.49 |
| 990 | GLN | NE2 | 46.323 | 24.719 | 32.620 | 41.49 |
| 991 | GLN | H | 50.243 | 24.612 | 35.941 | 20.00 |
| 992 | GLN | HA | 48.926 | 21.997 | 36.641 | 20.00 |
| 993 | GLN | 1HB | 47.226 | 22.901 | 35.438 | 20.00 |
| 994 | GLN | 2HB | 48.003 | 21.889 | 34.282 | 20.00 |
| 995 | GLN | 1HG | 49.283 | 24.268 | 33.676 | 20.00 |
| 996 | GLN | 2HG | 47.866 | 24.901 | 34.612 | 20.00 |
| 997 | GLN | 1HE2 | 45.658 | 24.510 | 31.912 | 20.00 |
| 998 | GLN | 2HE2 | 46.171 | 25.495 | 33.241 | 20.00 |
| 999 | GLU | N | 50.320 | 20.649 | 35.092 | 41.15 |
| 1000 | GLU | CA | 51.547 | 19.859 | 34.850 | 41.70 |
| 1001 | GLU | C | 51.834 | 19.728 | 33.311 | 39.31 |
| 1002 | GLU | O | 52.984 | 19.644 | 32.860 | 38.68 |
| 1003 | GLU | CB | 51.430 | 18.558 | 35.655 | 45.57 |
| 1004 | GLU | CG | 51.679 | 18.866 | 37.145 | 54.22 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1005 | GLU | CD | 50.777 | 17.977 | 38.035 | 60.23 |
| 1006 | GLU | OE1 | 49.587 | 18.325 | 38.117 | 63.36 |
| 1007 | GLU | OE2 | 51.253 | 16.964 | 38.605 | 62.48 |
| 1008 | GLU | H | 49.451 | 20.221 | 35.343 | 20.00 |
| 1009 | GLU | HA | 52.415 | 20.380 | 35.254 | 20.00 |
| 1010 | GLU | 1HB | 52.138 | 17.803 | 35.321 | 20.00 |
| 1011 | GLU | 2HB | 50.436 | 18.128 | 35.508 | 20.00 |
| 1012 | GLU | 1HG | 51.411 | 19.888 | 37.403 | 20.00 |
| 1013 | GLU | 2HG | 52.719 | 18.720 | 37.428 | 20.00 |
| 1014 | ASP | N | 50.713 | 19.782 | 32.532 | 38.53 |
| 1015 | ASP | CA | 50.859 | 19.700 | 31.061 | 37.73 |
| 1016 | ASP | C | 51.793 | 20.877 | 30.583 | 33.50 |
| 1017 | ASP | O | 52.946 | 20.793 | 30.147 | 35.46 |
| 1018 | ASP | CB | 49.374 | 19.842 | 30.492 | 43.21 |
| 1019 | ASP | CG | 49.448 | 20.048 | 28.963 | 49.96 |
| 1020 | ASP | OD1 | 50.358 | 19.411 | 28.396 | 53.55 |
| 1021 | ASP | OD2 | 48.668 | 20.859 | 28.386 | 52.89 |
| 1022 | ASP | H | 49.807 | 19.888 | 32.924 | 20.00 |
| 1023 | ASP | HA | 51.321 | 18.751 | 30.761 | 20.00 |
| 1024 | ASP | 1HB | 48.803 | 20.635 | 30.964 | 20.00 |
| 1025 | ASP | 2HB | 48.830 | 18.915 | 30.646 | 20.00 |
| 1026 | ASN | N | 51.117 | 22.012 | 30.774 | 28.37 |
| 1027 | ASN | CA | 51.658 | 23.198 | 30.253 | 21.99 |
| 1028 | ASN | C | 51.272 | 24.281 | 31.204 | 20.24 |
| 1029 | ASN | O | 50.088 | 24.519 | 31.310 | 21.87 |
| 1030 | ASN | CB | 51.062 | 23.311 | 28.867 | 19.04 |
| 1031 | ASN | CG | 51.901 | 24.202 | 27.972 | 18.04 |
| 1032 | ASN | OD1 | 52.747 | 24.954 | 28.409 | 19.25 |
| 1033 | ASN | ND2 | 51.670 | 24.083 | 26.677 | 15.06 |
| 1034 | ASN | H | 50.148 | 21.879 | 30.992 | 20.00 |
| 1035 | ASN | HA | 52.742 | 23.147 | 30.225 | 20.00 |
| 1036 | ASN | 1HB | 50.053 | 23.709 | 28.917 | 20.00 |
| 1037 | ASN | 2HB | 50.976 | 22.339 | 28.367 | 20.00 |
| 1038 | ASN | 1HD2 | 52.136 | 24.800 | 26.133 | 20.00 |
| 1039 | ASN | 2HD2 | 51.105 | 23.357 | 26.296 | 20.00 |
| 1040 | ASP | N | 52.310 | 24.934 | 31.781 | 18.00 |
| 1041 | ASP | CA | 52.359 | 26.033 | 32.774 | 18.78 |
| 1042 | ASP | C | 52.269 | 27.339 | 32.022 | 17.35 |
| 1043 | ASP | O | 52.385 | 28.381 | 32.643 | 18.81 |
| 1044 | ASP | CB | 53.678 | 26.048 | 33.673 | 19.48 |
| 1045 | ASP | CG | 55.010 | 26.577 | 33.066 | 23.10 |
| 1046 | ASP | OD1 | 55.075 | 26.798 | 31.865 | 24.35 |
| 1047 | ASP | OD2 | 56.022 | 26.809 | 33.756 | 29.58 |
| 1048 | ASP | H | 53.213 | 24.652 | 31.479 | 20.00 |
| 1049 | ASP | HA | 51.485 | 25.929 | 33.416 | 20.00 |
| 1050 | ASP | 1HB | 53.905 | 25.042 | 34.027 | 20.00 |
| 1051 | ASP | 2HB | 53.466 | 26.618 | 34.583 | 20.00 |
| 1052 | TYR | N | 52.126 | 27.268 | 30.658 | 16.55 |
| 1053 | TYR | CA | 52.342 | 28.547 | 29.854 | 12.98 |
| 1054 | TYR | C | 51.059 | 29.382 | 29.617 | 12.27 |
| 1055 | TYR | O | 50.072 | 28.908 | 29.056 | 12.81 |
| 1056 | TYR | CB | 53.128 | 28.308 | 28.524 | 10.36 |
| 1057 | TYR | CG | 53.307 | 29.633 | 27.752 | 12.42 |
| 1058 | TYR | CD1 | 54.305 | 30.529 | 28.014 | 10.55 |
| 1059 | TYR | CD2 | 52.385 | 30.073 | 26.782 | 11.80 |
| 1060 | TYR | CE1 | 54.386 | 31.783 | 27.545 | 11.79 |
| 1061 | TYR | CE2 | 52.453 | 31.353 | 26.260 | 10.71 |
| 1062 | TYR | CZ | 53.524 | 32.198 | 26.519 | 9.67 |
| 1063 | TYR | OH | 53.938 | 33.401 | 26.004 | 10.99 |
| 1064 | TYR | H | 52.132 | 26.366 | 30.228 | 20.00 |
| 1065 | TYR | HA | 53.022 | 29.162 | 30.449 | 20.00 |
| 1066 | TYR | 1HB | 52.598 | 27.575 | 27.914 | 20.00 |
| 1067 | TYR | 2HB | 54.096 | 27.862 | 28.732 | 20.00 |
| 1068 | TYR | HD1 | 55.008 | 30.232 | 28.857 | 20.00 |
| 1069 | TYR | HD2 | 51.588 | 29.416 | 26.475 | 20.00 |
| 1070 | TYR | HE1 | 55.198 | 32.442 | 27.833 | 20.00 |
| 1071 | TYR | HE2 | 51.561 | 31.484 | 25.630 | 20.00 |
| 1072 | TYR | HH | 53.565 | 33.505 | 25.119 | 20.00 |
| 1073 | ILE | N | 51.111 | 30.653 | 30.018 | 13.06 |
| 1074 | ILE | CA | 50.146 | 31.725 | 29.683 | 12.41 |
| 1075 | ILE | C | 50.996 | 32.948 | 29.283 | 11.32 |
| 1076 | ILE | O | 52.043 | 33.149 | 29.862 | 12.19 |
| 1077 | ILE | CB | 49.059 | 32.003 | 30.788 | 12.98 |
| 1078 | ILE | CG1 | 48.065 | 33.056 | 30.196 | 8.76 |
| 1079 | ILE | CG2 | 49.639 | 32.315 | 32.217 | 10.91 |
| 1080 | ILE | CD1 | 46.906 | 33.342 | 31.116 | 9.88 |
| 1081 | ILE | H | 51.869 | 30.910 | 30.612 | 20.00 |
| 1082 | ILE | HA | 49.636 | 31.400 | 28.775 | 20.00 |
| 1083 | ILE | HB | 48.500 | 31.076 | 30.889 | 20.00 |
| 1084 | ILE | 1HG1 | 47.659 | 32.732 | 29.240 | 20.00 |
| 1085 | ILE | 2HG1 | 48.584 | 33.993 | 30.018 | 20.00 |
| 1086 | ILE | 1HG2 | 50.271 | 33.197 | 32.211 | 20.00 |
| 1087 | ILE | 2HG2 | 50.242 | 31.487 | 32.577 | 20.00 |
| 1088 | ILE | 3HG2 | 48.844 | 32.475 | 32.935 | 20.00 |
| 1089 | ILE | 1HD1 | 47.243 | 33.841 | 32.021 | 20.00 |
| 1090 | ILE | 2HD1 | 46.420 | 32.423 | 31.431 | 20.00 |
| 1091 | ILE | 3HD1 | 46.150 | 33.978 | 30.654 | 20.00 |
| 1092 | ASN | N | 50.614 | 33.705 | 28.262 | 9.16 |
| 1093 | ASN | CA | 51.251 | 34.994 | 27.951 | 9.65 |
| 1094 | ASN | C | 50.836 | 36.013 | 28.977 | 10.37 |
| 1095 | ASN | O | 49.889 | 36.738 | 28.762 | 10.07 |
| 1096 | ASN | CB | 50.740 | 35.386 | 26.534 | 9.08 |
| 1097 | ASN | CG | 51.559 | 36.512 | 25.985 | 9.54 |
| 1098 | ASN | OD1 | 51.733 | 37.578 | 26.614 | 10.96 |
| 1099 | ASN | ND2 | 52.102 | 36.212 | 24.777 | 9.06 |
| 1100 | ASN | H | 49.891 | 33.381 | 27.666 | 20.00 |
| 1101 | ASN | HA | 52.326 | 34.865 | 28.001 | 20.00 |
| 1102 | ASN | 1HB | 49.721 | 35.743 | 26.595 | 20.00 |
| 1103 | ASN | 2HB | 50.681 | 34.548 | 25.844 | 20.00 |
| 1104 | ASN | 1HD2 | 52.677 | 36.857 | 24.276 | 20.00 |
| 1105 | ASN | 2HD2 | 51.947 | 35.294 | 24.398 | 20.00 |
| 1106 | ALA | N | 51.472 | 36.004 | 30.161 | 9.41 |
| 1107 | ALA | CA | 51.160 | 37.001 | 31.204 | 10.05 |
| 1108 | ALA | C | 52.418 | 37.231 | 31.951 | 11.58 |
| 1109 | ALA | O | 53.203 | 36.292 | 32.110 | 12.92 |
| 1110 | ALA | CB | 50.197 | 36.373 | 32.229 | 7.50 |
| 1111 | ALA | H | 52.104 | 35.256 | 30.340 | 20.00 |
| 1112 | ALA | HA | 50.721 | 37.888 | 30.752 | 20.00 |
| 1113 | ALA | 1HB | 50.631 | 35.477 | 32.665 | 20.00 |
| 1114 | ALA | 2HB | 49.277 | 36.060 | 31.754 | 20.00 |
| 1115 | ALA | 3HB | 49.933 | 37.050 | 33.037 | 20.00 |
| 1116 | SER | N | 52.522 | 38.468 | 32.470 | 10.51 |
| 1117 | SER | CA | 53.663 | 38.902 | 33.299 | 11.23 |
| 1118 | SER | C | 53.285 | 39.621 | 34.550 | 10.85 |
| 1119 | SER | O | 52.423 | 40.474 | 34.557 | 12.48 |
| 1120 | SER | CB | 54.393 | 39.958 | 32.386 | 7.55 |
| 1121 | SER | OG | 54.544 | 39.424 | 30.979 | 10.45 |
| 1122 | SER | H | 51.738 | 39.068 | 32.307 | 20.00 |
| 1123 | SER | HA | 54.292 | 38.048 | 33.555 | 20.00 |
| 1124 | SER | 1HB | 55.364 | 40.197 | 32.840 | 20.00 |
| 1125 | SER | 2HB | 53.966 | 41.002 | 32.539 | 20.00 |
| 1126 | SER | HG | 53.779 | 38.963 | 30.539 | 20.00 |
| 1127 | LEU | N | 54.089 | 39.317 | 35.577 | 11.48 |
| 1128 | LEU | CA | 53.997 | 40.074 | 36.831 | 12.53 |
| 1129 | LEU | C | 54.875 | 41.328 | 36.773 | 13.15 |
| 1130 | LEU | O | 56.106 | 41.237 | 36.710 | 13.65 |
| 1131 | LEU | CB | 54.509 | 39.118 | 37.938 | 13.18 |
| 1132 | LEU | CG | 54.050 | 39.236 | 39.386 | 15.58 |
| 1133 | LEU | CD1 | 53.078 | 40.321 | 39.819 | 15.45 |
| 1134 | LEU | CD2 | 55.183 | 39.160 | 40.327 | 15.90 |
| 1135 | LEU | H | 54.798 | 38.633 | 35.444 | 20.00 |
| 1136 | LEU | HA | 52.955 | 40.335 | 37.005 | 20.00 |
| 1137 | LEU | 1HB | 55.596 | 39.023 | 37.872 | 20.00 |
| 1138 | LEU | 2HB | 54.181 | 38.124 | 37.632 | 20.00 |
| 1139 | LEU | HG | 53.486 | 38.316 | 39.575 | 20.00 |
| 1140 | LEU | 1HD1 | 52.149 | 40.243 | 39.258 | 20.00 |
| 1141 | LEU | 2HD1 | 53.486 | 41.319 | 39.654 | 20.00 |
| 1142 | LEU | 3HD1 | 52.812 | 40.238 | 40.873 | 20.00 |
| 1143 | LEU | 1HD2 | 55.856 | 39.996 | 40.139 | 20.00 |
| 1144 | LEU | 2HD2 | 55.743 | 38.233 | 40.214 | 20.00 |
| 1145 | LEU | 3HD2 | 54.838 | 39.213 | 41.361 | 20.00 |
| 1146 | ILE | N | 54.198 | 42.491 | 36.870 | 12.91 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1147 | ILE | CA | 54.849 | 43.764 | 37.188 | 13.87 |
| 1148 | ILE | C | 54.768 | 44.035 | 38.703 | 16.47 |
| 1149 | ILE | O | 53.759 | 44.202 | 39.394 | 16.73 |
| 1150 | ILE | CB | 54.282 | 44.944 | 36.382 | 13.55 |
| 1151 | ILE | CG1 | 54.385 | 44.786 | 34.837 | 12.82 |
| 1152 | ILE | CG2 | 54.940 | 46.250 | 36.798 | 16.67 |
| 1153 | ILE | CD1 | 54.103 | 43.394 | 34.279 | 12.75 |
| 1154 | ILE | H | 53.200 | 42.393 | 36.826 | 20.00 |
| 1155 | ILE | HA | 55.895 | 43.661 | 36.897 | 20.00 |
| 1156 | ILE | HB | 53.217 | 45.012 | 36.617 | 20.00 |
| 1157 | ILE | 1HG1 | 55.383 | 45.077 | 34.511 | 20.00 |
| 1158 | ILE | 2HG1 | 53.700 | 45.497 | 34.362 | 20.00 |
| 1159 | ILE | 1HG2 | 56.026 | 46.220 | 36.689 | 20.00 |
| 1160 | ILE | 2HG2 | 54.753 | 46.467 | 37.845 | 20.00 |
| 1161 | ILE | 3HG2 | 54.556 | 47.094 | 36.229 | 20.00 |
| 1162 | ILE | 1HD1 | 53.156 | 42.977 | 34.619 | 20.00 |
| 1163 | ILE | 2HD1 | 54.904 | 42.685 | 34.471 | 20.00 |
| 1164 | ILE | 3HD1 | 54.016 | 43.465 | 33.195 | 20.00 |
| 1165 | LYS | N | 55.961 | 44.052 | 39.204 | 16.38 |
| 1166 | LYS | CA | 56.155 | 44.186 | 40.594 | 19.03 |
| 1167 | LYS | C | 56.848 | 45.516 | 40.860 | 18.79 |
| 1168 | LYS | O | 58.065 | 45.591 | 40.884 | 18.39 |
| 1169 | LYS | CB | 56.939 | 42.956 | 40.929 | 24.89 |
| 1170 | LYS | CG | 56.912 | 42.866 | 42.439 | 36.70 |
| 1171 | LYS | CD | 57.328 | 41.533 | 43.051 | 45.35 |
| 1172 | LYS | CE | 57.186 | 41.692 | 44.560 | 49.89 |
| 1173 | LYS | NZ | 57.538 | 40.467 | 45.290 | 53.29 |
| 1174 | LYS | H | 56.745 | 43.962 | 38.586 | 20.00 |
| 1175 | LYS | HA | 55.199 | 44.202 | 41.123 | 20.00 |
| 1176 | LYS | 1HB | 57.961 | 43.013 | 40.539 | 20.00 |
| 1177 | LYS | 2HB | 56.467 | 42.081 | 40.482 | 20.00 |
| 1178 | LYS | 1HG | 55.910 | 43.036 | 42.726 | 20.00 |
| 1179 | LYS | 2HG | 57.473 | 43.692 | 42.872 | 20.00 |
| 1180 | LYS | 1HD | 58.364 | 41.333 | 42.777 | 20.00 |
| 1181 | LYS | 2HD | 56.711 | 40.725 | 42.648 | 20.00 |
| 1182 | LYS | 1HE | 56.135 | 41.919 | 44.779 | 20.00 |
| 1183 | LYS | 2HE | 57.770 | 42.540 | 44.932 | 20.00 |
| 1184 | LYS | 1HZ | 58.555 | 40.282 | 45.176 | 20.00 |
| 1185 | LYS | 2HZ | 57.015 | 39.665 | 44.873 | 20.00 |
| 1186 | LYS | 3HZ | 57.314 | 40.520 | 46.304 | 20.00 |
| 1187 | MET | N | 56.027 | 46.767 | 41.062 | 17.44 |
| 1188 | MET | CA | 56.634 | 47.846 | 41.393 | 17.07 |
| 1189 | MET | C | 57.007 | 47.929 | 42.923 | 17.04 |
| 1190 | MET | O | 56.147 | 48.095 | 43.790 | 16.87 |
| 1191 | MET | CB | 55.675 | 48.907 | 40.957 | 15.46 |
| 1192 | MET | CG | 55.291 | 48.734 | 39.503 | 15.47 |
| 1193 | MET | SD | 56.753 | 48.529 | 38.450 | 16.71 |
| 1194 | MET | CE | 57.080 | 50.195 | 38.026 | 12.89 |
| 1195 | MET | H | 55.032 | 46.464 | 41.035 | 20.00 |
| 1196 | MET | HA | 57.546 | 47.951 | 40.808 | 20.00 |
| 1197 | MET | 1HB | 56.133 | 49.884 | 41.087 | 20.00 |
| 1198 | MET | 2HB | 54.772 | 48.927 | 41.568 | 20.00 |
| 1199 | MET | 1HG | 54.709 | 49.588 | 39.160 | 20.00 |
| 1200 | MET | 2HG | 54.618 | 47.892 | 39.385 | 20.00 |
| 1201 | MET | 1HE | 57.389 | 50.721 | 38.923 | 20.00 |
| 1202 | MET | 2HE | 56.172 | 50.653 | 37.664 | 20.00 |
| 1203 | MET | 3HE | 57.869 | 50.255 | 37.283 | 20.00 |
| 1204 | GLU | N | 58.311 | 47.763 | 43.214 | 20.27 |
| 1205 | GLU | CA | 58.778 | 47.729 | 44.589 | 22.54 |
| 1206 | GLU | C | 58.455 | 49.032 | 45.367 | 22.33 |
| 1207 | GLU | O | 57.551 | 49.145 | 46.174 | 24.08 |
| 1208 | GLU | CB | 60.261 | 47.369 | 44.550 | 26.36 |
| 1209 | GLU | CG | 60.752 | 46.542 | 45.777 | 35.25 |
| 1210 | GLU | CD | 62.306 | 46.400 | 45.765 | 40.00 |
| 1211 | GLU | OE1 | 63.007 | 47.377 | 46.070 | 43.15 |
| 1212 | GLU | OE2 | 62.798 | 45.322 | 45.423 | 43.54 |
| 1213 | GLU | H | 58.846 | 47.524 | 42.399 | 20.00 |
| 1214 | GLU | HA | 58.235 | 46.912 | 45.065 | 20.00 |
| 1215 | GLU | 1HB | 60.894 | 48.246 | 44.415 | 20.00 |
| 1216 | GLU | 2HB | 60.457 | 46.747 | 43.675 | 20.00 |
| 1217 | GLU | 1HG | 60.308 | 45.548 | 45.809 | 20.00 |
| 1218 | GLU | 2HG | 60.494 | 47.045 | 46.708 | 20.00 |
| 1219 | GLU | N | 59.176 | 50.055 | 45.053 | 23.41 |
| 1220 | GLU | CA | 58.964 | 51.347 | 45.670 | 24.81 |
| 1221 | GLU | C | 57.479 | 51.755 | 45.865 | 24.74 |
| 1222 | GLU | O | 57.051 | 52.142 | 46.947 | 24.77 |
| 1223 | GLU | CB | 59.765 | 52.321 | 44.797 | 26.99 |
| 1224 | GLU | CG | 59.810 | 53.801 | 45.255 | 35.79 |
| 1225 | GLU | CD | 60.222 | 54.688 | 44.049 | 45.06 |
| 1226 | GLU | OE1 | 59.969 | 54.335 | 42.876 | 48.32 |
| 1227 | GLU | OE2 | 60.747 | 55.769 | 44.308 | 49.68 |
| 1228 | GLU | H | 59.978 | 49.853 | 44.499 | 20.00 |
| 1229 | GLU | HA | 59.422 | 51.306 | 46.657 | 20.00 |
| 1230 | GLU | 1HB | 59.378 | 52.294 | 43.798 | 20.00 |
| 1231 | GLU | 2HB | 60.779 | 51.944 | 44.681 | 20.00 |
| 1232 | GLU | 1HG | 60.583 | 53.892 | 46.009 | 20.00 |
| 1233 | GLU | 2HG | 58.858 | 54.133 | 45.660 | 20.00 |
| 1234 | ALA | N | 56.670 | 51.652 | 44.799 | 22.17 |
| 1235 | ALA | CA | 55.246 | 52.057 | 44.836 | 21.64 |
| 1236 | ALA | C | 54.539 | 51.006 | 45.549 | 22.46 |
| 1237 | ALA | O | 53.160 | 51.123 | 45.691 | 24.05 |
| 1238 | ALA | CB | 54.806 | 52.202 | 43.393 | 20.53 |
| 1239 | ALA | H | 57.053 | 51.248 | 43.967 | 20.00 |
| 1240 | ALA | HA | 55.174 | 53.008 | 45.366 | 20.00 |
| 1241 | ALA | 1HB | 54.756 | 51.228 | 42.929 | 20.00 |
| 1242 | ALA | 2HB | 55.522 | 52.775 | 42.815 | 20.00 |
| 1243 | ALA | 3HB | 53.829 | 52.664 | 43.317 | 20.00 |
| 1244 | GLN | N | 55.030 | 49.944 | 45.995 | 23.74 |
| 1245 | GLN | CA | 54.391 | 48.860 | 46.644 | 27.80 |
| 1246 | GLN | C | 53.125 | 48.391 | 45.853 | 26.92 |
| 1247 | GLN | O | 52.149 | 47.989 | 46.495 | 27.71 |
| 1248 | GLN | CB | 54.140 | 49.267 | 48.138 | 32.88 |
| 1249 | GLN | CG | 55.326 | 49.006 | 49.110 | 40.36 |
| 1250 | GLN | CD | 55.212 | 47.532 | 49.760 | 47.19 |
| 1251 | GLN | OE1 | 54.421 | 47.292 | 50.673 | 52.84 |
| 1252 | GLN | NE2 | 56.012 | 46.546 | 49.265 | 46.59 |
| 1253 | GLN | H | 55.964 | 49.826 | 45.665 | 20.00 |
| 1254 | GLN | HA | 55.085 | 48.022 | 46.580 | 20.00 |
| 1255 | GLN | 1HB | 53.282 | 48.717 | 48.513 | 20.00 |
| 1256 | GLN | 2HB | 53.816 | 50.302 | 48.171 | 20.00 |
| 1257 | GLN | 1HG | 55.368 | 49.735 | 49.918 | 20.00 |
| 1258 | GLN | 2HG | 56.264 | 49.080 | 48.553 | 20.00 |
| 1259 | GLN | 1HE2 | 55.903 | 45.690 | 49.757 | 20.00 |
| 1260 | GLN | 2HE2 | 56.637 | 46.689 | 48.503 | 20.00 |
| 1261 | ARG | N | 53.166 | 48.361 | 44.464 | 23.43 |
| 1262 | ARG | CA | 52.057 | 47.713 | 43.751 | 18.91 |
| 1263 | ARG | C | 52.453 | 46.726 | 42.694 | 16.84 |
| 1264 | ARG | O | 53.318 | 47.057 | 41.916 | 17.96 |
| 1265 | ARG | CB | 51.320 | 48.807 | 43.076 | 18.58 |
| 1266 | ARG | CG | 50.098 | 48.257 | 42.395 | 16.36 |
| 1267 | ARG | CD | 49.034 | 49.322 | 42.305 | 17.70 |
| 1268 | ARG | NE | 48.208 | 49.346 | 43.527 | 17.29 |
| 1269 | ARG | CZ | 47.441 | 50.424 | 43.806 | 15.94 |
| 1270 | ARG | NH1 | 47.297 | 51.403 | 42.891 | 13.68 |
| 1271 | ARG | NH2 | 46.819 | 50.417 | 44.975 | 18.40 |
| 1272 | ARG | H | 54.018 | 48.616 | 44.002 | 20.00 |
| 1273 | ARG | HA | 51.427 | 47.185 | 44.462 | 20.00 |
| 1274 | ARG | 1HB | 51.976 | 49.317 | 42.372 | 20.00 |
| 1275 | ARG | 2HB | 51.053 | 49.558 | 43.825 | 20.00 |
| 1276 | ARG | 1HG | 49.683 | 47.403 | 42.929 | 20.00 |
| 1277 | ARG | 2HG | 50.353 | 47.899 | 41.397 | 20.00 |
| 1278 | ARG | 1HD | 48.372 | 49.152 | 41.452 | 20.00 |
| 1279 | ARG | 2HD | 49.446 | 50.319 | 42.247 | 20.00 |
| 1280 | ARG | HE | 48.258 | 48.588 | 44.171 | 20.00 |
| 1281 | ARG | 1HH1 | 46.755 | 52.223 | 43.004 | 20.00 |
| 1282 | ARG | 2HH1 | 47.752 | 51.289 | 41.992 | 20.00 |
| 1283 | ARG | 1HH2 | 46.269 | 51.202 | 45.245 | 20.00 |
| 1284 | ARG | 2HH2 | 46.898 | 49.595 | 45.539 | 20.00 |
| 1285 | SER | N | 51.766 | 45.572 | 42.683 | 13.82 |
| 1286 | SER | CA | 51.692 | 44.596 | 41.633 | 12.48 |
| 1287 | SER | C | 50.434 | 44.551 | 40.727 | 11.37 |
| 1288 | SER | O | 49.287 | 44.615 | 41.157 | 13.16 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1289 | SER | CB | 51.817 | 43.113 | 42.100 | 12.86 |
| 1290 | SER | OG | 53.028 | 42.834 | 42.899 | 19.01 |
| 1291 | SER | H | 51.167 | 45.419 | 43.464 | 20.00 |
| 1292 | SER | HA | 52.523 | 44.871 | 41.005 | 20.00 |
| 1293 | SER | 1HB | 51.950 | 42.559 | 41.136 | 20.00 |
| 1294 | SER | 2HB | 50.804 | 42.672 | 42.377 | 20.00 |
| 1295 | SER | HG | 53.168 | 43.269 | 43.803 | 20.00 |
| 1296 | TYR | N | 50.787 | 44.235 | 39.430 | 11.99 |
| 1297 | TYR | CA | 49.732 | 44.002 | 38.418 | 10.12 |
| 1298 | TYR | C | 50.149 | 42.759 | 37.675 | 10.62 |
| 1299 | TYR | O | 51.329 | 42.534 | 37.602 | 11.32 |
| 1300 | TYR | CB | 49.562 | 45.151 | 37.368 | 10.39 |
| 1301 | TYR | CG | 49.764 | 46.542 | 37.950 | 10.08 |
| 1302 | TYR | CD1 | 51.063 | 46.952 | 38.255 | 10.55 |
| 1303 | TYR | CD2 | 48.695 | 47.416 | 38.159 | 10.53 |
| 1304 | TYR | CE1 | 51.305 | 48.211 | 38.707 | 12.90 |
| 1305 | TYR | CE2 | 48.895 | 48.689 | 38.649 | 12.10 |
| 1306 | TYR | CZ | 50.180 | 49.106 | 38.885 | 13.13 |
| 1307 | TYR | OH | 50.199 | 50.433 | 39.253 | 13.22 |
| 1308 | TYR | H | 51.751 | 44.131 | 39.179 | 20.00 |
| 1309 | TYR | HA | 48.782 | 43.799 | 38.924 | 20.00 |
| 1310 | TYR | 1HB | 48.582 | 45.095 | 36.888 | 20.00 |
| 1311 | TYR | 2HB | 50.285 | 45.040 | 36.555 | 20.00 |
| 1312 | TYR | HD1 | 51.873 | 46.248 | 38.135 | 20.00 |
| 1313 | TYR | HD2 | 47.680 | 47.117 | 37.910 | 20.00 |
| 1314 | TYR | HE1 | 52.383 | 48.243 | 38.882 | 20.00 |
| 1315 | TYR | HE2 | 48.058 | 49.352 | 38.782 | 20.00 |
| 1316 | TYR | HH | 50.979 | 50.728 | 39.691 | 20.00 |
| 1317 | ILE | N | 49.222 | 42.018 | 37.068 | 10.35 |
| 1318 | ILE | CA | 49.503 | 41.053 | 35.972 | 7.97 |
| 1319 | ILE | C | 49.087 | 41.676 | 34.586 | 9.78 |
| 1320 | ILE | O | 47.914 | 41.999 | 34.387 | 10.25 |
| 1321 | ILE | CB | 48.760 | 39.736 | 36.289 | 9.05 |
| 1322 | ILE | CG1 | 49.269 | 39.172 | 37.681 | 10.20 |
| 1323 | ILE | CG2 | 48.976 | 38.754 | 35.095 | 8.37 |
| 1324 | ILE | CD1 | 48.737 | 37.834 | 38.236 | 8.33 |
| 1325 | ILE | H | 48.275 | 42.270 | 37.213 | 20.00 |
| 1326 | ILE | HA | 50.572 | 40.865 | 35.958 | 20.00 |
| 1327 | ILE | HB | 47.694 | 39.953 | 36.380 | 20.00 |
| 1328 | ILE | 1HG1 | 49.048 | 39.919 | 38.429 | 20.00 |
| 1329 | ILE | 2HG1 | 50.359 | 39.121 | 37.645 | 20.00 |
| 1330 | ILE | 1HG2 | 50.043 | 38.615 | 34.936 | 20.00 |
| 1331 | ILE | 2HG2 | 48.543 | 39.117 | 34.167 | 20.00 |
| 1332 | ILE | 3HG2 | 48.537 | 37.783 | 35.302 | 20.00 |
| 1333 | ILE | 1HD1 | 49.021 | 37.050 | 37.542 | 20.00 |
| 1334 | ILE | 2HD1 | 47.661 | 37.804 | 38.225 | 20.00 |
| 1335 | ILE | 3HD1 | 49.128 | 37.549 | 39.212 | 20.00 |
| 1336 | LEU | N | 50.086 | 41.866 | 33.670 | 8.73 |
| 1337 | LEU | CA | 49.787 | 42.333 | 32.269 | 8.66 |
| 1338 | LEU | C | 49.661 | 41.053 | 31.404 | 11.10 |
| 1339 | LEU | O | 50.565 | 40.223 | 31.418 | 12.49 |
| 1340 | LEU | CB | 50.852 | 43.343 | 31.645 | 9.65 |
| 1341 | LEU | CG | 50.557 | 44.804 | 32.004 | 10.58 |
| 1342 | LEU | CD1 | 51.628 | 45.857 | 31.658 | 11.19 |
| 1343 | LEU | CD2 | 50.324 | 44.924 | 33.515 | 12.47 |
| 1344 | LEU | H | 50.995 | 41.592 | 33.979 | 20.00 |
| 1345 | LEU | HA | 48.813 | 42.831 | 32.284 | 20.00 |
| 1346 | LEU | 1HB | 50.867 | 43.235 | 30.561 | 20.00 |
| 1347 | LEU | 2HB | 51.845 | 43.080 | 32.000 | 20.00 |
| 1348 | LEU | HG | 49.634 | 45.070 | 31.499 | 20.00 |
| 1349 | LEU | 1HD1 | 51.749 | 45.864 | 30.559 | 20.00 |
| 1350 | LEU | 2HD1 | 52.586 | 45.584 | 32.073 | 20.00 |
| 1351 | LEU | 3HD1 | 51.364 | 46.862 | 31.958 | 20.00 |
| 1352 | LEU | 1HD2 | 51.193 | 44.547 | 34.051 | 20.00 |
| 1353 | LEU | 2HD2 | 49.440 | 44.385 | 33.853 | 20.00 |
| 1354 | LEU | 3HD2 | 50.173 | 45.958 | 33.809 | 20.00 |
| 1355 | THR | N | 48.531 | 40.850 | 30.708 | 10.83 |
| 1356 | THR | CA | 48.266 | 39.641 | 29.888 | 8.06 |
| 1357 | THR | C | 47.699 | 40.039 | 28.466 | 9.10 |
| 1358 | THR | O | 47.222 | 41.124 | 28.225 | 8.53 |
| 1359 | THR | CB | 47.333 | 38.650 | 30.660 | 8.87 |
| 1360 | THR | OG1 | 47.456 | 37.292 | 30.225 | 11.27 |
| 1361 | THR | CG2 | 45.834 | 39.019 | 30.813 | 8.63 |
| 1362 | THR | H | 47.838 | 41.569 | 30.829 | 20.00 |
| 1363 | THR | HA | 49.265 | 39.242 | 29.728 | 20.00 |
| 1364 | THR | HB | 47.726 | 38.689 | 31.711 | 20.00 |
| 1365 | THR | HG1 | 47.258 | 36.919 | 29.323 | 20.00 |
| 1366 | THR | 1HG2 | 45.238 | 39.174 | 29.907 | 20.00 |
| 1367 | THR | 2HG2 | 45.766 | 39.973 | 31.337 | 20.00 |
| 1368 | THR | 3HG2 | 45.335 | 38.315 | 31.484 | 20.00 |
| 1369 | GLN | N | 47.760 | 39.180 | 27.461 | 7.55 |
| 1370 | GLN | CA | 47.071 | 39.610 | 26.199 | 7.51 |
| 1371 | GLN | C | 45.534 | 39.436 | 26.344 | 8.15 |
| 1372 | GLN | O | 45.108 | 38.664 | 27.188 | 9.26 |
| 1373 | GLN | CB | 47.562 | 38.744 | 25.030 | 7.72 |
| 1374 | GLN | CG | 47.407 | 37.252 | 25.399 | 7.48 |
| 1375 | GLN | CD | 47.989 | 36.233 | 24.490 | 7.54 |
| 1376 | GLN | OE1 | 47.581 | 35.092 | 24.452 | 13.65 |
| 1377 | GLN | NE2 | 49.116 | 36.537 | 23.918 | 6.16 |
| 1378 | GLN | H | 48.093 | 38.257 | 27.639 | 20.00 |
| 1379 | GLN | HA | 47.281 | 40.663 | 25.990 | 20.00 |
| 1380 | GLN | 1HB | 48.615 | 38.974 | 24.855 | 20.00 |
| 1381 | GLN | 2HB | 47.022 | 38.964 | 24.104 | 20.00 |
| 1382 | GLN | 1HG | 46.374 | 36.962 | 25.596 | 20.00 |
| 1383 | GLN | 2HG | 47.973 | 37.052 | 26.297 | 20.00 |
| 1384 | GLN | 1HE2 | 49.523 | 35.662 | 23.730 | 20.00 |
| 1385 | GLN | 2HE2 | 49.492 | 37.437 | 23.695 | 20.00 |
| 1386 | GLY | N | 44.700 | 40.048 | 25.468 | 8.70 |
| 1387 | GLY | CA | 43.381 | 39.512 | 25.333 | 8.95 |
| 1388 | GLY | C | 43.447 | 37.969 | 25.067 | 10.89 |
| 1389 | GLY | O | 44.117 | 37.488 | 24.141 | 12.56 |
| 1390 | GLY | H | 45.110 | 40.695 | 24.840 | 20.00 |
| 1391 | GLY | 1HA | 42.923 | 40.000 | 24.471 | 20.00 |
| 1392 | GLY | 2HA | 42.825 | 39.769 | 26.226 | 20.00 |
| 1393 | PRO | N | 42.703 | 37.161 | 25.868 | 11.90 |
| 1394 | PRO | CA | 42.702 | 35.712 | 25.665 | 10.45 |
| 1395 | PRO | C | 42.336 | 35.222 | 24.206 | 12.59 |
| 1396 | PRO | O | 41.485 | 35.804 | 23.503 | 12.30 |
| 1397 | PRO | CB | 41.616 | 35.253 | 26.615 | 10.51 |
| 1398 | PRO | CG | 41.508 | 36.340 | 27.662 | 11.89 |
| 1399 | PRO | CD | 41.846 | 37.636 | 26.938 | 9.07 |
| 1400 | PRO | HA | 43.706 | 35.498 | 26.026 | 20.00 |
| 1401 | PRO | 1HB | 41.830 | 34.304 | 27.113 | 20.00 |
| 1402 | PRO | 2HB | 40.642 | 35.140 | 26.128 | 20.00 |
| 1403 | PRO | 1HG | 40.578 | 36.362 | 28.234 | 20.00 |
| 1404 | PRO | 2HG | 42.309 | 36.169 | 28.380 | 20.00 |
| 1405 | PRO | 1HD | 42.340 | 38.326 | 27.629 | 20.00 |
| 1406 | PRO | 2HD | 40.938 | 38.092 | 26.560 | 20.00 |
| 1407 | LEU | N | 42.979 | 34.139 | 23.738 | 13.19 |
| 1408 | LEU | CA | 42.570 | 33.451 | 22.471 | 14.02 |
| 1409 | LEU | C | 41.455 | 32.441 | 22.773 | 13.93 |
| 1410 | LEU | O | 41.173 | 32.179 | 23.932 | 12.95 |
| 1411 | LEU | CB | 43.705 | 32.668 | 21.783 | 13.39 |
| 1412 | LEU | CG | 44.875 | 33.411 | 21.125 | 14.69 |
| 1413 | LEU | CD1 | 46.091 | 33.381 | 21.981 | 13.28 |
| 1414 | LEU | CD2 | 44.589 | 34.682 | 20.356 | 12.21 |
| 1415 | LEU | H | 43.863 | 33.945 | 24.174 | 20.00 |
| 1416 | LEU | HA | 42.170 | 34.195 | 21.784 | 20.00 |
| 1417 | LEU | 1HB | 43.310 | 32.178 | 20.906 | 20.00 |
| 1418 | LEU | 2HB | 44.080 | 31.757 | 22.250 | 20.00 |
| 1419 | LEU | HG | 45.188 | 32.734 | 20.321 | 20.00 |
| 1420 | LEU | 1HD1 | 46.300 | 32.381 | 22.362 | 20.00 |
| 1421 | LEU | 2HD1 | 46.027 | 34.045 | 22.844 | 20.00 |
| 1422 | LEU | 3HD1 | 46.952 | 33.682 | 21.388 | 20.00 |
| 1423 | LEU | 1HD2 | 44.522 | 35.528 | 21.034 | 20.00 |
| 1424 | LEU | 2HD2 | 43.657 | 34.594 | 19.801 | 20.00 |
| 1425 | LEU | 3HD2 | 45.373 | 34.903 | 19.634 | 20.00 |
| 1426 | PRO | N | 40.810 | 31.845 | 21.721 | 16.81 |
| 1427 | PRO | CA | 39.625 | 31.072 | 21.951 | 17.34 |
| 1428 | PRO | C | 39.955 | 29.842 | 22.707 | 16.85 |
| 1429 | PRO | O | 39.063 | 29.280 | 23.267 | 18.24 |
| 1430 | PRO | CB | 39.185 | 30.662 | 20.513 | 17.12 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1431 | PRO | CG | 39.775 | 31.705 | 19.619 | 19.47 |
| 1432 | PRO | CD | 41.112 | 31.934 | 20.286 | 16.45 |
| 1433 | PRO | HA | 38.865 | 31.652 | 22.479 | 20.00 |
| 1434 | PRO | 1HB | 38.100 | 30.601 | 20.422 | 20.00 |
| 1435 | PRO | 2HB | 39.579 | 29.685 | 20.211 | 20.00 |
| 1436 | PRO | 1HG | 39.869 | 31.368 | 18.588 | 20.00 |
| 1437 | PRO | 2HG | 39.170 | 32.614 | 19.648 | 20.00 |
| 1438 | PRO | 1HD | 41.526 | 32.906 | 20.005 | 20.00 |
| 1439 | PRO | 2HD | 41.807 | 31.143 | 19.988 | 20.00 |
| 1440 | ASN | N | 41.232 | 29.451 | 22.729 | 15.30 |
| 1441 | ASN | CA | 41.785 | 28.298 | 23.484 | 14.86 |
| 1442 | ASN | C | 42.556 | 28.687 | 24.770 | 15.36 |
| 1443 | ASN | O | 43.108 | 27.833 | 25.417 | 15.84 |
| 1444 | ASN | CB | 42.877 | 27.529 | 22.617 | 14.48 |
| 1445 | ASN | CG | 44.147 | 28.314 | 22.038 | 16.03 |
| 1446 | ASN | OD1 | 44.043 | 29.255 | 21.263 | 19.68 |
| 1447 | ASN | ND2 | 45.329 | 27.892 | 22.449 | 15.67 |
| 1448 | ASN | H | 41.818 | 29.895 | 22.060 | 20.00 |
| 1449 | ASN | HA | 40.954 | 27.643 | 23.757 | 20.00 |
| 1450 | ASN | 1HB | 42.375 | 27.105 | 21.737 | 20.00 |
| 1451 | ASN | 2HB | 43.249 | 26.672 | 23.187 | 20.00 |
| 1452 | ASN | 1HD2 | 46.001 | 28.521 | 22.054 | 20.00 |
| 1453 | ASN | 2HD2 | 45.568 | 27.139 | 23.052 | 20.00 |
| 1454 | THR | N | 42.650 | 29.978 | 25.133 | 15.02 |
| 1455 | THR | CA | 43.391 | 30.291 | 26.417 | 12.29 |
| 1456 | THR | C | 42.474 | 31.036 | 27.517 | 11.96 |
| 1457 | THR | O | 42.852 | 31.476 | 28.583 | 11.69 |
| 1458 | THR | CB | 44.719 | 31.008 | 26.014 | 10.87 |
| 1459 | THR | OG1 | 44.565 | 32.343 | 25.555 | 10.92 |
| 1460 | THR | CG2 | 45.584 | 30.273 | 25.027 | 10.49 |
| 1461 | THR | H | 42.262 | 30.664 | 24.515 | 20.00 |
| 1462 | THR | HA | 43.646 | 29.369 | 26.917 | 20.00 |
| 1463 | THR | HB | 45.361 | 30.992 | 26.941 | 20.00 |
| 1464 | THR | HG1 | 43.754 | 32.671 | 25.107 | 20.00 |
| 1465 | THR | 1HG2 | 45.153 | 30.085 | 24.039 | 20.00 |
| 1466 | THR | 2HG2 | 45.915 | 29.312 | 25.408 | 20.00 |
| 1467 | THR | 3HG2 | 46.499 | 30.848 | 24.857 | 20.00 |
| 1468 | CYS | N | 41.161 | 31.075 | 27.244 | 14.04 |
| 1469 | CYS | CA | 40.171 | 31.667 | 28.138 | 14.17 |
| 1470 | CYS | C | 40.085 | 30.933 | 29.493 | 12.97 |
| 1471 | CYS | O | 39.963 | 31.492 | 30.591 | 13.90 |
| 1472 | CYS | CB | 38.786 | 31.617 | 27.536 | 13.16 |
| 1473 | CYS | SG | 38.550 | 32.838 | 26.281 | 15.24 |
| 1474 | CYS | H | 40.878 | 30.770 | 26.336 | 20.00 |
| 1475 | CYS | HA | 40.460 | 32.696 | 28.339 | 20.00 |
| 1476 | CYS | 1HB | 38.031 | 31.820 | 28.305 | 20.00 |
| 1477 | CYS | 2HB | 38.541 | 30.623 | 27.152 | 20.00 |
| 1478 | CYS | HG | 38.695 | 32.291 | 25.082 | 20.00 |
| 1479 | GLY | N | 40.243 | 29.645 | 29.298 | 13.25 |
| 1480 | GLY | CA | 40.387 | 28.785 | 30.429 | 14.11 |
| 1481 | GLY | C | 41.808 | 28.832 | 31.180 | 14.77 |
| 1482 | GLY | O | 41.877 | 28.613 | 32.340 | 15.71 |
| 1483 | GLY | H | 40.296 | 29.275 | 28.376 | 20.00 |
| 1484 | GLY | 1HA | 40.315 | 27.866 | 29.861 | 20.00 |
| 1485 | GLY | 2HA | 39.548 | 29.026 | 31.088 | 20.00 |
| 1486 | HIS | N | 42.939 | 29.144 | 30.573 | 15.04 |
| 1487 | HIS | CA | 44.200 | 29.473 | 31.244 | 13.49 |
| 1488 | HIS | C | 43.971 | 30.831 | 31.942 | 14.38 |
| 1489 | HIS | O | 44.520 | 31.190 | 32.974 | 15.19 |
| 1490 | HIS | CB | 45.303 | 29.659 | 30.149 | 12.89 |
| 1491 | HIS | CG | 45.443 | 28.449 | 29.222 | 14.63 |
| 1492 | HIS | ND1 | 45.683 | 28.487 | 27.875 | 13.48 |
| 1493 | HIS | CD2 | 45.237 | 27.096 | 29.517 | 16.55 |
| 1494 | HIS | CE1 | 45.572 | 27.255 | 27.426 | 14.33 |
| 1495 | HIS | NE2 | 45.317 | 26.382 | 28.410 | 15.87 |
| 1496 | HIS | H | 42.914 | 28.968 | 29.590 | 20.00 |
| 1497 | HIS | HA | 44.420 | 28.687 | 31.970 | 20.00 |
| 1498 | HIS | 1HB | 46.257 | 29.992 | 30.558 | 20.00 |
| 1499 | HIS | 2HB | 44.992 | 30.483 | 29.501 | 20.00 |
| 1500 | HIS | HD1 | 45.880 | 29.274 | 27.336 | 20.00 |
| 1501 | HIS | HD2 | 44.997 | 26.700 | 30.496 | 20.00 |
| 1502 | HIS | HE1 | 45.646 | 26.975 | 26.381 | 20.00 |
| 1503 | PHE | N | 43.159 | 31.695 | 31.311 | 12.72 |
| 1504 | PHE | CA | 43.089 | 33.072 | 31.837 | 12.68 |
| 1505 | PHE | C | 42.415 | 33.006 | 33.201 | 13.22 |
| 1506 | PHE | O | 42.872 | 33.545 | 34.203 | 12.12 |
| 1507 | PHE | CB | 42.315 | 33.909 | 30.774 | 12.82 |
| 1508 | PHE | CG | 42.032 | 35.335 | 31.183 | 9.60 |
| 1509 | PHE | CD1 | 40.875 | 35.627 | 31.879 | 8.18 |
| 1510 | PHE | CD2 | 42.919 | 36.384 | 30.909 | 8.54 |
| 1511 | PHE | CE1 | 40.653 | 36.859 | 32.368 | 11.79 |
| 1512 | PHE | CE2 | 42.654 | 37.665 | 31.367 | 11.03 |
| 1513 | PHE | CZ | 41.535 | 37.845 | 32.118 | 10.70 |
| 1514 | PHE | H | 42.743 | 31.410 | 30.457 | 20.00 |
| 1515 | PHE | HA | 44.103 | 33.467 | 31.947 | 20.00 |
| 1516 | PHE | 1HB | 41.355 | 33.453 | 30.563 | 20.00 |
| 1517 | PHE | 2HB | 42.841 | 33.912 | 29.814 | 20.00 |
| 1518 | PHE | HD1 | 40.158 | 34.849 | 32.083 | 20.00 |
| 1519 | PHE | HD2 | 43.824 | 36.183 | 30.347 | 20.00 |
| 1520 | PHE | HE1 | 39.765 | 37.060 | 32.953 | 20.00 |
| 1521 | PHE | HE2 | 43.281 | 38.521 | 31.136 | 20.00 |
| 1522 | PHE | HZ | 41.317 | 38.835 | 32.490 | 20.00 |
| 1523 | TRP | N | 41.278 | 32.289 | 33.173 | 12.17 |
| 1524 | TRP | CA | 40.450 | 32.222 | 34.411 | 12.15 |
| 1525 | TRP | C | 41.113 | 31.433 | 35.595 | 12.77 |
| 1526 | TRP | O | 41.043 | 31.813 | 36.756 | 12.89 |
| 1527 | TRP | CB | 39.015 | 31.707 | 34.001 | 13.28 |
| 1528 | TRP | CG | 38.226 | 32.858 | 33.399 | 13.46 |
| 1529 | TRP | CD1 | 37.724 | 32.964 | 32.065 | 13.99 |
| 1530 | TRP | CD2 | 37.952 | 34.113 | 34.051 | 12.69 |
| 1531 | TRP | NE1 | 37.180 | 34.195 | 31.900 | 13.76 |
| 1532 | TRP | CE2 | 37.314 | 34.931 | 33.090 | 12.21 |
| 1533 | TRP | CE3 | 38.279 | 34.589 | 35.303 | 11.54 |
| 1534 | TRP | CZ2 | 36.958 | 36.217 | 33.415 | 11.49 |
| 1535 | TRP | CZ3 | 37.922 | 35.900 | 35.617 | 12.46 |
| 1536 | TRP | CH2 | 37.265 | 36.700 | 34.699 | 11.61 |
| 1537 | TRP | H | 40.911 | 31.965 | 32.302 | 20.00 |
| 1538 | TRP | HA | 40.399 | 33.229 | 34.783 | 20.00 |
| 1539 | TRP | 1HB | 38.472 | 31.313 | 34.862 | 20.00 |
| 1540 | TRP | 2HB | 39.104 | 30.873 | 33.295 | 20.00 |
| 1541 | TRP | HD1 | 37.760 | 32.155 | 31.345 | 20.00 |
| 1542 | TRP | HE1 | 36.707 | 34.474 | 31.085 | 20.00 |
| 1543 | TRP | HE3 | 38.784 | 33.971 | 36.026 | 20.00 |
| 1544 | TRP | HZ2 | 36.450 | 36.835 | 32.687 | 20.00 |
| 1545 | TRP | HZ3 | 38.094 | 36.300 | 36.599 | 20.00 |
| 1546 | TRP | HH2 | 36.986 | 37.699 | 34.976 | 20.00 |
| 1547 | GLU | N | 41.780 | 30.326 | 35.178 | 13.48 |
| 1548 | GLU | CA | 42.730 | 29.627 | 35.996 | 12.78 |
| 1549 | GLU | C | 43.768 | 30.566 | 36.534 | 13.54 |
| 1550 | GLU | O | 43.972 | 30.594 | 37.732 | 13.56 |
| 1551 | GLU | CB | 43.388 | 28.531 | 35.219 | 11.88 |
| 1552 | GLU | CG | 44.436 | 27.771 | 36.130 | 15.11 |
| 1553 | GLU | CD | 45.202 | 26.754 | 35.308 | 17.43 |
| 1554 | GLU | OE1 | 44.936 | 26.639 | 34.112 | 19.12 |
| 1555 | GLU | OE2 | 46.076 | 26.069 | 35.793 | 19.81 |
| 1556 | GLU | H | 41.624 | 30.031 | 34.237 | 20.00 |
| 1557 | GLU | HA | 42.211 | 29.204 | 36.855 | 20.00 |
| 1558 | GLU | 1HB | 43.840 | 28.925 | 34.313 | 20.00 |
| 1559 | GLU | 2HB | 42.624 | 27.820 | 34.904 | 20.00 |
| 1560 | GLU | 1HG | 43.929 | 27.252 | 36.939 | 20.00 |
| 1561 | GLU | 2HG | 45.161 | 28.434 | 36.597 | 20.00 |
| 1562 | MET | N | 44.363 | 31.442 | 35.736 | 11.71 |
| 1563 | MET | CA | 45.348 | 32.380 | 36.339 | 12.23 |
| 1564 | MET | C | 44.716 | 33.407 | 37.337 | 11.68 |
| 1565 | MET | O | 45.324 | 33.773 | 38.327 | 11.24 |
| 1566 | MET | CB | 46.127 | 33.111 | 35.218 | 9.82 |
| 1567 | MET | CG | 46.844 | 34.402 | 35.674 | 11.63 |
| 1568 | MET | SD | 47.623 | 35.297 | 34.348 | 15.04 |
| 1569 | MET | CE | 46.176 | 36.105 | 33.568 | 11.38 |
| 1570 | MET | H | 44.302 | 31.230 | 34.763 | 20.00 |
| 1571 | MET | HA | 46.042 | 31.771 | 36.918 | 20.00 |
| 1572 | MET | 1HB | 45.456 | 33.358 | 34.395 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1573 | MET | 2HB | 46.859 | 32.430 | 34.785 | 20.00 |
| 1574 | MET | 1HG | 47.575 | 34.147 | 36.441 | 20.00 |
| 1575 | MET | 2HG | 46.154 | 35.105 | 36.154 | 20.00 |
| 1576 | MET | 1HE | 45.659 | 36.709 | 34.305 | 20.00 |
| 1577 | MET | 2HE | 45.493 | 35.347 | 33.206 | 20.00 |
| 1578 | MET | 3HE | 46.520 | 36.723 | 32.753 | 20.00 |
| 1579 | VAL | N | 43.503 | 33.877 | 37.018 | 12.17 |
| 1580 | VAL | CA | 42.734 | 34.719 | 37.923 | 10.63 |
| 1581 | VAL | C | 42.543 | 33.925 | 39.336 | 13.77 |
| 1582 | VAL | O | 42.754 | 34.422 | 40.455 | 14.26 |
| 1583 | VAL | CB | 41.481 | 35.257 | 37.215 | 10.58 |
| 1584 | VAL | CG1 | 41.931 | 36.174 | 36.095 | 8.22 |
| 1585 | VAL | CG2 | 40.524 | 36.097 | 38.147 | 10.48 |
| 1586 | VAL | H | 43.171 | 33.627 | 36.109 | 20.00 |
| 1587 | VAL | HA | 43.374 | 35.574 | 38.158 | 20.00 |
| 1588 | VAL | HB | 40.927 | 34.414 | 36.800 | 20.00 |
| 1589 | VAL | 1HG1 | 42.614 | 35.675 | 35.400 | 20.00 |
| 1590 | VAL | 2HG1 | 42.457 | 37.043 | 36.488 | 20.00 |
| 1591 | VAL | 3HG1 | 41.073 | 36.507 | 35.505 | 20.00 |
| 1592 | VAL | 1HG2 | 41.087 | 36.909 | 38.606 | 20.00 |
| 1593 | VAL | 2HG2 | 40.113 | 35.494 | 38.956 | 20.00 |
| 1594 | VAL | 3HG2 | 39.722 | 36.595 | 37.623 | 20.00 |
| 1595 | TRP | N | 42.224 | 32.627 | 39.175 | 13.52 |
| 1596 | TRP | CA | 42.001 | 31.790 | 40.338 | 14.59 |
| 1597 | TRP | C | 43.264 | 31.610 | 41.155 | 15.04 |
| 1598 | TRP | O | 43.328 | 32.070 | 42.288 | 16.22 |
| 1599 | TRP | CB | 41.340 | 30.544 | 39.858 | 12.97 |
| 1600 | TRP | CG | 40.867 | 29.820 | 41.069 | 17.46 |
| 1601 | TRP | CD1 | 41.606 | 28.897 | 41.786 | 21.61 |
| 1602 | TRP | CD2 | 39.602 | 29.940 | 41.731 | 19.79 |
| 1603 | TRP | NE1 | 40.899 | 28.456 | 42.861 | 23.85 |
| 1604 | TRP | CE2 | 39.653 | 29.065 | 42.870 | 22.70 |
| 1605 | TRP | CE3 | 38.464 | 30.605 | 41.428 | 21.09 |
| 1606 | TRP | CZ2 | 38.576 | 28.895 | 43.700 | 21.76 |
| 1607 | TRP | CZ3 | 37.360 | 30.412 | 42.267 | 21.15 |
| 1608 | TRP | CH2 | 37.413 | 29.570 | 43.399 | 21.23 |
| 1609 | TRP | H | 42.074 | 32.302 | 38.246 | 20.00 |
| 1610 | TRP | HA | 41.294 | 32.332 | 40.966 | 20.00 |
| 1611 | TRP | 1HB | 42.030 | 29.916 | 39.289 | 20.00 |
| 1612 | TRP | 2HB | 40.487 | 30.754 | 39.199 | 20.00 |
| 1613 | TRP | HD1 | 42.618 | 28.612 | 41.516 | 20.00 |
| 1614 | TRP | HE1 | 41.220 | 27.834 | 43.554 | 20.00 |
| 1615 | TRP | HE3 | 38.407 | 31.218 | 40.555 | 20.00 |
| 1616 | TRP | HZ2 | 38.667 | 28.250 | 44.569 | 20.00 |
| 1617 | TRP | HZ3 | 36.437 | 30.916 | 42.045 | 20.00 |
| 1618 | TRP | HH2 | 36.555 | 29.455 | 44.032 | 20.00 |
| 1619 | GLU | N | 44.259 | 30.940 | 40.543 | 16.06 |
| 1620 | GLU | CA | 45.592 | 30.695 | 41.135 | 15.05 |
| 1621 | GLU | C | 46.223 | 31.929 | 41.826 | 16.50 |
| 1622 | GLU | O | 46.831 | 31.834 | 42.894 | 18.37 |
| 1623 | GLU | CB | 46.473 | 30.020 | 40.099 | 13.43 |
| 1624 | GLU | CG | 45.967 | 28.568 | 39.973 | 13.77 |
| 1625 | GLU | CD | 46.558 | 27.837 | 38.747 | 14.43 |
| 1626 | GLU | OE1 | 47.458 | 28.382 | 38.119 | 15.87 |
| 1627 | GLU | OE2 | 46.113 | 26.745 | 38.435 | 15.61 |
| 1628 | GLU | H | 44.114 | 30.564 | 39.620 | 20.00 |
| 1629 | GLU | HA | 45.422 | 29.979 | 41.932 | 20.00 |
| 1630 | GLU | 1HB | 47.522 | 30.030 | 40.407 | 20.00 |
| 1631 | GLU | 2HB | 46.364 | 30.567 | 39.152 | 20.00 |
| 1632 | GLU | 1HG | 44.895 | 28.546 | 39.840 | 20.00 |
| 1633 | GLU | 2HG | 46.191 | 27.991 | 40.858 | 20.00 |
| 1634 | GLN | N | 45.999 | 33.062 | 41.202 | 14.99 |
| 1635 | GLN | CA | 46.714 | 34.258 | 41.610 | 14.10 |
| 1636 | GLN | C | 45.841 | 35.103 | 42.496 | 14.79 |
| 1637 | GLN | O | 46.292 | 36.113 | 42.957 | 14.03 |
| 1638 | GLN | CB | 47.074 | 35.107 | 40.341 | 13.84 |
| 1639 | GLN | CG | 48.001 | 34.423 | 39.298 | 14.77 |
| 1640 | GLN | CD | 49.291 | 33.960 | 40.073 | 20.12 |
| 1641 | GLN | OE1 | 49.843 | 34.780 | 40.814 | 21.85 |
| 1642 | GLN | NE2 | 49.740 | 32.664 | 39.964 | 18.11 |
| 1643 | GLN | H | 45.582 | 33.013 | 40.294 | 20.00 |
| 1644 | GLN | HA | 47.620 | 34.012 | 42.178 | 20.00 |
| 1645 | GLN | 1HB | 47.560 | 36.034 | 40.653 | 20.00 |
| 1646 | GLN | 2HB | 46.157 | 35.450 | 39.856 | 20.00 |
| 1647 | GLN | 1HG | 48.269 | 35.110 | 38.493 | 20.00 |
| 1648 | GLN | 2HG | 47.536 | 33.553 | 38.850 | 20.00 |
| 1649 | GLN | 1HE2 | 50.530 | 32.405 | 40.514 | 20.00 |
| 1650 | GLN | 2HE2 | 49.411 | 31.946 | 39.364 | 20.00 |
| 1651 | LYS | N | 44.583 | 34.682 | 42.756 | 14.24 |
| 1652 | LYS | CA | 43.720 | 35.355 | 43.752 | 15.01 |
| 1653 | LYS | C | 43.390 | 36.821 | 43.456 | 12.96 |
| 1654 | LYS | O | 43.245 | 37.665 | 44.331 | 13.31 |
| 1655 | LYS | CB | 44.218 | 35.116 | 45.226 | 19.21 |
| 1656 | LYS | CG | 44.427 | 33.587 | 45.521 | 21.85 |
| 1657 | LYS | CD | 44.580 | 33.241 | 47.008 | 29.47 |
| 1658 | LYS | CE | 45.043 | 31.802 | 47.295 | 31.82 |
| 1659 | LYS | NZ | 46.358 | 31.625 | 46.658 | 37.86 |
| 1660 | LYS | H | 44.246 | 33.917 | 42.208 | 20.00 |
| 1661 | LYS | HA | 42.775 | 34.834 | 43.635 | 20.00 |
| 1662 | LYS | 1HB | 43.461 | 35.509 | 45.903 | 20.00 |
| 1663 | LYS | 2HB | 45.135 | 35.675 | 45.430 | 20.00 |
| 1664 | LYS | 1HG | 45.269 | 33.231 | 44.929 | 20.00 |
| 1665 | LYS | 2HG | 43.538 | 33.081 | 45.155 | 20.00 |
| 1666 | LYS | 1HD | 43.644 | 33.429 | 47.532 | 20.00 |
| 1667 | LYS | 2HD | 45.293 | 33.928 | 47.452 | 20.00 |
| 1668 | LYS | 1HE | 44.353 | 31.026 | 46.952 | 20.00 |
| 1669 | LYS | 2HE | 45.156 | 31.662 | 48.378 | 20.00 |
| 1670 | LYS | 1HZ | 47.041 | 32.309 | 47.036 | 20.00 |
| 1671 | LYS | 2HZ | 46.295 | 31.809 | 45.636 | 20.00 |
| 1672 | LYS | 3HZ | 46.730 | 30.665 | 46.798 | 20.00 |
| 1673 | SER | N | 43.292 | 37.085 | 42.172 | 14.72 |
| 1674 | SER | CA | 42.944 | 38.424 | 41.776 | 14.22 |
| 1675 | SER | C | 41.469 | 38.644 | 41.990 | 15.12 |
| 1676 | SER | O | 40.653 | 37.731 | 41.873 | 14.48 |
| 1677 | SER | CB | 43.222 | 38.649 | 40.258 | 12.78 |
| 1678 | SER | OG | 44.599 | 38.384 | 39.786 | 13.54 |
| 1679 | SER | H | 43.501 | 36.368 | 41.511 | 20.00 |
| 1680 | SER | HA | 43.424 | 39.132 | 42.463 | 20.00 |
| 1681 | SER | 1HB | 42.684 | 39.566 | 39.862 | 20.00 |
| 1682 | SER | 2HB | 42.553 | 37.916 | 39.760 | 20.00 |
| 1683 | SER | HG | 45.445 | 38.774 | 40.181 | 20.00 |
| 1684 | ARG | N | 41.194 | 39.943 | 42.269 | 13.87 |
| 1685 | ARG | CA | 39.838 | 40.374 | 42.565 | 14.62 |
| 1686 | ARG | C | 39.210 | 41.125 | 41.397 | 14.77 |
| 1687 | ARG | O | 38.037 | 41.061 | 41.111 | 13.72 |
| 1688 | ARG | CB | 39.935 | 41.251 | 43.846 | 14.39 |
| 1689 | ARG | CG | 38.548 | 41.299 | 44.523 | 23.02 |
| 1690 | ARG | CD | 37.577 | 42.376 | 44.071 | 27.49 |
| 1691 | ARG | NE | 36.501 | 42.588 | 45.040 | 30.20 |
| 1692 | ARG | CZ | 35.270 | 42.112 | 45.005 | 29.90 |
| 1693 | ARG | NH1 | 34.915 | 40.949 | 44.459 | 31.36 |
| 1694 | ARG | NH2 | 34.360 | 42.901 | 45.542 | 30.49 |
| 1695 | ARG | H | 41.983 | 40.543 | 42.411 | 20.00 |
| 1696 | ARG | HA | 39.228 | 39.487 | 42.741 | 20.00 |
| 1697 | ARG | 1HB | 40.353 | 42.237 | 43.656 | 20.00 |
| 1698 | ARG | 2HB | 40.624 | 40.744 | 44.518 | 20.00 |
| 1699 | ARG | 1HG | 38.665 | 41.371 | 45.589 | 20.00 |
| 1700 | ARG | 2HG | 38.050 | 40.344 | 44.361 | 20.00 |
| 1701 | ARG | 1HD | 37.164 | 42.250 | 43.068 | 20.00 |
| 1702 | ARG | 2HD | 38.127 | 43.313 | 44.077 | 20.00 |
| 1703 | ARG | HE | 36.646 | 43.361 | 45.657 | 20.00 |
| 1704 | ARG | 1HH1 | 33.929 | 40.756 | 44.381 | 20.00 |
| 1705 | ARG | 2HH1 | 35.573 | 40.273 | 44.127 | 20.00 |
| 1706 | ARG | 1HH2 | 33.407 | 42.577 | 45.455 | 20.00 |
| 1707 | ARG | 2HH2 | 34.560 | 43.766 | 45.978 | 20.00 |
| 1708 | GLY | N | 40.103 | 41.883 | 40.761 | 15.17 |
| 1709 | GLY | CA | 39.769 | 42.723 | 39.598 | 13.10 |
| 1710 | GLY | C | 40.451 | 42.232 | 38.273 | 12.93 |
| 1711 | GLY | O | 41.570 | 41.712 | 38.267 | 12.18 |
| 1712 | GLY | H | 41.036 | 41.839 | 41.124 | 20.00 |
| 1713 | GLY | 1HA | 40.096 | 43.738 | 39.816 | 20.00 |
| 1714 | GLY | 2HA | 38.686 | 42.743 | 39.482 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1715 | VAL | N | 39.674 | 42.483 | 37.168 | 13.38 |
| 1716 | VAL | CA | 40.227 | 42.427 | 35.793 | 10.87 |
| 1717 | VAL | C | 39.995 | 43.725 | 35.172 | 9.66 |
| 1718 | VAL | O | 38.888 | 44.245 | 35.106 | 10.04 |
| 1719 | VAL | CB | 39.570 | 41.284 | 34.982 | 10.73 |
| 1720 | VAL | CG1 | 39.639 | 39.894 | 35.612 | 11.72 |
| 1721 | VAL | CG2 | 40.122 | 41.100 | 33.537 | 10.72 |
| 1722 | VAL | H | 38.722 | 42.761 | 37.332 | 20.00 |
| 1723 | VAL | HA | 41.295 | 42.251 | 35.853 | 20.00 |
| 1724 | VAL | HB | 38.516 | 41.544 | 34.929 | 20.00 |
| 1725 | VAL | 1HG1 | 39.229 | 39.859 | 36.619 | 20.00 |
| 1726 | VAL | 2HG1 | 40.675 | 39.558 | 35.682 | 20.00 |
| 1727 | VAL | 3HG1 | 39.100 | 39.172 | 34.999 | 20.00 |
| 1728 | VAL | 1HG2 | 41.197 | 40.918 | 33.522 | 20.00 |
| 1729 | VAL | 2HG2 | 39.948 | 41.984 | 32.925 | 20.00 |
| 1730 | VAL | 3HG2 | 39.637 | 40.265 | 33.032 | 20.00 |
| 1731 | VAL | N | 41.057 | 44.256 | 34.606 | 8.51 |
| 1732 | VAL | CA | 40.949 | 45.502 | 33.785 | 7.91 |
| 1733 | VAL | C | 41.098 | 45.261 | 32.275 | 8.39 |
| 1734 | VAL | O | 42.171 | 44.892 | 31.831 | 9.71 |
| 1735 | VAL | CB | 41.905 | 46.631 | 34.279 | 6.14 |
| 1736 | VAL | CG1 | 41.684 | 47.022 | 35.734 | 7.70 |
| 1737 | VAL | CG2 | 41.778 | 47.812 | 33.395 | 6.32 |
| 1738 | VAL | H | 41.884 | 43.822 | 34.895 | 20.00 |
| 1739 | VAL | HA | 39.938 | 45.889 | 33.912 | 20.00 |
| 1740 | VAL | HB | 42.928 | 46.278 | 34.202 | 20.00 |
| 1741 | VAL | 1HG1 | 41.809 | 46.162 | 36.389 | 20.00 |
| 1742 | VAL | 2HG1 | 40.681 | 47.425 | 35.882 | 20.00 |
| 1743 | VAL | 3HG1 | 42.394 | 47.791 | 36.054 | 20.00 |
| 1744 | VAL | 1HG2 | 40.751 | 48.182 | 33.347 | 20.00 |
| 1745 | VAL | 2HG2 | 42.150 | 47.616 | 32.391 | 20.00 |
| 1746 | VAL | 3HG2 | 42.380 | 48.634 | 33.780 | 20.00 |
| 1747 | MET | N | 40.029 | 45.551 | 31.499 | 8.82 |
| 1748 | MET | CA | 40.098 | 45.371 | 30.025 | 8.53 |
| 1749 | MET | C | 40.050 | 46.649 | 29.219 | 9.29 |
| 1750 | MET | O | 39.015 | 47.259 | 29.225 | 9.66 |
| 1751 | MET | CB | 38.784 | 44.680 | 29.671 | 8.63 |
| 1752 | MET | CG | 38.641 | 44.332 | 28.205 | 9.02 |
| 1753 | MET | SD | 37.443 | 43.055 | 27.893 | 13.59 |
| 1754 | MET | CE | 37.600 | 42.908 | 26.065 | 7.30 |
| 1755 | MET | H | 39.197 | 45.854 | 31.962 | 20.00 |
| 1756 | MET | HA | 40.941 | 44.743 | 29.751 | 20.00 |
| 1757 | MET | 1HB | 37.913 | 45.199 | 30.067 | 20.00 |
| 1758 | MET | 2HB | 38.900 | 43.841 | 30.315 | 20.00 |
| 1759 | MET | 1HG | 39.586 | 43.983 | 27.797 | 20.00 |
| 1760 | MET | 2HG | 38.320 | 45.209 | 27.645 | 20.00 |
| 1761 | MET | 1HE | 38.649 | 42.746 | 25.840 | 20.00 |
| 1762 | MET | 2HE | 37.313 | 43.833 | 25.576 | 20.00 |
| 1763 | MET | 3HE | 37.023 | 42.066 | 25.702 | 20.00 |
| 1764 | LEU | N | 41.108 | 47.023 | 28.523 | 8.05 |
| 1765 | LEU | CA | 41.161 | 48.369 | 27.911 | 6.79 |
| 1766 | LEU | C | 40.878 | 48.480 | 26.338 | 8.29 |
| 1767 | LEU | O | 41.027 | 49.534 | 25.740 | 8.17 |
| 1768 | LEU | CB | 42.531 | 48.968 | 28.277 | 8.82 |
| 1769 | LEU | CG | 42.851 | 48.939 | 29.793 | 9.33 |
| 1770 | LEU | CD1 | 41.825 | 49.803 | 30.601 | 6.68 |
| 1771 | LEU | CD2 | 44.286 | 49.352 | 29.927 | 8.69 |
| 1772 | LEU | H | 41.914 | 46.450 | 28.660 | 20.00 |
| 1773 | LEU | HA | 40.405 | 48.977 | 28.396 | 20.00 |
| 1774 | LEU | 1HB | 42.648 | 49.982 | 27.900 | 20.00 |
| 1775 | LEU | 2HB | 43.278 | 48.364 | 27.763 | 20.00 |
| 1776 | LEU | HG | 42.807 | 47.915 | 30.157 | 20.00 |
| 1777 | LEU | 1HD1 | 40.826 | 49.357 | 30.594 | 20.00 |
| 1778 | LEU | 2HD1 | 41.756 | 50.793 | 30.148 | 20.00 |
| 1779 | LEU | 3HD1 | 42.127 | 49.940 | 31.640 | 20.00 |
| 1780 | LEU | 1HD2 | 44.381 | 50.415 | 29.708 | 20.00 |
| 1781 | LEU | 2HD2 | 44.933 | 48.881 | 29.208 | 20.00 |
| 1782 | LEU | 3HD2 | 44.686 | 49.148 | 30.922 | 20.00 |
| 1783 | ASN | N | 40.414 | 47.337 | 25.761 | 8.85 |
| 1784 | ASN | CA | 40.131 | 47.123 | 24.392 | 10.85 |
| 1785 | ASN | C | 38.659 | 46.635 | 24.231 | 10.96 |
| 1786 | ASN | O | 38.021 | 46.324 | 25.247 | 11.52 |
| 1787 | ASN | CB | 41.197 | 46.126 | 23.941 | 10.56 |
| 1788 | ASN | CG | 40.890 | 44.664 | 24.261 | 10.18 |
| 1789 | ASN | OD1 | 40.432 | 43.836 | 23.484 | 13.30 |
| 1790 | ASN | ND2 | 41.203 | 44.346 | 25.480 | 6.84 |
| 1791 | ASN | H | 39.979 | 46.747 | 26.435 | 20.00 |
| 1792 | ASN | HA | 40.182 | 48.082 | 23.880 | 20.00 |
| 1793 | ASN | 1HB | 42.177 | 46.387 | 24.344 | 20.00 |
| 1794 | ASN | 2HB | 41.276 | 46.154 | 22.858 | 20.00 |
| 1795 | ASN | 1HD2 | 41.057 | 43.367 | 25.597 | 20.00 |
| 1796 | ASN | 2HD2 | 41.445 | 44.908 | 26.261 | 20.00 |
| 1797 | ARG | N | 38.180 | 46.553 | 22.953 | 12.81 |
| 1798 | ARG | CA | 36.927 | 45.848 | 22.626 | 12.84 |
| 1799 | ARG | C | 37.350 | 44.502 | 22.051 | 13.06 |
| 1800 | ARG | O | 38.503 | 44.343 | 21.679 | 13.72 |
| 1801 | ARG | CB | 35.917 | 46.694 | 21.830 | 15.06 |
| 1802 | ARG | CG | 35.700 | 48.081 | 22.459 | 23.73 |
| 1803 | ARG | CD | 34.608 | 48.863 | 21.755 | 34.40 |
| 1804 | ARG | NE | 34.599 | 48.708 | 20.298 | 44.56 |
| 1805 | ARG | CZ | 35.344 | 49.461 | 19.525 | 51.42 |
| 1806 | ARG | NH1 | 36.112 | 50.366 | 20.022 | 54.99 |
| 1807 | ARG | NH2 | 35.346 | 49.337 | 18.230 | 53.99 |
| 1808 | ARG | H | 38.768 | 46.870 | 22.206 | 20.00 |
| 1809 | ARG | HA | 36.453 | 45.621 | 23.579 | 20.00 |
| 1810 | ARG | 1HB | 34.965 | 46.180 | 21.772 | 20.00 |
| 1811 | ARG | 2HB | 36.260 | 46.803 | 20.803 | 20.00 |
| 1812 | ARG | 1HG | 36.626 | 48.660 | 22.436 | 20.00 |
| 1813 | ARG | 2HG | 35.439 | 47.990 | 23.514 | 20.00 |
| 1814 | ARG | 1HD | 34.562 | 49.917 | 22.003 | 20.00 |
| 1815 | ARG | 2HD | 33.643 | 48.479 | 22.083 | 20.00 |
| 1816 | ARG | HE | 34.015 | 48.023 | 19.871 | 20.00 |
| 1817 | ARG | 1HH1 | 36.646 | 50.991 | 19.465 | 20.00 |
| 1818 | ARG | 2HH1 | 36.185 | 50.455 | 21.013 | 20.00 |
| 1819 | ARG | 1HH2 | 35.928 | 49.944 | 17.707 | 20.00 |
| 1820 | ARG | 2HH2 | 34.791 | 48.643 | 17.775 | 20.00 |
| 1821 | VAL | N | 36.412 | 43.522 | 22.089 | 13.43 |
| 1822 | VAL | CA | 36.678 | 42.221 | 21.443 | 16.12 |
| 1823 | VAL | C | 36.936 | 42.341 | 19.861 | 16.48 |
| 1824 | VAL | O | 37.508 | 41.501 | 19.204 | 14.56 |
| 1825 | VAL | CB | 35.416 | 41.364 | 21.767 | 14.79 |
| 1826 | VAL | CG1 | 35.507 | 40.697 | 23.158 | 14.80 |
| 1827 | VAL | CG2 | 35.222 | 40.300 | 20.662 | 16.58 |
| 1828 | VAL | H | 35.544 | 43.637 | 22.538 | 20.00 |
| 1829 | VAL | HA | 37.574 | 41.806 | 21.888 | 20.00 |
| 1830 | VAL | HB | 34.531 | 42.004 | 21.742 | 20.00 |
| 1831 | VAL | 1HG1 | 35.515 | 41.454 | 23.937 | 20.00 |
| 1832 | VAL | 2HG1 | 36.431 | 40.123 | 23.260 | 20.00 |
| 1833 | VAL | 3HG1 | 34.687 | 40.009 | 23.336 | 20.00 |
| 1834 | VAL | 1HG2 | 36.123 | 39.694 | 20.523 | 20.00 |
| 1835 | VAL | 2HG2 | 34.966 | 40.732 | 19.690 | 20.00 |
| 1836 | VAL | 3HG2 | 34.404 | 39.618 | 20.907 | 20.00 |
| 1837 | MET | N | 36.406 | 43.407 | 19.280 | 17.62 |
| 1838 | MET | CA | 36.626 | 43.711 | 17.914 | 19.41 |
| 1839 | MET | C | 36.901 | 45.186 | 17.748 | 17.22 |
| 1840 | MET | O | 36.164 | 46.011 | 18.235 | 16.41 |
| 1841 | MET | CB | 35.353 | 43.277 | 17.172 | 22.53 |
| 1842 | MET | CG | 35.669 | 43.239 | 15.645 | 30.44 |
| 1843 | MET | SD | 34.456 | 42.296 | 14.726 | 36.43 |
| 1844 | MET | CE | 33.433 | 43.769 | 14.332 | 32.23 |
| 1845 | MET | H | 35.921 | 44.042 | 19.872 | 20.00 |
| 1846 | MET | HA | 37.494 | 43.147 | 17.583 | 20.00 |
| 1847 | MET | 1HB | 34.536 | 43.972 | 17.357 | 20.00 |
| 1848 | MET | 2HB | 35.027 | 42.298 | 17.516 | 20.00 |
| 1849 | MET | 1HG | 36.598 | 42.694 | 15.471 | 20.00 |
| 1850 | MET | 2HG | 35.835 | 44.229 | 15.216 | 20.00 |
| 1851 | MET | 1HE | 34.049 | 44.530 | 13.845 | 20.00 |
| 1852 | MET | 2HE | 33.035 | 44.226 | 15.235 | 20.00 |
| 1853 | MET | 3HE | 32.615 | 43.541 | 13.649 | 20.00 |
| 1854 | GLU | N | 37.970 | 45.511 | 17.065 | 17.49 |
| 1855 | GLU | CA | 38.300 | 46.936 | 16.903 | 18.64 |
| 1856 | GLU | C | 38.818 | 47.158 | 15.437 | 17.88 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1857 | GLU | O | 39.395 | 46.229 | 14.856 | 18.32 |
| 1858 | GLU | CB | 39.271 | 47.483 | 17.997 | 16.54 |
| 1859 | GLU | CG | 39.163 | 46.802 | 19.374 | 16.82 |
| 1860 | GLU | CD | 40.244 | 47.335 | 20.294 | 15.94 |
| 1861 | GLU | OE1 | 41.417 | 47.016 | 20.261 | 15.52 |
| 1862 | GLU | OE2 | 39.878 | 48.107 | 21.133 | 15.98 |
| 1863 | GLU | H | 38.603 | 44.799 | 16.761 | 20.00 |
| 1864 | GLU | HA | 37.372 | 47.509 | 16.964 | 20.00 |
| 1865 | GLU | 1HB | 39.171 | 48.563 | 18.106 | 20.00 |
| 1866 | GLU | 2HB | 40.290 | 47.331 | 17.643 | 20.00 |
| 1867 | GLU | 1HG | 39.267 | 45.731 | 19.339 | 20.00 |
| 1868 | GLU | 2HG | 38.189 | 47.010 | 19.799 | 20.00 |
| 1869 | LYS | N | 38.446 | 48.382 | 14.874 | 19.17 |
| 1870 | LYS | CA | 38.777 | 48.777 | 13.484 | 20.14 |
| 1871 | LYS | C | 38.520 | 47.522 | 12.524 | 18.74 |
| 1872 | LYS | O | 39.311 | 47.173 | 11.670 | 18.86 |
| 1873 | LYS | CB | 40.278 | 49.240 | 13.415 | 21.50 |
| 1874 | LYS | CG | 40.703 | 50.654 | 13.986 | 24.11 |
| 1875 | LYS | CD | 42.172 | 50.552 | 14.578 | 28.82 |
| 1876 | LYS | CE | 43.021 | 51.809 | 14.894 | 30.30 |
| 1877 | LYS | NZ | 42.319 | 53.111 | 14.983 | 32.58 |
| 1878 | LYS | H | 37.978 | 49.029 | 15.463 | 20.00 |
| 1879 | LYS | HA | 38.115 | 49.580 | 13.155 | 20.00 |
| 1880 | LYS | 1HB | 40.638 | 49.186 | 12.388 | 20.00 |
| 1881 | LYS | 2HB | 40.863 | 48.468 | 13.917 | 20.00 |
| 1882 | LYS | 1HG | 40.032 | 50.973 | 14.782 | 20.00 |
| 1883 | LYS | 2HG | 40.674 | 51.390 | 13.184 | 20.00 |
| 1884 | LYS | 1HD | 42.764 | 49.942 | 13.889 | 20.00 |
| 1885 | LYS | 2HD | 42.152 | 49.930 | 15.476 | 20.00 |
| 1886 | LYS | 1HE | 43.736 | 51.897 | 14.065 | 20.00 |
| 1887 | LYS | 2HE | 43.661 | 51.644 | 15.777 | 20.00 |
| 1888 | LYS | 1HZ | 41.751 | 53.142 | 15.851 | 20.00 |
| 1889 | LYS | 2HZ | 41.700 | 53.243 | 14.157 | 20.00 |
| 1890 | LYS | 3HZ | 43.009 | 53.887 | 15.036 | 20.00 |
| 1891 | GLY | N | 37.431 | 46.797 | 12.782 | 18.79 |
| 1892 | GLY | CA | 37.164 | 45.601 | 11.983 | 17.83 |
| 1893 | GLY | C | 37.939 | 44.731 | 12.298 | 19.02 |
| 1894 | GLY | O | 37.645 | 43.318 | 11.675 | 18.80 |
| 1895 | GLY | H | 36.805 | 47.142 | 13.472 | 20.00 |
| 1896 | GLY | 1HA | 37.364 | 48.858 | 10.936 | 20.00 |
| 1897 | GLY | 2HA | 36.104 | 45.378 | 12.101 | 20.00 |
| 1898 | SER | N | 38.905 | 44.320 | 13.292 | 16.08 |
| 1899 | SER | CA | 39.607 | 43.056 | 13.660 | 17.76 |
| 1900 | SER | C | 39.296 | 42.486 | 15.005 | 16.07 |
| 1901 | SER | O | 38.995 | 43.233 | 15.902 | 15.80 |
| 1902 | SER | CB | 41.114 | 43.073 | 13.410 | 21.32 |
| 1903 | SER | OG | 41.466 | 43.211 | 11.962 | 29.95 |
| 1904 | SER | H | 39.281 | 45.222 | 13.434 | 20.00 |
| 1905 | SER | HA | 39.189 | 42.275 | 13.020 | 20.00 |
| 1906 | SER | 1HB | 41.468 | 42.062 | 13.716 | 20.00 |
| 1907 | SER | 2HB | 41.685 | 43.644 | 14.204 | 20.00 |
| 1908 | SER | HG | 41.217 | 43.991 | 11.368 | 20.00 |
| 1909 | LEU | N | 39.354 | 41.139 | 15.085 | 16.19 |
| 1910 | LEU | CA | 39.179 | 40.408 | 16.344 | 14.22 |
| 1911 | LEU | C | 40.426 | 40.584 | 17.073 | 14.90 |
| 1912 | LEU | O | 41.500 | 40.325 | 16.507 | 16.30 |
| 1913 | LEU | CB | 38.953 | 38.890 | 16.239 | 13.16 |
| 1914 | LEU | CG | 37.613 | 38.637 | 15.495 | 12.66 |
| 1915 | LEU | CD1 | 36.379 | 39.491 | 16.079 | 15.43 |
| 1916 | LEU | CD2 | 37.330 | 37.112 | 15.281 | 13.88 |
| 1917 | LEU | H | 39.542 | 40.665 | 14.226 | 20.00 |
| 1918 | LEU | HA | 38.395 | 40.914 | 16.899 | 20.00 |
| 1919 | LEU | 1HB | 38.892 | 38.447 | 17.234 | 20.00 |
| 1920 | LEU | 2HB | 39.763 | 38.405 | 15.689 | 20.00 |
| 1921 | LEU | HG | 39.743 | 39.052 | 14.496 | 20.00 |
| 1922 | LEU | 1HD1 | 36.551 | 40.564 | 16.142 | 20.00 |
| 1923 | LEU | 2HD1 | 36.136 | 39.140 | 17.085 | 20.00 |
| 1924 | LEU | 3HD1 | 35.484 | 39.341 | 15.469 | 20.00 |
| 1925 | LEU | 1HD2 | 37.257 | 36.579 | 16.225 | 20.00 |
| 1926 | LEU | 2HD2 | 38.130 | 36.677 | 14.681 | 20.00 |
| 1927 | LEU | 3HD2 | 36.393 | 36.951 | 14.742 | 20.00 |
| 1928 | LYS | N | 40.213 | 41.120 | 18.298 | 14.30 |
| 1929 | LYS | CA | 41.214 | 41.721 | 19.186 | 11.19 |
| 1930 | LYS | C | 41.424 | 40.990 | 20.578 | 10.51 |
| 1931 | LYS | O | 42.491 | 41.101 | 21.208 | 11.24 |
| 1932 | LYS | CB | 40.927 | 43.219 | 19.400 | 11.90 |
| 1933 | LYS | CG | 41.294 | 44.096 | 18.204 | 15.22 |
| 1934 | LYS | CD | 42.782 | 44.088 | 18.074 | 16.86 |
| 1935 | LYS | CE | 43.416 | 44.879 | 16.995 | 20.26 |
| 1936 | LYS | NZ | 44.866 | 44.759 | 17.227 | 18.45 |
| 1937 | LYS | H | 39.250 | 41.290 | 18.494 | 20.00 |
| 1938 | LYS | HA | 42.072 | 41.565 | 18.549 | 20.00 |
| 1939 | LYS | 1HB | 41.453 | 43.590 | 20.273 | 20.00 |
| 1940 | LYS | 2HB | 39.873 | 43.359 | 19.638 | 20.00 |
| 1941 | LYS | 1HG | 40.989 | 45.121 | 18.373 | 20.00 |
| 1942 | LYS | 2HG | 40.822 | 43.779 | 17.280 | 20.00 |
| 1943 | LYS | 1HD | 43.048 | 43.070 | 17.823 | 20.00 |
| 1944 | LYS | 2HD | 43.172 | 44.442 | 19.028 | 20.00 |
| 1945 | LYS | 1HE | 43.122 | 45.933 | 17.063 | 20.00 |
| 1946 | LYS | 2HE | 43.135 | 44.495 | 16.012 | 20.00 |
| 1947 | LYS | 1HZ | 45.192 | 43.803 | 17.446 | 20.00 |
| 1948 | LYS | 2HZ | 45.137 | 45.336 | 18.077 | 20.00 |
| 1949 | LYS | 3HZ | 45.463 | 45.200 | 16.489 | 20.00 |
| 1950 | CYS | N | 40.378 | 40.163 | 20.958 | 10.35 |
| 1951 | CYS | CA | 40.307 | 39.378 | 22.205 | 10.12 |
| 1952 | CYS | C | 39.140 | 38.345 | 22.075 | 13.34 |
| 1953 | CYS | O | 38.199 | 38.571 | 21.322 | 13.61 |
| 1954 | CYS | CB | 39.998 | 40.335 | 23.357 | 13.04 |
| 1955 | CYS | SG | 39.948 | 39.653 | 25.023 | 11.06 |
| 1956 | CYS | H | 39.554 | 40.270 | 20.385 | 20.00 |
| 1957 | CYS | HA | 41.260 | 38.903 | 22.390 | 20.00 |
| 1958 | CYS | 1HB | 39.044 | 40.818 | 23.189 | 20.00 |
| 1959 | CYS | 2HB | 40.715 | 41.148 | 23.356 | 20.00 |
| 1960 | CYS | HG | 41.059 | 39.958 | 25.695 | 20.00 |
| 1961 | ALA | N | 39.220 | 37.197 | 22.807 | 11.84 |
| 1962 | ALA | CA | 38.076 | 36.310 | 22.861 | 11.47 |
| 1963 | ALA | C | 36.942 | 36.970 | 23.673 | 13.20 |
| 1964 | ALA | O | 37.135 | 37.777 | 24.550 | 10.87 |
| 1965 | ALA | CB | 38.542 | 34.974 | 23.518 | 9.90 |
| 1966 | ALA | H | 39.961 | 37.072 | 23.467 | 20.00 |
| 1967 | ALA | HA | 37.727 | 36.169 | 21.837 | 20.00 |
| 1968 | ALA | 1HB | 38.943 | 35.142 | 24.518 | 20.00 |
| 1969 | ALA | 2HB | 39.334 | 34.524 | 22.920 | 20.00 |
| 1970 | ALA | 3HB | 37.722 | 34.257 | 23.606 | 20.00 |
| 1971 | GLN | N | 35.725 | 36.522 | 23.415 | 12.25 |
| 1972 | GLN | CA | 34.645 | 36.830 | 24.422 | 13.18 |
| 1973 | GLN | C | 34.789 | 35.908 | 25.674 | 13.71 |
| 1974 | GLN | O | 34.306 | 34.800 | 25.733 | 14.92 |
| 1975 | GLN | CB | 33.424 | 36.554 | 23.562 | 13.64 |
| 1976 | GLN | CG | 32.149 | 37.021 | 24.112 | 14.19 |
| 1977 | GLN | CD | 32.229 | 38.437 | 24.551 | 14.78 |
| 1978 | GLN | OE1 | 32.151 | 38.741 | 25.725 | 20.52 |
| 1979 | GLN | NE2 | 32.162 | 39.286 | 23.542 | 13.59 |
| 1980 | GLN | H | 35.602 | 35.916 | 22.635 | 20.00 |
| 1981 | GLN | HA | 34.723 | 37.882 | 24.718 | 20.00 |
| 1982 | GLN | 1HB | 33.359 | 35.487 | 23.379 | 20.00 |
| 1983 | GLN | 2HB | 33.554 | 37.017 | 22.589 | 20.00 |
| 1984 | GLN | 1HG | 31.839 | 36.429 | 24.969 | 20.00 |
| 1985 | GLN | 2HG | 31.338 | 36.929 | 23.379 | 20.00 |
| 1986 | GLN | 1HE2 | 31.885 | 40.195 | 23.842 | 20.00 |
| 1987 | GLN | 2HE2 | 32.304 | 39.058 | 22.593 | 20.00 |
| 1988 | TYR | N | 35.597 | 36.366 | 26.628 | 12.19 |
| 1989 | TYR | CA | 36.060 | 35.379 | 27.613 | 11.14 |
| 1990 | TYR | C | 35.168 | 35.400 | 28.882 | 10.72 |
| 1991 | TYR | O | 35.292 | 34.588 | 29.784 | 12.61 |
| 1992 | TYR | CB | 37.551 | 35.557 | 27.877 | 10.70 |
| 1993 | TYR | CG | 37.814 | 36.894 | 28.483 | 12.19 |
| 1994 | TYR | CD1 | 37.736 | 37.113 | 29.882 | 10.21 |
| 1995 | TYR | CD2 | 38.194 | 37.946 | 27.679 | 11.16 |
| 1996 | TYR | CE1 | 38.060 | 38.311 | 30.487 | 12.37 |
| 1997 | TYR | CE2 | 38.525 | 39.175 | 28.244 | 10.83 |
| 1998 | TYR | CZ | 38.452 | 39.353 | 29.637 | 11.09 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 1999 | TYR | OH | 38.741 | 40.615 | 30.127 | 11.70 |
| 2000 | TYR | H | 36.006 | 37.267 | 26.500 | 20.00 |
| 2001 | TYR | HA | 35.959 | 34.369 | 27.208 | 20.00 |
| 2002 | TYR | 1HB | 38.106 | 35.477 | 26.945 | 20.00 |
| 2003 | TYR | 2HB | 37.949 | 34.775 | 28.517 | 20.00 |
| 2004 | TYR | HD1 | 37.433 | 36.298 | 30.508 | 20.00 |
| 2005 | TYR | HD2 | 38.288 | 37.831 | 26.601 | 20.00 |
| 2006 | TYR | HE1 | 38.028 | 38.353 | 31.577 | 20.00 |
| 2007 | TYR | HE2 | 38.875 | 39.932 | 27.553 | 20.00 |
| 2008 | TYR | HH | 37.890 | 41.054 | 30.183 | 20.00 |
| 2009 | TRP | N | 34.243 | 36.345 | 28.877 | 11.94 |
| 2010 | TRP | CA | 33.260 | 36.444 | 29.897 | 12.84 |
| 2011 | TRP | C | 31.795 | 36.329 | 29.296 | 14.59 |
| 2012 | TRP | O | 31.599 | 36.587 | 28.134 | 14.57 |
| 2013 | TRP | CB | 33.665 | 37.712 | 30.717 | 12.85 |
| 2014 | TRP | CG | 33.087 | 38.919 | 30.092 | 13.65 |
| 2015 | TRP | CD1 | 31.828 | 39.488 | 30.403 | 14.58 |
| 2016 | TRP | CD2 | 33.657 | 39.662 | 29.006 | 12.43 |
| 2017 | TRP | NE1 | 31.613 | 40.540 | 29.550 | 14.02 |
| 2018 | TRP | CE2 | 32.726 | 40.705 | 28.701 | 12.63 |
| 2019 | TRP | CE3 | 34.809 | 39.538 | 28.302 | 13.32 |
| 2020 | TRP | CZ2 | 33.067 | 41.598 | 27.737 | 12.31 |
| 2021 | TRP | CZ3 | 35.137 | 40.434 | 27.306 | 11.49 |
| 2022 | TRP | CH2 | 34.278 | 41.483 | 27.035 | 14.96 |
| 2023 | TRP | H | 34.167 | 36.958 | 28.097 | 20.00 |
| 2024 | TRP | HA | 33.359 | 35.577 | 30.550 | 20.00 |
| 2025 | TRP | 1HB | 34.750 | 37.815 | 30.805 | 20.00 |
| 2026 | TRP | 2HB | 33.287 | 37.655 | 31.738 | 20.00 |
| 2027 | TRP | HD1 | 31.145 | 39.100 | 31.149 | 20.00 |
| 2028 | TRP | HE1 | 30.758 | 41.024 | 29.513 | 20.00 |
| 2029 | TRP | HE3 | 35.482 | 38.710 | 28.515 | 20.00 |
| 2030 | TRP | HZ2 | 32.368 | 42.385 | 27.492 | 20.00 |
| 2031 | TRP | HZ3 | 36.048 | 40.298 | 26.745 | 20.00 |
| 2032 | TRP | HH2 | 34.554 | 42.186 | 26.270 | 20.00 |
| 2033 | PRO | N | 30.771 | 35.903 | 30.090 | 16.00 |
| 2034 | PRO | CA | 29.379 | 35.863 | 29.628 | 15.76 |
| 2035 | PRO | C | 28.711 | 37.138 | 29.353 | 16.40 |
| 2036 | PRO | O | 28.872 | 38.116 | 30.195 | 18.51 |
| 2037 | PRO | CB | 28.648 | 35.085 | 30.686 | 12.06 |
| 2038 | PRO | CG | 29.535 | 35.324 | 31.918 | 15.79 |
| 2039 | PRO | CD | 30.937 | 35.297 | 31.426 | 15.75 |
| 2040 | PRO | HA | 29.331 | 35.310 | 28.691 | 20.00 |
| 2041 | PRO | 1HB | 28.646 | 34.019 | 30.437 | 20.00 |
| 2042 | PRO | 2HB | 27.601 | 35.373 | 30.852 | 20.00 |
| 2043 | PRO | 1HG | 29.349 | 36.293 | 32.360 | 20.00 |
| 2044 | PRO | 2HG | 29.365 | 34.566 | 32.684 | 20.00 |
| 2045 | PRO | 1HD | 31.323 | 34.282 | 31.325 | 20.00 |
| 2046 | PRO | 2HD | 31.591 | 35.885 | 32.067 | 20.00 |
| 2047 | GLN | N | 27.952 | 37.249 | 28.248 | 18.99 |
| 2048 | GLN | CA | 27.291 | 38.520 | 27.956 | 21.65 |
| 2049 | GLN | C | 25.891 | 38.588 | 28.499 | 22.14 |
| 2050 | GLN | O | 25.303 | 39.651 | 28.554 | 20.49 |
| 2051 | GLN | CB | 27.240 | 38.783 | 26.497 | 26.00 |
| 2052 | GLN | CG | 28.579 | 39.267 | 26.045 | 32.71 |
| 2053 | GLN | CD | 28.474 | 39.304 | 24.551 | 36.57 |
| 2054 | GLN | OE1 | 28.270 | 38.247 | 23.966 | 35.28 |
| 2055 | GLN | NE2 | 28.566 | 40.493 | 23.988 | 40.87 |
| 2056 | GLN | H | 28.103 | 36.536 | 27.563 | 20.00 |
| 2057 | GLN | HA | 27.828 | 39.333 | 28.450 | 20.00 |
| 2058 | GLN | 1HB | 26.462 | 39.506 | 26.222 | 20.00 |
| 2059 | GLN | 2HB | 27.001 | 37.849 | 25.971 | 20.00 |
| 2060 | GLN | 1HG | 29.420 | 38.737 | 26.370 | 20.00 |
| 2061 | GLN | 2HG | 28.769 | 40.372 | 26.438 | 20.00 |
| 2062 | GLN | 1HE2 | 28.441 | 40.574 | 23.007 | 20.00 |
| 2063 | GLN | 2HE2 | 28.815 | 41.241 | 24.593 | 20.00 |
| 2064 | LYS | N | 25.408 | 37.425 | 28.909 | 20.39 |
| 2065 | LYS | CA | 24.255 | 37.495 | 29.783 | 19.10 |
| 2066 | LYS | C | 24.218 | 36.437 | 30.788 | 16.46 |
| 2067 | LYS | O | 24.860 | 35.417 | 30.584 | 16.58 |
| 2068 | LYS | CB | 23.043 | 37.308 | 28.996 | 22.59 |
| 2069 | LYS | CG | 22.991 | 36.049 | 28.192 | 24.94 |
| 2070 | LYS | CD | 21.840 | 36.224 | 27.229 | 30.53 |
| 2071 | LYS | CE | 21.248 | 37.656 | 27.135 | 32.07 |
| 2072 | LYS | NZ | 19.951 | 37.638 | 26.450 | 40.14 |
| 2073 | LYS | H | 25.913 | 36.568 | 28.818 | 20.00 |
| 2074 | LYS | HA | 24.207 | 38.466 | 30.286 | 20.00 |
| 2075 | LYS | 1HB | 23.084 | 38.211 | 28.385 | 20.00 |
| 2076 | LYS | 2HB | 22.156 | 37.389 | 29.639 | 20.00 |
| 2077 | LYS | 1HG | 22.886 | 35.151 | 28.800 | 20.00 |
| 2078 | LYS | 2HG | 23.896 | 35.943 | 27.603 | 20.00 |
| 2079 | LYS | 1HD | 21.052 | 35.524 | 27.493 | 20.00 |
| 2080 | LYS | 2HD | 22.158 | 35.907 | 26.237 | 20.00 |
| 2081 | LYS | 1HE | 21.938 | 38.332 | 26.616 | 20.00 |
| 2082 | LYS | 2HE | 21.014 | 38.102 | 28.111 | 20.00 |
| 2083 | LYS | 1HZ | 19.364 | 37.019 | 27.058 | 20.00 |
| 2084 | LYS | 2HZ | 20.056 | 37.233 | 25.501 | 20.00 |
| 2085 | LYS | 3HZ | 19.574 | 38.608 | 26.433 | 20.00 |
| 2086 | GLU | N | 23.400 | 36.776 | 31.841 | 15.88 |
| 2087 | GLU | CA | 23.136 | 36.118 | 33.111 | 15.37 |
| 2088 | GLU | C | 22.807 | 34.620 | 32.974 | 15.69 |
| 2089 | GLU | O | 23.432 | 33.804 | 33.626 | 13.68 |
| 2090 | GLU | CB | 22.083 | 36.964 | 33.900 | 16.72 |
| 2091 | GLU | CG | 22.625 | 38.280 | 34.481 | 14.29 |
| 2092 | GLU | CD | 22.320 | 39.420 | 33.579 | 18.80 |
| 2093 | GLU | OE1 | 22.205 | 39.180 | 32.359 | 21.62 |
| 2094 | GLU | OE2 | 22.216 | 40.551 | 34.077 | 21.27 |
| 2095 | GLU | H | 22.923 | 37.629 | 31.683 | 20.00 |
| 2096 | GLU | HA | 24.072 | 36.180 | 33.655 | 20.00 |
| 2097 | GLU | 1HB | 21.726 | 36.367 | 34.740 | 20.00 |
| 2098 | GLU | 2HB | 21.182 | 37.117 | 33.295 | 20.00 |
| 2099 | GLU | 1HG | 23.692 | 38.268 | 34.620 | 20.00 |
| 2100 | GLU | 2HG | 22.172 | 38.502 | 35.438 | 20.00 |
| 2101 | GLU | N | 21.816 | 34.259 | 32.125 | 18.42 |
| 2102 | GLU | CA | 21.276 | 32.842 | 31.945 | 20.95 |
| 2103 | GLU | C | 22.156 | 31.928 | 31.090 | 20.76 |
| 2104 | GLU | O | 21.994 | 30.705 | 31.057 | 20.49 |
| 2105 | GLU | CB | 19.952 | 32.834 | 31.234 | 20.78 |
| 2106 | GLU | CG | 19.309 | 34.201 | 31.354 | 25.93 |
| 2107 | GLU | CD | 19.642 | 35.143 | 30.246 | 25.99 |
| 2108 | GLU | OE1 | 19.653 | 34.697 | 29.122 | 28.63 |
| 2109 | GLU | OE2 | 19.906 | 36.310 | 30.524 | 25.53 |
| 2110 | GLU | H | 21.335 | 35.045 | 31.723 | 20.00 |
| 2111 | GLU | HA | 21.174 | 32.451 | 32.958 | 20.00 |
| 2112 | GLU | 1HB | 19.298 | 32.082 | 31.685 | 20.00 |
| 2113 | GLU | 2HB | 20.022 | 32.547 | 30.179 | 20.00 |
| 2114 | GLU | 1HG | 19.417 | 34.671 | 32.332 | 20.00 |
| 2115 | GLU | 2HG | 18.245 | 34.072 | 31.265 | 20.00 |
| 2116 | LYS | N | 23.111 | 32.603 | 30.414 | 21.38 |
| 2117 | LYS | CA | 24.125 | 31.842 | 29.692 | 21.50 |
| 2118 | LYS | C | 25.526 | 31.935 | 30.345 | 21.97 |
| 2119 | LYS | O | 26.347 | 32.738 | 29.892 | 22.57 |
| 2120 | LYS | CB | 24.088 | 32.258 | 28.172 | 22.92 |
| 2121 | LYS | CG | 22.714 | 31.845 | 27.594 | 27.23 |
| 2122 | LYS | CD | 22.552 | 31.376 | 26.144 | 35.59 |
| 2123 | LYS | CE | 23.728 | 30.647 | 25.664 | 43.39 |
| 2124 | LYS | NZ | 24.007 | 29.243 | 26.485 | 46.48 |
| 2125 | LYS | H | 23.100 | 33.602 | 30.448 | 20.00 |
| 2126 | LYS | HA | 23.905 | 30.779 | 29.750 | 20.00 |
| 2127 | LYS | 1HB | 24.907 | 31.743 | 27.668 | 20.00 |
| 2128 | LYS | 2HB | 24.269 | 33.331 | 28.039 | 20.00 |
| 2129 | LYS | 1HG | 21.975 | 32.616 | 27.813 | 20.00 |
| 2130 | LYS | 2HG | 22.353 | 30.996 | 28.180 | 20.00 |
| 2131 | LYS | 1HD | 22.496 | 32.263 | 25.506 | 20.00 |
| 2132 | LYS | 2HD | 21.598 | 30.867 | 26.006 | 20.00 |
| 2133 | LYS | 1HE | 24.630 | 31.088 | 25.626 | 20.00 |
| 2134 | LYS | 2HE | 23.573 | 30.193 | 24.616 | 20.00 |
| 2135 | LYS | 1HZ | 23.210 | 28.580 | 26.409 | 20.00 |
| 2136 | LYS | 2HZ | 24.158 | 29.477 | 27.490 | 20.00 |
| 2137 | LYS | 3HZ | 24.854 | 28.748 | 26.137 | 20.00 |
| 2138 | GLU | N | 25.773 | 31.078 | 31.373 | 21.26 |
| 2139 | GLU | CA | 27.139 | 30.999 | 31.912 | 22.94 |
| 2140 | GLU | C | 28.092 | 30.064 | 31.083 | 21.77 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2141 | GLU | O | 27.645 | 29.223 | 30.310 | 23.33 |
| 2142 | GLU | CB | 27.231 | 30.453 | 33.369 | 22.83 |
| 2143 | GLU | CG | 26.205 | 29.525 | 33.954 | 28.82 |
| 2144 | GLU | CD | 25.370 | 28.477 | 33.224 | 29.12 |
| 2145 | GLU | OE1 | 25.536 | 27.271 | 33.488 | 33.37 |
| 2146 | GLU | OE2 | 24.429 | 28.906 | 32.545 | 28.44 |
| 2147 | GLU | H | 25.059 | 30.466 | 31.701 | 20.00 |
| 2148 | GLU | HA | 27.582 | 31.996 | 31.877 | 20.00 |
| 2149 | GLU | 1HB | 27.261 | 31.330 | 34.014 | 20.00 |
| 2150 | GLU | 2HB | 28.206 | 30.000 | 33.571 | 20.00 |
| 2151 | GLU | 1HG | 25.454 | 30.212 | 34.324 | 20.00 |
| 2152 | GLU | 2HG | 26.595 | 29.090 | 34.874 | 20.00 |
| 2153 | MET | N | 29.391 | 30.275 | 31.312 | 18.83 |
| 2154 | MET | CA | 30.416 | 29.603 | 30.511 | 17.54 |
| 2155 | MET | C | 31.128 | 28.585 | 31.349 | 19.07 |
| 2156 | MET | O | 31.491 | 28.947 | 32.433 | 20.58 |
| 2157 | MET | CB | 31.427 | 30.660 | 30.153 | 16.27 |
| 2158 | MET | CG | 30.870 | 31.714 | 29.186 | 16.56 |
| 2159 | MET | SD | 32.137 | 32.886 | 28.710 | 19.88 |
| 2160 | MET | CE | 33.223 | 31.855 | 27.860 | 18.70 |
| 2161 | MET | H | 29.589 | 30.862 | 32.098 | 20.00 |
| 2162 | MET | HA | 29.978 | 29.130 | 29.625 | 20.00 |
| 2163 | MET | 1HB | 32.321 | 30.175 | 29.762 | 20.00 |
| 2164 | MET | 2HB | 31.744 | 31.163 | 31.066 | 20.00 |
| 2165 | MET | 1HG | 30.026 | 32.258 | 29.604 | 20.00 |
| 2166 | MET | 2HG | 30.521 | 31.214 | 28.283 | 20.00 |
| 2167 | MET | 1HE | 32.744 | 31.511 | 26.943 | 20.00 |
| 2168 | MET | 2HE | 33.506 | 30.974 | 28.415 | 20.00 |
| 2169 | MET | 3HE | 34.117 | 32.425 | 27.610 | 20.00 |
| 2170 | ILE | N | 31.339 | 27.348 | 30.934 | 18.63 |
| 2171 | ILE | CA | 32.211 | 26.451 | 31.678 | 20.60 |
| 2172 | ILE | C | 33.493 | 28.318 | 30.901 | 20.37 |
| 2173 | ILE | O | 33.409 | 26.217 | 29.700 | 23.05 |
| 2174 | ILE | CB | 31.480 | 25.129 | 31.975 | 24.01 |
| 2175 | ILE | CG1 | 30.423 | 25.362 | 33.119 | 25.81 |
| 2176 | ILE | CG2 | 32.435 | 24.026 | 32.386 | 24.90 |
| 2177 | ILE | CD1 | 29.015 | 25.092 | 32.627 | 27.88 |
| 2178 | ILE | H | 30.974 | 27.074 | 30.050 | 20.00 |
| 2179 | ILE | HA | 32.485 | 26.885 | 32.636 | 20.00 |
| 2180 | ILE | HB | 30.985 | 24.804 | 31.061 | 20.00 |
| 2181 | ILE | 1HG1 | 30.463 | 26.402 | 33.452 | 20.00 |
| 2182 | ILE | 2HG1 | 30.652 | 24.754 | 34.001 | 20.00 |
| 2183 | ILE | 1HG2 | 33.016 | 24.304 | 33.266 | 20.00 |
| 2184 | ILE | 2HG2 | 33.118 | 23.779 | 31.571 | 20.00 |
| 2185 | ILE | 3HG2 | 31.883 | 23.113 | 32.621 | 20.00 |
| 2186 | ILE | 1HD1 | 28.917 | 24.029 | 32.403 | 20.00 |
| 2187 | ILE | 2HD1 | 28.793 | 25.634 | 31.710 | 20.00 |
| 2188 | ILE | 3HD1 | 28.264 | 25.343 | 33.374 | 20.00 |
| 2189 | PHE | N | 34.683 | 26.352 | 31.568 | 19.97 |
| 2190 | PHE | CA | 35.937 | 26.121 | 30.909 | 18.46 |
| 2191 | PHE | C | 36.319 | 24.745 | 31.318 | 19.73 |
| 2192 | PHE | O | 36.707 | 24.506 | 32.444 | 18.94 |
| 2193 | PHE | CB | 36.932 | 27.287 | 31.208 | 16.35 |
| 2194 | PHE | CG | 36.422 | 28.683 | 31.025 | 14.87 |
| 2195 | PHE | CD1 | 36.522 | 29.299 | 29.779 | 13.55 |
| 2196 | PHE | CD2 | 35.733 | 29.310 | 32.097 | 16.14 |
| 2197 | PHE | CE1 | 35.830 | 30.461 | 29.569 | 14.72 |
| 2198 | PHE | CE2 | 35.066 | 30.492 | 31.858 | 14.63 |
| 2199 | PHE | CZ | 35.099 | 31.052 | 30.579 | 14.92 |
| 2200 | PHE | H | 34.651 | 26.525 | 32.549 | 20.00 |
| 2201 | PHE | HA | 35.764 | 26.097 | 29.830 | 20.00 |
| 2202 | PHE | 1HB | 37.703 | 27.282 | 30.445 | 20.00 |
| 2203 | PHE | 2HB | 37.090 | 27.353 | 32.285 | 20.00 |
| 2204 | PHE | HD1 | 37.082 | 28.849 | 28.984 | 20.00 |
| 2205 | PHE | HD2 | 35.695 | 28.842 | 33.075 | 20.00 |
| 2206 | PHE | HE1 | 35.848 | 30.933 | 28.597 | 20.00 |
| 2207 | PHE | HE2 | 34.533 | 30.984 | 32.644 | 20.00 |
| 2208 | PHE | HZ | 34.566 | 31.975 | 30.381 | 20.00 |
| 2209 | GLU | N | 36.121 | 23.790 | 30.412 | 23.42 |
| 2210 | GLU | CA | 36.337 | 22.339 | 30.733 | 27.04 |
| 2211 | GLU | C | 37.729 | 21.979 | 30.888 | 26.67 |
| 2212 | GLU | O | 38.100 | 21.211 | 31.739 | 27.77 |
| 2213 | GLU | CB | 35.728 | 21.345 | 29.766 | 32.84 |
| 2214 | GLU | CG | 34.183 | 21.469 | 29.799 | 43.59 |
| 2215 | GLU | CD | 33.519 | 20.760 | 28.583 | 52.36 |
| 2216 | GLU | OE1 | 33.847 | 21.115 | 27.436 | 54.69 |
| 2217 | GLU | OE2 | 32.681 | 19.880 | 28.790 | 55.07 |
| 2218 | GLU | H | 35.751 | 24.069 | 29.529 | 20.00 |
| 2219 | GLU | HA | 35.881 | 22.173 | 31.709 | 20.00 |
| 2220 | GLU | 1HB | 35.996 | 20.309 | 30.011 | 20.00 |
| 2221 | GLU | 2HB | 36.098 | 21.541 | 28.755 | 20.00 |
| 2222 | GLU | 1HG | 33.904 | 22.517 | 29.697 | 20.00 |
| 2223 | GLU | 2HG | 33.744 | 21.100 | 30.727 | 20.00 |
| 2224 | ASP | N | 38.560 | 22.594 | 30.081 | 25.27 |
| 2225 | ASP | CA | 39.984 | 22.349 | 30.299 | 24.77 |
| 2226 | ASP | C | 40.545 | 22.756 | 31.677 | 24.82 |
| 2227 | ASP | O | 41.386 | 22.063 | 32.189 | 26.69 |
| 2228 | ASP | CB | 40.679 | 23.052 | 29.135 | 25.87 |
| 2229 | ASP | CG | 40.734 | 24.550 | 29.259 | 28.11 |
| 2230 | ASP | OD1 | 39.805 | 25.153 | 29.754 | 27.95 |
| 2231 | ASP | OD2 | 41.734 | 25.112 | 28.924 | 30.09 |
| 2232 | ASP | H | 38.274 | 23.318 | 29.453 | 20.00 |
| 2233 | ASP | HA | 40.119 | 21.276 | 30.225 | 20.00 |
| 2234 | ASP | 1HB | 40.199 | 22.776 | 28.195 | 20.00 |
| 2235 | ASP | 2HB | 41.699 | 22.679 | 29.067 | 20.00 |
| 2236 | THR | N | 40.124 | 23.834 | 32.305 | 22.69 |
| 2237 | THR | CA | 40.690 | 24.144 | 33.672 | 20.10 |
| 2238 | THR | C | 39.585 | 23.979 | 34.752 | 20.10 |
| 2239 | THR | O | 39.768 | 24.233 | 35.885 | 20.15 |
| 2240 | THR | CB | 41.135 | 25.633 | 33.587 | 18.17 |
| 2241 | THR | OG1 | 40.007 | 26.430 | 33.110 | 15.16 |
| 2242 | THR | CG2 | 42.544 | 25.763 | 32.851 | 16.50 |
| 2243 | THR | H | 39.685 | 24.464 | 31.679 | 20.00 |
| 2244 | THR | HA | 41.531 | 23.510 | 33.937 | 20.00 |
| 2245 | THR | HB | 41.412 | 25.917 | 34.651 | 20.00 |
| 2246 | THR | HG1 | 39.736 | 26.169 | 32.225 | 20.00 |
| 2247 | THR | 1HG2 | 42.651 | 25.408 | 31.820 | 20.00 |
| 2248 | THR | 2HG2 | 43.224 | 25.098 | 33.381 | 20.00 |
| 2249 | THR | 3HG2 | 42.971 | 26.751 | 32.905 | 20.00 |
| 2250 | ASN | N | 38.400 | 23.517 | 34.414 | 21.38 |
| 2251 | ASN | CA | 37.484 | 23.164 | 35.497 | 23.28 |
| 2252 | ASN | C | 36.941 | 24.311 | 36.323 | 23.35 |
| 2253 | ASN | O | 36.879 | 24.212 | 37.538 | 24.28 |
| 2254 | ASN | CB | 38.125 | 22.180 | 36.450 | 27.97 |
| 2255 | ASN | CG | 37.063 | 21.199 | 36.881 | 32.19 |
| 2256 | ASN | OD1 | 36.007 | 21.054 | 36.300 | 34.42 |
| 2257 | ASN | ND2 | 37.398 | 20.416 | 37.882 | 31.14 |
| 2258 | ASN | H | 38.197 | 23.360 | 33.445 | 20.00 |
| 2259 | ASN | HA | 36.637 | 22.771 | 34.958 | 20.00 |
| 2260 | ASN | 1HB | 38.630 | 22.649 | 37.291 | 20.00 |
| 2261 | ASN | 2HB | 38.876 | 21.572 | 35.956 | 20.00 |
| 2262 | ASN | 1HD2 | 36.827 | 19.614 | 38.005 | 20.00 |
| 2263 | ASN | 2HD2 | 38.154 | 20.743 | 38.435 | 20.00 |
| 2264 | LEU | N | 36.523 | 25.343 | 35.557 | 22.74 |
| 2265 | LEU | CA | 36.054 | 26.662 | 36.015 | 21.67 |
| 2266 | LEU | C | 34.666 | 26.976 | 35.433 | 20.94 |
| 2267 | LEU | O | 34.360 | 26.609 | 34.348 | 21.39 |
| 2268 | LEU | CB | 37.062 | 27.693 | 35.512 | 21.84 |
| 2269 | LEU | CG | 38.192 | 28.179 | 36.501 | 23.37 |
| 2270 | LEU | CD1 | 39.526 | 28.185 | 35.755 | 17.13 |
| 2271 | LEU | CD2 | 38.304 | 27.532 | 37.894 | 21.62 |
| 2272 | LEU | H | 36.596 | 25.109 | 34.588 | 20.00 |
| 2273 | LEU | HA | 35.977 | 26.636 | 37.101 | 20.00 |
| 2274 | LEU | 1HB | 36.570 | 28.580 | 35.111 | 20.00 |
| 2275 | LEU | 2HB | 37.540 | 27.261 | 34.632 | 20.00 |
| 2276 | LEU | HG | 37.973 | 29.219 | 36.721 | 20.00 |
| 2277 | LEU | 1HD1 | 39.471 | 28.735 | 34.816 | 20.00 |
| 2278 | LEU | 2HD1 | 39.850 | 27.168 | 35.542 | 20.00 |
| 2279 | LEU | 3HD1 | 40.281 | 28.627 | 36.394 | 20.00 |
| 2280 | LEU | 1HD2 | 38.454 | 26.455 | 37.798 | 20.00 |
| 2281 | LEU | 2HD2 | 37.409 | 27.696 | 38.497 | 20.00 |
| 2282 | LEU | 3HD2 | 39.149 | 27.916 | 38.459 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2283 | LYS | N | 33.788 | 27.630 | 36.164 | 21.10 |
| 2284 | LYS | CA | 32.465 | 28.108 | 35.683 | 19.53 |
| 2285 | LYS | C | 32.490 | 29.604 | 35.894 | 18.34 |
| 2286 | LYS | O | 33.087 | 30.091 | 36.832 | 20.22 |
| 2287 | LYS | CB | 31.333 | 27.455 | 36.480 | 20.94 |
| 2288 | LYS | CG | 29.922 | 27.807 | 36.039 | 22.87 |
| 2289 | LYS | CD | 28.975 | 26.839 | 36.717 | 29.27 |
| 2290 | LYS | CE | 27.555 | 27.322 | 37.117 | 32.16 |
| 2291 | LYS | NZ | 27.241 | 26.588 | 38.379 | 36.84 |
| 2292 | LYS | H | 34.067 | 27.812 | 37.110 | 20.00 |
| 2293 | LYS | HA | 32.356 | 27.890 | 34.626 | 20.00 |
| 2294 | LYS | 1HB | 31.418 | 27.687 | 37.535 | 20.00 |
| 2295 | LYS | 2HB | 31.452 | 26.379 | 36.378 | 20.00 |
| 2296 | LYS | 1HG | 29.776 | 27.833 | 34.960 | 20.00 |
| 2297 | LYS | 2HG | 29.738 | 28.789 | 36.395 | 20.00 |
| 2298 | LYS | 1HD | 29.460 | 26.460 | 37.618 | 20.00 |
| 2299 | LYS | 2HD | 28.872 | 25.967 | 36.075 | 20.00 |
| 2300 | LYS | 1HE | 26.811 | 27.141 | 36.334 | 20.00 |
| 2301 | LYS | 2HE | 27.560 | 28.394 | 37.332 | 20.00 |
| 2302 | LYS | 1HZ | 28.022 | 26.733 | 39.071 | 20.00 |
| 2303 | LYS | 2HZ | 27.136 | 25.563 | 38.252 | 20.00 |
| 2304 | LYS | 3HZ | 26.383 | 26.914 | 38.881 | 20.00 |
| 2305 | LEU | N | 31.850 | 30.299 | 35.029 | 16.41 |
| 2306 | LEU | CA | 31.816 | 31.744 | 35.238 | 16.41 |
| 2307 | LEU | C | 30.414 | 32.310 | 34.879 | 16.89 |
| 2308 | LEU | O | 29.861 | 31.985 | 33.848 | 16.71 |
| 2309 | LEU | CB | 32.856 | 32.320 | 34.286 | 15.09 |
| 2310 | LEU | CG | 33.093 | 33.868 | 34.349 | 13.98 |
| 2311 | LEU | CD1 | 33.803 | 34.225 | 33.001 | 15.42 |
| 2312 | LEU | CD2 | 33.869 | 34.360 | 35.697 | 16.75 |
| 2313 | LEU | H | 31.410 | 29.830 | 34.259 | 20.00 |
| 2314 | LEU | HA | 32.044 | 32.013 | 36.257 | 20.00 |
| 2315 | LEU | 1HB | 32.580 | 32.030 | 33.270 | 20.00 |
| 2316 | LEU | 2HB | 33.813 | 31.832 | 34.474 | 20.00 |
| 2317 | LEU | HG | 32.130 | 34.370 | 34.324 | 20.00 |
| 2318 | LEU | 1HD1 | 33.298 | 33.816 | 32.134 | 20.00 |
| 2319 | LEU | 2HD1 | 34.821 | 33.849 | 32.995 | 20.00 |
| 2320 | LEU | 3HD1 | 33.860 | 35.305 | 32.873 | 20.00 |
| 2321 | LEU | 1HD2 | 34.834 | 33.868 | 35.776 | 20.00 |
| 2322 | LEU | 2HD2 | 33.302 | 34.161 | 36.605 | 20.00 |
| 2323 | LEU | 3HD2 | 34.065 | 35.433 | 35.659 | 20.00 |
| 2324 | THR | N | 29.882 | 33.181 | 35.720 | 17.65 |
| 2325 | THR | CA | 28.551 | 33.725 | 35.460 | 17.51 |
| 2326 | THR | C | 28.621 | 35.167 | 35.480 | 16.95 |
| 2327 | THR | O | 29.498 | 35.674 | 36.178 | 16.10 |
| 2328 | THR | CB | 27.606 | 33.300 | 36.590 | 15.94 |
| 2329 | THR | OG1 | 27.778 | 31.872 | 36.920 | 15.73 |
| 2330 | THR | CG2 | 26.172 | 33.301 | 36.033 | 17.67 |
| 2331 | THR | H | 30.415 | 33.344 | 36.554 | 20.00 |
| 2332 | THR | HA | 28.182 | 33.409 | 34.478 | 20.00 |
| 2333 | THR | HB | 27.496 | 34.079 | 37.426 | 20.00 |
| 2334 | THR | HG1 | 28.648 | 31.469 | 37.142 | 20.00 |
| 2335 | THR | 1HG2 | 26.077 | 32.678 | 35.147 | 20.00 |
| 2336 | THR | 2HG2 | 25.823 | 34.300 | 35.797 | 20.00 |
| 2337 | THR | 3HG2 | 25.480 | 32.889 | 36.770 | 20.00 |
| 2338 | LEU | N | 27.703 | 35.781 | 34.691 | 15.85 |
| 2339 | LEU | CA | 27.556 | 37.232 | 34.739 | 16.51 |
| 2340 | LEU | C | 26.532 | 37.558 | 35.906 | 19.83 |
| 2341 | LEU | O | 25.356 | 37.257 | 35.814 | 20.59 |
| 2342 | LEU | CB | 27.158 | 37.822 | 33.324 | 15.58 |
| 2343 | LEU | CG | 26.882 | 39.324 | 33.346 | 15.08 |
| 2344 | LEU | CD1 | 26.057 | 39.756 | 32.155 | 13.12 |
| 2345 | LEU | CD2 | 28.113 | 40.188 | 33.679 | 15.75 |
| 2346 | LEU | H | 27.076 | 35.205 | 34.167 | 20.00 |
| 2347 | LEU | HA | 28.523 | 37.660 | 35.002 | 20.00 |
| 2348 | LEU | 1HB | 26.279 | 37.289 | 32.972 | 20.00 |
| 2349 | LEU | 2HB | 27.913 | 37.649 | 32.569 | 20.00 |
| 2350 | LEU | HG | 26.189 | 39.498 | 34.166 | 20.00 |
| 2351 | LEU | 1HD1 | 25.097 | 39.241 | 32.130 | 20.00 |
| 2352 | LEU | 2HD1 | 26.577 | 39.583 | 31.213 | 20.00 |
| 2353 | LEU | 3HD1 | 25.853 | 40.827 | 32.198 | 20.00 |
| 2354 | LEU | 1HD2 | 28.892 | 40.010 | 32.953 | 20.00 |
| 2355 | LEU | 2HD2 | 28.512 | 39.992 | 34.673 | 20.00 |
| 2356 | LEU | 3HD2 | 27.865 | 41.249 | 33.638 | 20.00 |
| 2357 | ILE | N | 27.041 | 38.159 | 37.021 | 18.46 |
| 2358 | ILE | CA | 26.043 | 38.466 | 38.063 | 18.30 |
| 2359 | ILE | C | 25.345 | 39.750 | 37.757 | 18.81 |
| 2360 | ILE | O | 24.145 | 39.889 | 37.903 | 19.41 |
| 2361 | ILE | CB | 26.654 | 38.493 | 39.445 | 17.44 |
| 2362 | ILE | CG1 | 27.314 | 37.152 | 39.761 | 16.16 |
| 2363 | ILE | CG2 | 25.700 | 38.914 | 40.537 | 17.37 |
| 2364 | ILE | CD1 | 26.469 | 35.848 | 39.622 | 15.26 |
| 2365 | ILE | H | 28.018 | 38.357 | 37.091 | 20.00 |
| 2366 | ILE | HA | 25.263 | 37.704 | 38.059 | 20.00 |
| 2367 | ILE | HB | 27.457 | 39.233 | 39.436 | 20.00 |
| 2368 | ILE | 1HG1 | 27.712 | 37.198 | 40.771 | 20.00 |
| 2369 | ILE | 2HG1 | 28.194 | 37.048 | 39.123 | 20.00 |
| 2370 | ILE | 1HG2 | 24.902 | 38.179 | 40.612 | 20.00 |
| 2371 | ILE | 2HG2 | 25.274 | 39.901 | 40.363 | 20.00 |
| 2372 | ILE | 3HG2 | 26.190 | 38.945 | 41.509 | 20.00 |
| 2373 | ILE | 1HD1 | 26.117 | 35.706 | 38.599 | 20.00 |
| 2374 | ILE | 2HD1 | 25.604 | 35.841 | 40.288 | 20.00 |
| 2375 | ILE | 3HD1 | 27.069 | 34.972 | 39.875 | 20.00 |
| 2376 | SER | N | 26.099 | 40.697 | 37.346 | 18.02 |
| 2377 | SER | CA | 25.432 | 41.954 | 36.914 | 19.40 |
| 2378 | SER | C | 26.370 | 42.826 | 36.013 | 21.38 |
| 2379 | SER | O | 27.551 | 42.619 | 36.115 | 22.64 |
| 2380 | SER | CB | 25.076 | 42.740 | 38.219 | 21.28 |
| 2381 | SER | OG | 26.035 | 43.743 | 38.695 | 24.51 |
| 2382 | SER | H | 27.087 | 40.552 | 37.291 | 20.00 |
| 2383 | SER | HA | 24.533 | 41.708 | 36.356 | 20.00 |
| 2384 | SER | 1HB | 24.803 | 42.025 | 39.038 | 20.00 |
| 2385 | SER | 2HB | 24.053 | 43.172 | 38.066 | 20.00 |
| 2386 | SER | HG | 26.904 | 43.995 | 38.253 | 20.00 |
| 2387 | GLU | N | 25.933 | 43.809 | 35.222 | 22.91 |
| 2388 | GLU | CA | 26.837 | 44.927 | 34.671 | 25.57 |
| 2389 | GLU | C | 26.217 | 46.306 | 34.923 | 25.11 |
| 2390 | GLU | O | 25.011 | 46.358 | 34.981 | 28.12 |
| 2391 | GLU | CB | 27.228 | 44.878 | 33.158 | 27.94 |
| 2392 | GLU | CG | 26.075 | 44.442 | 32.355 | 32.29 |
| 2393 | GLU | CD | 26.377 | 44.181 | 30.922 | 38.30 |
| 2394 | GLU | OE1 | 27.547 | 44.144 | 30.531 | 43.02 |
| 2395 | GLU | OE2 | 25.405 | 43.982 | 30.205 | 41.87 |
| 2396 | GLU | H | 24.982 | 43.809 | 34.916 | 20.00 |
| 2397 | GLU | HA | 27.770 | 44.930 | 35.236 | 20.00 |
| 2398 | GLU | 1HB | 27.987 | 44.106 | 33.047 | 20.00 |
| 2399 | GLU | 2HB | 27.650 | 45.808 | 32.773 | 20.00 |
| 2400 | GLU | 1HG | 25.222 | 45.118 | 32.423 | 20.00 |
| 2401 | GLU | 2HG | 25.745 | 43.467 | 32.706 | 20.00 |
| 2402 | ASP | N | 27.039 | 47.342 | 35.079 | 20.31 |
| 2403 | ASP | CA | 26.705 | 48.761 | 35.113 | 18.75 |
| 2404 | ASP | C | 27.443 | 49.451 | 33.921 | 19.30 |
| 2405 | ASP | O | 28.624 | 49.821 | 33.900 | 17.85 |
| 2406 | ASP | CB | 27.189 | 49.177 | 36.507 | 21.92 |
| 2407 | ASP | CG | 27.254 | 50.675 | 36.768 | 28.13 |
| 2408 | ASP | OD1 | 26.258 | 51.344 | 36.462 | 28.01 |
| 2409 | ASP | OD2 | 28.321 | 51.154 | 37.274 | 33.77 |
| 2410 | ASP | H | 28.005 | 47.105 | 35.158 | 20.00 |
| 2411 | ASP | HA | 25.624 | 48.883 | 35.026 | 20.00 |
| 2412 | ASP | 1HB | 28.199 | 48.802 | 36.674 | 20.00 |
| 2413 | ASP | 2HB | 26.569 | 48.727 | 37.282 | 20.00 |
| 2414 | ILE | N | 26.646 | 49.500 | 32.878 | 19.47 |
| 2415 | ILE | CA | 27.011 | 50.169 | 31.640 | 20.98 |
| 2416 | ILE | C | 26.884 | 51.689 | 31.756 | 22.51 |
| 2417 | ILE | O | 25.854 | 52.187 | 32.173 | 25.15 |
| 2418 | ILE | CB | 26.054 | 49.679 | 30.540 | 22.51 |
| 2419 | ILE | CG1 | 26.166 | 48.190 | 30.336 | 22.32 |
| 2420 | ILE | CG2 | 26.210 | 50.376 | 29.202 | 23.73 |
| 2421 | ILE | CD1 | 25.344 | 47.693 | 29.157 | 22.61 |
| 2422 | ILE | H | 25.726 | 49.152 | 33.013 | 20.00 |
| 2423 | ILE | HA | 28.044 | 49.924 | 31.444 | 20.00 |
| 2424 | ILE | HB | 25.034 | 49.883 | 30.893 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2425 | ILE | 1HG1 | 25.831 | 47.659 | 31.231 | 20.00 |
| 2426 | ILE | 2HG1 | 27.204 | 47.891 | 30.185 | 20.00 |
| 2427 | ILE | 1HG2 | 26.990 | 49.941 | 28.588 | 20.00 |
| 2428 | ILE | 2HG2 | 26.412 | 51.439 | 29.278 | 20.00 |
| 2429 | ILE | 3HG2 | 25.287 | 50.309 | 28.630 | 20.00 |
| 2430 | ILE | 1HD1 | 25.810 | 47.995 | 28.217 | 20.00 |
| 2431 | ILE | 2HD1 | 24.316 | 48.054 | 29.173 | 20.00 |
| 2432 | ILE | 3HD1 | 25.309 | 46.600 | 29.147 | 20.00 |
| 2433 | LYS | N | 27.927 | 52.396 | 31.334 | 21.11 |
| 2434 | LYS | CA | 28.007 | 53.844 | 31.411 | 20.45 |
| 2435 | LYS | C | 28.454 | 54.260 | 29.997 | 20.80 |
| 2436 | LYS | O | 28.625 | 53.399 | 29.162 | 22.26 |
| 2437 | LYS | CB | 29.094 | 54.210 | 32.440 | 22.37 |
| 2438 | LYS | CG | 28.926 | 53.803 | 33.916 | 25.62 |
| 2439 | LYS | CD | 28.269 | 54.939 | 34.702 | 29.83 |
| 2440 | LYS | CE | 27.931 | 54.725 | 36.183 | 33.05 |
| 2441 | LYS | NZ | 27.390 | 56.048 | 36.625 | 35.32 |
| 2442 | LYS | H | 28.708 | 51.893 | 30.963 | 20.00 |
| 2443 | LYS | HA | 27.026 | 54.274 | 31.645 | 20.00 |
| 2444 | LYS | 1HB | 29.330 | 55.273 | 32.393 | 20.00 |
| 2445 | LYS | 2HB | 30.013 | 53.731 | 32.121 | 20.00 |
| 2446 | LYS | 1HG | 29.915 | 53.631 | 34.341 | 20.00 |
| 2447 | LYS | 2HG | 28.387 | 52.862 | 34.018 | 20.00 |
| 2448 | LYS | 1HD | 27.317 | 55.140 | 34.208 | 20.00 |
| 2449 | LYS | 2HD | 28.840 | 55.855 | 34.583 | 20.00 |
| 2450 | LYS | 1HE | 28.821 | 54.455 | 36.758 | 20.00 |
| 2451 | LYS | 2HE | 27.183 | 53.930 | 36.298 | 20.00 |
| 2452 | LYS | 1HZ | 26.728 | 56.433 | 35.914 | 20.00 |
| 2453 | LYS | 2HZ | 28.153 | 56.770 | 36.673 | 20.00 |
| 2454 | LYS | 3HZ | 26.891 | 56.014 | 37.524 | 20.00 |
| 2455 | THR | N | 28.665 | 55.518 | 29.676 | 19.82 |
| 2456 | THR | CA | 28.839 | 55.815 | 28.253 | 21.59 |
| 2457 | THR | C | 30.207 | 55.342 | 27.586 | 20.83 |
| 2458 | THR | O | 30.252 | 54.972 | 26.399 | 22.59 |
| 2459 | THR | CB | 28.731 | 57.347 | 28.048 | 24.13 |
| 2460 | THR | OG1 | 29.994 | 57.972 | 28.523 | 24.73 |
| 2461 | THR | CG2 | 27.406 | 57.828 | 28.730 | 30.44 |
| 2462 | THR | H | 28.394 | 56.233 | 30.314 | 20.00 |
| 2463 | THR | HA | 28.017 | 55.332 | 27.719 | 20.00 |
| 2464 | THR | HB | 28.524 | 57.312 | 26.923 | 20.00 |
| 2465 | THR | HG1 | 30.033 | 58.957 | 28.697 | 20.00 |
| 2466 | THR | 1HG2 | 27.365 | 57.757 | 29.806 | 20.00 |
| 2467 | THR | 2HG2 | 26.606 | 57.179 | 28.402 | 20.00 |
| 2468 | THR | 3HG2 | 27.015 | 58.808 | 28.421 | 20.00 |
| 2469 | TYR | N | 31.305 | 55.374 | 28.446 | 17.73 |
| 2470 | TYR | CA | 32.678 | 55.061 | 27.957 | 15.97 |
| 2471 | TYR | CA | 33.341 | 53.758 | 28.591 | 15.46 |
| 2472 | TYR | C | 34.328 | 53.178 | 28.162 | 15.86 |
| 2473 | TYR | CB | 33.284 | 56.428 | 28.157 | 12.55 |
| 2474 | TYR | CG | 33.967 | 56.737 | 29.464 | 12.56 |
| 2475 | TYR | CD1 | 33.364 | 57.603 | 30.382 | 14.70 |
| 2476 | TYR | CD2 | 35.206 | 56.191 | 29.786 | 14.86 |
| 2477 | TYR | CE1 | 33.908 | 57.950 | 31.591 | 15.48 |
| 2478 | TYR | CE2 | 35.785 | 56.566 | 30.989 | 16.69 |
| 2479 | TYR | CZ | 35.129 | 57.413 | 31.908 | 16.96 |
| 2480 | TYR | OH | 35.664 | 57.737 | 33.129 | 15.71 |
| 2481 | TYR | H | 31.090 | 55.949 | 29.230 | 20.00 |
| 2482 | TYR | HA | 32.616 | 54.883 | 26.881 | 20.00 |
| 2483 | TYR | 1HB | 32.511 | 57.176 | 28.055 | 20.00 |
| 2484 | TYR | 2HB | 33.813 | 56.779 | 27.310 | 20.00 |
| 2485 | TYR | HD1 | 32.439 | 58.052 | 30.168 | 20.00 |
| 2486 | TYR | HD2 | 35.662 | 55.472 | 29.127 | 20.00 |
| 2487 | TYR | HE1 | 33.342 | 58.642 | 32.206 | 20.00 |
| 2488 | TYR | HE2 | 36.782 | 56.174 | 31.160 | 20.00 |
| 2489 | TYR | HH | 35.472 | 57.124 | 33.840 | 20.00 |
| 2490 | TYR | N | 32.720 | 53.248 | 29.650 | 14.74 |
| 2491 | TYR | CA | 33.167 | 52.050 | 30.352 | 14.03 |
| 2492 | TYR | C | 31.906 | 51.359 | 30.862 | 16.12 |
| 2493 | TYR | O | 30.824 | 51.930 | 30.915 | 17.82 |
| 2494 | TYR | CB | 34.251 | 52.412 | 31.375 | 12.74 |
| 2495 | TYR | CG | 33.728 | 53.134 | 32.579 | 15.40 |
| 2496 | TYR | CD1 | 33.475 | 52.431 | 33.758 | 13.77 |
| 2497 | TYR | CD2 | 33.476 | 54.490 | 32.544 | 18.58 |
| 2498 | TYR | CE1 | 33.015 | 53.078 | 34.883 | 15.81 |
| 2499 | TYR | CE2 | 32.944 | 55.161 | 33.649 | 17.84 |
| 2500 | TYR | CZ | 32.740 | 54.435 | 34.866 | 16.69 |
| 2501 | TYR | OH | 32.240 | 54.871 | 36.111 | 18.92 |
| 2502 | TYR | H | 31.850 | 53.689 | 29.886 | 20.00 |
| 2503 | TYR | HA | 33.628 | 51.368 | 29.650 | 20.00 |
| 2504 | TYR | 1HB | 35.016 | 53.026 | 30.901 | 20.00 |
| 2505 | TYR | 2HB | 34.748 | 51.510 | 31.713 | 20.00 |
| 2506 | TYR | HD1 | 33.656 | 51.367 | 33.806 | 20.00 |
| 2507 | TYR | HD2 | 33.632 | 55.018 | 31.619 | 20.00 |
| 2508 | TYR | HE1 | 32.854 | 52.539 | 35.807 | 20.00 |
| 2509 | TYR | HE2 | 32.615 | 56.155 | 33.358 | 20.00 |
| 2510 | TYR | HH | 31.864 | 55.766 | 36.179 | 20.00 |
| 2511 | THR | N | 32.096 | 50.092 | 31.166 | 14.21 |
| 2512 | THR | CA | 31.125 | 49.193 | 31.834 | 15.42 |
| 2513 | THR | C | 31.889 | 48.540 | 33.043 | 15.44 |
| 2514 | THR | O | 33.128 | 48.344 | 32.955 | 15.14 |
| 2515 | THR | CB | 30.572 | 48.077 | 30.896 | 16.15 |
| 2516 | THR | OG1 | 29.894 | 48.442 | 29.632 | 16.75 |
| 2517 | THR | CG2 | 29.525 | 47.168 | 31.562 | 15.21 |
| 2518 | THR | H | 33.038 | 49.794 | 31.028 | 20.00 |
| 2519 | THR | HA | 30.320 | 49.806 | 32.254 | 20.00 |
| 2520 | THR | HB | 31.408 | 47.328 | 30.806 | 20.00 |
| 2521 | THR | HG1 | 30.097 | 49.274 | 29.118 | 20.00 |
| 2522 | THR | 1HG2 | 28.699 | 47.761 | 31.955 | 20.00 |
| 2523 | THR | 2HG2 | 29.934 | 46.590 | 32.391 | 20.00 |
| 2524 | THR | 3HG2 | 29.096 | 46.451 | 30.861 | 20.00 |
| 2525 | VAL | N | 31.079 | 48.256 | 34.137 | 14.25 |
| 2526 | VAL | CA | 31.584 | 47.499 | 35.318 | 15.61 |
| 2527 | VAL | C | 30.715 | 46.291 | 35.625 | 15.76 |
| 2528 | VAL | O | 29.577 | 46.241 | 36.050 | 16.87 |
| 2529 | VAL | CB | 31.794 | 48.216 | 36.666 | 15.56 |
| 2530 | VAL | CG1 | 32.554 | 49.567 | 36.570 | 17.93 |
| 2531 | VAL | CG2 | 32.587 | 47.191 | 37.535 | 15.84 |
| 2532 | VAL | H | 30.179 | 48.701 | 34.161 | 20.00 |
| 2533 | VAL | HA | 32.559 | 47.126 | 35.001 | 20.00 |
| 2534 | VAL | HB | 30.835 | 48.422 | 37.142 | 20.00 |
| 2535 | VAL | 1HG1 | 31.976 | 50.307 | 36.013 | 20.00 |
| 2536 | VAL | 2HG1 | 33.491 | 49.416 | 36.039 | 20.00 |
| 2537 | VAL | 3HG1 | 32.779 | 49.960 | 37.562 | 20.00 |
| 2538 | VAL | 1HG2 | 33.506 | 46.870 | 37.041 | 20.00 |
| 2539 | VAL | 2HG2 | 32.017 | 46.297 | 37.790 | 20.00 |
| 2540 | VAL | 3HG2 | 32.878 | 47.622 | 38.492 | 20.00 |
| 2541 | ARG | N | 31.313 | 45.111 | 35.451 | 15.23 |
| 2542 | ARG | CA | 30.636 | 43.909 | 35.796 | 12.90 |
| 2543 | ARG | C | 31.149 | 43.269 | 37.138 | 14.57 |
| 2544 | ARG | O | 32.271 | 43.418 | 37.622 | 14.51 |
| 2545 | ARG | CB | 30.918 | 42.912 | 34.683 | 12.22 |
| 2546 | ARG | CG | 30.854 | 43.522 | 33.366 | 14.22 |
| 2547 | ARG | CD | 30.693 | 42.427 | 32.294 | 17.43 |
| 2548 | ARG | NE | 30.223 | 43.114 | 31.092 | 19.70 |
| 2549 | ARG | CZ | 30.925 | 43.891 | 30.263 | 18.02 |
| 2550 | ARG | NH1 | 32.183 | 44.065 | 30.512 | 20.75 |
| 2551 | ARG | NH2 | 30.350 | 44.466 | 29.248 | 22.30 |
| 2552 | ARG | H | 32.298 | 45.147 | 35.294 | 20.00 |
| 2553 | ARG | HA | 29.568 | 44.091 | 35.867 | 20.00 |
| 2554 | ARG | 1HB | 30.145 | 42.142 | 34.759 | 20.00 |
| 2555 | ARG | 2HB | 31.835 | 42.363 | 34.817 | 20.00 |
| 2556 | ARG | 1HG | 31.731 | 44.132 | 33.167 | 20.00 |
| 2557 | ARG | 2HG | 29.999 | 44.186 | 33.307 | 20.00 |
| 2558 | ARG | 1HD | 29.921 | 41.721 | 32.566 | 20.00 |
| 2559 | ARG | 2HD | 31.619 | 41.882 | 32.095 | 20.00 |
| 2560 | ARG | HE | 29.220 | 43.100 | 30.923 | 20.00 |
| 2561 | ARG | 1HH1 | 32.774 | 44.675 | 29.993 | 20.00 |
| 2562 | ARG | 2HH1 | 32.503 | 43.503 | 31.261 | 20.00 |
| 2563 | ARG | 1HH2 | 30.802 | 45.007 | 28.545 | 20.00 |
| 2564 | ARG | 2HH2 | 29.341 | 44.378 | 29.241 | 20.00 |
| 2565 | GLN | N | 30.217 | 42.477 | 37.624 | 15.95 |
| 2566 | GLN | CA | 30.475 | 41.509 | 38.662 | 15.20 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2567 | GLN | C | 30.211 | 40.123 | 38.070 | 14.98 |
| 2568 | GLN | O | 29.185 | 39.776 | 37.459 | 15.16 |
| 2569 | GLN | CB | 29.451 | 41.789 | 39.755 | 19.99 |
| 2570 | GLN | OG | 29.683 | 40.991 | 41.063 | 24.39 |
| 2571 | GLN | CD | 28.589 | 41.388 | 42.123 | 33.29 |
| 2572 | GLN | OE1 | 27.850 | 42.381 | 41.972 | 36.18 |
| 2573 | GLN | NE2 | 28.425 | 40.476 | 43.095 | 32.20 |
| 2574 | GLN | H | 29.312 | 42.543 | 37.204 | 20.00 |
| 2575 | GLN | HA | 31.495 | 41.611 | 39.033 | 20.00 |
| 2576 | GLN | 1HB | 28.462 | 41.527 | 39.400 | 20.00 |
| 2577 | GLN | 2HB | 29.459 | 42.847 | 40.009 | 20.00 |
| 2578 | GLN | 1HG | 30.642 | 41.250 | 41.495 | 20.00 |
| 2579 | GLN | 2HG | 29.662 | 39.915 | 40.893 | 20.00 |
| 2580 | GLN | 1HE2 | 27.641 | 40.580 | 43.693 | 20.00 |
| 2581 | GLN | 2HE2 | 29.140 | 39.806 | 43.302 | 20.00 |
| 2582 | LEU | N | 31.219 | 39.366 | 38.295 | 14.40 |
| 2583 | LEU | CA | 31.301 | 38.012 | 37.806 | 16.50 |
| 2584 | LEU | C | 31.384 | 37.122 | 39.071 | 17.55 |
| 2585 | LEU | O | 31.940 | 37.484 | 40.119 | 18.19 |
| 2586 | LEU | CB | 32.603 | 37.945 | 36.952 | 16.87 |
| 2587 | LEU | CG | 32.569 | 38.220 | 35.452 | 19.16 |
| 2588 | LEU | CD1 | 33.846 | 38.919 | 35.104 | 18.62 |
| 2589 | LEU | CD2 | 31.412 | 39.019 | 34.876 | 19.45 |
| 2590 | LEU | H | 31.971 | 39.750 | 38.837 | 20.00 |
| 2591 | LEU | HA | 30.417 | 37.737 | 37.232 | 20.00 |
| 2592 | LEU | 1HB | 32.962 | 36.918 | 37.027 | 20.00 |
| 2593 | LEU | 2HB | 33.381 | 38.510 | 37.469 | 20.00 |
| 2594 | LEU | HG | 32.559 | 37.262 | 34.932 | 20.00 |
| 2595 | LEU | 1HD1 | 34.685 | 38.249 | 35.290 | 20.00 |
| 2596 | LEU | 2HD1 | 33.982 | 39.781 | 35.756 | 20.00 |
| 2597 | LEU | 3HD1 | 33.894 | 39.241 | 34.066 | 20.00 |
| 2598 | LEU | 1HD2 | 31.346 | 40.006 | 35.343 | 20.00 |
| 2599 | LEU | 2HD2 | 30.471 | 38.515 | 35.066 | 20.00 |
| 2600 | LEU | 3HD2 | 31.492 | 39.169 | 33.798 | 20.00 |
| 2601 | GLU | N | 30.823 | 35.909 | 38.869 | 16.26 |
| 2602 | GLU | CA | 31.238 | 34.878 | 39.789 | 16.63 |
| 2603 | GLU | C | 32.084 | 33.768 | 39.058 | 15.84 |
| 2604 | GLU | O | 31.620 | 33.130 | 38.137 | 17.35 |
| 2605 | GLU | CB | 30.001 | 34.344 | 40.415 | 17.38 |
| 2606 | GLU | CG | 30.495 | 33.228 | 41.347 | 23.65 |
| 2607 | GLU | CD | 29.265 | 32.786 | 42.113 | 30.56 |
| 2608 | GLU | OE1 | 28.878 | 33.608 | 42.914 | 31.25 |
| 2609 | GLU | OE2 | 28.700 | 31.723 | 41.893 | 32.96 |
| 2610 | GLU | H | 30.319 | 35.716 | 38.030 | 20.00 |
| 2611 | GLU | HA | 31.850 | 35.274 | 40.600 | 20.00 |
| 2612 | GLU | 1HB | 29.288 | 33.951 | 39.680 | 20.00 |
| 2613 | GLU | 2HB | 29.485 | 35.129 | 40.974 | 20.00 |
| 2614 | GLU | 1HG | 31.213 | 33.593 | 42.076 | 20.00 |
| 2615 | GLU | 2HG | 30.933 | 32.393 | 40.798 | 20.00 |
| 2616 | LEU | N | 33.326 | 33.595 | 39.566 | 17.81 |
| 2617 | LEU | CA | 34.140 | 32.449 | 39.349 | 19.00 |
| 2618 | LEU | C | 33.940 | 31.282 | 40.390 | 21.54 |
| 2619 | LEU | O | 34.276 | 31.393 | 41.532 | 19.81 |
| 2620 | LEU | CD | 35.606 | 32.971 | 39.327 | 17.55 |
| 2621 | LEU | CG | 36.442 | 32.660 | 38.027 | 19.65 |
| 2622 | LEU | CD1 | 36.241 | 31.301 | 37.304 | 20.83 |
| 2623 | LEU | CD2 | 37.930 | 32.956 | 38.354 | 17.35 |
| 2624 | LEU | H | 33.557 | 34.257 | 40.273 | 20.00 |
| 2625 | LEU | HA | 33.888 | 32.074 | 38.357 | 20.00 |
| 2626 | LEU | 1HB | 36.140 | 32.604 | 40.202 | 20.00 |
| 2627 | LEU | 2HB | 35.640 | 34.051 | 39.468 | 20.00 |
| 2628 | LEU | HG | 36.150 | 33.394 | 37.288 | 20.00 |
| 2629 | LEU | 1HD1 | 35.238 | 31.140 | 36.918 | 20.00 |
| 2630 | LEU | 2HD1 | 36.429 | 30.499 | 38.028 | 20.00 |
| 2631 | LEU | 3HD1 | 36.940 | 31.166 | 36.483 | 20.00 |
| 2632 | LEU | 1HD2 | 38.241 | 32.718 | 39.355 | 20.00 |
| 2633 | LEU | 2HD2 | 38.125 | 34.026 | 38.251 | 20.00 |
| 2634 | LEU | 3HD2 | 38.604 | 32.454 | 37.658 | 20.00 |
| 2635 | GLU | N | 33.496 | 30.126 | 39.911 | 24.40 |
| 2636 | GLU | CA | 33.575 | 28.858 | 40.619 | 24.80 |
| 2637 | GLU | C | 34.665 | 27.956 | 40.054 | 25.64 |
| 2638 | GLU | O | 34.768 | 27.641 | 38.858 | 24.49 |
| 2639 | GLU | CB | 32.249 | 28.090 | 40.382 | 24.55 |
| 2640 | GLU | CG | 31.925 | 27.011 | 41.455 | 26.49 |
| 2641 | GLU | CD | 30.506 | 26.410 | 41.400 | 28.97 |
| 2642 | GLU | OE1 | 29.575 | 26.949 | 40.725 | 33.55 |
| 2643 | GLU | OE2 | 30.384 | 25.331 | 42.024 | 32.02 |
| 2644 | GLU | H | 33.173 | 30.112 | 38.963 | 20.00 |
| 2645 | GLU | HA | 33.711 | 29.057 | 41.677 | 20.00 |
| 2646 | GLU | 1HB | 32.211 | 27.646 | 39.397 | 20.00 |
| 2647 | GLU | 2HB | 31.442 | 28.819 | 40.405 | 20.00 |
| 2648 | GLU | 1HG | 32.032 | 27.435 | 42.451 | 20.00 |
| 2649 | GLU | 2HG | 32.627 | 26.180 | 41.374 | 20.00 |
| 2650 | ASN | N | 35.429 | 27.522 | 41.022 | 26.33 |
| 2651 | ASN | CA | 36.257 | 26.375 | 40.918 | 28.36 |
| 2652 | ASN | C | 35.484 | 25.105 | 41.356 | 29.60 |
| 2653 | ASN | O | 35.519 | 24.635 | 42.483 | 31.34 |
| 2654 | ASN | CB | 37.592 | 26.666 | 41.584 | 27.93 |
| 2655 | ASN | CG | 38.437 | 25.448 | 41.952 | 30.21 |
| 2656 | ASN | OD1 | 38.104 | 24.312 | 41.659 | 28.62 |
| 2657 | ASN | ND2 | 39.585 | 25.727 | 42.536 | 31.76 |
| 2658 | ASN | H | 35.202 | 27.900 | 41.924 | 20.00 |
| 2659 | ASN | HA | 36.506 | 26.230 | 39.865 | 20.00 |
| 2660 | ASN | 1HB | 37.424 | 27.336 | 42.384 | 20.00 |
| 2661 | ASN | 2HB | 38.200 | 27.247 | 40.895 | 20.00 |
| 2662 | ASN | 1HD2 | 40.189 | 24.947 | 42.678 | 20.00 |
| 2663 | ASN | 2HD2 | 39.765 | 26.675 | 42.775 | 20.00 |
| 2664 | LEU | N | 34.921 | 24.563 | 40.253 | 30.56 |
| 2665 | LEU | CA | 34.285 | 23.303 | 40.064 | 31.30 |
| 2666 | LEU | C | 35.081 | 22.185 | 40.712 | 35.28 |
| 2667 | LEU | O | 34.408 | 21.328 | 41.256 | 35.62 |
| 2668 | LEU | CB | 34.110 | 23.167 | 38.540 | 28.95 |
| 2669 | LEU | CG | 32.712 | 23.388 | 37.955 | 29.38 |
| 2670 | LEU | CD1 | 32.843 | 23.432 | 36.457 | 27.85 |
| 2671 | LEU | CD2 | 32.026 | 24.649 | 38.417 | 30.00 |
| 2672 | LEU | H | 35.069 | 25.106 | 39.427 | 20.00 |
| 2673 | LEU | HA | 33.325 | 23.325 | 40.583 | 20.00 |
| 2674 | LEU | 1HB | 34.448 | 22.177 | 38.227 | 20.00 |
| 2675 | LEU | 2HB | 34.784 | 23.849 | 38.045 | 20.00 |
| 2676 | LEU | HG | 32.087 | 22.541 | 38.236 | 20.00 |
| 2677 | LEU | 1HD1 | 33.274 | 22.495 | 36.092 | 20.00 |
| 2678 | LEU | 2HD1 | 33.477 | 24.257 | 36.130 | 20.00 |
| 2679 | LEU | 3HD1 | 31.871 | 23.548 | 35.979 | 20.00 |
| 2680 | LEU | 1HD2 | 32.635 | 25.524 | 38.200 | 20.00 |
| 2681 | LEU | 2HD2 | 31.877 | 24.617 | 39.498 | 20.00 |
| 2682 | LEU | 3HD2 | 31.046 | 24.777 | 37.961 | 20.00 |
| 2683 | THR | N | 36.468 | 22.190 | 40.736 | 37.71 |
| 2684 | THR | CA | 37.202 | 21.155 | 41.533 | 41.16 |
| 2685 | THR | C | 36.825 | 21.148 | 43.051 | 43.17 |
| 2686 | THR | O | 36.644 | 20.102 | 43.667 | 45.18 |
| 2687 | THR | CB | 38.736 | 21.197 | 41.432 | 44.16 |
| 2688 | THR | OG1 | 39.177 | 21.273 | 40.028 | 45.45 |
| 2689 | THR | CG2 | 39.401 | 20.134 | 42.369 | 44.74 |
| 2690 | THR | H | 36.994 | 22.868 | 40.211 | 20.00 |
| 2691 | THR | HA | 36.832 | 20.195 | 41.169 | 20.00 |
| 2692 | THR | HB | 38.994 | 22.162 | 41.936 | 20.00 |
| 2693 | THR | HG1 | 39.493 | 20.516 | 39.481 | 20.00 |
| 2694 | THR | 1HG2 | 39.074 | 19.099 | 42.217 | 20.00 |
| 2695 | THR | 2HG2 | 39.155 | 20.320 | 43.413 | 20.00 |
| 2696 | THR | 3HG2 | 40.498 | 20.158 | 42.403 | 20.00 |
| 2697 | THR | N | 36.755 | 22.357 | 43.620 | 43.51 |
| 2698 | THR | CA | 36.569 | 22.492 | 45.080 | 40.76 |
| 2699 | THR | C | 35.225 | 23.028 | 45.501 | 41.34 |
| 2700 | THR | O | 34.949 | 23.173 | 46.685 | 43.02 |
| 2701 | THR | CB | 37.422 | 23.692 | 45.561 | 39.25 |
| 2702 | THR | OG1 | 37.152 | 25.022 | 44.987 | 42.09 |
| 2703 | THR | CG2 | 38.908 | 23.417 | 45.377 | 37.92 |
| 2704 | THR | H | 36.887 | 23.135 | 43.004 | 20.00 |
| 2705 | THR | HA | 36.765 | 21.561 | 45.612 | 20.00 |
| 2706 | THR | HB | 37.364 | 23.699 | 46.689 | 20.00 |
| 2707 | THR | HG1 | 36.526 | 25.122 | 44.220 | 20.00 |
| 2708 | THR | 1HG2 | 39.205 | 23.284 | 44.335 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2709 | THR | 2HG2 | 39.175 | 22.506 | 45.911 | 20.00 |
| 2710 | THR | 3HG2 | 39.483 | 24.240 | 45.802 | 20.00 |
| 2711 | GLN | N | 34.476 | 23.431 | 44.476 | 40.94 |
| 2712 | GLN | CA | 33.352 | 24.345 | 44.557 | 41.20 |
| 2713 | GLN | C | 33.545 | 25.695 | 45.299 | 38.70 |
| 2714 | GLN | O | 32.586 | 26.414 | 45.546 | 38.13 |
| 2715 | GLN | CB | 32.149 | 23.549 | 45.037 | 45.37 |
| 2716 | GLN | CG | 31.786 | 22.523 | 43.980 | 51.51 |
| 2717 | GLN | CD | 30.414 | 21.959 | 44.267 | 56.44 |
| 2718 | GLN | OE1 | 30.270 | 21.226 | 45.234 | 58.04 |
| 2719 | GLN | NE2 | 29.438 | 22.272 | 43.407 | 61.09 |
| 2720 | GLN | H | 34.741 | 23.135 | 43.558 | 20.00 |
| 2721 | GLN | HA | 33.160 | 24.656 | 43.530 | 20.00 |
| 2722 | GLN | 1HB | 31.310 | 24.234 | 45.188 | 20.00 |
| 2723 | GLN | 2HB | 32.358 | 23.063 | 45.989 | 20.00 |
| 2724 | GLN | 1HG | 32.495 | 21.702 | 43.926 | 20.00 |
| 2725 | GLN | 2HG | 31.753 | 22.994 | 42.994 | 20.00 |
| 2726 | GLN | 1HE2 | 28.585 | 21.754 | 43.419 | 20.00 |
| 2727 | GLN | 2HE2 | 29.601 | 22.971 | 42.703 | 20.00 |
| 2728 | GLU | N | 34.762 | 26.092 | 45.656 | 37.29 |
| 2729 | GLU | CA | 34.911 | 27.514 | 46.023 | 37.74 |
| 2730 | GLU | C | 34.377 | 28.454 | 44.928 | 35.73 |
| 2731 | GLU | O | 34.427 | 28.209 | 43.728 | 34.94 |
| 2732 | GLU | CB | 36.317 | 27.954 | 46.489 | 43.18 |
| 2733 | GLU | CG | 36.377 | 29.427 | 47.019 | 51.01 |
| 2734 | GLU | CD | 37.799 | 29.866 | 47.427 | 57.11 |
| 2735 | GLU | OE1 | 38.637 | 29.023 | 47.594 | 59.70 |
| 2736 | GLU | OE2 | 38.063 | 31.062 | 47.546 | 59.23 |
| 2737 | GLU | H | 35.487 | 25.418 | 45.773 | 20.00 |
| 2738 | GLU | HA | 34.261 | 27.618 | 46.889 | 20.00 |
| 2739 | GLU | 1HB | 37.020 | 27.876 | 45.674 | 20.00 |
| 2740 | GLU | 2HB | 36.685 | 27.267 | 47.255 | 20.00 |
| 2741 | GLU | 1HG | 35.747 | 29.531 | 47.902 | 20.00 |
| 2742 | GLU | 2HG | 36.060 | 30.154 | 46.279 | 20.00 |
| 2743 | THR | N | 33.861 | 29.566 | 45.444 | 33.44 |
| 2744 | THR | CA | 33.250 | 30.618 | 44.592 | 31.67 |
| 2745 | THR | C | 33.937 | 31.934 | 44.874 | 30.34 |
| 2746 | THR | O | 34.285 | 32.227 | 46.011 | 31.62 |
| 2747 | THR | CB | 31.701 | 30.674 | 44.951 | 29.52 |
| 2748 | THR | OG1 | 31.012 | 29.973 | 43.882 | 31.41 |
| 2749 | THR | CG2 | 31.094 | 31.901 | 45.741 | 27.83 |
| 2750 | THR | H | 34.048 | 29.665 | 46.415 | 20.00 |
| 2751 | THR | HA | 33.482 | 30.372 | 43.553 | 20.00 |
| 2752 | THR | HB | 31.695 | 30.004 | 45.845 | 20.00 |
| 2753 | THR | HG1 | 30.437 | 30.433 | 43.203 | 20.00 |
| 2754 | THR | 1HG2 | 31.122 | 32.846 | 45.187 | 20.00 |
| 2755 | THR | 2HG2 | 31.678 | 32.101 | 46.635 | 20.00 |
| 2756 | THR | 3HG2 | 30.068 | 31.750 | 46.091 | 20.00 |
| 2757 | ARG | N | 34.107 | 32.738 | 43.860 | 27.40 |
| 2758 | ARG | CA | 34.538 | 34.090 | 44.139 | 22.96 |
| 2759 | ARG | C | 33.959 | 35.067 | 43.175 | 19.60 |
| 2760 | ARG | O | 33.722 | 34.760 | 42.031 | 18.08 |
| 2761 | ARG | CB | 36.078 | 34.229 | 44.003 | 24.02 |
| 2762 | ARG | CG | 36.854 | 33.227 | 44.797 | 27.06 |
| 2763 | ARG | CD | 38.285 | 33.547 | 44.508 | 30.34 |
| 2764 | ARG | NE | 39.183 | 32.683 | 45.219 | 31.08 |
| 2765 | ARG | CZ | 40.370 | 32.287 | 44.813 | 33.27 |
| 2766 | ARG | NH1 | 41.054 | 32.842 | 43.773 | 28.01 |
| 2767 | ARG | NH2 | 40.742 | 31.202 | 45.477 | 34.77 |
| 2768 | ARG | H | 33.782 | 32.444 | 42.964 | 20.00 |
| 2769 | ARG | HA | 34.184 | 34.369 | 45.135 | 20.00 |
| 2770 | ARG | 1HB | 36.387 | 35.247 | 44.261 | 20.00 |
| 2771 | ARG | 2HB | 36.342 | 34.082 | 42.952 | 20.00 |
| 2772 | ARG | 1HG | 36.606 | 32.197 | 44.535 | 20.00 |
| 2773 | ARG | 2HG | 36.637 | 33.357 | 45.857 | 20.00 |
| 2774 | ARG | 1HD | 38.521 | 34.562 | 44.846 | 20.00 |
| 2775 | ARG | 2HD | 38.485 | 33.476 | 43.435 | 20.00 |
| 2776 | ARG | HE | 38.854 | 32.134 | 45.993 | 20.00 |
| 2777 | ARG | 1HH1 | 41.905 | 32.439 | 43.426 | 20.00 |
| 2778 | ARG | 2HH1 | 40.666 | 33.647 | 43.339 | 20.00 |
| 2779 | ARG | 1HH2 | 41.602 | 30.761 | 45.232 | 20.00 |
| 2780 | ARG | 2HH2 | 40.159 | 30.814 | 46.201 | 20.00 |
| 2781 | GLU | N | 33.859 | 36.255 | 43.731 | 19.61 |
| 2782 | GLU | CA | 33.468 | 37.442 | 43.053 | 20.49 |
| 2783 | GLU | C | 34.699 | 38.231 | 42.582 | 18.35 |
| 2784 | GLU | O | 35.609 | 38.648 | 43.324 | 19.50 |
| 2785 | GLU | CB | 32.651 | 38.383 | 43.905 | 23.73 |
| 2786 | GLU | CG | 32.354 | 39.674 | 43.116 | 30.58 |
| 2787 | GLU | CD | 31.697 | 40.680 | 44.039 | 37.37 |
| 2788 | GLU | OE1 | 32.349 | 41.643 | 44.394 | 42.91 |
| 2789 | GLU | OE2 | 30.572 | 40.459 | 44.434 | 39.95 |
| 2790 | GLU | H | 34.048 | 36.277 | 44.708 | 20.00 |
| 2791 | GLU | HA | 32.845 | 37.134 | 42.209 | 20.00 |
| 2792 | GLU | 1HB | 33.179 | 38.620 | 44.825 | 20.00 |
| 2793 | GLU | 2HB | 31.718 | 37.904 | 44.224 | 20.00 |
| 2794 | GLU | 1HG | 31.671 | 39.438 | 42.299 | 20.00 |
| 2795 | GLU | 2HG | 33.211 | 40.145 | 42.652 | 20.00 |
| 2796 | ILE | N | 34.562 | 38.431 | 41.227 | 17.31 |
| 2797 | ILE | CA | 35.533 | 39.098 | 40.423 | 15.44 |
| 2798 | ILE | C | 34.806 | 40.329 | 39.820 | 13.03 |
| 2799 | ILE | O | 33.725 | 40.269 | 39.307 | 13.73 |
| 2800 | ILE | CB | 36.014 | 38.081 | 39.316 | 14.77 |
| 2801 | ILE | CG1 | 36.469 | 36.717 | 39.808 | 13.99 |
| 2802 | ILE | CG2 | 37.156 | 38.781 | 38.511 | 13.81 |
| 2803 | ILE | CD1 | 37.777 | 36.731 | 40.616 | 13.39 |
| 2804 | ILE | H | 33.698 | 38.103 | 40.833 | 20.00 |
| 2805 | ILE | HA | 36.373 | 39.393 | 41.053 | 20.00 |
| 2806 | ILE | HB | 35.178 | 37.891 | 38.645 | 20.00 |
| 2807 | ILE | 1HG1 | 36.634 | 36.068 | 38.940 | 20.00 |
| 2808 | ILE | 2HG1 | 35.686 | 36.219 | 40.382 | 20.00 |
| 2809 | ILE | 1HG2 | 37.976 | 39.123 | 39.142 | 20.00 |
| 2810 | ILE | 2HG2 | 36.753 | 39.664 | 38.013 | 20.00 |
| 2811 | ILE | 3HG2 | 37.571 | 38.142 | 37.731 | 20.00 |
| 2812 | ILE | 1HD1 | 37.651 | 37.273 | 41.553 | 20.00 |
| 2813 | ILE | 2HD1 | 38.583 | 37.221 | 40.068 | 20.00 |
| 2814 | ILE | 3HD1 | 38.126 | 35.731 | 40.878 | 20.00 |
| 2815 | LEU | N | 35.437 | 41.444 | 39.855 | 9.92 |
| 2816 | LEU | CA | 34.934 | 42.684 | 39.281 | 10.85 |
| 2817 | LEU | C | 35.639 | 42.986 | 37.908 | 12.45 |
| 2818 | LEU | O | 36.823 | 42.846 | 37.768 | 13.72 |
| 2819 | LEU | CB | 35.395 | 43.657 | 40.382 | 11.52 |
| 2820 | LEU | CG | 34.233 | 43.955 | 41.312 | 17.76 |
| 2821 | LEU | CD1 | 34.708 | 44.759 | 42.493 | 14.86 |
| 2822 | LEU | CD2 | 33.503 | 42.721 | 41.757 | 15.60 |
| 2823 | LEU | H | 36.344 | 41.402 | 40.277 | 20.00 |
| 2824 | LEU | HA | 33.859 | 42.644 | 39.125 | 20.00 |
| 2825 | LEU | 1HB | 35.739 | 44.594 | 39.965 | 20.00 |
| 2826 | LEU | 2HB | 36.256 | 43.272 | 40.931 | 20.00 |
| 2827 | LEU | HG | 33.518 | 44.568 | 40.763 | 20.00 |
| 2828 | LEU | 1HD1 | 35.021 | 45.750 | 42.182 | 20.00 |
| 2829 | LEU | 2HD1 | 35.528 | 44.252 | 42.999 | 20.00 |
| 2830 | LEU | 3HD1 | 33.915 | 44.895 | 43.226 | 20.00 |
| 2831 | LEU | 1HD2 | 34.144 | 41.977 | 42.215 | 20.00 |
| 2832 | LEU | 2HD2 | 32.928 | 42.261 | 40.949 | 20.00 |
| 2833 | LEU | 3HD2 | 32.747 | 43.012 | 42.487 | 20.00 |
| 2834 | HIS | N | 34.933 | 43.394 | 36.894 | 10.68 |
| 2835 | HIS | CA | 35.545 | 43.475 | 35.600 | 11.55 |
| 2836 | HIS | C | 35.323 | 44.872 | 35.144 | 12.79 |
| 2837 | HIS | O | 34.194 | 45.266 | 34.919 | 14.70 |
| 2838 | HIS | CB | 34.788 | 42.489 | 34.668 | 11.04 |
| 2839 | HIS | CG | 35.263 | 42.384 | 33.227 | 9.68 |
| 2840 | HIS | ND1 | 34.526 | 42.828 | 32.187 | 10.25 |
| 2841 | HIS | CD2 | 36.429 | 41.786 | 32.744 | 10.64 |
| 2842 | HIS | CE1 | 35.183 | 42.511 | 31.063 | 12.62 |
| 2843 | HIS | NE2 | 36.329 | 41.906 | 31.409 | 11.21 |
| 2844 | HIS | H | 33.982 | 43.625 | 37.069 | 20.00 |
| 2845 | HIS | HA | 36.601 | 43.242 | 35.581 | 20.00 |
| 2846 | HIS | 1HB | 33.743 | 42.742 | 34.647 | 20.00 |
| 2847 | HIS | 2HB | 34.856 | 41.492 | 35.083 | 20.00 |
| 2848 | HIS | HD1 | 33.677 | 43.272 | 32.321 | 20.00 |
| 2849 | HIS | HD2 | 37.206 | 41.325 | 33.337 | 20.00 |
| 2850 | HIS | HE1 | 34.876 | 42.676 | 30.032 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2851 | PHE | N | 36.438 | 45.608 | 34.939 | 12.23 |
| 2852 | PHE | CA | 36.352 | 47.028 | 34.537 | 10.89 |
| 2853 | PHE | C | 36.685 | 47.113 | 33.028 | 13.34 |
| 2854 | PHE | O | 37.811 | 46.965 | 32.583 | 13.55 |
| 2855 | PHE | CB | 37.334 | 47.858 | 35.441 | 10.80 |
| 2856 | PHE | CG | 37.058 | 47.717 | 36.947 | 11.64 |
| 2857 | PHE | CD1 | 37.655 | 46.741 | 37.702 | 11.60 |
| 2858 | PHE | CD2 | 36.134 | 48.520 | 37.567 | 14.48 |
| 2859 | PHE | CE1 | 37.264 | 46.493 | 39.006 | 12.91 |
| 2860 | PHE | CE2 | 35.739 | 48.287 | 38.862 | 15.96 |
| 2861 | PHE | CZ | 36.291 | 47.267 | 39.581 | 13.40 |
| 2862 | PHE | H | 37.310 | 45.176 | 35.152 | 20.00 |
| 2863 | PHE | HA | 35.335 | 47.384 | 34.690 | 20.00 |
| 2864 | PHE | 1HB | 37.275 | 48.922 | 35.204 | 20.00 |
| 2865 | PHE | 2HB | 38.366 | 47.564 | 35.244 | 20.00 |
| 2866 | PHE | HD1 | 38.413 | 46.111 | 37.256 | 20.00 |
| 2867 | PHE | HD2 | 35.694 | 49.334 | 37.003 | 20.00 |
| 2868 | PHE | HE1 | 37.715 | 45.660 | 39.525 | 20.00 |
| 2869 | PHE | HE2 | 34.999 | 48.915 | 39.328 | 20.00 |
| 2870 | PHE | HZ | 35.930 | 47.074 | 40.572 | 20.00 |
| 2871 | HIS | N | 35.639 | 47.337 | 32.230 | 11.63 |
| 2872 | HIS | CA | 35.829 | 47.375 | 30.802 | 10.69 |
| 2873 | HIS | C | 35.809 | 48.820 | 30.319 | 11.28 |
| 2874 | HIS | O | 34.778 | 49.477 | 30.311 | 10.79 |
| 2875 | HIS | CB | 34.731 | 46.513 | 30.278 | 11.78 |
| 2876 | HIS | CG | 34.919 | 46.186 | 28.833 | 10.24 |
| 2877 | HIS | ND1 | 35.782 | 46.799 | 27.957 | 13.45 |
| 2878 | HIS | CD2 | 34.178 | 45.239 | 28.132 | 9.09 |
| 2879 | HIS | CE1 | 35.554 | 46.232 | 26.766 | 8.49 |
| 2880 | HIS | NE2 | 34.587 | 45.287 | 26.854 | 12.97 |
| 2881 | HIS | H | 34.770 | 47.509 | 32.693 | 20.00 |
| 2882 | HIS | HA | 36.801 | 46.952 | 30.534 | 20.00 |
| 2883 | HIS | 1HB | 33.769 | 46.998 | 30.395 | 20.00 |
| 2884 | HIS | 2HB | 34.712 | 45.579 | 30.833 | 20.00 |
| 2885 | HIS | HD1 | 36.458 | 47.499 | 28.105 | 20.00 |
| 2886 | HIS | HD2 | 33.424 | 44.566 | 28.470 | 20.00 |
| 2887 | HIS | HE1 | 35.972 | 46.552 | 25.831 | 20.00 |
| 2888 | TYR | N | 36.961 | 49.274 | 29.879 | 10.13 |
| 2889 | TYR | CA | 37.059 | 50.545 | 29.109 | 11.53 |
| 2890 | TYR | C | 36.769 | 50.315 | 27.571 | 12.75 |
| 2891 | TYR | O | 37.466 | 49.547 | 26.883 | 11.94 |
| 2892 | TYR | CB | 38.465 | 51.130 | 29.407 | 12.91 |
| 2893 | TYR | CG | 38.500 | 52.618 | 29.205 | 14.41 |
| 2894 | TYR | CD1 | 38.303 | 53.125 | 27.967 | 12.62 |
| 2895 | TYR | CD2 | 38.816 | 53.503 | 30.229 | 14.67 |
| 2896 | TYR | CE1 | 38.422 | 54.506 | 27.769 | 14.22 |
| 2897 | TYR | CE2 | 38.884 | 54.882 | 30.077 | 15.77 |
| 2898 | TYR | CZ | 38.608 | 55.421 | 28.834 | 16.57 |
| 2899 | TYR | OH | 38.583 | 56.821 | 28.797 | 18.08 |
| 2900 | TYR | H | 37.739 | 48.639 | 29.964 | 20.00 |
| 2901 | TYR | HA | 36.319 | 51.229 | 29.522 | 20.00 |
| 2902 | TYR | 1HB | 39.183 | 50.677 | 28.729 | 20.00 |
| 2903 | TYR | 2HB | 38.782 | 50.884 | 30.426 | 20.00 |
| 2904 | TYR | HD1 | 38.125 | 52.492 | 27.111 | 20.00 |
| 2905 | TYR | HD2 | 39.029 | 53.064 | 31.176 | 20.00 |
| 2906 | TYR | HE1 | 38.636 | 54.616 | 26.713 | 20.00 |
| 2907 | TYR | HE2 | 39.100 | 55.550 | 30.901 | 20.00 |
| 2908 | TYR | HH | 38.117 | 57.229 | 28.064 | 20.00 |
| 2909 | THR | N | 35.664 | 50.941 | 27.075 | 13.66 |
| 2910 | THR | CA | 35.217 | 50.519 | 25.758 | 14.87 |
| 2911 | THR | C | 35.474 | 51.605 | 24.708 | 16.37 |
| 2912 | THR | O | 35.293 | 51.365 | 23.530 | 19.74 |
| 2913 | THR | CB | 33.766 | 50.067 | 25.763 | 13.92 |
| 2914 | THR | OG1 | 32.985 | 51.270 | 25.886 | 14.21 |
| 2915 | THR | CG2 | 33.452 | 48.853 | 26.638 | 14.13 |
| 2916 | THR | H | 35.138 | 51.598 | 27.614 | 20.00 |
| 2917 | THR | HA | 35.810 | 49.689 | 25.389 | 20.00 |
| 2918 | THR | HB | 33.665 | 49.671 | 24.715 | 20.00 |
| 2919 | THR | HG1 | 32.608 | 51.609 | 26.739 | 20.00 |
| 2920 | THR | 1HG2 | 33.804 | 48.858 | 27.675 | 20.00 |
| 2921 | THR | 2HG2 | 33.975 | 48.036 | 26.159 | 20.00 |
| 2922 | THR | 3HG2 | 32.412 | 48.517 | 26.599 | 20.00 |
| 2923 | THR | N | 35.980 | 52.791 | 25.104 | 17.79 |
| 2924 | THR | CA | 36.277 | 53.829 | 24.097 | 17.71 |
| 2925 | THR | C | 37.780 | 54.268 | 23.978 | 17.22 |
| 2926 | THR | O | 38.171 | 55.337 | 23.501 | 19.49 |
| 2927 | THR | CB | 35.414 | 55.056 | 24.407 | 20.00 |
| 2928 | THR | OG1 | 35.794 | 55.465 | 25.757 | 22.57 |
| 2929 | THR | CG2 | 33.969 | 54.696 | 24.541 | 17.86 |
| 2930 | THR | H | 35.848 | 53.085 | 26.052 | 20.00 |
| 2931 | THR | HA | 35.998 | 53.464 | 23.110 | 20.00 |
| 2932 | THR | HB | 35.386 | 55.656 | 23.415 | 20.00 |
| 2933 | THR | HG1 | 36.368 | 56.268 | 25.953 | 20.00 |
| 2934 | THR | 1HG2 | 33.838 | 53.994 | 25.327 | 20.00 |
| 2935 | THR | 2HG2 | 33.561 | 54.280 | 23.626 | 20.00 |
| 2936 | THR | 3HG2 | 33.378 | 55.567 | 24.814 | 20.00 |
| 2937 | TRP | N | 38.641 | 53.346 | 24.336 | 13.24 |
| 2938 | TRP | CA | 40.120 | 53.598 | 24.218 | 11.42 |
| 2939 | TRP | C | 40.640 | 52.873 | 22.987 | 11.23 |
| 2940 | TRP | O | 40.679 | 51.639 | 22.980 | 13.88 |
| 2941 | TRP | CB | 40.854 | 53.065 | 25.467 | 10.59 |
| 2942 | TRP | CG | 42.300 | 53.478 | 25.605 | 10.86 |
| 2943 | TRP | CD1 | 43.194 | 53.926 | 24.620 | 10.44 |
| 2944 | TRP | CD2 | 43.010 | 53.434 | 26.877 | 11.23 |
| 2945 | TRP | NE1 | 44.399 | 54.166 | 25.165 | 11.38 |
| 2946 | TRP | CE2 | 44.332 | 53.890 | 26.576 | 11.59 |
| 2947 | TRP | CE3 | 42.647 | 53.113 | 28.170 | 12.73 |
| 2948 | TRP | CZ2 | 45.251 | 54.034 | 27.615 | 9.06 |
| 2949 | TRP | CZ3 | 43.596 | 53.268 | 29.207 | 11.86 |
| 2950 | TRP | CH2 | 44.901 | 53.730 | 28.923 | 9.08 |
| 2951 | TRP | H | 38.223 | 52.591 | 24.823 | 20.00 |
| 2952 | TRP | HA | 40.290 | 54.667 | 24.218 | 20.00 |
| 2953 | TRP | 1HB | 40.803 | 51.977 | 25.516 | 20.00 |
| 2954 | TRP | 2HB | 40.369 | 53.437 | 26.358 | 20.00 |
| 2955 | TRP | HD1 | 42.974 | 54.062 | 23.567 | 20.00 |
| 2956 | TRP | HE1 | 45.198 | 54.476 | 24.680 | 20.00 |
| 2957 | TRP | HE3 | 41.644 | 52.763 | 28.381 | 20.00 |
| 2958 | TRP | HZ2 | 46.233 | 54.366 | 27.330 | 20.00 |
| 2959 | TRP | HZ3 | 43.327 | 53.028 | 30.234 | 20.00 |
| 2960 | TRP | HH2 | 45.624 | 53.867 | 29.709 | 20.00 |
| 2961 | PRO | N | 41.054 | 53.592 | 21.917 | 11.63 |
| 2962 | PRO | CA | 41.341 | 52.864 | 20.657 | 12.03 |
| 2963 | PRO | C | 42.762 | 52.223 | 20.620 | 10.91 |
| 2964 | PRO | O | 43.674 | 52.589 | 21.352 | 11.74 |
| 2965 | PRO | CB | 41.002 | 53.928 | 19.599 | 15.45 |
| 2966 | PRO | CG | 40.318 | 55.060 | 20.382 | 16.92 |
| 2967 | PRO | CD | 40.930 | 55.068 | 21.726 | 12.40 |
| 2968 | PRO | HA | 40.641 | 52.036 | 20.543 | 20.00 |
| 2969 | PRO | 1HB | 40.376 | 53.540 | 18.790 | 20.00 |
| 2970 | PRO | 2HB | 41.911 | 54.325 | 19.146 | 20.00 |
| 2971 | PRO | 1HG | 40.429 | 56.033 | 19.909 | 20.00 |
| 2972 | PRO | 2HG | 39.258 | 54.863 | 20.489 | 20.00 |
| 2973 | PRO | 1HD | 40.296 | 55.584 | 22.434 | 20.00 |
| 2974 | PRO | 2HD | 41.916 | 55.543 | 21.732 | 20.00 |
| 2975 | ASP | N | 42.866 | 51.223 | 19.711 | 9.83 |
| 2976 | ASP | CA | 44.171 | 50.530 | 19.648 | 13.50 |
| 2977 | ASP | C | 45.160 | 51.471 | 19.077 | 15.42 |
| 2978 | ASP | O | 44.802 | 52.201 | 18.172 | 16.15 |
| 2979 | ASP | CB | 44.065 | 49.223 | 18.819 | 14.19 |
| 2980 | ASP | CG | 45.153 | 48.241 | 19.221 | 17.10 |
| 2981 | ASP | OD1 | 45.877 | 48.540 | 20.150 | 16.38 |
| 2982 | ASP | OD2 | 45.270 | 47.155 | 18.676 | 16.84 |
| 2983 | ASP | H | 42.077 | 50.813 | 19.277 | 20.00 |
| 2984 | ASP | HA | 44.449 | 50.328 | 20.691 | 20.00 |
| 2985 | ASP | 1HB | 44.135 | 49.419 | 17.751 | 20.00 |
| 2986 | ASP | 2HB | 43.120 | 48.725 | 19.033 | 20.00 |
| 2987 | PHE | N | 46.329 | 51.527 | 19.651 | 15.66 |
| 2988 | PHE | CA | 47.349 | 52.538 | 19.450 | 13.22 |
| 2989 | PHE | C | 46.921 | 54.020 | 19.555 | 13.65 |
| 2990 | PHE | O | 47.504 | 54.923 | 18.956 | 14.13 |
| 2991 | PHE | CB | 48.233 | 52.272 | 18.290 | 15.03 |
| 2992 | PHE | CG | 48.749 | 50.895 | 18.233 | 16.37 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 2993 | PHE | CD1 | 49.950 | 50.591 | 18.833 | 12.85 |
| 2994 | PHE | CD2 | 48.009 | 49.927 | 17.529 | 15.04 |
| 2995 | PHE | CE1 | 50.376 | 49.294 | 18.803 | 10.54 |
| 2996 | PHE | CE2 | 48.460 | 48.659 | 17.407 | 12.82 |
| 2997 | PHE | CZ | 49.626 | 48.341 | 18.105 | 12.68 |
| 2998 | PHE | H | 46.546 | 50.666 | 20.113 | 20.00 |
| 2999 | PHE | HA | 47.975 | 52.405 | 20.321 | 20.00 |
| 3000 | PHE | 1HB | 49.022 | 53.011 | 18.302 | 20.00 |
| 3001 | PHE | 2HB | 47.662 | 52.452 | 17.380 | 20.00 |
| 3002 | PHE | HD1 | 50.490 | 51.363 | 19.335 | 20.00 |
| 3003 | PHE | HD2 | 47.070 | 50.181 | 17.066 | 20.00 |
| 3004 | PHE | HE1 | 51.281 | 48.969 | 19.299 | 20.00 |
| 3005 | PHE | HE2 | 47.901 | 47.906 | 16.873 | 20.00 |
| 3006 | PHE | HZ | 49.963 | 47.312 | 18.117 | 20.00 |
| 3007 | GLY | N | 45.887 | 54.153 | 20.424 | 12.17 |
| 3008 | GLY | CA | 45.240 | 55.436 | 20.680 | 12.74 |
| 3009 | GLY | C | 45.436 | 55.859 | 22.144 | 13.53 |
| 3010 | GLY | O | 46.132 | 55.250 | 22.953 | 12.80 |
| 3011 | GLY | H | 45.489 | 53.315 | 20.797 | 20.00 |
| 3012 | GLY | 1HA | 44.176 | 55.267 | 20.536 | 20.00 |
| 3013 | GLY | 2HA | 45.596 | 56.211 | 19.988 | 20.00 |
| 3014 | VAL | N | 44.801 | 56.938 | 22.435 | 14.29 |
| 3015 | VAL | CA | 44.812 | 57.503 | 23.722 | 13.36 |
| 3016 | VAL | C | 43.249 | 57.513 | 24.071 | 15.85 |
| 3017 | VAL | O | 42.426 | 57.380 | 23.136 | 16.84 |
| 3018 | VAL | CB | 45.673 | 58.788 | 23.744 | 12.64 |
| 3019 | VAL | CG1 | 45.201 | 59.840 | 22.763 | 13.96 |
| 3020 | VAL | CG2 | 47.178 | 58.444 | 23.585 | 12.56 |
| 3021 | VAL | H | 44.211 | 57.343 | 21.732 | 20.00 |
| 3022 | VAL | HA | 45.291 | 56.801 | 24.402 | 20.00 |
| 3023 | VAL | HB | 45.561 | 59.232 | 24.737 | 20.00 |
| 3024 | VAL | 1HG1 | 44.171 | 60.133 | 22.945 | 20.00 |
| 3025 | VAL | 2HG1 | 45.278 | 59.537 | 21.722 | 20.00 |
| 3026 | VAL | 3HG1 | 45.807 | 60.743 | 22.867 | 20.00 |
| 3027 | VAL | 1HG2 | 47.395 | 58.056 | 22.589 | 20.00 |
| 3028 | VAL | 2HG2 | 47.478 | 57.697 | 24.315 | 20.00 |
| 3029 | VAL | 3HG2 | 47.782 | 59.337 | 23.714 | 20.00 |
| 3030 | PRO | N | 42.963 | 57.517 | 25.476 | 16.09 |
| 3031 | PRO | CA | 41.668 | 57.936 | 26.088 | 14.29 |
| 3032 | PRO | C | 41.138 | 59.345 | 25.657 | 16.70 |
| 3033 | PRO | O | 41.887 | 60.270 | 25.348 | 15.47 |
| 3034 | PRO | CB | 42.035 | 58.106 | 27.586 | 12.24 |
| 3035 | PRO | CG | 43.260 | 57.208 | 27.767 | 11.83 |
| 3036 | PRO | CD | 44.019 | 57.339 | 26.463 | 14.99 |
| 3037 | PRO | HA | 40.885 | 57.194 | 25.936 | 20.00 |
| 3038 | PRO | 1HB | 41.236 | 57.797 | 28.246 | 20.00 |
| 3039 | PRO | 2HB | 42.288 | 59.134 | 27.841 | 20.00 |
| 3040 | PRO | 1HG | 43.844 | 57.437 | 28.646 | 20.00 |
| 3041 | PRO | 2HG | 42.915 | 56.182 | 27.868 | 20.00 |
| 3042 | PRO | 1HD | 44.640 | 56.472 | 26.300 | 20.00 |
| 3043 | PRO | 2HD | 44.642 | 58.226 | 26.489 | 20.00 |
| 3044 | GLU | N | 39.830 | 59.499 | 25.747 | 18.37 |
| 3045 | GLU | CA | 39.149 | 60.735 | 25.401 | 20.99 |
| 3046 | GLU | C | 39.701 | 61.877 | 26.121 | 22.01 |
| 3047 | GLU | O | 39.946 | 62.949 | 25.567 | 24.26 |
| 3048 | GLU | CB | 37.652 | 60.699 | 25.572 | 22.54 |
| 3049 | GLU | CG | 37.095 | 59.481 | 24.814 | 31.50 |
| 3050 | GLU | CD | 36.818 | 58.252 | 25.777 | 36.66 |
| 3051 | GLU | OE1 | 37.792 | 57.706 | 26.363 | 31.28 |
| 3052 | GLU | OE2 | 35.603 | 57.899 | 25.789 | 36.17 |
| 3053 | GLU | H | 39.307 | 58.672 | 25.934 | 20.00 |
| 3054 | GLU | HA | 39.384 | 60.894 | 24.354 | 20.00 |
| 3055 | GLU | 1HB | 37.225 | 61.596 | 25.130 | 20.00 |
| 3056 | GLU | 2HB | 37.322 | 60.660 | 26.604 | 20.00 |
| 3057 | GLU | 1HG | 37.751 | 59.146 | 24.012 | 20.00 |
| 3058 | GLU | 2HG | 36.147 | 59.734 | 24.345 | 20.00 |
| 3059 | SER | N | 39.960 | 61.603 | 27.399 | 20.38 |
| 3060 | SER | CA | 40.647 | 62.714 | 28.080 | 17.88 |
| 3061 | SER | C | 41.167 | 62.167 | 29.306 | 15.08 |
| 3062 | SER | O | 40.789 | 61.054 | 29.671 | 14.67 |
| 3063 | SER | CB | 39.666 | 63.853 | 28.431 | 16.14 |
| 3064 | SER | OG | 38.604 | 63.400 | 29.339 | 13.25 |
| 3065 | SER | H | 39.673 | 60.707 | 27.729 | 20.00 |
| 3066 | SER | HA | 41.461 | 63.055 | 27.454 | 20.00 |
| 3067 | SER | 1HB | 39.386 | 64.462 | 27.511 | 20.00 |
| 3068 | SER | 2HB | 40.217 | 64.669 | 28.926 | 20.00 |
| 3069 | SER | HG | 38.043 | 62.566 | 29.237 | 20.00 |
| 3070 | PRO | N | 42.046 | 62.978 | 29.961 | 17.02 |
| 3071 | PRO | CA | 42.562 | 62.555 | 31.277 | 16.44 |
| 3072 | PRO | C | 41.527 | 62.381 | 32.332 | 16.53 |
| 3073 | PRO | O | 41.596 | 61.476 | 33.162 | 15.74 |
| 3074 | PRO | CB | 43.653 | 63.578 | 31.636 | 16.53 |
| 3075 | PRO | CG | 43.993 | 64.277 | 30.294 | 18.72 |
| 3076 | PRO | CD | 42.716 | 64.193 | 29.431 | 16.72 |
| 3077 | PRO | HA | 43.044 | 61.584 | 31.179 | 20.00 |
| 3078 | PRO | 1HB | 44.530 | 63.132 | 32.109 | 20.00 |
| 3079 | PRO | 2HB | 43.256 | 64.327 | 32.324 | 20.00 |
| 3080 | PRO | 1HG | 44.374 | 65.291 | 30.432 | 20.00 |
| 3081 | PRO | 2HG | 44.794 | 63.718 | 29.803 | 20.00 |
| 3082 | PRO | 1HD | 42.963 | 64.147 | 28.370 | 20.00 |
| 3083 | PRO | 2HD | 42.115 | 65.075 | 29.631 | 20.00 |
| 3084 | ALA | N | 40.466 | 63.193 | 32.219 | 16.66 |
| 3085 | ALA | CA | 39.366 | 63.113 | 33.208 | 16.12 |
| 3086 | ALA | C | 38.576 | 61.824 | 33.103 | 15.23 |
| 3087 | ALA | O | 38.319 | 61.127 | 34.062 | 15.53 |
| 3088 | ALA | CB | 38.449 | 64.319 | 32.990 | 15.29 |
| 3089 | ALA | H | 40.478 | 63.899 | 31.513 | 20.00 |
| 3090 | ALA | HA | 39.809 | 63.153 | 34.207 | 20.00 |
| 3091 | ALA | 1HB | 38.110 | 64.430 | 31.968 | 20.00 |
| 3092 | ALA | 2HB | 38.976 | 65.236 | 33.241 | 20.00 |
| 3093 | ALA | 3HB | 37.586 | 64.273 | 33.637 | 20.00 |
| 3094 | SER | N | 38.207 | 61.442 | 31.920 | 15.32 |
| 3095 | SER | CA | 37.563 | 60.086 | 31.870 | 15.79 |
| 3096 | SER | C | 38.482 | 58.892 | 32.167 | 13.45 |
| 3097 | SER | O | 38.104 | 57.921 | 32.825 | 13.08 |
| 3098 | SER | CB | 37.106 | 59.914 | 30.447 | 17.95 |
| 3099 | SER | OG | 38.030 | 60.657 | 29.618 | 26.88 |
| 3100 | SER | H | 38.374 | 62.009 | 31.111 | 20.00 |
| 3101 | SER | HA | 36.720 | 60.060 | 32.554 | 20.00 |
| 3102 | SER | 1HB | 36.110 | 60.396 | 30.400 | 20.00 |
| 3103 | SER | 2HB | 36.640 | 58.920 | 30.206 | 20.00 |
| 3104 | SER | HG | 38.996 | 60.405 | 29.428 | 20.00 |
| 3105 | PHE | N | 39.774 | 59.018 | 31.727 | 13.85 |
| 3106 | PHE | CA | 40.788 | 57.998 | 32.090 | 12.76 |
| 3107 | PHE | C | 40.881 | 57.892 | 33.605 | 12.10 |
| 3108 | PHE | O | 40.898 | 56.801 | 34.114 | 14.79 |
| 3109 | PHE | CB | 42.188 | 58.355 | 31.403 | 14.01 |
| 3110 | PHE | CG | 43.256 | 57.467 | 32.071 | 12.89 |
| 3111 | PHE | CD1 | 43.459 | 56.157 | 31.644 | 10.70 |
| 3112 | PHE | CD2 | 44.026 | 57.962 | 33.147 | 15.33 |
| 3113 | PHE | CE1 | 44.455 | 55.390 | 32.240 | 13.65 |
| 3114 | PHE | CE2 | 44.962 | 57.161 | 33.827 | 13.88 |
| 3115 | PHE | CZ | 45.203 | 55.884 | 33.321 | 14.38 |
| 3116 | PHE | H | 40.011 | 59.805 | 31.151 | 20.00 |
| 3117 | PHE | HA | 40.420 | 57.039 | 31.724 | 20.00 |
| 3118 | PHE | 1HB | 42.428 | 59.353 | 31.538 | 20.00 |
| 3119 | PHE | 2HB | 42.148 | 58.111 | 30.338 | 20.00 |
| 3120 | PHE | HD1 | 42.865 | 55.751 | 30.834 | 20.00 |
| 3121 | PHE | HD2 | 43.878 | 58.976 | 33.489 | 20.00 |
| 3122 | PHE | HE1 | 44.653 | 54.393 | 31.863 | 20.00 |
| 3123 | PHE | HE2 | 45.523 | 57.524 | 34.685 | 20.00 |
| 3124 | PHE | HZ | 45.964 | 55.260 | 33.765 | 20.00 |
| 3125 | LEU | N | 40.947 | 59.079 | 34.274 | 13.17 |
| 3126 | LEU | CA | 41.247 | 59.248 | 35.713 | 11.98 |
| 3127 | LEU | C | 40.029 | 58.870 | 36.513 | 11.69 |
| 3128 | LEU | O | 40.128 | 58.021 | 37.389 | 10.86 |
| 3129 | LEU | CB | 41.632 | 60.677 | 36.115 | 11.49 |
| 3130 | LEU | CG | 43.049 | 61.075 | 35.775 | 9.71 |
| 3131 | LEU | CD1 | 44.161 | 60.504 | 36.812 | 12.65 |
| 3132 | LEU | CD2 | 43.046 | 62.608 | 35.515 | 12.34 |
| 3133 | LEU | H | 40.884 | 59.875 | 33.675 | 20.00 |
| 3134 | LEU | HA | 42.051 | 58.546 | 35.951 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3135 | LEU | 1HB | 41.509 | 60.842 | 37.187 | 20.00 |
| 3136 | LEU | 2HB | 40.927 | 61.358 | 35.635 | 20.00 |
| 3137 | LEU | HG | 43.285 | 60.627 | 34.817 | 20.00 |
| 3138 | LEU | 1HD1 | 44.121 | 59.416 | 36.874 | 20.00 |
| 3139 | LEU | 2HD1 | 43.969 | 60.871 | 37.820 | 20.00 |
| 3140 | LEU | 3HD1 | 45.175 | 60.780 | 36.532 | 20.00 |
| 3141 | LEU | 1HD2 | 42.831 | 63.130 | 36.448 | 20.00 |
| 3142 | LEU | 2HD2 | 42.314 | 62.959 | 34.794 | 20.00 |
| 3143 | LEU | 3HD2 | 44.031 | 62.930 | 35.184 | 20.00 |
| 3144 | ASN | N | 38.872 | 59.446 | 36.129 | 13.52 |
| 3145 | ASN | CA | 37.574 | 58.890 | 36.526 | 14.70 |
| 3146 | ASN | C | 37.456 | 57.332 | 36.437 | 13.68 |
| 3147 | ASN | O | 37.238 | 56.742 | 37.481 | 13.48 |
| 3148 | ASN | CB | 36.423 | 59.673 | 35.859 | 15.31 |
| 3149 | ASN | CG | 35.033 | 59.150 | 36.303 | 16.04 |
| 3150 | ASN | OD1 | 34.813 | 59.091 | 37.510 | 17.67 |
| 3151 | ASN | ND2 | 34.127 | 58.751 | 35.405 | 15.77 |
| 3152 | ASN | H | 38.965 | 60.202 | 35.486 | 20.00 |
| 3153 | ASN | HA | 37.544 | 59.107 | 37.591 | 20.00 |
| 3154 | ASN | 1HB | 36.509 | 59.883 | 34.794 | 20.00 |
| 3155 | ASN | 2HB | 36.434 | 60.658 | 36.318 | 20.00 |
| 3156 | ASN | 1HD2 | 33.321 | 58.374 | 35.886 | 20.00 |
| 3157 | ASN | 2HD2 | 34.246 | 58.811 | 34.418 | 20.00 |
| 3158 | PHE | N | 37.671 | 56.657 | 35.281 | 12.27 |
| 3159 | PHE | CA | 37.848 | 55.157 | 35.199 | 11.60 |
| 3160 | PHE | C | 38.826 | 54.528 | 36.216 | 11.61 |
| 3161 | PHE | O | 38.507 | 53.684 | 37.018 | 13.15 |
| 3162 | PHE | CB | 38.317 | 54.735 | 33.790 | 11.94 |
| 3163 | PHE | CG | 38.417 | 53.234 | 33.582 | 11.78 |
| 3164 | PHE | CD1 | 39.644 | 52.558 | 33.626 | 14.00 |
| 3165 | PHE | CD2 | 37.292 | 52.475 | 33.355 | 11.64 |
| 3166 | PHE | CE1 | 39.718 | 51.158 | 33.535 | 10.61 |
| 3167 | PHE | CE2 | 37.370 | 51.102 | 33.252 | 12.07 |
| 3168 | PHE | CZ | 38.565 | 50.426 | 33.352 | 10.24 |
| 3169 | PHE | H | 37.841 | 57.232 | 34.482 | 20.00 |
| 3170 | PHE | HA | 36.884 | 54.701 | 35.429 | 20.00 |
| 3171 | PHE | 1HB | 39.285 | 55.158 | 33.567 | 20.00 |
| 3172 | PHE | 2HB | 37.678 | 55.105 | 32.995 | 20.00 |
| 3173 | PHE | HD1 | 40.553 | 53.144 | 33.746 | 20.00 |
| 3174 | PHE | HD2 | 36.350 | 52.985 | 33.259 | 20.00 |
| 3175 | PHE | HE1 | 40.676 | 50.645 | 33.599 | 20.00 |
| 3176 | PHE | HE2 | 36.457 | 50.539 | 33.082 | 20.00 |
| 3177 | PHE | HZ | 38.602 | 49.351 | 33.281 | 20.00 |
| 3178 | LEU | N | 40.060 | 54.928 | 36.155 | 10.72 |
| 3179 | LEU | CA | 41.129 | 54.468 | 37.080 | 10.36 |
| 3180 | LEU | C | 40.671 | 54.520 | 38.579 | 11.41 |
| 3181 | LEU | O | 40.734 | 53.555 | 39.309 | 8.72 |
| 3182 | LEU | CB | 42.457 | 55.335 | 36.829 | 9.30 |
| 3183 | LEU | CG | 43.531 | 55.094 | 37.943 | 11.24 |
| 3184 | LEU | CD1 | 44.819 | 55.890 | 37.855 | 9.97 |
| 3185 | LEU | CD2 | 43.880 | 53.666 | 38.148 | 8.08 |
| 3186 | LEU | H | 40.230 | 55.612 | 35.446 | 20.00 |
| 3187 | LEU | HA | 41.306 | 53.427 | 36.811 | 20.00 |
| 3188 | LEU | 1HB | 42.214 | 56.395 | 36.816 | 20.00 |
| 3189 | LEU | 2HB | 42.881 | 55.113 | 35.846 | 20.00 |
| 3190 | LEU | HG | 43.084 | 55.415 | 38.883 | 20.00 |
| 3191 | LEU | 1HD1 | 44.605 | 56.957 | 37.902 | 20.00 |
| 3192 | LEU | 2HD1 | 45.361 | 55.713 | 36.926 | 20.00 |
| 3193 | LEU | 3HD1 | 45.489 | 55.647 | 38.679 | 20.00 |
| 3194 | LEU | 1HD2 | 44.339 | 53.255 | 37.248 | 20.00 |
| 3195 | LEU | 2HD2 | 43.033 | 53.027 | 38.390 | 20.00 |
| 3196 | LEU | 3HD2 | 44.625 | 53.549 | 38.936 | 20.00 |
| 3197 | PHE | N | 40.227 | 55.702 | 38.999 | 13.37 |
| 3198 | PHE | CA | 39.608 | 55.966 | 40.304 | 14.13 |
| 3199 | PHE | C | 38.419 | 55.074 | 40.584 | 14.10 |
| 3200 | PHE | O | 38.421 | 54.432 | 41.582 | 16.46 |
| 3201 | PHE | CB | 39.373 | 57.460 | 40.466 | 14.59 |
| 3202 | PHE | CG | 40.608 | 58.108 | 41.004 | 17.38 |
| 3203 | PHE | CD1 | 41.729 | 58.330 | 40.223 | 17.66 |
| 3204 | PHE | CD2 | 40.649 | 58.448 | 42.351 | 20.46 |
| 3205 | PHE | CE1 | 42.902 | 58.849 | 40.752 | 17.85 |
| 3206 | PHE | CE2 | 41.842 | 58.951 | 42.901 | 21.97 |
| 3207 | PHE | CZ | 42.980 | 59.145 | 42.099 | 19.00 |
| 3208 | PHE | H | 40.315 | 56.444 | 38.339 | 20.00 |
| 3209 | PHE | HA | 40.353 | 55.693 | 41.035 | 20.00 |
| 3210 | PHE | 1HB | 38.539 | 57.656 | 41.135 | 20.00 |
| 3211 | PHE | 2HB | 39.078 | 57.912 | 39.521 | 20.00 |
| 3212 | PHE | HD1 | 41.687 | 58.093 | 39.172 | 20.00 |
| 3213 | PHE | HD2 | 39.778 | 58.316 | 42.988 | 20.00 |
| 3214 | PHE | HE1 | 43.761 | 58.990 | 40.117 | 20.00 |
| 3215 | PHE | HE2 | 41.841 | 59.192 | 43.957 | 20.00 |
| 3216 | PHE | HZ | 43.888 | 59.517 | 42.548 | 20.00 |
| 3217 | LYS | N | 37.472 | 54.865 | 39.696 | 14.03 |
| 3218 | LYS | CA | 36.583 | 53.707 | 39.921 | 13.68 |
| 3219 | LYS | C | 37.382 | 52.381 | 40.226 | 13.76 |
| 3220 | LYS | O | 37.060 | 51.643 | 41.128 | 13.17 |
| 3221 | LYS | CB | 35.710 | 53.494 | 38.629 | 17.74 |
| 3222 | LYS | CG | 34.241 | 53.905 | 38.681 | 26.69 |
| 3223 | LYS | CD | 33.252 | 52.778 | 39.167 | 32.82 |
| 3224 | LYS | CE | 31.708 | 53.171 | 39.423 | 34.45 |
| 3225 | LYS | NZ | 30.586 | 52.149 | 39.327 | 39.18 |
| 3226 | LYS | H | 37.491 | 55.414 | 38.855 | 20.00 |
| 3227 | LYS | HA | 35.958 | 53.951 | 40.781 | 20.00 |
| 3228 | LYS | 1HB | 35.782 | 52.475 | 38.241 | 20.00 |
| 3229 | LYS | 2HB | 36.164 | 54.118 | 37.857 | 20.00 |
| 3230 | LYS | 1HG | 34.004 | 54.112 | 37.648 | 20.00 |
| 3231 | LYS | 2HG | 34.101 | 54.839 | 39.226 | 20.00 |
| 3232 | LYS | 1HD | 33.656 | 52.326 | 40.073 | 20.00 |
| 3233 | LYS | 2HD | 33.287 | 51.993 | 38.414 | 20.00 |
| 3234 | LYS | 1HE | 31.446 | 53.975 | 38.749 | 20.00 |
| 3235 | LYS | 2HE | 31.667 | 53.627 | 40.417 | 20.00 |
| 3236 | LYS | 1HZ | 30.720 | 51.336 | 39.961 | 20.00 |
| 3237 | LYS | 2HZ | 30.445 | 51.758 | 38.364 | 20.00 |
| 3238 | LYS | 3HZ | 29.655 | 52.552 | 39.548 | 20.00 |
| 3239 | VAL | N | 38.441 | 52.045 | 39.435 | 13.89 |
| 3240 | VAL | CA | 39.117 | 50.767 | 39.646 | 11.86 |
| 3241 | VAL | C | 39.668 | 50.735 | 41.109 | 11.86 |
| 3242 | VAL | O | 39.382 | 49.808 | 41.856 | 11.98 |
| 3243 | VAL | CB | 40.222 | 50.455 | 38.595 | 12.00 |
| 3244 | VAL | CG1 | 39.714 | 50.431 | 37.083 | 11.88 |
| 3245 | VAL | CG2 | 40.882 | 49.143 | 38.956 | 12.37 |
| 3246 | VAL | H | 38.644 | 52.666 | 38.678 | 20.00 |
| 3247 | VAL | HA | 38.347 | 50.001 | 39.562 | 20.00 |
| 3248 | VAL | HB | 40.980 | 51.236 | 38.654 | 20.00 |
| 3249 | VAL | 1HG1 | 39.334 | 51.404 | 36.781 | 20.00 |
| 3250 | VAL | 2HG1 | 38.911 | 49.717 | 36.936 | 20.00 |
| 3251 | VAL | 3HG1 | 40.521 | 50.193 | 36.388 | 20.00 |
| 3252 | VAL | 1HG2 | 40.141 | 48.344 | 38.985 | 20.00 |
| 3253 | VAL | 2HG2 | 41.338 | 49.168 | 39.940 | 20.00 |
| 3254 | VAL | 3HG2 | 41.657 | 48.868 | 38.246 | 20.00 |
| 3255 | ARG | N | 40.409 | 51.870 | 41.447 | 12.93 |
| 3256 | ARG | CA | 40.873 | 52.261 | 42.832 | 14.48 |
| 3257 | ARG | C | 39.825 | 52.066 | 43.972 | 16.45 |
| 3258 | ARG | O | 39.966 | 51.141 | 44.744 | 17.22 |
| 3259 | ARG | CB | 41.467 | 53.625 | 42.820 | 13.76 |
| 3260 | ARG | CG | 42.889 | 53.536 | 42.265 | 12.22 |
| 3261 | ARG | CD | 43.652 | 54.811 | 42.463 | 13.67 |
| 3262 | ARG | NE | 45.033 | 54.629 | 42.060 | 15.68 |
| 3263 | ARG | CZ | 46.003 | 55.526 | 42.281 | 14.21 |
| 3264 | ARG | NH | 45.760 | 56.603 | 42.913 | 12.91 |
| 3265 | ARG | NH2 | 47.224 | 55.411 | 41.884 | 12.03 |
| 3266 | ARG | H | 40.563 | 52.500 | 40.699 | 20.00 |
| 3267 | ARG | HA | 41.629 | 51.519 | 43.075 | 20.00 |
| 3268 | ARG | 1HB | 41.495 | 54.037 | 43.832 | 20.00 |
| 3269 | ARG | 2HB | 40.831 | 54.268 | 42.232 | 20.00 |
| 3270 | ARG | 1HG | 42.853 | 53.277 | 41.206 | 20.00 |
| 3271 | ARG | 2HG | 43.451 | 52.741 | 42.750 | 20.00 |
| 3272 | ARG | 1HD | 43.664 | 55.063 | 43.522 | 20.00 |
| 3273 | ARG | 2HD | 43.212 | 55.649 | 41.915 | 20.00 |
| 3274 | ARG | HE | 45.320 | 53.862 | 41.467 | 20.00 |
| 3275 | ARG | 1HH1 | 46.502 | 57.215 | 43.201 | 20.00 |
| 3276 | ARG | 2HH1 | 44.822 | 56.812 | 43.169 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3277 | ARG | 1HH2 | 47.930 | 56.047 | 42.164 | 20.00 |
| 3278 | ARG | 2HH2 | 47.472 | 54.665 | 41.247 | 20.00 |
| 3279 | GLU | N | 38.745 | 52.856 | 43.977 | 16.23 |
| 3280 | GLU | CA | 37.684 | 52.766 | 45.003 | 16.92 |
| 3281 | GLU | C | 37.252 | 51.348 | 45.300 | 16.63 |
| 3282 | GLU | O | 36.916 | 50.971 | 46.419 | 17.05 |
| 3283 | GLU | CB | 36.444 | 53.545 | 44.582 | 21.77 |
| 3284 | GLU | CG | 36.799 | 54.907 | 43.984 | 30.11 |
| 3285 | GLU | CD | 37.027 | 55.961 | 44.992 | 37.62 |
| 3286 | GLU | OE1 | 36.553 | 57.060 | 44.734 | 42.75 |
| 3287 | GLU | OE2 | 37.678 | 55.675 | 46.010 | 39.25 |
| 3288 | GLU | H | 38.672 | 53.569 | 43.277 | 20.00 |
| 3289 | GLU | HA | 38.104 | 53.180 | 45.920 | 20.00 |
| 3290 | GLU | 1HB | 35.743 | 53.654 | 45.404 | 20.00 |
| 3291 | GLU | 2HB | 35.911 | 53.001 | 43.806 | 20.00 |
| 3292 | GLU | 1HG | 36.049 | 55.234 | 43.267 | 20.00 |
| 3293 | GLU | 2HG | 37.756 | 54.964 | 43.507 | 20.00 |
| 3294 | SER | N | 37.245 | 50.596 | 44.208 | 16.50 |
| 3295 | SER | CA | 36.586 | 49.299 | 44.192 | 17.63 |
| 3296 | SER | C | 37.276 | 48.308 | 45.115 | 20.41 |
| 3297 | SER | O | 36.752 | 47.306 | 45.551 | 21.90 |
| 3298 | SER | CB | 36.543 | 48.757 | 42.749 | 14.84 |
| 3299 | SER | OG | 37.770 | 47.902 | 42.522 | 13.92 |
| 3300 | SER | H | 37.593 | 51.010 | 43.365 | 20.00 |
| 3301 | SER | HA | 35.572 | 49.436 | 44.561 | 20.00 |
| 3302 | SER | 1HB | 36.155 | 49.519 | 42.003 | 20.00 |
| 3303 | SER | 2HB | 35.639 | 48.112 | 42.750 | 20.00 |
| 3304 | SER | HG | 38.700 | 48.252 | 42.358 | 20.00 |
| 3305 | GLY | N | 38.524 | 48.565 | 45.371 | 20.72 |
| 3306 | GLY | CA | 39.194 | 47.651 | 46.288 | 20.75 |
| 3307 | GLY | C | 40.089 | 46.595 | 45.636 | 22.62 |
| 3308 | GLY | O | 40.792 | 45.813 | 46.284 | 25.75 |
| 3309 | GLY | H | 38.903 | 49.440 | 45.055 | 20.00 |
| 3310 | GLY | 1HA | 38.508 | 47.150 | 46.966 | 20.00 |
| 3311 | GLY | 2HA | 39.722 | 48.329 | 46.930 | 20.00 |
| 3312 | SER | N | 40.027 | 46.568 | 44.280 | 20.77 |
| 3313 | SER | CA | 40.726 | 45.501 | 43.613 | 20.37 |
| 3314 | SER | C | 42.153 | 45.729 | 43.531 | 22.30 |
| 3315 | SER | O | 42.854 | 44.771 | 43.336 | 22.94 |
| 3316 | SER | CB | 40.220 | 45.343 | 42.184 | 17.21 |
| 3317 | SER | OG | 38.756 | 45.469 | 42.138 | 16.17 |
| 3318 | SER | H | 39.321 | 47.129 | 43.860 | 20.00 |
| 3319 | SER | HA | 40.564 | 44.582 | 44.184 | 20.00 |
| 3320 | SER | 1HB | 40.511 | 44.313 | 41.903 | 20.00 |
| 3321 | SER | 2HB | 40.832 | 45.875 | 41.397 | 20.00 |
| 3322 | SER | HG | 38.200 | 46.170 | 42.594 | 20.00 |
| 3323 | LEU | N | 42.580 | 46.968 | 43.678 | 22.44 |
| 3324 | LEU | CA | 44.021 | 47.151 | 43.601 | 25.58 |
| 3325 | LEU | C | 44.758 | 46.978 | 44.971 | 29.18 |
| 3326 | LEU | O | 45.885 | 47.472 | 45.142 | 34.54 |
| 3327 | LEU | CB | 44.227 | 48.551 | 43.032 | 23.62 |
| 3328 | LEU | CG | 43.771 | 48.613 | 41.595 | 22.66 |
| 3329 | LEU | CD1 | 44.790 | 47.909 | 40.682 | 23.63 |
| 3330 | LEU | CD2 | 43.739 | 50.030 | 41.191 | 25.59 |
| 3331 | LEU | H | 41.920 | 47.692 | 43.869 | 20.00 |
| 3332 | LEU | HA | 44.457 | 46.425 | 42.916 | 20.00 |
| 3333 | LEU | 1HB | 45.272 | 48.860 | 43.086 | 20.00 |
| 3334 | LEU | 2HB | 43.668 | 49.264 | 43.642 | 20.00 |
| 3335 | LEU | HG | 42.768 | 48.203 | 41.473 | 20.00 |
| 3336 | LEU | 1HD1 | 44.838 | 46.837 | 40.861 | 20.00 |
| 3337 | LEU | 2HD1 | 45.797 | 48.314 | 40.814 | 20.00 |
| 3338 | LEU | 3HD1 | 44.523 | 48.057 | 39.636 | 20.00 |
| 3339 | LEU | 1HD2 | 44.730 | 50.484 | 41.260 | 20.00 |
| 3340 | LEU | 2HD2 | 43.082 | 50.610 | 41.825 | 20.00 |
| 3341 | LEU | 3HD2 | 43.390 | 50.156 | 40.166 | 20.00 |
| 3342 | SER | N | 44.047 | 46.362 | 45.949 | 27.88 |
| 3343 | SER | CA | 44.527 | 46.315 | 47.294 | 28.98 |
| 3344 | SER | C | 45.268 | 45.026 | 47.535 | 29.17 |
| 3345 | SER | O | 44.928 | 44.000 | 46.945 | 29.28 |
| 3346 | SER | CB | 43.294 | 46.473 | 48.203 | 29.56 |
| 3347 | SER | OG | 42.391 | 47.648 | 47.851 | 38.82 |
| 3348 | SER | H | 43.142 | 45.971 | 45.753 | 20.00 |
| 3349 | SER | HA | 45.282 | 47.090 | 47.412 | 20.00 |
| 3350 | SER | 1HB | 43.680 | 46.480 | 49.240 | 20.00 |
| 3351 | SER | 2HB | 42.704 | 45.533 | 48.129 | 20.00 |
| 3352 | SER | HG | 42.660 | 48.585 | 47.609 | 20.00 |
| 3353 | PRO | N | 46.350 | 45.122 | 48.386 | 28.99 |
| 3354 | PRO | CA | 47.235 | 44.009 | 48.606 | 28.15 |
| 3355 | PRO | C | 46.665 | 42.947 | 49.550 | 27.34 |
| 3356 | PRO | O | 47.292 | 41.932 | 49.843 | 28.43 |
| 3357 | PRO | CB | 48.430 | 44.664 | 49.261 | 29.14 |
| 3358 | PRO | CG | 47.828 | 45.786 | 50.081 | 28.91 |
| 3359 | PRO | CD | 46.762 | 46.306 | 49.144 | 28.77 |
| 3360 | PRO | HA | 47.507 | 43.522 | 47.670 | 20.00 |
| 3361 | PRO | 1HB | 49.098 | 45.079 | 48.505 | 20.00 |
| 3362 | PRO | 2HB | 49.021 | 43.976 | 49.861 | 20.00 |
| 3363 | PRO | 1HG | 47.380 | 45.394 | 50.989 | 20.00 |
| 3364 | PRO | 2HG | 48.563 | 46.532 | 50.377 | 20.00 |
| 3365 | PRO | 1HD | 47.199 | 47.044 | 48.471 | 20.00 |
| 3366 | PRO | 2HD | 45.931 | 46.753 | 49.695 | 20.00 |
| 3367 | GLU | N | 45.457 | 43.150 | 49.997 | 25.89 |
| 3368 | GLU | CA | 44.871 | 41.988 | 50.605 | 27.19 |
| 3369 | GLU | C | 44.368 | 41.012 | 49.552 | 26.00 |
| 3370 | GLU | O | 43.942 | 39.916 | 49.893 | 25.89 |
| 3371 | GLU | CB | 43.911 | 42.425 | 51.728 | 33.55 |
| 3372 | GLU | CG | 42.550 | 43.115 | 51.372 | 41.02 |
| 3373 | GLU | CD | 42.705 | 44.505 | 50.654 | 47.74 |
| 3374 | GLU | OE1 | 43.847 | 45.031 | 50.685 | 49.25 |
| 3375 | GLU | OE2 | 41.702 | 45.025 | 50.090 | 51.04 |
| 3376 | GLU | H | 44.923 | 43.947 | 49.758 | 20.00 |
| 3377 | GLU | HA | 45.628 | 41.417 | 51.145 | 20.00 |
| 3378 | GLU | 1HB | 44.457 | 43.059 | 52.424 | 20.00 |
| 3379 | GLU | 2HB | 43.665 | 41.517 | 52.278 | 20.00 |
| 3380 | GLU | 1HG | 41.959 | 43.265 | 52.272 | 20.00 |
| 3381 | GLU | 2HG | 41.958 | 42.466 | 50.731 | 20.00 |
| 3382 | HIS | N | 44.471 | 41.415 | 48.248 | 21.92 |
| 3383 | HIS | CA | 44.127 | 40.631 | 47.048 | 18.96 |
| 3384 | HIS | C | 45.367 | 40.200 | 46.240 | 17.83 |
| 3385 | HIS | O | 46.450 | 40.745 | 46.401 | 17.07 |
| 3386 | HIS | CB | 43.211 | 41.449 | 46.115 | 20.94 |
| 3387 | HIS | CG | 41.922 | 41.788 | 46.796 | 20.70 |
| 3388 | HIS | ND1 | 41.464 | 43.035 | 47.020 | 22.42 |
| 3389 | HIS | CD2 | 40.920 | 40.898 | 47.210 | 19.89 |
| 3390 | HIS | CE1 | 40.213 | 42.908 | 47.536 | 18.97 |
| 3391 | HIS | NE2 | 39.847 | 41.615 | 47.661 | 19.93 |
| 3392 | HIS | H | 44.691 | 42.370 | 48.072 | 20.00 |
| 3393 | HIS | HA | 43.622 | 39.722 | 47.371 | 20.00 |
| 3394 | HIS | 1HB | 42.958 | 40.907 | 45.199 | 20.00 |
| 3395 | HIS | 2HB | 43.680 | 42.390 | 45.807 | 20.00 |
| 3396 | HIS | HD1 | 41.918 | 43.894 | 46.893 | 20.00 |
| 3397 | HIS | HD2 | 41.004 | 39.919 | 47.163 | 20.00 |
| 3398 | HIS | HE1 | 39.593 | 43.730 | 47.851 | 20.00 |
| 3399 | GLY | N | 45.184 | 39.221 | 45.302 | 16.31 |
| 3400 | GLY | CA | 46.302 | 39.054 | 44.354 | 14.07 |
| 3401 | GLY | C | 46.385 | 40.252 | 43.419 | 12.35 |
| 3402 | GLY | O | 45.650 | 41.217 | 43.559 | 13.46 |
| 3403 | GLY | H | 44.287 | 38.802 | 45.246 | 20.00 |
| 3404 | GLY | 1HA | 46.107 | 38.168 | 43.769 | 20.00 |
| 3405 | GLY | 2HA | 47.243 | 38.952 | 44.893 | 20.00 |
| 3406 | PRO | N | 47.313 | 40.254 | 42.476 | 11.56 |
| 3407 | PRO | CA | 47.457 | 41.398 | 41.621 | 13.06 |
| 3408 | PRO | C | 46.319 | 41.572 | 40.614 | 12.70 |
| 3409 | PRO | O | 45.791 | 40.570 | 40.113 | 13.68 |
| 3410 | PRO | CB | 48.793 | 41.186 | 40.861 | 11.82 |
| 3411 | PRO | CG | 49.194 | 39.809 | 41.186 | 12.42 |
| 3412 | PRO | CD | 48.405 | 39.318 | 42.377 | 11.92 |
| 3413 | PRO | HA | 47.521 | 42.314 | 42.213 | 20.00 |
| 3414 | PRO | 1HB | 49.530 | 41.880 | 41.216 | 20.00 |
| 3415 | PRO | 2HB | 48.701 | 41.370 | 39.795 | 20.00 |
| 3416 | PRO | 1HG | 48.850 | 39.180 | 40.380 | 20.00 |
| 3417 | PRO | 2HG | 50.270 | 39.657 | 41.272 | 20.00 |
| 3418 | PRO | 1HD | 49.014 | 39.338 | 43.284 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3419 | PRO | 2HD | 48.052 | 38.297 | 42.234 | 20.00 |
| 3420 | VAL | N | 45.973 | 42.849 | 40.334 | 12.70 |
| 3421 | VAL | CA | 44.929 | 42.963 | 39.339 | 12.91 |
| 3422 | VAL | C | 45.483 | 42.510 | 37.953 | 13.19 |
| 3423 | VAL | O | 46.621 | 42.728 | 37.620 | 11.64 |
| 3424 | VAL | CB | 44.496 | 44.421 | 39.253 | 13.06 |
| 3425 | VAL | CG1 | 43.349 | 44.731 | 38.248 | 14.25 |
| 3426 | VAL | CG2 | 45.666 | 45.279 | 38.770 | 13.39 |
| 3427 | VAL | H | 46.382 | 43.579 | 40.884 | 20.00 |
| 3428 | VAL | HA | 44.101 | 42.315 | 39.632 | 20.00 |
| 3429 | VAL | HB | 44.216 | 44.757 | 40.258 | 20.00 |
| 3430 | VAL | 1HG1 | 42.439 | 44.202 | 38.530 | 20.00 |
| 3431 | VAL | 2HG1 | 43.570 | 44.460 | 37.215 | 20.00 |
| 3432 | VAL | 3HG1 | 43.120 | 45.801 | 38.259 | 20.00 |
| 3433 | VAL | 1HG2 | 45.922 | 45.076 | 37.665 | 20.00 |
| 3434 | VAL | 2HG2 | 46.576 | 45.157 | 39.298 | 20.00 |
| 3435 | VAL | 3HG2 | 45.433 | 46.341 | 38.734 | 20.00 |
| 3436 | VAL | N | 44.602 | 41.927 | 37.144 | 12.59 |
| 3437 | VAL | CA | 44.881 | 41.577 | 35.752 | 11.98 |
| 3438 | VAL | O | 44.531 | 42.778 | 34.849 | 12.38 |
| 3439 | VAL | O | 43.397 | 43.158 | 34.785 | 15.24 |
| 3440 | VAL | CB | 44.176 | 40.272 | 35.374 | 9.51 |
| 3441 | VAL | CG1 | 44.743 | 39.059 | 36.135 | 9.49 |
| 3442 | VAL | CG2 | 44.361 | 39.925 | 33.910 | 10.06 |
| 3443 | VAL | H | 43.709 | 41.713 | 37.540 | 20.00 |
| 3444 | VAL | HA | 45.954 | 41.413 | 35.671 | 20.00 |
| 3445 | VAL | HB | 43.115 | 40.379 | 35.597 | 20.00 |
| 3446 | VAL | 1HG1 | 44.479 | 39.140 | 37.183 | 20.00 |
| 3447 | VAL | 2HG1 | 45.824 | 38.965 | 36.047 | 20.00 |
| 3448 | VAL | 3HG1 | 44.325 | 38.113 | 35.792 | 20.00 |
| 3449 | VAL | 1HG2 | 45.410 | 39.826 | 33.635 | 20.00 |
| 3450 | VAL | 2HG2 | 43.899 | 40.660 | 33.252 | 20.00 |
| 3451 | VAL | 3HG2 | 43.873 | 38.976 | 33.702 | 20.00 |
| 3452 | VAL | N | 45.479 | 43.359 | 34.121 | 10.51 |
| 3453 | VAL | CA | 45.213 | 44.321 | 33.091 | 10.15 |
| 3454 | VAL | C | 45.520 | 43.549 | 31.813 | 11.07 |
| 3455 | VAL | O | 46.535 | 42.885 | 31.627 | 11.12 |
| 3456 | VAL | CB | 46.096 | 45.556 | 33.342 | 9.24 |
| 3457 | VAL | CG1 | 46.058 | 45.910 | 34.877 | 8.57 |
| 3458 | VAL | CG2 | 45.692 | 46.835 | 32.573 | 9.28 |
| 3459 | VAL | H | 46.407 | 43.018 | 34.253 | 20.00 |
| 3460 | VAL | HA | 44.159 | 44.590 | 33.110 | 20.00 |
| 3461 | VAL | HB | 47.120 | 45.295 | 33.080 | 20.00 |
| 3462 | VAL | 1HG1 | 46.514 | 45.136 | 35.496 | 20.00 |
| 3463 | VAL | 2HG1 | 45.048 | 46.086 | 35.240 | 20.00 |
| 3464 | VAL | 3HG1 | 46.642 | 46.804 | 35.079 | 20.00 |
| 3465 | VAL | 1HG2 | 44.720 | 47.202 | 32.917 | 20.00 |
| 3466 | VAL | 2HG2 | 45.588 | 46.664 | 31.520 | 20.00 |
| 3467 | VAL | 3HG2 | 46.421 | 47.627 | 32.738 | 20.00 |
| 3468 | HIS | N | 44.588 | 43.703 | 30.899 | 10.38 |
| 3469 | HIS | CA | 44.843 | 43.345 | 29.524 | 8.48 |
| 3470 | HIS | C | 44.257 | 44.454 | 28.566 | 10.06 |
| 3471 | HIS | O | 43.285 | 45.158 | 28.830 | 9.96 |
| 3472 | HIS | CB | 44.287 | 41.924 | 29.313 | 8.91 |
| 3473 | HIS | CG | 42.824 | 41.948 | 28.937 | 8.64 |
| 3474 | HIS | ND1 | 42.370 | 41.918 | 27.656 | 7.44 |
| 3475 | HIS | CD2 | 41.783 | 41.815 | 29.793 | 8.51 |
| 3476 | HIS | CE1 | 41.082 | 41.735 | 27.708 | 9.19 |
| 3477 | HIS | NE2 | 40.730 | 41.677 | 28.984 | 11.46 |
| 3478 | HIS | H | 43.749 | 44.180 | 31.164 | 20.00 |
| 3479 | HIS | HA | 45.921 | 43.222 | 29.367 | 20.00 |
| 3480 | HIS | 1HB | 44.424 | 41.327 | 30.215 | 20.00 |
| 3481 | HIS | 2HB | 44.812 | 41.427 | 28.502 | 20.00 |
| 3482 | HIS | HD1 | 42.926 | 41.960 | 26.851 | 20.00 |
| 3483 | HIS | HD2 | 41.793 | 41.781 | 30.873 | 20.00 |
| 3484 | HIS | HE1 | 40.391 | 41.585 | 26.885 | 20.00 |
| 3485 | CYS | N | 44.901 | 44.539 | 27.410 | 10.31 |
| 3486 | CYS | CA | 44.335 | 45.149 | 26.196 | 8.62 |
| 3487 | CYS | C | 44.351 | 44.032 | 25.182 | 9.41 |
| 3488 | CYS | O | 44.133 | 42.849 | 25.460 | 9.11 |
| 3489 | CYS | CB | 45.153 | 46.362 | 25.753 | 9.94 |
| 3490 | CYS | SG | 47.021 | 46.150 | 25.889 | 10.94 |
| 3491 | CYS | H | 45.698 | 43.931 | 27.402 | 20.00 |
| 3492 | CYS | HA | 43.311 | 45.451 | 26.378 | 20.00 |
| 3493 | CYS | 1HB | 44.769 | 47.265 | 26.233 | 20.00 |
| 3494 | CYS | 2HB | 44.846 | 46.673 | 24.780 | 20.00 |
| 3495 | CYS | HG | 47.564 | 46.018 | 24.675 | 20.00 |
| 3496 | SER | N | 44.663 | 44.316 | 23.984 | 9.15 |
| 3497 | SER | CA | 44.722 | 43.139 | 23.130 | 8.78 |
| 3498 | SER | C | 46.105 | 42.359 | 23.239 | 8.55 |
| 3499 | SER | O | 46.217 | 41.128 | 23.347 | 8.15 |
| 3500 | SER | CB | 44.389 | 43.699 | 21.683 | 7.93 |
| 3501 | SER | OG | 44.662 | 42.684 | 20.631 | 8.26 |
| 3502 | SER | H | 44.850 | 45.208 | 23.621 | 20.00 |
| 3503 | SER | HA | 43.891 | 42.482 | 23.434 | 20.00 |
| 3504 | SER | 1HB | 45.102 | 44.543 | 21.547 | 20.00 |
| 3505 | SER | 2HB | 43.440 | 44.339 | 21.661 | 20.00 |
| 3506 | SER | HG | 44.215 | 41.792 | 20.609 | 20.00 |
| 3507 | ALA | N | 47.234 | 43.166 | 23.239 | 8.61 |
| 3508 | ALA | CA | 48.571 | 42.556 | 23.451 | 7.66 |
| 3509 | ALA | C | 49.048 | 42.526 | 24.949 | 8.82 |
| 3510 | ALA | O | 49.906 | 41.719 | 25.386 | 11.75 |
| 3511 | ALA | CB | 49.495 | 43.448 | 22.703 | 7.00 |
| 3512 | ALA | H | 47.101 | 44.074 | 22.832 | 20.00 |
| 3513 | ALA | HA | 48.580 | 41.555 | 23.021 | 20.00 |
| 3514 | ALA | 1HB | 49.449 | 44.478 | 23.062 | 20.00 |
| 3515 | ALA | 2HB | 49.221 | 43.481 | 21.650 | 20.00 |
| 3516 | ALA | 3HB | 50.531 | 43.112 | 22.754 | 20.00 |
| 3517 | GLY | N | 48.451 | 43.474 | 25.731 | 8.66 |
| 3518 | GLY | CA | 48.838 | 43.523 | 27.166 | 8.32 |
| 3519 | GLY | C | 50.020 | 44.449 | 27.521 | 9.76 |
| 3520 | GLY | O | 50.750 | 44.217 | 28.493 | 10.12 |
| 3521 | GLY | H | 47.716 | 43.998 | 25.323 | 20.00 |
| 3522 | GLY | 1HA | 49.118 | 42.517 | 27.472 | 20.00 |
| 3523 | GLY | 2HA | 47.962 | 43.705 | 27.760 | 20.00 |
| 3524 | ILE | N | 50.209 | 45.476 | 26.649 | 11.14 |
| 3525 | ILE | CA | 51.393 | 46.367 | 26.588 | 12.07 |
| 3526 | ILE | C | 51.104 | 47.859 | 26.189 | 10.76 |
| 3527 | ILE | O | 51.483 | 48.766 | 26.906 | 12.85 |
| 3528 | ILE | CB | 52.535 | 45.757 | 25.705 | 8.68 |
| 3529 | ILE | CG1 | 52.223 | 45.596 | 24.220 | 9.17 |
| 3530 | ILE | CG2 | 52.925 | 44.361 | 26.249 | 8.98 |
| 3531 | ILE | CD1 | 53.481 | 45.306 | 23.388 | 7.46 |
| 3532 | ILE | H | 49.535 | 45.515 | 25.921 | 20.00 |
| 3533 | ILE | HA | 51.746 | 46.417 | 27.621 | 20.00 |
| 3534 | ILE | HB | 53.406 | 46.400 | 25.807 | 20.00 |
| 3535 | ILE | 1HG1 | 51.822 | 46.511 | 23.805 | 20.00 |
| 3536 | ILE | 2HG1 | 51.482 | 44.821 | 24.044 | 20.00 |
| 3537 | ILE | 1HG2 | 52.130 | 43.636 | 26.107 | 20.00 |
| 3538 | ILE | 2HG2 | 53.153 | 44.435 | 27.313 | 20.00 |
| 3539 | ILE | 3HG2 | 53.807 | 43.971 | 25.748 | 20.00 |
| 3540 | ILE | 1HD1 | 53.909 | 44.318 | 23.568 | 20.00 |
| 3541 | ILE | 2HD1 | 54.265 | 46.026 | 23.602 | 20.00 |
| 3542 | ILE | 3HD1 | 53.262 | 45.368 | 22.319 | 20.00 |
| 3543 | GLY | N | 50.417 | 48.135 | 25.062 | 10.38 |
| 3544 | GLY | CA | 50.161 | 49.536 | 24.720 | 9.10 |
| 3545 | GLY | C | 49.289 | 50.270 | 25.787 | 10.90 |
| 3546 | GLY | O | 49.707 | 51.067 | 26.645 | 10.20 |
| 3547 | GLY | H | 50.328 | 47.389 | 24.405 | 20.00 |
| 3548 | GLY | 1HA | 49.709 | 49.560 | 23.740 | 20.00 |
| 3549 | GLY | 2HA | 51.112 | 50.049 | 24.648 | 20.00 |
| 3550 | ARG | N | 48.015 | 49.955 | 25.638 | 11.01 |
| 3551 | ARG | CA | 47.000 | 50.422 | 26.563 | 10.63 |
| 3552 | ARG | C | 47.250 | 49.944 | 28.078 | 10.18 |
| 3553 | ARG | O | 47.128 | 50.731 | 28.993 | 10.97 |
| 3554 | ARG | CB | 45.607 | 50.070 | 26.013 | 9.12 |
| 3555 | ARG | CG | 45.144 | 50.880 | 24.746 | 9.78 |
| 3556 | ARG | CD | 43.773 | 50.426 | 24.185 | 7.58 |
| 3557 | ARG | NE | 44.049 | 49.233 | 23.356 | 8.89 |
| 3558 | ARG | CZ | 43.196 | 48.582 | 22.597 | 9.55 |
| 3559 | ARG | NH1 | 41.972 | 48.921 | 22.463 | 10.16 |
| 3560 | ARG | NH2 | 43.540 | 47.568 | 21.873 | 9.68 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3561 | ARG | H | 47.708 | 49.447 | 24.827 | 20.00 |
| 3562 | ARG | HA | 47.003 | 51.506 | 26.576 | 20.00 |
| 3563 | ARG | 1HB | 44.861 | 50.223 | 26.789 | 20.00 |
| 3564 | ARG | 2HB | 45.634 | 49.021 | 25.746 | 20.00 |
| 3565 | ARG | 1HG | 45.900 | 50.827 | 23.957 | 20.00 |
| 3566 | ARG | 2HG | 45.132 | 51.924 | 25.011 | 20.00 |
| 3567 | ARG | 1HD | 43.364 | 51.196 | 23.526 | 20.00 |
| 3568 | ARG | 2HD | 43.068 | 50.217 | 24.981 | 20.00 |
| 3569 | ARG | HE | 45.007 | 48.990 | 23.182 | 20.00 |
| 3570 | ARG | 1HH1 | 41.396 | 48.399 | 21.816 | 20.00 |
| 3571 | ARG | 2HH1 | 41.590 | 49.702 | 22.945 | 20.00 |
| 3572 | ARG | 1HH2 | 42.793 | 47.113 | 21.366 | 20.00 |
| 3573 | ARG | 2HH2 | 44.482 | 47.294 | 21.669 | 20.00 |
| 3574 | SER | N | 47.594 | 48.689 | 28.346 | 10.07 |
| 3575 | SER | CA | 47.913 | 48.208 | 29.693 | 8.26 |
| 3576 | SER | C | 49.065 | 48.962 | 30.267 | 10.19 |
| 3577 | SER | O | 48.901 | 49.340 | 31.398 | 10.34 |
| 3578 | SER | CB | 48.033 | 46.638 | 29.836 | 8.89 |
| 3579 | SER | OG | 46.922 | 45.809 | 29.211 | 11.05 |
| 3580 | SER | H | 47.665 | 48.073 | 27.569 | 20.00 |
| 3581 | SER | HA | 47.089 | 48.557 | 30.322 | 20.00 |
| 3582 | SER | 1HB | 48.069 | 46.443 | 30.939 | 20.00 |
| 3583 | SER | 2HB | 49.068 | 46.298 | 29.561 | 20.00 |
| 3584 | SER | HG | 46.279 | 46.160 | 28.550 | 20.00 |
| 3585 | GLY | N | 50.182 | 49.229 | 29.505 | 10.44 |
| 3586 | GLY | CA | 51.325 | 49.953 | 30.078 | 8.60 |
| 3587 | GLY | C | 50.896 | 51.373 | 30.405 | 9.62 |
| 3588 | GLY | O | 51.139 | 51.879 | 31.498 | 11.83 |
| 3589 | GLY | H | 50.224 | 48.899 | 28.558 | 20.00 |
| 3590 | GLY | 1HA | 52.103 | 49.991 | 29.311 | 20.00 |
| 3591 | GLY | 2HA | 51.649 | 49.439 | 30.989 | 20.00 |
| 3592 | THR | N | 50.155 | 52.015 | 29.454 | 11.37 |
| 3593 | THR | CA | 49.632 | 53.367 | 29.813 | 10.02 |
| 3594 | THR | C | 48.846 | 53.501 | 31.196 | 11.10 |
| 3595 | THR | O | 49.111 | 54.330 | 32.043 | 9.82 |
| 3596 | THR | CB | 48.658 | 53.726 | 28.649 | 9.53 |
| 3597 | THR | OG1 | 49.394 | 53.774 | 27.401 | 10.14 |
| 3598 | THR | CG2 | 48.212 | 55.179 | 28.705 | 8.73 |
| 3599 | THR | H | 50.061 | 51.610 | 28.544 | 20.00 |
| 3600 | THR | HA | 50.475 | 54.060 | 29.842 | 20.00 |
| 3601 | THR | HB | 47.638 | 53.223 | 28.821 | 20.00 |
| 3602 | THR | HG1 | 49.688 | 52.952 | 26.910 | 20.00 |
| 3603 | THR | 1HG2 | 49.090 | 55.745 | 28.772 | 20.00 |
| 3604 | THR | 2HG2 | 47.611 | 55.422 | 29.584 | 20.00 |
| 3605 | THR | 3HG2 | 47.726 | 55.537 | 27.806 | 20.00 |
| 3606 | PHE | N | 47.836 | 52.592 | 31.360 | 9.10 |
| 3607 | PHE | CA | 46.998 | 52.422 | 32.513 | 10.60 |
| 3608 | PHE | C | 47.763 | 52.282 | 33.849 | 10.58 |
| 3609 | PHE | O | 47.468 | 53.018 | 34.785 | 11.24 |
| 3610 | PHE | CB | 46.107 | 51.169 | 32.361 | 8.88 |
| 3611 | PHE | CG | 45.222 | 51.035 | 33.635 | 9.58 |
| 3612 | PHE | CD1 | 43.998 | 51.687 | 33.724 | 11.54 |
| 3613 | PHE | CD2 | 45.625 | 50.250 | 34.736 | 11.23 |
| 3614 | PHE | CE1 | 43.198 | 51.577 | 34.840 | 6.44 |
| 3615 | PHE | CE2 | 44.807 | 50.110 | 35.884 | 9.94 |
| 3616 | PHE | CZ | 43.575 | 50.768 | 35.919 | 6.47 |
| 3617 | PHE | H | 47.740 | 51.934 | 30.607 | 20.00 |
| 3618 | PHE | HA | 46.395 | 53.324 | 32.576 | 20.00 |
| 3619 | PHE | 1HB | 46.680 | 50.256 | 32.197 | 20.00 |
| 3620 | PHE | 2HB | 45.487 | 51.288 | 31.473 | 20.00 |
| 3621 | PHE | HD1 | 43.670 | 52.276 | 32.877 | 20.00 |
| 3622 | PHE | HD2 | 46.584 | 49.739 | 34.711 | 20.00 |
| 3623 | PHE | HE1 | 42.263 | 52.121 | 34.876 | 20.00 |
| 3624 | PHE | HE2 | 45.155 | 49.525 | 36.733 | 20.00 |
| 3625 | PHE | HZ | 42.947 | 50.692 | 36.793 | 20.00 |
| 3626 | CYS | N | 48.703 | 51.295 | 33.817 | 10.70 |
| 3627 | CYS | CA | 49.631 | 50.947 | 34.885 | 10.02 |
| 3628 | CYS | C | 50.699 | 52.006 | 35.192 | 10.89 |
| 3629 | CYS | O | 51.065 | 52.292 | 36.335 | 12.32 |
| 3630 | CYS | CB | 50.376 | 49.689 | 34.433 | 12.17 |
| 3631 | CYS | SG | 49.243 | 48.345 | 34.666 | 15.41 |
| 3632 | CYS | H | 48.709 | 50.767 | 32.964 | 20.00 |
| 3633 | CYS | HA | 49.055 | 50.755 | 35.790 | 20.00 |
| 3634 | CYS | 1HB | 51.208 | 49.519 | 35.117 | 20.00 |
| 3635 | CYS | 2HB | 50.793 | 49.726 | 33.426 | 20.00 |
| 3636 | CYS | HG | 48.768 | 48.009 | 33.459 | 20.00 |
| 3637 | LEU | N | 51.226 | 52.596 | 34.112 | 10.01 |
| 3638 | LEU | CA | 52.185 | 53.673 | 34.273 | 10.37 |
| 3639 | LEU | C | 51.674 | 54.833 | 35.143 | 10.12 |
| 3640 | LEU | O | 52.319 | 55.313 | 36.051 | 9.30 |
| 3641 | LEU | CB | 52.734 | 54.180 | 32.895 | 9.12 |
| 3642 | LEU | CG | 53.780 | 55.327 | 33.205 | 11.23 |
| 3643 | LEU | CD1 | 54.197 | 56.096 | 31.977 | 11.32 |
| 3644 | LEU | CD2 | 55.004 | 54.815 | 34.036 | 11.96 |
| 3645 | LEU | H | 50.866 | 52.331 | 33.223 | 20.00 |
| 3646 | LEU | HA | 53.005 | 53.241 | 34.825 | 20.00 |
| 3647 | LEU | 1HB | 51.930 | 54.585 | 32.286 | 20.00 |
| 3648 | LEU | 2HB | 53.201 | 53.374 | 32.332 | 20.00 |
| 3649 | LEU | HG | 53.317 | 56.100 | 33.819 | 20.00 |
| 3650 | LEU | 1HD1 | 53.342 | 56.567 | 31.505 | 20.00 |
| 3651 | LEU | 2HD1 | 54.636 | 55.435 | 31.232 | 20.00 |
| 3652 | LEU | 3HD1 | 54.937 | 56.849 | 32.198 | 20.00 |
| 3653 | LEU | 1HD2 | 55.470 | 53.966 | 33.544 | 20.00 |
| 3654 | LEU | 2HD2 | 54.680 | 54.473 | 35.013 | 20.00 |
| 3655 | LEU | 3HD2 | 55.757 | 55.589 | 34.178 | 20.00 |
| 3656 | ALA | N | 50.511 | 55.296 | 34.725 | 10.91 |
| 3657 | ALA | CA | 49.836 | 56.419 | 35.284 | 10.80 |
| 3658 | ALA | C | 49.353 | 56.116 | 36.768 | 11.33 |
| 3659 | ALA | O | 49.659 | 56.874 | 37.671 | 10.76 |
| 3660 | ALA | CB | 48.789 | 56.860 | 34.272 | 7.83 |
| 3661 | ALA | H | 50.129 | 54.843 | 33.918 | 20.00 |
| 3662 | ALA | HA | 50.597 | 57.196 | 35.359 | 20.00 |
| 3663 | ALA | 1HB | 48.087 | 56.053 | 34.063 | 20.00 |
| 3664 | ALA | 2HB | 49.263 | 57.110 | 33.316 | 20.00 |
| 3665 | ALA | 3HB | 48.242 | 57.733 | 34.616 | 20.00 |
| 3666 | ASP | N | 48.709 | 54.939 | 37.028 | 11.75 |
| 3667 | ASP | CA | 48.530 | 54.419 | 38.415 | 11.91 |
| 3668 | ASP | C | 49.770 | 54.521 | 39.379 | 11.55 |
| 3669 | ASP | O | 49.711 | 55.168 | 40.421 | 11.95 |
| 3670 | ASP | CB | 47.928 | 52.991 | 38.350 | 10.16 |
| 3671 | ASP | CG | 47.508 | 52.440 | 39.753 | 13.48 |
| 3672 | ASP | OD1 | 46.984 | 53.154 | 40.612 | 12.31 |
| 3673 | ASP | OD2 | 47.716 | 51.287 | 40.031 | 12.63 |
| 3674 | ASP | H | 48.369 | 54.406 | 36.245 | 20.00 |
| 3675 | ASP | HA | 47.781 | 55.068 | 38.858 | 20.00 |
| 3676 | ASP | 1HB | 48.599 | 52.290 | 37.857 | 20.00 |
| 3677 | ASP | 2HB | 47.011 | 53.008 | 37.763 | 20.00 |
| 3678 | THR | N | 50.869 | 53.897 | 38.951 | 10.97 |
| 3679 | THR | CA | 52.060 | 53.792 | 39.783 | 11.02 |
| 3680 | THR | C | 52.733 | 55.095 | 39.943 | 11.79 |
| 3681 | THR | O | 53.143 | 55.434 | 41.062 | 11.99 |
| 3682 | THR | CB | 53.122 | 52.827 | 39.159 | 11.07 |
| 3683 | THR | OG1 | 52.653 | 51.451 | 38.973 | 11.80 |
| 3684 | THR | CG2 | 54.351 | 52.594 | 40.065 | 10.36 |
| 3685 | THR | H | 50.727 | 53.360 | 38.110 | 20.00 |
| 3686 | THR | HA | 51.787 | 53.543 | 40.811 | 20.00 |
| 3687 | THR | HB | 53.646 | 53.341 | 38.290 | 20.00 |
| 3688 | THR | HG1 | 51.720 | 51.234 | 38.657 | 20.00 |
| 3689 | THR | 1HG2 | 54.046 | 52.144 | 41.006 | 20.00 |
| 3690 | THR | 2HG2 | 54.884 | 53.516 | 40.274 | 20.00 |
| 3691 | THR | 3HG2 | 55.051 | 51.906 | 39.588 | 20.00 |
| 3692 | CYS | N | 52.728 | 55.872 | 38.863 | 10.65 |
| 3693 | CYS | CA | 53.207 | 57.210 | 39.137 | 10.63 |
| 3694 | CYS | C | 52.322 | 58.003 | 40.111 | 12.96 |
| 3695 | CYS | O | 52.866 | 58.826 | 40.820 | 13.56 |
| 3696 | CYS | CB | 53.409 | 58.056 | 37.880 | 10.48 |
| 3697 | CYS | SG | 54.835 | 57.579 | 36.906 | 13.42 |
| 3698 | CYS | H | 52.373 | 55.549 | 37.978 | 20.00 |
| 3699 | CYS | HA | 54.197 | 57.134 | 39.592 | 20.00 |
| 3700 | CYS | 1HB | 53.582 | 59.091 | 38.184 | 20.00 |
| 3701 | CYS | 2HB | 52.512 | 58.066 | 37.258 | 20.00 |
| 3702 | CYS | HG | 54.517 | 56.537 | 36.129 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3703 | LEU | N | 50.996 | 57.761 | 40.200 | 10.64 |
| 3704 | LEU | CA | 50.209 | 58.546 | 41.149 | 11.23 |
| 3705 | LEU | C | 50.345 | 57.934 | 42.558 | 12.65 |
| 3706 | LEU | O | 50.250 | 58.570 | 43.589 | 14.44 |
| 3707 | LEU | CB | 48.712 | 58.588 | 40.748 | 9.49 |
| 3708 | LEU | CG | 48.459 | 59.449 | 39.550 | 8.57 |
| 3709 | LEU | CD1 | 48.546 | 60.918 | 39.903 | 10.68 |
| 3710 | LEU | CD2 | 47.149 | 59.075 | 38.926 | 11.48 |
| 3711 | LEU | H | 50.585 | 57.122 | 39.545 | 20.00 |
| 3712 | LEU | HA | 50.594 | 59.563 | 41.168 | 20.00 |
| 3713 | LEU | 1HB | 48.112 | 58.972 | 41.572 | 20.00 |
| 3714 | LEU | 2HB | 48.360 | 57.578 | 40.552 | 20.00 |
| 3715 | LEU | HG | 49.224 | 59.256 | 38.808 | 20.00 |
| 3716 | LEU | 1HD1 | 49.555 | 61.220 | 40.186 | 20.00 |
| 3717 | LEU | 2HD1 | 47.884 | 61.189 | 40.720 | 20.00 |
| 3718 | LEU | 3HD1 | 48.268 | 61.545 | 39.055 | 20.00 |
| 3719 | LEU | 1HD2 | 46.315 | 59.278 | 39.602 | 20.00 |
| 3720 | LEU | 2HD2 | 47.126 | 58.022 | 38.642 | 20.00 |
| 3721 | LEU | 3HD2 | 46.963 | 59.659 | 38.023 | 20.00 |
| 3722 | LEU | N | 50.587 | 56.660 | 42.564 | 13.24 |
| 3723 | LEU | CA | 50.835 | 56.004 | 43.863 | 12.90 |
| 3724 | LEU | C | 52.190 | 56.454 | 44.611 | 13.36 |
| 3725 | LEU | O | 52.395 | 56.408 | 45.830 | 15.00 |
| 3726 | LEU | CB | 50.904 | 54.505 | 43.469 | 12.90 |
| 3727 | LEU | CG | 49.835 | 53.569 | 43.939 | 17.31 |
| 3728 | LEU | CD1 | 49.263 | 53.990 | 45.326 | 17.90 |
| 3729 | LEU | CD2 | 50.526 | 52.220 | 43.957 | 17.91 |
| 3730 | LEU | H | 50.646 | 56.184 | 41.684 | 20.00 |
| 3731 | LEU | HA | 49.999 | 56.251 | 44.523 | 20.00 |
| 3732 | LEU | 1HB | 51.908 | 54.136 | 43.644 | 20.00 |
| 3733 | LEU | 2HB | 50.832 | 54.426 | 42.388 | 20.00 |
| 3734 | LEU | HG | 49.006 | 53.536 | 43.238 | 20.00 |
| 3735 | LEU | 1HD1 | 48.585 | 54.834 | 45.275 | 20.00 |
| 3736 | LEU | 2HD1 | 50.070 | 54.266 | 46.010 | 20.00 |
| 3737 | LEU | 3HD1 | 48.730 | 53.181 | 45.816 | 20.00 |
| 3738 | LEU | 1HD2 | 51.425 | 52.244 | 44.573 | 20.00 |
| 3739 | LEU | 2HD2 | 50.823 | 51.905 | 42.956 | 20.00 |
| 3740 | LEU | 3HD2 | 49.881 | 51.463 | 44.393 | 20.00 |
| 3741 | LEU | N | 53.129 | 56.820 | 43.760 | 14.06 |
| 3742 | LEU | CA | 54.476 | 57.023 | 44.220 | 15.83 |
| 3743 | LEU | C | 54.440 | 58.040 | 44.768 | 15.86 |
| 3744 | LEU | O | 54.749 | 58.682 | 45.911 | 15.48 |
| 3745 | LEU | CB | 55.357 | 56.970 | 42.985 | 15.91 |
| 3746 | LEU | CG | 56.668 | 56.200 | 43.023 | 18.29 |
| 3747 | LEU | CD1 | 56.873 | 55.755 | 41.585 | 20.36 |
| 3748 | LEU | CD2 | 56.800 | 55.028 | 43.983 | 16.23 |
| 3749 | LEU | H | 52.886 | 56.679 | 42.799 | 20.00 |
| 3750 | LEU | HA | 54.733 | 56.275 | 44.971 | 20.00 |
| 3751 | LEU | 1HB | 55.586 | 57.948 | 42.562 | 20.00 |
| 3752 | LEU | 2HB | 54.761 | 56.546 | 42.184 | 20.00 |
| 3753 | LEU | HG | 57.472 | 56.891 | 43.272 | 20.00 |
| 3754 | LEU | 1HD1 | 56.867 | 56.632 | 40.928 | 20.00 |
| 3755 | LEU | 2HD1 | 56.101 | 55.069 | 41.240 | 20.00 |
| 3756 | LEU | 3HD1 | 57.836 | 55.256 | 41.439 | 20.00 |
| 3757 | LEU | 1HD2 | 55.882 | 54.460 | 43.936 | 20.00 |
| 3758 | LEU | 2HD2 | 56.954 | 55.352 | 45.011 | 20.00 |
| 3759 | LEU | 3HD2 | 57.613 | 54.361 | 43.694 | 20.00 |
| 3760 | MET | N | 53.976 | 59.242 | 43.877 | 14.06 |
| 3761 | MET | CA | 53.624 | 60.606 | 44.191 | 16.10 |
| 3762 | MET | C | 52.765 | 60.733 | 45.517 | 18.37 |
| 3763 | MET | O | 53.079 | 61.547 | 46.384 | 17.82 |
| 3764 | MET | CB | 53.022 | 61.097 | 42.848 | 17.90 |
| 3765 | MET | CG | 52.600 | 62.534 | 42.880 | 22.88 |
| 3766 | MET | SD | 52.133 | 63.122 | 41.275 | 27.93 |
| 3767 | MET | CE | 53.674 | 62.882 | 40.484 | 21.01 |
| 3768 | MET | H | 53.802 | 58.889 | 42.947 | 20.00 |
| 3769 | MET | HA | 54.574 | 61.137 | 44.355 | 20.00 |
| 3770 | MET | 1HB | 52.142 | 60.514 | 42.589 | 20.00 |
| 3771 | MET | 2HB | 53.726 | 60.932 | 42.040 | 20.00 |
| 3772 | MET | 1HG | 53.414 | 63.117 | 43.298 | 20.00 |
| 3773 | MET | 2HG | 51.765 | 62.692 | 43.563 | 20.00 |
| 3774 | MET | 1HE | 53.737 | 61.868 | 40.089 | 20.00 |
| 3775 | MET | 2HE | 54.533 | 63.102 | 41.116 | 20.00 |
| 3776 | MET | 3HE | 53.709 | 63.582 | 39.649 | 20.00 |
| 3777 | ASP | N | 51.796 | 59.845 | 45.706 | 17.66 |
| 3778 | ASP | CA | 51.046 | 59.817 | 46.959 | 18.72 |
| 3779 | ASP | C | 51.866 | 59.517 | 48.249 | 20.72 |
| 3780 | ASP | O | 51.506 | 60.010 | 49.317 | 18.46 |
| 3781 | ASP | CB | 49.865 | 58.833 | 46.789 | 15.77 |
| 3782 | ASP | C | 48.692 | 59.223 | 47.720 | 15.78 |
| 3783 | ASP | OD1 | 47.921 | 60.098 | 47.335 | 15.30 |
| 3784 | ASP | OD2 | 48.573 | 58.745 | 48.849 | 12.03 |
| 3785 | ASP | H | 51.489 | 59.265 | 44.954 | 20.00 |
| 3786 | ASP | HA | 50.641 | 60.814 | 47.092 | 20.00 |
| 3787 | ASP | 1HB | 50.143 | 57.792 | 46.991 | 20.00 |
| 3788 | ASP | 2HB | 49.523 | 58.841 | 45.757 | 20.00 |
| 3789 | LYS | N | 52.983 | 58.760 | 48.131 | 22.67 |
| 3790 | LYS | CA | 53.674 | 58.145 | 49.290 | 26.79 |
| 3791 | LYS | C | 54.931 | 58.920 | 49.795 | 27.91 |
| 3792 | LYS | O | 55.952 | 58.446 | 50.319 | 27.25 |
| 3793 | LYS | CB | 53.901 | 56.634 | 49.079 | 31.63 |
| 3794 | LYS | CG | 55.221 | 56.174 | 48.432 | 36.21 |
| 3795 | LYS | CD | 55.564 | 54.732 | 48.920 | 41.15 |
| 3796 | LYS | CE | 54.502 | 53.672 | 48.501 | 45.83 |
| 3797 | LYS | NZ | 54.382 | 52.509 | 49.411 | 48.52 |
| 3798 | LYS | H | 53.168 | 58.421 | 47.202 | 20.00 |
| 3799 | LYS | HA | 52.971 | 58.231 | 50.127 | 20.00 |
| 3800 | LYS | 1HB | 53.037 | 56.222 | 48.565 | 20.00 |
| 3801 | LYS | 2HB | 53.878 | 56.200 | 50.076 | 20.00 |
| 3802 | LYS | 1HG | 56.072 | 56.800 | 48.691 | 20.00 |
| 3803 | LYS | 2HG | 55.142 | 56.208 | 47.346 | 20.00 |
| 3804 | LYS | 1HD | 55.694 | 54.725 | 50.001 | 20.00 |
| 3805 | LYS | 2HD | 56.528 | 54.416 | 48.507 | 20.00 |
| 3806 | LYS | 1HE | 54.738 | 53.304 | 47.496 | 20.00 |
| 3807 | LYS | 2HE | 53.519 | 54.136 | 48.398 | 20.00 |
| 3808 | LYS | 1HZ | 54.131 | 52.810 | 50.372 | 20.00 |
| 3809 | LYS | 2HZ | 55.273 | 51.969 | 49.417 | 20.00 |
| 3810 | LYS | 3HZ | 53.633 | 51.882 | 49.045 | 20.00 |
| 3811 | ARG | N | 54.783 | 60.192 | 49.561 | 29.18 |
| 3812 | ARG | CA | 55.920 | 61.072 | 49.744 | 30.25 |
| 3813 | ARG | C | 55.412 | 62.476 | 49.597 | 28.51 |
| 3814 | ARG | O | 55.983 | 63.400 | 50.172 | 29.83 |
| 3815 | ARG | CB | 57.138 | 60.726 | 48.833 | 35.96 |
| 3816 | ARG | CG | 56.825 | 60.702 | 47.353 | 35.60 |
| 3817 | ARG | CD | 57.971 | 60.140 | 46.489 | 39.72 |
| 3818 | ARG | NE | 58.346 | 58.740 | 46.746 | 44.72 |
| 3819 | ARG | CZ | 59.252 | 58.052 | 45.985 | 49.49 |
| 3820 | ARG | NH1 | 59.736 | 58.571 | 44.823 | 46.55 |
| 3821 | ARG | NH2 | 59.631 | 56.831 | 46.444 | 54.27 |
| 3822 | ARG | H | 53.921 | 60.398 | 49.096 | 20.00 |
| 3823 | ARG | HA | 56.222 | 60.959 | 50.792 | 20.00 |
| 3824 | ARG | 1HB | 57.517 | 59.753 | 49.136 | 20.00 |
| 3825 | ARG | 2HB | 57.954 | 61.419 | 49.015 | 20.00 |
| 3826 | ARG | 1HG | 56.572 | 61.699 | 46.997 | 20.00 |
| 3827 | ARG | 2HG | 55.957 | 60.080 | 47.195 | 20.00 |
| 3828 | ARG | 1HD | 58.897 | 60.700 | 46.658 | 20.00 |
| 3829 | ARG | 2HD | 57.668 | 60.138 | 45.441 | 20.00 |
| 3830 | ARG | HE | 57.974 | 58.277 | 47.547 | 20.00 |
| 3831 | ARG | 1HH1 | 60.317 | 57.968 | 44.264 | 20.00 |
| 3832 | ARG | 2HH1 | 59.524 | 59.501 | 44.534 | 20.00 |
| 3833 | ARG | 1HH2 | 60.241 | 56.297 | 45.852 | 20.00 |
| 3834 | ARG | 2HH2 | 59.320 | 56.463 | 47.308 | 20.00 |
| 3835 | LYS | N | 54.299 | 62.635 | 48.843 | 24.03 |
| 3836 | LYS | CA | 53.709 | 63.975 | 48.683 | 22.66 |
| 3837 | LYS | C | 54.836 | 65.076 | 48.313 | 22.19 |
| 3838 | LYS | O | 54.746 | 66.296 | 48.531 | 22.54 |
| 3839 | LYS | CB | 52.828 | 64.382 | 49.905 | 23.45 |
| 3840 | LYS | CG | 51.703 | 63.412 | 50.390 | 20.10 |
| 3841 | LYS | CD | 50.532 | 63.202 | 49.448 | 20.71 |
| 3842 | LYS | CE | 49.505 | 62.232 | 50.059 | 17.94 |
| 3843 | LYS | NZ | 48.450 | 61.958 | 49.071 | 27.72 |
| 3844 | LYS | H | 53.968 | 61.880 | 48.276 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3845 | LYS | HA | 53.071 | 63.873 | 47.806 | 20.00 |
| 3846 | LYS | 1HB | 52.363 | 65.342 | 49.684 | 20.00 |
| 3847 | LYS | 2HB | 53.494 | 64.560 | 50.747 | 20.00 |
| 3848 | LYS | 1HG | 51.304 | 63.828 | 51.315 | 20.00 |
| 3849 | LYS | 2HG | 52.136 | 62.454 | 50.672 | 20.00 |
| 3850 | LYS | 1HD | 50.884 | 62.812 | 48.489 | 20.00 |
| 3851 | LYS | 2HD | 50.052 | 64.161 | 49.235 | 20.00 |
| 3852 | LYS | 1HE | 49.049 | 62.670 | 50.950 | 20.00 |
| 3853 | LYS | 2HE | 49.952 | 61.283 | 50.363 | 20.00 |
| 3854 | LYS | 1HZ | 48.810 | 61.313 | 48.331 | 20.00 |
| 3855 | LYS | 2HZ | 48.109 | 62.817 | 48.578 | 20.00 |
| 3856 | LYS | 3HZ | 47.647 | 61.409 | 49.432 | 20.00 |
| 3857 | ASP | N | 55.889 | 64.482 | 47.680 | 21.48 |
| 3858 | ASP | CA | 56.806 | 65.251 | 46.882 | 22.85 |
| 3859 | ASP | C | 56.543 | 64.944 | 45.345 | 21.41 |
| 3860 | ASP | O | 57.198 | 64.103 | 44.713 | 21.48 |
| 3861 | ASP | CB | 58.216 | 64.968 | 47.416 | 25.58 |
| 3862 | ASP | CG | 59.244 | 65.767 | 46.566 | 29.64 |
| 3863 | ASP | OD1 | 58.862 | 66.819 | 45.964 | 31.77 |
| 3864 | ASP | OD2 | 60.408 | 65.344 | 46.549 | 30.41 |
| 3865 | ASP | H | 56.060 | 63.508 | 47.768 | 20.00 |
| 3866 | ASP | HA | 56.609 | 66.305 | 47.057 | 20.00 |
| 3867 | ASP | 1HB | 58.465 | 63.918 | 47.556 | 20.00 |
| 3868 | ASP | 2HB | 58.277 | 65.369 | 48.429 | 20.00 |
| 3869 | PRO | N | 55.539 | 65.638 | 44.744 | 20.58 |
| 3870 | PRO | CA | 55.308 | 65.416 | 43.295 | 22.04 |
| 3871 | PRO | C | 56.569 | 65.307 | 42.347 | 24.22 |
| 3872 | PRO | O | 56.572 | 64.547 | 41.372 | 22.77 |
| 3873 | PRO | CB | 54.441 | 66.653 | 42.852 | 23.82 |
| 3874 | PRO | CG | 53.958 | 67.350 | 44.156 | 22.76 |
| 3875 | PRO | CD | 54.861 | 66.824 | 45.284 | 22.17 |
| 3876 | PRO | HA | 54.784 | 64.489 | 43.157 | 20.00 |
| 3877 | PRO | 1HB | 53.643 | 66.360 | 42.176 | 20.00 |
| 3878 | PRO | 2HB | 55.022 | 67.367 | 42.285 | 20.00 |
| 3879 | PRO | 1HG | 53.966 | 68.430 | 44.056 | 20.00 |
| 3880 | PRO | 2HG | 52.945 | 67.022 | 44.344 | 20.00 |
| 3881 | PRO | 1HD | 54.292 | 66.563 | 46.162 | 20.00 |
| 3882 | PRO | 2HD | 55.589 | 67.586 | 45.557 | 20.00 |
| 3883 | SER | N | 57.644 | 66.017 | 42.810 | 26.49 |
| 3884 | SER | CA | 58.744 | 66.328 | 41.960 | 29.21 |
| 3885 | SER | C | 59.732 | 65.218 | 41.913 | 28.16 |
| 3886 | SER | O | 60.301 | 64.849 | 40.890 | 30.98 |
| 3887 | SER | CB | 59.304 | 67.616 | 42.594 | 32.36 |
| 3888 | SER | OG | 58.637 | 68.913 | 42.285 | 37.57 |
| 3889 | SER | H | 57.630 | 66.394 | 43.738 | 20.00 |
| 3890 | SER | HA | 58.429 | 66.385 | 40.908 | 20.00 |
| 3891 | SER | 1HB | 60.351 | 67.694 | 42.232 | 20.00 |
| 3892 | SER | 2HB | 59.521 | 67.454 | 43.682 | 20.00 |
| 3893 | SER | HG | 57.670 | 69.067 | 42.060 | 20.00 |
| 3894 | SER | N | 59.925 | 64.613 | 43.043 | 25.94 |
| 3895 | SER | CA | 60.809 | 63.466 | 42.969 | 23.97 |
| 3896 | SER | C | 60.407 | 62.308 | 41.968 | 23.07 |
| 3897 | SER | O | 61.251 | 61.419 | 41.868 | 23.41 |
| 3898 | SER | CB | 60.695 | 62.845 | 44.395 | 24.53 |
| 3899 | SER | OG | 59.325 | 62.461 | 44.856 | 26.18 |
| 3900 | SER | H | 59.459 | 64.900 | 43.888 | 20.00 |
| 3901 | SER | HA | 61.810 | 63.811 | 42.723 | 20.00 |
| 3902 | SER | 1HB | 61.331 | 63.648 | 45.113 | 20.00 |
| 3903 | SER | 2HB | 61.358 | 61.949 | 44.388 | 20.00 |
| 3904 | SER | HG | 58.514 | 63.013 | 44.586 | 20.00 |
| 3905 | VAL | N | 59.176 | 62.231 | 41.306 | 22.45 |
| 3906 | VAL | CA | 58.834 | 61.027 | 40.461 | 21.20 |
| 3907 | VAL | C | 59.182 | 61.249 | 38.947 | 21.26 |
| 3908 | VAL | O | 58.675 | 62.163 | 38.320 | 22.49 |
| 3909 | VAL | CB | 57.391 | 60.434 | 40.620 | 22.58 |
| 3910 | VAL | CG1 | 56.451 | 60.386 | 39.363 | 20.76 |
| 3911 | VAL | CG2 | 56.695 | 61.029 | 41.828 | 17.17 |
| 3912 | VAL | H | 58.588 | 63.040 | 41.291 | 20.00 |
| 3913 | VAL | HA | 59.500 | 60.233 | 40.807 | 20.00 |
| 3914 | VAL | HB | 57.535 | 59.380 | 40.863 | 20.00 |
| 3915 | VAL | 1HG1 | 56.888 | 59.787 | 38.559 | 20.00 |
| 3916 | VAL | 2HG1 | 56.252 | 61.381 | 38.973 | 20.00 |
| 3917 | VAL | 3HG1 | 55.488 | 59.919 | 39.577 | 20.00 |
| 3918 | VAL | 1HG2 | 56.539 | 62.101 | 41.733 | 20.00 |
| 3919 | VAL | 2HG2 | 57.252 | 60.803 | 42.729 | 20.00 |
| 3920 | VAL | 3HG2 | 55.729 | 60.556 | 41.956 | 20.00 |
| 3921 | ASP | N | 60.034 | 60.370 | 38.393 | 19.92 |
| 3922 | ASP | CA | 60.422 | 60.486 | 37.014 | 19.98 |
| 3923 | ASP | C | 59.593 | 59.489 | 36.190 | 17.61 |
| 3924 | ASP | O | 59.810 | 58.291 | 36.270 | 18.51 |
| 3925 | ASP | CB | 61.968 | 60.298 | 36.922 | 21.39 |
| 3926 | ASP | CG | 62.632 | 60.452 | 35.517 | 25.31 |
| 3927 | ASP | OD1 | 62.006 | 60.671 | 34.458 | 23.58 |
| 3928 | ASP | OD2 | 63.846 | 60.336 | 35.498 | 32.08 |
| 3929 | ASP | H | 60.462 | 59.701 | 38.992 | 20.00 |
| 3930 | ASP | HA | 60.181 | 61.487 | 36.644 | 20.00 |
| 3931 | ASP | 1HB | 62.267 | 59.369 | 37.393 | 20.00 |
| 3932 | ASP | 2HB | 62.408 | 61.078 | 37.534 | 20.00 |
| 3933 | ILE | N | 58.641 | 60.060 | 35.429 | 18.00 |
| 3934 | ILE | CA | 57.715 | 59.212 | 34.684 | 16.17 |
| 3935 | ILE | C | 58.457 | 58.121 | 33.908 | 16.20 |
| 3936 | ILE | O | 58.158 | 56.962 | 33.989 | 16.71 |
| 3937 | ILE | CB | 56.682 | 60.059 | 33.831 | 18.69 |
| 3938 | ILE | CG1 | 55.862 | 61.009 | 34.788 | 20.07 |
| 3939 | ILE | CG2 | 55.633 | 59.144 | 33.082 | 16.13 |
| 3940 | ILE | CD1 | 54.494 | 61.498 | 34.162 | 22.35 |
| 3941 | ILE | H | 58.643 | 61.059 | 35.410 | 20.00 |
| 3942 | ILE | HA | 57.154 | 58.675 | 35.450 | 20.00 |
| 3943 | ILE | HB | 57.226 | 60.649 | 33.091 | 20.00 |
| 3944 | ILE | 1HG1 | 56.474 | 61.858 | 35.081 | 20.00 |
| 3945 | ILE | 2HG1 | 55.628 | 60.471 | 35.709 | 20.00 |
| 3946 | ILE | 1HG2 | 55.008 | 58.573 | 33.774 | 20.00 |
| 3947 | ILE | 2HG2 | 56.178 | 58.446 | 32.443 | 20.00 |
| 3948 | ILE | 3HG2 | 54.982 | 59.699 | 32.406 | 20.00 |
| 3949 | ILE | 1HD1 | 53.818 | 60.694 | 33.876 | 20.00 |
| 3950 | ILE | 2HD1 | 54.710 | 62.086 | 33.280 | 20.00 |
| 3951 | ILE | 3HD1 | 53.924 | 62.104 | 34.865 | 20.00 |
| 3952 | LYS | N | 59.488 | 58.562 | 33.158 | 15.61 |
| 3953 | LYS | CA | 60.319 | 57.703 | 32.288 | 16.12 |
| 3954 | LYS | C | 61.173 | 56.727 | 33.130 | 15.62 |
| 3955 | LYS | O | 61.228 | 55.568 | 32.799 | 15.12 |
| 3956 | LYS | CB | 61.147 | 58.457 | 31.166 | 18.84 |
| 3957 | LYS | CG | 60.600 | 59.764 | 30.558 | 31.31 |
| 3958 | LYS | CD | 61.795 | 60.577 | 29.985 | 37.73 |
| 3959 | LYS | CE | 62.746 | 61.132 | 31.087 | 43.40 |
| 3960 | LYS | NZ | 62.754 | 62.577 | 31.255 | 47.06 |
| 3961 | LYS | H | 59.666 | 59.540 | 33.256 | 20.00 |
| 3962 | LYS | HA | 59.593 | 57.072 | 31.780 | 20.00 |
| 3963 | LYS | 1HB | 61.394 | 57.754 | 30.371 | 20.00 |
| 3964 | LYS | 2HB | 62.114 | 58.664 | 31.609 | 20.00 |
| 3965 | LYS | 1HG | 60.123 | 60.303 | 31.374 | 20.00 |
| 3966 | LYS | 2HG | 59.834 | 59.586 | 29.806 | 20.00 |
| 3967 | LYS | 1HD | 61.613 | 61.325 | 29.225 | 20.00 |
| 3968 | LYS | 2HD | 62.379 | 59.879 | 29.384 | 20.00 |
| 3969 | LYS | 1HE | 63.770 | 60.795 | 30.916 | 20.00 |
| 3970 | LYS | 2HE | 62.462 | 60.714 | 32.058 | 20.00 |
| 3971 | LYS | 1HZ | 61.799 | 62.973 | 31.456 | 20.00 |
| 3972 | LYS | 2HZ | 63.031 | 63.140 | 30.419 | 20.00 |
| 3973 | LYS | 3HZ | 63.326 | 62.866 | 32.070 | 20.00 |
| 3974 | LYS | N | 61.763 | 57.189 | 34.225 | 16.19 |
| 3975 | LYS | CA | 62.257 | 56.242 | 35.200 | 17.17 |
| 3976 | LYS | C | 61.293 | 55.010 | 35.671 | 15.81 |
| 3977 | LYS | O | 61.750 | 53.857 | 35.780 | 13.38 |
| 3978 | LYS | CB | 62.721 | 57.021 | 36.420 | 21.47 |
| 3979 | LYS | CG | 63.685 | 56.179 | 37.285 | 26.41 |
| 3980 | LYS | CD | 64.794 | 57.072 | 37.807 | 32.75 |
| 3981 | LYS | CE | 65.626 | 57.849 | 36.734 | 37.01 |
| 3982 | LYS | NZ | 67.041 | 58.078 | 37.149 | 41.44 |
| 3983 | LYS | H | 61.705 | 58.168 | 34.443 | 20.00 |
| 3984 | LYS | HA | 63.127 | 55.786 | 34.726 | 20.00 |
| 3985 | LYS | 1HB | 61.887 | 57.362 | 37.030 | 20.00 |
| 3986 | LYS | 2HB | 63.231 | 57.909 | 36.056 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 3987 | LYS | 1HG | 64.127 | 55.380 | 36.694 | 20.00 |
| 3988 | LYS | 2HG | 63.149 | 55.685 | 38.097 | 20.00 |
| 3989 | LYS | 1HD | 65.457 | 56.465 | 38.425 | 20.00 |
| 3990 | LYS | 2HD | 64.355 | 57.817 | 38.475 | 20.00 |
| 3991 | LYS | 1HE | 65.173 | 58.818 | 36.541 | 20.00 |
| 3992 | LYS | 2HE | 65.625 | 57.311 | 35.781 | 20.00 |
| 3993 | LYS | 1HZ | 67.519 | 57.178 | 37.364 | 20.00 |
| 3994 | LYS | 2HZ | 67.048 | 58.692 | 37.990 | 20.00 |
| 3995 | LYS | 3HZ | 67.545 | 58.575 | 36.382 | 20.00 |
| 3996 | VAL | N | 59.985 | 55.323 | 35.959 | 15.38 |
| 3997 | VAL | CA | 59.007 | 54.265 | 36.251 | 13.40 |
| 3998 | VAL | C | 58.622 | 53.424 | 35.039 | 12.42 |
| 3999 | VAL | O | 58.570 | 52.215 | 35.094 | 12.19 |
| 4000 | VAL | CB | 57.954 | 54.563 | 37.383 | 17.62 |
| 4001 | VAL | CG1 | 56.568 | 53.984 | 37.220 | 13.70 |
| 4002 | VAL | CG2 | 57.966 | 55.998 | 37.910 | 14.26 |
| 4003 | VAL | H | 59.750 | 56.303 | 35.924 | 20.00 |
| 4004 | VAL | HA | 59.627 | 53.531 | 36.757 | 20.00 |
| 4005 | VAL | HB | 58.323 | 54.004 | 38.246 | 20.00 |
| 4006 | VAL | 1HG1 | 56.577 | 52.930 | 36.941 | 20.00 |
| 4007 | VAL | 2HG1 | 56.042 | 54.545 | 36.459 | 20.00 |
| 4008 | VAL | 3HG1 | 55.990 | 54.074 | 38.141 | 20.00 |
| 4009 | VAL | 1HG2 | 57.755 | 56.693 | 37.096 | 20.00 |
| 4010 | VAL | 2HG2 | 58.937 | 56.269 | 38.321 | 20.00 |
| 4011 | VAL | 3HG2 | 57.210 | 56.147 | 38.681 | 20.00 |
| 4012 | LEU | N | 58.433 | 54.033 | 33.899 | 11.53 |
| 4013 | LEU | CA | 58.144 | 53.234 | 32.728 | 12.42 |
| 4014 | LEU | C | 59.278 | 52.236 | 32.445 | 11.91 |
| 4015 | LEU | O | 59.058 | 51.051 | 32.366 | 10.65 |
| 4016 | LEU | CB | 57.743 | 54.157 | 31.624 | 12.94 |
| 4017 | LEU | CG | 57.326 | 53.410 | 30.304 | 14.51 |
| 4018 | LEU | CD1 | 57.086 | 54.408 | 29.182 | 14.86 |
| 4019 | LEU | CD2 | 56.160 | 52.386 | 30.503 | 12.64 |
| 4020 | LEU | H | 58.437 | 55.031 | 33.911 | 20.00 |
| 4021 | LEU | HA | 57.258 | 52.666 | 32.990 | 20.00 |
| 4022 | LEU | 1HB | 58.593 | 54.808 | 31.418 | 20.00 |
| 4023 | LEU | 2HB | 56.941 | 54.822 | 31.950 | 20.00 |
| 4024 | LEU | HG | 58.192 | 52.818 | 30.000 | 20.00 |
| 4025 | LEU | 1HD1 | 57.963 | 55.014 | 29.049 | 20.00 |
| 4026 | LEU | 2HD1 | 56.240 | 55.060 | 29.390 | 20.00 |
| 4027 | LEU | 3HD1 | 56.896 | 53.878 | 28.248 | 20.00 |
| 4028 | LEU | 1HD2 | 55.276 | 52.909 | 30.864 | 20.00 |
| 4029 | LEU | 2HD2 | 56.404 | 51.623 | 31.245 | 20.00 |
| 4030 | LEU | 3HD2 | 55.893 | 51.869 | 29.585 | 20.00 |
| 4031 | LEU | N | 60.504 | 52.731 | 32.420 | 14.10 |
| 4032 | LEU | CA | 61.690 | 51.872 | 32.395 | 13.57 |
| 4033 | LEU | C | 61.761 | 50.752 | 33.479 | 11.98 |
| 4034 | LEU | O | 62.002 | 49.612 | 33.082 | 10.15 |
| 4035 | LEU | CB | 62.918 | 52.796 | 32.471 | 15.92 |
| 4036 | LEU | CG | 63.686 | 53.177 | 31.132 | 18.96 |
| 4037 | LEU | CD1 | 64.024 | 54.658 | 31.092 | 18.76 |
| 4038 | LEU | CD2 | 63.078 | 52.694 | 29.832 | 20.15 |
| 4039 | LEU | H | 60.599 | 53.726 | 32.457 | 20.00 |
| 4040 | LEU | HA | 61.655 | 51.323 | 31.457 | 20.00 |
| 4041 | LEU | 1HB | 63.669 | 52.330 | 33.103 | 20.00 |
| 4042 | LEU | 2HB | 62.658 | 53.693 | 33.033 | 20.00 |
| 4043 | LEU | HG | 64.658 | 52.680 | 31.172 | 20.00 |
| 4044 | LEU | 1HD1 | 64.621 | 54.977 | 31.950 | 20.00 |
| 4045 | LEU | 2HD1 | 63.112 | 55.255 | 31.098 | 20.00 |
| 4046 | LEU | 3HD1 | 64.604 | 54.927 | 30.204 | 20.00 |
| 4047 | LEU | 1HD2 | 62.022 | 52.950 | 29.855 | 20.00 |
| 4048 | LEU | 2HD2 | 63.159 | 51.613 | 29.727 | 20.00 |
| 4049 | LEU | 3HD2 | 63.545 | 53.169 | 28.966 | 20.00 |
| 4050 | ASP | N | 61.560 | 51.032 | 34.837 | 13.06 |
| 4051 | ASP | CA | 61.390 | 49.905 | 35.801 | 12.70 |
| 4052 | ASP | C | 60.231 | 48.923 | 35.403 | 11.44 |
| 4053 | ASP | O | 60.321 | 47.695 | 35.475 | 11.16 |
| 4054 | ASP | CB | 61.278 | 50.344 | 37.304 | 15.05 |
| 4055 | ASP | CG | 62.123 | 49.288 | 38.082 | 23.08 |
| 4056 | ASP | OD1 | 63.364 | 49.262 | 38.000 | 22.88 |
| 4057 | ASP | OD2 | 61.586 | 48.379 | 38.689 | 24.92 |
| 4058 | ASP | H | 61.491 | 51.996 | 35.102 | 20.00 |
| 4059 | ASP | HA | 62.301 | 49.314 | 35.656 | 20.00 |
| 4060 | ASP | 1HB | 60.255 | 50.372 | 37.670 | 20.00 |
| 4061 | ASP | 2HB | 61.732 | 51.315 | 37.466 | 20.00 |
| 4062 | MET | N | 59.093 | 49.516 | 34.944 | 13.08 |
| 4063 | MET | CA | 58.001 | 48.656 | 34.411 | 12.59 |
| 4064 | MET | C | 58.462 | 47.656 | 33.363 | 10.76 |
| 4065 | MET | O | 58.113 | 46.455 | 33.408 | 9.86 |
| 4066 | MET | CB | 56.904 | 49.483 | 33.836 | 14.18 |
| 4067 | MET | CG | 55.903 | 49.698 | 34.916 | 20.95 |
| 4068 | MET | SD | 54.280 | 50.357 | 34.340 | 25.25 |
| 4069 | MET | CE | 54.062 | 51.043 | 35.991 | 24.15 |
| 4070 | MET | H | 59.129 | 50.515 | 34.915 | 20.00 |
| 4071 | MET | HA | 57.666 | 48.053 | 35.256 | 20.00 |
| 4072 | MET | 1HB | 56.398 | 49.008 | 33.008 | 20.00 |
| 4073 | MET | 2HB | 57.229 | 50.450 | 33.479 | 20.00 |
| 4074 | MET | 1HG | 56.386 | 50.456 | 35.537 | 20.00 |
| 4075 | MET | 2HG | 55.734 | 48.842 | 35.576 | 20.00 |
| 4076 | MET | 1HE | 54.838 | 51.743 | 36.278 | 20.00 |
| 4077 | MET | 2HE | 54.045 | 50.220 | 36.708 | 20.00 |
| 4078 | MET | 3HE | 53.126 | 51.565 | 35.960 | 20.00 |
| 4079 | ARG | N | 59.282 | 48.214 | 32.437 | 11.81 |
| 4080 | ARG | CA | 59.642 | 47.419 | 31.226 | 14.09 |
| 4081 | ARG | C | 60.637 | 46.252 | 31.489 | 14.19 |
| 4082 | ARG | O | 60.925 | 45.526 | 30.551 | 15.37 |
| 4083 | ARG | CB | 59.943 | 48.311 | 29.993 | 15.27 |
| 4084 | ARG | CG | 59.098 | 49.556 | 29.941 | 20.41 |
| 4085 | ARG | CD | 58.376 | 49.966 | 28.632 | 22.57 |
| 4086 | ARG | NE | 59.200 | 50.017 | 27.449 | 21.00 |
| 4087 | ARG | CZ | 58.839 | 50.296 | 26.192 | 19.36 |
| 4088 | ARG | NH1 | 57.852 | 51.031 | 25.801 | 17.30 |
| 4089 | ARG | NH2 | 59.579 | 49.731 | 25.327 | 15.47 |
| 4090 | ARG | H | 59.531 | 49.173 | 32.573 | 20.00 |
| 4091 | ARG | HA | 58.706 | 46.936 | 30.961 | 20.00 |
| 4092 | ARG | 1HB | 59.788 | 47.723 | 29.092 | 20.00 |
| 4093 | ARG | 2HB | 60.999 | 48.599 | 29.991 | 20.00 |
| 4094 | ARG | 1HG | 59.729 | 50.392 | 30.254 | 20.00 |
| 4095 | ARG | 2HG | 58.294 | 49.528 | 30.682 | 20.00 |
| 4096 | ARG | 1HD | 57.908 | 50.943 | 28.745 | 20.00 |
| 4097 | ARG | 2HD | 57.606 | 49.239 | 28.396 | 20.00 |
| 4098 | ARG | HE | 60.107 | 49.639 | 27.637 | 20.00 |
| 4099 | ARG | 1HH1 | 57.601 | 51.294 | 24.882 | 20.00 |
| 4100 | ARG | 2HH1 | 57.261 | 51.372 | 26.542 | 20.00 |
| 4101 | ARG | 1HH2 | 59.524 | 49.940 | 24.352 | 20.00 |
| 4102 | ARG | 2HH2 | 60.246 | 49.058 | 25.646 | 20.00 |
| 4103 | LYS | N | 61.164 | 46.114 | 32.773 | 12.82 |
| 4104 | LYS | CA | 61.935 | 44.941 | 33.256 | 11.88 |
| 4105 | LYS | C | 61.085 | 43.713 | 33.410 | 11.52 |
| 4106 | LYS | O | 61.593 | 42.577 | 33.421 | 12.87 |
| 4107 | LYS | CB | 62.641 | 45.126 | 34.625 | 10.90 |
| 4108 | LYS | CG | 63.618 | 46.277 | 34.601 | 10.61 |
| 4109 | LYS | CD | 64.058 | 46.712 | 35.985 | 16.89 |
| 4110 | LYS | CE | 65.109 | 47.798 | 35.884 | 18.25 |
| 4111 | LYS | NZ | 65.603 | 48.012 | 37.220 | 18.64 |
| 4112 | LYS | H | 60.974 | 46.858 | 33.419 | 20.00 |
| 4113 | LYS | HA | 62.681 | 44.732 | 32.484 | 20.00 |
| 4114 | LYS | 1HB | 63.115 | 44.215 | 34.984 | 20.00 |
| 4115 | LYS | 2HB | 61.880 | 45.373 | 35.364 | 20.00 |
| 4116 | LYS | 1HG | 63.158 | 47.138 | 34.122 | 20.00 |
| 4117 | LYS | 2HG | 64.500 | 45.961 | 34.042 | 20.00 |
| 4118 | LYS | 1HD | 64.460 | 45.868 | 36.534 | 20.00 |
| 4119 | LYS | 2HD | 63.195 | 47.069 | 36.549 | 20.00 |
| 4120 | LYS | 1HE | 64.731 | 48.741 | 35.473 | 20.00 |
| 4121 | LYS | 2HE | 65.940 | 47.473 | 35.260 | 20.00 |
| 4122 | LYS | 1HZ | 65.673 | 47.094 | 37.707 | 20.00 |
| 4123 | LYS | 2HZ | 64.909 | 48.549 | 37.785 | 20.00 |
| 4124 | LYS | 3HZ | 66.557 | 48.423 | 37.253 | 20.00 |
| 4125 | PHE | N | 59.784 | 43.979 | 33.518 | 11.46 |
| 4126 | PHE | CA | 58.890 | 42.872 | 33.793 | 10.66 |
| 4127 | PHE | C | 58.071 | 42.350 | 32.647 | 10.63 |
| 4128 | PHE | O | 57.810 | 41.174 | 32.624 | 11.08 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 4129 | PHE | CB | 57.941 | 43.342 | 34.873 | 10.87 |
| 4130 | PHE | CG | 58.702 | 43.716 | 36.137 | 10.74 |
| 4131 | PHE | CD1 | 59.198 | 42.740 | 36.931 | 14.67 |
| 4132 | PHE | CD2 | 58.946 | 45.007 | 36.493 | 13.16 |
| 4133 | PHE | CE1 | 59.928 | 43.056 | 38.070 | 14.61 |
| 4134 | PHE | CE2 | 59.709 | 45.342 | 37.584 | 11.84 |
| 4135 | PHE | CZ | 60.231 | 44.342 | 38.364 | 12.78 |
| 4136 | PHE | H | 59.498 | 44.933 | 33.611 | 20.00 |
| 4137 | PHE | HA | 59.449 | 41.996 | 34.159 | 20.00 |
| 4138 | PHE | 1HB | 57.244 | 42.532 | 35.092 | 20.00 |
| 4139 | PHE | 2HB | 57.356 | 44.185 | 34.502 | 20.00 |
| 4140 | PHE | HD1 | 59.026 | 41.700 | 36.674 | 20.00 |
| 4141 | PHE | HD2 | 58.541 | 45.812 | 35.888 | 20.00 |
| 4142 | PHE | HE1 | 60.292 | 42.264 | 38.718 | 20.00 |
| 4143 | PHE | HE2 | 59.892 | 46.384 | 37.839 | 20.00 |
| 4144 | PHE | HZ | 60.833 | 44.580 | 39.223 | 20.00 |
| 4145 | ARG | N | 57.637 | 43.234 | 31.729 | 11.78 |
| 4146 | ARG | CA | 56.999 | 42.971 | 30.403 | 11.12 |
| 4147 | ARG | C | 57.537 | 43.989 | 29.272 | 10.70 |
| 4148 | ARG | O | 57.754 | 45.168 | 29.450 | 11.00 |
| 4149 | ARG | CB | 55.450 | 43.030 | 30.422 | 9.05 |
| 4150 | ARG | CG | 54.720 | 42.312 | 29.233 | 8.54 |
| 4151 | ARG | CD | 53.173 | 42.198 | 29.472 | 8.35 |
| 4152 | ARG | NE | 52.329 | 41.703 | 28.413 | 8.45 |
| 4153 | ARG | CZ | 52.240 | 40.450 | 27.919 | 8.44 |
| 4154 | ARG | NH1 | 52.939 | 39.527 | 28.425 | 8.74 |
| 4155 | ARG | NH2 | 51.413 | 40.156 | 26.940 | 9.54 |
| 4156 | ARG | H | 57.860 | 44.166 | 32.007 | 20.00 |
| 4157 | ARG | HA | 57.284 | 41.962 | 30.171 | 20.00 |
| 4158 | ARG | 1HB | 55.116 | 44.056 | 30.542 | 20.00 |
| 4159 | ARG | 2HB | 55.154 | 42.528 | 31.341 | 20.00 |
| 4160 | ARG | 1HG | 55.200 | 41.356 | 29.029 | 20.00 |
| 4161 | ARG | 2HG | 54.899 | 42.903 | 28.332 | 20.00 |
| 4162 | ARG | 1HD | 52.863 | 43.247 | 29.522 | 20.00 |
| 4163 | ARG | 2HD | 52.834 | 41.843 | 30.446 | 20.00 |
| 4164 | ARG | HE | 51.722 | 42.406 | 28.035 | 20.00 |
| 4165 | ARG | 1HH1 | 52.806 | 38.586 | 28.112 | 20.00 |
| 4166 | ARG | 2HH1 | 53.602 | 39.812 | 29.109 | 20.00 |
| 4167 | ARG | 1HH2 | 51.312 | 39.214 | 26.626 | 20.00 |
| 4168 | ARG | 2HH2 | 50.878 | 40.883 | 26.495 | 20.00 |
| 4169 | MET | N | 57.716 | 43.404 | 28.075 | 11.10 |
| 4170 | MET | CA | 58.186 | 44.260 | 26.962 | 10.52 |
| 4171 | MET | C | 57.024 | 45.223 | 26.500 | 12.21 |
| 4172 | MET | O | 55.843 | 44.858 | 26.471 | 11.69 |
| 4173 | MET | CB | 58.606 | 43.362 | 25.796 | 12.40 |
| 4174 | MET | CG | 57.434 | 42.486 | 25.214 | 13.12 |
| 4175 | MET | SD | 57.895 | 41.619 | 23.717 | 12.49 |
| 4176 | MET | CE | 59.286 | 40.641 | 24.231 | 14.52 |
| 4177 | MET | H | 57.157 | 42.590 | 27.946 | 20.00 |
| 4178 | MET | HA | 59.033 | 44.839 | 27.332 | 20.00 |
| 4179 | MET | 1HB | 59.421 | 42.716 | 26.125 | 20.00 |
| 4180 | MET | 2HB | 59.017 | 43.981 | 24.995 | 20.00 |
| 4181 | MET | 1HG | 56.537 | 43.061 | 24.993 | 20.00 |
| 4182 | MET | 2HG | 57.153 | 41.751 | 25.963 | 20.00 |
| 4183 | MET | 1HE | 58.999 | 40.071 | 25.111 | 20.00 |
| 4184 | MET | 2HE | 60.128 | 41.283 | 24.473 | 20.00 |
| 4185 | MET | 3HE | 59.569 | 39.950 | 23.436 | 20.00 |
| 4186 | GLY | N | 57.448 | 46.438 | 26.060 | 11.82 |
| 4187 | GLY | CA | 56.696 | 47.240 | 25.071 | 10.69 |
| 4188 | GLY | C | 55.505 | 47.941 | 25.724 | 11.80 |
| 4189 | GLY | O | 54.605 | 48.408 | 25.044 | 11.81 |
| 4190 | GLY | H | 58.395 | 46.587 | 26.326 | 20.00 |
| 4191 | GLY | 1HA | 56.379 | 46.563 | 24.277 | 20.00 |
| 4192 | GLY | 2HA | 57.369 | 47.983 | 24.659 | 20.00 |
| 4193 | LEU | N | 55.644 | 48.052 | 27.083 | 11.43 |
| 4194 | LEU | CA | 54.762 | 48.854 | 27.881 | 11.39 |
| 4195 | LEU | C | 54.798 | 50.309 | 27.386 | 12.20 |
| 4196 | LEU | O | 55.819 | 51.000 | 27.369 | 12.24 |
| 4197 | LEU | CB | 55.125 | 48.664 | 29.353 | 10.83 |
| 4198 | LEU | CG | 55.153 | 47.177 | 29.826 | 9.47 |
| 4199 | LEU | CD1 | 53.979 | 46.390 | 29.211 | 9.16 |
| 4200 | LEU | CD2 | 55.106 | 46.987 | 31.376 | 10.38 |
| 4201 | LEU | H | 56.255 | 47.429 | 27.563 | 20.00 |
| 4202 | LEU | HA | 53.765 | 48.452 | 27.684 | 20.00 |
| 4203 | LEU | 1HB | 54.363 | 49.187 | 29.928 | 20.00 |
| 4204 | LEU | 2HB | 56.038 | 49.177 | 29.650 | 20.00 |
| 4205 | LEU | HG | 56.074 | 46.731 | 29.458 | 20.00 |
| 4206 | LEU | 1HD1 | 54.146 | 46.270 | 28.145 | 20.00 |
| 4207 | LEU | 2HD1 | 53.059 | 46.958 | 29.330 | 20.00 |
| 4208 | LEU | 3HD1 | 53.845 | 45.402 | 29.632 | 20.00 |
| 4209 | LEU | 1HD2 | 54.239 | 47.489 | 31.812 | 20.00 |
| 4210 | LEU | 2HD2 | 56.013 | 47.373 | 31.822 | 20.00 |
| 4211 | LEU | 3HD2 | 55.039 | 45.931 | 31.632 | 20.00 |
| 4212 | ILE | N | 53.611 | 50.747 | 26.925 | 10.54 |
| 4213 | ILE | CA | 53.352 | 51.904 | 26.078 | 11.17 |
| 4214 | ILE | C | 53.942 | 51.707 | 24.614 | 13.75 |
| 4215 | ILE | O | 55.152 | 51.525 | 24.341 | 13.91 |
| 4216 | ILE | CB | 53.775 | 53.199 | 26.797 | 11.11 |
| 4217 | ILE | CG1 | 53.323 | 53.232 | 28.236 | 9.13 |
| 4218 | ILE | CG2 | 53.534 | 54.509 | 25.973 | 14.38 |
| 4219 | ILE | CD1 | 53.085 | 54.633 | 28.731 | 8.65 |
| 4220 | ILE | H | 52.857 | 50.110 | 27.076 | 20.00 |
| 4221 | ILE | HA | 52.300 | 51.849 | 25.895 | 20.00 |
| 4222 | ILE | HB | 54.854 | 53.154 | 26.854 | 20.00 |
| 4223 | ILE | 1HG1 | 54.057 | 52.753 | 28.875 | 20.00 |
| 4224 | ILE | 2HG1 | 52.434 | 52.641 | 28.395 | 20.00 |
| 4225 | ILE | 1HG2 | 52.489 | 54.771 | 26.013 | 20.00 |
| 4226 | ILE | 2HG2 | 53.837 | 54.423 | 24.931 | 20.00 |
| 4227 | ILE | 3HG2 | 54.073 | 55.352 | 26.405 | 20.00 |
| 4228 | ILE | 1HD1 | 52.339 | 55.011 | 28.055 | 20.00 |
| 4229 | ILE | 2HD1 | 53.956 | 55.277 | 28.718 | 20.00 |
| 4230 | ILE | 3HD1 | 52.642 | 54.642 | 29.720 | 20.00 |
| 4231 | GLN | N | 52.962 | 51.794 | 23.698 | 13.18 |
| 4232 | GLN | CA | 53.199 | 51.506 | 22.275 | 12.31 |
| 4233 | GLN | C | 53.430 | 52.716 | 21.367 | 14.51 |
| 4234 | GLN | O | 53.955 | 52.560 | 20.262 | 14.93 |
| 4235 | GLN | CB | 52.144 | 50.560 | 21.736 | 12.10 |
| 4236 | GLN | CG | 52.439 | 49.160 | 22.274 | 13.08 |
| 4237 | GLN | CD | 53.546 | 48.547 | 21.425 | 14.33 |
| 4238 | GLN | OE1 | 53.483 | 48.340 | 20.241 | 16.45 |
| 4239 | GLN | NE2 | 54.621 | 48.324 | 22.095 | 11.97 |
| 4240 | GLN | H | 52.069 | 52.116 | 24.025 | 20.00 |
| 4241 | GLN | HA | 54.053 | 50.882 | 22.198 | 20.00 |
| 4242 | GLN | 1HB | 52.148 | 50.567 | 20.649 | 20.00 |
| 4243 | GLN | 2HB | 51.163 | 50.906 | 22.068 | 20.00 |
| 4244 | GLN | 1HG | 51.565 | 48.532 | 22.129 | 20.00 |
| 4245 | GLN | 2HG | 52.700 | 49.128 | 23.334 | 20.00 |
| 4246 | GLN | 1HE2 | 55.255 | 47.877 | 21.463 | 20.00 |
| 4247 | GLN | 2HE2 | 54.687 | 48.534 | 23.072 | 20.00 |
| 4248 | THR | N | 52.999 | 53.889 | 21.847 | 14.47 |
| 4249 | THR | CA | 53.293 | 55.112 | 21.160 | 13.82 |
| 4250 | THR | C | 53.795 | 56.277 | 22.022 | 15.31 |
| 4251 | THR | O | 53.504 | 56.378 | 23.202 | 15.21 |
| 4252 | THR | CB | 52.018 | 55.721 | 20.549 | 12.44 |
| 4253 | THR | OG1 | 51.132 | 56.387 | 21.467 | 13.84 |
| 4254 | THR | CG2 | 51.116 | 54.688 | 19.900 | 12.80 |
| 4255 | THR | H | 52.517 | 53.881 | 22.722 | 20.00 |
| 4256 | THR | HA | 54.032 | 54.925 | 20.382 | 20.00 |
| 4257 | THR | HB | 52.313 | 56.216 | 19.551 | 20.00 |
| 4258 | THR | HG1 | 51.470 | 57.060 | 22.111 | 20.00 |
| 4259 | THR | 1HG2 | 50.910 | 53.814 | 20.510 | 20.00 |
| 4260 | THR | 2HG2 | 51.562 | 54.409 | 18.964 | 20.00 |
| 4261 | THR | 3HG2 | 50.153 | 55.136 | 19.640 | 20.00 |
| 4262 | ALA | N | 54.477 | 57.213 | 21.304 | 16.12 |
| 4263 | ALA | CA | 54.775 | 58.515 | 21.914 | 17.15 |
| 4264 | ALA | C | 53.591 | 59.401 | 22.373 | 17.06 |
| 4265 | ALA | O | 53.789 | 60.142 | 23.290 | 16.84 |
| 4266 | ALA | CB | 55.595 | 59.324 | 20.904 | 15.40 |
| 4267 | ALA | H | 54.845 | 56.937 | 20.420 | 20.00 |
| 4268 | ALA | HA | 55.376 | 58.310 | 22.799 | 20.00 |
| 4269 | ALA | 1HB | 55.020 | 59.526 | 19.991 | 20.00 |
| 4270 | ALA | 2HB | 56.466 | 58.733 | 20.623 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 4271 | ALA | 3HB | 55.932 | 60.276 | 21.309 | 20.00 |
| 4272 | ASP | N | 52.372 | 59.361 | 21.793 | 16.67 |
| 4273 | ASP | CA | 51.253 | 60.117 | 22.425 | 16.05 |
| 4274 | ASP | C | 50.459 | 59.397 | 23.628 | 14.16 |
| 4275 | ASP | O | 49.950 | 60.007 | 24.564 | 13.25 |
| 4276 | ASP | CB | 50.285 | 60.449 | 21.279 | 16.36 |
| 4277 | ASP | CG | 49.302 | 61.573 | 21.733 | 18.91 |
| 4278 | ASP | OD1 | 49.622 | 62.439 | 22.550 | 19.27 |
| 4279 | ASP | OD2 | 48.176 | 61.536 | 21.255 | 19.47 |
| 4280 | ASP | H | 52.169 | 58.892 | 20.940 | 20.00 |
| 4281 | ASP | HA | 51.675 | 61.041 | 22.821 | 20.00 |
| 4282 | ASP | 1HB | 49.700 | 59.570 | 21.004 | 20.00 |
| 4283 | ASP | 2HB | 50.796 | 60.835 | 20.398 | 20.00 |
| 4284 | GLN | N | 50.509 | 58.059 | 23.612 | 12.74 |
| 4285 | GLN | CA | 50.357 | 57.350 | 24.885 | 12.47 |
| 4286 | GLN | C | 51.372 | 57.732 | 25.883 | 13.42 |
| 4287 | GLN | O | 50.983 | 57.853 | 27.011 | 13.68 |
| 4288 | GLN | CB | 50.268 | 55.796 | 24.870 | 10.94 |
| 4289 | GLN | CG | 49.003 | 55.278 | 24.131 | 10.93 |
| 4290 | GLN | CD | 49.169 | 53.862 | 23.674 | 11.89 |
| 4291 | GLN | OE1 | 50.245 | 53.338 | 23.823 | 13.27 |
| 4292 | GLN | NE2 | 48.120 | 53.148 | 23.278 | 10.17 |
| 4293 | GLN | H | 50.220 | 57.686 | 22.728 | 20.00 |
| 4294 | GLN | HA | 49.410 | 57.687 | 25.306 | 20.00 |
| 4295 | GLN | 1HB | 50.120 | 55.691 | 25.933 | 20.00 |
| 4296 | GLN | 2HB | 51.199 | 55.298 | 24.622 | 20.00 |
| 4297 | GLN | 1HG | 48.722 | 55.880 | 23.275 | 20.00 |
| 4298 | GLN | 2HG | 48.157 | 55.324 | 24.814 | 20.00 |
| 4299 | GLN | 1HE2 | 48.192 | 52.170 | 23.170 | 20.00 |
| 4300 | GLN | 2HE2 | 47.274 | 53.670 | 23.184 | 20.00 |
| 4301 | LEU | N | 52.632 | 57.962 | 25.482 | 15.21 |
| 4302 | LEU | CA | 53.622 | 58.317 | 26.460 | 13.64 |
| 4303 | LEU | C | 53.221 | 59.639 | 27.103 | 14.41 |
| 4304 | LEU | O | 53.197 | 59.793 | 28.299 | 15.65 |
| 4305 | LEU | CB | 55.040 | 58.373 | 25.963 | 12.86 |
| 4306 | LEU | CG | 55.940 | 58.940 | 27.044 | 13.02 |
| 4307 | LEU | CD1 | 57.423 | 59.114 | 26.568 | 12.87 |
| 4308 | LEU | CD2 | 55.803 | 58.093 | 28.344 | 12.32 |
| 4309 | LEU | H | 52.853 | 57.713 | 24.542 | 20.00 |
| 4310 | LEU | HA | 53.697 | 57.475 | 27.137 | 20.00 |
| 4311 | LEU | 1HB | 55.109 | 58.990 | 25.075 | 20.00 |
| 4312 | LEU | 2HB | 55.368 | 57.378 | 25.665 | 20.00 |
| 4313 | LEU | HG | 55.643 | 59.956 | 27.299 | 20.00 |
| 4314 | LEU | 1HD1 | 57.503 | 59.794 | 25.718 | 20.00 |
| 4315 | LEU | 2HD1 | 57.826 | 58.155 | 26.246 | 20.00 |
| 4316 | LEU | 3HD1 | 58.066 | 59.498 | 27.365 | 20.00 |
| 4317 | LEU | 1HD2 | 55.984 | 57.030 | 28.190 | 20.00 |
| 4318 | LEU | 2HD2 | 54.823 | 58.181 | 28.813 | 20.00 |
| 4319 | LEU | 3HD2 | 56.521 | 58.432 | 29.090 | 20.00 |
| 4320 | ARG | N | 52.940 | 60.581 | 26.220 | 13.43 |
| 4321 | ARG | CA | 52.516 | 61.919 | 26.552 | 13.38 |
| 4322 | ARG | C | 51.245 | 61.967 | 27.425 | 14.16 |
| 4323 | ARG | O | 51.086 | 62.719 | 28.402 | 14.64 |
| 4324 | ARG | CB | 52.251 | 62.603 | 25.232 | 13.46 |
| 4325 | ARG | CG | 51.762 | 64.060 | 25.435 | 13.29 |
| 4326 | ARG | CD | 51.576 | 64.868 | 24.119 | 16.52 |
| 4327 | ARG | NE | 51.522 | 66.299 | 24.432 | 20.17 |
| 4328 | ARG | CZ | 50.397 | 67.002 | 24.409 | 19.49 |
| 4329 | ARG | NH1 | 49.216 | 66.446 | 24.187 | 20.88 |
| 4330 | ARG | NH2 | 50.463 | 68.265 | 24.567 | 21.32 |
| 4331 | ARG | H | 53.137 | 60.365 | 25.265 | 20.00 |
| 4332 | ARG | HA | 53.333 | 62.403 | 27.095 | 20.00 |
| 4333 | ARG | 1HB | 51.506 | 62.063 | 24.656 | 20.00 |
| 4334 | ARG | 2HB | 53.170 | 62.609 | 24.642 | 20.00 |
| 4335 | ARG | 1HG | 52.524 | 64.576 | 26.019 | 20.00 |
| 4336 | ARG | 2HG | 50.846 | 64.108 | 26.022 | 20.00 |
| 4337 | ARG | 1HD | 50.719 | 64.529 | 23.542 | 20.00 |
| 4338 | ARG | 2HD | 52.437 | 64.758 | 23.467 | 20.00 |
| 4339 | ARG | HE | 52.358 | 66.829 | 24.622 | 20.00 |
| 4340 | ARG | 1HH1 | 48.378 | 66.959 | 24.120 | 20.00 |
| 4341 | ARG | 2HH1 | 49.238 | 65.453 | 24.060 | 20.00 |
| 4342 | ARG | 1HH2 | 49.696 | 68.881 | 24.571 | 20.00 |
| 4343 | ARG | 2HH2 | 51.389 | 68.673 | 24.644 | 20.00 |
| 4344 | PHE | N | 50.335 | 61.083 | 26.968 | 13.41 |
| 4345 | PHE | CA | 49.001 | 61.017 | 27.582 | 13.00 |
| 4346 | PHE | C | 49.112 | 60.777 | 29.110 | 12.42 |
| 4347 | PHE | O | 48.608 | 61.592 | 29.880 | 14.84 |
| 4348 | PHE | CB | 48.098 | 60.098 | 26.822 | 12.87 |
| 4349 | PHE | CG | 46.828 | 60.022 | 27.581 | 13.08 |
| 4350 | PHE | CD1 | 45.801 | 60.881 | 27.276 | 15.82 |
| 4351 | PHE | CD2 | 46.705 | 59.168 | 28.680 | 13.48 |
| 4352 | PHE | CE1 | 44.667 | 60.910 | 28.097 | 14.88 |
| 4353 | PHE | CE2 | 45.574 | 59.191 | 29.498 | 14.71 |
| 4354 | PHE | CZ | 44.540 | 60.071 | 29.199 | 13.48 |
| 4355 | PHE | H | 50.562 | 60.635 | 26.109 | 20.00 |
| 4356 | PHE | HA | 48.585 | 62.029 | 27.497 | 20.00 |
| 4357 | PHE | 1HB | 48.536 | 59.108 | 26.759 | 20.00 |
| 4358 | PHE | 2HB | 47.915 | 60.462 | 25.813 | 20.00 |
| 4359 | PHE | HD1 | 45.882 | 61.539 | 26.423 | 20.00 |
| 4360 | PHE | HD2 | 47.512 | 58.491 | 28.940 | 20.00 |
| 4361 | PHE | HE1 | 43.859 | 61.581 | 27.846 | 20.00 |
| 4362 | PHE | HE2 | 45.506 | 58.535 | 30.360 | 20.00 |
| 4363 | PHE | HZ | 43.642 | 60.078 | 29.799 | 20.00 |
| 4364 | SER | N | 49.969 | 59.763 | 29.464 | 12.86 |
| 4365 | SER | CA | 50.587 | 59.542 | 30.810 | 13.82 |
| 4366 | SER | C | 51.041 | 60.698 | 31.656 | 15.06 |
| 4367 | SER | O | 50.771 | 60.701 | 32.874 | 15.36 |
| 4368 | SER | CB | 51.858 | 58.721 | 30.716 | 11.50 |
| 4369 | SER | OG | 51.516 | 57.632 | 29.848 | 19.07 |
| 4370 | SER | H | 50.242 | 59.181 | 28.697 | 20.00 |
| 4371 | SER | HA | 49.818 | 59.037 | 31.402 | 20.00 |
| 4372 | SER | 1HB | 52.010 | 58.296 | 31.729 | 20.00 |
| 4373 | SER | 2HB | 52.852 | 59.284 | 30.654 | 20.00 |
| 4374 | SER | HG | 51.270 | 57.729 | 28.858 | 20.00 |
| 4375 | TYR | N | 51.813 | 61.593 | 31.024 | 14.37 |
| 4376 | TYR | CA | 52.267 | 62.766 | 31.766 | 13.98 |
| 4377 | TYR | C | 51.058 | 63.681 | 31.998 | 14.72 |
| 4378 | TYR | O | 50.967 | 64.337 | 33.005 | 16.92 |
| 4379 | TYR | CB | 53.229 | 63.600 | 30.917 | 15.56 |
| 4380 | TYR | CG | 54.652 | 63.274 | 30.954 | 15.10 |
| 4381 | TYR | CD1 | 55.052 | 62.134 | 30.271 | 15.01 |
| 4382 | TYR | CD2 | 55.620 | 64.132 | 31.549 | 16.69 |
| 4383 | TYR | CE1 | 56.421 | 61.838 | 30.141 | 17.26 |
| 4384 | TYR | CE2 | 57.005 | 63.819 | 31.493 | 17.79 |
| 4385 | TYR | CZ | 57.399 | 62.668 | 30.725 | 18.91 |
| 4386 | TYR | OH | 58.714 | 62.271 | 30.439 | 22.03 |
| 4387 | TYR | H | 51.999 | 61.445 | 30.050 | 20.00 |
| 4388 | TYR | HA | 52.676 | 62.473 | 32.734 | 20.00 |
| 4389 | TYR | 1HB | 53.169 | 64.651 | 31.202 | 20.00 |
| 4390 | TYR | 2HB | 52.902 | 63.592 | 29.873 | 20.00 |
| 4391 | TYR | HD1 | 54.327 | 61.491 | 29.785 | 20.00 |
| 4392 | TYR | HD2 | 55.300 | 65.033 | 32.057 | 20.00 |
| 4393 | TYR | HE1 | 56.711 | 60.965 | 29.563 | 20.00 |
| 4394 | TYR | HE2 | 57.650 | 64.487 | 32.074 | 20.00 |
| 4395 | TYR | HH | 59.145 | 62.947 | 29.940 | 20.00 |
| 4396 | LEU | N | 50.119 | 63.730 | 31.072 | 14.60 |
| 4397 | LEU | CA | 48.847 | 64.446 | 31.233 | 13.80 |
| 4398 | LEU | C | 47.979 | 63.736 | 32.311 | 13.84 |
| 4399 | LEU | O | 47.376 | 64.413 | 33.100 | 15.22 |
| 4400 | LEU | CB | 48.123 | 64.423 | 29.847 | 15.22 |
| 4401 | LEU | CG | 47.836 | 65.699 | 28.996 | 17.91 |
| 4402 | LEU | CD1 | 47.984 | 65.297 | 27.542 | 17.36 |
| 4403 | LEU | CD2 | 48.732 | 66.869 | 29.241 | 17.38 |
| 4404 | LEU | H | 50.299 | 63.237 | 30.217 | 20.00 |
| 4405 | LEU | HA | 49.052 | 65.467 | 31.565 | 20.00 |
| 4406 | LEU | 1HB | 47.178 | 63.886 | 29.921 | 20.00 |
| 4407 | LEU | 2HB | 48.719 | 63.775 | 29.209 | 20.00 |
| 4408 | LEU | HG | 46.811 | 66.008 | 29.196 | 20.00 |
| 4409 | LEU | 1HD1 | 47.280 | 64.485 | 27.341 | 20.00 |
| 4410 | LEU | 2HD1 | 48.978 | 64.923 | 27.304 | 20.00 |
| 4411 | LEU | 3HD1 | 47.734 | 66.112 | 26.869 | 20.00 |
| 4412 | LEU | 1HD2 | 49.761 | 66.547 | 29.286 | 20.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 4413 | LEU | 2HD2 | 48.501 | 67.327 | 30.203 | 20.00 |
| 4414 | LEU | 3HD2 | 48.593 | 67.645 | 28.487 | 20.00 |
| 4415 | ALA | N | 47.923 | 62.376 | 32.381 | 13.18 |
| 4416 | ALA | CA | 47.070 | 61.732 | 33.394 | 12.65 |
| 4417 | ALA | C | 47.647 | 61.860 | 34.804 | 14.16 |
| 4418 | ALA | O | 46.924 | 62.169 | 35.735 | 14.00 |
| 4419 | ALA | CB | 46.896 | 60.294 | 33.069 | 13.02 |
| 4420 | ALA | H | 48.404 | 61.889 | 31.656 | 20.00 |
| 4421 | ALA | HA | 46.109 | 62.245 | 33.400 | 20.00 |
| 4422 | ALA | 1HB | 47.848 | 59.772 | 33.044 | 20.00 |
| 4423 | ALA | 2HB | 46.427 | 60.175 | 32.093 | 20.00 |
| 4424 | ALA | 3HB | 46.257 | 59.808 | 33.797 | 20.00 |
| 4425 | VAL | N | 48.993 | 61.669 | 34.953 | 11.78 |
| 4426 | VAL | CA | 49.638 | 61.928 | 36.266 | 12.53 |
| 4427 | VAL | C | 49.529 | 63.388 | 36.657 | 13.82 |
| 4428 | VAL | O | 49.106 | 63.654 | 37.760 | 12.86 |
| 4429 | VAL | CB | 51.060 | 61.470 | 36.199 | 11.66 |
| 4430 | VAL | CG1 | 51.011 | 59.975 | 35.935 | 13.24 |
| 4431 | VAL | CG2 | 51.884 | 61.820 | 37.450 | 9.92 |
| 4432 | VAL | H | 49.505 | 61.389 | 34.142 | 20.00 |
| 4433 | VAL | HA | 49.097 | 61.346 | 37.011 | 20.00 |
| 4434 | VAL | HB | 51.525 | 61.950 | 35.339 | 20.00 |
| 4435 | VAL | 1HG1 | 50.457 | 59.680 | 35.046 | 20.00 |
| 4436 | VAL | 2HG1 | 50.567 | 59.443 | 36.774 | 20.00 |
| 4437 | VAL | 3HG1 | 52.028 | 59.609 | 35.790 | 20.00 |
| 4438 | VAL | 1HG2 | 51.434 | 61.452 | 38.374 | 20.00 |
| 4439 | VAL | 2HG2 | 52.023 | 62.899 | 37.543 | 20.00 |
| 4440 | VAL | 3HG2 | 52.878 | 61.383 | 37.357 | 20.00 |
| 4441 | ILE | N | 49.859 | 64.316 | 35.726 | 12.29 |
| 4442 | ILE | CA | 49.777 | 65.753 | 36.099 | 13.94 |
| 4443 | ILE | C | 48.339 | 66.176 | 36.660 | 14.15 |
| 4444 | ILE | O | 48.117 | 66.660 | 37.773 | 14.06 |
| 4445 | ILE | CB | 50.394 | 66.654 | 34.959 | 13.50 |
| 4446 | ILE | CG1 | 51.944 | 66.544 | 34.796 | 14.91 |
| 4447 | ILE | CG2 | 50.076 | 68.142 | 35.160 | 12.74 |
| 4448 | ILE | CD1 | 52.435 | 66.779 | 33.323 | 13.99 |
| 4449 | ILE | H | 50.221 | 64.029 | 34.834 | 20.00 |
| 4450 | ILE | HA | 50.451 | 65.871 | 36.951 | 20.00 |
| 4451 | ILE | HB | 49.927 | 66.358 | 34.020 | 20.00 |
| 4452 | ILE | 1HG1 | 52.222 | 65.531 | 35.081 | 20.00 |
| 4453 | ILE | 2HG1 | 52.448 | 67.206 | 35.500 | 20.00 |
| 4454 | ILE | 1HG2 | 50.457 | 68.501 | 36.112 | 20.00 |
| 4455 | ILE | 2HG2 | 49.002 | 68.322 | 35.154 | 20.00 |
| 4456 | ILE | 3HG2 | 50.501 | 68.767 | 34.372 | 20.00 |
| 4457 | ILE | 1HD1 | 52.530 | 67.849 | 33.137 | 20.00 |
| 4458 | ILE | 2HD1 | 51.774 | 66.409 | 32.552 | 20.00 |
| 4459 | ILE | 3HD1 | 53.420 | 66.336 | 33.174 | 20.00 |
| 4460 | GLU | N | 47.359 | 65.839 | 35.881 | 13.27 |
| 4461 | GLU | CA | 45.989 | 66.067 | 36.314 | 12.79 |
| 4462 | GLU | C | 45.607 | 65.346 | 37.640 | 14.22 |
| 4463 | GLU | O | 45.016 | 65.931 | 38.541 | 14.98 |
| 4464 | GLU | CB | 45.069 | 65.673 | 35.120 | 11.88 |
| 4465 | GLU | CG | 43.617 | 66.022 | 35.440 | 12.69 |
| 4466 | GLU | CD | 43.489 | 67.515 | 35.873 | 18.61 |
| 4467 | GLU | OE1 | 44.197 | 68.391 | 35.267 | 19.68 |
| 4468 | GLU | OE2 | 42.684 | 67.786 | 36.795 | 20.07 |
| 4469 | GLU | H | 47.536 | 65.473 | 34.961 | 20.00 |
| 4470 | GLU | HA | 45.923 | 67.144 | 36.510 | 20.00 |
| 4471 | GLU | 1HB | 45.179 | 64.633 | 34.870 | 20.00 |
| 4472 | GLU | 2HB | 45.379 | 66.212 | 34.239 | 20.00 |
| 4473 | GLU | 1HG | 43.215 | 65.380 | 36.227 | 20.00 |
| 4474 | GLU | 2HG | 42.978 | 65.886 | 34.565 | 20.00 |
| 4475 | GLY | N | 46.045 | 64.072 | 37.760 | 14.10 |
| 4476 | GLY | CA | 45.654 | 63.221 | 38.876 | 11.35 |
| 4477 | GLY | C | 46.321 | 63.593 | 40.191 | 12.42 |
| 4478 | GLY | O | 45.815 | 63.292 | 41.292 | 14.09 |
| 4479 | GLY | H | 46.512 | 63.723 | 36.945 | 20.00 |
| 4480 | GLY | 1HA | 45.949 | 62.203 | 38.620 | 20.00 |
| 4481 | GLY | 2HA | 44.571 | 63.247 | 38.973 | 20.00 |
| 4482 | ALA | N | 47.519 | 64.244 | 40.018 | 12.11 |
| 4483 | ALA | CA | 48.374 | 64.823 | 41.082 | 13.24 |
| 4484 | ALA | C | 47.582 | 65.702 | 41.977 | 14.50 |
| 4485 | ALA | O | 47.596 | 65.589 | 43.194 | 15.74 |
| 4486 | ALA | CB | 49.490 | 65.703 | 40.494 | 12.85 |
| 4487 | ALA | H | 47.815 | 64.323 | 39.062 | 20.00 |
| 4488 | ALA | HA | 48.781 | 63.986 | 41.661 | 20.00 |
| 4489 | ALA | 1HB | 49.117 | 66.579 | 39.973 | 20.00 |
| 4490 | ALA | 2HB | 50.058 | 65.139 | 39.757 | 20.00 |
| 4491 | ALA | 3HB | 50.202 | 66.027 | 41.246 | 20.00 |
| 4492 | LYS | N | 46.816 | 66.546 | 41.296 | 15.43 |
| 4493 | LYS | CA | 45.724 | 67.345 | 41.899 | 17.97 |
| 4494 | LYS | C | 44.931 | 66.779 | 43.125 | 18.17 |
| 4495 | LYS | O | 44.899 | 67.351 | 44.214 | 16.72 |
| 4496 | LYS | CB | 44.741 | 67.668 | 40.789 | 17.36 |
| 4497 | LYS | CG | 45.473 | 68.507 | 39.735 | 20.89 |
| 4498 | LYS | CD | 44.411 | 69.357 | 39.059 | 19.35 |
| 4499 | LYS | CE | 44.941 | 70.273 | 37.899 | 21.45 |
| 4500 | LYS | NZ | 43.854 | 70.561 | 36.916 | 28.58 |
| 4501 | LYS | H | 46.970 | 66.537 | 40.302 | 20.00 |
| 4502 | LYS | HA | 46.194 | 68.257 | 42.271 | 20.00 |
| 4503 | LYS | 1HB | 43.929 | 68.238 | 41.230 | 20.00 |
| 4504 | LYS | 2HB | 44.281 | 66.774 | 40.403 | 20.00 |
| 4505 | LYS | 1HG | 46.030 | 67.909 | 39.021 | 20.00 |
| 4506 | LYS | 2HG | 46.191 | 69.182 | 40.190 | 20.00 |
| 4507 | LYS | 1HD | 43.864 | 69.945 | 39.793 | 20.00 |
| 4508 | LYS | 2HD | 43.678 | 68.654 | 38.678 | 20.00 |
| 4509 | LYS | 1HE | 45.750 | 69.766 | 37.367 | 20.00 |
| 4510 | LYS | 2HE | 45.330 | 71.199 | 38.323 | 20.00 |
| 4511 | LYS | 1HZ | 42.957 | 70.859 | 37.339 | 20.00 |
| 4512 | LYS | 2HZ | 43.637 | 69.601 | 36.519 | 20.00 |
| 4513 | LYS | 3HZ | 44.134 | 71.121 | 36.095 | 20.00 |
| 4514 | PHE | N | 44.281 | 65.638 | 42.830 | 17.06 |
| 4515 | PHE | CA | 43.646 | 64.836 | 43.843 | 17.26 |
| 4516 | PHE | C | 44.714 | 64.518 | 44.920 | 17.65 |
| 4517 | PHE | O | 44.482 | 64.738 | 46.105 | 17.35 |
| 4518 | PHE | CB | 42.997 | 63.581 | 43.127 | 16.04 |
| 4519 | PHE | CG | 42.385 | 62.573 | 44.092 | 18.17 |
| 4520 | PHE | CD1 | 43.226 | 61.617 | 44.720 | 18.77 |
| 4521 | PHE | CD2 | 41.030 | 62.660 | 44.476 | 17.46 |
| 4522 | PHE | CE1 | 42.767 | 60.863 | 45.818 | 18.56 |
| 4523 | PHE | CE2 | 40.577 | 61.903 | 45.587 | 17.26 |
| 4524 | PHE | CZ | 41.444 | 61.051 | 46.279 | 16.76 |
| 4525 | PHE | H | 44.444 | 65.270 | 41.908 | 20.00 |
| 4526 | PHE | HA | 42.892 | 65.451 | 44.341 | 20.00 |
| 4527 | PHE | 1HB | 43.750 | 63.045 | 42.548 | 20.00 |
| 4528 | PHE | 2HB | 42.235 | 63.919 | 42.431 | 20.00 |
| 4529 | PHE | HD1 | 44.244 | 61.511 | 44.366 | 20.00 |
| 4530 | PHE | HD2 | 40.363 | 63.332 | 43.956 | 20.00 |
| 4531 | PHE | HE1 | 43.447 | 60.182 | 46.317 | 20.00 |
| 4532 | PHE | HE2 | 39.540 | 61.973 | 45.889 | 20.00 |
| 4533 | PHE | HZ | 41.096 | 60.520 | 47.152 | 20.00 |
| 4534 | ILE | N | 45.904 | 64.058 | 44.464 | 17.16 |
| 4535 | ILE | CA | 46.963 | 63.619 | 45.424 | 16.95 |
| 4536 | ILE | C | 47.403 | 64.740 | 46.364 | 18.22 |
| 4537 | ILE | O | 47.734 | 64.521 | 47.537 | 19.58 |
| 4538 | ILE | CB | 48.233 | 63.056 | 44.686 | 16.65 |
| 4539 | ILE | CG1 | 47.877 | 61.897 | 43.715 | 15.20 |
| 4540 | ILE | CG2 | 49.381 | 62.644 | 45.664 | 17.33 |
| 4541 | ILE | CD1 | 47.124 | 60.747 | 44.386 | 16.00 |
| 4542 | ILE | H | 46.085 | 64.029 | 43.475 | 20.00 |
| 4543 | ILE | HA | 46.533 | 62.830 | 46.038 | 20.00 |
| 4544 | ILE | HB | 48.696 | 63.820 | 44.061 | 20.00 |
| 4545 | ILE | 1HG1 | 48.782 | 61.500 | 43.247 | 20.00 |
| 4546 | ILE | 2HG1 | 47.269 | 62.310 | 42.913 | 20.00 |
| 4547 | ILE | 1HG2 | 49.052 | 61.908 | 46.381 | 20.00 |
| 4548 | ILE | 2HG2 | 49.782 | 63.508 | 46.200 | 20.00 |
| 4549 | ILE | 3HG2 | 50.229 | 62.212 | 45.127 | 20.00 |
| 4550 | ILE | 1HD1 | 46.267 | 61.066 | 44.967 | 20.00 |
| 4551 | ILE | 2HD1 | 47.811 | 60.254 | 45.053 | 20.00 |
| 4552 | ILE | 3HD1 | 46.779 | 60.010 | 43.663 | 20.00 |
| 4553 | MET | N | 47.484 | 65.937 | 45.795 | 17.76 |
| 4554 | MET | CA | 48.123 | 67.010 | 46.548 | 17.15 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 4555 | MET | C | 47.180 | 67.601 | 47.549 | 18.59 |
| 4556 | MET | O | 47.634 | 68.088 | 48.582 | 18.92 |
| 4557 | MET | CB | 48.913 | 67.951 | 45.663 | 18.33 |
| 4558 | MET | CG | 50.089 | 67.168 | 45.027 | 18.10 |
| 4559 | MET | SD | 51.391 | 66.428 | 46.158 | 22.98 |
| 4560 | MET | CE | 51.905 | 67.914 | 47.025 | 22.14 |
| 4561 | MET | H | 47.175 | 66.080 | 44.861 | 20.00 |
| 4562 | MET | HA | 48.874 | 66.553 | 47.202 | 20.00 |
| 4563 | MET | 1HB | 49.285 | 68.791 | 46.230 | 20.00 |
| 4564 | MET | 2HB | 48.257 | 68.389 | 44.906 | 20.00 |
| 4565 | MET | 1HG | 50.607 | 67.834 | 44.333 | 20.00 |
| 4566 | MET | 2HG | 49.687 | 66.363 | 44.396 | 20.00 |
| 4567 | MET | 1HE | 51.085 | 68.420 | 47.548 | 20.00 |
| 4568 | MET | 2HE | 52.319 | 68.603 | 46.291 | 20.00 |
| 4569 | MET | 3HE | 52.687 | 67.673 | 47.749 | 20.00 |
| 4570 | GLY | N | 45.872 | 67.378 | 47.277 | 17.81 |
| 4571 | GLY | CA | 44.850 | 67.320 | 48.361 | 19.24 |
| 4572 | GLY | C | 43.474 | 67.982 | 48.080 | 18.12 |
| 4573 | GLY | O | 42.634 | 68.149 | 48.984 | 18.31 |
| 4574 | GLY | H | 45.672 | 66.962 | 46.387 | 20.00 |
| 4575 | GLY | 1HA | 45.269 | 67.841 | 49.231 | 20.00 |
| 4576 | GLY | 2HA | 44.716 | 66.282 | 48.674 | 20.00 |
| 4577 | ASP | N | 43.290 | 68.369 | 46.814 | 16.53 |
| 4578 | ASP | CA | 41.961 | 68.826 | 46.372 | 17.00 |
| 4579 | ASP | C | 41.035 | 67.607 | 46.048 | 18.13 |
| 4580 | ASP | O | 40.855 | 67.207 | 44.903 | 19.06 |
| 4581 | ASP | CB | 42.133 | 69.714 | 45.111 | 18.82 |
| 4582 | ASP | CG | 40.838 | 69.926 | 44.250 | 20.22 |
| 4583 | ASP | OD1 | 39.720 | 69.692 | 44.750 | 19.51 |
| 4584 | ASP | OD2 | 40.968 | 70.317 | 43.089 | 23.56 |
| 4585 | ASP | H | 44.012 | 68.210 | 46.144 | 20.00 |
| 4586 | ASP | HA | 41.478 | 69.396 | 47.157 | 20.00 |
| 4587 | ASP | 1HB | 42.844 | 69.226 | 44.444 | 20.00 |
| 4588 | ASP | 2HB | 42.546 | 70.691 | 45.349 | 20.00 |
| 4589 | SER | N | 40.427 | 66.964 | 47.031 | 18.73 |
| 4590 | SER | CA | 39.684 | 65.767 | 46.555 | 16.96 |
| 4591 | SER | C | 38.438 | 66.118 | 45.684 | 18.39 |
| 4592 | SER | O | 37.753 | 65.300 | 45.151 | 18.33 |
| 4593 | SER | CB | 39.548 | 64.762 | 47.784 | 17.13 |
| 4594 | SER | OG | 40.769 | 64.296 | 48.566 | 14.25 |
| 4595 | SER | H | 40.606 | 67.273 | 47.975 | 20.00 |
| 4596 | SER | HA | 40.219 | 65.218 | 45.768 | 20.00 |
| 4597 | SER | 1HB | 38.927 | 63.897 | 47.443 | 20.00 |
| 4598 | SER | 2HB | 38.817 | 65.230 | 48.491 | 20.00 |
| 4599 | SER | HG | 41.719 | 64.490 | 48.317 | 20.00 |
| 4600 | SER | N | 38.161 | 67.528 | 45.516 | 17.50 |
| 4601 | SER | CA | 37.016 | 68.024 | 44.673 | 18.74 |
| 4602 | SER | C | 37.183 | 67.715 | 43.164 | 17.75 |
| 4603 | SER | O | 36.183 | 67.406 | 42.477 | 16.68 |
| 4604 | SER | CB | 36.747 | 69.546 | 44.774 | 19.67 |
| 4605 | SER | OG | 37.500 | 70.494 | 43.897 | 21.88 |
| 4606 | SER | H | 38.797 | 68.224 | 45.866 | 20.00 |
| 4607 | SER | HA | 36.131 | 67.483 | 45.019 | 20.00 |
| 4608 | SER | 1HB | 36.605 | 69.852 | 45.852 | 20.00 |
| 4609 | SER | 2HB | 35.674 | 69.626 | 44.497 | 20.00 |
| 4610 | SER | HG | 38.484 | 70.378 | 43.663 | 20.00 |
| 4611 | VAL | N | 38.473 | 67.708 | 42.702 | 17.27 |
| 4612 | VAL | CA | 38.680 | 67.191 | 41.319 | 18.22 |
| 4613 | VAL | C | 37.910 | 65.970 | 40.883 | 18.73 |
| 4614 | VAL | O | 37.472 | 65.906 | 39.737 | 19.63 |
| 4615 | VAL | CB | 40.132 | 66.911 | 40.897 | 20.69 |
| 4616 | VAL | CG1 | 40.884 | 66.073 | 41.910 | 17.79 |
| 4617 | VAL | CG2 | 40.868 | 68.222 | 40.572 | 23.70 |
| 4618 | VAL | H | 39.207 | 68.134 | 43.257 | 20.00 |
| 4619 | VAL | HA | 38.305 | 67.980 | 40.690 | 20.00 |
| 4620 | VAL | HB | 40.169 | 66.379 | 39.947 | 20.00 |
| 4621 | VAL | 1HG1 | 40.410 | 65.103 | 42.049 | 20.00 |
| 4622 | VAL | 2HG1 | 40.897 | 66.580 | 42.855 | 20.00 |
| 4623 | VAL | 3HG1 | 41.920 | 65.935 | 41.604 | 20.00 |
| 4624 | VAL | 1HG2 | 41.042 | 68.758 | 41.495 | 20.00 |
| 4625 | VAL | 2HG2 | 40.304 | 68.883 | 39.916 | 20.00 |
| 4626 | VAL | 3HG2 | 41.836 | 68.034 | 40.111 | 20.00 |
| 4627 | GLN | N | 37.827 | 64.997 | 41.788 | 18.28 |
| 4628 | GLN | CA | 37.407 | 63.664 | 41.383 | 19.78 |
| 4629 | GLN | C | 35.957 | 63.564 | 40.980 | 23.25 |
| 4630 | GLN | O | 35.635 | 62.870 | 40.010 | 25.12 |
| 4631 | GLN | CB | 37.684 | 62.612 | 42.412 | 20.56 |
| 4632 | GLN | CG | 37.171 | 61.233 | 41.947 | 24.84 |
| 4633 | GLN | CD | 37.628 | 60.156 | 42.928 | 27.26 |
| 4634 | GLN | OE1 | 38.497 | 60.357 | 43.777 | 31.04 |
| 4635 | GLN | NE2 | 37.005 | 59.010 | 42.735 | 29.42 |
| 4636 | GLN | H | 38.155 | 65.203 | 42.714 | 20.00 |
| 4637 | GLN | HA | 37.983 | 63.430 | 40.496 | 20.00 |
| 4638 | GLN | 1HB | 37.199 | 62.866 | 43.353 | 20.00 |
| 4639 | GLN | 2HB | 38.752 | 62.567 | 42.609 | 20.00 |
| 4640 | GLN | 1HG | 37.541 | 60.972 | 40.956 | 20.00 |
| 4641 | GLN | 2HG | 36.077 | 61.187 | 41.899 | 20.00 |
| 4642 | GLN | 1HE2 | 37.189 | 58.293 | 43.411 | 20.00 |
| 4643 | GLN | 2HE2 | 36.335 | 58.854 | 42.017 | 20.00 |
| 4644 | ASP | N | 35.132 | 64.360 | 41.665 | 25.31 |
| 4645 | ASP | CA | 33.794 | 64.542 | 41.078 | 27.02 |
| 4646 | ASP | C | 33.714 | 65.515 | 39.851 | 25.79 |
| 4647 | ASP | O | 33.010 | 65.234 | 38.884 | 25.32 |
| 4648 | ASP | CB | 32.728 | 64.363 | 42.176 | 35.78 |
| 4649 | ASP | CG | 32.232 | 62.848 | 42.252 | 44.92 |
| 4650 | ASP | OD1 | 33.060 | 61.924 | 42.012 | 50.04 |
| 4651 | ASP | OD2 | 31.014 | 62.626 | 42.502 | 50.59 |
| 4652 | ASP | H | 35.428 | 64.744 | 42.538 | 20.00 |
| 4653 | ASP | HA | 33.606 | 63.669 | 40.453 | 20.00 |
| 4654 | ASP | 1HB | 31.871 | 64.981 | 41.929 | 20.00 |
| 4655 | ASP | 2HB | 33.104 | 64.706 | 43.143 | 20.00 |
| 4656 | GLN | N | 34.626 | 66.532 | 39.807 | 23.38 |
| 4657 | GLN | CA | 34.903 | 67.171 | 38.484 | 24.32 |
| 4658 | GLN | C | 35.209 | 66.229 | 37.269 | 23.16 |
| 4659 | GLN | O | 34.689 | 66.444 | 36.165 | 21.27 |
| 4660 | GLN | CB | 35.989 | 68.248 | 38.513 | 28.00 |
| 4661 | GLN | CG | 35.765 | 69.233 | 39.647 | 35.72 |
| 4662 | GLN | CD | 37.011 | 70.084 | 39.806 | 43.13 |
| 4663 | GLN | OE1 | 37.614 | 70.466 | 38.814 | 48.57 |
| 4664 | GLN | NE2 | 37.399 | 70.384 | 41.059 | 43.82 |
| 4665 | GLN | H | 35.105 | 66.754 | 40.660 | 20.00 |
| 4666 | GLN | HA | 33.969 | 67.668 | 38.222 | 20.00 |
| 4667 | GLN | 1HB | 36.001 | 68.784 | 37.562 | 20.00 |
| 4668 | GLN | 2HB | 36.973 | 67.792 | 38.594 | 20.00 |
| 4669 | GLN | 1HG | 35.574 | 68.757 | 40.601 | 20.00 |
| 4670 | GLN | 2HG | 34.922 | 69.879 | 39.419 | 20.00 |
| 4671 | GLN | 1HE2 | 38.245 | 70.918 | 41.061 | 20.00 |
| 4672 | GLN | 2HE2 | 36.969 | 70.145 | 41.925 | 20.00 |
| 4673 | TRP | N | 36.067 | 65.207 | 37.463 | 20.29 |
| 4674 | TRP | CA | 36.319 | 64.264 | 36.366 | 19.31 |
| 4675 | TRP | C | 35.089 | 63.487 | 35.918 | 19.07 |
| 4676 | TRP | O | 34.861 | 63.193 | 34.736 | 19.20 |
| 4677 | TRP | CB | 37.263 | 63.169 | 36.885 | 19.26 |
| 4678 | TRP | CG | 38.589 | 63.776 | 37.213 | 15.65 |
| 4679 | TRP | CD1 | 39.188 | 64.909 | 36.656 | 14.94 |
| 4680 | TRP | CD2 | 39.483 | 63.209 | 38.143 | 15.85 |
| 4681 | TRP | NE1 | 40.412 | 65.088 | 37.205 | 15.54 |
| 4682 | TRP | CE2 | 40.619 | 64.068 | 38.133 | 15.86 |
| 4683 | TRP | CE3 | 39.390 | 62.115 | 38.989 | 14.86 |
| 4684 | TRP | CZ2 | 41.699 | 63.722 | 38.904 | 16.78 |
| 4685 | TRP | CZ3 | 40.479 | 61.761 | 39.786 | 14.37 |
| 4686 | TRP | CH2 | 41.631 | 62.585 | 39.740 | 15.56 |
| 4687 | TRP | H | 36.508 | 65.153 | 38.360 | 20.00 |
| 4688 | TRP | HA | 36.722 | 64.799 | 35.513 | 20.00 |
| 4689 | TRP | 1HB | 37.452 | 62.427 | 36.116 | 20.00 |
| 4690 | TRP | 2HB | 36.849 | 62.663 | 37.759 | 20.00 |
| 4691 | TRP | HD1 | 38.745 | 65.543 | 35.900 | 20.00 |
| 4692 | TRP | HE1 | 41.059 | 65.811 | 37.001 | 20.00 |
| 4693 | TRP | HE3 | 38.490 | 61.508 | 38.989 | 20.00 |
| 4694 | TRP | HZ2 | 42.571 | 64.373 | 38.864 | 20.00 |
| 4695 | TRP | HZ3 | 40.436 | 60.909 | 40.460 | 20.00 |
| 4696 | TRP | HH2 | 42.485 | 62.328 | 40.349 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 4697 | LYS | N | 34.338 | 63.136 | 36.976 | 21.19 |
| 4698 | LYS | CA | 33.082 | 62.421 | 36.730 | 24.17 |
| 4699 | LYS | C | 32.154 | 63.264 | 35.758 | 25.28 |
| 4700 | LYS | O | 31.736 | 62.892 | 34.656 | 26.15 |
| 4701 | LYS | CB | 32.453 | 62.137 | 38.108 | 26.43 |
| 4702 | LYS | CG | 31.329 | 61.095 | 38.057 | 32.00 |
| 4703 | LYS | CD | 30.909 | 60.906 | 39.490 | 38.87 |
| 4704 | LYS | CE | 29.764 | 59.913 | 39.692 | 45.47 |
| 4705 | LYS | NZ | 29.279 | 60.040 | 41.099 | 51.74 |
| 4706 | LYS | H | 34.648 | 63.302 | 37.917 | 20.00 |
| 4707 | LYS | HA | 33.334 | 61.452 | 36.303 | 20.00 |
| 4708 | LYS | 1HB | 32.101 | 63.055 | 38.569 | 20.00 |
| 4709 | LYS | 2HB | 33.239 | 61.739 | 38.752 | 20.00 |
| 4710 | LYS | 1HG | 31.674 | 60.151 | 37.631 | 20.00 |
| 4711 | LYS | 2HG | 30.495 | 61.432 | 37.435 | 20.00 |
| 4712 | LYS | 1HD | 30.615 | 61.873 | 39.902 | 20.00 |
| 4713 | LYS | 2HD | 31.768 | 60.576 | 40.078 | 20.00 |
| 4714 | LYS | 1HE | 30.136 | 58.898 | 39.499 | 20.00 |
| 4715 | LYS | 2HE | 28.947 | 60.090 | 38.984 | 20.00 |
| 4716 | LYS | 1HZ | 29.033 | 61.040 | 41.269 | 20.00 |
| 4717 | LYS | 2HZ | 30.103 | 59.869 | 41.719 | 20.00 |
| 4718 | LYS | 3HZ | 28.496 | 59.397 | 41.317 | 20.00 |
| 4719 | GLU | N | 32.050 | 64.521 | 36.209 | 26.22 |
| 4720 | GLU | CA | 31.455 | 65.533 | 35.365 | 27.87 |
| 4721 | GLU | C | 32.006 | 65.577 | 33.869 | 26.53 |
| 4722 | GLU | O | 31.332 | 65.367 | 32.866 | 30.42 |
| 4723 | GLU | CB | 31.542 | 66.807 | 36.263 | 34.80 |
| 4724 | GLU | CG | 30.693 | 66.725 | 37.585 | 47.61 |
| 4725 | GLU | CD | 29.211 | 66.293 | 37.462 | 55.88 |
| 4726 | GLU | OE1 | 28.422 | 67.129 | 36.998 | 59.76 |
| 4727 | GLU | OE2 | 28.883 | 65.134 | 37.826 | 61.03 |
| 4728 | GLU | H | 32.243 | 64.712 | 37.176 | 20.00 |
| 4729 | GLU | HA | 30.410 | 65.251 | 35.271 | 20.00 |
| 4730 | GLU | 1HB | 31.181 | 67.661 | 35.698 | 20.00 |
| 4731 | GLU | 2HB | 32.564 | 67.009 | 36.547 | 20.00 |
| 4732 | GLU | 1HG | 30.708 | 67.672 | 38.117 | 20.00 |
| 4733 | GLU | 2HG | 31.080 | 65.993 | 38.276 | 20.00 |
| 4734 | LEU | N | 33.317 | 65.813 | 33.793 | 24.19 |
| 4735 | LEU | CA | 34.088 | 66.004 | 32.540 | 23.43 |
| 4736 | LEU | C | 34.108 | 64.773 | 31.610 | 24.08 |
| 4737 | LEU | O | 34.441 | 64.885 | 30.447 | 22.85 |
| 4738 | LEU | CB | 35.553 | 66.277 | 32.956 | 25.02 |
| 4739 | LEU | CG | 35.989 | 67.725 | 32.878 | 25.39 |
| 4740 | LEU | CD1 | 37.358 | 67.805 | 33.605 | 27.03 |
| 4741 | LEU | CD2 | 34.947 | 68.615 | 33.583 | 28.40 |
| 4742 | LEU | H | 33.756 | 65.871 | 34.690 | 20.00 |
| 4743 | LEU | HA | 33.699 | 66.832 | 31.949 | 20.00 |
| 4744 | LEU | 1HB | 36.274 | 65.707 | 32.372 | 20.00 |
| 4745 | LEU | 2HB | 35.693 | 65.929 | 33.976 | 20.00 |
| 4746 | LEU | HG | 36.089 | 68.033 | 31.838 | 20.00 |
| 4747 | LEU | 1HD1 | 38.106 | 67.202 | 33.097 | 20.00 |
| 4748 | LEU | 2HD1 | 37.284 | 67.450 | 34.634 | 20.00 |
| 4749 | LEU | 3HD1 | 37.742 | 68.825 | 33.641 | 20.00 |
| 4750 | LEU | 1HD2 | 34.769 | 68.729 | 34.605 | 20.00 |
| 4751 | LEU | 2HD2 | 33.982 | 68.644 | 33.078 | 20.00 |
| 4752 | LEU | 3HD2 | 35.307 | 69.642 | 33.676 | 20.00 |
| 4753 | SER | N | 33.842 | 63.591 | 32.146 | 23.22 |
| 4754 | SER | CA | 34.023 | 62.430 | 31.279 | 24.53 |
| 4755 | SER | C | 32.729 | 62.144 | 30.475 | 26.87 |
| 4756 | SER | O | 32.753 | 61.539 | 29.414 | 26.47 |
| 4757 | SER | CB | 34.168 | 61.268 | 32.238 | 23.92 |
| 4758 | SER | OG | 32.851 | 60.942 | 32.814 | 27.33 |
| 4759 | SER | H | 33.548 | 63.568 | 33.105 | 20.00 |
| 4760 | SER | HA | 34.900 | 62.512 | 30.638 | 20.00 |
| 4761 | SER | 1HB | 35.074 | 61.383 | 32.907 | 20.00 |
| 4762 | SER | 2HB | 34.520 | 60.416 | 31.633 | 20.00 |
| 4763 | SER | HG | 32.219 | 61.568 | 33.301 | 20.00 |
| 4764 | HIS | N | 31.582 | 62.546 | 31.085 | 29.80 |
| 4765 | HIS | CA | 30.257 | 62.150 | 30.557 | 33.13 |
| 4766 | HIS | O | 29.778 | 60.651 | 30.861 | 33.64 |
| 4767 | HIS | O | 29.195 | 59.996 | 29.999 | 31.30 |
| 4768 | HIS | CB | 30.150 | 62.548 | 29.063 | 36.51 |
| 4769 | HIS | CG | 30.638 | 63.959 | 28.940 | 40.71 |
| 4770 | HIS | ND1 | 31.746 | 64.287 | 28.246 | 43.97 |
| 4771 | HIS | CD2 | 30.108 | 65.137 | 29.519 | 42.68 |
| 4772 | HIS | CE1 | 31.894 | 65.632 | 28.386 | 43.60 |
| 4773 | HIS | NE2 | 30.917 | 66.174 | 29.151 | 42.67 |
| 4774 | HIS | H | 31.682 | 63.199 | 31.841 | 20.00 |
| 4775 | HIS | HA | 29.569 | 62.773 | 31.127 | 20.00 |
| 4776 | HIS | 1HB | 29.124 | 62.477 | 28.704 | 20.00 |
| 4777 | HIS | 2HB | 30.767 | 61.968 | 28.391 | 20.00 |
| 4778 | HIS | HD1 | 32.351 | 63.667 | 27.792 | 20.00 |
| 4779 | HIS | HD2 | 29.244 | 65.194 | 30.166 | 20.00 |
| 4780 | HIS | HE1 | 32.696 | 66.220 | 27.957 | 20.00 |
| 4781 | GLU | N | 30.038 | 60.148 | 32.122 | 35.19 |
| 4782 | GLU | CA | 29.812 | 58.725 | 32.461 | 36.70 |
| 4783 | GLU | C | 28.365 | 58.293 | 32.195 | 38.60 |
| 4784 | GLU | O | 28.187 | 57.171 | 31.764 | 37.53 |
| 4785 | GLU | CB | 30.385 | 58.171 | 33.820 | 35.82 |
| 4786 | GLU | CG | 29.685 | 58.624 | 35.121 | 36.20 |
| 4787 | GLU | CD | 30.185 | 57.959 | 36.421 | 38.96 |
| 4788 | GLU | OE1 | 31.324 | 57.527 | 36.458 | 36.60 |
| 4789 | GLU | OE2 | 29.434 | 57.837 | 37.399 | 41.14 |
| 4790 | GLU | H | 30.309 | 60.799 | 32.826 | 20.00 |
| 4791 | GLU | HA | 30.412 | 58.167 | 31.757 | 20.00 |
| 4792 | GLU | 1HB | 31.453 | 58.377 | 33.892 | 20.00 |
| 4793 | GLU | 2HB | 30.305 | 57.095 | 33.743 | 20.00 |
| 4794 | GLU | 1HG | 28.617 | 58.448 | 35.059 | 20.00 |
| 4795 | GLU | 2HG | 29.808 | 59.700 | 35.259 | 20.00 |
| 4796 | ASP | N | 27.355 | 59.161 | 32.427 | 42.63 |
| 4797 | ASP | CA | 25.947 | 58.715 | 32.232 | 46.40 |
| 4798 | ASP | C | 25.333 | 59.095 | 30.796 | 47.19 |
| 4799 | ASP | O | 25.663 | 60.179 | 30.242 | 46.38 |
| 4800 | ASP | CB | 25.156 | 59.121 | 33.508 | 50.98 |
| 4801 | ASP | CG | 25.757 | 58.386 | 34.723 | 57.85 |
| 4802 | ASP | OD1 | 25.724 | 57.146 | 34.731 | 60.50 |
| 4803 | ASP | OD2 | 26.292 | 59.021 | 35.648 | 61.02 |
| 4804 | ASP | OXT | 24.582 | 58.276 | 30.208 | 48.57 |
| 4805 | ASP | H | 27.519 | 60.002 | 32.926 | 20.00 |
| 4806 | ASP | HA | 25.950 | 57.622 | 32.219 | 20.00 |
| 4807 | ASP | 1HB | 24.118 | 58.815 | 33.431 | 20.00 |
| 4808 | ASP | 2HB | 25.188 | 60.198 | 33.649 | 20.00 |
| 1 | OC__ | C1 | 49.640 | 37.719 | 14.003 | 0.00 |
| 2 | OC__ | C2 | 50.787 | 38.141 | 14.736 | 0.00 |
| 3 | OC__ | C3 | 51.008 | 39.495 | 14.916 | 0.00 |
| 4 | OC__ | C4 | 50.154 | 40.364 | 14.322 | 0.00 |
| 5 | OC__ | C5 | 49.053 | 40.047 | 13.581 | 0.00 |
| 6 | OC__ | C6 | 48.782 | 38.701 | 13.402 | 0.00 |
| 7 | OC__ | 7H | 49.187 | 36.718 | 13.842 | 0.00 |
| 8 | OC__ | 8H | 48.426 | 40.820 | 13.123 | 0.00 |
| 9 | OC__ | H9 | 47.921 | 38.415 | 12.808 | 0.00 |
| 10 | OC__ | C10 | 52.036 | 40.299 | 15.636 | 0.00 |
| 11 | OC__ | N11 | 51.728 | 41.572 | 15.438 | 0.00 |
| 12 | OC__ | C12 | 50.628 | 41.640 | 14.622 | 0.00 |
| 13 | OC__ | O13 | 50.068 | 42.623 | 14.140 | 0.00 |
| 14 | OC__ | O14 | 52.998 | 39.925 | 16.291 | 0.00 |
| 15 | OC__ | O15 | 51.718 | 37.289 | 15.246 | 0.00 |
| 16 | OC__ | H16 | 51.994 | 36.801 | 14.488 | 0.00 |
| 17 | OC__ | C17 | 52.602 | 42.662 | 15.945 | 0.00 |
| 18 | OC__ | C18 | 51.989 | 43.758 | 16.830 | 0.00 |
| 19 | OC__ | H19 | 53.162 | 43.136 | 15.129 | 0.00 |
| 20 | OC__ | H20 | 53.441 | 42.237 | 16.493 | 0.00 |
| 21 | OC__ | O21 | 52.823 | 43.764 | 17.935 | 0.00 |
| 22 | OC__ | C22 | 52.911 | 44.965 | 18.630 | 0.00 |
| 23 | OC__ | C23 | 51.464 | 45.106 | 19.104 | 0.00 |
| 24 | OC__ | C24 | 50.401 | 44.489 | 18.575 | 0.00 |
| 25 | OC__ | C25 | 50.577 | 43.599 | 17.383 | 0.00 |
| 26 | OC__ | 6H2 | 52.083 | 44.717 | 16.324 | 0.00 |
| 27 | OC__ | H27 | 53.299 | 45.778 | 18.011 | 0.00 |
| 28 | OC__ | H28 | 53.618 | 44.846 | 19.458 | 0.00 |
| 29 | OC__ | 9H2 | 49.817 | 43.779 | 16.639 | 0.00 |
| 30 | OC__ | 0H3 | 50.512 | 42.573 | 17.745 | 0.00 |

TABLE C-continued

Table of the orthogonal three dimensional coordinates in Ångstroms and B factors (Å$^2$) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 31 | OC__ | S31 | 50.995 | 45.860 | 20.622 | 0.00 |
| 32 | OC__ | C32 | 49.309 | 45.615 | 20.276 | 0.00 |
| 33 | OC__ | C33 | 49.082 | 44.948 | 19.126 | 0.00 |
| 34 | OC__ | N34 | 48.236 | 46.161 | 21.034 | 0.00 |
| 35 | OC__ | C35 | 48.405 | 46.833 | 22.220 | 0.00 |
| 36 | OC__ | C36 | 47.021 | 47.267 | 22.889 | 0.00 |
| 37 | OC__ | O37 | 46.749 | 48.354 | 23.338 | 0.00 |
| 38 | OC__ | O38 | 46.116 | 46.291 | 23.042 | 0.00 |
| 39 | OC__ | O39 | 49.477 | 47.023 | 22.820 | 0.00 |
| 40 | OC__ | C40 | 47.697 | 44.874 | 18.500 | 0.00 |
| 41 | OC__ | O41 | 46.650 | 44.969 | 19.070 | 0.00 |
| 42 | OC__ | O42 | 47.614 | 44.562 | 17.174 | 0.00 |
| 43 | OC__ | 3H4 | 46.996 | 43.859 | 17.092 | 0.00 |
| 44 | OC__ | H44 | 45.261 | 46.650 | 23.184 | 0.00 |
| 45 | OC__ | H45 | 47.336 | 46.168 | 20.596 | 0.00 |
| 1 | TIP | OH2 | 55.419 | 44.829 | 16.389 | 20.00 |
| 2 | TIP | H1 | 55.536 | 44.889 | 17.342 | 20.00 |
| 3 | TIP | 2H | 55.300 | 45.765 | 16.164 | 20.00 |
| 4 | TIP | OH2 | 50.936 | 38.099 | 22.176 | 20.00 |
| 5 | TIP | 1H | 51.119 | 38.023 | 23.113 | 20.00 |
| 6 | TIP | H2 | 50.913 | 39.042 | 22.012 | 20.00 |
| 7 | TIP | OH2 | 29.774 | 30.704 | 38.242 | 20.00 |
| 8 | TIP | 1H | 29.956 | 30.628 | 39.179 | 20.00 |
| 9 | TIP | H2 | 29.750 | 31.647 | 38.078 | 20.00 |
| 10 | TIP | OH2 | 45.277 | 35.890 | 28.823 | 20.00 |
| 11 | TIP | 1H | 45.460 | 35.813 | 29.759 | 20.00 |
| 12 | TIP | H2 | 45.253 | 36.832 | 28.659 | 20.00 |
| 13 | TIP | OH2 | 58.027 | 40.785 | 28.285 | 20.00 |
| 14 | TIP | 1H | 58.210 | 40.709 | 29.222 | 20.00 |
| 15 | TIP | H2 | 58.004 | 41.728 | 28.121 | 20.00 |
| 16 | TIP | OH2 | 40.267 | 36.083 | 19.326 | 20.00 |
| 17 | TIP | H1 | 40.450 | 36.007 | 20.263 | 20.00 |
| 18 | TIP | 2H | 40.244 | 37.026 | 19.162 | 20.00 |
| 19 | TIP | OH2 | 53.647 | 32.258 | 38.649 | 20.00 |
| 20 | TIP | 1H | 53.830 | 32.182 | 39.585 | 20.00 |
| 21 | TIP | H2 | 53.623 | 33.200 | 38.484 | 20.00 |
| 22 | TIP | OH2 | 48.317 | 32.381 | 26.654 | 20.00 |
| 23 | TIP | 1H | 48.499 | 32.305 | 27.591 | 20.00 |
| 24 | TIP | H2 | 48.293 | 33.324 | 26.490 | 20.00 |
| 25 | TIP | OH2 | 38.532 | 50.364 | 24.358 | 20.00 |
| 26 | TIP | 1H | 38.714 | 50.288 | 25.294 | 20.00 |
| 27 | TIP | H2 | 38.508 | 51.307 | 24.194 | 20.00 |
| 28 | TIP | OH2 | 43.205 | 42.135 | 42.424 | 20.00 |
| 29 | TIP | 1H | 43.387 | 42.059 | 43.360 | 20.00 |
| 30 | TIP | 2H | 43.181 | 43.078 | 42.260 | 20.00 |
| 31 | TIP | OH2 | 38.345 | 49.997 | 21.607 | 20.00 |
| 32 | TIP | H1 | 38.528 | 49.921 | 22.543 | 20.00 |
| 33 | TIP | H2 | 38.321 | 50.940 | 21.443 | 20.00 |
| 34 | TIP | OH2 | 48.352 | 30.997 | 37.771 | 20.00 |
| 35 | TIP | 1H | 48.535 | 30.921 | 38.708 | 20.00 |
| 36 | TIP | H2 | 48.329 | 31.940 | 37.607 | 20.00 |
| 37 | TIP | OH2 | 48.526 | 24.351 | 23.768 | 20.00 |
| 38 | TIP | H1 | 48.709 | 24.275 | 24.705 | 20.00 |
| 39 | TIP | 2H | 48.502 | 25.294 | 23.604 | 20.00 |
| 40 | TIP | OH2 | 30.895 | 32.557 | 49.007 | 20.00 |
| 41 | TIP | H1 | 31.078 | 32.480 | 49.944 | 20.00 |
| 42 | TIP | 2H | 30.871 | 33.499 | 48.843 | 20.00 |
| 43 | TIP | OH2 | 48.519 | 50.061 | 21.813 | 20.00 |
| 44 | TIP | H1 | 48.702 | 49.985 | 22.750 | 20.00 |
| 45 | TIP | 2H | 48.495 | 51.003 | 21.649 | 20.00 |
| 46 | TIP | OH2 | 57.848 | 51.344 | 42.042 | 20.00 |
| 47 | TIP | H1 | 58.031 | 51.268 | 42.978 | 20.00 |
| 48 | TIP | 2H | 57.825 | 52.287 | 41.877 | 20.00 |
| 49 | TIP | OH2 | 54.834 | 35.583 | 21.192 | 20.00 |
| 50 | TIP | 1H | 55.017 | 35.507 | 22.129 | 20.00 |
| 51 | TIP | H2 | 54.811 | 36.525 | 21.028 | 20.00 |
| 52 | TIP | OH2 | 21.604 | 40.670 | 37.071 | 20.00 |
| 53 | TIP | H1 | 21.787 | 40.594 | 38.007 | 20.00 |
| 54 | TIP | 2H | 21.581 | 41.613 | 36.907 | 20.00 |
| 55 | TIP | OH2 | 61.252 | 32.808 | 37.483 | 20.00 |
| 56 | TIP | H1 | 61.435 | 32.732 | 38.420 | 20.00 |
| 57 | TIP | 2H | 61.229 | 33.751 | 37.319 | 20.00 |
| 58 | TIP | OH2 | 66.912 | 49.122 | 40.151 | 20.00 |
| 59 | TIP | H1 | 67.094 | 49.046 | 41.088 | 20.00 |
| 60 | TIP | 2H | 66.888 | 50.065 | 39.987 | 20.00 |
| 61 | TIP | OH2 | 23.155 | 25.413 | 25.818 | 20.00 |
| 62 | TIP | H1 | 23.337 | 25.337 | 26.755 | 20.00 |
| 63 | TIP | 2H | 23.131 | 26.355 | 25.654 | 20.00 |
| 64 | TIP | OH2 | 52.477 | 58.511 | 18.314 | 20.00 |
| 65 | TIP | H1 | 52.659 | 58.434 | 19.250 | 20.00 |
| 66 | TIP | 2H | 52.453 | 59.453 | 18.150 | 20.00 |
| 67 | TIP | OH2 | 33.877 | 44.186 | 23.766 | 20.00 |
| 68 | TIP | 1H | 34.060 | 44.110 | 24.702 | 20.00 |
| 69 | TIP | H2 | 33.853 | 45.129 | 23.602 | 20.00 |
| 70 | TIP | OH2 | 36.071 | 53.377 | 48.280 | 20.00 |
| 71 | TIP | H1 | 36.254 | 53.301 | 49.216 | 20.00 |
| 72 | TIP | 2H | 36.047 | 54.320 | 48.116 | 20.00 |
| 73 | TIP | OH2 | 57.951 | 22.393 | 22.291 | 20.00 |
| 74 | TIP | 1H | 58.133 | 22.317 | 23.228 | 20.00 |
| 75 | TIP | H2 | 57.927 | 23.335 | 22.127 | 20.00 |
| 76 | TIP | OH2 | 43.946 | 30.374 | 44.700 | 20.00 |
| 77 | TIP | 1H | 44.128 | 30.298 | 45.637 | 20.00 |
| 78 | TIP | H2 | 43.922 | 31.316 | 44.536 | 20.00 |
| 79 | TIP | OH2 | 23.284 | 48.767 | 33.067 | 20.00 |
| 80 | TIP | 1H | 23.466 | 48.691 | 34.004 | 20.00 |
| 81 | TIP | H2 | 23.260 | 49.710 | 32.903 | 20.00 |
| 82 | TIP | OH2 | 34.465 | 36.411 | 46.836 | 20.00 |
| 83 | TIP | 1H | 34.648 | 36.335 | 47.773 | 20.00 |
| 84 | TIP | H2 | 34.441 | 37.353 | 46.672 | 20.00 |
| 85 | TIP | OH2 | 47.183 | 59.524 | 19.471 | 20.00 |
| 86 | TIP | H1 | 47.365 | 59.448 | 20.407 | 20.00 |
| 87 | TIP | 2H | 47.159 | 60.467 | 19.307 | 20.00 |
| 88 | TIP | OH2 | 38.194 | 26.639 | 27.880 | 20.00 |
| 89 | TIP | 1H | 38.377 | 26.563 | 28.816 | 20.00 |
| 90 | TIP | H2 | 38.170 | 27.581 | 27.716 | 20.00 |
| 91 | TIP | OH2 | 63.749 | 46.405 | 40.207 | 20.00 |
| 92 | TIP | 1H | 63.932 | 46.329 | 41.143 | 20.00 |
| 93 | TIP | H2 | 63.726 | 47.347 | 40.043 | 20.00 |
| 94 | TIP | OH2 | 38.952 | 29.220 | 51.044 | 20.00 |
| 95 | TIP | 1H | 39.135 | 29.144 | 51.980 | 20.00 |
| 96 | TIP | H2 | 38.928 | 30.162 | 50.880 | 20.00 |
| 97 | TIP | OH2 | 22.585 | 40.880 | 29.562 | 20.00 |
| 98 | TIP | H1 | 22.768 | 40.804 | 30.498 | 20.00 |
| 99 | TIP | 2H | 22.562 | 41.823 | 29.398 | 20.00 |
| 100 | TIP | OH2 | 60.690 | 27.339 | 33.408 | 20.00 |
| 101 | TIP | 1H | 60.873 | 27.263 | 34.345 | 20.00 |
| 102 | TIP | H2 | 60.666 | 28.282 | 33.244 | 20.00 |
| 103 | TIP | OH2 | 44.387 | 24.820 | 39.848 | 20.00 |
| 104 | TIP | H1 | 44.570 | 24.744 | 40.784 | 20.00 |
| 105 | TIP | H2 | 44.363 | 25.763 | 39.684 | 20.00 |
| 106 | TIP | OH2 | 47.685 | 57.349 | 44.874 | 20.00 |
| 107 | TIP | 1H | 47.867 | 57.272 | 45.810 | 20.00 |
| 108 | TIP | H2 | 47.661 | 58.291 | 44.710 | 20.00 |
| 109 | TIP | OH2 | 67.071 | 45.345 | 34.784 | 20.00 |
| 110 | TIP | H1 | 67.254 | 45.268 | 35.720 | 20.00 |
| 111 | TIP | 2H | 67.047 | 46.287 | 34.620 | 20.00 |
| 112 | TIP | OH2 | 45.116 | 59.190 | 18.168 | 20.00 |
| 113 | TIP | H1 | 45.298 | 59.114 | 19.105 | 20.00 |
| 114 | TIP | 2H | 45.092 | 60.133 | 18.004 | 20.00 |
| 115 | TIP | OH2 | 60.283 | 64.299 | 18.011 | 20.00 |
| 116 | TIP | H1 | 60.466 | 64.223 | 18.947 | 20.00 |
| 117 | TIP | 2H | 60.259 | 65.241 | 17.847 | 20.00 |
| 118 | TIP | OH2 | 60.415 | 30.584 | 33.261 | 20.00 |
| 119 | TIP | H1 | 60.598 | 30.508 | 34.198 | 20.00 |
| 120 | TIP | 2H | 60.392 | 31.527 | 33.097 | 20.00 |
| 121 | TIP | OH2 | 60.024 | 47.287 | 40.698 | 20.00 |
| 122 | TIP | 1H | 60.207 | 47.211 | 41.634 | 20.00 |
| 123 | TIP | H2 | 60.001 | 48.230 | 40.534 | 20.00 |
| 124 | TIP | OH2 | 37.196 | 38.650 | 46.459 | 20.00 |
| 125 | TIP | H1 | 37.379 | 38.574 | 47.395 | 20.00 |
| 126 | TIP | 2H | 37.172 | 39.592 | 46.294 | 20.00 |
| 127 | TIP | OH2 | 46.215 | 64.400 | 22.087 | 20.00 |

TABLE C-continued

Table of the orthogonal three dimensional coordinates in Ångstroms and B factors (Å²) for Protein Tyrosine Phosphatase 1B complexed with 5-(4-hydroxy-1,3-dioxo-1,3-dihydro-isoindol-2-ylmethyl)-2-(oxalyl-amino)-4,7-dihydro-5H-thieno[2,3-c]pyran-3-carboxylic acid (Example 4).

| No | Amino acid | | X | Y | Z | B |
|---|---|---|---|---|---|---|
| 128 | TIP | H1 | 46.398 | 64.324 | 23.024 | 20.00 |
| 129 | TIP | 2H | 46.191 | 65.343 | 21.923 | 20.00 |
| 130 | TIP | OH2 | 32.296 | 42.095 | 24.175 | 20.00 |
| 131 | TIP | H1 | 32.479 | 42.019 | 25.112 | 20.00 |
| 132 | TIP | 2H | 32.272 | 43.038 | 24.011 | 20.00 |
| 133 | TIP | OH2 | 25.133 | 25.020 | 39.586 | 20.00 |
| 134 | TIP | 1H | 25.316 | 24.944 | 40.523 | 20.00 |
| 135 | TIP | 2H | 25.109 | 25.962 | 39.422 | 20.00 |
| 136 | TIP | OH2 | 63.940 | 65.238 | 29.552 | 20.00 |
| 137 | TIP | 1H | 64.123 | 65.162 | 30.489 | 20.00 |
| 138 | TIP | H2 | 63.917 | 66.181 | 29.388 | 20.00 |
| 139 | TIP | OH2 | 42.953 | 24.320 | 36.755 | 20.00 |
| 140 | TIP | H1 | 43.135 | 24.244 | 37.692 | 20.00 |
| 141 | TIP | 2H | 42.929 | 25.263 | 36.591 | 20.00 |
| 142 | TIP | OH2 | 31.728 | 20.196 | 39.928 | 20.00 |
| 143 | TIP | 1H | 31.910 | 20.120 | 40.864 | 20.00 |
| 144 | TIP | H2 | 31.704 | 21.139 | 39.764 | 20.00 |
| 145 | TIP | OH2 | 63.074 | 44.498 | 42.664 | 20.00 |
| 146 | TIP | H1 | 63.256 | 44.422 | 43.600 | 20.00 |
| 147 | TIP | H2 | 63.050 | 45.441 | 42.500 | 20.00 |
| 148 | TIP | OH2 | 57.929 | 49.570 | 22.490 | 20.00 |
| 149 | TIP | 1H | 58.112 | 49.494 | 23.426 | 20.00 |
| 150 | TIP | 2H | 57.906 | 50.513 | 22.325 | 20.00 |
| 151 | TIP | OH2 | 37.261 | 57.330 | 21.133 | 20.00 |
| 152 | TIP | 1H | 37.444 | 57.254 | 22.070 | 20.00 |
| 153 | TIP | 2H | 37.238 | 58.273 | 20.969 | 20.00 |
| 154 | TIP | OH2 | 49.491 | 44.986 | 44.949 | 20.00 |
| 155 | TIP | H1 | 49.673 | 44.910 | 45.886 | 20.00 |
| 156 | TIP | 2H | 49.467 | 45.929 | 44.785 | 20.00 |
| 157 | TIP | OH2 | 58.235 | 25.415 | 34.562 | 20.00 |
| 158 | TIP | 1H | 58.417 | 25.339 | 35.498 | 20.00 |
| 159 | TIP | H2 | 58.211 | 26.358 | 34.398 | 20.00 |
| 160 | TIP | OH2 | 39.581 | 24.265 | 39.192 | 20.00 |
| 161 | TIP | H1 | 39.763 | 24.189 | 40.129 | 20.00 |
| 162 | TIP | 2H | 39.557 | 25.208 | 39.028 | 20.00 |
| 163 | TIP | OH2 | 26.644 | 29.865 | 39.722 | 20.00 |
| 164 | TIP | H1 | 26.827 | 29.789 | 40.658 | 20.00 |
| 165 | TIP | 2H | 26.620 | 30.807 | 39.558 | 20.00 |
| 166 | TIP | OH2 | 46.323 | 43.759 | 44.595 | 20.00 |
| 167 | TIP | H1 | 46.506 | 43.683 | 45.532 | 20.00 |
| 168 | TIP | 2H | 46.300 | 44.701 | 44.431 | 20.00 |

TABLE D

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1 | GLU | N | 21.703 | 70.016 | 37.889 | 44.68 |
| 2 | GLU | CA | 20.473 | 69.206 | 37.782 | 43.88 |
| 3 | GLU | C | 20.313 | 68.401 | 36.438 | 42.17 |
| 4 | GLU | O | 20.963 | 68.696 | 35.441 | 41.34 |
| 5 | GLU | CB | 19.333 | 70.227 | 37.986 | 46.14 |
| 6 | GLU | CG | 17.913 | 69.694 | 38.169 | 53.54 |
| 7 | GLU | CD | 17.723 | 68.479 | 39.088 | 61.73 |
| 8 | GLU | OE1 | 16.693 | 68.363 | 39.735 | 64.31 |
| 9 | GLU | OE2 | 18.581 | 67.618 | 39.170 | 63.66 |
| 10 | MET | N | 19.366 | 67.432 | 36.416 | 39.32 |
| 11 | MET | CA | 18.893 | 66.684 | 35.226 | 34.55 |
| 12 | MET | C | 18.088 | 67.589 | 34.297 | 32.30 |
| 13 | MET | O | 18.046 | 67.444 | 33.093 | 32.26 |
| 14 | MET | CB | 17.971 | 65.501 | 35.627 | 34.25 |
| 15 | MET | CG | 16.763 | 65.884 | 36.525 | 32.80 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 16 | MET | SD | 15.642 | 64.525 | 36.918 | 29.12 |
| 17 | MET | CE | 16.780 | 63.485 | 37.833 | 28.64 |
| 18 | GLU | N | 17.444 | 68.545 | 34.943 | 32.02 |
| 19 | GLU | CA | 16.660 | 69.568 | 34.282 | 35.48 |
| 20 | GLU | C | 17.565 | 70.545 | 33.478 | 34.80 |
| 21 | GLU | O | 17.324 | 70.861 | 32.328 | 34.07 |
| 22 | GLU | CB | 15.843 | 70.226 | 35.377 | 37.66 |
| 23 | GLU | CG | 14.638 | 71.016 | 34.859 | 41.16 |
| 24 | GLU | CD | 13.640 | 71.228 | 36.010 | 44.68 |
| 25 | GLU | OE1 | 14.018 | 71.066 | 37.168 | 43.98 |
| 26 | GLU | OE2 | 12.488 | 71.540 | 35.734 | 47.38 |
| 27 | LYS | N | 18.704 | 70.909 | 34.098 | 35.30 |
| 28 | LYS | CA | 19.749 | 71.591 | 33.318 | 36.11 |
| 29 | LYS | C | 20.297 | 70.750 | 32.115 | 33.14 |
| 30 | LYS | O | 20.337 | 71.206 | 30.978 | 32.17 |
| 31 | LYS | CB | 20.887 | 72.023 | 34.258 | 40.81 |
| 32 | LYS | CG | 20.524 | 73.209 | 35.174 | 47.76 |
| 33 | LYS | CD | 21.621 | 73.495 | 36.226 | 53.62 |
| 34 | LYS | CE | 21.051 | 73.908 | 37.587 | 55.86 |
| 35 | LYS | NZ | 21.885 | 73.368 | 38.677 | 56.39 |
| 36 | GLU | N | 20.701 | 69.500 | 32.404 | 31.78 |
| 37 | GLU | CA | 21.112 | 68.597 | 31.321 | 30.77 |
| 38 | GLU | C | 20.053 | 68.489 | 30.194 | 30.69 |
| 39 | GLU | O | 20.353 | 68.592 | 29.020 | 29.85 |
| 40 | GLU | CB | 21.406 | 67.217 | 31.894 | 32.53 |
| 41 | GLU | CG | 21.384 | 66.134 | 30.814 | 37.49 |
| 42 | GLU | CD | 22.178 | 64.888 | 31.173 | 38.32 |
| 43 | GLU | OE1 | 22.206 | 64.433 | 32.300 | 42.27 |
| 44 | GLU | OE2 | 22.785 | 64.379 | 30.267 | 40.62 |
| 45 | PHE | N | 18.794 | 68.321 | 30.587 | 30.73 |
| 46 | PHE | CA | 17.727 | 68.276 | 29.603 | 32.45 |
| 47 | PHE | C | 17.750 | 69.480 | 28.642 | 34.85 |
| 48 | PHE | O | 17.904 | 69.288 | 27.453 | 33.64 |
| 49 | PHE | CB | 16.381 | 68.223 | 30.320 | 30.35 |
| 50 | PHE | CG | 15.294 | 67.870 | 29.350 | 26.13 |
| 51 | PHE | CD1 | 15.021 | 66.538 | 29.085 | 25.00 |
| 52 | PHE | CD2 | 14.582 | 68.860 | 28.688 | 22.62 |
| 53 | PHE | CE1 | 14.068 | 66.173 | 28.147 | 24.45 |
| 54 | PHE | CE2 | 13.636 | 68.508 | 27.740 | 23.14 |
| 55 | PHE | CZ | 13.391 | 67.166 | 27.459 | 23.15 |
| 56 | GLU | N | 17.650 | 70.698 | 29.207 | 38.88 |
| 57 | GLU | CA | 17.603 | 71.927 | 28.405 | 42.49 |
| 58 | GLU | C | 18.812 | 71.977 | 27.485 | 40.63 |
| 59 | GLU | O | 18.782 | 72.264 | 26.313 | 38.60 |
| 60 | GLU | CB | 17.758 | 73.128 | 29.336 | 48.61 |
| 61 | GLU | CG | 16.586 | 73.249 | 30.307 | 59.10 |
| 62 | GLU | CD | 15.360 | 73.806 | 29.606 | 67.27 |
| 63 | GLU | OE1 | 15.504 | 74.386 | 28.522 | 72.82 |
| 64 | GLU | OE2 | 14.274 | 73.680 | 30.153 | 69.58 |
| 65 | GLN | N | 19.926 | 71.681 | 28.084 | 38.72 |
| 66 | GLN | CA | 21.182 | 71.677 | 27.384 | 39.05 |
| 67 | GLN | C | 21.295 | 70.629 | 26.263 | 36.85 |
| 68 | GLN | O | 21.920 | 70.876 | 25.239 | 37.31 |
| 69 | GLN | CB | 22.160 | 71.459 | 28.488 | 43.39 |
| 70 | GLN | CG | 23.600 | 71.228 | 28.046 | 51.02 |
| 71 | GLN | CD | 24.424 | 70.842 | 29.287 | 57.42 |
| 72 | GLN | OE1 | 25.562 | 70.436 | 29.224 | 62.88 |
| 73 | GLN | NE2 | 23.787 | 70.955 | 30.441 | 59.65 |
| 74 | ILE | N | 20.644 | 69.479 | 26.488 | 33.52 |
| 75 | ILE | CA | 20.568 | 68.460 | 25.480 | 28.82 |
| 76 | ILE | C | 19.654 | 68.921 | 24.295 | 27.31 |
| 77 | ILE | O | 19.969 | 68.894 | 23.110 | 27.61 |
| 78 | ILE | CB | 20.239 | 67.069 | 25.944 | 27.67 |
| 79 | ILE | CG1 | 21.327 | 66.546 | 26.867 | 25.62 |
| 80 | ILE | CG2 | 20.110 | 66.093 | 24.775 | 24.46 |
| 81 | ILE | CD1 | 20.897 | 65.251 | 27.523 | 28.44 |
| 82 | ASP | N | 18.496 | 69.346 | 24.737 | 27.29 |
| 83 | ASP | CA | 17.539 | 69.884 | 23.816 | 28.22 |
| 84 | ASP | C | 18.093 | 71.055 | 22.974 | 29.77 |
| 85 | ASP | O | 17.950 | 71.106 | 21.763 | 29.46 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 86 | ASP | CB | 16.329 | 70.307 | 24.644 | 26.78 |
| 87 | ASP | CG | 15.094 | 69.454 | 24.346 | 25.32 |
| 88 | ASP | OD1 | 15.182 | 68.402 | 23.784 | 25.41 |
| 89 | ASP | OD2 | 14.023 | 69.884 | 24.659 | 25.96 |
| 90 | LYS | N | 18.772 | 71.968 | 23.654 | 34.04 |
| 91 | LYS | CA | 19.284 | 73.163 | 23.027 | 38.17 |
| 92 | LYS | C | 20.201 | 72.782 | 21.859 | 38.28 |
| 93 | LYS | O | 20.020 | 73.189 | 20.713 | 41.49 |
| 94 | LYS | CB | 20.015 | 74.041 | 24.063 | 43.91 |
| 95 | LYS | CG | 19.071 | 74.819 | 25.012 | 52.90 |
| 96 | LYS | CD | 19.799 | 75.829 | 25.904 | 58.71 |
| 97 | LYS | CE | 18.834 | 76.499 | 26.900 | 60.27 |
| 98 | LYS | NZ | 19.587 | 77.453 | 27.717 | 61.96 |
| 99 | SER | N | 21.163 | 71.912 | 22.177 | 35.28 |
| 100 | SER | CA | 22.098 | 71.545 | 21.090 | 33.50 |
| 101 | SER | C | 21.511 | 70.377 | 20.261 | 33.89 |
| 102 | SER | O | 22.246 | 69.714 | 19.554 | 35.89 |
| 103 | SER | CB | 23.342 | 70.937 | 21.788 | 32.34 |
| 104 | SER | OG | 22.978 | 69.903 | 22.780 | 34.77 |
| 105 | GLY | N | 20.201 | 70.097 | 20.417 | 32.04 |
| 106 | GLY | CA | 19.593 | 68.985 | 19.695 | 31.04 |
| 107 | GLY | C | 20.362 | 67.670 | 19.728 | 31.12 |
| 108 | GLY | O | 20.378 | 66.986 | 18.724 | 34.31 |
| 109 | SER | N | 20.977 | 67.282 | 20.858 | 29.06 |
| 110 | SER | CA | 21.777 | 66.031 | 20.725 | 26.56 |
| 111 | SER | C | 21.199 | 64.762 | 21.398 | 25.00 |
| 112 | SER | O | 21.940 | 63.835 | 21.667 | 26.10 |
| 113 | SER | CB | 23.233 | 66.335 | 21.115 | 28.79 |
| 114 | SER | OG | 23.361 | 67.063 | 22.382 | 32.58 |
| 115 | TRP | N | 19.855 | 64.639 | 21.554 | 22.56 |
| 116 | TRP | CA | 19.293 | 63.388 | 22.093 | 19.31 |
| 117 | TRP | C | 19.786 | 62.100 | 21.381 | 18.55 |
| 118 | TRP | O | 20.083 | 61.102 | 22.013 | 20.55 |
| 119 | TRP | CB | 17.751 | 63.440 | 22.080 | 17.74 |
| 120 | TRP | CG | 17.247 | 64.345 | 23.180 | 17.53 |
| 121 | TRP | CD1 | 16.779 | 65.654 | 23.022 | 14.15 |
| 122 | TRP | CD2 | 17.312 | 64.085 | 24.605 | 16.03 |
| 123 | TRP | NE1 | 16.593 | 66.177 | 24.251 | 16.66 |
| 124 | TRP | CE2 | 16.887 | 65.268 | 25.251 | 17.66 |
| 125 | TRP | CE3 | 17.675 | 63.004 | 25.350 | 11.39 |
| 126 | TRP | CZ2 | 16.898 | 65.347 | 26.623 | 18.08 |
| 127 | TRP | CZ3 | 17.676 | 63.059 | 26.745 | 10.09 |
| 128 | TRP | CH2 | 17.279 | 64.235 | 27.383 | 15.36 |
| 129 | ALA | N | 19.871 | 62.143 | 20.056 | 17.72 |
| 130 | ALA | CA | 20.202 | 60.910 | 19.307 | 17.15 |
| 131 | ALA | C | 21.652 | 60.428 | 19.547 | 15.94 |
| 132 | ALA | O | 21.895 | 59.243 | 19.607 | 16.09 |
| 133 | ALA | CB | 20.042 | 61.212 | 17.815 | 15.04 |
| 134 | ALA | N | 22.583 | 61.369 | 19.645 | 15.86 |
| 135 | ALA | CA | 23.953 | 61.087 | 20.057 | 16.56 |
| 136 | ALA | C | 24.062 | 60.639 | 21.520 | 17.32 |
| 137 | ALA | O | 24.632 | 59.609 | 21.781 | 18.09 |
| 138 | ALA | CB | 24.761 | 62.357 | 19.906 | 14.93 |
| 139 | ILE | N | 23.417 | 61.377 | 22.433 | 17.87 |
| 140 | ILE | CA | 23.245 | 60.832 | 23.789 | 19.03 |
| 141 | ILE | C | 22.763 | 59.345 | 23.796 | 18.11 |
| 142 | ILE | O | 23.305 | 58.438 | 24.409 | 18.57 |
| 143 | ILE | CB | 22.216 | 61.696 | 24.560 | 21.02 |
| 144 | ILE | CG1 | 22.665 | 63.159 | 24.647 | 20.66 |
| 145 | ILE | CG2 | 22.012 | 61.186 | 25.992 | 20.04 |
| 146 | ILE | CD1 | 24.097 | 63.283 | 25.120 | 18.89 |
| 147 | TYR | N | 21.674 | 59.132 | 23.082 | 16.17 |
| 148 | TYR | CA | 21.120 | 57.794 | 23.060 | 17.24 |
| 149 | TYR | C | 22.043 | 56.788 | 22.376 | 19.36 |
| 150 | TYR | O | 22.300 | 55.706 | 22.907 | 19.20 |
| 151 | TYR | CB | 19.754 | 57.851 | 22.383 | 15.19 |
| 152 | TYR | CG | 19.119 | 56.501 | 22.280 | 15.92 |
| 153 | TYR | CD1 | 18.853 | 55.782 | 23.434 | 14.65 |
| 154 | TYR | CD2 | 18.790 | 55.967 | 21.035 | 16.31 |
| 155 | TYR | CE1 | 18.267 | 54.556 | 23.417 | 13.96 |
| 156 | TYR | CE2 | 18.159 | 54.733 | 20.979 | 14.00 |
| 157 | TYR | CZ | 17.905 | 54.008 | 22.163 | 14.32 |
| 158 | TYR | OH | 17.345 | 52.759 | 21.944 | 11.00 |
| 159 | GLN | N | 22.561 | 57.160 | 21.194 | 21.20 |
| 160 | GLN | CA | 23.605 | 56.331 | 20.588 | 24.13 |
| 161 | GLN | C | 24.713 | 56.001 | 21.593 | 21.45 |
| 162 | GLN | O | 25.184 | 54.880 | 21.631 | 20.37 |
| 163 | GLN | CB | 24.248 | 56.982 | 19.353 | 34.41 |
| 164 | GLN | CG | 25.321 | 56.035 | 18.773 | 49.84 |
| 165 | GLN | CD | 26.136 | 56.556 | 17.565 | 62.54 |
| 166 | GLN | OE1 | 26.977 | 55.883 | 16.989 | 66.64 |
| 167 | GLN | NE2 | 25.813 | 57.794 | 17.172 | 67.57 |
| 168 | ASP | N | 25.085 | 57.002 | 22.391 | 21.19 |
| 169 | ASP | CA | 26.174 | 56.832 | 23.339 | 23.68 |
| 170 | ASP | C | 25.858 | 55.716 | 24.328 | 23.38 |
| 171 | ASP | O | 26.600 | 54.749 | 24.489 | 24.87 |
| 172 | ASP | CB | 26.451 | 58.140 | 24.079 | 28.19 |
| 173 | ASP | CG | 27.103 | 59.205 | 23.199 | 31.40 |
| 174 | ASP | OD1 | 27.483 | 58.905 | 22.061 | 34.52 |
| 175 | ASP | OD2 | 27.221 | 60.349 | 23.646 | 34.31 |
| 176 | ILE | N | 24.627 | 55.828 | 24.873 | 21.79 |
| 177 | ILE | CA | 24.154 | 54.745 | 25.716 | 20.54 |
| 178 | ILE | C | 24.220 | 53.381 | 24.999 | 20.53 |
| 179 | ILE | O | 24.664 | 52.384 | 25.562 | 19.96 |
| 180 | ILE | CB | 22.722 | 55.057 | 26.188 | 19.90 |
| 181 | ILE | CG1 | 22.746 | 56.121 | 27.295 | 18.92 |
| 182 | ILE | CG2 | 22.002 | 53.809 | 26.709 | 13.13 |
| 183 | ILE | CD1 | 21.427 | 56.904 | 27.348 | 23.15 |
| 184 | ARG | N | 23.711 | 53.345 | 23.741 | 20.41 |
| 185 | ARG | CA | 23.715 | 52.099 | 22.985 | 22.09 |
| 186 | ARG | C | 25.141 | 51.469 | 22.930 | 23.43 |
| 187 | ARG | O | 25.286 | 50.258 | 23.023 | 21.33 |
| 188 | ARG | CB | 23.088 | 52.300 | 21.584 | 24.59 |
| 189 | ARG | CG | 21.532 | 52.302 | 21.526 | 27.48 |
| 190 | ARG | CD | 20.912 | 52.327 | 20.101 | 32.84 |
| 191 | ARG | NE | 19.450 | 52.168 | 20.157 | 43.35 |
| 192 | ARG | CZ | 18.645 | 51.724 | 19.167 | 44.57 |
| 193 | ARG | NH1 | 19.112 | 51.575 | 17.953 | 46.24 |
| 194 | ARG | NH2 | 17.395 | 51.443 | 19.393 | 38.15 |
| 195 | HIS | N | 26.156 | 52.353 | 22.819 | 26.24 |
| 196 | HIS | CA | 27.538 | 51.876 | 22.706 | 29.54 |
| 197 | HIS | C | 28.137 | 51.358 | 24.001 | 30.14 |
| 198 | HIS | O | 28.822 | 50.348 | 24.027 | 31.41 |
| 199 | HIS | CB | 28.432 | 52.975 | 22.150 | 35.11 |
| 200 | HIS | CG | 28.242 | 52.899 | 20.676 | 45.77 |
| 201 | HIS | ND1 | 28.436 | 51.769 | 19.968 | 50.82 |
| 202 | HIS | CD2 | 27.726 | 53.883 | 19.830 | 48.72 |
| 203 | HIS | CE1 | 28.026 | 52.047 | 18.726 | 53.20 |
| 204 | HIS | NE2 | 27.594 | 53.318 | 18.613 | 51.96 |
| 205 | GLU | N | 27.850 | 52.116 | 25.059 | 29.74 |
| 206 | GLU | CA | 28.217 | 51.750 | 26.423 | 26.86 |
| 207 | GLU | C | 27.461 | 50.503 | 26.956 | 25.10 |
| 208 | GLU | O | 27.958 | 49.784 | 27.824 | 25.66 |
| 209 | GLU | CB | 27.885 | 52.987 | 27.258 | 29.73 |
| 210 | GLU | CG | 28.749 | 54.190 | 26.816 | 36.62 |
| 211 | GLU | CD | 28.227 | 55.576 | 27.238 | 42.17 |
| 212 | GLU | OE1 | 27.415 | 55.678 | 28.155 | 43.56 |
| 213 | GLU | OE2 | 28.663 | 56.549 | 26.634 | 42.82 |
| 214 | ALA | N | 26.224 | 50.276 | 26.460 | 22.66 |
| 215 | ALA | CA | 25.424 | 49.170 | 27.037 | 19.17 |
| 216 | ALA | C | 26.192 | 47.808 | 27.064 | 17.78 |
| 217 | ALA | O | 27.027 | 47.515 | 26.229 | 18.91 |
| 218 | ALA | CB | 24.115 | 49.032 | 26.262 | 11.88 |
| 219 | SER | N | 25.866 | 47.002 | 28.076 | 16.59 |
| 220 | SER | CA | 26.466 | 45.670 | 28.261 | 15.02 |
| 221 | SER | C | 26.067 | 44.661 | 27.239 | 15.21 |
| 222 | SER | O | 25.057 | 44.724 | 26.572 | 14.30 |
| 223 | SER | CB | 25.928 | 45.219 | 29.658 | 13.45 |
| 224 | SER | OG | 26.076 | 46.179 | 30.730 | 20.52 |
| 225 | ASP | N | 26.914 | 43.640 | 27.200 | 18.46 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 226 | ASP | CA | 26.637 | 42.515 | 26.346 | 18.64 |
| 227 | ASP | C | 27.079 | 41.224 | 27.054 | 16.04 |
| 228 | ASP | O | 28.233 | 41.010 | 27.385 | 17.44 |
| 229 | ASP | CB | 27.372 | 42.760 | 25.036 | 23.76 |
| 230 | ASP | CG | 26.832 | 41.802 | 23.989 | 28.93 |
| 231 | ASP | OD1 | 25.701 | 41.295 | 24.133 | 29.41 |
| 232 | ASP | OD2 | 27.537 | 41.564 | 23.023 | 33.21 |
| 233 | PHE | N | 26.075 | 40.401 | 27.320 | 14.88 |
| 234 | PHE | CA | 26.312 | 39.115 | 27.938 | 12.14 |
| 235 | PHE | C | 25.696 | 37.991 | 27.085 | 10.36 |
| 236 | PHE | O | 24.778 | 38.182 | 26.301 | 14.29 |
| 237 | PHE | CB | 25.708 | 39.121 | 29.344 | 9.41 |
| 238 | PHE | CG | 26.277 | 40.180 | 30.227 | 10.05 |
| 239 | PHE | CD1 | 27.508 | 39.992 | 30.862 | 12.58 |
| 240 | PHE | CD2 | 25.566 | 41.344 | 30.471 | 6.85 |
| 241 | PHE | CE1 | 28.002 | 40.930 | 31.768 | 9.43 |
| 242 | PHE | CE2 | 26.045 | 42.265 | 31.390 | 5.14 |
| 243 | PHE | CZ | 27.251 | 42.063 | 32.036 | 7.18 |
| 244 | PRO | N | 26.241 | 36.762 | 27.253 | 7.14 |
| 245 | PRO | CA | 25.755 | 35.675 | 26.473 | 6.52 |
| 246 | PRO | C | 24.277 | 35.394 | 26.679 | 9.69 |
| 247 | PRO | O | 23.748 | 35.569 | 27.762 | 12.15 |
| 248 | PRO | CB | 26.607 | 34.503 | 26.897 | 3.58 |
| 249 | PRO | CG | 27.467 | 34.928 | 28.059 | 4.26 |
| 250 | PRO | CD | 27.366 | 36.422 | 28.133 | 3.15 |
| 251 | CYS | N | 23.626 | 34.982 | 25.597 | 12.69 |
| 252 | CYS | CA | 22.261 | 34.498 | 25.720 | 14.65 |
| 253 | CYS | C | 22.172 | 33.102 | 25.112 | 17.19 |
| 254 | CYS | O | 21.342 | 32.783 | 24.256 | 16.47 |
| 255 | CYS | CB | 21.300 | 35.454 | 25.016 | 13.35 |
| 256 | CYS | SG | 21.382 | 37.237 | 25.396 | 15.48 |
| 257 | ARG | N | 23.129 | 32.258 | 25.541 | 18.46 |
| 258 | ARG | CA | 23.174 | 30.921 | 24.986 | 19.34 |
| 259 | ARG | C | 21.865 | 30.155 | 25.153 | 19.02 |
| 260 | ARG | O | 21.360 | 29.596 | 24.201 | 20.59 |
| 261 | ARG | CB | 24.339 | 30.190 | 25.590 | 24.24 |
| 262 | ARG | CG | 25.684 | 30.614 | 24.976 | 34.28 |
| 263 | ARG | CD | 26.506 | 31.531 | 25.846 | 42.36 |
| 264 | ARG | NE | 26.067 | 31.510 | 27.243 | 47.65 |
| 265 | ARG | CZ | 26.832 | 31.598 | 28.306 | 47.20 |
| 266 | ARG | NH1 | 28.125 | 31.583 | 28.117 | 46.56 |
| 267 | ARG | NH2 | 26.311 | 31.717 | 29.498 | 44.55 |
| 268 | VAL | N | 21.246 | 30.117 | 26.340 | 17.94 |
| 269 | VAL | CA | 20.046 | 29.252 | 26.364 | 16.39 |
| 270 | VAL | C | 18.870 | 29.732 | 25.445 | 16.62 |
| 271 | VAL | O | 18.228 | 28.961 | 24.769 | 20.22 |
| 272 | VAL | CB | 19.708 | 28.709 | 27.746 | 14.40 |
| 273 | VAL | CG1 | 18.301 | 29.008 | 28.203 | 13.66 |
| 274 | VAL | CG2 | 20.727 | 29.076 | 28.805 | 11.01 |
| 275 | ALA | N | 18.666 | 31.040 | 25.380 | 16.61 |
| 276 | ALA | CA | 17.795 | 31.721 | 24.438 | 13.61 |
| 277 | ALA | C | 18.036 | 31.352 | 23.035 | 12.12 |
| 278 | ALA | O | 17.160 | 31.403 | 22.187 | 12.55 |
| 279 | ALA | CB | 18.080 | 33.255 | 24.451 | 10.37 |
| 280 | LYS | N | 19.303 | 31.043 | 22.828 | 11.81 |
| 281 | LYS | CA | 19.667 | 30.701 | 21.490 | 12.07 |
| 282 | LYS | C | 19.712 | 29.217 | 21.190 | 13.74 |
| 283 | LYS | O | 19.996 | 28.858 | 20.061 | 17.30 |
| 284 | LYS | CB | 20.968 | 31.391 | 21.154 | 12.40 |
| 285 | LYS | CG | 20.822 | 32.884 | 20.934 | 13.01 |
| 286 | LYS | CD | 19.574 | 33.099 | 20.085 | 17.78 |
| 287 | LYS | CE | 19.498 | 34.385 | 19.324 | 22.14 |
| 288 | LYS | NZ | 18.143 | 34.532 | 18.753 | 25.46 |
| 289 | LEU | N | 19.358 | 28.374 | 22.149 | 13.01 |
| 290 | LEU | CA | 19.324 | 26.958 | 21.822 | 13.50 |
| 291 | LEU | C | 18.159 | 26.587 | 20.853 | 16.14 |
| 292 | LEU | O | 17.057 | 27.133 | 20.907 | 14.24 |
| 293 | LEU | CB | 19.105 | 26.163 | 23.118 | 11.77 |
| 294 | LEU | CG | 20.222 | 26.230 | 24.139 | 8.45 |
| 295 | LEU | CD1 | 21.462 | 25.514 | 23.666 | 2.00 |
| 296 | LEU | CD2 | 19.752 | 25.632 | 25.474 | 5.67 |
| 297 | PRO | N | 18.411 | 25.594 | 19.966 | 18.99 |
| 298 | PRO | CA | 17.420 | 25.201 | 18.974 | 20.81 |
| 299 | PRO | C | 16.038 | 24.817 | 19.486 | 21.23 |
| 300 | PRO | O | 15.028 | 25.094 | 18.853 | 23.12 |
| 301 | PRO | CB | 18.053 | 23.970 | 18.312 | 22.01 |
| 302 | PRO | CG | 19.544 | 24.226 | 18.419 | 20.31 |
| 303 | PRO | CD | 19.693 | 24.935 | 19.760 | 21.95 |
| 304 | LYS | N | 16.032 | 24.245 | 20.703 | 20.72 |
| 305 | LYS | CA | 14.730 | 23.878 | 21.253 | 20.41 |
| 306 | LYS | C | 13.860 | 25.101 | 21.665 | 22.87 |
| 307 | LYS | O | 12.648 | 25.010 | 21.812 | 25.57 |
| 308 | LYS | CB | 14.945 | 22.949 | 22.437 | 19.35 |
| 309 | LYS | CG | 15.755 | 23.579 | 23.575 | 18.95 |
| 310 | LYS | CD | 15.710 | 22.689 | 24.822 | 21.88 |
| 311 | LYS | CE | 16.801 | 23.034 | 25.823 | 28.88 |
| 312 | LYS | NZ | 16.535 | 22.399 | 27.128 | 34.05 |
| 313 | ASN | N | 14.556 | 26.233 | 21.841 | 20.66 |
| 314 | ASN | CA | 13.870 | 27.431 | 22.279 | 18.39 |
| 315 | ASN | C | 13.486 | 28.352 | 21.122 | 18.29 |
| 316 | ASN | O | 12.970 | 29.444 | 21.354 | 16.34 |
| 317 | ASN | CB | 14.739 | 28.164 | 23.298 | 16.54 |
| 318 | ASN | CG | 14.821 | 27.389 | 24.621 | 18.02 |
| 319 | ASN | OD1 | 13.969 | 26.599 | 24.993 | 18.28 |
| 320 | ASN | ND2 | 15.875 | 27.678 | 25.307 | 15.54 |
| 321 | LYS | N | 13.754 | 27.923 | 19.857 | 19.25 |
| 322 | LYS | CA | 13.464 | 28.846 | 18.745 | 20.87 |
| 323 | LYS | C | 12.043 | 29.452 | 18.860 | 18.97 |
| 324 | LYS | O | 11.823 | 30.654 | 18.781 | 18.79 |
| 325 | LYS | CB | 13.693 | 28.184 | 17.377 | 25.70 |
| 326 | LYS | CG | 14.211 | 29.179 | 16.316 | 33.55 |
| 327 | LYS | CD | 14.555 | 28.542 | 14.949 | 41.05 |
| 328 | LYS | CE | 15.066 | 29.579 | 13.926 | 44.78 |
| 329 | LYS | NZ | 14.971 | 29.087 | 12.537 | 44.25 |
| 330 | ASN | N | 11.091 | 28.544 | 19.113 | 15.61 |
| 331 | ASN | CA | 9.708 | 28.969 | 19.134 | 14.25 |
| 332 | ASN | C | 9.210 | 29.512 | 20.495 | 13.55 |
| 333 | ASN | O | 8.012 | 29.666 | 20.711 | 11.55 |
| 334 | ASN | CB | 8.855 | 27.796 | 18.681 | 14.58 |
| 335 | ASN | CG | 8.704 | 26.756 | 19.791 | 18.11 |
| 336 | ASN | OD1 | 9.204 | 26.857 | 20.899 | 19.64 |
| 337 | ASN | ND2 | 7.912 | 25.772 | 19.462 | 22.97 |
| 338 | ARG | N | 10.163 | 29.703 | 21.400 | 12.38 |
| 339 | ARG | CA | 9.830 | 30.375 | 22.640 | 12.69 |
| 340 | ARG | C | 10.255 | 31.846 | 22.554 | 11.47 |
| 341 | ARG | O | 10.045 | 32.608 | 23.480 | 10.92 |
| 342 | ARG | CB | 10.492 | 29.633 | 23.827 | 12.58 |
| 343 | ARG | CG | 9.840 | 28.263 | 24.143 | 7.25 |
| 344 | ARG | CD | 10.452 | 27.622 | 25.391 | 6.96 |
| 345 | ARG | NE | 9.754 | 26.378 | 25.717 | 10.56 |
| 346 | ARG | CZ | 9.591 | 25.939 | 26.964 | 12.63 |
| 347 | ARG | NH1 | 10.049 | 26.621 | 27.978 | 13.70 |
| 348 | ARG | NH2 | 8.970 | 24.830 | 27.205 | 13.18 |
| 349 | ASN | N | 10.877 | 32.231 | 21.416 | 11.45 |
| 350 | ASN | CA | 11.276 | 33.639 | 21.283 | 10.48 |
| 351 | ASN | C | 10.479 | 34.359 | 20.189 | 10.61 |
| 352 | ASN | O | 10.425 | 33.924 | 19.054 | 12.34 |
| 353 | ASN | CB | 12.749 | 33.695 | 20.923 | 9.53 |
| 354 | ASN | CG | 13.512 | 33.223 | 22.114 | 13.73 |
| 355 | ASN | OD1 | 13.255 | 33.613 | 23.245 | 15.94 |
| 356 | ASN | ND2 | 14.468 | 32.378 | 21.802 | 13.53 |
| 357 | ARG | N | 9.906 | 35.498 | 20.587 | 9.18 |
| 358 | ARG | CA | 9.132 | 36.240 | 19.605 | 7.77 |
| 359 | ARG | C | 9.980 | 36.947 | 18.540 | 6.85 |
| 360 | ARG | O | 9.628 | 37.017 | 17.379 | 6.50 |
| 361 | ARG | CB | 8.232 | 37.214 | 20.383 | 7.45 |
| 362 | ARG | CG | 7.408 | 38.017 | 19.428 | 5.78 |
| 363 | ARG | CD | 6.595 | 39.001 | 20.150 | 7.80 |
| 364 | ARG | NE | 5.520 | 38.392 | 20.894 | 7.84 |
| 365 | ARG | CZ | 4.356 | 38.086 | 20.319 | 6.71 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 366 | ARG | NH1 | 4.093 | 38.311 | 19.075 | 3.66 |
| 367 | ARG | NH2 | 3.466 | 37.541 | 21.012 | 3.47 |
| 368 | TYR | N | 11.110 | 37.522 | 18.982 | 8.09 |
| 369 | TYR | CA | 11.994 | 38.167 | 18.021 | 7.20 |
| 370 | TYR | C | 13.398 | 37.575 | 18.097 | 10.87 |
| 371 | TYR | O | 13.994 | 37.455 | 19.164 | 11.24 |
| 372 | TYR | CB | 12.115 | 39.628 | 18.386 | 5.76 |
| 373 | TYR | CG | 10.820 | 40.320 | 18.388 | 7.25 |
| 374 | TYR | CD1 | 10.123 | 40.388 | 17.212 | 10.32 |
| 375 | TYR | CD2 | 10.304 | 40.862 | 19.541 | 3.38 |
| 376 | TYR | CE1 | 8.881 | 40.994 | 17.151 | 12.06 |
| 377 | TYR | CE2 | 9.097 | 41.526 | 19.474 | 8.53 |
| 378 | TYR | CZ | 8.354 | 41.606 | 18.291 | 12.52 |
| 379 | TYR | OH | 7.116 | 42.223 | 18.267 | 12.22 |
| 380 | ARG | N | 13.917 | 37.304 | 16.886 | 12.71 |
| 381 | ARG | CA | 15.268 | 36.791 | 16.740 | 14.19 |
| 382 | ARG | C | 16.325 | 37.589 | 17.518 | 15.21 |
| 383 | ARG | O | 17.239 | 36.987 | 18.070 | 17.69 |
| 384 | ARG | CB | 15.618 | 36.796 | 15.242 | 16.20 |
| 385 | ARG | CG | 16.894 | 36.009 | 14.934 | 20.90 |
| 386 | ARG | CD | 17.513 | 36.381 | 13.600 | 24.13 |
| 387 | ARG | NE | 18.032 | 37.734 | 13.679 | 31.45 |
| 388 | ARG | CZ | 18.180 | 38.440 | 12.559 | 35.35 |
| 389 | ARG | NH1 | 18.031 | 37.849 | 11.400 | 34.27 |
| 390 | ARG | NH2 | 18.426 | 39.722 | 12.626 | 36.59 |
| 391 | ASP | N | 16.129 | 38.922 | 17.483 | 15.52 |
| 392 | ASP | CA | 17.068 | 39.945 | 17.947 | 14.40 |
| 393 | ASP | C | 16.939 | 40.307 | 19.430 | 12.23 |
| 394 | ASP | O | 17.780 | 41.001 | 19.966 | 11.34 |
| 395 | ASP | CB | 16.825 | 41.235 | 17.144 | 19.70 |
| 396 | ASP | CG | 17.502 | 41.193 | 15.756 | 24.49 |
| 397 | ASP | OD1 | 18.205 | 40.237 | 15.418 | 27.69 |
| 398 | ASP | OD2 | 17.350 | 42.135 | 14.999 | 25.18 |
| 399 | VAL | N | 15.836 | 39.831 | 20.061 | 13.80 |
| 400 | VAL | CA | 15.628 | 40.144 | 21.478 | 13.65 |
| 401 | VAL | C | 15.556 | 38.911 | 22.396 | 13.05 |
| 402 | VAL | O | 14.676 | 38.066 | 22.356 | 10.76 |
| 403 | VAL | CB | 14.512 | 41.187 | 21.704 | 14.37 |
| 404 | VAL | CG1 | 13.751 | 41.144 | 23.012 | 10.38 |
| 405 | VAL | CG2 | 13.935 | 41.930 | 20.498 | 12.19 |
| 406 | SER | N | 16.585 | 38.852 | 23.257 | 14.06 |
| 407 | SER | CA | 16.846 | 37.705 | 24.127 | 9.73 |
| 408 | SER | C | 17.249 | 38.159 | 25.487 | 8.28 |
| 409 | SER | O | 17.770 | 39.230 | 25.677 | 5.98 |
| 410 | SER | CB | 17.993 | 36.869 | 23.463 | 10.62 |
| 411 | SER | OG | 17.811 | 36.472 | 22.071 | 11.36 |
| 412 | PRO | N | 16.972 | 37.263 | 26.461 | 7.35 |
| 413 | PRO | CA | 17.450 | 37.352 | 27.792 | 8.44 |
| 414 | PRO | C | 18.908 | 36.905 | 27.921 | 11.00 |
| 415 | PRO | O | 19.259 | 35.821 | 27.503 | 13.36 |
| 416 | PRO | CB | 16.474 | 36.351 | 28.513 | 7.21 |
| 417 | PRO | CG | 16.182 | 35.277 | 27.531 | 11.53 |
| 418 | PRO | CD | 16.259 | 36.046 | 26.224 | 9.12 |
| 419 | PHE | N | 19.753 | 37.763 | 28.507 | 10.36 |
| 420 | PHE | CA | 21.035 | 37.197 | 28.928 | 8.56 |
| 421 | PHE | C | 20.847 | 35.981 | 29.853 | 10.75 |
| 422 | PHE | O | 19.894 | 35.899 | 30.634 | 12.42 |
| 423 | PHE | CB | 21.829 | 38.225 | 29.725 | 6.92 |
| 424 | PHE | CG | 21.969 | 39.566 | 29.090 | 4.90 |
| 425 | PHE | CD1 | 22.372 | 39.651 | 27.773 | 2.00 |
| 426 | PHE | CD2 | 21.749 | 40.718 | 29.841 | 3.60 |
| 427 | PHE | CE1 | 22.581 | 40.893 | 27.214 | 3.30 |
| 428 | PHE | CE2 | 21.964 | 41.964 | 29.276 | 2.19 |
| 429 | PHE | CZ | 22.390 | 42.047 | 27.962 | 2.00 |
| 430 | ASP | N | 21.804 | 35.056 | 29.764 | 11.92 |
| 431 | ASP | CA | 21.710 | 33.883 | 30.620 | 12.44 |
| 432 | ASP | C | 21.749 | 34.248 | 32.129 | 10.45 |
| 433 | ASP | O | 21.055 | 33.664 | 32.955 | 14.63 |
| 434 | ASP | CB | 22.852 | 32.934 | 30.260 | 13.15 |
| 435 | ASP | CG | 22.759 | 32.466 | 28.829 | 17.42 |
| 436 | ASP | OD1 | 21.740 | 31.969 | 28.404 | 17.02 |
| 437 | ASP | OD2 | 23.745 | 32.592 | 28.162 | 18.42 |
| 438 | HIS | N | 22.577 | 35.242 | 32.485 | 6.99 |
| 439 | HIS | CA | 22.781 | 35.415 | 33.933 | 7.65 |
| 440 | HIS | C | 21.522 | 35.922 | 34.692 | 11.47 |
| 441 | HIS | O | 21.329 | 35.728 | 35.891 | 12.59 |
| 442 | HIS | CB | 23.994 | 36.314 | 34.157 | 4.46 |
| 443 | HIS | CG | 23.699 | 37.794 | 34.137 | 5.10 |
| 444 | HIS | ND1 | 23.259 | 38.489 | 35.219 | 8.84 |
| 445 | HIS | CD2 | 23.892 | 38.696 | 33.091 | 5.96 |
| 446 | HIS | CE1 | 23.198 | 39.775 | 34.852 | 5.13 |
| 447 | HIS | NE2 | 23.568 | 39.921 | 33.577 | 7.85 |
| 448 | SER | N | 20.686 | 36.648 | 33.929 | 11.96 |
| 449 | SER | CA | 19.591 | 37.347 | 34.601 | 10.61 |
| 450 | SER | C | 18.221 | 36.722 | 34.179 | 11.50 |
| 451 | SER | O | 17.161 | 37.166 | 34.622 | 13.21 |
| 452 | SER | CB | 19.578 | 38.795 | 34.005 | 6.54 |
| 453 | SER | OG | 19.426 | 38.747 | 32.546 | 11.00 |
| 454 | ARG | N | 18.259 | 35.718 | 33.274 | 10.94 |
| 455 | ARG | CA | 16.999 | 35.170 | 32.768 | 12.70 |
| 456 | ARG | C | 16.139 | 34.506 | 33.898 | 14.39 |
| 457 | ARG | O | 16.647 | 33.926 | 34.844 | 12.31 |
| 458 | ARG | CB | 17.292 | 34.168 | 31.637 | 12.58 |
| 459 | ARG | CG | 17.894 | 32.846 | 32.135 | 14.19 |
| 460 | ARG | CD | 18.073 | 31.815 | 31.023 | 15.27 |
| 461 | ARG | NE | 18.531 | 30.520 | 31.560 | 15.37 |
| 462 | ARG | CZ | 17.720 | 29.463 | 31.683 | 15.74 |
| 463 | ARG | NH1 | 16.468 | 29.566 | 31.330 | 13.61 |
| 464 | ARG | NH2 | 18.150 | 28.339 | 32.167 | 13.65 |
| 465 | ILE | N | 14.811 | 34.584 | 33.745 | 16.19 |
| 466 | ILE | CA | 13.964 | 33.837 | 34.671 | 13.97 |
| 467 | ILE | C | 13.863 | 32.356 | 34.253 | 13.70 |
| 468 | ILE | O | 13.599 | 32.046 | 33.119 | 15.22 |
| 469 | ILE | CB | 12.583 | 34.496 | 34.725 | 14.29 |
| 470 | ILE | CG1 | 12.697 | 35.981 | 35.109 | 14.68 |
| 471 | ILE | CG2 | 11.695 | 33.761 | 35.745 | 14.23 |
| 472 | ILE | CD1 | 12.768 | 36.193 | 36.625 | 11.53 |
| 473 | LYS | N | 14.079 | 31.452 | 35.184 | 15.41 |
| 474 | LYS | CA | 13.901 | 30.039 | 34.865 | 16.79 |
| 475 | LYS | C | 12.555 | 29.531 | 35.391 | 17.35 |
| 476 | LYS | O | 12.222 | 29.772 | 36.539 | 19.31 |
| 477 | LYS | CB | 14.952 | 29.273 | 35.664 | 17.97 |
| 478 | LYS | CG | 16.348 | 29.641 | 35.224 | 20.00 |
| 479 | LYS | CD | 17.342 | 28.756 | 35.923 | 21.07 |
| 480 | LYS | CE | 18.757 | 29.183 | 35.586 | 25.86 |
| 481 | LYS | NZ | 19.661 | 28.132 | 36.065 | 29.41 |
| 482 | LEU | N | 11.827 | 28.807 | 34.546 | 17.14 |
| 483 | LEU | CA | 10.659 | 28.096 | 35.026 | 16.17 |
| 484 | LEU | C | 11.101 | 26.982 | 35.997 | 18.46 |
| 485 | LEU | O | 12.139 | 26.361 | 35.815 | 16.31 |
| 486 | LEU | CB | 9.925 | 27.512 | 33.820 | 16.73 |
| 487 | LEU | CG | 9.241 | 28.474 | 32.838 | 16.01 |
| 488 | LEU | CD1 | 9.233 | 28.140 | 31.340 | 18.22 |
| 489 | LEU | CD2 | 9.174 | 29.942 | 33.208 | 19.99 |
| 490 | HIS | N | 10.307 | 26.720 | 37.031 | 20.86 |
| 491 | HIS | CA | 10.504 | 25.539 | 37.856 | 22.12 |
| 492 | HIS | C | 9.967 | 24.256 | 37.160 | 26.50 |
| 493 | HIS | O | 9.214 | 23.488 | 37.729 | 29.06 |
| 494 | HIS | CB | 9.795 | 25.710 | 39.208 | 20.80 |
| 495 | HIS | CG | 10.244 | 26.940 | 39.961 | 18.49 |
| 496 | HIS | ND1 | 9.650 | 27.355 | 41.096 | 18.74 |
| 497 | HIS | CD2 | 11.279 | 27.836 | 39.657 | 17.16 |
| 498 | HIS | CE1 | 10.306 | 28.462 | 41.471 | 16.79 |
| 499 | HIS | NE2 | 11.293 | 28.776 | 40.626 | 15.80 |
| 500 | GLN | N | 10.416 | 24.000 | 35.928 | 31.86 |
| 501 | GLN | CA | 9.989 | 22.769 | 35.260 | 36.18 |
| 502 | GLN | C | 11.226 | 22.046 | 34.724 | 37.67 |
| 503 | GLN | O | 12.153 | 22.676 | 34.251 | 38.03 |
| 504 | GLN | CB | 8.969 | 23.068 | 34.141 | 38.37 |
| 505 | GLN | CG | 9.413 | 24.118 | 33.110 | 45.32 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 506 | GLN | CD | 8.538 | 24.115 | 31.844 | 51.67 |
| 507 | GLN | OE1 | 8.913 | 23.628 | 30.781 | 53.74 |
| 508 | GLN | NE2 | 7.325 | 24.611 | 32.016 | 51.04 |
| 509 | GLU | N | 11.195 | 20.711 | 34.825 | 40.34 |
| 510 | GLU | CA | 12.374 | 19.917 | 34.434 | 41.41 |
| 511 | GLU | C | 12.545 | 19.806 | 32.896 | 40.03 |
| 512 | GLU | O | 13.654 | 19.763 | 32.381 | 38.15 |
| 513 | GLU | CB | 12.223 | 18.535 | 35.054 | 45.95 |
| 514 | GLU | CG | 12.189 | 18.568 | 36.590 | 52.82 |
| 515 | GLU | CD | 11.488 | 17.315 | 37.138 | 60.20 |
| 516 | GLU | OE1 | 11.234 | 16.382 | 36.370 | 63.99 |
| 517 | GLU | OE2 | 11.181 | 17.291 | 38.322 | 61.75 |
| 518 | ASP | N | 11.382 | 19.779 | 32.207 | 39.83 |
| 519 | ASP | CA | 11.403 | 19.725 | 30.735 | 37.84 |
| 520 | ASP | C | 12.238 | 20.863 | 30.075 | 31.75 |
| 521 | ASP | O | 13.278 | 20.692 | 29.439 | 32.35 |
| 522 | ASP | CB | 9.941 | 19.774 | 30.258 | 45.12 |
| 523 | ASP | CG | 9.937 | 19.953 | 28.726 | 53.29 |
| 524 | ASP | OD1 | 10.589 | 19.165 | 28.040 | 57.18 |
| 525 | ASP | OD2 | 9.363 | 20.939 | 28.246 | 56.58 |
| 526 | ASN | N | 11.695 | 22.072 | 30.254 | 26.65 |
| 527 | ASN | CA | 12.390 | 23.201 | 29.678 | 21.86 |
| 528 | ASN | C | 12.099 | 24.449 | 30.528 | 20.05 |
| 529 | ASN | O | 11.018 | 25.025 | 30.494 | 21.82 |
| 530 | ASN | CB | 11.951 | 23.347 | 28.213 | 18.23 |
| 531 | ASN | CG | 12.778 | 24.425 | 27.560 | 15.37 |
| 532 | ASN | OD1 | 13.328 | 25.282 | 28.216 | 19.18 |
| 533 | ASN | ND2 | 12.889 | 24.375 | 26.266 | 5.53 |
| 534 | ASP | N | 13.138 | 24.890 | 31.233 | 17.24 |
| 535 | ASP | CA | 12.969 | 26.055 | 32.084 | 15.50 |
| 536 | ASP | C | 12.983 | 27.419 | 31.339 | 13.37 |
| 537 | ASP | O | 12.998 | 28.461 | 31.970 | 16.65 |
| 538 | ASP | CB | 14.049 | 26.012 | 33.173 | 19.65 |
| 539 | ASP | CG | 15.459 | 26.514 | 32.718 | 24.75 |
| 540 | ASP | OD1 | 15.644 | 27.054 | 31.628 | 25.78 |
| 541 | ASP | OD2 | 16.425 | 26.355 | 33.444 | 27.00 |
| 542 | TYR | N | 13.057 | 27.417 | 29.999 | 11.69 |
| 543 | TYR | CA | 13.282 | 28.673 | 29.271 | 9.17 |
| 544 | TYR | C | 11.981 | 29.477 | 29.069 | 8.95 |
| 545 | TYR | O | 10.979 | 28.944 | 28.618 | 10.59 |
| 546 | TYR | CB | 14.044 | 28.417 | 27.937 | 9.39 |
| 547 | TYR | CG | 14.285 | 29.690 | 27.182 | 7.68 |
| 548 | TYR | CD1 | 15.282 | 30.541 | 27.605 | 5.47 |
| 549 | TYR | CD2 | 13.461 | 30.068 | 26.121 | 6.70 |
| 550 | TYR | CE1 | 15.383 | 31.821 | 27.085 | 6.80 |
| 551 | TYR | CE2 | 13.539 | 31.330 | 25.557 | 5.20 |
| 552 | TYR | CZ | 14.498 | 32.243 | 26.073 | 8.53 |
| 553 | TYR | OH | 14.596 | 33.555 | 25.625 | 8.14 |
| 554 | ILE | N | 12.050 | 30.770 | 29.393 | 8.87 |
| 555 | ILE | CA | 11.093 | 31.830 | 29.070 | 10.50 |
| 556 | ILE | C | 11.899 | 33.107 | 28.707 | 10.84 |
| 557 | ILE | O | 12.881 | 33.469 | 29.342 | 11.65 |
| 558 | ILE | CB | 10.060 | 32.108 | 30.209 | 11.32 |
| 559 | ILE | CG1 | 9.000 | 33.151 | 29.783 | 10.88 |
| 560 | ILE | CG2 | 10.719 | 32.543 | 31.525 | 10.89 |
| 561 | ILE | CD1 | 7.704 | 33.146 | 30.591 | 8.77 |
| 562 | ASN | N | 11.470 | 33.812 | 27.665 | 8.42 |
| 563 | ASN | CA | 12.083 | 35.065 | 27.316 | 8.86 |
| 564 | ASN | C | 11.668 | 36.151 | 28.345 | 8.99 |
| 565 | ASN | O | 10.725 | 36.902 | 28.126 | 9.36 |
| 566 | ASN | CB | 11.679 | 35.428 | 25.878 | 7.09 |
| 567 | ASN | CG | 12.506 | 36.595 | 25.383 | 7.69 |
| 568 | ASN | OD1 | 12.723 | 37.602 | 26.057 | 9.31 |
| 569 | ASN | ND2 | 12.964 | 36.408 | 24.164 | 4.12 |
| 570 | ALA | N | 12.428 | 36.178 | 29.455 | 7.57 |
| 571 | ALA | CA | 12.160 | 37.033 | 30.608 | 8.59 |
| 572 | ALA | C | 13.456 | 37.271 | 31.452 | 9.69 |
| 573 | ALA | O | 14.277 | 36.377 | 31.571 | 9.38 |
| 574 | ALA | CB | 11.128 | 36.326 | 31.528 | 8.05 |
| 575 | SER | N | 13.603 | 38.481 | 32.012 | 8.59 |
| 576 | SER | CA | 14.773 | 38.835 | 32.876 | 9.14 |
| 577 | SER | C | 14.389 | 39.499 | 34.110 | 10.33 |
| 578 | SER | O | 13.476 | 40.308 | 34.125 | 12.06 |
| 579 | SER | CB | 15.574 | 39.938 | 32.054 | 7.95 |
| 580 | SER | OG | 15.690 | 39.635 | 30.644 | 8.20 |
| 581 | LEU | N | 15.179 | 39.173 | 35.149 | 9.68 |
| 582 | LEU | CA | 15.021 | 39.922 | 36.386 | 10.62 |
| 583 | LEU | C | 15.923 | 41.152 | 36.334 | 9.94 |
| 584 | LEU | O | 17.141 | 41.081 | 36.377 | 10.46 |
| 585 | LEU | CB | 15.343 | 38.989 | 37.549 | 10.83 |
| 586 | LEU | CG | 15.005 | 39.449 | 38.990 | 13.92 |
| 587 | LEU | CD1 | 13.816 | 40.385 | 39.226 | 12.88 |
| 588 | LEU | CD2 | 16.114 | 39.506 | 40.027 | 12.99 |
| 589 | ILE | N | 15.258 | 42.299 | 36.213 | 10.44 |
| 590 | ILE | CA | 15.971 | 43.551 | 36.356 | 10.17 |
| 591 | ILE | C | 16.048 | 43.883 | 37.879 | 13.89 |
| 592 | ILE | O | 15.070 | 44.274 | 38.505 | 15.18 |
| 593 | ILE | GB | 15.228 | 44.651 | 35.596 | 8.61 |
| 594 | ILE | CG1 | 15.428 | 44.579 | 34.073 | 6.44 |
| 595 | ILE | CG2 | 15.734 | 46.015 | 36.078 | 10.00 |
| 596 | ILE | CD1 | 15.155 | 43.216 | 33.468 | 5.57 |
| 597 | LYS | N | 17.239 | 43.734 | 38.432 | 15.52 |
| 598 | LYS | CA | 17.380 | 43.928 | 39.856 | 15.20 |
| 599 | LYS | C | 18.176 | 45.182 | 40.221 | 15.99 |
| 600 | LYS | O | 19.398 | 45.244 | 40.138 | 15.65 |
| 601 | LYS | CB | 18.123 | 42.725 | 40.331 | 18.92 |
| 602 | LYS | CG | 18.087 | 42.602 | 41.836 | 24.92 |
| 603 | LYS | CD | 18.365 | 41.191 | 42.268 | 32.15 |
| 604 | LYS | CE | 17.900 | 40.926 | 43.679 | 39.12 |
| 605 | LYS | NZ | 18.225 | 39.537 | 44.018 | 44.57 |
| 606 | MET | N | 17.397 | 46.178 | 40.655 | 15.97 |
| 607 | MET | CA | 17.988 | 47.464 | 40.974 | 16.08 |
| 608 | MET | C | 18.400 | 47.544 | 42.462 | 17.49 |
| 609 | MET | O | 17.579 | 47.794 | 43.332 | 17.67 |
| 610 | MET | CB | 16.968 | 48.533 | 40.607 | 14.83 |
| 611 | MET | CG | 16.626 | 48.573 | 39.119 | 13.99 |
| 612 | MET | SD | 18.121 | 48.583 | 38.091 | 17.00 |
| 613 | MET | CE | 18.404 | 50.363 | 38.012 | 4.51 |
| 614 | GLU | N | 19.696 | 47.328 | 42.741 | 19.80 |
| 615 | GLU | CA | 20.201 | 47.101 | 44.094 | 21.74 |
| 616 | GLU | C | 20.060 | 48.353 | 44.993 | 21.70 |
| 617 | GLU | O | 19.551 | 48.311 | 46.106 | 21.22 |
| 618 | GLU | CB | 21.652 | 46.627 | 44.007 | 24.29 |
| 619 | GLU | CG | 22.273 | 46.291 | 45.379 | 31.56 |
| 620 | GLU | CD | 23.780 | 45.945 | 45.252 | 36.04 |
| 621 | GLU | OE1 | 24.575 | 46.709 | 44.678 | 39.83 |
| 622 | GLU | OE2 | 24.167 | 44.887 | 45.726 | 40.03 |
| 623 | GLU | N | 20.500 | 49.491 | 44.427 | 22.15 |
| 624 | GLU | CA | 20.486 | 50.733 | 45.200 | 22.50 |
| 625 | GLU | C | 19.056 | 51.237 | 45.483 | 22.61 |
| 626 | GLU | O | 18.690 | 51.633 | 46.586 | 23.83 |
| 627 | GLU | CB | 21.321 | 51.751 | 44.448 | 23.01 |
| 628 | GLU | CG | 21.465 | 53.095 | 45.163 | 29.10 |
| 629 | GLU | CD | 21.921 | 54.170 | 44.157 | 35.50 |
| 630 | GLU | OE1 | 21.836 | 53.969 | 42.942 | 36.25 |
| 631 | GLU | OE2 | 22.346 | 55.218 | 44.595 | 38.56 |
| 632 | ALA | N | 18.218 | 51.181 | 44.432 | 23.89 |
| 633 | ALA | CA | 16.788 | 51.506 | 44.582 | 21.87 |
| 634 | ALA | C | 16.051 | 50.494 | 45.447 | 20.77 |
| 635 | ALA | O | 15.078 | 50.857 | 46.077 | 21.59 |
| 636 | ALA | CB | 16.112 | 51.586 | 43.207 | 19.61 |
| 637 | GLN | N | 16.555 | 49.262 | 45.482 | 22.52 |
| 638 | GLN | CA | 15.859 | 48.190 | 46.212 | 23.75 |
| 639 | GLN | C | 14.447 | 47.831 | 45.617 | 21.92 |
| 640 | GLN | O | 13.548 | 47.415 | 46.324 | 23.13 |
| 641 | GLN | CB | 15.781 | 48.573 | 47.700 | 28.00 |
| 642 | GLN | CG | 17.090 | 48.375 | 48.482 | 37.73 |
| 643 | GLN | CD | 17.102 | 46.993 | 49.161 | 45.98 |
| 644 | GLN | OE1 | 16.962 | 46.865 | 50.359 | 49.70 |
| 645 | GLN | NE2 | 17.222 | 45.958 | 48.347 | 46.64 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No  | Amino acid |     | X      | Y      | Z      | B     |
|-----|-----|------|--------|--------|--------|-------|
| 646 | ARG | N    | 14.293 | 47.996 | 44.288 | 19.87 |
| 647 | ARG | CA   | 13.167 | 47.433 | 43.520 | 15.56 |
| 648 | ARG | C    | 13.671 | 46.530 | 42.369 | 15.93 |
| 649 | ARG | O    | 14.589 | 46.892 | 41.649 | 19.66 |
| 650 | ARG | CB   | 12.378 | 48.566 | 42.894 | 12.31 |
| 651 | ARG | CG   | 11.026 | 48.114 | 42.359 | 8.59  |
| 652 | ARG | CD   | 9.975  | 49.222 | 42.284 | 8.75  |
| 653 | ARG | NE   | 9.454  | 49.581 | 43.583 | 9.44  |
| 654 | ARG | CZ   | 8.781  | 50.712 | 43.804 | 13.29 |
| 655 | ARG | NH1  | 8.507  | 51.573 | 42.868 | 14.59 |
| 656 | ARG | NH2  | 8.376  | 50.970 | 44.997 | 14.52 |
| 657 | SER | N    | 13.018 | 45.374 | 42.191 | 13.03 |
| 658 | SER | CA   | 13.174 | 44.563 | 40.969 | 11.10 |
| 659 | SER | C    | 11.905 | 44.484 | 40.133 | 9.85  |
| 660 | SER | O    | 10.797 | 44.430 | 40.625 | 7.17  |
| 661 | SER | CB   | 13.491 | 43.098 | 41.352 | 9.97  |
| 662 | SER | OG   | 14.257 | 42.832 | 42.565 | 16.33 |
| 663 | TYR | N    | 12.149 | 44.304 | 38.838 | 10.99 |
| 664 | TYR | CA   | 11.059 | 43.986 | 37.924 | 11.25 |
| 665 | TYR | C    | 11.428 | 42.738 | 37.134 | 11.69 |
| 666 | TYR | O    | 12.600 | 42.426 | 36.947 | 12.93 |
| 667 | TYR | CB   | 10.855 | 45.145 | 36.944 | 11.85 |
| 668 | TYR | CG   | 11.048 | 46.504 | 37.543 | 11.61 |
| 669 | TYR | CD1  | 12.330 | 46.990 | 37.697 | 13.15 |
| 670 | TYR | CD2  | 9.974  | 47.284 | 37.928 | 10.09 |
| 671 | TYR | CE1  | 12.574 | 48.223 | 38.239 | 12.30 |
| 672 | TYR | CE2  | 10.189 | 48.561 | 38.453 | 11.52 |
| 673 | TYR | CZ   | 11.477 | 49.041 | 38.615 | 11.57 |
| 674 | TYR | OH   | 11.518 | 50.318 | 39.128 | 16.85 |
| 675 | ILE | N    | 10.411 | 42.065 | 36.626 | 10.13 |
| 676 | ILE | CA   | 10.683 | 41.103 | 35.561 | 10.15 |
| 677 | ILE | C    | 10.210 | 41.646 | 34.208 | 11.23 |
| 678 | ILE | O    | 9.017  | 41.882 | 34.001 | 14.10 |
| 679 | ILE | CB   | 9.984  | 39.783 | 35.918 | 8.65  |
| 680 | ILE | CG1  | 10.575 | 39.226 | 37.221 | 5.54  |
| 681 | ILE | CG2  | 10.117 | 38.788 | 34.758 | 4.72  |
| 682 | ILE | CD1  | 9.885  | 37.981 | 37.750 | 3.41  |
| 683 | LEU | N    | 11.171 | 41.837 | 33.292 | 8.83  |
| 684 | LEU | CA   | 10.757 | 42.279 | 31.952 | 8.27  |
| 685 | LEU | C    | 10.642 | 41.089 | 31.042 | 9.63  |
| 686 | LEU | O    | 11.563 | 40.274 | 30.925 | 10.20 |
| 687 | LEU | CB   | 11.754 | 43.266 | 31.361 | 6.64  |
| 688 | LEU | CG   | 11.554 | 44.667 | 31.933 | 5.33  |
| 689 | LEU | CD1  | 12.441 | 45.790 | 31.363 | 7.20  |
| 690 | LEU | CD2  | 11.164 | 44.814 | 33.411 | 7.37  |
| 691 | THR | N    | 9.476  | 41.020 | 30.372 | 9.19  |
| 692 | THR | CA   | 9.353  | 39.941 | 29.424 | 7.94  |
| 693 | THR | C    | 8.748  | 40.395 | 28.068 | 7.09  |
| 694 | THR | O    | 8.236  | 41.487 | 27.941 | 6.68  |
| 695 | THR | CB   | 8.633  | 38.725 | 30.140 | 7.51  |
| 696 | THR | OG1  | 8.460  | 37.446 | 29.475 | 10.84 |
| 697 | THR | CG2  | 7.202  | 39.098 | 30.532 | 4.90  |
| 698 | GLN | N    | 8.895  | 39.560 | 27.025 | 5.28  |
| 699 | GLN | CA   | 8.176  | 39.853 | 25.785 | 4.05  |
| 700 | GLN | C    | 6.657  | 39.538 | 25.856 | 8.34  |
| 701 | GLN | O    | 6.182  | 38.810 | 26.707 | 9.07  |
| 702 | GLN | CB   | 8.778  | 38.943 | 24.733 | 4.35  |
| 703 | GLN | CG   | 8.435  | 37.461 | 24.941 | 3.62  |
| 704 | GLN | CD   | 9.043  | 36.521 | 23.968 | 7.57  |
| 705 | GLN | OE1  | 8.588  | 35.441 | 23.735 | 13.92 |
| 706 | GLN | NE2  | 10.151 | 36.927 | 23.436 | 7.22  |
| 707 | GLY | N    | 5.886  | 40.050 | 24.882 | 8.61  |
| 708 | GLY | CA   | 4.495  | 39.635 | 24.802 | 6.03  |
| 709 | GLY | C    | 4.380  | 38.143 | 24.529 | 6.11  |
| 710 | GLY | O    | 4.839  | 37.652 | 23.504 | 6.83  |
| 711 | PRO | N    | 3.737  | 37.417 | 25.464 | 7.87  |
| 712 | PRO | CA   | 3.639  | 35.977 | 25.333 | 7.10  |
| 713 | PRO | C    | 3.212  | 35.542 | 23.927 | 8.95  |
| 714 | PRO | O    | 2.432  | 36.210 | 23.249 | 9.13  |
| 715 | PRO | CB   | 2.617  | 35.533 | 26.387 | 7.90  |
| 716 | PRO | CG   | 2.452  | 36.716 | 27.320 | 8.31  |
| 717 | PRO | CD   | 3.076  | 37.939 | 26.655 | 8.22  |
| 718 | LEU | N    | 3.826  | 34.451 | 23.462 | 11.50 |
| 719 | LEU | CA   | 3.453  | 33.772 | 22.222 | 12.63 |
| 720 | LEU | C    | 2.284  | 32.817 | 22.537 | 10.92 |
| 721 | LEU | O    | 2.099  | 32.425 | 23.675 | 10.18 |
| 722 | LEU | CB   | 4.653  | 32.966 | 21.630 | 12.16 |
| 723 | LEU | CG   | 5.658  | 33.617 | 20.677 | 10.05 |
| 724 | LEU | CD1  | 7.130  | 33.604 | 21.085 | 9.84  |
| 725 | LEU | CD2  | 5.220  | 34.724 | 19.751 | 8.39  |
| 726 | PRO | N    | 1.493  | 32.446 | 21.503 | 11.77 |
| 727 | PRO | CA   | 0.410  | 31.494 | 21.723 | 12.03 |
| 728 | PRO | C    | 0.830  | 30.158 | 22.433 | 13.54 |
| 729 | PRO | O    | 0.089  | 29.551 | 23.183 | 15.14 |
| 730 | PRO | CB   | -0.132 | 31.242 | 20.320 | 9.15  |
| 731 | PRO | CG   | 0.277  | 32.454 | 19.478 | 10.31 |
| 732 | PRO | CD   | 1.572  | 32.919 | 20.123 | 10.84 |
| 733 | ASN | N    | 2.100  | 29.779 | 22.259 | 13.43 |
| 734 | ASN | CA   | 2.585  | 28.584 | 22.964 | 13.13 |
| 735 | ASN | C    | 3.324  | 28.859 | 24.291 | 11.81 |
| 736 | ASN | O    | 3.962  | 27.974 | 24.845 | 11.04 |
| 737 | ASN | CB   | 3.496  | 27.799 | 22.046 | 13.99 |
| 738 | ASN | CG   | 4.657  | 28.667 | 21.597 | 16.96 |
| 739 | ASN | OD1  | 4.503  | 29.783 | 21.131 | 22.38 |
| 740 | ASN | ND2  | 5.839  | 28.120 | 21.783 | 18.79 |
| 741 | THR | N    | 3.286  | 30.095 | 24.782 | 9.69  |
| 742 | THR | CA   | 4.037  | 30.277 | 26.042 | 9.51  |
| 743 | THR | C    | 3.210  | 31.147 | 27.020 | 11.20 |
| 744 | THR | O    | 3.752  | 31.735 | 27.945 | 11.31 |
| 745 | THR | CB   | 5.272  | 31.194 | 25.696 | 8.41  |
| 746 | THR | OG1  | 4.946  | 32.545 | 25.282 | 10.58 |
| 747 | THR | CG2  | 6.132  | 30.535 | 24.591 | 5.31  |
| 748 | CYS | N    | 1.877  | 31.177 | 26.815 | 12.27 |
| 749 | CYS | CA   | 1.007  | 31.799 | 27.822 | 12.45 |
| 750 | CYS | C    | 0.947  | 30.973 | 29.109 | 12.47 |
| 751 | CYS | O    | 0.771  | 31.526 | 30.183 | 14.18 |
| 752 | CYS | CB   | -0.422 | 32.004 | 27.341 | 8.19  |
| 753 | CYS | SG   | -0.524 | 32.997 | 25.849 | 9.18  |
| 754 | GLY | N    | 1.156  | 29.654 | 28.975 | 10.77 |
| 755 | GLY | CA   | 1.293  | 28.814 | 30.180 | 10.51 |
| 756 | GLY | C    | 2.589  | 29.054 | 30.979 | 13.69 |
| 757 | GLY | O    | 2.584  | 29.199 | 32.182 | 14.84 |
| 758 | HIS | N    | 3.719  | 29.198 | 30.259 | 14.08 |
| 759 | HIS | CA   | 4.993  | 29.584 | 30.868 | 11.53 |
| 760 | HIS | C    | 4.914  | 30.988 | 31.502 | 11.94 |
| 761 | HIS | O    | 5.482  | 31.244 | 32.554 | 14.08 |
| 762 | HIS | CB   | 6.065  | 29.732 | 29.789 | 10.46 |
| 763 | HIS | CG   | 6.166  | 28.534 | 28.894 | 10.11 |
| 764 | HIS | ND1  | 6.494  | 28.651 | 27.599 | 10.39 |
| 765 | HIS | CD2  | 5.952  | 27.176 | 29.154 | 10.94 |
| 766 | HIS | CE1  | 6.495  | 27.433 | 27.054 | 9.44  |
| 767 | HIS | NE2  | 6.173  | 26.529 | 27.977 | 9.56  |
| 768 | PHE | N    | 4.216  | 31.925 | 30.815 | 9.75  |
| 769 | PHE | CA   | 4.084  | 33.301 | 31.370 | 8.97  |
| 770 | PHE | C    | 3.385  | 33.272 | 32.732 | 9.22  |
| 771 | PHE | O    | 3.896  | 33.785 | 33.709 | 10.50 |
| 772 | PHE | CB   | 3.365  | 34.218 | 30.386 | 7.25  |
| 773 | PHE | CG   | 3.083  | 35.612 | 30.896 | 7.78  |
| 774 | PHE | CD1  | 1.951  | 35.897 | 31.664 | 11.43 |
| 775 | PHE | CD2  | 3.909  | 36.683 | 30.568 | 9.65  |
| 776 | PHE | CE1  | 1.682  | 37.195 | 32.100 | 9.78  |
| 777 | PHE | CE2  | 3.605  | 37.988 | 30.955 | 8.16  |
| 778 | PHE | CZ   | 2.499  | 38.243 | 31.737 | 5.91  |
| 779 | TRP | N    | 2.224  | 32.595 | 32.770 | 9.57  |
| 780 | TRP | CA   | 1.478  | 32.437 | 34.017 | 9.40  |
| 781 | TRP | C    | 2.170  | 31.539 | 35.067 | 10.21 |
| 782 | TRP | O    | 2.124  | 31.827 | 36.254 | 12.41 |
| 783 | TRP | CB   | 0.044  | 32.007 | 33.682 | 8.88  |
| 784 | TRP | CG   | -0.686 | 33.205 | 33.102 | 10.66 |
| 785 | TRP | CD1  | -1.211 | 33.295 | 31.810 | 11.90 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 786 | TRP | CD2 | -0.933 | 34.478 | 33.751 | 10.70 |
| 787 | TRP | NE1 | -1.748 | 34.526 | 31.630 | 13.39 |
| 788 | TRP | CE2 | -1.595 | 35.307 | 32.790 | 11.80 |
| 789 | TRP | CE3 | -0.672 | 34.978 | 35.004 | 10.81 |
| 790 | TRP | CZ2 | -1.912 | 36.601 | 33.125 | 9.91 |
| 791 | TRP | CZ3 | -1.002 | 36.282 | 35.341 | 6.82 |
| 792 | TRP | CH2 | -1.615 | 37.109 | 34.389 | 9.18 |
| 793 | GLU | N | 2.885 | 30.502 | 34.607 | 11.17 |
| 794 | GLU | CA | 3.798 | 29.745 | 35.468 | 8.99 |
| 795 | GLU | C | 4.825 | 30.644 | 36.135 | 8.16 |
| 796 | GLU | O | 4.957 | 30.683 | 37.347 | 10.61 |
| 797 | GLU | CB | 4.501 | 28.631 | 34.698 | 9.22 |
| 798 | GLU | CG | 5.405 | 27.764 | 35.612 | 10.50 |
| 799 | GLU | CD | 6.236 | 26.726 | 34.837 | 11.31 |
| 800 | GLU | OE1 | 6.063 | 26.619 | 33.627 | 15.64 |
| 801 | GLU | OE2 | 7.056 | 26.019 | 35.406 | 11.72 |
| 802 | MET | N | 5.477 | 31.465 | 35.308 | 6.74 |
| 803 | MET | CA | 6.436 | 32.428 | 35.835 | 7.30 |
| 804 | MET | C | 5.812 | 33.362 | 36.919 | 9.58 |
| 805 | MET | O | 6.404 | 33.616 | 37.963 | 11.01 |
| 806 | MET | CB | 7.044 | 33.189 | 34.659 | 4.95 |
| 807 | MET | CG | 7.808 | 34.437 | 35.117 | 8.57 |
| 808 | MET | SD | 8.586 | 35.351 | 33.769 | 10.82 |
| 809 | MET | CE | 7.136 | 36.296 | 33.246 | 5.07 |
| 810 | VAL | N | 4.592 | 33.892 | 36.686 | 11.04 |
| 811 | VAL | CA | 4.040 | 34.817 | 37.683 | 10.24 |
| 812 | VAL | C | 3.700 | 34.069 | 38.978 | 12.49 |
| 813 | VAL | O | 3.978 | 34.571 | 40.066 | 12.79 |
| 814 | VAL | CB | 2.754 | 35.438 | 37.092 | 8.52 |
| 815 | VAL | CG1 | 2.812 | 36.052 | 35.686 | 3.31 |
| 816 | VAL | CG2 | 1.750 | 36.088 | 38.062 | 6.62 |
| 817 | TRP | N | 3.107 | 32.838 | 38.856 | 13.65 |
| 818 | TRP | CA | 2.909 | 31.996 | 40.053 | 12.02 |
| 819 | TRP | C | 4.227 | 31.749 | 40.844 | 11.70 |
| 820 | TRP | O | 4.326 | 32.034 | 42.034 | 12.54 |
| 821 | TRP | CB | 2.217 | 30.672 | 39.710 | 10.42 |
| 822 | TRP | CG | 1.863 | 29.951 | 41.001 | 12.86 |
| 823 | TRP | CD1 | 2.696 | 29.101 | 41.739 | 14.68 |
| 824 | TRP | CD2 | 0.644 | 30.071 | 41.772 | 14.87 |
| 825 | TRP | NE1 | 2.072 | 28.715 | 42.886 | 15.11 |
| 826 | TRP | CE2 | 0.810 | 29.275 | 42.935 | 15.72 |
| 827 | TRP | CE3 | -0.539 | 30.710 | 41.553 | 15.15 |
| 828 | TRP | CZ2 | -0.194 | 29.217 | 43.858 | 16.05 |
| 829 | TRP | CZ3 | -1.558 | 30.644 | 42.477 | 14.60 |
| 830 | TRP | CH2 | -1.389 | 29.889 | 43.623 | 17.06 |
| 831 | GLU | N | 5.226 | 31.223 | 40.140 | 12.34 |
| 832 | GLU | CA | 6.504 | 30.890 | 40.783 | 13.26 |
| 833 | GLU | C | 7.246 | 32.102 | 41.352 | 15.44 |
| 834 | GLU | O | 7.808 | 32.021 | 42.444 | 18.46 |
| 835 | GLU | CB | 7.401 | 30.155 | 39.785 | 11.02 |
| 836 | GLU | CG | 6.906 | 28.742 | 39.525 | 9.86 |
| 837 | GLU | CD | 7.513 | 28.097 | 38.292 | 10.94 |
| 838 | GLU | OE1 | 8.355 | 28.663 | 37.634 | 13.74 |
| 839 | GLU | OE2 | 7.119 | 26.985 | 38.017 | 12.82 |
| 840 | GLN | N | 7.186 | 33.233 | 40.614 | 15.26 |
| 841 | GLN | CA | 7.871 | 34.449 | 41.042 | 15.75 |
| 842 | GLN | C | 7.052 | 35.265 | 42.051 | 16.17 |
| 843 | GLN | O | 7.555 | 36.199 | 42.665 | 16.73 |
| 844 | GLN | CB | 8.228 | 35.289 | 39.806 | 16.31 |
| 845 | GLN | CG | 9.155 | 34.556 | 38.822 | 16.92 |
| 846 | GLN | CD | 10.425 | 34.083 | 39.552 | 19.20 |
| 847 | GLN | OE1 | 11.001 | 34.783 | 40.362 | 19.09 |
| 848 | GLN | NE2 | 10.810 | 32.870 | 39.299 | 15.74 |
| 849 | LYS | N | 5.771 | 34.861 | 42.227 | 15.25 |
| 850 | LYS | CA | 4.934 | 35.484 | 43.254 | 13.27 |
| 851 | LYS | C | 4.651 | 36.977 | 42.993 | 13.03 |
| 852 | LYS | O | 4.524 | 37.792 | 43.895 | 10.75 |
| 853 | LYS | CB | 5.567 | 35.249 | 44.622 | 16.84 |
| 854 | LYS | CG | 5.787 | 33.755 | 44.877 | 20.72 |
| 855 | LYS | CD | 6.097 | 33.446 | 46.349 | 23.31 |
| 856 | LYS | CE | 6.774 | 32.099 | 46.522 | 26.45 |
| 857 | LYS | NZ | 7.947 | 31.999 | 45.619 | 30.79 |
| 858 | SER | N | 4.552 | 37.327 | 41.701 | 14.11 |
| 859 | SER | CA | 4.152 | 38.693 | 41.351 | 13.84 |
| 860 | SER | C | 2.681 | 38.899 | 41.621 | 14.27 |
| 861 | SER | O | 1.854 | 38.015 | 41.464 | 13.39 |
| 862 | SER | CB | 4.462 | 38.899 | 39.829 | 13.28 |
| 863 | SER | OG | 5.745 | 38.417 | 39.369 | 13.97 |
| 864 | ARG | N | 2.389 | 40.117 | 42.068 | 15.30 |
| 865 | ARG | CA | 1.022 | 40.497 | 42.358 | 15.25 |
| 866 | ARG | C | 0.390 | 41.239 | 41.189 | 14.31 |
| 867 | ARG | O | -0.817 | 41.375 | 41.116 | 11.90 |
| 868 | ARG | CB | 1.055 | 41.352 | 43.620 | 16.01 |
| 869 | ARG | CG | -0.333 | 41.453 | 44.243 | 21.04 |
| 870 | ARG | CD | -0.934 | 42.809 | 43.980 | 23.71 |
| 871 | ARG | NE | -1.985 | 43.095 | 44.935 | 25.68 |
| 872 | ARG | CZ | -3.145 | 42.448 | 44.880 | 25.46 |
| 873 | ARG | NH1 | -3.278 | 41.374 | 44.164 | 22.79 |
| 874 | ARG | NH2 | -4.168 | 42.930 | 45.529 | 27.74 |
| 875 | GLY | N | 1.276 | 41.733 | 40.301 | 12.62 |
| 876 | GLY | CA | 0.899 | 42.673 | 39.263 | 10.16 |
| 877 | GLY | C | 1.631 | 42.376 | 37.956 | 10.24 |
| 878 | GLY | O | 2.792 | 41.984 | 37.944 | 9.74 |
| 879 | VAL | N | 0.909 | 42.597 | 36.861 | 10.10 |
| 880 | VAL | CA | 1.554 | 42.588 | 35.545 | 9.04 |
| 881 | VAL | C | 1.189 | 43.904 | 34.860 | 7.92 |
| 882 | VAL | O | 0.021 | 44.276 | 34.795 | 8.52 |
| 883 | VAL | CB | 0.955 | 41.434 | 34.717 | 7.21 |
| 884 | VAL | CG1 | 0.741 | 40.059 | 35.377 | 10.00 |
| 885 | VAL | CG2 | 1.208 | 41.428 | 33.216 | 6.46 |
| 886 | VAL | N | 2.225 | 44.560 | 34.356 | 6.18 |
| 887 | VAL | CA | 2.002 | 45.766 | 33.558 | 5.67 |
| 888 | VAL | C | 2.204 | 45.440 | 32.090 | 5.05 |
| 889 | VAL | O | 3.294 | 45.104 | 31.685 | 8.26 |
| 890 | VAL | CB | 2.942 | 46.867 | 34.051 | 4.27 |
| 891 | VAL | CG1 | 2.627 | 47.146 | 35.522 | 5.59 |
| 892 | VAL | CG2 | 2.821 | 48.193 | 33.311 | 5.52 |
| 893 | MET | N | 1.129 | 45.564 | 31.315 | 6.05 |
| 894 | MET | CA | 1.132 | 45.435 | 29.850 | 6.12 |
| 895 | MET | C | 1.159 | 46.791 | 29.168 | 5.90 |
| 896 | MET | O | 0.263 | 47.591 | 29.379 | 6.94 |
| 897 | MET | CB | -0.222 | 44.895 | 29.428 | 6.49 |
| 898 | MET | CG | -0.347 | 44.620 | 27.938 | 5.59 |
| 899 | MET | SD | -1.592 | 43.356 | 27.620 | 10.50 |
| 900 | MET | CE | -1.470 | 43.249 | 25.807 | 2.00 |
| 901 | LEU | N | 2.146 | 47.028 | 28.319 | 5.40 |
| 902 | LEU | CA | 2.242 | 48.428 | 27.799 | 5.78 |
| 903 | LEU | C | 1.866 | 48.558 | 26.299 | 7.49 |
| 904 | LEU | O | 2.091 | 49.581 | 25.666 | 7.99 |
| 905 | LEU | CB | 3.632 | 48.997 | 28.075 | 6.33 |
| 906 | LEU | CG | 3.952 | 49.053 | 29.593 | 8.42 |
| 907 | LEU | CD1 | 3.064 | 50.026 | 30.390 | 6.57 |
| 908 | LEU | CD2 | 5.400 | 49.460 | 29.834 | 5.25 |
| 909 | ASN | N | 1.336 | 47.445 | 25.747 | 6.12 |
| 910 | ASN | CA | 1.077 | 47.367 | 24.327 | 8.78 |
| 911 | ASN | C | -0.348 | 46.840 | 24.026 | 10.77 |
| 912 | ASN | O | -0.979 | 46.296 | 24.907 | 11.62 |
| 913 | ASN | CB | 2.125 | 46.458 | 23.685 | 10.20 |
| 914 | ASN | CG | 1.956 | 45.019 | 24.175 | 10.50 |
| 915 | ASN | OD1 | 1.469 | 44.137 | 23.509 | 13.52 |
| 916 | ASN | ND2 | 2.370 | 44.830 | 25.401 | 11.44 |
| 917 | ARG | N | -0.798 | 46.974 | 22.777 | 12.13 |
| 918 | ARG | CA | -1.993 | 46.274 | 22.315 | 12.77 |
| 919 | ARG | C | -1.619 | 44.915 | 21.703 | 11.64 |
| 920 | ARG | O | -0.553 | 44.743 | 21.149 | 13.53 |
| 921 | ARG | CB | -2.716 | 47.222 | 21.340 | 15.99 |
| 922 | ARG | CG | -3.045 | 48.546 | 22.066 | 23.40 |
| 923 | ARG | CD | -4.252 | 49.313 | 21.496 | 32.56 |
| 924 | ARG | NE | -4.304 | 49.380 | 20.020 | 44.25 |
| 925 | ARG | CZ | -3.229 | 49.594 | 19.246 | 50.26 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 926 | ARG | NH1 | −2.041 | 49.756 | 19.777 | 51.39 |
| 927 | ARG | NH2 | −3.324 | 49.640 | 17.948 | 53.49 |
| 928 | VAL | N | −2.522 | 43.925 | 21.780 | 11.90 |
| 929 | VAL | CA | −2.168 | 42.689 | 21.057 | 13.18 |
| 930 | VAL | C | −2.076 | 42.945 | 19.536 | 12.04 |
| 931 | VAL | O | −1.410 | 42.208 | 18.850 | 12.44 |
| 932 | VAL | CB | −3.314 | 41.697 | 21.330 | 14.90 |
| 933 | VAL | CG1 | −3.544 | 41.230 | 22.786 | 14.45 |
| 934 | VAL | CG2 | −3.739 | 40.733 | 20.196 | 13.17 |
| 935 | MET | N | −2.781 | 43.975 | 19.030 | 13.86 |
| 936 | MET | CA | −2.503 | 44.415 | 17.669 | 16.37 |
| 937 | MET | C | −1.936 | 45.845 | 17.600 | 15.93 |
| 938 | MET | O | −2.532 | 46.816 | 18.063 | 15.73 |
| 939 | MET | CB | −3.734 | 44.308 | 16.776 | 19.13 |
| 940 | MET | CG | −3.319 | 44.384 | 15.289 | 25.05 |
| 941 | MET | SD | −4.505 | 43.645 | 14.175 | 30.99 |
| 942 | MET | CE | −4.816 | 45.133 | 13.287 | 28.20 |
| 943 | GLU | N | −0.776 | 45.915 | 16.938 | 15.17 |
| 944 | GLU | CA | −0.179 | 47.200 | 16.644 | 16.14 |
| 945 | GLU | C | 0.459 | 47.173 | 15.260 | 18.85 |
| 946 | GLU | O | 1.028 | 46.175 | 14.830 | 20.26 |
| 947 | GLU | CB | 0.888 | 47.527 | 17.679 | 15.90 |
| 948 | GLU | CG | 0.407 | 47.344 | 19.109 | 17.76 |
| 949 | GLU | CD | 1.416 | 47.771 | 20.137 | 18.82 |
| 950 | GLU | OE1 | 2.568 | 47.438 | 19.990 | 16.03 |
| 951 | GLU | OE2 | 1.021 | 48.466 | 21.072 | 15.57 |
| 952 | LYS | N | 0.322 | 48.325 | 14.571 | 22.41 |
| 953 | LYS | CA | 0.947 | 48.444 | 13.227 | 23.76 |
| 954 | LYS | C | 0.631 | 47.250 | 12.303 | 21.76 |
| 955 | LYS | O | 1.464 | 46.702 | 11.599 | 21.77 |
| 956 | LYS | CB | 2.450 | 48.721 | 13.386 | 24.05 |
| 957 | LYS | CG | 2.681 | 50.181 | 13.822 | 23.31 |
| 958 | LYS | CD | 3.794 | 50.330 | 14.847 | 25.30 |
| 959 | LYS | CE | 4.085 | 51.801 | 15.113 | 28.40 |
| 960 | LYS | NZ | 2.832 | 52.557 | 15.212 | 27.38 |
| 961 | GLY | N | −0.656 | 46.844 | 12.413 | 20.87 |
| 962 | GLY | CA | −1.177 | 45.815 | 11.522 | 19.66 |
| 963 | GLY | C | −0.875 | 44.362 | 11.919 | 19.12 |
| 964 | GLY | O | −1.358 | 43.436 | 11.269 | 19.90 |
| 965 | SER | N | −0.076 | 44.207 | 12.978 | 17.43 |
| 966 | SER | CA | 0.409 | 42.896 | 13.385 | 16.48 |
| 967 | SER | C | 0.010 | 42.558 | 14.786 | 15.10 |
| 968 | SER | O | −0.199 | 43.426 | 15.622 | 15.11 |
| 969 | SER | CB | 1.956 | 42.955 | 13.330 | 18.82 |
| 970 | SER | OG | 2.476 | 43.387 | 12.036 | 30.66 |
| 971 | LEU | N | −0.028 | 41.228 | 14.996 | 14.24 |
| 972 | LEU | CA | −0.222 | 40.624 | 16.300 | 13.02 |
| 973 | LEU | C | 1.075 | 40.659 | 17.114 | 12.02 |
| 974 | LEU | O | 2.026 | 39.930 | 16.888 | 12.03 |
| 975 | LEU | CB | −0.717 | 39.195 | 16.092 | 13.63 |
| 976 | LEU | CG | −2.160 | 39.215 | 15.545 | 10.24 |
| 977 | LEU | CD1 | −3.226 | 40.017 | 16.301 | 10.97 |
| 978 | LEU | CD2 | −2.646 | 37.927 | 14.916 | 9.61 |
| 979 | LYS | N | 1.105 | 41.571 | 18.084 | 11.18 |
| 980 | LYS | CA | 2.290 | 41.882 | 18.858 | 8.96 |
| 981 | LYS | C | 2.390 | 41.095 | 20.161 | 7.30 |
| 982 | LYS | O | 3.376 | 41.101 | 20.884 | 6.49 |
| 983 | LYS | CB | 2.258 | 43.376 | 19.126 | 12.36 |
| 984 | LYS | CG | 2.527 | 44.152 | 17.844 | 14.52 |
| 985 | LYS | CD | 3.978 | 44.105 | 17.484 | 16.12 |
| 986 | LYS | CE | 4.345 | 44.924 | 16.271 | 20.42 |
| 987 | LYS | NZ | 5.804 | 45.081 | 16.202 | 23.02 |
| 988 | CYS | N | 1.319 | 40.356 | 20.402 | 6.54 |
| 989 | CYS | CA | 1.256 | 39.673 | 21.686 | 10.66 |
| 990 | CYS | C | 0.100 | 38.668 | 21.635 | 14.07 |
| 991 | CYS | O | −0.882 | 38.889 | 20.936 | 18.36 |
| 992 | CYS | CB | 1.133 | 40.710 | 22.839 | 9.20 |
| 993 | CYS | SG | 0.873 | 40.094 | 24.504 | 5.00 |
| 994 | ALA | N | 0.214 | 37.548 | 22.367 | 13.71 |
| 995 | ALA | CA | −0.970 | 36.706 | 22.498 | 11.28 |
| 996 | ALA | C | −2.054 | 37.332 | 23.451 | 13.57 |
| 997 | ALA | O | −1.787 | 38.061 | 24.405 | 13.87 |
| 998 | ALA | CB | −0.506 | 35.347 | 22.988 | 5.96 |
| 999 | GLN | N | −3.315 | 36.986 | 23.148 | 13.22 |
| 1000 | GLN | CA | −4.355 | 37.267 | 24.134 | 11.86 |
| 1001 | GLN | C | −4.194 | 36.315 | 25.338 | 9.90 |
| 1002 | GLN | O | −4.748 | 35.227 | 25.329 | 8.51 |
| 1003 | GLN | CB | −5.696 | 36.958 | 23.442 | 11.64 |
| 1004 | GLN | CG | −6.901 | 37.307 | 24.331 | 12.96 |
| 1005 | GLN | CD | −6.930 | 38.782 | 24.786 | 15.38 |
| 1006 | GLN | OE1 | −7.275 | 39.155 | 25.885 | 18.48 |
| 1007 | GLN | NE2 | −6.501 | 39.645 | 23.923 | 10.76 |
| 1008 | TYR | N | −3.353 | 36.690 | 26.311 | 10.20 |
| 1009 | TYR | CA | −2.959 | 35.652 | 27.305 | 11.34 |
| 1010 | TYR | C | −3.874 | 35.622 | 28.587 | 10.00 |
| 1011 | TYR | O | −3.692 | 34.809 | 29.480 | 12.22 |
| 1012 | TYR | CB | −1.451 | 35.764 | 27.671 | 9.57 |
| 1013 | TYR | CG | −1.092 | 37.093 | 28.295 | 10.61 |
| 1014 | TYR | CD1 | −1.112 | 37.261 | 29.674 | 11.35 |
| 1015 | TYR | CD2 | −0.748 | 38.189 | 27.492 | 10.24 |
| 1016 | TYR | CE1 | −0.865 | 38.489 | 30.277 | 10.01 |
| 1017 | TYR | CE2 | −0.500 | 39.429 | 28.066 | 8.22 |
| 1018 | TYR | CZ | −0.564 | 39.588 | 29.448 | 8.65 |
| 1019 | TYR | OH | −0.317 | 40.841 | 29.955 | 7.28 |
| 1020 | TRP | N | −4.815 | 36.557 | 28.642 | 9.43 |
| 1021 | TRP | CA | −5.714 | 36.690 | 29.792 | 10.16 |
| 1022 | TRP | C | −7.175 | 36.690 | 29.287 | 10.75 |
| 1023 | TRP | O | −7.442 | 37.154 | 28.187 | 8.67 |
| 1024 | TRP | CB | −5.341 | 37.945 | 30.612 | 8.10 |
| 1025 | TRP | CG | −5.788 | 39.222 | 29.929 | 8.50 |
| 1026 | TRP | CD1 | −6.970 | 39.931 | 30.199 | 9.41 |
| 1027 | TRP | CD2 | −5.138 | 39.917 | 28.835 | 8.04 |
| 1028 | TRP | NE1 | −7.089 | 40.994 | 29.356 | 8.02 |
| 1029 | TRP | CE2 | −5.979 | 41.032 | 28.508 | 8.86 |
| 1030 | TRP | CE3 | −3.990 | 39.680 | 28.138 | 6.23 |
| 1031 | TRP | CZ2 | −5.626 | 41.863 | 27.469 | 7.39 |
| 1032 | TRP | CZ3 | −3.641 | 40.518 | 27.068 | 8.40 |
| 1033 | TRP | CH2 | −4.457 | 41.614 | 26.747 | 8.65 |
| 1034 | PRO | N | −8.137 | 36.145 | 30.127 | 11.94 |
| 1035 | PRO | CA | −9.538 | 36.107 | 29.746 | 11.58 |
| 1036 | PRO | C | 10.158 | 37.512 | 29.637 | 14.25 |
| 1037 | PRO | O | 10.022 | 38.396 | 30.486 | 14.80 |
| 1038 | PRO | CB | 10.225 | 35.238 | 30.819 | 8.41 |
| 1039 | PRO | CG | −9.311 | 35.278 | 32.027 | 5.08 |
| 1040 | PRO | CD | −7.939 | 35.615 | 31.474 | 10.33 |
| 1041 | GLN | N | 10.892 | 37.626 | 28.524 | 15.45 |
| 1042 | GLN | CA | 11.657 | 38.851 | 28.328 | 18.38 |
| 1043 | GLN | C | 13.068 | 38.858 | 28.949 | 19.02 |
| 1044 | GLN | O | 13.747 | 39.861 | 28.892 | 20.54 |
| 1045 | GLN | CB | 11.682 | 39.166 | 26.841 | 20.69 |
| 1046 | GLN | CG | 10.255 | 39.453 | 26.327 | 27.58 |
| 1047 | GLN | CD | 10.336 | 39.675 | 24.835 | 28.97 |
| 1048 | GLN | OE1 | 10.447 | 38.767 | 24.036 | 27.29 |
| 1049 | GLN | NE2 | 10.375 | 40.949 | 24.506 | 28.60 |
| 1050 | LYS | N | 13.516 | 37.738 | 29.523 | 19.10 |
| 1051 | LYS | CA | 14.764 | 37.856 | 30.269 | 18.50 |
| 1052 | LYS | C | 14.946 | 36.717 | 31.217 | 15.91 |
| 1053 | LYS | O | 14.342 | 35.680 | 31.035 | 16.84 |
| 1054 | LYS | CB | 15.921 | 37.842 | 29.309 | 24.10 |
| 1055 | LYS | CG | 15.932 | 36.706 | 28.297 | 25.36 |
| 1056 | LYS | CD | 16.993 | 36.968 | 27.238 | 29.33 |
| 1057 | LYS | CE | 17.243 | 38.464 | 27.014 | 37.08 |
| 1058 | LYS | NZ | 18.344 | 38.699 | 26.095 | 42.94 |
| 1059 | GLU | N | 15.801 | 36.951 | 32.206 | 14.50 |
| 1060 | GLU | CA | 15.976 | 36.171 | 33.393 | 14.90 |
| 1061 | GLU | C | 16.338 | 34.709 | 33.088 | 18.20 |
| 1062 | GLU | O | 15.719 | 33.790 | 33.632 | 21.55 |
| 1063 | GLU | CB | 17.056 | 36.856 | 34.217 | 15.32 |
| 1064 | GLU | CG | 16.575 | 38.151 | 34.874 | 13.30 |
| 1065 | GLU | CD | 16.724 | 39.424 | 34.004 | 16.29 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1066 | GLU | OE1 | 16.616 | 39.376 | 32.782 | 16.80 |
| 1067 | GLU | OE2 | 16.964 | 40.491 | 34.568 | 16.60 |
| 1068 | GLU | N | 17.317 | 34.475 | 32.183 | 19.29 |
| 1069 | GLU | CA | 17.820 | 33.133 | 31.855 | 19.57 |
| 1070 | GLU | C | 16.760 | 32.233 | 31.213 | 21.30 |
| 1071 | GLU | O | 16.888 | 31.007 | 31.232 | 20.15 |
| 1072 | GLU | CB | 18.964 | 33.205 | 30.827 | 18.63 |
| 1073 | GLU | CG | 19.852 | 34.414 | 31.027 | 16.44 |
| 1074 | GLU | CD | 19.393 | 35.654 | 30.276 | 16.06 |
| 1075 | GLU | OE1 | 19.651 | 35.750 | 29.079 | 17.52 |
| 1076 | GLU | OE2 | 18.763 | 36.522 | 30.864 | 15.56 |
| 1077 | LYS | N | 15.763 | 32.878 | 30.564 | 21.95 |
| 1078 | LYS | CA | 14.806 | 32.104 | 29.783 | 24.05 |
| 1079 | LYS | C | 13.376 | 32.240 | 30.376 | 24.41 |
| 1080 | LYS | O | 12.539 | 32.989 | 29.869 | 24.56 |
| 1081 | LYS | CB | 14.884 | 32.562 | 28.310 | 26.00 |
| 1082 | LYS | CG | 16.297 | 32.545 | 27.708 | 32.43 |
| 1083 | LYS | CD | 16.445 | 31.919 | 26.320 | 39.12 |
| 1084 | LYS | CE | 15.519 | 30.736 | 26.063 | 47.59 |
| 1085 | LYS | NZ | 16.271 | 29.672 | 25.392 | 51.15 |
| 1086 | GLU | N | 13.140 | 31.494 | 31.483 | 24.94 |
| 1087 | GLU | CA | 11.782 | 31.372 | 32.025 | 23.85 |
| 1088 | GLU | C | 10.831 | 30.682 | 31.032 | 20.25 |
| 1089 | GLU | O | 11.227 | 29.985 | 30.119 | 19.30 |
| 1090 | GLU | CB | 11.754 | 30.531 | 33.308 | 26.32 |
| 1091 | GLU | CG | 13.084 | 30.345 | 34.016 | 32.27 |
| 1092 | GLU | CD | 13.812 | 29.168 | 33.377 | 33.00 |
| 1093 | GLU | OE1 | 13.258 | 28.077 | 33.359 | 32.06 |
| 1094 | GLU | OE2 | 14.929 | 29.369 | 32.909 | 35.48 |
| 1095 | MET | N | −9.550 | 30.894 | 31.280 | 17.49 |
| 1096 | MET | CA | −8.526 | 30.188 | 30.550 | 15.38 |
| 1097 | MET | C | −7.902 | 29.097 | 31.442 | 16.86 |
| 1098 | MET | O | −7.471 | 29.361 | 32.554 | 18.95 |
| 1099 | MET | CB | −7.489 | 31.239 | 30.146 | 12.45 |
| 1100 | MET | CG | −8.055 | 32.218 | 29.122 | 11.06 |
| 1101 | MET | SD | −6.888 | 33.465 | 28.615 | 15.30 |
| 1102 | MET | CE | −5.835 | 32.442 | 27.602 | 13.48 |
| 1103 | ILE | N | −7.819 | 27.879 | 30.942 | 15.12 |
| 1104 | ILE | CA | −6.944 | 26.908 | 31.605 | 16.59 |
| 1105 | ILE | C | −5.708 | 26.614 | 30.770 | 17.15 |
| 1106 | ILE | O | −5.788 | 26.242 | 29.614 | 19.86 |
| 1107 | ILE | CB | −7.708 | 25.631 | 31.971 | 18.08 |
| 1108 | ILE | CG1 | −8.632 | 25.919 | 33.163 | 23.46 |
| 1109 | ILE | CG2 | −6.764 | 24.493 | 32.352 | 17.34 |
| 1110 | ILE | CD1 | 10.089 | 25.551 | 32.914 | 24.91 |
| 1111 | PHE | N | −4.558 | 26.751 | 31.426 | 16.66 |
| 1112 | PHE | CA | −3.307 | 26.461 | 30.755 | 16.55 |
| 1113 | PHE | C | −2.838 | 25.024 | 31.123 | 19.38 |
| 1114 | PHE | O | −2.330 | 24.746 | 32.201 | 19.28 |
| 1115 | PHE | CB | −2.336 | 27.588 | 31.105 | 12.36 |
| 1116 | PHE | CG | −2.824 | 28.944 | 30.818 | 10.57 |
| 1117 | PHE | CD1 | −2.749 | 29.439 | 29.534 | 8.04 |
| 1118 | PHE | CD2 | −3.334 | 29.723 | 31.855 | 11.55 |
| 1119 | PHE | CE1 | −3.201 | 30.723 | 29.284 | 10.42 |
| 1120 | PHE | CE2 | −3.787 | 31.007 | 31.608 | 11.87 |
| 1121 | PHE | CZ | −3.719 | 31.506 | 30.311 | 12.28 |
| 1122 | GLU | N | −3.116 | 24.104 | 30.205 | 21.82 |
| 1123 | GLU | CA | −3.039 | 22.720 | 30.661 | 25.19 |
| 1124 | GLU | C | −1.584 | 22.256 | 30.878 | 24.14 |
| 1125 | GLU | O | −1.290 | 21.361 | 31.659 | 25.33 |
| 1126 | GLU | CB | −3.639 | 21.787 | 29.605 | 31.07 |
| 1127 | GLU | CG | −5.166 | 21.765 | 29.396 | 39.94 |
| 1128 | GLU | CD | −5.454 | 20.639 | 28.364 | 48.24 |
| 1129 | GLU | OE1 | −5.364 | 20.905 | 27.164 | 52.05 |
| 1130 | GLU | OE2 | −5.724 | 19.507 | 28.772 | 51.99 |
| 1131 | ASP | N | −0.697 | 22.914 | 30.136 | 23.00 |
| 1132 | ASP | CA | 0.712 | 22.482 | 30.155 | 22.21 |
| 1133 | ASP | C | 1.446 | 22.782 | 31.508 | 20.47 |
| 1134 | ASP | O | 2.261 | 22.031 | 32.033 | 19.77 |
| 1135 | ASP | CB | 1.332 | 23.130 | 28.915 | 21.00 |
| 1136 | ASP | CG | 1.430 | 24.643 | 29.079 | 22.61 |
| 1137 | ASP | OD1 | 0.486 | 25.282 | 29.556 | 26.49 |
| 1138 | ASP | OD2 | 2.454 | 25.190 | 28.734 | 21.60 |
| 1139 | THR | N | 1.068 | 23.914 | 32.079 | 19.14 |
| 1140 | THR | CA | 1.645 | 24.175 | 33.404 | 16.22 |
| 1141 | THR | C | 0.561 | 24.054 | 34.479 | 18.50 |
| 1142 | THR | O | 0.848 | 24.327 | 35.628 | 20.38 |
| 1143 | THR | CB | 2.051 | 25.710 | 33.412 | 14.66 |
| 1144 | THR | OG1 | 0.989 | 26.641 | 33.065 | 13.92 |
| 1145 | THR | CG2 | 3.261 | 25.983 | 32.480 | 11.30 |
| 1146 | ASN | N | −0.686 | 23.637 | 34.105 | 19.33 |
| 1147 | ASN | CA | −1.730 | 23.331 | 35.094 | 19.95 |
| 1148 | ASN | C | −2.154 | 24.539 | 35.987 | 21.85 |
| 1149 | ASN | O | −2.161 | 24.482 | 37.214 | 22.33 |
| 1150 | ASN | CB | −1.180 | 22.269 | 36.021 | 24.72 |
| 1151 | ASN | CG | −2.334 | 21.494 | 36.646 | 27.53 |
| 1152 | ASN | OD1 | −3.342 | 21.190 | 36.060 | 30.68 |
| 1153 | ASN | ND2 | −2.193 | 21.200 | 37.881 | 26.04 |
| 1154 | LEU | N | −2.484 | 25.635 | 35.297 | 22.78 |
| 1155 | LEU | CA | −2.886 | 26.899 | 35.936 | 22.24 |
| 1156 | LEU | C | −4.265 | 27.315 | 35.376 | 22.59 |
| 1157 | LEU | O | −4.561 | 27.167 | 34.194 | 23.95 |
| 1158 | LEU | CB | −1.875 | 28.025 | 35.599 | 21.01 |
| 1159 | LEU | CG | −0.701 | 28.404 | 36.548 | 17.04 |
| 1160 | LEU | CD1 | 0.610 | 28.303 | 35.804 | 13.07 |
| 1161 | LEU | CD2 | −0.612 | 27.764 | 37.930 | 14.04 |
| 1162 | LYS | N | −5.087 | 27.901 | 36.222 | 20.53 |
| 1163 | LYS | CA | −6.322 | 28.485 | 35.725 | 17.91 |
| 1164 | LYS | C | −6.339 | 30.003 | 35.942 | 17.68 |
| 1165 | LYS | O | −5.903 | 30.515 | 36.958 | 16.29 |
| 1166 | LYS | CB | −7.441 | 27.691 | 36.368 | 17.25 |
| 1167 | LYS | CG | −8.807 | 28.050 | 35.869 | 18.58 |
| 1168 | LYS | CD | −9.895 | 27.178 | 36.443 | 22.19 |
| 1169 | LYS | CE | 11.140 | 27.885 | 36.932 | 22.34 |
| 1170 | LYS | NZ | 11.879 | 26.984 | 37.836 | 24.46 |
| 1171 | LEU | N | −6.846 | 30.705 | 34.934 | 17.39 |
| 1172 | LEU | CA | −7.006 | 32.157 | 34.943 | 15.35 |
| 1173 | LEU | C | −8.477 | 32.621 | 34.637 | 16.31 |
| 1174 | LEU | O | −9.075 | 32.259 | 33.636 | 16.43 |
| 1175 | LEU | CB | −5.961 | 32.752 | 34.009 | 12.86 |
| 1176 | LEU | CG | −5.853 | 34.284 | 34.126 | 9.27 |
| 1177 | LEU | CD1 | −5.021 | 34.787 | 32.956 | 8.45 |
| 1178 | LEU | CD2 | −5.200 | 34.687 | 35.454 | 9.53 |
| 1179 | THR | N | −9.012 | 33.479 | 35.526 | 13.25 |
| 1180 | THR | CA | 10.354 | 34.063 | 35.463 | 12.10 |
| 1181 | THR | C | 10.355 | 35.563 | 35.597 | 13.46 |
| 1182 | THR | O | −9.718 | 36.088 | 36.499 | 15.11 |
| 1183 | THR | CB | 11.097 | 33.461 | 36.694 | 12.89 |
| 1184 | THR | OG1 | 10.946 | 32.013 | 36.745 | 11.16 |
| 1185 | THR | CG2 | 12.589 | 33.673 | 36.530 | 13.73 |
| 1186 | LEU | N | 11.097 | 36.253 | 34.707 | 12.69 |
| 1187 | LEU | CA | 11.361 | 37.680 | 34.900 | 13.21 |
| 1188 | LEU | C | 12.268 | 37.840 | 36.109 | 16.36 |
| 1189 | LEU | O | 13.383 | 37.337 | 36.138 | 17.33 |
| 1190 | LEU | CB | 12.105 | 38.280 | 33.697 | 9.27 |
| 1191 | LEU | CG | 12.355 | 39.790 | 33.774 | 5.96 |
| 1192 | LEU | CD1 | 13.113 | 40.189 | 32.520 | 3.05 |
| 1193 | LEU | CD2 | 11.034 | 40.574 | 33.866 | 2.04 |
| 1194 | ILE | N | 11.767 | 38.531 | 37.113 | 16.98 |
| 1195 | ILE | CA | 12.711 | 38.814 | 38.209 | 16.56 |
| 1196 | ILE | C | 13.488 | 40.095 | 37.970 | 15.67 |
| 1197 | ILE | O | 14.677 | 40.183 | 38.224 | 16.31 |
| 1198 | ILE | CB | 12.058 | 38.673 | 39.567 | 14.46 |
| 1199 | ILE | CG1 | 11.521 | 37.227 | 39.718 | 13.21 |
| 1200 | ILE | CG2 | 13.057 | 39.124 | 40.658 | 11.57 |
| 1201 | ILE | CD1 | 12.570 | 36.104 | 39.539 | 7.88 |
| 1202 | SER | N | 12.769 | 41.053 | 37.410 | 16.03 |
| 1203 | SER | CA | 13.492 | 42.181 | 36.859 | 17.37 |
| 1204 | SER | C | 12.449 | 43.133 | 36.298 | 19.23 |
| 1205 | SER | O | 11.276 | 42.946 | 36.557 | 19.21 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1206 | SER | CB | 14.107 | 42.990 | 38.027 | 20.04 |
| 1207 | SER | OG | 13.123 | 43.511 | 39.003 | 20.18 |
| 1208 | GLU | N | 12.886 | 44.193 | 35.634 | 22.29 |
| 1209 | GLU | CA | 11.982 | 45.230 | 35.140 | 23.93 |
| 1210 | GLU | C | 12.557 | 46.663 | 35.235 | 23.31 |
| 1211 | GLU | O | 13.754 | 46.861 | 35.283 | 27.00 |
| 1212 | GLU | CB | 11.701 | 44.924 | 33.697 | 24.38 |
| 1213 | GLU | CG | 12.961 | 44.717 | 32.896 | 25.56 |
| 1214 | GLU | CD | 12.581 | 44.588 | 31.426 | 31.45 |
| 1215 | GLU | OE1 | 11.402 | 44.721 | 31.054 | 32.20 |
| 1216 | GLU | OE2 | 13.483 | 44.345 | 30.651 | 36.07 |
| 1217 | ASP | N | 11.671 | 47.634 | 35.279 | 21.18 |
| 1218 | ASP | CA | 11.995 | 49.030 | 35.441 | 17.82 |
| 1219 | ASP | C | 11.395 | 49.764 | 34.225 | 18.72 |
| 1220 | ASP | O | 10.200 | 50.051 | 34.108 | 20.93 |
| 1221 | ASP | CB | 11.443 | 49.430 | 36.814 | 22.34 |
| 1222 | ASP | CG | 11.406 | 50.932 | 37.034 | 28.58 |
| 1223 | ASP | OD1 | 12.354 | 51.602 | 36.636 | 27.70 |
| 1224 | ASP | OD2 | 10.412 | 51.436 | 37.597 | 33.90 |
| 1225 | ILE | N | 12.306 | 49.980 | 33.282 | 18.31 |
| 1226 | ILE | CA | 11.933 | 50.554 | 32.008 | 19.98 |
| 1227 | ILE | C | 11.874 | 52.099 | 32.025 | 20.84 |
| 1228 | ILE | O | 12.850 | 52.781 | 32.267 | 20.15 |
| 1229 | ILE | CB | 12.946 | 50.053 | 30.978 | 20.01 |
| 1230 | ILE | CG1 | 12.853 | 48.540 | 30.856 | 20.02 |
| 1231 | ILE | CG2 | 12.762 | 50.696 | 29.607 | 19.35 |
| 1232 | ILE | CD1 | 13.722 | 47.987 | 29.733 | 21.08 |
| 1233 | LYS | N | 10.700 | 52.617 | 31.682 | 22.09 |
| 1234 | LYS | CA | 10.548 | 54.069 | 31.550 | 21.26 |
| 1235 | LYS | C | 10.289 | 54.430 | 30.108 | 20.78 |
| 1236 | LYS | O | 10.038 | 53.563 | 29.266 | 22.79 |
| 1237 | LYS | CB | −9.402 | 54.433 | 32.459 | 22.27 |
| 1238 | LYS | CG | −9.721 | 54.009 | 33.868 | 22.36 |
| 1239 | LYS | CD | 10.326 | 55.177 | 34.630 | 25.91 |
| 1240 | LYS | CE | 10.825 | 54.813 | 36.002 | 28.42 |
| 1241 | LYS | NZ | 11.309 | 56.052 | 36.589 | 30.51 |
| 1242 | THR | N | 10.327 | 55.686 | 29.733 | 19.62 |
| 1243 | THR | CA | 10.249 | 56.059 | 28.237 | 20.98 |
| 1244 | THR | C | −8.822 | 55.510 | 27.732 | 20.84 |
| 1245 | THR | O | −8.780 | 55.122 | 26.657 | 22.93 |
| 1246 | THR | CB | −9.822 | 57.568 | 28.309 | 19.41 |
| 1247 | THR | OG1 | −8.833 | 57.806 | 29.314 | 22.97 |
| 1248 | THR | CG2 | 11.069 | 58.348 | 28.636 | 24.19 |
| 1249 | TYR | N | −7.719 | 55.518 | 28.646 | 20.25 |
| 1250 | TYR | CA | −6.458 | 55.219 | 28.007 | 18.72 |
| 1251 | TYR | C | −5.770 | 53.922 | 28.602 | 18.44 |
| 1252 | TYR | O | −4.685 | 53.476 | 28.203 | 20.29 |
| 1253 | TYR | CB | −5.607 | 56.494 | 28.042 | 16.14 |
| 1254 | TYR | CG | −4.897 | 56.888 | 29.314 | 13.33 |
| 1255 | TYR | CD1 | −5.465 | 57.864 | 30.081 | 14.09 |
| 1256 | TYR | CD2 | −3.682 | 56.427 | 29.721 | 13.30 |
| 1257 | TYR | CE1 | −5.016 | 58.191 | 31.311 | 17.45 |
| 1258 | TYR | CE2 | −3.090 | 56.866 | 30.874 | 19.22 |
| 1259 | TYR | CZ | −3.767 | 57.715 | 31.696 | 19.65 |
| 1260 | TYR | OH | −3.079 | 58.078 | 32.801 | 20.24 |
| 1261 | TYR | N | −6.461 | 53.351 | 29.591 | 15.06 |
| 1262 | TYR | CA | −5.915 | 52.151 | 30.228 | 14.61 |
| 1263 | TYR | C | −7.010 | 51.388 | 30.962 | 15.66 |
| 1264 | TYR | O | −8.023 | 51.956 | 31.320 | 17.43 |
| 1265 | TYR | CB | −4.719 | 52.522 | 31.134 | 15.82 |
| 1266 | TYR | CG | −5.118 | 53.115 | 32.443 | 19.10 |
| 1267 | TYR | CD1 | −5.449 | 52.289 | 33.528 | 21.07 |
| 1268 | TYR | CD2 | −5.158 | 54.491 | 32.606 | 21.69 |
| 1269 | TYR | CE1 | −5.830 | 52.813 | 34.755 | 19.08 |
| 1270 | TYR | CE2 | −5.580 | 55.003 | 33.823 | 22.03 |
| 1271 | TYR | CZ | −5.883 | 54.185 | 34.902 | 20.70 |
| 1272 | TYR | OH | −6.221 | 54.746 | 36.125 | 20.35 |
| 1273 | THR | N | −6.777 | 50.103 | 31.213 | 13.79 |
| 1274 | THR | CA | −7.774 | 49.326 | 31.968 | 14.01 |
| 1275 | THR | C | −7.068 | 48.551 | 33.024 | 13.51 |
| 1276 | THR | O | −6.050 | 47.935 | 32.736 | 12.55 |
| 1277 | THR | CB | −8.369 | 48.336 | 30.922 | 15.24 |
| 1278 | THR | OG1 | −9.115 | 48.941 | 29.853 | 15.88 |
| 1279 | THR | CG2 | −9.278 | 47.291 | 31.615 | 12.04 |
| 1280 | VAL | N | −7.636 | 48.525 | 34.247 | 13.29 |
| 1281 | VAL | CA | −7.079 | 47.585 | 35.204 | 14.30 |
| 1282 | VAL | C | −8.024 | 46.398 | 35.369 | 14.29 |
| 1283 | VAL | O | −9.217 | 46.546 | 35.469 | 15.36 |
| 1284 | VAL | CB | −6.887 | 48.311 | 36.548 | 13.88 |
| 1285 | VAL | CG1 | −6.372 | 49.756 | 36.536 | 8.84 |
| 1286 | VAL | CG2 | −6.537 | 47.465 | 37.788 | 13.68 |
| 1287 | ARG | N | −7.465 | 45.214 | 35.420 | 12.81 |
| 1288 | ARG | CA | −8.229 | 44.025 | 35.644 | 11.72 |
| 1289 | ARG | C | −7.772 | 43.342 | 36.930 | 12.76 |
| 1290 | ARG | O | −6.620 | 43.342 | 37.320 | 12.68 |
| 1291 | ARG | CB | −8.045 | 43.128 | 34.450 | 11.12 |
| 1292 | ARG | CG | −8.286 | 43.859 | 33.139 | 15.30 |
| 1293 | ARG | CD | −8.261 | 42.904 | 31.963 | 20.03 |
| 1294 | ARG | NE | −8.786 | 43.590 | 30.765 | 23.64 |
| 1295 | ARG | CZ | −7.985 | 44.278 | 29.965 | 22.07 |
| 1296 | ARG | NH1 | −6.692 | 44.288 | 30.189 | 21.13 |
| 1297 | ARG | NH2 | −8.468 | 44.954 | 28.976 | 24.55 |
| 1298 | GLN | N | −8.730 | 42.732 | 37.569 | 15.02 |
| 1299 | GLN | CA | −8.427 | 41.791 | 38.595 | 17.49 |
| 1300 | GLN | C | −8.600 | 40.390 | 38.060 | 15.96 |
| 1301 | GLN | O | −9.647 | 40.036 | 37.541 | 14.32 |
| 1302 | GLN | CB | −9.382 | 42.030 | 39.713 | 22.81 |
| 1303 | GLN | CG | −9.262 | 41.053 | 40.854 | 32.87 |
| 1304 | GLN | CD | 10.405 | 41.347 | 41.813 | 39.46 |
| 1305 | GLN | OE1 | 11.408 | 41.967 | 41.482 | 41.19 |
| 1306 | GLN | NE2 | 10.187 | 40.875 | 43.013 | 42.57 |
| 1307 | LEU | N | −7.538 | 39.630 | 38.194 | 15.65 |
| 1308 | LEU | CA | −7.498 | 38.264 | 37.718 | 15.53 |
| 1309 | LEU | C | −7.483 | 37.312 | 38.917 | 15.62 |
| 1310 | LEU | O | −7.009 | 37.654 | 39.984 | 17.25 |
| 1311 | LEU | CB | −6.202 | 38.112 | 36.903 | 16.62 |
| 1312 | LEU | CG | −6.242 | 38.575 | 35.434 | 14.27 |
| 1313 | LEU | CD1 | −4.942 | 38.991 | 34.790 | 16.50 |
| 1314 | LEU | CD2 | −7.496 | 39.201 | 34.857 | 12.30 |
| 1315 | GLU | N | −7.982 | 36.101 | 38.711 | 15.87 |
| 1316 | GLU | CA | −7.649 | 35.059 | 39.670 | 14.28 |
| 1317 | GLU | C | −6.819 | 34.006 | 38.952 | 12.82 |
| 1318 | GLU | O | −7.183 | 33.521 | 37.900 | 11.62 |
| 1319 | GLU | CB | −8.912 | 34.480 | 40.323 | 15.74 |
| 1320 | GLU | CG | −8.504 | 33.348 | 41.273 | 20.52 |
| 1321 | GLU | CD | −9.616 | 32.843 | 42.174 | 22.26 |
| 1322 | GLU | OE1 | 10.040 | 33.589 | 43.047 | 26.87 |
| 1323 | GLU | OE2 | 10.020 | 31.708 | 42.012 | 16.51 |
| 1324 | LEU | N | −5.679 | 33.708 | 39.578 | 13.74 |
| 1325 | LEU | CA | −4.780 | 32.673 | 39.137 | 14.23 |
| 1326 | LEU | C | −4.851 | 31.471 | 40.119 | 16.97 |
| 1327 | LEU | O | −4.491 | 31.577 | 41.289 | 13.98 |
| 1328 | LEU | CB | −3.391 | 33.307 | 39.131 | 13.18 |
| 1329 | LEU | CG | −2.359 | 32.718 | 38.152 | 14.58 |
| 1330 | LEU | CD1 | −2.685 | 31.494 | 37.300 | 13.64 |
| 1331 | LEU | CD2 | −0.889 | 32.995 | 38.428 | 15.94 |
| 1332 | GLU | N | −5.312 | 30.327 | 39.601 | 18.45 |
| 1333 | GLU | CA | −5.299 | 29.116 | 40.366 | 18.22 |
| 1334 | GLU | C | −4.243 | 28.118 | 39.888 | 19.24 |
| 1335 | GLU | O | −4.250 | 27.596 | 38.789 | 17.31 |
| 1336 | GLU | CB | −6.667 | 28.458 | 40.354 | 18.17 |
| 1337 | GLU | CG | −6.781 | 27.377 | 41.470 | 20.37 |
| 1338 | GLU | CD | −8.058 | 26.570 | 41.332 | 22.37 |
| 1339 | GLU | OE1 | −8.995 | 26.977 | 40.666 | 21.04 |
| 1340 | GLU | OE2 | −8.108 | 25.474 | 41.879 | 25.85 |
| 1341 | ASN | N | −3.345 | 27.828 | 40.804 | 22.37 |
| 1342 | ASN | CA | −2.546 | 26.649 | 40.584 | 25.92 |
| 1343 | ASN | C | −3.387 | 25.377 | 40.755 | 25.53 |
| 1344 | ASN | O | −3.572 | 24.897 | 41.861 | 25.67 |
| 1345 | ASN | CB | −1.325 | 26.765 | 41.500 | 27.66 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1346 | ASN | CG | −0.601 | 25.427 | 41.717 | 27.77 |
| 1347 | ASN | OD1 | −1.077 | 24.341 | 41.436 | 27.56 |
| 1348 | ASN | ND2 | 0.571 | 25.533 | 42.244 | 29.56 |
| 1349 | LEU | N | −3.807 | 24.821 | 39.627 | 23.83 |
| 1350 | LEU | CA | −4.652 | 23.629 | 39.641 | 22.45 |
| 1351 | LEU | C | −4.106 | 22.430 | 40.435 | 24.96 |
| 1352 | LEU | O | −4.848 | 21.603 | 40.937 | 26.15 |
| 1353 | LEU | CB | −4.919 | 23.245 | 38.197 | 16.54 |
| 1354 | LEU | CG | −6.200 | 23.824 | 37.584 | 15.77 |
| 1355 | LEU | CD1 | −6.355 | 23.781 | 36.061 | 13.72 |
| 1356 | LEU | CD2 | −6.966 | 24.930 | 38.291 | 12.99 |
| 1357 | THR | N | −2.783 | 22.364 | 40.547 | 26.74 |
| 1358 | THR | CA | −2.184 | 21.257 | 41.276 | 27.87 |
| 1359 | THR | C | −2.387 | 21.269 | 42.779 | 29.27 |
| 1360 | THR | O | −2.324 | 20.235 | 43.438 | 30.62 |
| 1361 | THR | CB | −0.656 | 21.271 | 40.960 | 28.76 |
| 1362 | THR | OG1 | −0.222 | 21.276 | 39.580 | 28.70 |
| 1363 | THR | CG2 | 0.076 | 20.197 | 41.798 | 28.43 |
| 1364 | THR | N | −2.626 | 22.437 | 43.328 | 28.69 |
| 1365 | THR | CA | −2.904 | 22.402 | 44.775 | 28.99 |
| 1366 | THR | C | −4.201 | 23.179 | 45.033 | 32.17 |
| 1367 | THR | O | −4.673 | 23.210 | 46.146 | 34.29 |
| 1368 | THR | CB | −1.808 | 23.352 | 45.374 | 25.58 |
| 1369 | THR | OG1 | −1.906 | 24.712 | 44.893 | 24.80 |
| 1370 | THR | CG2 | −0.413 | 22.844 | 44.960 | 21.97 |
| 1371 | GLN | N | −4.726 | 23.838 | 43.975 | 34.19 |
| 1372 | GLN | CA | −5.903 | 24.683 | 44.149 | 36.02 |
| 1373 | GLN | C | −5.651 | 25.904 | 45.068 | 34.54 |
| 1374 | GLN | O | −6.560 | 26.502 | 45.630 | 34.82 |
| 1375 | GLN | CB | −7.056 | 23.797 | 44.633 | 40.16 |
| 1376 | GLN | CG | −7.447 | 22.737 | 43.605 | 46.76 |
| 1377 | GLN | CD | −8.777 | 22.111 | 44.000 | 50.73 |
| 1378 | GLN | OE1 | −9.050 | 21.806 | 45.145 | 50.25 |
| 1379 | GLN | NE2 | −9.586 | 21.893 | 42.985 | 53.71 |
| 1380 | GLU | N | −4.364 | 26.264 | 45.184 | 33.22 |
| 1381 | GLU | CA | −4.084 | 27.590 | 45.723 | 33.18 |
| 1382 | GLU | C | −4.526 | 28.672 | 44.740 | 30.34 |
| 1383 | GLU | O | −4.574 | 28.507 | 43.524 | 28.93 |
| 1384 | GLU | CB | −2.597 | 27.807 | 45.960 | 37.35 |
| 1385 | GLU | CG | −2.029 | 27.073 | 47.151 | 45.79 |
| 1386 | GLU | CD | −0.503 | 27.118 | 47.092 | 53.23 |
| 1387 | GLU | OE1 | 0.090 | 28.186 | 47.253 | 54.41 |
| 1388 | GLU | OE2 | 0.110 | 26.083 | 46.854 | 58.44 |
| 1389 | THR | N | −4.771 | 29.824 | 45.341 | 27.29 |
| 1390 | THR | CA | −5.321 | 30.882 | 44.519 | 21.75 |
| 1391 | THR | C | −4.702 | 32.231 | 44.866 | 20.39 |
| 1392 | THR | O | −4.480 | 32.572 | 46.024 | 21.88 |
| 1393 | THR | CB | −6.901 | 30.855 | 44.831 | 20.91 |
| 1394 | THR | OG1 | −7.887 | 30.317 | 43.926 | 18.30 |
| 1395 | THR | CG2 | −7.402 | 32.239 | 45.242 | 22.13 |
| 1396 | ARG | N | −4.478 | 33.010 | 43.805 | 17.74 |
| 1397 | ARG | CA | −3.917 | 34.344 | 44.023 | 15.94 |
| 1398 | ARG | C | −4.593 | 35.365 | 43.131 | 15.58 |
| 1399 | ARG | O | −4.922 | 35.078 | 41.994 | 14.33 |
| 1400 | ARG | CB | −2.434 | 34.314 | 43.653 | 16.13 |
| 1401 | ARG | CG | −1.673 | 33.304 | 44.487 | 18.13 |
| 1402 | ARG | CD | −0.197 | 33.503 | 44.382 | 18.87 |
| 1403 | ARG | NE | 0.471 | 32.485 | 45.132 | 20.71 |
| 1404 | ARG | CZ | 1.666 | 32.149 | 44.780 | 21.27 |
| 1405 | ARG | NH1 | 2.351 | 32.800 | 43.866 | 19.60 |
| 1406 | ARG | NH2 | 2.163 | 31.120 | 45.349 | 22.46 |
| 1407 | GLU | N | −4.737 | 36.564 | 43.664 | 16.20 |
| 1408 | GLU | CA | −5.232 | 37.648 | 42.820 | 17.96 |
| 1409 | GLU | C | −4.066 | 38.466 | 42.226 | 18.25 |
| 1410 | GLU | O | −3.223 | 39.023 | 42.925 | 19.75 |
| 1411 | GLU | CB | −6.054 | 38.623 | 43.649 | 20.78 |
| 1412 | GLU | CG | −6.513 | 39.851 | 42.845 | 23.52 |
| 1413 | GLU | CD | −6.777 | 40.984 | 43.840 | 31.18 |
| 1414 | GLU | OE1 | −5.867 | 41.331 | 44.491 | 35.95 |
| 1415 | GLU | OE2 | −7.849 | 41.495 | 43.990 | 33.07 |
| 1416 | ILE | N | −4.131 | 38.557 | 40.902 | 16.64 |
| 1417 | ILE | CA | −3.169 | 39.310 | 40.109 | 12.04 |
| 1418 | ILE | C | −3.880 | 40.515 | 39.527 | 11.07 |
| 1419 | ILE | O | −4.862 | 40.403 | 38.819 | 11.62 |
| 1420 | ILE | CB | −2.704 | 38.444 | 38.926 | 9.49 |
| 1421 | ILE | CG1 | −2.292 | 37.027 | 39.359 | 8.19 |
| 1422 | ILE | CG2 | −1.679 | 39.155 | 38.027 | 6.71 |
| 1423 | ILE | CD1 | −1.062 | 36.953 | 40.271 | 8.86 |
| 1424 | LEU | N | −3.314 | 41.663 | 39.796 | 12.20 |
| 1425 | LEU | CA | −3.765 | 42.894 | 39.153 | 11.34 |
| 1426 | LEU | C | −3.068 | 43.084 | 37.797 | 10.98 |
| 1427 | LEU | O | −1.855 | 43.017 | 37.679 | 11.20 |
| 1428 | LEU | CB | −3.376 | 43.996 | 40.135 | 11.87 |
| 1429 | LEU | CG | −4.459 | 44.428 | 41.136 | 14.45 |
| 1430 | LEU | CD1 | −3.851 | 45.049 | 42.374 | 13.48 |
| 1431 | LEU | CD2 | −5.510 | 43.382 | 41.494 | 14.58 |
| 1432 | HIS | N | −3.887 | 43.335 | 36.774 | 11.21 |
| 1433 | HIS | CA | −3.409 | 43.599 | 35.405 | 10.35 |
| 1434 | HIS | C | −3.599 | 45.056 | 35.037 | 11.82 |
| 1435 | HIS | O | −4.720 | 45.529 | 34.960 | 13.04 |
| 1436 | HIS | CB | −4.223 | 42.719 | 34.475 | 10.25 |
| 1437 | HIS | CG | −3.735 | 42.604 | 33.061 | 5.26 |
| 1438 | HIS | ND1 | −4.371 | 43.183 | 32.017 | 4.31 |
| 1439 | HIS | CD2 | −2.622 | 41.907 | 32.605 | 3.49 |
| 1440 | HIS | CE1 | −3.660 | 42.851 | 30.935 | 4.28 |
| 1441 | HIS | NE2 | −2.608 | 42.086 | 31.264 | 4.14 |
| 1442 | PHE | N | −2.489 | 45.762 | 34.785 | 10.90 |
| 1443 | PHE | CA | −2.577 | 47.192 | 34.424 | 10.08 |
| 1444 | PHE | C | −2.213 | 47.405 | 32.956 | 10.93 |
| 1445 | PHE | O | −1.070 | 47.258 | 32.553 | 12.60 |
| 1446 | PHE | CB | −1.586 | 48.018 | 35.254 | 8.89 |
| 1447 | PHE | CG | −1.856 | 47.856 | 36.714 | 10.34 |
| 1448 | PHE | CD1 | −1.223 | 46.858 | 37.441 | 9.37 |
| 1449 | PHE | CD2 | −2.739 | 48.705 | 37.357 | 12.07 |
| 1450 | PHE | CE1 | −1.474 | 46.722 | 38.787 | 8.64 |
| 1451 | PHE | CE2 | −2.995 | 48.564 | 38.714 | 7.54 |
| 1452 | PHE | CZ | −2.359 | 47.577 | 39.417 | 6.90 |
| 1453 | HIS | N | −3.227 | 47.745 | 32.158 | 10.22 |
| 1454 | HIS | CA | −3.060 | 47.678 | 30.720 | 10.82 |
| 1455 | HIS | C | −3.094 | 49.072 | 30.056 | 11.67 |
| 1456 | HIS | O | −4.145 | 49.698 | 29.957 | 13.22 |
| 1457 | HIS | CB | −4.194 | 46.789 | 30.220 | 11.88 |
| 1458 | HIS | CG | −4.060 | 46.522 | 28.750 | 9.09 |
| 1459 | HIS | ND1 | −3.037 | 46.925 | 27.987 | 14.21 |
| 1460 | HIS | CD2 | −4.958 | 45.845 | 27.938 | 9.60 |
| 1461 | HIS | CE1 | −3.331 | 46.498 | 26.751 | 10.85 |
| 1462 | HIS | NE2 | −4.488 | 45.829 | 26.687 | 11.12 |
| 1463 | TYR | N | −1.914 | 49.518 | 29.591 | 11.21 |
| 1464 | TYR | CA | −1.813 | 50.801 | 28.897 | 12.13 |
| 1465 | TYR | C | −2.155 | 50.619 | 27.389 | 13.01 |
| 1466 | TYR | O | −1.497 | 49.865 | 26.675 | 12.08 |
| 1467 | TYR | CB | −0.388 | 51.305 | 29.131 | 11.51 |
| 1468 | TYR | CG | −0.235 | 52.799 | 29.078 | 14.44 |
| 1469 | TYR | CD1 | −0.475 | 53.489 | 27.919 | 15.45 |
| 1470 | TYR | CD2 | 0.267 | 53.497 | 30.164 | 13.74 |
| 1471 | TYR | CE1 | −0.140 | 54.860 | 27.837 | 15.14 |
| 1472 | TYR | CE2 | 0.460 | 54.871 | 30.142 | 13.53 |
| 1473 | TYR | CZ | 0.229 | 55.578 | 28.981 | 12.44 |
| 1474 | TYR | OH | 0.435 | 56.939 | 28.993 | 13.99 |
| 1475 | THR | N | −3.213 | 51.285 | 26.911 | 13.59 |
| 1476 | THR | CA | −3.606 | 50.873 | 25.519 | 15.13 |
| 1477 | THR | C | −3.481 | 52.067 | 24.538 | 16.95 |
| 1478 | THR | O | −3.906 | 51.956 | 23.403 | 20.50 |
| 1479 | THR | CB | −5.144 | 50.574 | 25.606 | 13.16 |
| 1480 | THR | OG1 | −5.954 | 51.612 | 26.206 | 15.62 |
| 1481 | THR | CG2 | −5.433 | 49.321 | 26.462 | 10.17 |
| 1482 | THR | N | −2.858 | 53.182 | 24.942 | 15.57 |
| 1483 | THR | CA | −2.577 | 54.214 | 23.880 | 14.73 |
| 1484 | THR | C | −1.085 | 54.620 | 23.940 | 15.24 |
| 1485 | THR | O | −0.720 | 55.737 | 23.634 | 16.37 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1486 | THR | CB | -3.210 | 55.519 | 24.477 | 15.29 |
| 1487 | THR | OG1 | -2.750 | 55.685 | 25.838 | 16.09 |
| 1488 | THR | CG2 | -4.765 | 55.520 | 24.411 | 14.63 |
| 1489 | TRP | N | -0.197 | 53.698 | 24.382 | 13.79 |
| 1490 | TRP | CA | 1.223 | 53.979 | 24.245 | 12.12 |
| 1491 | TRP | C | 1.772 | 53.276 | 22.951 | 11.93 |
| 1492 | TRP | O | 1.876 | 52.056 | 22.904 | 14.64 |
| 1493 | TRP | CB | 1.906 | 53.454 | 25.513 | 13.19 |
| 1494 | TRP | CG | 3.394 | 53.773 | 25.583 | 10.47 |
| 1495 | TRP | CD1 | 4.221 | 54.197 | 24.541 | 8.59 |
| 1496 | TRP | CD2 | 4.228 | 53.714 | 26.768 | 11.45 |
| 1497 | TRP | NE1 | 5.472 | 54.391 | 24.988 | 9.33 |
| 1498 | TRP | CE2 | 5.529 | 54.103 | 26.358 | 11.57 |
| 1499 | TRP | CE3 | 3.999 | 53.379 | 28.077 | 8.59 |
| 1500 | TRP | CZ2 | 6.546 | 54.155 | 27.292 | 8.09 |
| 1501 | TRP | CZ3 | 5.036 | 53.437 | 29.007 | 7.89 |
| 1502 | TRP | CH2 | 6.317 | 53.825 | 28.620 | 3.96 |
| 1503 | PRO | N | 2.127 | 54.031 | 21.860 | 11.54 |
| 1504 | PRO | CA | 2.430 | 53.374 | 20.577 | 9.51 |
| 1505 | PRO | C | 3.765 | 52.621 | 20.539 | 9.46 |
| 1506 | PRO | O | 4.738 | 53.105 | 21.091 | 9.47 |
| 1507 | PRO | CB | 2.388 | 54.494 | 19.532 | 5.29 |
| 1508 | PRO | CG | 1.818 | 55.684 | 20.278 | 4.86 |
| 1509 | PRO | CD | 2.158 | 55.495 | 21.745 | 8.47 |
| 1510 | ASP | N | 3.775 | 51.454 | 19.864 | 8.54 |
| 1511 | ASP | CA | 5.035 | 50.736 | 19.645 | 10.50 |
| 1512 | ASP | C | 6.154 | 51.662 | 19.076 | 12.96 |
| 1513 | ASP | O | 5.907 | 52.405 | 18.129 | 15.10 |
| 1514 | ASP | CB | 4.794 | 49.507 | 18.750 | 10.62 |
| 1515 | ASP | CG | 5.909 | 48.497 | 18.955 | 11.09 |
| 1516 | ASP | OD1 | 6.834 | 48.771 | 19.704 | 16.40 |
| 1517 | ASP | OD2 | 5.840 | 47.423 | 18.386 | 12.44 |
| 1518 | PHE | N | 7.320 | 51.664 | 19.747 | 12.20 |
| 1519 | PHE | CA | 8.430 | 52.587 | 19.427 | 11.72 |
| 1520 | PHE | C | 8.102 | 54.085 | 19.493 | 12.78 |
| 1521 | PHE | O | 8.865 | 54.904 | 18.986 | 12.60 |
| 1522 | PHE | CB | 9.015 | 52.330 | 18.045 | 9.10 |
| 1523 | PHE | CG | 9.636 | 50.969 | 17.921 | 9.42 |
| 1524 | PHE | CD1 | 10.917 | 50.751 | 18.407 | 7.65 |
| 1525 | PHE | CD2 | 8.923 | 49.930 | 17.329 | 7.68 |
| 1526 | PHE | CE1 | 11.479 | 49.496 | 18.292 | 7.82 |
| 1527 | PHE | CE2 | 9.488 | 48.677 | 17.203 | 7.43 |
| 1528 | PHE | CZ | 10.762 | 48.468 | 17.686 | 6.08 |
| 1529 | GLY | N | 6.979 | 54.401 | 20.157 | 11.81 |
| 1530 | GLY | CA | 6.677 | 55.764 | 20.535 | 10.61 |
| 1531 | GLY | C | 6.660 | 55.972 | 22.034 | 13.38 |
| 1532 | GLY | O | 7.313 | 55.303 | 22.839 | 14.97 |
| 1533 | VAL | N | 5.865 | 56.984 | 22.375 | 14.24 |
| 1534 | VAL | CA | 5.933 | 57.538 | 23.723 | 13.51 |
| 1535 | VAL | C | 4.501 | 57.778 | 24.246 | 14.35 |
| 1536 | VAL | O | 3.562 | 57.882 | 23.459 | 15.05 |
| 1537 | VAL | CB | 6.733 | 58.845 | 23.784 | 11.74 |
| 1538 | VAL | CG1 | 6.121 | 60.069 | 23.102 | 10.72 |
| 1539 | VAL | CG2 | 8.255 | 58.752 | 23.835 | 12.09 |
| 1540 | PRO | N | 4.336 | 57.872 | 25.595 | 15.06 |
| 1541 | PRO | CA | 3.040 | 58.236 | 26.137 | 16.11 |
| 1542 | PRO | C | 2.530 | 59.619 | 25.634 | 17.94 |
| 1543 | PRO | O | 3.317 | 60.468 | 25.242 | 18.05 |
| 1544 | PRO | CB | 3.302 | 58.226 | 27.645 | 13.63 |
| 1545 | PRO | CG | 4.528 | 57.385 | 27.893 | 12.41 |
| 1546 | PRO | CD | 5.346 | 57.630 | 26.643 | 13.69 |
| 1547 | GLU | N | 1.202 | 59.808 | 25.668 | 20.58 |
| 1548 | GLU | CA | 0.652 | 61.098 | 25.215 | 24.47 |
| 1549 | GLU | C | 1.250 | 62.298 | 25.940 | 22.91 |
| 1550 | GLU | O | 1.492 | 63.361 | 25.390 | 25.20 |
| 1551 | GLU | CB | -0.850 | 61.158 | 25.409 | 32.07 |
| 1552 | GLU | CG | -1.590 | 60.311 | 24.379 | 47.45 |
| 1553 | GLU | CD | -3.087 | 60.502 | 24.517 | 58.57 |
| 1554 | GLU | OE1 | -3.532 | 61.222 | 25.432 | 65.04 |
| 1555 | GLU | OE2 | -3.790 | 59.928 | 23.682 | 61.51 |
| 1556 | SER | N | 1.500 | 62.076 | 27.234 | 18.37 |
| 1557 | SER | CA | 2.197 | 63.131 | 27.944 | 15.28 |
| 1558 | SER | C | 2.757 | 62.537 | 29.222 | 14.24 |
| 1559 | SER | O | 2.365 | 61.449 | 29.650 | 14.09 |
| 1560 | SER | CB | 1.096 | 64.150 | 28.335 | 16.36 |
| 1561 | SER | OG | -0.038 | 63.590 | 29.064 | 13.71 |
| 1562 | PRO | N | 3.694 | 63.279 | 29.870 | 16.15 |
| 1563 | PRO | CA | 4.138 | 62.933 | 31.224 | 15.80 |
| 1564 | PRO | C | 3.004 | 62.717 | 32.253 | 14.92 |
| 1565 | PRO | O | 3.058 | 61.827 | 33.071 | 16.83 |
| 1566 | PRO | CB | 5.050 | 64.111 | 31.635 | 15.53 |
| 1567 | PRO | CG | 5.523 | 64.712 | 30.308 | 13.98 |
| 1568 | PRO | CD | 4.387 | 64.458 | 29.311 | 14.91 |
| 1569 | ALA | N | 1.938 | 63.509 | 32.155 | 13.73 |
| 1570 | ALA | CA | 0.888 | 63.387 | 33.176 | 11.80 |
| 1571 | ALA | C | 0.126 | 62.067 | 33.107 | 12.67 |
| 1572 | ALA | O | -0.162 | 61.442 | 34.116 | 15.33 |
| 1573 | ALA | CB | -0.118 | 64.507 | 32.976 | 10.12 |
| 1574 | SER | N | -0.196 | 61.656 | 31.875 | 13.30 |
| 1575 | SER | CA | -0.925 | 60.382 | 31.746 | 13.82 |
| 1576 | SER | C | -0.019 | 59.148 | 32.010 | 13.05 |
| 1577 | SER | O | -0.412 | 58.220 | 32.690 | 15.15 |
| 1578 | SER | CB | -1.429 | 60.366 | 30.317 | 14.32 |
| 1579 | SER | OG | -0.511 | 60.907 | 29.312 | 19.74 |
| 1580 | PHE | N | 1.239 | 59.221 | 31.521 | 12.50 |
| 1581 | PHE | CA | 2.228 | 58.251 | 32.002 | 12.76 |
| 1582 | PHE | C | 2.343 | 58.176 | 33.577 | 11.82 |
| 1583 | PHE | O | 2.186 | 57.121 | 34.169 | 11.88 |
| 1584 | PHE | CB | 3.615 | 58.605 | 31.431 | 13.14 |
| 1585 | PHE | CG | 4.637 | 57.656 | 32.013 | 16.05 |
| 1586 | PHE | CD1 | 4.686 | 56.327 | 31.585 | 14.24 |
| 1587 | PHE | CD2 | 5.489 | 58.064 | 33.038 | 13.37 |
| 1588 | PHE | CE1 | 5.556 | 55.424 | 32.196 | 13.11 |
| 1589 | PHE | CE2 | 6.349 | 57.150 | 33.644 | 11.48 |
| 1590 | PHE | CZ | 6.383 | 55.827 | 33.237 | 9.34 |
| 1591 | LEU | N | 2.617 | 59.319 | 34.219 | 11.77 |
| 1592 | LEU | CA | 2.708 | 59.367 | 35.689 | 11.73 |
| 1593 | LEU | C | 1.410 | 58.893 | 36.391 | 10.70 |
| 1594 | LEU | O | 1.438 | 58.216 | 37.408 | 10.38 |
| 1595 | LEU | CB | 3.025 | 60.798 | 36.167 | 9.36 |
| 1596 | LEU | CG | 4.478 | 61.159 | 35.960 | 5.68 |
| 1597 | LEU | CD1 | 5.549 | 60.306 | 36.660 | 9.00 |
| 1598 | LEU | CD2 | 4.835 | 62.638 | 35.814 | 3.73 |
| 1599 | ASN | N | 0.271 | 59.271 | 35.828 | 10.41 |
| 1600 | ASN | CA | -0.968 | 58.792 | 36.423 | 11.16 |
| 1601 | ASN | C | -1.089 | 57.240 | 36.314 | 11.19 |
| 1602 | ASN | O | -1.352 | 56.580 | 37.305 | 13.76 |
| 1603 | ASN | CB | -2.069 | 59.596 | 35.747 | 11.22 |
| 1604 | ASN | CG | -3.518 | 59.183 | 36.219 | 12.14 |
| 1605 | ASN | OD1 | -3.896 | 59.472 | 37.330 | 14.92 |
| 1606 | ASN | ND2 | -4.309 | 58.498 | 35.428 | 8.22 |
| 1607 | PHE | N | -0.805 | 56.671 | 35.119 | 10.54 |
| 1608 | PHE | CA | -0.779 | 55.193 | 35.030 | 10.34 |
| 1609 | PHE | C | 0.248 | 54.567 | 36.012 | 11.26 |
| 1610 | PHE | O | -0.042 | 53.601 | 36.688 | 14.43 |
| 1611 | PHE | CB | -0.512 | 54.781 | 33.582 | 10.28 |
| 1612 | PHE | CG | -0.425 | 53.288 | 33.361 | 9.79 |
| 1613 | PHE | CD1 | 0.808 | 52.629 | 33.406 | 11.60 |
| 1614 | PHE | CD2 | -1.556 | 52.540 | 33.059 | 9.63 |
| 1615 | PHE | CE1 | 0.895 | 51.260 | 33.146 | 9.17 |
| 1616 | PHE | CE2 | -1.479 | 51.172 | 32.813 | 8.28 |
| 1617 | PHE | CZ | -0.255 | 50.534 | 32.852 | 7.12 |
| 1618 | LEU | N | 1.439 | 55.168 | 36.111 | 11.04 |
| 1619 | LEU | CA | 2.470 | 54.642 | 36.987 | 9.37 |
| 1620 | LEU | C | 2.018 | 54.681 | 38.463 | 10.19 |
| 1621 | LEU | O | 2.198 | 53.743 | 39.237 | 10.47 |
| 1622 | LEU | CB | 3.736 | 55.476 | 36.727 | 8.63 |
| 1623 | LEU | CG | 4.917 | 55.081 | 37.636 | 6.66 |
| 1624 | LEU | CD1 | 6.117 | 56.024 | 37.650 | 2.00 |
| 1625 | LEU | CD2 | 5.215 | 53.570 | 37.847 | 4.01 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1626 | PHE | N | 1.397 | 55.809 | 38.841 | 11.88 |
| 1627 | PHE | CA | 0.953 | 55.953 | 40.219 | 12.54 |
| 1628 | PHE | C | −0.257 | 55.057 | 40.464 | 11.68 |
| 1629 | PHE | O | −0.343 | 54.449 | 41.499 | 13.53 |
| 1630 | PHE | CB | 0.677 | 57.419 | 40.583 | 18.00 |
| 1631 | PHE | CG | 1.923 | 58.166 | 41.007 | 19.08 |
| 1632 | PHE | CD1 | 3.029 | 58.239 | 40.174 | 19.03 |
| 1633 | PHE | CD2 | 1.996 | 58.784 | 42.248 | 20.54 |
| 1634 | PHE | CE1 | 4.208 | 58.855 | 40.582 | 18.32 |
| 1635 | PHE | CE2 | 3.162 | 59.434 | 42.649 | 23.62 |
| 1636 | PHE | CZ | 4.284 | 59.461 | 41.825 | 21.78 |
| 1637 | LYS | N | −1.164 | 54.891 | 39.512 | 11.07 |
| 1638 | LYS | CA | −2.120 | 53.796 | 39.650 | 12.85 |
| 1639 | LYS | C | −1.477 | 52.463 | 40.008 | 14.04 |
| 1640 | LYS | O | −1.967 | 51.768 | 40.896 | 16.37 |
| 1641 | LYS | CB | −2.922 | 53.586 | 38.373 | 16.95 |
| 1642 | LYS | CG | −4.318 | 54.180 | 38.510 | 21.62 |
| 1643 | LYS | CD | −5.385 | 53.142 | 38.905 | 25.54 |
| 1644 | LYS | CE | −6.673 | 53.761 | 39.500 | 25.67 |
| 1645 | LYS | NZ | −7.774 | 52.779 | 39.478 | 30.26 |
| 1646 | VAL | N | −0.356 | 52.121 | 39.336 | 14.89 |
| 1647 | VAL | CA | 0.251 | 50.822 | 39.694 | 14.57 |
| 1648 | VAL | C | 0.969 | 50.877 | 41.070 | 14.27 |
| 1649 | VAL | O | 0.927 | 49.926 | 41.836 | 14.66 |
| 1650 | VAL | CB | 1.287 | 50.408 | 38.602 | 12.16 |
| 1651 | VAL | CG1 | 0.967 | 50.623 | 37.128 | 10.83 |
| 1652 | VAL | CG2 | 2.179 | 49.194 | 38.894 | 11.91 |
| 1653 | ARG | N | 1.645 | 52.008 | 41.379 | 14.32 |
| 1654 | ARG | CA | 2.136 | 52.229 | 42.754 | 15.07 |
| 1655 | ARG | C | 1.031 | 52.174 | 43.854 | 14.33 |
| 1656 | ARG | O | 1.086 | 51.389 | 44.780 | 14.82 |
| 1657 | ARG | CB | 2.852 | 53.578 | 42.830 | 17.02 |
| 1658 | ARG | CG | 4.273 | 53.559 | 42.279 | 13.14 |
| 1659 | ARG | CD | 4.819 | 54.963 | 42.208 | 14.56 |
| 1660 | ARG | NE | 6.213 | 54.951 | 41.816 | 17.25 |
| 1661 | ARG | CZ | 7.151 | 55.597 | 42.478 | 14.40 |
| 1662 | ARG | NH1 | 6.810 | 56.358 | 43.478 | 11.54 |
| 1663 | ARG | NH2 | 8.404 | 55.427 | 42.163 | 14.05 |
| 1664 | GLU | N | 0.019 | 52.995 | 43.747 | 13.57 |
| 1665 | GLU | CA | −1.064 | 52.972 | 44.716 | 15.15 |
| 1666 | GLU | C | −1.655 | 51.587 | 44.982 | 15.15 |
| 1667 | GLU | O | −2.117 | 51.259 | 46.064 | 17.25 |
| 1668 | GLU | CB | −2.186 | 53.776 | 44.127 | 17.33 |
| 1669 | GLU | CG | −1.783 | 55.240 | 44.116 | 26.73 |
| 1670 | GLU | CD | −2.040 | 55.944 | 45.433 | 33.22 |
| 1671 | GLU | OE1 | −1.492 | 57.025 | 45.592 | 34.31 |
| 1672 | GLU | OE2 | −2.768 | 55.425 | 46.287 | 38.92 |
| 1673 | SER | N | −1.601 | 50.783 | 43.914 | 15.09 |
| 1674 | SER | CA | −2.190 | 49.461 | 43.984 | 15.03 |
| 1675 | SER | C | −1.471 | 48.479 | 44.930 | 16.60 |
| 1676 | SER | O | −1.954 | 47.372 | 45.132 | 19.63 |
| 1677 | SER | CB | −2.078 | 48.789 | 42.605 | 13.60 |
| 1678 | SER | OG | −0.807 | 48.101 | 42.352 | 12.81 |
| 1679 | GLY | N | −0.289 | 48.848 | 45.456 | 16.76 |
| 1680 | GLY | CA | 0.383 | 47.836 | 46.262 | 17.69 |
| 1681 | GLY | C | 1.256 | 46.857 | 45.477 | 21.84 |
| 1682 | GLY | O | 2.059 | 46.140 | 46.045 | 25.25 |
| 1683 | SER | N | 1.187 | 46.859 | 44.143 | 21.52 |
| 1684 | SER | CA | 1.899 | 45.727 | 43.512 | 18.70 |
| 1685 | SER | C | 3.343 | 45.801 | 43.485 | 21.56 |
| 1686 | SER | O | 3.983 | 44.799 | 43.241 | 23.22 |
| 1687 | SER | CB | 1.526 | 45.671 | 41.996 | 17.25 |
| 1688 | SER | OG | 0.078 | 45.551 | 41.812 | 15.02 |
| 1689 | LEU | N | 3.832 | 47.043 | 43.689 | 22.71 |
| 1690 | LEU | CA | 5.267 | 47.260 | 43.621 | 25.21 |
| 1691 | LEU | C | 5.971 | 46.987 | 44.956 | 28.44 |
| 1692 | LEU | O | 7.168 | 47.166 | 45.123 | 32.40 |
| 1693 | LEU | CB | 5.530 | 48.678 | 43.103 | 23.08 |
| 1694 | LEU | CG | 5.152 | 48.831 | 41.627 | 22.44 |
| 1695 | LEU | CD1 | 6.028 | 47.953 | 40.742 | 22.73 |
| 1696 | LEU | CD2 | 5.302 | 50.276 | 41.155 | 22.80 |
| 1697 | SER | N | 5.140 | 46.673 | 45.939 | 30.11 |
| 1698 | SER | CA | 5.719 | 46.649 | 47.256 | 33.16 |
| 1699 | SER | C | 6.475 | 45.373 | 47.510 | 31.90 |
| 1700 | SER | O | 6.234 | 44.343 | 46.911 | 34.68 |
| 1701 | SER | CB | 4.546 | 46.921 | 48.203 | 37.54 |
| 1702 | SER | OG | 4.262 | 48.388 | 48.292 | 42.64 |
| 1703 | PRO | N | 7.461 | 45.477 | 48.448 | 28.58 |
| 1704 | PRO | CA | 8.460 | 44.430 | 48.554 | 26.29 |
| 1705 | PRO | C | 7.977 | 43.176 | 49.267 | 25.94 |
| 1706 | PRO | O | 8.685 | 42.192 | 49.313 | 25.90 |
| 1707 | PRO | CB | 9.540 | 45.047 | 49.415 | 25.82 |
| 1708 | PRO | CG | 8.802 | 46.052 | 50.292 | 27.01 |
| 1709 | PRO | CD | 7.625 | 46.520 | 49.442 | 26.00 |
| 1710 | GLU | N | 6.753 | 43.231 | 49.826 | 25.30 |
| 1711 | GLU | CA | 6.147 | 41.998 | 50.313 | 25.00 |
| 1712 | GLU | C | 5.678 | 41.030 | 49.167 | 23.01 |
| 1713 | GLU | O | 5.322 | 39.874 | 49.383 | 23.82 |
| 1714 | GLU | CB | 5.055 | 42.375 | 51.309 | 32.49 |
| 1715 | GLU | CG | 4.100 | 43.491 | 50.809 | 45.13 |
| 1716 | GLU | CD | 2.635 | 43.121 | 51.003 | 53.12 |
| 1717 | GLU | OE1 | 2.305 | 41.954 | 51.249 | 57.67 |
| 1718 | GLU | OE2 | 1.825 | 44.041 | 50.923 | 54.61 |
| 1719 | HIS | N | 5.757 | 41.530 | 47.916 | 19.60 |
| 1720 | HIS | CA | 5.382 | 40.713 | 46.750 | 16.53 |
| 1721 | HIS | C | 6.608 | 40.318 | 45.908 | 14.85 |
| 1722 | HIS | O | 7.657 | 40.935 | 46.002 | 18.13 |
| 1723 | HIS | CB | 4.469 | 41.549 | 45.834 | 16.49 |
| 1724 | HIS | CG | 3.186 | 41.819 | 46.543 | 16.48 |
| 1725 | HIS | ND1 | 2.705 | 43.052 | 46.753 | 19.82 |
| 1726 | HIS | CD2 | 2.315 | 40.880 | 47.113 | 17.11 |
| 1727 | HIS | CE1 | 1.564 | 42.877 | 47.445 | 17.32 |
| 1728 | HIS | NE2 | 1.308 | 41.580 | 47.657 | 16.80 |
| 1729 | GLY | N | 6.441 | 39.313 | 45.037 | 10.74 |
| 1730 | GLY | CA | 7.480 | 39.072 | 44.033 | 8.36 |
| 1731 | GLY | C | 7.639 | 40.271 | 43.101 | 10.21 |
| 1732 | GLY | O | 6.842 | 41.204 | 43.135 | 10.12 |
| 1733 | PRO | N | 8.672 | 40.305 | 42.215 | 11.23 |
| 1734 | PRO | CA | 8.791 | 41.488 | 41.376 | 11.31 |
| 1735 | PRO | C | 7.586 | 41.597 | 40.436 | 13.76 |
| 1736 | PRO | O | 7.115 | 40.556 | 39.982 | 15.58 |
| 1737 | PRO | CB | 10.071 | 41.270 | 40.602 | 11.62 |
| 1738 | PRO | CG | 10.485 | 39.825 | 40.768 | 10.97 |
| 1739 | PRO | CD | 9.655 | 39.266 | 41.909 | 10.99 |
| 1740 | VAL | N | 7.067 | 42.823 | 40.180 | 12.46 |
| 1741 | VAL | CA | 6.099 | 43.008 | 39.084 | 10.53 |
| 1742 | VAL | C | 6.698 | 42.540 | 37.776 | 8.69 |
| 1743 | VAL | O | 7.876 | 42.742 | 37.532 | 5.62 |
| 1744 | VAL | CB | 5.714 | 44.493 | 39.007 | 12.64 |
| 1745 | VAL | CG1 | 4.325 | 44.836 | 38.477 | 13.13 |
| 1746 | VAL | CG2 | 6.817 | 45.499 | 38.640 | 14.34 |
| 1747 | VAL | N | 5.857 | 41.916 | 36.948 | 8.33 |
| 1748 | VAL | CA | 6.266 | 41.620 | 35.592 | 10.28 |
| 1749 | VAL | C | 5.777 | 42.727 | 34.650 | 10.89 |
| 1750 | VAL | O | 4.589 | 42.975 | 34.553 | 14.16 |
| 1751 | VAL | CB | 5.588 | 40.298 | 35.212 | 7.81 |
| 1752 | VAL | CG1 | 5.790 | 39.085 | 36.150 | 3.89 |
| 1753 | VAL | CG2 | 5.488 | 39.993 | 33.708 | 9.30 |
| 1754 | VAL | N | 6.693 | 43.374 | 33.943 | 8.73 |
| 1755 | VAL | CA | 6.230 | 44.364 | 32.984 | 8.66 |
| 1756 | VAL | C | 6.557 | 43.846 | 31.596 | 11.40 |
| 1757 | VAL | O | 7.631 | 43.296 | 31.372 | 11.10 |
| 1758 | VAL | CB | 7.079 | 45.597 | 33.283 | 4.62 |
| 1759 | VAL | CG1 | 7.273 | 45.981 | 34.747 | 5.26 |
| 1760 | VAL | CG2 | 7.039 | 46.751 | 32.271 | 6.18 |
| 1761 | HIS | N | 5.625 | 44.053 | 30.653 | 11.47 |
| 1762 | HIS | CA | 5.949 | 43.726 | 29.291 | 9.12 |
| 1763 | HIS | C | 5.390 | 44.767 | 28.325 | 10.76 |
| 1764 | HIS | O | 4.416 | 45.484 | 28.572 | 9.76 |
| 1765 | HIS | CB | 5.537 | 42.311 | 28.991 | 7.01 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1766 | HIS | CG | 4.100 | 42.188 | 28.648 | 6.87 |
| 1767 | HIS | ND1 | 3.610 | 42.276 | 27.377 | 6.42 |
| 1768 | HIS | CD2 | 3.046 | 41.886 | 29.498 | 7.35 |
| 1769 | HIS | CE1 | 2.317 | 42.030 | 27.445 | 3.34 |
| 1770 | HIS | NE2 | 1.946 | 41.795 | 28.713 | 6.66 |
| 1771 | CYS | N | 6.034 | 44.779 | 27.145 | 9.68 |
| 1772 | CYS | CA | 5.396 | 45.284 | 25.959 | 8.47 |
| 1773 | CYS | C | 5.349 | 44.168 | 24.910 | 8.61 |
| 1774 | CYS | O | 5.015 | 43.037 | 25.183 | 9.39 |
| 1775 | CYS | CB | 6.155 | 46.470 | 25.439 | 9.17 |
| 1776 | CYS | SG | 7.918 | 46.279 | 25.682 | 10.04 |
| 1777 | SER | N | 5.732 | 44.480 | 23.683 | 8.84 |
| 1778 | SER | CA | 5.746 | 43.399 | 22.743 | 8.32 |
| 1779 | SER | C | 7.091 | 42.628 | 22.814 | 9.11 |
| 1780 | SER | O | 7.164 | 41.412 | 22.865 | 6.41 |
| 1781 | SER | CB | 5.589 | 44.028 | 21.316 | 4.93 |
| 1782 | SER | OG | 5.503 | 43.095 | 20.188 | 2.00 |
| 1783 | ALA | N | 8.209 | 43.407 | 22.865 | 8.74 |
| 1784 | ALA | CA | 9.538 | 42.795 | 23.004 | 5.14 |
| 1785 | ALA | C | 9.982 | 42.703 | 24.478 | 8.48 |
| 1786 | ALA | O | 10.901 | 41.977 | 24.865 | 8.15 |
| 1787 | ALA | CB | 10.555 | 43.604 | 22.223 | 2.07 |
| 1788 | GLY | N | 9.283 | 43.536 | 25.298 | 7.00 |
| 1789 | GLY | CA | 9.738 | 43.634 | 26.670 | 7.25 |
| 1790 | GLY | C | 10.994 | 44.521 | 26.895 | 9.02 |
| 1791 | GLY | O | 11.684 | 44.322 | 27.873 | 8.42 |
| 1792 | ILE | N | 11.272 | 45.454 | 25.949 | 8.13 |
| 1793 | ILE | CA | 12.439 | 46.358 | 26.075 | 6.90 |
| 1794 | ILE | C | 12.129 | 47.884 | 25.909 | 6.67 |
| 1795 | ILE | O | 12.517 | 48.706 | 26.735 | 6.93 |
| 1796 | ILE | CB | 13.600 | 45.878 | 25.157 | 7.40 |
| 1797 | ILE | CG1 | 13.304 | 45.896 | 23.645 | 6.63 |
| 1798 | ILE | CG2 | 14.029 | 44.484 | 25.566 | 6.11 |
| 1799 | ILE | CD1 | 14.447 | 45.330 | 22.799 | 2.00 |
| 1800 | GLY | N | 11.389 | 48.259 | 24.844 | 5.07 |
| 1801 | GLY | CA | 11.257 | 49.697 | 24.559 | 3.39 |
| 1802 | GLY | C | 10.479 | 50.506 | 25.591 | 7.26 |
| 1803 | GLY | O | 11.016 | 51.213 | 26.448 | 8.47 |
| 1804 | ARG | N | 9.146 | 50.302 | 25.486 | 9.36 |
| 1805 | ARG | CA | 8.119 | 50.783 | 26.438 | 7.15 |
| 1806 | ARG | C | 8.349 | 50.290 | 27.911 | 8.03 |
| 1807 | ARG | O | 8.254 | 51.041 | 28.878 | 5.27 |
| 1808 | ARG | CB | 6.735 | 50.387 | 25.888 | 4.52 |
| 1809 | ARG | CG | 6.355 | 51.122 | 24.594 | 7.50 |
| 1810 | ARG | CD | 4.963 | 50.741 | 24.037 | 5.39 |
| 1811 | ARG | NE | 5.123 | 49.454 | 23.386 | 2.97 |
| 1812 | ARG | CZ | 4.249 | 48.999 | 22.515 | 6.48 |
| 1813 | ARG | NH1 | 3.100 | 49.567 | 22.403 | 8.00 |
| 1814 | ARG | NH2 | 4.539 | 48.025 | 21.692 | 6.37 |
| 1815 | SER | N | 8.704 | 48.990 | 28.053 | 8.64 |
| 1816 | SER | CA | 8.988 | 48.505 | 29.429 | 11.85 |
| 1817 | SER | C | 10.194 | 49.159 | 30.098 | 13.94 |
| 1818 | SER | O | 10.135 | 49.549 | 31.256 | 14.70 |
| 1819 | SER | CB | 9.251 | 46.983 | 29.317 | 9.42 |
| 1820 | SER | OG | 8.298 | 46.180 | 28.561 | 10.50 |
| 1821 | GLY | N | 11.295 | 49.287 | 29.298 | 13.08 |
| 1822 | GLY | CA | 12.465 | 50.017 | 29.805 | 12.72 |
| 1823 | GLY | C | 12.183 | 51.482 | 30.203 | 12.38 |
| 1824 | GLY | O | 12.630 | 51.952 | 31.232 | 11.48 |
| 1825 | THR | N | 11.373 | 52.164 | 29.392 | 13.33 |
| 1826 | THR | CA | 10.876 | 53.522 | 29.710 | 12.47 |
| 1827 | THR | C | 10.128 | 53.607 | 31.051 | 11.44 |
| 1828 | THR | O | 10.480 | 54.379 | 31.932 | 10.01 |
| 1829 | THR | CB | 9.919 | 53.908 | 28.580 | 13.96 |
| 1830 | THR | OG1 | 10.500 | 53.936 | 27.312 | 14.77 |
| 1831 | THR | CG2 | 9.296 | 55.291 | 28.720 | 14.36 |
| 1832 | PHE | N | 9.086 | 52.761 | 31.159 | 10.63 |
| 1833 | PHE | CA | 8.301 | 52.618 | 32.390 | 10.77 |
| 1834 | PHE | C | 9.161 | 52.415 | 33.683 | 13.07 |
| 1835 | PHE | O | 9.077 | 53.163 | 34.662 | 13.04 |
| 1836 | PHE | CB | 7.336 | 51.445 | 32.182 | 7.40 |
| 1837 | PHE | CG | 6.474 | 51.211 | 33.370 | 8.91 |
| 1838 | PHE | CD1 | 5.294 | 51.939 | 33.535 | 9.56 |
| 1839 | PHE | CD2 | 6.833 | 50.260 | 34.332 | 11.15 |
| 1840 | PHE | CE1 | 4.472 | 51.724 | 34.635 | 6.80 |
| 1841 | PHE | CE2 | 6.011 | 50.042 | 35.441 | 12.86 |
| 1842 | PHE | CZ | 4.826 | 50.776 | 35.585 | 8.20 |
| 1843 | CYS | N | 10.001 | 51.358 | 33.587 | 11.48 |
| 1844 | CYS | CA | 10.913 | 51.025 | 34.674 | 11.25 |
| 1845 | CYS | C | 11.955 | 52.098 | 34.908 | 10.61 |
| 1846 | CYS | O | 12.298 | 52.389 | 36.041 | 11.12 |
| 1847 | CYS | CB | 11.666 | 49.694 | 34.478 | 12.63 |
| 1848 | CYS | SG | 10.535 | 48.313 | 34.271 | 13.23 |
| 1849 | LEU | N | 12.490 | 52.692 | 33.840 | 7.85 |
| 1850 | LEU | CA | 13.512 | 53.666 | 34.153 | 7.84 |
| 1851 | LEU | C | 12.924 | 54.861 | 34.963 | 9.98 |
| 1852 | LEU | O | 13.454 | 55.271 | 36.001 | 9.91 |
| 1853 | LEU | CB | 14.179 | 54.130 | 32.867 | 8.17 |
| 1854 | LEU | CG | 15.152 | 55.294 | 33.101 | 8.10 |
| 1855 | LEU | CD1 | 15.641 | 55.866 | 31.788 | 10.22 |
| 1856 | LEU | CD2 | 16.308 | 54.805 | 33.900 | 5.46 |
| 1857 | ALA | N | 11.765 | 55.366 | 34.479 | 9.15 |
| 1858 | ALA | CA | 11.145 | 56.409 | 35.272 | 8.72 |
| 1859 | ALA | C | 10.859 | 55.961 | 36.758 | 9.37 |
| 1860 | ALA | O | 11.252 | 56.616 | 37.720 | 8.82 |
| 1861 | ALA | CB | 9.933 | 56.906 | 34.502 | 6.08 |
| 1862 | ASP | N | 10.206 | 54.798 | 36.899 | 12.15 |
| 1863 | ASP | CA | 9.882 | 54.384 | 38.274 | 12.54 |
| 1864 | ASP | C | 11.120 | 54.327 | 39.195 | 12.62 |
| 1865 | ASP | O | 11.125 | 54.868 | 40.301 | 14.12 |
| 1866 | ASP | CB | 9.135 | 53.047 | 38.255 | 10.97 |
| 1867 | ASP | CG | 8.677 | 52.635 | 39.683 | 13.96 |
| 1868 | ASP | OD1 | 8.123 | 53.446 | 40.424 | 11.13 |
| 1869 | ASP | OD2 | 8.896 | 51.507 | 40.090 | 16.12 |
| 1870 | THR | N | 12.183 | 53.716 | 38.673 | 11.33 |
| 1871 | THR | CA | 13.409 | 53.627 | 39.496 | 12.31 |
| 1872 | THR | C | 14.030 | 54.924 | 39.818 | 12.62 |
| 1873 | THR | O | 14.421 | 55.178 | 40.946 | 13.17 |
| 1874 | THR | CB | 14.390 | 52.694 | 38.719 | 12.56 |
| 1875 | THR | OG1 | 13.877 | 51.364 | 38.413 | 12.72 |
| 1876 | THR | CG2 | 15.640 | 52.493 | 39.580 | 10.83 |
| 1877 | CYS | N | 14.069 | 55.784 | 38.801 | 11.92 |
| 1878 | CYS | GA | 14.552 | 57.116 | 39.077 | 10.93 |
| 1879 | CYS | C | 13.771 | 57.825 | 40.199 | 11.91 |
| 1880 | CYS | O | 14.365 | 58.424 | 41.096 | 13.19 |
| 1881 | CYS | CB | 14.542 | 57.925 | 37.797 | 10.56 |
| 1882 | CYS | SG | 15.955 | 57.393 | 36.809 | 11.98 |
| 1883 | LEU | N | 12.437 | 57.700 | 40.148 | 10.59 |
| 1884 | LEU | CA | 11.658 | 58.318 | 41.208 | 11.97 |
| 1885 | LEU | C | 11.860 | 57.690 | 42.599 | 12.62 |
| 1886 | LEU | O | 12.008 | 58.369 | 43.598 | 16.19 |
| 1887 | LEU | CB | 10.156 | 58.266 | 40.800 | 11.83 |
| 1888 | LEU | CG | 9.808 | 59.325 | 39.729 | 7.13 |
| 1889 | LEU | CD1 | 10.407 | 60.753 | 39.850 | 6.19 |
| 1890 | LEU | CD2 | 8.408 | 59.256 | 39.129 | 7.45 |
| 1891 | LEU | N | 11.933 | 56.374 | 42.599 | 10.74 |
| 1892 | LEU | GA | 12.298 | 55.683 | 43.835 | 12.52 |
| 1893 | LEU | C | 13.630 | 56.165 | 44.485 | 14.94 |
| 1894 | LEU | O | 13.753 | 56.451 | 45.664 | 14.86 |
| 1895 | LEU | CB | 12.445 | 54.210 | 43.454 | 14.62 |
| 1896 | LEU | CG | 12.070 | 53.202 | 44.542 | 18.58 |
| 1897 | LEU | CD1 | 11.573 | 53.687 | 45.902 | 18.58 |
| 1898 | LEU | CD2 | 12.714 | 51.819 | 44.495 | 18.21 |
| 1899 | LEU | N | 14.657 | 56.205 | 43.622 | 16.93 |
| 1900 | LEU | CA | 15.944 | 56.730 | 44.029 | 16.68 |
| 1901 | LEU | C | 15.899 | 58.125 | 44.634 | 17.07 |
| 1902 | LEU | O | 16.407 | 58.365 | 45.718 | 17.96 |
| 1903 | LEU | CB | 16.865 | 56.799 | 42.823 | 15.86 |
| 1904 | LEU | CG | 17.819 | 55.637 | 42.653 | 16.83 |
| 1905 | LEU | CD1 | 18.150 | 55.210 | 41.239 | 20.58 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 1906 | LEU | CD2 | 17.889 | 54.560 | 43.724 | 20.85 |
| 1907 | MET | N | 15.289 | 59.030 | 43.862 | 17.43 |
| 1908 | MET | CA | 15.045 | 60.372 | 44.363 | 17.74 |
| 1909 | MET | C | 14.356 | 60.343 | 45.749 | 20.59 |
| 1910 | MET | O | 14.705 | 61.087 | 46.653 | 19.57 |
| 1911 | MET | CB | 14.202 | 61.069 | 43.311 | 15.42 |
| 1912 | MET | CG | 14.045 | 62.573 | 43.556 | 22.27 |
| 1913 | MET | SD | 13.221 | 63.451 | 42.216 | 26.88 |
| 1914 | MET | CE | 14.257 | 62.910 | 40.846 | 20.89 |
| 1915 | ASP | N | 13.406 | 59.399 | 45.879 | 21.94 |
| 1916 | ASP | CA | 12.588 | 59.263 | 47.068 | 20.62 |
| 1917 | ASP | C | 13.373 | 58.964 | 48.367 | 22.12 |
| 1918 | ASP | O | 13.158 | 59.545 | 49.428 | 21.16 |
| 1919 | ASP | CB | 11.560 | 58.168 | 46.825 | 17.54 |
| 1920 | ASP | CG | 10.247 | 58.505 | 47.525 | 17.97 |
| 1921 | ASP | OD1 | 10.130 | 59.552 | 48.186 | 16.33 |
| 1922 | ASP | OD2 | 9.323 | 57.702 | 47.398 | 16.58 |
| 1923 | LYS | N | 14.304 | 58.014 | 48.244 | 24.18 |
| 1924 | LYS | CA | 14.838 | 57.506 | 49.461 | 30.25 |
| 1925 | LYS | C | 15.855 | 58.477 | 50.159 | 31.26 |
| 1926 | LYS | O | 16.111 | 58.474 | 51.360 | 31.16 |
| 1927 | LYS | CB | 15.431 | 56.139 | 49.330 | 34.06 |
| 1928 | LYS | CG | 16.631 | 56.140 | 48.175 | 37.83 |
| 1929 | LYS | CD | 16.505 | 54.826 | 47.413 | 40.81 |
| 1930 | LYS | CE | 15.165 | 53.967 | 47.642 | 45.68 |
| 1931 | LYS | NZ | 15.491 | 52.600 | 48.093 | 49.67 |
| 1932 | ARG | N | 16.448 | 59.284 | 49.291 | 32.87 |
| 1933 | ARG | CA | 17.298 | 60.331 | 49.838 | 34.54 |
| 1934 | ARG | C | 16.556 | 61.652 | 49.897 | 32.47 |
| 1935 | ARG | O | 16.969 | 62.544 | 50.607 | 35.59 |
| 1936 | ARG | CB | 18.529 | 60.438 | 48.950 | 40.97 |
| 1937 | ARG | CG | 18.224 | 60.378 | 47.464 | 42.29 |
| 1938 | ARG | CD | 19.440 | 59.951 | 46.685 | 46.58 |
| 1939 | ARG | NE | 19.789 | 58.566 | 46.787 | 51.13 |
| 1940 | ARG | CZ | 20.305 | 57.917 | 45.732 | 51.55 |
| 1941 | ARG | NH1 | 20.573 | 58.530 | 44.593 | 50.19 |
| 1942 | ARG | NH2 | 20.556 | 56.659 | 45.871 | 52.57 |
| 1943 | LYS | N | 15.477 | 61.744 | 49.085 | 28.06 |
| 1944 | LYS | CA | 14.887 | 63.034 | 48.739 | 23.26 |
| 1945 | LYS | C | 15.871 | 63.979 | 48.006 | 22.95 |
| 1946 | LYS | O | 15.846 | 65.185 | 48.145 | 24.32 |
| 1947 | LYS | CB | 14.280 | 63.666 | 49.994 | 20.64 |
| 1948 | LYS | CG | 13.096 | 62.885 | 50.574 | 17.75 |
| 1949 | LYS | CD | 11.829 | 63.028 | 49.746 | 16.37 |
| 1950 | LYS | CE | 10.610 | 62.496 | 50.484 | 18.59 |
| 1951 | LYS | NZ | 9.607 | 61.996 | 49.547 | 18.19 |
| 1952 | ASP | N | 16.744 | 63.378 | 47.216 | 22.49 |
| 1953 | ASP | CA | 17.804 | 64.139 | 46.613 | 22.01 |
| 1954 | ASP | C | 17.837 | 63.901 | 45.057 | 22.36 |
| 1955 | ASP | O | 18.396 | 63.068 | 44.529 | 20.34 |
| 1956 | ASP | CB | 19.135 | 63.784 | 47.280 | 22.14 |
| 1957 | ASP | CG | 20.281 | 64.530 | 46.551 | 24.82 |
| 1958 | ASP | OD1 | 20.036 | 65.282 | 45.596 | 27.44 |
| 1959 | ASP | OD2 | 21.408 | 64.386 | 46.894 | 28.31 |
| 1960 | PRO | N | 17.129 | 64.817 | 44.351 | 22.38 |
| 1961 | PRO | CA | 17.082 | 64.625 | 42.912 | 22.74 |
| 1962 | PRO | C | 18.394 | 64.663 | 42.163 | 23.45 |
| 1963 | PRO | O | 18.563 | 64.065 | 41.106 | 23.06 |
| 1964 | PRO | CB | 16.208 | 65.798 | 42.474 | 22.60 |
| 1965 | PRO | CG | 15.495 | 66.302 | 43.723 | 20.02 |
| 1966 | PRO | CD | 16.375 | 65.912 | 44.883 | 22.19 |
| 1967 | SER | N | 19.308 | 65.388 | 42.820 | 25.88 |
| 1968 | SER | CA | 20.553 | 65.744 | 42.163 | 28.66 |
| 1969 | SER | C | 21.583 | 64.640 | 42.365 | 28.70 |
| 1970 | SER | O | 22.595 | 64.553 | 41.674 | 34.40 |
| 1971 | SER | CB | 20.987 | 67.189 | 42.600 | 32.17 |
| 1972 | SER | OG | 20.078 | 68.376 | 42.408 | 38.47 |
| 1973 | SER | N | 21.286 | 63.704 | 43.228 | 24.95 |
| 1974 | SER | CA | 22.122 | 62.506 | 43.080 | 22.47 |
| 1975 | SER | C | 21.408 | 61.415 | 42.208 | 24.29 |
| 1976 | SER | O | 21.632 | 60.237 | 42.481 | 28.47 |
| 1977 | SER | CB | 21.899 | 61.880 | 44.476 | 19.35 |
| 1978 | SER | OG | 20.447 | 61.522 | 44.588 | 19.02 |
| 1979 | VAL | N | 20.496 | 61.724 | 41.238 | 23.38 |
| 1980 | VAL | CA | 20.110 | 60.629 | 40.317 | 21.74 |
| 1981 | VAL | C | 20.696 | 60.973 | 38.944 | 21.15 |
| 1982 | VAL | O | 20.505 | 62.041 | 38.378 | 21.56 |
| 1983 | VAL | CB | 18.614 | 60.127 | 40.291 | 22.27 |
| 1984 | VAL | CG1 | 17.992 | 60.001 | 38.888 | 19.64 |
| 1985 | VAL | CG2 | 17.642 | 60.735 | 41.319 | 19.29 |
| 1986 | ASP | N | 21.402 | 60.004 | 38.419 | 19.17 |
| 1987 | ASP | CA | 21.900 | 60.033 | 37.078 | 18.10 |
| 1988 | ASP | C | 21.109 | 59.025 | 36.194 | 15.54 |
| 1989 | ASP | O | 21.381 | 57.837 | 36.153 | 15.08 |
| 1990 | ASP | CB | 23.343 | 59.668 | 37.302 | 19.38 |
| 1991 | ASP | CG | 24.180 | 59.829 | 36.067 | 22.12 |
| 1992 | ASP | OD1 | 23.681 | 59.769 | 34.927 | 18.04 |
| 1993 | ASP | OD2 | 25.375 | 60.010 | 36.276 | 24.29 |
| 1994 | ILE | N | 20.110 | 59.581 | 35.484 | 15.98 |
| 1995 | ILE | CA | 19.186 | 58.824 | 34.619 | 14.13 |
| 1996 | ILE | C | 19.943 | 57.927 | 33.639 | 13.36 |
| 1997 | ILE | O | 19.658 | 56.735 | 33.541 | 14.33 |
| 1998 | ILE | CB | 18.150 | 59.751 | 33.905 | 14.98 |
| 1999 | ILE | CG1 | 17.376 | 60.610 | 34.912 | 15.47 |
| 2000 | ILE | CG2 | 17.135 | 58.986 | 33.014 | 15.21 |
| 2001 | ILE | CD1 | 16.406 | 61.621 | 34.258 | 15.57 |
| 2002 | LYS | N | 20.940 | 58.512 | 32.906 | 13.55 |
| 2003 | LYS | CA | 21.574 | 57.679 | 31.868 | 14.54 |
| 2004 | LYS | C | 22.324 | 56.502 | 32.481 | 12.60 |
| 2005 | LYS | O | 22.324 | 55.397 | 31.976 | 14.35 |
| 2006 | LYS | CB | 22.600 | 58.431 | 31.039 | 19.78 |
| 2007 | LYS | CG | 22.050 | 59.595 | 30.233 | 28.21 |
| 2008 | LYS | CD | 23.189 | 60.536 | 29.694 | 33.36 |
| 2009 | LYS | CE | 24.131 | 61.030 | 30.806 | 38.77 |
| 2010 | LYS | NZ | 24.213 | 62.457 | 30.838 | 39.28 |
| 2011 | LYS | N | 22.936 | 56.831 | 33.609 | 13.28 |
| 2012 | LYS | CA | 23.649 | 55.839 | 34.394 | 15.81 |
| 2013 | LYS | C | 22.728 | 54.716 | 34.947 | 16.74 |
| 2014 | LYS | O | 23.120 | 53.553 | 35.015 | 17.00 |
| 2015 | LYS | CB | 24.324 | 56.596 | 35.524 | 18.25 |
| 2016 | LYS | CG | 25.428 | 55.816 | 36.190 | 24.61 |
| 2017 | LYS | CD | 26.426 | 56.748 | 36.886 | 31.08 |
| 2018 | LYS | CE | 27.219 | 57.609 | 35.891 | 33.12 |
| 2019 | LYS | NZ | 28.384 | 58.196 | 36.565 | 38.51 |
| 2020 | VAL | N | 21.473 | 55.107 | 35.320 | 15.03 |
| 2021 | VAL | CA | 20.508 | 54.123 | 35.787 | 12.06 |
| 2022 | VAL | C | 19.952 | 53.242 | 34.667 | 10.81 |
| 2023 | VAL | O | 19.752 | 52.042 | 34.805 | 10.34 |
| 2024 | VAL | CB | 19.461 | 54.608 | 36.785 | 11.58 |
| 2025 | VAL | CG1 | 18.054 | 54.087 | 36.638 | 10.48 |
| 2026 | VAL | CG2 | 19.699 | 55.895 | 37.544 | 10.22 |
| 2027 | LEU | N | 19.772 | 53.885 | 33.526 | 10.79 |
| 2028 | LEU | CA | 19.436 | 53.099 | 32.349 | 8.94 |
| 2029 | LEU | C | 20.548 | 52.062 | 32.020 | 8.48 |
| 2030 | LEU | O | 20.294 | 50.918 | 31.723 | 8.83 |
| 2031 | LEU | CB | 19.293 | 54.082 | 31.185 | 10.94 |
| 2032 | LEU | CG | 18.735 | 53.416 | 29.924 | 12.07 |
| 2033 | LEU | CD1 | 18.531 | 54.306 | 28.709 | 12.15 |
| 2034 | LEU | CD2 | 17.687 | 52.271 | 30.071 | 12.74 |
| 2035 | LEU | N | 21.797 | 52.491 | 32.138 | 8.39 |
| 2036 | LEU | CA | 22.910 | 51.562 | 31.944 | 9.03 |
| 2037 | LEU | C | 23.023 | 50.436 | 33.014 | 9.12 |
| 2038 | LEU | O | 23.321 | 49.296 | 32.672 | 11.52 |
| 2039 | LEU | CB | 24.196 | 52.402 | 31.926 | 12.18 |
| 2040 | LEU | CG | 24.764 | 52.758 | 30.531 | 14.87 |
| 2041 | LEU | CD1 | 25.445 | 54.117 | 30.349 | 13.96 |
| 2042 | LEU | CD2 | 24.118 | 52.171 | 29.284 | 16.58 |
| 2043 | ASP | N | 22.759 | 50.740 | 34.317 | 10.70 |
| 2044 | ASP | CA | 22.692 | 49.615 | 35.266 | 12.69 |
| 2045 | ASP | C | 21.562 | 48.644 | 34.854 | 12.49 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 2046 | ASP | O | 21.672 | 47.428 | 34.883 | 13.96 |
| 2047 | ASP | CB | 22.578 | 50.077 | 36.745 | 12.75 |
| 2048 | ASP | CG | 23.504 | 49.125 | 37.609 | 19.37 |
| 2049 | ASP | OD1 | 24.668 | 49.405 | 37.774 | 18.61 |
| 2050 | ASP | OD2 | 23.102 | 48.048 | 38.058 | 18.50 |
| 2051 | MET | N | 20.479 | 49.260 | 34.346 | 13.94 |
| 2052 | MET | CA | 19.382 | 48.416 | 33.885 | 12.52 |
| 2053 | MET | C | 19.769 | 47.475 | 32.725 | 11.34 |
| 2054 | MET | O | 19.403 | 46.298 | 32.750 | 10.85 |
| 2055 | MET | CB | 18.218 | 49.297 | 33.477 | 12.33 |
| 2056 | MET | CG | 17.250 | 49.543 | 34.624 | 15.57 |
| 2057 | MET | SD | 15.727 | 50.299 | 34.084 | 17.56 |
| 2058 | MET | CE | 15.056 | 50.546 | 35.719 | 21.12 |
| 2059 | ARG | N | 20.500 | 48.014 | 31.717 | 10.37 |
| 2060 | ARG | CA | 20.829 | 47.189 | 30.532 | 11.63 |
| 2061 | ARG | C | 21.931 | 46.116 | 30.833 | 12.35 |
| 2062 | ARG | O | 22.276 | 45.276 | 30.016 | 14.86 |
| 2063 | ARG | CB | 21.135 | 48.021 | 29.251 | 7.82 |
| 2064 | ARG | CG | 20.382 | 49.348 | 29.129 | 10.04 |
| 2065 | ARG | CD | 19.630 | 49.616 | 27.841 | 10.30 |
| 2066 | ARG | NE | 20.491 | 49.785 | 26.689 | 13.76 |
| 2067 | ARG | CZ | 20.030 | 50.198 | 25.490 | 13.60 |
| 2068 | ARG | NH1 | 18.843 | 50.675 | 25.351 | 14.69 |
| 2069 | ARG | NH2 | 20.742 | 50.080 | 24.428 | 14.13 |
| 2070 | LYS | N | 22.428 | 46.114 | 32.087 | 9.97 |
| 2071 | LYS | CA | 23.169 | 44.943 | 32.556 | 9.28 |
| 2072 | LYS | C | 22.295 | 43.656 | 32.712 | 10.67 |
| 2073 | LYS | O | 22.771 | 42.535 | 32.720 | 11.47 |
| 2074 | LYS | CB | 23.764 | 45.238 | 33.939 | 10.01 |
| 2075 | LYS | CG | 24.737 | 46.407 | 33.949 | 8.63 |
| 2076 | LYS | CD | 25.212 | 46.730 | 35.354 | 11.76 |
| 2077 | LYS | CE | 26.300 | 47.806 | 35.387 | 8.10 |
| 2078 | LYS | NZ | 26.725 | 47.986 | 36.771 | 8.13 |
| 2079 | PHE | N | 20.978 | 43.866 | 32.874 | 9.59 |
| 2080 | PHE | CA | 20.099 | 42.748 | 33.170 | 6.82 |
| 2081 | PHE | C | 19.223 | 42.333 | 31.987 | 7.73 |
| 2082 | PHE | O | 18.813 | 41.194 | 31.885 | 9.01 |
| 2083 | PHE | CB | 19.214 | 43.172 | 34.302 | 7.16 |
| 2084 | PHE | CG | 20.005 | 43.498 | 35.521 | 6.83 |
| 2085 | PHE | CD1 | 20.451 | 42.470 | 36.348 | 11.66 |
| 2086 | PHE | CD2 | 20.290 | 44.810 | 35.847 | 7.67 |
| 2087 | PHE | CE1 | 21.108 | 42.746 | 37.544 | 9.99 |
| 2088 | PHE | CE2 | 20.987 | 45.098 | 37.012 | 9.82 |
| 2089 | PHE | CZ | 21.389 | 44.069 | 37.871 | 10.60 |
| 2090 | ARG | N | 18.928 | 43.295 | 31.101 | 6.54 |
| 2091 | ARG | CA | 18.312 | 42.935 | 29.815 | 5.34 |
| 2092 | ARG | C | 18.778 | 43.936 | 28.745 | 6.76 |
| 2093 | ARG | O | 18.946 | 45.121 | 29.033 | 6.23 |
| 2094 | ARG | CB | 16.793 | 42.959 | 29.957 | 6.13 |
| 2095 | ARG | CG | 16.003 | 42.371 | 28.786 | 4.01 |
| 2096 | ARG | CD | 14.522 | 42.202 | 29.163 | 6.42 |
| 2097 | ARG | NE | 13.698 | 41.832 | 28.004 | 7.85 |
| 2098 | ARG | CZ | 13.475 | 40.588 | 27.608 | 7.40 |
| 2099 | ARG | NH1 | 14.082 | 39.611 | 28.213 | 5.55 |
| 2100 | ARG | NH2 | 12.650 | 40.317 | 26.626 | 8.19 |
| 2101 | MET | N | 18.984 | 43.449 | 27.517 | 6.50 |
| 2102 | MET | CA | 19.373 | 44.300 | 26.373 | 5.07 |
| 2103 | MET | C | 18.264 | 45.269 | 25.893 | 4.52 |
| 2104 | MET | O | 17.077 | 45.011 | 25.922 | 5.43 |
| 2105 | MET | CB | 19.754 | 43.386 | 25.208 | 5.61 |
| 2106 | MET | CG | 18.602 | 42.498 | 24.719 | 8.08 |
| 2107 | MET | SD | 19.100 | 41.534 | 23.260 | 10.26 |
| 2108 | MET | CE | 20.352 | 40.481 | 24.035 | 6.83 |
| 2109 | GLY | N | 18.702 | 46.408 | 25.380 | 5.33 |
| 2110 | GLY | CA | 17.798 | 47.158 | 24.511 | 6.72 |
| 2111 | GLY | C | 16.765 | 48.002 | 25.246 | 7.88 |
| 2112 | GLY | O | 15.895 | 48.607 | 24.644 | 8.44 |
| 2113 | LEU | N | 16.917 | 48.057 | 26.575 | 7.79 |
| 2114 | LEU | CA | 15.991 | 48.835 | 27.389 | 7.90 |
| 2115 | LEU | C | 15.847 | 50.280 | 26.931 | 9.43 |
| 2116 | LEU | O | 16.811 | 51.025 | 26.952 | 11.69 |
| 2117 | LEU | CB | 16.435 | 48.759 | 28.855 | 5.63 |
| 2118 | LEU | CG | 16.114 | 47.411 | 29.485 | 3.21 |
| 2119 | LEU | CD1 | 14.875 | 46.664 | 28.964 | 2.00 |
| 2120 | LEU | CD2 | 16.413 | 47.234 | 30.993 | 6.08 |
| 2121 | ILE | N | 14.635 | 50.617 | 26.473 | 8.21 |
| 2122 | ILE | CA | 14.424 | 51.874 | 25.755 | 8.00 |
| 2123 | ILE | C | 15.014 | 51.906 | 24.344 | 9.79 |
| 2124 | ILE | O | 16.216 | 51.821 | 24.151 | 9.69 |
| 2125 | ILE | CB | 14.907 | 53.103 | 26.533 | 7.76 |
| 2126 | ILE | CG1 | 14.427 | 53.121 | 27.981 | 5.80 |
| 2127 | ILE | CG2 | 14.511 | 54.386 | 25.776 | 8.24 |
| 2128 | ILE | CD1 | 14.710 | 54.364 | 28.762 | 7.02 |
| 2129 | GLN | N | 14.092 | 52.024 | 23.368 | 10.99 |
| 2130 | GLN | CA | 14.319 | 51.678 | 21.966 | 11.79 |
| 2131 | GLN | C | 14.653 | 52.880 | 21.069 | 11.05 |
| 2132 | GLN | O | 15.337 | 52.751 | 20.058 | 11.93 |
| 2133 | GLN | CB | 13.190 | 50.852 | 21.454 | 13.66 |
| 2134 | GLN | CG | 13.408 | 49.365 | 21.794 | 17.35 |
| 2135 | GLN | CD | 14.613 | 48.766 | 21.039 | 17.85 |
| 2136 | GLN | OE1 | 14.671 | 48.808 | 19.824 | 17.92 |
| 2137 | GLN | NE2 | 15.638 | 48.402 | 21.798 | 14.72 |
| 2138 | THR | N | 14.146 | 54.045 | 21.454 | 10.48 |
| 2139 | THR | CA | 14.523 | 55.241 | 20.676 | 10.99 |
| 2140 | THR | C | 15.015 | 56.439 | 21.584 | 10.88 |
| 2141 | THR | O | 14.872 | 56.440 | 22.812 | 13.32 |
| 2142 | THR | CB | 13.206 | 55.801 | 20.036 | 10.39 |
| 2143 | THR | OG1 | 12.406 | 56.499 | 21.045 | 11.13 |
| 2144 | THR | CG2 | 12.332 | 54.665 | 19.508 | 5.92 |
| 2145 | ALA | N | 15.526 | 57.490 | 20.947 | 11.27 |
| 2146 | ALA | CA | 16.040 | 58.653 | 21.696 | 12.40 |
| 2147 | ALA | C | 14.922 | 59.563 | 22.293 | 12.72 |
| 2148 | ALA | O | 15.128 | 60.317 | 23.230 | 12.68 |
| 2149 | ALA | CB | 16.884 | 59.495 | 20.743 | 9.84 |
| 2150 | ASP | N | 13.739 | 59.440 | 21.699 | 13.07 |
| 2151 | ASP | CA | 12.627 | 60.217 | 22.243 | 13.49 |
| 2152 | ASP | C | 11.999 | 59.518 | 23.460 | 11.38 |
| 2153 | ASP | O | 11.668 | 60.167 | 24.429 | 11.43 |
| 2154 | ASP | CB | 11.563 | 60.373 | 21.157 | 14.90 |
| 2155 | ASP | CG | 10.713 | 61.587 | 21.478 | 15.65 |
| 2156 | ASP | OD1 | 11.277 | 62.628 | 21.814 | 20.35 |
| 2157 | ASP | OD2 | 9.504 | 61.478 | 21.405 | 15.09 |
| 2158 | GLN | N | 11.911 | 58.184 | 23.464 | 8.92 |
| 2159 | GLN | CA | 11.597 | 57.530 | 24.722 | 9.07 |
| 2160 | GLN | C | 12.604 | 57.887 | 25.843 | 9.83 |
| 2161 | GLN | O | 12.229 | 58.053 | 26.996 | 11.31 |
| 2162 | GLN | CB | 11.618 | 56.017 | 24.539 | 6.40 |
| 2163 | GLN | CG | 10.410 | 55.426 | 23.789 | 7.52 |
| 2164 | GLN | CD | 10.618 | 53.949 | 23.490 | 8.30 |
| 2165 | GLN | OE1 | 11.688 | 53.402 | 23.681 | 10.49 |
| 2166 | GLN | NE2 | 9.596 | 53.335 | 22.960 | 5.63 |
| 2167 | LEU | N | 13.876 | 58.036 | 25.429 | 10.38 |
| 2168 | LEU | CA | 14.899 | 58.532 | 26.365 | 9.22 |
| 2169 | LEU | C | 14.542 | 59.919 | 26.917 | 11.76 |
| 2170 | LEU | O | 14.608 | 60.227 | 28.096 | 14.48 |
| 2171 | LEU | CB | 16.257 | 58.651 | 25.674 | 5.69 |
| 2172 | LEU | CG | 17.350 | 58.976 | 26.691 | 3.16 |
| 2173 | LEU | CD1 | 18.730 | 59.387 | 26.183 | 3.34 |
| 2174 | LEU | CD2 | 17.399 | 58.164 | 27.984 | 6.48 |
| 2175 | ARG | N | 14.189 | 60.765 | 25.959 | 11.77 |
| 2176 | ARG | CA | 13.847 | 62.121 | 26.325 | 11.99 |
| 2177 | ARG | C | 12.535 | 62.202 | 27.128 | 12.66 |
| 2178 | ARG | O | 12.373 | 63.015 | 28.034 | 15.67 |
| 2179 | ARG | CB | 13.757 | 62.891 | 25.023 | 10.45 |
| 2180 | ARG | CG | 13.274 | 64.311 | 25.258 | 11.84 |
| 2181 | ARG | CD | 12.982 | 64.996 | 23.947 | 14.66 |
| 2182 | ARG | NE | 12.991 | 66.432 | 24.187 | 15.50 |
| 2183 | ARG | CZ | 11.861 | 67.087 | 24.321 | 13.39 |
| 2184 | ARG | NH1 | 10.719 | 66.475 | 24.238 | 14.80 |
| 2185 | ARG | NH2 | 11.867 | 68.349 | 24.532 | 9.72 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 2186 | PHE | N | 11.590 | 61.331 | 26.796 | 10.85 |
| 2187 | PHE | CA | 10.374 | 61.254 | 27.565 | 10.59 |
| 2188 | PHE | C | 10.713 | 60.835 | 28.993 | 9.21 |
| 2189 | PHE | O | 10.219 | 61.439 | 29.914 | 13.15 |
| 2190 | PHE | CB | 9.413 | 60.250 | 26.930 | 12.58 |
| 2191 | PHE | CG | 8.132 | 60.221 | 27.703 | 13.60 |
| 2192 | PHE | CD1 | 7.110 | 61.104 | 27.388 | 14.76 |
| 2193 | PHE | CD2 | 7.968 | 59.339 | 28.773 | 15.39 |
| 2194 | PHE | CE1 | 5.934 | 61.118 | 28.132 | 14.58 |
| 2195 | PHE | CE2 | 6.799 | 59.362 | 29.523 | 15.49 |
| 2196 | PHE | CZ | 5.785 | 60.254 | 29.206 | 13.29 |
| 2197 | SER | N | 11.598 | 59.856 | 29.173 | 9.61 |
| 2198 | SER | CA | 12.076 | 59.508 | 30.549 | 11.91 |
| 2199 | SER | C | 12.490 | 60.695 | 31.440 | 13.91 |
| 2200 | SER | O | 12.041 | 60.822 | 32.561 | 15.55 |
| 2201 | SER | CB | 13.309 | 58.607 | 30.361 | 9.99 |
| 2202 | SER | OG | 12.988 | 57.388 | 29.633 | 13.54 |
| 2203 | TYR | N | 13.369 | 61.576 | 30.916 | 12.72 |
| 2204 | TYR | CA | 13.660 | 62.827 | 31.602 | 13.18 |
| 2205 | TYR | C | 12.385 | 63.670 | 31.910 | 14.92 |
| 2206 | TYR | O | 12.138 | 64.043 | 33.043 | 17.21 |
| 2207 | TYR | CB | 14.553 | 63.660 | 30.712 | 13.16 |
| 2208 | TYR | CG | 16.002 | 63.282 | 30.776 | 14.18 |
| 2209 | TYR | CD1 | 16.411 | 62.111 | 30.180 | 16.94 |
| 2210 | TYR | CD2 | 16.947 | 64.100 | 31.406 | 15.60 |
| 2211 | TYR | CE1 | 17.734 | 61.726 | 30.172 | 18.68 |
| 2212 | TYR | CE2 | 18.295 | 63.765 | 31.403 | 16.96 |
| 2213 | TYR | CZ | 18.682 | 62.574 | 30.758 | 19.92 |
| 2214 | TYR | OH | 20.008 | 62.233 | 30.655 | 20.96 |
| 2215 | LEU | N | 11.559 | 63.956 | 30.883 | 14.29 |
| 2216 | LEU | CA | 10.249 | 64.563 | 31.141 | 11.73 |
| 2217 | LEU | C | 9.468 | 63.942 | 32.331 | 13.72 |
| 2218 | LEU | O | 9.041 | 64.636 | 33.258 | 13.88 |
| 2219 | LEU | CB | 9.443 | 64.482 | 29.866 | 11.89 |
| 2220 | LEU | CG | 9.673 | 65.629 | 28.871 | 15.00 |
| 2221 | LEU | CD1 | 9.334 | 65.412 | 27.398 | 15.00 |
| 2222 | LEU | CD2 | 10.774 | 66.642 | 29.158 | 14.31 |
| 2223 | ALA | N | 9.318 | 62.599 | 32.273 | 13.35 |
| 2224 | ALA | CA | 8.564 | 61.864 | 33.295 | 12.89 |
| 2225 | ALA | C | 9.213 | 62.040 | 34.696 | 13.12 |
| 2226 | ALA | O | 8.582 | 62.474 | 35.653 | 13.73 |
| 2227 | ALA | CB | 8.309 | 60.393 | 32.891 | 10.58 |
| 2228 | VAL | N | 10.503 | 61.743 | 34.779 | 11.11 |
| 2229 | VAL | CA | 11.204 | 61.933 | 36.054 | 10.33 |
| 2230 | VAL | C | 11.237 | 63.384 | 36.609 | 10.96 |
| 2231 | VAL | O | 10.993 | 63.608 | 37.784 | 12.23 |
| 2232 | VAL | CB | 12.606 | 61.377 | 35.913 | 10.20 |
| 2233 | VAL | CG1 | 12.546 | 59.906 | 35.484 | 11.84 |
| 2234 | VAL | CG2 | 13.332 | 61.458 | 37.253 | 10.96 |
| 2235 | ILE | N | 11.560 | 64.377 | 35.760 | 10.85 |
| 2236 | ILE | CA | 11.577 | 65.764 | 36.191 | 8.53 |
| 2237 | ILE | C | 10.208 | 66.186 | 36.747 | 9.55 |
| 2238 | ILE | O | 10.125 | 66.781 | 37.812 | 13.70 |
| 2239 | ILE | CB | 12.040 | 66.687 | 35.033 | 12.52 |
| 2240 | ILE | CG1 | 13.570 | 66.56 | 434.80 | 611.25 |
| 2241 | ILE | CG2 | 11.699 | 68.16 | 435.33 | 53.61 |
| 2242 | ILE | CD1 | 14.012 | 67.08 | 733.57 | 12.56 |
| 2243 | GLU | N | 9.121 | 65.820 | 36.020 | 9.61 |
| 2244 | GLU | CA | 7.751 | 66.097 | 36.515 | 9.71 |
| 2245 | GLU | C | 7.388 | 65.403 | 37.845 | 11.33 |
| 2246 | GLU | O | 6.888 | 65.977 | 38.806 | 9.63 |
| 2247 | GLU | CB | 6.755 | 65.653 | 35.442 | 9.81 |
| 2248 | GLU | CG | 5.280 | 65.882 | 35.870 | 17.01 |
| 2249 | GLU | CD | 4.989 | 67.337 | 36.130 | 20.22 |
| 2250 | GLU | OE1 | 5.765 | 68.150 | 35.672 | 20.12 |
| 2251 | GLU | OE2 | 4.011 | 67.716 | 36.770 | 21.83 |
| 2252 | GLY | N | 7.672 | 64.081 | 37.850 | 12.33 |
| 2253 | GLY | CA | 7.383 | 63.246 | 39.008 | 12.09 |
| 2254 | GLY | C | 8.175 | 63.692 | 40.243 | 13.63 |
| 2255 | GLY | O | 7.770 | 63.523 | 41.398 | 15.75 |
| 2256 | ALA | N | 9.326 | 64.327 | 39.971 | 12.57 |
| 2257 | ALA | CA | 10.116 | 64.799 | 41.081 | 14.07 |
| 2258 | ALA | C | 9.322 | 65.821 | 41.954 | 16.52 |
| 2259 | ALA | O | 9.483 | 65.941 | 43.167 | 16.67 |
| 2260 | ALA | CB | 11.371 | 65.387 | 40.495 | 12.23 |
| 2261 | LYS | N | 8.393 | 66.507 | 41.280 | 16.77 |
| 2262 | LYS | CA | 7.541 | 67.398 | 42.059 | 18.39 |
| 2263 | LYS | C | 6.832 | 66.678 | 43.258 | 17.76 |
| 2264 | LYS | O | 6.865 | 67.105 | 44.408 | 19.35 |
| 2265 | LYS | CB | 6.506 | 68.005 | 41.124 | 17.12 |
| 2266 | LYS | CG | 7.090 | 68.856 | 39.992 | 14.36 |
| 2267 | LYS | CD | 5.966 | 69.306 | 39.075 | 15.39 |
| 2268 | LYS | CE | 6.435 | 70.134 | 37.894 | 16.39 |
| 2269 | LYS | NZ | 5.285 | 70.300 | 36.996 | 21.56 |
| 2270 | PHE | N | 6.264 | 65.515 | 42.907 | 14.95 |
| 2271 | PHE | CA | 5.549 | 64.731 | 43.913 | 14.55 |
| 2272 | PHE | C | 6.529 | 64.115 | 44.923 | 15.10 |
| 2273 | PHE | O | 6.356 | 64.173 | 46.135 | 14.00 |
| 2274 | PHE | CB | 4.737 | 63.652 | 43.197 | 14.81 |
| 2275 | PHE | CG | 4.063 | 62.700 | 44.139 | 15.08 |
| 2276 | PHE | CD1 | 4.788 | 61.680 | 44.744 | 16.62 |
| 2277 | PHE | CD2 | 2.722 | 62.833 | 44.438 | 14.90 |
| 2278 | PHE | CE1 | 4.201 | 60.834 | 45.687 | 14.26 |
| 2279 | PHE | CE2 | 2.122 | 61.981 | 45.359 | 13.81 |
| 2280 | PHE | CZ | 2.854 | 60.983 | 45.992 | 11.28 |
| 2281 | ILE | N | 7.602 | 63.516 | 44.369 | 15.29 |
| 2282 | ILE | CA | 8.620 | 62.994 | 45.271 | 14.87 |
| 2283 | ILE | C | 9.098 | 64.058 | 46.323 | 18.20 |
| 2284 | ILE | O | 9.269 | 63.810 | 47.523 | 18.22 |
| 2285 | ILE | CB | 9.781 | 62.450 | 44.423 | 13.45 |
| 2286 | ILE | CG1 | 9.314 | 61.364 | 43.436 | 10.62 |
| 2287 | ILE | CG2 | 10.886 | 61.886 | 45.294 | 11.70 |
| 2288 | ILE | CD1 | 8.566 | 60.206 | 44.086 | 4.61 |
| 2289 | MET | N | 9.239 | 65.281 | 45.809 | 18.52 |
| 2290 | MET | CA | 9.792 | 66.326 | 46.640 | 18.33 |
| 2291 | MET | C | 8.732 | 67.081 | 47.515 | 19.20 |
| 2292 | MET | O | 8.959 | 68.195 | 47.962 | 19.72 |
| 2293 | MET | CB | 10.605 | 67.243 | 45.721 | 17.77 |
| 2294 | MET | CG | 11.851 | 66.555 | 45.143 | 19.38 |
| 2295 | MET | SD | 12.907 | 65.705 | 46.383 | 20.87 |
| 2296 | MET | CE | 13.821 | 67.149 | 46.923 | 16.05 |
| 2297 | GLY | N | 7.574 | 66.434 | 47.745 | 18.14 |
| 2298 | GLY | CA | 6.695 | 66.952 | 48.792 | 18.26 |
| 2299 | GLY | C | 5.452 | 67.686 | 48.275 | 20.47 |
| 2300 | GLY | O | 4.563 | 68.022 | 49.049 | 22.07 |
| 2301 | ASP | N | 5.356 | 67.942 | 46.965 | 20.50 |
| 2302 | ASP | CA | 4.108 | 68.483 | 46.437 | 17.37 |
| 2303 | ASP | C | 3.162 | 67.337 | 46.013 | 17.32 |
| 2304 | ASP | O | 2.919 | 67.081 | 44.841 | 18.62 |
| 2305 | ASP | CB | 4.439 | 69.421 | 45.276 | 19.62 |
| 2306 | ASP | CG | 3.154 | 70.077 | 44.730 | 24.90 |
| 2307 | ASP | OD1 | 2.113 | 69.959 | 45.386 | 26.11 |
| 2308 | ASP | OD2 | 3.181 | 70.716 | 43.684 | 25.14 |
| 2309 | SER | N | 2.580 | 66.630 | 46.985 | 16.61 |
| 2310 | SER | CA | 1.600 | 65.618 | 46.540 | 16.15 |
| 2311 | SER | C | 0.437 | 66.083 | 45.684 | 16.64 |
| 2312 | SER | O | −0.191 | 65.274 | 45.017 | 19.31 |
| 2313 | SER | CB | 1.018 | 64.974 | 47.843 | 16.12 |
| 2314 | SER | OG | 1.977 | 64.473 | 48.858 | 18.84 |
| 2315 | SER | N | 0.137 | 67.393 | 45.713 | 16.18 |
| 2316 | SER | CA | −1.081 | 67.847 | 45.042 | 14.76 |
| 2317 | SER | C | −1.003 | 67.619 | 43.503 | 14.88 |
| 2318 | SER | O | −2.019 | 67.519 | 42.820 | 15.72 |
| 2319 | SER | CB | −1.161 | 69.349 | 45.254 | 13.96 |
| 2320 | SER | OG | −0.260 | 70.137 | 44.401 | 22.60 |
| 2321 | VAL | N | 0.253 | 67.507 | 43.003 | 13.31 |
| 2322 | VAL | CA | 0.437 | 67.281 | 41.570 | 14.74 |
| 2323 | VAL | C | −0.202 | 65.960 | 41.092 | 15.66 |
| 2324 | VAL | O | −0.608 | 65.824 | 39.951 | 13.81 |
| 2325 | VAL | CB | 1.896 | 67.243 | 41.083 | 15.18 |

TABLE D-continued

Table of the orthogonal three dimensional coordinates in Ångstroms and B factors (Å$^2$) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 2326 | VAL | CG1 | 2.814 | 66.190 | 41.711 | 12.54 |
| 2327 | VAL | CG2 | 2.515 | 68.549 | 40.598 | 15.63 |
| 2328 | GLN | N | -0.243 | 64.979 | 42.006 | 16.96 |
| 2329 | GLN | CA | -0.793 | 63.684 | 41.636 | 18.92 |
| 2330 | GLN | C | -2.226 | 63.773 | 41.066 | 21.43 |
| 2331 | GLN | O | -2.521 | 63.253 | 39.993 | 24.69 |
| 2332 | GLN | CB | -0.734 | 62.761 | 42.839 | 17.47 |
| 2333 | GLN | CG | -1.288 | 61.371 | 42.515 | 18.74 |
| 2334 | GLN | CD | -0.938 | 60.331 | 43.569 | 18.38 |
| 2335 | GLN | OE1 | -0.084 | 60.526 | 44.399 | 19.34 |
| 2336 | GLN | NE2 | -1.630 | 59.234 | 43.514 | 18.40 |
| 2337 | ASP | N | -3.081 | 64.507 | 41.797 | 23.31 |
| 2338 | ASP | CA | -4.435 | 64.639 | 41.265 | 24.99 |
| 2339 | ASP | C | -4.498 | 65.555 | 40.036 | 24.90 |
| 2340 | ASP | O | -5.371 | 65.464 | 39.191 | 27.85 |
| 2341 | ASP | CB | -5.359 | 65.090 | 42.386 | 30.46 |
| 2342 | ASP | CG | -5.898 | 63.864 | 43.139 | 38.34 |
| 2343 | ASP | OD1 | -6.096 | 62.796 | 42.538 | 41.41 |
| 2344 | ASP | OD2 | -6.133 | 63.968 | 44.331 | 40.64 |
| 2345 | GLN | N | -3.481 | 66.421 | 39.920 | 24.19 |
| 2346 | GLN | CA | -3.341 | 67.176 | 38.686 | 24.10 |
| 2347 | GLN | C | -3.036 | 66.310 | 37.465 | 22.53 |
| 2348 | GLN | O | -3.619 | 66.479 | 36.402 | 22.16 |
| 2349 | GLN | CB | -2.236 | 68.189 | 38.854 | 27.88 |
| 2350 | GLN | CG | -2.519 | 69.162 | 39.994 | 35.96 |
| 2351 | GLN | CD | -1.452 | 70.219 | 39.986 | 41.70 |
| 2352 | GLN | OE1 | -1.042 | 70.696 | 38.939 | 46.03 |
| 2353 | GLN | NE2 | -0.989 | 70.532 | 41.190 | 41.69 |
| 2354 | TRP | N | -2.111 | 65.357 | 37.651 | 20.33 |
| 2355 | TRP | CA | -1.847 | 64.398 | 36.574 | 17.39 |
| 2356 | TRP | C | -3.136 | 63.679 | 36.183 | 17.81 |
| 2357 | TRP | O | -3.426 | 63.468 | 35.016 | 19.79 |
| 2358 | TRP | CB | -0.830 | 63.332 | 36.993 | 13.77 |
| 2359 | TRP | CG | 0.516 | 63.940 | 37.335 | 10.55 |
| 2360 | TRP | CD1 | 1.046 | 65.159 | 36.878 | 9.50 |
| 2361 | TRP | CD2 | 1.470 | 63.387 | 38.256 | 8.89 |
| 2362 | TRP | NE1 | 2.254 | 65.372 | 37.454 | 9.63 |
| 2363 | TRP | CE2 | 2.563 | 64.307 | 38.309 | 9.34 |
| 2364 | TRP | CE3 | 1.485 | 62.233 | 38.992 | 7.20 |
| 2365 | TRP | CZ2 | 3.624 | 64.047 | 39.152 | 6.71 |
| 2366 | TRP | CZ3 | 2.570 | 61.964 | 39.836 | 8.42 |
| 2367 | TRP | CH2 | 3.652 | 62.866 | 39.910 | 6.38 |
| 2368 | LYS | N | -3.920 | 63.356 | 37.205 | 19.50 |
| 2369 | LYS | CA | -5.171 | 62.681 | 36.902 | 22.56 |
| 2370 | LYS | C | -6.181 | 63.495 | 36.071 | 23.90 |
| 2371 | LYS | O | -6.735 | 63.007 | 35.084 | 23.96 |
| 2372 | LYS | CB | -5.799 | 62.361 | 38.218 | 24.50 |
| 2373 | LYS | CG | -7.008 | 61.458 | 38.044 | 28.26 |
| 2374 | LYS | CD | -7.501 | 61.118 | 39.433 | 34.93 |
| 2375 | LYS | CE | -8.576 | 60.059 | 39.389 | 39.02 |
| 2376 | LYS | NZ | -9.083 | 59.968 | 40.759 | 41.94 |
| 2377 | GLU | N | -6.383 | 64.761 | 36.493 | 23.93 |
| 2378 | GLU | CA | -7.181 | 65.678 | 35.682 | 24.58 |
| 2379 | GLU | C | -6.649 | 65.760 | 34.242 | 21.99 |
| 2380 | GLU | O | -7.318 | 65.458 | 33.269 | 22.01 |
| 2381 | GLU | CB | -7.206 | 67.072 | 36.321 | 30.24 |
| 2382 | GLU | CG | -7.960 | 67.120 | 37.657 | 42.65 |
| 2383 | GLU | CD | -9.484 | 67.012 | 37.473 | 50.82 |
| 2384 | GLU | OE1 | 10.159 | 68.045 | 37.475 | 54.25 |
| 2385 | GLU | OE2 | -9.972 | 65.894 | 37.327 | 54.41 |
| 2386 | LEU | N | -5.361 | 66.102 | 34.158 | 21.08 |
| 2387 | LEU | CA | -4.739 | 66.203 | 32.844 | 22.45 |
| 2388 | LEU | C | -4.934 | 65.008 | 31.923 | 23.20 |
| 2389 | LEU | O | -5.055 | 65.104 | 30.712 | 23.99 |
| 2390 | LEU | CB | -3.233 | 66.395 | 33.046 | 20.54 |
| 2391 | LEU | CG | -2.790 | 67.845 | 33.160 | 18.96 |
| 2392 | LEU | CD1 | -1.487 | 68.124 | 33.900 | 20.13 |
| 2393 | LEU | CD2 | -3.847 | 68.949 | 33.168 | 19.21 |
| 2394 | SER | N | -4.864 | 63.864 | 32.562 | 23.38 |
| 2395 | SER | CA | -4.721 | 62.687 | 31.728 | 22.92 |
| 2396 | SER | C | -6.100 | 62.254 | 31.142 | 23.30 |
| 2397 | SER | O | -6.151 | 61.450 | 30.228 | 24.72 |
| 2398 | SER | CB | -4.319 | 61.591 | 32.750 | 22.16 |
| 2399 | SER | OG | -5.473 | 60.975 | 33.415 | 27.77 |
| 2400 | HIS | N | -7.184 | 62.819 | 31.732 | 25.90 |
| 2401 | HIS | CA | -8.537 | 62.618 | 31.210 | 28.59 |
| 2402 | HIS | C | -9.030 | 61.156 | 31.255 | 30.18 |
| 2403 | HIS | O | -9.507 | 60.620 | 30.270 | 30.25 |
| 2404 | HIS | CB | -8.602 | 63.146 | 29.769 | 30.95 |
| 2405 | HIS | CG | -8.313 | 64.620 | 29.712 | 34.62 |
| 2406 | HIS | ND1 | -7.438 | 65.162 | 28.838 | 36.95 |
| 2407 | HIS | CD2 | -8.885 | 65.653 | 30.480 | 34.71 |
| 2408 | HIS | CE1 | -7.474 | 66.484 | 29.058 | 38.33 |
| 2409 | HIS | NE2 | -8.339 | 66.806 | 30.042 | 36.25 |
| 2410 | GLU | N | -8.866 | 60.555 | 32.442 | 32.02 |
| 2411 | GLU | CA | -8.880 | 59.114 | 32.550 | 32.12 |
| 2412 | GLU | C | 10.319 | 58.458 | 32.274 | 34.76 |
| 2413 | GLU | O | 10.404 | 57.302 | 31.847 | 35.29 |
| 2414 | GLU | CB | -8.241 | 58.464 | 33.758 | 32.31 |
| 2415 | GLU | CG | -8.829 | 58.921 | 35.045 | 34.00 |
| 2416 | GLU | CD | -8.282 | 58.062 | 36.156 | 35.79 |
| 2417 | GLU | OE1 | -7.104 | 57.728 | 36.149 | 34.22 |
| 2418 | GLU | OE2 | -9.052 | 57.673 | 37.019 | 40.13 |
| 2419 | ASP | N | 11.327 | 59.215 | 32.616 | 37.80 |
| 2420 | ASP | CA | 12.729 | 58.834 | 32.627 | 40.36 |
| 2421 | ASP | C | 13.412 | 58.996 | 31.213 | 42.09 |
| 2422 | ASP | OCT1 | 13.102 | 59.944 | 30.481 | 43.37 |
| 2423 | ASP | CB | 13.289 | 59.623 | 33.836 | 41.96 |
| 2424 | ASP | CG | 12.785 | 58.974 | 35.133 | 47.10 |
| 2425 | ASP | OD1 | 12.786 | 57.758 | 35.206 | 47.56 |
| 2426 | ASP | OD2 | 12.374 | 59.654 | 36.072 | 50.59 |
| 2427 | ASP | OCT2 | 14.223 | 58.147 | 30.834 | 44.87 |
| 2428 | HOH | O | 1.590 | 36.257 | 19.829 | 22.41 |
| 2429 | HOH | O | 8.296 | 45.178 | 41.518 | 8.41 |
| 2430 | HOH | O | 9.270 | 50.471 | 21.734 | 19.65 |
| 2431 | HOH | O | 7.577 | 61.174 | 51.241 | 16.06 |
| 2432 | HOH | O | 18.943 | 38.939 | 37.699 | 17.27 |
| 2433 | HOH | O | 22.811 | 45.617 | 27.594 | 16.66 |
| 2434 | HOH | O | 6.371 | 36.383 | 28.124 | 13.20 |
| 2435 | HOH | O | 9.209 | 32.873 | 26.183 | 14.51 |
| 2436 | HOH | O | 16.479 | 44.901 | 44.793 | 23.25 |
| 2437 | HOH | O | 8.760 | 29.925 | 27.422 | 20.25 |
| 2438 | HOH | O | 4.215 | 58.428 | 19.845 | 22.23 |
| 2439 | HOH | O | 9.419 | 63.753 | 24.541 | 24.52 |
| 2440 | HOH | O | -0.851 | 27.498 | 26.895 | 29.29 |
| 2441 | HOH | O | 15.941 | 25.654 | 27.134 | 22.26 |
| 2442 | HOH | O | 19.413 | 32.977 | 27.432 | 12.77 |
| 2443 | HOH | O | 27.512 | 49.614 | 31.335 | 40.23 |
| 2444 | HOH | O | -0.436 | 61.801 | 47.891 | 47.15 |
| 2445 | HOH | O | 21.459 | 47.078 | 25.096 | 17.33 |
| 2446 | HOH | O | 2.837 | 27.864 | 27.715 | 17.29 |
| 2447 | HOH | O | 5.024 | 60.810 | 49.088 | 29.47 |
| 2448 | HOH | O | 20.997 | 29.985 | 32.990 | 39.54 |
| 2449 | HOH | O | 10.885 | 59.567 | 51.200 | 19.14 |
| 2450 | HOH | O | 16.023 | 56.714 | 18.058 | 21.46 |
| 2451 | HOH | O | 8.071 | 59.483 | 19.187 | 23.78 |
| 2452 | HOH | O | 22.091 | 57.680 | 39.956 | 22.67 |
| 2453 | HOH | O | 19.064 | 49.798 | 21.891 | 21.33 |
| 2454 | HOH | O | -5.143 | 44.798 | 23.400 | 15.49 |
| 2455 | HOH | O | 1.980 | 66.688 | 31.326 | 25.33 |
| 2456 | HOH | O | 17.162 | 41.413 | 37.458 | 26.52 |
| 2457 | HOH | O | -1.859 | 60.380 | 39.401 | 20.12 |
| 2458 | HOH | O | -4.668 | 51.480 | 41.919 | 15.16 |
| 2459 | HOH | O | 4.708 | 30.728 | 44.704 | 22.73 |
| 2460 | HOH | O | 9.740 | 65.513 | 50.805 | 38.71 |
| 2461 | HOH | O | 1.814 | 50.953 | 17.669 | 30.06 |
| 2462 | HOH | O | 15.786 | 35.633 | 20.587 | 12.33 |
| 2463 | HOH | O | 1.462 | 57.677 | 45.374 | 23.51 |
| 2464 | HOH | O | 9.068 | 56.054 | 44.758 | 18.52 |
| 2465 | HOH | O | 25.060 | 34.834 | 23.092 | 34.44 |

TABLE D-continued

Table of the orthogonal three dimensional coordinates in Ångstroms and B factors (Å²) for Protein Tyrosine Phosphatase 1B complexed with 2-(oxalyl-amino)-7-(1,1,3-trioxo-1H-benzo[d]isothiazol-3-yloxomethyl)-4,7-dihydro-5H-thieno[2,3-c]pyran-3-carboxylic acid and the water molecule which forms hydrogen bonds with the pyran oxygen atom, the side chain oxygen atom and aspartic acid 48 (Example XX).

| No | Amino acid | | X | Y | Z | B |
|---|---|---|---|---|---|---|
| 2466 | HOH | O | 1.037 | 20.342 | 34.088 | 47.03 |
| 2467 | HOH | O | 16.506 | 29.904 | 19.735 | 17.43 |
| 2468 | HOH | O | 20.557 | 38.125 | 16.713 | 33.14 |
| 2469 | HOH | O | 10.887 | 44.145 | 44.506 | 27.05 |
| 2470 | HOH | O | 12.790 | 34.400 | 33.238 | 10.97 |
| 2471 | HOH | O | 13.677 | 30.353 | 37.505 | 59.66 |
| 2472 | HOH | O | −3.086 | 57.405 | 41.033 | 36.02 |
| 2473 | HOH | O | 12.385 | 42.893 | 25.595 | 46.73 |
| 2474 | HOH | O | 21.344 | 47.271 | 40.333 | 20.06 |
| 2475 | HOH | O | 25.419 | 45.911 | 39.851 | 27.74 |
| 2476 | HOH | O | 9.958 | 57.066 | 20.295 | 16.04 |
| 2477 | HOH | O | 13.824 | 63.678 | 20.576 | 37.51 |
| 2478 | HOH | O | 1.949 | 34.748 | 41.972 | 16.46 |
| 2479 | HOH | O | 11.924 | 25.680 | 18.786 | 24.92 |
| 2480 | HOH | O | 8.764 | 31.931 | 16.917 | 30.52 |
| 2481 | HOH | O | −4.221 | 36.972 | 46.588 | 28.63 |
| 2482 | HOH | O | 13.821 | 31.194 | 39.085 | 34.61 |
| 2483 | HOH | O | 6.696 | 27.669 | 43.269 | 29.04 |
| 2484 | HOH | O | 0.694 | 24.349 | 39.414 | 33.75 |
| 2485 | HOH | O | 3.032 | 49.405 | 45.063 | 12.51 |
| 2486 | HOH | O | 9.849 | 48.468 | 46.210 | 29.19 |
| 2487 | HOH | O | 23.380 | 28.613 | 22.797 | 25.48 |
| 2488 | HOH | O | 10.046 | 47.774 | 27.577 | 19.52 |
| 2489 | HOH | O | 21.363 | 43.357 | 41.852 | 34.99 |
| 2490 | HOH | O | 19.727 | 38.364 | 41.922 | 52.15 |
| 2491 | HOH | O | 13.859 | 55.007 | 29.048 | 33.35 |
| 2492 | HOH | O | 14.515 | 57.104 | 53.219 | 21.80 |
| 2493 | HOH | O | −9.836 | 29.524 | 39.997 | 26.93 |
| 2494 | HOH | O | 15.693 | 44.242 | 14.713 | 25.00 |
| 2495 | HOH | O | −0.431 | 50.825 | 24.089 | 17.41 |
| 2496 | HOH | O | 4.304 | 42.234 | 42.012 | 13.63 |
| 2497 | HOH | O | 7.488 | 43.798 | 44.456 | 22.44 |
| 2498 | HOH | O | −7.835 | 34.880 | 45.632 | 36.15 |
| 2499 | HOH | O | 2.138 | 68.198 | 50.281 | 19.61 |
| 2500 | HOH | O | 2.980 | 26.111 | 37.904 | 31.74 |
| 2501 | HOH | O | 7.532 | 71.080 | 47.284 | 47.61 |
| 2502 | HOH | O | 23.456 | 43.284 | 24.031 | 33.57 |
| 2503 | HOH | O | 12.879 | 33.827 | 17.029 | 41.26 |
| 2504 | HOH | O | 20.888 | 52.812 | 40.217 | 32.00 |
| 2505 | HOH | O | −9.383 | 62.551 | 34.350 | 30.07 |
| 2506 | HOH | O | −8.835 | 48.846 | 24.502 | 42.77 |
| 2507 | HOH | O | 9.650 | 31.084 | 37.437 | 29.51 |
| 2508 | HOH | O | 26.005 | 51.793 | 38.260 | 31.70 |
| 2509 | HOH | O | 24.046 | 63.460 | 39.268 | 43.53 |
| 2510 | HOH | O | 19.228 | 57.561 | 17.667 | 36.93 |
| 2511 | HOH | O | 29.104 | 43.058 | 29.224 | 34.73 |
| 2512 | HOH | O | −3.271 | 63.254 | 48.607 | 39.25 |
| 2513 | HOH | O | −8.324 | 51.286 | 27.830 | 31.97 |
| 2514 | HOH | O | 21.456 | 64.000 | 35.006 | 51.35 |
| 2515 | HOH | O | −8.889 | 27.216 | 28.324 | 24.05 |
| 2516 | HOH | O | −7.122 | 39.723 | 21.296 | 25.00 |
| 2517 | HOH | O | 8.123 | 69.041 | 34.700 | 34.79 |
| 2518 | HOH | O | 11.982 | 38.083 | 21.811 | 25.95 |
| 2519 | HOH | O | 4.694 | 64.020 | 48.437 | 21.02 |
| 2520 | HOH | O | 17.885 | 25.230 | 29.617 | 36.99 |
| 2521 | HOH | O | 19.286 | 25.222 | 33.390 | 42.05 |
| 2522 | HOH | O | −8.562 | 44.803 | 26.142 | 51.85 |
| 2523 | HOH | O | −2.242 | 26.527 | 23.393 | 43.07 |
| 2524 | HOH | O | 15.970 | 32.954 | 18.673 | 44.57 |
| 2525 | HOH | O | 16.957 | 72.759 | 19.740 | 41.48 |
| 2526 | HOH | O | 18.945 | 40.529 | 27.705 | 20.81 |
| 2527 | HOH | O | −6.563 | 33.542 | 23.890 | 44.78 |
| 2528 | HOH | O | 0.655 | 54.144 | 15.969 | 48.10 |
| 2529 | HOH | O | 15.452 | 42.847 | 26.665 | 67.31 |
| 2530 | HOH | O | −5.796 | 57.757 | 39.132 | 35.87 |
| 2531 | HOH | O | 19.494 | 43.627 | 13.835 | 34.84 |
| 2532 | HOH | O | 8.922 | 55.846 | 16.058 | 55.98 |
| 2533 | HOH | O | 12.263 | 58.246 | 17.626 | 37.03 |
| 2534 | HOH | O | 14.753 | 66.276 | 52.641 | 30.00 |
| 2535 | HOH | O | −0.697 | 58.698 | 48.711 | 56.27 |
| 2536 | HOH | O | 4.631 | 63.608 | 25.321 | 39.92 |
| 2537 | HOH | O | 26.057 | 51.777 | 34.940 | 56.34 |
| 2538 | HOH | O | 25.752 | 58.882 | 40.841 | 54.74 |
| 2539 | HOH | O | 15.383 | 70.120 | 19.035 | 43.73 |
| 2540 | HOH | O | −8.062 | 21.118 | 40.565 | 30.10 |
| 2541 | HOH | O | −5.664 | 37.797 | 19.071 | 34.90 |
| 2542 | HOH | O | 21.557 | 47.692 | 21.844 | 42.58 |
| 2543 | HOH | O | 16.120 | 23.050 | 31.744 | 38.14 |
| 2544 | HOH | O | 14.291 | 55.688 | 33.958 | 43.49 |
| 2545 | HOH | O | 22.485 | 41.730 | 21.237 | 47.32 |
| 2546 | HOH | O | −3.228 | 63.778 | 28.090 | 44.59 |
| 2547 | HOH | O | 26.949 | 48.396 | 41.531 | 41.13 |
| 2548 | HOH | O | 23.942 | 39.006 | 22.657 | 43.94 |
| 2549 | HOH | O | 9.207 | 24.849 | 23.061 | 41.15 |
| 2550 | HOH | O | 6.750 | 71.340 | 43.221 | 54.51 |
| 2551 | HOH | O | 30.844 | 41.630 | 25.787 | 45.95 |
| 2552 | HOH | O | −3.732 | 34.406 | 21.323 | 35.90 |
| 2553 | HOH | O | −4.730 | 60.259 | 28.099 | 41.23 |
| 2554 | HOH | O | 25.149 | 31.323 | 20.979 | 58.72 |
| 2555 | HOH | O | 14.035 | 68.161 | 21.262 | 57.00 |
| 2556 | HOH | O | 12.454 | 34.648 | 27.576 | 54.08 |
| 2557 | HOH | O | 24.417 | 50.046 | 45.237 | 40.59 |
| 2558 | HOH | O | 5.535 | 36.921 | 48.195 | 32.86 |
| 2559 | HOH | O | 23.831 | 29.039 | 31.600 | 46.72 |
| 2560 | HOH | O | 21.844 | 62.478 | 48.694 | 45.22 |
| 2561 | HOH | O | 24.579 | 48.404 | 30.338 | 31.47 |
| 2562 | HOH | O | 14.659 | 31.918 | 30.697 | 18.81 |
| 2563 | HOH | O | −1.318 | 30.530 | 47.378 | 31.01 |
| 2564 | LIG | O1 | 13.892 | 44.198 | 17.349 | 17.64 |
| 2565 | LIG | C2 | 13.816 | 45.044 | 18.486 | 15.35 |
| 2566 | LIG | C3 | 12.387 | 45.372 | 18.768 | 14.39 |
| 2567 | LIG | C4 | 11.353 | 45.039 | 17.981 | 14.98 |
| 2568 | LIG | C5 | 11.543 | 44.211 | 16.758 | 12.97 |
| 2569 | LIG | C6 | 12.784 | 43.377 | 17.076 | 16.70 |
| 2570 | LIG | S7 | 11.937 | 46.075 | 20.258 | 13.76 |
| 2571 | LIG | C8 | 10.288 | 45.912 | 19.771 | 14.99 |
| 2572 | LIG | C9 | 10.047 | 45.402 | 18.557 | 16.33 |
| 2573 | LIG | C10 | 8.663 | 45.297 | 17.953 | 14.29 |
| 2574 | LIG | O11 | 8.537 | 45.250 | 16.765 | 16.29 |
| 2575 | LIG | O12 | 7.552 | 45.243 | 18.690 | 11.51 |
| 2576 | LIG | N13 | 9.206 | 46.366 | 20.611 | 15.13 |
| 2577 | LIG | C14 | 9.318 | 47.070 | 21.737 | 13.37 |
| 2578 | LIG | C15 | 7.975 | 47.489 | 22.364 | 13.19 |
| 2579 | LIG | O16 | 7.777 | 48.528 | 22.914 | 14.53 |
| 2580 | LIG | O17 | 7.008 | 46.559 | 22.413 | 13.61 |
| 2581 | LIG | O18 | 10.375 | 47.351 | 22.323 | 12.30 |
| 2582 | LIG | C19 | 14.638 | 46.212 | 18.060 | 13.64 |
| 2583 | LIG | O20 | 15.877 | 45.679 | 17.667 | 12.90 |
| 2584 | LIG | C21 | 16.713 | 45.231 | 18.698 | 11.97 |
| 2585 | LIG | C22 | 17.949 | 44.543 | 18.423 | 14.27 |
| 2586 | LIG | C23 | 18.635 | 44.315 | 19.609 | 13.98 |
| 2587 | LIG | S24 | 17.780 | 44.784 | 21.023 | 15.89 |
| 2588 | LIG | N25 | 16.601 | 45.291 | 20.050 | 12.72 |
| 2589 | LIG | C26 | 18.462 | 44.268 | 17.177 | 16.50 |
| 2590 | LIG | C27 | 19.670 | 43.576 | 17.086 | 13.27 |
| 2591 | LIG | C28 | 20.396 | 43.313 | 18.253 | 13.47 |
| 2592 | LIG | C29 | 19.871 | 43.620 | 19.501 | 12.46 |
| 2593 | LIG | O30 | 18.420 | 45.879 | 21.625 | 15.41 |
| 2594 | LIG | O31 | 17.376 | 43.603 | 21.782 | 15.88 |

The invention claimed is:

1. A method of inhibiting at least one intracellular or membrane-associated PTPase that has aspartic acid (Asp) in position 48 using the numbering for PTP1B, the method comprising exposing said at least one PTPase in which inhibition is intended to an inhibitor compound which fits spatially into the active site and the vicinity thereof, said compound comprising the following features and moieties:

I. a phosphate isostere which forms a salt bridge to the guanidinium group of arginine 221 and a hydrogen bond with a hydrogen atom donated by the backbone amide nitrogens of arginine 221 and glycine 220 such that the distance between the centroid of the phosphate isostere group and (I) the centroid of said guanidinium group ranges from 3.50–4.20 Å, (II) said arginine 221 backbone amide nitrogen ranges from 3.5–4.2 Å, and (III) said glycine 220 backbone amide nitrogen ranges from 2.7–3.5 Å; and II. (a) a carboxylic acid group or (b) a carboxylic acid isostere group selected from the following 5-membered heterocycles

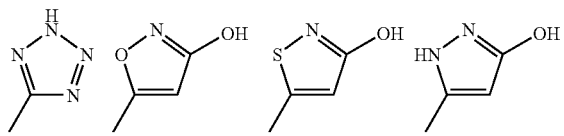

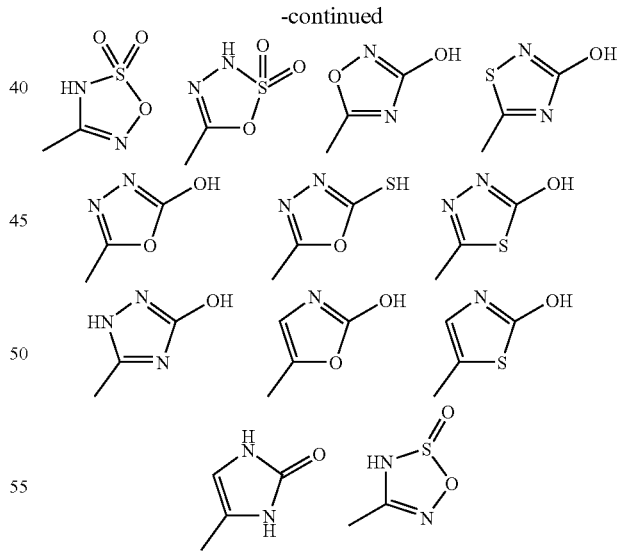

-continued wherein said acid or said isostere group forms a salt bridge to the side chain amino group of lysine 120 wherein the distance between the centroid of said carboxylic acid or carboxylic acid isostere and the side chain nitrogen atom of said lysine 120 ranges from 3.4–4.1 Å; and III. a hydrophobic group that interacts with the aromatic ring of tyrosine 46 such that the distance between the centroid of said hydrophobic group and the centroid of the aromatic ring of said tyrosine 46 ranges from 4.4–5.1 Å; and at least one of features IV through V:

IV. a hydrophobic group that interacts with the aromatic ring of phenylalanine 182 such that the distance between the centroid of said hydrophobic group and the centroid of the aromatic ring of said phenylalanine 182 ranges from 4.4–5.1 Å; and V. a hydrophobic group that interacts with the imidazole ring of histidine 182 such that the distance between the centroid of said hydrophobic group and the centroid of the aromatic ring of said histidine 182 ranges from 4.4–6.5 Å; and one or more of the following features VI–XXXVII:

VI. an amino group which forms a salt bridge to the side chain carboxylic acid group of aspartic acid 48 such that the distance between the nitrogen atom of said amino group and the centroid of said side chain carboxylic acid group of aspartic acid 48 ranges from 3.4–4.1 Å; and VII. two oxygen atoms which form hydrogen bonds via a water molecule to the side chain carboxylic acid group of aspartic acid 48 such that the distance between each of the two oxygen atoms and the centroid of said water molecule ranges from 2.5–3.6 Å and that the distance between said water molecule and the centroid of said side chain carboxylic acid group of aspartic acid 48 ranges from 2.5–3.6 Å and that the distance between said two oxygen atoms ranges from 2.5–3.0 Å; and VIII. a hydrophobic group that interacts with the side chain methylene groups of tyrosine 46 such that the distance between the centroid of said hydrophobic group and the centroid of the methylene groups of said tyrosine 46 ranges from 4.4–5.1 Å;

IX. a hydrophilic group that forms a hydrogen bond or forms a salt bridge with aspartic acid 181 such that the distance between the centroid of said hydrophilic group and the centroid of the carboxylic acid of said aspartic acid 181 ranges from 4.4–5.1 Å;

X. a hydrophobic group that interacts with tyrosine 46 and the methylene side chain atoms of arginine 47 such that the distance between the centroid of said hydrophobic group and the centroid of the aromatic ring of said tyrosine 46 ranges from 4.7–5.2 Å and the centroid of the methylene side chain atoms of said arginine 47 ranges from 4.5–5.5 Å;

XI. a hydrophilic group that forms a hydrogen bond with the one or more hydrogen atoms donated by the guanidinium group of arginine 47 such that the distance between the centroid of said hydrophilic group and the guanidinium group of said arginine 47 ranges from 2.7–3.5 Å;

XII. a hydrophilic group that forms a hydrogen bond with the hydrogen atom donated by the backbone amide nitrogen of arginine 47 such that the distance between the centroid of said hydrophilic group and the amide nitrogen group of said arginine 47 ranges from 2.7–4.0 Å;

XIII. a hydrophilic group that forms a hydrogen bond with the hydrogen atom donated by the backbone amide nitrogen of aspartic acid 48 such that the distance between the centroid of said hydrophilic group and the amide nitrogen group of said aspartic acid 48 ranges from 2.7–4.0 Å;

XIV. a hydrophilic group that interacts with the backbone amide carbonyl group of asparagine 44 such that the distance between the centroid of said hydrophilic group and the amide carbonyl group of said asparagine 44 ranges from 2.7–4.0 Å;

XV. a hydrophilic group that forms a hydrogen bond with one or more hydrogen atoms donated by the guanidinium group of arginine 45 such that the distance between the centroid of said hydrophilic group and the centroid of the guanidinium group of said arginine 45 ranges from 2.7–4.0 Å;

XVI. a hydrophilic group that forms a salt bridge with the guanidinium group of arginine 45 such that the distance between the centroid of said hydrophilic group and the centroid of the guanidinium group of said arginine 45 ranges from 2.7–4.0 Å;

XVII. a hydrophobic group that interacts with the side chain methylene groups of arginine 45 such that the distance between the centroid of said hydrophilic group and the centroid of the methylene groups of said arginine 45 ranges from 4.4–5.1 Å;

XVIII. a hydrophilic group that forms a hydrogen bond with the backbone amide carbonyl group of arginine 45 such that the distance between the centroid of said hydrophilic group and the amide carbonyl group of said arginine 45 ranges from 2.7–4.0 Å;

XIX. a hydrophilic group that forms a hydrogen bond with the side chain hydroxy group of tyrosine 46 such that the distance between the centroid of said hydrophilic group and the hydroxy group of said tyrosine 46 ranges from 2.7–4.0 Å;

XX. a hydrophilic group that forms a hydrogen bond with the side chain amino group of lysine 41 such that the distance between the centroid of said hydrophilic group and the amino group of said lysine 41 ranges from 2.7–4.0 Å;

XXI. a hydrophobic group that interacts with the side chain methylene groups of lysine 41 such that the distance between the centroid of said hydrophilic group and the centroid of the methylene groups of said lysine 41 ranges from 4.4–5.1 Å;

XXII. a hydrophobic group that interacts with the side chain methylene groups of leucine 88 such that the distance between the centroid of said hydrophilic group and the centroid of the methylene groups of said leucine 88 ranges from 4.4–5.1 Å;

XXIII. a hydrophilic group that forms a hydrogen bond with the side chain hydroxy group of serine 118 such that the distance between the centroid of said hydrophilic group and the hydroxy group of said serine 118 ranges from 2.7–4.0 Å;

XXIV. a hydrophilic group that forms a hydrogen bond with the backbone amide carbonyl group of leucine 119 such that the distance between the centroid of said hydrophilic group and the amide carbonyl group of said leucine 119 ranges from 2.7–4.0 Å;

XXV. a hydrophilic group that forms a hydrogen bond with the one of the hydrogen atoms donated by the side chain amide nitrogen of glutamine 262 such that the distance between the centroid of said hydrophilic group and the amide nitrogen group of said glutamine 262 ranges from 2.7–4.0 Å;

XXVI. a hydrophilic group that forms a hydrogen bond with the hydrogen atom donated by the backbone amide group nitrogen of glycine 259 such that the distance between the centroid of said hydrophilic group and the amide nitrogen group of said glycine 259 ranges from 2.7–4.0 Å;

XXVII. a hydrophilic group that forms a hydrogen bond with one or more hydrogen atoms donated by the side chain guanidinium group of arginine 254 such that the distance between the centroid of said hydrophilic group and the centroid of the guanidinium group of said arginine 254 ranges from 2.7–4.0 Å;

XXVIII. a hydrophilic group that forms a salt bridge with the guanidinium group of arginine 254 such that the distance between the centroid of said hydrophilic group and the centroid of the guanidinium group of said arginine 254 ranges from 2.7–4.0 Å;

XXIX. a hydrophobic group that interacts with the side chain methylene groups of arginine 254 such that the distance between the centroid of said hydrophilic group and the centroid of the methylene groups of said arginine 254 ranges from 4.4–5.1 Å;

XXX. a hydrophilic group that forms a hydrogen bond with one or more hydrogen atoms donated by the guanidinium group of arginine 24 such that the distance between the centroid of said hydrophilic group and the centroid of the guanidinium group of said arginine 24 ranges from 2.7–4.0 Å;

XXXI. a hydrophilic group that forms a salt bridge with the guanidinium group of arginine 24 such that the distance between the centroid of said hydrophilic group and the centroid of the guanidinium group of said arginine 24 ranges from 2.7–4.0 Å;

XXXII. a hydrophobic group that interacts with the side chain methylene groups of arginine 24 such that the distance between the centroid of said hydrophilic group and the centroid of the methylene groups of said arginine 24 ranges from 4.4–5.1 Å;

XXXIII. a hydrophilic group that forms a hydrogen bond with the backbone amide carbonyl group of aspartic acid 48 such that the distance between the centroid of said hydrophilic group and the backbone amide carbonyl group of said aspartic acid 48 ranges from 2.7–3.5 Å;

XXXIV. a hydrophobic group that interacts with the side chain atoms of methionine 258 such that the distance between the centroid of said hydrophobic group and the centroid of the side chain of said methionine 258 ranges from 4.5–6.2 Å;

XXXV. a hydrophobic group that interacts with glycine 259 such that the distance between the centroid of said hydrophobic group and the centroid of the alpha-carbon atom of said glycine 259 ranges from 4.5–6.2 Å;

XXXVI. a hydrophobic group that interacts with phenylalanine 52 such that the distance between the centroid of said hydrophobic group and the centroid of the aromatic group of said phenylalanine 52 ranges from 4.1–9.1 Å; or XXXVII. a hydrophobic group that interacts with methionine 258, glycine 259 and phenylalanine 52 being part of a hydrophobic pocket such that the distance between the centroid of said hydrophobic group and (i) the centroid of the side chain of said methionine 258 ranges from 4.1–7.2 Å, (ii) the centroid of said glycine 259 ranges from 4.7–7.7 Å, and (iii) the centroid of the side chain of said phenylalanine 52 ranges from 4.1–9.1 Å, wherein said compound is of the Formula 1

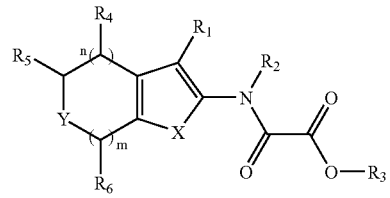

Formula 1 wherein n is 0, 1 or 2, with the proviso that n is 1 or 2 when m is 0;

m is 0, 1 or 2, with the proviso that m is 1 or 2 when n is 0;

X is S, O, or $NR_8$;

Y is $NR_7$, O, S, SO, or $SO_2$;

$R_1$ is hydrogen, $COOR_3$, or selected from the following 5-membered heterocycles:

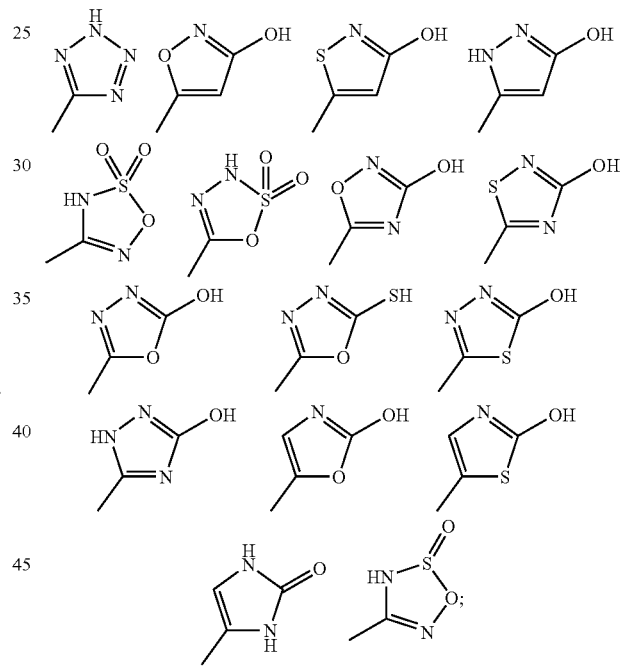

$R_2$ is hydrogen, $C_1$–$C_6$alkyl, hydroxy, or $NR_9R_{10}$;

$R_3$ is hydrogen, $C_1$–$C_6$alkyl, aryl$C_1$–$C_6$alkyl, $C_1$–$C_6$alkylcarbonyloxy$C_1$–$C_6$alkyl, or $C_1$–$C_6$alkylcarbonyloxyaryl$C_1$–$C_6$alkyl;

$R_4$, $R_5$ and $R_6$ are independently hydrogen, trihalomethyl, $C_1$–$C_6$alkyl, aryl, aryl$C_1$–$C_6$alkyl, hydroxy, oxo, carboxy, carboxy$C_1$–$C_6$alkyl, $C_1$–$C_6$alkyloxy-carbonyl, aryloxycarbonyl, aryl$C_1$–$C_6$alkyloxycarbonyl, $C_1$–$C_6$alkyloxy, $C_1$–$C_6$alkyloxy$C_1$–$C_6$alkyl, aryloxy, aryl$C_1$–$C_6$alkyloxy, aryl$C_1$–$C_6$alkyloxy$C_1$–$C_6$alkyl, thio, $C_1$–$C_6$alkylthio, $C_1$–$C_6$alkylthio$C_1$–$C_6$alkyl, arylthio, aryl$C_1$–$C_6$alkylthio, aryl$C_1$–$C_6$alkylthio$C_1$–$C_6$alkyl, $NR_9R_{10}$, $C_1$–$C_6$alkylamino$C_1$–$C_6$alkyl, aryl$C_1$–$C_6$alkylamino$C_1$–$C_6$alkyl, di(aryl$C_1$–$C_6$alkyl)amino$C_1$–$C_6$alkyl, $C_1$–$C_6$alkylcarbonyl, $C_1$–$C_6$alkylcarbonyl$C_1$–$C_6$alkyl, arylC$_1$–C$_6$alkylcarbonyl,
arylC$_1$–C$_6$alkylcarbonylC$_1$–C$_6$alkyl,
C$_1$–C$_6$alkylcarboxy, C$_1$–C$_6$alkylcarboxyC$_1$–C$_6$-alkyl,
arylcarboxy, arylcarboxyC$_1$–C$_6$alkyl,
arylC$_1$–C$_6$alkylcarboxy,
arylC$_1$–C$_6$alkylcarboxyC$_1$–C$_6$alkyl,
C$_1$–C$_6$alkylcarbonylamino, C$_1$–C$_6$alkylcarbonylaminoC$_1$–C$_6$alkyl, -carbonylNR$_7$C$_1$–C$_6$alkylCOR$_{13}$,
arylC$_1$–C$_6$alkylcarbonyl-amino,
arylC$_1$–C$_6$alkylcarbonylaminoC$_1$–C$_6$alkyl,
CONR$_9$R$_{10}$, or C$_1$–C$_6$alkyl-CONR$_9$R$_{10}$ wherein the alkyl and aryl groups are optionally substituted and R$_{13}$ is NR$_9$R$_{10}$, or C$_1$–C$_6$alkylNR$_9$R$_{10}$; R$_7$ is hydrogen, C$_1$–C$_6$alkyl, aryl, arylC$_1$–C$_6$alkyl, C$_1$–C$_6$alkylcarbonyl, C$_1$–C$_6$alkyloxocarbonyl, arylcarbonyl, aryloxocarbonyl, arylC$_1$–C$_6$alkylcarbonyl, arylC$_1$–C$_6$alkyloxocarbonyl, C$_1$–C$_6$alkylcarboxy, arylC$_1$–C$_6$alkylcarboxy, R$_9$R$_{10}$NcarbonylC$_1$–C$_6$alkyl wherein R$_9$ and R$_0$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted;

R$_8$ is hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkyl-carboxy wherein the alkyl and aryl groups are optionally substituted;

R$_9$ and R$_{10}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy wherein the alkyl and aryl groups are optionally substituted; or R$_9$ and R$_{10}$ are together with the nitrogen to which they are attached forming a saturated, partially saturated or aromatic cyclic, bicyclic or tricyclic ring system containing from 3 to 14 carbon atoms and from 0 to 3 additional heteroatoms selected from nitrogen, oxygen or sulphur, the ring system can optionally be substituted with at least one C$_1$–C$_6$alkyl, aryl, arylC$_1$–C$_6$alkyl, hydroxy, oxo, C$_1$–C$_6$alkyloxy, arylC$_1$–C$_6$alkyloxy, C$_1$–C$_6$alkyloxyC$_1$–C$_6$alkyl, NR$_{11}$R$_{12}$ or C$_1$–C$_6$alkylamino-C$_1$–C$_6$alkyl, wherein R$_{11}$ and R$_{12}$ are independently selected from hydrogen, C$_1$–C$_6$alkyl, aryl, arylC$_1$–C$_6$alkyl, C$_1$–C$_6$alkylcarbonyl, arylcarbonyl, arylC$_1$–C$_6$alkylcarbonyl, C$_1$–C$_6$alkylcarboxy or arylC$_1$–C$_6$alkylcarboxy; wherein the alkyl and aryl groups are optionally substituted; or R$_9$ and R$_{10}$ are independently a saturated or partial saturated cyclic 5, 6 or 7 membered amine, imide or lactam;

or a salt thereof with a pharmaceutically acceptable acid or a base, or any optical isomer or mixture of isomers thereof, or any tautomer thereof.

2. The method of claim 1 wherein the compound is selected from the following:

5-(4-Chloro-1,3-dioxo-1,3-dihydro-isoindol-2-ylmethyl)-2-(oxalyl-amino)-4,7-dihydro-5H-thieno[2,3-c]pyran-3-carboxylic acid;

7-(2,4-Dioxo-thiazolidin-3-ylmethyl)-2-(oxalyl-amino)-4,7-dihydro-5H-thieno[2,3-c]pyran-3-carboxylic acid;

5-(4,5,6,7-Tetrachloro-1,3-dioxo-1,3-dihydro-isoindol-2-ylmethyl)-2-(oxalyl-amino)-4,7-dihydro-5H-thieno[2,3-c]pyran-3-carboxylic acid;

7-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(1,3-Dioxo-1,3-dihydro-benzo[f]isoindol-2-ylmethyl)-2-(oxalyl-amino)-4,7-dihydro-5H-thieno[2,3-c]pyran-3-carboxylic acid;

Oxalic acid (3-carboxy-2-(oxalyl-amino)-4,7-dihydro-5H-thieno[2,3-c]pyran-5-ylmethyl) ester methyl ester;

Oxalic acid (3-carboxy-2-(oxalyl-amino)-4,7-dihydro-5H-thieno[2,3-c]pyran-5-ylmethyl) ester;

7-Hydroxymethyl-2-(oxalyl-amino)-4,7-dihydro-5H-thieno[2,3-c]pyran-3-carboxylic acid;

7-(((Benzo[1,3]dioxole-5-carbonyl)-amino)-methyl)-2-(oxalyl-amino)-4,7-dihydro-5H-thieno[2,3-c]pyran-3-carboxylic acid;

5-(3-Imidazol-1-yl-2,5-dioxo-pyrrolidin-1-ylmethyl)-2-(oxalyl-amino)-4,7-dihydro-5H-thieno[2,3-c]pyran-3-carboxylic acid;

2-(Oxalyl-amino)-5-phenylcarbamoyl-4,7-dihydro-5H-thieno[2,3-c]pyran-3-carboxylic acid;

2-(Oxalyl-amino)-5-phenylcarbamoyl-4,7-dihydro-5H-thieno[2,3-c]pyran-3-carboxylic acid;

2-(Oxalyl-amino)-4,7-dihydro-5H-thieno[2,3-c]pyran-3,7-dicarboxylic acid 7-ethyl ester;

7-Benzylcarbamoyl-2-(oxalyl-amino)-4,7-dihydro-5H-thieno[2,3-c]pyran-3-carboxylic acid;

5-(5,7-Dioxo-5,7-dihydro-pyrrolo[3,4-b]pyrazin-6-ylmethyl)-2-(oxalyl-amino)-4,7-dihydro-5H-thieno[2,3-c]pyran-3-carboxylic acid;

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;

7-(1,3-Dioxo-1,3-dihydro-isoindol-2-yloxymethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

7-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

7-(3-(2,4-Dimethoxy-phenyl)-ureidomethyl)-2-(oxalyl-amino)-4,7-dihydro-5H-thieno[2,3-c]pyran-3-carboxylic acid;

2-((3-Carboxy-2-(oxalyl-amino)-4,7-dihydro-5H-thieno[2,3-c]pyran-5-ylmethyl)-carbamoyl)-nicotinic acid;

5-(4-Fluoro-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Benzyloxy-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

7-(5,7-Dioxo-5,7-dihydro-[1,3]dioxolo[4,5-f]isoindol-6-ylmethyl2-(oxalyl-amino)-4,7-dihydro-5H-thieno[2,3-c]pyran-3-carboxylic acid;

7-(2,4-Dioxo-5-pyridin-2-ylmethylene-thiazolidin-3-yl-methyl)-2-(oxalyl-amino)-4,7-dihydro-5H-thieno[2,3-c]pyran-3-carboxylic acid;

7-(2,4-Dioxo-5-pyridin-2-ylmethyl-thiazolidin-3-ylmethyl)-2-(oxalyl-amino)-4,7-dihydro-5H-thieno[2,3-c]pyran-3-carboxylic acid;

7-(5-(4-Methoxy-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(4-Acetylamino-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(3,5-Dimethoxy-benzylidene)-2,4-dioxo-thiazolidin-3-ylmethyl)-2-(oxalyl-amino)-4,7-dihydro-5H-thieno[2,3-c]pyran-3-carboxylic acid;

7-(5-(1H-Imidazol-4(5)-ylmethylene)-2,4-dioxo-thiazolidin-3-ylmethyl)-2-(oxalyl-amino)-4,7-dihydro-5H-thieno[2,3-c]pyran-3-carboxylic acid;

7-((2-(4-Methanesulfonyl-phenyl)-acetylamino)-methyl)-2-(oxalyl-amino)-4,7-dihydro-5H-thieno[2,3-c]pyran-3-carboxylic acid;

5-(1,3-Dioxo-4,7-epoxido-1,3,4,5,6,7-hexahydro-isoindol-2-ylmethyl)-2-(oxalyl-amino)-4,7-dihydro-5H-thieno[2,3-c]pyran-3-carboxylic acid;

7-((2-Amino-3-phenyl-propionylamino)methyl)-2-(oxalyl-amino)-4,7-dihydro-5H-thieno[2,3-c]pyran-3-carboxylic acid;

7-(((2R)-2-Amino-3-phenyl-propionylamino)-methyl)-2-(oxalyl-amino)-4,7-dihydro-5H-thieno[2,3-c]pyran-3-carboxylic acid;

7-((2-Acetylamino-3-(4-hydroxy-phenyl)-propionylamino)-methyl)-2-(oxalyl-amino)-4,7-dihydro-5H-thieno[2,3-c]pyran-3-carboxylic acid;

7-((2-Acetylamino-3-methyl-butyrylamino)methyl)-2-(oxalyl-amino)-4,7-dihydro-5H-thieno[2,3-c]pyran-3-carboxylic acid;

5-(5-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Acetylamino-1,3-dioxo-1,3-dihydro-isoindol-2-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-b]pyridin-6-ylmethyl)-2-(oxalyl-amino)-4,7-dihydro-5H-thieno[2,3-c]pyran-3-carboxylic acid;

5-(5,7-Dioxo-5,7-dihydro-pyrrolo[3,4-c]pyridin-6-ylmethyl)-2-(oxalyl-amino)-4,7-dihydro-5H-thieno[2,3-c]pyran-3-carboxylic acid;

5-(5-Nitro-1,3-dioxo-1,3-dihydro-isoindol-2-ylmethyl)-2-(oxalyl-amino)-4,7-dihydro-5H-thieno[2,3-c]pyran-3-carboxylic acid;

5-(5-Hydroxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

5-(4-Nitro-1,3-dioxo-1,3-dihydro-isoindol-2-ylmethyl)-2-(oxalyl-amino)-4,7-dihydro-5H-thieno[2,3-c]pyran-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyran-3-carboxylic acid;

2-(Oxalyl-amino)-7-(3-oxo-3H-benzo[d]isoxazol-2-ylmethyl)-4,7-dihydro-5H-thieno[2,3-c]pyran-3-carboxylic acid;

5-(1,3-Dioxo-1,3-dihydro-isoindol-2-ylmethyl)-2-(oxalyl-amino)-4,5,6,7-tetrahydro-thieno[2,3-c]pyridine-3,6-dicarboxylic acid 6-ethyl ester;

5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

(L)-5-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1-oxo-1,3-dihydro-isoindol-2-ylmethyl)-4,5,6,7-tetrahydro-thieno[2,3-c]pyridine-3-carboxylic acid;

or a pharmaceutically acceptable salt thereof.

3. The method of claim 1 wherein the compound is selected from the following:

5-(5-Methoxy-1,3-dioxo-1,3-dihydro-isoindol-2-ylmethyl)-2-(oxalyl-amino)-4,7-dihydro-5H-thieno[2,3-c]pyran-3-carboxylic acid;

7-(((Benzo[1,3]dioxole-5-carbonyl)amino)methyl)-2-(oxalyl-amino)-4,7-dihydro-5H-thieno[2,3-c]pyran-3-carboxylic acid;

5-(4-(4-Chloro-phenylsulfanyl)-6-methyl-1,3-dioxo-1,3-dihydro-pyrrolo[3,4-c]pyridin-2-ylmethyl)-2-(oxalyl-amino)-4,7-dihydro-5H-thieno[2,3-c]pyran-3-carboxylic acid;

7-(3-(2,4-Dimethoxy-phenyl)-ureidomethyl)-2-(oxalyl-amino)-4,7-dihydro-5H-thieno[2,3-c]pyran-3-carboxylic acid;

7-((2-(4-Methanesulfonyl-phenyl)acetylamino)methyl)-2-(oxalyl-amino)-4,7-dihydro-5H-thieno[2,3-c]pyran-3-carboxylic acid;

7-((2-Acetylamino-3-(4-hydroxy-phenyl)propionylamino)methyl)-2-(oxalyl-amino)-4,7-dihydro-5H-thieno[2,3-c]pyran-3-carboxylic acid;

5-(S)-(1,3-Dioxo-1,3-dihydro-isoindol-2-ylmethyl)-2-(oxalyl-amino)-4,5,6,7-tetrahydro-thieno[2,3-c]pyridine-3-carboxylic acid;

7-(4-Hydroxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(S)-(1-oxo-1,3-dihydro-isoindol-2-ylmethyl)-4,5,6,7-tetrahydro-thieno[2,3-c]pyridine-3-carboxylic acid;

5-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(4-Hydroxy-1-oxo-1,3-dihydro-isoindol-2-ylmethyl)-6-methyl-2-(oxalyl-amino)-4,5,6,7-tetrahydro-thieno[2,3-c]pyridine-3-carboxylic acid;

5-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

7-((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Benzyloxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

5-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

7-(7-Hydroxy-1-oxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(1,3-Dioxo-1,3-dihydro-isoindol-2-ylmethyl)-6-(4-methoxy-benzyl)-2-(oxalyl-amino)-4,5,6,7-tetrahydro-thieno[2,3-c]pyridine-3-carboxylic acid;

7-(((5-Benzyloxy-1H-indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-(((6-Bromo-2-p-tolyl-quinoline-4-carbonyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((5-methyl-2-phenyl-2H-[1,2,3]triazole-4-carbonyl)amino)methyl)-2-(oxalyl-amino)-4,5,6,7-tetrahydro-thieno[2,3-c]pyridine-3-carboxylic acid;

7-(((1H-Indole-3-carbonyl)amino)methyl)-6-(4-methoxy-benzyl)-2-(oxalyl-amino)-4,5,6,7-tetrahydro-thieno[2,3-c]pyridine-3-carboxylic acid;

7-((4-Ethoxy-2-hydroxy-benzoylamino)methyl)-6-(4-methoxy-benzyl)-2-(oxalyl-amino)-4,5,6,7-tetrahydro-thieno[2,3-c]pyridine-3-carboxylic acid;

7-((4-Benzoylamino-benzoylamino)methyl)-6-(4-methoxy-benzyl)-2-(oxalyl-amino)-4,5,6,7-tetrahydro-thieno[2,3-c]pyridine-3-carboxylic acid;

7-(((Biphenyl-4-carbonyl)-amino)methyl)-6-(4-methoxy-benzyl)-2-(oxalyl-amino)-4,5,6,7-tetrahydro-thieno[2,3-c]pyridine-3-carboxylic acid;

7-(((1H-Indole-2-carbonyl)amino)methyl)-6-(4-methoxy-benzyl)-2-(oxalyl-amino)-4,5,6,7-tetrahydro-thieno[2,3-c]pyridine-3-carboxylic acid;

7-((3-Biphenyl-4-yl-acryloylamino)methyl)-6-(4-methoxy-benzyl)-2-(oxalyl-amino)-4,5,6,7-tetrahydro-thieno[2,3-c)pyridine-3-carboxylic acid;

6-(4-Methoxy-benzyl)-7-(((5-methoxy-1H-indole-2-carbonyl)amino)methyl)-2-(oxalyl-amino)-4,5,6,7-tetrahydro-thieno[2,3-c]pyridine-3-carboxylic acid;

7-((4-Benzyl-benzoylamino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-7-(((naphthalene-1-carbonyl)amino)methyl)-2-(oxalyl-amino)-4,5,6,7-tetrahydro-thieno[2,3-c]pyridine-3-carboxylic acid;

6-(4-Methoxy-benzyl)-5-((2-naphthalen-2-yl-ethylamino)methyl)-2-(oxalyl-amino)-4,5,6,7-tetrahydro-thieno[2,3-c]pyridine-3-carboxylic acid;

5-((2-Benzo[1,3]dioxol-5-yl-acetylamino)methyl)-2-(oxalyl-amino)-4,5,6,7-tetrahydro-thieno[2,3-c]pyridine-3-carboxylic acid;

5-((2-Dibenzofuran-2-yl-ethyl)amino)methyl)-6-(4-methoxy-benzyl)-2-(oxalyl-amino)-4,5,6,7-tetrahydro-thieno[2,3-c]pyridine-3-carboxylic acid;

6-(4-Methoxy-benzyl)-5-((2-(5-methoxy-2-methyl-H-indol-3-yl)-acetylamino)methyl)-2-(oxalyl-amino)-4,5,6,7-tetrahydro-thieno[2,3-c]pyridine-3-carboxylic acid;

5-(R)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(7-Methoxy-1-oxo-1,3-dihydro-isoindol-2-ylmethyl)-2-(oxalyl-amino)-4,5,6,7-tetrahydro-thieno[2,3-c]pyridine-3-carboxylic acid;

5-(S)-(4-Hydroxy-1-oxo-1,3-dihydro-isoindol-2-ylmethyl)-2-(oxalyl-amino)-4,5,6,7-tetrahydro-thieno[2,3-c]pyridine-3-carboxylic acid;

2-(S)-(Oxalyl-amino)-5-((4-phenoxy-benzylamino)methyl)-4,5,6,7-tetrahydro-thieno[2,3-c]pyridine-3-carboxylic acid;

5-(S)-((4-Acetylamino-benzylamino)methyl)-2-(oxalyl-amino)-4,5,6,7-tetrahydro-thieno[2,3-c]pyridine-3-carboxylic acid;

7-(S)-((Acetyl-(4-phenoxy-benzyl)amino)methyl)-2-(oxalyl-amino)-4,5,6,7-tetrahydro-thieno[2,3-c]pyridine-3-carboxylic acid;

7-(S)-((Acetyl-benzyl-amino)methyl)-2-(oxalyl-amino)-4,5,6,7-tetrahydro-thieno[2,3-c]pyridine-3-carboxylic acid;

5-(S)-(((1,1-Dioxo-1H-benzo[d]isothiazol-3-ylamino)methyl)-2-(oxalyl-amino)-4,5,6,7-tetrahydro-thieno[2,3-c]pyridine-3-carboxylic acid;

5-(4-Benzyloxy-1,3-dioxo-1,3-dihydro-isoindol-2-ylmethyl)-2-(oxalyl-amino)-4,5,6,7-tetrahydro-thieno[2,3-c]pyridine-3-carboxylic acid;

5-(6-Methoxy-4-methoxycarbonyl-1-oxo-1,3-dihydro-isoindol-2-ylmethyl)-2-(oxalyl-amino)-4,5,6,7-tetrahydro-thieno[2,3-c]pyridine-3-carboxylic acid;

2-(Oxalyl-amino)-5-(1,1,3-trioxo-1,3-dihydro-1H-benzo[d]isothiazol-2-ylmethyl)-4,7-dihydro-5H-thieno[2,3-c]pyridine-3-carboxylic acid;

2-(Oxalyl-amino)-7-(1,1,3-trioxo-1,3-dihydro-1H-benzo[d]isothiazol-2-ylmethyl)-4,7-dihydro-5H-thieno[2,3-c]pyridine-3-carboxylic acid;

7-(R)-Carbamoyl-2-(oxalyl-amino)-4,5,6,7-tetrahydro-thieno[2,3-c]pyridine-3-carboxylic acid;

2-(Oxalyl-amino)-5-(S)-(2-oxo-tetrahydro-thiophen-3-yl-carbamoyl)-4,5,6,7-tetrahydro-thieno[2,3-c]pyridine-3-carboxylic acid;

2-(Oxalyl-amino)-5-(S)-phenylcarbamoyl-4,5,6,7-tetrahydro-thieno[2,3-c]pyridine-3-carboxylic acid;

2-(Oxalyl-amino)-7-(R)-phenylcarbamoyl-4,5,6,7-tetrahydro-thieno[2,3-c]pyridine-3-carboxylic acid;

5-(R),7-(R)-Bis-benzyloxymethyl-2-(oxalyl-amino)-4,5,6,7-tetrahydro-thieno[2,3-c]pyridine-3-carboxylic acid;

6-Benzyl-2-(oxalyl-amino)-5-(1,1,3-trioxo-1,3-dihydro-1,6-benzo[d]isothiazol-2-ylmethyl)-4,5,6,7-tetrahydro-thieno[2,3-c]pyridine-3-carboxylic acid;

or a pharmaceutically acceptable salt thereof.

4. The method of claim 1, wherein said exposing step is effected by administering said compound to a mammal in need of said inhibition.

5. The method of claim 4 wherein said mammal has a disease selected from the group consisting of autoimmune diseases, acute and chronic inflammation, osteoporosis, cancers, type I diabetes, type II diabetes, and obesity.

6. The method of claim 4 wherein said mammal is a human.

* * * * *